US012539427B2

(12) United States Patent

Forsell

(10) Patent No.: US 12,539,427 B2
(45) Date of Patent: Feb. 3, 2026

(54) TREATMENT OF GERD

(71) Applicant: Peter Forsell, Obwalden (CH)

(72) Inventor: Peter Forsell, Obwalden (CH)

( * ) Notice: Subject to any disclaimer, the term of this patent is extended or adjusted under 35 U.S.C. 154(b) by 34 days.

(21) Appl. No.: 18/404,930

(22) Filed: Jan. 5, 2024

(65) Prior Publication Data

US 2024/0226581 A1 Jul. 11, 2024

Related U.S. Application Data

(63) Continuation-in-part of application No. 18/576,400, filed as application No. PCT/EP2022/068597 on Jul. 5, 2022, which is a continuation-in-part of application No. 17/367,656, filed on Jul. 6, 2021, now Pat. No. 12,097,138, application No. 18/404,930 is a continuation-in-part of application No. PCT/EP2023/087772, filed on Dec. 22, 2023.

(51) Int. Cl.
*A61N 1/375* (2006.01)
*A61N 1/05* (2006.01)
*A61N 1/36* (2006.01)

(52) U.S. Cl.
CPC ....... *A61N 1/37518* (2017.08); *A61N 1/0509* (2013.01); *A61N 1/36007* (2013.01)

(58) Field of Classification Search
CPC .............. A61N 1/37518; A61N 1/0509; A61N 1/36007; A61B 2017/00827
See application file for complete search history.

(56) References Cited

U.S. PATENT DOCUMENTS

| | | | | |
|---|---|---|---|---|
| 2004/0260316 A1 | 12/2004 | Knudson et al. | | |
| 2005/0283235 A1 | 12/2005 | Kugler et al. | | |
| 2010/0312356 A1* | 12/2010 | Forsell | A61B 1/32 623/23.65 | |
| 2011/0202041 A1 | 8/2011 | Forsell | | |

(Continued)

FOREIGN PATENT DOCUMENTS

| | | | |
|---|---|---|---|
| AU | 2018267675 A1 | 12/2018 | |
| EP | 3072480 A1 | 9/2016 | |

(Continued)

*Primary Examiner* — Erin Mcgrath

(57) ABSTRACT

A surgical method of treating reflux disease comprising the steps of dissecting the fundus at least partially down on the posterior side thereof; in the approximate direction towards bursa Omentalis, as well as away from the spleen. The method further comprising the steps of dissecting the esophagus such that the esophagus is disconnected from the surrounding tissue at least 3 cm in a cranial direction from the angle of his and connecting the fundus to the esophagus by placing at least two posterior single sutures in a posterior suture line, or a posterior continuous suture line, connecting the fundus to the esophagus, on the sinister-posterior side of the esophagus, and placing at least two anterior sutures, in an anterior suture line, or an anterior continuous suture line, connecting the fundus to the esophagus, on the sinister-anterior side of the esophagus. The method further comprises placing an implantable movement restriction device between the angle of His and the diaphragm, such that the lower esophageal sphincter is prevented from sliding through the esophageal hiatus.

20 Claims, 114 Drawing Sheets

(56) References Cited

U.S. PATENT DOCUMENTS

| | | | | |
|---|---|---|---|---|
| 2015/0374352 | A1* | 12/2015 | Inoue | A61B 17/00234 128/898 |
| 2018/0161037 | A1 | 6/2018 | Fadahunsi | |
| 2019/0029688 | A1 | 1/2019 | Shelton, IV et al. | |
| 2020/0246169 | A1 | 8/2020 | Forsell | |
| 2021/0378811 | A1 | 12/2021 | Forsell | |

FOREIGN PATENT DOCUMENTS

| | | | |
|---|---|---|---|
| EP | 3388034 | A1 | 10/2018 |
| WO | 2003020183 | A1 | 3/2003 |
| WO | 2009048380 | A1 | 4/2009 |

* cited by examiner

Fig.23I´

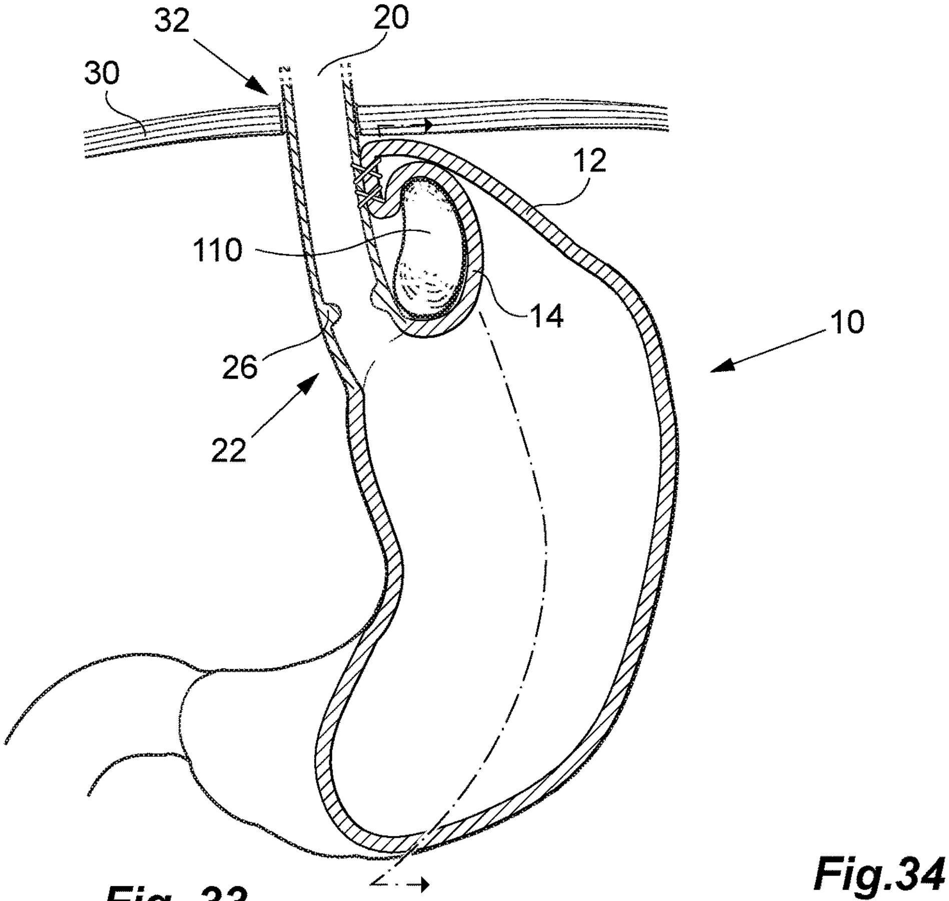
Fig. 33
Fig.34
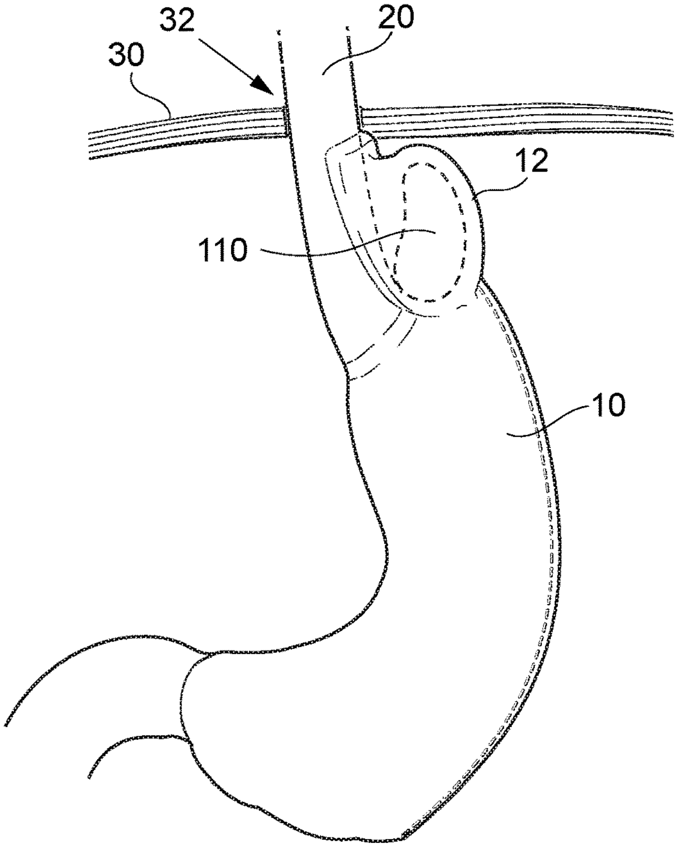

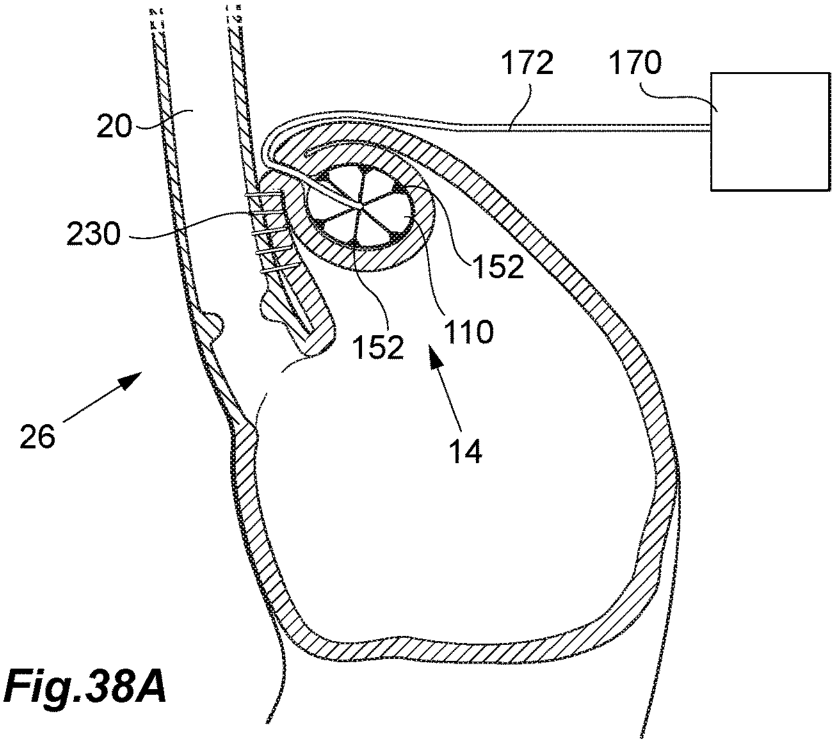
Fig.38A
Fig. 38B
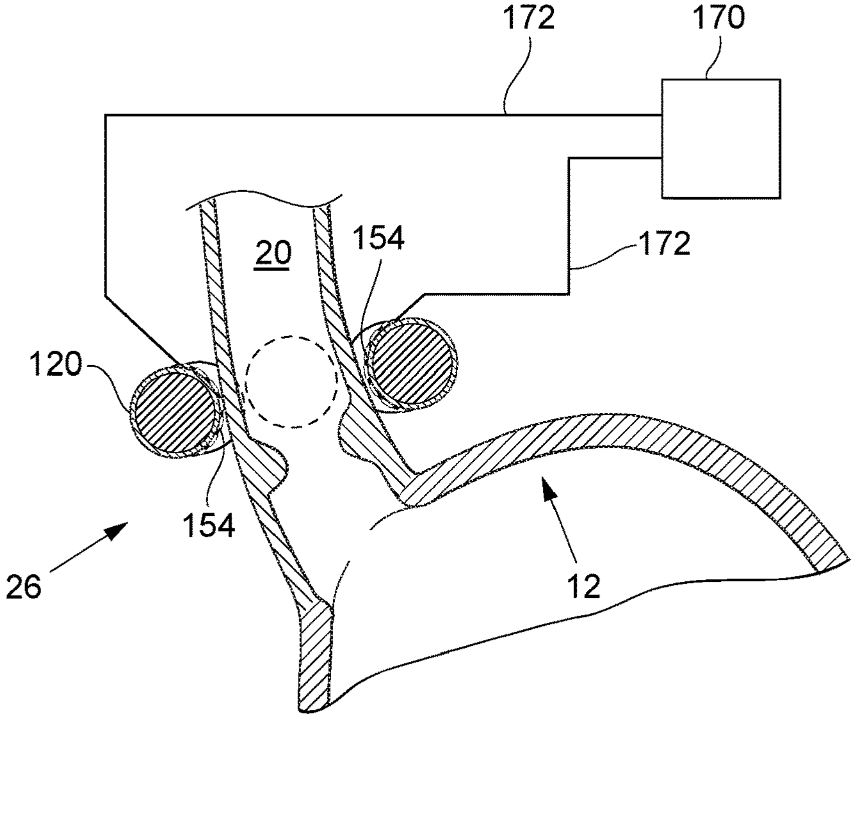

*Fig. 39W´*
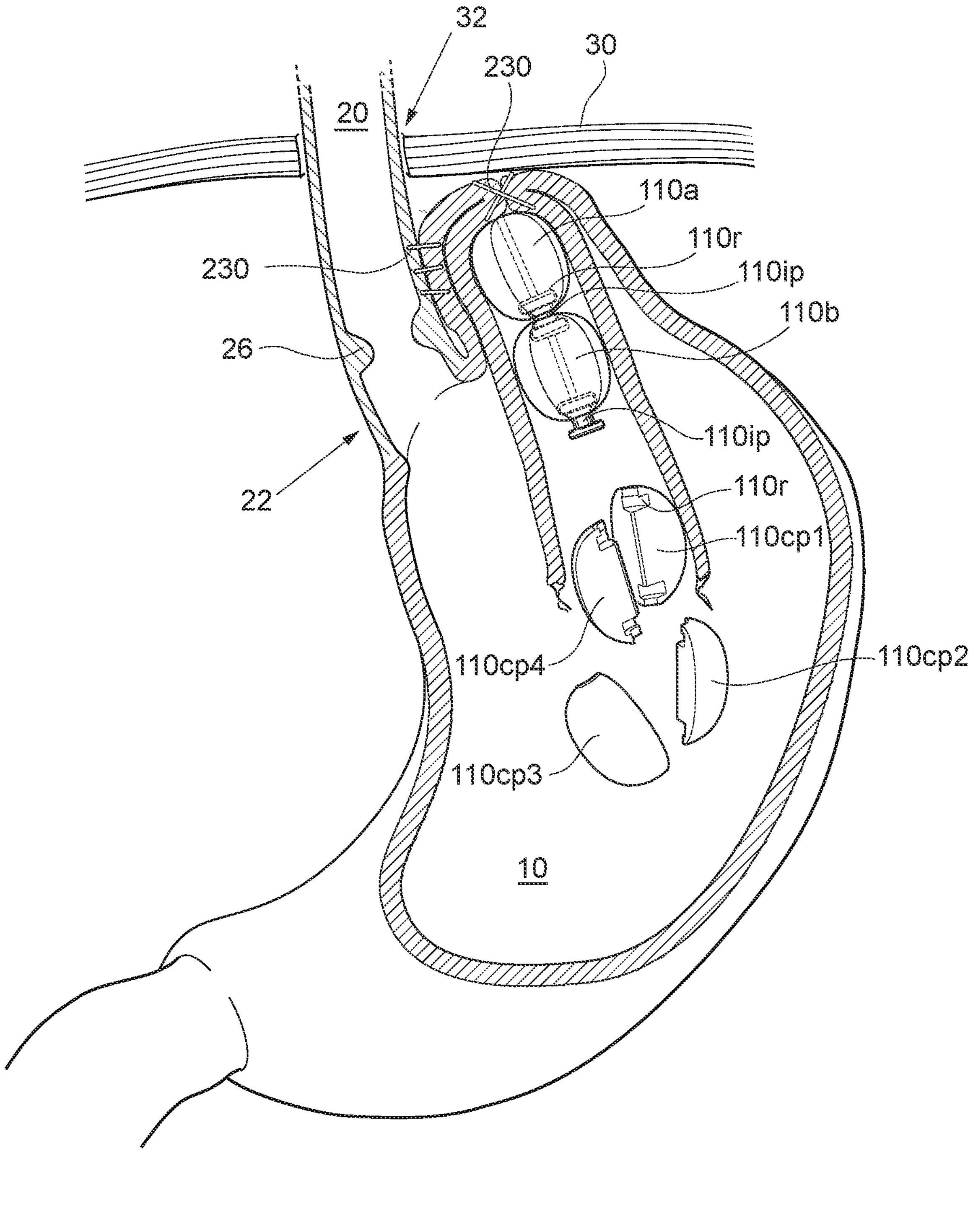

Fig.40N´
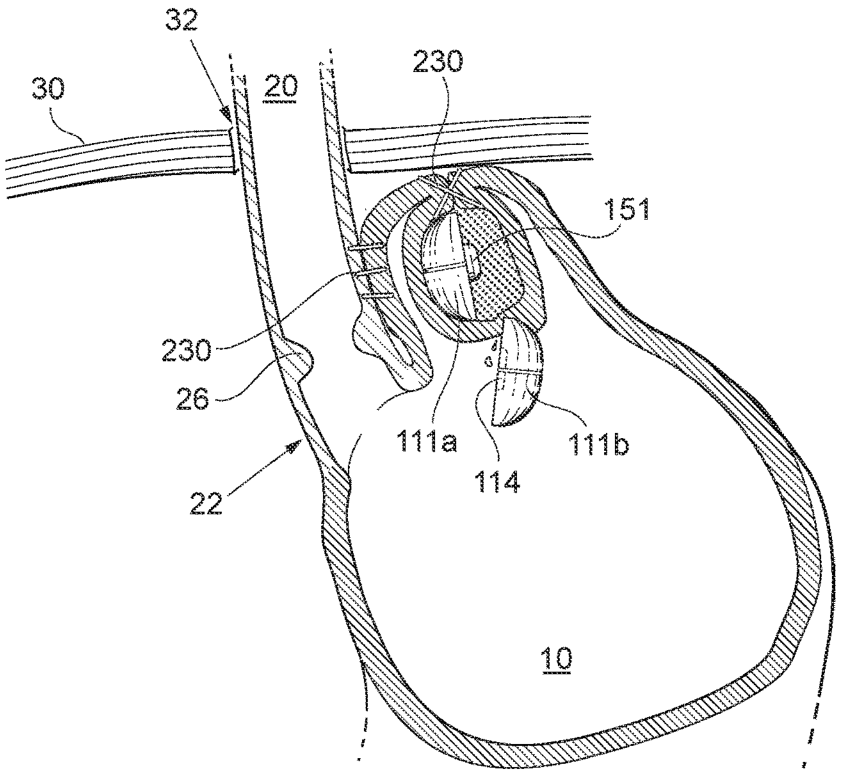
Fig.40N´´
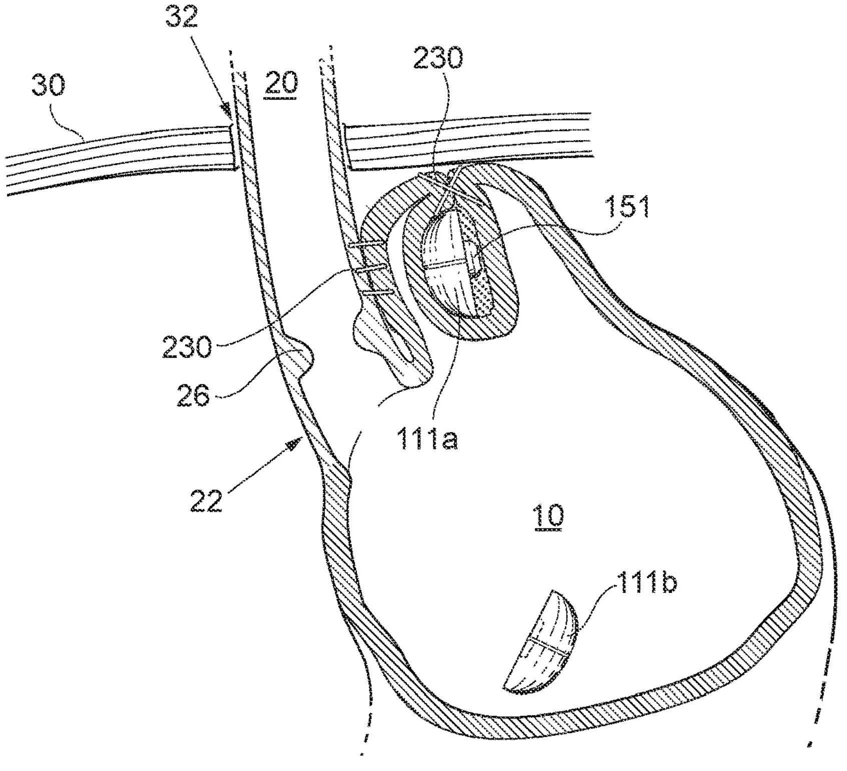

Fig.40P´

*Fig.40P˝*
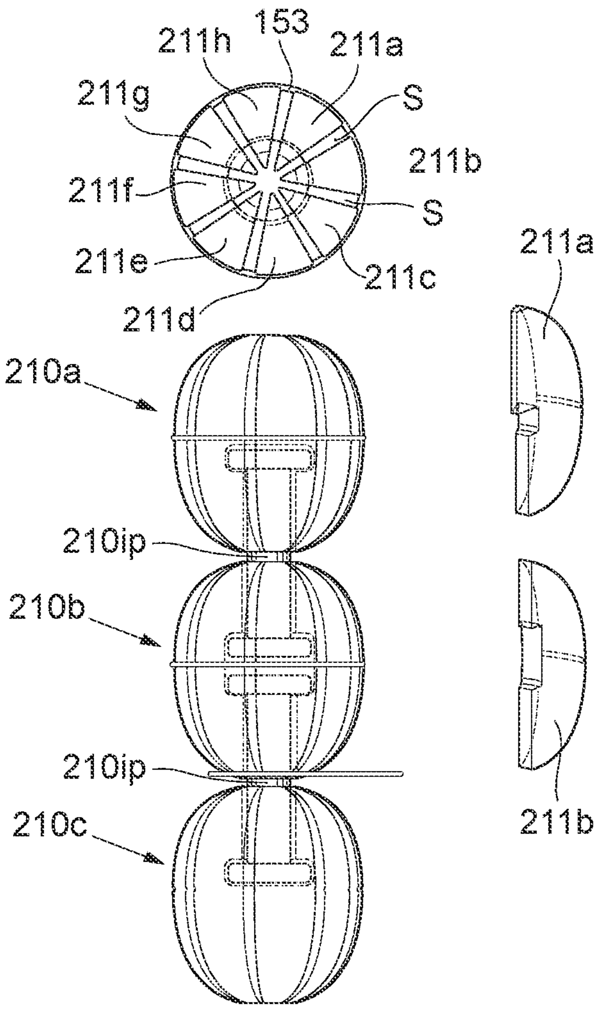

Fig.40SC´
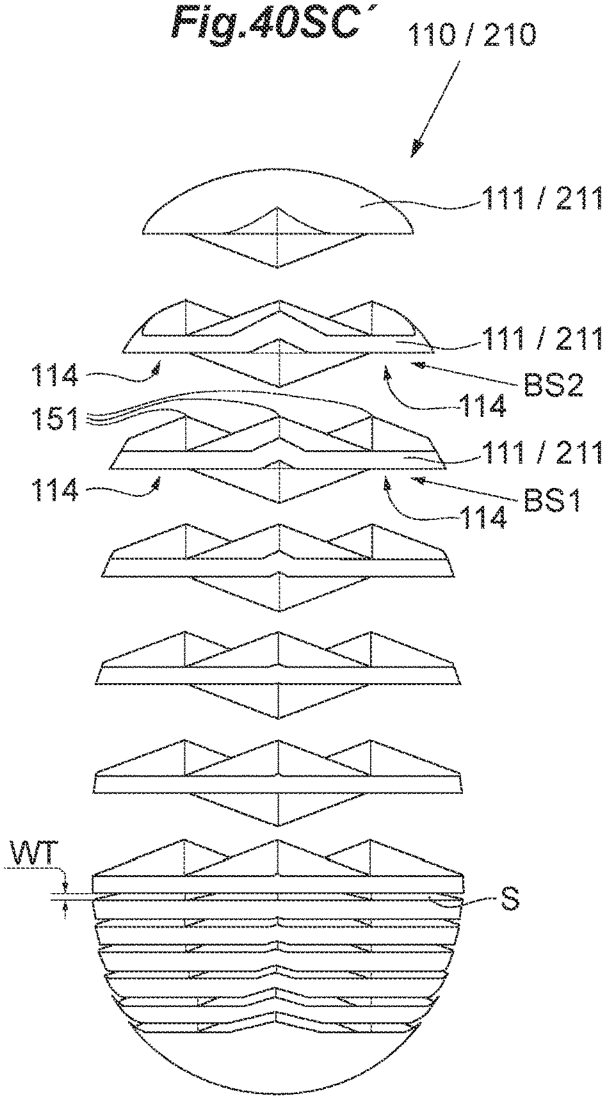
Fig.40SD´
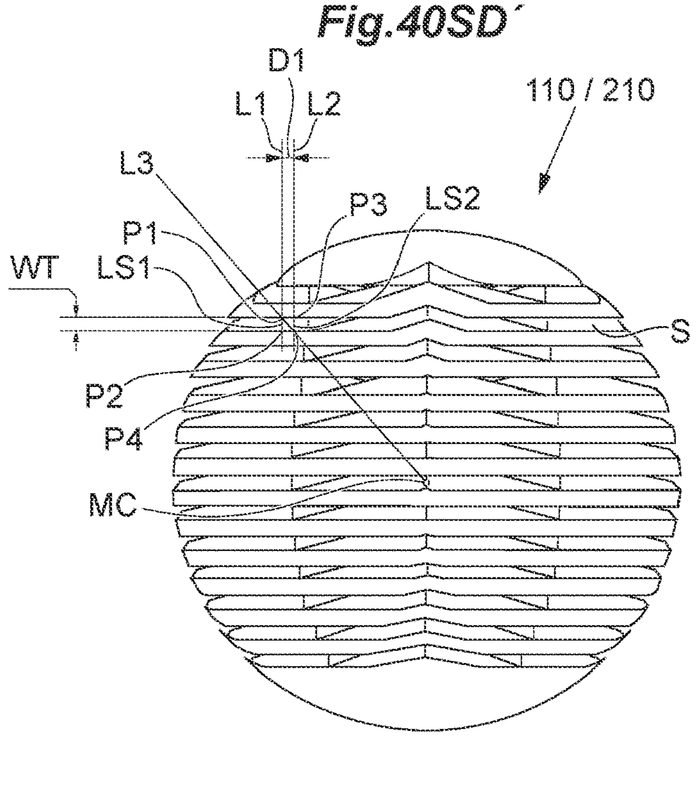

Fig.40SE´
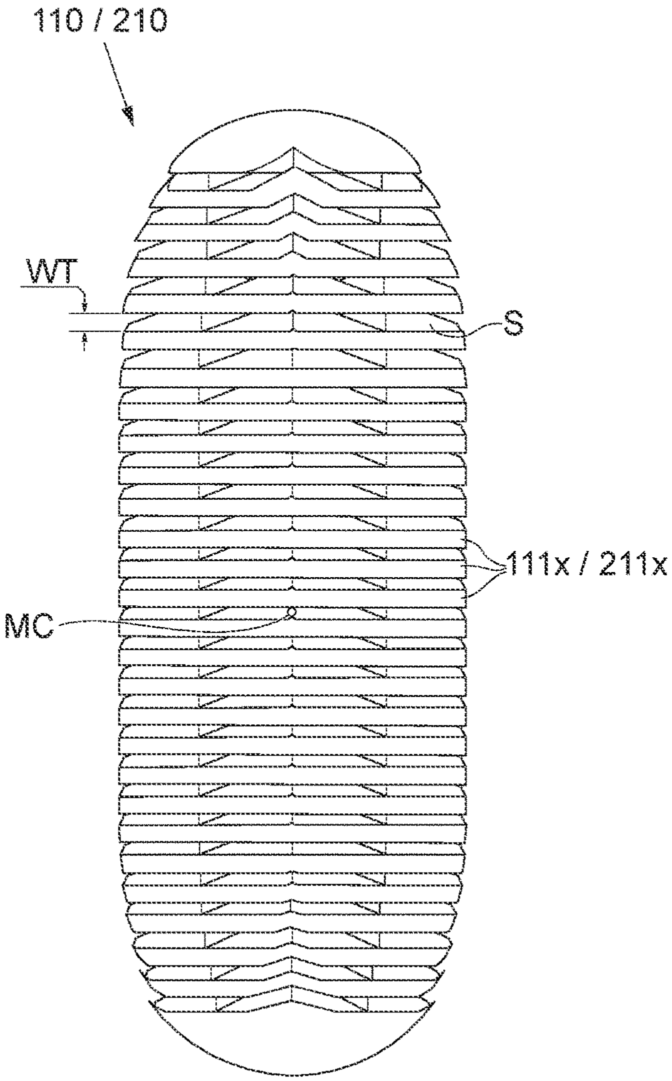
Fig.40SF´
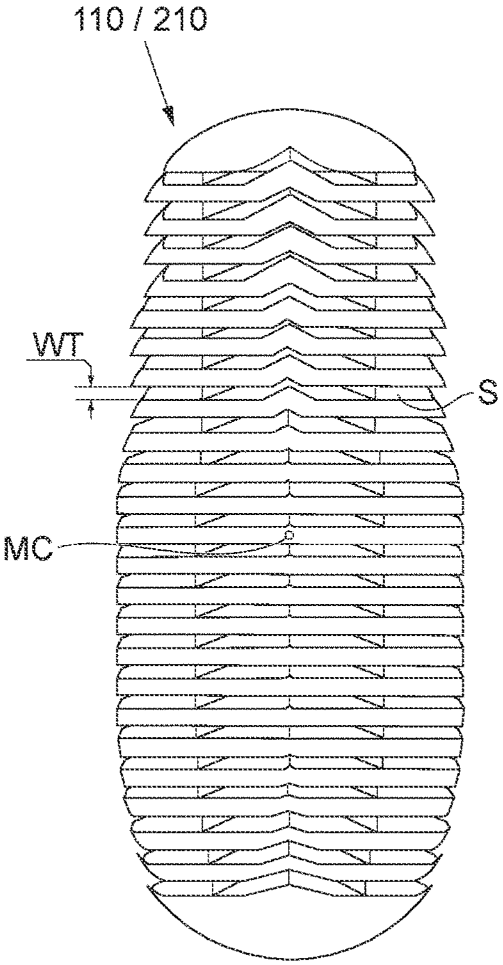

Fig.40SE´´
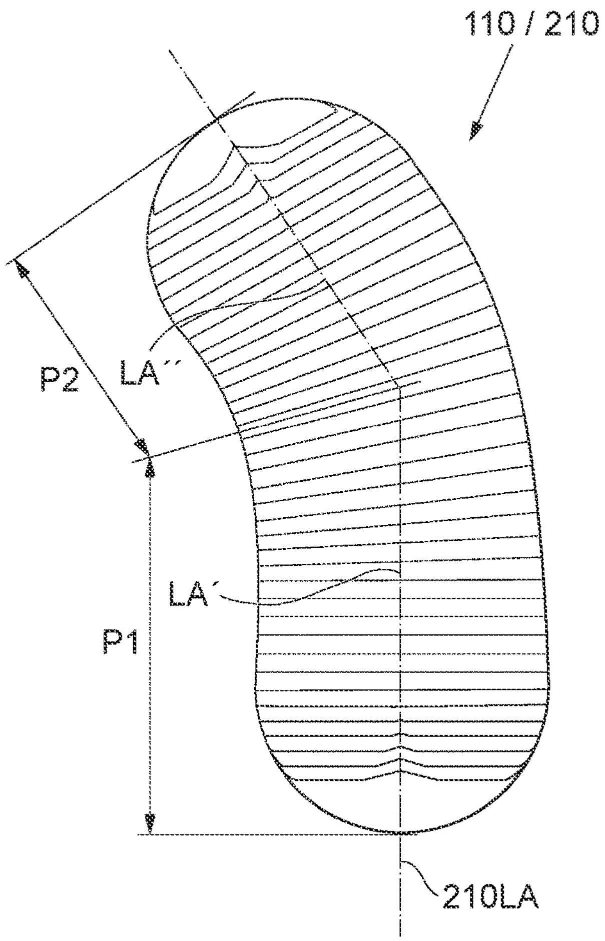
Fig.40SE´´´
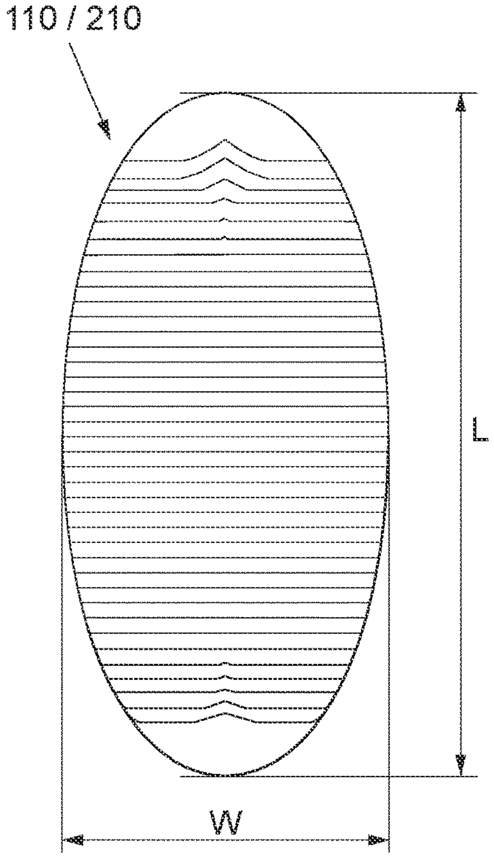

TREATMENT OF GERD

This application is a continuation-in-part of U.S. application Ser. No. 18/576,400, filed Jan. 4, 2024, which is the national stage entry of International Application No. PCT/EP2022/068597, filed 5 Jul. 2022, which designated the U.S., is a continuation-in-part of U.S. application Ser. No. 17/367,656, filed on 6 Jul. 2021, and claims priority of Swedish Application No. 2151027-6, filed 30 Aug. 2021 and Swedish Application No. 2250227-2, filed 18 Feb. 2022; this application is also a continuation-in-part of International Application No. PCT/EP2023/087772, filed Dec. 22, 2023; the entire contents of each of which are hereby incorporated by reference in this application.

TECHNICAL FIELD

The present inventive concept generally relates to medial implants. More specifically the inventive concept relates to medical implants for treating gastroesophageal reflux disease (GERD).

BACKGROUND

Gastroesophageal reflux disease (GERD), or reflux disease, is a condition resulting in mucosal damage in the esophagus caused by recurring occurrence of acid reflux in the esophagus. GERD can be treated in a number of different ways, including both medical and surgical treatments. An example of a surgical treatment is Nissen fundoplication surgery, in which the upper curve of the stomach (the fundus) is wrapped around the lower esophageal sphincter (LES) to strengthen the sphincter, prevent acid reflux, and repair a hiatal hernia. This method however risks causing a constriction of the food passageway, making it more difficult for the patient to swallow.

Another example is the Anglechik prosthesis, in which a device formed like a horseshoe is placed around the esophagus above the cardia. The intended effect is to prevent the cardia from slipping up into the thorax cavity. However, this device is associated with a number of complications, including migrating through and damaging the esophagus. Further, the body tends to react to a medical implant, partly because the implant is a foreign object, and partly because the implant interacts mechanically with tissue of the body. Exposing tissue to long-term engagement with, or pressure from, an implant may deprive the cells of oxygen and nutrients, which may lead to deterioration of the tissue, atrophy and eventually necrosis.

It would therefore be advantageous to provide more efficient and/or less damaging techniques for treating GERD.

SUMMARY

It is an object of the present inventive concept to overcome, or at least alleviate, at least some of the drawbacks associated with the above-mentioned treatments of GERD. Further and/or alternative objectives may be understood from the following.

A method for treating reflux disease of a human patient by implanting a movement restriction device is provided. The movement restriction device is arranged to restrict movement of the cardia of the patient's stomach towards the diaphragm to hinder the cardia from sliding through the diaphragm opening into the patient's thorax. The method comprises attaching the fundus of the stomach of the patient to the esophagus of the patient in a first position, attaching the fundus of the stomach of the patient to the esophagus of the patient in a second position, at a distance from the first position in a cranial-caudal direction, and positioning the movement restriction device between the first and second position, such that the movement restriction device is secured in the cranial-caudal direction by the attachments between the fundus and the esophagus in the first and second positions.

According to one embodiment, the step of attaching the fundus of the stomach of the patient to the esophagus of the patient in a second position is preceded by the step of positioning the movement restriction device between the first and second position.

According to one embodiment, at least one of the steps of: attaching the fundus of the stomach of the patient to the esophagus of the patient in a first position, and attaching the fundus of the stomach of the patient to the esophagus of the patient in a second position comprises suturing or stapling the fundus to the esophagus.

According to one embodiment, the steps of attaching the fundus of the stomach of the patient to the esophagus of the patient in a first position and attaching the fundus of the stomach of the patient to the esophagus of the patient in a second position are preceded by the step of dissecting the stomach of the patient.

According to one embodiment, at least one of the steps of attaching the fundus of the stomach of the patient to the esophagus of the patient in a first position and attaching the fundus of the stomach of the patient to the esophagus of the patient in a second position is performed using a translaminar instrument configured to be inserted through the esophagus of the patient.

According to one embodiment, the step of positioning the movement restriction device between the first and second position is performed using an abdominal instrument configured to enter the abdomen of the patient through an incision made in the skin of the patient.

At least one of the steps of attaching the fundus of the stomach of the patient to the esophagus of the patient in a first position and attaching the fundus of the stomach of the patient to the esophagus of the patient in a second position may be performed using an abdominal instrument configured to enter the abdomen of the patient through an incision made in the skin of the patient.

The step of attaching the fundus of the stomach of the patient to the esophagus of the patient in a first position may comprise attaching the fundus of the stomach of the patient to the esophagus of the patient at a distance from the angle of His exceeding 5 mm, or exceeding 10 mm, or exceeding 20 mm or exceeding 30 mm.

The step of positioning the movement restriction device between the first and second position may comprise positioning the center of mass of the movement restriction device in a plane extending perpendicular to the cranial-caudal direction at a distance from the angle of His exceeding 20 mm, or exceeding 30 mm.

The step of positioning the movement restriction device between the first and second position may comprise positioning the upper-most point of the movement restriction device in a plane extending perpendicular to the cranial caudal direction at a distance from an upper-most point of the cardia exceeding 5 mm, or exceeding 10 mm.

The step of positioning the movement restriction device between the first and second position may comprise positioning the center of mass of the movement restriction device in a plane extending perpendicular to the cranial-caudal direction at a distance from an upper-most point of the cardia exceeding 1 mm, or exceeding 5 mm, or exceeding 10 mm.

The movement restriction device may in any of the embodiments herein have a rounded shape, which may be a spherical shape.

The step of positioning the movement restriction device may comprise positioning a movement restriction device encircling at least ⅓ of the esophagus in a plane extending perpendicular to the cranial-caudal direction, or positioning a movement restriction device encircling at least ½ of the esophagus in a plane extending perpendicular to the cranial-caudal direction, or positioning a movement restriction device encircling at least ⅔ of the esophagus in a plane extending perpendicular to the cranial-caudal direction, or positioning a movement restriction device encircling the esophagus in a plane extending perpendicular to the cranial-caudal direction.

The step of positioning the movement restriction device may comprise positioning a movement restriction device comprising a curved outer surface, such that the curved outer surface faces the esophagus. The curved outer surface may comprise a radius of curvature corresponding to or exceeding the radius of curvature of the esophagus, such that the curved outer surface comprises a radius of curvature corresponding to or exceeding the radius of curvature of the esophagus.

The step of positioning the movement restriction device may comprise positioning a movement restriction device comprising an electrode arrangement configured to electrically stimulate muscle tissue of the portion of the fundus and/or the serosa to improve the conditions for long term implantation of the movement restriction device.

The method may in any of the embodiments comprise implanting an implantable energy source configured to provide the electrode with electrical power. The implantable energy source may be arranged inside the movement restriction device or may be placed subcutaneously. The method may further comprise implanting an implantable charger configured to be electrically connected to the implantable energy source and enable charging of the implantable energy source by the external energy source.

The method may further comprise implanting a controller configured to be operably connected to the electrode arrangement for controlling the electrical stimulation of the muscle tissue. The controller may be configured to control the electrical stimulation such that the muscle tissue is stimulated by a series of electrical pulses PL1, PL2, PL3, PL4. The electrical stimulation signal may comprise a pulse frequency of 0.15-0.25 Hz, a pulse duration of 20-30 ms and a pulse amplitude of 3-10 mA. The controller may comprise a wireless remote control.

According to one embodiment, the step of positioning the movement restriction device comprises positioning a movement restriction device having a constricting state for hindering fluid from passing from the stomach into the esophagus and an expanded state for allowing food to pass into the stomach in response to the patient swallowing. The step of positioning the movement restriction device may comprise positioning a movement restriction device configured to exert an encircling pressure on the esophagus in the constricting state.

According to one embodiment, the step of positioning the movement restriction device comprises positioning a movement restriction device comprising at least one attractor for resiliently attracting adjacent portions of the movement restriction device to generate the encircling pressure. The attractor may comprise an clastic element or at least two mutually attracting magnets. The apparatus may further comprise a link connecting a first and a second one of said at least two magnets to each other.

The step of positioning the movement restriction device may comprise positioning a non-adjustable movement restriction device or in the alternative the step of positioning the movement restriction device may comprises positioning a movement restriction device having an adjustable volume.

An apparatus for treating reflux disease of a human patient is further provided. The apparatus comprises an implantable movement restriction device having a shape and size allowing it to be arranged to rest against a fundus wall portion of the patient's stomach, such that the movement restriction device is implanted at a position between the patient's diaphragm and a portion of the fundus wall, and such that movement of the cardia of the patient's stomach towards the diaphragm is restricted to hinder the cardia from sliding through the diaphragm opening into the patient's thorax. The apparatus further comprises a first electrode arrangement configured to engage and electrically stimulate muscle tissue of the fundus wall portion to exercise the muscle tissue to improve the conditions for long term implantation of the movement restriction device, and a second electrode arrangement configured to engage and electrically stimulate the cardiac sphincter for causing contraction of the cardiac sphincter.

According to one embodiment, the first electrode arrangement is arranged on an outer surface of the movement restriction device. The first electrode arrangement may comprise a plurality of electrode elements, each of which being configured to engage and electrically stimulate the muscle tissue.

The first electrode arrangement may comprise a coiled wire for increasing a contact surface between the first electrode arrangement and the muscle tissue and for allowing the first electrode arrangement to follow contraction and relaxation of the muscle tissue.

At least one of the first and second electrode arrangement may comprise a bare electrode portion configured to form a metal-tissue interface with the muscle tissue, thereby allowing faradaic charge transfer to the be predominant charge transfer mechanism over said interface.

At least one of the first and second electrode arrangement may comprise an electrode portion at least partly covered by a dielectric material configured to form a dielectric-tissue interface with the muscle tissue, thereby allowing for a faradaic portion of the charge transfer mechanism over said interface to be reduced.

According to one embodiment, the second electrode arrangement comprises at least two electrode elements configured to be arranged on opposing sides of the cardiac sphincter.

The apparatus may further comprise a holder configured to support the at least two electrode elements at the opposing sides of the cardiac sphincter.

According to one embodiment, the apparatus may further comprise an implantable energy source configured to provide the electrode with electrical power. The implantable energy source may be arranged inside the movement restriction device or outside the movement restriction device, such as subcutaneously. The implantable energy source may comprises a primary cell and/or a secondary cell.

The apparatus in any of the preceding embodiments may further comprise a controller configured to be operably connected to the electrode arrangement for controlling the electrical stimulation of the muscle tissue. The controller may be configured to control the electrical stimulation such that the muscle tissue is stimulated by a series of electrical pulses PL1, PL2, PL3, PL4. The controller may be configured to control the electrical stimulation such that a pulse of a first polarity is followed by a pulse of a second, reversed polarity.

According to one embodiment, the controller is configured to generate a pulsed electrical stimulation signal comprising a pulse frequency F of 0.01-150 Hz.

According to one embodiment, the electrical stimulation signal comprises a pulse duration D of 0.01-100 ms.

According to one embodiment, the electrical stimulation signal comprises a pulse amplitude A of 1-15 mA.

According to one embodiment, the electrical stimulation signal comprises a pulse frequency of 0.15-0.25 Hz, a pulse duration of 20-30 ms and a pulse amplitude of 3-10 mA.

The electrical stimulation signal may comprise a build-up period X1 of 0.01-2 s in which the amplitude is gradually increasing, a stimulation period X2 of 1-60 s, and a stimulation pause X4 of 0.01-60 s, wherein the electrical signal comprises a pulse frequency of 1-50 Hz and a pulse duration of 0.1-10 ms.

The controller may comprise a wireless remote control and the controller may be configured to indicate a functional status of the implantable energy source. The functional status may indicate a charge level of the implantable energy source.

According to one embodiment, the functional status indicates a temperature of at least one of the implantable energy source, the muscle tissue and the electrode arrangement.

According to one embodiment, the implantable energy source is configured to be charged by an external energy source arranged outside the patient's body.

According to one embodiment, the apparatus further comprises an implantable charger configured to be electrically connected to the implantable energy source and enable charging of the implantable energy source by the external energy source.

The charger may comprise an electromagnetic coil configured to receive electrical power wirelessly from the external energy source, and the charger may be configured to control the charging of the implantable energy source based on the functional status.

According to one embodiment, the charger is configured to control the charging of the implantable energy source by controlling a receipt of electrical power from the external energy source at the implantable charger.

According to one embodiment, the charger is configured to control the charging of the implantable energy source by controlling a transmission of electrical power from the external energy source to the implantable charger.

The apparatus may further comprise an implantable sensor S1 configured to sense actions potentials generated by pacemaker cells of the muscle tissue, and wherein the controller is configured to control the electrical simulation based at least partly on the sensed action potentials, and according to one embodiment, the controller is configured to generate electrical pulses amplifying the sensed action potentials.

The volume of the movement restriction device may be non-adjustable after implantation, in the alternative, a volume of the movement restriction device is adjustable after implantation.

The movement restriction device may further comprise an injection port for allowing a fluid to be injected or extracted from the inside of the movement restriction device so as to vary a volume of the movement restriction device after implantation.

The movement restriction device may comprise a biocompatible outer surface configured to rest against the fundus wall portion.

The movement restriction device may be substantially spherical or egg-shaped.

The movement restriction device may be configured to be at least partially invaginated by the fundus wall.

The movement restriction device in any of the embodiment herein may be configured to be introduced in the patient's body by means of a gastroscope or an intraluminal instrument.

The movement restriction device may be configured to change its shape to allow it to pass through a trocar during insertion into the patient's body.

According to one embodiment, the movement restriction device is formed of at least two distinct and separable parts configured to be assembled into the movement restriction device after insertion in the patient's body.

A minimum width of the movement restriction device in any of the embodiments herein, as measured from side to side, may be 20 mm or larger, or 30 mm or larger, such as 40 mm or larger.

A minimum outer circumference of the movement restriction device may be 150 mm or less, such as 130 mm or less, such as 110 mm or less, such as 90 mm or less, such as 70 mm or less, such as 50 mm or less, such as 30 mm or less.

An apparatus for treating reflux disease of a human patient is further provided. The apparatus comprises an implantable movement restriction device configured to be fixated between an upper portion of the stomach and the thoracic diaphragm of the patient, for restricting the movement of the cardia of the patient towards the thoracic diaphragm. The implantable movement restriction device has a first cross-sectional distance and a second cross-sectional distance, and the movement restriction device is configured to be implanted such that the first cross-sectional distance is more parallel than perpendicular to the cranial-caudal axis of the patient, and the second cross-sectional distance is more perpendicular than parallel to the cranial-caudal axis of the patient. The implantable movement restriction device is adjustable in situ, such that the shape of the implantable movement restriction device can be adjusted by the adjustment of the length of the first cross-sectional distance, such that the length of the first cross-sectional distance can be increased relative to the length of the second cross-sectional distance.

According to one embodiment, the shape of the implantable movement restriction device can be adjusted by an increase of the length of the first cross-sectional distance relative to the length of the second cross-sectional distance while the length of a circumference of a cross-section of the implantable movement restriction device, in a plane parallel to the coronal plane of the patient remains constant.

According to one embodiment, the shape of the implantable movement restriction device can be adjusted to an elongated shape by an increase of the length of the first cross-sectional distance relative to the length of the second cross-sectional distance.

According to one embodiment, the shape of the implantable movement restriction device can be adjusted by an increase of the length of the first cross-sectional distance relative to the length of the second cross-sectional distance, such that the length of the circumference of a cross-section of the implantable movement restriction device, in a plane parallel to the coronal plane of the patient, is increased relative to the length of the circumference of a cross-section of the implantable movement restriction device, in a plane parallel to the transverse plane of the patient.

According to one embodiment, the implantable movement restriction device comprises a lower portion configured to, directly or indirectly, engage the stomach of the patient in a region of the angle of his, such that the function of the implantable movement restriction device is supported by tissue of the stomach in the region of the angle of his.

According to one embodiment, the implantable movement restriction device comprises an upper portion configured to, directly or indirectly, engage the thoracic diaphragm of the patient, and wherein the upper portion comprises at least one curvature.

According to one embodiment, the implantable movement restriction device is configured to be at least partially invaginated by the stomach wall.

The implantable movement restriction device may be configured to be at least partially invaginated by the stomach wall of the fundus.

According to one embodiment, the movement restriction device comprises a curved cross-section in a plane parallel to the transverse plane of the patient. The curve may be configured to partially enclose the esophagus of the patient. According to one embodiment, the movement restriction device is configured to encircle at least ⅓ of the esophagus in a plane parallel to the transverse plane of the patient, in another embodiment, the movement restriction device is configured to encircle at least ½ of the esophagus in a plane parallel to the transverse plane of the patient, in another embodiment, the movement restriction device comprises a C-shaped cross-section in a plane parallel to the transverse plane of the patient, and the C-shaped cross-section is configured to partially enclose the esophagus of the patient, in another embodiment, the movement restriction device is configured to encircle at least ⅔ of the esophagus in a plane parallel to the transverse plane of the patient.

According to one embodiment, a cross-section of the movement restriction device in a plane parallel to the transverse plane of the patient comprises a closed curve configured to enclose the esophagus of the patient.

According to one embodiment, the movement restriction device is hydraulically adjustable. The movement restriction device may comprise a conduit configured to connect the hydraulically adjustable movement restriction device to an implantable injection port.

The movement restriction device may comprise an injection port, such that the hydraulically adjustable movement restriction device can be adjusted by the injection or withdrawal of a hydraulic fluid into the hydraulically adjustable movement restriction device. A portion of the movement restriction device may comprise a bellows, and wherein the injection or withdrawal of a hydraulic fluid into the hydraulically adjustable movement restriction adjusts a length of the bellows.

According to one embodiment, the movement restriction device comprises a wall enclosing a hydraulic adjustment chamber, and the thickness of the wall varies, which affects the alteration of the shape of the movement restriction device as fluid is injected into or withdrawn from the movement restriction device.

According to one embodiment, the shape of the movement restriction device is altered by a thinner portion of the wall enclosing the hydraulic adjustment chamber being deformed more than thicker portions of the wall enclosing the hydraulic adjustment chamber.

According to one embodiment, the movement restriction device is mechanically adjustable and may comprise a mechanical operation device.

According to one embodiment, the movement restriction device comprises a transferring element configured to transfer at least one of: electrical energy, and mechanical force to the mechanically adjustable movement restriction device.

According to one embodiment, the transferring element comprises at least one of: an electrical lead, a shaft for transferring rotating force, and a shaft for transferring linear force.

According to one embodiment, the mechanical operation device comprises an electrical motor.

The mechanical operation device may comprise a transmission configured to transform a rotating force generated by the electrical motor into a linear force for adjusting the length of the first cross-sectional distance.

According to one embodiment, a portion of the movement restriction device comprises a bellows, and operation of the mechanical operation device adjusts a length of the bellows.

In other embodiments, the movement restriction device is electrically adjustable.

According to one embodiment, the movement restriction device comprises at least one material configured to alter shape when exposed to an electrical current or an electrical voltage. Such a material may comprise at least one electroactive polymer which could be an electroactive polymer selected from a list consisting of: ferroelectric polymers, electrostrictive graft polymers, electrostrictive paper, piezoelectric polymers and liquid crystal elastomers.

According to one embodiment, the movement restriction device further comprises a transferring element configured to transfer electrical energy to the movement restriction device.

According to one embodiment, the length of the first cross-sectional distance is adjustable in situ such that the length of the first cross-sectional distance is 1.2 times the length of the second cross-sectional distance, or 1.3 times the length of the second cross-sectional distance, or 1.5 times the length of the second cross-sectional distance.

According to one embodiment, the length of the first cross-sectional distance is adjustable in situ such that the length of the circumference of a cross-section of the implantable movement restriction device, in a plane parallel to the coronal plane of the patient, is 1.2 times the length of the circumference of a cross-section of the implantable movement restriction device, in a plane parallel to the transverse plane of the patient, or 1.3 times the length of the circumference of a cross-section of the implantable movement restriction device, in a plane parallel to the transverse plane of the patient, or 1.5 times the length of the circumference of a cross-section of the implantable movement restriction device, in a plane parallel to the transverse plane of the patient.

According to one embodiment, the length of the first cross-sectional distance is adjustable in situ such that the center of mass of the movement restriction device in a plane parallel to the transverse plane of the patient is positioned at a distance from the angle of His exceeding 20 mm, or exceeding 30 mm.

According to one embodiment, the length of the first cross-sectional distance is adjustable in situ such that the center of mass of the movement restriction device in a plane parallel to the transverse plane of the patient is positioned at a distance from an upper-most point of the cardia exceeding 5 mm, or exceeding 10 mm.

In any of the embodiments herein, the movement restriction device may comprise at least two parts.

In any of the embodiments herein, the apparatus may further comprise an implantable energy source configured to provide the adjustable implantable movement restriction device with electrical power. The implantable energy source may be arranged inside the movement restriction device or arranged subcutaneously.

In any of the embodiments herein, the apparatus may further comprise at least one electrode for electrically stimulating at least one tissue portion of the patient.

According to one embodiment, the movement restriction device comprises has a constricting state for hindering fluid from passing from the stomach into the esophagus and an expanded state for allowing food to pass into the stomach in response to the patient swallowing. The movement restriction device may comprise at least one attractor for resiliently attracting adjacent portions of the movement restriction device to generate an encircling pressure on the esophagus and the attractor may comprise an clastic element.

According to one embodiment, the attractor comprises at least two mutually attracting magnets.

An apparatus for treating reflux disease of a human patient is further provided. The apparatus comprises an implantable movement restriction device configured to be fixated between an upper portion of the stomach and the thoracic diaphragm of the patient, for restricting the movement of the cardia of the patient towards the thoracic diaphragm. The implantable movement restriction device comprises a first portion having a first volume enclosed by material of the implantable movement restriction device, and a second portion, different from the first portion, having a second volume enclosed by material of the implantable movement restriction device. The first volume and the second volumes are equally large and the first volume has a higher density than the second volume, and the second volume has a density below 1000 kg/m3.

According to one embodiment, the first volume comprises a first solid material, and the first solid material may comprise a polymer material.

According to one embodiment, the first solid material comprises at least one of silicone-based material and a polyurethane-based material.

According to one embodiment, the second volume comprises a second solid material, and the second solid material may comprise a polymer material. The second solid material may comprise at least one of a polypropylene-based and a polyethylene-based material.

The first volume may comprise a solid material having a density above 1000 kg/m3 and the second volume may comprise a solid material having a density below 1000 kg/m3.

According to one embodiment, the second volume comprises a fluid, which may be a liquid having a density a below 1000 kg/m3, such as a liquid selected from a list of oil-based liquids, and alcohol-based liquids.

According to one embodiment, the second volume comprises a gas, and the second volume may comprise a plurality of volumes of gas enclosed by an enclosing material.

According to one embodiment, the second volume comprises a solid polymer material enclosing the enclosing material, and the enclosing material is harder than the solid polymer material.

According to one embodiment, the plurality of volumes of gas enclosed by an enclosing material makes up at least 10 volume percent of the second volume, more preferably at least 20 volume percent of the second volume, and even more preferably at least 30 volume percent of the second volume.

The enclosing material may comprise glass.

According to one embodiment, the movement restriction device has an average density below 1100 kg/m3, or below 1050 kg/m3, or below 1000 kg/m3.

According to one embodiment, the movement restriction device comprises a first cross-sectional distance and a second cross-sectional distance. The movement restriction device may be configured to be implanted such that the first cross-sectional distance is more parallel than perpendicular to the cranial-caudal axis of the patient, and the second cross-sectional distance is more perpendicular than parallel to the cranial-caudal axis of the patient. The implantable movement restriction device may be adjustable in situ, such that the shape of the implantable movement restriction device can be adjusted by the adjustment of the length of the first cross-sectional distance, such that the length of the first cross-sectional distance can be increased relative to the length of the second cross-sectional distance.

According to one embodiment, the shape of the implantable movement restriction device can be adjusted by an increase of the length of the first cross-sectional distance relative to the length of the second cross-sectional distance while the length of a circumference of a cross-section of the implantable movement restriction device, in a plane parallel to the coronal plane of the patient remains constant.

According to one embodiment, the implantable movement restriction device comprises a lower portion configured to, directly or indirectly, engage the stomach of the patient in a region of the angle of his, such that the function of the implantable movement restriction device is supported by tissue of the stomach in the region of the angle of his.

According to one embodiment, the implantable movement restriction device comprises an upper portion configured to, directly or indirectly, engage the thoracic diaphragm of the patient, and wherein the upper portion comprises at least one curvature.

The implantable movement restriction device may in any of the embodiments herein be at least partially invaginated by the stomach wall.

According to one embodiment, the implantable movement restriction device is configured to be at least partially invaginated by the stomach wall of the fundus.

According to one embodiment, the implantable movement restriction device comprises at least one circular cross-section.

The implantable movement restriction device may in any of the embodiments herein comprise at least two parts, and the at least two parts may be configured to be assembled to form the implantable movement restriction device. The at least two parts may be configured to be connected to each other to form the implantable movement restriction device.

According to one embodiment, the apparatus further comprising an interconnecting part configured to connect to the at least two parts, and at least one of the two parts and the interconnecting part comprises a connecting recess, and at least one of the two parts and the interconnecting part comprises a connecting protrusion, and wherein at least one connecting protrusion and one connecting recess are configured to be interconnected for forming the implantable movement restriction device.

According to one embodiment, the movement restriction device comprises a curved cross-section in a plane parallel to the transverse plane of the patient, and wherein the curve is configured to partially enclose the esophagus of the patient.

According to one embodiment, the movement restriction device is configured to encircle at least ⅓ of the esophagus in a plane parallel to the transverse plane of the patient, or configured to encircle at least ½ of the esophagus in a plane parallel to the transverse plane of the patient, or configured to encircle at least ⅔ of the esophagus in a plane parallel to the transverse plane of the patient.

According to one embodiment, the movement restriction device comprises a C-shaped cross-section in a plane parallel to the transverse plane of the patient, and wherein the C-shaped cross-section is configured to partially enclose the esophagus of the patient.

According to one embodiment, a cross-section of the movement restriction device in a plane parallel to the transverse plane of the patient comprises a closed curve configured to enclose the esophagus of the patient.

According to one embodiment, the movement restriction device has a constricting state for hindering fluid from passing from the stomach into the esophagus and an expanded state for allowing food to pass into the stomach in response to the patient swallowing. The movement restriction device may comprise at least one attractor for resiliently attracting adjacent portions of the movement restriction device to generate an encircling pressure in the esophagus. The attractor may comprise an elastic element or at least two mutually attracting magnets.

An apparatus for treating reflux disease of a human patient is further provided. The apparatus comprises an implantable movement restriction device configured to be at least partly invaginated by the stomach wall of the patient for restricting the movement of the cardia of the patient towards the thoracic diaphragm. The implantable movement restriction device has a first cross-sectional distance and a second cross-sectional distance, the first cross-sectional distance has a first length and the second cross-sectional distance has a second length. The first length is more than 1.5 times the second length. The movement restriction device is configured to be implanted such that the first cross-sectional distance is more parallel than perpendicular to the cranial-caudal axis of the patient, and the second cross-sectional distance is more perpendicular than parallel to the cranial-caudal axis of the patient. The implantable movement restriction device comprises at least a first and a second part configured to be connected to form the implantable movement restriction device. The center of gravity of the first part is positioned on a plane extending perpendicularly from a first half of the first cross-sectional distance and the center of gravity of the second part is positioned on a plane extending perpendicularly from a second half of the first cross-sectional distance, a lower portion of the first part comprises a first connecting portion and the upper portion of the second part comprises a second connecting portion. The first and second connecting portions are configured to be connected to each other and the first and second connecting portions are configured to remain connected to each other by at least one of the first and second parts being supported or compressed by the invagination of the implantable movement restriction device in the stomach wall of the patient, and the first and second parts are capable of disconnecting and separating if the support or compression from at least one of the first and second parts the stomach wall decreases.

The first and second connecting portions may be configured to be directly connected to each other, or may be configured to be indirectly connected to each other by an interconnecting part.

According to one embodiment, at least one of: the first part, the second part, and the interconnecting part comprises a connecting recess, and at least one of: the first part, the second part, and the interconnecting part comprises a connecting protrusion and wherein at least one connecting protrusion and one connecting recess are configured to be interconnected for forming the implantable movement restriction device.

According to one embodiment, at least one of the first and second connecting portions comprises a resilient connecting portion and wherein the resilient connecting portion is, directly or indirectly, supported or compressed by the invagination of the implantable movement for connecting, directly or indirectly, the first part to the second part.

According to one embodiment, the resilient connecting portion comprises a resilient protrusion configured to engage a recess for connecting, directly or indirectly, the first part to the second part. The resilient protrusion may be configured to connect and disconnect from a recess in a direction substantially perpendicular to the direction of the first cross-sectional distance.

According to one embodiment, first part comprises a first sub-part a second sub-part, and/or the second part comprises a first sub-part and a second sub-part.

Each of the first and second sub-parts may comprise a connecting portion, and each of the first and second sub-parts may be configured to connect and disconnect from the connecting portion of the first part, or the second part of the interconnecting part in a direction substantially perpendicular to the direction of the first cross-sectional distance.

According to one embodiment, the first sub-part and the second sub-part are configured to remain connected to each other by at least one of the first and second parts being supported or compressed by the invagination of the implantable movement restriction device in the stomach wall of the patient, and wherein the first sub-part and the second sub-part are capable of disconnecting from each other and separating if the support or compression from the stomach wall on at least one of the first and second parts decreases.

According to one embodiment, the first part comprises a first and second sub-part, and the first and second sub-parts are configured to remain connected by the first and second sub-parts being supported or compressed by the connecting portion of the second part.

According to one embodiment, the second part is configured to exert a supporting or compressing force on the first part derived from a supporting or compressing force exerted by the stomach wall on the second part.

According to one embodiment, the first part comprises a first sub-part and a second sub-part, and the second part comprises a first sub-part and a second sub-part, and the first and second sub-parts of the first part are configured to remain connected to each other by a supporting or compressing force exerted by at least one of the second part and the stomach wall. The first and second sub-parts of the second part are configured to remain connected to each other by a supporting or compressing force exerted by the stomach wall.

According to one embodiment, the implantable movement restriction device further comprises a third part, and the lower portion of the second part comprises a third connecting portion and the upper portion of the third part comprises a fourth connecting portion, such that the first, second and third parts can be connected for forming the implantable medical device.

According to one embodiment, the second part is configured to exert a supporting or compressing force on the first part derived from a supporting or compressing force exerted by the third part on the second part. The third part may be configured to exert a supporting or compressing force on the second part derived from a supporting or compressing force exerted by the stomach wall on the third part.

According to one embodiment, the apparatus further comprises a second interconnecting part, and the third and fourth connecting portions are configured to be connected to the second interconnecting part, such that the first interconnecting part connects the first part to the second part and the second interconnecting part connects the third part to the fourth part.

According to one embodiment, the first and second resilient connecting portions are supported or compressed by a supporting or compressing force exerted by the third part on the second part.

According to one embodiment, the first part comprises a first sub-part and a second sub-part, the second part comprises a first sub-part and a second sub-part, and the third part comprises a first sub-part and a second sub-part. The first and second sub-parts of the first part are configured to remain connected to each other by a supporting or compressing force exerted by at least one of the second part and the stomach wall, the first and second sub-parts of the second part are configured to remain connected to each other by a supporting or compressing force exerted by at least one of the third part and the stomach wall, and the first and second sub-parts of the third part are configured to remain connected to each other by a supporting or compressing force exerted by the stomach wall.

According to one embodiment, the first part comprises a first, a second and a third sub-part and/or the second part comprises a first, a second and a third sub-part, and/or the third part comprises a first, a second and a third sub-part.

According to one embodiment, the first part comprises a first, second, third and fourth sub-part, and/or the second part comprises a first, second, third and fourth sub-part, and/or the third part comprises a first, second, third and fourth sub-part.

According to one embodiment, the movement restriction device is elongated and the first length is more than 2 times the second length, preferably more than 2.5 times the second length and even more preferably more than 3 times the second length.

According to one embodiment, the implantable movement restriction device comprises at least one circular cross-section.

The implantable movement restriction device may comprise a first, second and third cross-section in planes spaced apart and parallel to each other, wherein the first and third cross-sections have the same area, and the second cross-section is located between the first and third cross-section and have a smaller area. According to one embodiment, the implantable movement restriction device further comprises a fourth and fifth cross-section in planes spaced apart and parallel to the planes of the first, second and third cross-sections, wherein the third and fifth cross-sections have the same area, and the fourth cross-section is located between the third and fifth cross-sections and have a smaller area.

According to one embodiment, the implantable movement restriction device may be configured to be fully invaginated.

A first portion of the implantable movement restriction device may have a first volume enclosed by material of the implantable movement restriction device, and a second portion of the movement restriction device, separate from the first portion, may have a second volume enclosed by material of the implantable movement restriction device, The first volume and the second volumes are equally large and the first volume has a higher density than the second volume and the second volume has a density below 1000 kg/m3.

According to one embodiment, the first volume comprises a first solid material, and the first solid material may comprise a polymer material, such as a silicone-based material or a polyurethane-based material.

According to one embodiment, the second volume comprises a second solid material. The second solid material may comprise a polymer material, such as a polypropylene-based and a polyethylene-based material.

In any one of the embodiments herein, the first volume may comprise a solid material having a density above 1000 kg/m3 and the second volume may comprise a solid material having a density below 1000 kg/m3.

In any one of the embodiments herein, the second volume may comprises a fluid, which could be a liquid having a density a below 1000 kg/m3, such as an oil-based liquid or an alcohol-based liquid.

In any one of the embodiments herein, the second volume may comprise a gas, and the second volume may comprise a plurality of volumes of gas enclosed by an enclosing material.

According to one embodiment, the second volume may comprise a solid polymer material enclosing the enclosing material, and the enclosing material may be harder than the solid polymer material.

According to one embodiment, the plurality of volumes of gas enclosed by an enclosing material makes up at least 10 volume percent of the second volume, more preferably at least 20 volume percent of the second volume, and even more preferably at least 30 volume percent of the second volume. The enclosing material may comprise glass.

According to one embodiment, the movement restriction device has an average density below 1100 kg/m3, or an average density below 1050 kg/m3, or an average density below 1000 kg/m3.

According to one embodiment, the movement restriction device comprises a first cross-sectional distance and a second cross-sectional distance. The implantable movement restriction device may be adjustable in situ, such that the shape of the implantable movement restriction device can be adjusted by the adjustment of the length of the first cross-sectional distance, such that the length of the first cross-sectional distance can be increased relative to the length of the second cross-sectional distance.

According to one embodiment, the shape of the implantable movement restriction device can be adjusted by an increase of the length of the first cross-sectional distance relative to the length of the second cross-sectional distance while the length of a circumference of a cross-section of the implantable movement restriction device, in a plane parallel to the coronal plane of the patient remains constant.

The first part may in any of the embodiments herein comprise an upper portion configured to, directly or indirectly, engage the thoracic diaphragm of the patient, and the upper portion may comprise at least one curvature.

An apparatus for treating reflux disease of a human patient is further provided. The apparatus comprises an implantable movement restriction device configured to be at least partly invaginated by the stomach wall of the patient for restricting the movement of the cardia of the patient towards the thoracic diaphragm. The implantable movement restriction device comprising sensor configured to sense at least one of a force and a pressure, for monitoring a pressure or force exerted by the implantable movement restriction device on the stomach wall of the patient.

According to one embodiment, the sensor is fixated to a surface of the implantable movement restriction device and/or integrated in the implantable movement restriction device. The sensor could comprise a strain gauge-based sensor, such as a piezoresistive or piezoelectric strain gauge-based sensor or an optical strain gauge-based sensor. In the alternative, the sensor could comprise a capacitive sensor or an electromagnetic sensor.

According to one embodiment, the implantable movement restriction device comprises at least one enclosed chamber comprising a fluid, and the sensor is configured the sense a pressure in the fluid. The apparatus may further comprise at least one conduit and a sensor unit configured to house the sensor, and the conduit could be in fluid connection with the enclosed chamber of the implantable movement restriction device and with the sensor unit, such that the sensor can sense the pressure in the fluid in the enclosed chamber of the implantable movement restriction device through the fluid connection provided by the conduit.

According to one embodiment, the apparatus further comprises an implantable energy source for powering the sensor and an implantable controller connected to the sensor. The implantable controller may comprise a wireless transceiver configured to receive a sensor signal from the sensor and transmit a wireless signal derived from the sensor signal to a unit external to the body of the patient.

According to one embodiment, the implantable movement restriction device has a size such that the implantable movement restriction device can be fully invaginated by the fundus wall of the patient.

The apparatus may further comprise at least one lead connected to the sensor, and the lead may be configured to connect the sensor to an external device configured to remain outside the patient's body. The apparatus may further comprise a connector for detachably connecting the sensor to the lead, such that the lead can be disconnected from the sensor.

In alternative embodiments, the sensor may be detachably attached to the implantable movement restriction device, such that the sensor can be detached from the implantable movement restriction device by pulling on the lead and the sensor may be detachably attached to the implantable movement restriction device using an adhesive.

The implantable movement restriction device may in any of the embodiments herein have a size of less than 200 cm2, preferably less than 100 cm2, and more preferably less than 50 cm2.

According to one embodiment, the movement restriction device is elongated, and a first cross-sectional distance has a first length, and a second cross-sectional distance has a second length. The first length is more than 1.2 times the second length, preferably more than 1.5 times the second length and even more preferably more than 2 times the second length.

According to one embodiment, the implantable movement restriction device comprises at least one circular cross-section.

According to one embodiment, the implantable movement restriction device comprises a first, second and third cross-section in planes spaced apart and parallel to each other. The first and third cross-sections have the same area, and the second cross-section is located between the first and third cross-section and have a smaller area.

According to one embodiment, the implantable movement restriction device comprises at least two parts, or at least three parts, or at least 4 parts.

According to one embodiment, the at least two parts are configured to be assembled to form the implantable movement restriction device and the at least two parts may be configured to be connected to each other to form the implantable movement restriction device.

According to one embodiment, the movement restriction device comprises a curved cross-section in a plane parallel to the transverse plane of the patient, and the curve is configured to partially enclose the esophagus of the patient.

According to one embodiment, the movement restriction device comprises a curved cross-section in a plane parallel to the transverse plane of the patient. The curve may be configured to partially enclose the esophagus of the patient. According to one embodiment, the movement restriction device is configured to encircle at least ⅓ of the esophagus in a plane parallel to the transverse plane of the patient, in another embodiment, the movement restriction device is configured to encircle at least ½ of the esophagus in a plane parallel to the transverse plane of the patient, in another embodiment, the movement restriction device comprises a C-shaped cross-section in a plane parallel to the transverse plane of the patient, and the C-shaped cross-section is configured to partially enclose the esophagus of the patient, in another embodiment, the movement restriction device is configured to encircle at least ⅔ of the esophagus in a plane parallel to the transverse plane of the patient.

According to one embodiment, a cross-section of the movement restriction device in a plane parallel to the transverse plane of the patient comprises a closed curve configured to enclose the esophagus of the patient.

The implantable movement restriction device may in any of the embodiments comprise at least one circular cross-section.

A surgical instrument for assisting in a surgical procedure for implanting an implantable movement restriction device is further provided. The movement restriction device is configured to be at least partly invaginated by the stomach wall of the patient for restricting the movement of the cardia of the patient towards the thoracic diaphragm. The surgical instrument comprises a handling portion configured to remain outside of the body of the patient in use, a distal portion configured to be inserted into the body of the patient, and a lead at least partially attached to the distal portion and configured to be connected to a sensor for sensing at least one of a force and a pressure, for monitoring a pressure or force exerted by the implantable movement restriction device on the stomach wall of the patient during implantation.

According to one embodiment, the distal portion comprises a holding device connected to the handling portion and configured to be inserted into the body of the patient and to engage the movement restriction device.

According to one embodiment, the holding device comprises an elongated portion configured to be inserted into the implantable movement restriction device.

According to one embodiment, the holding device comprises a gripping portion configured to grip the implantable movement restriction device.

The surgical instrument may be configured for placement of the implantable movement restriction device, and the surgical instrument further comprises a sleeve connected to the handling portion, and the holding device is configured to be partially placed within the sleeve and be displaceable in relation to the sleeve. The handling of the handling portion creates relative displacement of the holding device in relation to the sleeve, which disengages the holding device from the movement restriction device for performing the placement of the movement restriction device.

According to one embodiment, the distal portion is bent in relation to the primary length axis of the surgical instrument, and the distal portion may be bent more than 20° in relation to the primary length axis of the instrument.

According to one embodiment, the distal portion is flexible or bendable.

According to one embodiment, the bending of the distal portion is controllable from the handling portion.

According to one embodiment, the surgical instrument is an abdominal instrument configured to be inserted into the abdomen of the patent during an open surgical procedure. In the alternative, the surgical instrument is a laparoscopic instrument configured to be inserted into the abdomen of the patient through a trocar, and in yet another alternative, the surgical instrument is a gastroscopic instrument configured to be inserted into the body of the patient through the esophagus of the patient.

According to one embodiment, the surgical instrument further comprises the sensor. The sensor may be configured to be detachably attached to the implantable movement restriction device, such that the sensor can be detached from the implantable movement restriction device and removed from the body of the patient during the surgical procedure.

According to one embodiment, the sensor is configured to be attached to a surface of the implantable movement restriction device or attached in the implantable movement restriction device. The sensor may be configured to be detachably attached to the implantable movement restriction device using an adhesive. The surgical instrument may further comprise a connector for detachably connecting the sensor to the lead, such that the lead can be disconnected from the sensor. The sensor could comprise a strain gauge-based sensor, such as a piezoresistive or piezoelectric strain gauge-based sensor, or an optical strain gauge-based sensor, or a capacitive sensor, or an electromagnetic sensor.

According to one embodiment, the implantable movement restriction device comprises at least one enclosed chamber comprising a fluid, and the sensor is a sensor configured the sense a pressure in a fluid.

According to one embodiment, the surgical instrument further comprises an energy source for powering the sensor and a controller connected to the sensor. The controller may be an external device configured to remain on the outside of the patient when the surgical instrument is in use, and the controller is configured to receive a sensor signal from the sensor via the lead and provide an output on the basis the sensor signal.

According to one embodiment, the controller comprises an output device configured to provide an output to a person, the output device comprises at least one unit selected from a list consisting of a unit providing audio output, a unit providing visual output, such as a lighting unit or a display unit, and a unit providing haptic output.

An apparatus for treating reflux disease of a human patient is further provided, the apparatus comprising an elongated core having a length allowing the core to at least partly encircle the esophagus of the patient. The core comprises a first length variability function allowing the core to be arranged in a constricting state for hindering fluid from passing from the stomach 10 into the esophagus and in an expanded state for allowing food to pass into the stomach in response to the patient swallowing; and a second length variability function for post-operatively adjusting the length that the core has in its constricting state.

According to one embodiment, the second length variability function comprises a hydraulic length variability function and may comprise at least one hydraulic chamber, and the length of the core can be post-operatively adjusted by injection of a fluid into, or withdrawal of a fluid from, the at least one hydraulic chamber. The hydraulic chamber may comprise at least one pleated portion, such as at least one bellows.

According to one embodiment, the elongated core comprises a wall enclosing the hydraulic chamber, and the thickness of the wall varies affecting the alteration of the shape of the hydraulic chamber as fluid is injected into or withdrawn from the hydraulic chamber.

According to one embodiment, the shape of the movement restriction device may be altered by the thinner portion of the wall enclosing the hydraulic adjustment chamber being deformed more than thicker portions of the wall enclosing the hydraulic adjustment chamber.

According to one embodiment, the hydraulic chamber comprises at least one implantable injection port, or is connected to at least one implantable injection port.

According to one embodiment, the second length variability function comprises a mechanical length variability function, and the mechanical length variability function may comprise a powered mechanical length variability function.

According to one embodiment, the powered mechanical length variability function may comprise at least one of: an electrical motor, an electromagnet, and an electroactive material.

According to one embodiment, the movement restriction device comprises a transferring element configured to transfer at least one of electrical energy, and mechanical force to the mechanical length variability function.

According to one embodiment, the transferring element comprises at least one of: an electrical lead, a shaft for transferring rotating force, and a shaft for transferring linear force.

The mechanical operation device may comprise a transmission configured to transform a rotating force generated by the electrical motor into a linear force for adjusting the length of the first cross-sectional distance.

According to one embodiment, the first length variability function comprises a plurality of portions that are movable relative to each other.

According to one embodiment, the first length variability function comprises an attractor for resiliently attracting adjacent portions of the elongated core to one another. The attractor may comprise an elastic element or may comprise at least two mutually attracting magnets.

According to one embodiment, the apparatus further comprises a link connecting a first and a second one of said at least two magnets to each other.

According to one embodiment, the elongated core is configured to exert an encircling pressure on the esophagus in the constricting state.

According to one embodiment, the apparatus comprises two end portions configured to be coupled to each other to form a closed ring around the esophagus and the end portions may be configured to be releasably attached to each other and may comprise a respective interlockable attacher.

According to one embodiment, the elongated core comprises a plurality of bodies configured to be arranged in an annular array around the esophagus.

According to one embodiment, the elongated core further comprises a plurality of links, each of which extending between a respective pair of bodies arranged adjacent to each other.

According to one embodiment, at least one of the plurality of bodies comprises the second length variability function for post-operatively adjusting the length of the core in its constricting state.

According to one embodiment, at least one of the plurality of bodies comprises the hydraulic chamber for post-operatively adjusting the length of the core in its constricting state.

The elongated core may have a size allowing at least a portion of the elongated core to protrude above the cardiac sphincter of the patient, when implanted, such that movement of the cardia towards the diaphragm is restricted to hinder the cardia from sliding through the diaphragm opening 32 into the patient's thorax.

According to one embodiment, the elongated core has a maximum height exceeding 2 cm, as measured in a normal direction to the plane in which the elongated core extends when encircling the esophagus. In alternative embodiments, the maximum height may be 3 cm or more, such as 4 cm or more, such as 5 cm or more.

According to one embodiment, the elongated core is configured to be implanted such that a portion of the elongated core having the maximum height is arranged at the fundus side of the esophagus.

According to one embodiment, the elongated core has a first cross-sectional distance and a second cross-sectional distance, and wherein the elongated core is configured to be implanted such that the first cross-sectional distance is more parallel than perpendicular to the cranial-caudal axis of the patient, and the second cross-sectional distance is more perpendicular than parallel to the cranial-caudal axis of the patient, and the elongated core is adjustable in situ, such that the shape of the elongated core can be adjusted by the adjustment of the length of the first cross-sectional distance, such that the length of the first cross-sectional distance can be increased relative to the length of the second cross-sectional distance.

According to one embodiment, the shape of the elongated core can be adjusted by an increase of the length of the first cross-sectional distance relative to the length of the second cross-sectional distance while the length of a circumference of a cross-section of the elongated core, in a plane parallel to the coronal plane of the patient remains constant.

According to one embodiment, the shape of a cross-section of the elongated core can be adjusted to an elongated shape by an increase of the length of the first cross-sectional distance relative to the length of the second cross-sectional distance.

According to one embodiment, the elongated core comprises a lower portion configured to, directly or indirectly, engage the stomach of the patient in a region of the angle of his, such that the function of the elongated core is supported by tissue of the stomach in the region of the angle of his.

According to one embodiment, the elongated core comprises an upper portion configured to, directly or indirectly, engage the thoracic diaphragm of the patient, and the upper portion comprises at least one curvature.

The elongated core in any of the embodiments herein may be configured to be at least partially invaginated by the stomach wall.

According to one embodiment, the elongated core is configured to be at least partially invaginated by the stomach wall of the fundus.

According to one embodiment, the movement restriction device comprises a curved cross-section in a plane parallel to the transverse plane of the patient. The curve may be configured to partially enclose the esophagus of the patient. According to one embodiment, the movement restriction device is configured to encircle at least ⅓ of the esophagus in a plane parallel to the transverse plane of the patient, in another embodiment, the movement restriction device is configured to encircle at least ½ of the esophagus in a plane parallel to the transverse plane of the patient, in another embodiment, the movement restriction device comprises a C-shaped cross-section in a plane parallel to the transverse plane of the patient, and the C-shaped cross-section is configured to partially enclose the esophagus of the patient, in another embodiment, the movement restriction device is configured to encircle at least ⅔ of the esophagus in a plane parallel to the transverse plane of the patient.

The second length variability function may in any of the embodiments herein be configured for post-operatively adjusting the length that the core has in its constricting state with more than 5%, or with more than 10%, or with more than 15% or with more than 20%.

The apparatus may in any of the embodiments herein comprise at least one electrode for electrically stimulating at least one tissue portion of the patient.

An apparatus for treating reflux disease of a human patient is further provided. The apparatus comprises an elongated core having a length allowing the elongated core to at least partly encircle the esophagus of the patient. The elongated core comprises a first length variability function allowing the core to be arranged in a constricting state for hindering fluid from passing from the stomach into the esophagus and in an expanded state for allowing food to pass into the stomach in response to the patient swallowing; and a protruding portion configured to protrude from the first length variability function in a direction more parallel than perpendicular to the cranial-caudal axis of the patient, in a substantially cranial direction, when the elongated core is implanted. The protruding portion is configured to protrude a distance of at least 10 mm in a substantially cranial direction from a plane extending perpendicularly from the cranial-caudal axis of the patient and comprising the center of gravity of the elongated core, and the protruding portion is configured to directly or indirectly engage the thoracic diaphragm of the patient for restricting the movement of the cardia of the patient.

The protruding portion may protrude a distance of at least 20 mm in a substantially cranial direction from a plane extending perpendicularly from the cranial-caudal axis of the patient and comprising the center of gravity of the elongated core.

The protruding portion may be configured to protrude in a substantially cranial direction from a plane extending perpendicularly from the cranial-caudal axis of the patient and comprising the center of gravity of the elongated core, a distance such that an upper portion of the protruding portion is placed at least 5 mm above the cardiac sphincter.

The protruding portion may be configured to protrude in a substantially cranial direction from a plane extending perpendicularly from the cranial-caudal axis of the patient and comprising the center of gravity of the elongated core, a distance such that an upper portion of the protruding portion is placed at least 10 mm above the cardiac sphincter.

The protruding portion may be configured to protrude in a substantially cranial direction from a plane extending perpendicularly from the cranial-caudal axis of the patient and comprising the center of gravity of the elongated core, a distance such that an upper portion of the protruding portion is placed at least 15 mm above the cardiac sphincter.

The elongated core may have a first cross-sectional area in a first plane extending perpendicularly from the cranial-caudal axis of the patient, and the protruding portion may have a second cross-sectional area in a second plane parallel to the first plane, and the first cross-sectional area may be more than 1.5 times the size of the second cross-sectional area.

According to one embodiment, the second cross-sectional area is an average cross-sectional area of the protruding portion.

According to one embodiment, the protruding portion has a third cross-sectional area in a third plane parallel to the first plane, and the second plane is positioned between the first and third planes, and the third cross-sectional area is more than 1.5 times the size of the second cross-sectional area.

According to one embodiment, the apparatus further comprises a second elongated core having a length allowing the second elongated core to at least partly encircle the esophagus of the patient. The protruding portion may connect the first elongated core to the second elongated core.

According to one embodiment, the elongated core comprises a lower portion configured to, directly or indirectly, engage the stomach of the patient in a region of the angle of his, such that the function of the elongated core is supported by tissue of the stomach in the region of the angle of his.

According to one embodiment, the protruding portion comprises an upper portion configured to, directly or indirectly, engage the thoracic diaphragm of the patient, and the upper portion comprises at least one curvature.

According to one embodiment, at least one of the first elongated core, the second elongate core and the protruding portion may be configured to be at least partially invaginated by the stomach wall.

According to one embodiment, the protruding portion is adjustable in situ, such that the length that the protruding portion protrudes from the plane extending perpendicularly from the cranial-caudal axis of the patient and comprising the center of gravity of the elongated core can be adjusted. The protruding portion may be hydraulically adjustable and may further comprises a conduit configured to connect the hydraulically adjustable protruding portion to an implantable injection port.

According to one embodiment, at least one of the protruding portion and the elongated core comprises an injection port, such that the hydraulically adjustable protruding portion can be adjusted by the injection or withdrawal of a hydraulic fluid into the injection port.

According to one embodiment, the protruding portion comprises a bellows, and injection or withdrawal of a hydraulic fluid into the injection port adjusts a length of the bellows.

According to one embodiment, the protruding portion comprises a wall enclosing a hydraulic adjustment chamber, and the thickness of the wall varies affecting the alteration of the shape of the protruding portion as fluid is injected into or withdrawn from the protruding portion. The shape of the protruding portion may be altered by the thinner portion of the wall enclosing the hydraulic adjustment chamber being deformed more than thicker portions of the wall enclosing the hydraulic adjustment chamber.

According to one embodiment, the protruding portion is mechanically adjustable and the apparatus may comprise a mechanical operation device for mechanically adjusting the protruding portion.

According to one embodiment, the movement restriction device comprises a transferring element configured to transfer at least one of: electrical energy, and mechanical force to the mechanically adjustable protruding portion.

According to one embodiment, the transferring element comprises at least one of an electrical lead, a shaft for transferring rotating force, and a shaft for transferring linear force.

The mechanical operation device may comprise an electrical motor, and may comprises a transmission configured to transform a rotating force generated by the electrical motor into a linear force for adjusting the length of the protruding portion.

A portion of the protruding portion comprises a bellows, and wherein the operation of the mechanical operation device adjusts a length of the bellows.

According to one embodiment, the protruding portion is electrically adjustable, and the apparatus may comprise at least one material configured to alter shape when exposed to an electrical current or an electrical voltage. The material may be at least one electroactive polymer, which could be at least one electroactive polymer selected from a list consisting of: ferroelectric polymers, electrostrictive graft polymers, electrostrictive paper, piezoelectric polymers and liquid crystal elastomers.

In any of the embodiments herein, the length of the protruding portion may be adjustable in situ more than 1.2 times, or more than 1.3 times, or more than 1.5 times.

According to one embodiment, the elongated core comprises a curved cross-section in a plane parallel to the transverse plane of the patient, and wherein the curve is configured to partially enclose the esophagus of the patient.

According to one embodiment, the movement restriction device comprises a curved cross-section in a plane parallel to the transverse plane of the patient. The curve may be configured to partially enclose the esophagus of the patient. According to one embodiment, the movement restriction device is configured to encircle at least ⅓ of the esophagus in a plane parallel to the transverse plane of the patient, in another embodiment, the movement restriction device is configured to encircle at least ½ of the esophagus in a plane parallel to the transverse plane of the patient, in another embodiment, the movement restriction device comprises a C-shaped cross-section in a plane parallel to the transverse plane of the patient, and the C-shaped cross-section is configured to partially enclose the esophagus of the patient, in another embodiment, the movement restriction device is configured to encircle at least ⅔ of the esophagus in a plane parallel to the transverse plane of the patient.

According to one embodiment, a cross-section of the elongated core in a plane parallel to the transverse plane of the patient may comprise a closed curve configured to enclose the esophagus of the patient.

According to one embodiment, the first length variability function comprises an attractor for resiliently attracting adjacent portions of the elongated core to one another. The attractor may comprise an elastic element or at least two mutually attracting magnets. The apparatus may further comprise a link connecting a first and a second one of said at least two magnets to each other.

According to one embodiment, the elongated core is configured to exert an encircling pressure on the esophagus in the constricting state.

According to one embodiment, the apparatus comprises two end portions configured to be coupled to each other to form a closed ring around the esophagus. The end portions may be configured to be releasably attached to each other and may comprise a respective interlockable attacher.

The elongated core may comprise a plurality of bodies configured to be arranged in an annular array around the esophagus.

According to one embodiment, the elongated core further comprises a plurality of links, each of which extending between a respective pair of bodies arranged adjacent to each other.

According to one embodiment, the elongated core is configured to be implanted such that the protruding portion is arranged at the fundus side of the esophagus.

The apparatus may further comprise a second length variability function configured for post-operatively adjusting the length that the elongated core has in its constricting state with more than 5%, or with more than 10%, or with more than 15% or with more than 20%.

The apparatus may in any of the embodiments herein comprise at least one electrode for electrically stimulating at least one tissue portion of the patient.

A method for treating reflux disease of a human patient by implanting a movement restriction device is further provided. The movement restriction device is arranged to restrict movement of the cardia of the patient's stomach towards the diaphragm to hinder the cardia from sliding through the diaphragm opening into the patient's thorax. The movement restriction device comprises a curved inner surface configured to face the curved outer surface of the esophagus. The method comprising positioning and fixating the movement restriction device such that the curved inner surface encircles at least ⅓ of the esophagus in a plane extending perpendicular to the cranial-caudal axis, and the center of mass of the movement restriction device is placed in a plane extending perpendicular to the cranial-caudal axis, and wherein the shortest distance from a point on the plane to the angle of His exceeds 20 mm.

According to one embodiment, the method comprises the step of attaching the fundus of the stomach of the patient to the esophagus of the patient in a first position below the center of mass of the movement restriction device, such that the movement restriction device is supported by the attachment of the fundus to the esophagus.

The step of attaching the fundus of the stomach of the patient to the esophagus of the patient in a first position may comprise attaching the fundus of the stomach of the patient to the esophagus of the patient at a distance from the angle of His exceeding 5 mm.

According to one embodiment, the step of positioning and fixating the movement restriction device comprises positioning and fixating the movement restriction device such that the upper most point of the movement restriction device is placed in a second plane extending perpendicular to the cranial-caudal axis, and the shortest distance from a point on the second plane to the angle of His exceeds 40 mm.

According to one embodiment, the step of positioning and fixating the movement restriction device comprises positioning and fixating the movement restriction device such that the upper most point of the movement restriction device is placed in a second plane extending perpendicular to the cranial-caudal axis, and wherein the shortest distance from a point on the second plane to the angle of His exceeds 50 mm.

According to one embodiment, the step of positioning and fixating the movement restriction device comprises positioning and fixating the movement restriction device such that the lower most point of the movement restriction device is placed in a third plane extending perpendicular to the cranial-caudal axis, and wherein the shortest distance from a point on the third plane to the angle of His exceeds 10 mm.

According to one embodiment, the step of positioning and fixating the movement restriction device comprises positioning and fixating the movement restriction device such that the lower most point of the movement restriction device is placed in a third plane extending perpendicular to the cranial-caudal axis, and wherein the shortest distance from a point on the third plane to the angle of His exceeds 20 mm.

According to one embodiment, the step of positioning and fixating the movement restriction device comprises positioning and fixating the movement restriction device such that the upper most point of the movement restriction device is placed in a second plane extending perpendicular to the cranial-caudal axis, and wherein the shortest distance from a point on the second plane to an upper-most point of the cardia exceeds 5 mm.

According to one embodiment, the step of positioning and fixating the movement restriction device comprises positioning and fixating the movement restriction device such that the upper most point of the movement restriction device is placed in a second plane extending perpendicular to the cranial-caudal axis, and wherein the shortest distance from a point on the second plane to an upper-most point of the cardia exceeds 10 mm.

According to one embodiment, the step of positioning and fixating the movement restriction device comprises positioning the center of mass of the movement restriction device in the second plane extending perpendicular to the cranial-caudal direction, and wherein the shortest distance from a point on the second plane to an upper-most point of the cardia exceeds 5 mm.

According to one embodiment, the step of positioning and fixating the movement restriction device comprises positioning the center of mass of the movement restriction device in the second plane extending perpendicular to the cranial-caudal direction, and wherein the shortest distance from a point on the second plane to an upper-most point of the cardia exceeds 10 mm.

According to one embodiment, the step of positioning and fixating the movement restriction device comprises positioning a movement restriction device encircling at least ½ of the esophagus in a plane extending perpendicular to the cranial-caudal direction.

According to one embodiment, the step of positioning and fixating the movement restriction device comprises positioning a movement restriction device encircling at least ⅔ of the esophagus in a plane extending perpendicular to the cranial-caudal direction.

According to one embodiment, the step of positioning and fixating the movement restriction device comprises positioning a movement restriction device encircling the esophagus in a plane extending perpendicular to the cranial-caudal direction.

According to one embodiment, the curved inner surface configured to face the curved outer surface of the esophagus comprises a radius of curvature corresponding to or exceeding the radius of curvature of the esophagus, such that the curved inner surface comprises a radius of curvature corresponding to or exceeding the radius of curvature of the esophagus.

According to one embodiment, the step of positioning and fixating the movement restriction device comprises positioning a movement restriction device comprising an electrode arrangement configured to electrically stimulate muscle tissue of the portion of the fundus and/or the serosa to improve the conditions for long term implantation of the movement restriction device.

According to one embodiment, the method further comprises implanting an implantable energy source configured to provide the electrode with electrical power.

According to one embodiment, the step of positioning and fixating the movement restriction device comprises positioning a movement restriction device having a constricting state for hindering fluid from passing from the stomach into the esophagus and an expanded state for allowing food to pass into the stomach in response to the patient swallowing.

According to one embodiment, the step of positioning the movement restriction device comprises positioning a movement restriction device configured to exert an encircling pressure on the esophagus in the constricting state.

According to one embodiment, the step of positioning and fixating the movement restriction device comprises positioning a movement restriction device comprising at least one attractor for resiliently attracting adjacent portions of the movement restriction device to generate the encircling pressure.

The attractor may comprise an clastic element or at least two mutually attracting magnets. The apparatus may further comprise a link connecting a first and a second one of said at least two magnets to each other.

According to one embodiment, the step of positioning and fixating the movement restriction device comprises positioning and fixating a movement restriction device having an adjustable volume.

According to further aspects, it is an object to reduce the risk of migration of the implantable movement restriction device disclosed herein. Migration of the movement restriction device is generally undesirable as it may decrease the effectiveness of the treatment of reflux disease in a human patient receiving the movement restriction device.

According to one aspect, there is provided an apparatus for treating reflux disease of a human patient. The apparatus comprises an implantable movement restriction device configured to be at least partly invaginated by the stomach wall of the patient for restricting the movement of the cardia of the patient towards the thoracic diaphragm. The implantable movement restriction device is comprising a surface friction reducing coating covering at least a part of the surface of the implantable movement restriction device. The surface friction reducing coating is configured to reduce the friction between the implantable movement restriction device and the tissue of the stomach wall by which the implantable movement restriction device is at least partially invaginated. It has been realized that the application of a surface friction reducing coating covering at least a part of the surface of the implantable movement restriction device advantageously prevents or reduces the risk of migration of the implantable movement restriction device. When implanted, the surface friction reducing coating maximizes contact with surrounding tissue, and it provides lubrication for the movement restriction device.

Typically, the surface friction reducing coating is covering at least 20%, such as at least 30%, such as at least 40%, such as at least 50%, such as at least 60%, such as at least 70%, such as at least 80%, such as at least 90%, such as at least 95% of the surface of the movement restriction device. According to one embodiment, the surface friction reducing coating is covering the entire surface of the movement restriction device. A higher degree of surface coverage is associated with a higher reduction of the risk of migration of the implantable movement restriction device.

In preferred embodiments, the surface friction reducing coating is selected from natural polymers; polysaccharide coatings, oils, hydrogels, and lubricating jellies.

In certain embodiments, the surface friction reducing coating comprises one or more natural polymers dissolved in water. Preferred natural polymers are selected from polysaccharides, such as native and modified celluloses, native and modified starches, xanthan gum, guar gum, carrageenan, alginate, pectin, and combinations thereof. A preferred polymer is methylcellulose, such as hydroxypropyl methylcellulose (HPMC) and carboxymethylcellulose. Another preferred polymer is ethylcellulose, such as hydroxyethylcellulose.

An example of a useful hydrogel is a poly(propylene fumarate-co-ethylene glycol) hydrogel.

In some embodiments, the surface friction reducing coating is selected from racine oil, mineral oil, glycerin, and polyethylene glycol (PEG). A preferred agent is PEG. It is further preferred to use PEG with larger size (>5 kDa) as it remains in tissues for several days before being cleared.

The surface friction reducing coating may furthermore comprise an active agent selected from bactericides, antibiotics, bacteriostatics, analgesics and anesthetics.

Examples of bactericides and bacteriostatics which are useful in the surface friction reducing coating include antibiotics. Antibiotics are naturally occurring or synthetic substances that are used to kill or inhibit the growth of bacteria. Some examples of antibiotics include penicillin (e.g. penicillin and amoxicillin), cephalosporins (e.g. cephalexin and cefuroxime), macrolides (e.g. erythromycin and azithromycin), tetracyclines (e.g. tetracycline and doxycycline), quinolones (e.g. ciprofloxacin and levofloxacin), sulfonamides (e.g. sulfamethoxazole and trimethoprim), aminoglycosides (e.g. gentamicin and tobramycin). Other examples of bactericides and bacteriostatics which are useful in the surface friction reducing coating include bacteriophages.

Examples of analgesics which are useful in the surface friction reducing coating include anti-inflammatory analgesics (e.g. acetaminophen, aspirin, COX inhibitors, nonsteroidal anti-inflammatory drugs (NSAIDs), such as ibuprofen and naproxen) and opioids (e.g. codeine, fentanyl, hydrocodone, meperidine, methadone, naloxone, naltrexone and oxycodone).

Examples of anesthetics which are useful in the surface friction reducing coating include local anesthetics which can be either ester- or amide-based. Examples of ester local anesthetics include procaine, amethocaine, cocaine, benzocaine, tetracaine. Examples of amide local anesthetics include lidocaine, prilocaine, bupivacaine, levobupivacaine, ropivacaine, mepivacaine, dibucaine and etidocaine. A preferred anesthetic is lidocaine, preferably in a concentration of 1-10% (w/v), such as 1-5% (w/v), such as 1-3% (w/v), such as about 2% (w/v).

In certain embodiments, the surface friction reducing coating provides antiseptic properties to the movement restriction device.

The surface friction reducing coating may also contain pH-adjusting compounds, including weak acids, weak bases and buffers.

In some embodiments, the surface friction reducing coating provides softening of adjacent tissues. This may further prevents or reduce the risk of migration of the implantable movement restriction device.

In certain embodiments, the surface friction reducing coating is a viscous medium. A viscous coating composition is a type of liquid or semi-solid material that is used to create a protective layer or film on a surface. This type of coating is characterized by its thick, sticky consistency, which allows it to adhere to the surface and form a durable, long-lasting layer. There are many different types of viscous coating compositions available, each with its own unique properties and characteristics.

It is preferred that the viscous medium is a viscous aqueous medium, such as a viscous aqueous liquid, such as a viscous aqueous solution. The viscous aqueous medium may be a viscoelastic medium. A preferred viscoelastic medium is a gel. The viscous medium may also be a viscous liquid.

Viscosity can be e.g. determined at 20° C. using a shear rate controlled rheometer (Model 302, Anton Paar, Germany), using a parallel plate geometry (plate diameter 50 mm, gap 100 μm). In this setup, the viscosity of water is approximately constant at 1 mPa·s, at shear rates between 0-100 s-1. For avoidance of doubt, viscous media as defined herein are considerably more viscous than water. Viscous media as defined herein typically exhibit a viscosity of at least 10 mPa·s, such as at least 50 mPa·s at shear rates between 0-100 s-1, such as at 50 s-1. Preferably, viscous media as defined herein exhibit a viscosity of at least 100 mPa·s, such as at least 200 mPa·s at shear rates between 0-100 s-1, such as at 50 s-1. The specific values above are relevant for this specific setup, but the skilled person can easily determine corresponding values for viscosity in other experimental setups. Typically, the surface friction reducing coating has a higher viscosity than water.

The surface friction reducing coating may comprise preservatives. Examples of preservatives include antimicrobial preservatives, e.g. sorbic acid, parabens and lactic acid. A preferred type of preservatives is parabens, e.g. methylparaben and propylparaben.

Preferably, the surface friction reducing coating is configured to remain in a pouch for housing the implantable movement restriction device for a time period exceeding 7 days, preferably exceeding 14 days, such as exceeding 21 days or 28 days.

Specific examples of the surface friction reducing coating are:

(1) Xylocaine jelly, containing 0.1-10% (w/v) xylocaine (lidocaine hydrochloride). The composition also contains methylparaben, propylparaben, hydroxypropyl methylcellulose, and sodium hydroxide and/or hydrochloric acid to adjust pH to 6.0-7.0.
(2) Xylocaine viscous composition, containing 0.1-10% (w/v) xylocaine (lidocaine hydrochloride). The composition also contains carboxymethylcellulose sodium, methylparaben, propylparaben, purified water and saccharin sodium.
(3) Surgical lubricant, containing hydroxypropyl methylcellulose, propylene glycol, chlorhexidine gluconate, and sterile water.
(4) Poly(propylene fumarate-co-ethylene glycol) hydrogels
(5) Polyethylene glycol (PEG) polymers, >5 kDa
(6) Lubricating glycerin jelly, containing water, PEG, glycerin, carbomer, sodium hydroxide, methylparaben, propylparaben.
(7) Lidocaine jelly, containing 0.1-10% (w/v) lidocaine hydrochloride. The composition also contains glycerol, hydrochloric acid, hydroxyethylcellulose, sodium hydroxide, and water.

In some embodiments disclosed herein, the implantable movement restriction device has a size such that the implantable movement restriction device can be fully invaginated by the fundus wall of the patient as set out herein. Preferably, the implantable movement restriction device has a size of less than 200 cm2, preferably less than 100 cm2, and more preferably less than 50 cm2.

In certain embodiments disclosed herein, the movement restriction device is elongated. A first cross-sectional distance has a first length, and a second cross-sectional distance has a second length, wherein the first length is more than 1.2 times the second length, preferably more than 1.5 times the second length and even more preferably more than 2 times the second length.

In some embodiments disclosed herein, implantable movement restriction device (100) comprises at least one circular cross-section. In certain embodiments, the implantable movement restriction device (100) comprises a first, second and third cross-section in planes spaced apart and parallel to each other, wherein the first and third cross-sections have the same area, and the second cross-section is located between the first and third cross-section and have a smaller area.

In certain embodiments disclosed herein, the implantable movement restriction device comprises at least two parts, or at least three parts, or at least 4 parts. Optionally, the at least two parts are configured to be assembled to form the implantable movement restriction device. Further optionally, the at least two parts are configured to be connected to each other to form the implantable movement restriction device.

In some embodiments disclosed herein, the movement restriction device comprises a curved cross-section in a plane parallel to the transverse plane of the patient, and wherein the curve is configured to partially enclose the esophagus of the patient. Advantageously, the movement restriction device is configured to encircle at least ⅓ of the esophagus in a plane parallel to the transverse plane of the patient, and preferably at least ½ of the esophagus in a plane parallel to the transverse plane of the patient. In certain embodiments disclosed herein, the movement restriction device comprises a C-shaped cross-section in a plane parallel to the transverse plane of the patient, and wherein the C-shaped cross-section is configured to partially enclose the esophagus of the patient. Optionally, the movement restriction device is configured to encircle at least ⅔ of the esophagus in a plane parallel to the transverse plane of the patient. In specific embodiments, a cross-section of the movement restriction device in a plane parallel to the transverse plane of the patient comprises a closed curve configured to enclose the esophagus of the patient.

In some embodiments disclosed herein, the implantable movement restriction device (100) comprises at least one circular cross-section.

According to related aspects, there is also provided a method for treating reflux disease of a human patient by implanting a movement restriction device (100). The method comprises: at least partially invaginating the movement restriction device in the stomach of the patient such that the movement restriction device restricts movement of the cardia (22) of the patient's stomach (10) towards the thoracic diaphragm (30) to hinder the cardia from sliding through the diaphragm opening (32) into the patient's thorax, wherein the surface of the movement restriction device is at least partially covered by a surface friction reducing coating.

There is furthermore provided a friction-reducing composition for use in the method as defined herein as a surface friction reducing coating.

There is also provided a use of a composition selected from natural polymers, polysaccharide coatings, oils, hydrogels, and lubricating jellies as a surface friction reducing coating of at least part of the surface of an implantable movement restriction device for treating reflux disease of a human patient, wherein the movement restriction device (100) is configured to be at least partially invaginated by a stomach wall of a patient and arranged to restrict movement of the cardia (22) of a patient's stomach (10) towards the diaphragm (30) to hinder the cardia from sliding through the diaphragm opening (32) into the patient's thorax.

When implanted, the surface friction reducing coating maximizes contact with surrounding tissue, and it provides lubrication for the movement restriction device.

In certain embodiments, the method comprises the step of applying the surface friction reducing coating onto the movement restriction device prior to implantation in the body of the patient. This implies that the coating is applied ex vivo. In other embodiments, the method comprises the step applying the surface friction reducing coating in situ between the movement restriction device and tissue of the stomach wall of the patient.

In some embodiments, the method comprises the steps of:
- partially invaginating the movement restriction device in the stomach of the patient,
- applying the surface friction reducing coating in situ between the movement restriction device and tissue of the stomach wall of the patient, and
- further invaginating the movement restriction device in the stomach of the patient.

Optionally, the step of at least partially invaginating the movement restriction device in the stomach of the patient comprises fully invaginating the movement restriction device in the stomach of the patient.

In certain embodiments, the method is a laparoscopic surgical method, and the method further comprises the step of introducing the movement restriction device into the body of the patient through a laparoscopic trocar after the surface friction reducing coating has been applied.

In other embodiments, the method is a laparoscopic surgical method, and the step of applying the surface friction reducing coating in situ between the movement restriction device and tissue of the stomach wall of the patient comprises applying the surface friction reducing coating in situ using a laparoscopic instrument inserted into the body of the patient though a laparoscopic trocar.

In some embodiments, the method is a gastroscopic method, and the method further comprises the step of introducing the movement restriction device into the body of the patient through the esophagus of the patient after the surface friction reducing coating has been applied.

In certain embodiments, the method is a gastroscopic method, and the step of applying the surface friction reducing coating in situ between the movement restriction device and tissue of the stomach wall of the patient comprises applying the surface friction reducing coating in situ using a gastroscopic instrument inserted into the body of the patient though the esophagus.

Typically, the surface friction reducing coating is covering at least 20%, such as at least 30%, such as at least 40%, such as at least 50%, such as at least 60%, such as at least 70%, such as at least 80%, such as at least 90%, such as at least 95% of the surface of the movement restriction device. According to one embodiment, the surface friction reducing coating is covering the entire surface of the movement restriction device. A higher degree of surface coverage is associated with a higher reduction of the risk of migration of the implantable movement restriction device.

In some embodiments, the step of at least partially invaginating a movement restriction device comprises at least partially invaginating a movement restriction device comprising a surface friction reducing coating covering the entire surface of the movement restriction device.

In preferred embodiments, the step of at least partially invaginating a movement restriction device comprises at least partially invaginating a movement restriction device comprising a surface friction reducing coating selected from natural polymers, polysaccharide coatings, oils, hydrogels, and lubricating jellies.

In certain embodiments, the surface friction reducing coating comprises one or more natural polymers dissolved in water. Preferred natural polymers are selected from polysaccharides, such as native and modified celluloses, native and modified starches, xanthan gum, guar gum, carrageenan, alginate, pectin, and combinations thereof. A preferred polymer is methylcellulose, such as hydroxypropyl methylcellulose (HPMC) and carboxymethylcellulose. Another preferred polymer is ethylcellulose, such as hydroxyethylcellulose.

An example of a useful hydrogel is a poly(propylene fumarate-co-ethylene glycol) hydrogel.

In some embodiments, the surface friction reducing coating is selected from racine oil, mineral oil, glycerin, and polyethylene glycol (PEG). A preferred agent is PEG. It is further preferred to use PEG with larger size (>5 kDa) as it remains in tissues for several days before being cleared.

The surface friction reducing coating may furthermore comprise an active agent selected from bactericides, antibiotics, bacteriostatics, analgesics and anesthetics.

Examples of bactericides and bacteriostatics which are useful in the surface friction reducing coating include antibiotics. Antibiotics are naturally occurring or synthetic substances that are used to kill or inhibit the growth of bacteria. Some examples of antibiotics include penicillin (e.g. penicillin and amoxicillin), cephalosporins (e.g. cephalexin and cefuroxime), macrolides (e.g. erythromycin and azithromycin), tetracyclines (e.g. tetracycline and doxycycline), quinolones (e.g. ciprofloxacin and levofloxacin), sulfonamides (e.g. sulfamethoxazole and trimethoprim), aminoglycosides (e.g. gentamicin and tobramycin). Other examples of bactericides and bacteriostatics which are useful in the surface friction reducing coating include bacteriophages.

Examples of analgesics which are useful in the surface friction reducing coating include anti-inflammatory analgesics (e.g. acetaminophen, aspirin, COX inhibitors, nonsteroidal anti-inflammatory drugs (NSAIDs), such as ibuprofen and naproxen) and opioids (e.g. codeine, fentanyl, hydrocodone, meperidine, methadone, naloxone, naltrexone and oxycodone).

Examples of anesthetics which are useful in the surface friction reducing coating include local anesthetics which can be either ester- or amide-based. Examples of ester local anesthetics include procaine, amethocaine, cocaine, benzocaine, tetracaine. Examples of amide local anesthetics include lidocaine, prilocaine, bupivacaine, levobupivacaine, ropivacaine, mepivacaine, dibucaine and etidocaine. A preferred anesthetic is lidocaine, preferably in a concentration of 1-10% (w/v), such as 1-5% (w/v), such as 1-3% (w/v), such as about 2% (w/v).

In certain embodiments, the surface friction reducing coating provides antiseptic properties to the movement restriction device.

The surface friction reducing coating may also contain pH-adjusting compounds, including weak acids, weak bases and buffers.

In some embodiments, the surface friction reducing coating provides softening of adjacent tissues. This may further prevents or reduce the risk of migration of the implantable movement restriction device.

In certain embodiments, the surface friction reducing coating is a viscous medium. A viscous coating composition is a type of liquid or semi-solid material that is used to create a protective layer or film on a surface. This type of coating is characterized by its thick, sticky consistency, which allows it to adhere to the surface and form a durable, long-lasting layer. There are many different types of viscous coating compositions available, each with its own unique properties and characteristics.

It is preferred that the viscous medium is a viscous aqueous medium, such as a viscous aqueous liquid, such as a viscous aqueous solution. The viscous aqueous medium may be a viscoelastic medium. A preferred viscoelastic medium is a gel. The viscous medium may also be a viscous liquid.

Viscosity can be e.g. determined at 20° C. using a shear rate controlled rheometer (Model 302, Anton Paar, Germany), using a parallel plate geometry (plate diameter 50 mm, gap 100 μm). In this setup, the viscosity of water is approximately constant at 1 mPa·s, at shear rates between 0-100 s-1. For avoidance of doubt, viscous media as defined herein are considerably more viscous than water. Viscous media as defined herein typically exhibit a viscosity of at least 10 mPa s, such as at least 50 mPa·s at shear rates between 0-100 s-1, such as at 50 s-1. Preferably, viscous media as defined herein exhibit a viscosity of at least 100 mPa·s, such as at least 200 mPa·s at shear rates between 0-100 s-1, such as at 50 s-1. The specific values above are relevant for this specific setup, but the skilled person can easily determine corresponding values for viscosity in other experimental setups. Typically, the surface friction reducing coating has a higher viscosity than water.

The surface friction reducing coating may comprise preservatives. Examples of preservatives include antimicrobial preservatives, e.g. sorbic acid, parabens and lactic acid. A preferred type of preservatives is parabens, e.g. methylparaben and propylparaben.

Preferably, the surface friction reducing coating is configured to remain in a pouch for housing the implantable movement restriction device for a time period exceeding 7 days, preferably exceeding 14 days, such as exceeding 21 days or 28 days.

Specific examples of the surface friction reducing coating are:

(1) Xylocaine jelly, containing 0.1-10% (w/v) xylocaine (lidocaine hydrochloride). The composition also contains methylparaben, propylparaben, hydroxypropyl methylcellulose, and sodium hydroxide and/or hydrochloric acid to adjust pH to 6.0-7.0.

(2) Xylocaine viscous composition, containing 0.1-10% (w/v) xylocaine (lidocaine hydrochloride). The composition also contains carboxymethylcellulose sodium, methylparaben, propylparaben, purified water and saccharin sodium.

(3) Surgical lubricant, containing hydroxypropyl methylcellulose, propylene glycol, chlorhexidine gluconate, and sterile water.

(4) Poly(propylene fumarate-co-ethylene glycol) hydrogels (5) Polyethylene glycol (PEG) polymers, >5 kDa (6) Lubricating glycerin jelly, containing water, PEG, glycerin, carbomer, sodium hydroxide, methylparaben, propylparaben.

(7) Lidocaine jelly, containing 0.1-10% (w/v) lidocaine hydrochloride. The composition also contains glycerol, hydrochloric acid, hydroxyethylcellulose, sodium hydroxide, and water.

In some embodiments disclosed herein, the implantable movement restriction device has a size such that the implantable movement restriction device can be fully invaginated by the fundus wall of the patient as set out herein. Preferably, the implantable movement restriction device has a size of less than 200 cm2, preferably less than 100 cm2, and more preferably less than 50 cm2. The step of at least partially invaginating a movement restriction device may comprise at least partially invaginating a movement restriction device having a size such that the implantable movement restriction device can be fully invaginated by the fundus wall of the patient. Preferably, the step of at least partially invaginating a movement restriction device comprises at least partially invaginating a movement restriction device having a size of less than 200 cm2, preferably less than 100 cm2, and more preferably less than 50 cm2.

In some embodiments, the step of at least partially invaginating a movement restriction device comprises at least partially invaginating a movement restriction device being elongated and having a first cross-sectional distance having a first length, and a second cross-sectional distance having a second length, and wherein the first length is more than 1.2 times the second length, preferably more than 1.5 times the second length and even more preferably more than 2 times the second length.

In certain embodiments, the step of at least partially invaginating a movement restriction device comprises at least partially invaginating a movement restriction device comprising at least one circular cross-section.

In some embodiments, the step of at least partially invaginating a movement restriction device comprises at least partially invaginating a movement restriction device comprising a first, second and third cross-section in planes spaced apart and parallel to each other, wherein the first and third cross-sections have the same area, and the second cross-section is located between the first and third cross-section and have a smaller area.

In certain embodiments, the step of at least partially invaginating a movement restriction device comprises at least partially invaginating a movement restriction device comprising at least two parts, or at least three parts, or at least 4 parts. Preferably, the step of at least partially invaginating a movement restriction device comprises assembling at least two parts for forming the implantable movement restriction device.

In some embodiments, the step of at least partially invaginating a movement restriction device comprises at least partially invaginating a movement restriction device comprising a curved cross-section in a plane parallel to the transverse plane of the patient, and wherein the curve is configured to partially enclose the esophagus of the patient.

In certain embodiments, the step of at least partially invaginating a movement restriction device comprises at least partially invaginating a movement restriction device comprising at least one circular cross-section.

According to an aspect, an apparatus for treating reflux disease of a human patient is provided, comprising an implantable movement restriction device and an electrode arrangement. The implantable movement restriction device has a shape and size that allows it to be arranged to rest against a fundus wall portion of the patient's stomach and to be at least partly invaginated by the fundus wall portion, such that the movement restriction device is implanted at a position between the patient's diaphragm and a lower portion of the fundus wall, and such that movement of the cardia of the patient's stomach towards the diaphragm is restricted to hinder the cardia from sliding through the diaphragm opening into the patient's thorax. The electrode arrangement is configured to be arranged between the movement restriction device and the fundus wall portion and to engage and electrically stimulate muscle tissue of the fundus wall portion to exercise the muscle tissue to improve the conditions for long term implantation of the movement restriction device.

According to an aspect, an apparatus for treating reflux disease of a human patient is provided, comprising an at least partly ring-shaped implantable movement restriction device and an electrode arrangement. The implantable movement restriction device comprises a first portion configured to be at least partly invaginated by a first wall portion of the patient's stomach and arranged such that at least a part of the first portion is arranged above the cardiac notch of the patient's stomach, and such that movement of the cardia towards the diaphragm is restricted to prevent the cardia from sliding through the diaphragm opening into the patient's thorax. The electrode arrangement is configured to be arranged between the movement restriction device and the first wall portion and to electrically stimulate muscle tissue of the first wall portion to exercise the muscle tissue to improve the conditions for long term implantation of the movement restriction device.

According to an aspect, an apparatus for treating reflux disease of a human patient is provided, comprising an elongated core and a tubular cover. The elongated core has a length allowing the core to at least partly encircle the esophagus of the patient, wherein the length is variable to allow the core to be arranged in a constricting state for hindering fluid from passing from the stomach into the esophagus and in an expanded state for allowing food to pass into the stomach in response to the patient swallowing. The tubular cover is configured to encloses at least a part of the core and comprises a plurality of portions adapted to bend relative to each other to allow the core to change between the constricting state and the expanded state, when the cover is at least partly covered by fibrotic tissue, without being substantially hindered or impeded by the presence of said fibrotic tissue.

According to an aspect, an apparatus for treating reflux disease of a human patient is provided, comprising an elongated core having a length allowing the core to at least partly encircle the esophagus of the patient, wherein the length is variable to allow the core to be arranged in a constricting state for hindering fluid from passing from the stomach into the esophagus and in an expanded state for allowing food to pass into the stomach in response to the patient swallowing. The apparatus further comprises an electrode arrangement comprising an electrode element supported by the core and configured to be arranged between the apparatus and the esophagus and to electrically stimulate muscle tissue of the esophagus.

According to an aspect, an apparatus for treating reflux disease of a human patient, is provided comprising a tubular device having a length allowing the tubular device to at least partly encircle the esophagus of the patient, wherein the length is variable to allow the tubular cover to be arranged in a constricting state for hindering fluid from passing from the stomach into the esophagus and in an expanded state for allowing food to pass into the stomach in response to the patient swallowing. The outer surface of the tubular device may comprise a plurality of portions adapted to bend relative to each other to allow the tubular device to change between the constricting state and the expanded state, when the outer surface is at least partly covered by fibrotic tissue, without being substantially hindered or impeded by the presence of said fibrotic tissue.

According to an aspect, an apparatus for treating reflux disease of a human patient is provided, comprising an elongated core having a length allowing the core to at least partly encircle the esophagus of the patient. The length may be variable to allow the core to be arranged in a constricting state for hindering fluid from passing from the stomach into the esophagus and in an expanded state for allowing food to pass into the stomach in response to the patient swallowing. Further, the elongated core has a size allowing at least a portion of the elongated core to protrude above the cardiac sphincter of the patient, when implanted, such that movement of the cardia towards the diaphragm is restricted to hinder the cardia from sliding through the diaphragm opening into the patient's thorax.

According to an aspect, an apparatus for treating reflux disease of a human patient is provided, which is adapted to at least partly encircle the esophagus (20) of the patient. The apparatus comprises a first implantable portion and a second implantable portion, wherein the first implantable portion has a shape and size allowing it to be arranged to rest against a fundus wall portion of the patient's stomach and to be at least partly invaginated by the fundus wall portion, such that the first implantable portion is implanted at a position between the patient's diaphragm and a lower portion of the fundus wall, and such that movement of the cardia of the patient's stomach towards the diaphragm is restricted to hinder the cardia from sliding through the diaphragm opening into the patient's thorax. The second implantable portion is elongated to at least partly encircle the esophagus and has a variable length for allowing the apparatus be arranged in a constricting state for hindering fluid from passing from the stomach into the esophagus and in an expanded state for allowing food to pass into the stomach in response to the patient swallowing.

According to an aspect, an apparatus for treating reflux disease of a human patient is provided, which is adapted to at least partly encircle the esophagus of the patient. The apparatus comprises a movement restriction device, an elongated support device and an electrode arrangement. The movement restriction device has a shape and size allowing it to be arranged to rest against a fundus wall portion of the patient's stomach and to be at least partly invaginated by the fundus wall portion, such that the first implantable portion is implanted at a position between the patient's diaphragm and a lower portion of the fundus wall, and such that movement of the cardia of the patient's stomach towards the diaphragm is restricted to hinder the cardia from sliding through the diaphragm opening into the patient's thorax. The elongated support device is connected to the movement restriction device and configured to at least partly encircle the esophagus. The electrode arrangement comprises an electrode element supported by the support device and configured to electrically stimulate muscle tissue of the esophagus. Further, the support device comprises a rigidity that allows the position of the electrode element relative to the esophagus to be determined mainly by the position and orientation of the movement restriction device.

According to an aspect, a method for treating reflux disease of a human patient is provided. The method involves implanting a movement restriction device such that the movement restriction device is arranged to restrict movement of the cardia of the patient's stomach towards the diaphragm to hinder the cardia from sliding through the diaphragm opening into the patient's thorax. The method comprises placing the movement restriction device such that a lower portion of the movement restriction device rests against the serosa at the angle of His, and such that an upper portion of the movement restriction device defines a gap between the movement restriction device and the patient's esophagus, when the lower portion rests against the angle of His. The method further comprises arranging a portion of the fundus of the stomach in the gap and attaching the fundus to the patient's esophagus to at least partly enclose the movement restriction device by the portion of the fundus.

According to an aspect, an apparatus for treating reflux disease of a human patient is provided, comprising an implantable movement restriction device and an elongated attacher configured to be attached to the movement restriction device and to be at least partly invaginated by a wall portion of the patient's stomach. The attacher comprises a shape and size allowing it to be invaginated by the wall portion to hinder rotation of the movement restriction device. The attacher is further configured to be invaginated by the wall portion such that the movement restriction device is arranged at a position between the patient's diaphragm and the wall portion, distant from the patient's esophagus, to restrict movement of the cardia of the patient's stomach towards the diaphragm to hinder the cardia from sliding through the diaphragm opening into the patient's thorax.

According to an aspect, the elongated attacher is configured to be attached to the movement restriction device and to be at least one of; partly invaginated by a wall portion of the patient's stomach and sutured to a previously sutured line of staplers in a surgically modified stomach. The attacher comprises a shape and size allowing it to be invaginated by or sutured to the stapler reinforced wall portion to both hold the device in position as well as hinder rotation of the movement restriction device. The attacher is configured to be sutured to or invaginated by the wall portion such that the movement restriction device is arranged at a position between the patient's diaphragm and the wall portion, close to esophagus, however, not contacting the patient's esophagus, high above the LES to restrict movement of the cardia of the patient's stomach towards the diaphragm to also hinder the cardia from sliding through the diaphragm opening into the patient's thorax.

According to an aspect, an apparatus for treating reflux disease of a human patient comprises an implantable movement restriction device and an elongated attacher configured to be attached to the movement restriction device and to be at least one of, partly invaginated by a wall portion of the patient's stomach and sutured to a previously sutured line of staplers in a surgically modified stomach. The attacher comprises a shape and size allowing it to be invaginated by or sutured to the stapler reinforced wall portion to both hold the device in position as well as hinder rotation of the movement restriction device. The attacher is configured to be sutured to or invaginated by the wall portion such that the movement restriction device is arranged at a position between the patient's diaphragm and the wall portion, close to esophagus, however, not contacting the patient's esophagus, high above the LES to restrict movement of the cardia of the patient's stomach towards the diaphragm to also hinder the cardia from sliding through the diaphragm opening into the patient's thorax.

According to an aspect, an apparatus for treating reflux disease of a human patient, comprising an at least partly ring-shaped implantable movement restriction device configured to be arranged such that at a first, lower portion of the movement restriction device is arranged at the cardia of the patient's stomach and such that a second, upper portion of the movement restriction device is arranged to abut the diaphragm of the patient, such that movement of the cardia towards the diaphragm is restricted to prevent the cardia from sliding through the diaphragm opening into the patient's thorax. The apparatus is further configured to be arranged to define a gap or spacing between the second, upper portion of the movement restriction device and the outside of the esophagus when the apparatus is implanted. The apparatus may be formed of the movement restriction device as disclosed herein, or at least comprise such a movement restriction device.

According to an aspect, a method of treating reflux disease in a human patient is provided, involving implanting an apparatus comprising a movement restriction device and an elongated support device, such that the support device at least partly encircles the esophagus of the patient and such that the movement restriction device is at arranged on the fundus side of the esophagus to restrict the movement of the cardia in relation to the diaphragm to hinder the cardia to from sliding through the diaphragm opening into the patient's thorax. The method comprises the steps of introducing the apparatus into the abdominal cavity, placing the apparatus such that the movement restriction device rests against the outside of the stomach's fundus, wrapping a portion of the fundus around at least a part of the movement restriction device, affixing the fundus to the esophagus such that the movement restriction device is arranged at a position between the diaphragm and the cardiac sphincter, and such that a part of the fundus is arranged between the movement restriction device and the esophagus and arranging the support device to at least partly encircle the esophagus. The movement restriction device and the second portion form a ring-shaped body extending through the pouch to at least partly encircle the esophagus.

According to an aspect, a method for affixing a fundus portion of the stomach of a human patient to the patient's esophagus is provided, wherein the fundus portion extends from the angle of His and in a direction away from the esophagus. The method comprises folding the fundus portion towards the esophagus such that the fundus portion rests against the esophagus, from the angle of His and upwards along the esophagus, and affixing the fundus portion to the esophagus by means of fasteners arranged along a first line and a second line. The first line and the second line extend along the esophagus and are arranged such that a distance between the first line and the second line increases with an increasing distance from the angle of His.

According to an aspect, an apparatus for treating reflux disease in a human patient according to any of the above aspects is provided. The apparatus comprises an electrode arrangement for electrically stimulating the patient's muscle tissue to exercise the muscle tissue to improve the conditions for long term implantation of the apparatus, as outlined above. The apparatus further comprises an implantable energy source configured to provide the electrode arrangement with electrical power, a controller operably connected to the electrode arrangement for controlling the electrical stimulation of the muscle tissue.

According to an aspect, an apparatus for treating reflux disease of a human patient according to any one of the above aspects is provided. The apparatus comprises an electrode arrangement, an implantable energy source configured to provide the apparatus with electrical power, an external energy source configured be arranged outside of the patient's body and configured to provide energy to the implantable energy source, and an implantable charger configured to be electrically connected to the implantable energy source and enable charging of the implantable energy source by the external energy source.

According to an aspect, there is provided an apparatus for treating reflux disease of a human patient, comprising: an implantable movement restriction device having a shape and size allowing it to be arranged to rest against a fundus wall portion of the patient's stomach (10), such that the movement restriction device is implanted at a position between the patient's diaphragm (30) and a portion of the fundus wall, and such that movement of the cardia (22) of the patient's stomach towards the diaphragm is restricted to hinder the cardia from sliding through the diaphragm opening into the patient's thorax, wherein the implantable movement restriction device comprises an outer surface configured to rest against the stomach wall portion, and wherein an average surface roughness measured on the outer surface is no more than 300'000 μm.

According to an aspect, there is provided an apparatus for treating reflux disease of a human patient, comprising: an implantable movement restriction device having a shape and size allowing it to be arranged to rest against a fundus wall portion of the patient's stomach, such that the movement restriction device is implanted at a position between the patient's diaphragm and a portion of the fundus wall, and such that movement of the cardia of the patient's stomach towards the diaphragm is restricted to hinder the cardia from sliding through the diaphragm opening into the patient's thorax, wherein the implantable movement restriction device comprises an outer surface configured to rest against the stomach wall portion, and wherein an indentation hardness on the Shore A scale measured on the outer surface is at least 50, or in the range of 50 to 65, or in the range 5-25 or in the range >25-50, or >65.

According to an aspect, there is provided an apparatus for treating reflux disease of a human patient, comprising an implantable movement restriction device having a shape and size allowing it to be arranged to rest against a fundus wall portion of the patient's stomach, such that the movement restriction device is implanted at a position between the patient's diaphragm and a portion of the fundus wall, and such that movement of the cardia of the patient's stomach towards the diaphragm is restricted to hinder the cardia from sliding through the diaphragm opening into the patient's thorax, wherein the implantable movement restriction device comprises a plurality of segments, wherein the plurality of segments are comprised of a core part and a plurality of outer parts, and wherein the core part has an average density of above 1000 kg/m3

According to an embodiment, an apparatus for treating reflux disease of a human patient according to any one of the above aspects is provided. The apparatus when comprises an electrode arrangement, and a controller configured to be operably connected to the electrode arrangement for controlling the electrical stimulation of the muscle tissue. The controller comprises an implantable communicator for transmitting and/or receiving a signal to/from the outside of the patient's body.

According to an embodiment of the above aspects, the electrode arrangement may be arranged on an outer surface of the movement restriction device.

According to some embodiments of the above aspects, the electrode arrangements may comprise a plurality of electrode elements, wherein each of the electrode elements is configured to engage and electrically stimulate the muscle tissue. The electrode arrangement may further comprise a coiled wire for increasing a contact surface between the electrode arrangement and the muscle tissue and for allowing the electrode arrangement to follow contraction and relaxation of the muscle tissue.

According to some embodiments of the above aspects, the electrode arrangement may comprise a bare electrode portion configured to form a metal-tissue interface with the muscle tissue so as to allow faradaic charge transfer to the be predominant charge transfer mechanism over the interface. Alternatively, or additionally the electrode arrangement may comprise an electrode portion that is at least partly covered by a dielectric material configured to form a dielectric-tissue interface with the muscle tissue so as to allowing a faradaic portion of the charge transfer mechanism over the interface to be reduced.

According to some embodiments, the electrode arrangement may be configured to be arranged to electrically stimulate the cardiac sphincter to cause the cardiac sphincter to contract. The electrode arrangement may comprise at least two electrode elements configured to be arranged on opposing sides of the cardiac sphincter. Further, the apparatus may comprise a holder configured to support the at least two electrode elements at the opposing sides of the cardiac sphincter.

Exemplary embodiments of a movement restriction device according to at least some of the above aspects will now be discussed.

According to an embodiment, a volume of the movement restriction device may be non-adjustable after implantation. According to another embodiment, the volume of the movement restriction device may be adjustable after implantation. The volume may be adjustable invasively or non-invasively. In an example, the movement restriction device comprises an injection port for allowing a fluid to be injected or extracted from the inside of the movement restriction device so as to vary the volume of the movement restriction device after implantation.

According to an embodiment, the movement restriction device may comprise a biocompatible outer surface configured to rest against the fundus wall portion.

According to an embodiment, the movement restriction device may be substantially spherical or egg-shaped. In an example, the movement restriction device may have a portion configured to be arranged to point away from the esophagus when implanted. In a further example, a lower portion of the movement restriction device may be wider that an upper portion.

According to an embodiment, the movement restriction device may be configured to be invaginated when placed on the outside of the fundus wall portion. In another embodiment, the movement restriction device may be configured to be invaginated when placed on the inside of the fundus wall portion.

According to an embodiment, the movement restriction device may be configured to be introduced in the patient's body by means of a gastroscope or an intraluminal instrument. The movement restriction device may for example be configured to change its shape to allow it to pass through a trocar during insertion into the patient's body.

According to an embodiment, the movement restriction device may be formed of at least two distinct and separable parts configured to be assembled into the movement restriction device after insertion in the patient's body.

According to an embodiment, a minimum width of the movement restriction device, as measured from side to side, may be 20 mm or larger, such as 30 mm or larger, such as 40 mm or larger, such as 50 mm or larger.

According to some embodiments, the movement restriction device may comprise a first and a second portion, wherein the first and second portions are configured to be arranged on opposite sides of the cardia. In an example, the movement restriction device may be configured to be arranged such that a gap is formed between the second portion of the movement restriction device and the esophagus. In an example, the second portion of the movement restriction device may be configured to be at least partly invaginated by a second wall portion of the stomach.

According to an embodiment, the movement restriction device may be configured to be arranged such that a portion of the first wall portion is arranged between the first portion of the movement restriction device and the esophagus.

According to an embodiment, the movement restriction device may be configured to be at least partly invaginated by the first wall portion along at least half of the toroidal length of the movement restriction device.

According to an embodiment, the movement restriction device may be configured to be invaginated when placed on the outside of the stomach wall.

According to an embodiment, the movement restriction device may comprise two end portions configured to be coupled to each other to form a closed ring. The end portions may be configured to be releasably attached to each other.

According to an embodiment, a poloidal circumference of the movement restriction device may be larger for the first portion and for the second portion. In an example, a minimum width of the first portion of the movement restriction device, as measured from side to side, is 20 mm or larger, such as 30 mm or larger, such as 40 mm or larger, such as 50 mm or larger. Alternatively, the width may be defined as a height measured along a normal to the plane in which the circumference extends.

According to an embodiment, the movement restriction device may have a shape conforming to a torus.

According to an embodiment, the movement restriction device may have C-shaped cross section.

According to an embodiment, an upper portion of the movement restriction device may comprise a recess defined in the outer surface of the movement restriction device.

According to an embodiment, a lower portion of the movement restriction device may comprise a curved outer surface, which may be arranged to face the esophagus. The curved outer surface may comprise a radius of curvature corresponding to or exceeding the radius of curvature of the esophagus.

According to an embodiment, an elongated support, protruding from the movement restriction device, may be at least partly invaginated in the fundus before the fundus is attached to the esophagus. The support may be oriented along the esophagus.

Exemplary embodiments of a core and a cover according to at least some of the above aspects will now be discussed.

According to some embodiments, the core may be configured to allow a transition from the constricting state into the expanded state caused by the food passing through esophagus. The core may be configured to exert an encircling pressure on the esophagus in the constricting state.

According to an embodiment, the apparatus may further comprise an attractor for resiliently attracting adjacent portions of the core to one another to generate the encircling pressure. The attractor may comprise an elastic element, and/or at least two mutually attracting magnets. Further, the apparatus may comprise a link connecting a first and a second one of said at least two magnets to each other. The link may be configured to extend into at least one of said magnets in response to said magnets moving towards each other.

According to some embodiments, the core may comprise two end portions configured to be coupled to each other to form a closed ring around the esophagus. The end portions may be configured to be releasably attached to each other and may comprise a respective interlockable attacher.

According to an embodiment, the core may comprise a plurality of core elements configured to be arranged in an annular array around the esophagus. The core may further comprise a plurality of links, wherein each link may extend between a respective pair of core elements arranged adjacent to each other. The links may be configured to allow the respective core elements to move towards and away from each other, and may be configured to extend into at least one of the core elements of the respective pair of core elements as the core elements move towards each other.

According to an embodiment, the cover may comprise an array of tubular segments.

According to some embodiments, the cover may comprise a biocompatible outer surface for long-term implantation. The cover may for example be configured to rest against an outer surface of the esophagus and may further comprise a surface for promoting tissue growth. The cover may for example be formed of a polymer material, such as silicone. In further examples, the cover may be formed of or comprise a carbon-based material, such as carbon fiber material.

According to some embodiments, the cover may be formed of a material having a thickness of 0.1-10 mm, such as 1-5 mm. The cover may comprise at least one predefined fold along which the cover is allowed to fold in response to the core varying its length. The cover may in some examples comprise lowered and elevated portions allowing the cover to vary its length while maintaining its surface area. Thus, the cover may be configured to be compressible and expandable in its length direction, wherein the length is varied mainly due to the folding of the cover rather than elastic properties of the material. Thus, the cover may be considered to be formed of an inelastic material. In some examples, a length of the cover enclosing the at least a part of the core may exceed a length of the at least a part of the core when the at least a part of the core is arranged in the constricting state.

Exemplary embodiments of the attacher, which comprises a shape and size that allows it to be invaginated by the wall portion to hinder rotation of the movement restriction device as set out above in connection with some of the aspects, will now be described in the following.

According to some embodiments, a first end portion of the attacher may be configured to be invaginated by the wall portion and a second end portion to be attached to the movement restriction device. The first portion and the second portion may extend in different directions relative to each other, wherein the first portion may be configured to be invaginated by the wall portion to hinder rotation of the movement restriction device around a first axis, and wherein the second portion may be configured to be invaginated by the wall portion to hinder rotation of the movement restriction device around a second axis, different from the first axis. The first and second portions of the attacher may be curved to follow a curvature of the wall portion. The first portion and the second portion may be arranged at an angle to each other, the angle being in the interval of 60-120 degrees, such as 90 degrees.

According to some embodiments, the attacher may be configured to be releasably attached to the movement restriction device. The attacher may be configured to allow a position of the movement restriction device to be adjusted after invagination of the attachment means. In some examples, the apparatus may be configured to allow a distance between the movement restriction device and the attacher to be varied to allow the position of the movement restriction device relative to the diaphragm to be adjusted. Further, the apparatus may be configured to allow an orientation of the movement restriction device relative to the attachments means to be varied to allow the position of the movement restriction device relative to the diaphragm to the adjusted.

In an embodiment, the attacher may comprise a third portion, configured to be arranged to protrude from the wall portion when implanted, and to define a distance between the wall portion and the movement restriction device. The third portion may comprise a curvature allowing the third portion to be arranged to point away from the esophagus when implanted.

According to an embodiment, the movement restriction device and the attacher may be integrally formed into a single piece.

According to an embodiment, each of the movement restriction device and the attachments means may comprise a biocompatible outer surface. The attacher may comprises an outer surface configured to promote tissue growth. In some examples, the attacher may be formed of a metal. In further examples, the movement restriction device may be formed of a polymer.

According to an embodiment, an outer surface of the movement restriction device may comprise a material for hindering growth of fibrotic tissue.

Exemplary embodiments of the method of treating reflux disease in a human patient by implanting an apparatus comprising a movement restriction device and an elongated support device, as set out in some of the above aspects, will now be discussed in the following.

According to an embodiment, the apparatus may be placed such that the movement restriction device rests against the outside of the fundus at a position between the cardiac sphincter and the portion of the fundus that is to be affixed to the esophagus.

According to an embodiment, the apparatus may be placed such that the portion of the fundus that is affixed to the esophagus is arranged between the cardiac sphincter and the movement restriction device.

According to an embodiment, the pouch may be formed to be open in a least two positions to form a tunnel through which the apparatus extends.

According to an embodiment, the portion of the fundus may be affixed to the patient's diaphragm.

According to an embodiment, affixing the portion of the fundus to the esophagus may include suturing or stapling.

According to an embodiment, the support device may comprise a first and a second end portion between which the esophagus can be introduced. The first and second end portions can be coupled to each other so as to fixate the support device to the esophagus in an encircling manner.

According to an embodiment, the method may further comprise inserting a needle or a tube-like instrument into the patient's abdomen, using the needle or tube-like instrument to fill the abdomen with a gas, placing at least two laparoscopic trocars in the abdomen, inserting a camera through one of the laparoscopic trocars into the abdomen, inserting at least one dissecting tool through one the laparoscopic trocars, dissecting a portion of the stomach, and at least partly closing the pouch by means of sutures, such as barbed sutures, or staples.

In the following, exemplary embodiments of the method for affixing a fundus portion of the stomach of a human patient to the patient's esophagus according to the above aspect will now be described.

According to an embodiment, the abdominal part of the esophagus and the fundus can be divided by a plane into a ventral and a dorsal side. The method may comprise providing the first line on the dorsal side of the plane and the second line on the ventral side of the plane. The first line may begin less than 1 cm above the angle of His and the second line began less than 3 cm above the angle of His. The second line may in some examples begin at a distance less than 2 cm from the first line.

According to an embodiment, a separating angle between the first line and the second line may be in the range of 90-150 degrees.

According to some embodiments, the method may comprise providing an additional fastener between the first line and the second line, at the top of the fundus portion.

In some examples, the fasteners may comprise staples. In some examples, the fasteners may comprise sutures, such as for example barbed sutures. The first line of fasteners may for example comprise a first continuous suture, and the second line of fasteners a second continuous suture.

According to some embodiments, the method may further comprises placing a movement restriction device on the fundus, forming a pouch in the fundus, arranging the movement restriction device at least partly in the pouch, and invaginating the movement restriction device by the fundus by at least partly closing the pouch by fasteners. The movement restriction device may be arranged at a position between the diaphragm and the cardiac sphincter to hinder the cardia from sliding through the diaphragm opening into the patient's thorax. The movement restriction device may be invaginated after affixing the fundus portion to the esophagus. Further, the pouch may be formed to be open in a least two positions to form a tunnel through which the movement restriction device may extend. In an example, the fundus may be affixed to the diaphragm.

According to some embodiments an energy source may be provided. The energy source may be configured to be implanted in the body of the patient. The energy source may be configured to provide energy consuming components of the implant with electrical power. Examples of energy consuming components include controllers, sensors, electrodes, and the like, as outlined above in connection with the previous embodiments and examples. Thus, in some embodiments the energy source may be configured to provide the electrode arrangement, or electrode, as outlined above with electrical power.

The implantable energy source may be configured to be arranged inside, or integrated with, the implanted device, such as the movement restriction device, support device, attachment means, core, or cover according to any of the embodiments and examples described above. In some examples the energy source, or a part of the energy source, may be configured to be implanted outside the apparatus or implanted device, such as for example subcutaneously.

The energy source may comprise a primary cell, or galvanic cell, designed to be discarded after use, and not recharged like a secondary cell. Alternatively, or additionally the energy source may comprise a secondary cell, or rechargeable battery, designed to be recharged repeatedly.

According to some embodiments, the implantable energy source may be configured to be charged by an external energy source, i.e., an energy source arranged outside the patient's body. This may for example be achieved by means of an implantable charger, which may be configured to be electrically connected to the implantable energy source and to enable charging of the implantable energy source by the external energy source. Thus, the charger may be configured to transmit the electrical power from the outside of the patient's body to the implanted energy source. The transmission may for example be performed wirelessly from the external source, and the charger may in some examples comprise an electromagnetic coil for facilitating the transfer.

According to some embodiments, the charger may be configured to control the charging of the implantable energy source by controlling a receipt of electrical power from the external energy source at the implantable charger, and/or by controlling a transmission of electrical power from the external energy source to the implantable charger.

According to some embodiments, the charging of the implantable energy source may be controlled based on a functional status of the implanted energy source. This may for example be realized by controlling the electrical power delivered or emitted by an external energy source, or by controlling the electrical power received by a charger as outlined above. Further, the charging may in some examples be controlled by controlling the electrical power delivered by the charger to the implantable energy source, either by controlling the power output from the charger or by controlling the power received or absorbed by the implantable energy source. Thus, it will be appreciated that the charging of the implantable energy source may be controlled by varying or controlling the electrical power, supplied by the external energy source, at any point along the way to the implantable energy source. As exemplified above, the electrical power that is supplied to the implantable energy source may hence be controlled at the external energy source, at the charger or at the implantable energy source itself.

The functional status of the implanted energy source may for example include a charge level or a temperature. The temperature may for example be related to the energy source, the muscle tissue, or a part of the implant such as the electrode arrangement. Thus, the charging may be reduced or even stopped in case the charge level (or accumulated energy) reaches an upper limit, or in case the temperature exceeds a predetermined interval.

According to some embodiments, there may be provided a controller (or processor or control circuitry) for controlling various parts or functions of the implanted device or apparatus according to any of the embodiments described above. The controller may for example be configured to include the functional status of the implanted energy source in a signal that is transmitted to the outside of the body.

The controller may be configured to be operable connected to the electrode arrangement for controlling the electrical stimulation of the muscle tissue. The stimulation may for example be controlled such that the muscle tissue is stimulated by a series of electrical pulses. The electrical pulses may be characterized by their voltage and/or current. In some examples, a pulse of a first polarity may be followed by a pulse of a second, reversed polarity. The first polarity may for example be a positive current and the second polarity a negative current relative a current flow direction. Alternatively, or additionally the first polarity may be characterized by a positive voltage relative to a reference such as ground, and the second polarity by a negative voltage.

The controller may be configured to generate a pulsed electrical stimulation signal comprising a pulse frequency of 0.01-150 Hz. The pulse duration may be 0.01-100 ms, and the pulse amplitude in the interval 1-15 mA. Specific examples of electrical stimulation signals may be characterized by a pulse frequency of 0.15-0.25 Hz, a pulse duration of 20-30 ms and a pulse amplitude of 3-10 mA.

The controller may further be configured to generate a pulsed electrical stimulation signal having a varying composition, including different periods including build-up periods in which the amplitude is gradually increasing, stimulation periods in which the stimulation is ongoing, and pause periods wherein the stimulation is paused. Thus, in an example, the electrical stimulation signal may comprise a build-up period of 0.01-2 s, a stimulation period of 1-60 s, and a stimulation pause of 0.01-60 s. During the build-up period and the stimulation period the signal may comprises a pulse frequency of 1-50 Hz and a pulse duration of 0.1-10 ms. These periods may be varied and combined depending on the desired stimulation of the muscle tissue and may further be varied based on a response which fort example may be monitored by means of a sensor connected to the controller. The sensor may for example be configured to measure a motoric response in the muscle tissue, which may be measured as a mechanical movement or an electrical response.

According to some embodiments, there may be provided an implantable sensor for sensing action potentials generated by pacemaker cells of the muscle tissue. The sensor may be communicatively coupled to the controller, which may be configured to control the electrical stimulation based at least partly on the sensed action potentials. This may be particularly advantageous when stimulating smooth muscle tissue, which may exhibit period contractions that are paced by the pacemaker cells. The present embodiments thus allow for the electrical stimulation signal to be tailored to amplify the sensed action potentials.

According to some embodiments, the controller may comprise an external controller configured to be arranged outside the patient's body, and an internal controller, or implantable controller, configured to be arranged inside the patient's body. The wireless remote control may comprise an external signal transmitter configured to communicate with the internal controller. The internal controller may thus be configured to receive a signal transmitted by the external signal transmitter and to control an operation of the apparatus or medical implant based on the signal. The signal may in some examples be selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.

According to an embodiment of the movement restriction device defined in any one of the aspects above, the average surface roughness is Ra as defined according to ISO 21920-2:2021.

According to an embodiment of the movement restriction device defined in any one of the aspects above the average surface roughness is Sa as defined according to ISO 25178-2:2021.

According to an embodiment of the movement restriction device defined in any one of the aspects above the average surface roughness is in the range of 0.1-0.5 μm.

According to an embodiment of the movement restriction device defined in any one of the aspects above the average surface roughness is in the range of 0.1-0.3 μm.

According to an embodiment of the movement restriction device defined in any one of the aspects above the implantable movement restriction device comprises a polymer material.

According to an embodiment of the movement restriction device defined in any one of the aspects above implantable movement restriction device comprises at least one of a silicone-based material and a polyurethane-based material.

According to an embodiment of the movement restriction device defined in any one of the aspects above second solid material comprises at least one of a polypropylene-based and a polyethylene-based material.

According to an embodiment of the movement restriction device defined in any one of the aspects above, an indentation hardness on the Shore A scale measured on the outer surface is at least 50.

According to an embodiment of the movement restriction device defined in any one of the aspects above indentation hardness is indentation hardness is measured by the durometer method defined in part 4 of ISO 48-4:2018.

According to an embodiment of the movement restriction device defined in any one of the aspects above an indentation hardness on the Shore A scale measured on the outer surface is no more than 70.

According to an embodiment of the movement restriction device defined in any one of the aspects above an indentation hardness on the Shore A scale measured on the outer surface is in the range of 55 to 65.

According to an embodiment, the implantable movement restriction device comprises a core part and at least one outer part, configured to be assembled to the implantable movement restriction device.

According to an embodiment, the core part comprises a fluid.

According to an embodiment, the core part comprises a liquid having a density a below 1000 kg/m3.

According to an embodiment, the liquid comprises at least one selected from a list of:

oil-based liquids, and alcohol based liquids.

According to an embodiment, the core part comprises a gas.

According to an embodiment, the core part comprises a plurality of volumes of gas enclosed by an enclosing material.

According to an embodiment, the core part comprises a solid polymer material enclosing the enclosing material, and wherein the enclosing material is harder than the solid polymer material.

According to an embodiment, the plurality of volumes of gas enclosed by an enclosing material makes up at least 10 volume percent of the second volume, more preferably at least 20 volume percent of the second volume, and even more preferably at least 30 volume percent of the at least one outer part, and even more preferably at least 40 volume percent of the second volume, and even more preferably at least 50 volume percent of the second volume, and even more preferably at least 60 volume percent of the second volume, and even more preferably at least 70 volume percent of the second volume, and even more preferably at least 80 volume percent of the second volume, and even more preferably at least 90 volume percent of the second volume.

According to an embodiment, the enclosing material comprises glass.

According to an embodiment, the implantable movement restriction device comprises a contrast agent.

According to an embodiment, the implantable movement restriction device comprises the contrast agent BaSO4.

According to an embodiment, the implantable movement restriction device comprises the contrast agent in an amount of 1-15% by weight of the implantable movement restriction device.

According to an embodiment, the implantable movement restriction device comprises the contrast agent in an amount of 1-6% by weight of the implantable movement restriction device.

According to an embodiment, the implantable movement restriction device comprises the contrast agent in an amount of 8-15% by weight of the implantable movement restriction device.

In some embodiments, the core part comprises the contrast agent in an amount of 8-15% by weight of the core part.

In some embodiments, the at least one outer part comprises the contrast agent in an amount of 1-6% by weight of the implantable movement restriction device.

The various apparatuses and methods according to the above aspects can be combined with any of the features, examples and effects described in the present application.

According to an embodiment of the movement restriction device defined in any one of the aspects above, the indentation hardness is indentation hardness is measured by the durometer method defined in part 4 of ISO 48-4:2018.

According to an embodiment of the movement restriction device defined in any one of the aspects above an indentation hardness on the Shore A scale measured on the outer surface is no more than 70.

According to an embodiment of the movement restriction device defined in any one of the aspects above an indentation hardness on the Shore A scale measured on the outer surface is in the range of 55 to 65.

According to an embodiment, the core part comprises a fluid.

According to an embodiment, the core part comprises a liquid having a density a below 1000 kg/m3.

According to an embodiment, the liquid comprises at least one selected from a list of: oil-based liquids, and alcohol based liquids.

According to an embodiment, the core part comprises a gas.

According to an embodiment, the core part comprises a plurality of volumes of gas enclosed by an enclosing material.

According to an embodiment, the core part comprises a solid polymer material enclosing the enclosing material, and wherein the enclosing material is harder than the solid polymer material.

According to an embodiment, the plurality of volumes of gas enclosed by an enclosing material makes up at least 10 volume percent of the second volume, more preferably at least 20 volume percent of the second volume, and even more preferably at least 30 volume percent of the at least one outer part.

According to an embodiment, the enclosing material comprises glass.

An implantable medical device for treating reflux disease is further provided. The implantable medical device comprises a movement restriction device configured to be fixated to the stomach wall for hindering movement of the lower esophageal sphincter relative to the thoracic diaphragm. The movement restriction device comprises a first part, a second part, and a first distance element. The first and second part are configured to be connected to each other for forming at least a portion of a functional movement restriction device.

The first and second part are capable of disconnecting from each other, such that the first and second part individually can pass through the gastro-intestinal tract, and the first distance element is configured to create a space located between the first and second part. The space is configured to allow in-growth of fibrotic tissue between portions of the first and second parts. The space is confined at least partially by a first surface of the first part and a second surface of the second part and wherein the first and second surfaces are positioned opposite each other when the first and second parts are connected. A line segment of a first straight line is bounded by a first point on the first surface and a second point on the second surface, the line segment of the first straight line is more than 1 mm. A line segment of a second straight line is bounded by a third point on the first surface and a fourth point on the second surface. The line segment of the second straight line is more than 1 mm and the first straight line is parallel to the second straight line. The first and second straight lines intersect a third straight line which also intersects the center of gravity of the functional movement restriction device, and a distance between the first and second straight lines is more than 2 mm for allowing in-growth of fibrotic tissue for aiding in the fixation of the functional movement restriction device to the stomach wall.

According to one embodiment, the first distance element is integrated in at least one of the first and second part, and the first distance element may protrude from a surface of at least one of the first and second part.

According to one embodiment, the implantable medical device further comprises a first separate distance part comprising the first distance element.

According to one embodiment, at least one of the first and second part may further comprise a recess configured to receive a portion of the first distance element.

The first distance element may in any of the embodiments herein comprise at least a first and second portion configured to be placed at a distance from each other.

According to one embodiment, the implantable medical device further comprises at least a third part, and the first, second and third parts may be configured to be connected to each other for forming at least a portion of the functional movement restriction device.

The implantable medical device according to any one of the embodiments herein may further comprise a second distance element, and the first distance element may be configured to create a space between the first and second part and the second distance element may be configured to create a space between the first and third part. The first and second distance element may be portions of a separate distance part.

According to one embodiment, at least one of the first, second and third parts may comprise a recess configured to receive a portion of the distance element.

According to one embodiment, the space created by the distance element may have a volume exceeding 100 mm3.

According to one embodiment, the space forms a recess in the implantable medical device, and the recess has a depth exceeding 2 mm and a width exceeding 1 mm.

According to one embodiment, the distance element is configured to prevent at least one of: rotation between the first and second part, linear movement between the first and second part in a first direction, and linear movement between the first and second part in a first and second direction.

According to one embodiment, the first separate distance part is configured to be placed centrally in the functional movement restriction device, and the center of gravity of the first separate distance part may substantially coincide with the center of gravity of the functional movement restriction device.

According to one embodiment, the first separate distance part comprises at least one rim comprising at least a first and a second surface. The first surface of the rim may be configured to engage a surface of the first part and the second surface of the flange is configured to engage a surface of the second part. The first and second surfaces of the at least one rim may be parallel. The first separate distance part may comprise at least two rims. The first rim may comprise at least a first and a second surface, the first surface of the first rim may be configured to engage a surface of the first part and the second surface of the first rim may be configured to engage a surface of the second part. The second rim may comprise at least a first and a second surface, and the first surface of the second rim may be configured to engage a surface of the first part and the second surface of the second rim may be configured to engage a surface of the third part.

According to one embodiment, the first surfaces of the first rim and the first surface of the second rim are angled relative to each other with an angle in the range 20°-70°.

According to one embodiment, the first surfaces of the first rim and the first surface of the second rim are angled relative to each other with an angle in the range 40°-50°.

According to one embodiment, the first surfaces of the first rim and the first surface of the second rim are perpendicular.

According to one embodiment, the first distance element may be configured to engage the recess in at least one of the first and second part in a direction of a length axis of the distance element, and the portion of the first distance element configured to enter the recess of the second part may comprise at least one surface being angled relative to the length axis of the distance element.

According to one embodiment, the surface of the first distance element being angled may be configured to face a surface of the recess in at least one of the first and second part being angled with an angle different from the angle of the first distance element, and wherein a point on the angled surface of the first distance element is configured to abut a point on the angled surface of the recess.

According to one embodiment, the angled surface of the first distance element abuts the angled surface of the recess over a length being less than half of the length of the angled surface of the first distance element.

According to one embodiment, the angled surface of the first distance element abuts the angled surface of the recess over a length being less than one third of the length of the angled surface of the first distance element.

According to one embodiment, the angled surface of the first distance element abuts the angled surface of the recess over a length being less than half of the depth of the recess, measured in a direction coinciding with the direction of the length axis of the first distance element, when the portion of the first distance element is inserted into the recess.

According to one embodiment, the portion of the first distance element configured to enter the recess of the second part comprises a tapered portion.

According to one embodiment, the tapered portion is tapered with an angle in the range 20°-100°.

According to one embodiment, the recess in at least one of the first and second part is tapered, such that two surfaces on opposite sides of the tapered portion of the first distance element faces two surfaces on opposite sides of the tapered recess, when the tapered portion of the first distance element is inserted into the recess. The tapered recess may be tapered with an angle in the range 30°-135°.

According to one embodiment, the tapered portion of the first distance element is tapered with a first angle and the tapered recess in at least one of the first and second part is tapered with a second angle, and the second angle is larger than the first angle. The second angle may be more than 3° larger than the first angle, or more than 5° larger than the first angle, or more than 10° larger than the first angle.

According to one embodiment, the tapered portion of the first distance element, and the tapered recess in at least one of the first and second part is conical or frustum-conical.

According to one embodiment, the tapered portion of the first distance element has the shape of a pyramid with a polygonal base.

According to one embodiment, the portion of the first distance element configured to enter the recess of the first or second part comprises at least one surface having a curvature.

According to one embodiment, the surface of the first distance element having a curvature is configured to face a surface of the recess in at least one of the first and second part. A point on the surface of the first distance element having the curvature is configured to abut a point on the surface of the recess.

According to one embodiment, the surface of the first distance element having a curvature abuts the surface of the recess over a length being less than half of the length of the angled surface of the first distance element, when the first distance element has been positioned in the recess in at least one of the first and second part.

According to one embodiment, the surface of the first distance element having a curvature abuts the surface of the recess over a length being less than one third of the length of the angled surface of the first distance element, when the portion of the first distance element is inserted into the recess.

According to one embodiment, the surface of the first distance element having a curvature abuts the surface of the recess over a length being less than one third of the length of the angled surface of the first distance element, when the portion of the first distance element is inserted into the recess.

According to one embodiment, the surface of the first distance element having a curvature abuts the surface of the recess over a length being less than half of the depth of the recess, measured in a direction coinciding with the direction of the length axis of the first distance element, when the portion of the first distance element is inserted into the recess.

According to one embodiment, the portion of the first distance element configured to enter the recess of the second part comprises at least one surface having a first and second curvature extending in perpendicular directions. The portion of the first distance element configured to enter the recess of the second part may comprise at least one spherical surface.

According to one embodiment, the recess in at least one of the first and second part is tapered, such that two curved surfaces on opposite sides of the portion of the first distance element configured to enter the recess of the first or second part faces two surfaces on opposite sides of the tapered recess, when the portion of the first distance element configured to enter the recess of the first or second part is inserted into the recess.

According to one embodiment, the recess in at least one of the first and second part comprises at least one surface having a curvature. The recess in at least one of the first and second part may comprise at least one surface having a first and second curvature extending in perpendicular directions.

According to one embodiment, the recess in at least one of the first and second part comprises at least one spherical surface.

According to one embodiment, the portion of the first distance element configured to enter the recess of the first or second part comprises at least one surface having a curvature with a first radius and the recess in at least one of the first and second part comprises at least one surface having a curvature with a second radius. The second radius is according to one embodiment longer than the first radius.

According to one embodiment, the portion of the first distance element configured to enter the recess of the first or second part comprises at least one surface having a first and second curvature extending in perpendicular directions.

According to one embodiment, the recess in at least one of the first and second part comprises at least one surface having a first and second curvature extending in perpendicular directions, and the sum of the radii of the first and second curvatures of the recess in at least one of the first and second part is longer than the sum of the radii of the first and second curvature of the portion of the first distance element configured to enter the recess.

According to one embodiment, the functional movement restriction device or the boundary of the functional movement restriction device may be elongated. The functional movement restriction device may be elongated such that a longest length is more than 1.5 times a widest width.

According to one embodiment, the functional movement restriction device comprises a bend, and the functional movement restriction device comprises a bent center axis following the elongation of the functional movement restriction device.

According to one embodiment, a first portion of the functional movement restriction device is configured to be positioned such that a first portion of the bent center axis is parallel to the caudal-cranial axis of the patient, and a second portion of the bent center axis is angled relative to the caudal-cranial axis of the patient, with an angle exceeding 5°.

According to one embodiment, the second portion of the bent center axis is configured to be positioned in the stomach such that it is angled towards the esophagus.

According to one embodiment, at least one of the first and second part has a shape corresponding to an ellipsoid wedge or a truncated ellipsoid wedge.

According to one embodiment, at least one of the first and second part has a shape corresponding to a spherical wedge or a truncated spherical wedge.

At least one of the first and second part may have a shape corresponding to a portion of an ellipsoid wedge or a portion of a truncated ellipsoid wedge.

According to one embodiment, at least one of the first and second part has a shape corresponding to a hemiellipsoid wedge or a truncated hemiellipsoid wedge.

At least one of the first and second part may have a shape corresponding to a portion of a spherical wedge or a portion of a truncated spherical wedge.

According to one embodiment, at least one of the first and second part has a shape corresponding to a hemispherical wedge or a truncated hemispherical wedge.

According to one embodiment, at least one of the first and second part has a shape corresponding to an ellipsoid segment or a portion of an ellipsoid segment.

According to one embodiment, at least one of the first and second part has a shape corresponding to a spherical segment or a portion of a spherical segment.

The functional movement restriction device, or the boundary of the functional movement restriction device, may in any of the embodiments have a shape corresponding to an ellipsoid or a truncated ellipsoid.

According to one embodiment, the functional movement restriction device, or the boundary of the functional movement restriction device, has a shape corresponding to a sphere or a truncated sphere.

According to one embodiment, at least the periphery of at least one of the first and second part has a shape corresponding to a cylinder.

According to one embodiment, the combined periphery of the first and second part has a shape corresponding to a cylinder.

According to one embodiment, the periphery of the first part has a shape corresponding to a first cylinder having a first radius, and the periphery of the second part has a shape corresponding to a second cylinder having a second radius, and the first and second radii are different.

According to one embodiment, the functional movement restriction device, or the boundary of the functional movement restriction device, comprises a stadium shaped cross-section, or a truncated stadium shaped cross-section.

According to one embodiment, the functional movement restriction device comprises a bent stadium shaped cross-section, or a truncated bent stadium shaped cross-section.

According to one embodiment, a periphery of the first part has a shape corresponding to a cylinder or an ellipsoid segment, and a periphery of the second part has a shape corresponding to a cylinder or an ellipsoid segment, and the first part comprises at least one protrusion protruding from a first base surface and the second part comprises at least one recess in a first base surface, and the at least one protrusion is adapted to be placed at least partially in the at least one recess. The at least one protrusion may be adapted to engage the at least one recess and the first part may further comprise at least one recess in a second base surface.

The position of the at least one protrusion may coincide with the position of the at least one recess, such that the recess overlaps the protrusion when the first part is viewed in a direction normal to the first base surface. The at least one recess may recess into the at least one protrusion.

According to one embodiment, the at least one protrusion may have the shape of a pyramid with a polygonal base.

According to one embodiment, the first part further comprises at least one protrusion in a second base surface, and the second part may further comprise at least one protrusion in a second base surface. The second part may further comprise at least one recess in a second base surface.

According to one embodiment, the implantable medical device further comprises a third part, and the first part further comprises a recess in a second base surface, the second part further comprises a protrusion protruding from a second base surface, the third part comprises a protrusion protruding from a first base surface and a recess in a second base surface, the protrusion of the first part is configured to be at least partially inserted into the recess of the second part, the protrusion of the second part is configured to be at least partially inserted into the recess of the third part, and the first, second and third parts are configured to be assembled for forming at least a portion of a functional implantable medical device, and wherein the recesses and protrusions stabilize the parts relative to each other when assembled.

According to one embodiment, the area of the first base surface of the first part is smaller than the area of the first base surface of the second part.

According to one embodiment, the at least one protrusion protruding from the first base surface of the first part comprises the distance element.

According to one embodiment, the medical device is further configured to treat obesity by the movement restriction device being configured to protrude into the stomach and thereby reducing the volume of the cavity of the stomach. For the purpose of treating obesity, the functional movement restriction device may have a volume in the range 100 cm3-1000 cm3, or in the range 100 cm3-500 cm3. For the purpose of treating obesity, the functional implantable medical device may have a length in the range 2.5 cm-15 cm or in the range 5 cm-15 cm, or in the range 7 cm-15 cm, or in the range 8 cm-15 cm, or in the range 8 cm-12 cm.

The movement restriction device may in any of the embodiments herein comprises a surface friction reducing coating covering at least a part of the surface of the movement restriction device. The surface friction reducing coating may be configured to reduce the friction between the movement restriction device and the tissue of the stomach wall by which the movement restriction device is at least partially invaginated.

The implantable medical device may further comprise a sensor configured to sense at least one of a force and a pressure, for monitoring a pressure or force exerted by the implantable movement restriction device on the stomach wall of the patient.

According to one embodiment, the movement restriction device comprises a first portion having a first volume enclosed by material of the implantable movement restriction device and a second portion, different from the first portion, having a second volume enclosed by material of the implantable movement restriction device. The first volume and the second volumes may be equally large and the first volume may have a higher density than the second volume, and the second volume may have a density below 1000 kg/m3.

According to one embodiment, the implantable medical device may be configured to be fixated to the stomach wall of the patient to act as a movement restriction device for hindering movement of the lower esophageal sphincter relative to the thoracic diaphragm. The movement restriction device comprises a first part, a second part, and a distance element. The first and second part may be configured to be connected to each other for forming at least a portion of a functional movement restriction device. The first and second parts are capable of disconnecting from each other if at least one of the first and second part becomes positioned inside of the stomach, such that the first and second part individually can pass through the gastro-intestinal tract, and the distance element is configured to create a space between the first and second part. The space is configured to allow in-growth of fibrotic tissue between portions of the first and second parts, and the space forms a recess in the functional movement restriction device. The recess may be more than 1 mm wide and more than 2 mm deep for allowing in-growth of fibrotic tissue for aiding in the fixation of the functional movement restriction device to the stomach wall.

According to one embodiment, the first distance element is integrated in at least one of the first and second part, and the first distance element may protrude from a surface of at least one of the first and second part.

According to one embodiment, the implantable medical device further comprises a first separate distance part comprising the first distance element.

According to one embodiment, at least one of the first and second part may further comprise a recess configured to receive a portion of the first distance element.

The first distance element may in any of the embodiments herein comprise at least a first and second portion configured to be placed at a distance from each other.

According to one embodiment, the implantable medical device further comprises at least a third part, and the first, second and third parts may be configured to be connected to each other for forming at least a portion of the functional movement restriction device.

The implantable medical device according to any one of the embodiments herein may further comprise a second distance element, and the first distance element may be configured to create a space between the first and second part and the second distance element may be configured to create a space between the first and third part. The first and second distance element may be portions of a separate distance part.

According to one embodiment, at least one of the first, second and third parts may comprise a recess configured to receive a portion of the distance element.

According to one embodiment, the space created by the distance element may have a volume exceeding 100 mm3.

According to one embodiment, the space forms a recess in the implantable medical device, and the recess has a depth exceeding 2 mm and a width exceeding 1 mm.

According to one embodiment, the distance element is configured to prevent at least one of: rotation between the first and second part, linear movement between the first and second part in a first direction, and linear movement between the first and second part in a first and second direction.

According to one embodiment, the first separate distance part is configured to be placed centrally in the functional movement restriction device, and the center of gravity of the first separate distance part may substantially coincide with the center of gravity of the functional movement restriction device.

According to one embodiment, the first separate distance part comprises at least one rim comprising at least a first and a second surface. The first surface of the rim may be configured to engage a surface of the first part and the second surface of the flange is configured to engage a surface of the second part. The first and second surfaces of the at least one rim may be parallel. The first separate distance part may comprise at least two rims. The first rim may comprise at least a first and a second surface, the first surface of the first rim may be configured to engage a surface of the first part and the second surface of the first rim may be configured to engage a surface of the second part. The second rim may comprise at least a first and a second surface, and the first surface of the second rim may be configured to engage a surface of the first part and the second surface of the second rim may be configured to engage a surface of the third part.

According to one embodiment, the first surfaces of the first rim and the first surface of the second rim are angled relative to each other with an angle in the range 20°-70°.

According to one embodiment, the first surfaces of the first rim and the first surface of the second rim are angled relative to each other with an angle in the range 40°-50°.

According to one embodiment, the first surfaces of the first rim and the first surface of the second rim are perpendicular.

According to one embodiment, the first distance element may be configured to engage the recess in at least one of the first and second part in a direction of a length axis of the distance element, and the portion of the first distance element configured to enter the recess of the second part may comprise at least one surface being angled relative to the length axis of the distance element.

According to one embodiment, the surface of the first distance element being angled may be configured to face a surface of the recess in at least one of the first and second part being angled with an angle different from the angle of the first distance element, and wherein a point on the angled surface of the first distance element is configured to abut a point on the angled surface of the recess.

According to one embodiment, the angled surface of the first distance element abuts the angled surface of the recess over a length being less than half of the length of the angled surface of the first distance element.

According to one embodiment, the angled surface of the first distance element abuts the angled surface of the recess over a length being less than one third of the length of the angled surface of the first distance element.

According to one embodiment, the angled surface of the first distance element abuts the angled surface of the recess over a length being less than half of the depth of the recess, measured in a direction coinciding with the direction of the length axis of the first distance element, when the portion of the first distance element is inserted into the recess.

According to one embodiment, the portion of the first distance element configured to enter the recess of the second part comprises a tapered portion.

According to one embodiment, the tapered portion is tapered with an angle in the range 20°-100°.

According to one embodiment, the recess in at least one of the first and second part is tapered, such that two surfaces on opposite sides of the tapered portion of the first distance element faces two surfaces on opposite sides of the tapered recess, when the tapered portion of the first distance element is inserted into the recess. The tapered recess may be tapered with an angle in the range 30°-135°.

According to one embodiment, the tapered portion of the first distance element is tapered with a first angle and the tapered recess in at least one of the first and second part is tapered with a second angle, and the second angle is larger than the first angle. The second angle may be more than 3° larger than the first angle, or more than 5° larger than the first angle, or more than 10° larger than the first angle.

According to one embodiment, the tapered portion of the first distance element, and the tapered recess in at least one of the first and second part is conical or frustum-conical.

According to one embodiment, the tapered portion of the first distance element has the shape of a pyramid with a polygonal base.

According to one embodiment, the portion of the first distance element configured to enter the recess of the first or second part comprises at least one surface having a curvature.

According to one embodiment, the surface of the first distance element having a curvature is configured to face a surface of the recess in at least one of the first and second part. A point on the surface of the first distance element having the curvature is configured to abut a point on the surface of the recess.

According to one embodiment, the surface of the first distance element having a curvature abuts the surface of the recess over a length being less than half of the length of the angled surface of the first distance element, when the first distance element has been positioned in the recess in at least one of the first and second part.

According to one embodiment, the surface of the first distance element having a curvature abuts the surface of the recess over a length being less than one third of the length of the angled surface of the first distance element, when the portion of the first distance element is inserted into the recess.

According to one embodiment, the surface of the first distance element having a curvature abuts the surface of the recess over a length being less than one third of the length of the angled surface of the first distance element, when the portion of the first distance element is inserted into the recess.

According to one embodiment, the surface of the first distance element having a curvature abuts the surface of the recess over a length being less than half of the depth of the recess, measured in a direction coinciding with the direction of the length axis of the first distance element, when the portion of the first distance element is inserted into the recess.

According to one embodiment, the portion of the first distance element configured to enter the recess of the second part comprises at least one surface having a first and second curvature extending in perpendicular directions. The portion of the first distance element configured to enter the recess of the second part may comprise at least one spherical surface.

According to one embodiment, the recess in at least one of the first and second part is tapered, such that two curved surfaces on opposite sides of the portion of the first distance element configured to enter the recess of the first or second part faces two surfaces on opposite sides of the tapered recess, when the portion of the first distance element configured to enter the recess of the first or second part is inserted into the recess.

According to one embodiment, the recess in at least one of the first and second part comprises at least one surface having a curvature. The recess in at least one of the first and second part may comprise at least one surface having a first and second curvature extending in perpendicular directions.

According to one embodiment, the recess in at least one of the first and second part comprises at least one spherical surface.

According to one embodiment, the portion of the first distance element configured to enter the recess of the first or second part comprises at least one surface having a curvature with a first radius and the recess in at least one of the first and second part comprises at least one surface having a curvature with a second radius. The second radius is according to one embodiment longer than the first radius.

According to one embodiment, the portion of the first distance element configured to enter the recess of the first or second part comprises at least one surface having a first and second curvature extending in perpendicular directions.

According to one embodiment, the recess in at least one of the first and second part comprises at least one surface having a first and second curvature extending in perpendicular directions, and the sum of the radii of the first and second curvatures of the recess in at least one of the first and second part is longer than the sum of the radii of the first and second curvature of the portion of the first distance element configured to enter the recess.

According to one embodiment, the functional movement restriction device or the boundary of the functional movement restriction device may be elongated. The functional movement restriction device may be elongated such that a longest length is more than 1.5 times a widest width.

According to one embodiment, the functional movement restriction device comprises a bend, and the functional movement restriction device comprises a bent center axis following the elongation of the functional movement restriction device.

According to one embodiment, a first portion of the functional movement restriction device is configured to be positioned such that a first portion of the bent center axis is parallel to the caudal-cranial axis of the patient, and a second portion of the bent center axis is angled relative to the caudal-cranial axis of the patient, with an angle exceeding 5°.

According to one embodiment, the second portion of the bent center axis is configured to be positioned in the stomach such that it is angled towards the esophagus.

According to one embodiment, at least one of the first and second part has a shape corresponding to an ellipsoid wedge or a truncated ellipsoid wedge.

According to one embodiment, at least one of the first and second part has a shape corresponding to a spherical wedge or a truncated spherical wedge.

At least one of the first and second part may have a shape corresponding to a portion of an ellipsoid wedge or a portion of a truncated ellipsoid wedge.

According to one embodiment, at least one of the first and second part has a shape corresponding to a hemiellipsoid wedge or a truncated hemiellipsoid wedge.

At least one of the first and second part may have a shape corresponding to a portion of a spherical wedge or a portion of a truncated spherical wedge.

According to one embodiment, at least one of the first and second part has a shape corresponding to a hemispherical wedge or a truncated hemispherical wedge.

According to one embodiment, at least one of the first and second part has a shape corresponding to an ellipsoid segment or a portion of an ellipsoid segment.

According to one embodiment, at least one of the first and second part has a shape corresponding to a spherical segment or a portion of a spherical segment.

The functional movement restriction device, or the boundary of the functional movement restriction device, may in any of the embodiments have a shape corresponding to an ellipsoid or a truncated ellipsoid.

According to one embodiment, the functional movement restriction device, or the boundary of the functional movement restriction device, has a shape corresponding to a sphere or a truncated sphere.

According to one embodiment, at least the periphery of at least one of the first and second part has a shape corresponding to a cylinder.

According to one embodiment, the combined periphery of the first and second part has a shape corresponding to a cylinder.

According to one embodiment, the periphery of the first part has a shape corresponding to a first cylinder having a first radius, and the periphery of the second part has a shape corresponding to a second cylinder having a second radius, and the first and second radii are different.

According to one embodiment, the functional movement restriction device, or the boundary of the functional movement restriction device, comprises a stadium shaped cross-section, or a truncated stadium shaped cross-section.

According to one embodiment, the functional movement restriction device comprises a bent stadium shaped cross-section, or a truncated bent stadium shaped cross-section.

According to one embodiment, a periphery of the first part has a shape corresponding to a cylinder or an ellipsoid segment, and a periphery of the second part has a shape corresponding to a cylinder or an ellipsoid segment, and the first part comprises at least one protrusion protruding from a first base surface and the second part comprises at least one recess in a first base surface, and the at least one protrusion is adapted to be placed at least partially in the at least one recess. The at least one protrusion may be adapted to engage the at least one recess and the first part may further comprise at least one recess in a second base surface.

The position of the at least one protrusion may coincide with the position of the at least one recess, such that the recess overlaps the protrusion when the first part is viewed in a direction normal to the first base surface. The at least one recess may recess into the at least one protrusion.

According to one embodiment, the at least one protrusion may have the shape of a pyramid with a polygonal base.

According to one embodiment, the first part further comprises at least one protrusion in a second base surface, and the second part may further comprise at least one protrusion in a second base surface. The second part may further comprise at least one recess in a second base surface.

According to one embodiment, the implantable medical device further comprises a third part, and the first part further comprises a recess in a second base surface, the second part further comprises a protrusion protruding from a second base surface, the third part comprises a protrusion protruding from a first base surface and a recess in a second base surface, the protrusion of the first part is configured to be at least partially inserted into the recess of the second part, the protrusion of the second part is configured to be at least partially inserted into the recess of the third part, and the first, second and third parts are configured to be assembled for forming at least a portion of a functional implantable medical device, and wherein the recesses and protrusions stabilize the parts relative to each other when assembled.

According to one embodiment, the area of the first base surface of the first part is smaller than the area of the first base surface of the second part.

According to one embodiment, the at least one protrusion protruding from the first base surface of the first part comprises the distance element.

According to one embodiment, the medical device is further configured to treat obesity by the movement restriction device being configured to protrude into the stomach and thereby reducing the volume of the cavity of the stomach. For the purpose of treating obesity, the functional movement restriction device may have a volume in the range 100 cm3-1000 cm3, or in the range 100 cm3-500 cm3. For the purpose of treating obesity, the functional implantable medical device may have a length in the range 2.5 cm-15 cm or in the range 5 cm-15 cm, or in the range 7 cm-15 cm, or in the range 8 cm-15 cm, or in the range 8 cm-12 cm.

The movement restriction device may in any of the embodiments herein comprises a surface friction reducing coating covering at least a part of the surface of the movement restriction device. The surface friction reducing coating may be configured to reduce the friction between the movement restriction device and the tissue of the stomach wall by which the movement restriction device is at least partially invaginated.

The implantable medical device may further comprise a sensor configured to sense at least one of a force and a pressure, for monitoring a pressure or force exerted by the implantable movement restriction device on the stomach wall of the patient.

According to one embodiment, the movement restriction device comprises a first portion having a first volume enclosed by material of the implantable movement restriction device and a second portion, different from the first portion, having a second volume enclosed by material of the implantable movement restriction device. The first volume and the second volumes may be equally large and the first volume may have a higher density than the second volume, and the second volume may have a density below 1000 kg/m3.

An implantable medical device for treating reflux disease, the implantable medical device comprising a movement restriction device configured to be fixated to the stomach wall for hindering movement of the lower esophageal sphincter relative to the thoracic diaphragm is further provided. The movement restriction device comprises a first part and a second part. The first and second parts are configured to be connected to each other for forming at least a portion of a functional movement restriction device. The first and second parts are capable of disconnecting from each other, such that the first and second part individually can pass through the gastro-intestinal tract, and a periphery of the first part has a shape corresponding to a cylinder or an ellipsoid segment, and a periphery of the second part has a shape corresponding to a cylinder or an ellipsoid segment. The first part comprises at least one protrusion protruding from a first base surface and the second part comprises at least one recess in a first base surface, and the at least one protrusion is adapted to be placed at least partially in the at least one recess for stabilizing the first and second parts relative to each other.

According to one embodiment, at least one protrusion of a first part the movement restriction device is adapted to engage at least one recess of a second part of the movement restriction device.

According to one embodiment, the first part further comprises at least one recess in a second base surface.

According to one embodiment, the position of the at least one protrusion coincides with the position of the at least one recess, such that the recess overlaps the protrusion when the first part is viewed in a direction normal to the first base surface. The at least one recess may recess into the at least one protrusion.

According to one embodiment, the at least one protrusion is adapted to engage the at least one recess in a direction of a length axis of the protrusion, and the portion of the protrusion adapted to be placed at least partially in the at least one recess comprises at least one surface being angled relative to the length axis of the protrusion.

According to one embodiment, the surface of the protrusion is being angled is configured to face a surface of the recess in the second part being angled with an angle different from the angle of the protrusion. A point on the angled surface of the protrusion is configured to abut a point on the angled surface of the recess.

According to one embodiment, the angled surface of the protrusion abuts the angled surface of the recess over a length being less than half of the length of the angled surface of the protrusion.

An angled surface of the protrusion may abut the angled surface of the recess over a length being less than one third of the length of the angled surface of protrusion.

According to one embodiment, the angled surface of the protrusion abuts the angled surface of the recess over a length being less than half of the depth of the recess, measured in a direction coinciding with the direction of the length axis of the protrusion, when the portion of the protrusion is inserted into the recess.

According to one embodiment, the portion of the protrusion configured to enter the recess of the second part comprises a tapered portion, and the tapered portion may be tapered with an angle in the range 20°-150°.

According to one embodiment, the recess in at least one of the first and second part is tapered, such that two surfaces on opposite sides of the tapered portion of the protrusion faces two surfaces on opposite sides of the tapered recess, when the tapered portion of the first distance element is inserted into the recess. The tapered recess may be tapered with an angle in the range 30°-155°.

According to one embodiment, the tapered portion of the protrusion is tapered with a first angle and the tapered recess in at least one of the first and second part is tapered with a second angle, and the second angle is larger than the first angle. The second angle may be more than 3° larger than the first angle, or more than 5° larger than the first angle, or more than 10° larger than the first angle.

According to one embodiment, the at least one protrusion has the shape of a pyramid with a polygonal base.

According to one embodiment, the first part further comprises at least one protrusion in a second base surface, and the second part further comprises at least one protrusion in a second base surface. The second part may further comprise at least one recess in a second base surface.

According to one embodiment, the implantable medical device further comprises a third part. The first part further comprises a recess in a second base surface, the second part further comprises a protrusion protruding from a second base surface, the third part comprises a protrusion protruding from a first base surface and a recess in a second base surface. The protrusion of the first part is configured to be at least partially inserted into the recess of the second part, the protrusion of the second part is configured to be at least partially inserted into the recess of the third part, and wherein the first, second and third parts are configured to be assembled for forming at least a portion of a functional implantable medical device, and wherein the recesses and protrusions stabilize the parts relative to each other when assembled.

According to one embodiment, the area of the first base surface of the first part is smaller than the area of the first base surface of the second part.

The functional movement restriction device, or the boundary of the functional movement restriction device, may in any of the embodiments have a shape corresponding to an ellipsoid or a truncated ellipsoid.

According to one embodiment, the functional movement restriction device, or the boundary of the functional movement restriction device, has a shape corresponding to a sphere or a truncated sphere.

According to one embodiment, at least the periphery of at least one of the first and second part has a shape corresponding to a cylinder.

According to one embodiment, the combined periphery of the first and second part has a shape corresponding to a cylinder.

According to one embodiment, the periphery of the first part has a shape corresponding to a first cylinder having a first radius, and the periphery of the second part has a shape corresponding to a second cylinder having a second radius, and the first and second radii are different.

According to one embodiment, the functional movement restriction device, or the boundary of the functional movement restriction device, comprises a stadium shaped cross-section, or a truncated stadium shaped cross-section.

According to one embodiment, the functional movement restriction device comprises a bent stadium shaped cross-section, or a truncated bent stadium shaped cross-section.

According to one embodiment, the functional movement restriction device or the boundary of the functional movement restriction device may be elongated. The functional movement restriction device may be elongated such that a longest length is more than 1.5 times a widest width.

According to one embodiment, the functional movement restriction device comprises a bend, and the functional movement restriction device comprises a bent center axis following the elongation of the functional movement restriction device.

According to one embodiment, a first portion of the functional movement restriction device is configured to be positioned such that a first portion of the bent center axis is parallel to the caudal-cranial axis of the patient, and a second portion of the bent center axis is angled relative to the caudal-cranial axis of the patient, with an angle exceeding 5°.

According to one embodiment, the second portion of the bent center axis is configured to be positioned in the stomach such that it is angled towards the esophagus.

According to one embodiment, the protrusion comprises a first distance element configured to create a space located between the first and second part. The space is configured to allow in-growth of fibrotic tissue between portions of the first and second parts, and wherein the space is confined at least partially by a first surface of the first part and a second surface of the second part and wherein the first and second surfaces are positioned opposite each other when the first and second parts are connected. A line segment of a first straight line is bounded by a first point on the first surface and a second point on the second surface. The line segment of the first straight line is more than 1 mm. A line segment of a second straight line is bounded by a third point on the first surface and a fourth point on the second surface. The line segment of the second straight line is more than 1 mm and the first straight line is parallel to the second straight line. The first and second straight lines intersect a third straight line which also intersects the center of gravity of the functional movement restriction device, and a distance between the first and second straight lines is more than 2 mm for allowing in-growth of fibrotic tissue for aiding in the fixation of the functional movement restriction device to the stomach wall.

According to one embodiment, the protrusion comprises a first distance element configured to create a space located between the first and second part. The space is configured to allow in-growth of fibrotic tissue between portions of the first and second parts and the space forms a recess in the functional implantable medical device. The recess is more than 1 mm wide and more than 2 mm deep for allowing in-growth of fibrotic tissue for aiding in the fixation of the functional implantable medical device to the stomach wall.

According to one embodiment, the medical device is further configured to treat obesity by the movement restriction device being configured to protrude into the stomach and thereby reducing the volume of the cavity of the stomach. For the purpose of treating obesity, the functional movement restriction device may have a volume in the range 100 cm3-1000 cm3, or in the range 100 cm3-500 cm3. For the purpose of treating obesity, the functional implantable medical device may have a length in the range 2.5 cm-15 cm or in the range 5 cm-15 cm, or in the range 7 cm-15 cm, or in the range 8 cm-15 cm, or in the range 8 cm-12 cm.

The movement restriction device may in any of the embodiments herein comprises a surface friction reducing coating covering at least a part of the surface of the movement restriction device. The surface friction reducing coating may be configured to reduce the friction between the movement restriction device and the tissue of the stomach wall by which the movement restriction device is at least partially invaginated.

The implantable medical device may further comprise a sensor configured to sense at least one of a force and a pressure, for monitoring a pressure or force exerted by the implantable movement restriction device on the stomach wall of the patient.

According to one embodiment, the movement restriction device comprises a first portion having a first volume enclosed by material of the implantable movement restriction device and a second portion, different from the first portion, having a second volume enclosed by material of the implantable movement restriction device. The first volume and the second volumes may be equally large and the first volume may have a higher density than the second volume, and the second volume may have a density below 1000 kg/m3.

An apparatus for treating reflux disease of a human patient is further provided. The apparatus comprising an implantable movement restriction device having a shape and size allowing it to be arranged to rest against a fundus wall portion of the patient's stomach, such that the movement restriction device is implanted at a position between the thoracic diaphragm of the patient and a portion of the fundus wall, and such that movement of the lower esophageal sphincter of the patient's stomach towards the thoracic diaphragm is restricted to hinder the lower esophageal sphincter from sliding through the opening in the thoracic diaphragm into the patient's thorax. The apparatus further comprising an electrode arrangement configured to engage and electrically stimulate the lower esophageal sphincter for causing contraction of the lower esophageal sphincter. The apparatus further comprising an electric impedance sensor configured to measure a change in electrical impedance in the tissue of the lower esophageal sphincter or in the esophagus tissue for detecting the patient swallowing, and a stimulation controller configured to control the electrical stimulation of the lower esophageal sphincter in response to signals from the electric impedance sensor.

According to one embodiment, the apparatus further comprises a reference electrode connected to the stimulation controller, and wherein the stimulation controller is configured to generate the output from the sensor based on an electrical interaction between the electric impedance sensor and the reference electrode.

According to one embodiment, the stimulation controller is configured to generate a time-varying signal having a frequency component that varies in the range of 1-10 KHz.

According to one embodiment, the stimulation controller is configured to generate a time-varying signal having a frequency component that varies in the range of 2-8 kHz.

According to one embodiment, the stimulation controller is configured to generate a time-varying signal having a frequency component that varies in the range of 4-6 kHz.

According to one embodiment, the electrode arrangement comprises at least two electrode elements configured to be arranged on opposing sides of the lower esophageal sphincter.

According to one embodiment, the apparatus further comprises a holder configured to support the at least two electrode elements at the opposing sides of the cardiac sphincter.

According to one embodiment, the apparatus further comprises an implantable energy source configured to provide the electrode with electrical power.

According to one embodiment, the implantable energy source is arranged inside the movement restriction device.

An implantable medical device for treating obesity is further provided. The implantable medical device is configured to be fixated to the stomach wall and protrude into the stomach and thereby reduce the volume of the cavity of the stomach. The implantable medical device comprises a first part, a second part, and a first distance element. The first and second parts are configured to be connected to each other for forming at least a portion of a functional implantable medical device. The first and second parts are capable of disconnecting from each other, such that the first and second part individually can pass through the gastro-intestinal tract. The first distance element is configured to create a space located between the first and second part. The space is configured to allow in-growth of fibrotic tissue between portions of the first and second parts. The space is confined at least partially by a first surface of the first part and a second surface of the second part. The first and second surfaces are positioned opposite each other when the first and second parts are connected. A line segment of a first straight line is bounded by a first point on the first surface and a second point on the second surface, and the line segment of the first straight line is more than 1 mm. A line segment of a second straight line is bounded by a third point on the first surface and a fourth point on the second surface, and the line segment of the second straight line is more than 1 mm. The first straight line is parallel to the second straight line, the first and second straight lines intersect a third straight line which also intersects the center of gravity of the functional medical device. A distance between the first and second straight lines is more than 2 mm for allowing in-growth of fibrotic tissue for aiding in the fixation of the functional implantable medical device to the stomach wall.

The functional implantable medical device may have a volume in the range 100 $cm^3$-1000 $cm^3$, or preferably in the range 100 $cm^3$-500 $cm^3$.

The functional implantable medical device may have a length in the range 2.5 cm-15 cm, or more preferably a length in the range 5 cm-15 cm and even more preferably a length in the range 7 cm-15 cm, or even more preferably a length in the range 8 cm-15 cm, and even more preferably a length in the range 8 cm-12 cm.

According to one embodiment, the first distance element is integrated in at least one of the first and second part, and the first distance element may protrude from a surface of at least one of the first and second part.

According to one embodiment, the implantable medical device further comprises a first separate distance part comprising the first distance element.

According to one embodiment, at least one of the first and second part may further comprise a recess configured to receive a portion of the first distance element.

The first distance element may in any of the embodiments herein comprise at least a first and second portion configured to be placed at a distance from each other.

According to one embodiment, the implantable medical device further comprises at least a third part, and the first, second and third parts may be configured to be connected to each other for forming at least a portion of the functional movement restriction device.

The implantable medical device according to any one of the embodiments herein may further comprise a second distance element, and the first distance element may be configured to create a space between the first and second part and the second distance element may be configured to create a space between the first and third part. The first and second distance element may be portions of a separate distance part.

According to one embodiment, at least one of the first, second and third parts may comprise a recess configured to receive a portion of the distance element.

According to one embodiment, the space created by the distance element may have a volume exceeding 100 mm3.

According to one embodiment, the space forms a recess in the implantable medical device, and the recess has a depth exceeding 2 mm and a width exceeding 1 mm.

According to one embodiment, the distance element is configured to prevent at least one of: rotation between the first and second part, linear movement between the first and second part in a first direction, and linear movement between the first and second part in a first and second direction.

According to one embodiment, the first separate distance part is configured to be placed centrally in the functional movement restriction device, and the center of gravity of the first separate distance part may substantially coincide with the center of gravity of the functional movement restriction device.

According to one embodiment, the first separate distance part comprises at least one rim comprising at least a first and a second surface. The first surface of the rim may be configured to engage a surface of the first part and the second surface of the flange is configured to engage a surface of the second part. The first and second surfaces of the at least one rim may be parallel. The first separate distance part may comprise at least two rims. The first rim may comprise at least a first and a second surface, the first surface of the first rim may be configured to engage a surface of the first part and the second surface of the first rim may be configured to engage a surface of the second part. The second rim may comprise at least a first and a second surface, and the first surface of the second rim may be configured to engage a surface of the first part and the second surface of the second rim may be configured to engage a surface of the third part.

According to one embodiment, the first surfaces of the first rim and the first surface of the second rim are angled relative to each other with an angle in the range 20°-70°.

According to one embodiment, the first surfaces of the first rim and the first surface of the second rim are angled relative to each other with an angle in the range 40°-50°.

According to one embodiment, the first surfaces of the first rim and the first surface of the second rim are perpendicular.

According to one embodiment, the first distance element may be configured to engage the recess in at least one of the first and second part in a direction of a length axis of the distance element, and the portion of the first distance element configured to enter the recess of the second part may comprise at least one surface being angled relative to the length axis of the distance element.

According to one embodiment, the surface of the first distance element being angled may be configured to face a surface of the recess in at least one of the first and second part being angled with an angle different from the angle of the first distance element, and wherein a point on the angled surface of the first distance element is configured to abut a point on the angled surface of the recess.

According to one embodiment, the angled surface of the first distance element abuts the angled surface of the recess over a length being less than half of the length of the angled surface of the first distance element.

According to one embodiment, the angled surface of the first distance element abuts the angled surface of the recess over a length being less than one third of the length of the angled surface of the first distance element.

According to one embodiment, the angled surface of the first distance element abuts the angled surface of the recess over a length being less than half of the depth of the recess, measured in a direction coinciding with the direction of the length axis of the first distance element, when the portion of the first distance element is inserted into the recess.

According to one embodiment, the portion of the first distance element configured to enter the recess of the second part comprises a tapered portion.

According to one embodiment, the tapered portion is tapered with an angle in the range 20°-100°.

According to one embodiment, the recess in at least one of the first and second part is tapered, such that two surfaces on opposite sides of the tapered portion of the first distance element faces two surfaces on opposite sides of the tapered recess, when the tapered portion of the first distance element is inserted into the recess. The tapered recess may be tapered with an angle in the range 30°-135°.

According to one embodiment, the tapered portion of the first distance element is tapered with a first angle and the tapered recess in at least one of the first and second part is tapered with a second angle, and the second angle is larger than the first angle. The second angle may be more than 3° larger than the first angle, or more than 5° larger than the first angle, or more than 10° larger than the first angle.

According to one embodiment, the tapered portion of the first distance element, and the tapered recess in at least one of the first and second part is conical or frustum-conical.

According to one embodiment, the tapered portion of the first distance element has the shape of a pyramid with a polygonal base.

According to one embodiment, the portion of the first distance element configured to enter the recess of the first or second part comprises at least one surface having a curvature.

According to one embodiment, the surface of the first distance element having a curvature is configured to face a surface of the recess in at least one of the first and second part. A point on the surface of the first distance element having the curvature is configured to abut a point on the surface of the recess.

According to one embodiment, the surface of the first distance element having a curvature abuts the surface of the recess over a length being less than half of the length of the angled surface of the first distance element, when the first distance element has been positioned in the recess in at least one of the first and second part.

According to one embodiment, the surface of the first distance element having a curvature abuts the surface of the recess over a length being less than one third of the length of the angled surface of the first distance element, when the portion of the first distance element is inserted into the recess.

According to one embodiment, the surface of the first distance element having a curvature abuts the surface of the recess over a length being less than one third of the length of the angled surface of the first distance element, when the portion of the first distance element is inserted into the recess.

According to one embodiment, the surface of the first distance element having a curvature abuts the surface of the recess over a length being less than half of the depth of the recess, measured in a direction coinciding with the direction of the length axis of the first distance element, when the portion of the first distance element is inserted into the recess.

According to one embodiment, the portion of the first distance element configured to enter the recess of the second part comprises at least one surface having a first and second curvature extending in perpendicular directions. The portion of the first distance element configured to enter the recess of the second part may comprise at least one spherical surface.

According to one embodiment, the recess in at least one of the first and second part is tapered, such that two curved surfaces on opposite sides of the portion of the first distance element configured to enter the recess of the first or second part faces two surfaces on opposite sides of the tapered recess, when the portion of the first distance element configured to enter the recess of the first or second part is inserted into the recess.

According to one embodiment, the recess in at least one of the first and second part comprises at least one surface having a curvature. The recess in at least one of the first and second part may comprise at least one surface having a first and second curvature extending in perpendicular directions.

According to one embodiment, the recess in at least one of the first and second part comprises at least one spherical surface.

According to one embodiment, the portion of the first distance element configured to enter the recess of the first or second part comprises at least one surface having a curvature with a first radius and the recess in at least one of the first and second part comprises at least one surface having a curvature with a second radius. The second radius is according to one embodiment longer than the first radius.

According to one embodiment, the portion of the first distance element configured to enter the recess of the first or second part comprises at least one surface having a first and second curvature extending in perpendicular directions.

According to one embodiment, the recess in at least one of the first and second part comprises at least one surface having a first and second curvature extending in perpendicular directions, and the sum of the radii of the first and second curvatures of the recess in at least one of the first and second part is longer than the sum of the radii of the first and second curvature of the portion of the first distance element configured to enter the recess.

According to one embodiment, the functional implantable medical device or the boundary of the functional implantable medical device may be elongated. The functional implantable medical device may be elongated such that a longest length is more than 1.5 times a widest width.

According to one embodiment, the functional implantable medical device comprises a bend, and the functional implantable medical device comprises a bent center axis following the elongation of the functional implantable medical device.

According to one embodiment, a first portion of the functional implantable medical device is configured to be positioned such that a first portion of the bent center axis is parallel to the caudal-cranial axis of the patient, and a second portion of the bent center axis is angled relative to the caudal-cranial axis of the patient, with an angle exceeding 5°.

According to one embodiment, the second portion of the bent center axis is configured to be positioned in the stomach such that it is angled towards the esophagus.

According to one embodiment, at least one of the first and second part has a shape corresponding to an ellipsoid wedge or a truncated ellipsoid wedge.

According to one embodiment, at least one of the first and second part has a shape corresponding to a spherical wedge or a truncated spherical wedge.

At least one of the first and second part may have a shape corresponding to a portion of an ellipsoid wedge or a portion of a truncated ellipsoid wedge.

According to one embodiment, at least one of the first and second part has a shape corresponding to a hemiellipsoid wedge or a truncated hemiellipsoid wedge.

At least one of the first and second part may have a shape corresponding to a portion of a spherical wedge or a portion of a truncated spherical wedge.

According to one embodiment, at least one of the first and second part has a shape corresponding to a hemispherical wedge or a truncated hemispherical wedge.

According to one embodiment, at least one of the first and second part has a shape corresponding to an ellipsoid segment or a portion of an ellipsoid segment.

According to one embodiment, at least one of the first and second part has a shape corresponding to a spherical segment or a portion of a spherical segment.

The functional movement restriction device, or the boundary of the functional implantable medical device, may in any of the embodiments have a shape corresponding to an ellipsoid or a truncated ellipsoid.

According to one embodiment, the functional implantable medical device, or the boundary of the functional implantable medical device, has a shape corresponding to a sphere or a truncated sphere.

According to one embodiment, at least the periphery of at least one of the first and second part has a shape corresponding to a cylinder.

According to one embodiment, the combined periphery of the first and second part has a shape corresponding to a cylinder.

According to one embodiment, the periphery of the first part has a shape corresponding to a first cylinder having a first radius, and the periphery of the second part has a shape corresponding to a second cylinder having a second radius, and the first and second radii are different.

According to one embodiment, the functional implantable medical device, or the boundary of the functional implantable medical device, comprises a stadium shaped cross-section, or a truncated stadium shaped cross-section.

According to one embodiment, the functional implantable medical device comprises a bent stadium shaped cross-section, or a truncated bent stadium shaped cross-section.

According to one embodiment, a periphery of the first part has a shape corresponding to a cylinder or an ellipsoid segment, and a periphery of the second part has a shape corresponding to a cylinder or an ellipsoid segment, and the first part comprises at least one protrusion protruding from a first base surface and the second part comprises at least one recess in a first base surface, and the at least one protrusion is adapted to be placed at least partially in the at least one recess. The at least one protrusion may be adapted to engage the at least one recess and the first part may further comprise at least one recess in a second base surface.

The position of the at least one protrusion may coincide with the position of the at least one recess, such that the recess overlaps the protrusion when the first part is viewed in a direction normal to the first base surface. The at least one recess may recess into the at least one protrusion.

According to one embodiment, the at least one protrusion may have the shape of a pyramid with a polygonal base.

According to one embodiment, the first part further comprises at least one protrusion in a second base surface, and the second part may further comprise at least one protrusion in a second base surface. The second part may further comprise at least one recess in a second base surface.

According to one embodiment, the implantable medical device further comprises a third part, and the first part further comprises a recess in a second base surface, the second part further comprises a protrusion protruding from a second base surface, the third part comprises a protrusion protruding from a first base surface and a recess in a second base surface, the protrusion of the first part is configured to be at least partially inserted into the recess of the second part, the protrusion of the second part is configured to be at least partially inserted into the recess of the third part, and the first, second and third parts are configured to be assembled for forming at least a portion of a functional implantable medical device, and wherein the recesses and protrusions stabilize the parts relative to each other when assembled.

According to one embodiment, the area of the first base surface of the first part is smaller than the area of the first base surface of the second part.

According to one embodiment, the at least one protrusion protruding from the first base surface of the first part comprises the distance element.

The implantable medical device may in any of the embodiments herein comprises a surface friction reducing coating covering at least a part of the surface of the implantable medical device. The surface friction reducing coating may be configured to reduce the friction between the implantable medical device and the tissue of the stomach wall by which the implantable medical device is at least partially invaginated.

The implantable medical device may further comprise a sensor configured to sense at least one of a force and a pressure, for monitoring a pressure or force exerted by the implantable medical device on the stomach wall of the patient.

According to one embodiment, the implantable medical device comprises a first portion having a first volume enclosed by material of the implantable medical device and a second portion, different from the first portion, having a second volume enclosed by material of the implantable medical device. The first volume and the second volumes may be equally large and the first volume may have a higher density than the second volume, and the second volume may have a density below 1000 kg/m3.

An implantable medical device for treating reflux disease is further provided. The implantable medical device comprises a movement restriction device configured to be fixated to the stomach wall for hindering movement of the lower esophageal sphincter relative to the thoracic diaphragm. The movement restriction device comprises a central part, and at least two outer parts. The central part and the at least two outer parts are configured to be connected to each other for forming at least a portion of a functional movement restriction device. The central part and the at least two outer parts are capable of disconnecting from each other, such that the central part and the at least two outer parts individually can pass through the gastro-intestinal tract. The outer surface of the functional movement restriction device comprises at least four flat surfaces separated from each other and interspaced by at least four curved surfaces, and the combined area of the at least four flat surfaces is in the interval 10%-20% of the total surface area of the functional movement restriction device. According to one embodiment, the functional movement restriction device comprises at least five flat surfaces. According to one embodiment, the outer surface of the functional movement restriction device comprises at least six flat surfaces. According to one embodiment, the outer surface of the functional movement restriction device comprises at least seven flat surfaces. According to one embodiment, the outer surface of the functional movement restriction device comprises at least eight flat surfaces.

The flat surfaces in any of the embodiments may be elliptical or circular or polygonal.

An implantable medical device for treating reflux disease is further provided. The implantable medical device comprises a movement restriction device configured to be fixated to the stomach wall for hindering movement of the lower esophageal sphincter relative to the thoracic diaphragm. The movement restriction device comprises a central part, and at least two outer parts. The central part and the at least two outer parts are configured to be connected to each other for forming at least a portion of a functional movement restriction device. The central part and the at least two outer parts are capable of disconnecting from each other, such that the central part and the at least two outer parts individually can pass through the gastro-intestinal tract. According to one embodiment, at least one of the functional movement restriction device and the boundary of the functional movement restriction device has a volume in the range 10 $cm^3$-30 $cm^3$ and according to another embodiment, the functional movement restriction device or the boundary of the functional movement restriction device has a volume in the range 12 $cm^3$-25 $cm^3$, and according to another embodiment, the functional movement restriction device or the boundary of the functional movement restriction device has a volume in the range 15 $cm^3$-25 $cm^3$, and according to another embodiment, the functional movement restriction device or the boundary of the functional movement restriction device has a volume in the range 15 $cm^3$-22 $cm^3$.

An implantable medical device for treating reflux disease is further provided. The implantable medical device comprises a movement restriction device configured to be fixated to the stomach wall for hindering movement of the lower esophageal sphincter relative to the thoracic diaphragm, the movement restriction device comprises at least two parts, wherein the parts are configured to be connected to each other for forming at least a portion of a functional movement restriction device, and the at least two parts are capable of disconnecting from each other, such that the at least two parts individually can pass through the gastro-intestinal tract. The functional movement restriction device has a height in the range 1 inch-3.5 cm or a height in the range 3 cm-6 cm, or a height in the range 3 cm-5 cm, or a height in the range 3.5 cm-6 cm, or a height in the range 4 cm-5 cm, or a height in the range 4 cm-6 cm.

The implantable medical device may further comprise a central part, and the at least two parts may be configured to be connected to the central part for forming at least a portion of the functional movement restriction device. The central part and the at least two parts may be capable of disconnecting from each other, such that the central part and the at least two parts individually can pass through the gastro-intestinal tract.

An implantable medical device for treating reflux disease is further provided. The implantable medical device comprises a movement restriction device configured to be fixated to the stomach wall for hindering movement of the lower esophageal sphincter relative to the thoracic diaphragm. The movement restriction device comprises a central part, and at least two outer parts. The central part and the at least two outer parts are configured to be connected to each other for forming at least a portion of a functional movement restriction device. The central part and the at least two outer parts are capable of disconnecting from each other, such that the central part and the at least two outer parts individually can pass through the gastro-intestinal tract. At least one of the two outer parts comprises a wedge-shaped portion and the central part comprises a wedge-shaped portion. The wedge-shaped portion of the at least one outer part is configured to be placed in the wedge-shaped portion of the central part, and the wedge-shaped portion of the at least one outer part is wedge-shaped with a first angle. The wedge-shaped portion of the central part is wedge-shaped with a second angle, and wherein the first angle is more than 7° larger than the second angle. According to one embodiment, the first angle is more than 10° larger than the second angle, and according to another embodiment, the first angle is more than 12° larger than the second angle, and according to another embodiment, the first angle is more than 15° larger than the second angle. The wedge-shaped portion of the at least one outer part may comprise a wedge-shaped recess configured to engage a wedge-shaped protrusion of the central part, or the at least one outer part may comprise a wedge-shaped protrusion configured to engage a wedge-shaped recess of the central part. The wedge-shaped portion of the central part may comprise a wedge-shaped recess or a wedge-shaped protrusion.

An implantable medical device for treating reflux disease is further provided. The implantable medical device comprises a movement restriction device configured to be fixated to the stomach wall for hindering movement of the lower esophageal sphincter relative to the thoracic diaphragm. The movement restriction device comprises a central part, and at least two outer parts. The central part and the at least two outer parts are configured to be connected to each other for forming at least a portion of a functional movement restriction device. The central part and the at least two outer parts are capable of disconnecting from each other, such that the central part and the at least two outer parts individually can pass through the gastro-intestinal tract. At least one of the two outer parts comprises a wedge-shaped portion and the central part comprises a wedge-shaped portion. The wedge-shaped portion of the central part is configured to be placed in the wedge-shaped portion of the central part, and the wedge-shaped portion of the at least one outer part is wedge-shaped with a first angle, and the wedge-shaped portion of the central part is wedge-shaped with a second angle, and the second angle is more than 7° larger than the first angle. According to one embodiment, the second angle is more than 10° larger than the first angle, and according to another embodiment, the second angle is more than 12° larger than the first angle, and according to another embodiment, the second angle is more than 15° larger than the first angle.

The wedge-shaped portion of the at least one outer part may comprise a wedge-shaped recess or a wedge-shaped protrusion. The wedge-shaped portion of the central part may comprise a wedge-shaped recess or may comprise a wedge-shaped protrusion.

An implantable medical device for treating reflux disease is further provided. The implantable medical device comprises a movement restriction device configured to be fixated to the stomach wall for hindering movement of the lower esophageal sphincter relative to the thoracic diaphragm. The movement restriction device comprises a central part, and at least two outer parts. The central part and the at least two outer parts are configured to be connected to each other for forming at least a portion of a functional movement restriction device. The central part and the at least two outer parts are capable of disconnecting from each other, such that the central part and the at least two outer parts individually can pass through the gastro-intestinal tract. At least one of the two outer parts comprises a contacting surface configured to be placed in contact with a contacting surface of the central part, and at least one of the contacting surfaces of the at least one outer part and the contacting surface of the central part is curved.

According to one embodiment, the contacting surface of the at least one outer part and the contacting surface of the central part is convex.

According to one embodiment, at least one of the contacting surfaces of the at least one outer part and the contacting surface of the central part is concave.

According to one embodiment, at least one of the contacting surfaces of the at least one outer part and the contacting surface of the central part comprises an elliptic point.

According to one embodiment, the contacting surface of the at least one outer part contacts the contacting surface of the central part over less than half of the area of the contacting surface of the at least one outer part.

According to one embodiment, the contacting surface of the at least one outer part contacts the contacting surface of the central part over less than one third of the area of the contacting surface of the at least one outer part.

An implantable medical device for treating reflux disease is further provided. The implantable medical device comprises a movement restriction device configured to be fixated to the stomach wall for hindering movement of the lower esophageal sphincter relative to the thoracic diaphragm. The movement restriction device comprises a central part, and at least two outer parts. The central part and the at least two outer parts are configured to be connected to each other for forming at least a portion of a functional movement restriction device. The central part and the at least two outer parts are capable of disconnecting from each other, such that the central part and the at least two outer parts individually can pass through the gastro-intestinal tract. The central part comprises at least three vertically extending rims being spaced apart, and each the at least three vertically extending rims have at least one contacting surface configured to contact at least one surface of the at least two outer parts. At least a portion of the at least three vertically extending rims is wedge-shaped with an angle in the range 20°-60°.

According to one embodiment, a portion of the at least three vertically extending rims is wedge-shaped with an angle exceeding 25°.

According to one embodiment, a portion of the at least three vertically extending rims is wedge-shaped with an angle exceeding 30°.

According to one embodiment, a portion of the at least three vertically extending rims is wedge-shaped with an angle exceeding 35°.

The wedge-shaped portion of the at least one vertically extending rim may be tapered in a direction away from the center of gravity of the central part.

According to one embodiment, the vertically extending rim has an elongated wedge-shaped portion, and wherein the elongated wedge-shaped portion of the vertically extending rim is tapered in a direction of the elongation of the vertically extending rim.

The implantable medical device may further comprise at least one horizontally extending rim extending substantially perpendicularly from at least one of the vertically extending rims, and the horizontally extending rim may comprise a wedge-shaped portion. The wedge-shaped portion of the horizontally extending rim may be tapered in a direction away from the center of gravity of the central part.

According to one embodiment, the wedge-shaped portion of the horizontally extending rim is wedge-shaped with an angle in the range 20°-60°.

An implantable medical device for treating reflux disease is further provided. The implantable medical device comprises a movement restriction device configured to be fixated to the stomach wall for hindering movement of the lower esophageal sphincter relative to the thoracic diaphragm. The movement restriction device comprises a central part, and at least two outer parts. The central part and the at least two outer parts are configured to be connected to each other for forming at least a portion of a functional movement restriction device. The central part and the at least two outer parts are capable of disconnecting from each other, such that the central part and the at least two outer parts individually can pass through the gastro-intestinal tract. The central part comprises at least one horizontally extending rim extending in a direction perpendicular to the vertical plane and wherein the central part has at least one contacting surface configured to contact at least one surface of the at least two outer parts. A portion of the horizontally extending rim is wedge-shaped with an angle in the range 20°-60°.

According to one embodiment, a portion of the horizontally extending rim is wedge-shaped with an angle exceeding 25°, or with an angle exceeding 30°, or with an angle exceeding 35°.

According to one embodiment, the wedge-shaped portion of the horizontally extending rim is tapered in a direction away from the center of gravity of the central part.

According to one embodiment, the implantable medical device further comprises at least two vertically extending rims extending substantially perpendicularly from the horizontally extending rim.

According to one embodiment, the vertically extending rims comprises wedge-shaped portions.

According to one embodiment, the wedge-shaped portion of the vertically extending rims are tapered in a direction away from the center of gravity of the central part.

According to one embodiment, the wedge-shaped portions of the vertically extending rims are wedge-shaped with an angle in the range 20°-60°.

An implantable medical device for treating reflux disease is further provided. The implantable medical device comprises a movement restriction device configured to be fixated to the stomach wall for hindering movement of the lower esophageal sphincter relative to the thoracic diaphragm. The movement restriction device comprises a central part, and at least two outer parts. The central part and the at least two outer parts are configured to be connected to each other for forming at least a portion of a functional movement restriction device. The central part and the at least two outer parts are capable of disconnecting from each other, such that the central part and the at least two outer parts individually can pass through the gastro-intestinal tract. The mass of the central part exceeds the mass of at least one of the outer parts.

According to one embodiment, the mass of the central part exceeds the mass of at least one of the outer parts by at least 10%.

According to one embodiment, the mass of the central part exceeds the mass of at least one of the outer parts by at least 20%.

According to one embodiment, the mass of the central part exceeds the mass of at least one of the outer parts by at least 30%.

According to one embodiment, the volume of the central part exceeds the volume of at least one of the outer parts by at least 10%.

According to one embodiment, the volume of the central part exceeds the volume of at least one of the outer parts by at least 20%.

According to one embodiment, the volume of the central part exceeds the volume of at least one of the outer parts by at least 30%.

An implantable medical device for treating reflux disease is further provided. The implantable medical device comprises a movement restriction device configured to be fixated to the stomach wall for hindering movement of the lower esophageal sphincter relative to the thoracic diaphragm. The movement restriction device comprises a central part, and at least two outer parts. The central part and the at least two outer parts are configured to be connected to each other for forming at least a portion of a functional movement restriction device. The central part and the at least two outer parts are capable of disconnecting from each other, such that the central part and the at least two outer parts individually can pass through the gastro-intestinal tract. The longest cross-sectional distance of at least one of the outer parts exceeds the longest cross-sectional distance of the central part by at least 20%.

According to one embodiment, the longest cross-sectional distance of at least one of the outer parts exceeds the longest cross-sectional distance of the central part by at least 30%.

According to one embodiment, the longest cross-sectional distance of at least one of the outer parts exceeds the longest cross-sectional distance of the central part by at least 40%.

According to one embodiment, the longest cross-sectional distance of at least one of the outer parts exceeds the longest cross-sectional distance of the central part by at least 50%.

An implantable medical device for treating reflux disease is further provided, the implantable medical device comprises a movement restriction device configured to be fixated to the stomach wall for hindering movement of the lower esophageal sphincter relative to the thoracic diaphragm.

According to one embodiment, at least one of the movement restriction device and the boundary of the movement restriction device has a surface area in the range 20 $cm^2$-50 $cm^2$.

According to one embodiment, at least one of the movement restriction device and the boundary of the movement restriction device has a surface area in the range 25 $cm^2$-50 $cm^2$.

According to one embodiment, at least one of the movement restriction device and the boundary of the movement restriction device has a surface area in the range 25 $cm^2$-40 $cm^2$.

According to one embodiment, at least one of the movement restriction device and the boundary of the movement restriction device has a surface area in the range 20 $cm^2$-40 $cm^2$.

According to one embodiment, at least one of the movement restriction device and the boundary of the movement restriction device has a surface area in the range 20 $cm^2$-35 $cm^2$.

According to one embodiment, at least one of the movement restriction device and the boundary of the movement restriction device has a surface area in the range 20 $cm^2$-30 $cm^2$.

According to other embodiments, at least one of the movement restriction device and the boundary of the movement restriction device has a surface area in the range >23 cm2-50 cm2, 22.5 cm2-45 cm2. 21 cm2-41 cm2, 19 cm2-29 cm2, >41 cm2, 22.5 cm2-225 and >225-599 cm2, 20.5 cm2-200 cm2, >200 cm2-350 cm2, >350 cm2-450 cm2 or >450-599 cm2.

According to one embodiment, the movement restriction device is elongated and has a height, being a longest cross-sectional distance, and a width, being a longest cross-sectional distance perpendicular to the height, and wherein the height is in the range 1.2 times-2 times longer than the width. According to one embodiment, the height is in the range 1.3 times-2 times longer than the width. According to one embodiment, the height is in the range 1.2 times-1.8 times longer than the width. According to one embodiment, the height is in the range 1.3 times-1.6 times longer than the width.

According to one embodiment, the movement restriction device has a height in the range 3 cm-5 cm, or a height of >1 inch or in the range 1 inch-3.5 cm or in the range 3.5 cm-6 cm, or a height in the range 4 cm-5 cm, or a height in the range 4 cm-6 cm.

According to one embodiment, at least one of the movement restriction device and the boundary of the movement restriction device has a volume in the range 7.3 $cm^3$-8 $cm^3$, or in the range >6.6 $cm^3$-<7.3 $cm^3$, or in the range >5.8 $cm^3$-6.6 $cm^3$, or in the range 5.0 $cm^3$-5.8 $cm^3$, or in the range >8 $cm^3$-<200 $cm^3$, or in the range 10 $cm^3$-30 $cm^3$ and according to another embodiment, the movement restriction device or the boundary of the movement restriction device has a volume in the range 12 $cm^3$-25 $cm^3$, and according to another embodiment, the movement restriction device or the boundary of the movement restriction device has a volume in the range 15 $cm^3$-25 $cm^3$, and according to another embodiment, the movement restriction device or the boundary of the movement restriction device has a volume in the range 15 $cm^3$-22 $cm^3$.

An implantable medical device for treating reflux disease is further provided, the implantable medical device comprises a movement restriction device configured to be fixated to the stomach wall for hindering movement of the lower esophageal sphincter relative to the thoracic diaphragm, the movement restriction device comprises at least two parts, wherein the parts are configured to be connected to each other for forming at least a portion of a functional movement restriction device, and the at least two parts are capable of disconnecting from each other, such that the at least two parts individually can pass through the gastro-intestinal tract. At least one of the functional movement restriction device and the boundary of the functional movement restriction device has a surface area in the range 20 $cm^2$-50 $cm^2$.

According to one embodiment, at least one of the functional movement restriction device and the boundary of the functional movement restriction device has a surface area in the range 25 $cm^2$-50 $cm^2$.

According to one embodiment, at least one of the functional movement restriction device and the boundary of the functional movement restriction device has a surface area in the range 25 $cm^2$-40 $cm^2$.

According to one embodiment, at least one of the functional movement restriction device and the boundary of the functional movement restriction device has a surface area in the range 20 $cm^2$-40 $cm^2$.

According to one embodiment, at least one of the functional movement restriction device and the boundary of the functional movement restriction device has a surface area in the range 20 $cm^2$-35 $cm^2$.

According to one embodiment, at least one of the functional movement restriction device and the boundary of the functional movement restriction device has a surface area in the range 20 $cm^2$-30 $cm^2$.

According to other embodiments, at least one of the movement restriction device and the boundary of the movement restriction device has a surface area in the range >23 cm2-50 cm2, 22.5 cm2-45 cm2, 21 cm2-41 cm2, 19 cm2-29 cm2, >41 cm2, 22.5 cm2-225 and >225-599 cm2, 20.5 cm2-200 cm2, >200 cm2-350 cm2, >350 cm2-450 cm2 or >450-599 cm2.

According to one embodiment, the functional movement restriction device is elongated and has a height, being a longest cross-sectional distance, and a width, being a longest cross-sectional distance perpendicular to the height, and wherein the height is in the range 1.2 times-2 times longer than the width. According to one embodiment, the height is in the range 1.3 times-2 times longer than the width. According to one embodiment, the height is in the range 1.2 times-1.8 times longer than the width. According to one embodiment, the height is in the range 1.3 times-1.6 times longer than the width.

According to one embodiment, the functional movement restriction device has a height of more than 1 inch or in the range 1 inch-3.5 cm, or in the range 3 cm-5 cm, or a height in the range 3.5 cm-6 cm, or a height in the range 4 cm-5 cm, or a height in the range 4 cm-6 cm.

According to one embodiment, the implantable medical device further comprises a central part, and the at least two parts are configured to be connected to the central part for forming at least a portion of the functional movement restriction device. The central part and the at least two parts are capable of disconnecting from each other, such that the central part and the at least two parts individually can pass through the gastro-intestinal tract.

An implantable medical device for treating reflux disease is further provided. The implantable medical device comprises a movement restriction device configured to be fixated to the stomach wall for hindering movement of the lower esophageal sphincter relative to the thoracic diaphragm. The movement restriction device comprises at least two parts, wherein the parts are configured to be connected to each other for forming at least a portion of a functional movement restriction device. The at least two parts are capable of disconnecting from each other, such that the at least two parts individually can pass through the gastro-intestinal tract. The functional movement restriction device is elongated and has a height, being a longest cross-sectional distance, and a width, being a longest cross-sectional distance perpendicular to the height, and wherein the height is the range 1.2-2 times longer than the width. According to one embodiment, the height is in the range 1.3-2 times longer than the width. According to one embodiment, the height is in the range 1.2-1.8 times longer than the width. According to one embodiment, the height is in the range 1.3-1.6 times longer than the width.

According to one embodiment, the functional movement restriction device has a height of >1 inch.

According to one embodiment, the functional movement restriction device has a height in the range 1 inch-3.5 cm.

According to one embodiment, the functional movement restriction device has a height in the range 3 cm-5 cm.

According to one embodiment, the functional movement restriction device has a height in the range 3.5 cm-6 cm.

According to one embodiment, the functional movement restriction device has a height in the range 4 cm-5 cm.

According to one embodiment, the functional movement restriction device has a height in the range 4 cm-6 cm.

The implantable medical device may further comprise a central part, and the at least two parts may be configured to be connected to the central part for forming at least a portion of the functional movement restriction device. The central part and the at least two parts may be capable of disconnecting from each other, such that the central part and the at least two parts individually can pass through the gastro-intestinal tract.

A surgical method of treating reflux disease is further provided. The surgical method comprises steps of dissecting the fundus at least partially down on the posterior side thereof, in the approximate direction towards bursa Omentalis, as well as away from the spleen, dissecting the esophagus such that the esophagus is disconnected from the surrounding tissue at least 3 cm in a cranial direction from the angle of his, connecting the fundus to the esophagus by: placing at least two posterior single sutures or staplers in a posterior suture line, or by a continuous suture line, connecting the fundus to the esophagus, on the sinister-posterior side of the esophagus, and placing at least two anterior sutures or staplers in a anterior suture line, or by a continuous suture line, connecting the fundus to the esophagus, on the sinister-anterior side of the esophagus. The surgical method further comprises the step of placing an implantable movement restriction device to the fundus between the angle of His and the diaphragm, such that the lower esophageal sphincter is prevented from sliding through the esophageal hiatus.

According to one embodiment the surgical method step of dissecting the fundus at least partially on the posterior side thereof comprises at least partially freeing the fundus from at least one of the gastrophrenic ligament and the gastrosplenic ligament. The step of dissecting the fundus at least partially on the posterior side thereof may comprise dissecting the fundus at least 0.5 cm posterior to a coronal plane intersecting a most cranial point of the fundus, or dissecting the fundus at least partially on the posterior side thereof at least 1 cm posterior to a coronal plane intersecting a most cranial point of the fundus.

According to one embodiment the surgical method step of dissecting the fundus further comprises dissecting the gastric brevis/short gastrics and ligating at least one of them.

According to one embodiment the surgical method step of dissecting the fundus further comprises dissecting the gastric brevis/short gastrics and ligating at least two of them.

According to one embodiment the surgical method step of dissecting the fundus further comprises dissecting the gastric brevis/short gastrics and ligating at least three of them.

According to one embodiment the surgical method step of dissecting the fundus at least partially on the posterior side thereof may comprise dissecting the fundus at least 0.5 cm posterior to the most anterior fixation point of the gastrophrenic ligament on the fundus, or at least 1 cm posterior to the most anterior fixation point of the gastrophrenic ligament on the fundus.

According to one embodiment the surgical method step of dissecting the fundus at least partially on the posterior side thereof comprises dissecting the fundus at least 0.5 cm posterior to an extension of the greater curvature of the stomach in the region of the fundus, or at least 1 cm posterior to an extension of the greater curvature of the stomach in the region of the fundus.

According to one embodiment the surgical method step of dissecting the esophagus comprises dissecting the esophagus such that the esophagus is disconnected from the surrounding tissue at least 4 cm in a cranial direction from the angle of his, preferably at least 5 cm in a cranial direction from the angle of his and most preferably at least 6 cm in a cranial direction from the angle of his.

According to one embodiment the surgical method step of dissecting the esophagus such that the esophagus is disconnected from the surrounding tissue comprises dissecting the esophagus into mediastinum. The step of dissecting the esophagus into mediastinum may comprise dissecting the esophagus into mediastinum such that the esophagus is disconnected from the surrounding tissue at least 1 cm in a cranial direction from the distal edge of the esophageal hiatus, preferably at least 2 cm in a cranial direction from the distal edge of the esophageal hiatus and most preferably at least 3 cm in a cranial direction from the distal edge of the esophageal hiatus.

According to one embodiment, the step of dissecting the esophagus into mediastinum comprises dissecting the esophagus into mediastinum such that the esophagus is disconnected from the surrounding tissue providing at least 4 cm of abdominal esophagus in a cranial direction from the distal edge of the repaired esophageal hiatus, preferably at least 5 cm of abdominal esophagus and most preferably at least 6 cm of abdominal esophagus from the distal edge of the repaired esophageal hiatus.

According to one embodiment, the step of dissecting the esophagus such that the esophagus is disconnected from the surrounding tissue comprises identifying the anterior and posterior nervus vagus trunk to avoid risk for nerve damage.

According to one embodiment, the step of dissecting the esophagus into mediastinum comprises dissecting the esophagus distally from a point 2 cm distally from the esophageal plexus of the vagus nerve, preferably from a point 1 cm distally from the esophageal plexus of the vagus nerve, more preferably from a point 0.5 cm distally from the esophageal plexus of the vagus nerve.

According to one embodiment, the step of dissecting the esophagus comprises freeing the esophagus from the crus muscles.

According to one embodiment, the surgical method step of placing at least two posterior sutures or staplers, connecting the fundus to the esophagus, on the sinister-posterior side of the esophagus, comprises placing at least two continuous sutures connecting the fundus to the esophagus, on the sinister-posterior side of the esophagus.

According to one embodiment, the surgical method step of placing at least two anterior sutures or staplers, connecting the fundus to the esophagus, on the sinister-anterior side of the esophagus comprises placing at least two continuous sutures connecting the fundus to the esophagus, on the sinister-anterior side of the esophagus.

In any of the embodiments herein, at least one of starting and ending of the continuous sutures may be performed in the serosa of the stomach wall for securing the sutures to the serosa of the stomach wall.

According to one embodiment, the surgical method step of placing at least two posterior sutures or staplers, connecting the fundus to the esophagus, on the sinister-posterior side of the esophagus comprises placing at least two lateral sutures substantially along a cranial-caudal axis, on the sinister-posterior side of the esophagus.

According to one embodiment, the surgical method step of placing at least two anterior sutures or staplers, connecting the fundus to the esophagus, on the sinister-anterior side of the esophagus comprises placing at least two lateral sutures substantially along a cranial-caudal axis, on the sinister-anterior side of the esophagus.

According to one embodiment, the surgical method step of placing at least two posterior sutures or staplers, connecting the fundus to the esophagus, on the sinister-posterior side of the esophagus, comprises placing the at least two posterior sutures or staplers at least 0.5 cm posterior to a coronal plane intersecting a most cranial point of the fundus.

According to one embodiment the surgical method step of placing at least two anterior sutures or staplers, connecting the fundus to the esophagus, on the sinister-anterior side of the esophagus, comprises placing the at least two anterior sutures or staplers at least 0.5 cm anterior from the coronal plane intersecting the most cranial point of the fundus.

According to one embodiment, the surgical method step of placing at least two posterior sutures or staplers, connecting the fundus to the esophagus, on the sinister-posterior side of the esophagus comprises placing the most caudal suture or stapler at least 0.5 cm from the angle of His.

According to one embodiment the surgical method step of placing at least two anterior sutures or staplers, connecting the fundus to the esophagus, on the sinister-anterior side of the esophagus comprises placing the most caudal suture or stapler at least 0.5 cm from the angle of His.

According to one embodiment, the step of placing at least two posterior sutures, connecting the fundus to the esophagus, on the sinister-posterior side of the esophagus comprises placing the most caudal suture, and the step of placing at least two anterior sutures, connecting the fundus to the esophagus, on the sinister-anterior side of the esophagus comprises placing the most caudal suture, comprising placing at least one of the most caudal suture in the region of the angle of His.

According to one embodiment, the step of placing at least two posterior sutures, connecting the fundus to the esophagus, on the sinister-posterior side of the esophagus comprises placing the most caudal suture, and the step of placing at least two anterior sutures, connecting the fundus to the esophagus, on the sinister-anterior side of the esophagus comprises placing the most caudal suture, comprising placing at least one of the two most caudal sutures in the region at least 1.5 cm above the angle of His.

According to one embodiment the surgical method step of placing at least two posterior sutures or staplers, connecting the fundus to the esophagus, on the sinister-posterior side of the esophagus comprises placing the most caudal suture or stapler at least 1.5 cm from the angle of His.

According to one embodiment the surgical method step of placing at least two anterior sutures or staplers, connecting the fundus to the esophagus, on the sinister-anterior side of the esophagus comprises placing the most caudal suture or stapler at least 1.5 cm from the angle of His.

According to one embodiment the surgical method step of placing the most caudal suture or stapler of the at least two posterior sutures or staplers, connecting the fundus to the esophagus, on the sinister-posterior side of the esophagus at least 0.5 cm from the angle of His and placing the most caudal suture or stapler of the at least two anterior sutures or staplers, connecting the fundus to the esophagus, on the sinister-anterior side of the esophagus at least 1.5 cm from the angle of His.

According to one embodiment the surgical method step of placing the most caudal suture or stapler of the at least two posterior sutures or staplers, connecting the fundus to the esophagus, on the sinister-posterior side of the esophagus at least 1.5 cm from the angle of His and placing the most caudal suture or stapler of the at least two anterior sutures or staplers, connecting the fundus to the esophagus, on the sinister-anterior side of the esophagus at least 0.5 cm from the angle of His.

According to one embodiment the surgical method step of connecting the fundus to the esophagus further comprises placing at least one central suture or stapler on a cranial-caudal axis extending between the at least two posterior sutures or staplers or continuous line and the at least two anterior sutures or staplers or continuous line. Placing at least one suture most cranial and preferable a line of sutures in between the posterior and anterior suture line, placing with a distance of one cm of esophagus circumference to both the anterior and posterior suture lines.

According to one embodiment, the step of connecting the fundus to the esophagus further comprises placing at least one central suture on a cranial-caudal axis extending between the at least two posterior sutures or continuous suture line and the at least two anterior sutures or continuous suture line, placing a third continuous suture line in between the posterior and anterior suture line, placing with a targeted distance of one cm of esophagus circumference to both the anterior and posterior suture lines.

The step of placing at least one central suture or stapler on a cranial-caudal axis may comprise placing at least one central in-between suture line or stapler being disconnected from the at least two anterior suture line or staplers and from the at least two posterior suture line or staplers, for maintaining the possibility of radial expansion the esophagus for limiting the disk of dysphagia.

According to one embodiment the surgical method step of placing at least two posterior sutures or staplers or continuous suture, connecting the fundus to the esophagus, on the sinister-posterior side of the esophagus, and placing at least two anterior sutures or a continuous suture or staplers, connecting the fundus to the esophagus, on the sinister-anterior side of the esophagus, comprises using an at least partially barbed suture.

In any of the surgical methods described herein, the step of stabilizing an implantable movement restriction device to the fundus may comprise placing a continuous multi-bite/purse-string tope roof suture in the region of the greater curvature of the stomach, in the region of the fundus, such that the stomach tissue can be contracted and formed to a hat over the implantable movement restriction device when implanted by pulling the ends of the purse-string sutures. The step of placing roof sutures may comprise placing at least one of the continuous purse-string roof sutures at least 1 cm, preferably 2 cm, behind the greater curvature of the stomach, in the caudal region of the fundus.

According to one embodiment the step of placing the continuous purse-string roof sutures may comprise placing the continuous purse-string roof sutures using an at least partially un-barbed suture, leaving a loose suture loop.

According to one embodiment the surgical method step of placing the continuous purse-string roof sutures may comprise starting or ending the continuous purse-string roof sutures at least 1 cm away from the esophagus to stomach anterior suture line.

According to one embodiment, the surgical method step of placing the continuous purse-string roof sutures may comprise placing the continuous purse-string roof sutures using a suture ending with a loop and lacking barbes close to the loop, such that the suture can be drawn through the loop for contracting the stomach tissue, but in a loose loop manner.

In any of the surgical methods described herein, the step of fixating the implantable movement restriction device to the fundus may comprise inserting the implantable movement restriction device into the abdomen of the patient. The step of inserting the implantable movement restriction device into the abdomen of the patient may comprise inserting the implantable movement restriction device into the abdomen of the patient using an insertion instrument having an elongated abdominal portion.

According to one embodiment, the surgical method step of fixating the implantable movement restriction device to the fundus may comprise pushing the implantable movement restriction device into the fundus in a cranial direction using the instrument having the elongated abdominal portion. The step of pushing the implantable movement restriction device into the fundus in a dorsal-cranial direction using the instrument having the elongated abdominal portion may comprise pushing the implantable movement restriction device using the elongated insertion instrument such that a portion of the implantable movement restriction device ends up dorsal to the roof sutures, forming a hat to the movement restriction device, for placing the movement restriction device in the fundus for facilitating the subsequent invagination in a high-up in fundus position.

According to one embodiment, the step of fixating the implantable movement restriction device to the fundus comprises placing a continuous purse-string base of floor suture in the region below the movement restriction device or proximal on fundus/proximal on the elongated insertion instrument holding the implantable movement restriction device to stabilize its position. The step of placing continuous purse-string floor sutures in the region of the caudal end of the implantable movement restriction device may comprise placing at least two of the continuous purse-string floor suture bites following an arc, preferable patient left to right at least from the equator to equator in an arc around the movement restriction device to stabilize its position. In cases when the at least two continuous purse-string floor sutures are placed following an arc the continuous purse-string floor sutures may be placed following an arc below the elongated abdominal portion of the instrument holding the implantable movement restriction device.

According to one embodiment, the step of placing continuous purse-string base or floor suture in the region of the caudal end of the implantable movement restriction device may comprise placing the continuous purse-string base sutures such that the continuous purse-string base suture bites forms a closed curve, closed loop to bring stomach from left and right of the elongated insertion instrument to contact each other above the instrument.

According to one embodiment, the step of stabilizing the implantable movement restriction device in relation to the fundus may comprise placing at least one suture or stapler from stomach wall around the movement restriction device and around the elongated insertion instrument to close the suture loop to above the elongated abdominal portion of the instrument holding the implantable movement restriction device.

According to one embodiment, the step of placing continuous purse-string base sutures in the region of the caudal end of the implantable movement restriction device may comprise placing one of the continuous purse-string base sutures from stomach wall to stomach wall above the elongated abdominal portion of the instrument holding the implantable movement restriction device.

The step of fixating the implantable movement restriction device to the fundus may comprise releasing the elongated abdominal portion of the instrument from the implantable movement restriction device.

According to one embodiment, the step of stabilizing the implantable movement restriction device to the fundus may comprise placing at least one suture or stapler to close the opening in the stomach wall in the region from which the elongated abdominal portion of the instrument was removed, for closing the hole through which the elongated abdominal portion of the instrument passed.

According to one embodiment, the step of placing continuous purse-string base sutures may comprise placing continuous purse-string base sutures using an at least unbarbed suture for enabling the contraction and relaxation of the stomach wall during the surgical procedure.

According to one embodiment, the step of stabilizing the implantable movement restriction device to the fundus comprises contracting a first portion of the stomach wall by pulling on the purse-string roof sutures and contracting a second portion of the stomach wall by pulling on the purse-string base sutures. The implantable movement restriction device may thus be fixated in the stomach wall between the first contracted portion and the second contracted portion.

The surgical method according to any one of the preceding embodiments may further comprise the step of fixating the implantable movement restriction device to the fundus by invaginating the remaining not yet covered implantable movement restriction device in the fundus wall from the outside thereof suturing caudal to cranial with single sutures or a continuous suture. The step of invaginating the implantable movement restriction device in the fundus wall from the outside thereof may comprise placing at least two more sutures or staplers from stomach wall to stomach wall for connecting stomach wall to stomach wall around the implantable movement restriction device and thereby enclose the implantable movement restriction device in a pouch formed by the stomach wall of the fundus. The step of invaginating the implantable movement restriction device may comprise ending the invagination by fixating the suture to the serosa of the stomach wall for long term fixation.

According to one embodiment, the step of fixating the implantable movement restriction device to the fundus comprises contracting the first portion of the stomach wall by pulling on the purse-string roof sutures and determining the length of the loop formed by the purse-string roof sutures by securing the purse-string roof sutures to the serosa of the stomach wall.

A surgical method of treating reflux disease is further provided. The surgical method comprises the steps of connecting the fundus to the esophagus by: placing at least two posterior lateral sutures or staplers or at least one continuous suture line substantially along a cranial-caudal axis on the sinister-posterior side of the esophagus, connecting the fundus to the esophagus on the sinister-posterior side of the esophagus, and placing at least two anterior lateral sutures or staplers or at least one continuous suture line substantially along a cranial-caudal axis on the sinister-posterior side of the esophagus, connecting the fundus to the esophagus on the sinister-posterior side of the esophagus or on the sinister side of esophagus. The surgical method further comprises the step of stabilizing an implantable movement restriction device to the fundus, such that the lower esophageal sphincter is prevented from sliding through the esophageal hiatus.

According to one embodiment, the surgical method step of placing at least two posterior sutures or staplers, connecting the fundus to the esophagus, on the sinister-posterior side of the esophagus, comprises placing at least two continuous sutures connecting the fundus to the esophagus, on the sinister-posterior side of the esophagus.

According to one embodiment, the surgical method step of placing at least two anterior sutures or staplers, connecting the fundus to the esophagus, on the sinister-anterior side of the esophagus comprises placing at least two continuous sutures connecting the fundus to the esophagus, on the sinister-anterior side of the esophagus.

In any of the embodiments herein, at least one of starting and ending of the continuous sutures may be performed in the serosa of the stomach wall for securing the sutures to the serosa of the stomach wall.

According to one embodiment, the surgical method step of placing at least two posterior sutures or staplers, connecting the fundus to the esophagus, on the sinister-posterior side of the esophagus comprises placing at least two lateral sutures substantially along a cranial-caudal axis, on the sinister-posterior side of the esophagus.

According to one embodiment, the surgical method step of placing at least two anterior sutures or staplers, connecting the fundus to the esophagus, on the sinister-anterior side of the esophagus comprises placing at least two lateral sutures substantially along a cranial-caudal axis, on the sinister-anterior side of the esophagus.

According to one embodiment, the surgical method step of placing at least two posterior sutures or staplers, connecting the fundus to the esophagus, on the sinister-posterior side of the esophagus, comprises placing the at least two posterior sutures or staplers at least 0.5 cm posterior to a coronal plane intersecting a most cranial point of the fundus.

According to one embodiment the surgical method step of placing at least two anterior sutures or staplers, connecting the fundus to the esophagus, on the sinister-anterior side of the esophagus, comprises placing the at least two anterior sutures or staplers at least 0.5 cm anterior from the coronal plane intersecting the most cranial point of the fundus.

According to one embodiment, the surgical method step of placing at least two posterior sutures or staplers, connecting the fundus to the esophagus, on the sinister-posterior side of the esophagus comprises placing the most caudal suture or stapler at least 0.5 cm from the angle of His.

According to one embodiment the surgical method step of placing at least two anterior sutures or staplers, connecting the fundus to the esophagus, on the sinister-anterior side of the esophagus comprises placing the most caudal suture or stapler at least 0.5 cm from the angle of His.

According to one embodiment the step of placing at least two posterior sutures, connecting the fundus to the esophagus, on the sinister-posterior side of the esophagus comprises placing the most caudal suture, and the step of placing at least two anterior sutures, connecting the fundus to the esophagus, on the sinister-anterior side of the esophagus comprises placing the most caudal suture, comprising placing at least one of the most caudal suture in the region of the angle of His.

According to one embodiment, the step of placing at least two posterior sutures, connecting the fundus to the esophagus, on the sinister-posterior side of the esophagus comprises placing the most caudal suture, and the step of placing at least two anterior sutures, connecting the fundus to the esophagus, on the sinister-anterior side of the esophagus comprises placing the most caudal suture, comprising placing at least one of the two most caudal sutures in the region at least 1.5 cm above the angle of His.

According to one embodiment the surgical method step of placing at least two posterior sutures or staplers, connecting the fundus to the esophagus, on the sinister-posterior side of the esophagus comprises placing the most caudal suture or stapler at least 1.5 cm from the angle of His.

According to one embodiment the surgical method step of placing at least two anterior sutures or staplers, connecting the fundus to the esophagus, on the sinister-anterior side of the esophagus comprises placing the most caudal suture or stapler at least 1.5 cm from the angle of His.

According to one embodiment the surgical method step of placing the most caudal suture or stapler of the at least two posterior sutures or staplers, connecting the fundus to the esophagus, on the sinister-posterior side of the esophagus at least 0.5 cm from the angle of His and placing the most caudal suture or stapler of the at least two anterior sutures or staplers, connecting the fundus to the esophagus, on the sinister-anterior side of the esophagus at least 1.5 cm from the angle of His.

According to one embodiment the surgical method step of placing the most caudal suture or stapler of the at least two posterior sutures or staplers, connecting the fundus to the esophagus, on the sinister-posterior side of the esophagus at least 1.5 cm from the angle of His and placing the most caudal suture or stapler of the at least two anterior sutures or staplers, connecting the fundus to the esophagus, on the sinister-anterior side of the esophagus at least 0.5 cm from the angle of His.

According to one embodiment the surgical method step of connecting the fundus to the esophagus further comprises placing at least one central suture or stapler on a cranial-caudal axis extending between the at least two posterior sutures or continuous suture line and the at least two anterior sutures or staplers or continuous suture line, placing at least one suture most cranial and preferable a line of sutures in between the posterior and anterior suture lines, placing with a distance of one cm of esophagus circumference to both the anterior and posterior suture lines.

According to one embodiment, the step of connecting the fundus to the esophagus further comprises placing at least one central suture on a cranial-caudal axis extending between the at least two posterior sutures or one continuous suture line and the at least two anterior sutures or one continuous suture line, placing at least one suture most cranial and preferable a line of sutures in between the posterior and anterior suture line, placing with a targeted distance of 1 cm of esophagus circumference to both the anterior and posterior suture lines.

The step of placing at least one central suture or stapler on a cranial-caudal axis may comprise placing at least one central suture or stapler in between the anterior and posterior suture lines and being disconnected therefrom, for maintaining the possibility of radial expansion the esophagus for limiting the disk of dysphagia.

According to one embodiment the surgical method step of placing at least two posterior sutures or staplers, connecting the fundus to the esophagus, on the sinister-posterior side of the esophagus, and placing at least two anterior sutures or staplers or continuous suture, connecting the fundus to the esophagus, on the sinister-anterior side of the esophagus, comprises using an at least partially barbed suture.

A surgical method of treating reflux disease is further provided. The surgical method comprises the steps of dissecting the fundus at least partially caudal on the posterior side thereof, in the approximate direction of bursa Omentalis, as well as away from the spleen area, wherein the step of dissecting the fundus at least partially on the posterior side thereof comprises at least partially freeing the fundus from at least one of the gastrophrenic ligament and the gastrosplenic ligament, and stabilizing an implantable movement restriction device in relation to the fundus, such that the lower esophageal sphincter is prevented from moving towards of through the esophageal hiatus.

The step of dissecting the fundus at least partially on the posterior side thereof may comprise dissecting the fundus at least 0.5 cm posterior to a coronal plane intersecting a most cranial point of the fundus or dissecting the fundus at least partially on the posterior side thereof at least 1 cm posterior to a coronal plane intersecting a most cranial point of the fundus.

According to one embodiment the surgical method step of dissecting the fundus at least partially on the posterior side thereof may comprise dissecting the fundus at least 0.5 cm posterior to the most anterior fixation point of the gastrophrenic ligament on the fundus, or at least 1 cm posterior to the most anterior fixation point of the gastrophrenic ligament on the fundus.

According to one embodiment the surgical method step of dissecting the fundus at least partially on the posterior side thereof comprises dissecting the fundus at least 0.5 cm posterior to an extension of the greater curvature of the stomach in the region of the fundus, or at least 1 cm posterior to an extension of the greater curvature of the stomach in the region of the fundus.

According to one embodiment, the step of dissecting the fundus further comprises to dissect the gastric brevis/short gastrics and ligating at least one of them.

According to one embodiment, the step of dissecting the fundus further comprises to dissect the gastric brevis/short gastrics and ligating at least two of them.

According to one embodiment, the step of dissecting the fundus further comprises to dissect the gastric brevis/short gastrics and ligating at least three of them.

In any of the surgical methods described herein, the step of fixating the implantable movement restriction device to the fundus may comprise placing continuous purse-string roof sutures in the region of the greater curvature of the stomach, in the region of the fundus, such that the stomach tissue can be contracted and forming a hat over the implantable movement restriction device when implanted by pulling the ends of the purse-string sutures. The step of placing roof sutures may comprise placing at least one of the continuous purse-string roof sutures at least 1 cm, preferably 2 cm behind sail of the greater curvature of the stomach, in the region of the fundus, leaving a loose suture loop.

According to one embodiment the step of placing the continuous purse-string roof sutures may comprise placing the continuous purse-string roof sutures using an at least partially un-barbed suture.

According to one embodiment the surgical method step of placing the continuous purse-string roof sutures may comprise starting or ending the continuous purse-string roof sutures at least 1 cm away from the esophagus to stomach anterior suture line.

According to one embodiment, the surgical method step of placing the continuous purse-string roof sutures may comprise placing the continuous purse-string roof sutures using a suture ending with a loop, such that the needle of the suture can be drawn through the loop for contracting the stomach tissue, in a loose loop manner, without fully close the suture loop due to lack of barbes close to the loop for the needle entrance.

According to one embodiment, the step of placing the continuous purse-string roof suture comprises using a barbed free suture that preferable only partly should be closed or loosely closed for contracting the stomach tissue, forming a hat over the implantable movement restriction device when implanted, but in a loose manner.

In any of the surgical methods described herein, the step of stabilizing the implantable movement restriction device to the fundus may comprise inserting the implantable movement restriction device into the abdomen of the patient. The step of inserting the implantable movement restriction device into the abdomen of the patient may comprise inserting the implantable movement restriction device into the abdomen of the patient using an elongated insertion instrument having an elongated abdominal portion.

According to one embodiment, the surgical method step of stabilizing the implantable movement restriction device to the fundus may comprise pushing the implantable movement restriction device into the fundus in a cranial-dorsal direction using the instrument having the elongated abdominal portion. The step of pushing the implantable movement restriction device into the fundus in a dorsal-cranial direction using the instrument having the elongated abdominal portion may comprise pushing the implantable movement restriction device into the fundus in a dorsal-cranial direction using the instrument such that a portion of the implantable movement restriction device ends up dorsal to the roof sutures, forming a hat for the movement restriction device, for placing the movement restriction device in the fundus for facilitating the subsequent invagination in a high-up in fundus position.

According to one embodiment, the step of stabilizing the implantable movement restriction device to the fundus comprises placing continuous purse-string base or floor sutures in the region below of the caudal end of the implantable movement restriction device being proximal on fundus and proximal on the elongated insertion instrument, holding the implantable movement restriction device to stabilize its position. The step of placing continuous purse-string floor sutures in the region of the caudal end of the implantable movement restriction device may comprise placing at least two of the continuous purse-string floor suture bites following an arc. In cases when the at least two continuous purse-string floor sutures are placed following an arc the continuous purse-string floor sutures may be placed following an arc around the movement restriction device with bites as a purse string also below the elongated abdominal portion of the instrument holding the implantable movement restriction device.

According to one embodiment, the step of placing continuous purse-string base sutures in the region of the caudal end of the implantable movement restriction device may comprise placing the continuous purse-string base sutures such that the continuous purse-string base sutures forms a closed curve by bringing stomach from left and right of the elongated insertion instrument to contact each other above the instrument when closing the suture loop.

According to one embodiment, the step of fixating the implantable movement restriction device to the fundus may comprise placing at least one suture or stapler from stomach wall to stomach wall above the elongated abdominal portion of the instrument holding the implantable movement restriction device.

According to one embodiment, the step of placing continuous purse-string base sutures in the region of the caudal end of the implantable movement restriction device may comprise placing one of the continuous purse-string base sutures from stomach wall to stomach wall above the elongated abdominal portion of the instrument holding the implantable movement restriction device.

The step of fixating the implantable movement restriction device to the fundus may comprise releasing the elongated abdominal portion of the instrument from the implantable movement restriction device.

According to one embodiment, the step of stabilizing the implantable movement restriction device in relation to the fundus may comprise placing at least one suture or stapler from stomach wall to stomach wall around the movement restriction device and around the elongated insertion instrument to close the suture loop in the region from which the elongated abdominal portion of the instrument was removed, for closing the hole through which the elongated abdominal portion of the instrument passed.

According to one embodiment, the step of placing continuous purse-string base sutures in the region of the caudal end of the implantable movement restriction device may comprise placing continuous purse-string base sutures using an at least un-barbed suture for enabling the contraction and relaxation of the stomach wall during the surgical procedure.

According to one embodiment, the step of stabilizing the implantable movement restriction device to the fundus comprises contracting a first portion of the stomach wall by pulling on the purse-string roof sutures and contracting a second portion of the stomach wall by pulling on the purse-string base sutures. The implantable movement restriction device may thus be fixated in the stomach wall between the first contracted portion and the second contracted portion.

The surgical method according to any one of the preceding embodiments may further comprise the step of stabilizing the implantable movement restriction device to the fundus by invaginating the implantable movement restriction device in the fundus wall from the outside thereof. The step of invaginating the implantable movement restriction device in the fundus wall from the outside thereof may comprise placing at least two sutures or staplers from stomach wall to stomach wall for connecting stomach wall to stomach wall around the implantable movement restriction device and thereby enclose the implantable movement restriction device in a pouch formed by the stomach wall of the fundus. The step of invaginating the implantable movement restriction device may comprise ending the invagination by stabilizing the suture to the serosa of the stomach wall for long term fixation.

According to one embodiment, the step of fixating the implantable movement restriction device to the fundus comprises contracting the first portion of the stomach wall by pulling on the purse-string roof sutures and determining the length of the loop formed by the purse-string roof sutures by securing the purse-string roof sutures to the serosa of the stomach wall.

A surgical method of treating reflux disease is further provided. The surgical method comprises the steps of: dissecting the esophagus such that the esophagus is disconnected from the surrounding tissue at least 3 cm in a cranial direction from the angle of his and stabilizing an implantable movement restriction device to the fundus, such that the lower esophageal sphincter is prevented from moving towards the diaphragm and/or sliding through the esophageal hiatus.

According to one embodiment the surgical method step of dissecting the esophagus comprises dissecting the esophagus such that the esophagus is disconnected from the surrounding tissue at least 4 cm in a cranial direction from the angle of his, preferably at least 5 cm in a cranial direction from the angle of his and most preferably at least 6 cm in a cranial direction from the angle of his.

According to one embodiment the surgical method step of dissecting the esophagus such that the esophagus is disconnected from the surrounding tissue comprises dissecting the esophagus into mediastinum. The step of dissecting the esophagus into mediastinum may comprise dissecting the esophagus into mediastinum such that the esophagus is disconnected from the surrounding tissue at least 3 cm in a cranial direction from the distal edge of the esophageal hiatus, preferably at least 4 cm in a cranial direction from the distal edge of the esophageal hiatus and most preferably at least 5 cm in a cranial direction from the distal edge of the esophageal hiatus.

According to one embodiment, the step of dissecting the esophagus into mediastinum comprises dissecting the esophagus into mediastinum such that the esophagus is disconnected from the surrounding tissue providing at least 4 cm of abdominal esophagus in a cranial direction from the distal edge of the repaired esophageal hiatus, preferably at least 5 cm of abdominal esophagus and most preferably at least 6 cm of abdominal esophagus from the distal edge of the repaired esophageal hiatus.

According to one embodiment, the step of dissecting the esophagus such that the esophagus is disconnected from the surrounding tissue comprises identifying the anterior and posterior nervus vagus trunc to avoid risk for nerve damage.

According to one embodiment, the surgical method step of placing at least two posterior sutures or staplers or at least one continuous suture line, connecting the fundus to the esophagus, on the sinister-posterior side of the esophagus, comprises placing at least two continuous sutures or at least one continuous suture line connecting the fundus to the esophagus, on the sinister-posterior side of the esophagus.

According to one embodiment, the surgical method step of placing at least two anterior sutures or staplers, connecting the fundus to the esophagus, on the sinister-anterior side of the esophagus comprises placing at least one continuous sutures connecting the fundus to the esophagus, on the sinister-anterior side of the esophagus.

In any of the embodiments herein, at least one of starting and ending of the continuous sutures may be performed in the serosa of the stomach wall for securing the sutures to the serosa of the stomach wall.

According to one embodiment, the surgical method step of placing at least two posterior sutures or staplers or at least one continuous suture line, connecting the fundus to the esophagus, on the sinister-posterior side of the esophagus comprises placing at least two lateral sutures substantially along a cranial-caudal axis, on the sinister-posterior side of the esophagus.

According to one embodiment, the surgical method step of placing at least two anterior sutures or staplers or at least one continuous suture line, connecting the fundus to the esophagus, on the sinister-anterior side of the esophagus comprises placing at least two lateral sutures or at least one continuous suture line substantially along a cranial-caudal axis, on the sinister-anterior side of the esophagus.

According to one embodiment, the surgical method step of placing at least two posterior sutures or staplers or at least one continuous suture line, connecting the fundus to the esophagus, on the sinister-posterior side of the esophagus, comprises placing the at least two posterior sutures or staplers or at least one continuous suture line at least 0.5 cm posterior to a coronal plane intersecting a most cranial point of the fundus.

According to one embodiment the surgical method step of placing at least two anterior sutures or staplers or at least one continuous suture line, connecting the fundus to the esophagus, on the sinister-anterior side of the esophagus, comprises placing the at least two anterior sutures or staplers or at least one continuous suture line at least 0.5 cm anterior from the coronal plane intersecting the most cranial point of the fundus.

According to one embodiment, the surgical method step of placing at least two posterior sutures or staplers or at least one continuous suture line, connecting the fundus to the esophagus, on the sinister-posterior side of the esophagus comprises placing the most caudal suture or stapler or at least one continuous suture line at least 0.5 cm from the angle of His.

According to one embodiment the surgical method step of placing at least two anterior sutures or staplers or at least one continuous suture line, connecting the fundus to the esophagus, on the sinister-anterior side of the esophagus comprises placing the most caudal suture or stapler at least 0.5 cm from the angle of His.

According to one embodiment the surgical method step of placing at least two posterior sutures or staplers or at least one continuous suture line, connecting the fundus to the esophagus, on the sinister-posterior side of the esophagus comprises placing the most caudal suture or stapler or at least one continuous suture line at least 1.5 cm from the angle of His.

According to one embodiment the surgical method step of placing at least two anterior sutures or staplers, connecting the fundus to the esophagus, on the sinister-anterior side of the esophagus comprises placing the most caudal suture or stapler at least 1.5 cm from the angle of His.

According to one embodiment the surgical method step of placing the most caudal suture or stapler or at least one continuous suture line of the at least two posterior sutures or staplers, connecting the fundus to the esophagus, on the sinister-posterior side of the esophagus at least 0.5 cm from the angle of His and placing the most caudal suture or stapler or at least one continuous suture line of the at least two anterior sutures or staplers, connecting the fundus to the esophagus, on the sinister-anterior side of the esophagus at least 1.5 cm from the angle of His.

According to one embodiment the surgical method step of placing the most caudal suture or stapler or at least one continuous suture line of the at least two posterior sutures or staplers or at least one continuous suture line, connecting the fundus to the esophagus, on the sinister-posterior side of the esophagus at least 1.5 cm from the angle of His and placing the most caudal suture or stapler or at least one continuous suture line of the at least two anterior sutures or staplers or at least one continuous suture line, connecting the fundus to the esophagus, on the sinister-anterior side of the esophagus at least 0.5 cm from the angle of His.

According to one embodiment the surgical method step of connecting the fundus to the esophagus further comprises placing at least one central suture or stapler or at least one continuous suture line on a cranial-caudal axis extending between the at least two posterior sutures or staplers and the at least two anterior sutures or staplers. The step of placing at least one central suture or stapler or at least one continuous suture line on a cranial-caudal axis may comprise placing at least one central suture or stapler being disconnected from the at least two anterior sutures or staplers and from the at least two posterior sutures or staplers, and placing at least one suture most cranial and preferable a line of sutures in between the posterior and anterior suture line, placing with a distance of 1 cm of esophagus circumference to both the anterior and posterior suture lines for maintaining the possibility of radial expansion the esophagus for limiting the disk of dysphagia.

According to one embodiment, the step of connecting the fundus to the esophagus further comprises placing at least one central suture on a cranial-caudal axis extending between the at least two posterior sutures or continuous suture line and the at least two anterior sutures or continuous suture line, placing a third continuous suture line in between the posterior and anterior suture line, placing with a targeted distance of one cm of esophagus circumference to both the anterior and posterior suture lines.

According to one embodiment the surgical method step of placing at least two posterior sutures or staplers or continuous suture, connecting the fundus to the esophagus, on the sinister-posterior side of the esophagus, and placing at least two anterior sutures or staplers or at least one continuous suture line, connecting the fundus to the esophagus, on the sinister-anterior side of the esophagus, comprises using an at least partially barbed suture.

A further surgical method for treating reflux disease of a human patient by implanting a movement restriction device such that the movement restriction device is arranged to restrict movement of the cardia of the patient's stomach towards the diaphragm is provided, to hinder the cardia from moving towards and potentially sliding through the diaphragm opening into the patient's thorax. The method comprises: placing the movement restriction device such that a lower portion of the movement restriction device rests against the serosa of a surgically modified stomach on the greater curvature side of the stomach partly extirpated, such that an upper portion of the movement restriction device defines; a small gap between the movement restriction device positioned close to the diaphragm and the patient's esophagus, when the lower portion rests against the surgically modified stomach. The method may further comprise arranging a portion of fat from the gastrophrenic and/or gastrosplenic ligament and/or greater omentum to cover the movement restriction device on at least one of the left, ventral and cranial side of the movement restriction device with the intention to avoid adherences to the nearby organs. The movement restriction device may have a rounded shape. The part of the movement restriction device mounted towards the stomach may be configured like an U-shaped arm.

A surgical kit for performing a surgical procedure for treating reflux disease is further provided. The surgical could include the movement restriction device according to any of the embodiments described herein. The kit surgical kit further comprises a lubricant including at least a bacteriostatic substance for use with the implantable movement restriction device, and at least one resorbable suture without barbs.

The bacteriostatic substance may comprise at least one of the substances Chlorhexidine and Lidocain.

The at least one resorbable suture may comprise at least one of the following materials: Polyglactin, GlycolideDioxanone, Trimethylene carbonat, Catgut, Collagen, Polylactide. Copolymer, Poly-4-hydroxybutyrate, PHA, Tephaflex, Polycaprolactone, Polyhydroxyalkanoates, Maxon, PDS, Polyglycolide.

According to one embodiment, the surgical kit further comprises at least one at least partially barbed suture which may be a suture comprising a barbed portion and a portion without barbs, the portion without barbs may be at least 2 cm long, or at least 3 cm long.

According to one embodiment, the at least one partially barbed suture comprises a loop for use in fixating the at least one partially barbed suture.

According to one embodiment, the at least one partially barbed suture comprises at least one of the following materials: PTFE, GoreTex®, PP, and Polyester.

According to one embodiment, the at least one barbed suture comprises at least one of the following materials: PTFE, GoreTex®, PP, and Polyester.

According to one embodiment, the at least one suture without barbs comprises at least one of the following materials: PTFE, GoreTex®, PP, and Polyester.

According to one embodiment, at least one of: the partially barbed suture, the at least one barbed suture, and the at least one suture without barbs, is a monofilament suture.

According to one embodiment, at least one of: the partially barbed suture, the at least one barbed suture, and at least one suture without barbs is a braided suture.

According to one embodiment, the suture comprises a coating.

According to one embodiment, the movement restriction device comprises at least two parts, wherein the parts are configured to be connected to each other for forming at least a portion of a functional movement restriction device, and the at least two parts are capable of disconnecting from each other, such that the at least two parts individually can pass through the gastro-intestinal tract.

According to one embodiment, the surgical kit further comprises a central part, wherein the at least two parts are configured to be connected to the central part for forming at least a portion of the functional movement restriction device, the central part and the at least two parts are capable of disconnecting from each other, such that the central part and the at least two parts individually can pass through the gastro-intestinal tract.

The various apparatuses and methods according to the above aspects can be combined with any of the features, examples and effects described in the present application.

BRIEF DESCRIPTION OF THE DRAWINGS

The above, as well as additional object, features and advantages of the present inventive concept will be better understood through the following illustrative and non-limiting detailed description, with reference to the appended drawings.

FIG. 19A shows the apparatus in an expanded state and FIG. 19B shows the apparatus in a constricting state.

FIGS. 29-38B are schematic views of various examples of apparatuses for treating reflux disease.

FIG. 39B' is a schematic illustration of the anatomy of the stomach of a human patient.

FIGS. 39AA and 39AB are schematic views of two examples of apparatuses and methods for treating reflux disease.

FIG. 39AC is a schematic view of an instrument for use in a method for implanting a movement restriction device.

FIGS. 39AD-39AG are schematic views of apparatus for the treatment of reflux disease shown in further detail.

FIGS. 39AH-39AJ are schematic views of various examples of apparatuses and methods for treating reflux disease.

FIGS. 40AB-40AD are schematic views of an apparatuses for treating reflux disease in further detail.

FIGS. 40AE-40AH are schematic views of details of distance elements of apparatuses for treating reflux disease.

FIGS. 65A-F. and 66A-N illustrate communication systems according to some embodiments.

DETAILED DESCRIPTION

Figure 1:
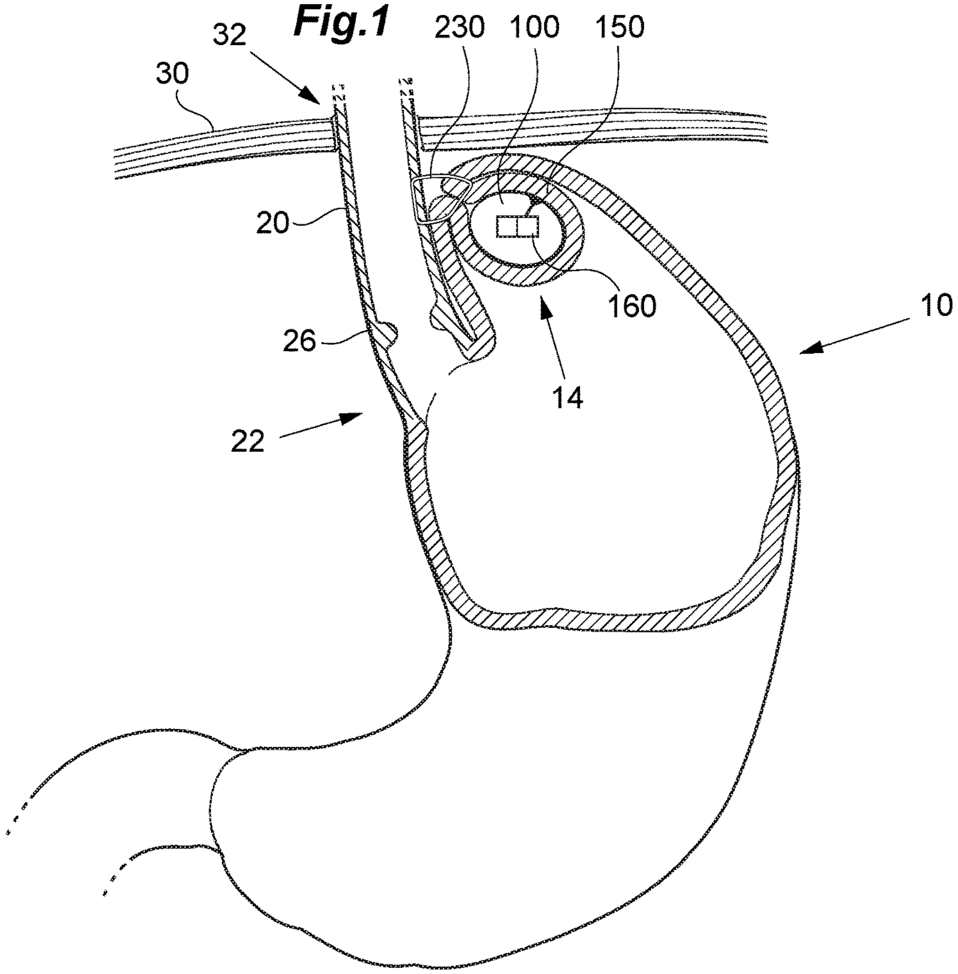
FIGS. 1-11 are schematic views of various examples of apparatuses for treating reflux disease, wherein the apparatuses are implanted in the body of the patient.

In the following a detailed description of embodiments of the invention will be given with reference to the accompanying drawings. It will be appreciated that the drawings are for illustration only and are not in any way restricting the scope of the invention. Thus, any references to directions, such as "up" or "down", are only referring to the directions shown in the figures. It should be noted that the features having the same reference numerals have the same function, a feature in one embodiment could thus be exchanged for a feature from another embodiment having the same reference numeral unless clearly contradictory. The descriptions of the features having the same reference numerals should thus be seen as complementing each other in describing the fundamental idea of the feature and thereby showing the features versatility.

Throughout the description/specification and claims, the terms segment and part are to be considered as equivalent and are in the same way for describing parts of the medical devices.

The boundary of an element is to be understood as the outer periphery that encompasses all of the points of the element without creating recesses. It can be illustrated by the surface created by placing the element in a plastic bag and tightening the plastic around the element such that the surface of the plastic bag takes the shortest route between points in the periphery of the element which are separated by a recess.

Functional implantable medical device/functional movement restriction device is to be understood as the shape and state which the functional implantable medical device/functional movement restriction device is in when it can perform its intended function. E.g. a functional implantable medical device configured to be assembled from a plurality of parts is not functional until assembled.

Throughout the description/specification and claims it should be understood that the implantable medical devices described herein in some embodiments may function as a movement restriction device and/or as an obesity treatment devices.

FIG. 1 is a schematic illustration of an apparatus 100 according to some embodiments of the present disclosure. The apparatus 100 may be used for treatment of a human patient suffering from gastroesophageal reflux disease (GERD), also referred to as reflux disease. As illustrated in the present figure, the apparatus 100 may comprise a movement restriction device 110 configured to be implanted in the stomach 10 for hindering the cardia 22 from sliding through the diaphragm opening 32, and an electrode arrangement 150 for stimulating and exercising muscle tissue of the stomach 10 to improve the conditions for long-term implantation.

The movement restriction device 110 may be arranged to rest against a fundus wall portion 14 of the stomach 10. In the present example, the movement restriction device 110 is arranged to rest against the outside of the stomach wall. However, the movement restriction device 110 may in alternative examples and implementations be arranged to rest against the inside of the stomach wall.

The movement restriction device 110 may have a shape and size that allows it to be fully or at least partly invaginated by the fundus wall portion 14. This may be achieved by forming a pouch or recess in the fundus wall portion 14 and at least partly closing the opening of the pouch or recess so as to hinder the movement restriction device 110 to be removed from the fundus wall portion 14. The invagination by the fundus wall portion 14 allows for the movement restriction device 110 to be implanted at a position between the patient's diaphragm 30 and a lower portion of the fundus wall 12, such that movement of the cardia 22 towards the diaphragm 30 is restricted. By restricting this movement, the cardia 22 may be hindered from sliding up towards, and possibly through, the diaphragm opening 32 into the patient's thorax, and the supporting pressure against the cardiac sphincter 26 exerted from the abdomen can therefore be maintained.

As illustrated in the example in FIG. 1, the movement restriction device 110 may be coupled, of affixed to the esophagus 20 at a position above the cardiac sphincter 26. The affixation of the movement restriction device 110 may preferably be of an indirect nature, achieved by affixing a part of the fundus 12 to the esophagus 20 such that the invagination can act as a mechanical stop against the diaphragm 30 when the esophagus is moving upwards through the diaphragm opening 32. Further, in order to protect the tissue of the esophagus 20 from being damaged by the movement restriction device 110, the movement restriction device 110 may be implanted such that a part of the fundus is arranged between the movement restriction device 110 and the outside of the esophagus 20.

The shape and size of the movement restriction device 110 is an important factor for allowing the invagination to act as a mechanical stop against the diaphragm 30. Preferably, the movement restriction device 110 may have a size and shape that allows for the invagination to be sufficiently large to hinder the fundus wall portion 14 to slide through the diaphragm opening 32 together with the cardia. Further, the movement restriction device 110 may have a size and shape that allows it to be invaginated by the fundus 12 of the stomach without causing an unjustified reduction of the total volume of the stomach cavity. In addition to this, the movement restriction device 110 may at the same time be sufficiently small to allow it to generate a mechanical stop against the diaphragm muscle while leaving the food passageway substantially intact and unaffected. Thus, the movement restriction device 110 disclosed herein advantageously allows for the symptoms of reflux disease to be addressed while reducing the risk for compressing the food passageway.

To facilitate invagination and reduce the risk for damaging the tissue of the fundus wall portion 14 the movement restriction device 110 may have a substantially smooth outer surface. Any corners, edges, joints, or seams may be rounded so as not to damage or irritate the tissue against which the movement restriction device 110 may rest when implanted. In some examples the movement restriction device 110 may have a rounded shape, for example conforming to a sphere, a spheroid, or an egg.

The minimum width of the movement restriction device 110, as measured from side to side, may in some examples be 30 mm or larger, such as 40 mm or larger. Additionally, or alternatively a minimum outer circumference of the movement restriction device 110 may be 150 mm or less, such as 130 mm or less, such as 110 mm or less. In further examples, the minimum outer circumference may be 90 mm or less, such as 70 mm or less, such as 50 mm or less, and such that 30) mm or less. It will however be appreciated that the dimensions of the movement restriction device may vary according to the anatomy of the actual individual into which the movement restriction device 110 is to be implanted. The size and shape of the movement restriction device 110 may be adapted to the individual patient to allow for the invagination to act as a mechanical stop as outlined above and thereby have an effect on reflux disease.

The movement restriction device 110 may be formed of a biocompatible material that is suitable for long-term implantation in the human body. Alternatively, or additionally, the outer surface of the movement restriction device 110 may be provided with a layer or coating of such a material. Examples of biocompatible materials include titanium or a medical grade metal alloy, such as medical grade stainless steel. In an alternative, movement restriction device 110 may be made from of comprise a ceramic material such as zirconium carbide, or a stiff medical grade polymer material such as Ultra-high-molecular-weight polyethylene (UHMWPE) or Polytetrafluoroethylene (PTFE) or a thermoplastic polyester such as polylactide (PLA). Movement restriction device 110 could also comprise at least one composite material, such as any combination of metallic/ceramic and polymer materials or a polymer material reinforced with organic or inorganic fibers, such as carbon or mineral fibers. Further, the movement restriction device may comprise an enclosure made from one of or a combination of: a carbon based material (such as graphite, silicon carbide, or a carbon fiber material), a boron material, a polymer material (such as silicone, Peck®, polyurethane, UHWPE or PTFE,), a metallic material (such as titanium, stainless steel, tantalum, platinum, niobium or aluminum), a ceramic material (such as zirconium dioxide, aluminum oxide or tungsten carbide) or glass.

Further, the movement restriction device 110 may according to some examples be configured to be introduced into the patient's body by means of a gastroscope or an intraluminal instrument, thereby allowing the apparatus 100 to be implanted by means of natural orifice transluminal endoscopic surgery (NOTES). Hence, the movement restriction device 110 may have a shape and size allowing it to be introduced and pass through a tubular instrument. In some examples, the movement restriction device 110 may be configured to change its shape, preferably resiliently, to temporarily assume a smallest width that allows for the movement restriction device 110 to pass through such an instrument.

The apparatus 100 may further comprise an electrode arrangement 150 configured to be arranged between the movement restriction device 110 and the stomach wall portion 14 when the apparatus 100 is implanted. The electrode arrangement 150 may be configured to electrically stimulate muscle tissue of the stomach wall portion 14 so as to exercise the muscle tissue and thereby improve the conditions for long term implantation of the movement restriction device 110. The electrode arrangement 14 may comprise at least one electrode element 152, which may be configured to abut the tissue against which the movement restriction device 110 is arranged to rest when implanted and to transmit electrical impulses to the muscle tissue. It is appreciated that the electrode element 152 may be arranged in direct contact with the muscle tissue, or in indirect contact via intermediate tissue such as for example connective tissue or fibrous tissue. Thus, the electrode arrangement 150 may be configured to rest against, abut or engage the tissue at least partly surrounding the implanted movement restriction device 110. The interaction between the electrode arrangement 150 and the muscle tissue will be described in greater detail in connection with FIGS. 38-41.

The electrode element 152 may be attached directly to an outer surface of the movement restriction device 110, as shown in FIG. 1. In some examples, however, the electrode element 152 may be arranged on a support, such as a flexible patch, which may be configured to be attached to the medical implant. In further examples the electrode arrangement 150 may be provided as a separate item, physically distinct from the movement restriction device 110.

The apparatus 100 may further comprise an implantable energy source 160, which may be configured to supply the electrode arrangement 150 with electrical power for the electrical stimulation of the muscle tissue. The energy source 160 may be integrated in the in the movement restriction device 110 as shown in the present figure, wherein the energy source 160 is placed inside the movement restriction device 110 and electrically connected to the electrode element 152 arranged between the outer surface of the movement restriction device 110 and the fundus wall portion 14. The energy source 160 may in some examples be arranged outside the movement restriction device 110 as well, forming as a separate structural entity that can be implanted in the abdomen or elsewhere, such as subcutaneously.

According to some examples the energy source 160 may comprise a primary cell, i.e., a battery designed to not be recharged. In further examples, the energy source 160 may comprise a secondary cell designed to be recharged, preferably by means of an external energy source located outside the patient's body. Various examples of charging of the energy source 160) and powering of the electrode arrangement 150 is described in connection with FIGS. 42-44, together with examples of how to control and operate the electrode arrangement 150.

Figure 2:
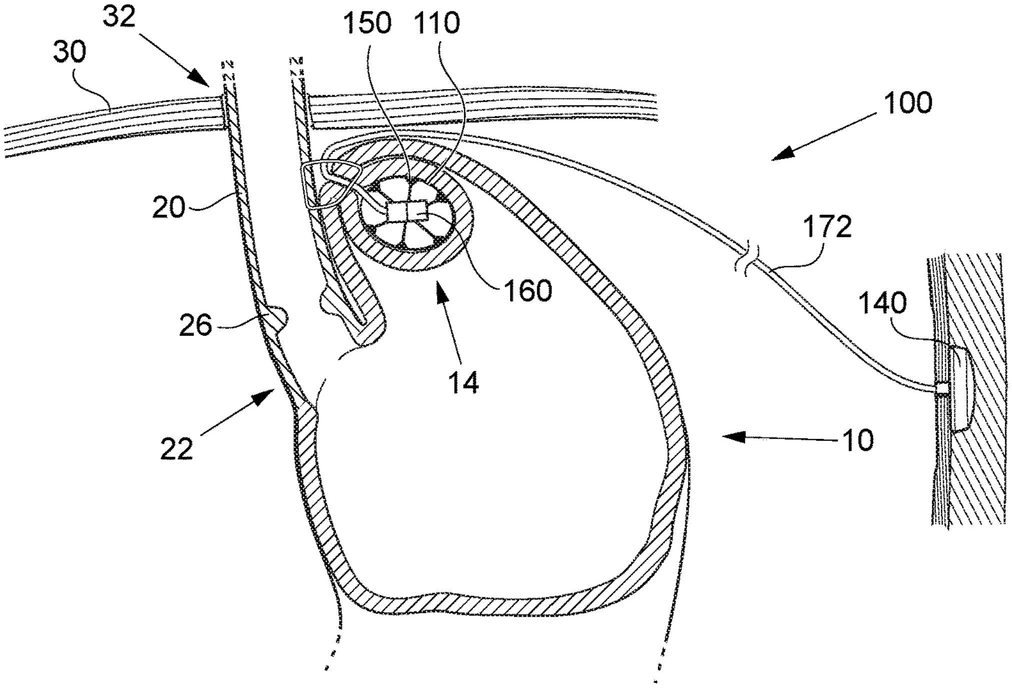

FIG. 2 is a schematic illustration of an apparatus 100 according to some embodiments, which may be similarly configured as the embodiments discussed with reference to FIG. 1. Hence, the apparatus 100 is shown when implanted in a patient to treat reflux disease, and may comprise a movement restriction device 110 and an electrode arrangement 150 for generating an electric signal causing the muscle cells of the fundus wall portion 14 to contract and relax repeatedly. This action, or exercising of the cells by means of the electrode arrangement as shown in FIGS. 1 and 2 has been found to have a positive impact in terms of preventing deterioration and damage of the tissue and help increasing tolerance of the tissue for pressure and mechanical forces generated by the medical implant.

The present example differs from the one of FIG. 1 in that the movement restriction device is coupled to a user interface allowing the patient or persons, such as medical staff, to interact with the apparatus 100. More specifically, the user interface may allow for communication with the implant and/or control of the operation of the implant. It may also comprise means for supplying power to the implant. The user interface may for example comprise a remote unit 140, such as a regulator or a push-button, that is connected to the movement restriction device 110 via a communication channel 172 such as a wiring or electrical lead. The remote unit 140 may for example be implanted subcutaneously so as to facilitate access from outside the body. Features and functions of the remote unit 140 is further described with reference to FIGS. 46-64. A user, such as the patient himself or a medical staff may interact with the remote unit 140 to regulate or control the electrical stimulation of the muscle tissue. The remote unit 140 may for example be used to initiate or end the stimulation, or to adjust the electrical signal used for the stimulation, as described in connection with FIGS. 38-41. The regulation and control of the electrical stimulation may be provided by a controller 170, which may be arranged within the movement restriction device 110, integrated in the remote unit 140, or implanted elsewhere in the body or arranged external to the body. In case of the controller being arranged outside the body, control signals may be sent to the implanted apparatus via the remote unit 140. Such a controller may for example comprise an energy source, an electric switch, or an injection port for varying a volume of the movement restriction device, depending on actual circumstances and application of the implant.

The electrode arrangement 150 may comprise a plurality of electrode elements 152 distributed over the outer surface of the movement restriction device 110 so as to allow for the tissue abutting the movement restriction device to be electrically stimulated and exercised. Each of the electrode elements 152 may comprise a contact pad, or contact surface, configured to form a junction with the surrounding tissue and which is electrically connected to a circuitry inside the movement restriction device 110. The circuitry may be configured to generate an electrical signal, for example comprising a pattern of electrical pulses, that is transmitted to the muscle tissue via the electrode elements 152.

Figure 3A:
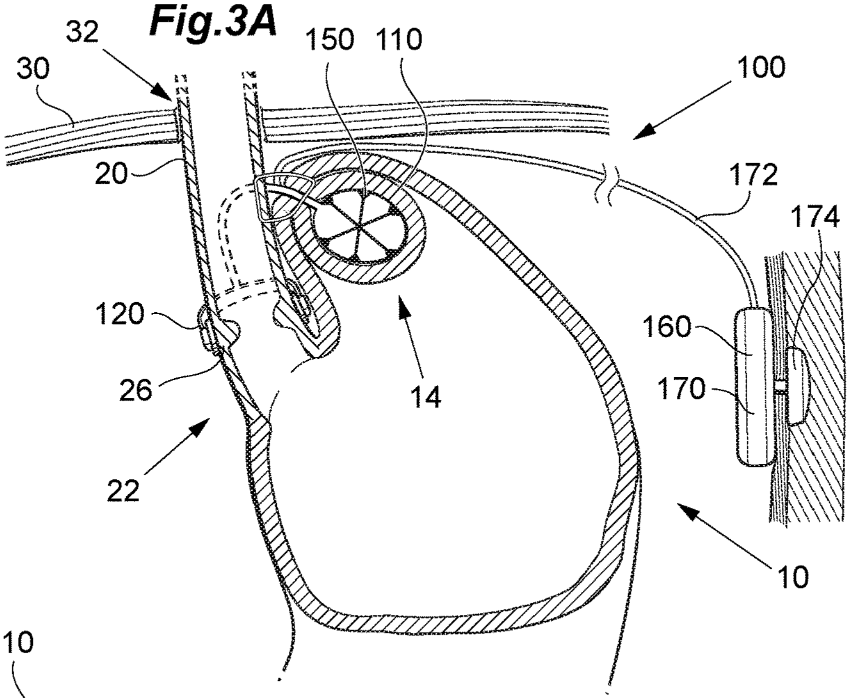
Figure 3B:
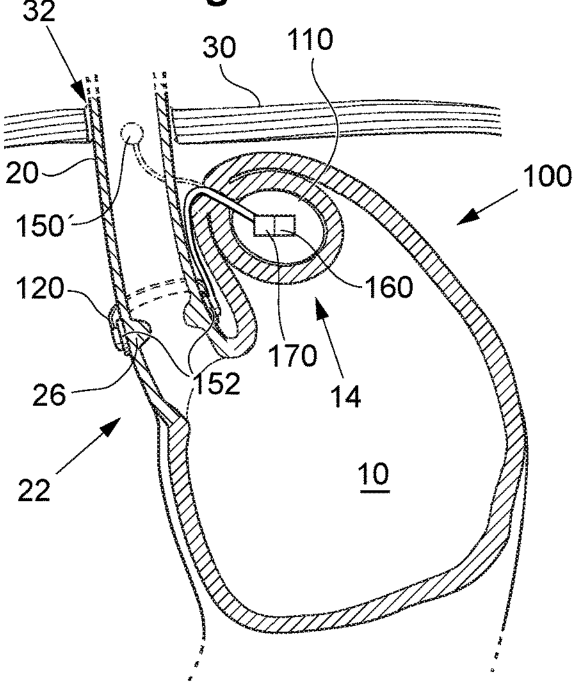

FIGS. 3A and 3B illustrates an apparatus 100 for treating reflux disease of a human patient, when implanted in the patient. The apparatus 100 may be similarly configured as the apparatuses disclosed in connection with FIGS. 1-3B, with the difference of an elongated support device 120 which may be configured to at least partly encircle the esophagus 20. Hence, the apparatus 100 of FIGS. 3A and 3B may comprise a movement restriction device 110 configured to be implanted to hinder the cardia from sliding through the diaphragm opening as discussed above, and an elongated support device 120 that may be connected to the movement restriction device 110 in a manner that allows the elongated support device 120 to be held in place around the esophagus 20 by the movement restriction device 110. The elongated support device 120 may comprise a mechanical stability, or rigidity that allows for its position relative to the esophagus 20 to be determined mainly by the position and orientation of the movement restriction device 110. Thus, the elongated support device 120 may be implanted and kept in position without having to be secured to the tissue of the esophagus 20. In FIG. 3B, the elongated support device 120 incorporates a lead for transferring the electrical stimulation signal from the controller 170 to the stimulation elements 152 and optionally to the suppression electrode 150'. The elongated support device 120 travels from the invaginated movement restriction device 110 in the space between the fundus tissue and the esophagus tissue and in a caudal direction to the region of the lower esophageal sphincter. The vertical portion of the elongated support device 120 may be placed between two the suture rows further elaborated on with reference to FIGS. 22A-23K.

The elongated support device 120 may be formed as a bracket or brace having a shape that allows it to follow at least a part of the outside of the esophagus 20. In some examples, the elongated support device 120 may have a shape conforming to a "C". The elongated support device 120 may be formed of the same material as the movement restriction device 110, or by a different material. Examples of materials include metals and polymers. Further, the elongated support device 120 may comprise a surface layer or coating configured to hinder or reduce growth of fibrotic tissue.

The elongated support device 120 may be integrally formed with the movement restriction device 110, such that the movement restriction device 110 and the elongated support device 120 form a single piece. The elongated support device 120 may hence be referred to as a protrusion of the movement restriction device 110, having a length and orientation relative to the body of the movement restriction device 110 that allows for the protrusion to be arranged at least partly around the esophagus 20. In alternative examples the elongated support device 120 and the movement restriction device 110 may be formed as separate pieces that can be joined or attached to each other when implanted.

Similar to the movement restriction device 110, the elongated support device 120 may be formed of a biocompatible material that is suitable for long-term implantation in the human body. Alternatively, or additionally, the outer surface of the elongated support device 120 may be provided with a layer or coating of such a material. Examples of biocompatible materials include titanium or a medical grade metal alloy, such as medical grade stainless steel. In an alternative, support device 120 may be made from of comprise a ceramic material such as zirconium carbide, or a stiff medical grade polymer material such as Ultra-high-molecular-weight polyethylene (UHMWPE) or Polytetrafluoroethylene (PTFE) or a thermoplastic polyester such as polylactide (PLA). The support device 120 could also comprise at least one composite material, such as any combination of metallic/ceramic and polymer materials or a polymer material reinforced with organic or inorganic fibers, such as carbon or mineral fibers. Further, the support device 120 may comprise an enclosure made from one of or a combination of: a carbon based material (such as graphite, silicon carbide, or a carbon fiber material), a boron material, a polymer material (such as silicone, Peek®, polyurethane, UHWPE or PTFE,), a metallic material (such as titanium, stainless steel, tantalum, platinum, niobium or aluminum), a ceramic material (such as zirconium dioxide, aluminum oxide or tungsten carbide) or glass.

The apparatus 100 may further comprise an electrode arrangement 150 comprising an electrode element 154 that is supported by the elongated support device 120, or holder 120 and configured to electrically stimulate muscle tissue of the esophagus 20. The electrode element 154 may hence be arranged between the holder 120 and the outside of the esophagus 20 and configured to transmit an electrical stimulation signal to the tissue of the esophagus 20.

The electrical stimulation of the tissue may be similar as the stimulation described above for the movement restriction device 110, i.e., for exercising the muscle tissue to improve the conditions for long term implantation. However, in additional or alternative examples the electrical stimulation may be configured to cause the cardiac sphincter 26 to contract. In the present example in FIG. 3 the apparatus 100 may be provided with an electrode arrangement 150 for electrical stimulation of the muscle tissue close to the implanted movement restriction device 110 and for electrical stimulation of the cardiac sphincter muscle 26. However, it is appreciated that the electrode arrangement 150 may comprise an electrode element 154 for the stimulation of the cardiac sphincter 26 only. In other words, the electrode arrangement 150 at the movement restriction device 110 may be optional.

The electrode arrangement 150 may comprise at least two electrode elements 154 that are supported by the elongated support device 120 at two different positions of the cardia 22, preferably at opposing sides, so as to allow for the cardiac sphincter 26 to be electrically stimulated. The electrode arrangement 150 may be controlled to alternate between at least two modes, i.e., an operation mode in which the cardiac sphincter 26 is stimulated with electrical energy and a resting mode, in which the cardiac sphincter 26 is not stimulated to allow the muscle tissue to recover.

The electrode arrangement 150 may further be operable to apply a suppression signal for suppressing action potentials, which are induced by the electrical stimulation of the tissue at the movement restriction device or the cardiac sphincter, propagating in an antidromic direction, i.e., towards the brain. In different words, the suppression signal may be employed to inhibit or block stimulation-induced action potentials from causing undesired responses in the patient when propagating towards the brain. The suppressing signal may for example be delivered to the vagus nerve at a position cranial to the plurality of electrode elements 152 arranged between the holder 120 and the outside of the esophagus 20. By delivering the suppression signal at a position between the delivery point of the stimulation signal and the brain, the nerve can be blocked or inhibited to a degree that prevents or at least reduces further propagation of action potentials induced by the stimulation signal. In FIG. 3B, an optional suppression electrode 150' is coupled to the outer wall of the esophagus 20, preferably at a position allowing the suppression signal to be delivered to the vagus nerve.

The suppression signal may be a time-varying signal, having a frequency component that varies in the range of 1-10 kHz, such as 2-8 kHz, such as 4-6 kHz, for which the nerve's capability of conveying action potentials has been observed to be reduced or even eliminated. Frequencies in the range of 1-10 kHz may be considered as relatively high frequencies, compared to the frequencies typically used for the electrical stimulation signal. The electrical stimulation signal has showed to generate an effector response when comprising frequencies in the range of, e.g., 0.1-100 Hz. The electrical stimulation signal may thus be referred to as a low-frequency signal, whereas the suppression signal may be referred to as a high-frequency signal.

By combining the electrical stimulation delivered by the electrode elements 152 with the suppression signal delivered by the suppression electrode 150', a substantially unidirectional stimulation may be achieved, in which the effector tissue (such as the tissue at the movement restriction device or the cardiac sphincter) can be stimulated without causing undesired stimulation or responses in tissue cranial to the suppression electrode 150'.

In some examples, the controller 170 is configured to drive the electrode arrangement 150 such that the stimulation signal and the suppression signal are delivered in sequence, with a delay of the suppression signal timed to generally match a conduction velocity of the stimulation signal in the nervous tissue, such as the vagus nerve, between the electrode element(s) 152, 154 delivering the stimulation signal and the suppression electrode 150 delivering the suppression signal.

In some examples, the controller 170 is configured to drive the electrode arrangement 150 such that each of the stimulation signal and the suppression signal is a time-varying signal, wherein the stimulation signal is a low-frequency signal (such as in the range of 0.1-100 Hz) and the suppression signal is a high-frequency signal (such as in the range of 1-10 kHz).

In some examples, the stimulation electrode element 152, 154 and the suppression electrode 150' are configured to be arranged spaced apart along a nerve, such as the vagus nerve, and/or along the esophagus. As mentioned above, the suppression electrode 150' may be arranged cranial to the stimulation electrode element 152, 154.

In some examples, the suppression electrode 150' may be a patch electrode configured to be attached to a portion of the stomach wall, a portion of the esophagus, and/or the vagus nerve.

In some examples, the suppression electrode 150' may be arranged in a cuff arranged to at least partly encircle the esophagus and to cause the suppression electrode 150' to touch the tissue of the esophagus.

In some examples, a sensor device may be provided, which is configured to generate a sensor signal indicating action potentials propagating in the vagus nerve, wherein the action potentials are induced by the electrical stimulation signal. The controller may be configured to generate the suppression signal based on the sensor signal, thereby allowing the suppression signal to be adapted or fine-tuned based on the action potentials propagating in the nerve.

In some examples, a sensor device may be provided to detect the patient swallowing. The sensor device may be configured to sense actions potentials generated by pacemaker cells of the muscle tissue. The stimulation controller (170) is then configured to control the electrical simulation based at least partly on the sensed action potentials, such that the electrical stimulation seizes when the patient swallows. In alternative embodiments, the sensor may sense swallowing by sensing other types of parameters. As such the sensor could comprise a motility sensor, which could be a piezo electric or piezo resistive motility sensor, or an accelerometer. In the alternative, a acoustic sensor, such as a microphone, may be used to sense the patient swallowing by picking up the sound generated by the patient swallowing. In the alternative, an optical sensor may be used for sensing the opacity alteration over the esophagus as food passes. A strain sensor could also be used for sensing the expansion of the esophagus as food passes. The sensor may be an EIM (Electrical Impedance Myography) sensor configured to measure a change in electrical impedance in the tissue of the lower esophageal sphincter or in the esophagus tissue to detect the patient swallowing or to detect the muscles response to the stimulation signal. The electromyographic sensor may be configured to measure an electric activity in the tissue of the lower esophageal sphincter or in the esophagus tissue. The sensor device may also or instead comprise an electric impedance sensor configured to measure a change in electrical impedance in the tissue of the lower esophageal sphincter or in the esophagus tissue. The sensor electrode may be configured to be arranged at the tissue of the lower esophageal sphincter or in the esophagus tissue and may further comprise a reference electrode. The sensor device or controller (170) may be configured to generate the sensor signal based on an electrical interaction between the sensor electrode and the reference electrode. The sensor device may in the alternative be configured to measure mechanical movement in the lower esophageal sphincter or in the esophagus tissue in response to the stimulation signal. For this purpose, the sensor device may comprise a strain gauge configured to measure a contraction or relaxation of the effector tissue in response to the stimulation signal.

As a complement or alternative, swallowing may be measured by measuring parameters related to a heart rate of the patient, a blood pressure of the patient or a rate of respiration of the patient.

The response from the sensor may be determined by the controller (170) which may be configured to determine a response measure based on the sensor signal, the response measure being indicative of the response in the lower esophageal sphincter or in the esophagus tissue. The controller may have a be configured to compare the response measure with a predetermined reference measure; and control the stimulation device to: increase an intensity of the stimulation signal in response to the response measure being below the reference measure, and reduce the intensity of the stimulation signal in response to the response measure exceeding the reference measure. The controller (170) may be configured to: increase the intensity of the stimulation signal by increasing at least one of a frequency, current amplitude, and voltage amplitude of the stimulation signal; and reduce the intensity of the stimulation signal by reducing at least one of the frequency, current amplitude, and voltage amplitude of the stimulation signal. The predetermined reference measure may be based on a previous measurement of the effector response in the patient.

The apparatus 100 may further comprise a user interface, comprising a remote unit 140 and a communication channel 172 which may be similarly configured to the example described above in connection with FIG. 2. The user interface may allow for the patient, or medical staff, to choose when the electrode arrangement 150 should be in the operation mode and when it should be in the resting mode. For example, for some patients is may be sufficient to keep the stimulation temporarily "on" when the patient experiences reflux symptoms, such as at night the patient is lying down, whereas other patients may need the cardiac sphincter 26 to be stimulated continuously, with the exception of when eating.

The user interface may further allow for the power of the electrical signal to be adjusted over time. For example, the power used for the stimulation may be increased to compensate for an increased resistance at the junction between the electrode element 154 and the tissue caused by formation of fibrotic tissue.

As indicated in the present figure, the apparatus 100 may comprise an energy source 160 for supplying the electrode arrangement 150 with electrical power. The energy source 160 may be implantable, for example at a location outside the movement restriction device 110, such as subcutaneously as illustrated in FIG. 3. The communication channel 172 may hence be configured to convey the electrical power, i.e., the electrical signal, from the energy source 160 to electrode arrangement 150. The communication channel 172 may for example comprise an electrical conductor for electrically connecting the electrode arrangement 150 of the elongated support device 120 (and, optionally, the movement restriction device 110) with the energy source 160.

It will be appreciated that the movement restriction device 110 may be implanted in the fundus wall portion 14 is a number of different ways, and that FIGS. 1-3 are merely illustrative examples. In FIGS. 1-3 the movement restriction device 110 is invaginated in the fundus wall portion 14 from outside the stomach. A plurality of stomach-to-stomach sutures or staples may be applied to maintain the invagination intact and the movement restriction device 110 in the desired position relative to the cardia 22 and the diaphragm 30 of a standing patient. This allows for a growth of fibrotic tissue for keeping the invagination intact over time.

Figure 4:
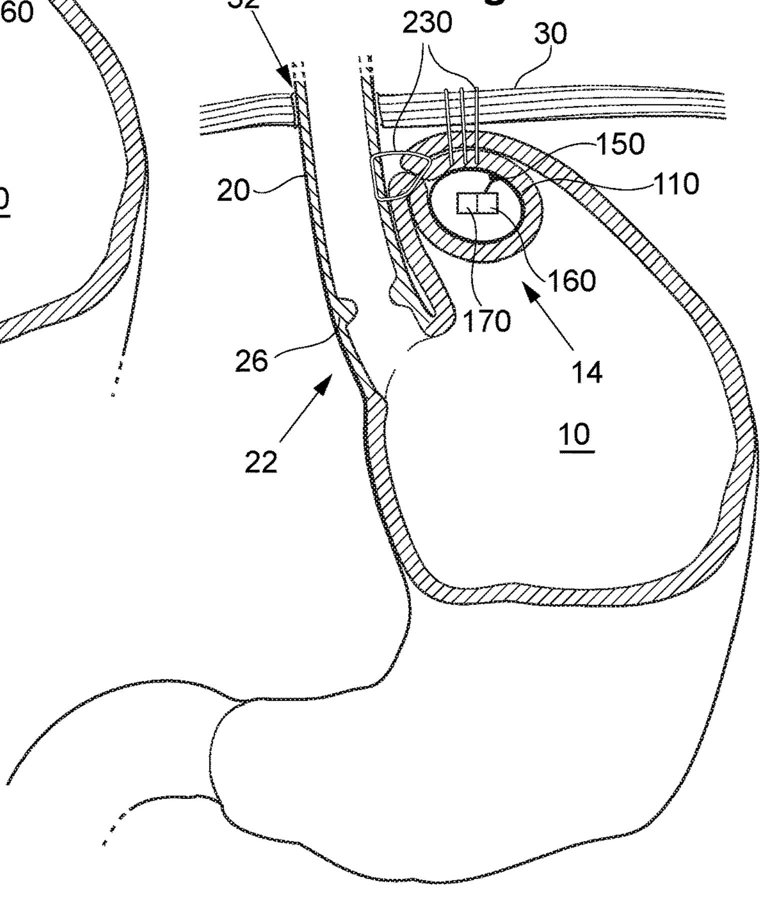

Additionally, or alternatively, an affixation may be provided between the fundus wall portion 14 and the diaphragm 30, and/or the fundus wall portion 14 and the esophagus 20 as illustrated in FIG. 4. The movement restriction device 110 depicted in FIG. 4 may be similarly configured as the embodiments discussed in connection with FIGS. 1-3, and FIG. 4 hence discloses a movement restriction device 110 implanted in in the fundus 12 and arranged at a position above the cardia 22 so as to provide a mechanical stop reducing the symptoms of reflux disease. The movement restriction device 110 may also comprise an electrode arrangement 150 for electrically stimulating and exercising the muscle tissue affected by the implanted device 110, as described above.

However, in the example shown in FIG. 4, the movement restriction device 110 is invaginated from the inside of the stomach 10, instead of from the outside of the stomach 10. The movement restriction device 110 is hence adapted to rest against a portion of the inside wall of the fundus wall portion 14 in a position between the diaphragm 30 and at least a portion of the lower part of the invaginated stomach fundus wall 12. After invagination, a number of stomach-to-stomach sutures or staples may be applied from the inside of the stomach 10 to keep the invagination intact and to allow growth of tissue to keep the invagination over time. Additional affixations may be provided between the outside of the fundus wall portion 14 and the esophagus 20 and/or the diaphragm muscle 30 to hold the movement restriction device 110 in the desired position.

Figure 5:
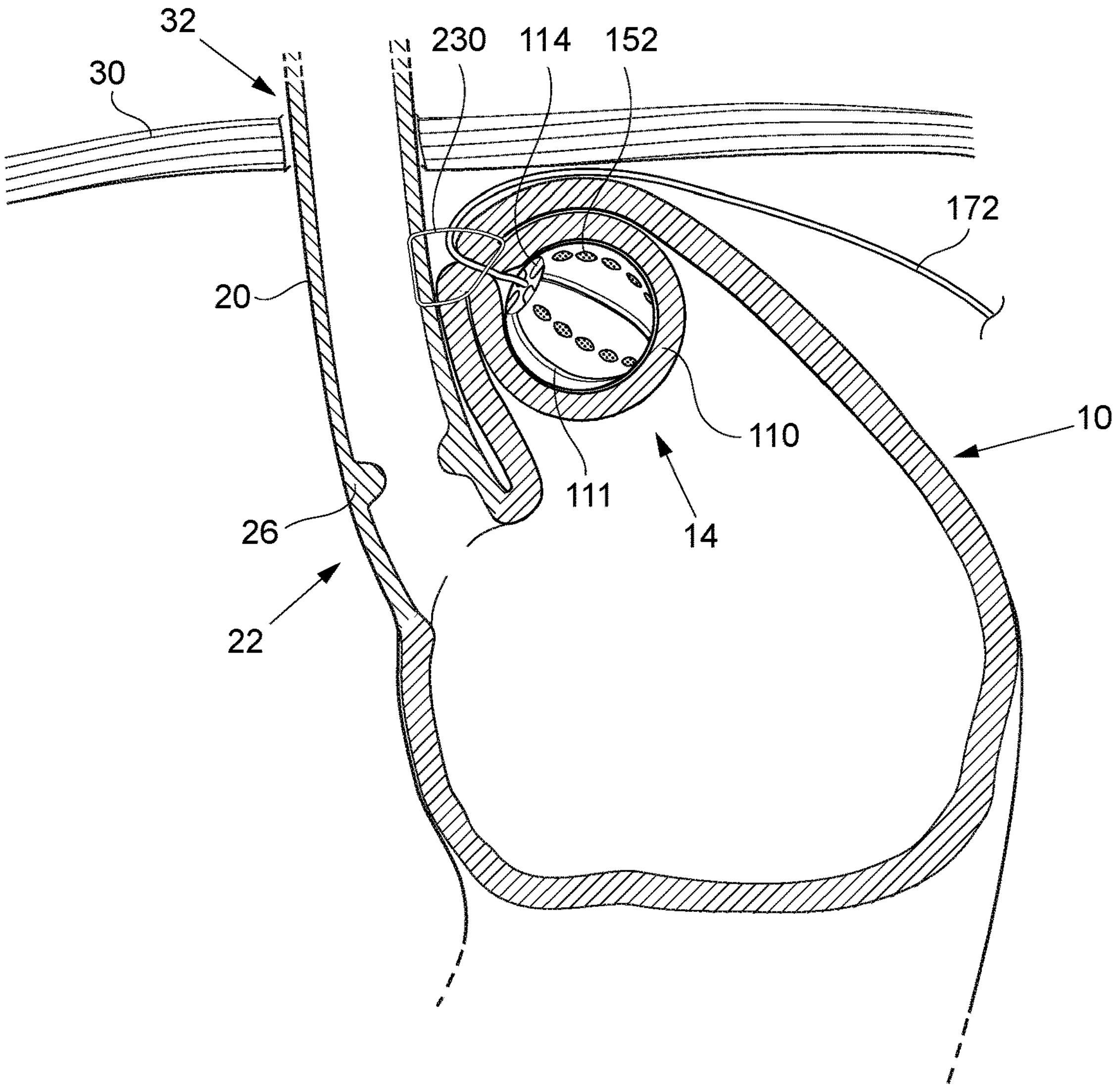

The movement restriction device 110 disclosed in FIGS. 1-4 may have several different configurations and may not necessarily be limited to the schematic versions outlined therein. Other configurations and designs are conceivable within the inventive concept, as defined by the appended claims. An example of such a variant is illustrated in FIG. 5, showing a movement restriction device 110 similar to the ones in FIGS. 1-4 but formed of a plurality of segments 111 that are configured to be attached to be assembled into a complete movement restriction device 110. The segments 111 may for example be secured to each other by means of mutually engaging structures such as protruding slits and receiving recesses/grooves 114, snap-fit connectors, or the like. In the present example, the movement restriction device 110 may be formed of five segments 111: four outer parts and an inner, core part around which the outer parts may be arranged to form a rounded and substantially smooth body suitable for invagination. The segments 111 may be configured to be securely attached to each other, or to be loosely fitted and kept in their right position when invaginated by the surrounding fundus wall 12. In some examples, the segments 111 may be secured to each other by means of a wire. The wire may be biodegradable and eventually dissolved. The segments 111 may be configured to be introduced in the body of the patient separately, one by one, and assembled into the movement restriction device 110 in connection with being implanted.

As shown in the present figure, a plurality of electrode elements 152 may be arranged on an outer surface of the segments 111, i.e., the surface of the outer parts that is to be arranged to rest against the fundus wall portion 14 when the assembled movement restriction device 110 is implanted. The segments 111 may be electrically connected to each other to allow for an electrical stimulation signal to be transmitted to the electrode elements 152 on the outer surface of the movement restriction device 110.

The movement restriction device 110 according to any of the above-mentioned examples may have a volume that is adjustable or non-adjustable after implantation. In case of a non-adjustable volume, the movement restriction device 110 may be formed of a body (or several segments) being solid, i.e., which is not hollow and/or comprises substantially the same material throughout. This may allow for the shape to be varied, for example during insertion into the body, such as through a tubular instrument, while the volume may be substantially the same. In case the movement restriction device 110 is adjustable in terms of volume, the device may be formed of a body (or several segments) comprising one or several cavities or voids capable of accumulating an releasing a fluid for causing a corresponding expansion and reduction of the movement restriction device 110. The fluid may for example be a gas or a liquid, such as a gel, which may be introduced and extracted from the movement restriction device 110 prior to implantation, during the implantation procedure, or after it has been implanted.

FIGS. **6*a* and 6*b* illustrate an example of a movement restriction device 110, similar to the ones discussed with reference to FIGS. 1-5, comprising a fluid communication port 115, or injection port, that can be used to add or remove a fluid to/from the inside of the movement restriction device 110 to thereby vary its volume. It may be desired to adjust the volume of the movement restriction device 110 post-operatively in order to fine tune or adjust the movement restriction device's 110** capability of acting as a mechanical stop against the diaphragm. It may for example be determined after the implantation, in a subsequent evaluation of the results of the operation, that an implant of another size would have been more optimal for the specific patient. This may be solved by adjusting the volume of the implant posit-operatively.

Figure 6A:
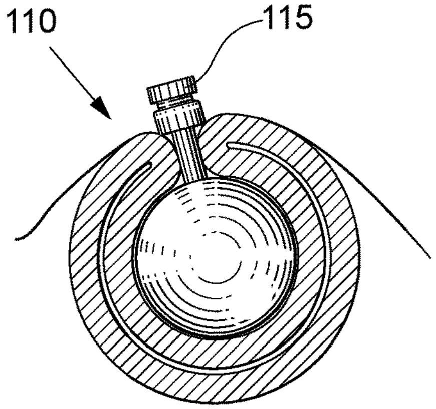
Figure 6B:
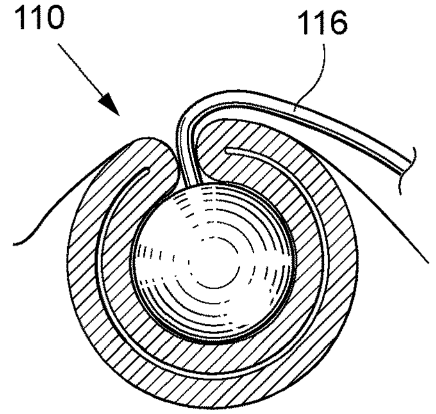

As shown in the present figures, the port 115 may be positioned such that it is accessible from outside the invagination, i.e., such that the port 115 can be accessed by an instrument or connection without having to penetrate the fundus wall portion 14. In FIG. **6*a* the port protrudes to the outside of the invagination, passing between sutures or staples used for at least partly closing the pouch in which the movement restriction device 110 is arranged. The port 115 may thus be available for connection to a tube or a syringe from the abdominal region of the patient. In FIG. 6*b* the port 115 is positioned inside the invagination and accessed by a tube 116 that is connected to the port 115** and extends into the abdominal region of the patient.

The volume of the movement restriction device 110 may according to some examples be adjustable non-invasively after implantation. A non-invasive adjustment may be allowed by means of the tube 116, that may be connected to the port 115 and led to the outside of the patient's body or to an implanted volume regulator, such as a pump or a reservoir, for non-invasive regulation of the volume of the movement restriction device 110. According to other examples, the volume of the movement restriction device 110 may be adjustable invasively, e.g. by means of an instrument that is inserted into the patient's body and connected directly to the port 115 or the tube 116 for adding or removing fluid from the movement restriction device 110. Alternatively, or additionally, an instrument such as a syringe may be inserted directly into the inside of the movement restriction device 110, penetrating and passing through the surrounding fundus wall portion 14 on the way to the movement restriction device 110.

It will be appreciated that the adjustable and non-adjustable characteristics of the volume of the movement restriction device 110 generally refer to a permanent state of the movement restriction device 110. In other words, an adjustment of the volume may, in the above context, result in a new volume that is substantially constant over time until the amount of fluid in the movement restriction device 110 is varied again. This may be contrasted with temporary changes of the volume, which for example may be caused by a temporary or resilient compression of the material forming the movement restriction device 110. Such a temporary change in volume may for example occur during introduction of the movement restriction device 110 into the body, e.g. via a tubular instrument. In other words, the movement restriction device 110 according to the examples outlined above with reference FIGS. 1-6 may be flexible or elastic, allowing the device 110 to at least temporarily assume different shapes and, in some examples, volumes, in response to being exposed to external mechanical forces.

An apparatus for treating reflux disease, as outlined above, will now be described with reference to FIGS. 7-13. The figures schematically illustrate an apparatus 100 comprising an at least partly ring-shaped implantable movement restriction device comprising a first portion 110 configured to be at least partly invaginated by a first wall portion of the patient's stomach 10 and arranged such that at least a part of the first portion of the apparatus 100 is arranged above the cardia 22 of the patient's stomach 10, and such that movement of the cardia towards the diaphragm is restricted to prevent the cardia 22 from sliding through the diaphragm opening 32 into the patient's thorax. The configuration and function of the first portion 110 of the apparatus 100 may hence be similar to the movement restriction devices 110 previously described with reference to FIGS. 1-6. Further, the apparatus 100 may comprise an electrode arrangement 150 which may be similar to the electrode arrangement 150 described in connection with the examples of FIGS. 1-6, and may hence be configured to be arranged between the first portion 110 of the apparatus 100 and the first wall portion 14 to electrically stimulate muscle tissue of the first wall portion 14 to exercise the muscle tissue and thereby improve the conditions for long term implantation of the apparatus 100.

The apparatus 100 may further comprise a second portion 120, which may be configured to be arranged on an opposite side of the cardia 22, as seen from the first portion 110. The first portion 110 and the second portion 120 may together form the at least partly ring-shaped movement restriction device 110, 120, which as indicated in the present figures may be configured to be arranged to at least partly encircle the esophagus 20 of the patient. The first portion 110 may for example be configured to be arranged on the fundus side of the esophagus 20, whereas the second portion 120 may be configured to be arranged on the side of the esophagus 20, i.e., the side opposing the fundus 12. The movement restriction device 110 may in some examples be formed of a substantially smooth, ring-shaped body configured to encircle the esophagus 20. The movement restriction device 110 may for example have a shape conforming to a torus, with the first portion 110 forming the part arranged at the fundus side of the esophagus and the second portion 120 forming the part arranged at the opposite side of the esophagus 20.

Figure 7:
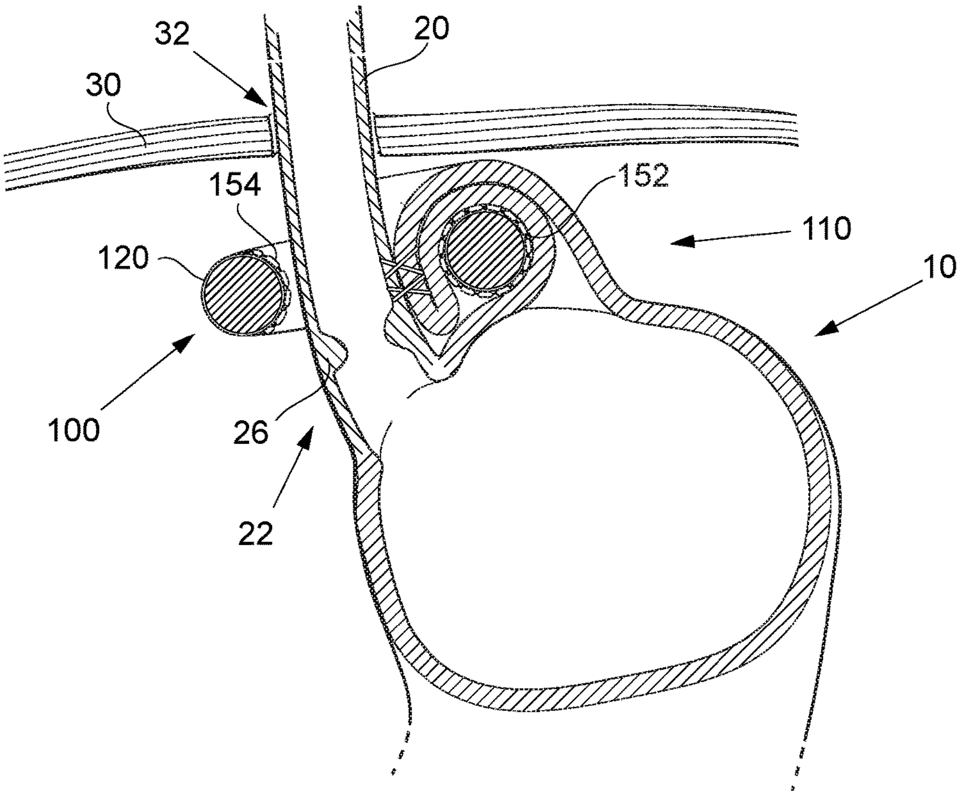
Figure 8:
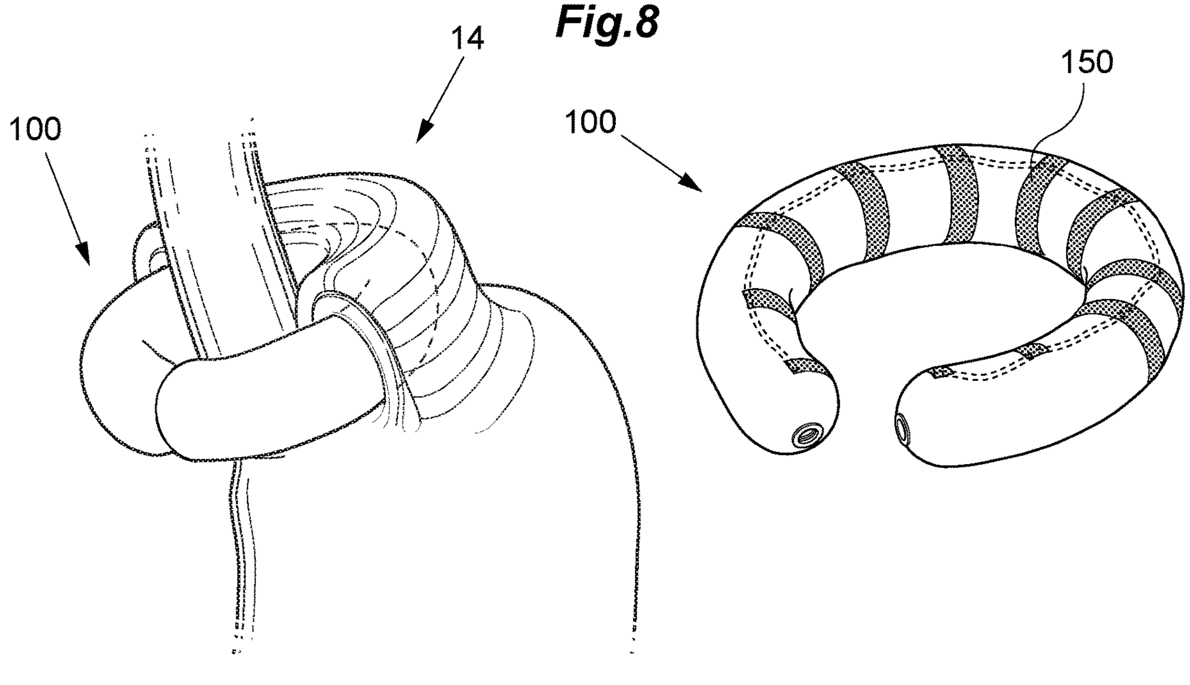
Figure 9:
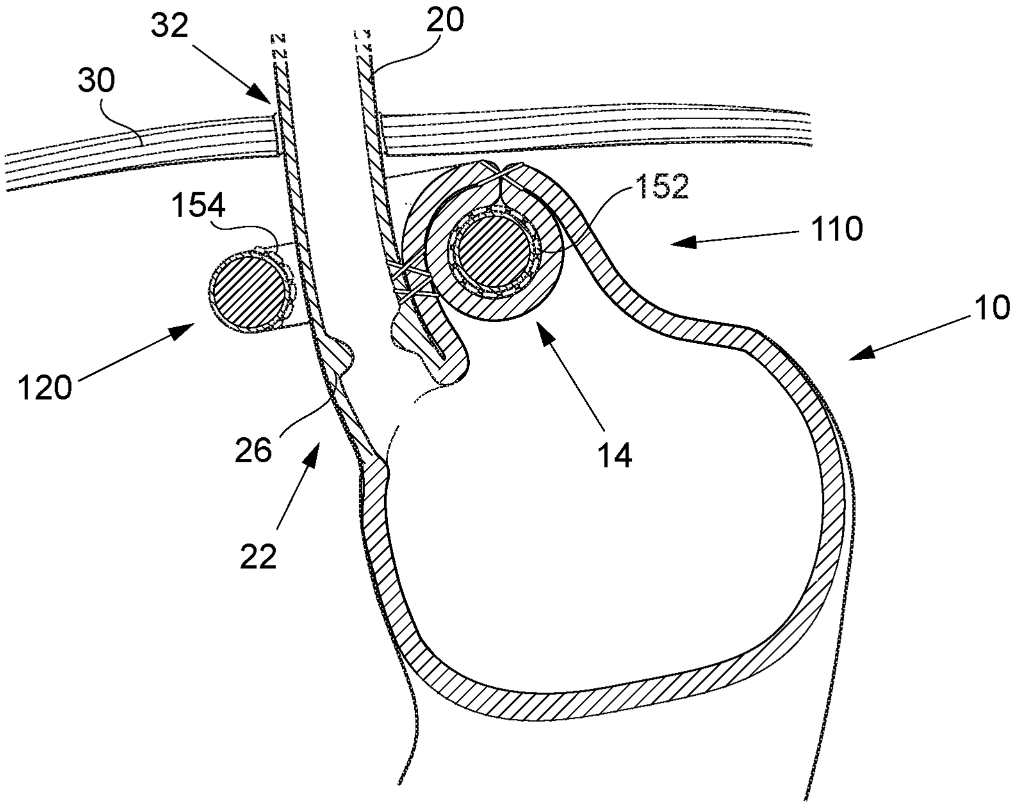

The ring-shaped body of the movement restriction device 110 may comprise an opening, or be possible to open, so as to allow the body to be arranged around the esophagus. After the movement restriction device 110 has been placed around the esophagus 20, the movement restriction device 110) may be affixed in a desired position, preferably at least partly above the cardia 22, by for example invaginating at least one of the first portion 110 and the second portion 120 by the outer wall of the stomach 10, or by wrapping a part of the stomach wall around at least a part of the ring-shaped body. Preferably, the movement restriction device 110 is implanted such that a part of the stomach wall is arranged between the movement restriction device 110 and the outside of the esophagus 20 to as to protect the tissue of the esophagus from being damaged by the movement restriction device 110, 120 abutting the tissue of the esophagus 20. As illustrated in the examples of FIGS. 7-9 a part of the fundus 12 may be arranged between the first portion 110 and the esophagus 20 and at the same time provide an affixation of the device to the stomach 10. Further, the movement restriction device may be provided with a shape and size allowing for a gap to be defined and maintained between the second portion 120 and the side of the esophagus opposite to the fundus side. Due to the affixation of the first portion 110 to the fundus 12, the separating gap between the second portion 120 and the tissue of the esophagus 20 may be maintained after implantation.

Figure 10:
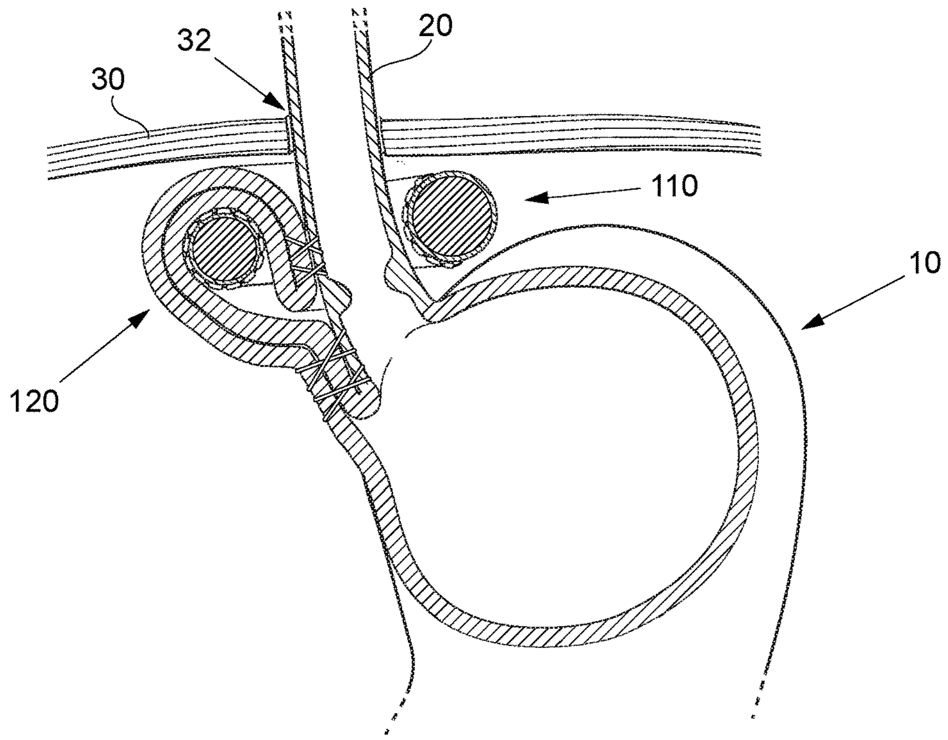

FIG. 10 shows an alternative example, in which the second portion 120 of the movement restriction device 110, 120 is arranged with a part of the stomach wall between the second portion 120 and the esophagus 20, on the side of the esophagus 20 opposing the fundus 12. On the fundus side, however, the first portion 110 may be arranged to define a distance or gap to the esophagus 20, similar to what is described FIGS. 7-9.

Figure 11:
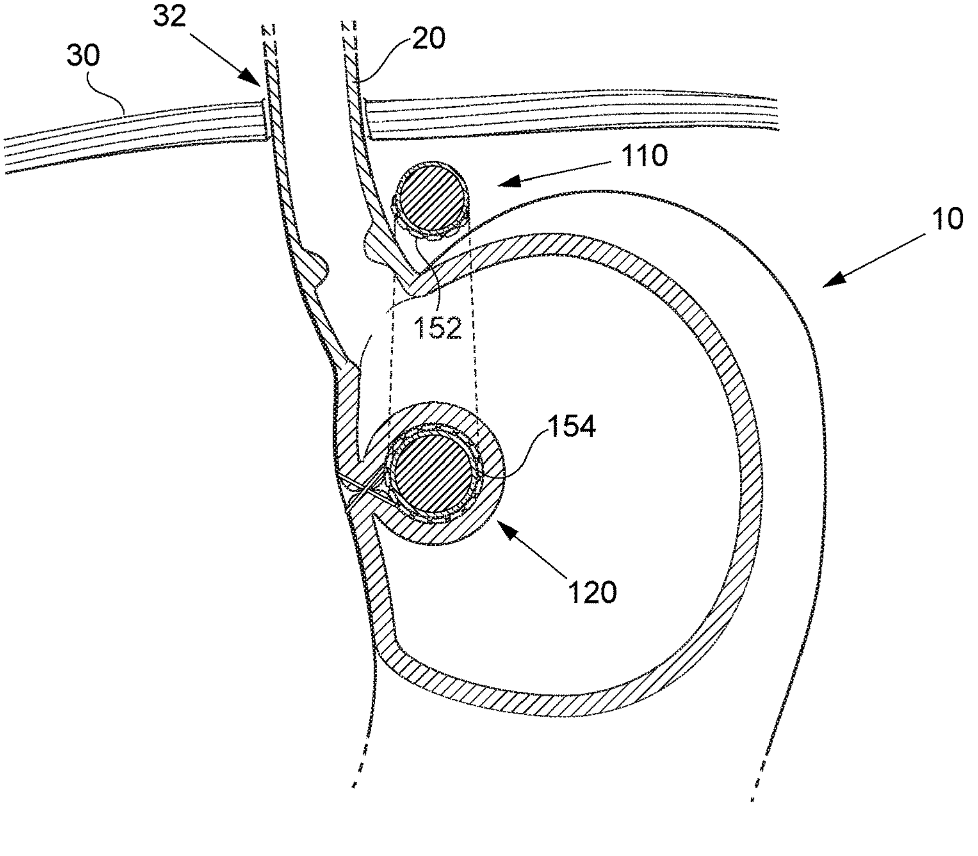

FIG. 11 shows a further example, wherein the first portion 110 may be placed at the angle of His and the second portion 120 invaginated by a pouch protruding into the stomach wall on the opposite side of the esophagus 20. The pouch may be arranged further down, compared to the example in FIG. 10. As a result, the first portion 110 and the second portion 120 may in FIG. 10 be implanted at substantially the same height relative to the cardia, whereas in FIG. 11 only the first portion 110 is implanted at least partly above the cardia 12.

Figure 12:
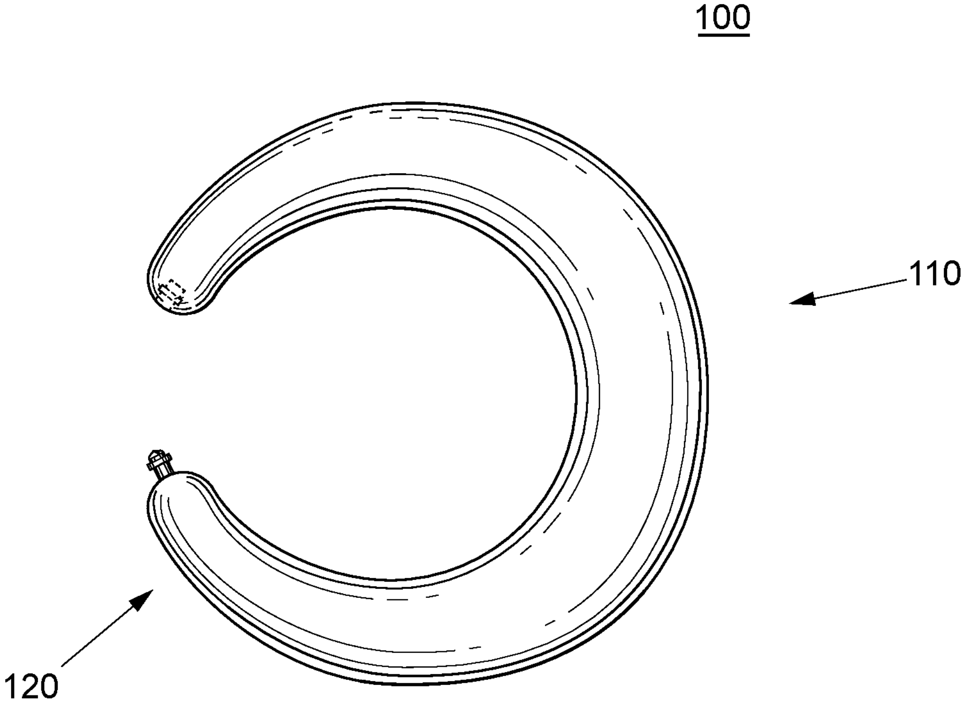
FIGS. 12-18J are schematic views of further examples of apparatuses for treating reflux disease.
Figure 13:
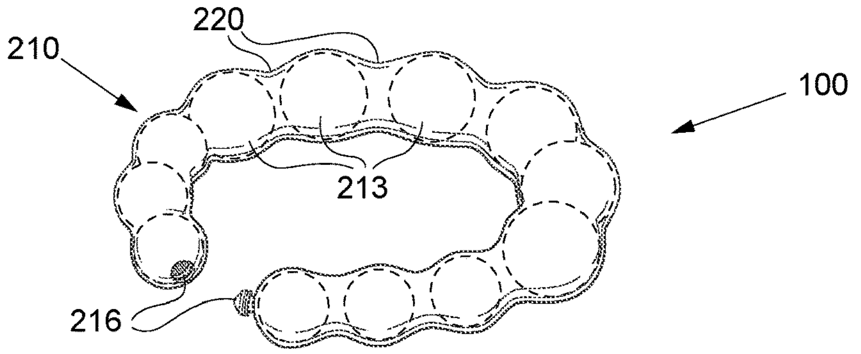

FIGS. 12 and 13 show various examples of at least partly ring-shaped movement restriction devices 110, 120, wherein the first portion 110 and the second portion 120 may be integrally formed into a single piece as shown in FIG. 12, or be formed of a plurality of core elements 213 arranged in a cover 220 as shown in FIG. 13. The movement restriction devices 110, 120 may for example conform to a torus, which may be closed or at least partly closed when implanted. Similar to the apparatuses illustrated in FIG. 7-11, the apparatus may be implanted in a position wherein it at least partly encircles the esophagus 20 and may function as a movement restriction device. The apparatuses may further comprise an electrode arrangement 150.

The electrode arrangement 150 of the examples shown in FIGS. 7-13 may comprise one or several electrode elements 152, 154, which may be arranged between at least one of the first portion 110 and the second portion 120 and the tissue against which the respective portion 110, 120 rests and operate according to principles similar to the ones discussed with reference to FIGS. 1-6. Thus, the electrode arrangement 150 may be configured to electrically stimulate and exercise muscle tissue of the fundus wall 12 or the esophagus 20 to improve conditions for long term implantation, and in some examples to electrically stimulate the cardiac sphincter muscle 26 so as to cause the sphincter to contract. In the latter case, the second portion 120 may be configured to act as an elongated support device for the electrode elements 154 for the cardiac sphincter stimulation, similar to the examples disclosed in connection with the previous figures.

The apparatus 100 may be configured to be at least partly invaginated, or covered, by the stomach wall along at least half of the toroidal length (i.e., the length as seen in the direction of the circumference encircling the esophagus). An example is illustrated in FIG. 8, wherein a toroidally shaped apparatus is at least partly covered by the fundus 12 along at least half the toroidal length. A similar arrangement is illustrated in FIGS. 7, 9, 10 and 11, wherein at least 25%, such as for example 50%, of the circumferential length of the apparatus may be at least partly invaginated or covered by stomach wall tissue.

As shown in the perspective views of FIGS. 8, 12 and 13 the apparatus 100 may be substantially ring-shaped and may comprises two end portions configured to be coupled to each other to form a closed ring. The end portions are configured to be releasably attached to each other, for example by means of a locking mechanism 216 or a fastener 216.

In case of the apparatus being at least partly ring-shaped, or conforming to a torus, the size of the apparatus may be characterized by its poloidal circumference and its toroidal circumference. The poloidal direction may be understood as a direction following a small circular ring around the surface, while the toroidal direction follows a large circular ring around the torus or ring, encircling the central void in which the esophagus may be arranged. In some examples, the poloidal circumference of the apparatus may be larger for the first portion 110 than for the second portion 120, as shown in FIGS. 12 and 13. Preferably, the first portion 110, forming the movement restriction device 110, may have a larger poloidal circumference so as to provide a mechanical stop hindering movement of the cardia towards and/or through the opening in the diaphragm.

In some examples, the first portion 110 may have a minimal width or cross section, as measured orthogonal to the toroidal direction, being 30 mm or larger, such as 40 mm or larger.

In some examples, a minimum poloidal circumference of the first portion 110 of the movement restriction device may be 150 mm or less, such as 130 mm or less, such as 110 mm or less, such as 90 mm or less, such as 70 mm or less, such as 50 mm or less, such as 30 mm or less.

In some examples, a maximum width of a cross section taken across a length direction (i.e. across toroidal direction) of the first portion 110, or movement restriction device 110, may be larger than a maximum width of a cross section taken across a length direction of the second portion 120, or support device 120.

The apparatus 100 may be affixed to the stomach wall in several different ways, all of which may include to at least partly wrap the stomach wall 10 around at least a portion of the apparatus 100 and affixing the stomach wall 10 to itself and/or to the esophagus 20. Some non-limiting examples of placing and affixing the apparatus 100 at the stomach wall 10 will now be discussed with reference to the ring-shaped movement restriction device 110, 120 disclosed in FIGS. 7-13.

In FIG. 7, the movement restriction device has been placed around the esophagus 20, such that the first portion 110 is arranged at the fundus side and the second portion 120 at the opposing side of the esophagus. A part of the fundus wall 12 has then been wrapped around the first portion 110 of the movement restriction device, from the outside of the device and into the center hole of the ring-shaped body, such that the part of the fundus wall 12 is arranged between the inner periphery of the ring-shaped body and the esophagus 20. The part of the fundus wall 12 that is wrapped around the first portion 110 may be considered as a "flap" formed of the fundus wall, which may be formed outside the ring-shape and pushed into the hole defined by the ring-shape and affixed to the esophagus 20.

FIG. 8 shows a perspective view of an apparatus 100 which may be similar to the one in FIG. 7, illustrating the affixation of the first portion 110 of the movement restriction device 110, 120 to the fundus 12. The part of the fundus that is wrapped around the first portion 110 and affixed to the esophagus may form a tunnel through which the ring-shaped body may extend on its way around the esophagus.

FIG. 9 shows an another example, in which the fundus portion closest to the angle of His has been folded to rest against the esophagus, from the angle of His and upwards along the esophagus, and affixed to the esophagus with one or several lines of fasteners, such as staples or sutures, extending along the esophagus. The first portion 110 of the movement restriction device may then be invaginated by another portion of the fundus, arranged further away from the angle of His, such that the movement restriction device is kept in place by the affixation to the esophagus and encircling the esophagus such that the second portion 120 is arranged on the opposite side of the esophagus 20.

Put differently, the method according to FIGS. 7 and 8 may result in the first portion 110 being arranged between the esophagus 20 and the portion of the fundus that is affixed to the esophagus 20, whereas the method according to FIG. 9 may result in the portion of the fundus 12 that is affixed to the esophagus 20 being arranged between the esophagus 20 and the first portion 110 of the movement restriction device. In the former example a part of the fundus may be pushed into the hole of the ring-shaped body from below, whereas in the latter example a part of the fundus may be pushed into the hole from above.

FIG. 10 shows a similar method as in FIG. 7, with the difference that it is the stomach wall on the side opposite to the fundus, i.e., the non-fundus side of the stomach wall, that is wrapped around the second portion 120 and introduced into the hole defined by the ring-shaped body and affixed to the esophagus. The portion of the stomach wall 10 closest to the esophagus 20 may further be folded to rest against the esophagus 20 and affixed to the esophagus 20 similar to the example of FIG. 9 so as to allow the second portion 120 of the movement restriction device to be arranged higher up, and preferably above the cardiac sphincter 26. The portion of the stomach wall closest to the esophagus 20 may be attached to the esophagus 20 before the stomach wall is wrapped around the second portion 120 and introduced into the hole defined by the ring-shaped body.

An apparatus for treating reflux disease of a human patient according to some examples will now be described with reference to FIGS. 14-21. FIGS. 14-21 illustrate an apparatus 100 comprising an elongated core 210 having a length that allows the core 210 to be arranged to at least partly encircle the esophagus 20 of an adult human the patient. The length is variable to allow the core 210 to be arranged in a constricting state for hindering fluid from passing from the stomach 10 into the esophagus 20, and in an expanded state for allowing food to pass into the stomach 10 in response to the patient swallowing. The apparatus may hence by used for treating reflux disease by assisting contraction of the cardiac sphincter 26 and hindering stomach contents to rise up into the esophagus 20. The transition from the constricting state into the expanded state may be caused by the food passing through esophagus 20, wherein the core 210 may be configured to exert an encircling pressure on the esophagus 20 in at least the constricting state. The encircling pressure may for example be generated by an attractor 212 configured to resiliently attracting adjacent portions 213 of the core to one another. Further, the apparatus 100 may according to some example comprise an electrode arrangement 150 comprising an electrode element 154 configured to be arranged between the apparatus 100 and the esophagus 20 and to electrically stimulate muscle tissue of the esophagus 20. The electrical stimulation may for example employed to stimulate the muscle tissue of the outer wall of the esophagus 20 so as to exercise the muscle tissue to improve the conditions for long term implantation of the apparatus 100, and/or to stimulate the cardiac sphincter 26 of the patient to cause the cardiac sphincter 26 to contract.

Figure 14:
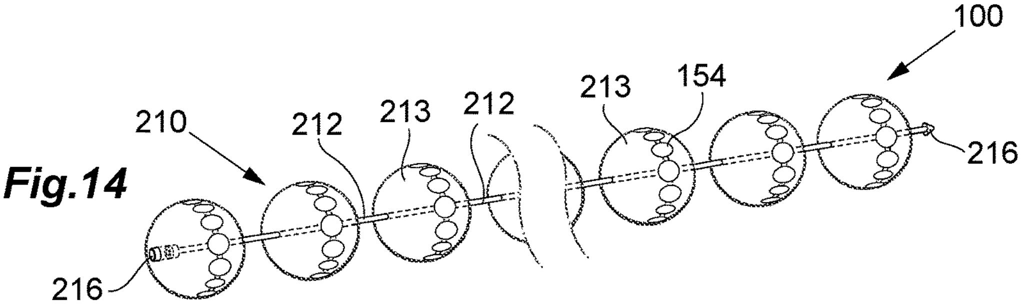

FIG. 14 shows a core 210 comprising an array of adjacent portions 213, wherein neighboring portions 213 of the array are interconnected by an attractor 212. The portions 213 of the array may for example be ball-shaped, having a substantially smooth outer surface suitable for resting against the tissue of the outer wall of the esophagus 20. The portions 213 may for example be formed of a metal or a polymer and may preferably comprise a biocompatible outer surface suitable for long-term implantation in the body. The attractors 212, connecting neighboring portions 213 to each other, may comprise an elastic element, such as an elastic band or string, allowing for the portions 213 to be resiliently pushed away from each other when entering the expanded state (e.g. in response to the patient swallowing a bolus of food), and pulling the neighboring portions 213 towards each other again to assume the constricting state for hinder stomach contents for pass into the esophagus 20. The core 210 may comprise a plurality of attractors 212, wherein each of the attractors 212 may have a first end connected to a first one of the portions 213 and a second end to a second one of the portions 213. Thus, each attractor 212 may be arranged to extend from a first one of a pair of neighboring portions 213 to the other one of the pair of neighboring portions 213. Alternatively, a single attractor 212 may be arranged to interconnect more than two portions 213 of the core 210. As indicated in FIG. 14, the attractor 212 may be formed of a string or band extending through each of the portions 213 of the core 210.

The core 210) may further comprise an attacher 216, or locking means, arranged at the end portions of the array of neighboring portions 213. The attacher 216 may for example comprise a first part, arranged at a first end portion, which can be inserted in, or attached to, a second part arranged at the other end portion of the core 210. Examples of attachers 216 include interlocking components, snap fasteners, and a screw assembles.

Alternatively, or additionally, resiliency of the core 210, which allows it to assume the expanded state and the constricting state and to exert an encircling pressure on the esophagus 20, may be achieved at least part by means of attractive forces between permanent magnets. In this case, the portions of the array may comprise permanent magnets 213, which may be arranged such that there is a mutual attraction between neighboring magnets 213 of the array. The magnets 213 may be attached to each other by a connector or link, such as a band or string 212 as outlined above, which may or may not be clastic so as to further contribute to the resiliency of the core and its ability to exert an encircling pressure on the esophagus 20. The magnets 213 may in some examples be referred to as attractors.

Figure 15:
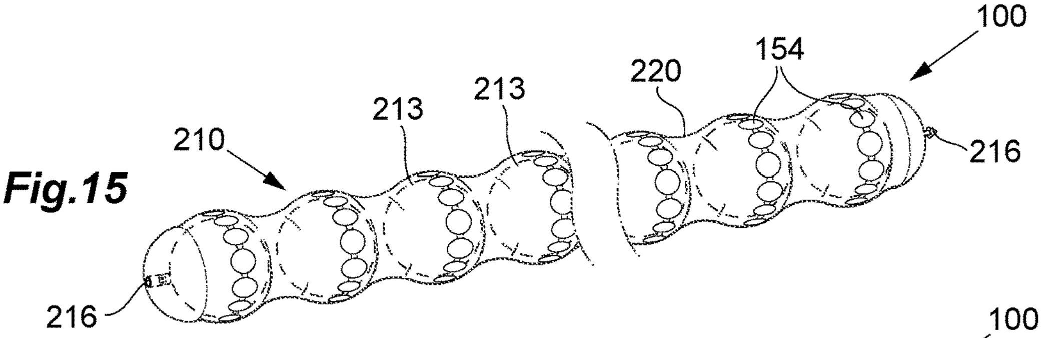

FIG. 15 shows an example wherein the core 210 comprises a plurality of magnetic portions 213, or permanent magnets 213 arranged in an array extending along the length direction of the elongated core 210. The example in FIG. 15 may thus be similarly configured as the apparatus 100 shown in FIG. 14, with the difference that the present apparatus 100) comprises a tubular cover 220 enclosing at least a part of the core 210. The cover 220 may comprise a plurality of portions 222 adapted to bend relative to each other to allow the core 210 to change between the constricting state and the expanded state, when the cover 220 is at least partly covered by fibrotic tissue, without being substantially hindered or impeded by the presence of the fibrotic tissue.

The implantation of a foreign body into the human body tends to cause an inflammatory response. The response generally persists until the foreign body has been encapsulated in a relatively dense layer of fibrotic connective tissue, which protects the human body from the foreign body. The process may start with the implant immediately and spontaneously acquiring a layer of host proteins. The blood protein-modified surface enables cells to attach to the surface, enabling monocytes and macrophages to interact on the surface of the implant. The macrophages secrete proteins that modulate fibrosis and in turn develop the fibrosis capsule around the foreign body, i.e., the implant. In practice, a fibrosis capsule may be formed of a dense layer of excess fibrous connective tissue. The inelastic properties of the fibrotic capsule may lead to hardening, tightness, deformity, and distortion of the implant, which in severe cases may result in revision surgery. On a medical device implanted in the abdomen, in the region of the stomach, the fibrotic capsule has been observed to typically grow a thickness of about 0.5-2 mm.

The presence of such a capsule of fibrotic tissue risks to hinder movement of the elongated core 210 of the apparatus 100 as described in connection with the examples of FIGS. 14-21. In particular, the presence of a relatively thick and inelastic layer of fibrotic tissue may hinder the core's 210 ability to change between the expanded state and the constricting state. To address this issue, the elongated core 210 may be arranged in, or at least partly covered by, the cover 220, which allows the core 210 to change its length without being substantially hindered by fibrotic tissue surrounding the cover 220. This is allowed by the cover 220 being capable of changing its length without stretching the material of which the cover 220 is formed. While the fibrotic tissue may be inelastic and thereby withstanding stretching, it may be easier to bend or fold. Thus, the cover 220 can be considered to make use of the fact that the fibrotic tissue may be more flexible than elastic in its nature, which allows for the apparatus to change its length (or circumference, as it is arranged around the esophagus 20) by folding or bending a plurality of portions of the core relative to each other. Put differently, the cover 220 may be configured to maintain a substantially constant surface as the core changes between the expanded state and the constricting state, thereby allowing for the length of the elongated core 210 to vary without stretching the surrounding fibrotic tissue to a corresponding degree. The cover 220 may thus have a length that exceeds a length of the core 210 when the core 210 is arranged in the constricting state.

FIG. 15 shows an example of a cover 220 which is tubular and arranged to accommodate an array of permanent magnets 213. The permanent magnets 213 may be attached to each other, for example by means of an attractor 212 as discussed above in connection with FIG. 14, or be freely arranged in the cover 220, without any interconnections. In some examples, the permanent magnets 213 may be affixed to the cover 220, such that each permanent magnet 213 may be maintained at a predetermined position relative to the cover 220. When going from the expanded state to the constricting state, neighboring magnets 213 may be pulled towards each other such that the distance between the magnets 213 in the array is reduced. The cover 220 may follow this movement by allowing the portions of the cover 220 arranged between the magnets 213 to fold or bend relative the portions of the cover 220 arranged at the respective magnets 213, such that the cover 220 is configured to be compressible and expandable in its length direction.

The cover 220 may comprises a biocompatible outer surface suitable for long-term implantation in the human body, and preferably for long-term implantation in a position where it rests against an outer surface of the esophagus 20. In some examples, the cover comprises a surface promoting tissue growth. The cover 220 may for example be formed of or at least comprise a polymer material (such as silicone, Peck®, polyurethane, UHWPE or PTFE,). Further, the cover may have a wall thickness of 0.1-5 mm. In some examples the cover 220 may be provided with a coating, such as Parylene, polytetrafluoroethylene (PTFE), or polyurethane, or a combination of such coatings, for improving the resistance to wear.

Further, the cover may comprise an electrode arrangement 150, similar to the one discussed above in connection with the examples of FIG. 14. The electrode arrangement 150 may hence comprise at least one electrode element 154 configured to be arranged between the cover 220 and the esophagus 20 for electrically stimulating muscle tissue of the esophagus 20. The electrode element 154 may for example be configured to stimulate muscle tissue at the outer surface of the esophagus so as to improve the conditions for long-term implantation, and/or the cardiac sphincter 26 so as to cause it to contract.

Figure 16:
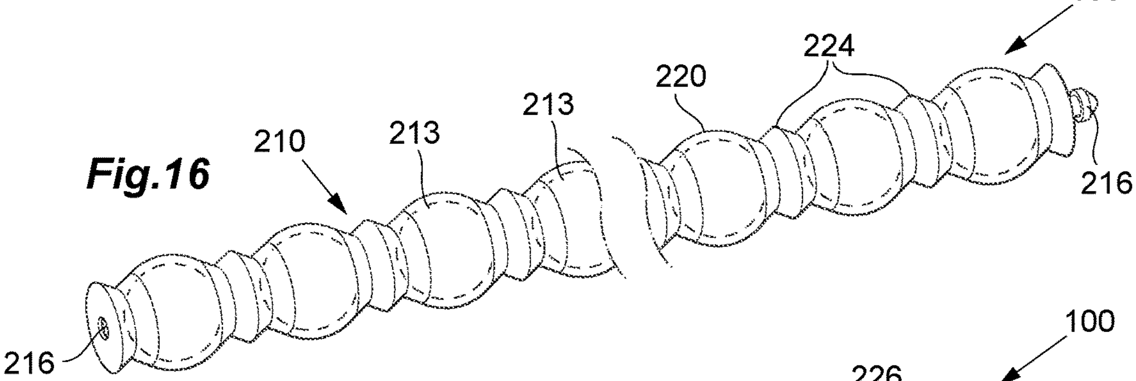

FIG. 16 shows an example of an apparatus 100 that may be similarly configured as the apparatuses discussed in connection with FIGS. 14 and 15. However, as indicated in the present figure, the cover 220 may comprise at least one predefined fold 224 along which the cover is allowed to fold in response to the core 210 varying its length. In some examples, the cover 220 may comprise a bellows-shaped structure of a plurality of lowered portions 225 and elevated portions 226 that allow the cover 220 to vary its length while maintaining its surface area substantially constant. A distance between two elevated portions 226 may be long enough to prevent growth of fibrotic tissue directly connecting to adjacent elevated portions 226. Thus, fibrotic tissue may grow on the surfaces of the lowered portions 225 and the elevated portions 226, but due to the distance between adjacent elevated portion 226 fibrotic tissue may be hindered from growing directly from one elevated portion 226 to another elevated portion 226 without first passing over the intermediate lowered portion 225. The cover 220 may hence comprise a ridges and grooves, or elevated 226 and lowered 225 portions dimensioned such that the connective tissue follows the surface of the elevated 226 and lowered 225 portions and leaves a separating gap between neighboring elevated portions 226, or ridges. In case the fibrotic tissue has a thickness of about 0.5-1.5 mm, as an example, the distance between adjacent elevated portions 226 may be greater than twice the maximum thickness of the fibrotic tissue, i.e., greater than about 3 mm.

Figure 17:
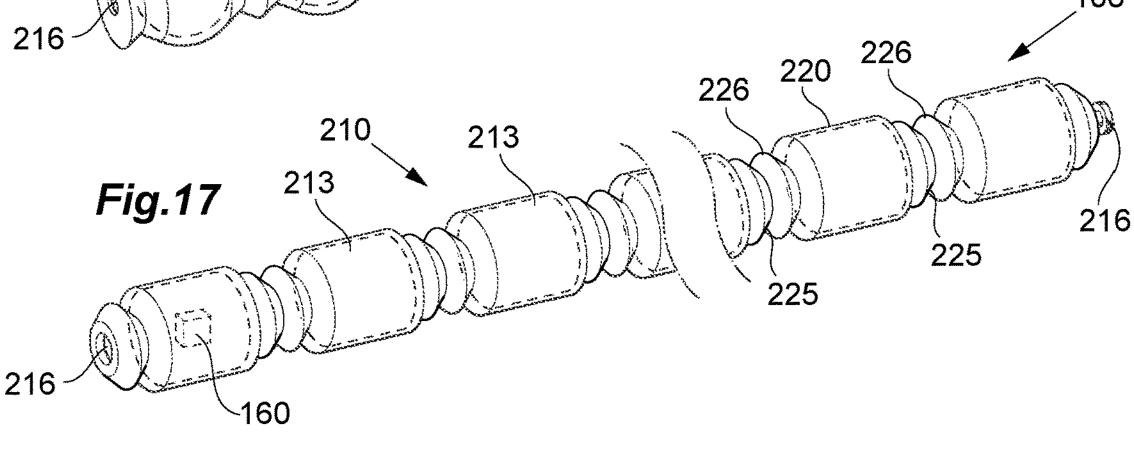

FIG. 17 shows an apparatus 100 which may be similarly configured to the examples of FIGS. 14-16. However, FIG. 17 further discloses an implantable energy source 160 for supplying the electrode arrangement 150 with electrical power for the electrical stimulation of the muscle tissue. The energy source 160 may be integrated in the in the elongated core 210, such as in one or several of the portions 213, as shown in the present figure. However, the energy source 160 may in some examples be arranged outside the apparatus 100 as well, forming as a separate structural entity that can be implanted in the abdomen or elsewhere, such as subcutaneously. The energy source 160 may comprise a primary cell, i.e., a battery designed to not be recharged. In further examples, the energy source 160 may comprise a secondary cell designed to be recharged, preferably by means of an external energy source located outside the patient's body. Various examples of charging of the energy source 160 and powering of the electrode arrangement 150 is described in connection with FIGS. 42-44, together with examples of how to control and operate the electrode arrangement 150.

Figure 18A:
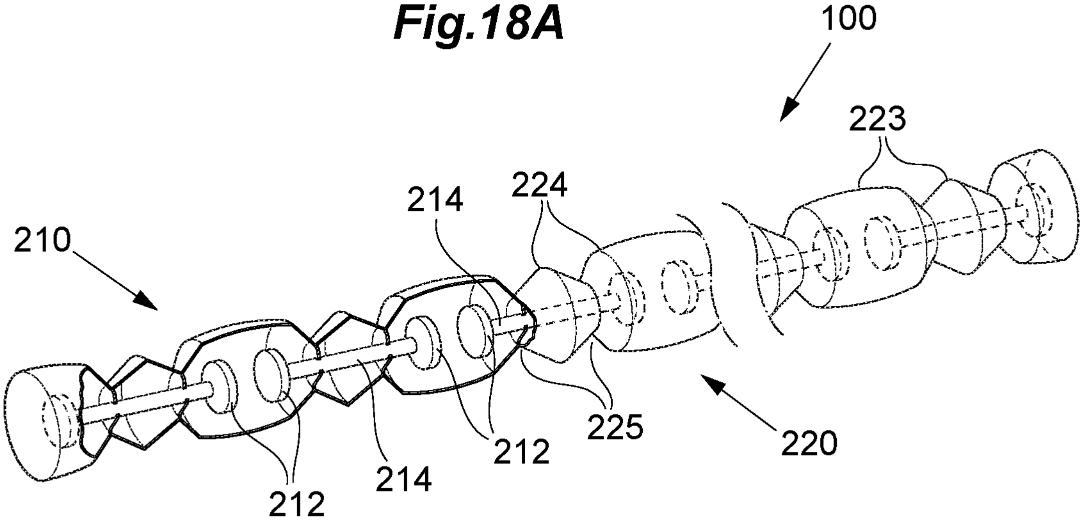
Figure 18B:
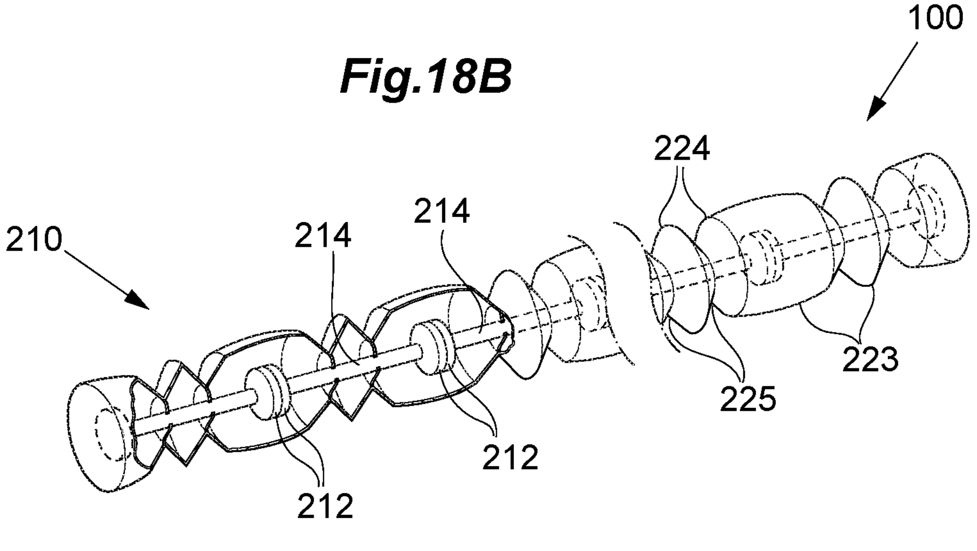

FIGS. 18*a* and 18*b* show an apparatus 100 which may be similarly configured as the examples shown in FIGS. 14-17. The apparatus 100 may comprise an elongated core 210 having a variable length which allows the apparatus to be arranged to at least partially encircle the esophagus 20 in a constricting state for hindering stomach contents from passing into the esophagus 20, and an expanded state for allowing a food bolus to pass into the stomach 10 in response to the patient swallowing. The encircling pressure exerted on the esophagus 20 may be generated by a plurality of attractors 212, which in the present example may comprise permanent magnets arranged in mutually attracting pairs. In FIGS. 18*a* and 18*b* the elongated core 210 is formed of an array of links 214, such as rods or levers, extending along the length direction of the elongated core 210 and having a permanent magnet 213 attached to its respective end portion. By arranging the magnets 213 of the end portions of the links 214 such that magnets 213 of neighboring links attract each other, the attracting forces between the magnets 213 can be utilized to cause the elongated core to transition from an expanded state shown in FIG. 18*a* to a constricting state shown in FIG. 18*b*. In the constricting state indicated in FIG. 18*b*, adjacent magnets 213 are arranged closer to each other than in the expanded state in FIG. 18*a*. If allowed to move freely, adjacent magnets 213 may abut each other. When the patient swallows food or liquids, the passing matter may cause the esophagus 20 to expand radially. This expansion may generate an expanding force acting on the apparatus 100, which may eventually overcome the attracting forces between the magnets 213 and thereby cause the core 210 to expand its circumference and assume the expanded state. Once the food or liquid has passed the apparatus 100, the attracting (or constricting) forces within the apparatus 100 may once again overcome the expanding forces of the esophagus 20, and the core 210 may hence reduce its circumference and the apparatus 100 return to the constricting state.

The apparatus 100 may further comprise a cover 220 enclosing at least a part of the elongated core 210. The cover 220 may be similar to the cover 220 discussed in connection with FIGS. 15-17 and may be configured to hinder fibrotic tissue from growing directly on the elongated core 210. Further, the cover 220 may be configured to provide mechanical support to the elements of the elongated core 210, such as the links 214 provided with the magnets 213. The cover 220 may be tubular, comprising a wall at least partially surrounding or encasing the elongated core 210 and having an at least partly hollow interior capable of accommodating the elements of the core 210. According to the example of the present figure, the cover 220 may comprise an array of tubular segments 222 distributed along the length of the elongated core 210. In the present example, a segment 222 may be configured to accommodate at least two mutually attracting magnets 213, wherein a first one of the magnets 213 may be attached to an end portion of a first link 214 and a second of the magnets 213 may be attached to an end portion of a second, neighboring link 214 of the elongated core 213. The variation of the length of the core 210, as the apparatus 100 transitions between the expanded state and the constricting state, may thus be achieved by said magnets moving towards and away from each other in the length direction of the core 210 and within the segment 222 in which they are accommodated.

The cover 220 may be configured to follow/allow the variation of length of the core 210 by means of a first portion and a second portion of the cover 220 bending relative to each other so as to compensate for the varying length without stretching the material of the cover 220. The first portion and the second portions may be separated by a fold 224 as indicated in the figure and may further be considered as a lowered portion 225 and an elevated portion 226, respectively. Put differently, the segment 222 of the cover 220 may be configured to act as a bellows compressing and expanding in response to the elongated core 210 contracting and expanding. The cover 220 may comprise one or several further segment 223 arranged between neighboring segments 222 comprising the magnets 213 as outlined above and accommodating a portion of the link 214 interconnecting the magnets 213.

The dimensions and configuration of the cover 220 may be adapted to allow fibrotic tissue to at least partly encapsule the outside of the cover 220, preferably in a layer following the outer contour of the segments such that the different portions of the cover 220 may bend and fold relative to each other while bending, rather that stretching, the fibrotic tissue.

The cover 220 may further comprise an electrode arrangement 150, similar to the cover 220 disclosed in FIGS. 15 and 16, for electrically stimulating muscle tissue of the esophagus 20. Preferably, the electrical stimulation may be adjusted to compensate for the presence of fibrotic tissue, which may prevent the electrode element from directly abutting or engaging the muscle tissue. Thus, the presence of fibrotic tissue in the interface or junction between the electrical element and the muscle tissue may be compensated for by adjusting the electrical stimulation signal accordingly, as will be discussed in more detail in connection with FIGS. 38-41.

Figure 18C:
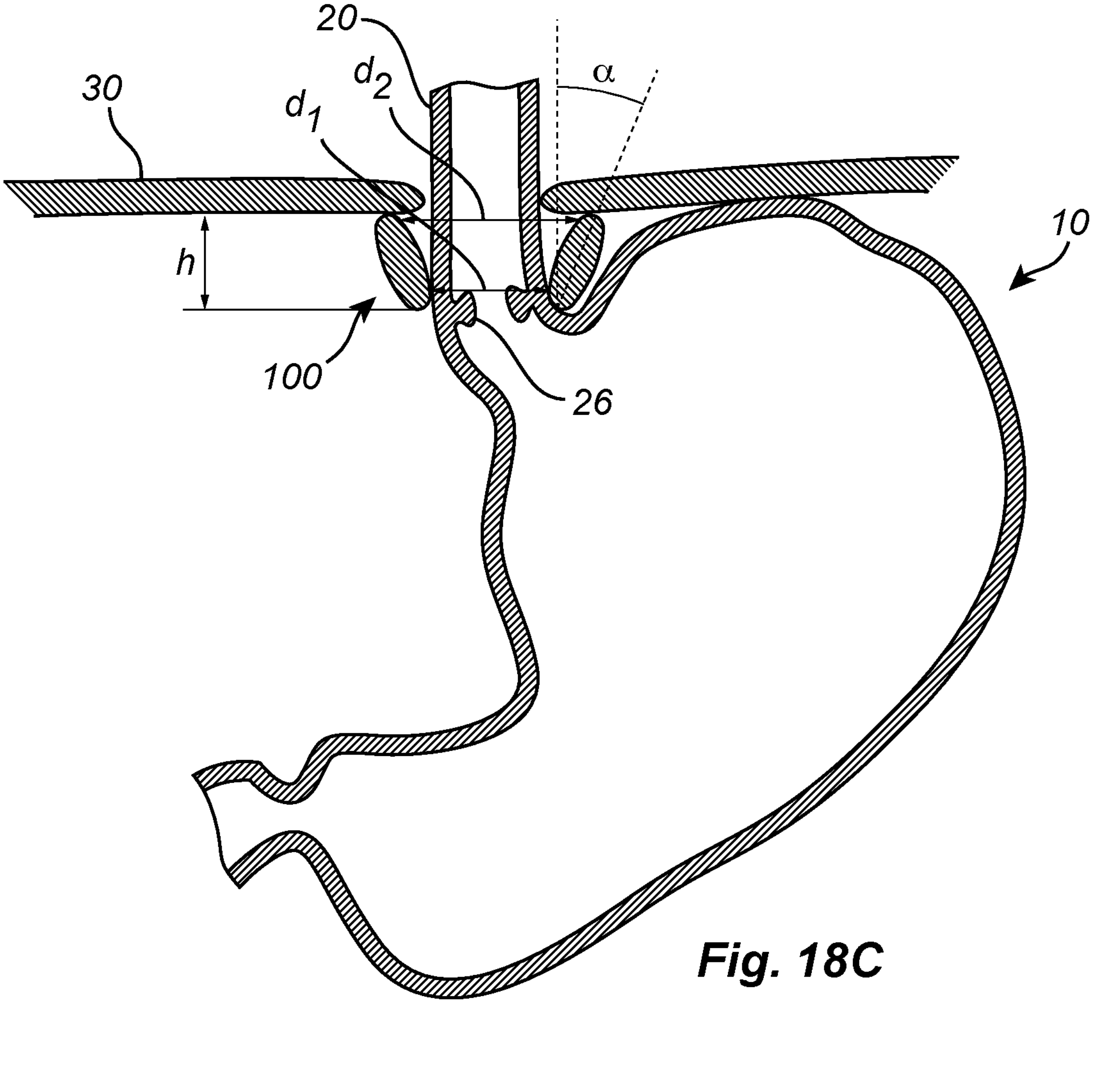
Figure 18D:
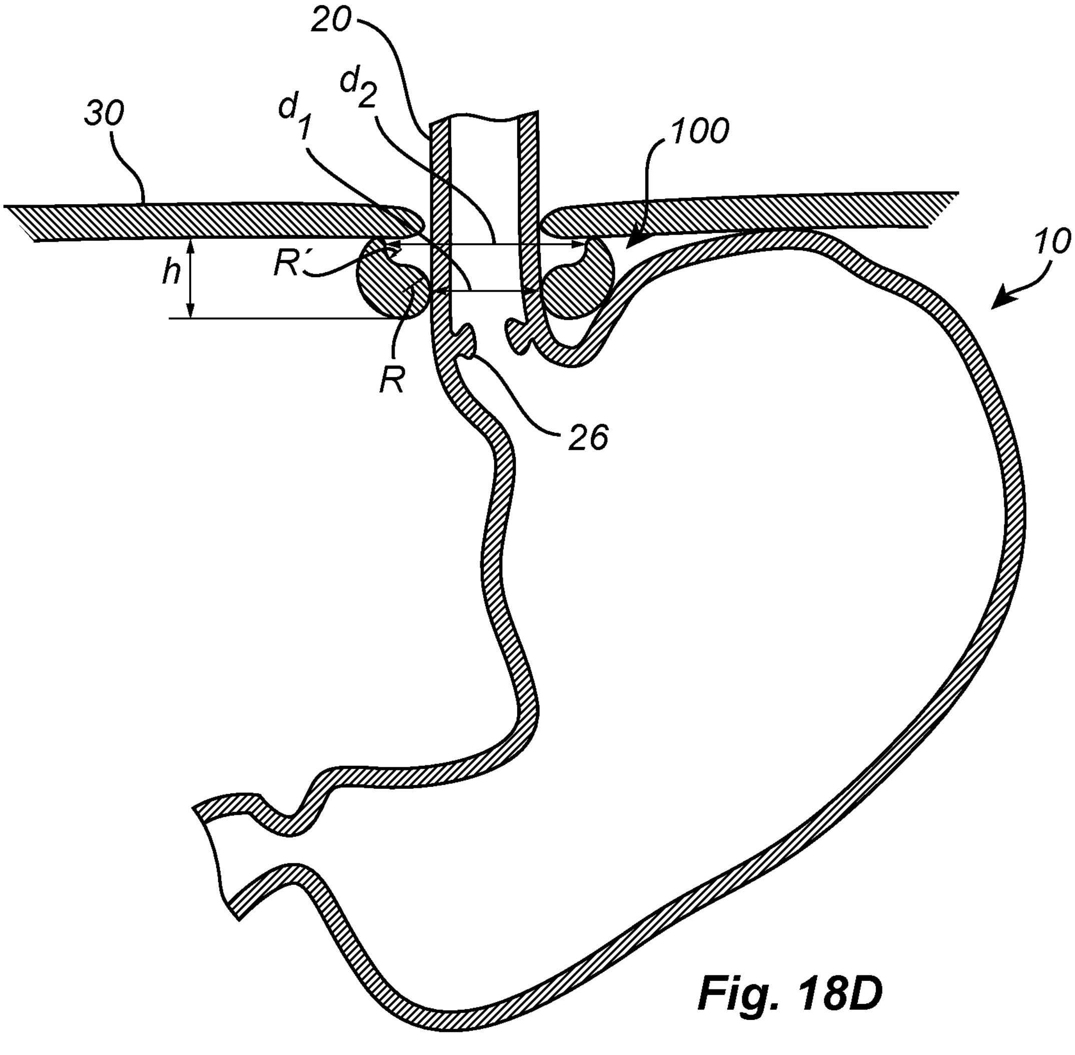
Figure 18E:
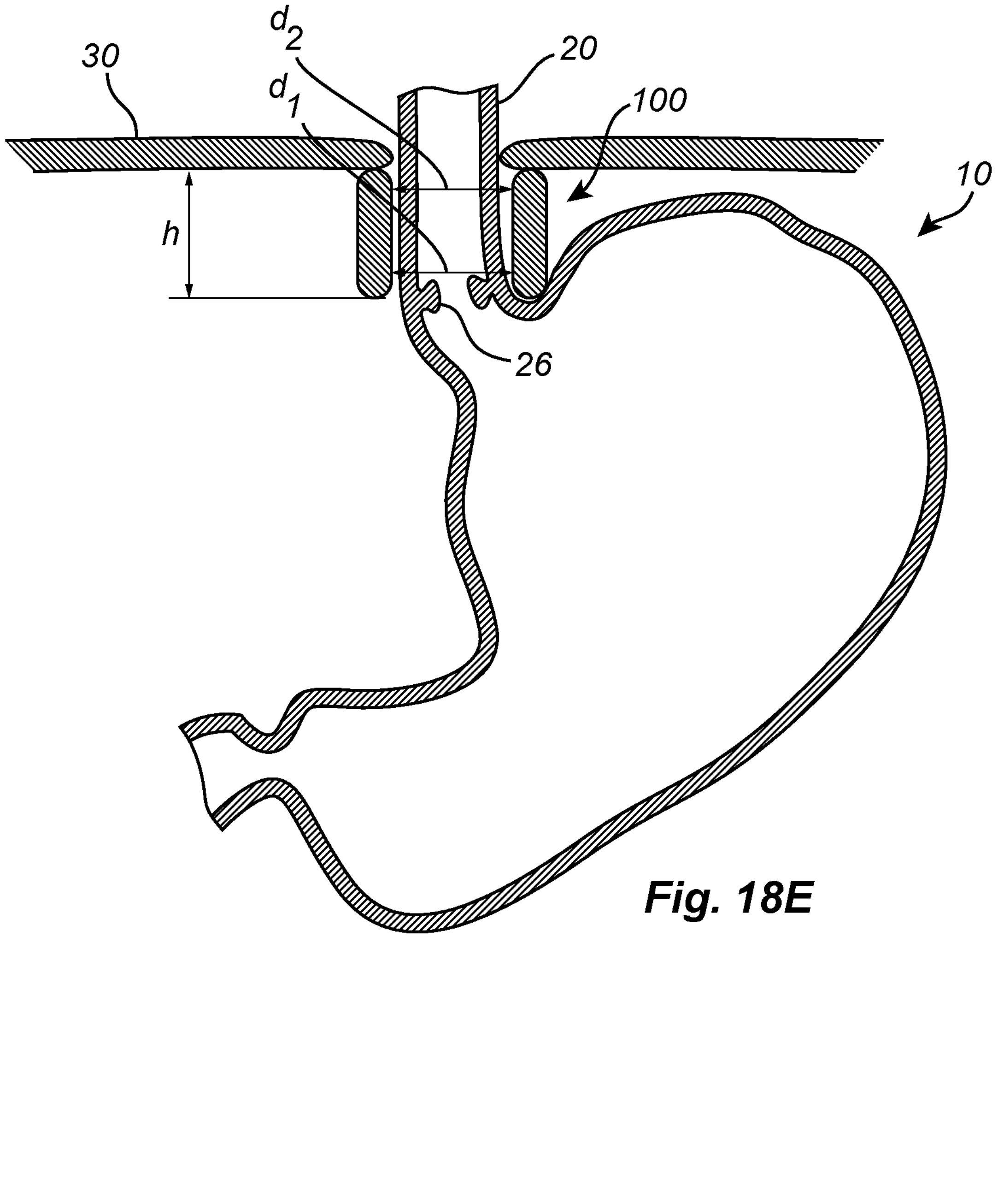

FIGS. 18C-J shows examples of an apparatus 100 which may be similarly configured as the embodiments discussed in connection with FIGS. 7-17 and 18A-B. However, as illustrated in FIGS. 18C-E the apparatus 100 may be configured to, when implanted, have a limited or none touching contact with tissue at the outside of the esophagus 20 at positions between the cardiac sphincter 26 and the diaphragm 30. While the outermost layer of the stomach wall 10, the tissue also being referred to as serosa, may be relatively robust and insensitive to mechanical contact with implants, the tissue forming the outermost layer of the esophagus 20 has been observed to be more sensitive to contact with implants, eventually leading to tissue damages and migration. Please refer to the description of FIG. 39 for more details regarding the serosa and the tissue of the esophagus 20. The serosa may extend also to the cardia and may cover a lower portion of the esophagus 20. The serosa has been observed to cover the lower portion of the esophagus 20 extending to the cardiac sphincter 26, above which there may be no serosa layer on the outside of the esophagus. The exemplifying embodiments shown in FIGS. 18C-J are provided to illustrate a beneficial arrangement in which the apparatus has a reduced impact on the non-serosa covered part of the esophagus 20. The apparatus 100, which may be configured to be arranged to at least partly encircle the esophagus 20, may for instance be formed as a gastric band similar to the ones disclosed above. Preferably, the apparatus 100 band is arranged to not abut or touch the outside of the esophagus 20, at least on upper regions not covered by the more robust serosa layer that also covers the outside of the stomach 10. This may be achieved by providing, or arranging, a apparatus 100 having an increasing inner width $d_1$, $d_2$ or diameter in a direction away from the stomach/cardiac notch. The width d1 may hence be smaller closer to the cardiac sphincter 26 to allow the apparatus 100 to exert a supporting or constricting pressure on the cardiac sphincter 26, and increase to a larger width d2 in the direction towards the diaphragm 30 so as to reduce the risk of the apparatus 100 touching or exerting a substantial pressure on the outside of the esophagus 20. As illustrated in the figures, the apparatus 100 may extend along a height h when implanted, allowing the apparatus to abut the diaphragm 30 and thereby act as a stop hindering the cardia from sliding towards and possibly past the diaphragm opening. The increasing inner width d1, d2 of the apparatus may also be expressed as the inner surface of the apparatus inclining in relation to the outer wall of the esophagus 20, or pointing away from the same. The increasing width is in FIG. 18C illustrated by the angle α, indicating the difference between the inner surface of the apparatus 100 and the outer surface of the esophagus 20 in a direction towards the diaphragm opening.

In other examples, the portions of the apparatus 100 may be provided with a convex part with radius R arranged at the cardia, or cardiac sphincter 26, and configured to abut, or rest against, the serosa layer of the cardia. It may further be provided with a concave part with radius R', arranged to face the esophagus 20 and such that a spacing or gap is formed between the concave surface of the apparatus 100 and the esophagus 20. Similar to FIG. 18C, the apparatus 100 may have a height h, when correctly implanted in the patient, allowing the apparatus 100 to touch or abut the diaphragm 30.

In yet an example, the apparatus 100 may conform to cylinder having a substantially constant width d1, d2 that is larger than the outer width of the esophagus 32. With this arrangement, the apparatus can be arranged around, or at least partly enclose, the esophagus 20 to provide a mechanical stop against the diaphragm (due to its height h) to prevent the cardiac sphincter 26 from moving towards and possibly past the diaphragm 30, in a similar way as described above, while still leaving a spacing or gap to the tissue of the outside of the esophagus 20. Beneficially, this reduces the risk of the apparatus 100 touching the more sensitive tissue of the esophagus 20 not covered by serosa and hence the risk of damaging the esophagus 20 during long term implantation.

Figure 18F:
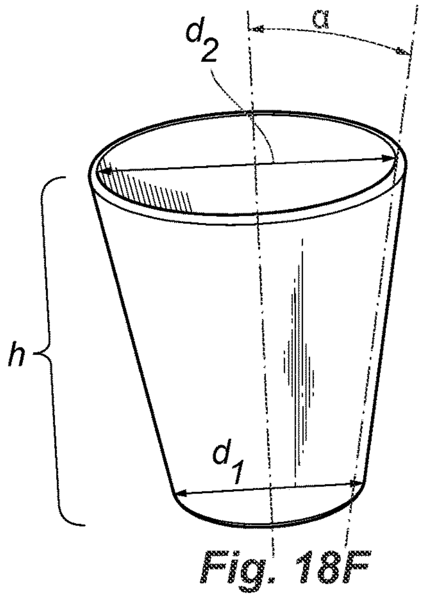
Figure 18G:
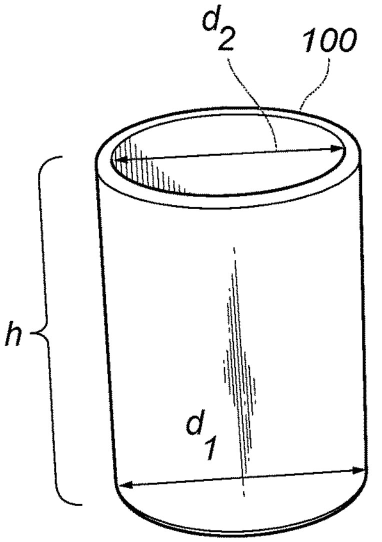

The apparatuses 100 described in the above figures, such as FIGS. 18C-E, may be formed as a substantially cylindrical band or sleeve that can be arranged around the esophagus 20. A few examples are illustrated in FIGS. 18F-J, having a lower width d1 (adapted to be arranged at the cardia) and an upper width d2 (adapted to be arranged at, or closer to, the diaphragm 30). The cylindrical shape may have a substantially uniform cross section as illustrated in FIGS. 18E and 18G, or a conical shape with a widening cross section as illustrated in FIGS. 18C and 18F.

Figure 18H:
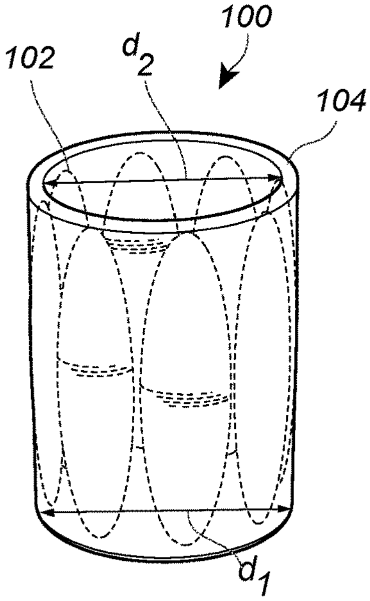
Figure 18I:
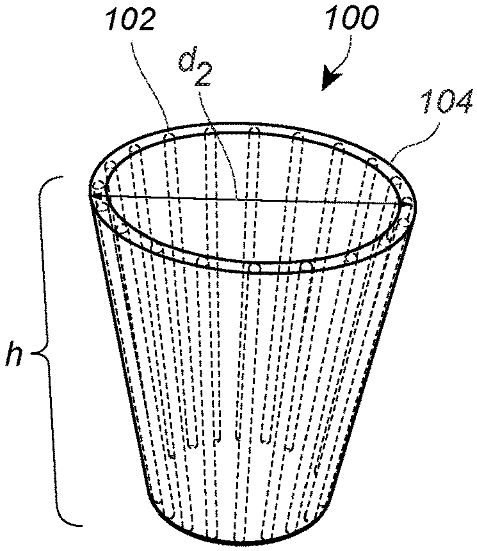

In the embodiment shown in FIGS. 18F and 18I, the upper width d2 is more than 1.2 times the lower width d1, or preferably more than 1.3 times the lower width d1, or preferably more than 1.4 times the lower width d1. The angle α is more than 3°, or preferably more than 5°, or preferably more than 7°, or preferably more than 10°. The height h is preferably exceeding 20 mm, more preferably exceeding 30 mm and more preferably exceeding 40 mm.

Figure 18J:
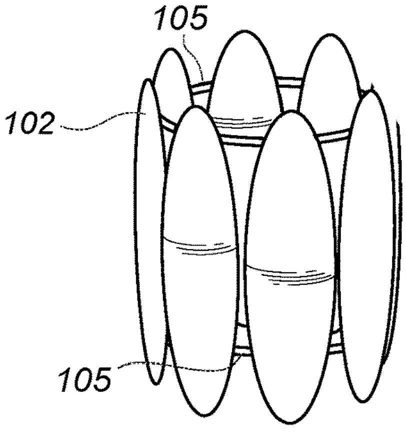

The apparatuses 100 described in the above figures may in some examples comprise a plurality of bodies 102 enclosed or at least partly secured in a holding means 104, 105 such as an elastic or flexible member, configured to keep the bodies 102 in an intended position in the apparatus. As illustrated in FIGS. 18H-J, the bodies 102 may be elongated, such as ellipsoids or rod shaped, or ball shaped. The bodies 102 may be attached to, or held in place by, a holding means 104, 105 being a flexible or elastic sheet of a biocompatible fabric or polymer material, such as silicone, or one or several strings or wires 105. The holding means 104, 105 may in some examples form a sleeve configured to be arranged around the lower part of the esophagus 20, and to be flexible to allow at least the lower portion of the apparatus to vary its width as the patient swallows and a bolus passes through the esophagus 20. The bodies may be provided with a shape allowing them to point away from the esophagus at the upper portion of the implanted apparatus. This may be achieved by providing the bodies with a surface, facing the esophagus, which bends or tapers away from the esophagus when moving upwards from the bottom portion of the implanted apparatus. Further, the bodies 102 may be magnetic, as previously discussed. The magnetic attracting forces between neighboring bodies 102 may be employed to maintain a pressure on the lower part of the esophagus, such as the cardia or cardiac sphincter 26.

Figure 19A:
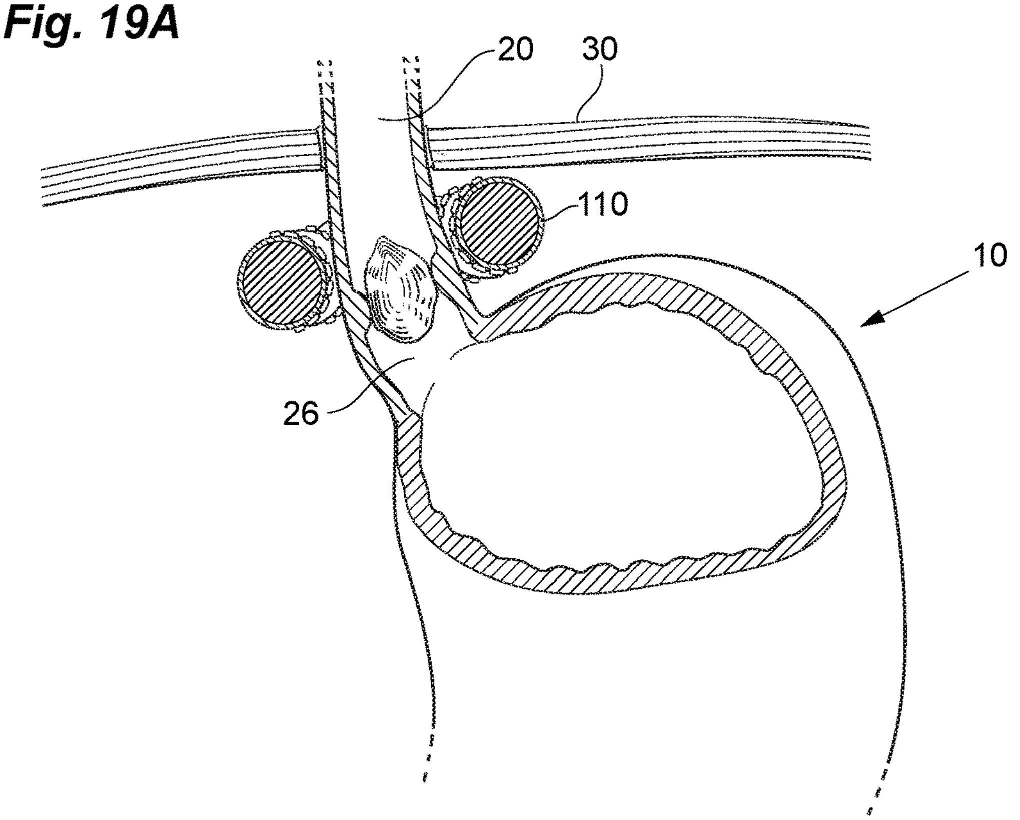
FIGS. 19A and 19B are schematic views of an example of an apparatus for treating reflux disease, wherein the apparatus is implanted in the body of the patient.
Figure 19B:
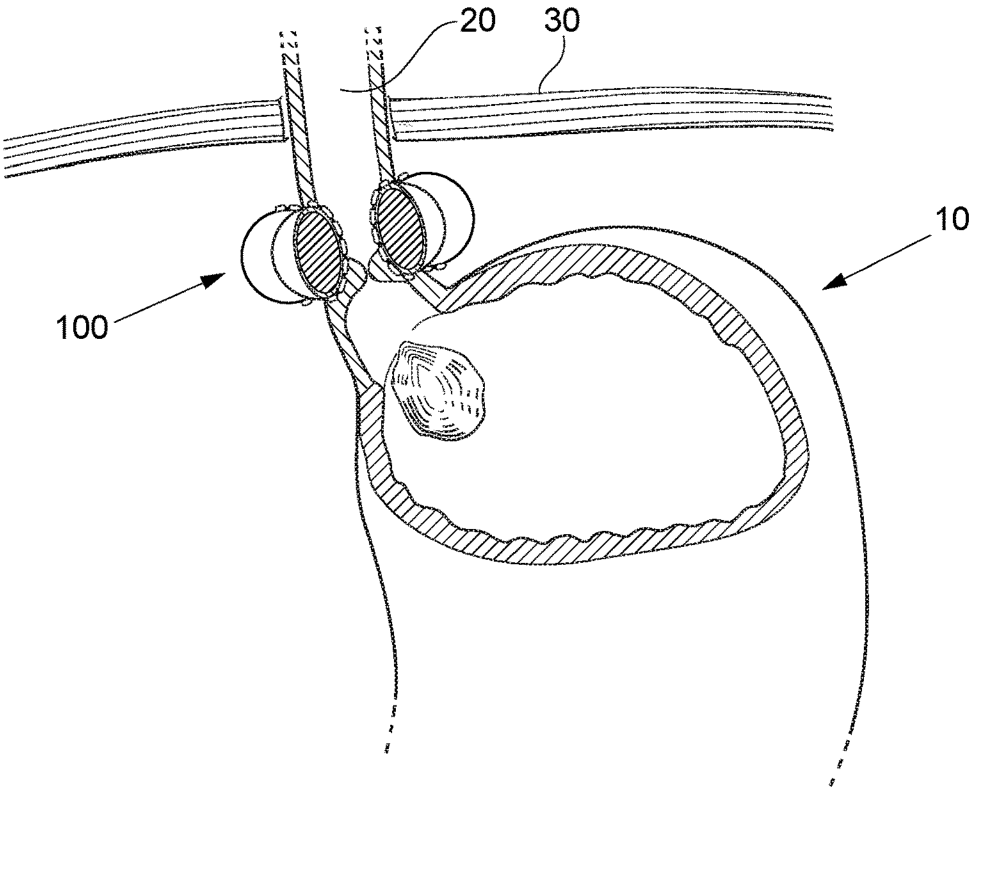

FIGS. 19*a* and 19*b* illustrate an apparatus 100 according to any of the examples shown in FIGS. 14-18 when implanted around the esophagus 20 of a human patient. Preferably, the apparatus 100 may be placed at the same height as the cardiac sphincter 26 so as to help the sphincter to contract. The apparatus 100 may be affixed to the esophagus 20 so as to maintain its desired position, for example by means of sutures of staples. The affixation by means of attachers such as staples or sutures may be of a temporary nature, and the apparatus 100 may be more permanently affixed by fibrotic tissue eventually encapsulating the apparatus 100. In further examples, the apparatus 100 may be arranged at the junction between the esophagus 20 and the stomach 10.

The apparatus 100 may be configured to exert an encircling pressure on the esophagus 26 so as to constrict the esophagus 26 and thereby reduce the risk for stomach content from entering the esophagus 26. The resilient forces within the apparatus 100, causing the elongated core 210 to contract, may be generated by an elastic means, such as an elastic band or a spring, or by magnetic attraction as outlined above, and may be balanced so as to allow food and liquids to pass through the esophagus 20 in response to the patient swallowing, and to allow stomach contents to pass through the esophagus 20 in response to the patient belching or vomiting.

The apparatus 100 may further comprise an electrode arrangement 150 as outlined above, for electrically stimulating and constricting the cardiac sphincter 26 and/or exercising the muscle tissue of the esophagus 20 so as to improve the conditions for long-term implantation.

Figure 20A:
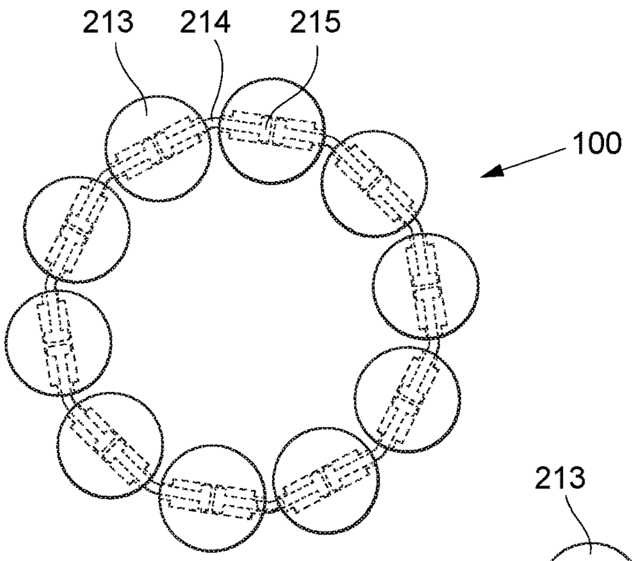
FIGS. 20A-21 are schematic views of various examples of apparatuses for treating reflux disease.
Figure 20B:
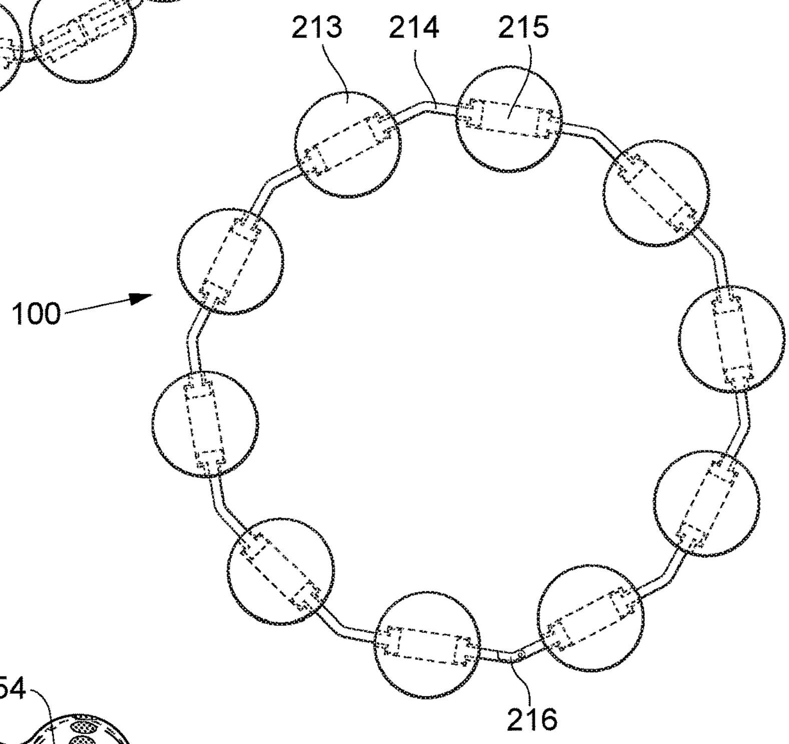

FIGS. 20*a* and 20*b* show an apparatus 100 according to an example, which may be similarly configured as the apparatuses 100 discussed above with reference to FIGS. 14-19. The apparatus 100 comprises an elongated core 210 comprising an array of adjacent portions, or core elements 213, which can be moved towards each other and away from each other in the array so as to vary the length of the elongated core 210. Further, the end portions 216 of the core 210 may attached to each other so as to form an annular or ring-shaped array, having a variable circumference and being possible to arrange to at least partly encircle the esophagus 20 of the patient. At least two of the core elements 213, or bodies 213, in the array may be provided with a respective permanent magnet adapted to attract each other and thereby generate a contracting force within the core 210.

The core 210 may further comprise a plurality of links 214 connecting the bodies 213 of the array to each other. The links 214 may be relatively rigid so as to provide mechanical support and guide the bodies 213 of the array in their movement towards and away from each other. Thus, the links 214 may be configured to maintain substantially the same shape during the operation of the apparatus, i.e., as the elongated core 210 changes between the expanded state and the constricting state. The links 214 may be configured to extend into at least one of the bodies 213 it interconnects in response to the bodies 213 moving towards each other. As indicated in the present figures, the body 213 may comprise a channel or passage 215 extending into the interior of the body 213. The channel 215 may be configured to allow an end portion of the link 214 to slide back and forth along the channel 215 in response to the core 210 varying its length. The end portion of the link 214 may further comprise a stop or abutment hindering the link 214 from leaving the channel 215 and thereby disconnect the bodies 213 of the array from each other.

FIG. 20*a* show the elongated core 210 in the constricting state. In the particular example illustrated in the figure, the elongated core 210 has assumed a minimum length (or circumference) defined by the bodies 213 of the array abutting each other. It will however be appreciated that the constricting state may be assumed also without the bodies 213 of the array touching each other. It may suffice if the bodies 213 of the array are arranged closer to each other than in the expanded state.

The constricting state may be maintained by the attractive forces between adjacent bodies 213 in the array. The forces may be overcome by expanding forces from within the esophagus 20, pushing the bodies 213 of the array apart so that the elongated core 210 assumed the expanded state instead. The expanding forces may for example be caused by the patient swallowing food, belching, or vomiting. Preferably, the attractive forces are strong enough to hinder or at least reduce passage of stomach contents into the esophagus in other cases than when the patient belches or vomits.

FIG. 20*b* shows the apparatus 100 in FIG. 20*a* in the expanded state, and in the particular example in a maximally expanded state defined by the stop 217 at the ends of the links 214.

Similar to the previous examples of the apparatus 100, an electrode arrangement 150 may be provided between the bodies 213 of the array and the surrounding tissue when implanted. The electrode arrangement 150 may for example comprise one or several electrode elements 154 arranged on the outer surface of one of several of the bodies 213 of the array. Similar to the examples discussed with reference to FIGS. 1-19, the electrode element(s) 154 may be configured to operate as a cathode during the stimulation, using the tissue of the human body as the anode. Alternatively, or additionally, a first one of the electrode elements 154 may be configured to operate as a cathode and a second one of the electrode elements 154 as an anode, allowing an electric signal to pass between the electrode elements 154, using the tissue of the human body as an electrical conductor. In some examples, the electrode arrangement 150 may be configured to provide at least two electrode elements 154 on opposing sides of the cardiac sphincter 26 so as to facilitate contraction of the sphincter 26.

Figure 21:
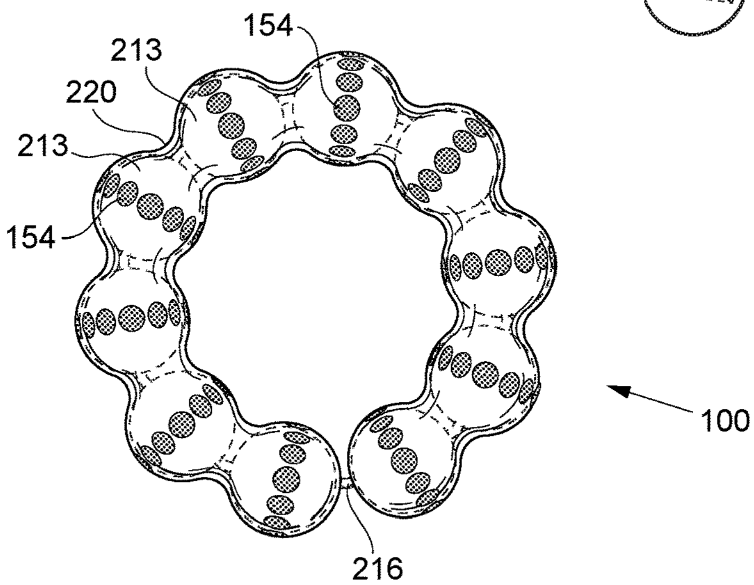

The apparatus 100 in FIGS. 20*a* and 20*b* may further comprise a cover 220, which may be similarly configured as the examples described in connection with e.g. FIGS. 15-19. An example of such an apparatus 100 is shown in FIG. 21, in which the elongated core 210 of FIGS. 20*a* and 20*b* is at least partly enclosed in a cover 220 allowing the core 210 to change between the constricting state and the expanded state without being substantially hindered or impeded by the presence of fibrotic tissue on the outer surface of the cover 220. Similar to the previous examples, an electrode arrangement 150 may be arranged between the cover 220 and the tissue against which the cover 220 rests when implanted. The electrode arrangement 150 may for example be arranged on the outer surface of the cover 220.

A method for implanting the apparatus 100 according in the body of a patient will now be discussed with reference to the examples illustrated in FIGS. 22A 22*d*. The present method may be used for affixing the apparatus 100 in the desired position by invaginating or wrapping at least a part of the device in the fundus 12 of the stomach 10, may hence be considered as an alternative to the placement shown in for example FIGS. 19*a* and 19*b*, wherein the apparatus 100 instead is arranged to encircle the esophagus without being invaginated or wrapped in a portion of the fundus 12. Preferably, the following method may be used when implanting a movement restriction device for reinforcing the fundus 12 to interact with the diaphragm and hindering movement of the cardia 22 up into the thorax.

Preferably, the apparatus 100 may be placed relatively high-up, above the upper edge of the lower esophageal sphincter (LES) so as to improve the effect on the reflux disease symptoms and allow the angle of His to assume its original, anatomically correct position and the LES to remain the abdomen. The present method can be divided into two separate parts: a first part in which a part of the stomach wall 14 is attached to the esophagus 20 so as to provide a “platform” positioning the apparatus 100 at the desired high, and a second part in which the apparatus 100 is placed in a pouch formed in the outside of the fundus, or wrapped in a portion of the fundus wall.

Figure 22A:
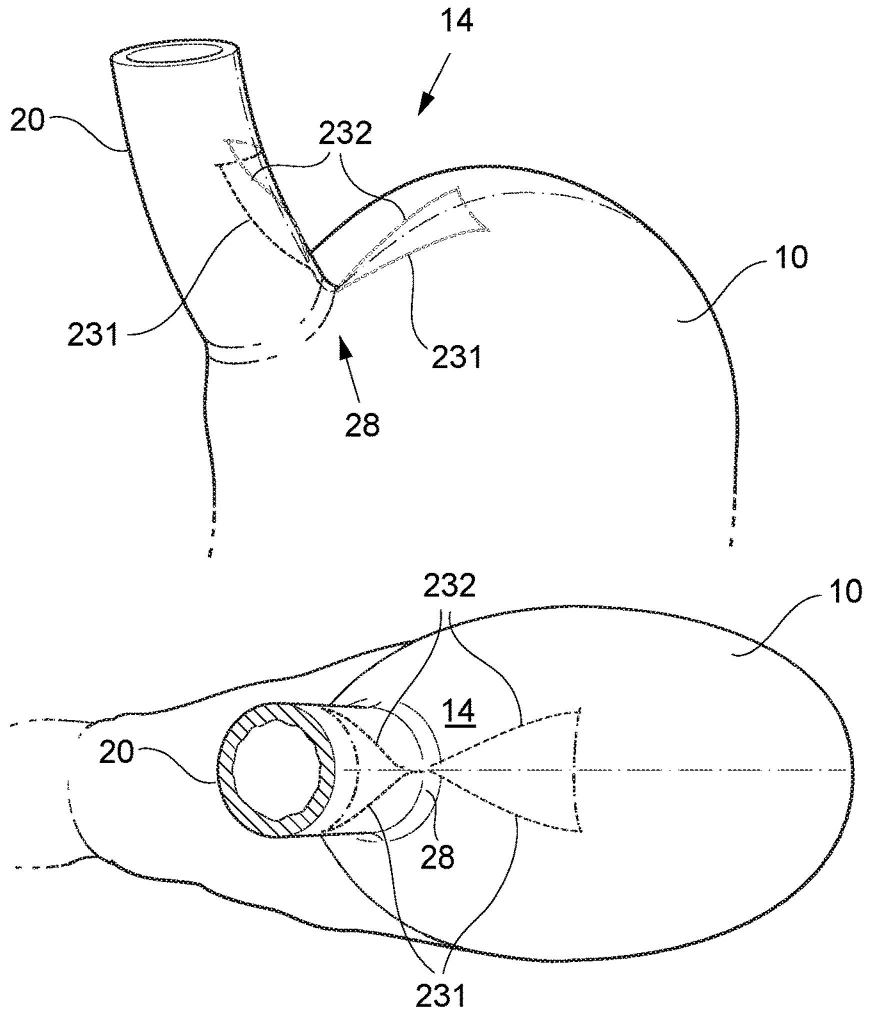
FIGS. 22A-23K are schematic views of various examples of methods for treating reflux disease and/or implanting an apparatus for treating reflux disease.
Figure 22B:
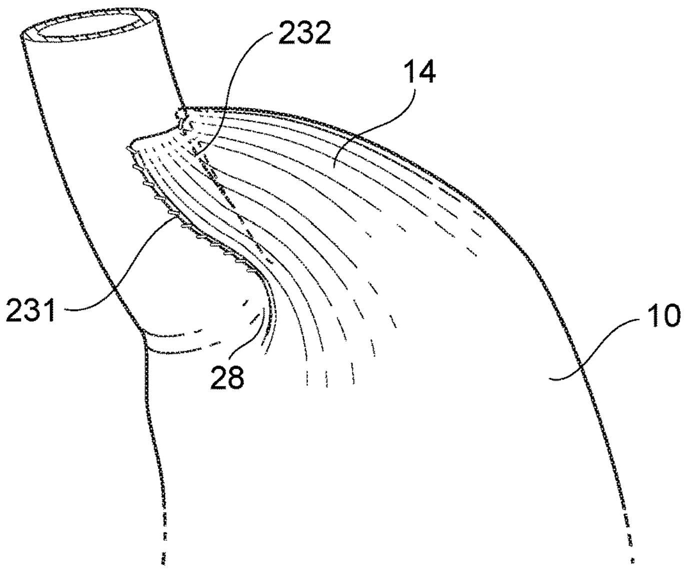

The first part of the method is illustrated in FIGS. 22A-22B, wherein a fundus portion 14, extending from the angle of His 28 and in a direction away from the esophagus, is affixed to the esophagus 20 after the esophagus 20 has been dissected in mediastinum. According to the method, the fundus portion 14 may be folded towards the esophagus 20 such that the fundus portion 14 rests against the esophagus 20, from the angle of His 28 and upwards along the esophagus 20. The fundus portion 14 may then be affixed to the esophagus 20 by means of fasteners 230 arranged along a first line 231 and a second line 232. The first line 231 and the second line 232 may extend along the esophagus 20 and may be arranged such that a distance between the first line 231 and the second line 232 increases with an increasing distance from the angle of His 28. The positions of the first line 231 and the second line 232 are indicated by the dashed lines in FIGS. 22*a* and 22*b*, before the fundus portion 14 has been folded against and affixed to the esophagus 20. The fasteners 230 may for example comprise staples or sutures and may preferably be of a non-resorbable type). In case of the fasteners 230 comprising sutures, the first line 231 and the second line 232 may comprise a respective continuous suture.

The abdominal part of the esophagus 20 and the fundus 12 may be divided by a plane into a ventral and a dorsal side. In this case, the first line 231 may be considered to be arranged on the dorsal side of the plane, whereas the second line 232 may be arranged on the ventral side of the plane. The first line 231 and the second line 232 may in some example be placed at an angle of 45-75 degrees relative to the plane, such as for example 60 degrees. Put differently, a separating angle between the first line 231 and the second line 232 may be in the range of 90-150 degrees, such as for example 120 degrees. In some examples, the maximum separation between the two lines 231, 232, at the top of the lines 231, 232, may be about 2-3 cm, such as about 2.5 cm. The orientation of the lines of fasteners can be considered to describe a “V” or “Y”, with the lines being separated at the top and gradually tapering towards each other towards the angle of His 28. Optionally, an additional fastener, such as a staple or suture, may be provided at the top of the “V” or “Y” shapes. Alternatively, a third line of sutures 233 may be provided between the first and second lines 231, 232.

In some examples, the method may comprise beginning the first line 231 less than 1 cm, such as about 0.5 cm, above the angle of His and beginning the second line 232 less than 3 cm, such as about 2 cm above the angle of His. Preferably, the second line 232 may be started less than 2 cm, such as about 1 cm, more ventral than the first line 231.

Figure 22C:
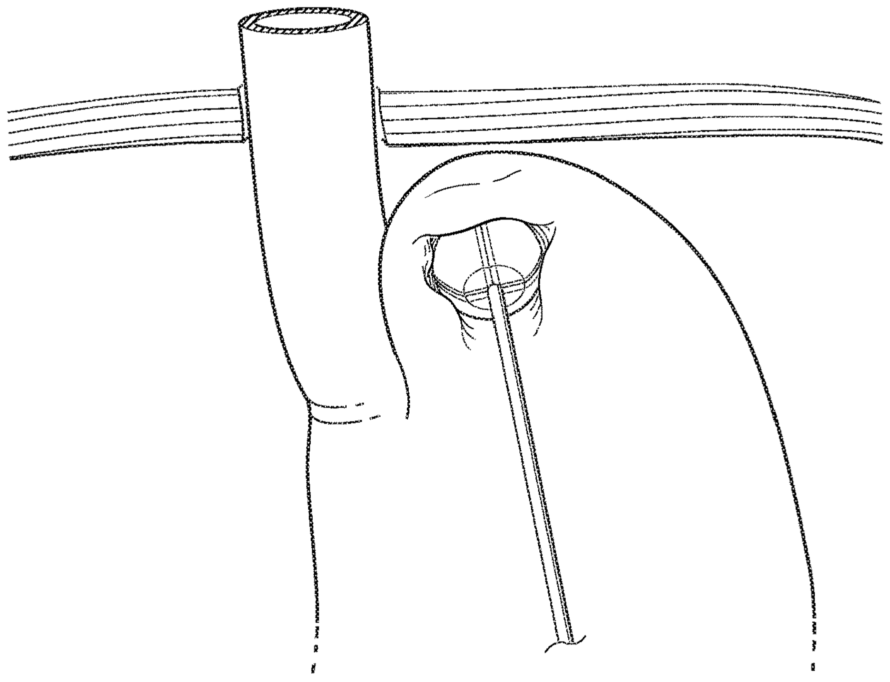
Figure 22D:
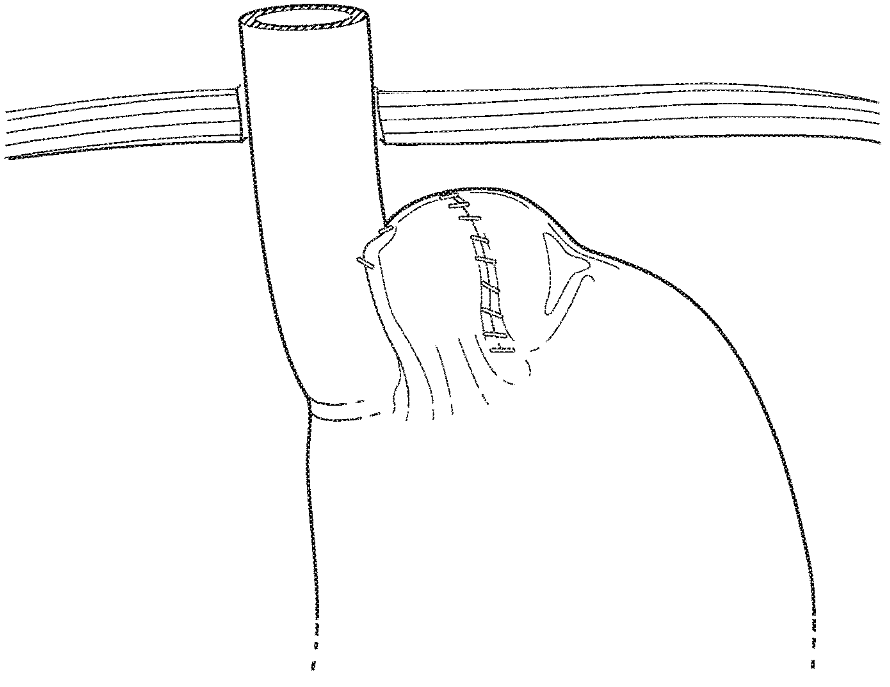

FIG. 22B shows the stomach 10 in FIGS. 22*a* and 22*b* after the fundus wall portion 14 has been affixed to the esophagus 20 according to the method outlined above. The method may now be followed by the implantation of the apparatus 100, such as for example the movement restriction device as shown in FIGS. 1-11. The apparatus 100 may be placed relatively high-up on the outside of the stomach fundus wall 12 and invaginated or covered by stomach tissue. This may be achieved by forming a pouch or recess 240 in the fundus 12, placing at least a part of the apparatus 100 in the pouch or recess 240, and at least partly closing the pouch or recess by fasteners 242 as illustrated in FIGS. 22C and 22D. Preferably, the apparatus 100 is placed such that the top of the apparatus 100 is positioned at a distance from the LES that exceeds the total height of the apparatus 100 so as to reduce the risk of the LES sliding through the diaphragm opening 32. Alternatively, the top of the apparatus may be arranged further down, such at a distance from the LES exceeding half of the total height of the apparatus 100. Arranging the apparatus even further down may lead to an increased risk for the LES sliding into the thorax and thereby a malfunction of apparatus 100.

Preferably, the apparatus 100 is placed relatively close to the esophagus 20, such that the distance between the apparatus 100 and the esophagus 20 primarily is determined by the thickness of the doubled stomach wall 14 placed between the apparatus 100 and the esophagus 20. This distance may for example be less than 2 cm, such as less than 1.5 cm, depending on the thickness of the stomach wall 14.

A further surgical method of treating reflux disease using an implantable movement restriction device will now be described with reference to FIGS. 23A-23K.

Figure 23A:
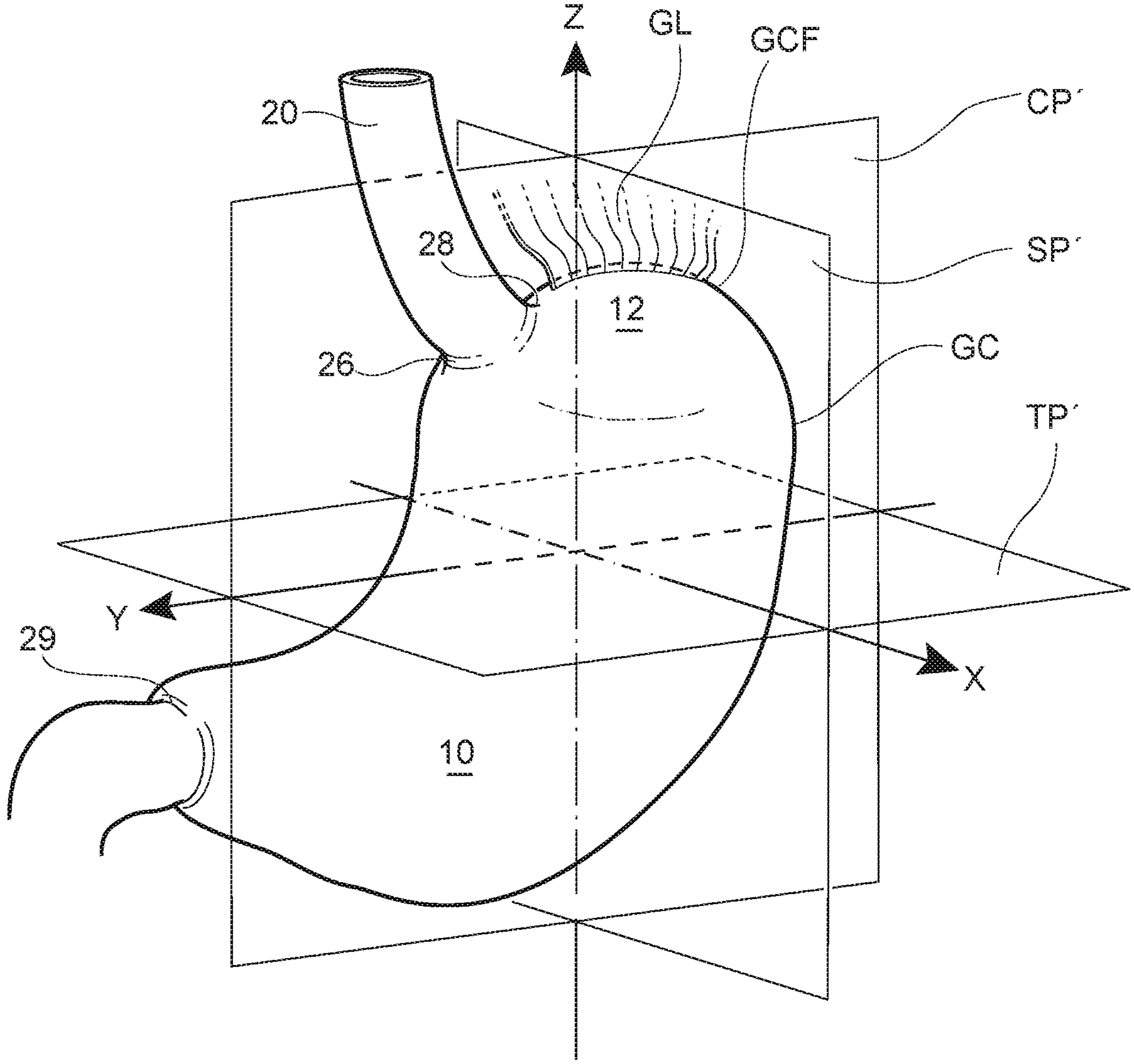

FIG. 23A is a schematic illustration of the stomach 10 of the patient substantially as oriented in the human body. The orientation of the planes of the human body are further described with reference to FIG. 39B. In the schematic illustration of FIG. 23A, a coronal stomach plane CP' is parallel to the coronal plane (CP of FIG. 39B) of the body and divides the stomach 10 into a dorsal and ventral section. A parasagittal stomach plane SP', parallel to the sagittal plane (SP in FIG. 39B) divides the stomach 10 into a right and left section and a transverse stomach plane TP' parallel to the transverse umbilical plane (TP in FIG. 39B) divides the stomach 10 into an upper and a lower section. Illustrated in the right portion of the figure is the greater curvature GC of the stomach 10 which forms a long, convex, lateral border of the stomach 10. The greater curvature GC starts at the angle of his 28 (cardiac notch) and curves to the right as it continues medially ending at the pyloric antrum 29. The gastrophrenic ligament GL is attached to the stomach 10 substantially along the greater curvature GC, mainly along the fundus portion of the greater curvature GCF. The gastrophrenic ligament GL is a thin layer of peritoneal tissue and forms part of the greater omentum. The gastrophrenic ligament GL attaches the fundus portion of the greater curvature GCF of the stomach 10 to the thoracic diaphragm.

Figure 23B:
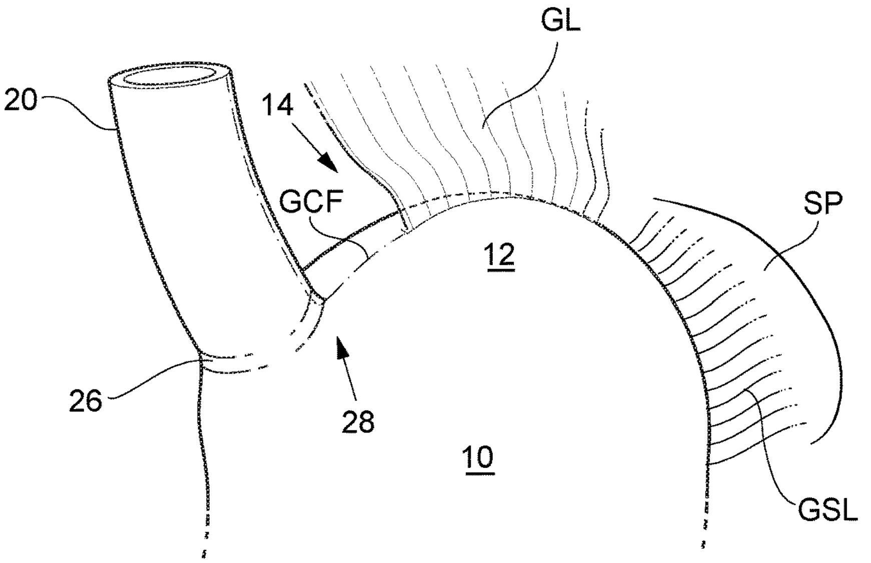

FIG. 23B shows a more detailed view of the proximal (or upper) portion of the stomach 10, where the fixation of the gastrophrenic ligament GL to the fundus portion of the greater curvature GCF of the stomach 10 can be viewed in further detail. On the sinister side of the stomach 10, the gastrosplenic ligament GSL is fixated substantially to the greater curvature GC of the stomach 10 and extends between the stomach 10 and the spleen SP. The gastrosplenic ligament GSL also forms part of the greater omentum.

Figure 23C:
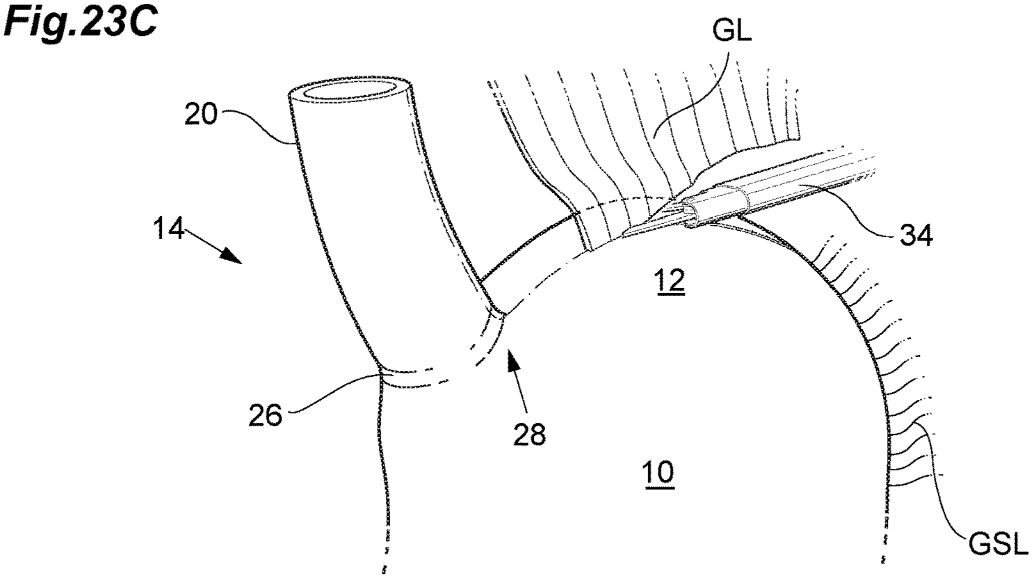

FIG. 23C shows the proximal portion of the stomach 10, when an ultra-sonic dissection instrument 34 dissects the fundus 12 at least partially on the posterior side thereof. In the dissection step shown in FIG. 23B, the fundus 12 is partially freed from the fixation to the gastrophrenic ligament GL. The dissection may extend further along the sinister side of the stomach 10, following the greater curvature GC, such that the fundus 12 may be freed also from the gastrosplenic ligament GSL. In the procedure illustrated in FIG. 23C, the ultra-sonic dissection instrument 34 is a laparoscopic ultra-sonic dissection instrument 34 used in a laparoscopic procedure. A laparoscopic procedure starts with the introduction of a needle or cannula into the abdomen through which a gas is introduced (usually carbon dioxide) by means of a laparoscopic insufflator. When the abdomen has been inflated, the working trocars are inserted in positions such that the surgical area can be reached.

In the procedure illustrated in FIG. 23C, the ultra-sonic dissection instrument 34 is inserted through a working trocar such that the ultra-sonic dissection instrument 34 can reach the fundus region.

Figure 23D:
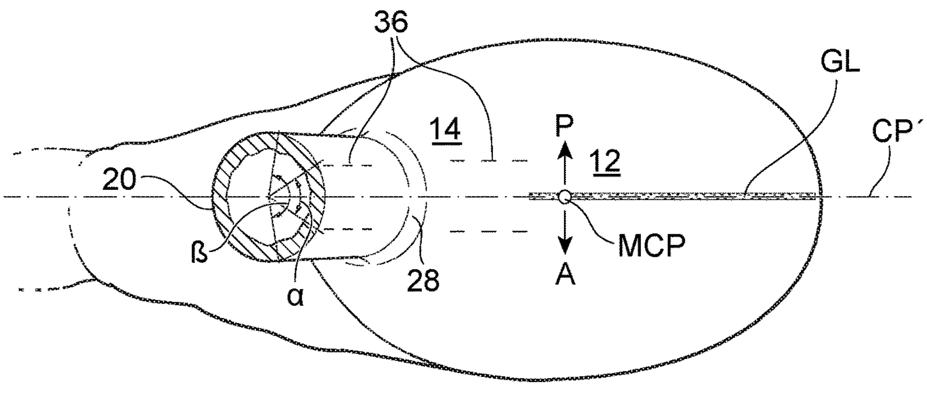

In the procedure illustrated in FIGS. 23C and 23D, the step of dissecting the fundus 12 at least partially on the posterior side P thereof comprises dissecting the fundus 12 at least 0.5 cm posterior P to the coronal stomach plane CP', more specifically dissecting the fundus at least 1 cm posterior P to a coronal stomach plane CP', and even more specifically dissecting the fundus at least 2 cm posterior P to a coronal stomach plane CP'. The coronal stomach plane CP' intersects the most cranial point MCP of the fundus 12. In other words, the step of dissecting the fundus 12 at least partially on the posterior side P thereof comprises dissecting the fundus at least 0.5 cm posterior P to the most anterior fixation point of the gastrophrenic ligament on the fundus 12, more specifically at least 1 cm posterior P to the most anterior fixation point of the gastrophrenic ligament GL on the fundus 12, and even more specifically at least 2 cm posterior P to the most anterior fixation point of the gastrophrenic ligament GL. In other words, the step of dissecting the fundus 12 at least partially on the posterior side P as shown in FIG. 23C, comprises dissecting the fundus at least 0.5 cm posterior to extension of the greater curvature GC of the stomach 10 in the region of the fundus 12, more specifically at least 1 cm posterior to extension of the greater curvature GC of the stomach 10 in the region of the fundus 12, even more specifically at least 2 cm posterior to extension of the greater curvature GC of the stomach 10 in the region of the fundus 12.

Figure 23E:
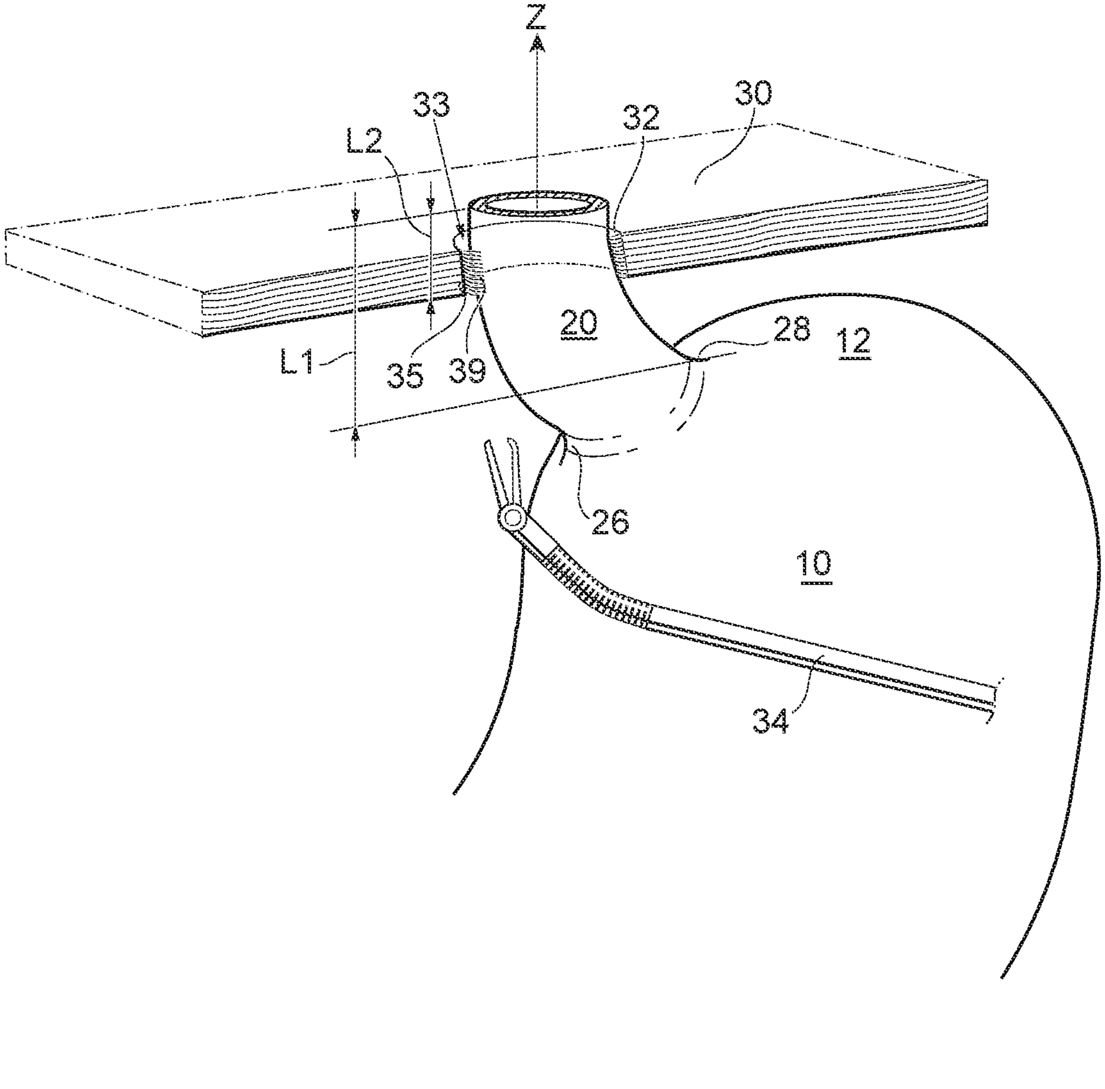
Figure 23F:
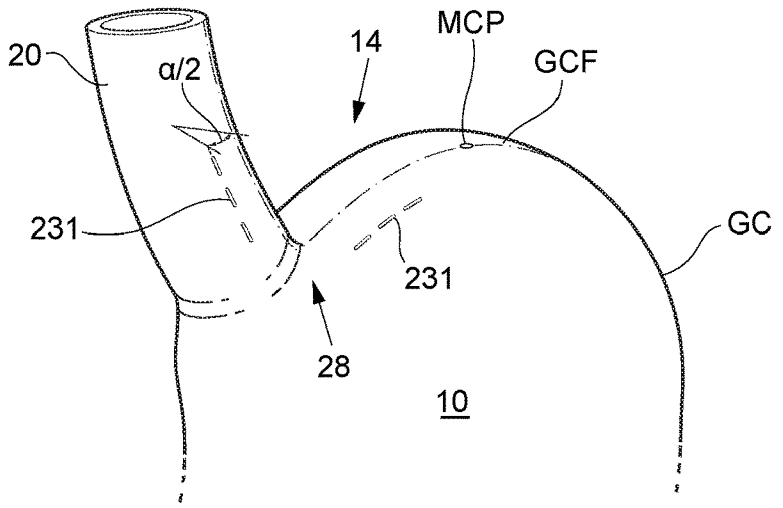

FIG. 23E shows the procedural step of dissecting the esophagus 20 such that the esophagus 20 is disconnected from the surrounding tissue with a length L1 of at least 3 cm in a cranial direction Z from the angle of his 28, more specifically at least 4 cm, more specifically at least 5 cm, more specifically at least 6 cm, and even more specifically at least 7 cm, in a cranial direction Z from the angle of his 28. In the procedural step shown in FIG. 23E, the step of dissecting the esophagus 20 such that the esophagus 20 is disconnected from the surrounding tissue comprises dissecting the esophagus 20 into mediastinum 33. 1. The mediastinum 33 is the central compartment of the thoracic cavity and lies within the thorax. The mediastinum 33 is enclosed on the right and left by pleurae, by the chest wall in front and the spine at the back. It extends from the sternum in front to the vertebral column behind and contains all the organs of the thorax except the lungs. In the procedural step shown in FIG. 23E, the step of dissecting the esophagus 20 into mediastinum 33 comprises dissecting the esophagus 20 into mediastinum 33 such that the esophagus 20 is disconnected from the surrounding tissue at least 1 cm in a cranial direction Z from the distal edge 35 of the esophageal hiatus 32, preferably at least 2 cm in a cranial direction Z from the distal edge 35 of the esophageal hiatus 32 and most preferably at least 3 cm in a cranial direction Z from the distal edge 35 of the esophageal hiatus 32. The dissection is performed by removing, preferably by cutting using an ultra-sonic dissection instrument 34, the connection of the adventitia 39 with neighboring structures, such as the thoracic diaphragm 30 and the pleurae. The step of dissecting the esophagus 20 into mediastinum 33 may comprise dissecting the esophagus 20 distally (in distal direction towards the stomach) from a point on the esophagus 2 cm distally from the esophageal plexus of the vagus nerve, such that the esophagus 20 is freed from the vagus nerve distally from such a point. Preferably, the esophagus 20 is dissected in distal direction from a point 1 cm distally from the esophageal plexus of the vagus nerve, and even more preferably from a point 0.5 cm distally from the esophageal plexus of the vagus nerve. The step of dissecting the esophagus 20 preferably comprises freeing the esophagus 20 from the crus muscles.

In the surgical procedure for treating reflux disease described with reference to FIGS. 23A-23K, the steps of dissecting the fundus 12 and dissecting the esophagus 20 are followed by the step of connecting (or plicating) the fundus 12 to the esophagus 20. FIG. 23D shows the prepared and dissected fundus 12 and esophagus 20. The dotted lines 36 on the fundus 12 and the esophagus 20 indicates plication positions, i.e. the positions on which the sutures or staplers connecting the fundus 12 to the esophagus 20 should be placed. In the procedural step described in FIG. 23D, two lateral rows of sutures are placed between the fundus 12 and the esophagus 20, from the fundus 12 to the esophagus 20. In the embodiment shown in FIG. 23D, the suturing starts in the serosa of the fundus 12, in which position the suture is fixated either by means of a knot or by means of barbs on the suture. The suturing is then made from stomach tissue to esophagus tissue with continuous stitches. In the embodiment shown in FIG. 23D, posterior sutures are placed laterally along a cranial-caudal axis for connecting the fundus 12 to the esophagus 20 on the sinister-posterior side of the esophagus 20, and anterior sutures are placed laterally along a cranial-caudal axis for connecting the fundus 12 to the esophagus 20 on the sinister-anterior side of the esophagus 20. In the procedure described with reference to FIGS. 23D-23H, the procedure is described using continuous sutures. However, in alternative procedures, it is equally conceivable that the plication (i.e. the connection of the fundus to the esophagus) is performed using single stiches which requires a knot for every stitch. In the procedure described with reference to FIGS. 23D-23H, the step of placing the posterior sutures 232 for connecting the fundus 12 to the esophagus 20, on the sinister-posterior side of the esophagus 20, is performed such that the sutures are positioned laterally on a cranial-caudal axis Z' at least 0.5 cm posterior P to a coronal stomach plane CP' intersecting a most cranial point MCP of the fundus 12, more specifically at least 1 cm, and even more specifically at least 1.5 cm posterior P to the coronal stomach plane CP'. Further, in the procedure described with reference to FIGS. 23D-23H, the step of placing the anterior sutures 231 for connecting the fundus 12 to the esophagus 20, on the sinister-anterior side of the esophagus 20, is performed such that the sutures are positioned laterally on a cranial-caudal axis Z" at least 0.5 cm anterior A to the coronal stomach plane CP' intersecting the most cranial point MCP of the fundus 12, more specifically at least 1 cm, and even more specifically at least 1.5 cm anterior A to the coronal stomach plane CP'.

Figure 23G:
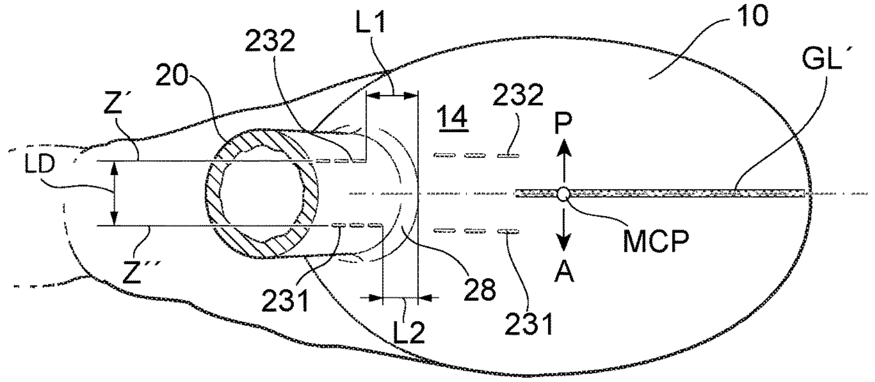

The esophagus 20 is a substantially cylindrical tube extending from the pharynx to the lower esophageal sphincter 26. FIGS. 23D and 23G shows the cross-section surface of the esophagus 20 as being substantially circular. In the embodiment of the procedure described with reference to FIGS. 23A-23H, the plication of the fundus to the esophagus 20 is performed as two lateral rows of sutures along two cranial-caudal axis positioned with an angle α between each other relative to a cranial-caudal center axis of the esophagus 20. The angle α is preferably about 80° but may be in the range 30°-160°. The aim with having a distance between the lateral rows of sutures 231, 232 (such that an angle α is created) is that the esophagus 20 should maintain its substantially cylindrical shape. If the sutures 231, 232 are placed too narrowly, the risk is that the pull from the fundus 12 deforms the esophagus 20 such that it assumes a more oval shape. If, on the other hand, the sutures are places too far apart, the risk is that pressure on the esophagus 20 exerted by the fundus 12 causes collapse of the esophagus 20, i.e. risking that the sinister side of the esophagus 20 protrudes into the esophagus 20 reducing the passageway through the esophagus 20 which may create swallowing difficulties or pain during swallowing (dysphagia or odynophagia). The angle β shown in FIG. 23D indicates the largest probable angle whilst maintaining a functioning esophagus 20, the angle β being about 160°. The lateral distance LD between the lateral rows of sutures 231, 232 is in the embodiment shown in FIGS. 23D-23K exceeding 1 cm, more specifically exceeding 1.5 cm and even more specifically about 2 cm.

FIG. 23G shows the fundus 12 and esophagus 20 in a top view slightly from the sinister side. In FIG. 23G it can be seen how the potential placement positions for the sutures 231, 232 extends on the sinister side of the esophagus 20, one on the sinister-posterior side of the esophagus 20 following a cranial-caudal axis Z' and one on the sinister-anterior side of the esophagus 20 following another, parallel, cranial-caudal axis Z". Both cranial-caudal axis Z', Z" are also parallel with the cranial-caudal center axis of the esophagus 20. In the embodiment of the procedure illustrated in FIG. 23G, the sinister-posterior suture row 232 starts at a distance L1 of about 1.5 cm from the angle of his 28, in the cranial direction, whereas the sinister-anterior suture row 231 starts about 0.5 cm from the angle of his 28, in the cranial direction. I.e. the most caudal suture in the sinister-posterior suture row 232 starts at a distance L1 exceeding 1 cm, or more specifically about 1.5 cm, from the angle of his 28, whereas the most caudal suture in the sinister-anterior suture row starts at a distance L2 exceeding 0.3 cm, or more specifically about 0.5 cm, from the angle of his 28. This is to make sure that at least one of the two suture rows 231, 232 do not include sutures placed in the lower esophageal sphincter 26, such that the radial expansion of the lower esophageal sphincter 26 which is necessary for unhindered swallowing remains unaffected by the plication of the fundus 12 to the esophagus 20. In alternative embodiments of the procedure, it is equally conceivable that the most caudal suture in the sinister-anterior suture row 231 starts at a distance of about 1.5 cm from the angle of his 28 and the most caudal suture in the sinister-posterior suture row 232 starts at a distance of about 0.5 cm from the angle of his 28.

Figure 23H:
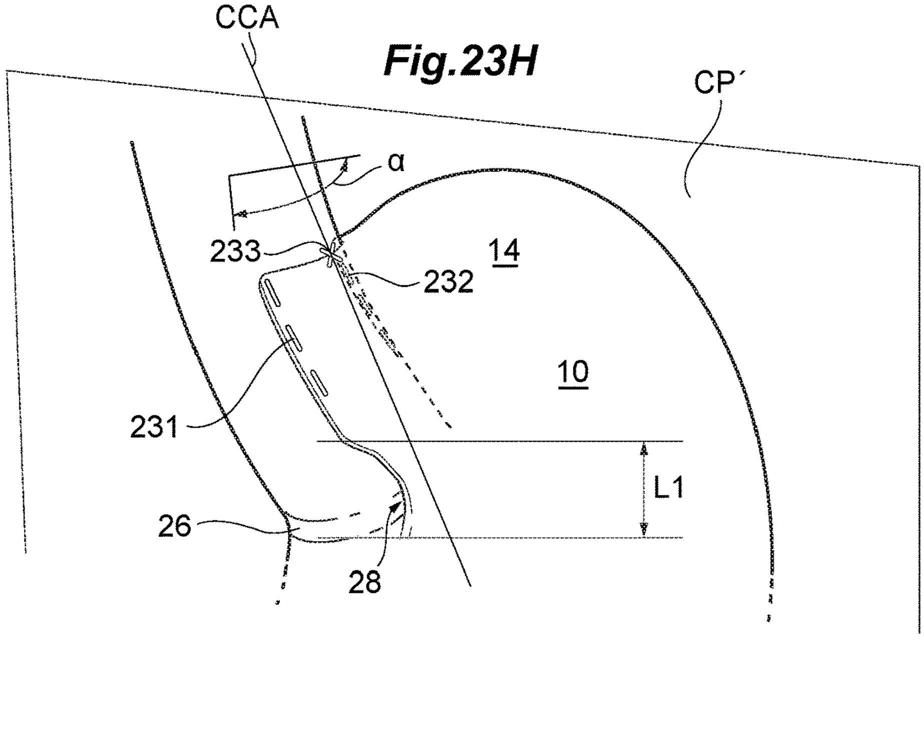

FIG. 23H shows an elevated frontal view of the stomach and esophagus when the plication with an anterior row of sutures 231 and a posterior row of sutures 232 has fixated the fundus 12 to the esophagus 20. FIG. 23H further shows the conclusion of the plication by the placement of a single central suture 233 on a cranial-caudal axis CCA extending between the at posterior suture row 232 and the anterior suture row 231. The central suture 233 is disconnected from the anterior sutures 231 and from the posterior sutures 232 for maintaining the possibility of radial expansion the esophagus 20 for limiting the disk of dysphagia. The central suture 233 supports the two most cranial sutures of the anterior and posterior suture rows 231, 232 by absorbing some of the weight of the fundus portion 14 plicated to the esophagus 20.

The anterior and posterior suture rows 231, 232, connecting the fundus 12 to the esophagus 20, when performed using continuous sutures are preferably performed using at least partially barbed suture.

Figure 23I:
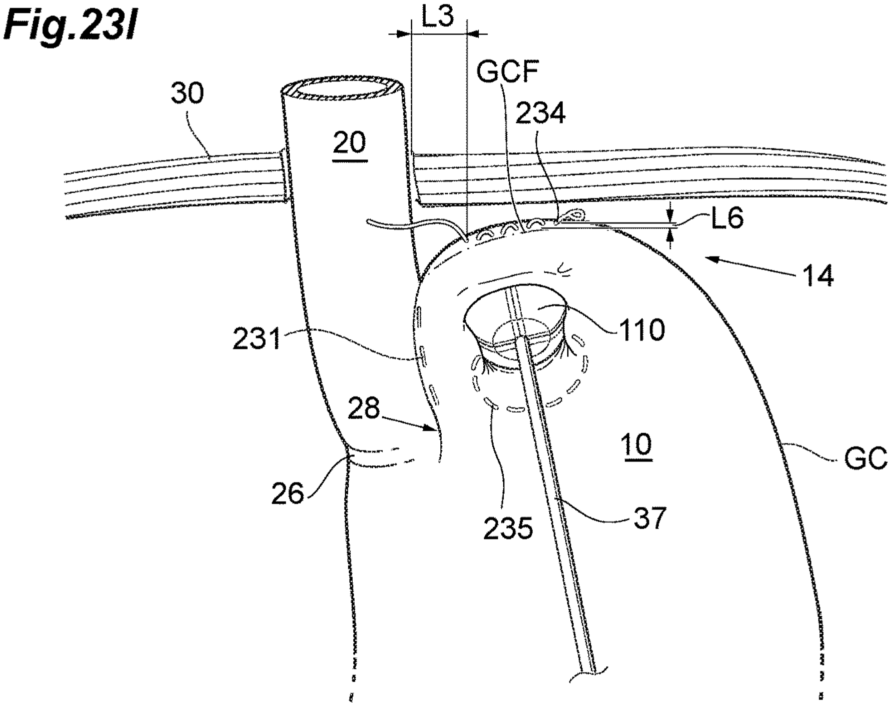
Figure 23I:
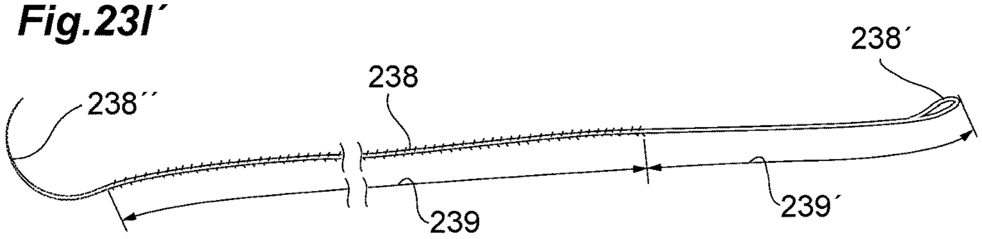

FIG. 23I shows an elevated frontal view of the stomach 10 and esophagus 20 when the plication has been performed such that the free fundus 12 has been attached to the esophagus 20. The next step of the procedure disclosed with reference to FIGS. 23A-23K is the step of fixating the implantable movement restriction device 110 to the freed fundus portion 14, such that the lower esophageal sphincter 26 is prevented from sliding through the esophageal hiatus 32. The movement restriction device 110 fixated in the procedure described with reference to FIG. 23I could be a movement restriction device 110 according to any one of the embodiments herein. More specifically, the movement restriction device 110 could be any of the functional movement restriction devices 110 (and/or functional volume filling devices) shown in FIGS. 1, 2, 3, 4, 5, 6A, 6B, 23B, 23C, 25, 29, 3031A-31F, 32, 33, 34, 35, 36, 37A, 37B, 39C, 39E, 39G, 39H, 39I, 39N-39O', 39Q-39T', 39U, 39U', 39V, 39V', 39AA, 39AC, 40AA-40AD, 40BA-40CA, 40DA-40EA, 40FA-40FD, 40GA-40GD, 40HA-40HC, 40IA-40IC, 40JA-40JC, 40KA-40KB, 40LA-40LB, 40MA-40MC, 40N-40N", 40SA-40SD, 40SC'-40SD', 40SE-40SF, 40SE'-40SF', 40SE"-40SE'".

The procedural step of fixating the movement restriction device 110 is commenced by the placement of continuous purse-string roof sutures 234 in the region of the greater curvature of the fundus GCF of the stomach, such that the stomach tissue can be contracted by pulling the ends of the purse-string sutures 234. More specifically, the purse-string roof sutures 234 are placed posteriorly to the greater curvature of the fundus GCF, even more specifically the purse-string roof sutures 234 are placed at a length L6 of at least 1 cm behind the greater curvature of the fundus GCF, or at a length L6 of more than 1.5 cm behind the greater curvature of the fundus GCF, in the region of the fundus portion 14. The continuous purse-string roof sutures 234 are preferably placed with an at least partially un-barbed suture, as the level of contraction of the stomach tissue in the region of the roof sutures 234 should be kept adjustable until the invagination steps have been concluded, to reduce the risk that the stomach tissue is wrapped too tightly around the movement restriction device 110. In the embodiment of the procedure described with reference to FIG. 23I, the suture used for the purse-string roof sutures 234 is a partially barbed and partially un-barbed suture having a loop at the end. The suture 238 specifically used in the procedural step described in the embodiment shown in FIG. 23I is shown in further detail in FIG. 23I'. The suture 238 starts at the needle 238" and has a loop 238' in the end. The end portion 239' is un-barbed, whereas the portion of the suture 239" closest to the needle 238" is barbed such that it gripes the tissue and locks in the tissue in the backwards direction. In the embodiment shown in FIGS. 23I and 23I', the un-barbed end portion 239' has a length exceeding 1 cm, more specifically a length exceeding 2 cm, to ensure that the contraction of the stomach tissue in the region of the roof sutures 234 is kept adjustable until the invagination steps have been concluded.

In the embodiment of the procedure described with reference to FIG. 23I, the step of placing the continuous purse-string roof sutures comprises starting or ending the continuous purse-string roof sutures at a length L3 from the esophagus 20 being at least 0.5 cm.

When the purse-string roof sutures 234 have been placed, the procedure is continued with the insertion of the implantable movement restriction device 110 into the abdomen of the patient. The implantable movement restriction device 110 is introduced through a trocar into the abdomen and held by an insertion instrument 37 having an elongated abdominal portion. The implantable movement restriction device 110 is held in place and pushed from below into the fundus of the stomach in a dorsal-cranial direction, such that a portion of the implantable movement restriction device 110 ends up behind (dorsal to) the roof sutures 234.

In the embodiment of the procedure described with reference to FIG. 23I, the procedure further comprises the step of placing continuous purse-string base sutures 235 in the region of the caudal end of the implantable movement restriction device 110. The continuous purse-string floor sutures 235 are placed following an arc below the elongated abdominal portion of the instrument 37 holding the implantable movement restriction device 110.

Figure 23J:
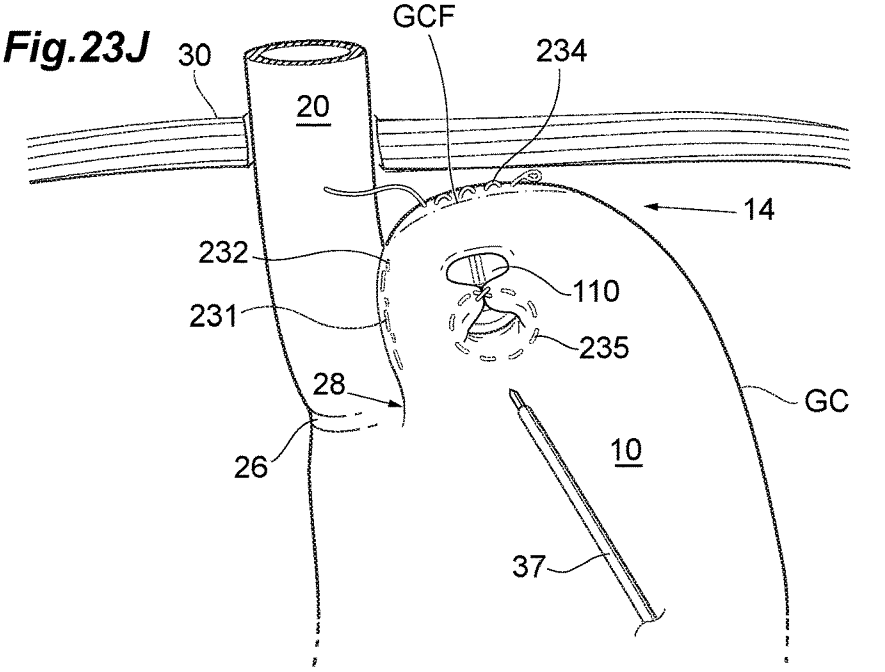
Figure 23K:
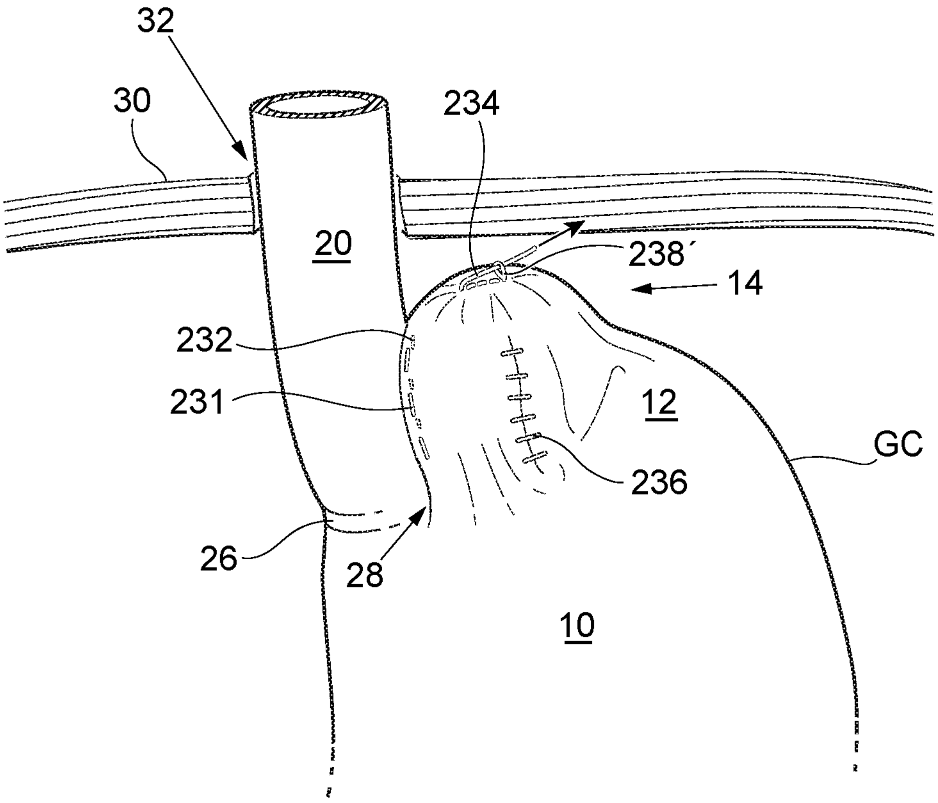

FIG. 23J shows the continuous placement of purse-string base sutures 235 are continuously placed such that the continuous purse-string base sutures 235 forms a closed curve or loop. The curve or loop is closed by at least one stomach-to-stomach suture placed above the elongated abdominal portion of the instrument 37 connecting stomach tissue to stomach tissue above the elongated abdominal portion of the instrument 37. When the continuous purse-string base sutures 235 have been completed, the implantable movement restriction device 110 is released from the instrument 37 and held in place in the fundus portion 14 by the contracted tissue of the roof sutures 234 and base sutures 235. The continuous purse-string base sutures 235 are preferably performed using an at least un-barbed suture for enabling the contraction and relaxation of the stomach wall during the surgical procedure.

The preparation of the base and the roof is followed by the closing of the pouch such that the implantable movement restriction device 110 becomes completely enclosed by the tissue wall of the fundus portion 14. The closing of the pouch is performed by stomach-to-stomach sutures commencing in the most caudal (or distal) portion of the pouch by the closing of the hole left by the instrument 37 by means of stomach-to-stomach sutures 236. The suturing the continues from side to side in the cranial (or proximal) direction until the closing sutures reaches the roof sutures 234, after which the closing sutures are fixated to the stomach wall. The closing of the pouch is preferably performed with sutures comprising Polypropylene (PP), which may be a barbed or un-barbed PP suture. The procedure is then concluded by the start of the roof suture 234 being inserted through the loop in the end of the suture and gently pulled the purse-string roof sutures 234 to contract tissue in the proximal region of the fundus just enough to keep the implantable movement restriction device 110 invaginated without tension of the fundus tissue. The suture is preferably fixated to the serosa, as the relatively thick muscular layer of the serosa creates good long-term fixation of the suture. To further fixate the implantable movement restriction device 110 before final invagination, the step of closing the roof suture 234 may be performed before the removal of the instrument 37 to ensure that the implantable movement restriction device 110 is firmly fixated in the stomach before the instrument 37 is removed.

If the implantable movement restriction device 110 is invaginated too tight, the tension in the fundus tissue creates pressure on the fundus tissue which risks hampering the oxygenation of the fundus tissue which may lead to degeneration of the tissue which increases the risk that the implantable movement restriction device 110 migrates through the tissue wall and ends up inside of the stomach cavity.

In the surgical procedure described above, the roof sutures is preferably performed with an un-barbed suture or a partially unbarbed suture. In embodiments in which the roof sutures are performed using a partially unbarbed suture, the portion without barbs is at least 2 cm long, or preferably at least 3 cm long. The suture for use in the roof suture can be a monofilament suture or a braided suture which may comprise a coating for reducing the risk of infection. The suture for use in the roof suture could have a loop in the end for facilitating the fixation of the suture.

The purse-string base sutures is preferably performed with an un-barbed suture, which may be a polyester suture. The suture may be a monofilament suture, such as "Prolene", or braided polyester suture which may be coated. In the alternative, the sutures may comprise PTFE or Gore-Tex®.

A few examples of apparatuses for treating reflux disease of a human patient will now be described with reference to FIGS. 24-27. The apparatuses 100 may be configured to operate by combining a restriction of movement of the cardia towards the diaphragm, as discussed in connection with for example FIGS. 1-11, with electrical stimulation for contracting the cardiac sphincter 26, as disclosed in connection with for example FIGS. 3 and 14-20, and/or an encircling pressure on the esophagus 20, as discussed with reference to the examples of FIGS. 14-20, for hindering stomach contents from rising through the esophagus 20. Hence, the apparatuses 100 of FIGS. 24-27 may be configured to at least partly encircle the esophagus 20, and may comprise a first implantable portion 110 (also referred to as a movement restriction device) having a shape and size allowing it to be arranged to rest against a fundus wall portion 14 of the patient's stomach 10 and to be at least partly invaginated or covered by the fundus wall portion 14, such that the first implantable portion 110 is implanted at a position between the patient's diaphragm 30 and a lower portion of the fundus wall 14, and such that movement of the cardia 22 of the patient's stomach 10 towards the diaphragm 30 is restricted to hinder the cardia 22 from sliding through the diaphragm opening (diaphragm hiatus) 32 into the patient's thorax. The apparatus may further comprise a second implantable portion 120 (also referred to as an elongated support device), which may be configured to at least partly encircle the esophagus 20. In some examples, the second implantable portion 120 may have a variable length for allowing the apparatus 100 to be arranged in a constricting state for hindering fluid from passing from the stomach

10 and upwards through the esophagus 20, and in an expanded state for allowing food to pass into the stomach 10 in response to the patient swallowing. In some examples, the second implantable portion 120 is formed as an elongated support device 120 connected to the first implantable portion 110 (or movement restriction device) and configured to support an electrode arrangement 150 such that it is positioned at the esophagus 20. The support device 120 may comprise a rigidity that allows the position of the electrode arrangement 150 relative to the esophagus 20 to be determined mainly by the position and orientation of the movement restriction device 110.

Figure 24:
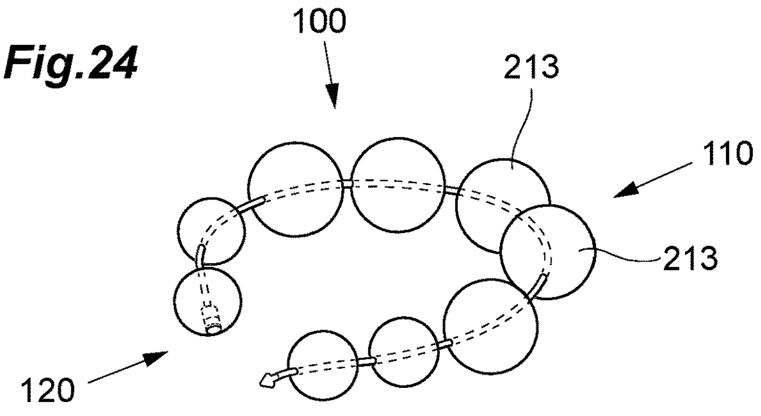
FIGS. 24-27 are schematic views of various examples of apparatuses for at least partly encircling the esophagus to treat reflux disease.

More specifically, FIG. 24 shows an apparatus 100 comprising a plurality of core elements 213 arranged in an array and connected to each other by means of a plurality of links 214. At least one of the core elements 213 may be larger than the other core elements 213 of the array and may be configured to form the first implantable portion 110 to be affixed to the fundus 12, for example by invagination or by at least partly covering the at least one larger core element 213 by stomach tissue. The at least one larger core element 213 may thus form a movement restriction device as discussed above in connection with FIGS. 1-6. The smaller ones of the core elements 213 may form the second implantable portion 120 and may be arranged to encircle at least a part of the esophagus 20. The second implantable portion 120 may have a variable length so as to allow the apparatus 100 to change between the expanded state and the constricting state as outlined above in the previous examples. A maximum width of a cross section taken across a length direction of the first implantable portion 110 may preferably be larger than a maximum width of a cross section taken across a length direction of the second implantable portion 120.

The first implantable portion 110 may be configured to have a substantially fixed size and shape during operation of the apparatus, whereas the second implantable portion 120 may be configured to vary its length, and hence the constriction of the esophagus 20, in response to the patient swallowing and, preferably, belching or vomiting. The second portion 120 may thus be arrangeable in an expanded state in which a food bolus may pass through the cardiac sphincter 26, and in a constricting state in which the second portion 120 exerts an encircling pressure on the esophagus 20 so as to help the cardiac sphincter 26 to close or at least constrict the passageway of the esophagus 20.

An electrode arrangement 150, similarly configured as the electrode arrangement 150 discussed above in connection with for example FIGS. 1 and 14, may be arranged between the first portion 110 and the fundus wall portion 14, and/or between the second portion 120 and the esophagus 20. The electrode arrangement 150) may comprise one or several electrode elements 152, 154 for electrically stimulating and thereby exercising muscle tissue affected by the implanted apparatus 100, and/or for electrically stimulating and thereby contracting the cardiac sphincter 26.

The combined apparatus 100 shown in FIG. 24 advantageously employs several different mechanisms for addressing reflux symptoms. Firstly, the first portion 110, acting as a mechanical stop against the diaphragm muscle 30, makes use of the technique to hinder the cardia 22 from sliding through the diaphragm opening 32 into the thorax. Secondly, the second portion 120, acting as a constricting device, utilizes the technique to assist the cardiac sphincter 26 in its closing movement so as to further improve the closing or constrictive function of the sphincter 26. Thirdly, the electrode arrangement 150 may be employed to electrically stimulate the cardiac sphincter muscle 26 so as to further stimulate constricting.

Figure 25:
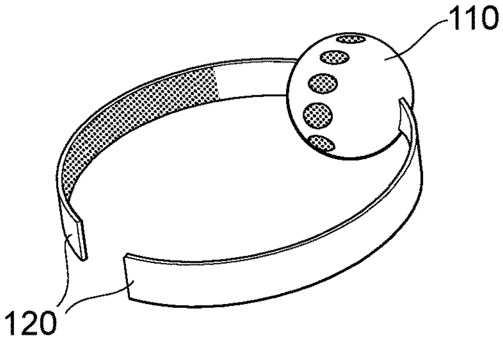

FIG. 25 shows an apparatus 100, which may be similarly configured as the embodiment discussed above with reference to FIG. 24. However, the present apparatus 100 may differ in that the second portion comprises an elongated support device 120 similar to the one disclosed in for example FIG. 3. Thus, while the first portion 110 may be invaginated or at least partly covered by the fundus tissue and arranged to act as a movement restriction device, the second portion 120 may, instead of the array of core elements shown in FIG. 24, comprise an elongated support device 120 that is attached to the first portion 110 and configured to at least partly encircle the esophagus 20. Preferably, the support device 110 is configured to support the electrode element 154 at a position where it can electrically stimulate muscle tissue of the esophagus 20. In some examples the support device 120 may be formed as a band 120 configured to be arranged around at least a part of the esophagus 20, and wherein a first and a second end portion of the band is coupled to the first implantable portion 110. Alternatively, or additionally, the support device 120 may comprise a rigidity that allows the position of the electrode element relative to the esophagus to be determined mainly by the position and orientation of the movement restriction device. This allows for the elongated support device 120, and thus the electrode element 154, to be arranged and maintained in a desired position at the esophagus 20 without being affixed, such as sutures or staples, directly to the tissue of the esophagus 20. Instead, the location and orientation of the first portion 110, which may be affixed to the fundus 12, may be adjusted until the electrode element 154 is arranged at the desired position.

Figure 26:
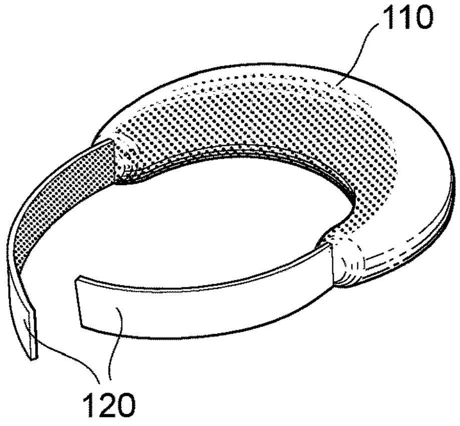

FIG. 26 shows an apparatus 100 which may be similarly configured as the embodiment of FIG. 25. The present apparatus 100 may however differ in that the first portion 110, which may be configured to function as a movement restriction device 110, may be formed as a segment of a ring-shape, such as a segment of a torus as indicated in the embodiments of for example FIGS. 7-11. The function and configuration may be similar to the ones of the embodiment of FIG. 26, allowing for the electrode element 154 to be positioned at the esophagus 20 without having to be affixed directly to the esophagus 20 by means of for example sutures or staples. The first portion 110 may have a curvature that conforms to a curvature of the esophagus 20, allowing for an inner curvature of the segment to be arranged to phase an outer surface of the esophagus 20, on the fundus side of the esophagus 20. The first portion 110 may for example be configured to be arranged to rest directly against the esophagus 20, such as at the angle of His 28, or be affixed to the fundus 12 in a way that allows for fundus tissue to be positioned between the first portion 110 and the esophagus 20. The at least partly ring-shaped first portion 110 may advantageously improve the stability of the apparatus 100 when implanted, allowing for the first portion 110 to be more securely affixed to the fundus 12 with a reduced risk for rotations to occur over time.

Figure 27:
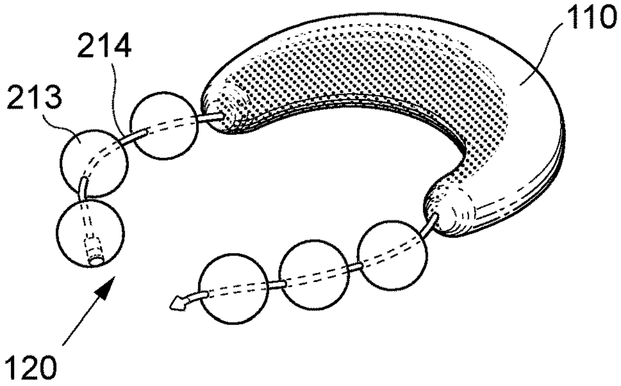

FIG. 27 shows an apparatus 100 which may be similarly configured as the embodiment of FIG. 26. The present apparatus 100 may however differ in that the second portion 120 may comprise a plurality of core elements 213 arranged in an array and connected to each other by means of a plurality of links 214, similar to what is described in connection with the embodiment of FIG. 24. The core elements 213 of the second implantable portion 120 may hence be arranged to encircle at least a part of the esophagus 20, and the second implantable portion 120 may have a variable length so as to allow the apparatus 100 to change between the expanded state and the constricting state as outlined above in the previous examples. The first portion 110, or the restriction device 110, may be similar to the corresponding portion of the embodiment of FIG. 26.

The apparatus 100 according to the embodiments described above in connection to FIGS. 1-13 and 24-27 may be implanted in the body and affixed by the fundus in several different ways. As previously described, the implantation method may involve placing the first portion 110 (or movement restriction device 110) in a pouch formed in the inside or outside wall of the fundus 12, or at least partly covering the first portion 110 by fundus tissue, and affixing the first portion 110 by stomach-to-stomach sutures, before the fundus 12 is affixed to the esophagus 20 and/or diaphragm 30 so as to arrange the apparatus 100 in a predetermined or desired position in the body. Further exemplary methods will now be described with reference to FIG. 28.

The apparatus 100 according to any of the embodiments described above in connection to FIGS. 1-13 and 24-27 may be affixed to the fundus such that the first portion 110, also referred to as a movement restriction device 110, is at arranged on the fundus side of the esophagus to restrict the movement of the stomach notch in relation to the diaphragm to hinder the cardia to from sliding through the diaphragm opening into the patient's thorax. This may be achieved by a method which may be referred to as "tunneling", i.e., at least partly wrapping or covering a part of the apparatus 100 in fundus tissue forming a pouch or cavity that is open in two ends so that the apparatus can extend through the pouch or cavity. Thus, the method may comprise placing the apparatus 100 such that the movement restriction device 110 rests against the outside of the stomach's fundus 12, wrapping a portion of the fundus 12 around at least a part of the movement restriction device 110, and affixing the fundus 12 to the esophagus 20 such that the movement restriction device 110 is arranged at a position between the diaphragm 30 and the cardiac sphincter 26, and such that a part of the fundus 12 is arranged between the movement restriction device 110 and the esophagus 20.

Figure 28:
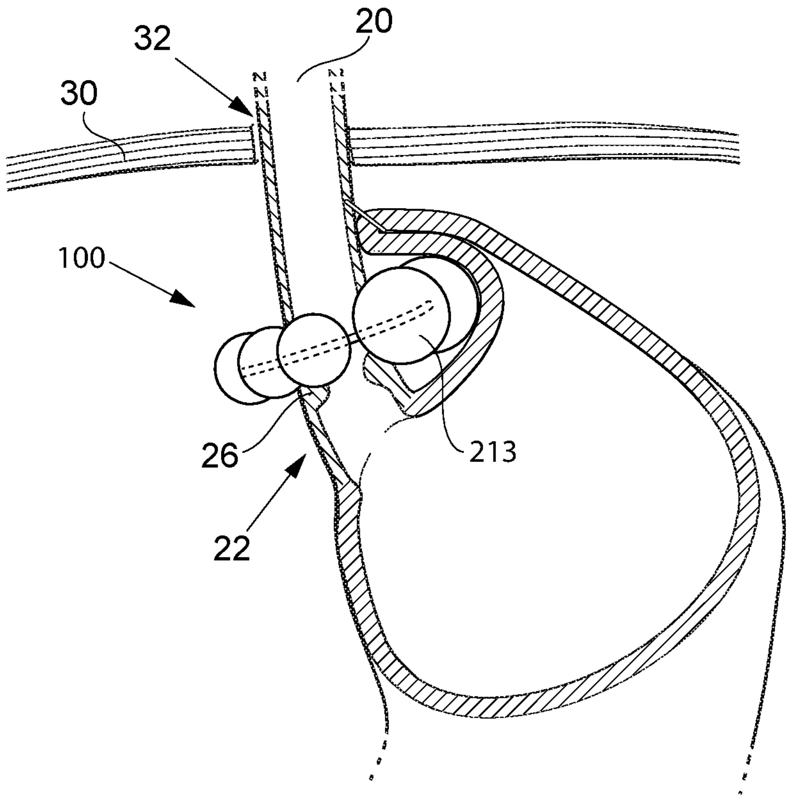
FIG. 28 schematically illustrates how an apparatus for treating reflux disease can be implanted in the patient.

FIG. 28 shows an apparatus 100, wherein the first portion 110 has been placed to rest at the outside of the fundus 12 at a position between the esophagus 20 and a portion of the fundus 12 that is wrapped over at least a part of the first portion 110 and introduced between the first portion 110 and the esophagus 20. In the present example, the apparatus 100 is ring-shaped so as to at least partly encircle the esophagus 20. The ring-shaped body formed by the first and second portions 110, 120 may thus define an inner hole, through which the esophagus 20 may extend and into which a portion of the fundus 12 may be introduced and affixed to the esophagus 20. The resulting structure, by which the apparatus 100 is affixed in the body of the patient, may thus be understood as a "tunnel" having a first opening a second opening through which the apparatus 100 may extend.

Alternatively, or additionally the apparatus 100 may be implanted by first affixing a portion of the fundus 12 arranged between the first portion 110 of the apparatus 100 and the esophagus 20 to the outside of the esophagus 20, in a similar manner as discussed above in connection with FIGS. 22 and 23. A portion of the fundus extending from the angle of His may thus be folded upwards, along the esophagus 20 and affixed to the esophagus 20, for example by means of fixators extending along a first and a second line arranged such that a distance between the lines increases with an increasing distance from the angle of His. The first portion 110 of the apparatus 100 may then be invaginated, or at least partly covered by, a portion of the fundus which is not affixed to the esophagus 20. The resulting structure may thus be understood as a "tunnel". The apparatus 100 may be affixed and secured in a position relative the esophagus 20 by means of stomach-to-esophagus fixators (such as sutures or staples) shown in FIG. 28, or invaginated and secured by means of stomach-to-stomach fixators. Additional fixators may in some examples be provided to also affix the fundus 12 to the diaphragm 30 (not shown in FIG. 28).

While the exemplary apparatus 100 shown in FIG. 28 is a ring-shaped apparatus formed of a first portion 110 and a second portion 120, it will be appreciated that other configurations of the apparatus 100 is possible as well. The apparatus may for example comprise only a first portion 110, i.e., not have a second portion 120, thereby being a movement restriction device 110 similar to the one disclosed in for example FIGS. 1-6. Alternatively, the apparatus may be formed as an encircling torus as indicated in FIGS. 7-13, or comprise a core and, optionally, a cover as illustrated in FIGS. 14-21. In further examples, the apparatus 100 may be similarly configured as the examples illustrated with reference to any of FIGS. 24-27.

Generally, the apparatus 100 may be implanted in the body of the patient by means of laparoscopic surgery. In an example, the method may comprise the steps of inserting a needle or a tube-like instrument into the patient's abdomen and using the needle or tube-like instrument to fill the abdomen with a gas. Then, at least two laparoscopic trocars may be placed in the abdomen, and a camera be inserted through one of the laparoscopic trocars into the abdomen. At least one dissecting tool may be inserted through one the laparoscopic trocars and be used for dissecting an area around esophagus in mediastinum. The apparatus may be introduced into the abdominal cavity, for example via one of the trocars, and placed as illustrated above. The fundus may be affixed to itself (forming the invagination) and/or to the esophagus using sutures or staples such that the apparatus 100 is secured in a desired position relative to the cardia 22 the diaphragm 30.

The apparatus 100 according to the embodiments described above in connection to FIGS. 1-13 and 24-27 may be placed at, or in the vicinity of, the junction between the esophagus 20 and the stomach 10. The position of the apparatus 100 may be secured by wrapping or folding a portion of the fundus 12 over the apparatus 100 and affixing the fundus portion to the esophagus 20, as indicated in FIGS. 29-31 and 33. The position where the esophagus 20 meets the stomach 10 may be referred to as the angle of His 28, or cardiac notch. With this placement, the apparatus 100 may be supported by the junction, abutting a portion of the outside wall of the fundus 12 extending from the angle of His and, preferably, also a lower portion of the outside wall of the esophagus 20. The outermost layer of the stomach wall may generally be formed of a serous membrane, also referred to as serosa, which is a smooth tissue membrane wall protecting the stomach wall. Duc to the protective nature of the serosa, it may be desirable to place the apparatus 100 to rest against the serosa when implanted. The serosa has been observed to cover also a part of the outside wall of the esophagus 20, close to the stomach 10, and it may therefore be advisable to allow the apparatus 100 to rest also against a lower part of the esophagus 20, covered by serosa, while avoiding placing the apparatus 100 against other parts of the esophagus 20 which are not covered by serosa. This may be achieved either by folding the fundus 12 such that fundus tissue is arranged between the apparatus 100 and the esophagus 20, as shown in for example FIGS. 1-3, 7-10 and 28. Alternatively. or additionally, this may be achieved by means of an apparatus 100, such as a movement restriction device 110) similar to the previous embodiments of FIGS. 1-3, 7-10 and 28, having a shape that allows for the device 100 to be placed such that an upper portion points or tapers away from the esophagus 20. Referring to FIGS. 29-33, the disclosed examples of movement restriction devices 110 may have a side phasing the esophagus 20, wherein a curvature of that side allows the movement restriction device 110 to be arranged such that a gap is defined between the movement restriction device 110 and the esophagus 20 along at least a portion of the esophagus 20. As indicated in the examples of the present figures, the gap may increase with an increasing distance from the junction between the esophagus 20 and the stomach 10. Put differently, the apparatus 100 may comprise an outer shape that allows it to be positioned to rest against a lower portion of the esophagus 20, comprising serosa, and to fall away, or point away, from the esophagus 20 as seen in an upward direction along the esophagus 20, towards regions of the esophagus 20 that generally are not covered by serosa. Preferably, the movement restriction device 110 has a rounded, substantially smooth outer surface so as to make it suitable for implantation.

These characteristics of the shape allows for the movement restriction device 110 to be placed to rest against, and supported by, the lowest portion of the esophagus 20 and extend upwards, towards the diaphragm 30, while avoiding contacting or abutting portions of the esophagus 20 which are arranged further up and generally not covered by a protecting layer of serosa Preferably, the movement restriction device 110, when arranged in such a position, may comprise an upper portion having an extension that is large enough to allow the movement restriction device 110 to function as a mechanical stop against the diaphragm 30, hindering the cardia 22 from sliding upwards through the diaphragm opening (diaphragm hiatus) 32 and thereby reducing the risk for reflux symptoms. Preferably, the movement restriction device 110 may be configured to abut the serosa of the part of the esophagus 20 extending below the cardiac sphincter 26, and leave a gap to the outer surface of part of the esophagus 20 above the cardiac sphincter 26. By allowing an upper portion of the movement restriction device 110 to extend above the cardiac sphincter 26 and towards the diaphragm 30, the top portion of the movement restriction device 110 may be positioned sufficiently high to hinder the cardiac sphincter 26 from sliding through the diaphragm opening into the patient's thorax.

Figure 30:
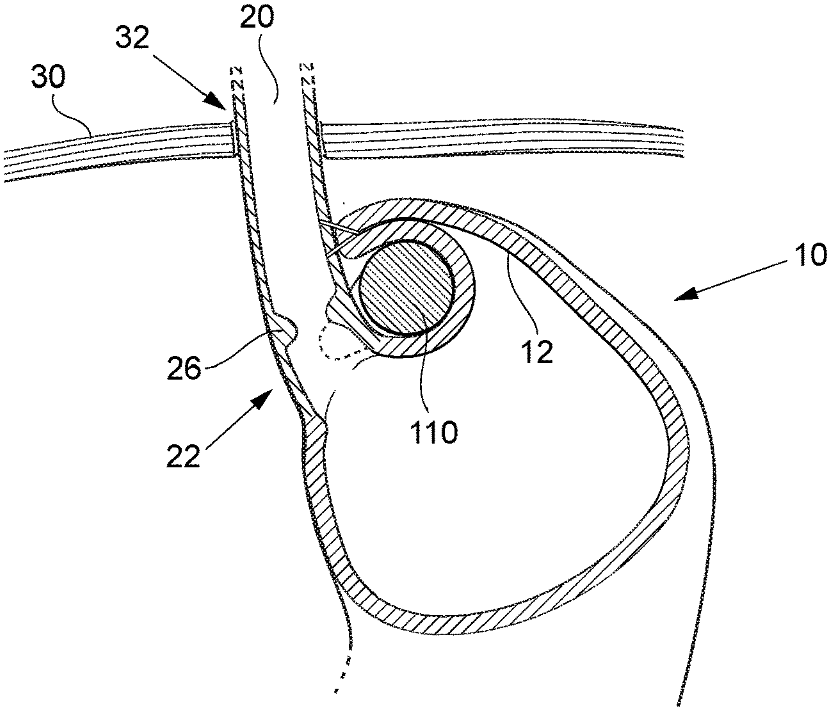

FIG. 30 shows a movement restriction device 110 having a lower portion with a curvature that allows for the movement restriction device 110 to at least partly follow the circumferential curvature of the esophagus 20. Thus, the movement restriction device 110 may be configured to be arranged at the junction between the esophagus 20 and the stomach 10, and such that it at least partly encircles the lower portion of the esophagus 20, which generally is covered with serosa. The movement restriction device 110 may thus be provided with C-shaped cross section along the surface adapted to be arranged to follow the circumference of the esophagus 20. Similar to what is described above, the movement restriction device 110 may point slightly away from the esophagus 20 further up along the esophagus 20, to define a separating gap between the outer surface of the esophagus 20 (which generally does not comprise any serosa further away from the angle of His) and the outer surface of the movement restriction device 110. The movement restriction device 110 may hence comprise at least two different curvatures—a first one along the circumferential curvature of the esophagus 20, and a second one allowing the upper portion of the movement restriction device 110 to fall away from the esophagus 20. The first curvature, adapted to phase the circumferential curvature of the esophagus, may comprise a radius of curvature that corresponds to or exceeds the radius of curvature of the esophagus 20.

Figure 29:
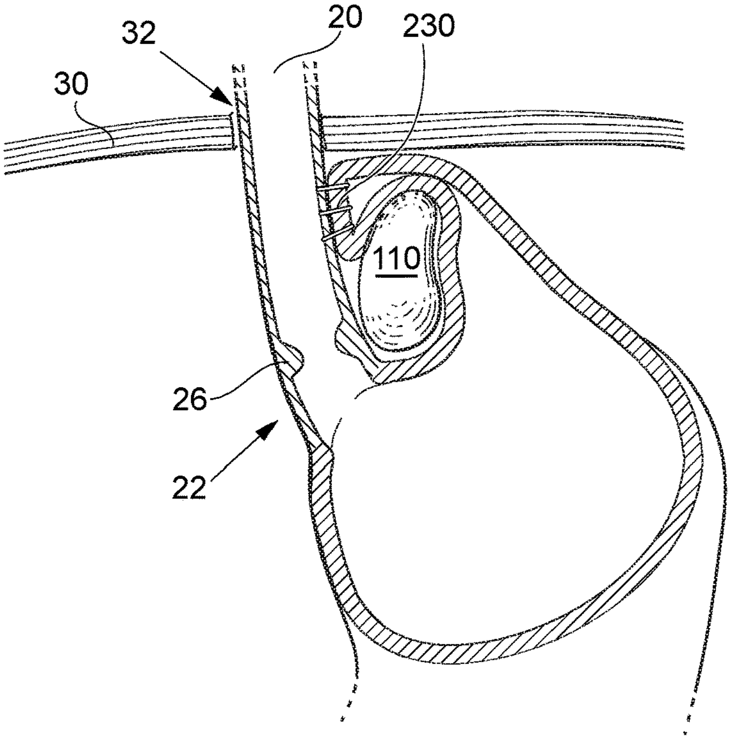

FIGS. 31A-F illustrate various examples of movement restriction devices 110, which may be similarly configured as the ones discussed with reference to the embodiments shown in FIGS. 29 and 30. It should be noted that the illustrations are schematic and not necessarily to scale. The actual shape and size of the movement restriction device 110 may vary depending on the physiology of the individual patient and may advantageously be adapted accordingly. A few characteristics may however be common to all examples illustrated in FIGS. 31A-F. The movement restriction device 110 may have a size and outer curvature that allows it to be arranged to rest against, and supported by, the lowest portion of the esophagus 20 and/or the portion of the fundus 12 arranged close to the esophagus 20, and extend upwards, towards the diaphragm 30, while avoiding contacting or abutting portions of the esophagus 20 which are arranged further up and generally not covered by a protecting layer of serosa.

The movement restriction devices 110 may be formed of a biocompatible material that is suitable for long-term implantation in the human body. Alternatively, or additionally, the outer surface of the movement restriction device 110 may be provided with a layer or coating of such a material. Examples of biocompatible materials include titanium or a medical grade metal alloy, such as medical grade stainless steel. In an alternative, movement restriction device 110 may be made from of comprise a ceramic material such as zirconium carbide, or a stiff medical grade polymer material such as Ultra-high-molecular-weight polyethylene (UHMWPE) or Polytetrafluoroethylene (PTFE) or a thermoplastic polyester such as polylactide (PLA). Movement restriction device 110 could also comprise at least one composite material, such as any combination of metallic/ceramic and polymer materials or a polymer material reinforced with organic or inorganic fibers, such as carbon or mineral fibers. Further, the movement restriction device may comprise an enclosure made from one of or a combination of: a carbon based material (such as graphite, silicon carbide, or a carbon fiber material), a boron material, a polymer material (such as silicone, Peek®, polyurethane, UHWPE or PTFE), a metallic material (such as titanium, stainless steel, tantalum, platinum, niobium or aluminum), a ceramic material (such as zirconium dioxide, aluminum oxide or tungsten carbide) or glass.

Preferably, the movement restriction device comprises a polymer material (such as silicone, Peek®, polyurethane, UHWPE or PTFE. Preferably, the movement restriction device comprises a biocompatible silicone-based material, such as liquid silicone rubber.

In some embodiments, the implantable movement restriction device comprises a biocompatible silicone based material, such as biocompatible silicone based material a density above 1000 kg/m3, more specifically above 1050 kg/m3, and even more specifically above 1100 kg/m3.

In addition to the polymer material, the movement restriction device may further comprise a contrast agent, in order to increase the visibility of the movement restriction device in X-ray imaging. An example of a preferred contrast agent is barium sulfate, BaSO4.

Preferably, the implantable movement restriction device comprises silicone, such as liquid silicone rubber, and BaSO4 as a contrast agent. During the manufacture of the implantable movement restriction device, which may be manufactured by means of injection moulding, BaSO4 powder is added to the polymer resin to form a mixture. The mixture is then injection moulded into the desired shape of the movement restriction device.

The movement restriction device may comprise barium sulfate in an amount of up to 15% by weight of the movement restriction device, such as in the range of 1-15% % by weight of the movement restriction device, preferably in the range of 1-10% by weight of the movement restriction device, such as of about 4-10% by weight of the movement restriction device.

Preferably, movement restriction device may comprise BaSO4 in an amount of 1-6% by weight of the movement restriction device.

Alternatively, the movement restriction device may comprise BaSO4 in an amount of 8-15% by weight of the movement restriction device.

BaSO4 has a density of approximately 4490 kg/m3, which is significantly higher than the density of biocompatible silicone-based material. Consequently, it may in some embodiments be advantageous to add a second polymer to the implantable movement restriction device, in order to reduce the overall weight. This is discussed in greater detail below, with reference to FIGS. 31 E-F and FIGS. 39Q-39 V'.

Further, each one of the movement restriction devices 110 shown in FIGS. 31A-F comprises an outer surface 110*a*. When implanted, the outer surface is configured to rest against the stomach wall portion. In particular, the outer surface 110*a* may have a size and outer curvature that allows it to be arranged to rest against, and supported by, the lowest portion of the esophagus 20 and/or the portion of the fundus 12 arranged close to the esophagus 20, and extend upwards, towards the diaphragm 30, while avoiding contacting or abutting portions of the esophagus 20 which are arranged further up and generally not covered by a protecting layer of serosa. The outer surface 100*a* is intended to denote the surface which defines the shape and size of the movement restriction device 110.

Preferably, the material of the outer surface may be a polymer material such as silicone, Peek®, polyurethane, UHWPE or PTFE. Preferably, the outer surface comprises a biocompatible silicone-based material, such as liquid silicone rubber such as biocompatible silicone based material a density above 1000 kg/m3, more specifically above 1050 kg/m3, and even more specifically above 1100 kg/m3 It has surprisingly been found that it is advantageous if an average surface roughness measured on the outer surface 110*a* is no more than 300'000 μm. A low surface roughness of the outer surface has been found to positively reduce the friction between the stomach wall and the movement restriction device 110. This is particularly advantageous in embodiments where the implantable movement restriction device 110 is intended to at least partially invaginated by the stomach wall. A high surface roughness generally corresponds to a high friction between the stomach wall and the movement restriction device 110. High friction between the stomach wall and the movement restriction device 110 could potentially cause the stomach wall to temporarily stick to the movement restriction device, in particular during the implantation surgery, which makes it difficult to position the device at its intended position against the stomach wall.

A low surface roughness has furthermore proven advantageous in that it reduces the wear between the implantable movement restriction device and the stomach wall, thereby reducing the risk of damage of the stomach wall during long-term use of the implantable movement restriction device. Such damage could include inflammation, and such damage could potentially lead to that the implant migrates through the tissue wall of the stomach wall.

The term "average surface roughness" may be used interchangeably with the term "arithmetic average surface roughness".

The average surface roughness as used herein may refer to the average profile surface roughness parameter Ra as defined according to ISO 21920-2:2021.

Alternatively, the average surface roughness as used herein may refer to the average surface roughness parameter Sa as defined according to ISO 25178-2:2021.

The average surface roughness may be determined in an Atomic Force Microscope (AFM) or by other means known to the person skilled in the art.

Surface roughness measurement are known to the skilled person in the art.

In some embodiments, the average surface roughness is in the range >0.5 μm-10 μm, >10-80 μm, >80-200 μm, >200-10'000 μm, >10'000-500'000 μm.

In some embodiments, the average surface roughness is less than 0.50 μm, such as less than 0.45 μm, such as less than 0.40 μm, such as less than 0.35 μm, such as less than 0.30 μm, such as less than 0.25 μm, 0.20 μm, such as less than 0.15 μm, such as less than 0.20 μm, such as less than 0.05 μm, such as less than 0.01 μm In some embodiments, the average surface roughness in the range of from 0.01 μm to 0.50 μm, in the range of from 0.01 μm to 0.45 μm, in the range of from 0.01 μm to 0.40 μm, such as in the range of from 0.01 μm to 0.35 μm, such as in the range of from 0.1 μm to 0.30 μm, such as in the range of from 0.01 μm to 0.25 μm.

In some embodiments, the average surface roughness measured anywhere according to the above-referenced ISO standards, on the outer surface of the implantable movement restriction device never exceeds 300'000 μm. This means that the complete outer surface of the implantable movement restriction device should has an average surface roughness of less than 300'000 μm.

Consequently, it should not matter whether the average surface roughness is measured as the profile parameter Ra as defined according to ISO 21920-2:2021, or as the area parameter Sa as defined according to ISO 25178-2:2021. Both methods of measurement should yield an average surface roughness of less than 300'000 μm, measured anywhere on the outer surface (i.e. a surface intended to abut the stomach wall) of the movement restriction device.

Figure 31A:
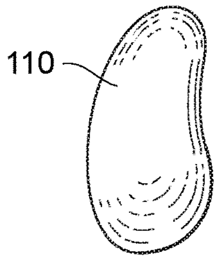
Figure 31B:
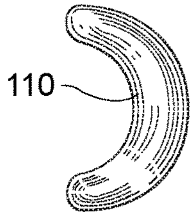
Figure 31C:
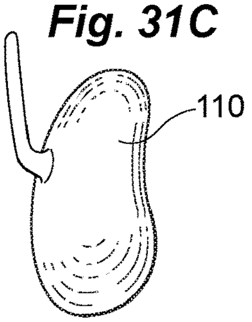
Figure 31D:
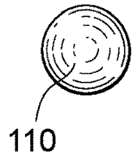
Figure 31E:
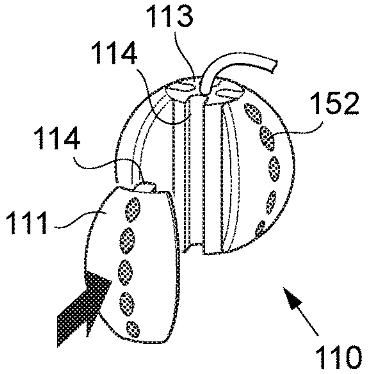
Figure 31F:
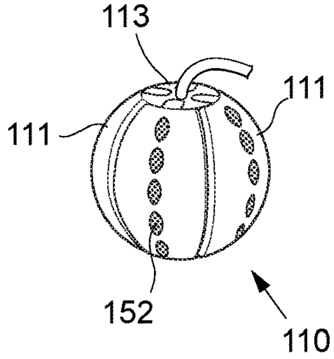

In the event that the movement restriction device comprises electrodes on its outer surface as shown in e.g. FIGS. 31E-F, the average surface roughness should be measured at a position on the outer surface not containing electrodes.

The movement restriction devices 110 may be formed of a biocompatible material that is suitable for long-term implantation in the human body. Alternatively, or additionally, the outer surface of the movement restriction device 110 may be provided with a layer or coating of such a material. Examples of biocompatible materials include titanium or a medical grade metal alloy, such as medical grade stainless steel. In an alternative, movement restriction device 110 may be made from of comprise a ceramic material such as zirconium carbide, or a stiff medical grade polymer material such as Ultra-high-molecular-weight polyethylene (UHMWPE) or Polytetrafluoroethylene (PTFE) or a thermoplastic polyester such as polylactide (PLA). Movement restriction device 110 could also comprise at least one composite material, such as any combination of metallic/ceramic and polymer materials or a polymer material reinforced with organic or inorganic fibers, such as carbon or mineral fibers. Further, the movement restriction device may comprise an enclosure made from one of or a combination of: a carbon based material (such as graphite, silicon carbide, or a carbon fiber material), a boron material, a polymer material (such as silicone, Peek®), polyurethane, UHWPE or PTFE), a metallic material (such as titanium, stainless steel, tantalum, platinum, niobium or aluminum), a ceramic material (such as zirconium dioxide, aluminum oxide or tungsten carbide) or glass.

Preferably, the movement restriction device comprises a polymer material (such as silicone, Peek®, polyurethane, UHWPE or PTFE. Preferably, the movement restriction device comprises silicone, such as liquid silicone rubber.

In addition to the polymer material, the movement restriction device may further comprise a contrast medium, in order to make A movement restriction device comprising a polymer material can be manufactured by means known to the skilled person in the art, such as injection moulding.

For example, when injection moulding is used to manufacture the implantable movement restriction device, an average surface roughness measured on the outer surface of the of less than 300'000 μm can be obtained by utilizing a mould having a corresponding low surface roughness. Typically, the surface roughness of a moulded polymer object matches the surface roughness of the mould utilized in the injection moulding.

Additionally or alternatively, an average surface roughness measured on the outer surface of the of less than 300'000 μm can be obtained by polishing or etching of the manufactured movement restriction device.

The provision of a mould with a low surface roughness can be obtained for example by mechanically treating the mould surface, such as by grinding, polishing, blasting or the like. It may also be obtained chemically by utilizing a suitable etchant.

It is equally conceivable that any one of the movement restriction devices shown in the present disclosure in e.g. FIG. 1, 2, 3, 4, 5, 6A, 6B, 7, 8, 9, 10, 11, 12 13, 14, 15, 16, 17, 18A-J, 19A-B, 20A-B, 21, 22, 23 A-C, 24, 25, 26, 27, 28, 29, 30, 32, 33, 34, 35, 36, 37 A-C, 38 A-B, 39 A-AJ comprises an average surface roughness measured on the outer surface 110*a* of no more than 300'000 μm, as defined in the aspect above.

In aspects and embodiments of the present invention, it has surprisingly been found that the implantable movement restriction devices as shown in FIGS. 31A-F should preferably exhibit an indentation hardness on the Shore A scale measured on the outer surface of at least 50. The indentation hardness is an indication of the hardness of the material, and thus its capability to elastically compress. It has been found that an implantable movement restriction device having exhibiting an indentation hardness on the Shore A scale measured on the outer surface of more than 50 is sufficiently sturdy to be handled by the surgeon during implantation of the implantable movement restriction device.

In such aspects and embodiment, at least the outer surface of the movement restriction device comprises a polymer material. The Shore A scale is suitable for measuring the hardness of elastomeric polymers such as those suitable for use on the outer surface of the implantable movement restriction device. In some embodiments, all parts of the implantable movement restriction device being enclosed by the outer surface are made of a polymer, such as an elastomeric polymer such as at least one of a silicone-based material and a polyurethane-based material. Preferably, they are made of, such as medical-grade silicone, also known as medical grade polysiloxane, such as of liquid silicone rubber (LSR). Other examples include Peck®), polyurethane, polyethylene-based (such as UHWPE) or PTFE, polypropylene-based, a SRP-based, a PPSU-based, a PSU-based, carbon-based material, or bio ceramic-based, material or any mixture thereof.

It has been found that a degree of elastic compressibility in the implantable movement restriction device is advantageous, since it allows the implantable movement restriction device to be compressed slightly by the surgical tools during the implantation surgery, which allows the surgeon to better hold on to the implantable movement restriction device. Consequently, in some embodiments, the indentation hardness on the Shore A scale measured on the outer surface (110*a*) is no more than 70.

Preferably, the indentation hardness is measured by the durometer method defined in part 4 of ISO 48-4:2018.

In some embodiments, an indentation hardness on the Shore A scale measured on the outer surface (110*a*) is in the range of 50-70, such as in the range of from 51-70, such as in the range of from 51-70, such as in the range of from 52-70, such as in the range of from 53-70, such as in the range of from 54-70, such as in the range of from 55-70, such as in the range of from 56-70, such as in the range of from 57-70, such as in the range of from 58-70, such as in the range of from 59-70.

In some embodiments, an indentation hardness on the Shore A scale measured on the outer surface (110*a*) is in the range of 50-70, such as in the range of 50-69, such as in the range of 50-70, such as in the range of 50-68, such as in the range of 50-67, such as in the range of 50-66, such as in the range of 50-65, such as in the range of 50-64, such as in the range of 50-63, such as in the range of 50-62, such as in the range of 50-61, In some embodiments, an indentation hardness on the Shore A scale measured on the outer surface (110*a*) is in the range of 50-70, such as in the range of 51-69, such as in the range of 52-68, such as in the range of 53-67, such as in the range of 54-66, such as in the range of 55-65, such as in the range of 56-64, such as in the range of 57-63, such as in the range of 58-62, such as in the range of 59-61, such as of about 60.

Preferably, the implantable movement restriction devices 110 disclosed in the present application has an indentation hardness on the Shore A scale measured on the outer surface of at least 50, and average surface roughness measured on the outer surface 110*a* is no more than 300'000 μm.

It is equally conceivable that any one of the movement restriction devices shown in the present disclosure in e.g. FIG. 1, 2, 3, 4, 5, 6A, 6B, 7, 8, 9, 10, 11, 12 13, 14, 15, 16, 17, 18A-J, 19A-B, 20A-B, 21, 22, 23 A-C, 24, 25, 26, 27, 28, 29, 30, 32, 33, 34, 35, 36, 37 A-C, 38 A-B, 39 A-AJ exhibit an indentation hardness on the Shore A scale measured on the outer surface of at least 50, as defined in the aspect above.

FIG. 31A illustrates an example wherein the lower portion of the movement restriction device 110 is wider than the upper portion, such that the lower portion can rest against the angle of His while the upper portion may be arranged in a position defining a gap between the movement restriction device 110 and the esophagus, similar to what is described with reference to FIG. 29.

FIG. 31B illustrates a movement restriction device 110 having a curvature that can be arranged to follow the circumference of the esophagus 20 at the angle of His, and thereby at least partly encircle the esophagus 20, and a further curvature allowing the movement restriction device 20 to taper off from the esophagus, as seen along a length direction of the esophagus. The embodiment may be similarly configured as the one described with reference to FIG. 30.

Figure 32:
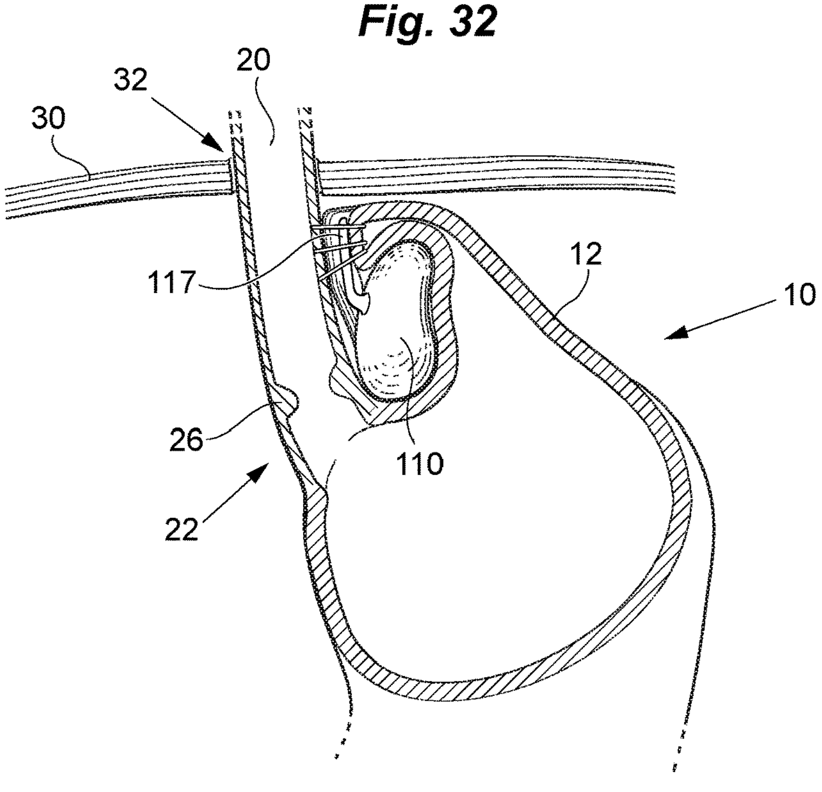

FIG. 31C shows the movement restriction device 110 in FIG. 31A with an elongated support 117 as shown in FIG. 32. The elongated support 117 may be attached to any of the examples of the movement restriction devices 110 discussed in the context of the present application for further improving the attachment of the movement restriction device 110 to the stomach 10 and reducing the risk for the movement restriction device 110 moving or changing is location and/or orientation relative to the esophagus 20. The support 117 may be configured to be affixed to the esophagus or fundus as discussed below with reference to FIG. 32.

FIG. 31D shows a further example of the movement restriction device 110, being substantially ball-shaped or spherical. For some patients it may be possible to arrange such a movement restriction device 110 at the angle of His and such that the upper part of the movement restriction device 110 do not abut the part of the esophagus 20 not covered by serosa. This depends on the anatomy and physiology of the actual patient, and further on the size and curvature of the movement restriction device 110. In some, non-limiting example the movement restriction device may have a shape conforming to a sphere having a diameter of 3 cm or more, such as 4 cm or more, such as 5 cm or more.

FIGS. 31E and F illustrate a movement restriction device 110 which may have a similar shaped and size as the embodiment shown in FIG. 31D, with the difference that the movement restriction device 110 may be formed of a plurality of segments 111 similar to the embodiment shown in FIG. 5. The embodiments of FIGS. 29-31 may further be combined with an electrode arrangement 150 for electrically stimulate and exercise the muscle tissue of the tissue against which the movement restriction device 110 rests when implanted, as discussed above in connection with for example FIGS. 1-5.

The movement restriction device 110 disclosed in FIGS. 31E-F is formed of a plurality of segments 111 that are configured to be attached to be assembled into a complete movement restriction device 110. The segments 111 may for example be secured to each other by means of mutually engaging structures 114 such as protruding slits and receiving grooves, snap-fit connectors, or the like. In the present example, the movement restriction device 110 may be formed of five segments 111: four outer parts 112 and an inner, core part 113 around which the outer parts 112 may be arranged to form a rounded and substantially smooth body suitable for invagination. The segments 111 may be configured to be securely attached to each other, or to be loosely fitted and kept in their right position when invaginated by the surrounding fundus wall 12. In some examples, the segments 111 may be secured to each other by means of a wire. The wire may be biodegradable and eventually dissolved. The segments 111 may be configured to be introduced in the body of the patient separately, one by one, and assembled into the movement restriction device 110 in connection with being implanted.

The movement restriction device illustrated in FIGS. 31E and F, wherein the plurality of segments are comprised of a core part and a plurality of outer parts, and wherein the core part has an average density of above 1000 kg/m3.

It has proven advantageous if the core part has a higher density than the outer parts. This way, the mass center of the device will be distributed towards the geometrical center of the movement restriction device.

Consequently, it may be advantageous to provide the contrast agent discussed above in the core part of the implantable movement restriction device.

In some embodiments, at least one outer part in the plurality of outer parts has an average density below 1000 kg/m3. The outer parts may then have a lower density, than the core parts.

The term "average density" is intended to refer to the density of the part in itself, irrespective of whether it is made of one or more materials, each having their own separate densities. The average density as defined herein is merely the weight if the part divided by its volume.

In some embodiments, the average density of the at least one outer part and the average density of the core part differ by at least 10 kg/m3, such as of at least 20 kg/m3.

Although the movement restriction device shown in FIGS. 31E and F is shown having a core part and 4 outer parts, it is equally conceivable that the implantable movement restriction device comprises a core part and 42 or 3 outer parts.

In some embodiments, all outer parts in the plurality of outer parts have an average density below 1000 kg/m3.

The core part may comprise a first solid material, being a biocompatible silicone-based material having a have an average density above 1000 kg/m3, more specifically above 1050 kg/m3, and even more specifically above 1100 kg/m3, and the at least one outer part may comprise second solid material has a may have an average density below 1100 kg/m3, more specifically below 1050 kg/m3, and even more specifically below 1000 kg/m3.

Figure 39A:
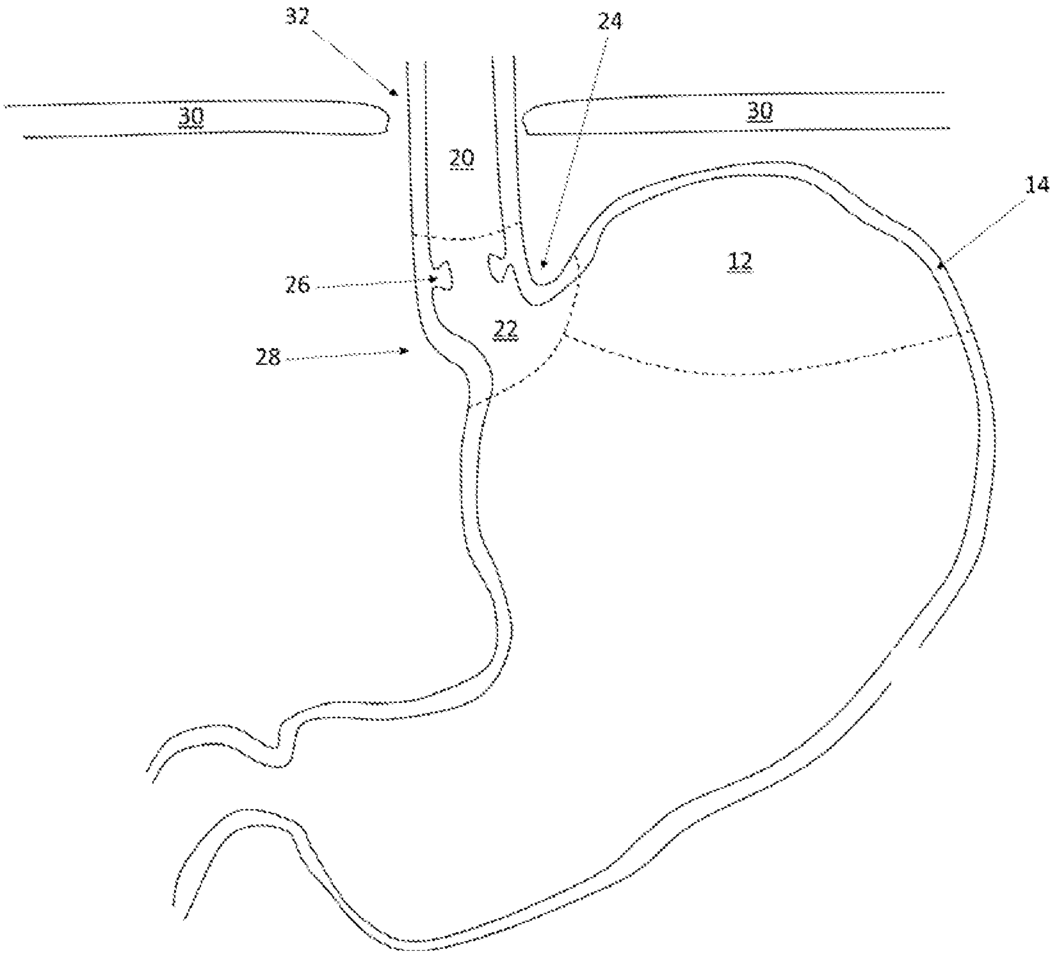
FIG. 39A is a schematic cross-section illustrating the anatomy of the stomach of a human patient.
Figure 39B:
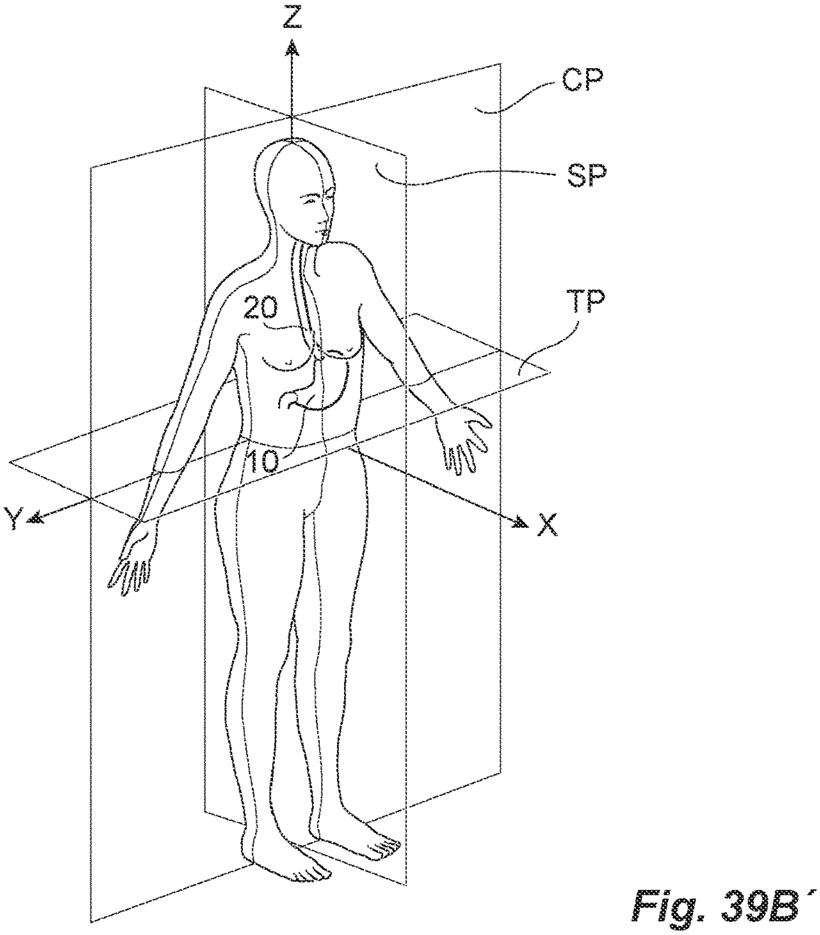
FIG. 39B is a schematic illustration of the anatomy of a human patient.
Figure 39B:
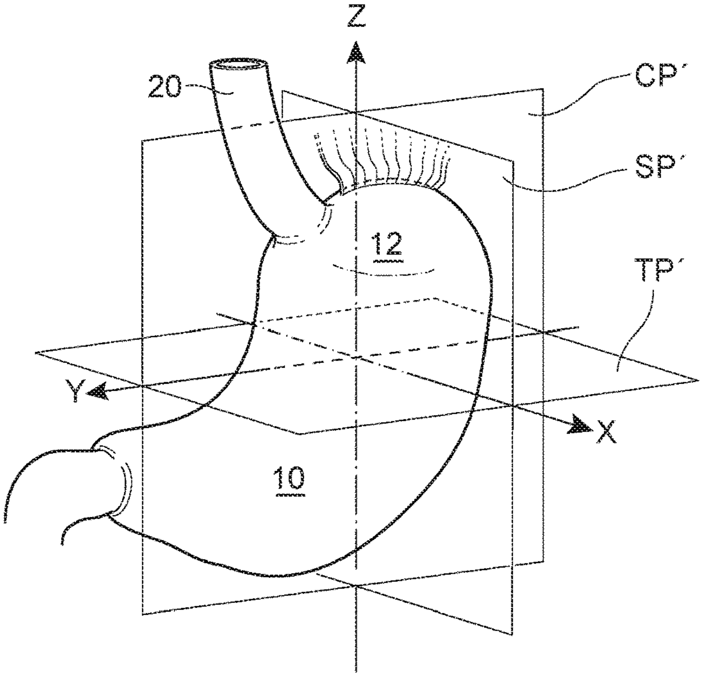
Figure 39C:
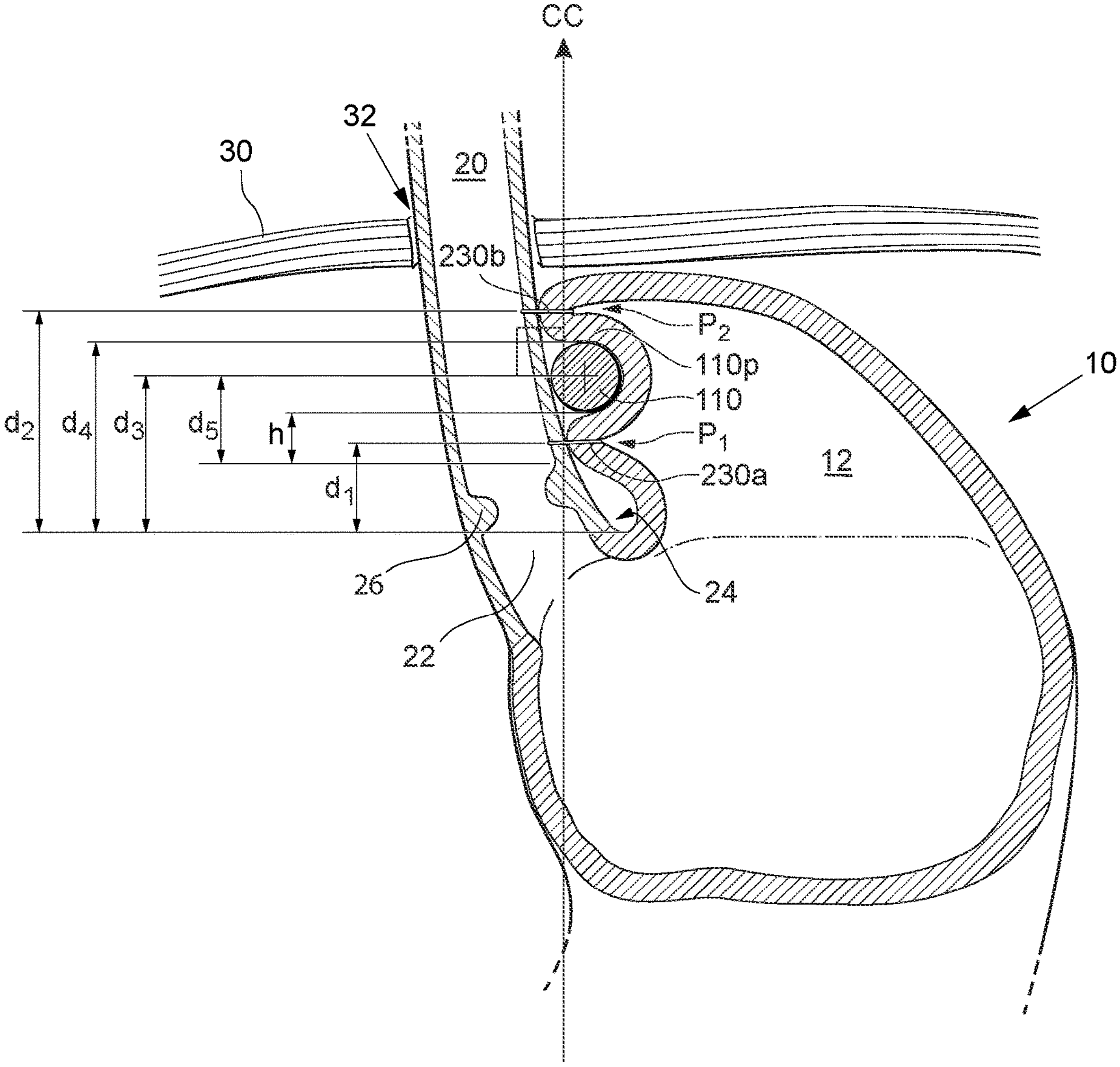
FIGS. 39C-39P' are schematic views of various examples of apparatuses and methods for treating reflux disease.
Figure 39D:
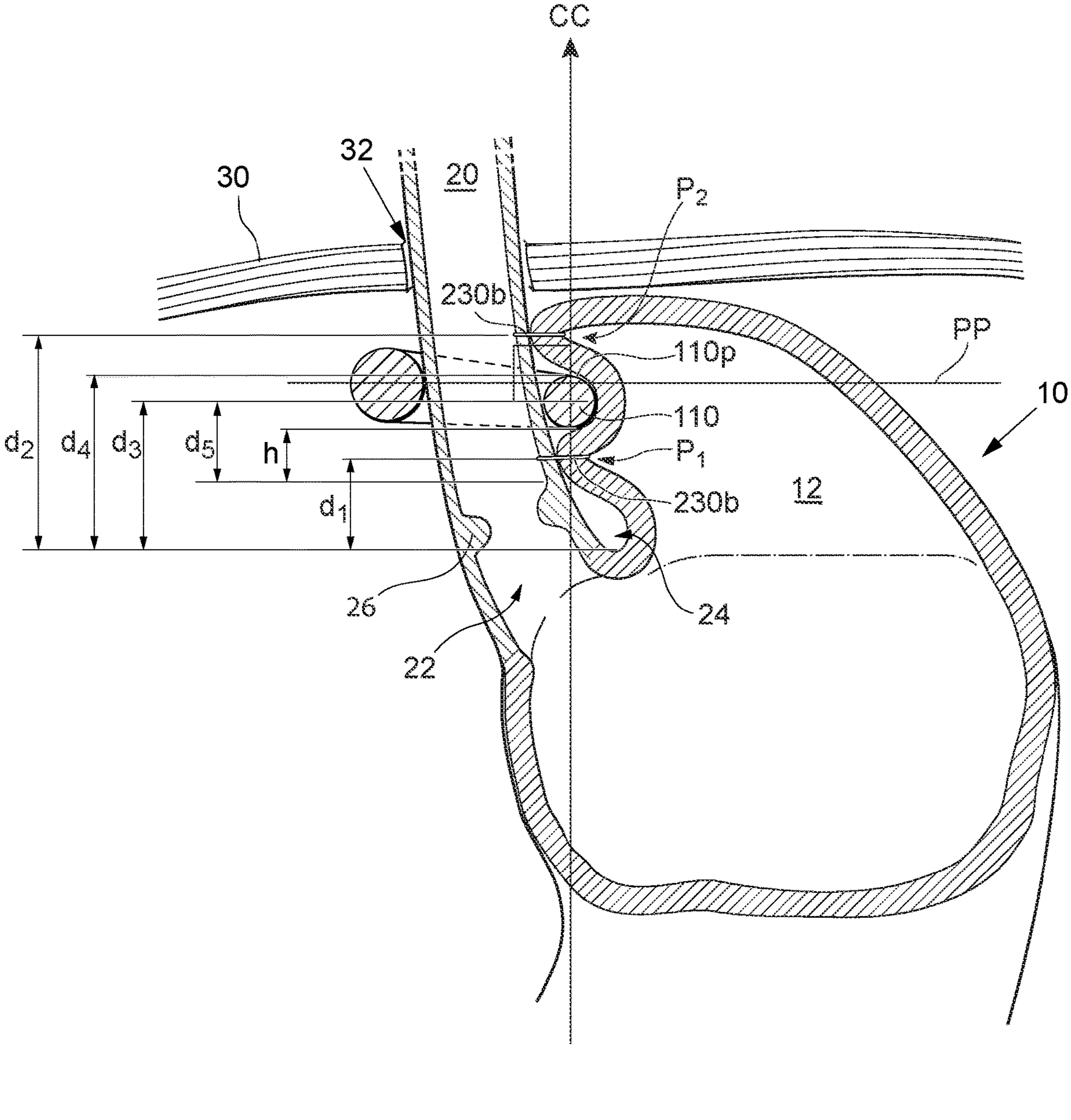
FIGS. 39Q-39V' are schematic cross-sectional views of various examples of movement restrictions devices for the treatment of reflux disease.
FIGS. 39W and 39W' are schematic cross-sectional views of an apparatus for the treatment of reflux disease and obesity.
FIGS. 39X-39Z" are schematic views of apparatus for the treatment of reflux disease and obesity shown in further detail.
Figure 39E:
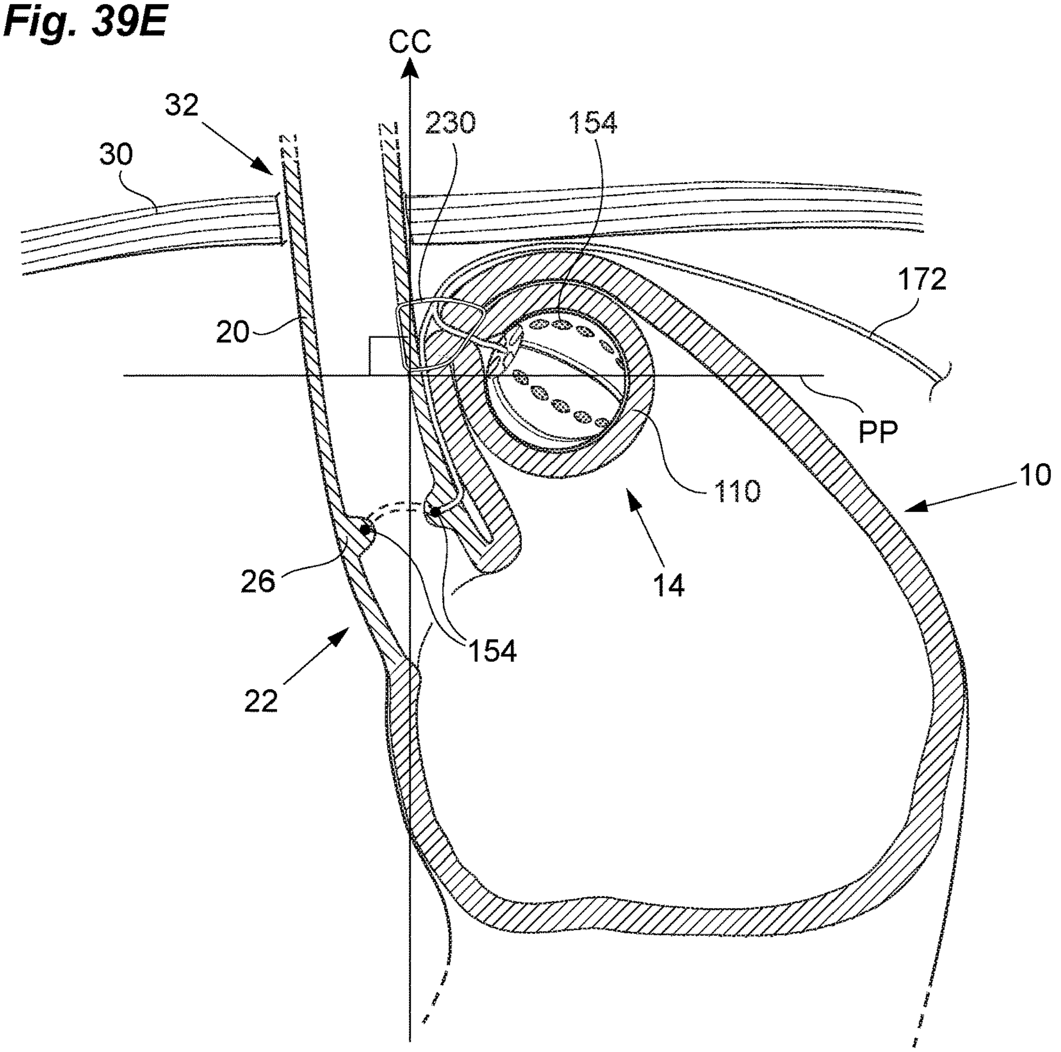
Figure 39F:
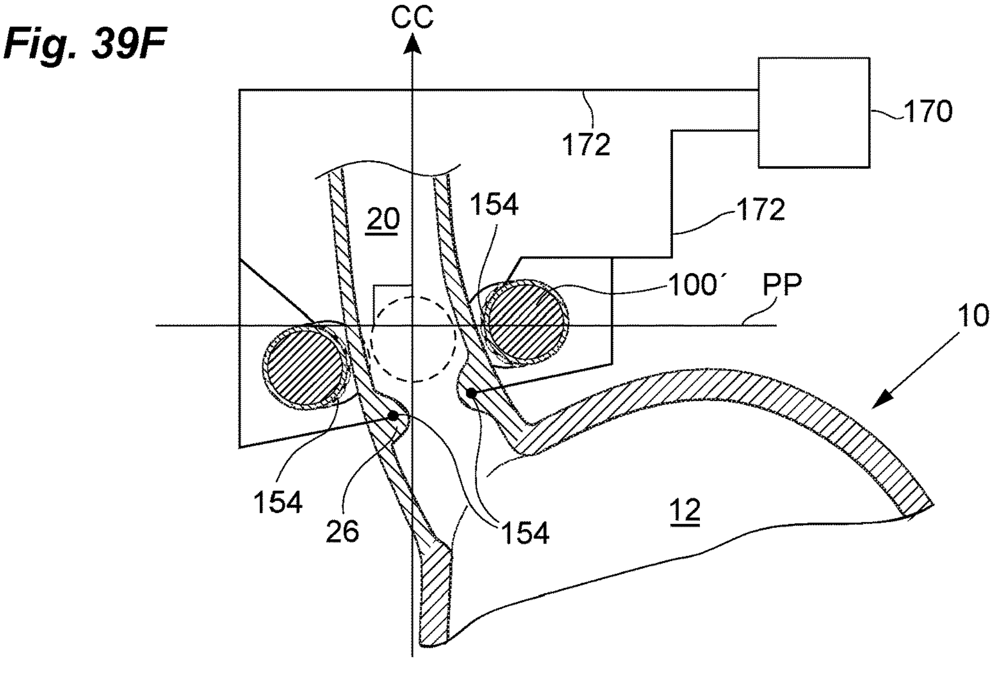
Figure 39G:
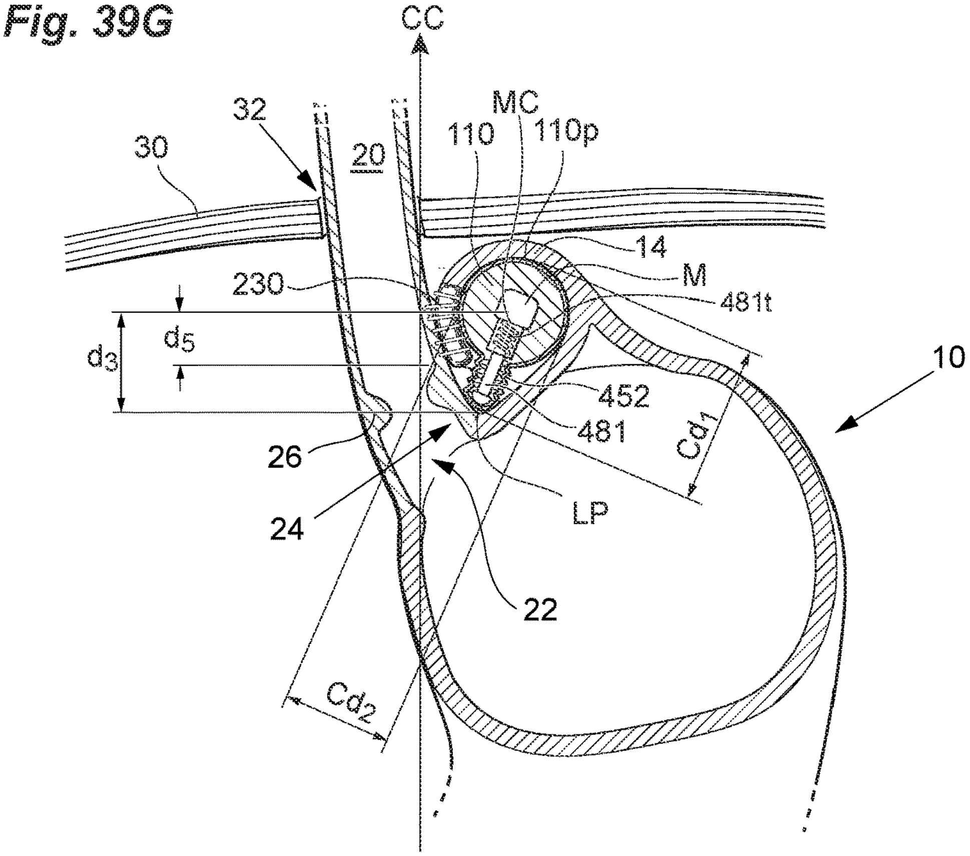
Figure 39H:
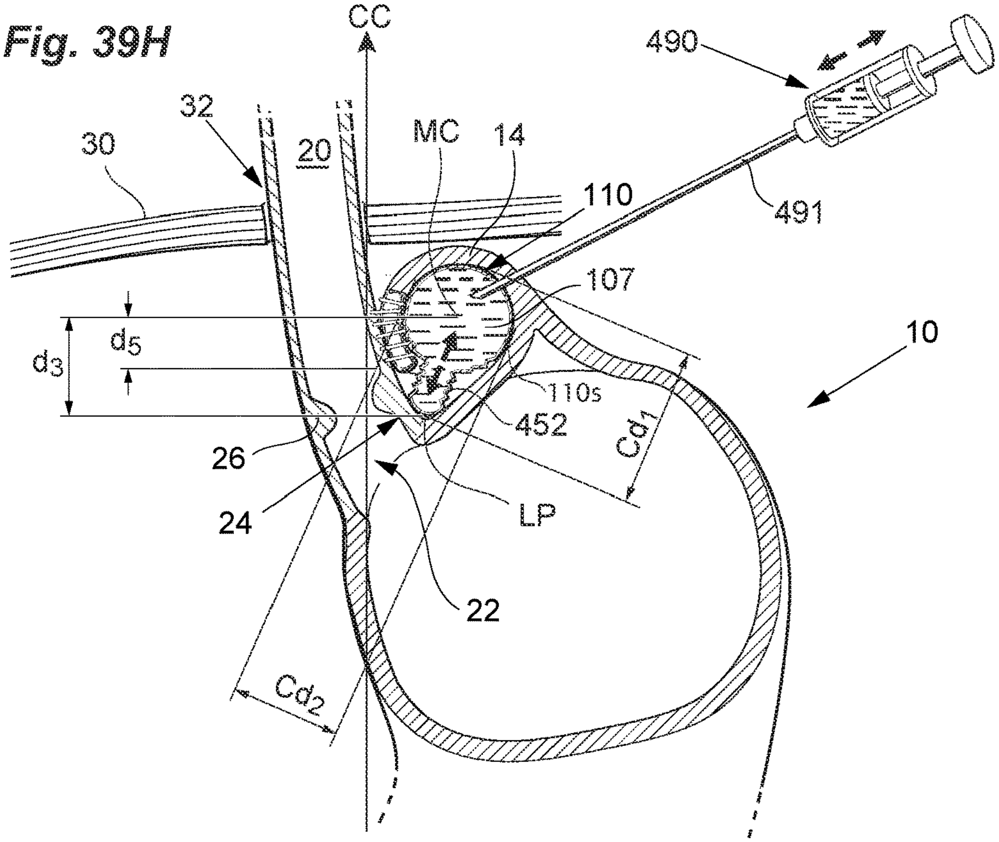
Figure 39I:
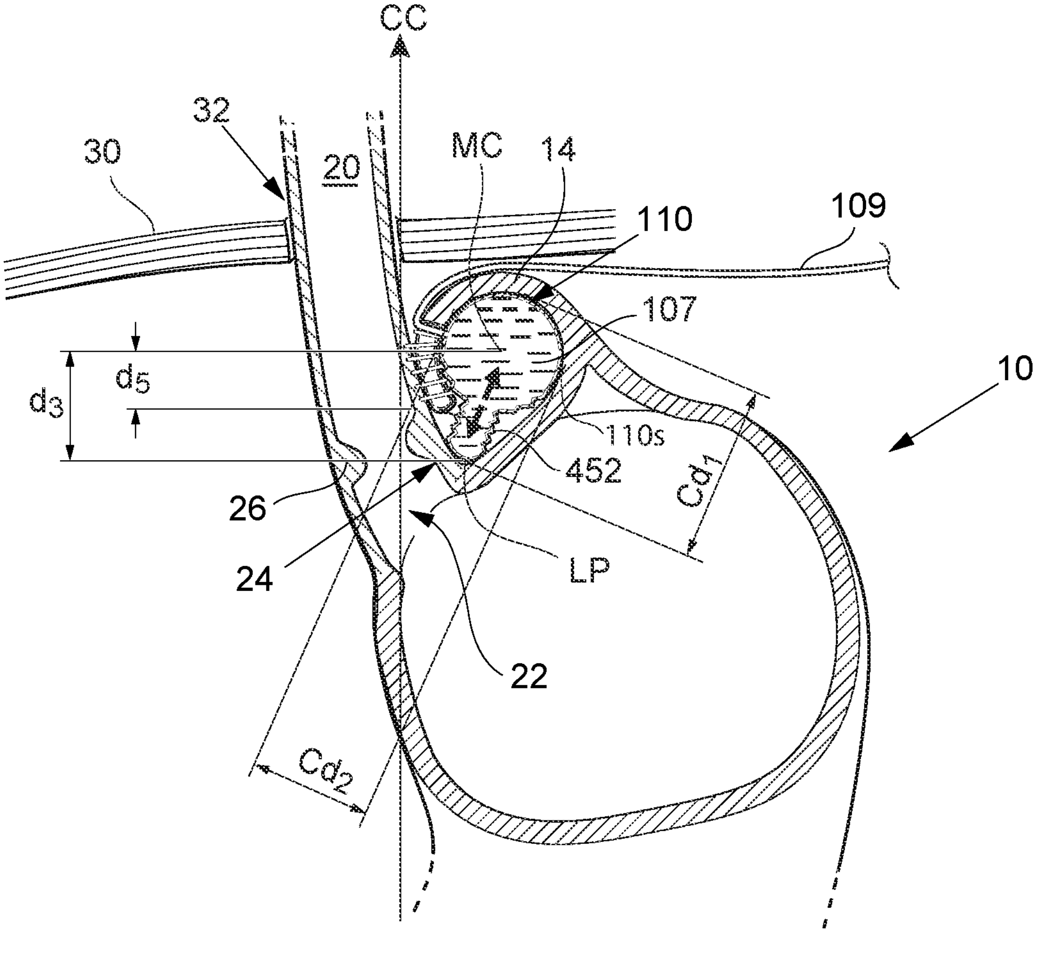
Figure 39J:
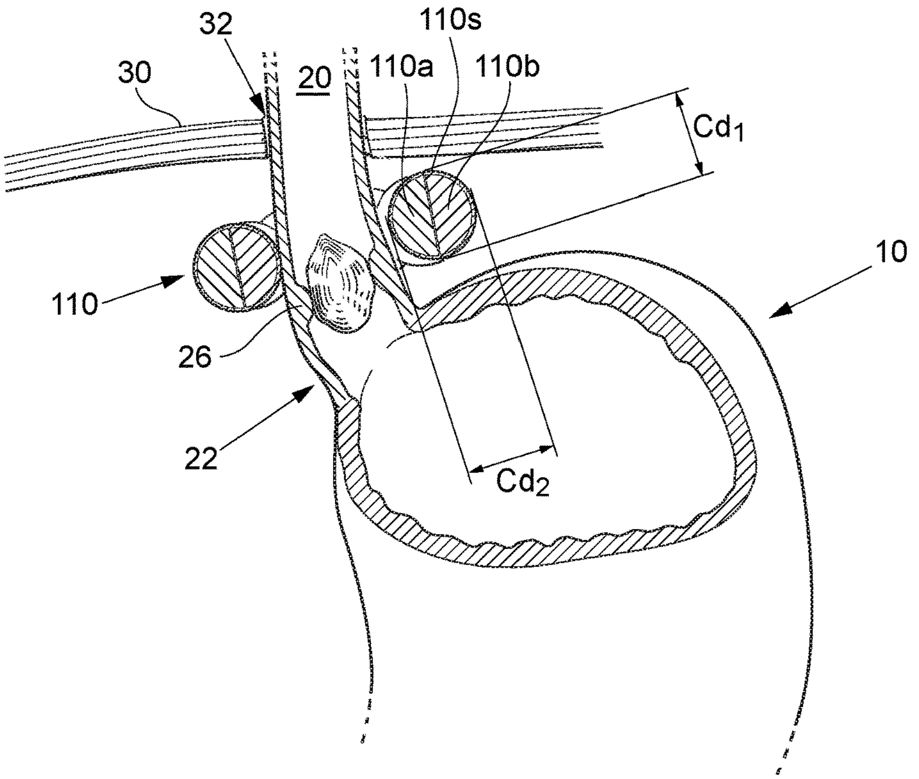
Figure 39J:
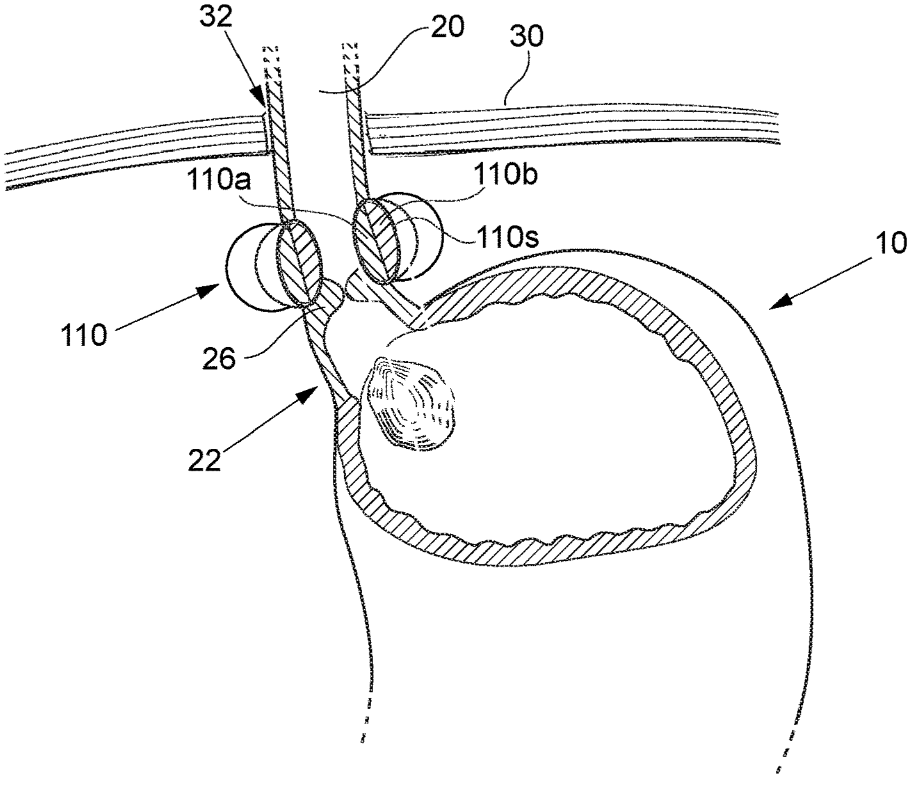
Figure 39K:
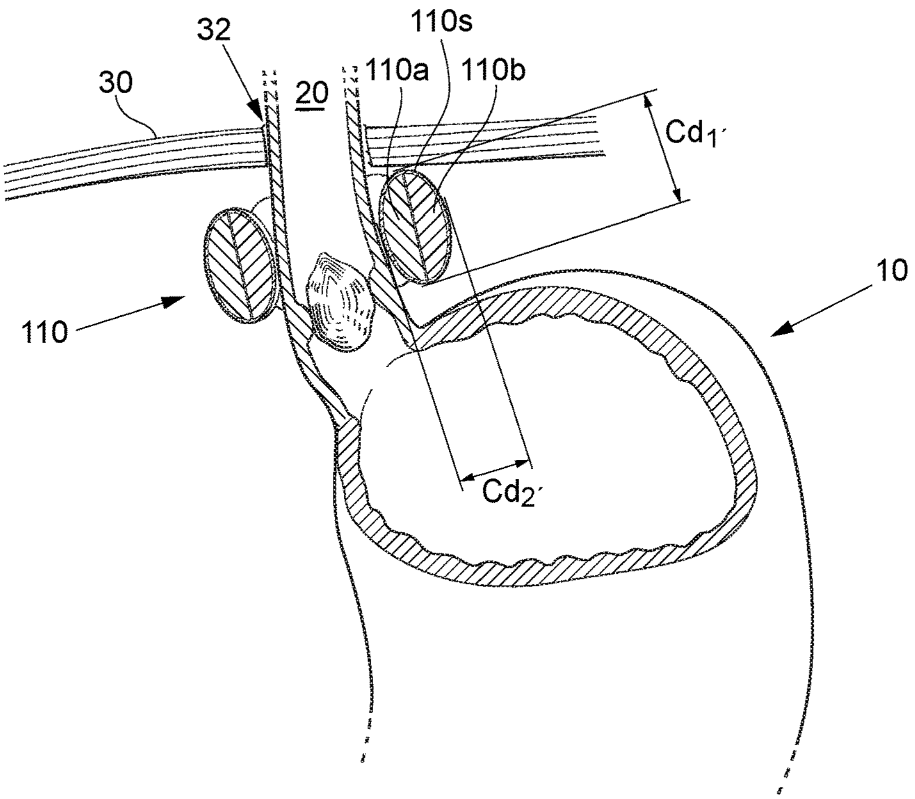
Figure 39K:
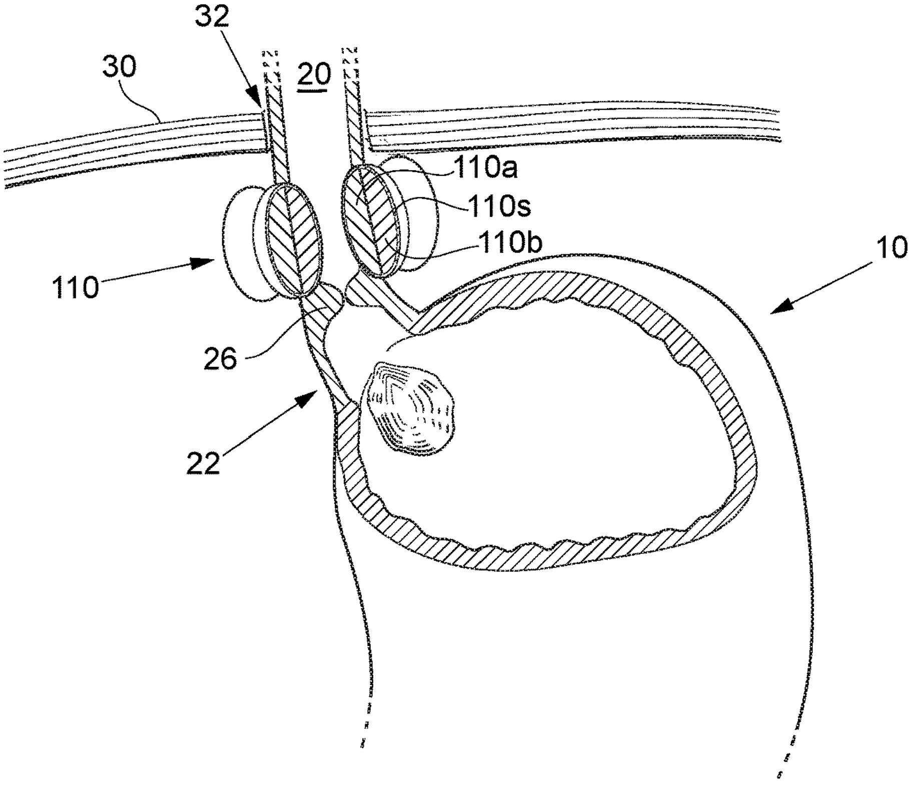
Figure 39L:
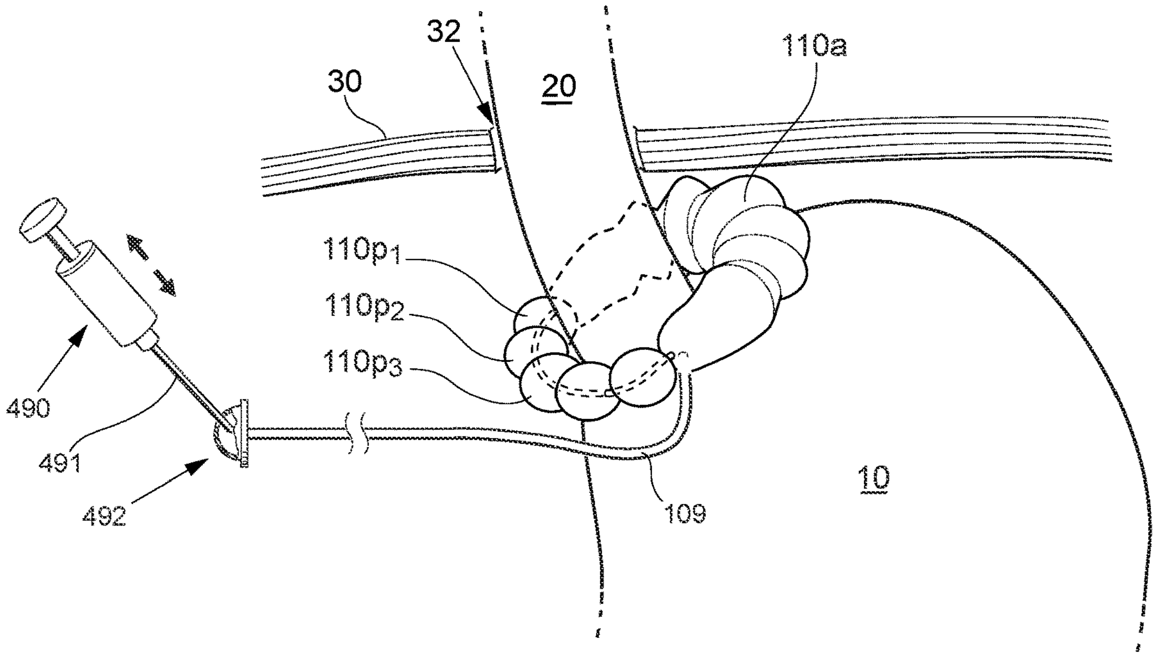
Figure 39M:
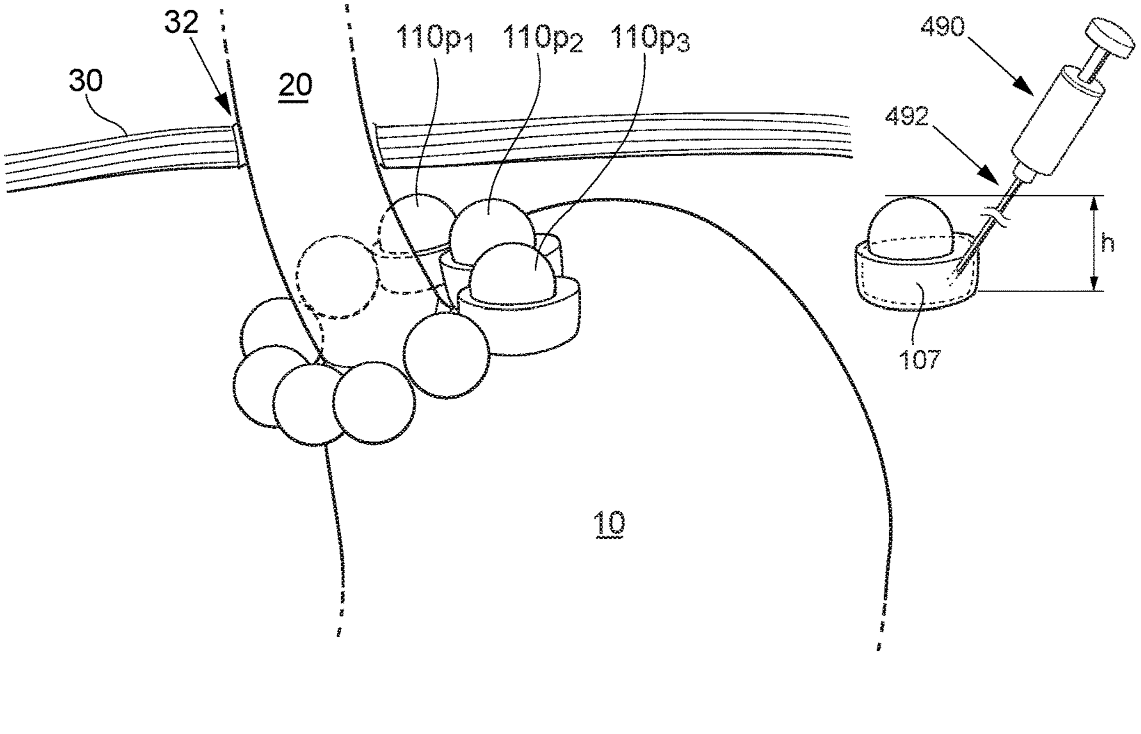
Figure 39N:
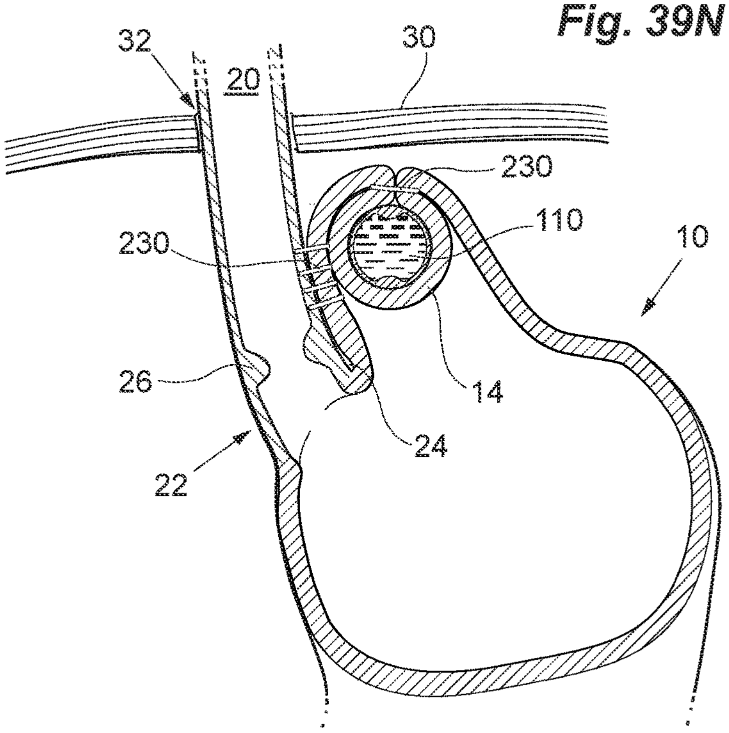
Figure 39N:
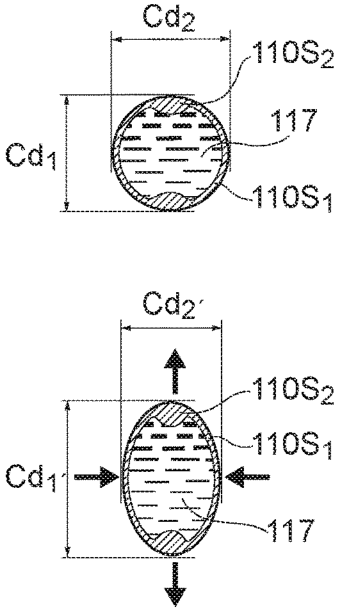
Figure 39O:
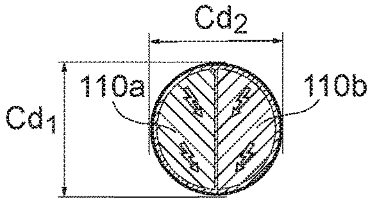
Figure 39O:
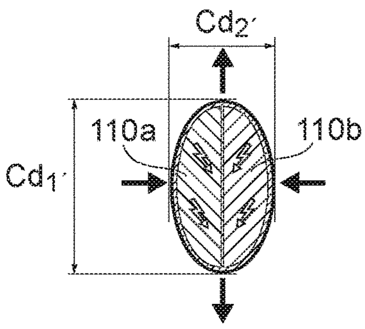
Figure 39P:
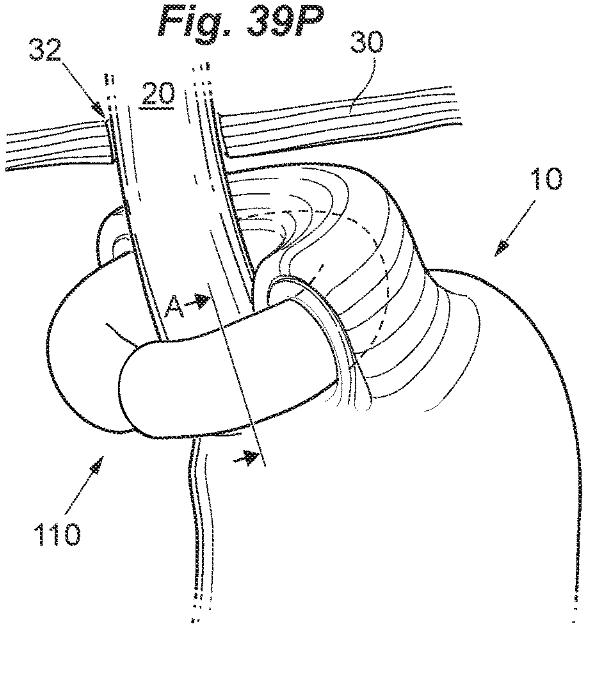
Figure 39P:
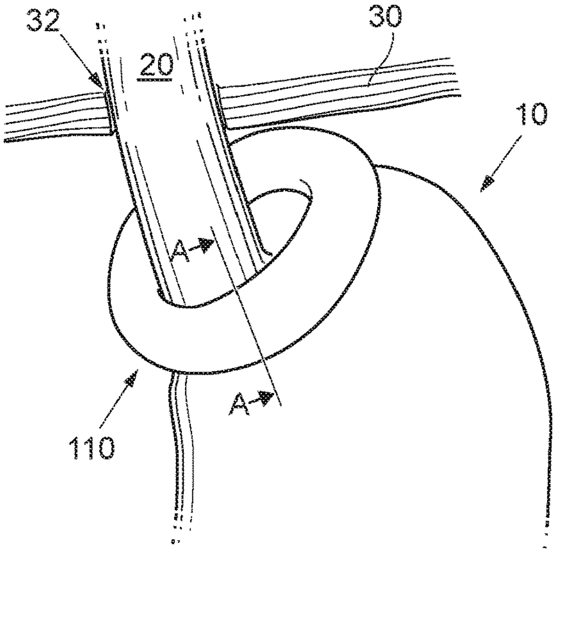
Figure 39Q:
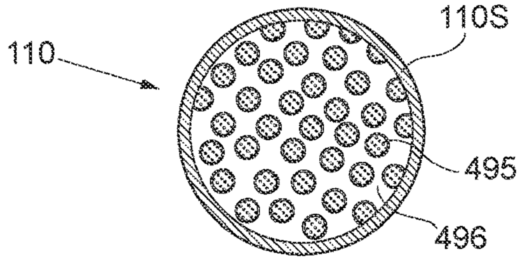
Figure 39Q:
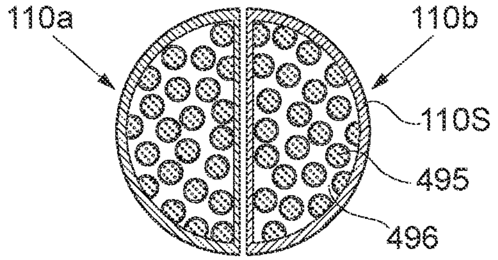

Similarly to the configuration shown in FIG. 39Q, the at least one outer part may comprise a biocompatible surface material 110*s* having an average density of about 1120 kg/m3, such as a biocompatible silicone-based surface material. However, it is equally conceivable that the biocompatible surface material 110*s* is a polyurethane-based surface material. The at least one outer part may further comprise an inner portion of the movement restriction device 110, enclosed by the biocompatible surface material, comprising a plurality of spheres 495 made from a glass-based material and enclosing a gas. The spheres 495 are stabilized in a polymer material 496, which could the same polymer material as in the biocompatible surface material 110*s*, or in the alternative a different polymer material, such as a polyethylene-based material or a polypropylene-based material. The combination of spheres 495 enclosing a gas and a stabilizing polymer material 496 results in an average density of the outer part below 1000 kg/m3. Reducing the weight of the outer part of the movement restriction device reduces the force that the implantable movement restriction device 110 exerts on the stomach wall, thus reducing the risk of wear, irritation and inflammation on the tissue wall which reduces the risk that the implant migrates through the tissue wall of the stomach wall.

In the embodiment shown in FIG. 39Q, the plurality of volumes of gas enclosed by an enclosing material makes up more than 10 volume percent of the second volume, more specifically more than 20 volume percent of the second volume, and even more specifically more than 30 volume percent of the second volume.

The core part is preferably made from a single polymer material such that an average density of the core part is of at least 1000 kg/m3. The core part may further comprise a contrast agent, such as BaSO4. It is particularly advantageous to position a majority of the contrast agent of the movement restriction device in the core part, as it is advantageous if the core part has a higher density than the outer parts. For example, the core part may comprise a contrast agent, preferably BaSO4 in an amount of 8-15% by weight of the core part. The at least one outer part may then be void of contrast agent, or comprise contrast agent in a lower amount, such as of 1-6% % by weight of the outer part. To compensate for the high density of the contrast agent, it is particularly advantageous if the at least one outer part further comprises a fluid, as discussed above. However, the core part may comprise an inner portion enclosed by the biocompatible surface material, comprising a plurality of spheres 495 made from a glass-based material and enclosing a gas. The spheres 495 are stabilized in a polymer material 496, which could the same polymer material as in the biocompatible surface material 110*s*, or in the alternative a different polymer material. However, the amount of gas in the core part should may be lower than the amount of gas in the at least one outer part, to ensure a higher density in the core part than in the at least one outer part. This means that the plurality of spheres in the core part may comprise fewer spheres per volume than the plurality of spheres in the at least one outer part. Alternatively, or additionally, the spheres in the core part may be smaller than the spheres of the at least one outer part.

Alternative, the amount of gas is the same in both the core part and the at least one outer part. The density can then be tailored by the adding more contrast agent to the core part than to the at least one outer part. For example, the core part may comprise contrast agent, preferably BaSO4 of 8-15% by weight of the outer part and the at least one outer part may be void of BaSO4 or comprise 1-6% of BaSO4 by weight of the at least one outer part. The BaSO4 will then be provided as a mixture with the stabilizing polymer material.

FIG. 32 shows an apparatus 100 which may be similarly configured as the embodiments discussed in connection with FIGS. 29-31, with the difference that the present example comprises an elongated support 117, or fastener, protruding from the movement restriction device 110. The elongated support 117, which may be shaped as a lever, may be configured to be oriented to extend along the esophagus 20 and affixed to the fundus 12 so as to provide additional mechanical support of the movement restriction device 110. The support 117 may be invaginated, or at least partly covered, by the fundus 12 tissue that may be wrapped around the movement restriction device 110 and affixed to the esophagus at least partly above the movement restriction device 110. The support 117 may protrude from the movement restriction device 110 with an angle that allows for the movement restriction device 110 to be arranged (and preferably secured over time) at a position reducing or avoiding direct contact between the movement restriction device 110 and regions of the esophagus 20 not comprising any serosa. The support 117 may be folded into, or at least partly invaginated by the fundus tissue in such a way that fundus tissue is arranged between the support 117 and the tissue of the esophagus 20.

FIGS. 33 and 34 illustrate an example wherein the apparatus 100 according to the embodiments of FIGS. 29-32 is used in combination with a bariatric procedure, such as for example sleeve gastrectomy. Sleeve gastrectomy, or gastric sleeve, is a surgical weight-loss procedure in the stomach is reduced in size by surgical (often laparoscopic) removal of a relatively large portion of the stomach along the greater curvature. In FIG. 34*a* the dashed line delimits the part that is to be removed, with the result shown in FIG. 34*b*. According to the present example, the implantation of the movement restriction device 110 and the sleeve gastrectomy may be performed during the same procedure, wherein the movement restriction device 110 may be positioned to rest against the angle of His and secured in this position by a portion of the fundus being affixed to the esophagus at a position above the movement restriction device 110 before the stomach is reduced along the greater curvature. It is advisable to implant the movement restriction device 110) before the sleeve gastrectomy is performed, so as to ensure that there is a sufficiently large portion of the fundus 12 available for the fixation of the movement restriction device 110. FIG. 34*b* shows the result, wherein the movement restriction device 110 may be encapsulated by the fundus 12 that is affixed to the esophagus 20 to form an enclosure accommodating the movement restriction device 110. The encapsulated movement restriction device 110 may thus form a mechanical stop hindering the cardia from sliding up through the diaphragm opening 32, while the overall volume of the stomach cavity has been reduced by the sleeve gastrectomy.

In case the stomach wall, such as the fundus, is not sufficiently large for allowing an apparatus according any of the embodiments of FIGS. 1-13 and 24-34, and in particular the movement restriction device 110 as discussed in connection with any of the previous embodiments, to be at least partly invaginated or covered by the stomach wall so that the apparatus may function as a movement restriction device of the cardia, an alternative apparatus shown in FIGS. 35-37 may be employed. The present apparatus may comprise an implantable movement restriction device 110 and an elongated attacher 117 configured to be attached to the movement restriction device and to be at least partly invaginated by a wall portion of the patient's stomach 10. As indicated in the present figures, the attacher 117 may comprise a shape and size allowing it to be invaginated by the wall portion to hinder rotation of the movement restriction device 110 when implanted. The attacher 117 may be configured to be invaginated by the outside of the wall portion such that the movement restriction device 110 is arranged at a position between the patient's diaphragm 30 and the wall portion of the stomach 10, distant from the patient's esophagus 20, to restrict movement of the cardia 22 of the patient's stomach towards the diaphragm 30 to hinder the cardia from sliding through the diaphragm opening 32 into the patient's thorax. The attacher 117 may also be referred to as a fixator, attaching means, support, and the like.

Thus, a first end portion of the attacher 117 may be configured to be affixed to the wall portion of the stomach 10 and a second end portion to be attached to the movement restriction device 110. The first end portion of the attacher 117 may be at least partly invaginated or covered by tissue of the stomach wall, which hence may be achieved using a relatively small portion of the outer wall of the stomach 10 compared to invaginating the entire movement restriction device 110 as discussed above in connection with the previous embodiments. The present embodiment hence allows for the movement restriction device 110 to be positioned so as to function as a mechanical stop of movement towards the diaphragm 30 also in cases when there is a relatively limited amount of stomach wall available. This may for example be the case after a gastric sleeve operation.

The attacher 117 may be releasably attached to the movement restriction device 110 to allow the surgeon to insert the attacher 117 and the movement restriction device 110 as separate items. Once inserted in the body of the patient, the movement restriction device 110 and the attacher 117 may be assembled into a single unit and then affixed to the outside of the stomach 110. The attacher 117 and the movement restriction device 110 may for example be secured to each other by means of interlocking attachment means, such as a snap fitting or a form fitting. The attacher 117 may also be attached to the movement restriction device 110 by means of a fastener means such as a threading, allowing the movement restriction device 110 to be screwed onto the attacher 117. In alterative examples, however, the movement restriction device 110 and the attacher 117 may integrally formed into a single piece.

Figure 35:
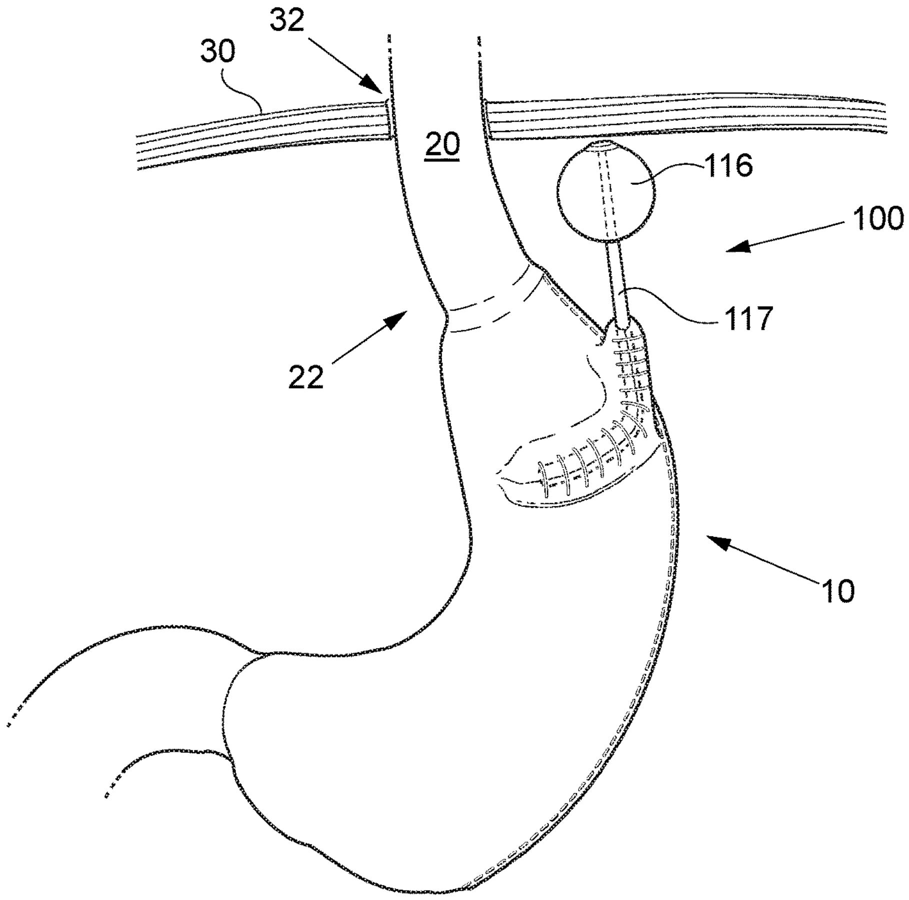
Figure 36:
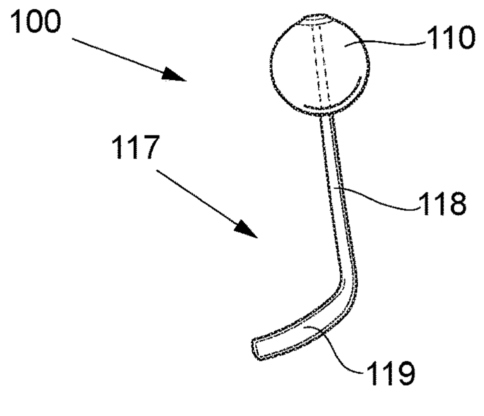

FIGS. 35 and 36 show an attacher 117 comprising a first portion 118 and a second portion 119 extending in different directions relative to each other, wherein the first portion 118 is configured to be invaginated by the wall portion to hinder rotation of the movement restriction device 110 around a first axis, and wherein the second portion 119 is configured to be invaginated by the wall portion to hinder rotation of the movement restriction device 110 around a second axis, different from the first axis. The first and second portions 118, 119 of the attacher 119 may further be curved to follow a curvature of the stomach. In some examples, the first portion 118 and the second portion 119 may be arranged at an angle to each other, wherein the angle for example may be in the interval of 60-120 degrees, such as about 90 degrees, so as to allow for the movement restriction device 110 to be mechanically supported by the stomach wall and movement of the restriction device 110 hindered in at least two different planes relative to the stomach portion. The attacher 117 may further comprise a third portion, being an extension of the second portion 119, which may be configured to be arranged to protrude from the wall portion when implanted to define a distance between the wall portion and the movement restriction device 110. In some examples, the third portion may comprise a curvature, which preferably may be adjustable, allowing the third portion to be arranged to point away from the esophagus 20 when implanted so as to reduce the risk for the movement restriction device 110 interfering with and constricting the esophagus 20.

The attacher 117 may be affixed to the stomach 10 in a procedure wherein the attacher 117 is placed onto the outer surface of the stomach 10, in a recess or fold which may be at least partly closed by means of stomach-to-stomach sutures or staples. Thus, the attached 117 may be at least partly covered and mechanically supported by tissue of the stomach wall. Eventually, the suture closing the recess or fold along the attacher 117 may be covered or encapsulated by fibrous tissue, further improving the affixation, and allowing for long-term implantation of the apparatus 100.

Preferably, the attacher 117 is formed or, or at least comprises an outer surface of a biocompatible material suitable for long-term implantation in the body. Examples of biocompatible materials include titanium or a medical grade metal alloy, such as medical grade stainless steel. Further examples include ceramic materials such as zirconium carbide, or a stiff medical grade polymer material such as Ultra-high-molecular-weight polyethylene (UHMWPE) or Polytetrafluoroethylene (PTFE) or a thermoplastic polyester such as polylactide (PLA). Further, the attacher 117 could comprise at least one composite material, such as any combination of metallic/ceramic and polymer materials or a polymer material reinforced with organic or inorganic fibers, such as carbon or mineral fibers.

The attacher 117 may also comprise an electrode arrangement 150 for electrical stimulation and exercise of the muscle tissue against which the attacher 117 rests when implanted. The electrode arrangement 150 may be configured and operate as any of the previous electrode arrangements 150 described with reference to FIGS. 1-34.

As illustrated in FIGS. 35-37, the movement restriction device 110 may have a rounded shape, for example conforming to a sphere, so as to reduce the risk for causing potential damage to surrounding tissue. The movement restriction device 117 may be formed of a polymer, or at least comprise an outer surface of such a material. The outer surface may further be provided with a material for hindering growth of fibrotic tissue. The outer surface may for example comprise a permanent or degradable polymer, containing an active pharmaceutical agent, coated on the movement restriction device 117. The coating may preferably allow for a gradual release of an antifibrotic drug. The eluted drug may thus be deposited at the contact point between the movement restriction device 110 and the tissue against which it abuts, such as the diaphragm 30, thereby providing targeted drug therapy. Examples of polymers include a blend of polyethylene-co-vinyl acetate (PEVA) and polybutyl methacrylate (PBMA) and poly(styrene-b-isobutylene-b-styrene), respectively. Further examples may include phosphorylcholine and poly(vinylidene fluoride-co-hexafluoropropylene) polymeric coatings, respectively.

Figure 37A:
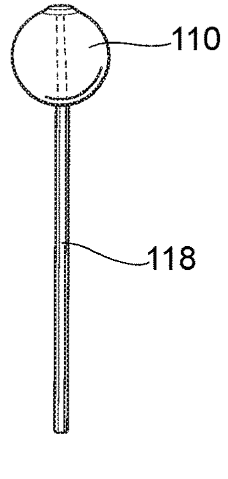
Figure 37B:
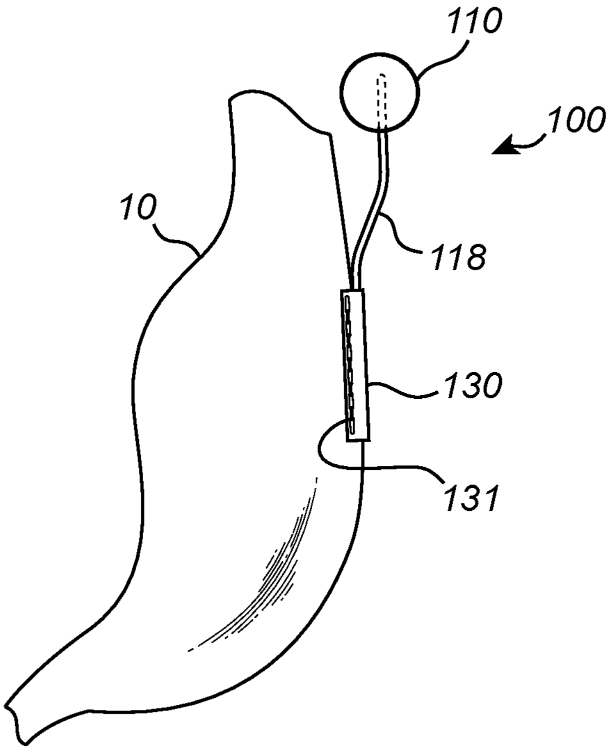
Figure 37C:
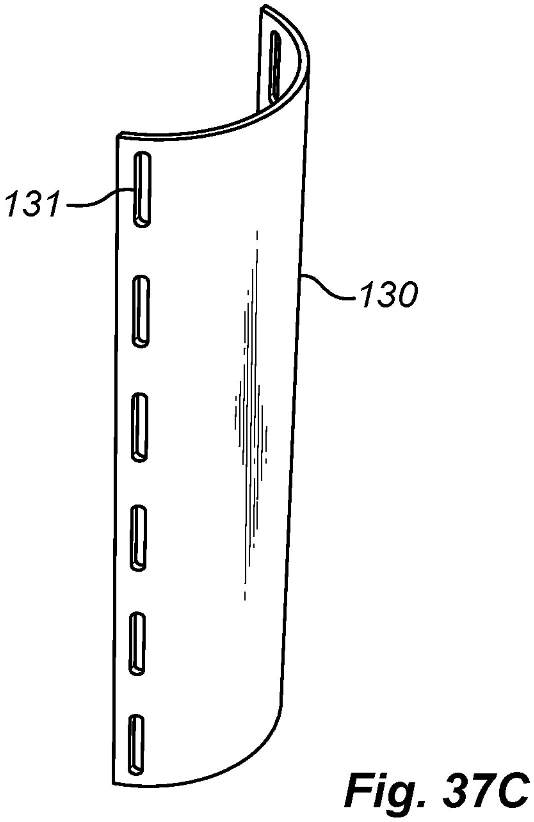

FIG. 37B shows the attacher 118 when secured to the stomach wall 10 at the sutures, or row of staples, used during the gastric sleeve surgery. Thus, the seam forming the sleeve may be provided with the additional purpose of securing the attacher 118, thereby reducing the need for additional surgery and interaction with the tissue of the stomach wall. Beneficially, to further improve the attachment to the stomach wall 10, a support device 130 may be arranged at the seam, as shown in FIG. 37C. In the present figures, a support device 130 in the form of a bar or flat rod, is disclosed. The bar may be formed or a sheet-like body with a rounded shape, such as a U-profile as indicated in the present figure, configured to follow an outer curvature of the stomach wall. The bar may be provided with a plurality of apertures 131 of through-holes through which the sutures may be threaded during the gastric sleeve surgery. The bar may hence be attached to the stomach wall by means of the same sutures or staples used for creating the gastric sleeve. The bar may further be configured to allow the attacher 118 to be securely attached thereto. In an example, the attacher 118 may be inserted between the bar 130 and the stomach 10 and held in place by the sutures or staples attaching the bar to the stomach wall. As illustrated in the example shown in the present figures, the attacher 118 may have a substantially rod-shaped portion configured to run at least partly along the bar 130 and then turning slightly away from stomach wall and the esophagus to reduce the risk of the movement restriction device 110, attached at the end portion of the attacher 118, touching or resting against the outside of the esophagus 20.

A further surgical method for treating reflux disease of a human patient by implanting a movement restriction device 110 such that the movement restriction device 110 is arranged to restrict movement of the cardia of the patient's stomach towards the diaphragm is provided, to hinder the cardia from moving towards and potentially sliding through the diaphragm opening into the patient's thorax. The method comprises: placing the movement restriction device 110 such that a lower portion of the movement restriction device rests against the serosa of the surgically modified stomach 10 on the greater curvature side of the stomach partly extirpated, such that an upper portion of the movement restriction device defines; a small gap between the movement restriction device positioned close to the diaphragm 30 and the patient's esophagus 20, when the lower portion rests against the surgically modified stomach. The method may further comprise arranging a portion of fat from the gastrophrenic and/or gastrosplenic ligament and/or greater omentum to cover the movement restriction device 110 on at least one of the left, ventral and cranial side of the movement restriction device with the intention to avoid adherences to the nearby organs. The movement restriction device 110 may have a rounded shape. The part of the movement restriction device 110 mounted towards the stomach may be configured like an U-shaped arm (117).

Further, the movement restriction device 110 may comprise an electrode arrangement 150 for electrical stimulation and exercise of the muscle tissue against which the movement restriction device 110 rests when implanted. The electrode arrangement 150 may be configured and operate as any of the previous electrode arrangements 150 described with reference to FIGS. 1-34

The movement restriction device 110 may have a shape and size that allows it to function as a mechanical stop abutting against the diaphragm 30, being sufficiently large to hinder the movement restriction device 110 from passing through the diaphragm 30 and sufficiently small so as to not push against the esophagus 20 and cause constriction of the food passageway. In some examples, a minimum width of the movement restriction device 110, as measured from side to side, may be 30 mm or larger, such as 40 mm or larger.

When implanted, the movement restriction device 110 may be supported by the attacher 117, which is affixed to the stomach 10, such that the movement restriction device 110 functions as a mechanical stop against the diaphragm 30 and thereby hinders the cardia 22 from sliding upwards towards the diaphragm opening 32. Preferably, the movement restriction device 110 may be arranged relatively close to the diaphragm opening 32, such as less than 2 cm away from the part of the esophagus 20 passing through diaphragm opening 32, without constricting the food passageway defined by the esophagus 20.

The position of the movement restriction device 110 relative to the diaphragm 30 and/or cardia may be adjusted after affixation of the attacher 117 to the stomach 10. The adjustment may for example be achieved by the attacher 117 being adjustable in terms of length and/or angle, wherein the attacher 117 for example may be extendible/retractable along the length directions, and/or bendable. This allows for the attacher to be affixed to a region on the outside of the stomach 10 which is suitable or even optimal for affixing the attacher 117, and for the movement restriction device 110 to be correctly aligned/positioned afterwards, without having to rearrange the affixation of the attacher 117 to the stomach 10.

In the following a detailed description of a method and system for electrically stimulating the muscle tissue against the apparatuses according to any of the embodiments discussed with reference to FIGS. 1-37 may rest when implanted. The electrical stimulation may be performed for exercising the muscle tissue and thereby improve the conditions for long term implantation. The electrical electrode arrangement described and the electrical electrodes comprised in the arrangement may be implemented in any of the embodiments of the apparatus described herein for the purpose of exercising the muscle tissue which is in contact with the apparatus, or mechanically affected by the apparatus.

The body tends to react to a medical implant, partly because the implant is a foreign object, and partly because the implant interacts mechanically with tissue of the body. Exposing tissue to long-term engagement with, or pressure from, an implant may deprive the cells of oxygen and nutrients, which may lead to deterioration of the tissue, atrophy and eventually necrosis. The interaction between the implant and the tissue may also result in fibrosis, in which the implant becomes at least partially encapsulated in fibrous tissue. It is therefore desirable to stimulate or exercise the cells to stimulate blood flow and increase tolerance of the tissue for pressure from the implanted apparatus.

Muscle tissue is generally formed of muscle cells that are joined together in tissue that can be either striated or smooth, depending on the presence or absence, respectively, of organized, regularly repeated arrangements of myofibrillar contractile proteins called myofilaments. Striated muscle tissue is further classified as either skeletal or cardiac muscle tissue. Skeletal muscle tissue is typically subject to conscious control and anchored by tendons to bone. Cardiac muscle tissue is typically found in the heart and not subject to voluntary control. A third type of muscle tissue is the so-called smooth muscle tissue, which is typically neither striated in structure nor under voluntary control. Smooth muscle tissue can be found within the walls of organs and in for example the wall of the stomach 10 and the esophagus 20.

The contraction of the muscle tissue may be activated both through the interaction of the nervous system as well as by hormones. The different muscle tissue types may vary in their response to neurotransmitters and endocrine substances depending on muscle type and the exact location of the muscle.

A nerve is an enclosed bundle of nerve fibers called axons, which are extensions of individual nerve cells or neurons. The axons are electrically excitable, due to maintenance of voltage gradients across their membranes, and provide a common pathway for the electrochemical nerve impulses called action potentials. An action potential is an all-or-nothing electrochemical pulse generated by the axon if the voltage across the membrane changes by a large enough amount over a short interval. The action potentials travel from one neuron to another by crossing a synapse, where the message is converted from electrical to chemical and then back to electrical.

The distal terminations of an axon are called axon terminals and comprise synaptic vesicles storing neurotransmitters. The axonal terminals are specialized to release the neurotransmitters into an interface or junction between the axon and the muscle cell. The released neurotransmitter binds to a receptor on the cell membrane of the muscle cell for a short period of time before it is dissociated and hydrolyzed by an enzyme located in the synapse. This enzyme quickly reduces the stimulus to the muscle, which allows the degree and timing of muscular contraction to be regulated delicately.

The action potential in a normal skeletal muscle cell is similar to the action potential in neurons and is typically about −90 mV. Upon activation, the intrinsic sodium/potassium channel of the cell membrane is opened, causing sodium to rush in and potassium to trickle out. As a result, the cell membrane reverses polarity and its voltage quickly jumps from the resting membrane potential of −90 mV to as high as +75 mV as sodium enters. The muscle action potential lasts roughly 2-4 ms, the absolute refractory period is roughly 1-3 ms, and the conduction velocity along the muscle is roughly 5 m/s. This change in polarity causes in turn the muscle cell to contract.

The contractile activity of smooth muscle cells is typically influenced by multiple inputs such as spontaneous electrical activity, neural and hormonal inputs, local changes in chemical composition, and stretch. This in contrast to the contractile activity of skeletal and cardiac muscle cells, which may rely on a single neural input. Some types of smooth muscle cells are able to generate their own action potentials spontaneously, which usually occur following a pacemaker potential or a slow wave potential. However, the rate and strength of the contractions can be modulated by external input from the autonomic nervous system. Autonomic neurons may comprise a series of axon-like swellings, called varicosities, forming motor units through the smooth muscle tissue. The varicosities comprise vesicles with neurotransmitters for transmitting the signal to the muscle cell.

The muscle cells described above, i.e., the cardiac, skeletal, and smooth muscle cells are known to react to external stimuli, such as electrical stimuli applied by electrodes. A distinction can be made between stimulation transmitted by a nerve and direct electrical stimulation of the muscle tissue. In case of stimulation via a nerve, an electrical signal may be provided to the nerve at a location distant from the actual muscle tissue, or at the muscle tissue, depending on the accessibility and extension of the nerve in the body. In case of direct stimulation of the muscle tissue, the electrical signal may be provided to the muscle cells by an electrode arranged in direct or close contact with the cells. However, other tissue such as fibrous tissue and nerves may of course be present at the interface between the electrode and the muscle tissue, which may result in the other tissue being subject to the electrical stimulation as well.

In the context of the present application, the electrical stimulation discussed in connection with the various aspects and embodiments may be provided to the tissue in direct or indirect contact with the implantable apparatus, such as for example the movement restriction device. Preferably, the electrical stimulation is provided by one or several electrode elements arranged at the interface or contact surface between the apparatus and the tissue. Thus, the electrical stimulation may, in terms of the present disclosure, be considered as a direct stimulation of the tissue. Particularly when contrasted to stimulation transmitted over a distance by a nerve, which may be referred to as an indirect stimulation or nerve stimulation.

Hence, an electrode arrangement comprising one or several electrode elements may be arranged in, partly in, on, or in close vicinity of the tissue that is to be exercised by means of an electrical signal, similar to what is described above in connection with the embodiments of FIGS. 1-37. Preferably, the electrode may be arranged to transmit the electrical signal to the portions of the tissue that is affected, or risks to be affected, by mechanical forces exerted by the medical implant. Thus, the electrode element may be considered to be arranged between the implanted apparatus and the tissue against which the apparatus is arranged to rest when implanted.

During operation of the implantable apparatus, or the electrode arrangement, the electric signal may cause the muscle cells to contract and relax repeatedly. This action of the cells may be referred to as exercise and may have a positive impact in terms of preventing deterioration and damage of the tissue. Further, the exercise may help increasing tolerance of the tissue for pressure and mechanical forces generated by the apparatus The interaction between the implanted electrode element and the tissue against which it rests is to a large extent determined by the properties at the junction between the tissue and the electrode element. The active electrically conducting surface of the electrode element (in the following referred to as "metal", even though other materials is equally conceivable) can either be uncoated resulting in a metal-tissue interface, or insulated with some type of dielectric material. The uncoated metal surface of the electrode element may also be referred to as a bare electrode. The interface between the electrode element and the tissue may influence the behavior of the electrode element since the electrical interaction with the tissue is transmitted via this interface. In the biological medium surrounding the electrode element, such as the actual tissue and any electrolyte that may be present in the junction, the current is carried by charged ions, while in the material of the electrode element the current is carried by electrons. Thus, in order for a continuous current to flow, there needs to be some type of mechanism to transfer charge between these two carriers.

In some examples, the electrode element may be a bare electrode wherein the metal may be exposed to the surrounding biological medium when implanted in, or at the muscle tissue that is to be stimulated. In this case there may be a charge transfer at a metal-electrolyte interface between the electrode element and the tissue. Due to the natural strive for thermodynamic equilibrium between the metal and the electrolyte, a voltage may be established across the interface which in turn may cause an attraction and ordering of ions from the electrolyte. This layer of charged ions at the metal surface may be referred to as a "double layer" and may physically account for some of the electrode capacitance.

Hence, both capacitive faradaic processes may take place at the electrode element. In a faradaic process, a transfer of charged particles across the metal-electrolyte interface may be considered as the predominant current transfer mechanism. Thus, in a faradaic process, after applying a constant current, the electrode charge, voltage, and composition tend to go to constant values. Instead, in a capacitive (non-faradaic) process charge is progressively stored at the metal surface and the current transfer is generally limited to the amount which can be passed by charging the interface.

In some examples, the electrode element may comprise a bare electrode portion, i.e., an electrode having an uncoated surface portion facing the tissue such that a conductor-tissue interface is provided between the electrode element and the tissue when the electrode element is implanted. This allows for the electric signal to be transmitted to the tissue by means of a predominantly faradaic charge transfer process. A bare electrode may be advantageous from a power consumption perspective since a faradaic process tends to be more efficient than a capacitive charge transfer process. Hence, a bare electrode may be used to increase the current transferred to the tissue for a given power consumption.

In some examples, the electrode element may comprise a portion that is at least partly covered by a dielectric material so as to form a dielectric-tissue interface with the muscle tissue when the electrode is implanted. This type of electrode element allows for a predominantly capacitive, or non-faradaic, transfer of the electric signal to the muscle tissue. This may be advantageous over the predominantly faradaic process associated with bare electrodes since faradaic charge transfer may be associated with several problems. Example of problems associated with faradaic charge transfer include undesirable chemical reactions such as metal oxidation, electrolysis of water, oxidation of saline, and oxidation of organics. Electrolysis of water may be damaging since it produces gases. Oxidation of saline can produce many different compounds, some of which are toxic. Oxidation of the metal may release metal ions and salts into the tissue which may be dangerous. Finally, oxidation of organics in a situation with an electrode element directly stimulating tissue may generate chemical products that are toxic.

These problems may be alleviated if the charge transfer by faradaic mechanisms is reduced, which may be achieved by using an electrode at least partly covered by a dielectric material. Preferably, the dielectric material is chosen to have as high capacitance as possible, restricting the currents flowing through the interface to a predominantly capacitive nature.

Several types of electrode elements can be combined with the present disclosure. The electrode element can for example be a plate electrode, comprising a plate-shaped active part forming the interface with the tissue. In other examples, the electrode may be a wire electrode, formed of a conducting wire that can be brought in electrical contact with the tissue. Further examples may include needle- or pin-shaped electrodes, having a point at the end which can be attached to or inserted in the muscle tissue. The electrodes may for example be encased in epoxy for electrical isolation and protection and comprise gold wires or contact pads for contacting the muscle tissue. Some of these examples of electrodes, methods of stimulating using electrodes, and how the electrode arrangements can be arranged in connection with implantable apparatuses such as described in connection with the embodiments of FIGS. 1-37 will be discussed below with reference to FIGS. 38-45.

FIGS. 38*a* and 38 *b* show embodiments of the apparatus 100, which may be similarly configured as the embodiments discussed with reference to any of the preceding FIGS. 1-37. Thus, FIG. 38*a* illustrates an apparatus 100 having a movement restriction device 110 configured to be affixed by the fundus 12 so as to hinder the cardia 22 from sliding upwards through the diaphragm opening, whereas FIG. 38*b* illustrates an apparatus 100 comprising a portion, such as an elongated core or support device 120, configured to at least partly encircle the esophagus 20. The encircling portion 120 may be configured to assist the cardiac sphincter in it closing of the esophagus, for example by applying an encircling pressure and/or by electrically stimulate the sphincter muscle so as to cause it to contract. The embodiments are illustrated in cross-sectional views when implanted and invaginated by the fundus 12 (movement restriction device in FIG. 38*a*) or placed around the esophagus (constricting/stimulating device in FIG. 38*b*).

The apparatus 100 in FIGS. 38*a* and 38*b* further comprises an electrode arrangement comprising a plurality of electrode elements 152, 154 for electrically stimulating the tissue of the fundus 12 and/or esophagus 20 for exercising the muscle tissue to improve the conditions for long term implantation of the apparatus 100, as discussed above. In the embodiment of FIG. 38*a* the electrode arrangement is arranged on an outer surface of the movement restriction device 110 and thus placed in abutment and in electrical contact with the tissue of the stomach fundus 12, to which the movement restriction device 110 may be affixed by means of invagination or at least partly covering the movement restriction device 110 by fundus wall tissue. In the embodiment of FIG. 38*b*, the electrode arrangement is arranged on an outer surface of a core element 213 and thus placed in abutment and in electrical contact with the tissue of the esophagus 20, around which the apparatus 100 may be arranged. As illustrated in FIG. 38*b*, the electrode arrangement may comprise at least two electrode elements 154 which may be placed on opposing sides of the esophagus 20 so as to cause the cardiac sphincter 26 to contract.

Each of the electrode elements 152, 154 of the electrode arrangement may be connected to a controller, such as a stimulation controller 170 by means of electrical conduits 172. The controller 170) may be configured to be operably connected to the electrode arrangement for controlling the electrical stimulation of the tissue. In the embodiment shown in FIG. 38*a*, the controller 170 may be configured to control the electrical stimulation such that the muscle tissue of the fundus 12 is stimulated by a series of electrical pulses. In the embodiment shown in FIG. 38*a*, the pulses may comprise a pulse of a first polarity followed by a pulse of a second, reversed polarity, and the pulsed electrical stimulation signal generated may comprise a pulse frequency of 0.01-150 Hz. In the embodiment shown in FIG. 38*a*, the electrical stimulation signal may comprise a pulse duration of 0.01-100 ms and a pulse amplitude of 1-15 mA. More specifically, in the embodiment of FIG. 38*a*, the electrical stimulation signal may comprise a pulse frequency of 0.15-0.25 Hz, a pulse duration of 20-30 ms and a pulse amplitude of 3-10 mA. Further, in the embodiment of FIG. 38*a*, the electrical stimulation signal may comprise a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.

The controller 170 of FIG. 38*a* may be integrated in an implantable controller, and the stimulation controller may be configured to receive input from a wireless remote control, directly or via a receiver of the implantable controller, for controlling the stimulation or for programming a stimulation routine for exercising the muscle tissue to improve the conditions for long term implantation of the implantable movement restriction device 110. The programming of a stimulation routine could for example be the programming of the frequency of the stimulation, or the current and/or voltage of the stimulation.

FIG. 38*b* shows an embodiment of the implantable apparatus 100 wherein the electrode elements 154 are connected to a stimulation controller 170 similarly configured as the one discussed with reference to FIG. 38*a*. The controller 170 may hence be configured to be operably connected to the electrode arrangement for controlling the electrical stimulation of the tissue of the esophagus 20. The stimulation of the tissue could for example be performed with electrical pulses, such as described with reference to FIG. 38*a*, or may in the alternative be controlled as a continuous low-energy current providing a continuous stimulation of the cardiac sphincter 26.

In the embodiments shown in FIGS. 38*a* and 38*b*, and preferably the movement restriction device 110, the implantable apparatus 100 may further comprise an implantable sensor 180 configured to sense actions potentials generated by pacemaker cells of the tissue of the stomach wall. The implantable sensor 180 may also be connected to the controller 170 by means of a sensor lead 173. The controller 170 may be configured to control the electrical simulation based at least partly on the sensed action potentials and may be configured to generate electrical pulses amplifying the sensed action potentials. The implantable sensor 180 may be implemented in any of the embodiments of implantable apparatuses 100 for treating reflux disease as disclosed in the present application.

As described above in connection with the embodiments illustrated in FIGS. 1-38, the apparatus may be implanted in the body so as to interact with different parts of the stomach and/or the esophagus. A first portion 110 of the apparatus may for example be affixed to the fundus 12 so as to function as a movement restriction device, and whereas a second portion 120 of the apparatus 100 may be arranged to at least partly encircle the esophagus in order to assist in preventing stomach content to rise through the esophagus 20.

FIG. 39A is a schematic cross section illustrating the general structure of a stomach of a healthy adult. The stomach is located in the patient's abdomen, below the diaphragm 30. Entering occurs through the esophagus 20, which may be an approximately 25 cm long fibromuscular tube passing from the thorax into the abdomen through an opening 32 in the diaphragm 30. The lower part of the esophagus 20 thus be referred to as the abdominal portion of the esophagus 20. The esophagus 20 may connect to the stomach via a shorter segment, typically less than 1 cm, called the cardia 22. The cardia 22 may hence be considered to form the junction or interface between the esophagus 20 and the stomach 10 and may be formed both of a portion of the esophagus 20 and a portion of the stomach. The cardia 22 may join the greater curvature of the stomach (to the right in the figure) in a cardiac notch 24, which creates an acute angle between the esophagus 20 and an upper stomach wall portion. The cardiac notch 24 may also be referred to as the angle of His. Typically, the angle may be around 75 degrees in a healthy adult. FIG. 39A further illustrates the cardiac sphincter 26, which may be located in the wall of the cardia 22. Functionally, the sphincter opens to allow food to pass into the stomach and then quickly closes to prevent stomach contents from flowing back into the esophagus 20. The fundus 12 is formed in the upper curved part of the stomach and may be located above the cardiac notch 24. It normally does not store food, but gas produced during digestion. The volume of an empty stomach of a healthy adult human may be around 50 ml, and the fundus 12 generally makes up a relatively small part of that volume. The outermost layer of the stomach wall is called serosa 14. The thickness off the serosa layer 14 may be around 1-2 mm, compared to the total stomach wall thicknesses which ranges from 3 to 4 mm. The serosa may extend also to the cardia 22 and may cover a lower portion of the esophagus 20. The serosa has been observed to cover the lower portion of the esophagus 20 extending to the cardiac sphincter 26, above which there may be no serosa layer on the outside of the esophagus.

FIG. 39B is a schematic illustration of a standing human in which the coronal plane CP, the sagittal plane SP and the transverse plane TP are shown. The coronal plane CP (also known as the frontal plane) is an anatomical plane that divides the body into dorsal and ventral sections (front and back). It is perpendicular to the sagittal plane SP and to the transverse plane TP. The coronal plane CP illustrated in FIG. 39B is a mid-coronal plane that transects the standing body into two halves in an imaginary line that cuts through both shoulders. The sagittal plane SP (also known as the longitudinal plane) is an anatomical plane that divides the body into right and left sections. In the embodiment shown in FIG. 39B, the sagittal plane SP is a median or mid-sagittal plane that runs through the midline of the standing person. The plane cuts the body into halves passing through midline structures such as the navel and spine. The transverse plane TP is the plane that divides the body into superior and inferior sections. In the illustration of FIG. 39B, the transverse plane TP is a transverse umbilical plane that passes through the abdomen at the level of the navel.

FIG. 39B' is a schematic illustration of the stomach of the patient when placed in the orientation as defined in FIG. 39B. I.e., a plane CP' parallel to the coronal plane divides the stomach into a dorsal and ventral section, a parasagittal plane SP' divides the stomach into a right and left section and a transverse plane TP' parallel to the transverse umbilical plane divides the stomach into an upper and a lower section FIG. 39C shows a cross-section of the upper portion of the stomach and a lower portion of the esophagus 20 passing through the esophageal hiatus (or diaphragm opening) 32 in the thoracic diaphragm 30. A method for treating reflux disease of a human patient by implanting a movement restriction device 110 has been performed, such that the movement restriction device 110 is arranged to restrict movement of the cardia 22 of the patient's stomach towards the diaphragm 30 to hinder the cardiac sphincter 26 from sliding through the diaphragm opening 32 into the patient's thorax. The method comprises attaching the fundus 12 of the stomach 10 of the patient to the esophagus 20 of the patient in a first position P1, attaching the fundus 12 of the stomach 10 of the patient to the esophagus 20 of the patient in a second position P2, at a distance from the first position P1 in a cranial-caudal direction CC. The method further comprises positioning the movement restriction device 110 between the first and second position P1, P2, such that the movement restriction device 110 is secured in the cranial-caudal direction CC by the attachments 230*a*,230*b* between the fundus 12 and the esophagus 20 in the first and second positions P1,P2.

The step of attaching the fundus 12 of the stomach 10 of the patient to the esophagus 20 of the patient in a second position P2 is preceded by the step of positioning the movement restriction device 110 between the first and second position P1. I.e. The surgeon first attaches the fundus 12 to the esophagus 20 at the first position P1, the positions the movement restriction device 110 against the stomach wall of the fundus and against the tissue of the esophagus 20 (in the particular embodiment shown in FIG. 39C), after which the surgeon attaches the fundus 12 to the esophagus 20 at the second position P2.

In the embodiment shown in FIG. 39C, the steps of attaching the fundus 12 of the stomach 10 of the patient to the esophagus 20 of the patient in a first position P1 comprises attaching the fundus 12 of the stomach 10 of the patient to the esophagus 20 using a fastener 230*a* in the form of at least one suture, and the step of attaching the fundus 12 of the stomach 10 of the patient to the esophagus 20 of the patient in a second position P2 comprises attaching the fundus 12 of the stomach 10 of the patient to the esophagus 20 using a fastener 230*b* in the form of at least one suture.

In the alternative, the fasteners 230*a*,230*b* in the form of at least one suture could be replaced by at least one staple.

The steps of attaching the fundus 12 of the stomach 10 of the patient to the esophagus 20 of the patient in a first position P1 and attaching the fundus 12 of the stomach 10 of the patient to the esophagus 20 of the patient in a second position P2 are preferably preceded by the step of dissecting the stomach 10 of the patient, such that the stomach 10 can be freely moved in relation to the esophagus 20.

The procedure of treating reflux disease of a human patient by implanting a movement restriction device 110 as shown in FIG. 39C can be performed as an abdominal-open surgical procedure, as an abdominal laparoscopic procedure through trocars placed through the skin of the patient, or at least one of the steps of the procedure could be performed using a translaminar instrument configured to be inserted through the esophagus of the patient. In embodiments in which a laparoscopic or transluminal instrument is used for the implantation of the movement restriction device 110, the movement restriction device 110 may be resilient and thereby configured to assume a shape such that the movement restriction device 110 can pass through a trocar or the esophagus 20 of the patient.

In the embodiment shown in FIG. 39, the steps of attaching the fundus 12 of the stomach 10 of the patient to the esophagus 20 of the patient in a first position P1 and attaching the fundus 12 of the stomach 10 of the patient to the esophagus 20 of the patient in a second position P2 is performed either using a translaminar instrument configured to be inserted through the esophagus of the patient or using an abdominal instrument configured to enter the abdomen of the patient through an incision made in the skin of the patient.

In the embodiment shown in FIG. 39C, the step of attaching the fundus 12 of the stomach 10 of the patient to the esophagus 20 of the patient in the first position P1 is performed such that the fundus 12 is attached to the esophagus 20 of the patient at a distance d1 from the angle of His 24 exceeding 5 mm, and more particularly exceeding 10 mm.

In the embodiment shown in FIG. 39C, the step of attaching the fundus 12 of the stomach 10 of the patient to the esophagus 20 of the patient in the second position P2 is performed such that the fundus 12 is attached to the esophagus 20 of the patient at a distance d2 from the angle of His 24 exceeding 20 mm, and more particularly exceeding 30 mm.

In the embodiment shown in FIG. 39C, the step of positioning the movement restriction device 110 between the first and second position P1, P2 comprises positioning the center of mass of the movement restriction device 110 in a plane extending perpendicular to the cranial-caudal CC direction at a distance d3 from the angle of His 24 exceeding 20 mm, and more particularly exceeding 30 mm.

In the embodiment shown in FIG. 39C, the step of positioning the movement restriction device 110 between the first and second position P1, P2 comprises positioning the upper-most point 110*p* of the movement restriction device 110 in a plane extending perpendicular to the cranial-caudal direction CC at a distance d4 from an upper-most point of the cardiac sphincter 26 exceeding 5 mm, and more particularly exceeding 10 mm.

In the embodiment shown in FIG. 39C, the step of positioning the movement restriction device 110 between the first and second position P1, P2 comprises positioning the center of mass of the movement restriction device 110 in a plane extending perpendicular to the cranial-caudal direction CC at a distance d5 from an upper-most point of the cardiac sphincter 26 exceeding 1 mm, and more particularly exceeding 5 mm, and more particularly exceeding 10 mm.

In the embodiment shown in FIG. 39C, the movement restriction device (110) has a rounded shape. More specifically, in the embodiment shown in FIG. 39C the movement restriction device (110) has a spherical shape.

FIG. 39D shows an embodiment similar to that shown in FIG. 39C, with the difference that in the embodiment shown in fog. 39D, the movement restriction device 110 at least partially encircling the esophagus of the patient. The encircling movement restriction device 110 could for example be one of the movement restriction devices described with reference to FIG. 7-21 or 24-28.

The movement restriction device 110 of the embodiment shown in FIG. 39D encircles more than ⅓ of the esophagus 20 in a plane PP extending perpendicular to the cranial-caudal direction CC, more particularly more than ½ of the esophagus 20 in the plane PP extending perpendicular to the cranial-caudal direction CC, more particularly more than ⅔ of the esophagus 20 in the plane PP extending perpendicular to the cranial-caudal direction CC, more particularly the entire esophagus 20 in the plane PP extending perpendicular to the cranial-caudal direction CC.

The movement restriction device 110 of the embodiment shown in FIG. 39D comprises a curved outer surface facing the esophagus, and in the embodiment shown in FIG. 39D, such curve is a portion of the torus shape of the movement restriction device 110 that encircles the esophagus. The curved outer surface facing the esophagus substantially has the same radius as the esophagus in the plane PP extending perpendicular to the cranial-caudal direction CC, such that the movement restriction device 110 may fit snuggly around the esophagus, which is needed in embodiments in which the movement restriction device 110 has a purpose of supporting the cardiac sphincter from the outside thereof.

In alternative embodiments, the curved outer surface comprising a radius of curvature exceeding the radius of curvature of the esophagus 20, such that a gap may be present between the esophagus and the movement restriction device 110 for allowing the movement restriction device 110 to expand as the patient swallows. The gap also reduces the risk that the movement restriction device 110 migrates through the tissue wall of the esophagus 20 which could be a consequence of erosive contact between the movement restriction device 110 and the esophagus 20.

In embodiments in which the movement restriction device 110 has a purpose of supporting the cardiac sphincter from the outside thereof, the movement restriction device 110 may comprise a movement restriction device 110 having a constricting state for hindering fluid from passing from the stomach into the esophagus and an expanded state for allowing food to pass into the stomach in response to the patient swallowing, and thus exerting an encircling pressure on the esophagus in the constricting state. Such movement restriction devices may comprise at least one attractor for resiliently attracting adjacent portions of the movement restriction device to generate the encircling pressure. The attractor may comprise an elastic element, or at least two mutually attracting magnets which may be connected by a link.

In any of the embodiments herein, there may be a gap exceeding 1 mm between the movement restriction device 110 and the esophagus, preferably exceeding 2 mm and most preferably exceeding 3 mm. The inner diameter of the encircling portion of the movement restriction device 110, in the plane PP extending perpendicular to the cranial-caudal direction CC, may be more than 5% longer than the outer diameter of the esophagus 20, or more than 10% longer than the outer diameter of the esophagus 20, or more than 20% longer than the outer diameter of the esophagus 20.

The movement restriction devices 110 shown in FIGS. 39C and 39D may comprise an electrode arrangement configured to electrically stimulate muscle tissue of the portion of the fundus and/or the serosa to improve the conditions for long term implantation of the movement restriction device 110. The electrode arrangement could be one of the electrode arrangements described with reference to any of FIGS. 1-5, 7-11, 14, 15, 21, 25, 31E, 31F, 38A, 38B and 40AA-45.

In embodiments in which the movement restriction devices 110 of FIGS. 39C and 39D comprises electrodes, the apparatus may further comprise an implantable energy source configured to provide the electrode with electrical power. Consequently, the method then comprises steps for implanting the implantable energy source and connecting the implantable energy source, directly or indirectly, to the electrode. The implantable energy source may be arranged inside the movement restriction device (as for example shown in FIG. 1) or may be placed subcutaneously (such as for example shown in FIG. 3).

In embodiments in which the movement restriction devices 110 of FIGS. 39C and 39D comprises electrodes, the apparatus may further comprise a controller configured to be operably connected to the electrode for controlling the electrical stimulation. Consequently, the method then comprises steps for implanting the controller and connecting the implantable energy source, directly or indirectly, to the controller. The controller may comprise a wireless remote control for controlling and communicating with the implantable controller. Control, communication with, and charging of the implantable controller from an external device, such as a wireless remote control, is further elaborated in in the description text referring to FIGS. 65A-66N.

The controller may control the electrical stimulation such that the muscle tissue is stimulated by a series of electrical pulses (such as described with reference to FIGS. 41 and 42). The electrical stimulation signal may for example comprises a pulse frequency of 0.15-0.25 Hz, a pulse duration of 20-30 ms and a pulse amplitude of 3-10 mA.

In the embodiment shown in FIGS. 39C and 39D, the movement restriction devices 110 are non-adjustable movement restriction device 110. However, in alternative embodiments, the movement restriction devices may have an adjustable volume, such as for example described with reference to FIGS. 39G-39O'.

FIG. 39E shows a cross-section of the upper portion of the stomach 10 and a lower portion of the esophagus 20 when a method for treating reflux disease of a human patient by implanting a movement restriction device 110 has been performed, such that the movement restriction device 110 is arranged to restrict movement of the cardia 22 of the patient's stomach towards the diaphragm 30 to hinder the cardiac sphincter 26 from sliding through the diaphragm opening 32 into the patient's thorax. The movement restriction device 110 has a shape and size allowing it to be arranged to rest against a fundus wall portion 14 of the patient's stomach 10, such that the movement restriction device 110 is implanted at a position between the patient's diaphragm 30 and a portion of the fundus wall 14, and such that movement of the cardiac sphincter 26 of the patient's stomach towards the diaphragm 30 is restricted to hinder the cardiac sphincter 26 from sliding through the diaphragm opening 32 into the patient's thorax.

In the embodiment shown in FIG. 39E, the movement restriction device comprises an electrode arrangement, comprising a plurality of electrodes 154 arranged on an outer surface of the movement restriction device 110 and configured to engage and electrically stimulate muscle tissue of the fundus wall portion 14 to exercise the muscle tissue to improve the conditions for long term implantation of the movement restriction device 110. Details of the particular embodiment of the movement restriction device 110 shown in FIG. 39E is further elaborated on with reference to FIG. 5.

In the embodiment shown in FIG. 39E, the implantable apparatus further comprises a second electrode arrangement comprising two electrodes 154 configured to engage and electrically stimulate the cardiac sphincter 26 for causing contraction of the cardiac sphincter 26, for supporting the cardiac sphincter and thereby reduce the risk that stomach contents leaks up into the esophagus 20.

The electrodes 154 may comprise a coiled wire for increasing a contact surface between the first electrode arrangement and the muscle tissue and for allowing the first electrode arrangement to follow contraction and relaxation of the muscle tissue. The electrodes 154 may comprise a bare electrode portion configured to form a metal-tissue interface with the muscle tissue, thereby allowing faradaic charge transfer to the be predominant charge transfer mechanism over said interface. The electrodes 154 may comprise an electrode portion at least partly covered by a dielectric material configured to form a dielectric-tissue interface with the muscle tissue, thereby allowing for a faradaic portion of the charge transfer mechanism over said interface to be reduced.

In the embodiment shown in FIG. 39E, the second electrode arrangement comprises at least two electrodes 154 configured to be arranged on opposing sides of the cardiac sphincter. The apparatus further comprises a holder in the form of the lead 172 configured to support the at least two electrode elements at the opposing sides of the cardiac sphincter 26. The lead also electrically and operably connects the electrodes to a stimulation controller (shown as 170 in FIG. 39F) for controlling the electrical stimulation.

The stimulation controller is in turn connected to an implantable energy source (such as a battery or capacitor) configured to provide the electrode 154 with electrical power. The implantable energy source may be arranged inside the movement restriction device (as for example shown in FIG. 1) or may be placed subcutaneously (such as for example shown in FIG. 3).

Consequently, the method of implanting the apparatuses of FIGS. 39E and 39F comprises steps for implanting the implantable energy source and the stimulation controller and connecting the electrodes 154, using the leads 172, directly or indirectly, to the implantable energy source and to the controller. The stimulation controller may be a part of a general implantable controller (further described with reference numeral 300 in FIGS. 46-66N), which may comprise a wireless remote control for controlling and communicating with the implantable controller. Control, communication with, and charging of the implantable controller from an external device, such as a wireless remote control, is further elaborated in in the description text referring to FIGS. 65A-66N.

The controller may control the electrical stimulation such that the muscle tissue is stimulated by a series of electrical pulses (such as described with reference to FIGS. 41 and 42). The stimulation controller could be configured to generate a pulsed electrical stimulation signal comprising a pulse frequency (F) of 0.01-150 Hz, having a pulse duration (D) of 0.01-100 ms and having a pulse amplitude (A) of 1-15 mA. In the embodiment of FIG. 39E, the electrical stimulation signal comprises a pulse frequency of 0.1-0.3 Hz, a pulse duration of 10-60 ms and a pulse amplitude of 3-30 mA, and a pulse of a first polarity is followed by a pulse of a second, reversed polarity. The electrical stimulation signal may comprise a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.

The implantable controller (300) may further be configured to indicate a functional status of the implantable energy source, which could be a charge level of the implantable energy source, or a temperature of at least one of the implantable energy source, the muscle tissue and the electrode arrangement. Keeping track of the temperature is critical for implantable stimulation apparatuses, as excessive temperatures can do great harm to the cells in the body of the patient.

The apparatus of FIGS. 39E and 39F further comprises an implantable sensor configured to sense actions potentials generated by pacemaker cells of the muscle tissue. The stimulation controller (170) is configured to control the electrical simulation based at least partly on the sensed action potentials, such that the electrical stimulation seizes when the patient swallows. In alternative embodiments, the sensor may sense swallowing by sensing other types of parameters. As such the sensor could comprise a motility sensor, which could be a piezo electric or piezo resistive motility sensor, or an accelerometer. In the alternative, a acoustic sensor, such as a microphone, may be used to sense the patient swallowing by picking up the sound generated by the patient swallowing. In the alternative, an optical sensor may be used for sensing the opacity alteration over the esophagus as food passes. A strain sensor could also be used for sensing the expansion of the esophagus as food passes.

In the embodiment shown in FIGS. 39E and 39F, the movement restriction devices 110 are non-adjustable movement restriction device 110. However, in alternative embodiments, the movement restriction devices may have an adjustable volume, such as for example described with reference to FIGS. 39G-39O'.

The procedure of placing the apparatus shown in FIGS. 39E and 39F may be performed as an abdominal-open surgical procedure, as an abdominal laparoscopic procedure through trocars placed through the skin of the patient, or at least one of the steps of the procedure could be performed using a translaminar instrument configured to be inserted through the esophagus of the patient. In embodiments in which a laparoscopic or transluminal instrument is used for the implantation of the movement restriction device 110, the movement restriction device 110 may be resilient and thereby configured to assume a shape such that the movement restriction device 110 can pass through a trocar or the esophagus 20 of the patient.

In the embodiment shown in FIG. 39E, a minimum width of the movement restriction device 110, as measured from side to side, is 18 mm or larger, such as 20 mm or larger. In the embodiment shown in FIG. 39E, a minimum outer circumference of the movement restriction device is 150 mm or less, such as 130 mm or less, such as 110 mm or less, such as 90 mm or less, such as 70 mm or less, such as 50 mm or less, such as 30 mm or less.

FIG. 39F shows an alternative embodiment of the apparatus described with reference to FIG. 39E. The difference being that in the embodiment of FIG. 39F, the apparatus comprises an encircling element 100' configured to be placed encircling the esophagus 20 of the patient.

The apparatus of FIG. 39F comprises a first electrode arrangement, comprising a plurality of electrodes 154 arranged on an outer surface of the encircling element 100' and configured to engage and electrically stimulate muscle tissue of the esophagus 20 to exercise the muscle tissue to improve the conditions for long term implantation of the encircling element 100" to thereby reduce the risk of damage to the tissue and/or migration of the encircling element 100' through the tissue wall of the esophagus 20.

In the embodiment shown in FIG. 39F, the implantable apparatus further comprises a second electrode arrangement comprising two electrodes 154 configured to engage and electrically stimulate the cardiac sphincter 26 for causing contraction of the cardiac sphincter 26, for supporting the cardiac sphincter and thereby reduce the risk that stomach contents leaks up into the esophagus 20.

In the embodiment shown in FIG. 39F, the center of mass of the encircling element 100' in a plane PP extending perpendicular to the cranial-caudal direction CC is placed at a distance from an upper-most point of the cardiac sphincter 26 exceeding 1 mm, and more particularly exceeding 3 mm.

The encircling element 100' could for example be one of the encircling elements 100' or movement restriction devices described with reference to FIG. 7-21 or 24-28.

The encircling element 100' shown in FIG. 39F encircles the esophagus completely, however, in alternative embodiments, it is equally conceivable that the encircling element 100' encircles more than ⅓ of the esophagus 20 in a plane PP extending perpendicular to the cranial-caudal direction CC, or more than ½ of the esophagus 20 in the plane PP extending perpendicular to the cranial-caudal direction CC, or more than ⅔ of the esophagus 20 in the plane PP extending perpendicular to the cranial-caudal direction CC.

The encircling element 100' of the embodiment shown in FIG. 39F comprises a curved outer surface facing the esophagus 20, and in the embodiment shown in FIG. 39F such curve is a portion of the torus shape of the encircling element 100' that encircles the esophagus 20. The curved outer surface facing the esophagus 20 substantially has the same radius as the esophagus 20 in the plane PP extending perpendicular to the cranial-caudal direction CC, such that the encircling element 100' may fit snuggly around the esophagus 20, which is needed in embodiments in which the encircling element 100' has a purpose of supporting the cardiac sphincter 26 from the outside thereof.

In alternative embodiments, the curved outer surface comprising a radius of curvature exceeding the radius of curvature of the esophagus 20, such that a gap may be present between the esophagus and the encircling element 100' for allowing the encircling element 100" to expand as the patient swallows. The gap also reduces the risk that the encircling element 100' migrates through the tissue wall of the esophagus 20 which could be a consequence of erosive contact between the encircling element 100' and the esophagus 20.

In embodiments in which the encircling element 100' has a purpose of supporting the cardiac sphincter 26 from the outside thereof, the movement restriction device 110 may comprise a encircling element 100' having a constricting state for hindering fluid from passing from the stomach into the esophagus 20 and an expanded state for allowing food to pass into the stomach in response to the patient swallowing, and thus exerting an encircling pressure on the esophagus 20 in the constricting state. Such encircling element 100' may comprise at least one attractor for resiliently attracting adjacent portions of the encircling element 100' to generate the encircling pressure. The attractor may comprise an elastic element, or at least two mutually attracting magnets which may be connected by a link.

In any of the embodiments herein, there may be a gap exceeding 1 mm between the encircling element 100' and the esophagus 20, preferably exceeding 2 mm and most preferably exceeding 3 mm. The inner diameter of the encircling portion of the encircling element 100', in the plane PP extending perpendicular to the cranial-caudal direction CC, may be more than 5% longer than the outer diameter of the esophagus 20, or more than 10% longer than the outer diameter of the esophagus 20, or more than 20% longer than the outer diameter of the esophagus 20.

The apparatus of FIG. 39F further comprises a stimulation controller 170 operably and electrically connected to the electrodes 154 by means of leads 172 for controlling the electrical stimulation. Consequently, the method of implanting the apparatus of FIG. 39F comprises steps for implanting the stimulation controller 170. The stimulation controller 170 may be part of—or connected to—a general implantable controller (further described with reference numeral 300 in FIGS. 46-66N). Communication with, and charging of the implantable controller from an external device, such as a wireless remote control, is further elaborated in in the description text referring to FIGS. 65A-66N.

Further details and examples of the operation of the stimulation electrodes of FIGS. 39E and 39F and the stimulation controller 170 is further described with reference to FIGS. 40AA-45.

FIGS. 39G and 39H shows a cross-section of the upper portion of the stomach 10 and a lower portion of the esophagus 20 when a method for treating reflux disease of a human patient by implanting a movement restriction device 110 has been performed, such that the movement restriction device 110 is arranged to restrict movement of the cardia 22 of the patient's stomach towards the diaphragm 30 to hinder the cardiac sphincter 26 from sliding through the diaphragm opening 32 into the patient's thorax. The movement restriction device 110 has a shape and size allowing it to be arranged to rest against a fundus wall portion 14 of the patient's stomach 10, such that the movement restriction device 110 is implanted at a position between the patient's diaphragm 30 and a portion of the fundus wall 14, and such that movement of the cardiac sphincter 26 of the patient's stomach towards the diaphragm 30 is restricted to hinder the cardiac sphincter 26 from sliding through the diaphragm opening 32 into the patient's thorax. The implantable movement restriction device 110 is in the embodiment shown in FIGS. 39G and 39H partially invaginated by the fundus wall of the patient, by the fundus wall being wrapped around the movement restriction device 110 from the frontal and dorsal side and fixated stomach-to-stomach and stomach-to-esophagus by means of fasteners 230 in the form of sutures or staplers.

The implantable movement restriction device 110 has a first cross-sectional distance cd1 more parallel than perpendicular to the cranial-caudal axis CC of the patient, and a second cross-sectional distance cd2 more perpendicular than parallel to the cranial-caudal axis CC of the patient.

The implantable movement restriction device 110 is adjustable in situ, such that the shape of the implantable movement restriction device 110 can be adjusted by the adjustment of the length of the first cross-sectional distance cd1, such that the length of the first cross-sectional distance cd1 can be increased relative to the length of the second cross-sectional distance cd2.

The implantable movement restriction device 110 comprises a lower portion LP configured to, directly or indirectly, engage the stomach 10 of the patient in a region of the angle of his 24, such that the function of the implantable movement restriction device 110 is supported by tissue of the stomach 10 in the region of the angle of his 24. I.e. the function as implantable movement restriction device 110 for restricting the movement of the cardia 22 relative to the thoracic diaphragm 30.

The implantable movement restriction device 110 further comprises an upper portion 110*p* configured to, directly or indirectly, engage the thoracic diaphragm 30 of the patient. The upper portion comprises at least one curvature such that a curved surface engages, directly or indirectly, the thoracic diaphragm 30 of the patient.

In the embodiment shown in FIG. 39G, the movement restriction device is mechanically adjustable by means of a mechanical operation device comprising a shaft 481 being capable of being extended or withdrawn inside of a pleated, bellows-shaped portion 481 configured for allowing adjustment of the length of the shaft even with the presence of fibrotic tissue growing on the bellows-shaped portion 481. The shaft comprises a threaded portion 481*t* configured to operably connect to threads of a nut-portion fixated to an electrical motor M for operating the nut-portion. The operation of the electrical motor M generates a rotating force which is translated into a linear force by the interaction of the threaded portion 481*t* of the shaft 481 and the threads in the nut-portion.

In the embodiment shown in FIG. 39G, the movement restriction device 110 comprises an integrated energy source (battery) and controller which controls and energizes the electrical motor of the mechanical operation device. However, in alternative embodiments, the apparatus may further comprise a transferring element configured to transfer at least one of: electrical energy, and mechanical force to the mechanically adjustable movement restriction device, from a remote unit. The function and features of such a remote unit 140 is further described with reference to FIGS. 2, 3 and 46-64. The transferring element could comprises at least one of: an electrical lead, a shaft for transferring rotating force, and a shaft for transferring linear force.

FIG. 39H shows an embodiment of the movement restriction device 110 similar to that shown in FIG. 39G in the sense that the movement restriction device 110 has an identical exterior surface and is implanted and fixated in the same way in the same position. The implantable movement restriction device 110 of FIG. 39H is also adjustable in situ, such that the shape of the implantable movement restriction device 110 can be adjusted by the adjustment of the length of the first cross-sectional distance cd1, such that the length of the first cross-sectional distance cd1 can be increased relative to the length of the second cross-sectional distance cd2. The difference being that the implantable movement restriction device 110 is hydraulically adjustable.

The implantable movement restriction device 110 of FIG. 39H comprises a hydraulic adjustment chamber 107 enclosed by the biocompatible surface material 110*s* of the implantable movement restriction device 110. The hydraulic adjustment chamber extends into a pleated bellows portion 452 comprising elevated and lowered portions enabling the adjustment of the first cross-sectional distance cd1, such that the distance that the implantable movement restriction device 110 extends between the angle of his 24 and the thoracic diaphragm 30 can be adjusted, such that the effect that the implantable movement restriction device 110 has on hindering the movement of the cardia 22 can be adjusted. I.e., injection or withdrawal of a hydraulic fluid into the hydraulic adjustment chamber 107 of the hydraulically adjustable movement restriction device 110 adjusts a length of the bellows 452.

In the embodiment of FIG. 39H, the implantable movement restriction device 110 comprises an injection port integrated in the surface material of the implantable movement restriction device 110. I.e. at least a portion of the wall of the implantable movement restriction device 110 comprises a self-sealing material which can be penetrated by an injection needle 491 of an injection device 490, such as a syringe. When the injection needle 491 is withdrawn from the hydraulic adjustment chamber and exits the surface material 110*s* through the self-sealing material, the self-sealing material self-seals such that the hydraulic fluid in the hydraulic adjustment chamber does not leak to the surrounding tissue. The hydraulically adjustable movement restriction device 110 of FIG. 39H can thus be adjusted by the injection or withdrawal of a hydraulic fluid into the hydraulic adjustment chamber 107 of the hydraulically adjustable movement restriction device 110.

FIG. 39I shows an embodiment of the implantable movement restriction device 110 very similar to the embodiment shown in FIG. 39H, the only difference being that in the embodiment shown in FIG. 39I, the injection port is not integrated in the material enclosing the hydraulic adjustment chamber 107. Instead, the apparatus shown in FIG. 39I comprises a conduit 109 connecting the hydraulic adjustment chamber 107 of the hydraulically adjustable movement restriction device 110 to a remote unit. The remote unit could simply be a subcutaneously placed injection port (such as shown in FIG. 39L) enabling the injection and withdrawal of hydraulic fluid into the conduit 109, and consequently into the hydraulic adjustment chamber 107 of the implantable movement restriction device 110. In the alternative, the remote unit could comprise a hydraulic pump, and energy source, a controller and means for wireless communication with an external device located outside the body of the patient. Remote units comprising a pump, an energy source and a controller is further described with reference to FIGS. 47A, 47B and 47C, and a controller and means for wireless communication with an external device located outside the body of the patient is further elaborated on with reference to FIGS. 65A-66N.

In the embodiments shown in FIGS. 39G-39P', the length of the first cross-sectional distance is adjustable in situ such that the length of the first cross-sectional distance cd1 is more than 1.2 times the length of the second cross-sectional distance cd2, and more specifically, more than 1.3 times the length of the second cross-sectional distance cd2, and even more specifically more than 1.5 times the length of the second cross-sectional distance cd2.

In FIGS. 39G, 39H, 39I, 39J, 39K, 39N, 39O and 39O', the implantable movement restriction devices are shown in a cross-section in a plane parallel to the coronal plane of the patient. And in the embodiments shown in FIGS. 39G-39P', the shape of the implantable movement restriction device 110 can be adjusted by an increase of the length of the first cross-sectional distance cd1 relative to the length of the second cross-sectional distance cd2, such that the length of the peripheral circumference of a cross-section of the implantable movement restriction device 110, in a plane parallel to the coronal plane of the patient, is increased relative to the length of the peripheral circumference of a cross-section of the implantable movement restriction device 110, in a plane parallel to the transverse plane of the patient. In particular, in the embodiments shown in FIGS. 39G-39P', the length of the first cross-sectional distance cd1 is adjustable such that the length of the peripheral circumference of the cross-section in the plane parallel to the coronal plane of the patient is more than 1.2 times the length of the peripheral circumference of a cross-section of the implantable movement restriction device, in a plane parallel to the transverse plane of the patient, or more specifically, more than 1.3 times the length of the peripheral circumference of the cross-section of the implantable movement restriction device in the plane parallel to the transverse plane of the patient, or more specifically, more than 1.5 times the length of the peripheral circumference of a cross-section of the implantable movement restriction device in a plane parallel to the transverse plane of the patient.

In the embodiments shown in FIGS. 39G-39I, the length of the first cross-sectional distance cd1 is adjustable in situ such that the center of mass me of the movement restriction devices 110 in a plane parallel to the transverse plane of the patient is positioned at a distance d3 from the angle of His 24 exceeding 20 mm, or exceeding 30 mm.

In the embodiments shown in FIGS. 39G-39I, the length of the first cross-sectional distance cd1 is adjustable in situ such that the center of mass me of the movement restriction device 110 in a plane parallel to the transverse plane of the patient is positioned at a distance d5 from an upper-most point of the cardiac sphincter 26 exceeding 5 mm, or exceeding 10 mm.

FIGS. 39J-39M shows an embodiment of the apparatus in which the movement restriction device 110 comprises movement restriction devices configured to encircle the esophagus 20 of the patient and having a constricting state (shown in FIGS. 39J' and 39K") for hindering fluid from passing from the stomach into the esophagus 20 and an expanded state (shown in FIGS. 39J and 39K) for allowing food to pass into the stomach 10 in response to the patient swallowing.

In the embodiments shown in FIGS. 39J-39K', the encircling movement restriction device 110 comprises attractors for resiliently attracting adjacent portions 110*p*1, 110*p*2, 110*p*3, . . . of the movement restriction device to generate an encircling pressure on the esophagus 20. In the embodiments shown in FIGS. 39J-39K' the attractors comprises an elastic elements placed between the adjacent portions 110*p*1, 110*p*2, 110*p*3, . . . . In the embodiments shown in FIGS. 39L and 39M, the attractors comprise mutually attracting magnets (such as further described with reference to FIGS. 18A, 18B, 20A, and 20B).

In the embodiments shown in FIGS. 39J-39K' and 39N-39P', the biocompatible surface material 110*s* of the movement restriction devices is resilient but substantially inelastic. As such, the shape of the implantable movement restriction devices 110 can be adjusted by an increase of the length of the first cross-sectional distance cd1 relative to the length of the second cross-sectional distance cd2 while the length of a peripheral circumference (comprising the biocompatible surface material 110*s*) of a cross-section of the implantable movement restriction device 110, in the plane parallel to the coronal plane of the patient remains constant.

FIGS. 39J and 39J' shows the encircling movement restriction device 110 in expanded and constricted state when the first and second cross-sectional distances cd1, cd2 are substantially equal. FIGS. 39K and 39K' shows the encircling movement restriction device 110 in expanded and constricted state when the length of the first cross-sectional distances cd1 has been adjusted such that the in the cross-section in the plane parallel to the coronal plane is elongated, by the length of the first cross-sectional distance cd1' being longer than the length of the second cross-sectional distance cd2'. In absolute terms, the length of the first cross-sectional distance cd1' has been made longer and the length of the second cross-sectional distance cd2' has been made shorter, such that the length of a peripheral circumference of the cross-section remains constant.

In the embodiments shown in FIGS. 39J-39K', the encircling movement restriction devices comprises a biocompatible surface material 110*s* and two parts 110*a*, 110*b* (in the state shown in FIGS. 39J and 39J' having semi-circular cross-sections). The two parts 110*a*, 110*b* are made from a material configured to change shape, such that the cross-section of the encircling movement restriction devices can assume the more elongated shape shown in FIGS. 39K and 39K'. In the embodiment shown in FIGS. 39J-39K', as well as in the embodiments shown in FIGS. 39O-39P', the material configured to change shape is an electrically adjustable material configured to alter shape when exposed to an electrical current or an electrical voltage. More specifically, in the embodiments shown in FIGS. 39J-39K', as well as in the embodiments shown in FIGS. 39O-39P', the adjustable material configured to alter shape comprises at least one electroactive polymer such as a ferroelectric polymers, an electrostrictive graft polymer, a electrostrictive paper, a piezoelectric polymers or a liquid crystal elastomers.

FIG. 39L shows an embodiment of the movement restriction device configured to encircle the esophagus 20 of the patient. The movement restriction device comprises a hydraulically adjustable portion 110*a*. The shape of the hydraulically adjustable portion can be altered by the injection or withdrawal of a hydraulic fluid to and from the hydraulically adjustable portion 110*a*, or more precisely from a hydraulic adjustment chamber of the hydraulically adjustable portion 110*a*. The hydraulically adjustable portion 110*a* is connected to portions 110*p*1, 110*p*2, 110*p*3, . . . comprising mutually attracting magnets (such as further described with reference to FIGS. 18A, 18B, 20A, and 20B) allowing the encircling movement restriction device to expand and contract enabling the patient to swallow. In the embodiment shown in FIG. 39L, a subcutaneously implantable injection port 492 is connected to a hydraulic adjustment chamber of the hydraulically adjustable portion 110*a* by means of a conduit 109. Injection of hydraulic fluid into the injection port by an injection needle 491 of an injection device 490 (such as a syringe) causes an expansion of the hydraulically adjustable portion 110*a*, such that a cross-sectional distances in a plane parallel to the coronal plane is elongated, increasing the height of the hydraulically adjustable portion 110*a* in the position between the upper portion of the stomach 10 and the thoracic diaphragm, causing a cross-section of the hydraulically adjustable portion 110*a* to assume an elongated shape, which increases the hydraulically adjustable portion's 110*a* effect as a movement restriction device for hindering the movement of the cardia in the direction towards the thoracic diaphragm.

FIG. 39M shows an alternative embodiment similar to the embodiment shown in FIG. 39L. The difference being that in the embodiment shown in FIG. 39M, the encircling movement restriction device comprises a plurality of adjustable portions 110*p*1, 110*p*2, 110*p*3 (namely three), each comprising a hydraulic adjustment chamber 107 and each being directly adjustable by injection or withdrawal of hydraulic fluid by means of an injection needle 492. As such, each of the adjustable portions 110*p*1, 110*p*2, 110*p*3 comprises an injection port comprising a self-scaling material integrated in the surface material of the adjustable portions, such that the height h of each of the adjustable portion 110*p*1, 110*p*2, 110*p*3 can be directly adjusted by the injection or withdrawal of hydraulic fluid into the reservoirs 107 of the adjustable portions 110*p*1, 110*p*2, 110*p*3. The advantage is that the height and thereby the space occupied by the movement restriction device between the upper portion of the stomach 10 and the thoracic diaphragm 30 can be more specifically adjusted by the individual adjustment of the respective adjustable portion 110*p*1, 110*p*2, 110*p*3.

FIG. 39N shows an embodiment of a hydraulically adjustable movement restriction device 110 in which the hydraulically adjustable movement restriction device 110 comprises a hydraulic adjustment chamber 107 enclosed by a biocompatible surface material (such as a silicone-based or polyurethane-based polymer material). The biocompatible surface material has a first thickness at a first portion 110*s*1 of the biocompatible surface material and a second thickness at a second portion 110*s*2 of the biocompatible surface material. The biocompatible surface material at the first portion is much thinner than the biocompatible surface material at the second portion. The shape of the implantable movement restriction device 110 can be adjusted to an elongated shape by an increase of the length of the first cross-sectional distance cd1 relative to the length of the second cross-sectional distance cd2. In absolute terms, the length of the first cross-sectional distance cd1 has been adjusted into a longer cross-sectional distance cd1' and the length of the second cross-sectional distance cd2 has been adjusted into a shorter cross-sectional distance cd2', but the length of a peripheral circumference of the cross-section remains constant. The hydraulically adjustable movement restriction device 110 of FIG. 39N may comprise an integrated injection port (such as described with reference to FIGS. 39H, 39M) or may be connected to a remote unit comprising an injection port or a pump by means of a conduit (such as described with reference to FIGS. 39I and 39L).

The varying thickness of the wall affects the alteration of the shape of the movement restriction device 110 as fluid is injected into or withdrawn from the hydraulic adjustment chamber 107 of the movement restriction device 110. I.e., the thinner portions of surface material 110*s*1 of the wall enclosing the hydraulic adjustment chamber 107 is deformed more than thicker portions of the wall 110*s*2 enclosing the hydraulic adjustment chamber 107, causing the movement restriction device 110 to assume an elongated shape as fluid is withdrawn from the hydraulic adjustment chamber 107.

FIGS. 39O-39P' shows an embodiment of the movement restriction device 110 configured to encircle the esophagus 20 of the patient. In the embodiment shown in FIGS. 39O-39P' the movement restriction device is electrically adjustable. The encircling movement restriction device 110 comprises two parts 110*a*, 110*b* made from a material configured to change shape such that the cross-section of the encircling movement restriction devices can assume the more elongated shape shown in FIG. 39O". In the embodiment shown in FIGS. 39O-39P', the material of the two parts 110*a*, 110*b* is a material configured to change shape when exposed to an electrical current or an electrical voltage. More specifically, in the embodiments shown in FIGS. 39O-39P', the adjustable material configured to alter shape comprises at least one electroactive polymer such as a ferroelectric polymers, an electrostrictive graft polymer, a electrostrictive paper, a piezoelectric polymers or a liquid crystal elastomers.

The movement restriction device 110 may comprise an integrated energy source and controller for enabling the electrical adjustment of the movement restriction device or may in the alternative be connected to a lead electrically connecting the electroactive polymer to a remote unit comprising an implantable energy source (such as a battery or capacitor) configured to provide the electroactive polymer with electrical power. The remote unit also comprises an implantable controller for controlling the current and/or voltage to the electroactive polymer. The function and features of such a remote unit 140 is further described with reference to FIGS. 2, 3 and 46-64. The implantable controller may be configured to communicate and receive instructions and/or energy from an external device for controlling and energizing the electroactive polymer. Control, communication, and charging of the implantable controller from an external device, such as a wireless remote control, is further elaborated in in the description text referring to FIGS. 65A-66N.

In the embodiment shown in FIG. 39P, the movement restriction device 110 is configured to be partially invaginated by the stomach wall of the patient, such that the portion of the encircling movement restriction device 110 placed on the sinister side of the esophagus 20 is invaginated by the stomach wall, which both fixates the movement restriction device 110 and protects the tissue wall of the esophagus and thoracic diaphragm from friction induced by the contact with the surface of the movement restriction device 110.

In the embodiment shown in FIG. 39P', the encircling movement restriction device 110 is configured to be placed freely around the esophagus 20. In the embodiment shown in FIG. 39P', the torus of the encircling movement restriction device 110 has an inner diameter being larger than the outer diameter of the esophagus 20, such that a gap is created between the movement restriction device 110 and the esophagus, such that the movement restriction device 110 does not engage the esophagus. In the embodiment shown in FIG. 39P', the inner diameter of the movement restriction device 110 is more than 10% larger than the esophagus which it is configured to be placed around, more specifically more than 20% larger than the esophagus which it is configured to be placed around, more than 30% larger than the esophagus which it is configured to be placed around.

In the embodiments shown in FIGS. 39O-39P', the length of the first cross-sectional distance cd1 is adjustable such that the length of the an adjusted first cross-sectional distance cd1' is more than 1.2 times the length of the first cross-sectional distance cd1, or more specifically, the adjusted first cross-sectional distance cd1' is more than 1.3 times the length of the first cross-sectional distance cd1, or more specifically, the adjusted first cross-sectional distance cd1' is more than 1.5 times the length of the first cross-sectional distance cd1. Further, the length of the adjusted first cross-sectional distance cd1' is more than 1.2 times the length of the adjusted second cross-sectional distance cd2', or more specifically, the adjusted first cross-sectional distance cd1' is more than 1.3 times the length of the adjusted second cross-sectional distance cd2', or more specifically, the adjusted first cross-sectional distance cd1' is more than 1.5 times the length of the adjusted second cross-sectional distance cd2'.

In the embodiments shown in FIGS. 39J, 39J', 39K, 39K', 39L, 39M, 39O-39P', the movement restriction device comprises a curved cross-section in a plane parallel to the transverse plane of the patient. The curve is configured to partially enclose the esophagus of the patient. In the embodiments shown in FIGS. 39J, 39J', 39K, 39K', 39L, 39M, 39O-39P' the movement restriction devices are configured to encircle the esophagus 20 entirely, and as such a cross-section of the movement restriction device in a plane parallel to the transverse plane of the patient comprises a closed curve enclosing the esophagus of the patient. In alternative embodiments it is however conceivable that the movement restriction devices are configured to encircle at least ⅓ of the esophagus in a plane parallel to the transverse plane of the patient, or at least ½ of the esophagus in a plane parallel to the transverse plane of the patient, or at least ⅔ of the esophagus in a plane parallel to the transverse plane of the patient. In some alternative embodiments, the movement restriction devices comprise a C-shaped cross-section in a plane parallel to the transverse plane of the patient, and the C-shaped cross-section is configured to partially enclose the esophagus of the patient.

The adjustable movement restriction devices shown in FIGS. 39G-39P' may additionally comprise at least one electrode for electrically stimulating at least one tissue portion of the patient. Further details and examples of the operation and control of the stimulation electrodes are provided with reference to FIGS. 40AA-45.

FIGS. 39Q-39 V' all show a central cross-sectional view of apparatuses for treating reflux disease of a human patient comprising implantable movement restriction devices 110 configured to be fixated between an upper portion of the stomach and the thoracic diaphragm of the patient, for restricting the movement of the cardia of the patient towards the thoracic diaphragm.

The embodiments of implantable movement restriction devices 110 shown with reference to FIGS. 39Q-39T' all comprises a first portion having a first volume enclosed by material of the implantable movement restriction device 110, and a second portion, different from the first portion, having a second volume enclosed by material of the implantable movement restriction device 110. The first volume and the second volumes are equally large, and the first volume has a higher density than the second volume, and the second volume has a density below 1000 kg/m3.

In the embodiment shown in FIG. 39Q, the first portion is a portion of the biocompatible surface material 110*s* of the implantable movement restriction device 110. The biocompatible surface material in the embodiment shown in FIG. 39Q is a silicone-based biocompatible surface material 110*s* having an average density of about 1120 kg/m3. However, it is equally conceivable that the biocompatible surface material 110*s* is a polyurethane-based surface material. The second portion is an inner portion of the movement restriction device 110 comprising a plurality of spheres 495 made from a glass-based material and enclosing a gas. The spheres 495 are stabilized in a polymer material 496, which could the same polymer material as in the biocompatible surface material 110*s*, or in the alternative a different polymer material. The combination of spheres 495 enclosing a gas and a stabilizing polymer material 496 results in an average density of the material of the second portion below 1000 kg/m3. Reducing the weight of the implantable movement restriction device reduces the force that the implantable movement restriction device 110 exerts on the stomach wall, thus reducing the risk of wear, irritation and inflammation on the tissue wall which reduces the risk that the implant migrates through the tissue wall of the stomach wall.

In the embodiment shown in FIG. 39Q, the plurality of volumes of gas enclosed by an enclosing material makes up more than 10 volume percent of the second volume, more specifically more than 20 volume percent of the second volume, and even more specifically more than 30 volume percent of the second volume.

The embodiment shown in FIG. 39Q' is the same as the embodiment shown in FIG. 39Q' as relates to the material of the first and second portions. However, in the embodiment shown in FIG. 39Q', the implantable movement restriction device comprises a first and second part or segment 111*a*, 111*b* configured to abut each other when implanted and in function. The first and second part or segment 111*a*, 111*b* are configured to fall apart or disconnect if the parts or segments 111*a*, 111*b* were to migrate through the stomach wall and inadvertently become located inside of the stomach of the patient. The smaller parts are then capable of passing through the intestinal system without creating a risk that the patient gets ileus. The first and second parts or segments 111*a*, 111*b* both comprises a flat surface. The flat surface of the first part or segment 111*a* is configured to engage the flat surface of the second part or segment 111*b*, such that the two parts or segments 111*a*, 111*b* rest against each other in a stable position.

Figure 39R:
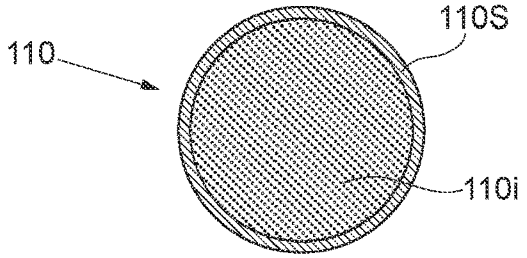
Figure 39R:
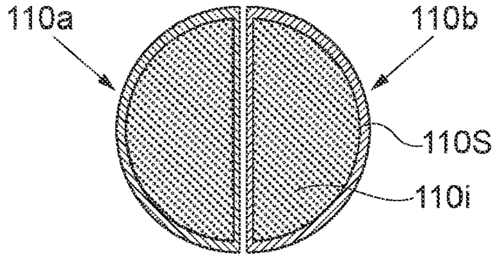

FIG. 39R shows a central cross-sectional view of an embodiment of the implantable movement restriction device 110 similar to that of the embodiment shown in FIG. 39Q. Just as in 39Q, the first portion comprises a biocompatible surface material 110*s*. However, the biocompatible surface material 110*s* of the first portion in FIG. 39R encloses a second solid material of an inner portion 110*i* of the implantable movement restriction device 110. The second solid material in the embodiment shown in FIG. 39R comprises a material having a density below 1000 kg/m3. In the specific embodiment shown in FIG. 39R, the second solid material is a low-density polyethylene. In alternative embodiments, it is equally conceivable that the second solid material is a polypropylene-based material. In the embodiment shown in FIG. 39R, the first solid material, being a biocompatible silicone-based material has a density above 1000 kg/m3, more specifically above 1050 kg/m3, and even more specifically above 1100 kg/m3, and the second solid material has a density below 1100 kg/m3, more specifically below 1050 kg/m3, and even more specifically below 1000 kg/m3.

The embodiment shown in FIG. 39R' has the same material composition as the implantable movement restriction device 110 shown in FIG. 39R. The difference being that the implantable movement restriction device of FIG. 39R' comprises a first and second part or segment 111*a*, 111*b* configured to abut each other when implanted and in function, for the same reasons as further elaborated on in relation to FIG. 39Q'.

Figure 39S:
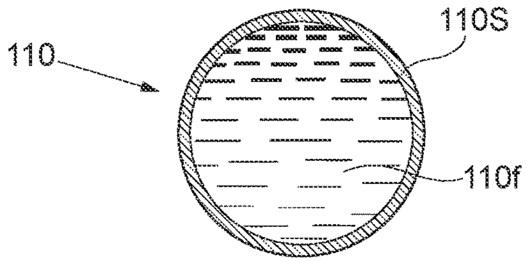
Figure 39S:
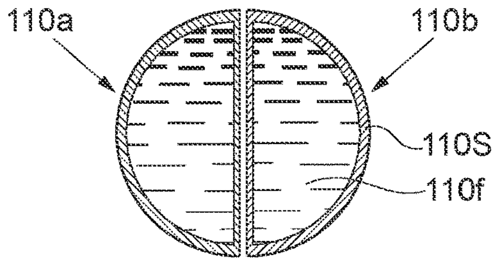

FIG. 39S shows a central cross-sectional view of an embodiment of the implantable movement restriction device 110 similar to that of the embodiment shown in FIGS. 39Q and 39R. Just as in 39Q and 39R, the first portion comprises a biocompatible surface material 110*s*. However, the biocompatible surface material 110*s* of the first portion in FIG. 39S encloses a fluid 110*f*. In the embodiment shown in FIG. 39S, the fluid is a liquid having a density a below 1000 kg/m3 in the form of an oil or fat-based liquid, which may be fat harvested from the patient, or a biocompatible synthetic substitute. In alternative embodiments, it is however conceivable that the liquid is an alcohol-based liquid. The liquid could be injected into the implantable movement restriction device 110 through an integrated injection port, which could be done during fabrication, prior to implantation or in-situ.

The embodiment shown in FIG. 39S' has the same material composition as the implantable movement restriction device 110 shown in FIG. 39S. The difference being that the implantable movement restriction device of FIG. 39S' comprises a first and second part or segment 111*a*, 111*b* configured to abut each other when implanted and in function, for the same reasons as further elaborated on in relation to FIG. 39Q'.

Figure 39T:
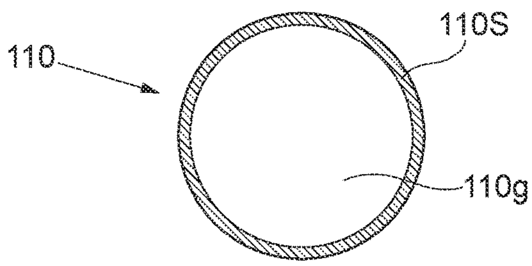
Figure 39T:
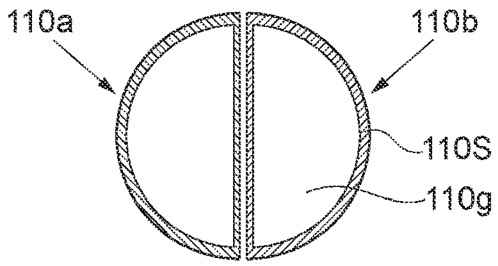

FIG. 39T shows a central cross-sectional view of an embodiment of the implantable movement restriction device 110 similar to that of the embodiment shown in FIGS. 39Q, 39R and 39S. Just as in 39Q, 39R and 39S, the first portion comprises a biocompatible surface material 110*s*. However, the biocompatible surface material 110*s* of the first portion in FIG. 39T encloses a gas 110*g*, which for example could be air, helium or nitrogen. The implantable movement restriction device 110 could be inflated by the gas during fabrication, prior to implantation or in-situ.

The embodiment shown in FIG. 39T' has the same material composition as the implantable movement restriction device 110 shown in FIG. 39T. The difference being that the implantable movement restriction device of FIG. 39T' comprises a first and second part or segment 111*a*, 111*b* configured to abut each other when implanted and in function, for the same reasons as further elaborated on in relation to FIG. 39Q'.

In the embodiments shown with reference to FIGS. 39Q', 39R', 39S' and 39T', the two parts are configured to be connected to each other simply by having flat surfaces abutting each other 31. However, in alternative embodiments, it is equally conceivable that the two parts are connected to each other by means of connecting recesses and protrusions on the respective parts, or by means of an interconnecting port placed between the two parts (such as for example disclosed with reference to FIGS. 39W-39Z").

Figure 39U:
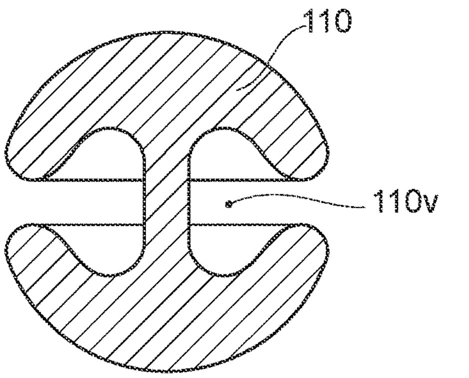
Figure 39U:
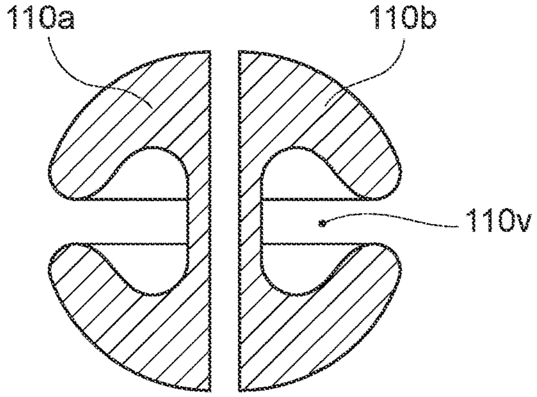

FIG. 39U shows a central cross-sectional view of a movement restriction device 110 having a shape in which the surface of the movement restriction device 110 comprises a recess in the form of an equatorial groove encircling the movement restriction device 110 and entering the material of the movement restriction device 110 such that a void 110*v* partially enclosed by the material of the movement restriction device 110 is created. The void 110*v* reduces the weight of the movement restriction device 110 and at the same time enables further fixation of the movement restriction device 110 by fibrotic tissue entering the recess and growing in the void 110*v*.

The embodiment shown in FIG. 39U' has the same outer shape as the implantable movement restriction device 110 shown in FIG. 39U. The difference being that the implantable movement restriction device of FIG. 39U' comprises a first and second part or segment 111*a*, 111*b* configured to abut each other when implanted and in function, for the same reasons as further elaborated on in relation to FIG. 39Q'.

In the embodiment shown in FIG. 39U, the implantable movement restriction devices 110 shown in FIGS. 39U and 39U' are rotationally symmetric and have a circular footprint in all directions.

Figure 39V:
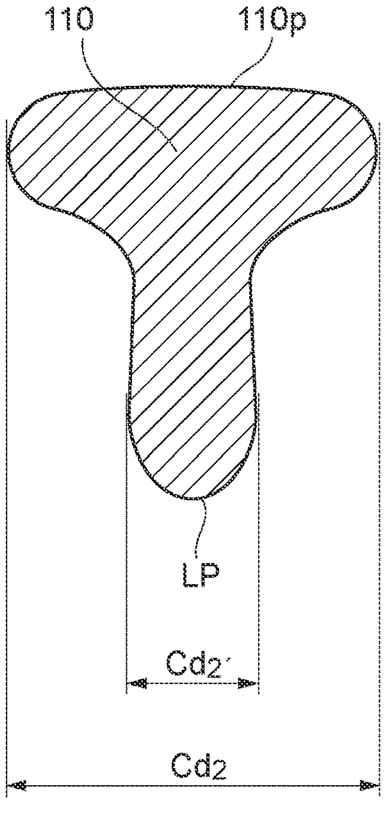
Figure 39V:
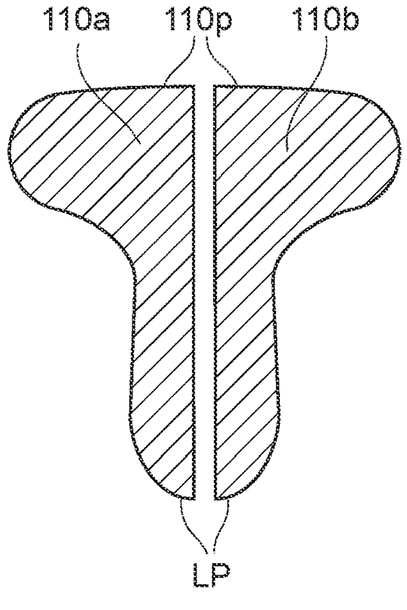

FIG. 39V shows a central cross-sectional view of a movement restriction device 110 having a shape in which the surface of the movement restriction device 110 has an upper portion 110*p* comprising a curvature and being configured to engage, directly or indirectly, the thoracic diaphragm of the patient, when implanted and in function. The upper portion 110*p* is wider than a lower portion LP. A length axis of the movement restriction device running from the lower portion LP to the upper portion, is configured to extend parallelly to the cranial-caudal axis of the patient, when the movement restriction device 110 is implanted and in function. The lower, narrower portion LP is configured to support and stabilize the upper portion 110*p*. In some embodiments, the lower portion LP is invaginated by the stomach wall of the patient, while the upper portion 110*p* is freely placed in the abdomen of the patient, directly engaging the thoracic diaphragm for hindering movement of the cardia of the patient. In the embodiment shown in FIGS. 39V and 39V', the upper portion 110*p* has a width cd2 being more than 2 times the width cd2' of the lower half of the movement restriction device 110. More specifically, the upper portion 110*p* has a width cd2 being more than 2.5 times the width cd2' of the lower half of the movement restriction device 110. I.e. the widest portion of the upper half of the movement restriction device 110 is 2 times or 2.5 times as wide as the widest portion of the lower half of the movement restriction device 110.

The embodiment shown in FIG. 39V' has the same outer shape as the implantable movement restriction device 110 shown in FIG. 39V. The difference being that the implantable movement restriction device of FIG. 39V' comprises a first and second part or segment 111*a*, 111*b* configured to abut each other when implanted and in function, for the same reasons as further elaborated on in relation to FIG. 39Q'.

The shapes and material compositions described with reference to FIGS. 39Q-39V' could be implemented in the embodiments disclosed in any one of FIGS. 1-21, 24-38B, 39C-39P' and 40AA-40SF' and could be altered to have an adjustable shape or volume such as described with reference to FIGS. 39G-39P'.

Figure 39W:
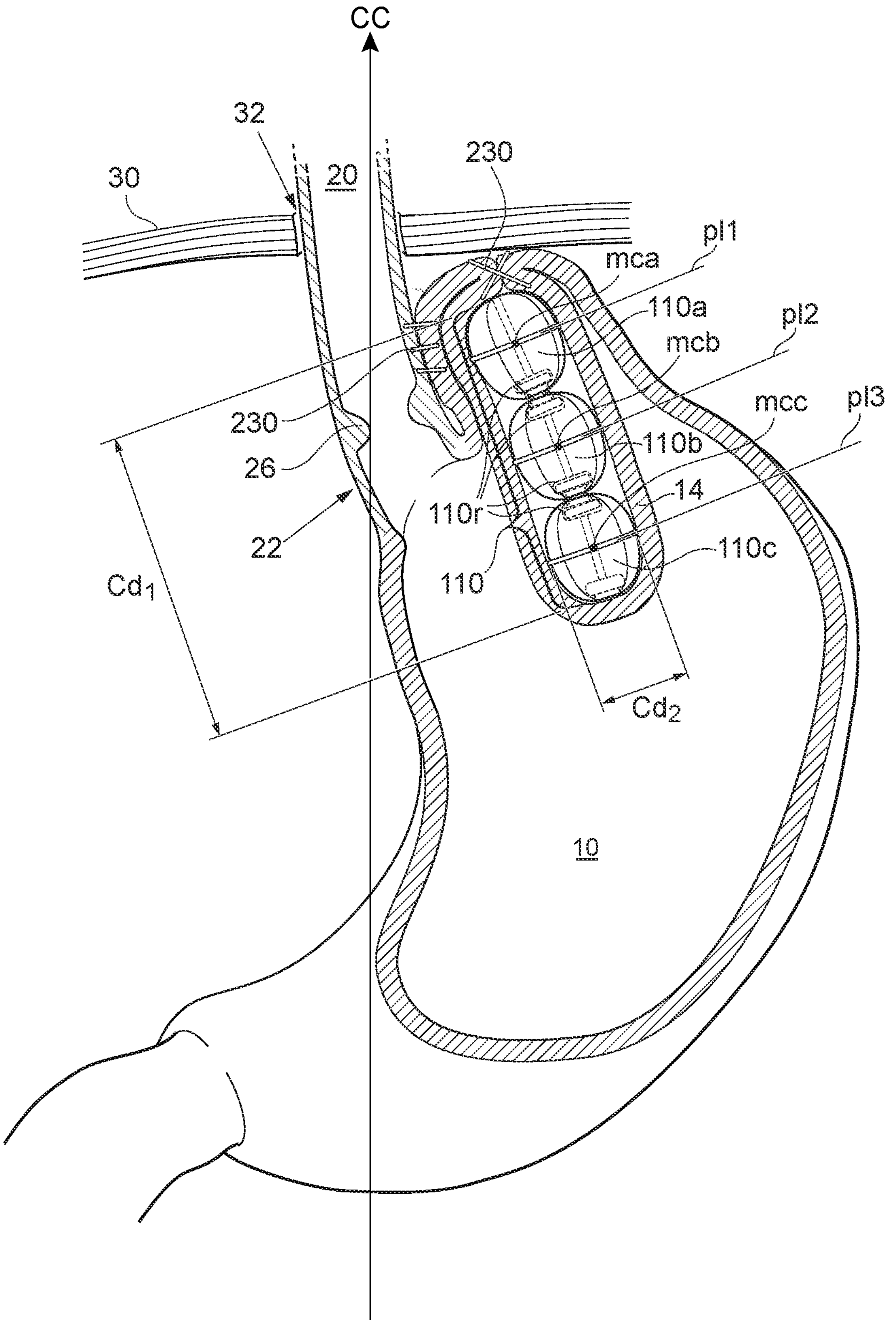

FIG. 39W shows an apparatus for treating reflux disease of a human patient comprises an implantable movement restriction device 110 configured to be at least partly invaginated by the stomach wall of the patient for restricting the movement of the cardia 22 of the patient towards the thoracic diaphragm 30. The implantable movement restriction device 110 has a first cross-sectional distance cd1 and a second cross-sectional distance cd2. The first cross-sectional distance cd1 has a first length and the second cross-sectional distance cd2 has a second length. The first length is more than 1.5 times the second length, more specifically the first length is more than 2 times the second length, more specifically the first length is more than 2.5 times the second length, more specifically the first length is more than 3 times the second length. The movement restriction device 110 is configured to be implanted such that the first cross-sectional distance cd1 is more parallel than perpendicular to the cranial-caudal axis CC of the patient, and the second cross-sectional distance cd2 is more perpendicular than parallel to the cranial-caudal axis CC of the patient. I.e., a length axis of the implantable movement restriction device 110 is more parallel than perpendicular to the cranial-caudal axis CC of the patient.

In the embodiment shown in FIG. 39W, the implantable movement restriction device is an assembled movement restriction device 110 comprising a first, second and third movement restriction device 110*a*, 110*b*, 110*c* configured to be connected to form the assembled implantable movement restriction device 110. The center of gravity mca of the first movement restriction device 110*a* is positioned on a plane pl1 extending perpendicularly from a first third of the first cross-sectional distance cd1 and the center of gravity mcb of the second movement restriction device 110*b* is positioned on a plane pl2 extending perpendicularly from a second third of the first cross-sectional distance cd1, and the center of gravity mcc of the third movement restriction device 110*c* is positioned on a plane pl3 extending perpendicularly from a third of the first cross-sectional distance cd1. A lower portion of the first movement restriction device 110*a* comprises a first connecting portion 110*r* and the upper portion of the second movement restriction device 110*b* comprises a second connecting portion 110*r*, and the first and second connecting portions are configured to be connected to each other. Further, a lower portion of the second movement restriction device 110*b* comprises a third connecting portion 110*r* and the upper portion of the third movement restriction device 110*c* comprises a fourth connecting portion 110*r*. The first and second connecting portions, as well as the third and fourth connecting portions, are configured to be connected to each other. The first and second as well as the third and fourth connecting portions are configured to remain connected to each other by at least one of the first, second and third movement restriction devices 110*a*-110*c* being supported or compressed by invagination of the implantable movement restriction device 110 in the stomach wall of the patient. The first, second and third movement restriction devices 110*a*, 110*b*, 110*c* are capable of disconnecting and separating if the support or compression from the stomach wall on at least one of the first, second and third movement restriction devices 110*a*, 110*b*, 110*c* decreases.

The apparatus shown in FIG. 39W could further be used for treating obesity, as the implantable movement restriction device 110 additionally takes up space in the stomach 10, which reduces the volume of the stomach 10 capable of being used for storing and digesting food. It is a clear advantage that the movement restriction device is elongated, as the stomach 10 has an elongated shape.

FIG. 39W' shows apparatus shown in FIG. 39W in a second state, in which the connection between the first, second and third movement restriction devices 110*a*-110*c* are shown in further detail. Each of the first, second and third movement restriction devices 110*a*-110*c* comprises four parts or segments, which in the third movement restriction device 110*c* is shown as 111*a*-111*d*. Each of these parts or segments 111*a*-111*d* comprises a connecting portion in the form of a recces 114. The recesses 114 of the parts 111*a*-111*d* are configured to be connected to an interconnecting part 110*ip* comprising a protrusion configured to engage the recesses 114 of the respective parts 111*a*-111*d* and further comprises a protrusion configured to engage recesses 114 of the parts or segments of the second movement restriction device 110*b*, such that the interconnecting part 110*ip* connects the first movement restriction device 110*a* to the second movement restriction device 110*b* and the second movement restriction device 110*b* to the third movement restriction device 110*c* along the length axis of the assembled movement restriction device 110. As such, the first, second and third connecting portions are configured to be indirectly connected to each other by the connections to the interconnecting parts 110*ip*.

In the state shown in FIG. 39W', the third movement restriction device 110*c* has inadvertently penetrated the stomach wall, causing the third part to fall into the stomach 10 from its invaginated position wrapped by the stomach wall. As the third movement restriction device 110*c* penetrates the stomach wall, the support and compression from the stomach wall on the third movement restriction device 110*c* decreases, which causes the parts or segments 111*a*-111*d* to separate from each other and thereby dislodge from the interconnecting part 110*ip* such that they disconnect from the second part 110*b* and enters the stomach 10 as individual smaller parts capable of passing through the gastro-intestinal system. In the embodiment shown in FIG. 39W', a single part 111*c* makes up less than $1/12^{th}$ of the volume of the movement restriction device 110. As such, the entire volume of the movement restriction device 110 can be more than 12 times a volume that can pass through the gastro-intestinal system of the patient.

The entire movement restriction device could have a volume exceeding 50 cm3, or a volume exceeding 75 cm3, or a volume exceeding 100 cm3. A single part or segment could have a volume smaller than 10 cm3, or smaller than 6 cm3, or smaller than 6 cm3.

Figure 39X:
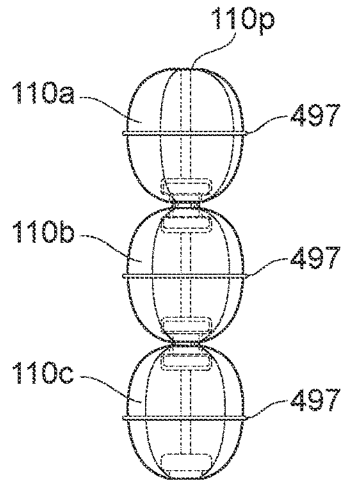
Figure 39X:
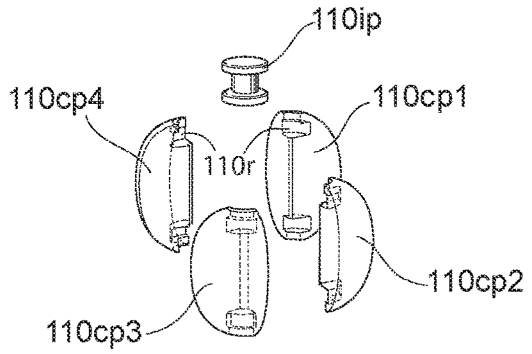

FIGS. 39X and 39X' shows the embodiment of the movement restriction device 110 shown in FIGS. 39W and 39W' before the movement restriction device 110 has been implanted in the patient. Each of the first, second and third parts 110*a*, 110*b*, 110*c* comprises an encircling string or band in the form of a resorbable suture 497 for keeping the movement restriction device 110 together before the movement restriction device is positioned in its invaginated position in the stomach, with the stomach wall in which the movement restriction device 110 has been invaginated supporting and compressing the movement restriction device 110. After implantation, the resorbable suture 497 is resorbed by the body after which the movement restriction device 110 is kept together by the support from the stomach wall in its invaginated position.

Figure 39Y:
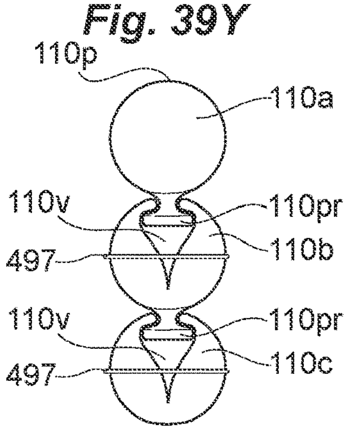
Figure 39Y:
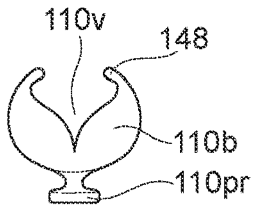
Figure 39Y:
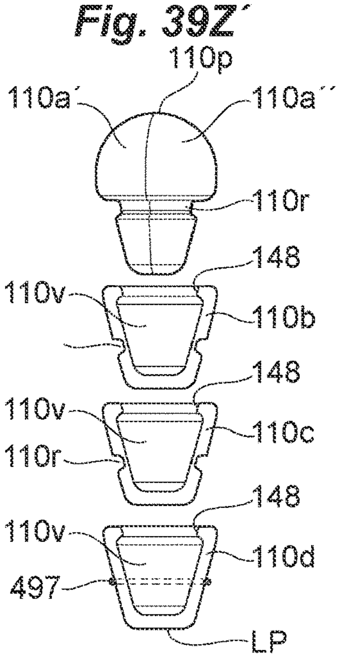

FIGS. 39Y and 39Y' shows an embodiment of the movement restriction device similar to that shown in FIGS. 39W-39X', the difference being that in the embodiment shown in FIGS. 39Y and 39Y', the connecting portions of the first, second and third parts 110*a*, 110*b*, 110*c* are directly connected to each other. The connecting portion of the lower portion of the first part 110*a* in the form of a protrusion 110*pr* is connected to a connecting portion of an upper portion of the second part 110*b* comprising resilient protrusions in the form of clasping elements 498 configured to clasp the protrusion 110*pr* of the connecting portion of the first part 110*b*. Resilient connecting portions in the form of clasping elements 498 of the third part 110*c* are in the same way configured to clasp the protrusion 110*pr* of the connecting portion of the third part 110*c*. In this way, the first, second and third parts 110*a*, 110*b*, 110*c* connects to each other to form the movement restriction device 110. The clasping elements 498 are biased outwards by means of elastic properties of the material of the second and third parts 110*b*, 110*c* and are kept in their clasping position by means of a resorbable suture 497 prior to implantation, and by the support and compressing force of the stomach wall when the implantable movement restriction device 110 is implanted and invaginated by the stomach wall. The resilient protrusions in the form of the clasping elements 498 are configured to connect and disconnect from the recess in a direction substantially perpendicular to the direction of the first cross-sectional distance, i.e. a direction substantially perpendicular to the length axis of the movement restriction device 110.

In the embodiment shown in FIGS. 39Y and 39Y', the second and third parts 110*b*, 110*c* have voids enclosed by the clasping elements 498, such voids also reduce the weight of the second and third parts 110*b*, 110*c*.

Figure 39Z:
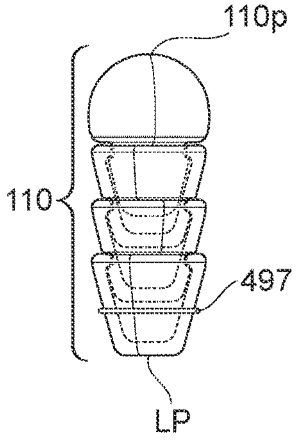
Figure 39Z:
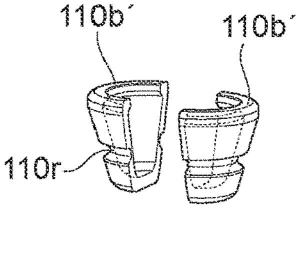
Figure 39A:
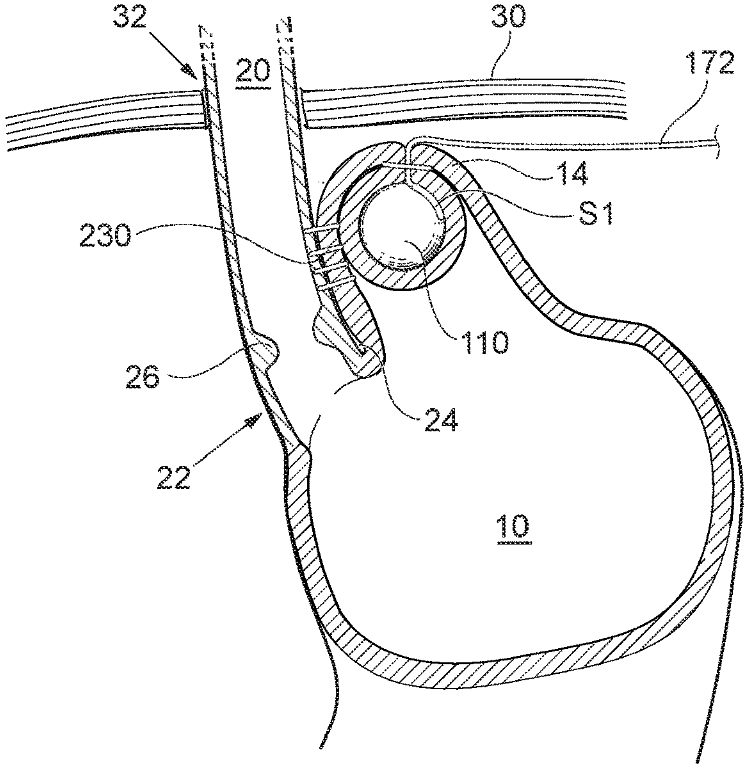
Figure 39A:
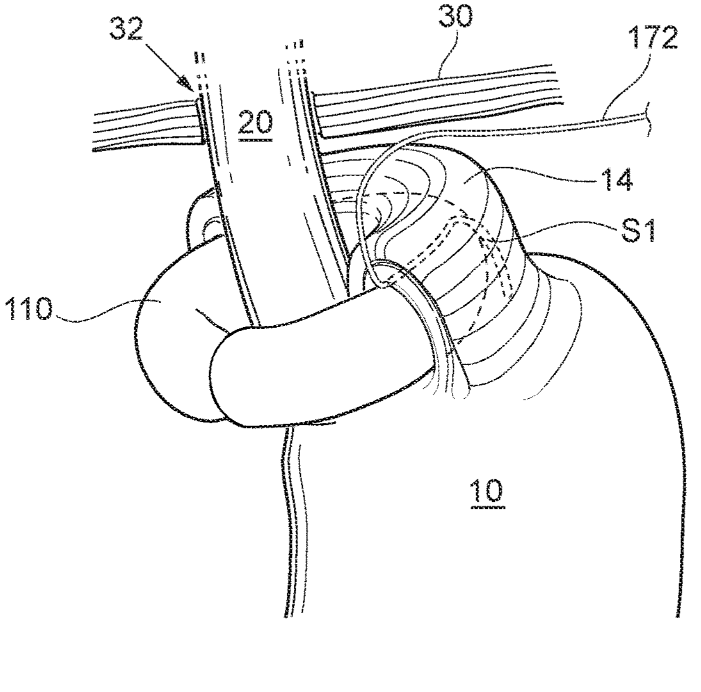
Figure 39A:
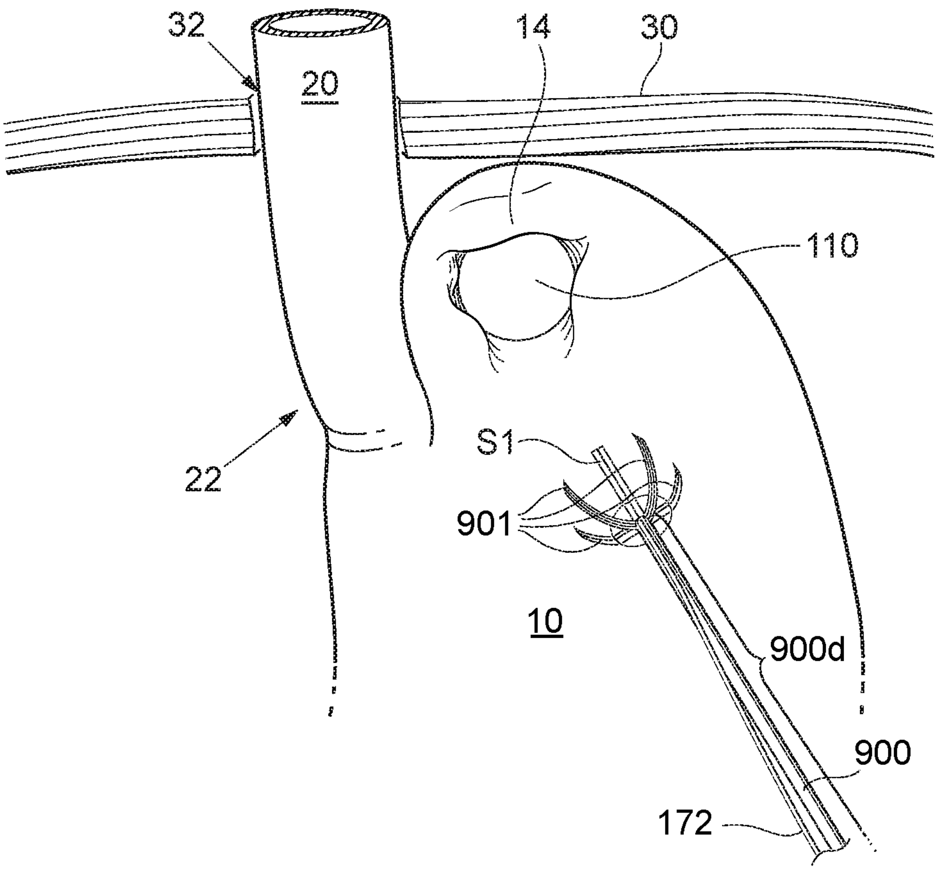
Figure 39A:
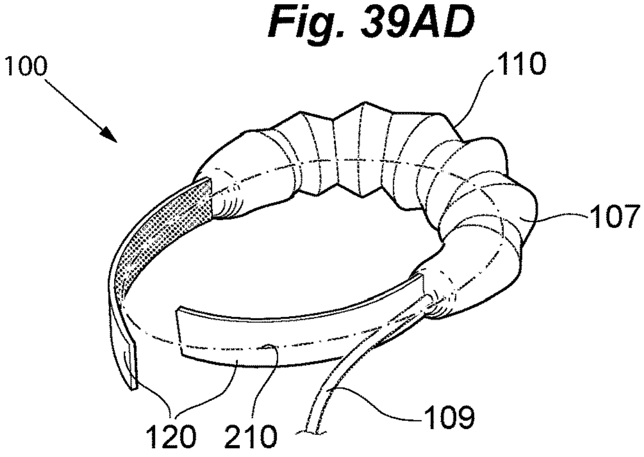
Figure 39A:
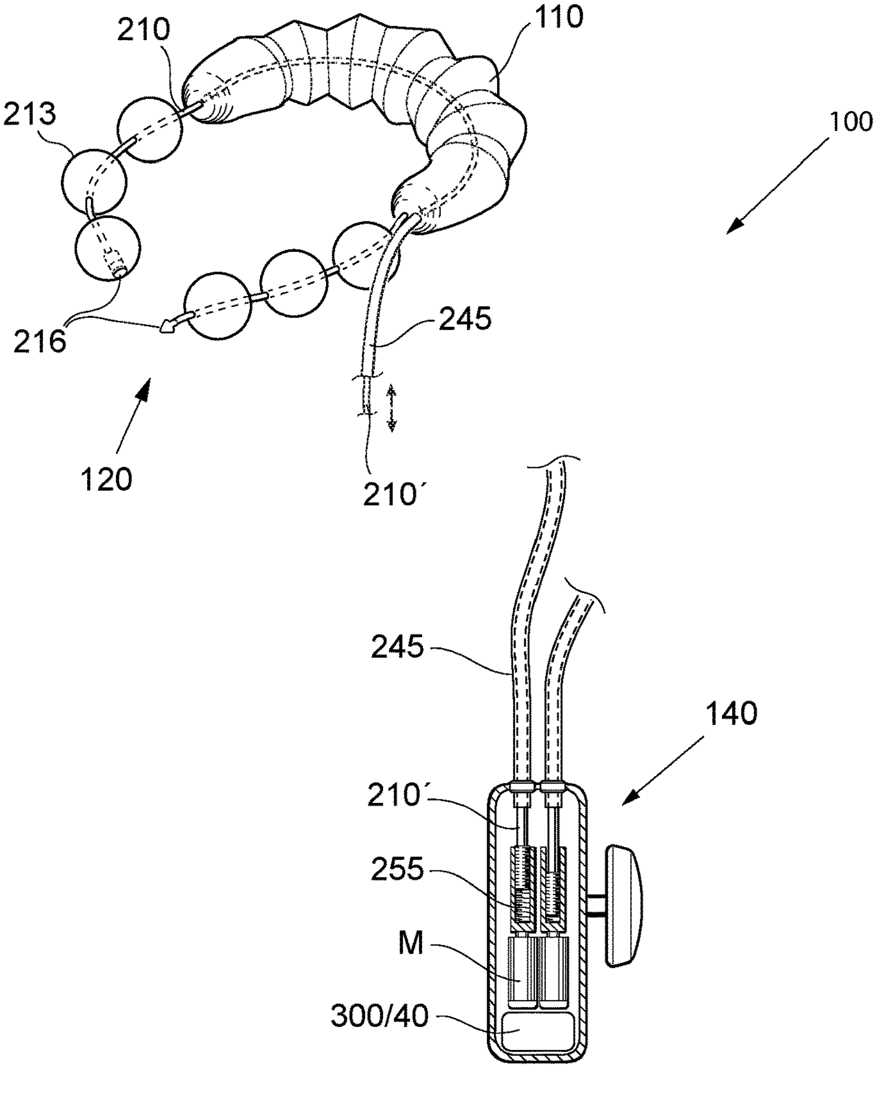
Figure 39A:
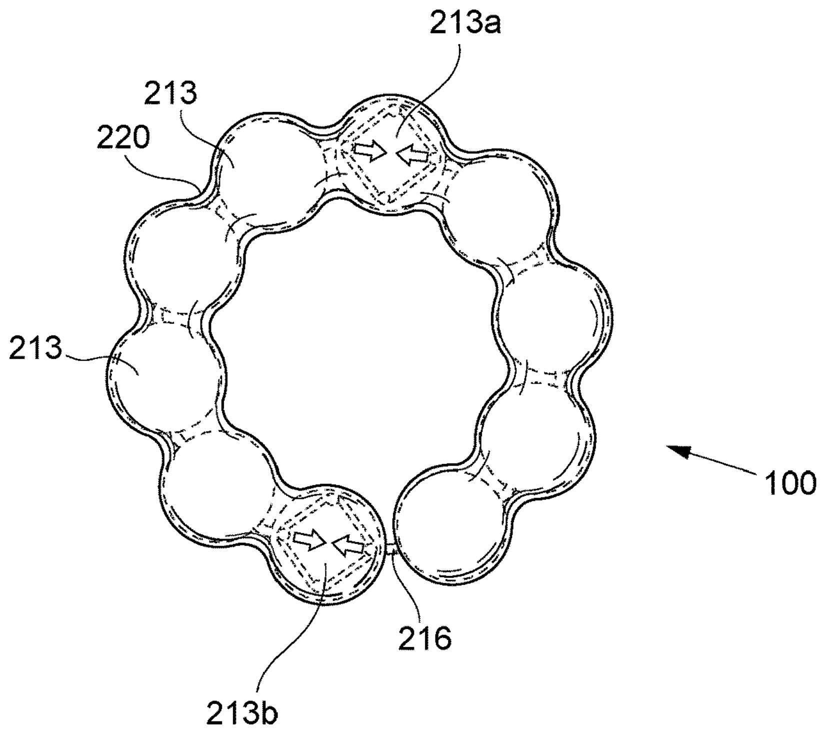
Figure 39A:
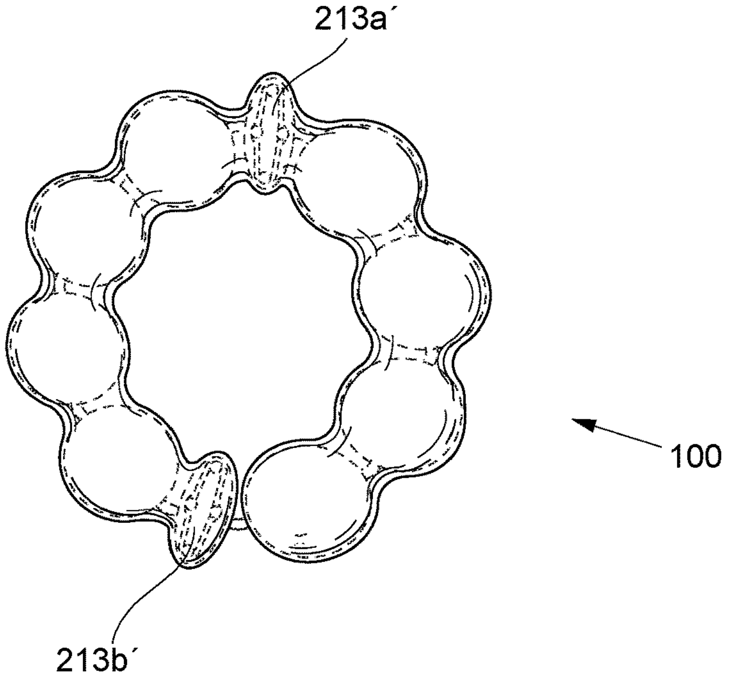
Figure 39A:
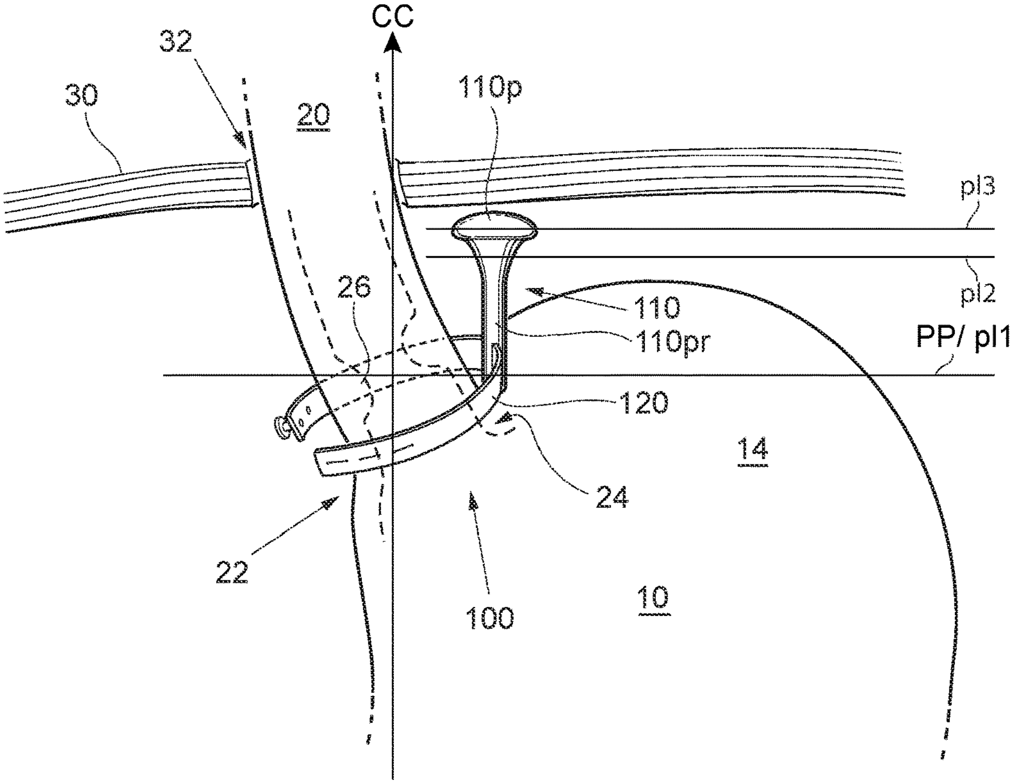
Figure 39A:
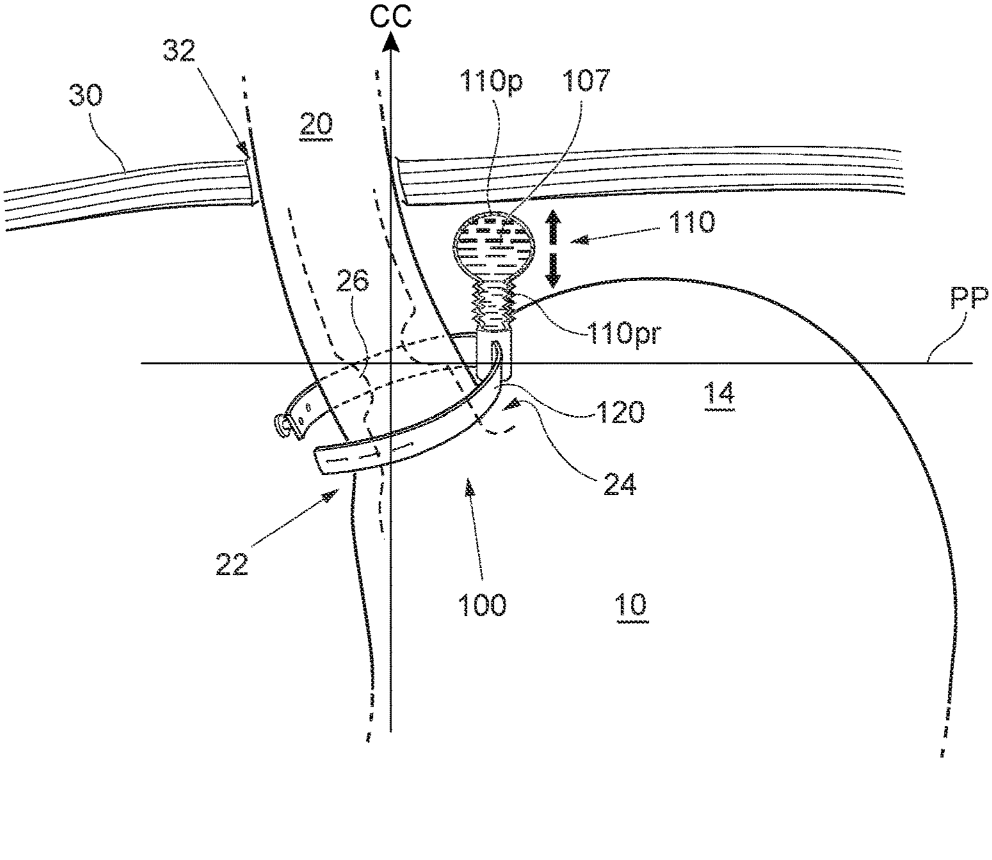
Figure 39A:
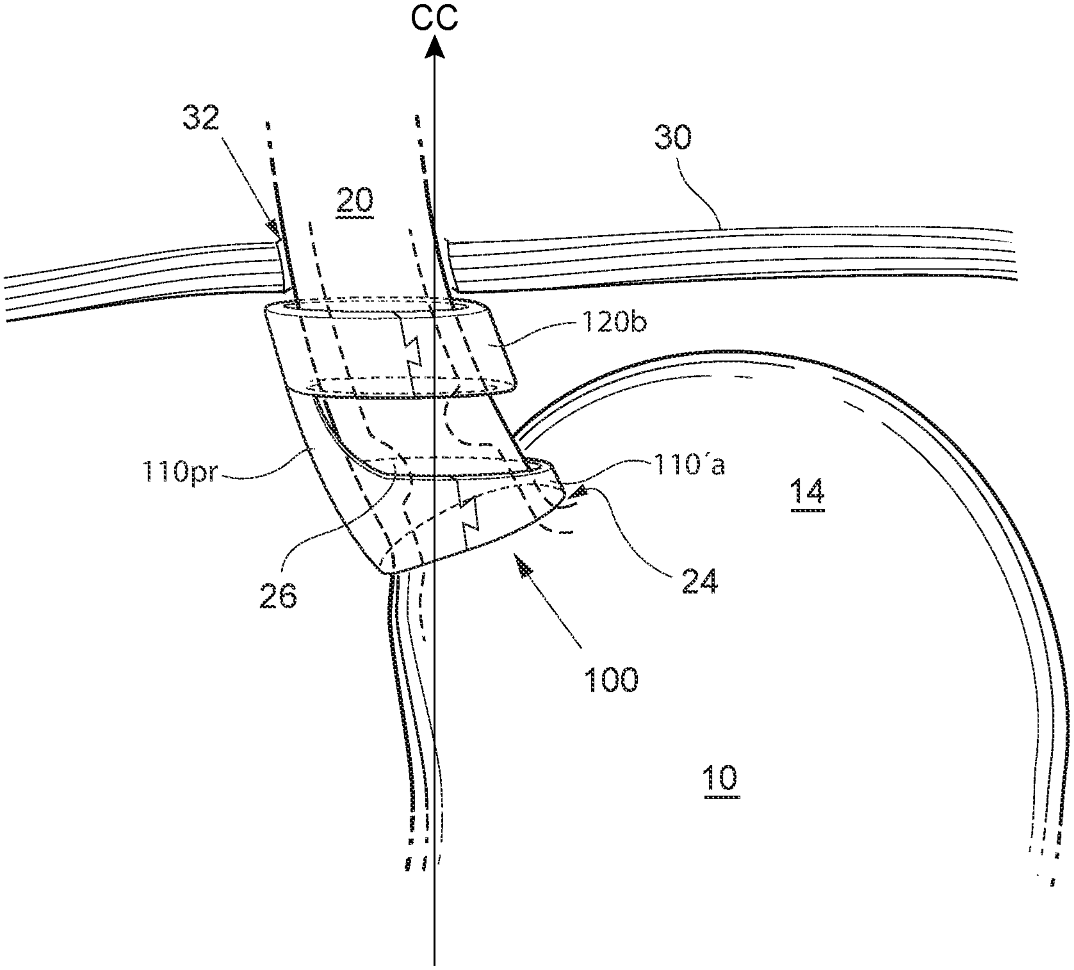

FIGS. 39Z and 39Z" shows an alternative embodiment, similar to the embodiment shown with reference to FIGS. 39W-39Y". In the embodiment shown in FIGS. 39W-39Y', the first part 110*a* comprises the upper portion of the implantable movement restriction device, and a first and second sub-part 110*a*', 110*a*" making up the first part 110*a*. The two sub-parts of the first part are kept together by the second part 110*b*. The first part 110*a* comprises an annular recess 110*r* in the form of a groove which is configured to house clasping elements 498 in the form of an annular protrusion protruding inwards on the upper portion of the second part 110*b*. The second part 110*b* is in turn comprised of a first and second sub-part 110*b*', 110*b*" enabling the second part to be severed for placement around—and surrounding the first part 110*a*. The third part 110*c* is identical to the second part 110*b*—in shape and function—and thus clasps the second part engaging the annular recess 110*r* of the second part 110*b*. The fourth part 110*d* differs in that it is an end part and thus do not comprise an annular recess for the connection of further parts. Instead, the fourth part 110*d* comprises an encircling string or band in the form of a resorbable suture 497 for keeping the fourth part 110*d* together and thereby successively the third, second and first parts 110*a*-110*c*. The resorbable suture 497 keeps the movement restriction device 110 together before the movement restriction device 110 is positioned in its invaginated position in the stomach. After implantation, the resorbable suture 497 is resorbed by the body after which the movement restriction device 110 is kept together by the support from the stomach wall in its invaginated position. The fourth part 110*d* is thus configured to exert a supporting or compressing force on the third part 110*c* derived from a supporting or compressing force exerted by the stomach wall on the fourth part 110*d*.

The resilient protrusions in the form of the clasping elements 498 are in the embodiment shown in FIGS. 39Z-39Z" configured to connect and disconnect from the recesses 110*r* in a direction substantially perpendicular to the direction of the first cross-sectional distance, i.e. the direction substantially perpendicular to the length axis of the movement restriction device 110.

In the embodiment shown in FIGS. 39Y and 39Y', the second, third and fourth parts 110*b*, 110*c*, 110*d* have voids 110*v* enclosed by the clasping elements 498, such voids 110*v* also reduce the weight of the second, third and fourth parts 110*b*, 110*c* and 110*d*.

In the embodiments shown in FIGS. 39Q-39Z' the implantable movement restriction devices 110 comprises at least one circular cross-section. In the embodiments shown in FIGS. 39W-39Z' the implantable movement restriction devices 110 comprises a circular cross-section perpendicular to the length extension of the implantable movement restriction devices 110 and thus to the first cross-sectional distance cd1.

In the embodiments shown in FIGS. 39W-39Y', the implantable movement restriction devices 110 comprises a first, second and third cross-section in planes spaced apart and parallel to each other. The first and third cross-sections have the same area, and the second cross-section is located between the first and third cross-section and have a smaller area. In FIG. 39W, the first and third cross-section are shown in planes pl1 and pl2, spaced apart and parallel to each. The second cross-section is placed centrally between the planes pl1 and pl2 in a plane (not shown) parallel to the planes pl1 and pl2, cutting through the intermediate part 110*ip* placed between the first and second parts 110*a*, 110*b*. The narrower portion between the first and second parts 110*a*, 110*b* can be used for the purpose of providing additional fixation, as the invagination can follow the outer surfaces of the respective parts and as such fixate the first and second parts along the length axis thereof. In the embodiment shown in FIG. 39W (and in the embodiments shown in FIGS. 39Y and 39Y'), the implantable movement restriction device 110 further comprises a fourth and fifth cross-section in planes spaced apart and parallel to the planes of the first, second and third cross-sections. The fifth cross-section plane being placed in the plane pl3 cutting through the center of gravity mcc of the third part 110*c*. The fourth cross-section is placed centrally between the planes pl2 and pl3 in a plane (not shown) parallel to the planes pl1, pl2 and pl3, cutting through the intermediate part placed between the second and third parts 110*b*, 110*c*. The third and fifth cross-sections have the same area, and the fourth cross-section is located between the third and fifth cross-sections and have a smaller area.

The embodiments of implantable movement restriction devices 110 shown in FIGS. 39W-39Z" can be fully invaginated by the stomach wall, such as shown in FIGS. 39W and 39W'. In the alternative, the movement restriction devices 110 shown in FIGS. 39W-39Z" can be partially invaginated such that some portion, such as the upper portion 110*p* protrudes up from the stomach towards the thoracic diaphragm.

The movement restriction devices shown in FIGS. 39W-39Z" may additionally comprise at least one electrode for electrically stimulating at least one tissue portion of the patient. Further details and examples of the operation and control of the stimulation electrodes are provided with reference to FIGS. 40AA-45.

The shapes and material compositions described with reference to FIGS. 39Q-39V' could be combined with the movement restriction devices shown in FIGS. 39W-39Z" to make the implant lighter. It is also possible that the movement restriction devices shown in FIGS. 39W-39Z", or individual parts or sub-parts of the movement restriction devices shown in FIGS. 39W-39Z" can have an adjustable shape or volume such as described with reference to FIGS. 39G-39P'.

FIG. 39AA shows a cross-section of the upper portion of the stomach 10 and a lower portion of the esophagus 20 passing through the esophageal hiatus (or diaphragm opening) 32 in the thoracic diaphragm 30. An apparatus comprising a movement restriction device 110 for treating reflux disease have been positioned and invaginated in the upper portion of the stomach 10. The movement restriction device restricts the movement of the cardia 22 of the patient 10 towards the thoracic diaphragm 30. In the embodiment shown in FIG. 39AA, the implantable movement restriction device 110 comprises a sensor S1 configured to sense at least one of a force and a pressure, for monitoring a pressure or force exerted by the implantable movement restriction device on the stomach wall of the patient. By monitoring the pressure or force exerted by the implantable movement restriction device on the stomach wall it can be established that the movement restriction device 110 is invaginated with suitable pressure for holding the movement restriction device 110 in place whilst not exerting too much pressure on the stomach wall of the patient which risks increasing the risk of damage to the stomach wall which increase the risk that the movement restriction device migrates through the stomach wall and becomes inadvertently positioned inside of the stomach.

According to the embodiment shown in FIG. 39AA, the sensor S1 is fixated to the surface of the implantable movement restriction device 110, such that the surface of the sensor S1 is exposed to the pressure exerted by the stomach wall on the implantable movement restriction device 110. The sensor S1 could be a strain gauge-based sensor, such as a piezoresistive or piezoelectric strain gauge-based sensor, or an optical strain gauge-based sensor, or a capacitive sensor, or an electromagnetic sensor.

In the embodiment shown in FIGS. 39AA and 39AB, the sensor is connected to a remote unit by means of a lead 172 for transferring an electrical signal between the sensor S1 and a remote unit (such as a remote unit further described with reference to FIGS. 46-64). The remote unit comprises an implantable energy source for powering the sensor S1 and an implantable controller for receiving signals from the sensor. The implantable controller may comprise a wireless transceiver, and the implantable controller is configured to receive a sensor signal from the sensor and transmit a wireless signal derived from the sensor signal to a unit external to the body of the patient. Control, communication with, and optional charging of the implantable energy source from an external device, is further elaborated on in the description text referring to FIGS. 65A-66N.

In alternative embodiments in which the movement restriction device is a movement restriction device comprising an enclosed chamber comprising a fluid, such as a compartment, reservoir or hydraulic adjustment chamber (such as further described with reference to FIGS. 39H, 39L, 39M, 39N, 39R, 39R', 39T and 39T') the sensor could be a sensor configured the sense a pressure in the fluid. The sensor could in such embodiments either be placed locally in the movement restriction device, or be placed in a remote unit (such as a remote unit further described with reference to FIGS. 46-64), and connected to the movement restriction device by means of a conduit (such as the conduit 109 shown in FIGS. 39I and 39L).

The apparatus may further comprise an implantable energy source, placed locally of placed in a remote unit, for powering the sensor and an implantable controller connected to the sensor for receiving sensor signals. The implantable controller may comprise a wireless transceiver, and the implantable controller is configured to receive a sensor signal from the sensor and transmit a wireless signal derived from the sensor signal to a unit external to the body of the patient.

In the embodiment shown in FIG. 39AA, the implantable movement restriction device 110 has a size such that the implantable movement restriction device 110 can be fully invaginated by the fundus wall of the patient.

In some embodiments, the sensor S1 is configured to only be used during implantation of the movement restriction device 110. What is most important is that the pressure is evaluated during the step of invaginating the movement restriction device in the stomach wall by suturing the tissue of the stomach wall with stomach-to-stomach sutures such that the movement restriction device becomes enclosed and fixated by the tissue of the stomach wall. After the procedure of invaginating the movement restriction device in the stomach has been concluded, the pressure normally remains substantially the same, which means that it is not necessary to keep monitoring the pressure exerted on the stomach wall after the invagination has been concluded. In such embodiments, the sensor S1 comprises at least one lead 172 connected to the sensor S1 and connecting the sensor S1 to an external device configured to remain outside the patient's body. The lead 172 is connected to the sensor S1 by means of a connector (not shown) such that the sensor S1 is detachably connected to the lead 172, such that the lead 172 can be disconnected from the sensor S1 after completion of the invagination, e.g., by pulling on the lead. In alternative embodiments, the sensor S1 is fixedly fixated to the lead, but the sensor S1 is detachably attached to the implantable movement restriction device, e.g. by means of an adhesive or a mechanical fixation element configured to disengage or rupture when exposed to a specific force.

The sensor for sensing force or pressure may be implemented in the movement restriction device according to any one of the embodiments herein, such as in the embodiments described with reference to FIGS. 1-38B and 39B-39AJ.

The sensor may be implemented in a movement restriction device having a size of less than 200 cm2, and preferably less than 100 cm2, and more preferably less than 50 cm2. The sensor may be implemented in a movement restriction device being elongated and having a first cross-sectional distance having a first length, and a second cross-sectional distance having a second length. The first length may be more than 1.2 times the second length, preferably more than 1.5 times the second length and even more preferably more than 2 times the second length. The sensor may be implemented in a movement restriction device comprising at least two parts, or at least three parts, or at least 4 parts and the parts may be configured to be assembled to form the implantable movement restriction device, e.g., by the at least two parts being configured to be connected to each other to form the implantable movement restriction device.

FIG. 39AB shows an embodiment of the movement restriction device comprising a sensor, in the same way as the embodiment shown in FIG. 39AA. The difference being that in the embodiment of FIG. 39AB, the movement restriction device 110 comprises a closed curve configured to encircle and enclose the esophagus 20 of the patient. The movement restriction device shown in FIG. 39AB is substantially torus-shaped and the portion of the torus shape placed on the sinister side of the esophagus 20 is configured to be invaginated by the stomach wall of the fundus 12. In the embodiment shown in FIG. 39AB, the invaginated portion of the torus shaped movement restriction device 110 placed on the sinister side of the esophagus 20 comprises about ½ of the entire torus shape. The invaginated portion of the torus shape comprises a curved inner surface facing the outer surface of the esophagus 20. The curved inner surface having a curvature such that it coincides with the curvature of the outer surface of the esophagus, when invaginated by the wall of the fundus. However, it is equally conceivable that the invaginated portion of the torus shape amount to only ⅓. Further details of the geometry of the movement restriction device of FIG. 39AB is described with reference to FIG. 8.

In yet alternative embodiments, the entire movement restriction device 110 has a C-shaped cross-section in a plane parallel to the transverse plane of the patient, and the C-shaped cross-section is configured to partially enclose the esophagus of the patient. In embodiments in which the movement restriction device has a C-shaped cross-section, the C-shaped cross-section is configured to not enclose less than ⅓ of the esophagus 20, or less than ¼ of the esophagus 20, or less than ⅕ of the esophagus 20.

The shapes and material compositions described with reference to FIGS. 39Q-39V' could be combined with the movement restriction devices shown in FIGS. 39AA and 39AB to make the implant lighter. It is also possible that the movement restriction devices shown in FIGS. 39AA-39AB can have an adjustable shape or volume such as described with reference to FIGS. 39G-39P'.

FIG. 39AC shows the upper portion of the stomach 10 and a lower portion of the esophagus 20 passing through the esophageal hiatus (or diaphragm opening) 32 in the thoracic diaphragm 30 when a movement restriction device according to any of the spherical movement restriction devices herein has been placed in a pouch created from the tissue of the fundus 12. The movement restriction device 110 has been positioned using a surgical instrument 900 for assisting in the placement of the movement restriction device 110. The surgical instrument 900 comprises a handling portion (not shown) configured to remain outside of the body of the patient in use, and a distal portion 900*d* configured to be inserted into the body of the patient. The instrument further comprises a lead at least partially attached to the distal portion 900*d* and configured to be connected to a sensor S1 for sensing at least one of a force and a pressure, for monitoring a pressure or force exerted by the implantable movement restriction device 110 on the stomach wall of the patient during implantation.

In the embodiment shown in FIG. 39AC, the distal portion comprises a holding device 901 comprising four holding members forming a gripping portion configured to grip the implantable movement restriction to engage and hold the movement restriction device during implantation.

In alternative embodiments, the holding device may comprise an elongated portion configured to be inserted into the implantable movement restriction device. The elongated portion may be placed inside of a sleeve forming the distal portion 900*d* and being connected to the handling portion. The elongated portion placed within the sleeve may be displaceable in relation to the sleeve, such that handling of the handling portion creates relative displacement of the holding device in relation to the sleeve, which disengages the holding device from the movement restriction device 110 for performing the placement of the movement restriction device 110.

In yet alternative embodiments, the distal portion is bent in relation to the primary length axis of the surgical instrument, with a bend that could exceed 10° in relation to the primary length axis of the instrument, or exceed 20° in relation to the primary length axis of the instrument, or exceed 30° in relation to the primary length axis of the instrument, or exceed 40° in relation to the primary length axis of the instrument.

In yet alternative embodiments, the distal portion is flexible and/or bendable for adjusting the angle of the distal portion in relation to the primary length axis of the instrument. The bending of the distal portion may be controllable from the handling portion.

In the embodiment shown in FIG. 39AC, the surgical instrument 900 is an abdominal instrument configured to be inserted into the abdomen of the patent during an open surgical procedure. The surgical instrument 900 may be a laparoscopic instrument configured to be inserted into the abdomen of the patient through a trocar.

In alternative embodiments, the surgical instrument 900 may be a transluminal instrument gastroscopic instrument configured to be inserted into the body of the patient through the esophagus 20 of the patient.

The sensor S1, is in the embodiment shown in FIG. 39AC comprised in the instrument 900, and fixedly connected to the lead 172, such that the sensor is removed from the movement restriction device 110 along with the surgical instrument 900, when the surgical instrument 900 is removed after the movement restriction device has been placed. As such, the sensor S1 is fixedly fixated to the lead, but the sensor S1 is detachably attached to the implantable movement restriction device, e.g. by means of an adhesive or a mechanical fixation element configured to disengage or rupture when exposed to a specific force. The sensor S1 could be attached to a surface of the implantable movement restriction device 110, or attached in the implantable movement restriction device 110, such as in a recess or hole in the implantable movement restriction device 110.

In alternative embodiments, the lead 172 may be connected to the sensor by means of a connector (not shown) such that the sensor is detachably connected to the lead 172, such that the lead 172 can be disconnected from the sensor S1 after completion of the invagination, e.g., by pulling on the lead. I.e. the sensor will remain in the body along with the movement restriction device, but without any operable connection to any controller.

Just as is described with reference to FIGS. 39AA and 39AB, the movement restriction device 110 may be a movement restriction device comprising an enclosed chamber comprising a fluid, such as a compartment, reservoir or hydraulic adjustment chamber (such as further described with reference to FIGS. 39H, 39L, 39M, 39N, 39R, 39R', 39T and 39T') and the sensor S1 could be a sensor configured the sense a pressure in the fluid. The sensor could in such embodiments either be placed locally in the movement restriction device, or be placed in the handling portion and connected to the movement restriction device by means of a conduit.

The handling portion may further comprise an energy source for powering the sensor, and a controller connected to the sensor for receiving sensor signals. The controller is in the embodiment shown in FIG. 39AC an external device configured to remain on the outside of the patient when the surgical instrument is in use, and the controller is configured to receive a sensor signal from the sensor via the lead 172 and provide an output on the basis the sensor signal. The output could be provided by an output device and could be provided to a person. The output device could comprises a unit providing audio output and/or a unit providing visual output, such as a lighting unit or a display unit, and/or a unit providing haptic output.

Just as is described with reference to FIGS. 39AA and 39AB, the sensor S1 could be a strain gauge-based sensor, such as a piezoresistive or piezoelectric strain gauge-based sensor, or an optical strain gauge-based sensor, or a capacitive sensor, or an electromagnetic sensor.

FIG. 39AD shows an apparatus 100 for treating reflux disease of a human patient. The apparatus comprises an implantable movement restriction device 110, and a support device 120 being a flat and relatively wide band configured to be placed around the esophagus. The movement restriction device 110 comprises a wider inflatable portion configured to be placed on the sinister side (or fundus side) of the esophagus for hindering movement of the cardia by means of the movement restriction device 110 directly or indirectly supporting against the thoracic diaphragm. The support device 120 has two ends configured to be connected to each other during implantation for securing the movement restriction device to the esophagus. In the embodiment shown in FIG. 39AD, the two ends of the support device 120 are configured to be sutured together such that the apparatus forms a closed curve encircling the esophagus. The movement restriction device 110 and the support device 120 forms an elongated core 210 forming the closed curve when the two ends of the support device 120 are connected. In the embodiment shown in FIG. 39AD, the apparatus 100 comprises a single variability function configured to alter the length of the elongated core 210 such that the length of the elongated core can be post-operatively adjusted for different persons and/or for changes in the anatomy in the body of the patient in the apparatus is implanted. In the embodiment shown in FIG. 39AD, the single variability function comprises a hydraulic adjustment chamber 107 enclosed by the surface material of the movement restriction device 110. The surface material enclosing the movement restriction device 110 is pleated such that the surface material forms a bellows with elevated and lowered portion, such that the movement restriction device 110 can be expanded and contracted for varying the length of the movement restriction device 110 and thereby the length of the encircling elongated core 210. The bellows enables the movement restriction device 110 can be expanded and contracted even as fibrotic tissue surrounds the bellows. In the embodiment shown in FIG. 39AD, the length variability function is a hydraulic length variability function and the hydraulic adjustment chamber 107 enclosed by the surface material is connected to a hydraulic operation device by means of a conduit 109. The hydraulic operation device is in the embodiment shown in FIG. 39AD placed in a remote unit, which could simply be a subcutaneously placed injection port (such as shown in FIG. 39L) enabling the injection and withdrawal of hydraulic fluid into the conduit 109, and consequently into the hydraulic adjustment chamber 107 of the implantable movement restriction device 110. In the alternative, the remote unit could comprise a hydraulic pump, and energy source, a controller and means for wireless communication with an external device located outside the body of the patient. Remote units comprising a pump, an energy source and a controller is further described with reference to FIGS. 47A, 47B and 47C, and a controller and means for wireless communication with an external device located outside the body of the patient is further elaborated on with reference to FIGS. 65A-66N.

In alternative embodiments, it is equally conceivable that the implantable movement restriction device 110 comprises an injection port integrated in the surface material of the implantable movement restriction device 110 for enabling injection of a fluid into, or withdrawal of a fluid from the hydraulic adjustment chamber 107, such as further described with reference to FIG. 39H.

In alternative embodiments, the thickness of the surface material forming the wall enclosing the hydraulic chamber may vary, which may affect the alteration of the shape of the hydraulic chamber as fluid is injected into or withdrawn from the hydraulic chamber. I.e. the shape of the movement restriction device 107 may be altered by thinner portion of the wall enclosing the hydraulic adjustment chamber 107 being deformed more than thicker portions of the wall enclosing the hydraulic adjustment chamber 107. An embodiment further describing how the shape of the hydraulic adjustment chamber 107 can be altered by means of variations in the wall thickness is described with reference to FIG. 39AA.

FIG. 39AE shows an apparatus 100 for treating reflux disease of a human patient similar to that shown in FIG. 39AE. In the embodiment shown in FIG. 39AE, the apparatus comprises a movement restriction device 110 and a support device 120 comprising multiple fixated to an elongated core 214 being a flat and relatively wide band configured to be placed around the esophagus. The difference being that in the embodiment shown in FIG. 39AE, the support device 120 comprises a first length variability function allowing the elongated core 210 to be arranged in a constricting state for hindering fluid from passing from the stomach into the esophagus and in an expanded state for allowing food to pass into the stomach in response to the patient swallowing. I.e. the elongated core 210 is configured to exert an encircling pressure on the esophagus in the constricting state. In the embodiment shown in FIG. 39AE, the first length variability function comprises an array of resiliently attracting adjacent portions 213 interconnected by the elongated core 210. In the embodiment shown in FIG. 39AE, the portions 213 of the array are ball-shaped, having a substantially smooth outer surface suitable for resting against the tissue of the outer wall of the esophagus. The portions 213 may for example be formed of a metal or a polymer and may preferably comprise a biocompatible outer surface suitable for long-term implantation in the body. The resiliently attracting adjacent portions 213 may be attracted to each other by means of an elastic element, such as the elongated core comprising an elastic band or string, or by means of magnets incorporated in the resiliently attracting adjacent portions 213. The resiliently attracting adjacent portions 213 allows the apparatus to enter an expanded state (e.g. in response to the patient swallowing a bolus of food), and assuming a constricting state for hindering stomach contents for pass into the esophagus when the patient is not swallowing. As indicated in FIG. 39AE, the core 210 comprises a string or band extending through each of the portions 213 of the support device. In the embodiment shown in FIG. 39AE, the elongated core 210 further comprises an attacher 216, or locking means, arranged at the end portions of the core 210 (or of the support device 120). The attacher 216 may for example comprise a first part, arranged at a first end portion, which can be inserted in, or attached to, a second part arranged at the other end portion of the core 210. Examples of attachers 216 include interlocking components, snap fasteners, and a screw assembles.

The first length variability function may be substituted for any of the length variability functions described with reference to FIG. 13-18B, 19A-21, 24 or 27.

The apparatus shown in FIG. 39AE further comprises a second length variability function for post-operatively adjusting the length that the core 210 has in its constricting state, variability function configured to alter the length of the elongated core 210 such that the length of the elongated core 210 can be post-operatively adjusted for different persons and/or for changes in the anatomy in the body of the patient in the apparatus is implanted. In the embodiment shown in FIG. 39AE, the second variability function comprises a mechanical length variability function. The elongated core 210 exits the surface material of the movement restriction device 110 through a sleeve 245. The length of the elongated core 210 can thus be adjusted by the pulling or releasing of the portion 210' of the elongated core 210 exiting the movement restriction device 110. Just as in the embodiment described with reference to FIG. 39AD, the surface material of the movement restriction device 110 is pleated such that the surface material forms a bellows with elevated and lowered portion, such that the movement restriction device 110 can be expanded and contracted for varying the length of the movement restriction device 110 and thereby the length of the encircling elongated core 210. The bellows enables the movement restriction device 110 to be expanded and contracted even as fibrotic tissue surrounds the bellows.

In the embodiment shown in FIG. 39AE, the mechanical length variability function is a powered mechanical length variability function, and the portion 210' of the elongated core 210 exiting the movement restriction device 110 is connected an electrical motor M (which may be substituted for an electromagnet or an electroactive material) placed in a remote unit 140. In the embodiment shown in FIG. 39AE, the portion 210' of the elongated core 210 exiting the movement restriction device acts as a shaft for transferring linear force, and the mechanical operation device comprises a transmission 255 configured to transform a rotating force generated by the electrical motor M into a linear force. The remote unit 140 further comprises an energy source 40 and a controller 300 for controlling the motor M and thereby the varying of the length of the elongated core 210.

In alternative embodiments, the portion 210' of the elongated core 210 used for varying of the length of the elongated core 210 may be just placed under the skin such that a small incision in the skin is needed to reach the portion 210' of the elongated core 210 for manual manipulation of the portion 210' of the elongated core 210.

In the embodiment shown in FIG. 39AE, the movement restriction device 110 part of the elongated core 210 is configured to protrude above the cardiac sphincter of the patient, when implanted, such that movement of the cardia towards the diaphragm is restricted to hinder the cardia from sliding through the diaphragm opening into the patient's thorax. The movement restriction device 110 part of the elongated core 210) has a maximum height exceeding 2 cm, as measured in a normal direction to the plane in which the elongated core extends when encircling the esophagus, the normal direction substantially coinciding with the cranial direction in the patient. More specifically, in the embodiment shown in FIG. 39AF, the movement restriction device 110 part of the elongated core 210 has a maximum height being 3 cm or more, more specifically more than 4 cm.

When implanted, the movement restriction device 110 portion of the apparatuses 100 of FIGS. 39AD and 39AE (or elongated core) may further have an adjustable height, such that the effect that the movement restriction device 110 has on restricting the movement of the cardia can be adjusted. In such embodiments, the elongated has a first cross-sectional distance and a second cross-sectional distance and when implanted the first cross-sectional distance is more parallel than perpendicular to the cranial-caudal axis of the patient, and the second cross-sectional distance is more perpendicular than parallel to the cranial-caudal axis of the patient. The elongated core can be adjusted in situ such that the shape of the elongated core can be adjusted by the adjustment of the length of the first cross-sectional distance, such that the length of the first cross-sectional distance can be increased relative to the length of the second cross-sectional distance. In some embodiments, the elongated core can be adjusted by an increase of the length of the first cross-sectional distance relative to the length of the second cross-sectional distance while the length of a circumference of a cross-section of the elongated core, in a plane parallel to the coronal plane of the patient remains constant.

Further details of adjustable shapes or volumes of the movement restriction device which may be applied to the movement restriction device 110 portion in the embodiments shown in FIGS. 39AD and 39AE are further elaborated on with reference to FIGS. 39G-39P".

When implanted, the movement restriction device 110 portion of the apparatuses 100 of FIGS. 39AD and 39AE (or elongated core) may be placed such that a lower portion of the elongated core 210, directly or indirectly, engages the stomach of the patient in a region of the angle of his, such that the function of the elongated core 210 as a movement restriction device 110 is supported by tissue of the stomach in the region of the angle of his.

The elongated core may be configured to be partially or fully invaginated by the stomach wall, preferably the stomach wall of the fundus. In some embodiments, the entire apparatus may be invaginated by the stomach wall, whereas in other embodiments, only the movement restriction device 110 portion of the apparatus is invaginated and the support device 120 is placed freely around the esophagus (such as for example shown in FIG. 39AB).

In the embodiments shown in FIGS. 39AD and 39AE, the movement restriction device 110 portion of the elongated core 210 configured to be placed on the sinister side of the esophagus comprises about ½ of the entire encircling elongated core 210. The curved inner surface is curved in a cross-section in a plane parallel to the transverse plane of the patient, and the curve is configured to partially enclose the esophagus of the patient and has a curvature such that it coincides with the curvature of the outer surface of the esophagus, when implanted. However, it is equally conceivable that the movement restriction device 110 portion of the elongated core 210 amount to only ⅓.

In the embodiments shown in FIGS. 39AD and 39AE, the movement restriction device 110 portion of the elongated core 210 has a C-shaped cross-section in a plane parallel to the transverse plane of the patient, when implanted. The C-shaped cross-section is configured to partially enclose the esophagus of the patient.

FIG. 39AF shows an embodiment of the apparatus 100 similar to the embodiment shown with reference to FIG. 13. The elongated core is formed by a plurality of core elements 213 annularly arranged to a ring-shape. Just as in the embodiment shown with reference to FIG. 13, the apparatus comprises a first length variability function allowing the core to be arranged in a constricting state for hindering fluid from passing from the stomach into the esophagus and in an expanded state for allowing food to pass into the stomach in response to the patient swallowing. The embodiment shown in FIG. 39AF differs from the embodiment shown in FIG. 13 in that the embodiment shown in FIG. 39AF further comprises a second length variability function for post-operatively adjusting the length that the core has in its constricting state, in the form of that two core elements 213*a*, 213*b* are collapsible by means of hinged portions inside of the two core elements 213*a*, 213*b*.

The core elements 213 are arranged in a cover 220 as shown in FIGS. 39AF and 39AG to enable length adjustment also when the cover 220 has been overgrown by fibrotic tissue. The two core elements 213*a*, 213*b* may be manually collapsible by pressing on the sides of the two core elements 213*a*, 213*b*, or the two core elements 213*a*, 213*b* may be energized such that the two core elements 213*a*, 213*b* may be collapsible for example by means of an electroactive material comprised in the two core elements 213*a*. 213*b*.

FIG. 39AG shows the embodiment shown in FIG. 39AF when the length of the elongated core has been shortened by the collapsing of the two core elements 213*a*, 213*b*.

In the embodiments shown in FIGS. 39AD-39AG, the second length variability function is configured for post-operatively adjusting the length of the elongated core 210 in its constricting state with more than 5%, more specifically with more than 10%, more specifically with more than 15%, or even more specifically with more than 20%.

The movement restriction devices shown in FIGS. 39AD-39AG may additionally comprise at least one electrode for electrically stimulating at least one tissue portion of the patient. Further details and examples of the operation and control of the stimulation electrodes are provided with reference to FIGS. 40AA-45.

The shapes and material compositions described with reference to FIGS. 39Q-39V' could be combined with the movement restriction devices shown in FIGS. 39AD-39AG to make the implant lighter.

FIG. 39AH shows an embodiment of an apparatus 100 for treating reflux disease of a human patient, the apparatus 100 comprises an elongated core in the form of a support element 120 having a length allowing the support element 120 to encircle the esophagus 20 of the patient. The apparatus further comprises a protruding portion 110*pr* configured to protrude from the support element 120 in a direction more parallel than perpendicular to the cranial-caudal axis CC of the patient, in a substantially cranial direction, when the apparatus is implanted. The protruding portion 110*pr* is configured to protrude a distance of at least 10 mm in a substantially cranial direction from a plane extending perpendicularly from the cranial-caudal axis CC of the patient and comprising the center of the support element 120. The protruding portion 110*pr* is configured to directly or indirectly engage the thoracic diaphragm 30 of the patient for restricting the movement of the cardia 22 of the patient.

The support element 120 may optionally comprise a length variability function allowing the support element 120 to be arranged in a constricting state for hindering fluid from passing from the stomach into the esophagus and in an expanded state for allowing food to pass into the stomach in response to the patient swallowing. In the embodiment shown in FIG. 39AH, the length variability function is incorporated in the support element 120 by the support element 120 being elastic. In alternative embodiments, the variability function could be based on magnetic force, such as for example described with reference to FIGS. 13-18B, 20A and 20B.

In the embodiment shown in FIG. 39AH, the protruding portion 110*pr* is configured to protrude a distance of at least 20 mm in a substantially cranial direction from a plane extending perpendicularly from the cranial-caudal axis CC of the patient and comprising the center of gravity of the support element 120.

In the embodiment shown in FIG. 39AH, the protruding portion 110*pr* is configured to protrude in a substantially cranial direction from a plane extending perpendicularly from the cranial-caudal axis CC of the patient and comprising the center of gravity of the support element 120 (or elongated core) a distance such that an upper portion 110*p* of the protruding portion 110*pr* is placed at least 5 mm above the cardiac sphincter 26, more specifically more than 10 mm above the cardiac sphincter, and even more specifically more than 15 mm above the cardiac sphincter. In the embodiment shown in FIG. 39AJ, the upper portion 110*p* is configured to, directly or indirectly, engage the thoracic diaphragm 30 of the patient, and the upper portion 110*p* comprises at least one curvature.

In the embodiment shown in FIG. 39AH, the support element 120 (or elongated core) has a first cross-sectional area in a first plane pl1 extending perpendicularly from the cranial-caudal axis CC of the patient, and the protruding portion has a second, average, cross-sectional area in a second plane pl2 parallel to the first plane pl1, and wherein the first cross-sectional area is more than 1.5 times the size of the second cross-sectional area. The protruding portion 110*pr* further has a third cross-sectional area in a third plane pl3 parallel to the first plane pl1, and wherein the second plane pl2 is positioned between the first and third planes pl1, pl2, and wherein the third cross-sectional area is more than 1.5 times the size of the second cross-sectional area.

The lower portion of the support element 120 (or elongated core) is in the embodiments shown in FIGS. 39AH, 39AI and 39AJ configured to, directly or indirectly, engage the stomach of the patient in a region of the angle of his 24, such that the function of the protruding portion 110*pr* as a movement restriction device is supported by tissue of the stomach in the region of the angle of his 24.

FIG. 39AI shows an embodiment of the apparatus 100 similar to that of the embodiment shown in FIG. 39AH. The difference being that in the embodiment in FIG. 39AI, the protruding portion 110*pr* is adjustable in situ, such that the length that the protruding portion 110*pr* protrudes from the plane PP extending perpendicularly from the cranial-caudal axis CC of the patient and comprising the center of gravity of the support element 120 (or elongated core) can be adjusted. In the embodiment shown in FIG. 39AI, the protruding portion 110*pr* is hydraulically adjustable by means of the protruding portion 110*pr* comprising a hydraulic adjustment chamber 107 comprising pleated portion forming a bellows. The apparatus could further comprise a conduit configured to connect the hydraulically adjustable protruding portion 110*pr* to an implantable injection port (such as for example shown with reference to FIG. 39I), or the implantable injection port could be comprised in the wall of the protruding portion 110*pr* (such as for example shown with reference to FIG. 39H). The injection or withdrawal of a hydraulic fluid into the injection port adjusts a length of the bellows and thereby the height of the protruding portion 110*pr.*

In alternative embodiments, the thickness of the surface material forming the wall enclosing the hydraulic chamber 107 may vary, which may affect the alteration of the shape of the protruding portion 110*pr* as fluid is injected into or withdrawn from the hydraulic chamber 107. I.e. the shape of the protruding portion 110*pr* may be altered by thinner portion of the wall enclosing the hydraulic adjustment chamber 107 being deformed more than thicker portions of the wall enclosing the hydraulic adjustment chamber 107. An embodiment further describing how the shape of the hydraulic adjustment chamber 107 can be altered by means of variations in the wall thickness is described with reference to FIG. 39AA.

In alternative embodiments, the protruding portion may be mechanically adjustable, and the hydraulic function described with reference to FIG. 39AI may be replaced by the mechanical function described with reference to FIG. 39G, or by an electroactive material configured to alter shape when exposed to an electrical current or an electrical voltage.

In the embodiment shown in FIG. 39AI, the length of the protruding portion is adjustable in situ more than 1.2 times. In alternative embodiments, the length of the protruding portion may be adjustable in situ more than 1.3 times, or more than 1.5 times.

FIG. 39AJ shows an alternative embodiment to the embodiments described with reference to FIGS. 39AH and 39AI. The difference being that in the embodiment of FIG. 39AJ, the apparatus comprises a first support element 120*a* (or elongated core) encircling the esophagus 20 and being supported by tissue of the stomach 10 in the region of the angle of his 24, and a second support element 120*b* (or elongated core) encircling the esophagus 20 and being placed at a distance from the first support element 120*a*. The second support element 120*b* being configured to directly or indirectly contact the thoracic diaphragm 30 and thereby act as a movement restriction device hindering the movement of the cardia. The first and second support elements 120*a*, 120*b* are connected to each other by means of the protruding portion 110*pr*. In the embodiment shown in FIG. 39AJ, the second support element 120*b* is placed at a distance from the first support element 120*a* exceeding 5 mm, more specifically exceeding 10 mm, in the direction of the cranial-caudal axis CC of the patient. The first and/or second support elements 120*a*, 120*b* may be configured to be invaginated by the stomach wall, preferably by the fundus 12.

The encircling support elements 120 of the embodiments shown in FIGS. 39AH-39AJ may be replaced by the adjustable encircling support elements 120 (or elongated cores) described with reference to FIGS. 39AD and 39AE.

The apparatuses shown in FIGS. 39AH-39AJ may additionally comprise at least one electrode for electrically stimulating at least one tissue portion of the patient. Further details and examples of the operation and control of the stimulation electrodes are provided with reference to FIGS. 40AA-45.

The shapes and material compositions described with reference to FIGS. 39Q-39V' could be combined with the movement restriction devices shown in FIGS. 39AH-39AJ to make the implant lighter.

Figure 40A:
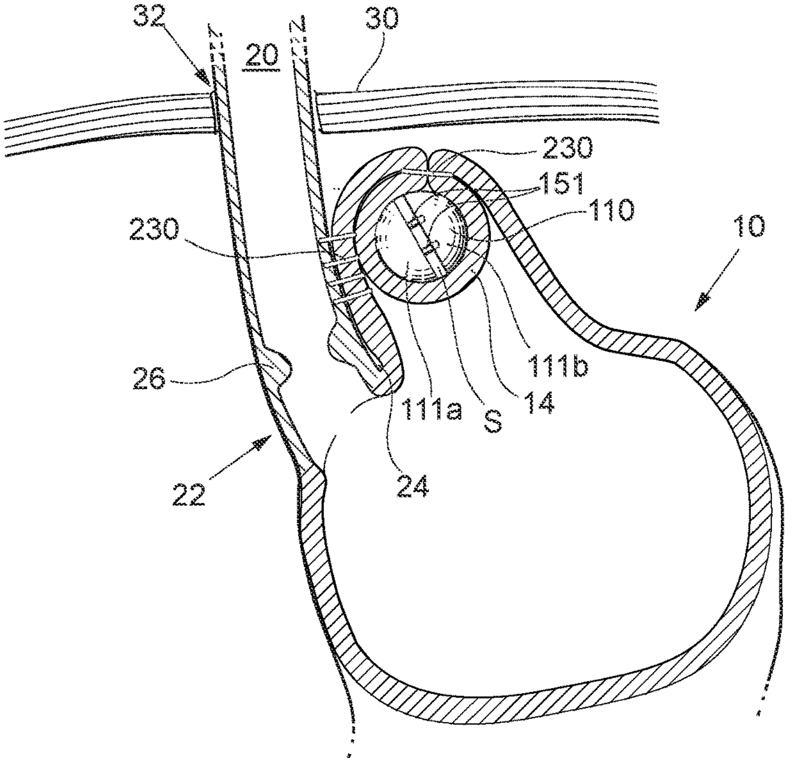
FIG. 40AA is a schematic view of an apparatus for treating reflux disease, when the apparatus is implanted in the body of the patient.
Figure 40A:
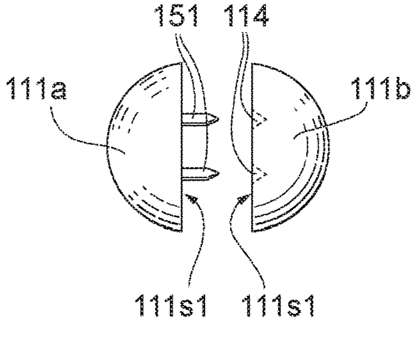
Figure 40A:
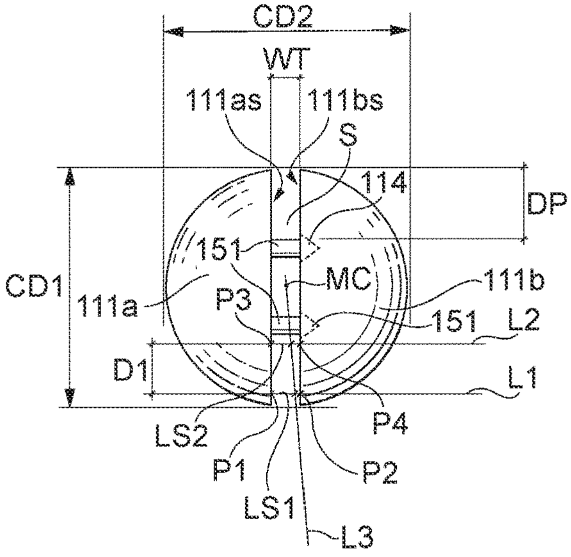
Figure 40A:
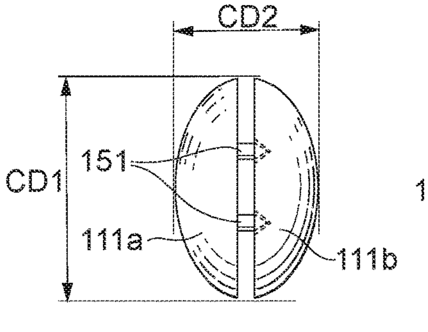
Figure 40A:
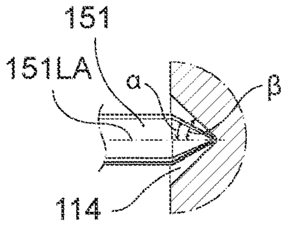
Figure 40A:
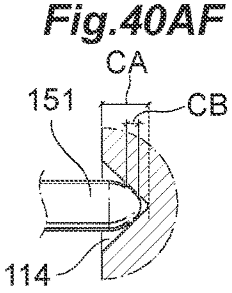
Figure 40A:
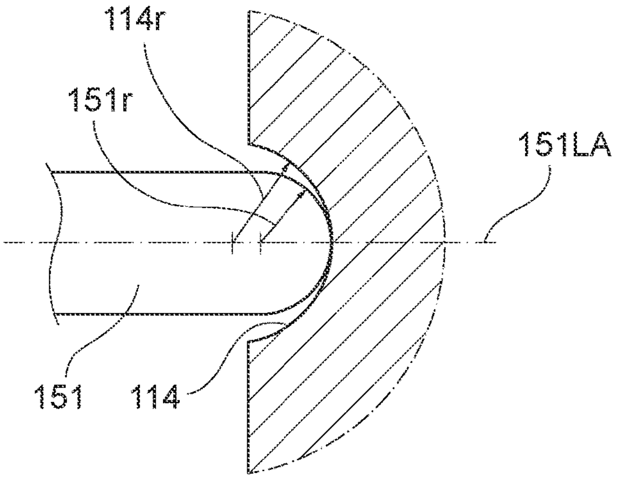
Figure 40A:
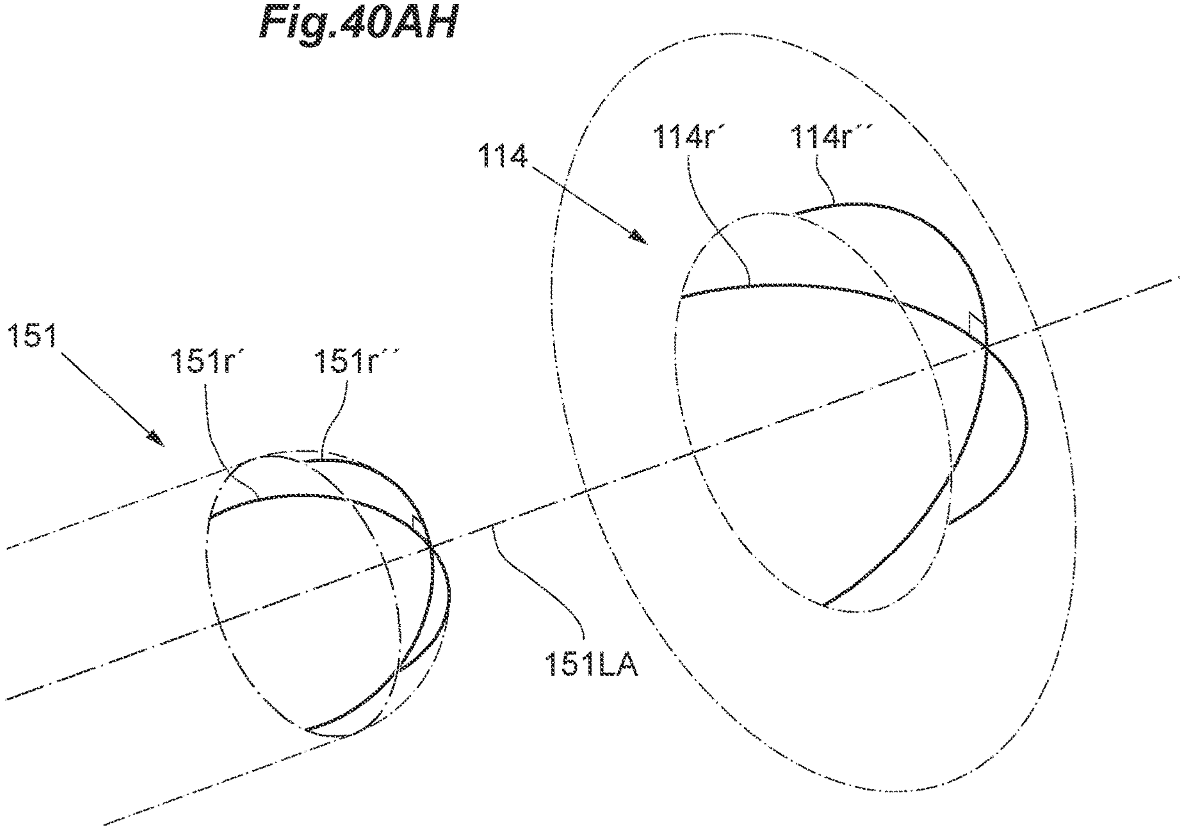

FIG. 40AA is a schematic illustration of an implantable medical device according to some embodiments of the present disclosure. In the embodiment shown in FIG. 40AA, the implantable medical device is used for treatment of a human patient suffering from gastroesophageal reflux disease (GERD), also referred to as reflux disease. As illustrated in FIG. 40AA, the implantable medical device comprises a movement restriction device 110 configured to be implanted in connection with the stomach 10 for hindering the cardia 22 and the lower esophageal sphincter 26 from sliding through the esophageal hiatus 32 into the thoracic diaphragm 30.

In the embodiment shown in FIG. 40AA, the movement restriction device 110 is arranged to rest against a fundus wall portion 14 of the stomach 10. In the present example, the movement restriction device 110 is arranged to rest against the outside of the stomach wall, against the outer serous membrane or serosa of the stomach. However, the movement restriction device 110 may in alternative examples and implementations be arranged to rest against the inside of the stomach wall and thus placed against the mucosa or submucosa of the stomach wall.

In the embodiment shown in FIG. 40AA, the movement restriction device 110 has a shape and size that allows it to be fully invaginated by the fundus wall portion 14. This is achieved by forming a pouch or recess in the fundus wall portion 14 and at least partly closing the opening of the pouch or recess so as to hinder the movement restriction device 110 from being removed from the fundus wall portion 14. The invagination by the fundus wall portion 14 allows the movement restriction device 110 to be implanted at a position between the patient's diaphragm 30 and a lower portion of the fundus wall 14, such that movement of the cardia 22 and the lower esophageal sphincter 26 towards the diaphragm 30 is restricted. By restricting this movement, the cardia 22 and the lower esophageal sphincter 26 may be hindered from sliding up towards, and possibly through, the esophageal hiatus 32 into the thoracic diaphragm 30 and into the patient's thorax, and the supporting pressure against the lower esophageal sphincter 26 or cardiac sphincter 26 exerted from the abdomen can therefore be maintained.

As illustrated in the embodiment shown in FIG. 40AA, the implantable medical device comprises fasteners 230 in the form of sutures or staplers 230 configured to fixate or couple the fundus wall 14 of the stomach 10 to the esophagus 20 such that the movement restriction device 110 is indirectly coupled or affixed to the esophagus 20 at a position above the cardiac sphincter 26. By the affixation of the movement restriction device 110 to the esophagus 20, the invaginated movement restriction device 110 can act as a mechanical stop against the thoracic diaphragm 30 when the esophagus 20 is moving upwards through the esophageal hiatus 32. In order to protect the tissue of the esophagus 20 from being damaged by the movement restriction device 110, the movement restriction device 110 is invaginated such that a part of the fundus is arranged between the movement restriction device 110 and the outside of the esophagus 20.

In the embodiment shown in FIG. 40AA, the movement restriction device 110 comprises a first part or segment 111*a*, being a first distinct separable piece, a second segment 111*b* being a second distinct separable piece, and a first distance element 151 in the form of a mutually engaging structure comprising two pins which are configured to be placed at a distance from each other and which are integrated in, and protruding from, the first segment 111*a* and entering two recesses (shown as 114 in FIGS. 40AB and 40AC) in the form of conical recesses 114 in the second part or segment 111*b*. When the first and second parts or segments 111*a*, 111*b* are connected to each other, the first and second segments 111*a*, 111*b* forms the functional movement restriction device 110 capable of hindering movement of the cardiac sphincter 26. In the embodiment shown in FIG. 40AA, the movement restriction device 110 is completely invaginated by the fundus wall 14, meaning that the movement restriction device 110 is placed in a pouch created from stomach wall and that the stomach wall 14 is sutured or stapled stomach tissue to stomach tissue such that the movement restriction device 110 is completely encapsulated by the stomach wall of the fundus. Attaching stomach tissue to stomach tissue allows the stomach tissue to grow together such that the movement restriction device 110 can be fixated in its invaginated position even if the suture or staplers are resorbed or repelled by the body. When the movement restriction device 110 is in constant contact with the tissue of the stomach 10, there is always a risk of erosive contact between the movement restriction device 110 and the human tissue which may create wear, irritation, and inflammation of the tissue wall. This may consequently lead to the movement restriction device 110 migrating through the tissue wall of the stomach 10 and inadvertently becoming located inside of the stomach 10 of the patient. In the embodiment shown in FIG. 40AA, the first and second parts or segments 111*a*, 111*b* are capable of disconnecting from each other such that the movement restriction device 110 falls apart, if at least one of the first and second part or segment 111*a*, 111*b* migrates into the stomach 10. As each of the first and second part or segment 111*a*, 111*b* are relatively small, the first and second part or segment 111*a*, 111*b* can individually pass through the gastro-intestinal tract without creating a risk of the patient getting ileus.

FIG. 40AB shows the movement restriction device 110 before the first and second parts or segments 111*a*, 111*b* are connected to each other showing that the distance element 151, in the form of the two pins, is integrate in the first part or segment 111*a* and configured to create a space S between the first and second parts or segments 111*a*, 111*b*. The space S is configured to allow in-growth of fibrotic tissue between portions of the first and second parts or segments 111*a*, 111*b* for aiding in the fixation of the first and second segments 111*a*, 111*b* to the body of the patient. In the embodiment shown in FIGS. 40AA-40AC, the first and second segments 111*a*, 111*b* are two hemispheres each having a flat surface 111*as*, 111*bs*. The two hemispheres substantially form a spherical functional movement restriction device 110 when connected. The flat surface 111*as* of the first segment 111*a* is configured to be mounted opposite to the flat surface 111*bs* of the second segment 111*b*, such that the plane of the flat surface 111*as* of the first segment 111*a* is parallel to the plane of the flat surface 111*bs* of the second segment 111*b*, when the first and second segments 111*a*, 111*b* are connected to form a functional movement restriction device 110.

FIG. 40AC shows the movement restriction device 110 in the connected state, when the first and second segments 111*a*, 111*b* forms the functional movement restriction device 110. When the functional movement restriction device 110 is in the connected state, a first line segment LS1 of a first straight line L1 is bounded by a first point P1 on the first surface 111*as* and a second point P2 on the second surface 111*bs*. A second line segment LS2 of a second straight line L2 is bounded by a third point P3 on the first surface 111*as* and a fourth point P4 on the second surface 111*bs*. The first line segment LS1 of the first straight line L1 is more than 1 mm, and the second line segment LS2 of the second straight line L2 is more than 1 mm. More preferably, the first line segment LS1 of the first straight line L1 is more than 2 mm, and the second line segment LS2 of the second straight line L2 is more than 2 mm. The first straight line L1 is parallel to the second straight line L2. The first and second straight lines L1, L2 intersect a third straight line L3, which also intersects the center of gravity me of the functional movement restriction device 110. A distance D1 between the first and second straight lines L1, L2 is more than 2 mm for allowing in-growth of fibrotic tissue for aiding in the fixation of the segments 111*a*, 111*b* of the functional movement restriction device 110 to the stomach wall.

In the embodiment shown in FIGS. 40AA-40AC, the outer boundary of the functional movement restriction device 110 forms a sphere having a first cross-sectional distance CD1 being parallel to a second cross-sectional distance CD2, and wherein the first and second cross-sectional distances CD1, CD2 have the same length. In the embodiment shown in FIGS. 40AA-40AC, the first and second cross-sectional distances CD1, CD2 have a length in the range 10 mm-35 mm, preferably in the range 15 mm-30 mm and more preferably in the range 15 mm-25 mm, such that the functional movement restriction device 110 is configured to be completely invaginated by the tissue wall 14 of the fundus of the stomach 10, or stomach fundus wall 14. The functional movement restriction device 110 needs to have a size large enough to act as a mechanical stop against the thoracic diaphragm 30. Preferably, the functional movement restriction device 110 have a size and shape sufficient to hinder the fundus wall portion 14 from sliding through the esophageal hiatus 32 into the thoracic diaphragm 30 together with the cardiac sphincter 26. Further, the functional movement restriction device 110 may have a size and shape that allows it to be invaginated by the fundus of the stomach 10 without causing an unjustified reduction of the total volume of the stomach cavity, such that the food passageway is left substantially intact and unaffected. Thus, the functional implantable medical device 100 disclosed herein advantageously allows the symptoms of reflux disease to be addressed while reducing the risk for compressing the food passageway.

In the embodiment shown in FIGS. 40AA-40AC, the distance between the first and second flat surface 111*as*, 111*bs* is more than 1 mm, preferably in the range 1 mm-7 mm, more preferably in the range 2 mm-5 mm. The distance creates a recess in the spherical body making up the functional implantable medical device 100 having a width WT in the range 1 mm-7 mm, more preferably in the range 2 mm-5 mm. The depth DP of the recess in the view of FIG. 40AC is exceeding 2 times the width WT. More specifically, the depth DP of the recess in the view of FIG. 40AC is in the range 2 mm-14 mm, preferably in the range 3 mm-10 mm, and more preferably in the range 4 mm-8 mm. As such, the total volume of the space S is in the range 45 mm3-5000 $mm^3$, preferably in the range 100 $mm^3$-2000 $mm^3$ and more preferably in the range 200 $mm^2$-1000 $mm^2$.

In the embodiment shown in FIGS. 40AA-40AC, and for the purpose of facilitating invagination and reducing the risk for damage to the tissue of the fundus wall portion 14, the functional movement restriction device 110 has a substantially smooth outer surface. In any event and in most embodiments described herein, corners, edges, joints, or seams should be rounded so as not to damage or irritate the tissue against which the functional movement restriction device 110 rests when implanted. In the embodiment shown in FIGS. 40AA-40AC, the functional movement restriction device 110 has a rounded shape conforming to a sphere.

However, in alternative embodiments the implantable movement restriction device 110 may have a rounded shape conforming to a spheroid, or an egg-shape.

The largest outer circumference of the functional movement restriction device 110 of the embodiment of FIGS. 40AA-40AC may be in the range 35 mm-100 mm, or in the range 50 mm-80 mm, or in the range 50 mm-70 mm. It will however be appreciated that the dimensions of the functional movement restriction device 110 may vary according to the anatomy of the actual individual into which the functional movement restriction device 110 is to be implanted. The size and shape of the functional movement restriction device 110 may be adapted to the individual patient to allow for the invagination to act as a mechanical stop as outlined above and thereby have an effect on reflux disease.

FIG. 40AD shows an alternative embodiment of the movement restriction device 110, similar to the movement restriction device shown in FIGS. 40AA-40AC, but with the difference that in the embodiment shown in FIG. 40AD, the first and second parts 111*a*, 111*b* have shapes corresponding to hemiellipsoids, such that the boundary of the functional movement restriction device 110 forms an ellipsoid when the first and second parts are connected, in which the first cross-sectional distance CD1 is longer than the second cross-sectional distance CD2. More specifically, in the embodiment shown in FIG. 40AD, the first cross-sectional distance CD1 is more than 1.2 times as long as the second cross-sectional distance CD2, or more specifically the first cross-sectional distance CD1 is more than 1.4 times as long as the second cross-sectional distance CD2. In the embodiment shown in FIG. 40AD, the first cross-sectional distance CD1 is the longest length of the movement restriction device 110, and the second cross-sectional distance CD2 is the widest width.

FIG. 40AE shows a detailed view of the portion of the distance element 151 entering the recess 114 in the second segment or part 111*b*. In the embodiment shown in FIGS. 40AA-40AE, the distance element 151 has a tapered end portion which is tapered with an angle α against the length axis 151LA of the distance element 151. The recess is conical, i.e. has a tapered shape with an angle β against the length axis 151LA of the distance element 151 in the direction of the length axis 151LA. In the embodiment shown in FIG. 40AE, angle β is larger than the angle α, more specifically more than 3° larger than the angle α, even more specifically more than 5° larger than the angle α, and even more specifically more than 7° larger than the angle α. The difference in angles α and β reduces the contacting surface between the distance element 151 and the recess 114 which reduces adherence between the surfaces of the distance element 151 and the surfaces of the recess 114.

In the embodiment shown in FIG. 40AF, the end portion of the distance element is rounded, i.e. have a curvature, such that the rounded surface engages the conical recess 114, which reduces the contacting surface between the distance element 151 and the recess 114 which reduces adherence between the surfaces of the distance element 151 and the surfaces of the recess 114. In the embodiment shown in FIG. 40AF, the surface of the portion of the distance element 151 having the curvature abuts the surface of the recess 114 over a length being less than half of the length of the angled surface of the distance element 151, when the distance element 151 has been positioned in the recess 114. More specifically, the surface of the portion of the distance element 151 having the curvature abuts the surface of the recess 114 over a length being less than one third of the length of the angled surface of the distance element 151, when the portion of the distance element 151 is inserted into the recess 114.

In the embodiment shown in FIG. 40AF, the portion of the distance element having the curvature abuts the surface of the recess 114 over a length CB being less than half of the depth CA of the recess 114, measured in a direction coinciding with the direction of the length axis 151LA of the distance element 151, when the portion of the first distance element is inserted into the recess.

FIG. 40AG shows an alternative embodiment of how the contacting surface between the distance element 151 and the recess 114 can be reduced. In the embodiment shown in FIG. 40AG, the portion of the distance element to be inserted in the recess 114 is rounded, or hemispherical, with a first radius 151*r*, whereas the recess is a hemispherical recess with a radius 114*r*. The radius 114*r* of the recess 114 is larger than the radius 151*r* of the distance element 151, which reduces the contacting surface between the distance element and the recess when the distance element 151 is positioned in the recess 114. More specifically, in the embodiment shown in FIG. 40AG, the hemispherical surface of the distance element 151 contacts the hemispherical surface of the recess 114 over less than 50% of the area of the hemispherical surface of the recess, of more specifically less than 60% of the area of the hemispherical surface, and even more specifically over less than 70% of the area of the hemispherical surface of the recess.

FIG. 40AH shows an alternative embodiment in which the recess 114 and the rounded portion of the distance element 151 have the shape of a hemi-ellipsoid, i.e. having two perpendicular radii 114*r*', 114*r*", 151*r*', 151*r*" being different. In the embodiment shown in FIG. 40AH the recess 114 have a first radius 114*r*' being equal to a first radius 151*r*' of the distance element 151, and a second radius 114*r*" being larger than a second radius 151*r*" of the distance element 151. As such, the two equal radii 114*r*', 151*r*' provides a long contacting surface providing stabilization, while the two different radii 151*r*'. 151*r*" provides a short contacting surface for reducing adhesion.

Figure 40B:
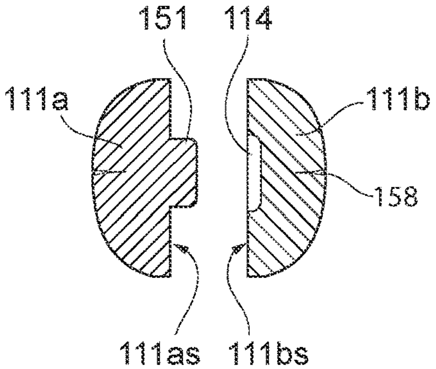
FIGS. 40BA-40ME are schematic views of an apparatuses for treating reflux disease in further detail.
Figure 40B:
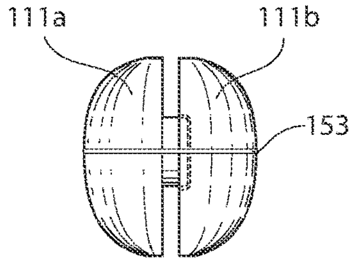
Figure 40B:
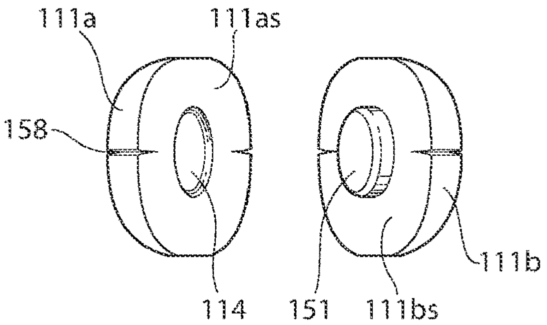

FIG. 40BA shows an alternative embodiment of the movement restriction device 110 in which the distance element 151 is integrated in the first segment 111*a* as a protruding cylindrical distance element 151. More specifically, in the embodiment shown in FIG. 40BA, the distance element 151 is materially integrated in the same piece of material as the first part or segment 111*a*, being manufactured e.g. by means of casting. In the embodiment shown in FIG. 40BA, the material of the first segment with the integrated distance element 151 is an clastic biocompatible silicone-based material. In the embodiment shown in FIG. 40BA, the second segment 111*b* comprises a recess 114 configured to receive a portion of the distance element 151 such that the portion of the distance element 151 placed in the recess 114 prevents the shifting of the first segment 111*a* relative to the second segment 111*b* in at least a direction parallel to the planes of the flat surfaces 111*as*, 111*bs* of the first and second segments 111*a*, 111*b*. In the embodiment shown in FIG. 40BA, the distance element 151, in the form of the protruding cylinder, protrudes 3 mm and the recess in the second segment 111*b* is cylindrical and has a depth of 1 mm, resulting in that the distance element 151 creates a distance between the flat surface 111*as* of the first segment 111*a* and the flat surface 111*bs* of the second segment 111*b* of 2 mm, which is sufficient to enable the in-growth of fibrotic tissue in the space S created between the flat surface 111*as* of the first segment 111*a* and the flat surface 111*bs* of the second segment 111*b*. In alternative embodiments, the integrated distance element may protrude 1.5 mm-10 mm and the recess may have a depth in the range 0.5 mm-4 mm, such that the distance between the first and second flat surfaces 111*as*, 111*bs* of the first and second segments 111*a*, 111*b* is in the range 1 mm-9.5 mm, preferably in the range 2 mm-5 mm.

FIG. 40BB shows the embodiment of FIG. 40BA when mounted. The two parts or segments 111*a*-111*b* are secured to each other by means of a wire 153 in the form of a resorbable suture 153 running in a groove 158 encircling the body of the movement restriction device 110.

FIG. 40BC shows an embodiment of the implantable medical device 100 similar to the embodiment shown in FIGS. 40BA and 40BB, with the difference that in the protruding distance element 151 has an oval cross-section in a plane parallel to the planes of the flat surfaces 111*as*, 111*bs* of the first and second segments 111*a*, 111*b*. The second segment 111*b* has a recess 114 having a corresponding oval cross-section, such that the shape of the distance element 151 and the recess 114 prevents relative rotation between the first and second part or segment 111*a*, 111*b*.

Figure 40C:
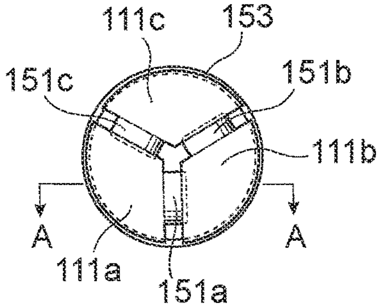
FIGS. 40N-40N" shows a schematic view of an implanted apparated for treating reflux disease, when the movement restriction device of the apparatus migrates through the stomach wall in its invaginated position.
FIGS. 40O-40SE'" shows schematic views of implantable medical devices for the treatment of reflux and/or obesity.
FIGS. 40TA-40TC schematically shows the insertion of parts of implantable medical devices shown in FIGS. 40SA-40SE'" for the treatment of reflux and/or obesity, as well as an instrument for use in such insertion.
FIGS. 40UA-40UI' schematically shows alternative shapes of implantable medical devices for the treatment of reflux and/or obesity and shapes of parts of implantable medical devices for the treatment of reflux and/or obesity.
Figure 40C:
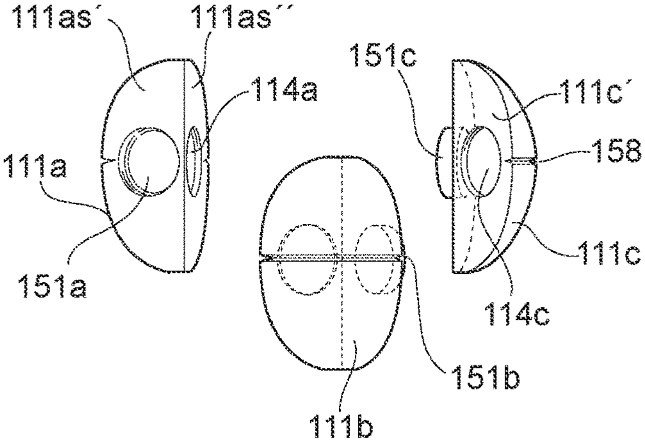
Figure 40C:
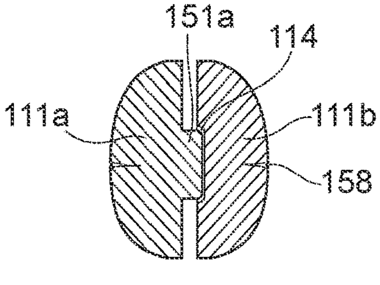

FIGS. 40CA-40CC shows an alternative embodiment of the movement restriction device 110, in which the movement restriction device 110 comprises a first, second and third segment or part 111*a*, 111*b*, 111*c*, each having the shape of an ellipsoid wedge. The first, second and third segments or parts 111*a*-111*c* are configured to be connected to each other for forming the movement restriction device 110. In the embodiment shown in FIGS. 40CA-40CC, each segment comprises an integrated distance element 151*a*, 151*b*, 151*c* in the form of a protruding cylindrical distance element and each segment comprises a recess 114*a*, 114*b*, 114*c* configured to receive a portion of the integrated distance elements 151*a*, 151*b*, 151*c* of the other segments 111*a*, 111*b*, 111*c*. The first segment 111*a* comprises a first integrated distance element 151*a*, protruding from a first flat surface 111*as*', configured to create a distance between the first part or segment 111*a* and the second part or segment 111*b*, the second segment 111*b* comprises a second integrated distance element 151*b*, protruding from a third flat surface 111*bs*', configured to create a distance between the second part or segment 111*b* and the third part or segment 111*c*, and the third part or segment 111*c* comprises a third integrated distance element 151*c*, protruding from a fifth flat surface 111*cs*', configured to create a distance between the third second segment 111*c* and the first segment 111*a*. The first segment 111*a* comprises a first recess 114*a*, in a second flat surface 111*as*", configured to receive a portion of the third distance element 151*c*, the second segment 111*b* comprises a second recess 114*b*, in a fourth flat surface 111*bs*", configured to receive a portion of the first distance element 151*a*, and the third segment 111*c* comprises a third recess 114*c*, in a sixth flat surface 111*cs*", configured to receive a portion of the second distance element 151*b*. The insertion of the distance elements 151*a*-151*c* in the respective recesses 114A-114C prevents the shifting of the segments 111*a*-111*c* relative to each other in a direction parallel to the planes of the flat surfaces 111*as*', 111*as*", 111*as*', 111*bs*", 111*cs*', 111*cs*" of the first and second segments 111*a*, 111*b*.

When mounted, the three segments 111*a*-111*c* are secured to each other by means of a wire 153 in the form of a resorbable suture 153 running in a groove 158 encircling the body of the movement restriction device 110.

Figure 40D:
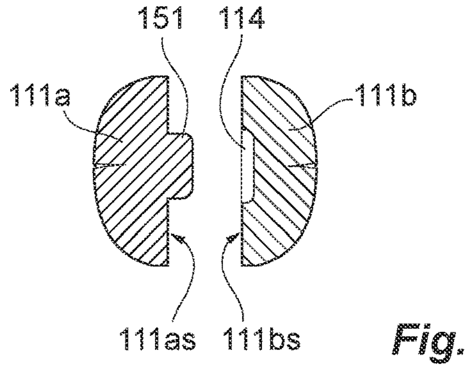
Figure 40D:
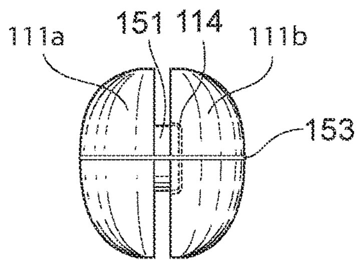
Figure 40D:
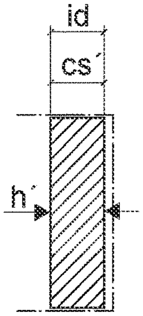
Figure 40D:
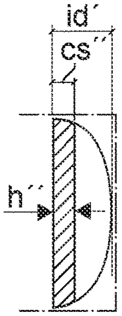
Figure 40D:
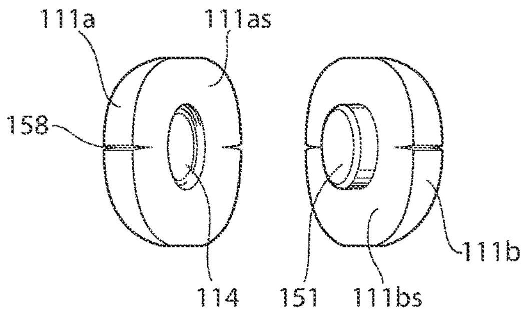

FIGS. 40DA-40DD shows an alternative embodiment of the movement restriction device 110, similar to that shown in FIGS. 40CA-40CC, with the difference that in the embodiment of FIGS. 40DA-40DD, the distance element 151 is rounded to reduce the contact surface between the distance element 151 and the recess 114 to facilitate disengagement between the distance element 151 and the recess 114. The first and second part or segment 111*a*, 111*b* of the movement restriction device 110, is in the embodiment shown in FIGS. 40DA-40DD made from a biocompatible elastic polymer material, such as a silicone or polyurethane based polymer material. Such biocompatible elastic polymer materials have a tendency to adhere to each other when placed in contact, especially over long periods of time. Also, the in-growth of fibrotic tissue and the infusion of bodily fluids into the movement restriction device further create adhesion between contacting surfaces of the parts or segments of the movement restriction device. In the embodiment shown in FIGS. 40DA, 40DB and 40DD, the contact area between the distance element 151 and the recess 114 has been reduced by the rounding of the outermost portion of the distance element 151, such as shown in further detail in FIG. 40DC". In 40DC', the cylindrical distance element 151 is shown in further detail, and in FIG. 40DC", the distance element 151 with the rounded outermost portion is shown in further detail. When the distance element is a cylindrical distance element 151, such as in FIG. 40DC', the height h' of the contacting surface cs' is equal to the insertion distance id, i.e., the distance that the cylindrical distance element 151 is inserted into the recess. However, in the rounded embodiment shown in FIG. 40DC", the contacting surface cs" has been reduced such that the height h" of the contacting surface cs" is less than 60% of the height h' of the contacting surface cs' of a cylindrical distance element 151 inserted the same distance id. More specifically, the contacting surface cs" has been reduced such that the height h" of the contacting surface cs" is less than 40% of the height h' of the contacting surface cs' of a cylindrical distance element 151 inserted the same distance id, and even more specifically, the contacting surface cs" has been reduced such that the height h" of the contacting surface cs" is less than 20% of the height h' of the contacting surface cs' of a cylindrical distance element 151 inserted the same distance id. As such, the area of the contacting surface has been reduced such that the contacting surface cs" of the rounded version is less than 60% of the area of the contacting surface cs' of the cylindrical version, more specifically less than 40% of the area of the contacting surface cs' of the cylindrical version, and even more specifically, less than 20% of the area of the contacting surface cs' of the cylindrical version.

Figure 40E:
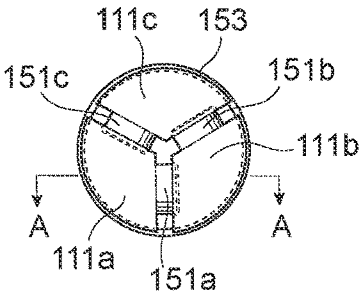
Figure 40E:
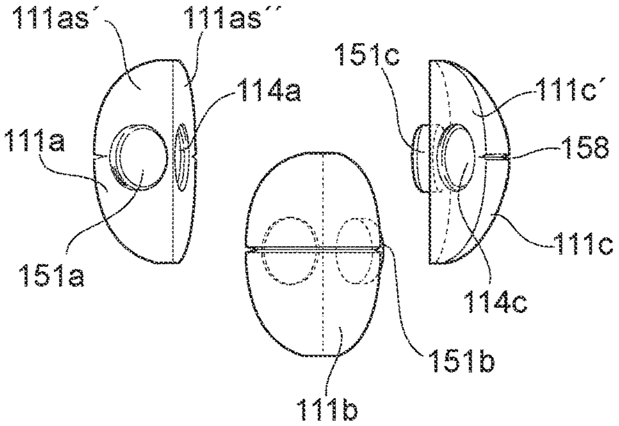
Figure 40E:
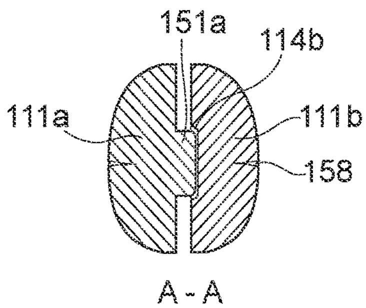

FIGS. 40EA-40EC shows an alternative embodiment of the movement restriction device 110, similar to that shown in FIGS. 40CA-40CC, with the difference that in the embodiment of FIGS. 40EA-40EC, the distance elements 151*a*-151*c* are rounded, in the same way as described with reference to FIGS. 40DA-40DD, to reduce the contact surface between the distance elements 151*a*-151*c* and the recesses 114*a*-114*c*, to facilitate disengagement between the distance elements 151*a*-151*c* and the recesses 114*a*-114*c*.

Figure 40F:
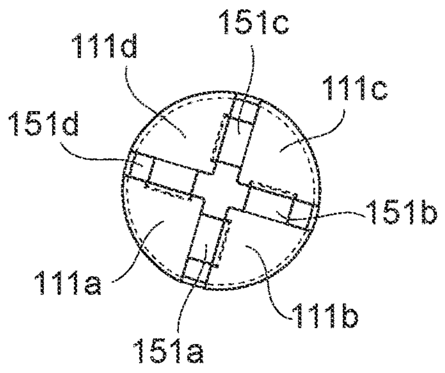
Figure 40F:
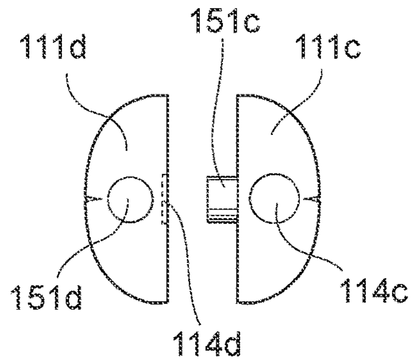
Figure 40F:
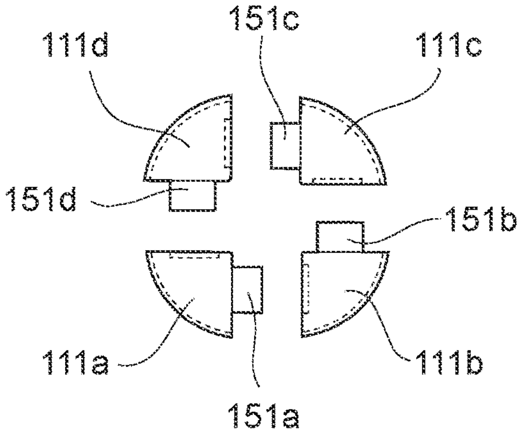
Figure 40F:
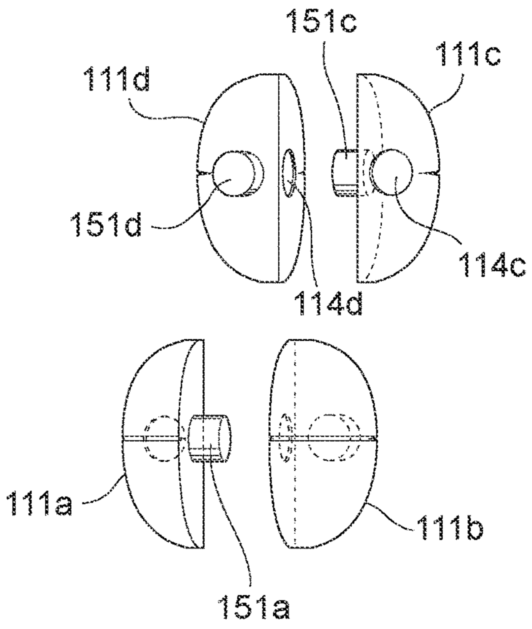

FIGS. 40FA-40FD shows an alternative embodiment of the movement restriction device 110, similar to that shown in FIGS. 40CA-40CC, with the difference that in the embodiment of FIGS. 40FA-40FD, the movement restriction device 110 comprises a first, second, third and fourth part or segment 111*a*, 111*b*, 111*c*, 111*d*. The first, second, third and fourth parts or segments 111*a*-111*d* each have the shape of an ellipsoid wedge, or more specifically, a spherical wedge, and are configured to be connected to each other for forming the movement restriction device 110 having a spherical boundary. In the embodiment shown in FIGS.

40FA-40FC, just as in the embodiment shown in FIGS. 40CA-40CC, each segment 111*a*-111*d* comprises an integrated distance element 151*a*, 151*b*, 151*c*, 151*d* in the form of a protruding cylindrical distance element and each segment comprises a recess 114*a*, 114*b*, 114*c*, 114*d* configured to receive a portion of the integrated distance elements 151*a*, 151*b*, 151*c*, 151*d* of the other segments 111*a*, 111*b*, 111*c*, 111*d*.

Figure 40G:
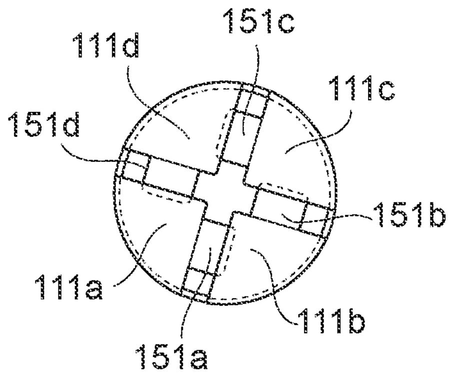
Figure 40G:
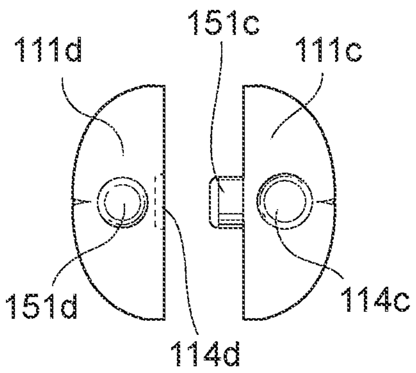
Figure 40G:
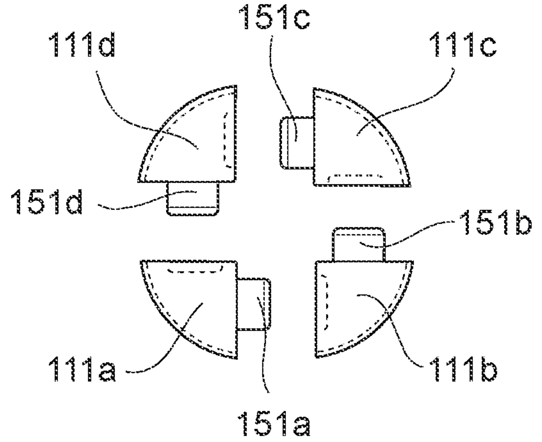
Figure 40G:
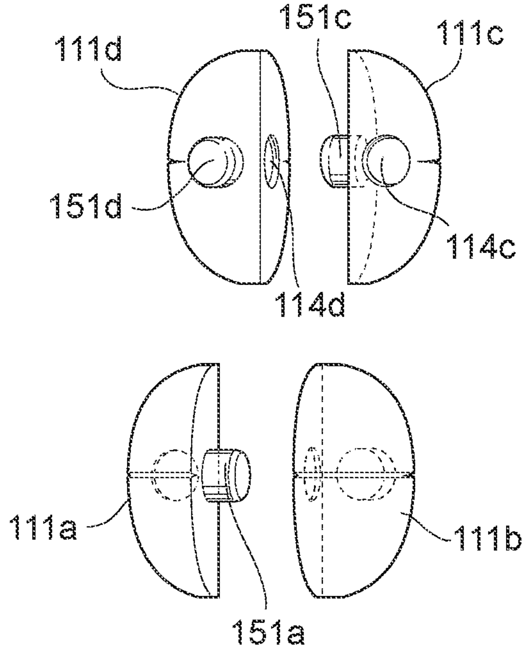

FIGS. 40GA-40GC shows an alternative embodiment of the movement restriction device 110, similar to that shown in FIGS. 40FA-40FC, with the difference that in the embodiment of FIGS. 40GA-40GC, the distance elements 151*a*-151*d* are rounded, in the same way as described with reference to FIGS. 40DA-40DD, to reduce the contact surface between the distance elements 151*a*-151*d* and the recesses 114*a*-114*d*, to facilitate disengagement between the distance elements 151*a*-151*d* and the recesses 114*a*-114*d*.

Figure 40H:
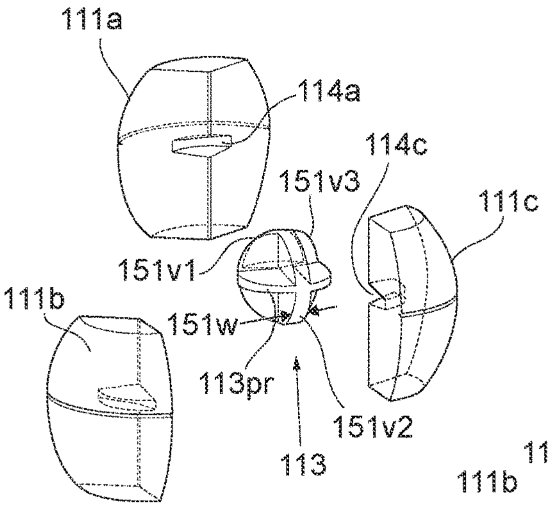
Figure 40H:
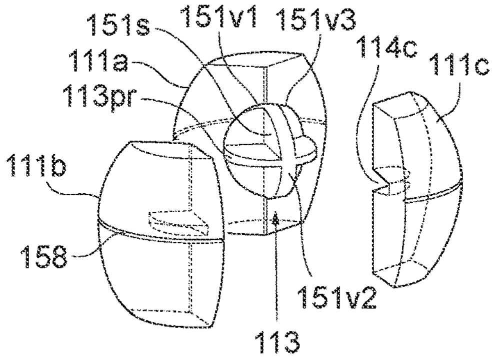
Figure 40H:
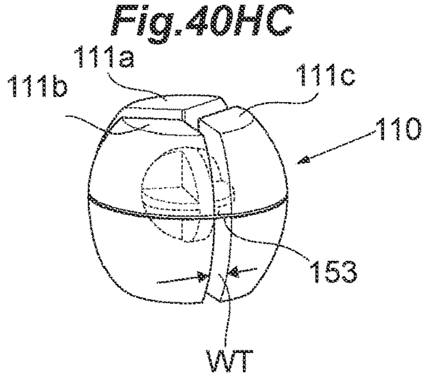

FIGS. 40HA-40HC shows an embodiment of the movement restriction device 110 in which the movement restriction device 110 comprises three segments 111*a*, 111*b*, 111*c*, just as in the embodiment shown in FIGS. 40CA-40CC, each of the segments 111*a*-111*c* has two flat surfaces configured to be positioned opposite corresponding flat surfaces of another segment when the movement restriction device 110 is mounted to a functional movement restriction device 110. In the embodiment shown in FIGS. 40HA-40HC, each of the parts or segments 111*a*-111*c* have the shape of a truncated ellipsoid wedge, or more specifically a truncated spherical wedge, such that the boundary of the parts 111*a*-111*c* forms a truncated sphere when connected. In the embodiment shown in FIGS. 40HA-40HC, the distance elements are portions of a separate, disconnectable centrally placed distance part 113 having the shape of a sphere from which six tetrahedrons with spherical base have been removed, leaving a sphere with six tetrahedrical recesses. The equatorial rim 113*pr* of the centrally placed distance part 113 is configured to enter the recesses 114*a*-114*c* of the three segments 111*a*-111*a* to assist in the formation of a functional movement restriction device 110 from the three segments 111*a*-111*c*, as the positioning of the equatorial rim 113*pr* in the recesses 114*a*-114*c* prevents the shifting of the segments 111*a*-111*c* relative to each other and relative to the centrally placed distance part 113. The vertically extending rims 151*v*1, 151*v*2, 151*v*3 are configured to be placed between the segments 111*a*-111*c*, for creating the distance between the segments 111*a*-111*c*. In the embodiment shown in FIGS. 40HA-40HC, flat surfaces of the vertically extending rims 151*v*1, 151*v*2, 151*v*3 (such as the flat surface denoted 151*s*) are configured to engage and abut the flat surfaces of the segments 111*a*-111*c*, when the movement restriction device 110 is in its mounted functional state. As such, the width 151*w* of the vertically extending rims 151*v*1, 151*v*2, 151*v*3 create the distance between the segments or parts 111*a*-111*c*, and the width of the distance WT thus corresponds to the width 151*w* of the vertically extending rims 151*v*1, 151*v*2, 151*v*3. In the embodiment shown in FIGS. 40HA-40HC, the vertically extending rims 151*v*1, 151*v*2, 151*v*3 have a width 151*w* of 2 mm for creating a 2 mm distance between the segments 111*a*-111*c* for creating three equidistantly placed recesses or grooves being 2 mm wide and about 3 mm deep running from the uppermost to the lowermost point of the functional movement restriction device 110 forming a space S for allowing the in-growth of fibrotic tissue aiding the fixation of the respective segment 111*a*-111*c* to the stomach of the patient. Preferably, the grooves are in the range 1 mm-10 mm wide and 1 mm-12 mm deep, more preferably in the range 2 mm-7 mm wide and 2 mm-8 mm deep, even more preferably in the range 2 mm-5 mm wide and 2 mm-5 mm deep.

FIG. 40HB shows the assembly of the functional movement restriction device 110 by the assembly of the three segments 111*a*-111*c* with the centrally located distance part 113.

FIG. 40HC shows the assembled functional movement restriction device 110 when a wire 153 in the form of a resorbable suture 153 has been placed encircling the functional movement restriction device 110 for holding the parts or segments 111*a*-111*c* together during implantation and before the assembled functional movement restriction device 110 has been properly secured by the in-growth of fibrotic tissue around and into the spaces formed in the assembled functional movement restriction device 110. The wire is held in place by being placed in an equatorial groove 158 configured to fixate the wire 153.

In the embodiment shown in FIGS. 40HA-40HC, the centrally located distance part 113 is created from the same biocompatible silicone material as the three segments 111*a*-111*c*. However, in alternative embodiments, the distance element may be made from another biocompatible material such as a less elastic biocompatible silicone material or another biocompatible polymer material such as polyurethane.

Figure 40I:
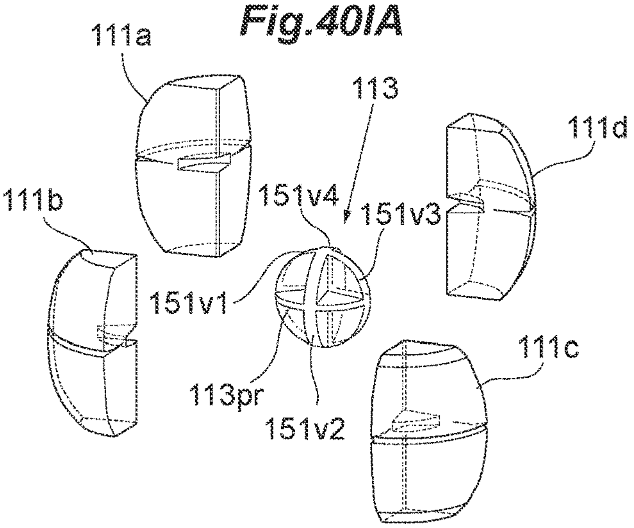
Figure 40I:
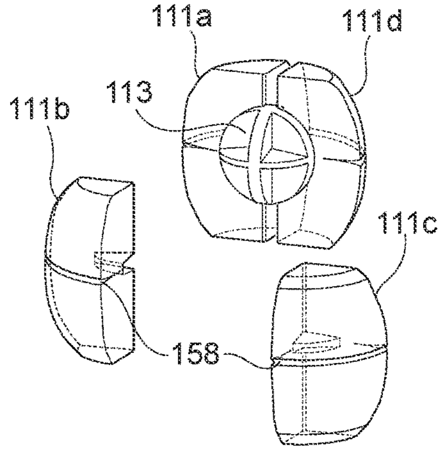
Figure 40I:
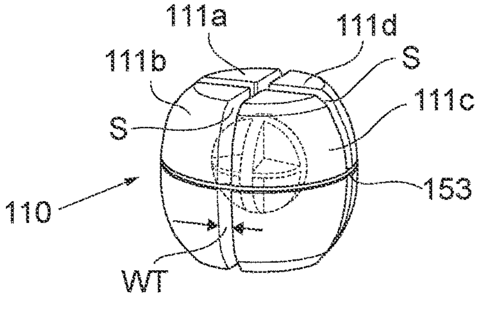

FIGS. 40IA-40IC shows an alternative embodiment of the movement restriction device 110, similar to that shown in FIGS. 40HA-40HC, with the difference that in the embodiment of FIGS. 40IA-40IC, the movement restriction device 110 comprises a first, second, third and fourth segment 111*a*, 111*b*, 111*c*, 111*d*. The first, second, third and fourth segments 111*a*-111*d* are in the same way as in FIGS. 40HA-40HC configured to be connected to a centrally placed part 113 which thus connects the segments 111*a*-111*d* to each other for forming the functional movement restriction device 110. In the embodiment shown in FIGS. 40IA-40IC, the centrally placed part 113 has the shape of a sphere from which eight tetrahedrons with spherical bases have been removed, leaving a sphere with eight tetrahedrical recesses, leaving the material of the centrally placed distance part 113 forming a plus-shape in the six plane views. In the embodiment shown in FIGS. 40IA-40IC, the four vertically extending rims 151*v*1-151*v*4 forms the distance elements configured to engage and abut the opposing flat surfaces of the segments 111*a*-111*d* for creating the distance between the segments 111*a*-111*d* for creating four equidistantly placed recesses or grooves positioned with right angles relative to each other and being about 2 mm wide and about 3 mm deep running from the uppermost to the lowermost point of the functional movement restriction device 110 forming a space S for allowing the in-growth of fibrotic tissue aiding the fixation of the respective segment 111*a*-111*d* to the stomach of the patient. Preferably, the grooves are in the range 1 mm-10 mm wide and 1 mm-12 mm deep, more preferably in the range 2 mm-7 mm wide and 2 mm-8 mm deep, even more preferably in the range 2 mm-5 mm wide and 2 mm-5 mm deep.

FIG. 40IB shows the assembly of the functional movement restriction device 110 by the assembly of the four segments 111*a*-111*d* with the centrally located distance part 113. FIG. 40IC shows the assembled functional movement restriction device 110 when a wire 153 in the form of a resorbable suture 153 has been placed in the equatorial groove 158 configured to fixate the wire 153.

Figure 40J:
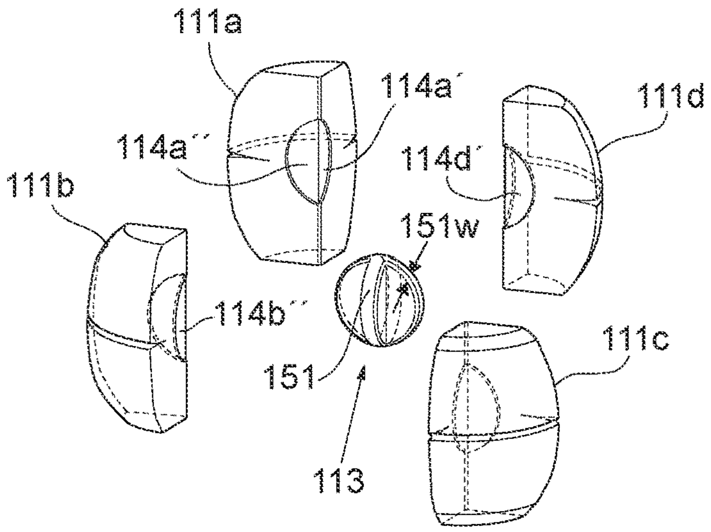
Figure 40J:
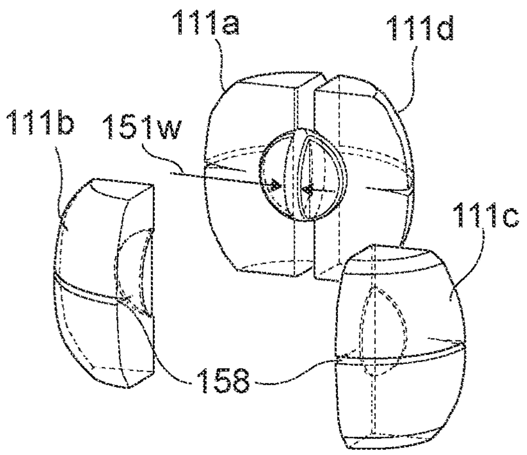
Figure 40J:
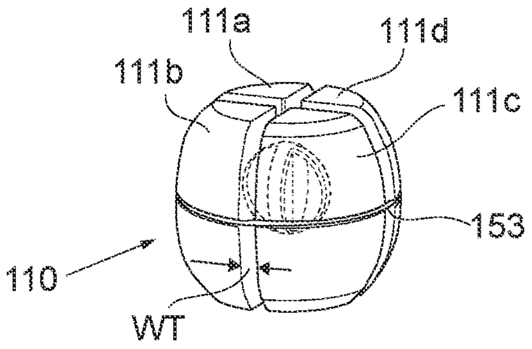

FIGS. 40JA-40JC shows an alternative embodiment of the movement restriction device 110, similar to that shown in FIGS. 40IA-40IC, with the difference that in the embodiment of FIGS. 40JA-40JC, the centrally placed distance part 113 lacks the equatorial rim (113*pr*). Instead, the opposing flat surfaces of the segments 111*a*-111*d* each comprise semi-circular recesses 114*a*'-114*d*" configured to receive portions of the vertically extending rims 151*v*1, 151*v*2, 151*v*3, 151*v*4, such that a portion of the vertically extending rims 151*v*1-151*v*4 are used for preventing the shifting of the segments 111*a*-111*d* relative to each other in a direction parallel to the planes of the opposing flat surfaces of the segments 111*a*-111*d*. The remainder of the width 151*w* of the vertically extending rims 151*v*1-151*v*4 are used for creating the distance between the segments 111*a*-111*d*, just as in the embodiment described with reference to FIGS. 40IA-40IC. In the embodiment shown in FIGS. 40JA-40JC, the centrally placed distance part 113 has the shape of a sphere from which four wedges have been removed, leaving a sphere with four wedge-formed recesses. In the embodiment shown in FIGS. 40JA-40JC, the vertically extending rims 151*v*1, 151*v*2, 151*v*3 have a width 151*w* of 4 mm and the semi-circular recesses 114*a*'-114*d*" have a depth of 1 mm, such that 1 mm+1 mm of the 4 mm width 151*w* is placed in the semi-circular recesses 114*a*'-114*d*" and the rest of the 4 mm width 151*w* creates a 2 mm distance between the segments 111*a*-111*d* for creating four equidistantly placed recesses or grooves positioned with right angles relative to each other and being about 2 mm wide and about 3 mm deep running from the uppermost to the lowermost point of the functional movement restriction device 110 forming a space S for allowing the in-growth of fibrotic tissue aiding the fixation of the respective segment 111*a*-111*d* to the stomach of the patient. Preferably, the grooves are in the range 1 mm-10 mm wide and 1 mm-12 mm deep, more preferably in the range 2 mm-7 mm wide and 2 mm-8 mm deep, even more preferably in the range 2 mm-5 mm wide and 2 mm-5 mm deep.

FIG. 40JB shows the assembly of the functional movement restriction device 110 by the assembly of the four segments 111*a*-111*d* with the centrally placed distance part 113.

FIG. 40JC shows the assembled functional movement restriction device 110 when a wire 153 in the form of a resorbable suture 153 has been placed in the equatorial groove 158 configured to fixate the wire 153.

Figure 40K:
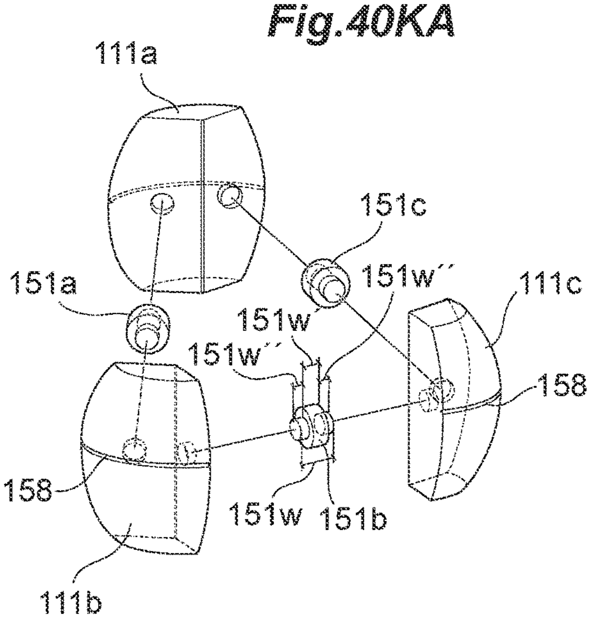
Figure 40K:
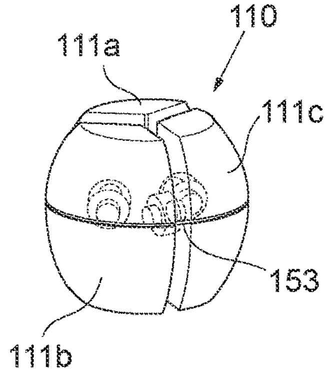

FIGS. 40KA-40KB shows an embodiment of the movement restriction device 110 in which the movement restriction device 110 comprises three segments 111*a*-111*c*, similar to the embodiment shown in FIGS. 40CA-40CC. Just as in the embodiment shown in FIGS. 40CA-40CC each of the segments 111*a*-111*c* has two flat surfaces configured to be positioned opposite corresponding flat surfaces of another segment when the movement restriction device 110 is mounted to a functional movement restriction device 110. In the embodiment shown in FIGS. 40CA-40CC, the distance elements 151*a*-151*c* are separate, disconnectable parts in the form of cylindrical distance elements 151*a*-151*c* having a width 151*w* for creating the distance between the segments 111*a*-111*c*. The cylindrical distance elements 151*a*-151*c* each have a cylindrical central portion having a first width 151*w*' configured to create the distance between the segments 111*a*-111*c*, and cylindrical end portions a smaller diameter and a width 151*w*". The cylindrical end portions are configured to enter cylindrical recesses 114 or blind holes in the opposing flat surfaces for securing and aligning the cylindrical distance elements 151*a*-151*c*. The positioning of the cylindrical end portions in the blind holes 114 prevents the shifting of the segments 111*a*-111*c* relative to each other and relative to the cylindrical distance elements 151*a*-151*c*. In the embodiment shown in FIGS. 40KA-40KB, the cylindrical distance elements 151*a*-151*c* have a total width 151*w* of 4 mm, of which the cylindrical central portions have widths 151*w*' of 2 mm and the cylindrical end portions have widths 151*w*" of 1 mm. As such, 1 mm+1 mm enters the bodies of the segments 111*a*-111*c* while 2 mm creates the 2 mm distance between the segments 111*a*-111*c*, for creating three equidistantly placed recesses or grooves being about 2 mm wide and about 3 mm deep running from the uppermost to the lowermost point of the functional movement restriction device 110 forming a space S for allowing the in-growth of fibrotic tissue aiding the fixation of the respective segment 111*a*-111*c* to the stomach of the patient. Preferably, the grooves are in the range 1 mm-10 mm wide and 1 mm-12 mm deep, more preferably in the range 2 mm-7 mm wide and 2 mm-8 mm deep, even more preferably in the range 2 mm-5 mm wide and 2 mm-5 mm deep.

FIG. 40KB shows the assembled functional movement restriction device 110 when a wire 153 in the form of a resorbable suture 153 has been placed in the equatorial groove 158 configured to fixate the wire 153.

Figure 40L:
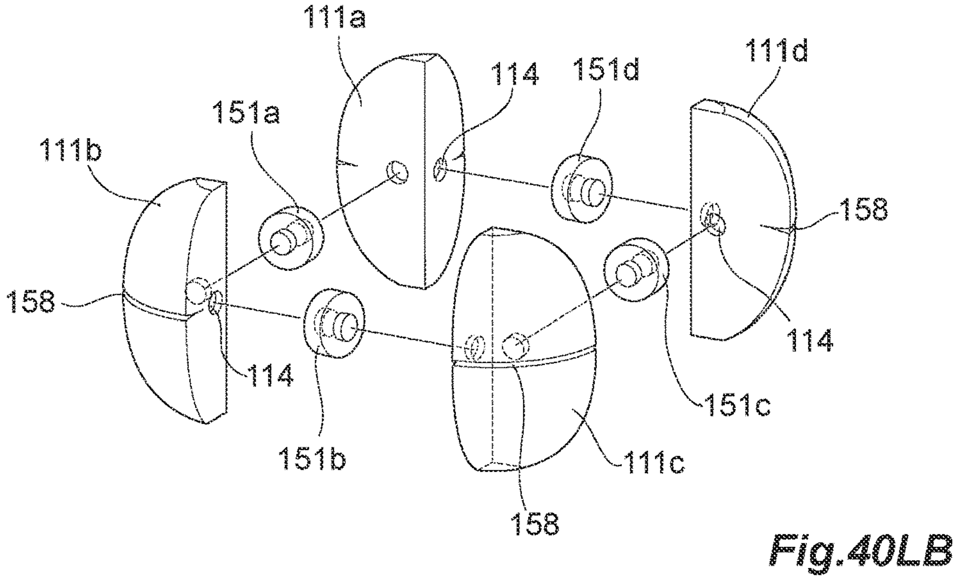
Figure 40L:
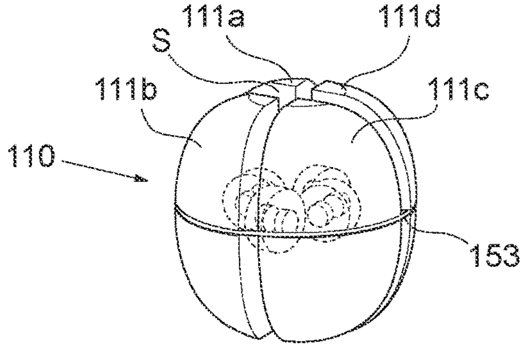

FIGS. 40LA-40LB shows an embodiment of the movement restriction device 110 very similar to the embodiment shown in the embodiment of FIGS. 40KA-40KB, with the difference that in the embodiment shown in FIGS. 40LA-40LB, the movement restriction device 110 comprises a first, second, third and fourth segment or part 111*a*, 111*b*, 111*c*, 111*d*. The four segments or parts 111*a*-111*d* are configured to be connected to each other for forming the movement restriction device 110. In the embodiment shown in FIGS. 40LA-40LB, just as in the embodiment shown in FIGS. 40KA-40KB, each segment 111*a*-111*d* are connected to two other segments, at a distance created by cylindrical distance elements 151*a*-151*d*.

FIG. 40LB shows the assembled functional movement restriction device 110 when a wire 153 in the form of a resorbable suture 153 has been placed in the equatorial groove 158 configured to fixate the wire 153. The assembled functional movement restriction device 110 has four equidistantly placed recesses or grooves positioned with right angles relative to each other and being about 2 mm wide and about 3 mm deep running from the uppermost to the lowermost point of the functional movement restriction device 110 forming a space S for allowing the in-growth of fibrotic tissue aiding the fixation of the respective segment 111*a*-111*d* to the stomach of the patient. Preferably, the grooves are in the range 1 mm-10 mm wide and 1 mm-12 mm deep, more preferably in the range 2 mm-7 mm wide and 2 mm-8 mm deep, even more preferably in the range 2 mm-5 mm wide and 2 mm-5 mm deep.

Figure 40M:
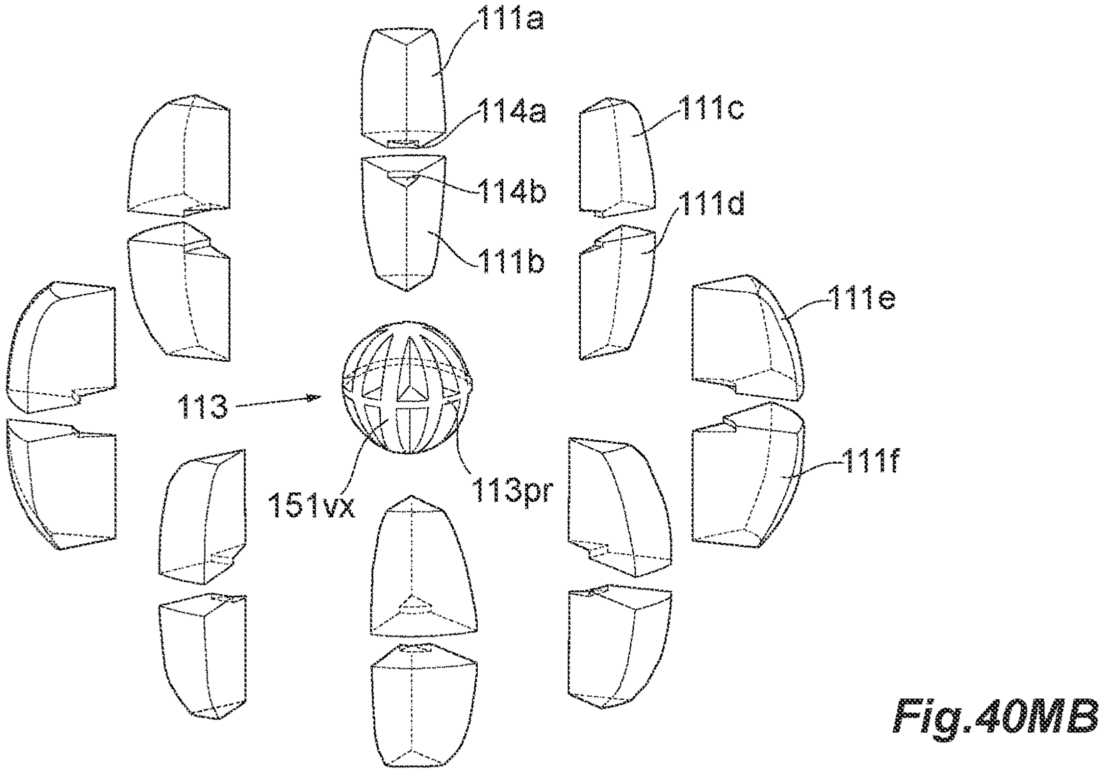
Figure 40M:
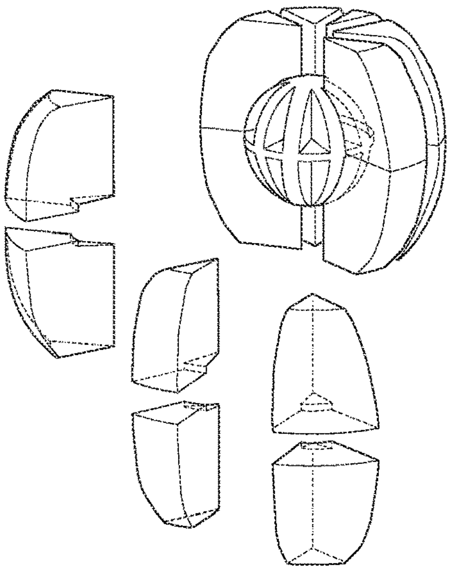
Figure 40M:
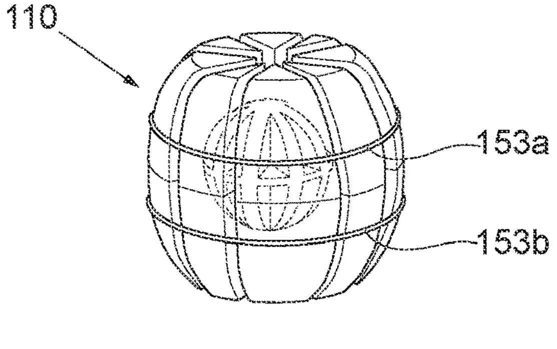
Figure 40M:
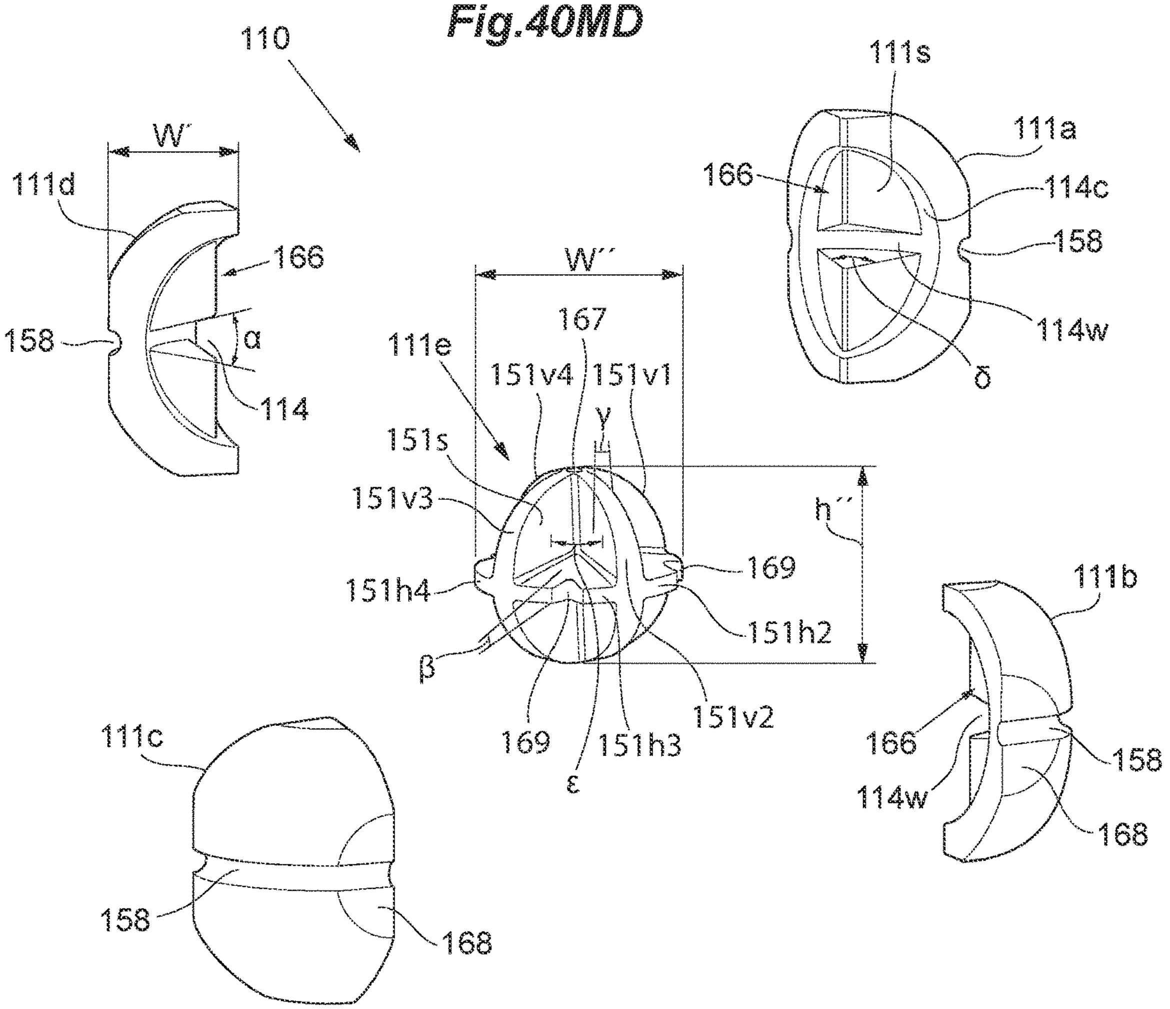
Figure 40M:
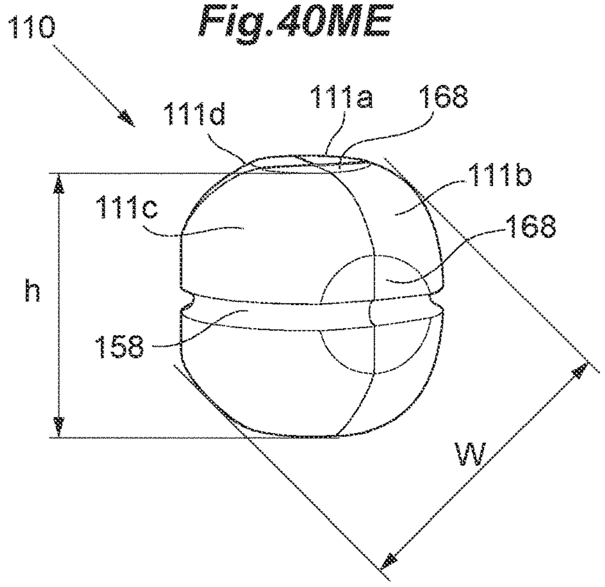

FIGS. 40MA-40MC shows an embodiment of the medical device in which the medical device comprises 16 parts 111*a*-111*p* and a one centrally placed distance part 113 configured to connect each of the 16 parts 111*a*-111*p* to each other at a distance. Each of the segments 111*a*-111*p* has the shape of a portion of a truncated ellipsoid wedge, or more specifically, a truncated hemiellipsoid wedge, or even more specifically, a truncated hemispherical wedge. Each of the segments 111*a*-111*p* has three flat surfaces configured to be positioned opposite corresponding flat surfaces of another segment when the movement restriction device 110 is mounted to a functional movement restriction device 110. Two of the flat surfaces are vertically extending flat surfaces of the wedges configured to be positioned opposing other vertically extending flat surfaces of the wedges, whereas one flat surface is a horizontally extending flat surface configured to be positioned opposite a corresponding horizontally extending flat surface of another part or segment. In the embodiment shown in FIGS. 40MA-40MC, the distance elements are portions of a separate, disconnectable centrally placed distance part 113 having the shape of a sphere in which a plurality of recesses have been made for accommodating a portion of the each of the 16 parts or segments 111*a*-111*p*. The horizontal and vertical rims are configured to be positioned between the 16 parts or segments 111*a*-111*p* and thereby creating distances between the 16 parts or segments 111*a*-111*p*. The width 151*w* of the horizontal and vertical rims create the distances between the segments or parts 111*a*-111*p*, and the width 151*w* of the horizontal and vertical rims thus corresponds to width of the distances created between the parts or segments. In the embodiment shown in FIGS. 40MA-40MC, the horizontal and vertical rims have a width 151*w* of 2 mm for creating a 2 mm distance between the segments 111*a*-111*p*. In the embodiment shown in FIGS. 40MA-40MC, the centrally placed distance part 113 creates eight vertically extending, equidistantly placed recesses or grooves being 2 mm wide and about 3 mm deep running from the uppermost to the lowermost point of the functional movement restriction device 110, and one horizontally extending recess or groove being 2 mm wide and about 3 mm deep running equatorially around the functional movement restriction device 110. The vertical and horizontal recesses or grooves forms spaces S allowing the in-growth of fibrotic tissue aiding the fixation of the respective segment 111*a*-111*c* to the stomach of the patient. Preferably, the grooves are in the range 1 mm-10 mm wide and 1 mm-12 mm deep, more preferably in the range 2 mm-7 mm wide and 2 mm-8 mm deep, even more preferably in the range 2 mm-5 mm wide and 2 mm-5 mm deep.

In the embodiment shown in FIGS. 40MA-40MC, the distances between each of the parts or segments are the same. However, in other embodiments, the distances between parts or segments may vary. In some embodiments, the vertically extending rims may create a first distance between vertically extending flat surfaces of the parts or segments, while horizontally extending rims may create a second, larger distance between horizontally extending flat surfaces of the parts or segments. This could be an advantage for example if it is of greater importance that the parts or segments are secured in a vertical direction than in a horizontal, as the in-growth of fibrotic tissue in a horizontal groove creates vertical fixation.

FIG. 40MB shows the assembly of the functional movement restriction device 110 by the assembly of the 16 segments 111*a*-111*p* with the centrally located distance part 113. FIG. 40MC shows the assembled functional movement restriction device 110 when three wires 153*a*-153*c*, two horizontally extending 153*a*, 153*b* and one vertically extending 153*c*, have been placed encircling the functional movement restriction device 110 for holding the parts or segments 111*a*-111*p* together during implantation and before the assembled functional movement restriction device 110 has been properly secured by the in-growth of fibrotic tissue around and into the spaces S formed in the assembled functional movement restriction device 110. The wires 153*a*-153*c* are held in place by being placed in encircling grooves 158 adapted to the thickness of the wires 153*a*-153*c*.

FIGS. 40MD and 40ME shows an embodiment of the medical device comprises a movement restriction device 110 comprising 5 parts 111*a*-111*e*-four outer parts 111*a*-111*d* and one centrally placed part 111*e* configured to engage and loosely connect the stabilize the outer parts relative to each other. In the embodiment shown in FIGS. 40MD and 40ME, the outer parts 111*a*-111*d* are not configured to be placed at a distance from each other, i.e. the central part 111*e* is not configured to act as a distance element between the parts. All parts are preferably made from a biocompatible implantable polymer material, such as medical grade silicone or medical grade polyurethane. The polymer material can preferably be mixed with a substance configured to make the implantable medical device more radiation opaque-such that the implant can be seen on an x-ray. Such a substance could for example be Barium sulfate which could be added in powder form to the polymer material and then mixed into a homogenous material. The concentration of Barium sulfate could be in the range 3%-20%, preferably in the range 5%-15%.

In the embodiment shown in the FIGS. 40MD and 40ME the central part 111*e* and the four outer parts 111*a*-111*d* are capable of disconnecting from each other, such that the central part and the at least two outer parts individually can pass through the gastro-intestinal tract. The outer surface of the functional movement restriction device 110, shown in FIG. 40ME, comprises six flat surfaces 168 separated from each other and interspaced by curved, convex, surfaces having elliptic points, more specifically being spherical surfaces. The flat surfaces 168 reduces the diameter of the movement restriction device when the movement restriction device is compressed and also reduces the devices tendency to rotate in its invaginated position. In the embodiment shown in FIGS. 40MD and 40ME, the combined area of the six flat surfaces exceeds 35% of the total outer surface area of the functional movement restriction device, however, in alternative embodiments, the functional movement restriction device may have fewer flat surfaces, such as three, four or five, or in the alternative, more flat surfaces, such as seven eight or nine. Also, in alternative embodiments, the combined area of the flat surfaces may exceed 40%, or may exceed 45% or may exceed 50% of the total outer surface area of the functional movement restriction device. In some implantations, increased movement of the movement restriction device may be beneficial for reducing the risk of migration and/or for not hampering the motility of the stomach. In such embodiments, the combined area of the flat surfaces may be reduced such that the combined area of the flat surfaces is in the interval 10%-20% of the total outer surface area of the functional movement restriction device. In the embodiment shown in the FIGS. 40MD and 40ME, the flat surfaces 168 are circular, however in alternative embodiments, the flat surfaces may be elliptic and elongated, stadium-shaped or polygonal.

In the embodiment shown in the FIGS. 40MD and 40ME the outer boundary of the functional movement restriction device has a volume in the range 7.3 cm3-8 cm3, or a volume in the range >6.6 cm3-<7.3 cm3, or a volume in the range >5.8 cm3-6.6 cm3, or a volume in the range 5.0 cm3-5.8 cm3, or a volume in the range, or a volume in the range >8 cm3-<200 cm3, or a volume in the range 10 cm$^3$-30 cm$^3$—for effectively working as a movement restriction device whilst still being possible to completely invaginate in the fundus. In the embodiment shown in FIGS. 40MD and 40ME the volume of the movement restriction device and the volume of the boundary of the movement restriction device are substantially the same (the only difference being the volume of the groove 158 running along the equator of the movement restriction device 110, which is included in the volume of the boundary of the movement restriction device). More specifically, in the embodiment shown in FIGS. 40MD and 40ME, the boundary of the functional movement restriction device has a volume in the range 7.3 $cm^3$-8 $cm^3$, or a volume in the range >6.6 $cm^3$-<7.3 $cm^3$, or a volume in the range >5.8 $cm^3$-6.6 $cm^3$, or a volume in the range 5.0 $cm^3$-5.8 $cm^3$ or a volume in the range 12 $cm^3$-25 $cm^3$, even more specifically, in the range 15 $cm^3$-25 $cm^3$ and even more specifically in the range 15 $cm^3$-22 $cm^3$, or a volume in the range >8 $cm^3$-<200 $cm^3$.

In the embodiment shown in the FIGS. 40MD and 40ME, the functional movement restriction device 110 has a height h in the range 3 cm-6 cm for ensuring that the distal part of the functional movement restriction device 110 is placed close to the thoracic diaphragm such that the functional movement restriction device 110 acts as a mechanical stop for hindering the movement of the lower esophageal sphincter, i.e. that the distal end of the movement restriction device ends up at a distance long enough from the angle of His. More specifically, in the embodiment shown in FIGS. 40MD and 40ME, the functional movement restriction device 110 has a height h in the range 3.5 cm-6 cm, and even more specifically a height in the range 4 cm-6 cm.

In the embodiment shown in the FIGS. 40MD and 40ME, the each of the four outer parts 111*a*-111*d* comprises a wedge-shaped portion 114*w*, being a wedge-shaped recess 114*w*, and the central part 111*e* comprises wedge-shaped portions 151*h*1-151*h*4 in the form of a horizontally extending rim 151*h*1-151*h*4 protruding horizontally from the center of gravity of the central part 111*e*. The wedge-shaped portions 151*h*1-151*h*4 of the central part 111*e* s of the four outer parts 111*a*-111*d* are configured to be placed in the wedge-shaped recesses 114*w* of the outer parts 111*a*-111*d* for stabilizing the outer parts 111*a*-111*d* in the vertical direction. In the embodiment shown in FIGS. 40MD and 40ME, the wedge-shaped portions 114*w* of the four outer parts 111*a*-111*d* are wedge-shaped with a first angle α. The wedge-shaped portions 151*h*1-151*h*4 of the central part 111*e* is wedge-shaped with a second angle β. The wedge-shaped portions 151*h*1-151*h*4 of the central part 111*e* are tapered in a direction from the center of gravity of the central part 111*e*. In the embodiment shown in the FIGS. 40MD and 40ME, the first angle α is more than 7° larger than the second angle β to reduce the contacting surface between the wedge-shaped portions 114*w* of the four outer parts 111*a*-111*d* and the wedge-shaped portions 151*h*1-151*h*4 of the central part 111*e*. In alternative embodiments, the first angle α, is more than 10° larger than the second angle β, or more than 12° larger than the second angle β, or more than 15° larger than the second angle β, two outer parts, and wherein a portion of the horizontally extending rim is wedge-shaped with an angle in the range 20°-60°.

In the embodiment shown in the FIGS. 40MD and 40ME, the wedge-shaped portion of the horizontally extending rim 151*h*1-151*h*4 is wedge-shaped with an angle exceeding 25°, or more specifically with an angle exceeding 30° and even more specifically with an angle exceeding 35°, for facilitating disengagement between the outer parts 111*a*-111*d* and the central part 111*e*.

In the embodiment shown in the FIGS. 40MD and 40ME, each of the four outer parts 111*a*-111*d* further comprises second wedge-shaped portions 166 in the form of two wedge-shaped protrusions 166, and the central part 111*e* comprises wedge-shaped recesses, or recesses having the form of tetrahedrons between the vertical surfaces 151*s* of the vertically extending rims 151*v*1.151*v*4 and the horizontally extending surfaces of the horizontally extending rims 151*h*1-151*h*4. The wedge-shaped portions 166 of the four outer parts 111*a*-111*d* are configured to be placed in the wedge-shaped recesses of the central part 111*e*, for stabilizing the outer parts 111*a*-111*d* relative to the central part 111*e* in the horizontal direction. In the embodiment shown in FIGS. 40MD and 40ME, the wedge-shaped portions 166 of the four outer parts 111*a*-111*d* are wedge-shaped with a fourth angle δ and the wedge-shaped portions of the central part 111*e* is wedge-shaped with a fifth angle ε. In the embodiment shown in the FIGS. 40MD and 40ME, the fifth angle ε is more than 7° larger than the fourth angle δ to reduce the contacting surface between the wedge-shaped portions 166 of the four outer parts 111*a*-111*d* and the wedge-shaped portions of the central part 111*e*. In alternative embodiments, the fifth angle ε is more than 10° larger than the fourth angle δ, or more than 12° larger than the fourth angle δ, or more than 15° larger than the fourth angle δ.

In the embodiment shown in the FIGS. 40MD and 40ME, the angle difference between the angle α and the angle β reduces the area of contact between the surfaces of the wedge-shaped recess 114*w* and the surfaces of the wedge-shaped protrusions 151*h*1-151*h*4 (portion of the horizontal rim). The inner surfaces of the wedge-shaped recess 114*w* contacts the outer surfaces of the wedge-shaped protrusions 151*h*1-151*h*4 over a length being less than half of the length of the wedge-shaped surfaces when the wedge-shaped protrusions 151*h*1-151*h*4 has been placed in the wedge-shaped recesses 114*w*. More specifically, the inner surfaces of the wedge-shaped recess 114*w* contacts the outer surfaces of the wedge-shaped protrusions 151*h*1-151*h*4 over a length being less than half of the length of the wedge-shaped surfaces. Also, in the embodiment shown in the FIGS. 40MD and 40ME, the inner surfaces of the wedge-shaped recess 114*w* contacts the outer surfaces of the wedge-shaped protrusions 151*h*1-151*h*4 over a length being less than half of the depth of the recess 114*w*, measured in a direction from the center of gravity of the central part 111*e*, when the movement restriction device 110 has been assembled.

In the embodiment shown in the FIGS. 40MD and 40ME, each of the outer parts 111*a*-111*d* comprises contacting surfaces 111*s* configured to be placed in contact with contacting surfaces 151*s* of the central part 111*e*. In the embodiment shown in the FIGS. 40MD and 40ME, the contacting surfaces 111*s* are curved, more specifically, the contacting surfaces 111*s* are convex, and even more specifically the contacting surfaces 111*s* comprises elliptic points—for reducing the contacting area between the contacting surfaces 111*s* and the contacting surfaces 151*s*. In the embodiment shown in the FIGS. 40MD and 40ME, the contacting surfaces 111*s* of the wedge-shaped portions 166 of the four outer parts 111*a*-111*d* contacts the contacting surfaces 151*s* of the central part 111*e* over less than half of the area of the contacting surfaces 111*s* of the wedge-shaped portions 166. More specifically, the contacting surfaces 111*s* of the wedge-shaped portions 166 of the four outer parts 111*a*-111*d* contacts the contacting surfaces 151*s* of the central part 111*e* over less than one third of the area of the contacting surfaces 111*s* of the wedge-shaped portions 166. In alternative embodiments, the contacting surfaces Ills of the wedge-shaped portions 166 of the four outer parts 111*a*-111*d* and/or the contacting surfaces 151*s* of the central part 111*e* may be concave for the purpose of reducing the contacting area between the surfaces 111*s*, 151*s*.

In the embodiment shown in the FIGS. 40MD and 40ME, the central part 111*e* comprises four vertically extending rims 151*v*1-151*v*4 being equidistant spaced apart. Each the four vertically extending rims have contacting surfaces 151*s* configured to contact surfaces 111*s* of the four outer parts. Each of the four vertically extending rims 151*v*1-151*v*4 are wedge-shaped in the vertical direction from the horizontal rim 151*h*1-151*h*4, such that the vertically extending rims 151*v*1-151*v*4 are tapered from the center (away from the center of gravity of the central part 111*c*) and upwards and downwards with an angle in the range 20°-60°, i.e. in a direction of the elongation of the vertically extending rims 151*v*1-151*v*4. More specifically, in the embodiment shown in the FIGS. 40MD and 40ME, the vertically extending rims are wedge-shaped with an angle exceeding 25°, more specifically, with an angle exceeding 30° and even more specifically with an angle exceeding 35°.

In the embodiment shown in the FIGS. 40MD and 40ME, the mass of the central part 111*e* exceeds the mass of at least one of the four outer parts 111*a*-111*d*. More specifically, the mass of the central part 111*e* exceeds the mass of at least one of the outer parts by more than 10%, or more specifically more than 20%, or even more specifically by more than 30%. Further, in the embodiment shown in the FIGS. 40MD and 40ME, the volume of the central part 111*e* exceeds the volume of at least one of the four outer parts 111*a*-111*d* by more than 10%, or more specifically by more than 20%, or even more specifically by more than 30%.

In alternative embodiments (not shown) the mass of at least one outer part may exceed the mass of the central parts. More specifically, the mass of one of the outer parts may exceed the mass of central part by more than 10%, or by more than 20%, or by more than 30%. Further, alternative embodiments the volume of at least one of the outer parts may exceed the volume of the central part 111*c* by more than 10%, or by more than 20%, or by more than 30%.

In the embodiment shown in the FIGS. 40MD and 40ME, the longest cross-sectional distance, being the vertical height h, of the outer parts 111*a*-111*d* exceeds the longest cross-sectional distance of the central part 111*e*, being the vertical height h", by more than 20%, or more specifically by more than 30%. In alternative embodiments, the longest cross-sectional distance h, of the outer parts 111*a*-111*d*, may exceed the longest cross-sectional distance of the central part 111*e* by more than 40% or by more than 50%.

In the embodiment shown in the FIGS. 40MD and 40ME, the central part 111*e* is elongated while the functional movement restriction device is spherical with six opposite cut surfaces (168). However, in alternative embodiments, the functional movement restriction device may be elongated and may have a height (h), being a longest cross-sectional distance, and a width (W), being a longest cross-sectional distance perpendicular to the height (h), and the height (h) may be in the range 1.2 times-2 times longer than the width (W). In further alternatives, the height may be in the range 1.3 times-2 times longer than the width, or the height may be in the range 1.2 times-1.8 times longer than the width, or the height may be in the range 1.3 times 1.6 times longer than the width. The functional movement restriction device may have a height of more than 1 inch or a height in the range 1 inch-3.5 cm, or in the range 3 cm-5 cm, or in the range 3.5 cm-6 cm, or in the range 4 cm-5 cm, or in the range 4 cm-6 cm.

Figure 40N:
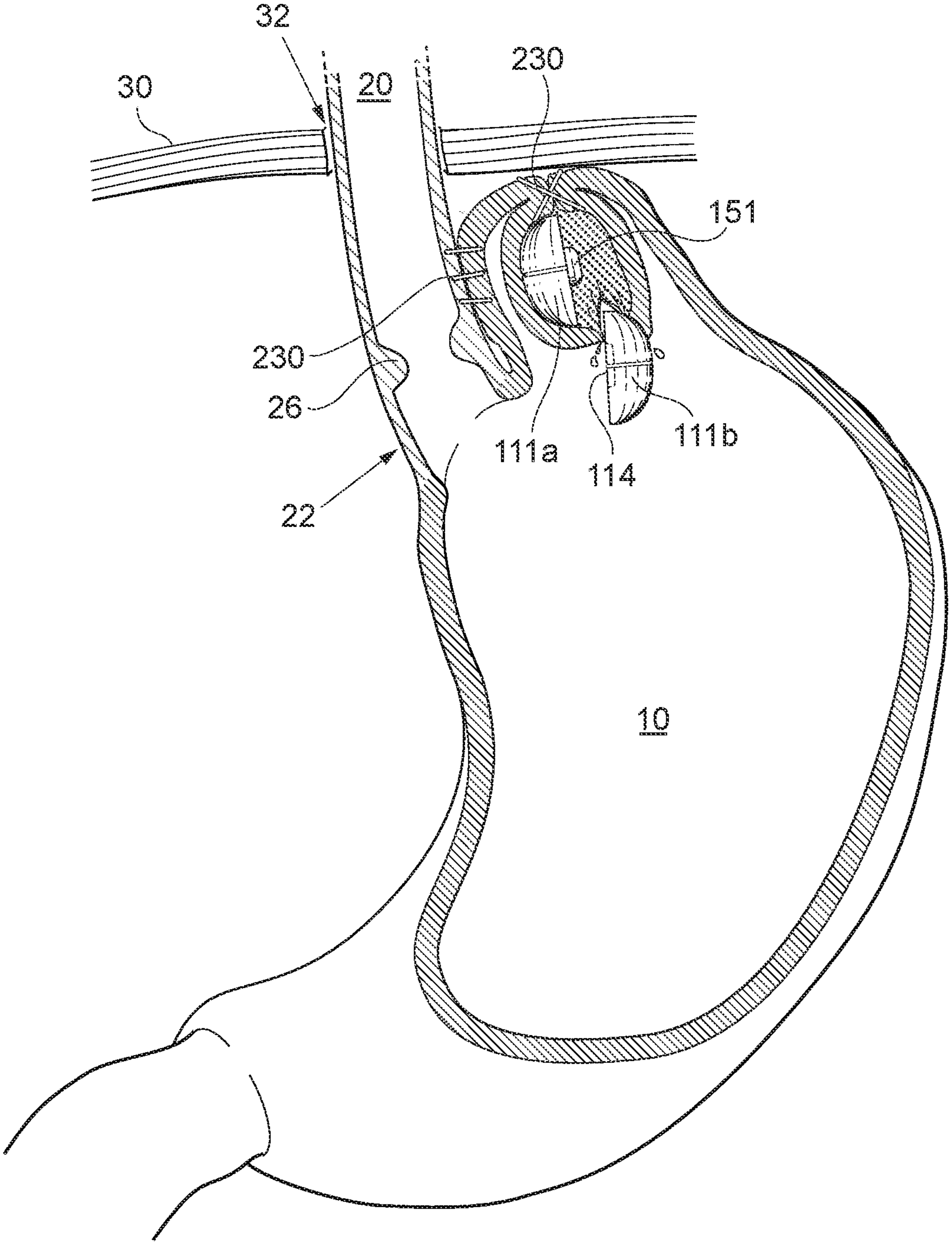

FIG. 40N shows the movement restriction device 110 according to the embodiment further described with reference to FIGS. 40DA-40DC when it has been implanted and fully invaginated by the stomach wall of the patient. Any foreign matter placed against the living tissue of the human body risks having an adverse effect on the living tissue. In the case of the movement restriction device disclosed herein, one risk is that if the invagination becomes too tight, the movement restriction device will exert a pressure on the tissue, which risks impeding the blood flow in the capillary vessels supplying the tissue and thereby reducing the oxygenation of the tissue. The reduced oxygenation may lead to tissue atrophy which in rare cases my lead to migration. I.e., the foreign body in the form of the movement restriction device 110 migrates into, and eventually through, the wall of the stomach, such that the movement restriction device 110 ends up inside of the stomach cavity. In the illustration in FIG. 40N, the space created by the distance element 151 enables the in-growth of fibrotic tissue between the first and second part or segment 111A, 111B, which individually fixates the first and second part or segment 111A, 111B to the stomach wall. In the illustration in FIG. 40N, pressure has been exerted on the tissue wall of the stomach by the second part or segment 111B, which has caused tissue atrophy subsequent migration of the second part or segment 111B through the wall of the pouch of stomach tissue in which the functional movement restriction device was placed. When the functional movement restriction device was implanted, the parts or segments 111*a*, 111*b* were held together by wires (shown as 153 throughout the description) in the form of resorbable sutures. However, after about two weeks, the sutures have been resorbed by the body and the functional movement restriction device is held together by the invagination in the stomach wall, i.e. by the tissue walls of the stomach forming a pouch in which the functional movement restriction device is positioned. When the second part or segment 111*b* starts migrating through the tissue wall, the enclosure provided by the stomach wall pouch, and thereby the withholding force exerted on the functional movement restriction device, disappear, which enables the two parts or segments to disconnect from each other, allowing only the second part or segment 111*b* to migrate through the tissue wall, while the first part or segment remains in its fixated position by means of a "flange" of fibrotic tissue which have grown into the space between the two parts or segments and which holds the first part or segment in its fixated position after the second part or segment has left the pouch of tissue wall.

FIG. 40N' shows the second part 111*b* in a state when it has migrated through the stomach wall is about to end up in the stomach cavity. As the migration happens relatively slowly, fibrotic tissue has been formed behind the migrating second part 111*b* and the tissue wall thus heals sequentially.

FIG. 40N" shows the movement restriction device in a state in which the second part 111*b* has migrated completely through the tissue wall of the stomach and the tissue wall behind the second part 111*b* has been completely healed, leaving the first part 111*a* positioned inside a fully enclosed tissue pouch. The remaining part or segment 111*a*, together with the pouch and fibrotic tissue, may suffice for working as a movement restriction device for hindering the cardia 22 and the lower esophageal sphincter 26 from sliding through the esophageal hiatus 32 into the thoracic diaphragm 30. The pouch of tissue wall may be partially filled with additional fibrotic tissue and may contract slightly as it now only needs to accommodate half of the volume of the functional movement restriction device. In this outcome, the second part or segment 111*b* leaves the body through the gastro-intestinal tract and the first part or segment 111*a* remains invaginated by the stomach wall and functioning as a movement restriction device—which means that the patient does not have to undergo any additional surgery. This is one clear advantage with the embodiments in which the movement restriction device is formed from a plurality of parts or segments connected to each other at a distance from each other for enabling individual fixation of the parts or segments by means of the in-growth of fibrotic tissue in spaces created between the parts or segments by the distance elements. The scenario described above and illustrated in FIGS. 40N-40N" is described in relation to the movement restriction device of the embodiment described with reference to FIGS. 40DA-40DC. However, the scenario is equally applicable to any of the movement restriction devices comprising a plurality of parts or segments, such as the embodiments described with reference to FIGS. 40AA-40AD, 40BA-40BC, 40CA-40CC, 40EA-40EC, 40FA-40FD, 40GA-40GD, 40HA-40HC, 40LA-40IC, 40JA-40JC, 40KA-40KB, 40LA-40LB, 40MA-40MC, 40P, 40O, 40Q, 40R, 40SA-40SD, 40SA', 40SB', 40SE, 40SF, 40SE', 40SF', 40SE", 40SE'". And the embodiments of FIGS. 31E, 31F, 39Q', 39R', 39S', 39T', 39U', 39V' when combined with a distance element, such as the distance element shown in FIG. 40DA.

Figure 40O:
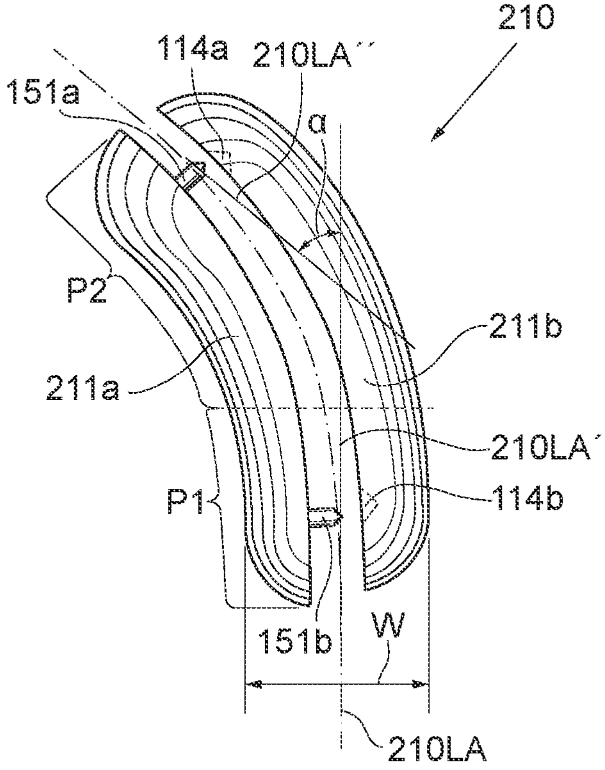
Figure 40P:
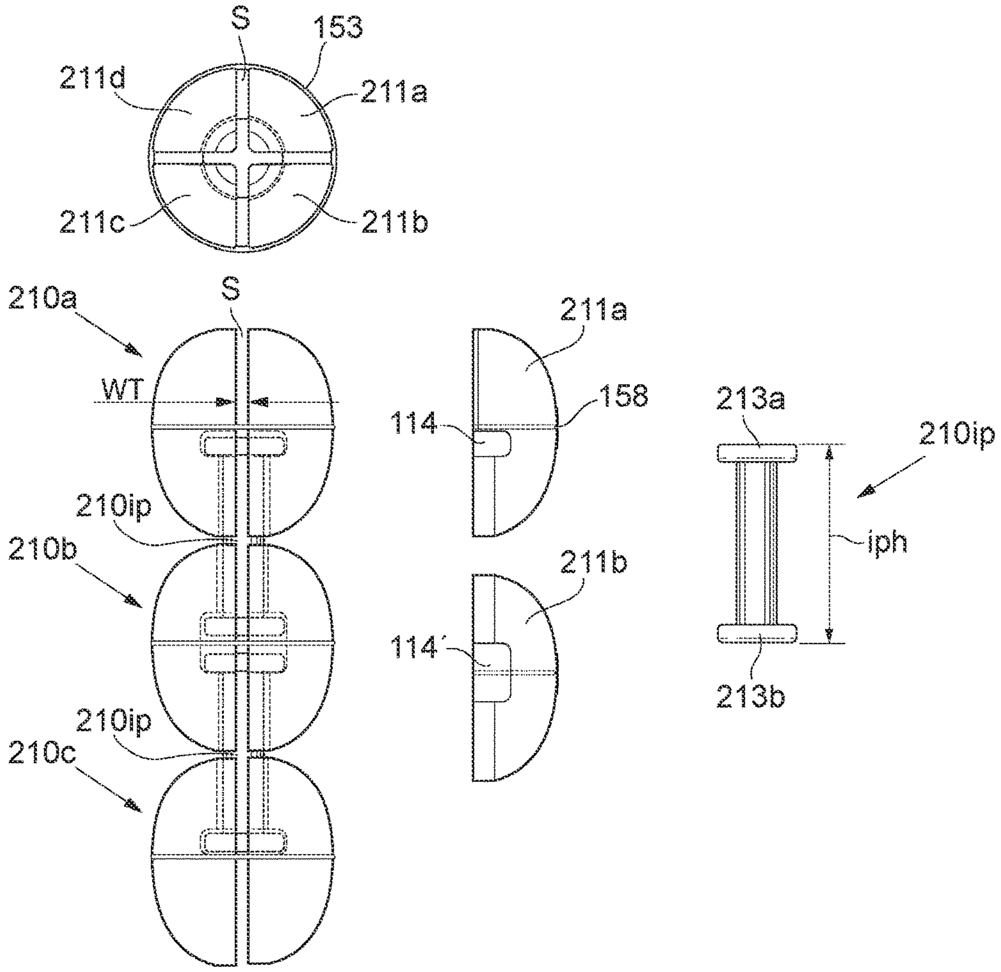
Figure 40P:
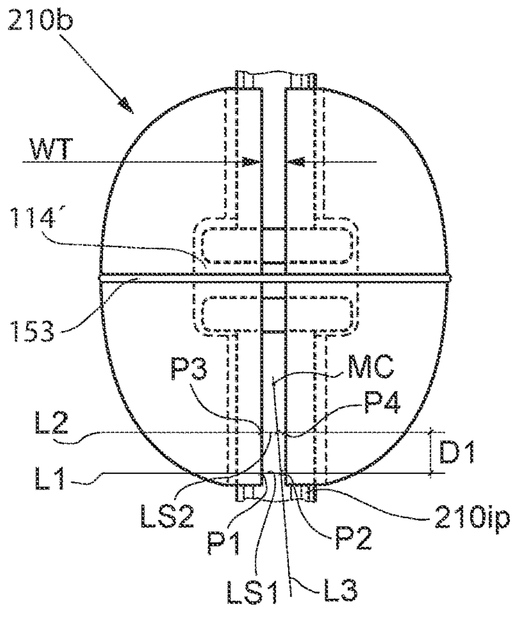

FIGS. 40P and 40P' shows an implantable medical device for treating obesity 210. The implantable obesity treatment device 210 is configured to be fixated to the stomach wall and comprises volume filling device(s) configured to protrude into the stomach and thereby reduce the volume of the cavity of the stomach, which reduces the patient's ability to cat. In the embodiment shown in FIGS. 40P and 40P', the obesity treatment device 210 comprises a first volume filling device 210*a*, a second volume filling device 210*b*, and a third volume filling device 210*c*. The boundaries of each of the three volume filling devices 210*a*-210*c* form ellipsoids. The first and second volume filling devices 210*a*, 210*b* are configured to be connected to each other by means of an interconnecting part 210*ip* and the second and third volume filling device 210*b*, 210*c* are configured to be connected to each other by means of another interconnecting part 210*ip*. Each of the first, second and third volume filling device 210*a*-210*c* comprises four parts 211*a*-211*d*, each having the shape of an ellipsoid wedge comprising two flat surfaces configured to be positioned opposite flat surfaces of respective other parts. The ellipsoid wedge further comprising an elliptic surface configured to form a portion of the outer surface of the functional assembled volume filling device. In FIG. 40P', a first part 211*a* is showed in isolation. In the embodiment shown in FIGS. 40P and 40P', the four parts 211*a*-211*d* are identical, i.e. the three additional parts 211*b*-211*d* are identical to the first part 211*a*. Turning now to the isolated view of the first part 211*a*. A recess 114 is positioned just below the equatorial line of the first part 211*a*, i.e. in the lower half of the first part 211*a*. The recess is configured to receive the upper protruding flange 213*a* of an interconnecting part 210*ip* configured to both connect the first and second volume filling device 210*a*, 210*b* to each other, and serve as a distance element for creating distances between the flat surfaces of the four parts 211*a*-211*d* of the volume filling devices 210*a*-210*c*, to enable the in-growth of fibrotic tissue into the space S between the flat surfaces of the four parts 211*a*-211*d* of the volume filling devices 210*a*-210*c*.

Just as in the embodiments of movement restriction devices described herein, the four parts 211*a*-211*d* are capable of disconnecting from each other, such that each of the four parts 211*a*-211*d* individually can pass through the gastro-intestinal tract in the event that one or more parts 211*a*-211*d* of the volume filling device migrates through the stomach wall and ends up inside the stomach.

The interconnecting part 210*ip* comprises an upper and lower protruding flange 213*a*, 213*b*. The protruding flanges 213*a*, 213*b* constitutes the part of the interconnecting part 210*ip* that is configured to create the space S located between the opposing flat surfaces of the first and second parts 211*a*, 211*b*, between the opposing flat surfaces of the second and third part 211*b*, 211*c*, between the opposing flat surfaces of the third and fourth part 211*c*, 211*d* and between the opposing flat surfaces of the fourth and first part 211*d*, 211*a*. The spaces S are configured to allow in-growth of fibrotic tissue between portions of the parts 211*a*-211*d*. The in-growth of fibrotic tissue between the parts 211*a*-211*d* assists in the individual fixation of the parts 211*a*-211*b* to the stomach wall. The individual fixation of the parts 211*a*-211*d* means that even if one or more parts (e.g. the first part 211*a*) migrates through the stomach wall and thus leaves its assembled, invaginated position, the remainder of the parts 211*b*-211*d* can remain in their assembled invaginated position. The remaining parts 211*b*-211*d*, together with the pouch and fibrotic tissue (and in the embodiment described in FIGS. 40P and 40P' the additional volume filling devices), may suffice for working as a volume filling device taking up enough volume in the stomach of the patient for reducing the patient's ability to eat. When the first part 211*a* disappears from its invaginated position, the pouch of tissue wall in which the volume filling devices 210*a*-210*c* are positioned may be partially filled with additional fibrotic tissue and may contract slightly as it now only needs to accommodate half of the volume of the functional movement restriction device. In this outcome, the first part 211*a* leaves the body through the gastro-intestinal tract and the remainder of the parts 211*b*-211*d* remains invaginated by the stomach wall and functions as a volume filling device—which means that the patient does not have to undergo any additional surgery. This is one clear advantage with the embodiments in which the volume filling device is formed from a plurality of parts connected to each other at a distance from each other for enabling individual fixation of the parts by means of the in-growth of fibrotic tissue in spaces created between the parts by the distance elements.

The spaces S between the parts 211*a*-211*d* are confined at least partially by a first surface of one part and a second surface of a second part. As an example, the space S between the first and second part 211*a*, 211*b* is confined by a first surface of the first part 211*a* and a second surface of the second part 211*b*. The first and second surfaces are positioned opposite each other when the first and second parts 211*a*, 211*b* are connected. A line segment LS1 of a first straight line L1 is bounded by a first point P1 on the first surface and a second point P2 on the second surface. The line segment LS1 of the first straight line L1 is more than 1 mm, a line segment LS2 of a second straight line L2 is bounded by a third point P3 on the first surface and a fourth point P4 on the second surface. The line segment LS2 of the second straight line L2 is more than 1 mm. The first straight line L1 is parallel to the second straight line L2. The first and second straight lines L1, L2 intersect a third straight line L3 which also intersects the center of gravity MC of the first volume filling device 210*a*. A distance D1 between the first and second straight lines L1, L2 is more than 2 mm for allowing in-growth of fibrotic tissue for aiding in the fixation of the parts of the volume filling devices and thereby the fixation of the functional implantable medical device, to the stomach wall.

In the embodiment shown in FIGS. 40P and 40P', the interconnecting part 210*ip* has the shape of a spool, with a central cylindrical portion, and an upper and lower protruding annular flange 213*a*, 213*b*. The interconnecting part 210*ip* has a height iph such that the interconnecting part 210*ip* reaches from just below the equatorial line of the first volume filling device 210*a* to just above the equatorial line of the second volume filling device 210*b*. As such, the height iph of the interconnecting part 210*ip* equals about the height of the first volume filling device 210*a*.

In the embodiment shown in FIG. 40P, each of the first, second and third volume filling device 210*a*, 210*b*, 210*c* have the shape of an ellipsoid having a height in the range 10 mm-40 mm, preferably in the range 15 mm-30 mm and a width in the range 10 mm-40 mm, preferably in the range 15 mm-30 mm. In the embodiment shown in FIG. 40P, the first, second and third volume filling device 210*a*, 210*b*, 210*c* are higher than they are wide, i.e. the height is longer than the width. However, in other embodiments, the first, second and third volume filling devices may be spherical such that the height and width are equal.

Turning now to the isolated view of the first part 211*b* of the second volume filling device 210*b*. The recess 114' in the first part 211*b* of the second volume filling device 210*b* is positioned centrally, such that the center of the recess is aligned with the equatorial line of the second volume filling device 210*b*. The recess 114' in the first part 211*b* of the second volume filling device 210*b* is twice the height of the recess 114 in the first part 211*a* of the first volume filling device 210*a*. As such, the recess 114' in the first part 211*b* of the second volume filling device 210*b* can accommodate both the lower protruding annular flange 213*b* of the interconnecting part 210*ip* which is interconnecting the first and second volume filling device 210*a*, 210*b*, and the upper protruding annular flange 213*a* of the interconnecting part 210*ip* which is interconnecting the second and third volume filling device 210*b*, 210*c*.

The four parts (denoted 211*a*-211*d* in the first volume filling device) of each of the three volume filling devices 210*a*-210*c* are held together by means of a wire 153 in the form of a resorbable suture 153 running in a groove 158 encircling the volume filling devices 210*a*-210*c*. The resorbable suture 153 is configured to hold the four parts of each of the volume filling devices together during implantation and before the assembled volume filling devices 210*a*-210*c* have been properly secured by the in-growth of fibrotic tissue around and into the spaces formed in the assembled functional volume filling devices 210*a*-210*c*. After the assembled functional volume filling devices 210*a*-210*c* has been implanted the resorbable suture 153 is resorbed by the environment in the body, and the assembled functional volume filling devices 210*a*-210*c* are kept in placed by means of the invagination and the in-growth of fibrotic tissue around and into the spaces formed in the assembled functional volume filling devices 210*a*-210*c*.

FIG. 40P" shows an embodiment of an implantable medical device for treating obesity 210 which is similar to the embodiment shown with reference to FIG. 40P'. The difference is that in the embodiment shown in FIG. 40P", each one of the four volume filling devices comprises four parts 211*a*-211*h* configured to be assembled into a volume filling device, and wherein each of the parts 211*a*-211*h* of the volume filling device are configured to be positioned at a distance from the neighboring part, such that a space S is created between surfaces of each of the parts 211*a*-211*h*.

FIG. 40O shows an embodiment of an implantable medical device for treating obesity 210 in which the implantable medical device comprises a single volume filling device comprised of two parts 211*a*, 211*b*. The boundary of the functional implantable volume filling device is elongated and bent and has the shape of a bent stadium. In the embodiment shown in FIG. 40O, the functional implantable medical device is elongated such that a longest length (following the center axis 210LA from the upper edge of the volume filling device 210 to the lower edge of the volume filling device 210) is more than 1.5 times a widest width W, more specifically such that a longest length is more than 2 times a widest width W, or even more specifically such that a longest length is more than 3 times a widest width W.

In the embodiment shown in FIG. 40O, the functional volume filling device comprises a bend and a bent center axis 210LA following the elongation of the functional volume filling device.

A first portion P1 of the functional implantable medical device is configured to be positioned such that a first portion 210LA' of the bent center axis 210LA is parallel to the caudal-cranial axis of the patient, and a second portion 210LA" of the bent center axis 210LA is angled relative to the caudal-cranial axis of the patient, with an angle $\alpha$ exceeding 5°, more specifically exceeding 10°, even more specifically exceeding 20° and even more specifically exceeding 30°. The second portion 210LA" of the bent center axis 210LA is configured to be positioned in the stomach such that it is angled towards the esophagus.

Similar to what is described with reference to FIG. 40AB, the first part 211*a* comprises a first distance element comprising two protruding distance elements 151*a*, 151*b* in the form of two pins which are placed at a distance from each other, and which are integrated in the first part 211*a* and configured to enter two conical recesses 114*a*, 114*b* in the second part 211*b*. When the first and second parts 211*a*, 211*b* are connected to each other, the first and second parts 211*a*, 211*b* form the functional volume filling device.

Just as in other embodiments described herein incorporating distance elements, the distance elements creates a space between the first and second parts 211*a*, 211*b* which enables the in-growth of fibrotic tissue, which individually fixates the first and second parts 211*a*, 211*b* to the stomach wall, such that each of the first and second parts 211*a*, 211*b* can remain individually fixated to the stomach wall in the event that one of the first and second parts 211*a*, 211*b* migrates through the stomach wall and ends up inside of the stomach.

Figure 40Q:
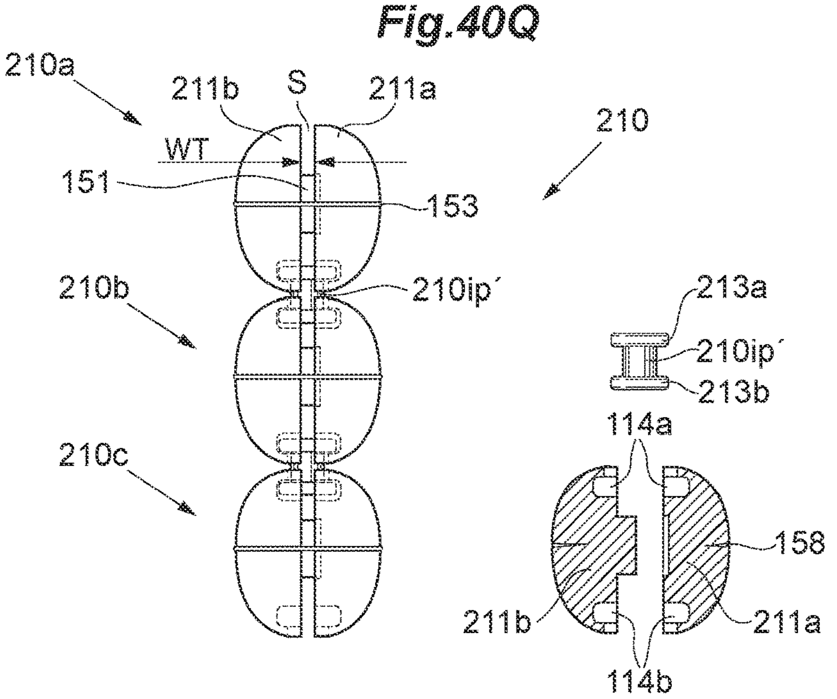

FIG. 40Q shows an embodiment of the implantable medical device 210 similar to the embodiment described with reference to FIGS. 40P' and 40P". The differences in the embodiment shown in FIG. 40Q is that each of the three volume filling devices 210*a*, 210*b*, 210*c* comprises two parts 211*a*, 211*b* which together forms the ellipsoid volume filling devices 210*a*-210*c* when assembled. A further difference is that the interconnecting parts 210*ip*' are shorter and adapted to interconnect the first volume filling device 210*a* to the second volume filling device 210*b*, and the second volume filling device 210*b* to the third volume filling device 210*c*. Each of the shorter interconnecting parts 210*ip*', also has the shape of a spool, with a central cylindrical portion, and an upper and lower protruding annular flange 213*a*. 213*b*. The upper protruding annular flange 213*a* of a first shorter interconnecting part 210*ip*' is configured to be positioned in recesses 114 in the lower part of the two parts 211*a*, 211*b* forming the first volume filling device 210*a*, and the lower protruding annular flange 213*b* is configured to be positioned in recesses 114*a* in the upper part of the two parts 211*a*, 211*b* forming the second volume filling device 210*b*, for interconnecting the first and second volume filling device. A second interconnecting part 210*ip*' is configured to be positioned in recesses 114*b* in the lower part of the two parts 211*a*, 211*b* forming the second volume filling device 210*b*, and the lower protruding annular flange 213*b* is configured to be positioned in recesses in the upper part of the two parts forming the third volume filling device 210*c*, for interconnecting the second and third volume filling device 210*b*, 210*c*.

The assembled, functional volume filling device 210 is elongated such that a longest length (following the center axis from the upper edge of the first volume filling device 210*a* to the lower edge of the third volume filling device 210*c*) is more than 1.5 times a widest width, more specifically such that a longest length is more than 2 times a widest width, or even more specifically such that a longest length is more than 3 times a widest width.

Figure 40R:
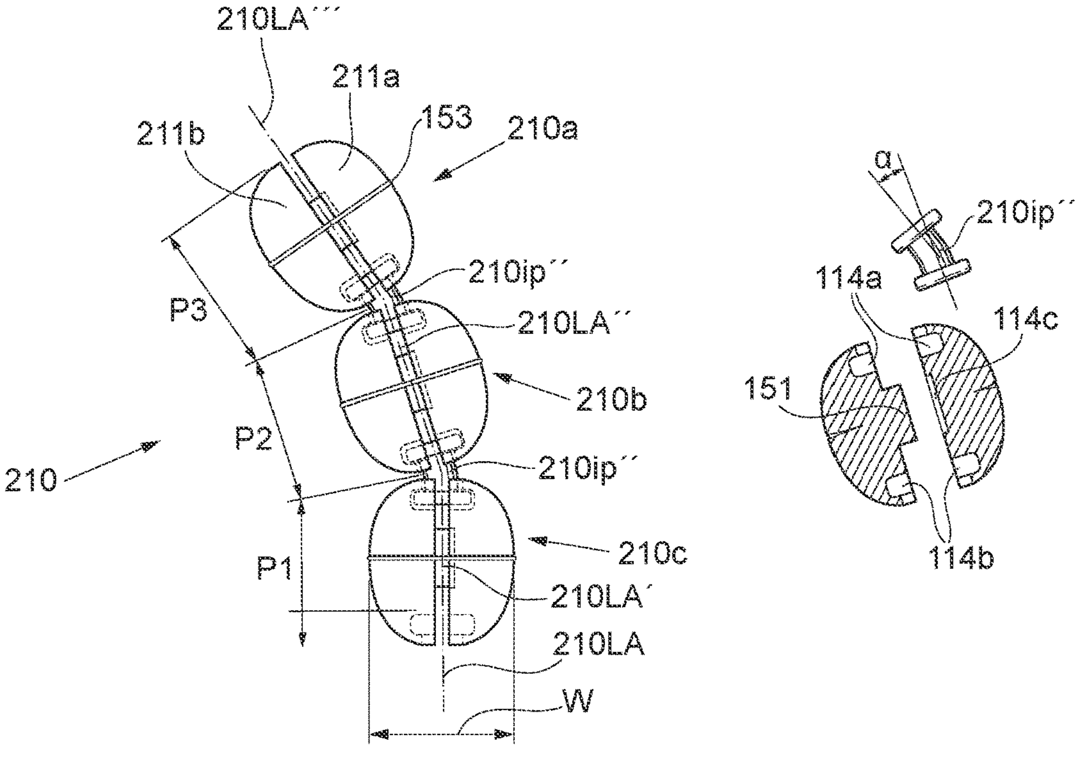

FIG. 40R shows an embodiment of the implantable medical device 210 similar to the embodiment described with reference to FIG. 40R. The differences in the embodiment shown in FIG. 40R is that the interconnecting parts 210*ip*" are angled such that the interconnecting parts 210*ip*" create an angled assembled volume filling device 210. In the embodiment shown in FIG. 40R, the interconnecting parts 210*ip*" are angled with an angle in the range 5°-45°, more specifically in the range 5°–30° and even more specifically in the range 10°-30°.

In the embodiment shown in FIG. 40R, a first portion P1 of the functional implantable medical device 210 is angled relative to a second portion P2 of the functional implantable medical device 210, which in turn is angled relative to a third portion P3 of the functional implantable medical device 210. More specifically, a first portion 210LA' of the center axis 210LA (which is the center axis 210LA' of the third volume filling device 210*c*) is angled relative to a second portion 210LA" of the center axis 210LA (which is the center axis 210LA" of the second volume filling device 210*b*) and the second portion 210LA" of the center axis 210LA is angled relative to a third portion 210LA'" of the center axis 210LA (which is the center axis 210LA'" of the first volume filling device 210*c*).

The third volume filling device 210*c* is configured to be positioned parallel to the caudal-cranial axis of the patient, such that the second volume filling device 210*b* and thereby the second portion 210LA" of the center axis 210LA is angled relative to the caudal-cranial axis of the patient, with an angle α in the range 5°-45°, more specifically in the range 5°-30° and even more specifically in the range 10°-30°. The first volume filling device 210*a* and thereby the third portion 210LA'" of the center axis 210LA is angled relative to the second portion 210LA" of the center axis 210LA, and thereby configured to be further angled relative to the caudal-cranial axis of the patient, with an angle α in the range 10°-45°, more specifically in the range 15°-45° and even more specifically in the range 15°-40°.

The assembled, functional, angled volume filling device 210 is elongated for better fitting in an invaginated position in the stomach. A longest length (following the center axis 210LA from the upper edge of the first volume filling device 210*a* to the lower edge of the third volume filling device 210) c) is more than 1.5 times a widest width W, more specifically such that a longest length is more than 2 times a widest width W, or even more specifically such that a longest length is more than 3 times a widest width W.

Figure 40S:
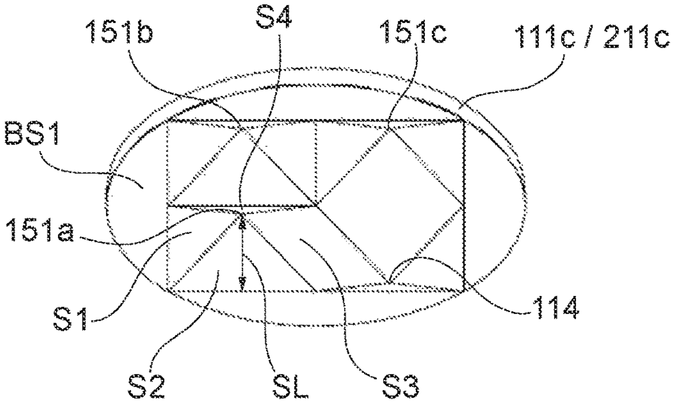
Figure 40S:
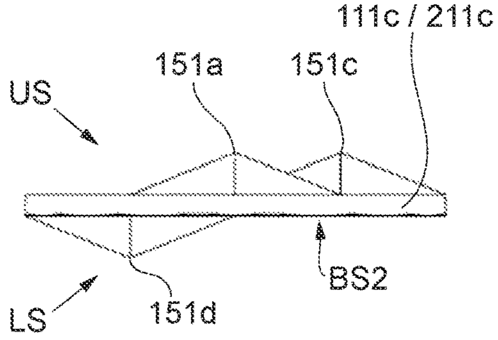
Figure 40S:
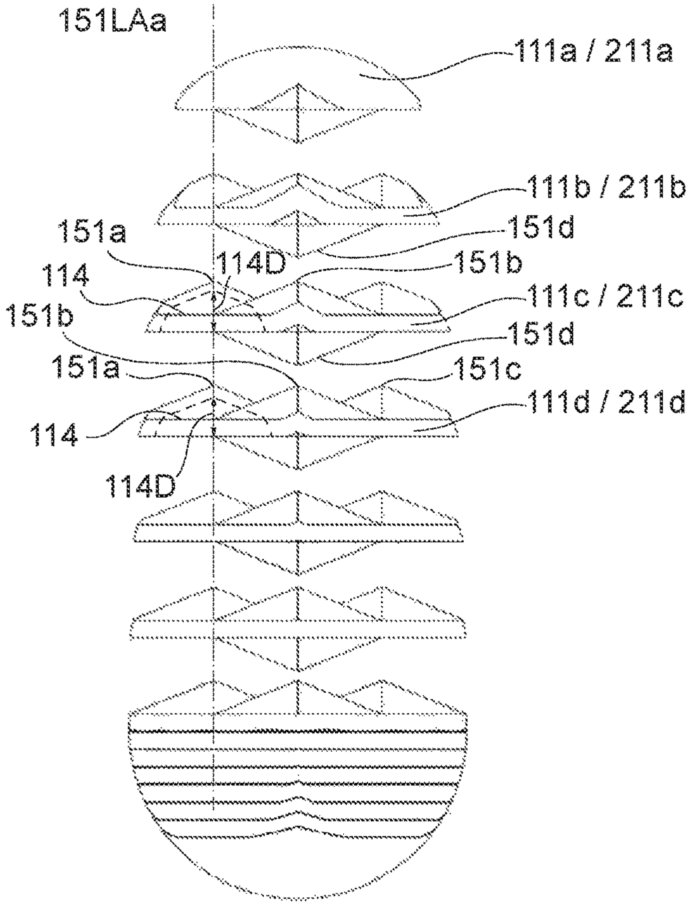
Figure 40S:
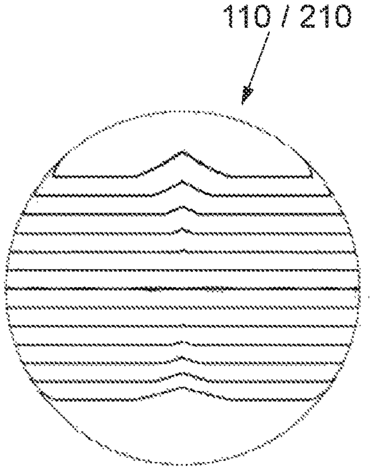
Figure 40S:
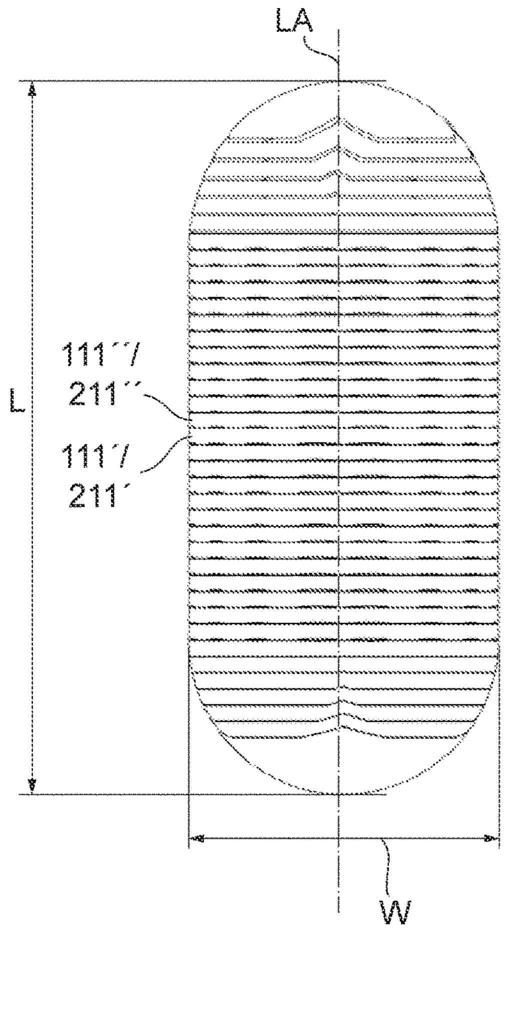
Figure 40S:
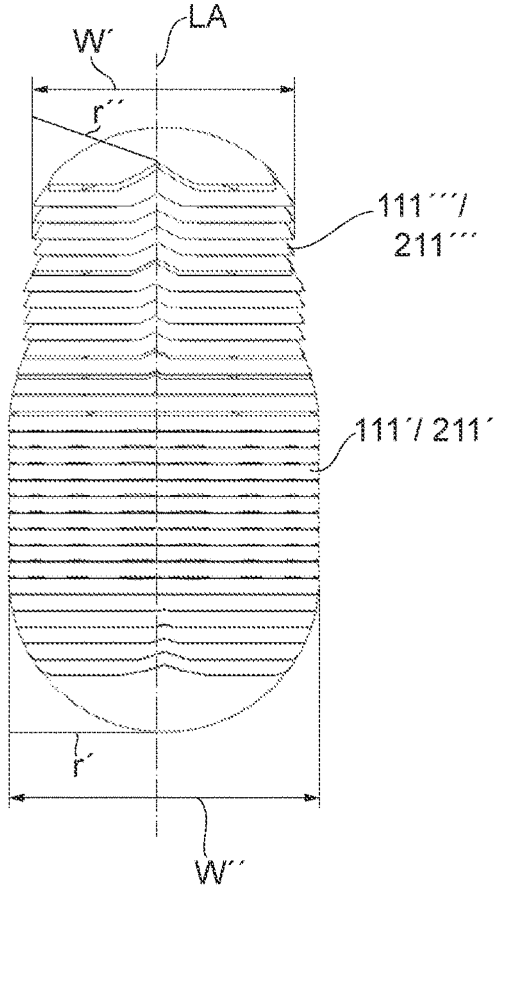

FIG. 40SA-40SD shows an embodiment of a medical device configured for implantation and for functioning as a movement restricting device 110, or a volume filling device 210, or as a movement restricting and volume filling device. In the embodiment shown in FIGS. 40SE-40SD, the movement restriction device 110/volume filling device 210 is configured to be fixated to the stomach wall for hindering movement of the lower esophageal sphincter relative to the thoracic diaphragm and/or for taking up volume in the stomach for reducing the patient's ability to eat. In the embodiment shown in FIGS. 40SA-40SD, the movement restriction device 110 and/or volume filling device 210 comprises several parts 111*a*/211*a*, 111*b*/211*b*, 111*c*/211*c* . . . configured to be connected to each other for forming the functional movement restriction and/or volume filling device. The parts 111*a*/211*a*, 111*b*/211*b*, 111*c*/211*c* . . . are capable of disconnecting from each other, such that the parts 111*a*/211*a*, 111*b*/211*b*, 111*c*/211*c* . . . individually can pass through the gastro-intestinal tract.

FIG. 40SA shows an elevated view of the third part 111*c*/211*c* in isolation. The third part 111*c*/211*c* is disc shaped and the periphery of the third part 111*c*/211*c* has an annular shape corresponding to an ellipsoid segment. The third part 111*c*/211*c* comprises three protrusions 151*a*, 151*b*, 151*c* protruding from a first base surface BS1. Each of the three protrusions 151*a*, 151*b*, 151*c* are configured to be placed in three corresponding recesses in the second part 111*b*/211*b* for stabilizing the second part 111*b*/211*b* relative to the third part 111*c*/211*c*. I.e. the position of the three protrusions 151*a*-151*c* coincides with the positions of three recesses, such that the recesses overlaps the protrusions 151*a*-151*c* when the first part 111*a*/211*a* is viewed in a direction normal to the first base surface BS1.

FIG. 40SB shows a side view of the third part 111*c*/211*c* in isolation. In the view of FIG. 40SB, the first and third protrusion 151*a*, 151*c* can be seen, as well as a fourth protrusion 151*d* protruding downwards from the second base surface BS2. The second base surface BS2, further comprises three recesses (not seen in in this view), each of which is recessing in the lower side LS of the third part 111*c*/211*c* and into the respective protrusions 151*a*-151*c* on the upper side US of the third part 111*c*/211*c*. As is seen in FIG. 40SC, each of the recesses in the third part 111*c*/211*c* are configured to receive protrusions 151*a*-151*c* protruding from the first base surface BS1 of the fourth part 111*d*/211*d*, for connecting the third part 111*c*/211*c* to the fourth part 111*c*/211*c*.

In the embodiment shown in FIGS. 40SA-40SD, the protrusions 151*a*-151*c* adapted to engage the recesses in the direction of a length axis 114LAa of the protrusions 151*a*-151*c*.

In the embodiment shown in FIGS. 40SA-40SD, the angled surfaces S1-S4 of the protrusion 151*a* and have the shape of a pyramid with a polygonal base, more specifically with a square base. As such, each of the protrusions 151*a*-151*c* have four surfaces S1-S4 being angled relative to the length axis 114LAa of the protrusion. Each of the four surfaces S1-S4 being angled relative to the length axis 151LAa of the protrusion are configured to face a surface of the recess in the second part 111*b*. In the embodiment shown in FIGS. 40SA-40SD, each of the four surfaces S1-S4 being angled are angled with an angle different from the angle of the surfaces of the recess, and at least one point on the angled surfaces S1-S4 of the protrusion 151*a* is configured to abut at least one point on the angled surfaces of the recess, such that the protrusion 151*a* engages and contacts the recess.

The parts 111*x*,211*x* are in the embodiment shown in FIGS. 40SA-40SF' made from a biocompatible clastic polymer material, such as a silicone or polyurethane based polymer material. Such biocompatible elastic polymer materials have a tendency to adhere to each other when placed in contact, especially over long periods of time. Also, the in-growth of fibrotic tissue and the infusion of bodily fluids into the movement restriction device further create adhesion between contacting surfaces of the parts 111*x*/211*x* of the movement restriction device. In the embodiment shown in FIGS. 40SA, 40SD, the contact area between the protrusions 151 and the recesses 114 has been reduced by that each of the four surfaces S1-S4 are angled with an angle different from the angle of the surfaces of the recesses 114

In the embodiment shown in FIGS. 40SA-40SD, the angled surfaces S1-S4 of the protrusion 151*a* abuts the angled surfaces of the recess over a length being less than half of the length SL of the angled surface of the protrusion, more specifically over a length being less than one third of the length SL of the angled surface of protrusion.

In the embodiment shown in FIGS. 40SA-40SD, the angled surfaces S1-S4 of the protrusion 151*a* abuts the angled surfaces of the recess 114 over a length being less than half of the depth 114D of the recess 114, measured in a direction coinciding with the direction of the length axis of the protrusion 151LAa, when the portion of the protrusion 151*a* is inserted into the recess 114.

In the embodiment shown in FIGS. 40SA-40SD, the angled surfaces S1-S4 of the protrusion 151*a* are tapered with an angle in the range 20°-150°.

In the embodiment shown in FIGS. 40SA-40SD, the recesses 114 in the second and third part 111*b*/211*b*, 111*c*, 211*c* are tapered, such that two surfaces on opposite sides of the tapered portion of the protrusion 151*a* faces two surfaces on opposite sides of the tapered recess 114, when the tapered portion is inserted into the recess 114. In the embodiment shown in FIGS. 40SA-40SD, the tapered recesses 114 are tapered with an angle in the range 30°-155°.

In the embodiment shown in FIGS. 40SA-40SD, the tapered portion of the protrusions 151*a*-151*c* are tapered with a first angle and the tapered recesses 114 in the second and third parts 111*b*/211*b*, 111*c*,211*c* are tapered with a second angle, and the second angle is larger than the first angle, specifically more than 3° larger than the first angle, more specifically more than 5° larger than the first angle and even more specifically more than 10° larger than the first angle.

As can be seen in FIGS. 40SB and 40SC, the second and third parts 111*b*/211*b*, 111*c*,211*c* further comprises a protrusion 151*d* in a second base surface BS2, which consequently is protruding downwards. In the third part 111*c*/211*c*, this means that the protrusion 151*d* is protruding towards the first base surface BS1 of the fourth part 111*d*/211*d* and configured to enter a recess in the first base surface BS1 of the fourth part 111*d*/211*d*.

In the embodiment shown in FIGS. 40SA-40SD, the parts (111*x*/211*x*) are segments of an ellipsoid, or more specifically segments of a sphere (as can be seen in FIG. 40SD). This means that all parts are annular and that all but the first (111*a*/211*a*) and last part are substantially disc shaped with a first base surface (BS1) facing upwards and a second base surface (BS2) facing downwards. The second part 111*b*/211*b* has a first radius, the third part 111*c*/211*c* has a second larger radius and the fourth part 111*d*/211*d* has a third even larger radius and so on until the centrally located part having the largest radius. As such, the area of the first base surface BS1 of the second part 111*b*/211*b* is larger than the area of the first base surface BS1 of the third part 111*c*/211*c*, and the area of the first base surface BS1 of the third part 111*c*/211*c* is larger than the area of the first base surface BS1 of the fourth part 111*d*/211*d*.

FIGS. 40SC' and 40SD' shows an embodiment of the medical device similar to the embodiment shown in FIGS. 40SA-40SD. The difference being that the protrusions 151 and recesses 114 are configured to function as distance elements for creating distance between the base surfaces BS1, BS2 of the parts, in particular at the periphery of the annular parts, such that annular grooves extending horizontally around the assembled functional movement restriction device 110 and/or volume filling device 210 are created. The annular grooves define spaces S located between the parts 111/211 configured to allow in-growth of fibrotic tissue between portions of the first and second parts 111/211. The space S is confined partially by a first surface of the first base surface BS1 of a first part 111/211 and a second surface of the second base surface BS2 of a second, adjacent part 111/211. The first and second surfaces are positioned opposite each other when the first and second parts 111/211 are connected. In the embodiment shown in FIGS. 40SC' and 40SD', a line segment LS1 of a first (theoretical) straight line L1 is bounded by a first point P1 on the first base surface BS1 and a second point P2 on the second base surface BS2. The line segment LS1 of the first straight line L1 is more than 1 mm, a line segment LS2 of a second straight line L2 is bounded by a third point P3 on the first base surface BS1 and a fourth point P4 on the second base surface BS2. The line segment LS2 of the second straight line L2 is more than 1 mm. The first straight line L1 is parallel to the second straight line L2. The first and second straight lines L1, L2 intersect a third straight line L3 which also intersects the center of gravity MC of the assembled functional movement restriction device 110 and/or volume filling device 210. A distance D1 between the first and second straight lines L1, L2 is more than 2 mm for allowing in-growth of fibrotic tissue for aiding in the fixation of the parts and thereby the fixation of the assembled functional movement restriction device 110 and/or volume filling device 210 to the stomach wall.

Just as in the embodiment described with reference to FIGS. 40SA-40SD, the contact area between the protrusions 151 and the recesses 114 has been reduced by the pyramid shaped protrusions 151 being angled with an angle different from the angle of the pyramid shape of the recesses 114, such the protrusions only contact the recesses over a portion of the distance that the protrusions 151 and the recesses 114 are placed facing each other.

FIG. 40SE shows an embodiment of a movement restriction device 110 and/or volume filling device 210 similar to the embodiment shown in FIGS. 40SA-40SD. The difference being that in the embodiment shown in FIG. 40SE, the assembled functional movement restriction device 110 and/or volume filling device 210 is elongated and has a stadium shaped cross-section. In the embodiment shown in FIG. 40SE, the functional assembled movement restriction device 110 and/or volume filling device 210 is elongated such that a longest length L (following the center axis LA from the upper edge the lower edge) is more than 1.5 times a widest width W, more specifically such that a longest length L is more than 2 times a widest width W, or even more specifically such that a longest length L is more than 3 times a widest width W. The assembled functional movement restriction device 110 and/or volume filling device 210 is configured to be positioned when implanted and at least partially invaginated in the stomach wall, such that it is parallel to the caudal-cranial axis of the patient.

FIG. 40SF shows an embodiment of a movement restriction device 110 and/or volume filling device 210 similar to the embodiment shown in FIG. 40SE. The difference being that in the embodiment shown in FIG. 40SF, the assembled functional movement restriction device 110 and/or volume filling device 210 is elongated with a varying width W', W'' or radii r',r''. The largest radius r'' of the upper ⅕ or the movement restriction device 110 and/or volume filling device 210 is more than 10% smaller than the largest radius r' of the lower ⅕ of the movement restriction device 110 and/or volume filling device 210. More specifically, the largest radius r" of the upper ⅕ or the movement restriction device 110 and/or volume filling device 210 is more than 20% smaller than the largest radius r' of the lower ⅕ of the movement restriction device 110 and/or volume filling device 210. As such, less stomach wall tissue is required for invagination of the upper portion of the movement restriction device 110 and/or volume filling device 210 which facilitates invagination of the upper portion in the fundus portion of the stomach, while the lower, larger, portion can be invaginated in the corpus portion of the stomach.

In the embodiment shown in FIG. 40SE, the periphery of several of the parts, such as 111'/211' and 111"/211" has a shape corresponding to a cylinder. In the embodiment shown in FIG. 40SE, the first and second parts 111'/211', 111"/211" have the same radii. As such, the combined periphery of the first and second parts 111'/211', 111"/211" has the shape corresponding to a cylinder.

In the embodiment shown in FIG. 40SF, the periphery of several of the parts, such as 111'/211' and 111"/211", also has a shape corresponding to a cylinder. However, in FIG. 40SF the periphery of the first part 111'/211' has a shape corresponding to a first cylinder having a first radius r', and the periphery of the second part 111'"/211'" has a shape corresponding to a second cylinder having a second, different, radius r". More specifically, the second radius is smaller than the first radius.

FIG. 40SE' shows an embodiment of the medical device similar to the embodiment shown in FIG. 40SE. The difference being that the protrusions 151 and recesses 114 are configured to function as distance elements for creating distances between the parts 111*x*/211*x*, in the same way as further described with reference to FIGS. 40SC' and 40SD'. The distance elements create annular grooves extending horizontally around the assembled functional movement restriction device 110 and/or volume filling device 210. The annular grooves define spaces S located between the parts 111*x*/211*x* configured to allow in-growth of fibrotic tissue between portions of the first and second parts 111*x*/211*x* for aiding in the fixation of the parts 111*x*/211*x* and thereby the fixation of the assembled functional movement restriction device 110 and/or volume filling device 210 to the stomach wall.

FIG. 40SF' shows an embodiment of the medical device similar to the embodiment shown in FIG. 40SF. The difference being that the protrusions 151 and recesses 114 are configured to function as distance elements for creating distances between the parts 111*x*/211*x*, in the same way as further described with reference to FIGS. 40SC' and 40SD'. The distance elements create annular grooves extending horizontally around the assembled functional movement restriction device 110 and/or volume filling device 210. The annular grooves define spaces S located between the parts 111*x*/211*x* configured to allow in-growth of fibrotic tissue between portions of the first and second parts 111*x*/211*x* for aiding in the fixation of the parts 111*x*/211*x* and thereby the fixation of the assembled functional movement restriction device 110 and/or volume filling device 210 to the stomach wall.

FIG. 40SE" shows an embodiment of the medical device similar to the embodiment shown in FIG. 40SE. The difference being that in the embodiment shown in FIG. 40SE", the assembled functional movement restriction device 110) and/or assembled functional volume filling device 210 comprises a bend. More specifically, a second portion P2 is angled relative to a first portion P1. More specifically, a second portion LA" of the center axis LA is angled relative to a first portion LA' of the center axis LA. The first portion P1 is configured to be positioned parallel to the caudal-cranial axis of the patient, such that the second portion P2 and thereby the second portion LA" of the center axis LA is angled relative to the caudal-cranial axis of the patient, towards the esophagus, with an angle α in the range 5°-45°, more specifically in the range 5°-30° and even more specifically in the range 10°-30°.

The assembled, functional, angled movement restriction device 110 and/or volume filling device 210 is elongated for better fitting in an invaginated position in the stomach. A longest length (following the center axis LA from the upper edge to the lower edge) is more than 1.5 times a widest width W, more specifically such that a longest length is more than 2 times a widest width W, or even more specifically such that a longest length is more than 3 times a widest width W.

The assembled, functional, angled movement restriction device 110 and/or volume filling device 210 has the shape of a bent stadium shape.

FIG. 40SE'" shows an embodiment of the medical device similar to the embodiment shown in FIG. 40SE. The difference being that in the embodiment shown in FIG. 40SE'", the assembled functional movement restriction device 110 and/or assembled functional volume filling device 210 has the shape of an ellipsoid. A longest length (following the center axis LA from the upper edge to the lower edge) is more than 1.5 times a widest width W, more specifically such that a longest length is more than 2 times a widest width W, or even more specifically such that a longest length is more than 3 times a widest width W.

The functional assembled movement restriction devices (110) and/or volume filling devices of the embodiments described with reference to FIGS. 40SA-40SE'" has volumes, exceeding 100 cm3, more specifically in the range 100 cm3-1000 cm3, even more specifically in the range 100 cm3-500 cm3 for occupying space in the stomach for reducing the patients ability to cat and/or for functioning as a movement restriction device for the treatment of GERD (as is further described with reference to FIG. 40AA).

The functional assembled movement restriction devices (110) and/or volume filling devices (210) of the embodiments described with reference to FIGS. 40SA-40SE'" has a length in the range 2.5 cm-15 cm, more specifically in the range 5 cm-15 cm, and even more specifically in the range 7 cm-15 cm and even more specifically in the range 8 cm-15 cm, and even more specifically in the range 8 cm-12 cm.

Figure 40T:
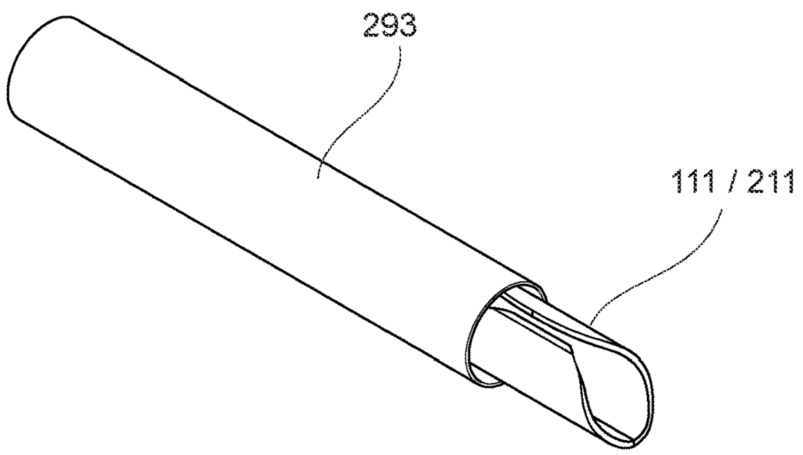
Figure 40T:
Figure 40T:
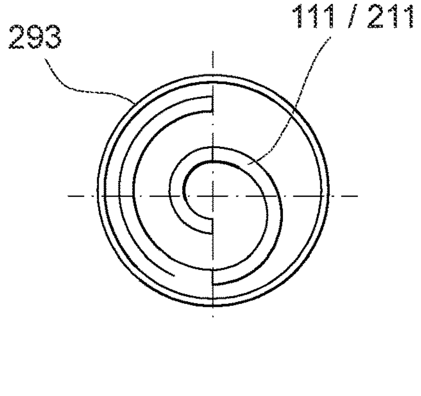

FIGS. 40TA-40TC shows, schematically, how the parts 111/211 of the movement restriction devices (110) and/or volume filling devices (210) of any of the embodiment of FIGS. 40SA-40SE'" can be inserted through a laparoscopic (or gastroscopic) cannula into the abdomen of the patient by means of an insertion sleeve 293. A part 111/211 is rolled into a roll which is then inserted into the insertion sleeve. The insertion sleeve 293 is then inserted directly into an incision in the abdomen of the patient or placed in a trocar or gastroscopic cannula for creating the passage into the abdomen. To enable transfer of the part 111/211 through the insertion sleeve 293, the part 111/211 is preferably lubricated with a biocompatible water-soluble lubricant. FIG. 40TA shows the insertion sleeve 293 in perspective view, FIG. 40TB shows the insertion sleeve 293 in a plane side view and FIG. 40TC shows the insertion sleeve 293 in cross-section. When the part 111/211 exits the insertion sleeve inside of the abdomen, the part resumes its flat shape and can then be assembled with other parts to form a functional movement restriction device (110) and/or functional volume filling device (210). The functional movement restriction device (110) and/or functional volume filling device (210) is thus assembled in situ.

Figure 40U:
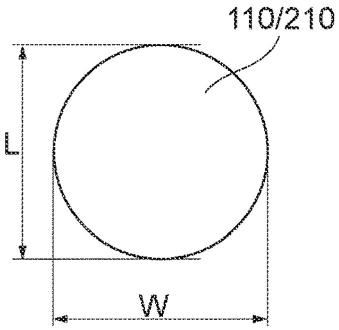
Figure 40U:
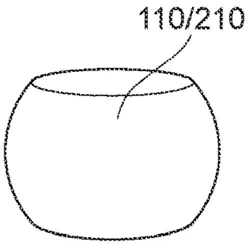
Figure 40U:
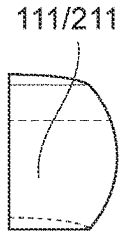
Figure 40U:
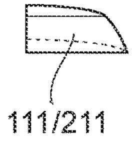
Figure 40U:
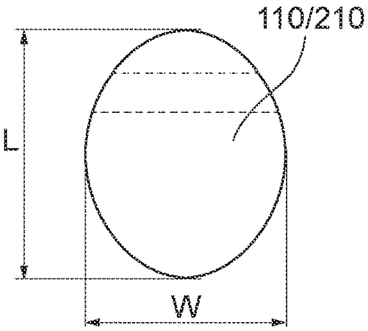
Figure 40U:
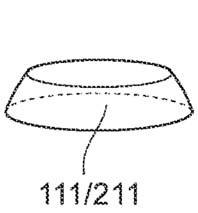
Figure 40U:
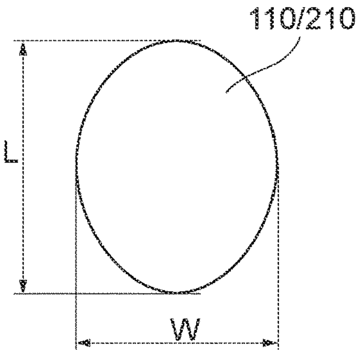
Figure 40U:
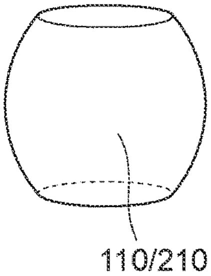
Figure 40U:
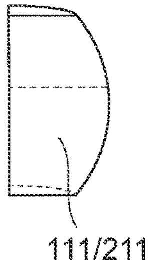
Figure 40U:
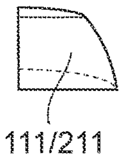
Figure 40U:
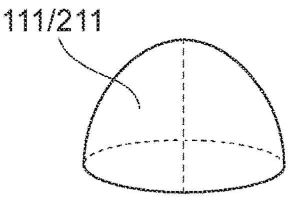
Figure 40U:
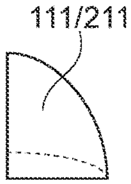
Figure 40U:
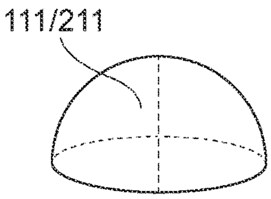
Figure 40U:
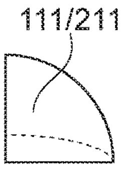

FIG. 40U-40UI' shows different geometric shapes of assembled functional movement restriction devices 110 and/or volume filling devices 210 and different geometric shapes of parts of movement restriction devices 111 and/or parts of volume filling devices 211.

1. FIGS. 40UA, 40UD and 40UE shows, schematically, examples of the functional movement restriction devices 110 and/or functional volume filling devices 210 having the shape of ellipsoids. More specifically, in FIGS. 40UD and 40UE the ellipsoids are ellipsoids in which the length L is longer than the width W, whereas in FIG. 40UA the ellipsoid is an ellipsoid having equally long length L and width W such that the ellipsoid is a sphere. Any of the functional movement restriction devices 110 and/or functional volume filling devices 210 shown in FIGS. 1, 2, 3, 4, 5, 6A, 6B, 23B, 23C, 25, 29, 3031A-31F, 32, 33, 34, 35, 36, 37A, 37B, 39C, 39E, 39G, 39H, 39I, 39N 39O', 39Q-39T', 39U, 39U', 39V, 39V', 39AA, 39AC, 40AA-40AD, 40BA-40CA, 40DA-40EA, 40FA-40FD, 40GA-40GD, 40HA-40HC, 40IA-40IC, 40JA-40JC, 40KA-40KB, 40LA-40LB, 40MA-40MC, 40N-40N", 40SA-40SD, 40SC'-40SD', 40SE-40SF, 40SE'-40SF', 40SE"-40SE'" may have the shape of an ellipsoid, which may be a spherical ellipsoid. It may also be the boundary of such functional movement restriction devices 110 and/or functional volume filling devices 210 that may have the shape of an ellipsoid, which may be a spherical ellipsoid. In any of the embodiments, the functional movement restriction device 110 or the boundary of the functional movement restriction device 110 may have a total surface area in the range >23 cm2-50 cm2, or in the range 22.5 cm2-45 cm2, or in the range 21 cm2-41 cm2, or in the range 19 cm2-29 cm2, or >41 cm2, or in the range 22.5 cm2-225, or in the range >225-599 cm2, such that the functional movement restriction device 110 functions as a mechanical stop for hindering the lower esophageal sphincter from sliding through the opening in the thoracis diaphragm. In embodiments in which the functional movement restriction device has an elongated shape, such as an ellipsoid, the functional movement restriction device 110 has a height or length L, being a longest cross-sectional distance, and a width W, being a longest cross-sectional distance perpendicular to the length L. The height or length L may be in the range 1.2 times-2 times longer than the width W, or may be in the range 1.3 times-2 times longer than the width W, or may be in the range 1.2 times-1.8 times longer than the width W, or may be in the range 1.3 times-1.6 times longer than the width W.

The height or length L of the functional movement restriction device 110 may be >1 inch or in the range 1 inch-3.5 cm, or in the range 3 cm-5 cm, or may be in the range 3.5 cm-6 cm, or may be in the range 4 cm-5 cm, or may be in the range 4 cm-6 cm for extending a sufficient distance between an area in the vicinity of the angle of His and the fundus for the functional movement restriction device 110 to functions as a mechanical stop for hindering the lower esophageal sphincter from sliding through the opening in the thoracis diaphragm.

FIGS. 40UB and 40UF shows, schematically, examples of the functional movement restriction devices 110 and/or functional volume filling devices 210 having the shape of truncated ellipsoids, i.e. ellipsoids in which the top and bottom portions have been cut-away leaving a flat surface at the top and bottom of the ellipsoid. More specifically, in FIG. 40UF the truncated ellipsoid is an ellipsoid in which the length L is longer than the width W, whereas in FIG. 40UB the truncated ellipsoid is a truncated sphere. Any of the functional movement restriction devices 110 and/or functional volume filling devices 210 shown in FIGS. 1, 2, 3, 4, 5, 6A, 6B, 23B, 23C, 25, 29, 3031A-31F, 32, 33, 34, 35, 36, 37A, 37B, 39C, 39E, 39G, 39H, 39I, 39N-39O', 39Q-39T', 39U, 39U', 39V, 39V', 39AA, 39AC, 40AA-40AD, 40BA-40CA, 40DA-40EA, 40FA-40FD, 40GA-40GD, 40HA-40HC, 40IA-40IC, 40JA-40JC, 40KA-40KB, 40LA-40LB, 40MA-40MC, 40N-40N", 40SA-40SD, 40SC'-40SD', 40SE-40SF, 40SE'-40SF', 40SE"-40SE'" may have the shape of a truncated ellipsoid, which may be a truncated sphere. It may also be the boundary of such functional movement restriction devices 110 and/or functional volume filling devices 210 that may have the shape of a truncated ellipsoid, which may be a truncated sphere.

FIGS. 40UC and 40UG shows, schematically, examples in which at least one part 111 of the functional movement restriction devices 110 and/or at least one part 211 of the functional volume filling devices 210 has the shape of a truncated ellipsoid wedge, i.e. a wedge of a truncated ellipsoids. More specifically, in FIG. 40UG the truncated ellipsoid wedge is a wedge of an ellipsoid in which the length L is longer than the width W, whereas in FIG. 40UB the truncated ellipsoid wedge is a wedge of a truncated sphere. Any of the functional movement restriction devices and/or functional volume filling devices shown in FIGS. 1, 2, 3, 4, 5, 6A, 6B, 23B, 23C, 25, 29, 3031A-31F. 32, 33, 34, 35, 36, 37A, 37B, 39C, 39E, 39G, 39H, 39I, 39N-39O', 39Q-39T', 39U, 39U', 39V, 39V', 39AA, 39AC, 40AA-40AD, 40BA-40CA, 40DA-40EA, 40FA-40FD, 40GA-40GD, 40HA-40HC, 40IA-40IC, 40JA-40JC, 40KA-40KB, 40LA-40LB, 40MA-40MC, 40N-40N". 40SA-40SD, 40SC'-40SD', 40SE-40SF, 40SE'-40SF', 40SE"-40SE'" may be assembled from several parts having the shape of a truncated ellipsoid wedge, which may be a wedge of a truncated sphere. It may also be the boundary of such functional movement restriction devices and/or functional volume filling devices that may be assembled from parts having the shape of a truncated ellipsoid wedge, which may be a wedge of a truncated sphere.

FIGS. 40UC' and 40UG' illustrates the fact that the truncated ellipsoid wedges may be further divided into parts having the shape of a portion of an ellipsoid wedge, which is for example further shown in the embodiment of FIG. 40MA-40MC.

FIG. 40UD' illustrates the fact that parts 111/211 may have the shape of an ellipsoid segment, which is for example further shown in the embodiment of FIG. 40SA-40SD'.

FIGS. 40UH and 40UI shows, schematically, examples in which at least one part 111 of the functional movement restriction devices 110 and/or at least one part 211 of the functional volume filling devices 210 has the shape of a hemi ellipsoid, i.e. half the shape of an ellipsoid. More specifically, in FIG. 40UH the hemi ellipsoid is half of an ellipsoid in which the length L is longer than the width W, whereas in FIG. 40UI the hemi ellipsoid is a hemisphere. Any of the functional movement restriction devices and/or functional volume filling devices shown in FIGS. 1, 2, 3, 4, 5, 6A, 6B, 23B, 23C, 25, 29, 3031A-31F, 32, 33, 34, 35, 36, 37A, 37B, 39C, 39E, 39G, 39H, 39I, 39N-39O', 39Q-39T', 39U, 39U', 39V, 39V', 39AA, 39AC, 40AA-40AD, 40BA-40CA, 40DA-40EA, 40FA-40FD, 40GA-40GD, 40HA-40HC, 40IA-40IC, 40JA-40JC, 40KA-40KB, 40LA-40LB, 40MA-40MC, 40N-40N", 40SA-40SD, 40SC'-40SD', 40SE-40SF, 40SE'-40SF', 40SE"-40SE'" may be assembled from two hemi ellipsoids, which may be hemispheres. It may also be the boundary of such functional movement restriction devices and/or functional volume filling devices that has a hemi ellipsoid shape.

FIGS. 40UH' and 40UI' illustrates the fact that the hemi ellipsoids may be further divided into parts having the shape of a hemi ellipsoid wedge, which may be a wedge of a hemisphere.

The assembled, functional, movement restriction devices (110) and/or volume filling devices (210) and/or parts (111) of the movement restriction devices and/or parts (211) of the volume filling devices of the embodiments described with reference to FIGS. 40AA-40SE''' are suitable made from a biocompatible material that is suitable for long-term implantation in the human body. Alternatively, or additionally, the outer surface of the movement restriction device 110 may be provided with a layer or coating of such a material. Examples of biocompatible materials include titanium or a medical grade metal alloy, such as medical grade stainless steel. In an alternative a ceramic material such as zirconium carbide may be used, or a stiff medical grade polymer material such as Ultra-high-molecular-weight polyethylene (UHMWPE) or Polytetrafluoroethylene (PTFE) or a thermoplastic polyester such as polylactide (PLA). The movement restriction devices (110) and/or volume filling devices (210) and/or parts (111) of the movement restriction devices and/or parts (211) of the volume filling devices could also comprise at least one composite material, such as any combination of metallic/ceramic and polymer materials or a polymer material reinforced with organic or inorganic fibers, such as carbon or mineral fibers. Further, the movement restriction devices (110) and/or volume filling devices (210) and/or parts (111) of the movement restriction devices and/or parts (211) of the volume filling devices may comprise an enclosure made from one of or a combination of: a carbon based material (such as graphite, silicon carbide, or a carbon fiber material), a boron material, a polymer material (such as silicone, Peek®), polyurethane, UHWPE or PTFE,), a SRP-based material, a PPSU-based material, a PSU-based material, a metallic material (such as titanium, stainless steel, tantalum, platinum, niobium or aluminum), a ceramic material (such as zirconium dioxide, aluminum oxide or tungsten carbide) or glass.

Further, the movement restriction devices (110) and/or volume filling devices (210) and/or parts (111) of the movement restriction devices and/or parts (211) of the volume filling devices may be configured to be introduced into the patient's body by means of a gastroscope or an intraluminal instrument, thereby allowing the movement restriction devices (110) and/or volume filling devices (210) and/or parts (111) of the movement restriction devices and/or parts (211) of the volume filling devices to be implanted by means of natural orifice transluminal endoscopic surgery (NOTES). Hence, the movement restriction devices (110) and/or volume filling devices (210) and/or parts (111) of the movement restriction devices and/or parts (211) of the volume filling devices may have a shape and size allowing it to be introduced and pass through a tubular instrument. In some examples, the movement restriction devices (110) and/or volume filling devices (210) and/or parts (111) of the movement restriction devices and/or parts (211) of the volume filling devices may be configured to change its shape, preferably resiliently, to temporarily assume a smallest width that allows the passage through such an instrument.

Methods and compositions for use in combination with the movement restriction devices (110) and/or volume filling devices (210) and/or parts (111) of the movement restriction devices and/or parts (211) of the volume filling devices for the purpose of reducing the risk of migration of the implantable movement restriction device will now be described. The methods and compositions may be used in combination with any movement restriction devices (110) and/or volume filling devices (210) and/or parts (111) of the movement restriction devices and/or parts (211) of the volume filling devices movement restriction devices, such as any of the movement restriction device described with reference to FIGS. 1-20A, 24-38B, 39C-39AJ and 40AA-40I'. The compositions described may further be used in the method described with reference to FIGS. 22A-23K.

According to one aspect, there is provided an apparatus for treating reflux disease of a human patient. The apparatus comprises an implantable movement restriction device (100) configured to be at least partly invaginated by the stomach wall of the patient for restricting the movement of the cardia (22) of the patient (10) towards the thoracic diaphragm (30). The implantable movement restriction device (100) is comprising a surface friction reducing coating covering at least a part of the surface of the implantable movement restriction device. The surface friction reducing coating is configured to reduce the friction between the implantable movement restriction device and the tissue of the stomach wall by which the implantable movement restriction device is at least partially invaginated. It has been realized that the application of a surface friction reducing coating covering at least a part of the surface of the implantable movement restriction device advantageously prevents or reduces the risk of migration of the implantable movement restriction device. When implanted, the surface friction reducing coating maximizes contact with surrounding tissue, and it provides lubrication for the movement restriction device.

Typically, the surface friction reducing coating is covering at least 20%, such as at least 30%, such as at least 40%, such as at least 50%, such as at least 60%, such as at least 70%, such as at least 80%, such as at least 90%, such as at least 95% of the surface of the movement restriction device. According to one embodiment, the surface friction reducing coating is covering the entire surface of the movement restriction device. A higher degree of surface coverage is associated with a higher reduction of the risk of migration of the implantable movement restriction device.

In preferred embodiments, the surface friction reducing coating is selected from natural polymers; polysaccharide coatings, oils, hydrogels, and lubricating jellies.

In certain embodiments, the surface friction reducing coating comprises one or more natural polymers dissolved in water. Preferred natural polymers are selected from polysaccharides, such as native and modified celluloses, native and modified starches, xanthan gum, guar gum, carrageenan, alginate, pectin, and combinations thereof. A preferred polymer is methylcellulose, such as hydroxypropyl methylcellulose (HPMC) and carboxymethylcellulose. Another preferred polymer is ethylcellulose, such as hydroxyethylcellulose.

An example of a useful hydrogel is a poly(propylene fumarate-co-ethylene glycol) hydrogel.

In some embodiments, the surface friction reducing coating is selected from racine oil, mineral oil, glycerin, and polyethylene glycol (PEG). A preferred agent is PEG. It is further preferred to use PEG with larger size (>5 kDa) as it remains in tissues for several days before being cleared.

The surface friction reducing coating may furthermore comprise an active agent selected from bactericides, antibiotics, bacteriostatics, analgesics and anesthetics.

Examples of bactericides and bacteriostatics which are useful in the surface friction reducing coating include antibiotics. Antibiotics are naturally occurring or synthetic substances that are used to kill or inhibit the growth of bacteria. Some examples of antibiotics include penicillin (e.g. penicillin and amoxicillin), cephalosporins (e.g. cephalexin and cefuroxime), macrolides (e.g. erythromycin and azithromycin), tetracyclines (e.g. tetracycline and doxycycline), quinolones (e.g. ciprofloxacin and levofloxacin), sulfonamides (e.g. sulfamethoxazole and trimethoprim), aminoglycosides (e.g. gentamicin and tobramycin). Other examples of bactericides and bacteriostatics which are useful in the surface friction reducing coating include bacteriophages.

Examples of analgesics which are useful in the surface friction reducing coating include anti-inflammatory analgesics (e.g. acetaminophen, aspirin, COX inhibitors, nonsteroidal anti-inflammatory drugs (NSAIDs), such as ibuprofen and naproxen) and opioids (e.g. codeine, fentanyl, hydrocodone, meperidine, methadone, naloxone, naltrexone and oxycodone).

Examples of anesthetics which are useful in the surface friction reducing coating include local anesthetics which can be either ester- or amide-based. Examples of ester local anesthetics include procaine, amethocaine, cocaine, benzocaine, tetracaine. Examples of amide local anesthetics include lidocaine, prilocaine, bupivacaine, levobupivacaine, ropivacaine, mepivacaine, dibucaine and etidocaine. A preferred anesthetic is lidocaine, preferably in a concentration of 1-10% (w/v), such as 1-5% (w/v), such as 1-3% (w/v), such as about 2% (w/v).

In certain embodiments, the surface friction reducing coating provides antiseptic properties to the movement restriction device.

The surface friction reducing coating may also contain pH-adjusting compounds, including weak acids, weak bases and buffers.

In some embodiments, the surface friction reducing coating provides softening of adjacent tissues. This may further prevent or reduce the risk of migration of the implantable movement restriction device.

In certain embodiments, the surface friction reducing coating is a viscous medium. A viscous coating composition is a type of liquid or semi-solid material that is used to create a protective layer or film on a surface. This type of coating is characterized by its thick, sticky consistency, which allows it to adhere to the surface and form a durable, long-lasting layer. There are many different types of viscous coating compositions available, each with its own unique properties and characteristics.

It is preferred that the viscous medium is a viscous aqueous medium, such as a viscous aqueous liquid, such as a viscous aqueous solution. The viscous aqueous medium may be a viscoelastic medium. A preferred viscoelastic medium is a gel. The viscous medium may also be a viscous liquid.

Viscosity can be e.g. determined at 20° C. using a shear rate controlled rheometer (Model 302, Anton Paar, Germany), using a parallel plate geometry (plate diameter 50 mm, gap 100 μm). In this setup, the viscosity of water is approximately constant at 1 mPa·s, at shear rates between 0-100 s-1. For avoidance of doubt, viscous media as defined herein are considerably more viscous than water. Viscous media as defined herein typically exhibit a viscosity of at least 10 mPa·s, such as at least 50 mPa·s at shear rates between 0-100 s-1, such as at 50 s-1. Preferably, viscous media as defined herein exhibit a viscosity of at least 100 mPa·s, such as at least 200 mPa·s at shear rates between 0-100 s-1, such as at 50 s-1. The specific values above are relevant for this specific setup, but the skilled person can easily determine corresponding values for viscosity in other experimental setups. Typically, the surface friction reducing coating has a higher viscosity than water.

The surface friction reducing coating may comprise preservatives. Examples of preservatives include antimicrobial preservatives, e.g. sorbic acid, parabens and lactic acid. A preferred type of preservatives is parabens, e.g. methylparaben and propylparaben.

Preferably, the surface friction reducing coating is configured to remain in a pouch for housing the implantable movement restriction device for a time period exceeding 7 days, preferably exceeding 14 days, such as exceeding 21 days or 28 days.

Specific examples of the surface friction reducing coating are:

(1) Xylocaine jelly, containing 0.1-10% (w/v) xylocaine (lidocaine hydrochloride). The composition also contains methylparaben, propylparaben, hydroxypropyl methylcellulose, and sodium hydroxide and/or hydrochloric acid to adjust pH to 6.0-7.0.
(2) Xylocaine viscous composition, containing 0.1-10% (w/v) xylocaine (lidocaine hydrochloride). The composition also contains carboxymethylcellulose sodium, methylparaben, propylparaben, purified water and saccharin sodium.
(3) Surgical lubricant, containing hydroxypropyl methylcellulose, propylene glycol, chlorhexidine gluconate, and sterile water.
(4) Poly(propylene fumarate-co-ethylene glycol) hydrogels
(5) Polyethylene glycol (PEG) polymers, >5 kDa
(6) Lubricating glycerin jelly, containing water, PEG, glycerin, carbomer, sodium hydroxide, methylparaben, propylparaben.
(7) Lidocaine jelly, containing 0.1-10% (w/v) lidocaine hydrochloride. The composition also contains glycerol, hydrochloric acid, hydroxyethylcellulose, sodium hydroxide, and water.

In some embodiments disclosed herein, the implantable movement restriction device has a size such that the implantable movement restriction device can be fully invaginated by the fundus wall of the patient as set out herein. Preferably, the implantable movement restriction device has a size of less than 200 cm3, preferably less than 100 cm3, and more preferably less than 50 cm3, or a volume in the range 7.3 cm3-8 cm3, or a volume in the range >6.6 cm3-<7.3 cm3, or a volume in the range >5.8 cm3-6.6 cm, or a volume in the range 5.0 cm3-5.8 cm3, or a volume in the range >8 cm3-<200 cm3.

In certain embodiments disclosed herein, the movement restriction device is elongated. A first cross-sectional distance has a first length, and a second cross-sectional distance has a second length, wherein the first length is more than 1.2 times the second length, preferably more than 1.5 times the second length and even more preferably more than 2 times the second length.

In some embodiments disclosed herein, implantable movement restriction device (100) comprises at least one circular cross-section. In certain embodiments, the implantable movement restriction device (100) comprises a first, second and third cross-section in planes spaced apart and parallel to each other, wherein the first and third cross-sections have the same area, and the second cross-section is located between the first and third cross-section and have a smaller area.

In certain embodiments disclosed herein, the implantable movement restriction device comprises at least two parts, or at least three parts, or at least 4 parts. Optionally, the at least two parts are configured to be assembled to form the implantable movement restriction device. Further optionally, the at least two parts are configured to be connected to each other to form the implantable movement restriction device.

In some embodiments disclosed herein, the movement restriction device comprises a curved cross-section in a plane parallel to the transverse plane of the patient, and wherein the curve is configured to partially enclose the esophagus of the patient. Advantageously, the movement restriction device is configured to encircle at least ⅓ of the esophagus in a plane parallel to the transverse plane of the patient, and preferably at least ½ of the esophagus in a plane parallel to the transverse plane of the patient. In certain embodiments disclosed herein, the movement restriction device comprises a C-shaped cross-section in a plane parallel to the transverse plane of the patient, and wherein the C-shaped cross-section is configured to partially enclose the esophagus of the patient. Optionally, the movement restriction device is configured to encircle at least ⅔ of the esophagus in a plane parallel to the transverse plane of the patient. In specific embodiments, a cross-section of the movement restriction device in a plane parallel to the transverse plane of the patient comprises a closed curve configured to enclose the esophagus of the patient.

In some embodiments disclosed herein, the implantable movement restriction device (100) comprises at least one circular cross-section.

According to related aspects, there is also provided a method for treating reflux disease of a human patient by implanting a movement restriction device (100). The method comprises: at least partially invaginating the movement restriction device in the stomach of the patient such that the movement restriction device restricts movement of the cardia (22) of the patient's stomach (10) towards the thoracic diaphragm (30) to hinder the cardia from sliding through the diaphragm opening (32) into the patient's thorax, wherein the surface of the movement restriction device is at least partially covered by a surface friction reducing coating.

There is furthermore provided a friction-reducing composition for use in the method as defined herein as a surface friction reducing coating.

There is also provided a use of a composition selected from natural polymers, polysaccharide coatings, oils, hydrogels, and lubricating jellies as a surface friction reducing coating of at least part of the surface of an implantable movement restriction device for treating reflux disease of a human patient, wherein the movement restriction device (100) is configured to be at least partially invaginated by a stomach wall of a patient and arranged to restrict movement of the cardia (22) of a patient's stomach (10) towards the diaphragm (30) to hinder the cardia from sliding through the diaphragm opening (32) into the patient's thorax.

When implanted, the surface friction reducing coating maximizes contact with surrounding tissue, and it provides lubrication for the movement restriction device.

In certain embodiments, the method comprises the step of applying the surface friction reducing coating onto the movement restriction device prior to implantation in the body of the patient. This implies that the coating is applied cx vivo. In other embodiments, the method comprises the step applying the surface friction reducing coating in situ between the movement restriction device and tissue of the stomach wall of the patient.

In some embodiments, the method comprises the steps of:

partially invaginating the movement restriction device in the stomach of the patient.

applying the surface friction reducing coating in situ between the movement restriction device and tissue of the stomach wall of the patient, and further invaginating the movement restriction device in the stomach of the patient.

Optionally, the step of at least partially invaginating the movement restriction device in the stomach of the patient comprises fully invaginating the movement restriction device in the stomach of the patient.

In certain embodiments, the method is a laparoscopic surgical method, and the method further comprises the step of introducing the movement restriction device into the body of the patient through a laparoscopic trocar after the surface friction reducing coating has been applied.

In other embodiments, the method is a laparoscopic surgical method, and the step of applying the surface friction reducing coating in situ between the movement restriction device and tissue of the stomach wall of the patient comprises applying the surface friction reducing coating in situ using a laparoscopic instrument inserted into the body of the patient though a laparoscopic trocar.

In some embodiments, the method is a gastroscopic method, and the method further comprises the step of introducing the movement restriction device into the body of the patient through the esophagus of the patient after the surface friction reducing coating has been applied.

In certain embodiments, the method is a gastroscopic method, and the step of applying the surface friction reducing coating in situ between the movement restriction device and tissue of the stomach wall of the patient comprises applying the surface friction reducing coating in situ using a gastroscopic instrument inserted into the body of the patient though the esophagus.

Typically, the surface friction reducing coating is covering at least 20%, such as at least 30%, such as at least 40%, such as at least 50%, such as at least 60%, such as at least 70%, such as at least 80%, such as at least 90%, such as at least 95% of the surface of the movement restriction device. According to one embodiment, the surface friction reducing coating is covering the entire surface of the movement restriction device. A higher degree of surface coverage is associated with a higher reduction of the risk of migration of the implantable movement restriction device.

In some embodiments, the step of at least partially invaginating a movement restriction device comprises at least partially invaginating a movement restriction device comprising a surface friction reducing coating covering the entire surface of the movement restriction device.

In preferred embodiments, the step of at least partially invaginating a movement restriction device comprises at least partially invaginating a movement restriction device comprising a surface friction reducing coating selected from natural polymers, polysaccharide coatings, oils, hydrogels, and lubricating jellies.

In certain embodiments, the surface friction reducing coating comprises one or more natural polymers dissolved in water. Preferred natural polymers are selected from polysaccharides, such as native and modified celluloses, native and modified starches, xanthan gum, guar gum, carrageenan, alginate, pectin, and combinations thereof. A preferred polymer is methylcellulose, such as hydroxypropyl methylcellulose (HPMC) and carboxymethylcellulose. Another preferred polymer is ethylcellulose, such as hydroxyethylcellulose.

An example of a useful hydrogel is a poly(propylene fumarate-co-ethylene glycol) hydrogel.

In some embodiments, the surface friction reducing coating is selected from racine oil, mineral oil, glycerin, and polyethylene glycol (PEG). A preferred agent is PEG. It is further preferred to use PEG with larger size (>5 kDa) as it remains in tissues for several days before being cleared.

The surface friction reducing coating may furthermore comprise an active agent selected from bactericides, antibiotics, bacteriostatics, analgesics and anesthetics.

Examples of bactericides and bacteriostatics which are useful in the surface friction reducing coating include antibiotics. Antibiotics are naturally occurring or synthetic substances that are used to kill or inhibit the growth of bacteria. Some examples of antibiotics include penicillin (e.g. penicillin and amoxicillin), cephalosporins (e.g. cephalexin and cefuroxime), macrolides (e.g. erythromycin and azithromycin), tetracyclines (e.g. tetracycline and doxycycline), quinolones (e.g. ciprofloxacin and levofloxacin), sulfonamides (e.g. sulfamethoxazole and trimethoprim), aminoglycosides (e.g. gentamicin and tobramycin). Other examples of bactericides and bacteriostatics which are useful in the surface friction reducing coating include bacteriophages.

Examples of analgesics which are useful in the surface friction reducing coating include anti-inflammatory analgesics (e.g. acetaminophen, aspirin, COX inhibitors, nonsteroidal anti-inflammatory drugs (NSAIDs), such as ibuprofen and naproxen) and opioids (e.g. codeine, fentanyl, hydrocodone, meperidine, methadone, naloxone, naltrexone and oxycodone).

Examples of anesthetics which are useful in the surface friction reducing coating include local anesthetics which can be either ester- or amide-based. Examples of ester local anesthetics include procaine, amethocaine, cocaine, benzocaine, tetracaine. Examples of amide local anesthetics include lidocaine, prilocaine, bupivacaine, levobupivacaine, ropivacaine, mepivacaine, dibucaine and etidocaine. A preferred anesthetic is lidocaine, preferably in a concentration of 1-10% (w/v), such as 1-5% (w/v), such as 1-3% (w/v), such as about 2% (w/v).

In certain embodiments, the surface friction reducing coating provides antiseptic properties to the movement restriction device.

The surface friction reducing coating may also contain pH-adjusting compounds, including weak acids, weak bases and buffers.

In some embodiments, the surface friction reducing coating provides softening of adjacent tissues. This may further prevent or reduce the risk of migration of the implantable movement restriction device.

In certain embodiments, the surface friction reducing coating is a viscous medium. A viscous coating composition is a type of liquid or semi-solid material that is used to create a protective layer or film on a surface. This type of coating is characterized by its thick, sticky consistency, which allows it to adhere to the surface and form a durable, long-lasting layer. There are many different types of viscous coating compositions available, each with its own unique properties and characteristics.

It is preferred that the viscous medium is a viscous aqueous medium, such as a viscous aqueous liquid, such as a viscous aqueous solution. The viscous aqueous medium may be a viscoelastic medium. A preferred viscoelastic medium is a gel. The viscous medium may also be a viscous liquid.

Viscosity can be e.g. determined at 20° C. using a shear rate controlled rheometer (Model 302, Anton Paar, Germany), using a parallel plate geometry (plate diameter 50 mm, gap 100 μm). In this setup, the viscosity of water is approximately constant at 1 mPa·s, at shear rates between 0-100 s-1. For avoidance of doubt, viscous media as defined herein are considerably more viscous than water. Viscous media as defined herein typically exhibit a viscosity of at least 10 mPa·s, such as at least 50 mPa·s at shear rates between 0-100 s-1, such as at 50 s-1. Preferably, viscous media as defined herein exhibit a viscosity of at least 100 mPa·s, such as at least 200 mPa·s at shear rates between 0-100 s-1, such as at 50 s-1. The specific values above are relevant for this specific setup, but the skilled person can easily determine corresponding values for viscosity in other experimental setups. Typically, the surface friction reducing coating has a higher viscosity than water.

The surface friction reducing coating may comprise preservatives. Examples of preservatives include antimicrobial preservatives, e.g. sorbic acid, parabens and lactic acid. A preferred type of preservatives is parabens, e.g. methylparaben and propylparaben.

Preferably, the surface friction reducing coating is configured to remain in a pouch for housing the implantable movement restriction device for a time period exceeding 7 days, preferably exceeding 14 days, such as exceeding 21 days or 28 days.

Specific examples of the surface friction reducing coating are:

(1) Xylocaine jelly, containing 0.1-10% (w/v) xylocaine (lidocaine hydrochloride). The composition also contains methylparaben, propylparaben, hydroxypropyl methylcellulose, and sodium hydroxide and/or hydrochloric acid to adjust pH to 6.0-7.0.

(2) Xylocaine viscous composition, containing 0.1-10% (w/v) xylocaine (lidocaine hydrochloride). The composition also contains carboxymethylcellulose sodium, methylparaben, propylparaben, purified water and saccharin sodium.

(3) Surgical lubricant, containing hydroxypropyl methylcellulose, propylene glycol, chlorhexidine gluconate, and sterile water.

(4) Poly(propylene fumarate-co-ethylene glycol) hydrogels (5) Polyethylene glycol (PEG) polymers, >5 kDa (6) Lubricating glycerin jelly, containing water, PEG, glycerin, carbomer, sodium hydroxide, methylparaben, propylparaben.

(7) Lidocaine jelly, containing 0.1-10% (w/v) lidocaine hydrochloride. The composition also contains glycerol, hydrochloric acid, hydroxyethylcellulose, sodium hydroxide, and water.

In some embodiments disclosed herein, the implantable movement restriction device has a size such that the implantable movement restriction device can be fully invaginated by the fundus wall of the patient as set out herein. Preferably, the implantable movement restriction device has a size of less than 200 cm2, preferably less than 100 cm2, and more preferably less than 50 cm2. The step of at least partially invaginating a movement restriction device may comprise at least partially invaginating a movement restriction device having a size such that the implantable movement restriction device can be fully invaginated by the fundus wall of the patient. Preferably, the step of at least partially invaginating a movement restriction device comprises at least partially invaginating a movement restriction device having a size of less than 200 cm2, preferably less than 100 cm2, and more preferably less than 50 cm2.

In some embodiments, the step of at least partially invaginating a movement restriction device comprises at least partially invaginating a movement restriction device being elongated and having a first cross-sectional distance having a first length, and a second cross-sectional distance having a second length, and wherein the first length is more than 1.2 times the second length, preferably more than 1.5 times the second length and even more preferably more than 2 times the second length.

In certain embodiments, the step of at least partially invaginating a movement restriction device comprises at least partially invaginating a movement restriction device comprising at least one circular cross-section.

In some embodiments, the step of at least partially invaginating a movement restriction device comprises at least partially invaginating a movement restriction device comprising a first, second and third cross-section in planes spaced apart and parallel to each other, wherein the first and third cross-sections have the same area, and the second cross-section is located between the first and third cross-section and have a smaller area.

In certain embodiments, the step of at least partially invaginating a movement restriction device comprises at least partially invaginating a movement restriction device comprising at least two parts, or at least three parts, or at least 4 parts. Preferably, the step of at least partially invaginating a movement restriction device comprises assembling at least two parts for forming the implantable movement restriction device.

In some embodiments, the step of at least partially invaginating a movement restriction device comprises at least partially invaginating a movement restriction device comprising a curved cross-section in a plane parallel to the transverse plane of the patient, and wherein the curve is configured to partially enclose the esophagus of the patient.

In certain embodiments, the step of at least partially invaginating a movement restriction device comprises at least partially invaginating a movement restriction device comprising at least one circular cross-section.

Figure 41A:
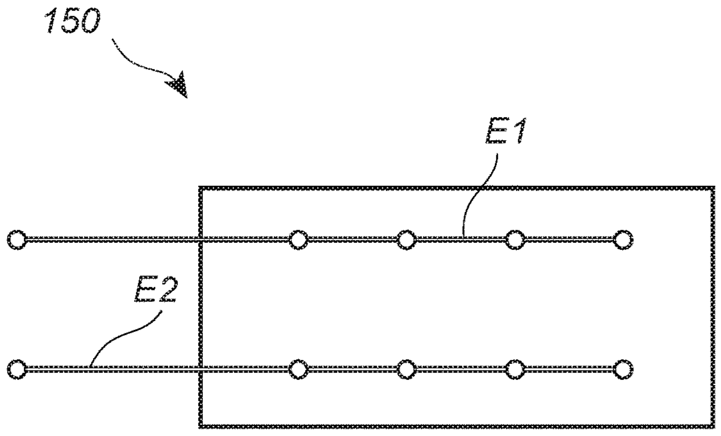
FIGS. 41A-D show various examples of electrode arrangements for electrically stimulating muscle tissue of the patient.
Figure 41B:
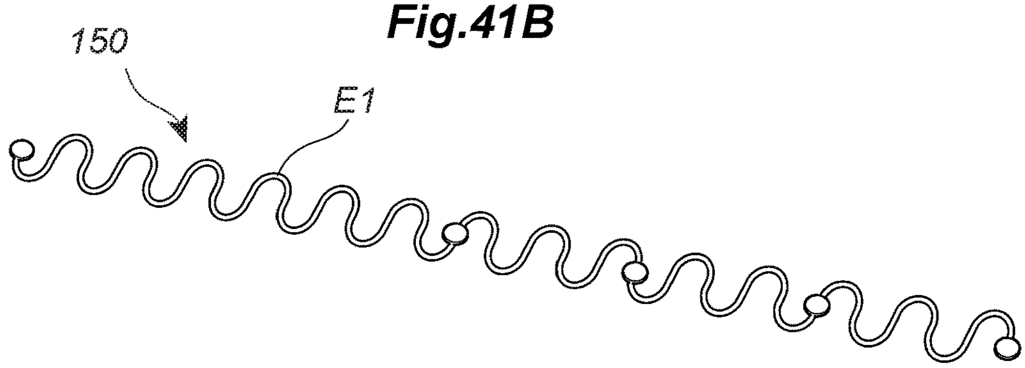
Figure 41C:
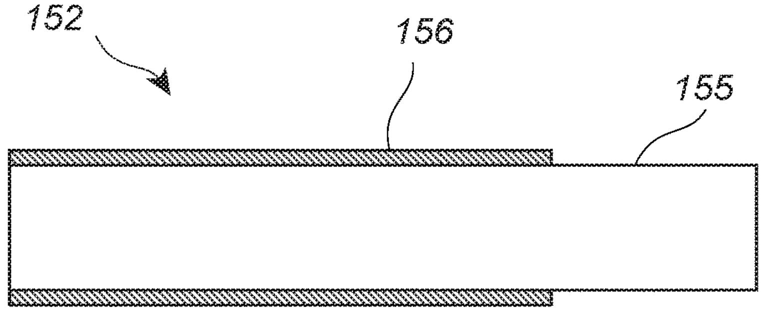
Figure 41D:
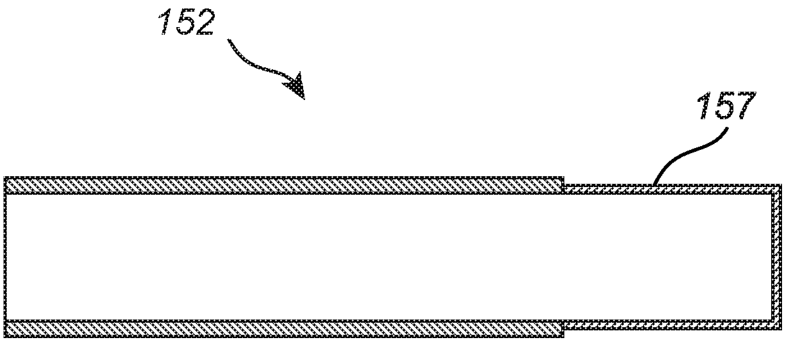

FIG. 41A is an example of a bipolar electrode arrangement 150, comprising a first and a second electrode element 152, 154 which may be similarly configured as the electrode elements discussed with reference to any of the previous embodiments. In the following figures, the first and second electrode elements will be distinguished by reference numerals E1 and E2, respectively. The first and second electrode elements E1, E2 may be connected to different electrical potentials. Thus, the first electrode element E1 can be operated as an anode and the second electrode element E2 can be operated as a cathode. In alternative embodiments, however, both electrode elements E1, E2 may be operated as cathodes, while using the tissue of the body as anode. The electrode elements E1, E2 may be attached directly to an outer surface of the implantable device, such as disclosed with reference to FIGS. 38A and 38B. In some examples the electrode elements E1, E2 may be arranged on a support, such as a flexible patch, which may be configured to be attached to the implantable constriction device. The electrode arrangement 150 can be arranged between the implantable constriction device and the tissue (such as disclosed with reference to FIGS. 38*a* and 38*b*) and may in some examples be provided as a separate, physically distinct item and in other examples be integrated in the apparatus 100. The electrode arrangement 150 may comprise one or several contact pads for increasing the contact surface between the electrode and the tissue when implanted. During operation, the electrical signal may be delivered to the muscle tissue by means of the first and second electrode elements E1, E2 so as to stimulate contraction of the muscle cells.

FIG. 40B is another example of an electrode arrangement 150, which in the present example may be a unipolar electrode element 152, 154. The electrode element E1 may for example be operated as a cathode when implanted. The electrode element 152 may be formed of a flat, coiled wire for increasing the contact surface between the electrode element 152 and the tissue. Further, the coiled configuration allows for a certain mechanical flexibility of the electrode element 152 such that it can follow the muscle tissue during contraction and relaxation.

FIG. 40C illustrates the end portion of a needle- or pin-shaped electrode arrangement 150, wherein the active portion of the electrode element 152 is provided as a bare electrode surface 155 at the end of the electrode element 152, protruding from an insulation 156 covering the rest of the electrode element 152. Thus, when implanted at or in the muscle tissue, the active, bare electrode surface 155 of the electrode element 152 may form a metal-tissue interface with the muscle tissue, wherein the interface may surround the end portion of the electrode element 152 so as to provide a relatively large contact surface. The present example is advantageous in that it can be inserted into the tissue, thereby allowing for a selective stimulation at a certain depth of the tissue.

FIG. 40D shows a similar electrode element 152 as the one in FIG. 40C, with the difference that the present electrode element 152 comprises an active portion that is covered by a dielectric material 157 so as to protect the electrode material from deterioration and to facilitate capacitive current transfer. The dielectric material 157 may for example be electrochemically deposited tantalum oxide, which allows the electrical charge to pass through the interface but reduces the risk for electrode corrosion, gas formation and metabolite reactions.

It will be appreciated that both faradaic and capacitive mechanisms may be present at the same time, irrespectively of the type of electrode used. Thus, capacitive charge transfer may be present also for a bare electrode forming a metal-tissue interface, and faradaic charge transfer may be present also for a coated electrode forming a dielectric-tissue interface. It has been found that the faradaic portion of the current delivered to the muscle tissue can be reduced or even eliminated by reducing the duration of the pulses of the electric signal. Reducing the pulse duration has turned out to be an efficient way of increasing the portion of the signal which can be passed through the interface as a capacitive current, rather than by a faradaic current. As a result, shorter pulses may produce less electrode and tissue damage.

The capacitive portion of the current may further be increased, relative to the faradaic portion, by reducing the amplitude of the current pulses of the electrical signal. Reducing the amplitude may reduce or suppress the chemical reactions at the interface between the electrode and the tissue, thereby reducing potential damage that may be caused by compounds and ions generated by such reactions.

In one example, the electrical stimulation may be controlled in such a manner that a positive pulse of the electrical signal is followed by a negative pulse (or, put differently, a pulse of a first polarity being followed by a pulse of a second, reversed polarity), preferably of the same amplitude and/or duration. Advantageously, the subsequent negative (or reversed) pulse may be used to reverse or at least moderate chemical reactions or changes taking place in the interface in response to the first, positive pulse. By generating a reversed pulse, the risk of deterioration of the electrode and/or the tissue at the interface between the electrode and the muscle tissue may be reduced.

Figure 42A:
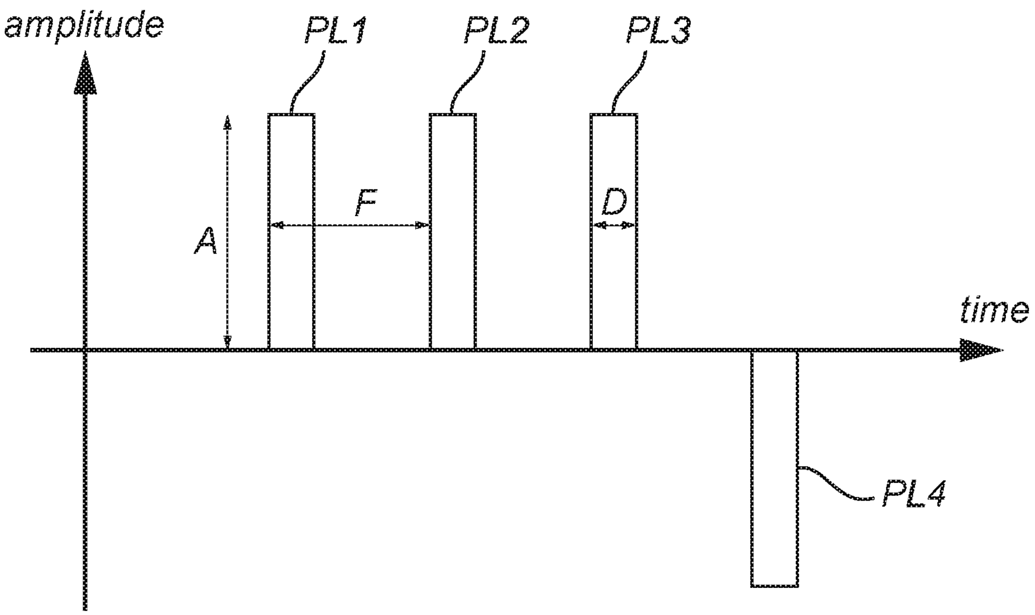
FIGS. 42A-42B illustrate a pulsed signal for electrically stimulating muscle tissue.

FIG. 42A shows an example of a pulsed electrical signal to be applied to an electrode for electrically stimulating muscle tissue via an electrode-tissue interface as discussed above. The electrical signal may be generated by a stimulation controller arranged outside the body or implanted in the body (as described with reference to FIGS. 38A and 38B). The stimulation controller 170 may be operatively connected to the electrode element 152, 154 by means of a lead 172, and the electrical signal shown in the present figure may either reflect the signal as generated at the stimulation controller 170, or the signal as delivered to the electrode element 152, 154 at the electrode-tissue interface. The characteristics of the electrical signal may be selected and varied determined on the electrical and properties at the electrode-tissue interface and on the actual response of the tissue. The electrical stimulation delivered to the muscle cells may depend on several factors, such as the configuration and placement of the electrode element 152, 154 at the tissue, the presence of fibrous material at the interface, the composition of the electrolyte in the interface, accumulation of non-conducting material on the electrode surfaces, etcetera. It is therefore suggested that the characteristics of the electric signal, as shown in the present figure, be selected, and varied based on an observed or estimated response from the stimulated tissue.

In the present example, the electrical signal is a pulsed signal comprising square waves PL1, PL2, PL3, PL4. However, other shapes of the pulses may be employed as well. The pulse signal may be periodic, as shown, or may be intermittent (i.e., multiple series of pulses separated by periods of no pulses). The pulses may have an amplitude A, which may be measured in volts, ampere, or the like. Each of the pulses of the signal may have a pulse width D. Likewise, if the signal is periodic, the pulse signal may have a period F that corresponds to a frequency of the signal. Further, the pulses may be either positive or negative in relation to a reference.

The pulse frequency may for example lie within the range of 0.01-150 hertz. More specifically, the pulse frequency may lie within at least one of the ranges of 0.1-1 Hz, 1-10 Hz., 10-50 Hz. and 50-150 Hz. It has been observed that relatively low pulse frequencies may be employed to imitate or enhance the slow wave potential associated with pacemaker cells of the smooth muscle tissue. Thus, it may be advantageous to use relatively low pulse frequencies, such as 0.01-0.1 Hz or frequencies below 1 Hz or a few Hz for such applications.

The pulse duration may for example lie within the range of 0.01-100 milliseconds, such as 0.1-20 milliseconds (ms), and preferably such as 1-5 ms. The natural muscle action potential has in some studies been observed to last about 2-4 ms, so it may be advantageous to use a pulse duration imitating that range.

The amplitude may for example lie within the range of 1-15 milliamperes (mA), such as 0.5-5 mA in which range a particularly good muscle contraction response has been observed in some studies.

In a preferred, specific example the electrical stimulation may hence be performed using a pulsed signal having a pulse frequency of 10 Hz, a pulse duration of 3 ms and an amplitude of 3 mA.

Figure 42B:
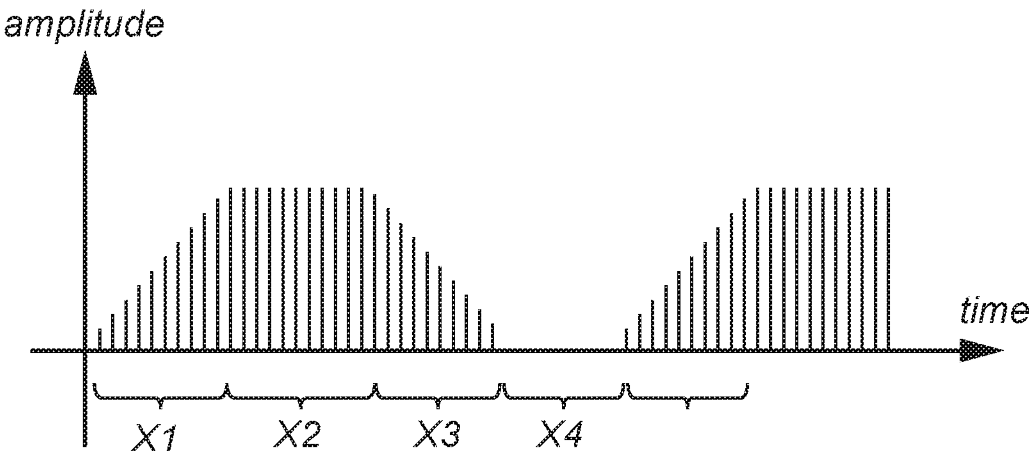

FIG. 42B shows an example of a pulsed signal, comprising build-up period X1, in which the amplitude is gradually increasing, a stimulation period X2 during which the muscle tissue is exposed to a contracting stimulation signal, a ramp down period X3 in which the amplitude is gradually decreasing, and a stimulation pause X4 before a new build-up period is initiated. The build-up period may for example be 0.01-2 seconds, the stimulation period 1-60 seconds, the ramp-down period 0.01-2 seconds, and the stimulation pause 0.01-60 seconds. The pulse frequency may for example be 1-50 Hz, the pulse duration 0.1-10 milliseconds and the amplitude during the stimulation period be 1-15 milliampere. The stimulation of skeletal muscle tissue may for example be performed using a frequency of 50 Hz. and pulses having a duration of 100 μs. The current amplitude may be 1, 2.5, 7.5 or 10 mA. In particular, a desired muscle contraction response has been experimentally observed within a range of 0.5 to 5.0 mA. In the present example, a coiled electrode may be used as a cathode. Another example design is a multi-stranded wire arranged in a helical design. They can be imbricated in the muscular wall of the fundus (or esophagus) and can be stimulated in any desired pattern. The stimulus parameters may for example be biphasic pulses, 10 to 40 Hz, lasting 0.1 to 5 ms, with a current density of 3 to 5 mA/cm2.

Figure 43:
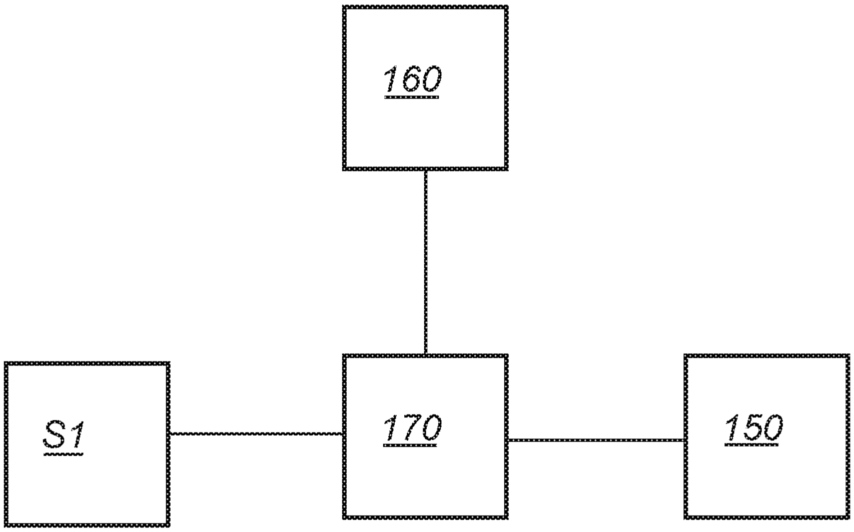
FIGS. 43-45 are schematic illustrations of systems for treating reflux disease.

FIG. 43 is a schematic outline of a system for electrically stimulating or exercising muscle cells to increase tolerance of the tissue for pressure from the apparatus 100. The system may be used in combination with the implantable apparatus 100 and may in some examples be comprised in such an apparatus 100. The system may comprise an electrode arrangement 150 which may be similarly configured as the electrodes arrangements/electrode elements discussed above in connection with the previous examples, an energy source 160 for providing the electrical energy required for generating the electrical signal, and a stimulation controller 170 controlling the generation of the electrical signal.

The electrode arrangement 150, which may comprise one or several electrode elements 152, 154, such as a bare electrode or an electrode at least partly covered by a dielectric material 157 shown in FIG. 39*d*, may be configured to be implanted in the muscle tissue to be stimulated, or to engage the muscle, so as to form an electrode-tissue interface through which the stimulating signal may be transferred. Alternatively, or additionally, the electrode element 152, 154 may be arranged in close vicinity to the muscle tissue such that an electrical coupling between the electrode element and the muscle tissue may be established. This may for example be the case when other tissue, such as connective tissue, is present between the implanted device and the muscle tissue.

The electrode may be electrically connected to the energy source 160, for example by means of a wiring or a lead 172, such that the electrical signal may be transferred to the electrode-tissue interface. In some examples, the electrode 152, 154 may be integrated with or attached to the apparatus, such as the movement restriction device 110, so that the electrode 152, 154 when implanted in the patient is arranged at the interface between the apparatus 100 and the muscle tissue. The electrode 152, 154 can thereby be used for exercising the muscle tissue that is mechanically affected by the implant.

The energy source 160 may for example be of a non-rechargeable type, such as a primary cell, or of a rechargeable type, such as a secondary cell. The energy source 160 may be rechargeable by energy transmitted from outside the body, from an external energy source, or be replaced by surgery. Further, the electrode arrangement 150 may be operably connected to a stimulation controller 170, which may comprise an electrical pulse generator, for generating the electrical pulse. The stimulation controller 170 may be integrated with the energy source 160 or provided as a separate, physically distinct unit which may be configured to be implanted in the body or operate from the outside of the body. In case of the latter, is may be advantageous to allow the external control unit to communicate wirelessly with the stimulation controller 150.

The system may according to some examples comprise a sensor S1 that is configured to sense a physical parameter of the body and/or the apparatus 100. The sensor S1 may for example be employed to sense or detect a bodily response to the electrical stimulation, such as for example a contraction of the stimulated muscle tissue. In an example, the sensor S1 may be configured to sense action potentials that are being sent to the muscle tissue. The action potentials may for example be generated by pacemaker cells of the muscle tissue, which may be registered by the sensor S1 and transmitted to the stimulation controller 170. The stimulation controller 170 may use the received signal when controlling the energy source 160, such that the generated electrical signal amplifies the sensed action potentials.

The energy source 160 may preferably be an implantable energy source 160 configured to be placed on the inside of the patient's body. Preferably, the implantable energy source 160 may comprise a secondary cell, which can be charged from the outside of the body so as to reduce the need for surgical battery replacement procedures. As indicated in the present figure, the implantable energy source 160 may be configured to be supplied with electrical energy from an external energy source 165 arranged outside the body. In such an example, the system may further comprise an implantable charger 190 configured to be electrically connected to the implantable energy source 160 and to enable charging of the implantable energy source 160 by the external energy source 165. The implantable charger 190 may for example be configured to be electrically connected to the implantable energy source 160 by means of a wiring or a lead 172, such that the electrical energy may be transferred from the implantable charger 190 to the implantable energy source 160. The implantable charger 190 may further be coupled to the external energy source 165 by a wireless coupling or by a wired coupling, using a wiring or lead 172 which may be similar to the one between the charger 190 and the implantable energy source 160. In case of the latter, the wiring or lead 172 may terminate in a terminal which may be access via the skin of the patient, either as a contact port surfacing the skin or being arranged under the skin. Electrical energy may then be transmitted to the charger 190 by connecting the external energy source 165 to the port, for example by incising the skin to expose the port and making it possible for the external energy source 165 to be plugged in.

Alternatively, the implantable charger 190 may be configured to receive energy from the external energy source 165 wirelessly, such as for example inductively. In this case, the charger 190 may comprise an electromagnetic coil configured to receive the electrical power wirelessly from the external energy source 165. The charger 190 may for example be arranged subcutaneously so as to facilitate inductive transfer of the energy via the skin of the patient.

The charging of the implantable energy source 160 may be controlled according to several different schemes. In an example, the charging of the implantable energy source 160 may be controlled by controlling the receipt of electrical power, from the external energy source, at the implantable charger 190. Put differently, the charger 190 may be configured to vary or control its capability of receiving electrical energy from the external energy source 165. Hence, the amount of electrical power delivered to the implantable energy source 160 may be regulated at the implantable charger 190 rather than at the external energy source 165, which hence may be allowed to transmit a substantially constant power. By varying the receipt at the charger 190, rather than the transmission at the external power source 165, the charging of the implantable energy source 160 may be performed without sending control signals to the external energy source 165. Instead, the intelligence required for regulating and controlling the charging of the implanted energy source 160 may be accommodated within the body of the patient, without the need of communication with the outside of the body.

In an alternative embodiment, the charging of the implantable energy source 160 may be controlled by controlling the transmission of electrical power at the external energy source 165. Thus, the charger 190 (or any other component of the apparatus/system arranged in the body) may send transmission instructions, for example via a control signal, to the external energy source 165 which may regulate its transmitting power accordingly.

The charging of the implantable energy source 160 may be controlled by the controller 170, which hence may be configured to issue control instructions to the implantable charger 190 and/or the external energy source 165, as discussed above. In some examples, the controller 170 may be configured to indicate a functional status of the implantable energy source 160, such as for example charge level, charging capacity, voltage and/or temperature of the implantable energy source 160. The functional status may for example be used for controlling the charging of the implantable energy source 160 as described above, and for indicating the status of the implantable energy source 160 to the patient or another, external entity such as medical staff. The functional status may for example be transmitted to the outside of the body, where it can be interpreted and used for diagnosis of the status/condition of the implanted apparatus. Further, the functional status may be transmitted to the outside of the body to provide a warning signal, for example indicating low battery or overheating. The transmission of a signal to/from the controller 170 is described in further detail in connection with the following FIGS. 44-48.

The functional status may for example be based on a signal from a sensor, such as a temperature sensor configured to sense a temperature of the implanted energy source 160, or a current or voltage meter configured to measure an electrical condition of the implanted energy source 160. The sensor output may be transmitted to the controller 170, for example by means of a wiring or lead 172, where it can be processed and acted upon in the form of an issued signal comprising control instructions for the charger 190/external energy source 165 and/or functional status information.

The functional status may in some examples be transmitted via a carrier signal to the outside of the body by means of a transmitter, which for example may be arranged subcutaneously. In some example the transmitter may be integrated in the charger 190.

Figure 44:
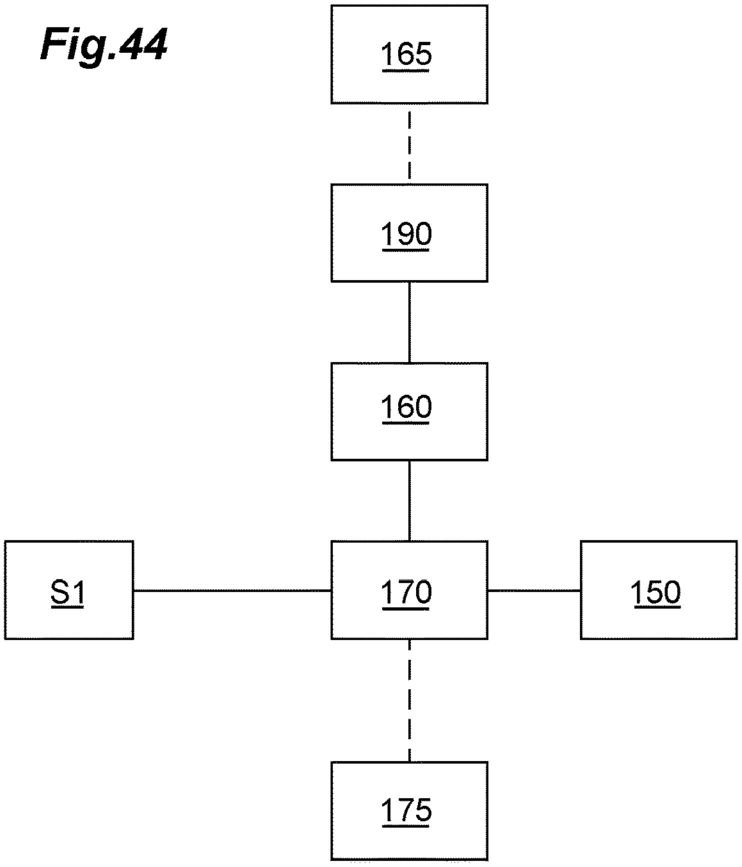

FIG. 44 shows a similar embodiment as the system described above with reference to FIG. 43. However, as indicated in the present figure, the system may further comprise an external signal transmitter 175, such as a wireless remote 175, which may be configured to be operably connected to the controller 170. The external signal transmitter 175 may be arranged to allow for the patient or another external entity, such as a service technician or medical staff, to interact with the controller 170. The external signal transmitter 175 may for example be used to control, or adjust, the operation of the implanted controller 170 in order to affect or adjust the electrical stimulation signal delivered to the tissue by the electrode arrangement 150. The external control of the controller 170 may for example serve the purpose of increasing or reducing an amplitude or frequency of the electrical stimulation signal, or for activating/deactivating the electrical stimulation. In an example, the external signal transmitter 175 may be used for increasing the electrical stimulation of the cardiac sphincter in response to experienced reflux symptoms. In this way, the patient may be allowed to increase the contraction of the cardiac sphincter so as to further hinder stomach contents from rising in the esophagus.

The signal, by which the external signal transmitter 175 is communicating with the implanted controller 170, may be selected from the group consisting of: a sound signal, an ultrasound signal, an electromagnetic signal, and infrared signal, a visible light signal, an ultra-violet light signal, a laser signal, a microwave signal, a radio wave signal, an X-ray radiation signal and a gamma radiation signal.

While illustrated as separate components/entities in the figure, it is appreciated that the implanted, or internal, controller 170 may be integrated in the implantable charger 190 and/or in the implantable energy source 160. Further, the external signal transmitter 175 may be integrated in the wireless remote.

Figure 45:
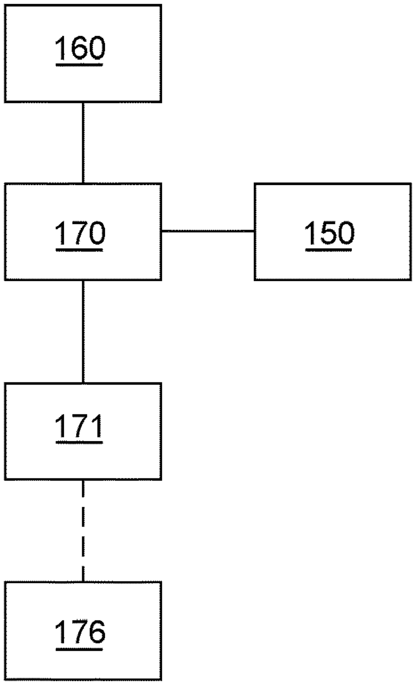

FIG. 45 is a schematic diagram of a system, or an apparatus, which may be similarly configured as the system described with reference to FIGS. 43 and 44. Hence, a system is disclosed, comprising an electrode arrangement 150 for exercising muscle tissue affected by an implanted apparatus according to any of the embodiments discussed above in connection with FIGS. 1-37, and a controller 170 configured to be operably connected to the electrode arrangement 150 for controlling the electrical stimulation of the muscle tissue. The controller 170 may be coupled to an implantable energy source 160 for providing the electrode arrangement with electrical power according to a stimulation signal or pattern generated by the controller 170.

FIG. 45 further illustrates an implantable communicator 171, which may be configured to transmitting a signal between the controller 170 and the outside of the patient's body, similar to what is described above in connection with FIG. 44. The communicator 171 may be comprised in the control unit 170 or provided as a separate unit. The communicator 171 may hence be used for transmitting the signal comprising the functional status of the implantable energy source 160, and for communicating with an external controller 176 used for controlling or adjusting the operation of the implantable controller 170. The external controller 176 may for example be comprised in a remote controller 175 as shown in FIG. 44.

The implantable controller 170, which also may be referred to as an internal controller or a stimulation controller 170, may be understood as any implantable unit capable of controlling the electrical stimulation of the tissue. A controller could include an electrical signal generator, a modulator or other electrical circuitry capable of delivering the electrical stimulation signal to the electrode arrangement. Further, the controller may be capable of processing control signals and generate the electrical stimulation signal in response thereto, and further to generate control signals for the control of other components of the system or apparatus, such as for example the implanted energy source 160 and/or the implantable charger 190. A control signal may thus be understood as any signal capable of carrying information and/or electric power such that a component of the system/apparatus can be directly or indirectly controlled.

The controller may comprise a processing unit, such as a CPU, for handling the control of the electrode arrangement 150 and other components of the system. The processing unit could be a single central processing unit or could comprise two or more processing units. The processing unit could comprise a general-purpose microprocessor and/or an instruction set processor and/or related chips sets and/or special purpose microprocessors such as ASICs (Application Specific Integrated Circuit). The processing unit may also comprise memory for storing instruction and/or data. The controller 170 could be adapted to keep track of different stimulation patterns and periods used for the stimulation of the muscle tissue, and in some examples also the action potentials sensed by the sensor S1. The controller 170 may further comprise a communicator, or communication unit 171 as outlined above, which may be configured for receiving and/or transmitting wireless or wired signals to/from outside the body. The communication unit 171 can enable programming the controller 170 form outside of body of the patient such that the operation of the electrode arrangement 150 can be programmed to function optimally.

The controller 170, as well as other implanted components such as the energy source 160, the charger 190, and the first or second portion 110, 120 of the apparatus 100, may be enclosed by an enclosure so as to protect the components from bodily fluids. The enclosures may be an enclosure made from one of or a combination of: a carbon-based material (such as graphite, silicon carbide, or a carbon fiber material), a boron material, a polymer material (such as silicone. Peck®), polyurethane, UHWPE or PTFE,), a metallic material (such as titanium, stainless steel, tantalum, platinum, niobium or aluminum), a ceramic material (such as zirconium dioxide, aluminum oxide or tungsten carbide) or glass. In any instance the enclosure should be made from a material with low permeability, such that migration of fluid through the walls of the enclosure is hindered.

Figure 46:
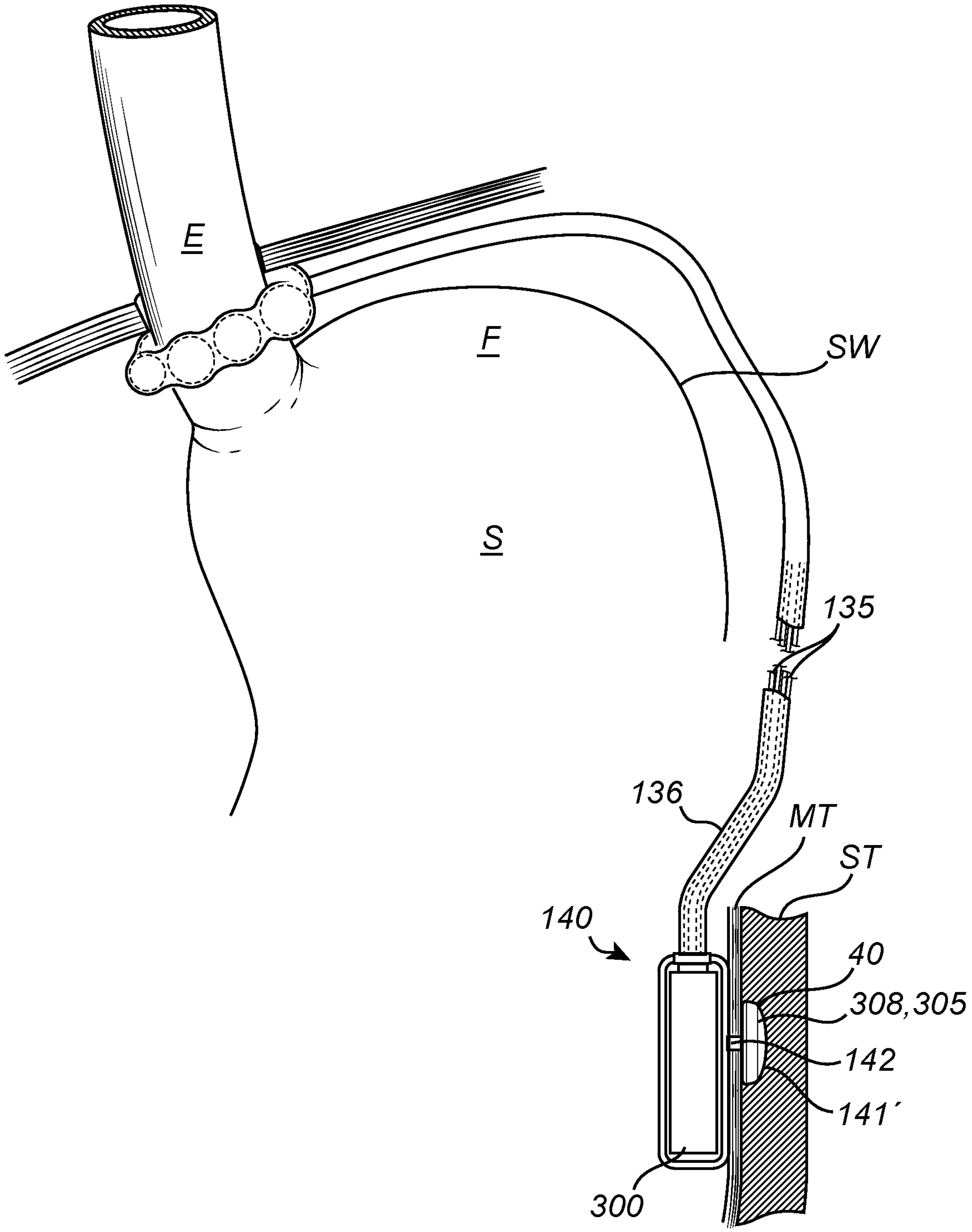
FIG. 46 shows a human patient in cross section when a system for treating reflux disease has been implanted.

FIG. 46 shows the stomach S of a patient (also referred to as stomach 10 in the above figures) when an apparatus 100 according to the embodiments described with reference to the previous figures has been arranged at least partly around the esophagus E (also referred to as esophagus 20 in the above figures). The apparatus 100 may be operated by means of electric leads 135 traveling inside of protective covers 136*a*, 136*b*, which combine to a single protective cover for guiding the electric leads 135 to a remote unit 140, or control unit 140, for remote operation of the apparatus 100. The operation may for instance relate to electrical stimulation and exercise of muscle tissue against which the apparatus 100 rests, as previously discussed.

In the embodiment of FIG. 46, the control unit comprises a first and second portion 141',141" placed on different sides of a portion of muscle tissue MT of the patient, and connected by means of a connecting portion placed through a hole in the muscle tissue MT. The second portion 141' is placed on the inside of the muscle tissue MT and the first portion is placed on the outside of the muscle tissue MT in the subcutaneous tissue ST. In the embodiment shown in FIG. 46, the controller 300 is placed in the second portion 141", and the implantable energy storage unit 40 is placed in the first portion 141'. The controller 300 and the implantable energy storage unit 40 are electrically connected by means of a lead running in the connecting portion, such that electrical energy and communication can be transferred from the second 141" to the first portion 141', and vice versa. In the embodiment of FIG. 46, the first portion 141' further comprises a wireless energy receiver 305 for receiving wireless energy for charging the implantable energy storage unit 40 and/or for powering the medical device, and a transceiver 308 for receiving and/or transmitting wireless signals to/from the outside the body. The implantable energy storage unit 40 may be any type of energy storage unit suitable for an implant, such as a re-chargeable battery or a solid-state battery, such as a thionyl-chlorid battery. The energy storage unit may be equipped with an energy storage unit indicator configured to indicate a functional status of the implantable energy storage unit. The functional status may indicate at least one of charge level and temperature of the implantable energy storage unit 40. For enabling indication of the temperature of the energy storage unit 40, the energy storage unit 40 or medical device 10 may comprising a temperature sensor.

The controller 300 may comprise at least one sensor or be configured to receive sensor input from the at least one sensor. The sensor could be a sensor configured to sense a physical parameter of the medical device system, such as at least one of:

A temperature of the medical device system, to avoid excessive heating of tissue connected to the medical device during operation of the medical device or charging of the energy storage unit 40. Excessive heating may also damage the medical device and/or the energy storage unit 40. Excessive heating may also be an indicator that something is wrong with the medical device 10 and may be used for triggering an alarm function for alerting the patient or physician.

A parameter related to the power consumption of the medical device system, to avoid excessive power consumption which may drain and/or damage the energy storage unit 40. Excessive power consumption may also be an indicator that something is wrong with the medical device 10 and may be used for triggering an alarm function for alerting the patient or physician.

A parameter related to strain in the medical device, such as the strain exerted on the esophagus in connection with the apparatus constricting the esophagus. Strain can be measured to avoid excessive strain which may damage medical device or the tissue of the patient. Excessive strain may also be an indicator that something is wrong with the medical device 10 and may be used for triggering an alarm function for alerting the patient or physician.

A parameter related to the wireless transfer of energy from a source external to the body of the patient. Excessive transfer of wireless energy may damage an implanted wireless energy received or the energy storage unit. It may also create excessive heating which may damage the tissue of the patient. The controller 300 may comprise a sensor or be configured to receive sensor input from a sensor configured to sense a physiological parameter of the patient. The physiological parameter of the patient may be:

A parameter related to the patient swallowing, such that the medical device can be controlled on the basis of the patient eating or drinking. A sensor configured to sense a parameter related to the patient swallowing could comprises a motility sensor, which could be a piezo electric or piezo resistive motility sensor, or an accelerometer. In the alternative, a acoustic sensor, such as a microphone, may be used to sense the patient swallowing by picking up the sound generated by the patient swallowing. In the alternative, an optical sensor may be used for sensing the opacity alteration over the esophagus as food passes. A strain sensor could also be used for sensing the expansion of the esophagus as food passes.

A local temperature, to avoid local excessive heating which may damage tissue of the patient.

A systemic temperature, to avoid systemic excessive heating which may cause fever and affect the overall well-being of the patient.

Blood saturation/oxygenation, or a parameter related to an ischemia marker such as lactate, to control and/or avoid that the flow of blood to some tissue portion is hampered by the implantation or operation of the medical device 10. Hampered blood flow may lead to tissue damage and in the worst cases to tissue necrosis.

Blood pressure, which may be an indication that the strain created by the medical device is in some way damaging to the overall wellbeing of the patient. Increased blood pressure may be used for triggering an alarm function for alerting the patient or physician.

pH, for determining the acidity of the stomach, which could be an indicator of the function of the digestive system and/or of the frequency of ingestion. The pH may be used for controlling the medical device 10 on the basis of the patient eating or drinking.

The controller 300 may further comprise a receiver for receiving patient generated control signals from a unit located external to the body of the patient. The receiver could be a wireless receiver configured to communicate with a transmitter located external to the body of the patient. The controller 300 may be configured to control the operation device 100 on the basis of the received patient generated control signal. The control signal could for example being that the patient indicates to the medical device 10 that the patient has finished a portion of food which causes the medical device 10 to operate to constrict the esophagus and/or the cardia. In the alternative, the controller 300 may be configured to control the operation device 100 on the basis of a signal related to a lapsed time or a time of day such that a constriction can be provided with certain intervals or during specific periods of the day. The controller 300 could further be configured to receive a signal from a sensor external to the body of the patient and use such signal for controlling the operation of the medical device 10. The sensor external to the body of the patient could be a sensor could be a sensor measuring a parameter related to the patient eating to create input for the control of the medical device 10. Such a parameter could be related to body temperature, blood pressure or the glucose level of the blood. In the alternative, the sensor could be a sensor sensing a parameter related to the external environment, such as the atmospheric pressure, which could affect the pressures in the medical device 10.

FIG. 46 shows a frontal view of a part of the abdomen of the patient when the medical device 10 (previously referred to as apparatus 100 in the figures) has been implanted. This is however only an example of an embodiment and it is clear that any of the embodiments of the medical device disclosed herein can be implanted and connected in the manner described with reference to FIG. 46. The apparatus, or medical device 10 is in the embodiment shown in FIG. 46 operated by a remote unit 140. This is however only an example of a remote unit for operation of the medical device 10 and it is clear that any of the embodiments of remote units disclosed herein can be implanted and connected in the manner described with reference to FIG. 46. The remote unit 140 comprises a first portion 141', a second portion 141", and a connecting portion 142, mechanically connecting the first and second portions 141',141". The second portion 141" is in the embodiment shown in FIG. 46 placed on the inside of muscular tissue MT of the abdominal wall AW of the patient, whereas the first portion 141' is placed on the outside of the muscular tissue MT of the abdominal wall AW, in the subcutaneous tissue ST. As such, the connecting portion 142 travels through a created hole in, or natural orifice between, the muscles of the muscular tissue MT. A cross-sectional area of the connecting portion 142, in a plane in the extension of the muscular tissue MT is smaller than a cross-sectional area of the first and second portions 141', 141", parallel to the cross-sectional area of the connecting portion 142. The cross-sectional areas of the first and second portions 141', 141" are also larger than the created hole or natural orifice though which the connecting portion 142 is placed. As such, the first and second portions 141',141" are unable to pass through the created hole or natural orifice and is as such fixated to the muscular tissue MT of the abdominal wall. This enables the remote unit 140 to be suspended and fixated to the muscle tissue MT of the abdominal wall AW. The connecting portion 142 may be a connecting portion 142 having a circular cross-section and an axial direction AD extending from the first portion 141' to the second portion 141". The plane in the extension of the muscular tissue MT, is in the embodiment of FIG. 46 perpendicular to the axial direction AD of the connecting portion 142 extending from the first portion 141' to the second portion 141".

The controller may be placed in the second portion 141", and the implantable energy storage unit is placed in the first portion 141'. The controller and the implantable energy storage unit are electrically connected to each other by means of a lead running in the connecting portion 142, such that electrical energy and communication can be transferred from the second 141" to the first portion 141', and vice versa. In the embodiment of FIG. 46, the first portion 141' further comprises a wireless energy receiver for receiving wireless energy for charging the implantable energy storage unit and/or for powering the medical device 10, and a transceiver for receiving and/or transmitting wireless signals to/from the outside the body. Further features and functions of the controller and the implantable energy storage unit are further described with reference to FIGS. 65*a-e* and 66*a-h*.

The abdominal wall AW is in most locations generally formed by a set of layers of skin, fat/fascia, muscles and the peritoneum. The deepest layer in the abdominal wall AW is the peritoneum PT, which covers many of the abdominal organs, for example the large and small intestines. The peritoneum PT is a serous membrane composed of a layer of mesothelium supported by a thin layer of connective tissue and serves as a conduit for abdominal organ's blood vessels, lymphatic vessels, and nerves. The area of the abdomen enclosed by the peritoneum PT is called the intraperitoneal space. The tissue and organs within the intraperitoneal space are called "intraperitoneal" (e.g., the stomach and intestines). The tissue and organs in the abdominal cavity that are located behind the intraperitoneal space are called "retroperitoneal" (e.g., the kidneys), and tissue and organs located below the intraperitoneal space are called "subperitoneal" or "infraperitoneal" (e.g., the bladder).

The peritoneum PT is connected to a layer of extraperitoneal fat EF which is connected to a layer or transversalis fascia TF. Connected to the transversalis fascia TF, at the area of the abdominal wall AW at which the section is extracted, is muscle tissue MT separated by layers of deep fascia DF. The deep fascia DF between the layers of muscle is thinner than the transversalis fascia TF and the Scarpa's fascia SF placed on the outside of the muscle tissue MT. Both the transversalis fascia TF and the Scarpa's fascia SF are relatively firm membranous sheets. At the area of the abdominal wall AW at which the section is extracted, the muscle tissue MT is composed of the transverse abdominal muscle TM (transversus abdominis), the internal oblique muscle IM (obliquus internus) and the external oblique muscle EM (obliquus externus). In other areas of the abdominal wall AW, the muscle tissue could also be composed of the rectus abdominis and the pyramidalis muscle.

The layer outside of the muscle tissue MT, beneath the skin SK of the patient is called subcutaneous tissue ST, also called the hypodermis, hypoderm, subcutis or superficial fascia. The main portion of the subcutaneous tissue ST is made up of Camper's fascia which consists primarily of loose connective tissue and fat. Generally, the subcutaneous tissue ST contains larger blood vessels and nerves than those found in the skin.

Placing the remote unit 140 at an area of the abdomen is advantageous as the intestines are easily displaced for making sufficient room for the remote unit 140, without the remote unit 140 affecting the patient too much in a sensational or visual way. Also, the placement of the remote unit 140 in the area of the abdomen makes it possible to fixate the remote unit 140 to the muscle tissue MT of the abdomen for creating an attachment keeping the remote unit 140 firmly in place. In the embodiment shown in FIG. 46, the first portion 141' of the remote unit 140 is placed on the left side of the patient in between the peritoneum PT and the muscle tissue MT. The first portion 141' is placed in the subcutaneous tissue ST between the muscle tissue MT and the skin SK of the patient. Placing the first portion 141' subcutaneously enables easy access to the first portion 141' for e.g. wireless communication using a wireless transceiver placed in the first portion 141', wireless charging of an implantable storage unit using a wireless energy receiver placed in the first portion 141', manual manipulation of for example a push button placed in the first portion 141', or maintenance or replacement of the first portion 141' via a small incision in the skin SK at the first portion 141'.

In the embodiment shown in FIG. 46, the electric leads 135 running inside of protective a cover 136 transports electric signals from the remote unit 140 to the main portion M of the medical device 10. The leads 135 run between the peritoneum PT and the muscle tissue MT vertically until the leads 135 reach the height of the main portion M of the medical device 10. At this height, the leads 135 enters the peritoneum PT and travels substantially horizontally to the main portion M of the medical device 10. As such, the leads 135 are placed inside of the intraperitoneal space for as short distance as possible which reduces the risk that implanted, foreign body, elements disturbs the intraperitoneal organs, reducing the risk of damage to organs, and reducing the risk that foreign body elements cause ileus.

In the embodiment shown in FIG. 46, the connecting portion 142 connects the first and second portions 141', 141" though three layers of muscle tissue MT, namely tissue of the transverse abdominal muscle TM, the internal oblique muscle IM and the external oblique muscle EM. In alternative embodiments, it is however conceivable that the second portion 141" is placed in between layers of muscle, such as between tissue of the transverse abdominal muscle TM, the internal oblique muscle IM, or between the internal oblique muscle IM and the external oblique muscle EM. As such, it is conceivable that in alternative embodiments, the connecting portion 142 connects the first and second portions 141', 141" through two layers of muscle tissue MT, or through one layer of muscle tissue MT.

In alternative embodiments, it is furthermore conceivable that the first portion 141' is placed in between layers of muscle, such as between tissue of external oblique muscle EM and the internal oblique muscle IM, or between the internal oblique muscle IM and the transverse abdominal muscle TM.

Figure 47A:
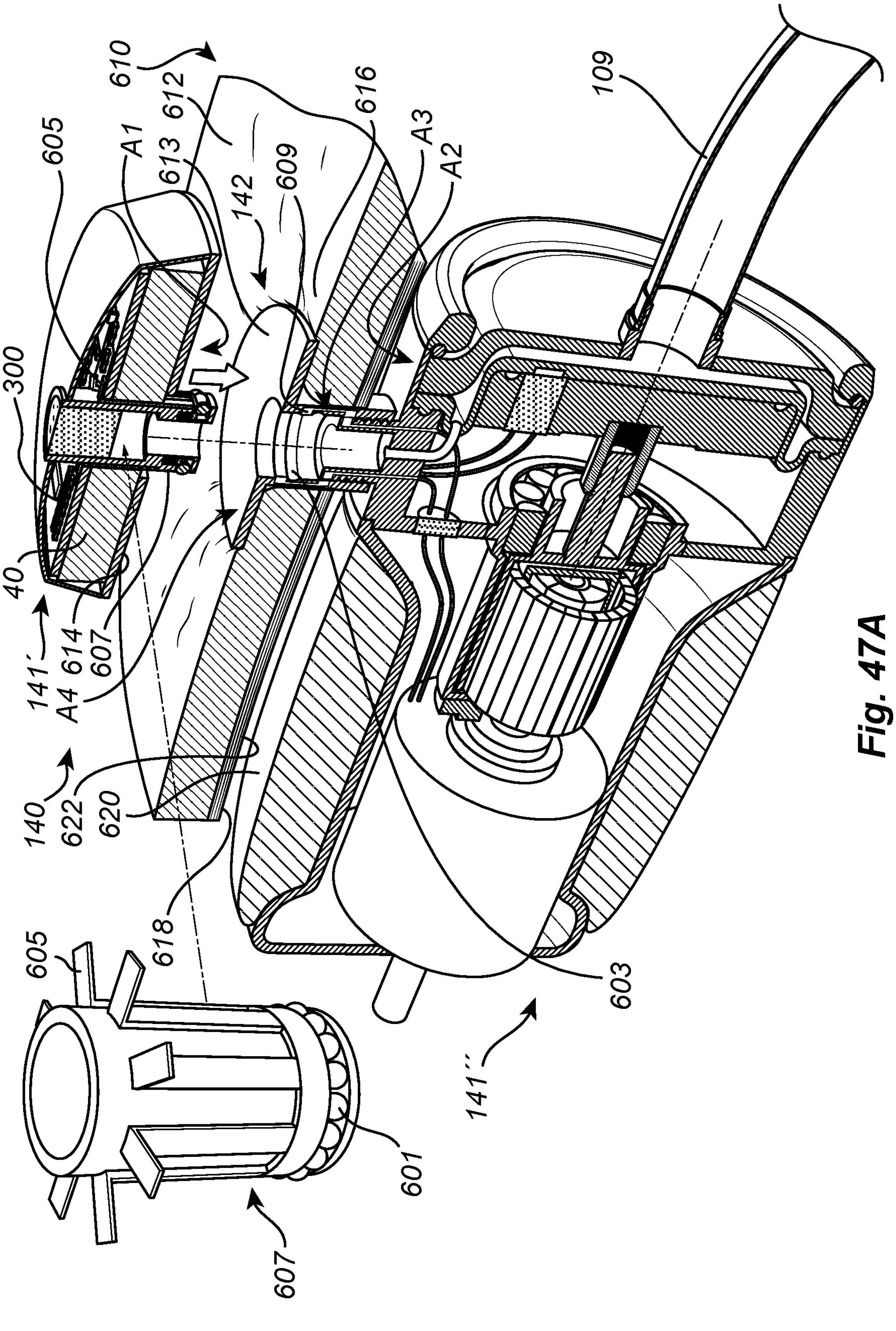
FIGS. 47A-B show a cross-sectional view of an implantable remote unit for powering an implantable medical device.
Figure 47B:
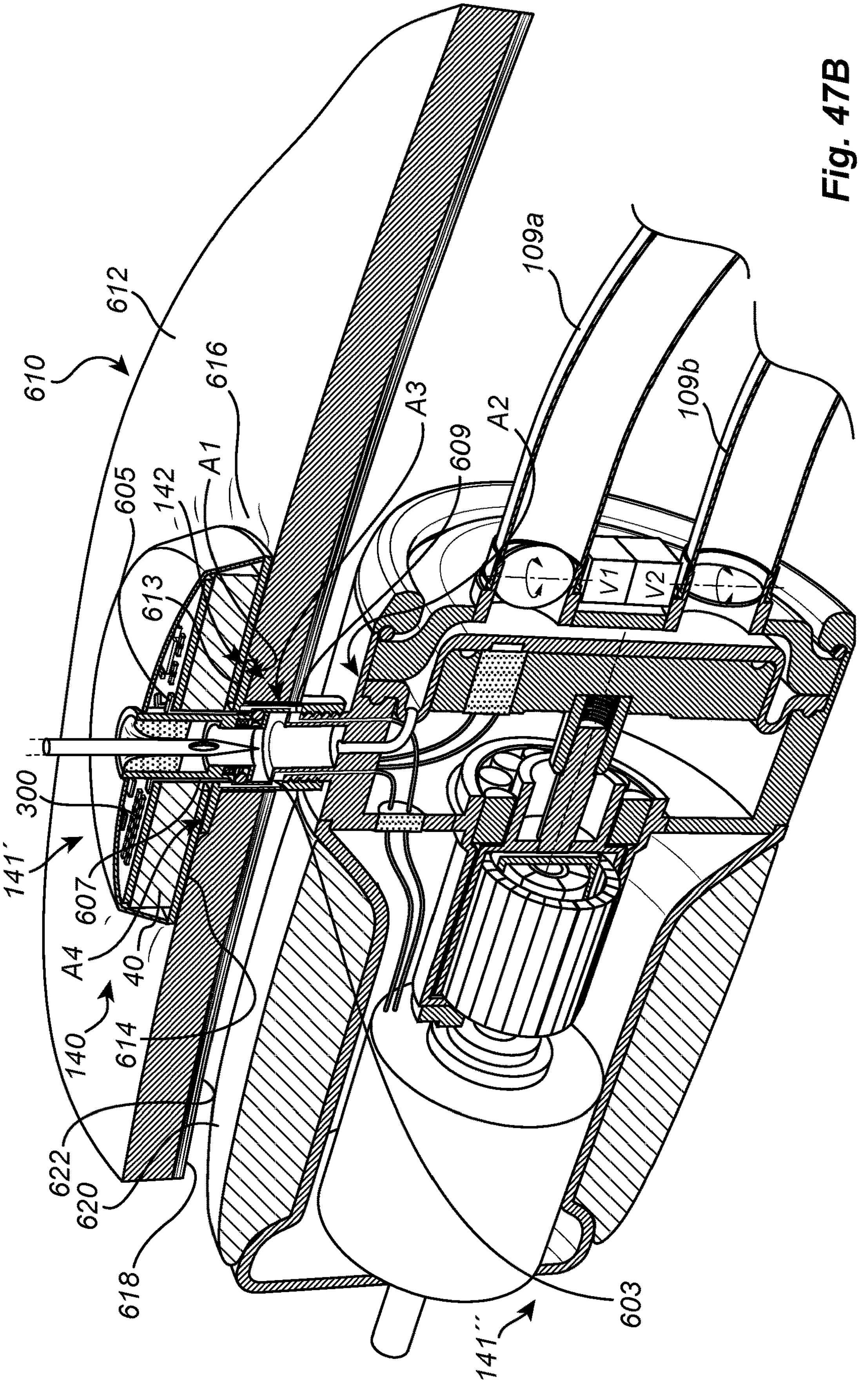
Figure 48:
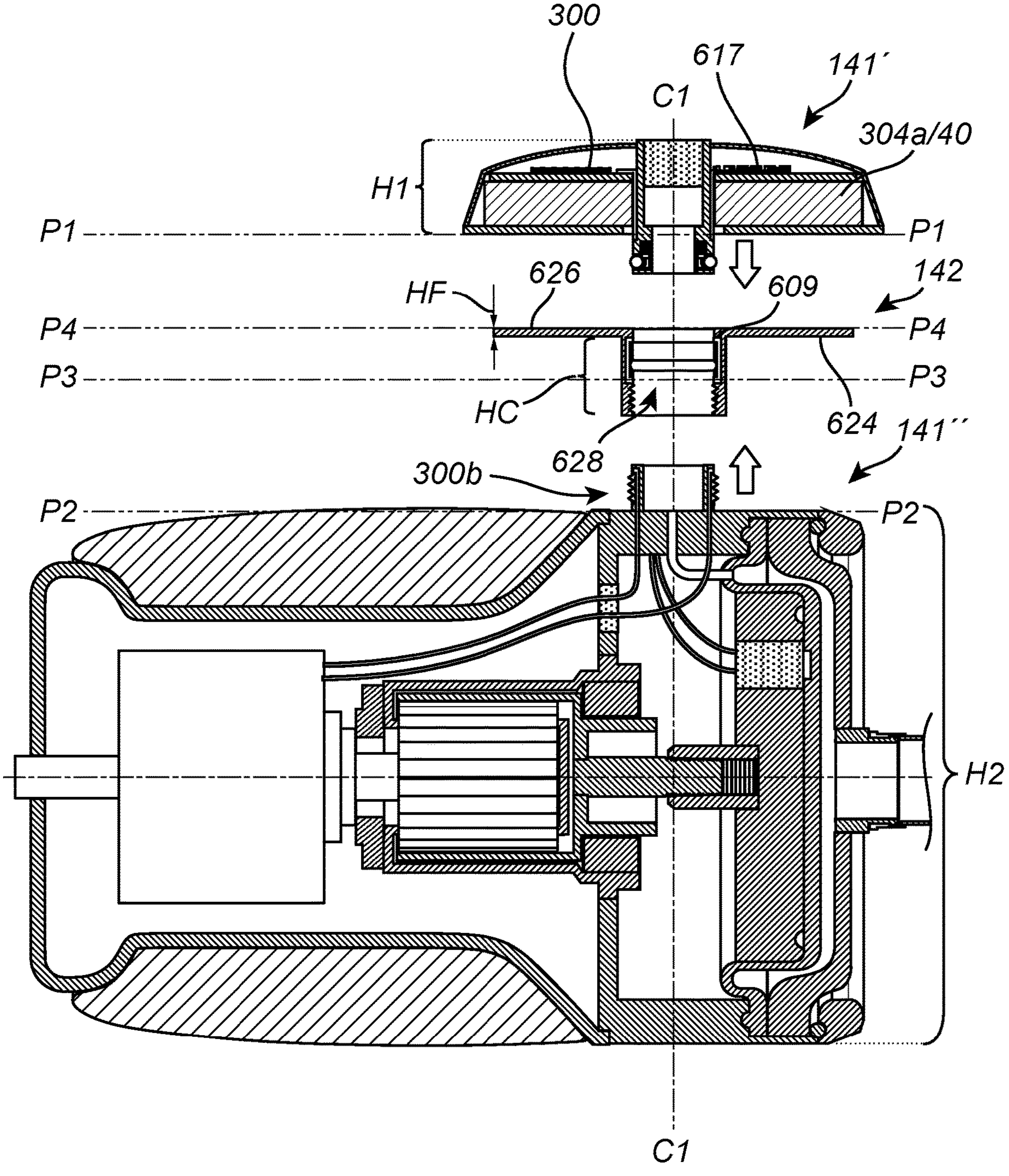
FIG. 48 shows an exploded cross-sectional view of an implantable remote unit for powering an implantable medical device.
Figure 49A:
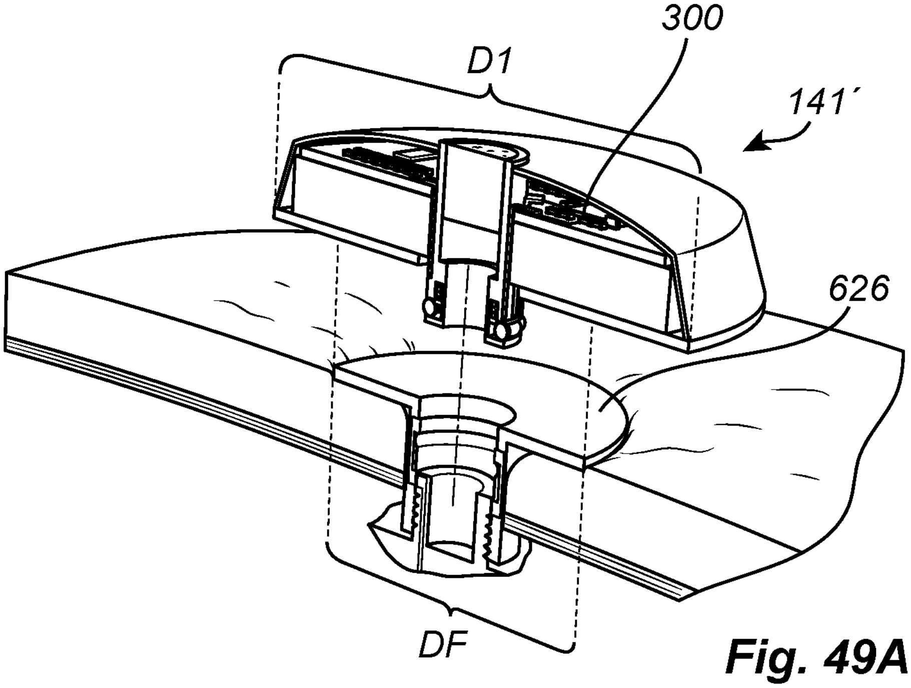
FIGS. 49A-C show a detailed cross-sectional view of a first unit of an implantable remote unit for powering an implantable medical device
Figure 49B:
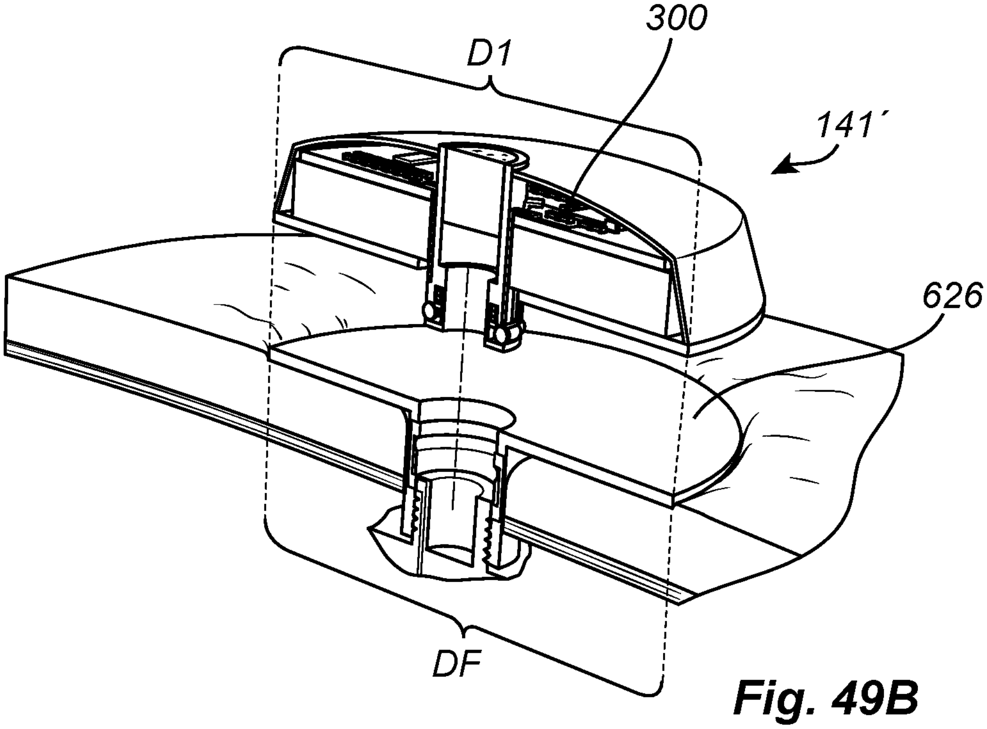
Figure 49C:
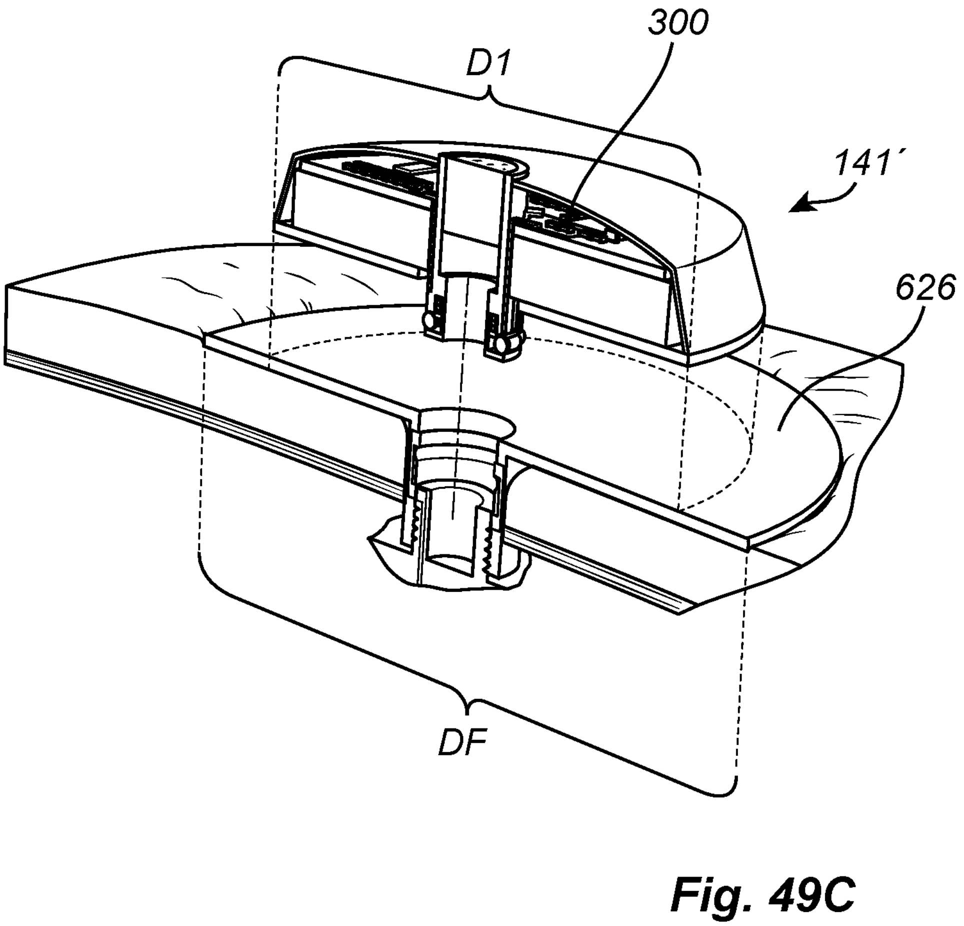

FIGS. 47*a*, 47*b* and 48 show an embodiment of a remote unit 140. The remote unit 140 is configured to be held in position by a tissue portion 610 of a patient. The remote unit 140 comprises a first portion 141' configured to be placed on a first side 612 of the tissue portion 610, the first portion 141' having a first cross-sectional area A1 in a first plane P1 and comprising a first surface 614 configured to face a first tissue surface 616 of the first side 612 of the tissue portion 610. The remote unit 140 further comprises a second portion 141" configured to be placed on a second side 618 of the tissue portion 610, the second side 618 opposing the first side 612, the second portion 141" having a second cross-sectional area A2 in a second plane P2 and comprising a second surface 620 configured to engage a second tissue surface 622 of the second side 618 of the tissue portion 610. The remote unit 140 further comprises a connecting portion 142 configured to be placed through a hole in the tissue portion 610 extending between the first and second sides 612, 618 of the tissue portion 610. The connecting portion 142 here has a third cross-sectional area A3 in a third plane P3 and a fourth cross-sectional area A4 in a fourth plane P4 and a third surface 624 configured to engage the first tissue surface 616 of the first side 612 of the tissue portion 610. The connecting portion 142 is configured to connect the first portion 141' to the second portion 141".

The connecting portion 142 thus has a portion being sized and shaped to fit through the hole in the tissue portion 610, such portion having the third cross-sectional area A3 Furthermore, the connecting portion 142 may have another portion being sized and shaped to not fit through the hole in the tissue portion 610, such portion having the fourth cross-sectional area A4. Likewise, the second portion 141" may have a portion being sized and shaped to not fit through the hole in the tissue portion 610, such portion having the second cross-sectional area A2. Thus, the connecting portion 142 may cooperate with the second portion 141" to keep the device in place in the hole of the tissue portion 610.

In the embodiment illustrated in FIG. 47*a*, the first portion 141' is configured to detachably connect, i.e. reversibly connect to the connecting portion 142 by a mechanical and/or magnetic mechanism. In the illustrated embodiment, a mechanic mechanism is used, wherein one or several spring-loaded spherical elements 601 lock in place in a groove 603 of the connecting portion 142 when the first portion 141' is inserted into the connecting portion 142. Other locking mechanisms are envisioned, including corresponding threads and grooves, self-locking elements, and twist and lock fittings.

The remote unit 140 is configured such that, when implanted, the first portion 141' will be placed closer to an outside of the patient than the second portion 141". Furthermore, in some implantation procedures the remote unit 140 may be implanted such that space will be available beyond the second portion, i.e. beyond the second side 618 of the tissue portion 610), whereas there may be as much space on the first side 612 of the tissue portion. Furthermore, tissue and/or skin may exert a force on the first portion 141" towards the tissue portion 610, and provide for that the second portion 141" does not travel through the hole in the tissue portion towards the first side 612 of the tissue portion. Thus, it is preferably if the remote unit 140 is primarily configured to prevent the first portion 141" from travelling through the hole in the tissue portion 612 towards the second side 618 of the tissue portion 610.

The first portion 141' may further comprise one or several connections 605 for transferring energy and/or communication signals to the second portion 141" via the connecting portion 142. The connections 605 in the illustrated embodiment are symmetrically arranged around a circumference of a protrusion 607 of the first portion 141' and are arranged to engage with a corresponding connection 609 arranged at an inner surface of the connecting portion 142. The protrusion 607 may extend in a central extension C1 of the central portion 142. The second portion 141" may also comprise one or several connections 611, which may be similarly arranged and configured as the connections 605 of the first portion 141'. For example, the one or several connections 611 may engage with the connection 609 of the connecting portion 142 to receive energy and/or communication signals from the first portion 141'. Although the protrusion 607 is illustrated separately in FIGS. 47*a* and 47*b*, it is to be understood that the protrusion 607 may be formed as one integral unit with the first portion 141'.

Other arrangements of connections are envisioned, such as asymmetrically arranged connections around the circumference of the protrusion 607. It is also envisioned that one or several connections may be arranged on the first surface 614 of the first portion 141', wherein the connections are arranged to engage with corresponding connections arranged on the opposing surface 613 of the connecting portion. Such connections on the opposing surface 613 may cover a relatively large area as compared to the connection 609, thus allowing a larger area of contact and a higher rate and/or signal strength of energy and/or communication signal transfer. Furthermore, it is envisioned that a physical connection between the first portion 141', connecting portion 142 and second portion 141" may be replaced or accompanied by a wireless arrangement, as described further in other parts of the present disclosure.

Any of the first surface 614 of the first portion 141', the second surface 620 of the second portion 141', the third surface 624 of the connecting portion 142, and an opposing surface 613 of the connecting portion 142, may be provided with at least one of ribs, barbs, hooks, a friction enhancing surface treatment, and a friction enhancing material, to facilitate the remote unit 140 being held in position by the tissue portion, and/or to facilitate that the different parts of the device are held in mutual position.

The opposing surface 613 of the connecting portion 142 and the first surface 614 of the first portion 141' may provide, fully or partly, a connection mechanism to detachably connect the first portion 141' to the connecting portion 142. Such connection mechanisms have been described previously in the presented disclosure, and can be arranged on one or both of the opposing surface 613 and the first surface 614, and will not be further described here.

The opposing surface 613 may be provided with a recess configured to house at least part of the first portion 141', In particular, such recess may be configured to receive at least a portion of the first portion 141', including the first surface 614. Similarly, the first surface 614 may be provided with a recess configured to house at least part of the connecting portion 142. In particular, such recess may be configured to receive at least a portion of the connecting portion 142, and in some embodiments such recess may be configured to receive at least one protruding element to at least partially enclose at least one protruding element or flange.

In the illustrated embodiment, the first portion 141' comprises a first energy storage unit 304*a* and a controller 300*a* comprising one or several processing units connected to the first energy storage unit 304*a*. The first energy storage unit 304*a* may be rechargeable by wireless transfer of energy. In some embodiments, the first energy storage unit 304*a* may be non-rechargeable. Upon reaching the life-time end of such first energy storage, a replacement first portion comprising a new first energy storage unit may simply be swapped in place for the first portion having the depleted first energy storage unit. The second portion 141" may further comprise a controller 300*b* comprising one or several processing units.

As will be described in other parts of the present disclosure, the first portion 141' and the second portion 141" may comprise one or several functional parts, such as receivers, transmitters, transceivers, control units, processing units, sensors, energy storage units, sensors, etc.

The remote unite 140 may be non-inflatable.

The first portion 141' may be detachably connected to at least one of the connecting portion 142 and the second portion 141".

As can be seen in FIG. 48, the first, second, third and fourth planes P1, P2, P3 and P4, are parallel to each other. Furthermore, in the illustrated embodiment, the third cross-sectional area A3 is smaller than the first, second and fourth cross-sectional areas A1, A2 and A4, such that the first portion 141', second portion 141" and connecting portion 142 are prevented from travelling through the hole in the tissue portion 610 in a direction perpendicular to the first, second and third planes P1, P2 and P3. Hereby, the second portion 141" and the connecting portion 142 can be held in position by the tissue portion 610 of the patient also when the first portion 141' is disconnected from the connecting portion 142.

It is to be understood that the illustrated planes P1, P2, P3 and P4 are merely an example of how such planes may intersect the remote unit 140. Other arrangements of planes are possible, as long as the conditions above are fulfilled, i.e. that the portions have cross-sectional areas, wherein the third cross-sectional area in the third plane P3 is smaller than the first, second and fourth cross-sectional areas, and that the planes P1, P2, P3 and P4 are parallel to each other.

The connecting portion 142 illustrated in FIG. 47*a* may be defined as a connecting portion 142 comprising a flange 626. The flange 626 thus comprises the fourth cross-sectional area A4 such that the flange 626 is prevented from travelling through the hole in the tissue portion 610 in a direction perpendicular to the first, second and third planes P1, P2 and P3. The flange 626 may protrude in a direction parallel to the first, second, third and fourth planes P1, P2. P3 and P4. This direction is perpendicular to a central extension C1 of the connecting portion 142.

The connecting portion 142 is not restricted to flanges, however. Other protruding elements may additionally or alternatively be incorporated into the connecting portion 142. As such, the connecting portion 142 may comprise at least one protruding element comprising the fourth cross-sectional area A4, such that the at least one protruding element is prevented from travelling through the hole in the tissue portion 610, such that the second portion 141" and the connecting portion 142 can be held in position by the tissue portion 610 of the patient also when the first portion 141' is disconnected from the connecting portion 142. The at least one protruding element may protrude in a direction parallel to the first, second, third and fourth planes P1, P2, P3 and P4. This direction is perpendicular to a central extension C1 of the connecting portion 142. As such, the at least one protruding element will also comprise the third surface configured to engage the first tissue surface 616 of the first side 612 of the tissue portion 610.

The connecting portion 142 may comprise a hollow portion 628. The hollow portion 628 may provide a passage between the first and second portions 141', 141". In particular, the hollow portion 628 may house a conduit for transferring fluid from the first portion 141' to the second portion 141". The hollow portion 628 may also comprise or house one or several connections or electrical leads for transferring energy and/or communication signals between the first portion 141' and the second portion 141".

Some relative dimensions of the remote unit 140 will now be described with reference to FIGS. 48 and 49A-49C, however it is to be understood that these dimensions may also apply to other embodiments of the remote unit 140). The at least one protruding element 626 may have a height HF in a direction perpendicular to the fourth plane being less than a height H1 of the first portion 141' in said direction. The height HF may alternatively be less than half of said height H1 of the first portion 141' in said direction, less than a quarter of said height H1 of the first portion 141' in said direction, or less than a tenth of said height H1 of the first portion 141' in said direction.

The height H1 of the first portion 141' in a direction perpendicular to the first plane may be less than a height H2 of the second portion 141" in said direction, such as less than half of said height H2 of the second portion 141" in said direction, less than a quarter of said height H2 of the second portion 141' in said direction, or less than a tenth of said height H2 of the second portion 141" in said direction.

The at least one protruding element 626 may have a diameter DF in the fourth plane being one of less than a diameter D1 of the first portion 141' in the first plane, equal to a diameter D1 of the first portion 141' in the first plane, and larger than a diameter D1 of the first portion 141' in the first plane. Similarly, the cross-sectional area of the at least one protruding element 626 in the fourth plane may be less, equal to, or larger than a cross-sectional area of the first portion in the first plane.

The at least one protruding element 626 may have a height HF in a direction perpendicular to the fourth plane being less than a height HC of the connecting portion 142 in said direction. Here, the height HC of the connecting portion 142 is defined as the height excluding the at least one protruding element, which forms part of the connecting portion 142. The height HF may alternatively be less than half of said height HC of the connecting portion 142 in said direction, less than a quarter of said height HC of the connecting portion 142 in said direction, or less than a tenth of said height HC of connecting portion 142 in said direction.

Figure 50A:
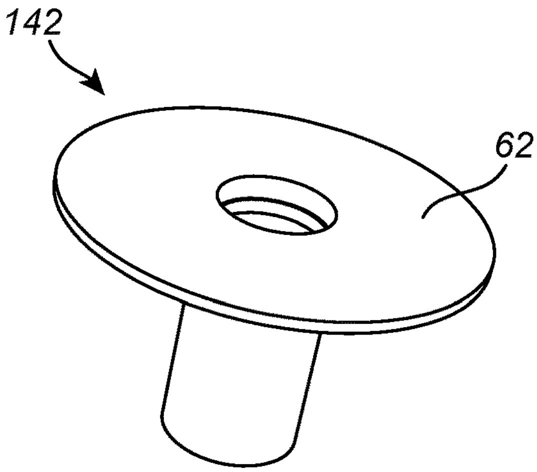
FIGS. 50A-B show alternative embodiments of connecting portions for an implantable remote unit.
Figure 50B:
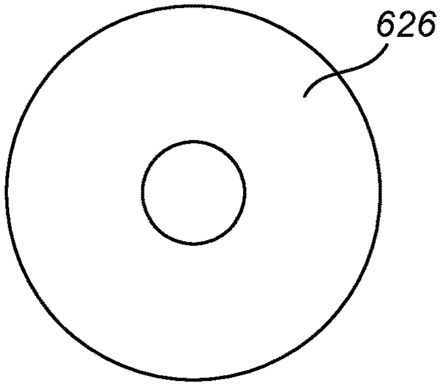

As shown in FIGS. 50A-50B, the at least one protruding element 626 may have an annular shape, such as a disk shape. However, elliptical, elongated and/or other polyhedral or irregular shapes are also possible. In the illustrated embodiment, the at least one protruding element 626 extends a full revolution around the center axis of the connecting portion 142. However, other arrangements are possible, wherein the at least one protruding element 626 constitute a partial circle sector. In the case of a plurality of protruding elements, such plurality of protruding elements may constitute several partial circle sectors.

As shown in FIGS. 51A-51B, 52A-52B, the connecting portion 142 may comprise at least two protruding elements 626, 627. For example, the connecting portion 142 may comprise at least three, four, five, fix, seven, eight, nine, ten protruding elements, and so on. In such embodiments, the at least two protruding elements 626, 627 may together comprise the fourth cross-sectional area, thus providing a necessary cross-sectional area to prevent the first portion and second portion from travelling through the hole in the tissue portion.

Figure 51A:
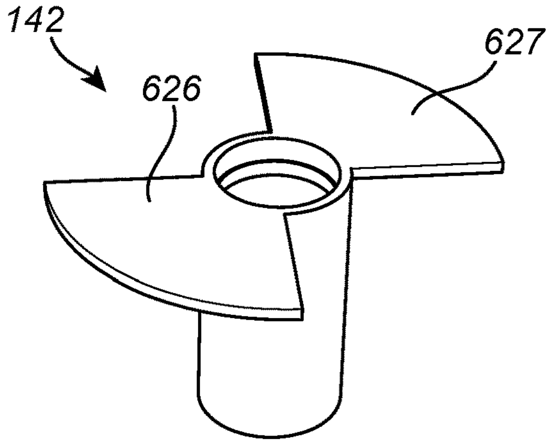
FIGS. 51A-B show, schematically, a kit of components forming an implantable remote unit.
Figure 51B:
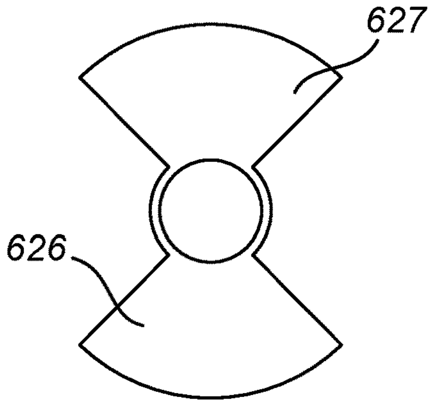
Figure 52A:
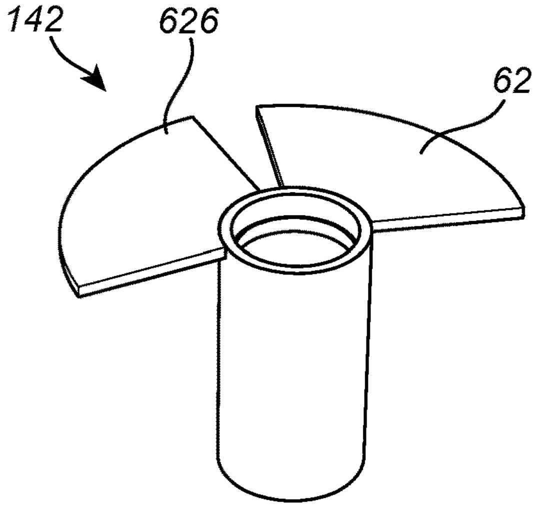
FIG. 52A-B show a detailed cross-sectional view of an embodiment of an implantable remote unit for powering an implantable medical device.
Figure 52B:
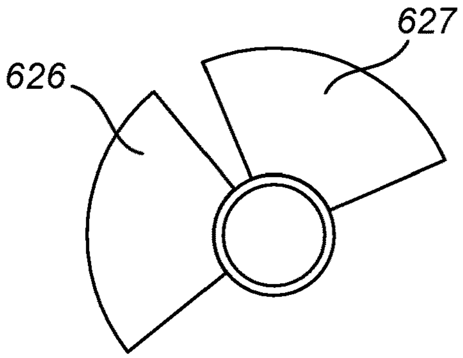

The at least two protruding elements 626, 627 may be symmetrically arranged about the central axis of the connecting portion, as shown in FIGS. 51*a*-51*b*, or asymmetrically arranged about the central axis of the connecting portion, as shown in FIGS. 52*a*-52*b*. In particular, the at least two protruding elements 626, 627 may be asymmetrically arranged so as to be located towards one side of the connecting portion 142, as shown in FIGS. 52*a*-52*b*. The arrangement of protruding element(s) may allow the remote unit 140, and in particular the connecting portion 142, to be placed in areas of the patient where space is limited in one or more directions.

The first portion 141' may comprise a first energy storage unit for supplying the remote unit 140 with energy.

Although one type or embodiment of the implantable remote unit 140, may fit most patients, it may be necessary to provide a selection of implantable remote units 140 or portions to be assembled into implantable remote units 140. For example, some patients may require different lengths, shapes, sizes, widths or heights depending on individual anatomy. Furthermore, some parts or portions of the implantable remote units 140 may be common among several different types or embodiments of remote units, while other parts or portions may be replaceable or interchangeable. Such parts or portions may include energy storage devices, communication devices, fluid connections, mechanical connections, electrical connections, and so on.

To provide flexibility and increase user friendliness, a kit of parts may be provided. The kit preferably comprises a group of one or more first portions, a group of one or more second portions, and a group of one or more connecting portions, the first portions, second portions and connecting portions being embodied as described throughout the present disclosure. At least one of the groups comprises at least two different types of said respective portions. By the term “type”, it is hereby meant a variety, class or embodiment of said respective portion.

In some embodiments of the kit, the group of one or more first portions, the group of one or more second portions, and the group of one or more connecting portions, comprise separate parts which may be assembled into a complete remote unit. The remote unit may thus be said to be modular, in that the first portion, the second portion, and/or the connecting portion may be interchanged for another type of the respective portion.

Figure 53:
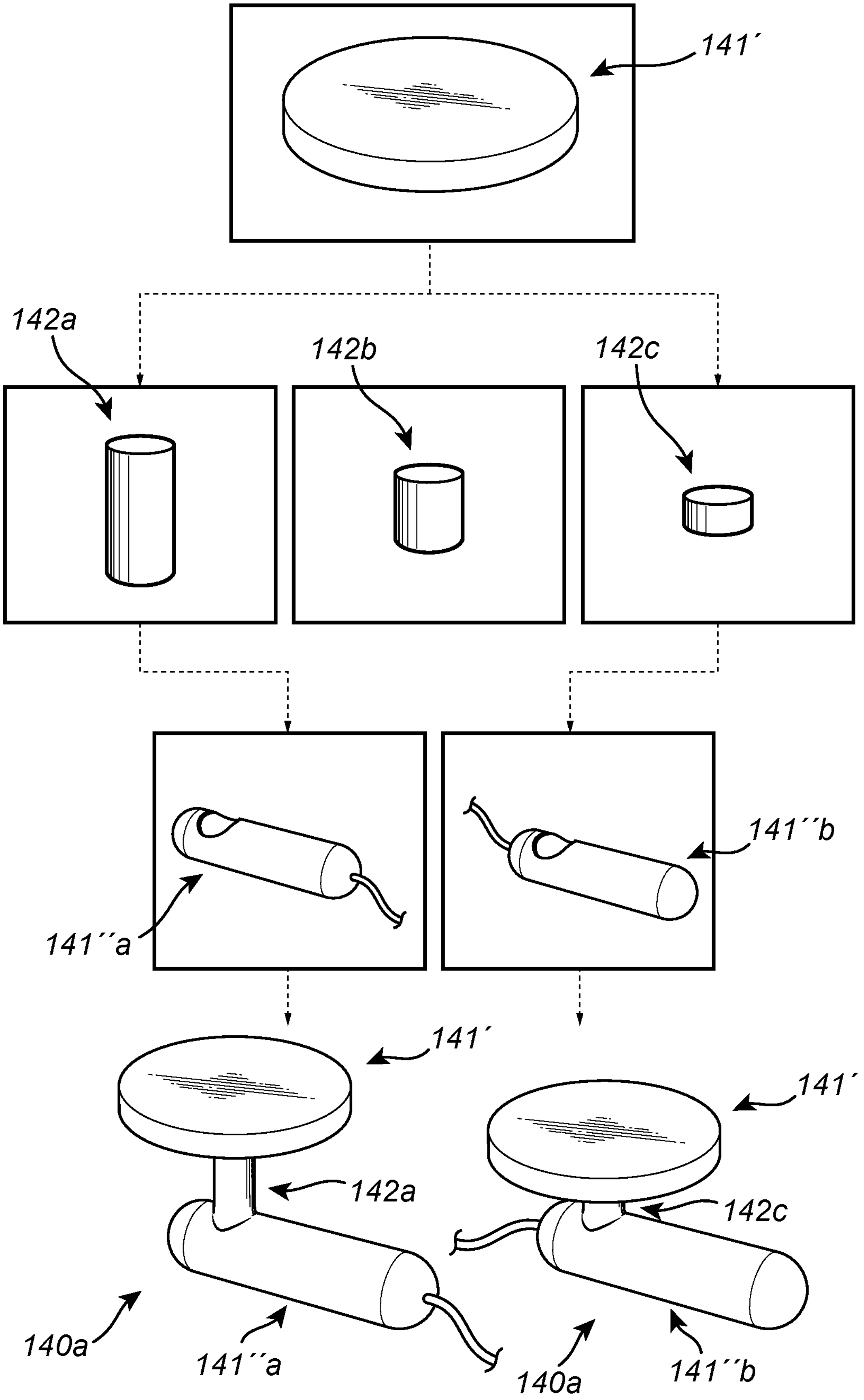
FIG. 53 shows a perspective elevated view from the right of an embodiment of an implantable remote unit for powering an implantable medical device.

In some embodiments, the connecting portion form part of the first portion or the second portion. With reference to FIG. 53, the kit for assembling the remote unit comprises a group 650 of one or more first portions 141', in the illustrated example a group of one first portion 141', a group 652 of one or more connecting portions 142, in the illustrated example a group of three connecting portions 142, and a group 654 of one or more second portions 141", in the illustrated example a group of two second portions 141". For simplicity, all types and combinations of first portions, second portions and connecting portions will not be illustrated or described in detail.

Accordingly, the group 652 of one or more connecting portions 142 comprise three different types of connecting portions 142. Here, the different types of connecting portions 142 comprise connecting portions 142*a*, 142*b*, 142*c* having different heights. Furthermore, the group 654 of one or more second portions 141" comprise two different types of second portions 141".

Here, the different types of second portions 141" comprise a second portion 141"*a* being configured to eccentrically connect to a connecting portion, having a first end and a second end as described in other parts of the present disclosure, wherein the second end of the second portion 141"*a* comprises or is configured for at least one connection for connecting to an implant being located in a caudal direction from a location of the remote unit in the patient, when the device is assembled. In the illustrated figure, the at least one connection is visualized as a lead or wire. However, other embodiments are possible, including the second end comprising a port, connector or other type of connective element for transmission of power, fluid, and/or signals.

Furthermore, the different types of second portions 141" comprise a second portion 141"*b* being configured to eccentrically connect to a connecting portion, having a first end and a second end as described in other parts of the present disclosure, wherein the first end of the second portion 141"*b* comprises or is configured for at least one connection for connecting to an implantable medical device for treating reflux disease of the patient, being located in a cranial direction from a location of the remote unit in the patient, when the device is assembled. In the illustrated figure, the at least one connection is visualized as a lead or wire. However, other embodiments are possible, including the first end comprising a port, connector or other type of connective element for transmission of power, fluid, and/or signals.

Thus, the remote unit may be modular, and different types of devices can be achieved by selecting and combining a first portion 141', a connecting portion 142, and a second portion 141", from each of the groups 652, 654, 656.

In the illustrated example, a first remote unit 140*a* is achieved by a selection of the first portion 141', the connecting portion 142*a*, and the second portion 141"*a*. Such remote unit 140*a* may be particularly advantageous in that the connecting portion 142*a* may be able to extend through a thick layer of tissue to connect the first portion 141' and the second portion 141"*a*. Another remote unit 140*b* is achieved by a selection of the first portion 141', the connecting portion 142*c*, and the second portion 141"*b*. Such device may be particularly advantageous in that the connecting portion 142*c* has a smaller footprint than the connecting portion 142*a*, i.e. occupying less space in the patient. Owing to the modular property of the remote units 140*a* and 140*b*, a practician or surgeon may select a suitable connecting portion as needed upon having assessed the anatomy of a patient. Furthermore, since remote units 140*a* and 140*b* share a common type of first portions 141', it will not be necessary for a practician or surgeon to maintain a stock of different first portions (or a stock of complete, assembled devices) merely for the sake of achieving a device having different connections located in the first end or second end of the second portion respectively, as in the case of second portions 141"*a*, 141"*b*.

The example illustrated in FIG. 53 is merely exemplifying to display the idea of a modular implantable remote unit 140. The group 650 of one or more first portions 141' may comprise a variety of different features, such as first portions with or without a first energy storage unit, with or without a first wireless energy receiver unit for receiving energy transmitted wirelessly by an external wireless energy transmitter, with or without an internal wireless energy transmitter, and/or other features as described throughout the present disclosure. Other features include different height, width, or length of the first portion. It is to be understood that first portions having one or more such features may be combined with a particular shape or dimensions to achieve a variety of first portions. The same applies to connecting portions and second portions.

Figure 54:
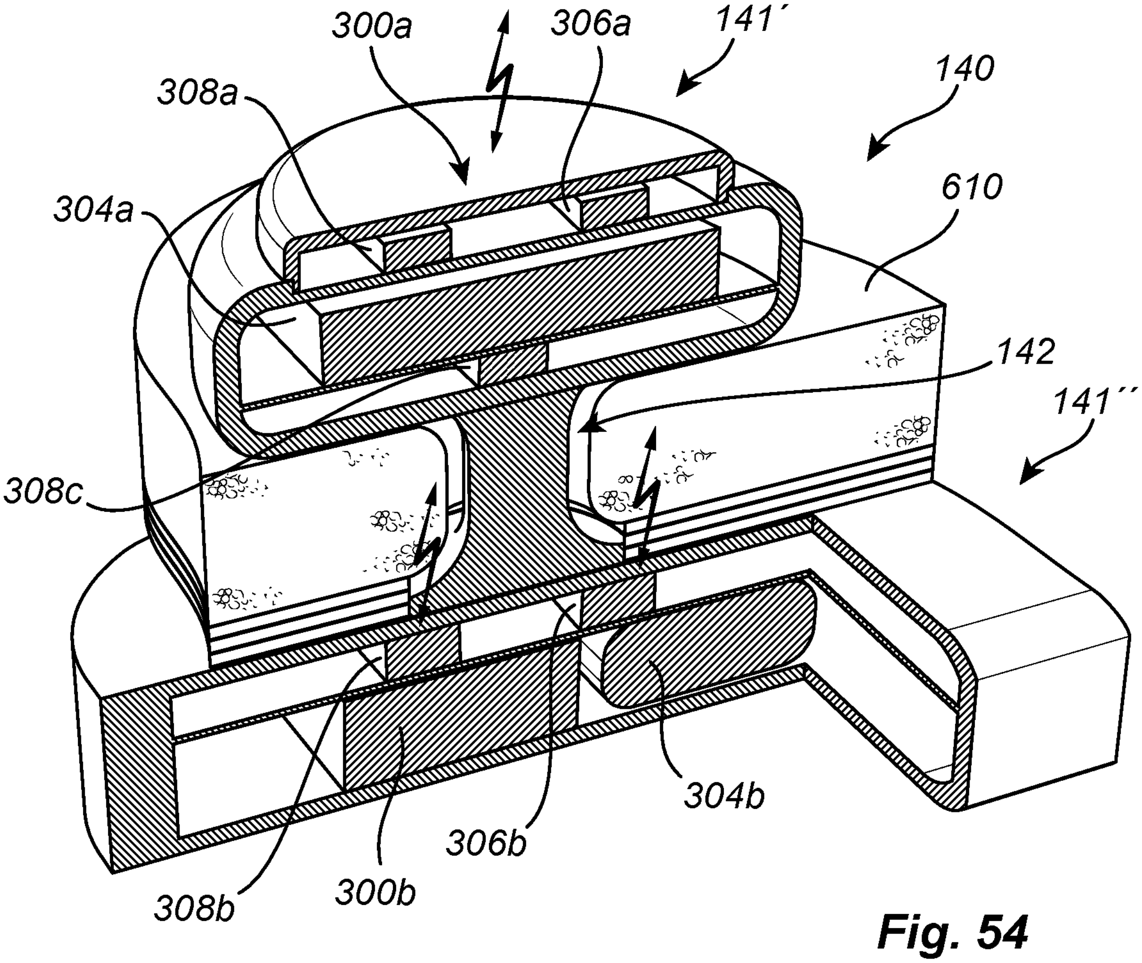
FIG. 54 shows a perspective elevated view from the right of a portion of an embodiment of an implantable remote unit for powering an implantable medical device.

With reference to FIG. 54, an embodiment of an implantable remote unit 140, will be described. The remote unit 140 is configured to be held in position by a tissue portion 610 of a patient. The remote unit 140 comprises a first portion 141' configured to be placed on a first side of the tissue portion 610, the first portion 141' having a first cross-sectional area in a first plane and comprising a first surface configured to face and/or engage a first tissue surface of the first side of the tissue portion 610. The device 140 further comprises a second portion 141" configured to be placed on a second side of the tissue portion 610, the second side opposing the first side, the second portion 141" having a second cross-sectional area in a second plane and comprising a second surface configured to engage a second tissue surface of the second side of the tissue portion 610. The remote unit 140 further comprises a connecting portion 142 configured to be placed through a hole in the tissue portion 610 extending between the first and second sides of the tissue portion 610. The connecting portion 142 here has a third cross-sectional area in a third plane. The connecting portion 142 is configured to connect the first portion 141' to the second portion 141". Here, the first portion 141' comprises a first wireless energy receiver 308*a* for receiving energy transmitted wirelessly by an external wireless energy transmitter, and an internal wireless energy transmitter 308*a* configured to transmit energy wirelessly to the second portion. Furthermore, the second portion here comprises a second wireless energy receiver 308*b* configured to receive energy transmitted wirelessly by the internal wireless energy transmitter 308*a*.

Although receivers and transmitters may be discussed and illustrated separately in the present disclosure, it is to be understood that the receivers and/or transmitters may be comprised in a transceiver. Furthermore, the receivers and/or transmitters in the first portion 141' and second portion 141" respectively may form part of a single receiving or transmitting unit configured for receiving or transmitting energy and/or communication signals, including data. Furthermore, the internal wireless energy transmitter and/or a first wireless communication receiver/transmitter may be a separate unit 308*c* located in a lower portion of the first portion 141', referred to as a proximal end of the first portion 141' in other parts of the present disclosure, close to the connecting portion 142 and the second portion 141". Such placement may provide for that energy and/or communication signals transmitted by the unit 308*c* will not be attenuated by internal components of the first portion 141' when being transmitted to the second portion 141". Such internal components may include a first energy storage unit 304*a*.

The first portion 141' here comprises a first energy storage unit 304*a* connected to the first wireless energy receiver 308*a*. The second portion comprises a second energy storage unit 304*b* connected to the second wireless energy receiver 308*b*. Such an energy storage unit may be a solid-state battery, such as a thionyl-chloride battery.

In some embodiments, the first wireless energy receiver 308*a* is configured to receive energy transmitted wirelessly by the external wireless energy transmitter and store the received energy in the first energy storage unit 304*a*. Furthermore, the internal wireless energy transmitter 308*a* is configured to wirelessly transmit energy stored in the first energy storage unit 304*a* to the second wireless energy receiver 308*b*, and the second wireless energy receiver 308*b* is configured to receive energy transmitted wirelessly by the internal wireless energy transmitter 308*a* and store the received energy in the second energy storage unit 305*b*.

The first energy storage unit 304*a* may be configured to store less energy than the second energy storage unit 304*b*, and/or configured to be charged faster than the second energy storage unit 304*b*. Hereby, charging of the first energy storage unit 304*a* may be relatively quick, whereas transfer of energy from the first energy storage unit 304*a* to the second energy storage unit 304*b* may be relatively slow. Thus, a user can quickly charge the first energy storage unit 304*a*, and will not during such charging be restricted for a long period of time by being connected to an external wireless energy transmitter, e.g. at a particular location. After having charged the first energy storage unit 304*a*, the user may move freely while energy slowly transfers from the first energy storage unit 304*a* to the second energy storage unit 304*b*, via the first wireless energy transmitter 308*a,c* and the second wireless energy receiver 308*b*.

The first portion may comprise a first controller comprising at least one processing unit 306*a*. The second portion may comprise a second controller comprising at least one processing unit 306*b*. At least one of the first and second processing unit 306*a*, 306*b* may be connected to a wireless transceiver 308*a,b,c* for communicating wirelessly with an external device.

The first controller may be connected to a first wireless communication receiver 308*a,c* in the first portion 141' for receiving wireless communication from an external device and/or from a wireless communication transmitter 308*b* in the second portion 141". Furthermore, the first controller may be connected to a first wireless communication transmitter 308*a,c* in the first portion 141' for transmitting wireless communication to a second wireless communication receiver 308*b* in the second portion 141". The second controller may be connected to the second wireless communication receiver 308*b* for receiving wireless communication from the first portion 141'. The second controller may further be connected to a second wireless communication transmitter 308*b* for transmitting wireless communication to the first portion 141'.

Figure 64:
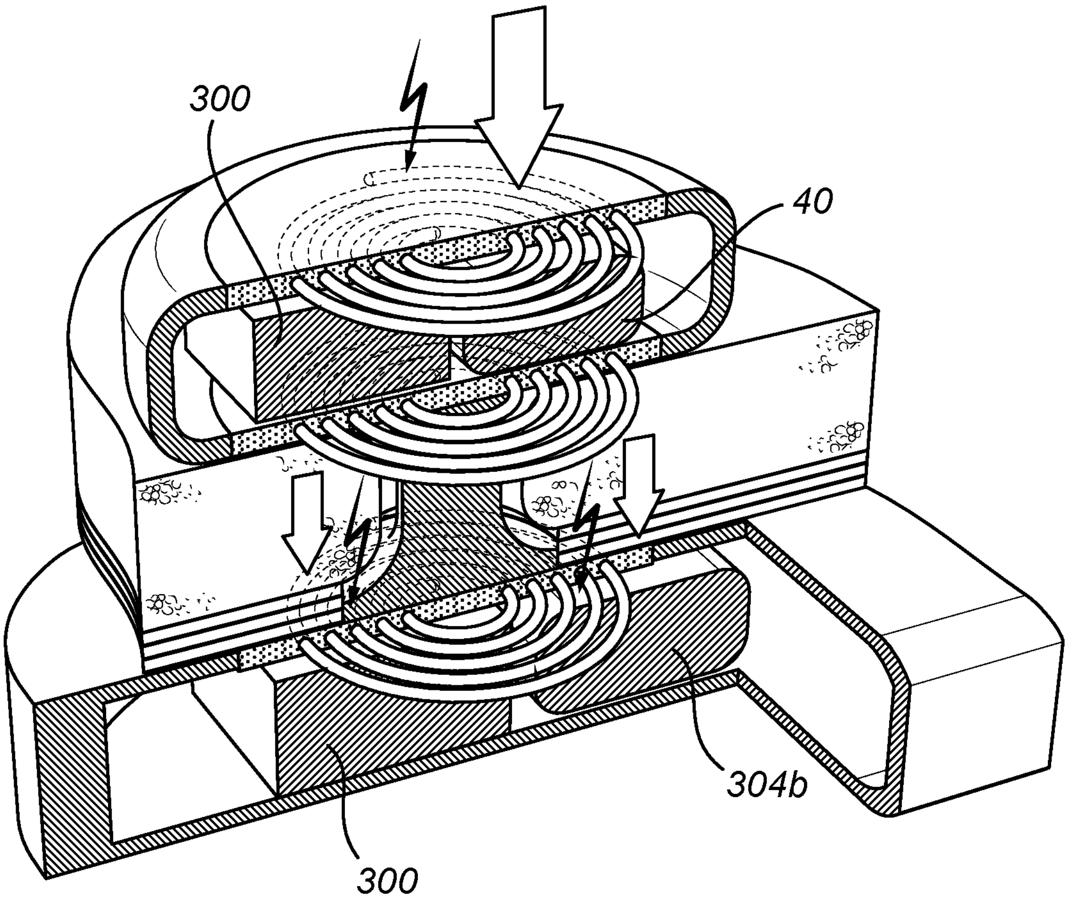
FIG. 64 shows a detailed cross-sectional view of an embodiment of an implantable remote unit for powering an implantable medical device.

In some embodiments, the first wireless energy receiver 308*a* comprises a first coil, and the wireless energy transmitter 308*a,c* comprises a second coil, as shown in FIG. 64.

The device may further comprise at least one sensor (not shown) for providing input to at least one of the first and second controller. Such sensor data may be transmitted to an external device via the first wireless communication transmitter 308*a* and/or the second wireless communication transmitter 308*b*. The sensor may be or comprise a sensor configured to sense a physical parameter of the device 140. The sensor may also be or comprise a sensor configured to sense at least one of a temperature of the remote unit 140, a temperature of an implantable device for stretching the stomach wall (which may be located in the main portion), a parameter related to the power consumption of the device, a parameter related to the power consumption of an stimulation device for stimulating muscle tissue touched by the implantable device, a parameter related to a status of at least one of the first and second energy storage unit 304*a*, 304*b*, and a parameter related to the wireless transfer of energy from a source external to the body of the patient. The sensor may also be or comprise a sensor configured to sense a physiological parameter of the patient, such as at least one of a parameter related to the patient swallowing, a local temperature, a systemic temperature, a blood saturation, a blood oxygenation, a blood pressure, a parameter related to an ischemia marker, or pH. The sensor configured to sense a parameter related to the patient swallowing may comprise at least one of a motility sensor, a acoustic sensor, an optical sensor, and a strain sensor. The sensor configured to sense pH may be configured to sense the acidity in the stomach.

The sensor may be configured to sense a temperature of the device 140, to avoid excessive heating of tissue connected to the device during operation of the device, or during operation of an external implant using the device, or charging of an energy storage unit in the device 140. Excessive heating may also damage the device and/or the energy storage unit. Excessive heating may also be an indicator that something is wrong with the device and may be used for triggering an alarm function for alerting the patient or physician. The sensor may also be configured to sense a parameter related to the power consumption of the device 140 or the power consumption of an external implant being powered by the device 140, to avoid excessive power consumption which may drain and/or damage the energy storage unit of the device 140. Excessive power consumption may also be an indicator that something is wrong with the device 140 and may be used for triggering an alarm function for alerting the patient or physician.

Figure 55:
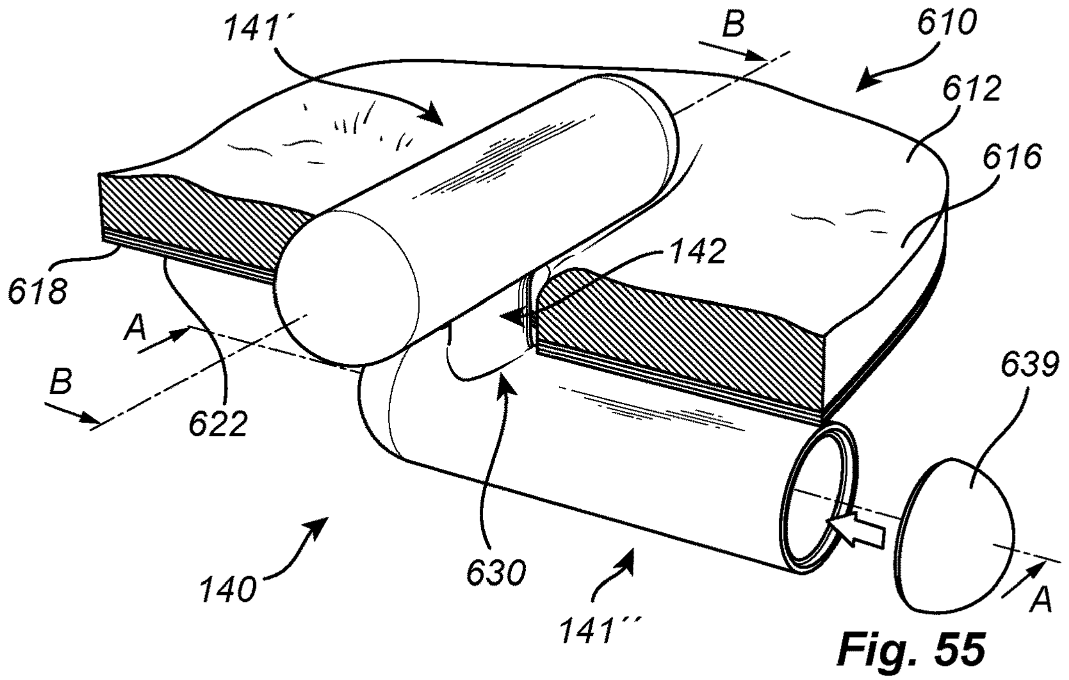
FIG. 55 shows a perspective elevated view from the right of a portion of an embodiment of an implantable remote unit for powering an implantable medical device.
Figure 58A:
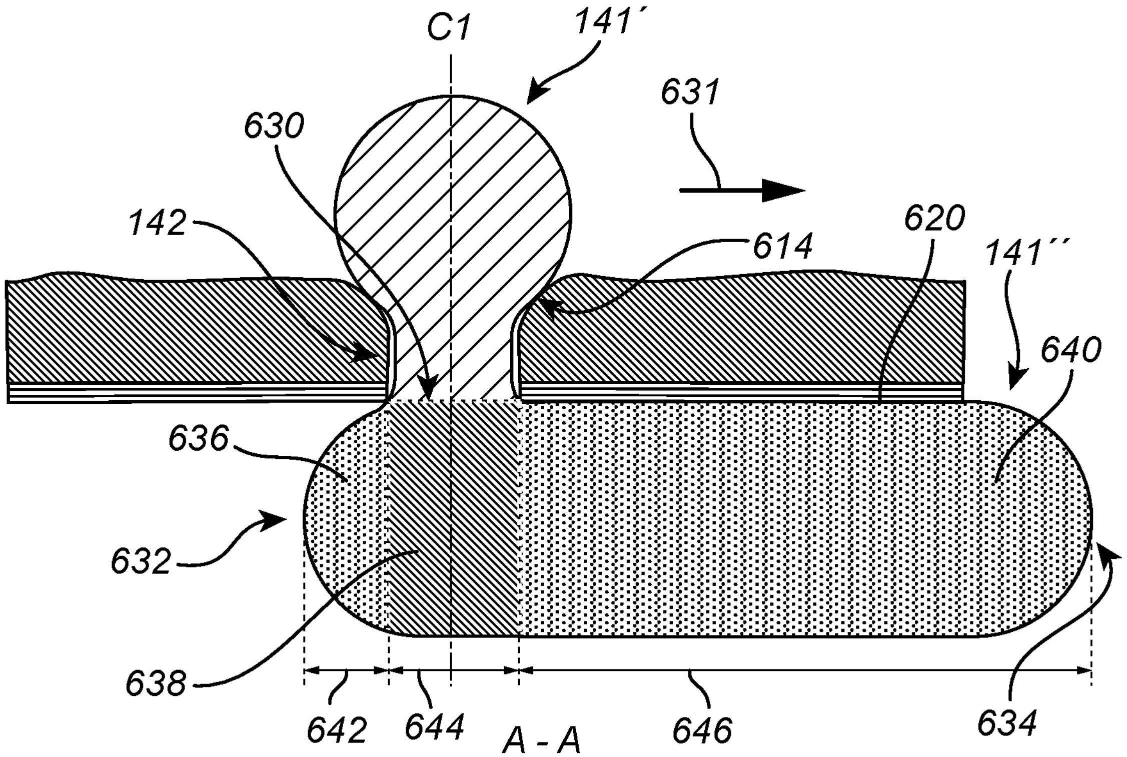
FIGS. 58A-D show cross-sectional plain side views of embodiments of an implantable remote unit for powering an implantable medical device.
Figure 58B:
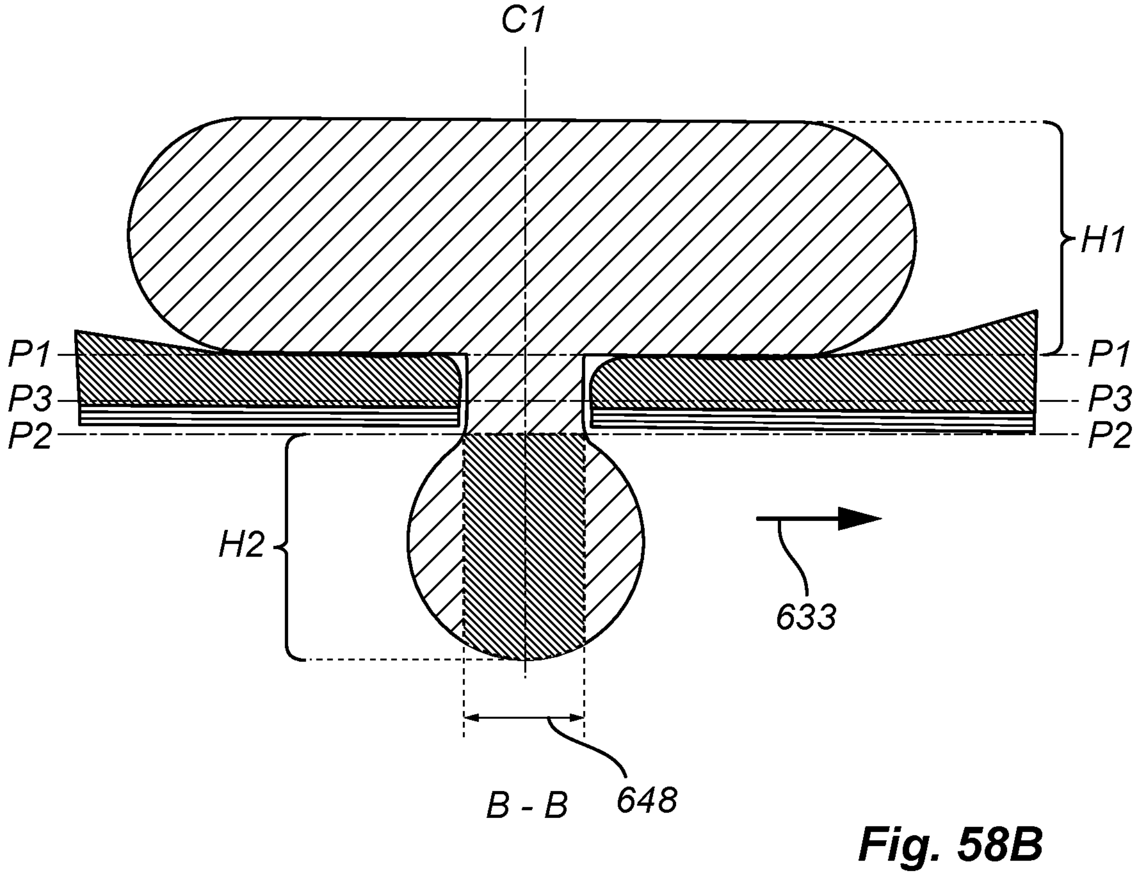
Figure 58C:
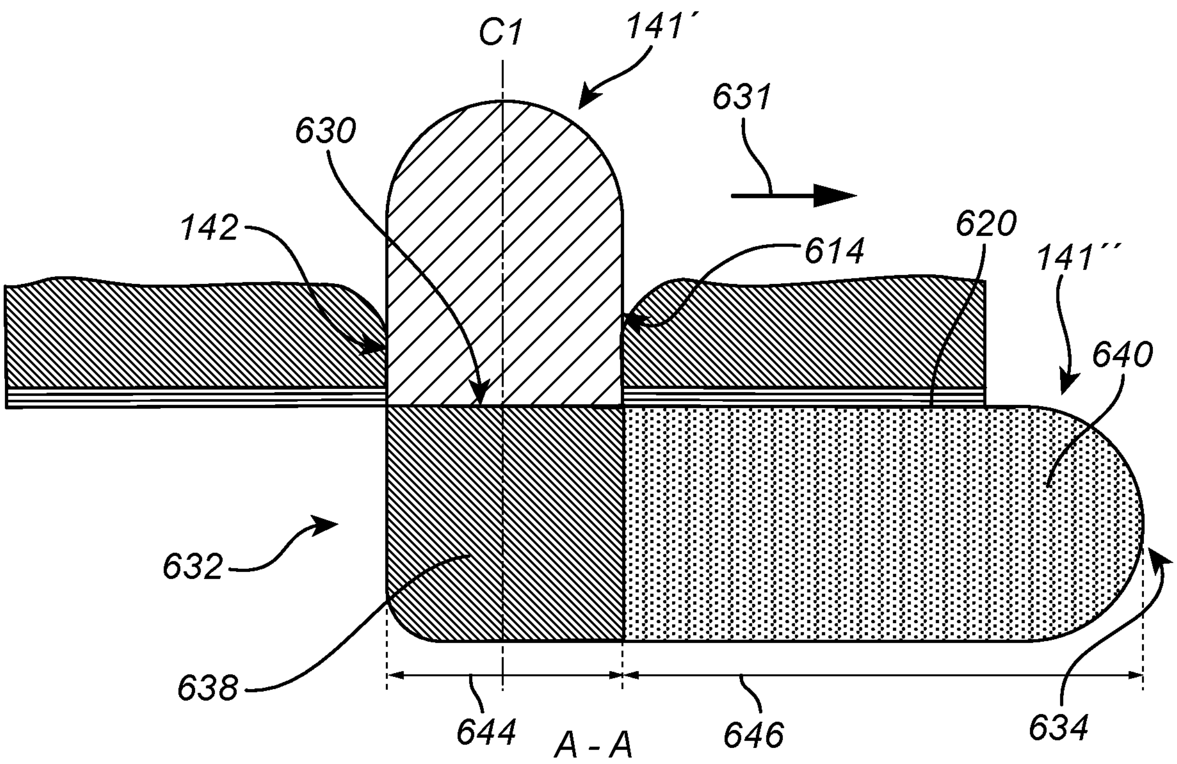
Figure 58D:
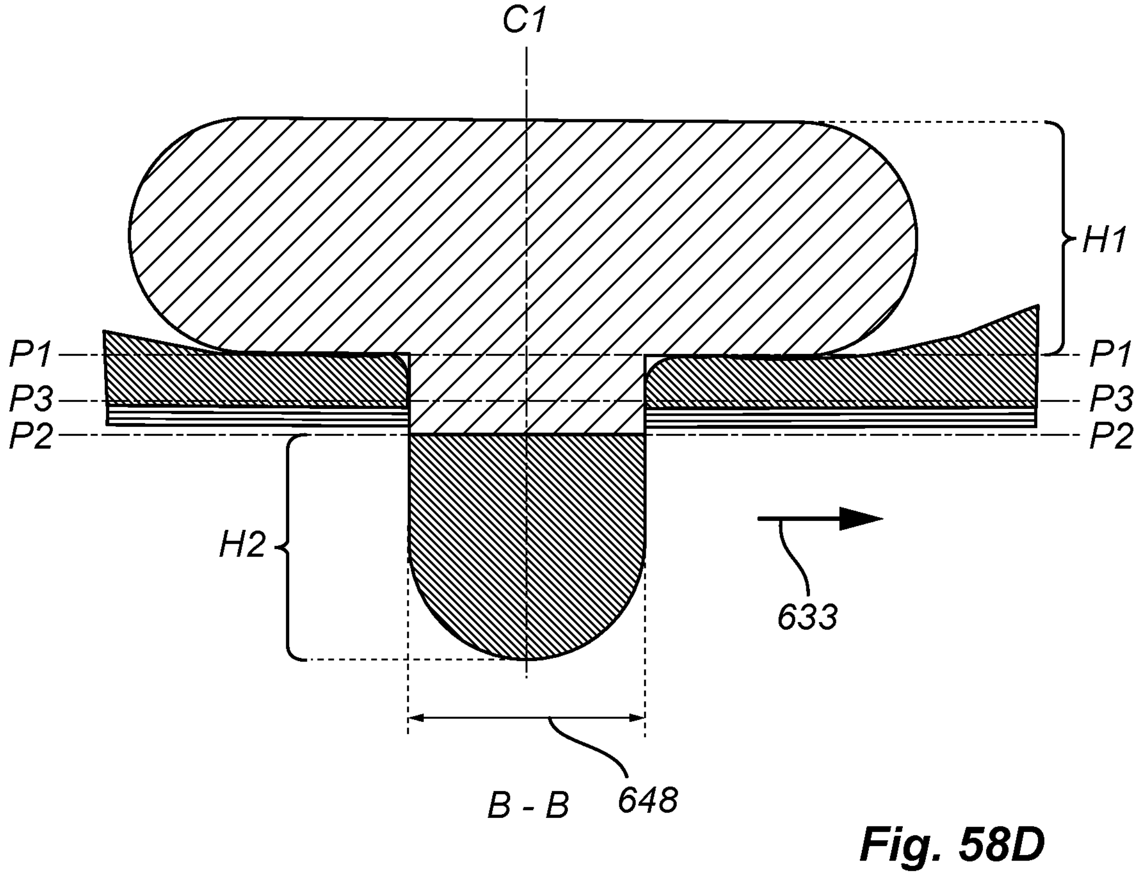

With reference to FIGS. 55, 58A and 58B, an embodiment of an implantable remote unit 140 will be described. The remote unit 140 is configured to be held in position by a tissue portion 610 of a patient.

The remote unit 140 comprises a first portion 141' configured to be placed on a first side 612 of the tissue portion 610, the first portion 141' having a first cross-sectional area A1 in a first plane P1 and comprising a first surface 614 configured to face and/or engage a first tissue surface 616 of the first side 612 of the tissue portion 610. The remote unit 140 further comprises a second portion 141" configured to be placed on a second side 618 of the tissue portion 610, the second side 618 opposing the first side 612, the second portion 141" having a second cross-sectional area A2 in a second plane P2 and comprising a second surface 620 configured to engage a second tissue surface 622 of the second side 618 of the tissue portion 610. The remote unit 140 further comprises a connecting portion 142 configured to be placed through a hole in the tissue portion 610 extending between the first and second sides 612, 618 of the tissue portion 610. The connecting portion 142 here has a third cross-sectional area A3 in a third plane P3. The connecting portion 142 is configured to connect the first portion 141' to the second portion 141". In the illustrated embodiment, a connecting interface 630 between the connecting portion 142 and the second portion 141" is eccentric with respect to the second portion 141".

The first portion 141' has an elongated shape in the illustrated embodiment of FIG. 55. Similarly, the second portion 141" has an elongated shape. However, the first portion 141' and/or second portion 141" may assume other shapes, such as a flat disk e.g. having a width and length being larger than the height, a sphere, an ellipsoid, or any other polyhedral or irregular shape, some of these being exemplified in FIGS. 55-57.

As illustrated in FIGS. 58A and 58B, the connecting interface 630 between the connecting portion 142 and the second portion 141" may be eccentric, with respect to the second portion 141" in a first direction 631, but not in a second direction 633 being perpendicular to the first direction. The first direction 631 is here parallel to the line A-A, to the second plane P2, and to a length of the second portion 141". The second direction 633 is here parallel to the line B-B, to the second plane P2, and to a width of the second portion 141". It is also possible that the connecting interface between the connecting portion 142 and the second portion 141" is eccentric, with respect to the second portion 141", in the first direction 631 as well as in the second direction 633 being perpendicular to the first direction 631.

Similarly, a connecting interface between the connecting portion 142 and the first portion 141' may be eccentric with respect to the first portion 141' in the first direction 631, and/or in the second direction 633.

The first portion 141', connecting portion 142 and second portion 141" may structurally form one integral unit. It is however also possible that the first portion 141' and the connecting portion 142 structurally form one integral unit, while the second portion 141" form a separate unit, or, that the second portion 141" and the connecting portion 142 structurally form one integral unit, while the first portion 141' form a separate unit.

Additionally, or alternatively, the second portion 141" may comprise a removable and/or interchangeable portion 639. In some embodiments, the removable portion 639 may form part of a distal region which will be further described in other parts of the present disclosure. A removable portion may also form part of a proximal region. Thus, the second portion 141" may comprise at least two removable portions, each being arranged at a respective end of the second portion 141". The removable portion 639 may house, hold or comprise one or several functional parts of the remote unit 140, such as gears, motors, connections, reservoirs, and the like as described in other parts of the present disclosure. An embodiment having such removable portion 639 will be able to be modified as necessary to circumstances of a particular patient.

In the case of the first portion 141', connecting portion 142 and second portion 141" structurally forming one integral unit, the eccentric connecting interface between the connecting portion 142 and the second portion 141", with respect to the second portion 141", will provide for that the remote unit 140 will be able to be inserted into the hole in the tissue portion. The remote unit 140 may for example be inserted into the hole at an angle, similar to how a foot is inserted into a shoe, to allow most or all of the second portion 141" to pass through the hole, before it is angled, rotated, and/or pivoted to allow any remaining portion of the second portion 141" to pass through the hole and allow the remote unit 140 to assume its intended position.

Figure 56:
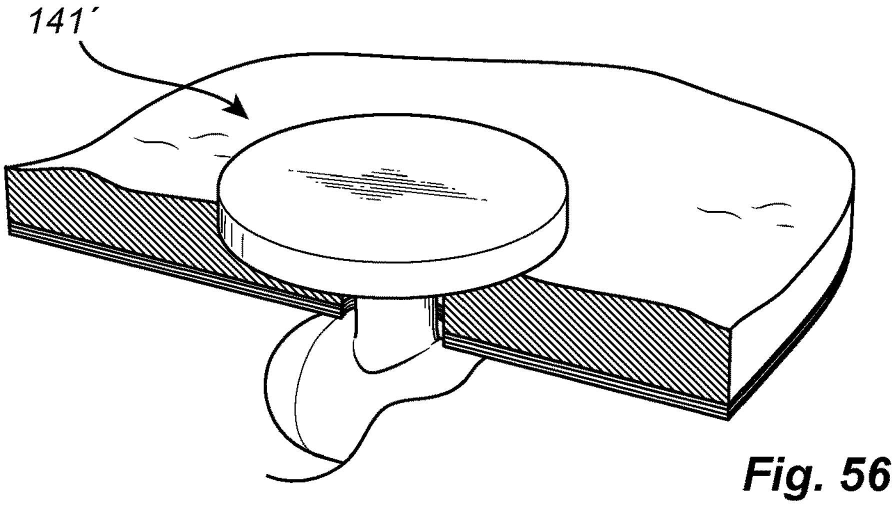
FIGS. 56-57 show cross-sectional plain side views of implantable remote units for powering an implantable medical device.
Figure 57:
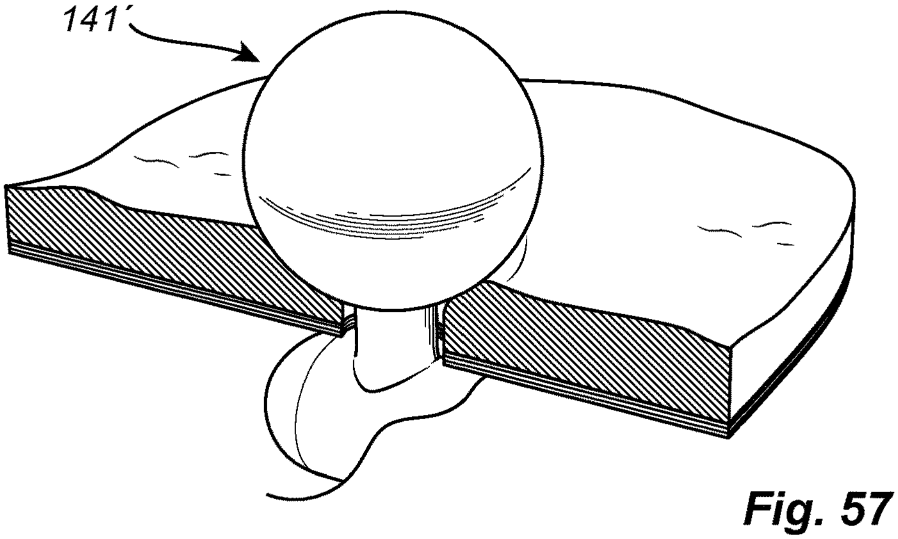

As illustrated in FIGS. 55-57, the first portion 141' may assume a variety of shapes, such as an oblong shape, a flat disk shape, a spherical shape, or any other polyhedral or irregular shape. Similarly, the second portion 141" may assume a variety of shapes, such as an oblong shape, a flat disk shape, a spherical shape, or any other polyhedral or irregular shape. The proposed shapes of the first and second portions 141', 141" may be mixed and combined to form embodiments not exemplified in the illustrated embodiments. For example, one or both of the first and second portions 141', 141" may have a flat oblong shape. In this context, the term "flat" is related to the height of the first or second portion 141', 141", i.e. in a direction parallel to a central extension C1 of the connecting portion 142. The term "oblong" is related to a length of the first or second portion 141', 141". A definition of such length is further discussed in other parts of the present disclosure.

With reference to FIGS. 58A-58B, the second portion 141" has a first end 632 and a second end 634 opposing the first end 632. The length of the second portion 141" is defined as the length between the first end 632 and the second end 634. The length of the second portion 141" is furthermore extending in a direction being different to the central extension C1 of the connecting portion 142. The first end 632 and second end 634 are separated in a direction parallel to the second plane P2. Similarly, the first portion 141' has a length between a first and a second end, the length extending in a direction being different to the central extension C1 of the connecting portion 142.

The second portion 141" may be curved along its length. For example, one or both ends of the second portion 141" may point in a direction being substantially different from the second plane P2, i.e. curving away from or towards the tissue portion when implanted. In some embodiments, the second portion 141" curves within the second plane P2, exclusively or in combination with curving in other planes. The second portion 141" may also be curved in more than one direction, i.e. along its length and along its width, the width extending in a direction perpendicular to the length.

The first and second ends 632, 634 of the second portion 141" may comprise an elliptical point respectively. For example, the first and second ends 632, 634 may comprise a hemispherical end cap respectively. It is to be understood that also the first and second ends of the first portion 141' may have such features.

The second portion 141" may have at least one circular cross-section along the length between the first end 632 and second end 634, as illustrated in FIG. 55. It is however possible for the second portion 141" to have at least one oval cross-section or at least one elliptical cross-section along the length between the first end 632 and the second end 634. Such cross-sectional shapes may also exist between ends in a width direction of the second portion 141". Similarly, such cross-sectional shapes may also exist between ends in a length and/or width direction in the first portion 141'.

In the following paragraphs, some features and properties of the second portion 141" will be described. It is however to be understood that these features and properties may also apply to the first portion 141'.

The second portion 141" has a proximal region 636, an intermediate region 638, and a distal region 640. The proximal region 636 extends from the first end 632 to an interface between the connecting portion 142 and the second portion 141", the intermediate region 638 is defined by the connecting interface 630 between the connecting portion 142 and the second portion 141", and the distal region 640 extends from the connecting interface 630 between the connecting portion 142 and the second portion 141" to the second end 634. The proximal region 636 is shorter than the distal region 640 with respect to the length of the second portion, i.e. with respect to the length direction 631. Thus, a heel (the proximal region) and a toc (the distal region) is present in the second portion 141".

The second surface 620, configured to engage with the second tissue surface 622 of the second side 618 of the tissue portion 610, is part of the proximal region 636 and the distal region 640. If a length of the second portion 141" is defined as x, and the width of the second portion 141" is defined as y along respective length and width directions 631, 633 being perpendicular to each other and substantially parallel to the second plane P2, the connecting interface between the connecting portion 142 and the second portion 141" is contained within a region extending from $x>0$ to $x<x/2$ and/or $y>0$ to $y<y/2$, x and y and 0 being respective end points of the second portion 141" along said length and width directions. In other words, the connecting interface between the connecting portion 142 and the second portion 141" is eccentric in at least one direction with respect to the second portion 141", such that a heel and a toe is formed in the second portion 141".

The first surface 614 configured to face and/or engage the first tissue surface 616 of the first side 612 of the tissue portion 610 may be substantially flat. In other words, the first portion 141' may comprise a substantially flat side facing towards the tissue portion 610. Furthermore, an opposing surface of the first portion 141', facing away from the tissue portion 610, may be substantially flat. Similarly, the second surface 620 configured to engage the second tissue surface 622 of the second side 618 of the tissue portion 610 may be substantially flat. In other words, the second portion 141" may comprise a substantially flat side facing towards the tissue portion 610. Furthermore, an opposing surface of the second portion 141", facing away from the tissue portion 610, may be substantially flat.

The second portion 141" may be tapered from the first end 632 to the second end 634, thus giving the second portion 141" different heights and/or widths along the length of the second portion 141". The second portion may also be tapered from each of the first end 632 and second end 634 towards the intermediate region 638 of the second portion 141".

Some dimensions of the first portion 141', the second portion 141" and the connecting portion 142 will now be disclosed. Any of the following disclosures of numerical intervals may include or exclude the end points of said intervals.

The first portion 141' may have a maximum dimension being in the range of 10 to 60 mm, such as in the range of 10 to 40 mm such as in the range of 10 to 30 mm, such as in the range of 10 to 25 mm, such as in the range of 15 to 40 mm, such as in the range of 15 to 35 mm, such as in the range of 15 to 30 mm, such as in the range of 15 to 25 mm. By the term "maximum dimension" it is hereby meant the largest dimension in any direction.

The first portion 141' may have a diameter being in the range of 10 to 60 mm, such as in the range of 10 to 40 mm such as in the range of 10 to 30 mm, such as in the range of 10 to 25 mm, such as in the range of 15 to 40 mm, such as in the range of 15 to 35 mm, such as in the range of 15 to 30 mm, such as in the range of 15 to 25 mm.

The connecting portion 142 may have a maximum dimension in the third plane P3 in the range of 2 to 20 mm, such as in the range of 2 to 15 mm, such as in the range of 2 to 10 mm, such as in the range of 5 to 10 mm, such as in the range of 8 to 20 mm, such as in the range of 8 to 15 mm, such as in the range of 8 to 10 mm.

The second portion 141" may have a maximum dimension being in the range of 30 to 90 mm, such as in the range of 30 to 70 mm, such as in the range of 30 to 60 mm, such as in the range of 30 to 40 mm, such as in the range of 35 to 90 mm, such as in the range of 35 to 70 mm, such as in the range of 35 to 60 mm, such as in the range of 35 to 40 mm.

The first portion has a first height H1, and the second portion has a second height H2, both heights being in a direction perpendicular to the first and second planes P1, P2. The first height may be smaller than the second height. However, in the embodiments illustrated in FIGS. 58A-58B, the first height H1 is substantially equal to the second height H2. Other height ratios are possible, for example the first height H1 may be less than ⅔ of the second height H2, such as less than ½ of the second height H2, such as less than ⅓ of the second height H2, such as less than ¼ of the second height H2, such as less than ⅕ of the second height H2, such as less than 1/10 of the second height H2.

As illustrated in FIGS. 58A-58B, the proximal region 636 has a length 642 being shorter than a length 646 of the distal region 640. The intermediate region 638 has a length 644, and a width 648. In some embodiments, the length 644 of the intermediate region 638 is longer than the width 648. In other words, the connecting interface between the connecting portion 142 and the second portion 141" may be elongated, having a longer dimension (in the exemplified case, the length) and a shorter dimension (in the exemplified case, the width). It is also possible that the length 644 of the intermediate region 638 is shorter than the width 648 of the intermediate region 638.

The length 646 of the distal region 640 is preferably longer than the length 644 of the intermediate region 638, however, an equally long distal region 640) and intermediate region 638, or a shorter distal region 640 than the intermediate region 638, is also possible. The length 642 of the proximal region 636 may be shorter than, equal to, or longer than the length 644 of the intermediate region 638.

The length 644 of the intermediate region 638 is preferably less than half of the length of the second portion 141", i.e. less than half of the combined length of the proximal region 636, the intermediate region 638, and the distal region 630. In some embodiments, the length 644 of the intermediate region 638 is less than a third of the length of the second portion 141", such as less than a fourth, less than a fifth, or less than a tenth of the length of the second portion 141".

The connecting portion may have one of an oval cross-section, an elongated cross-section, and a circular cross-section, in a plane parallel to the third plane P3. In particular, the connecting portion may have several different cross-sectional shapes along its length in the central extension C1.

FIGS. 45C-45D illustrate an embodiment similar to the one described in conjunction with FIGS. 58*a*-58*b*. However, the embodiment of FIGS. 58*c*-58*d* lacks a proximal portion, i.e. the second portion 141" does not comprise a "heel". Furthermore, such embodiment may have a connecting portion 142 having a length and width, in directions 631 and 633 respectively, being equal to a height of the second portion in a direction parallel to the central extension C1, as illustrated. Thus, the connecting portion 142 and the second portion 141" may be constituted by a substantially uniformly wide body.

In some embodiments the distal region 640 is configured to be directed downwards in a standing patient, i.e. in a caudal direction when the remote unit 140 is implanted. As illustrated in FIGS. 59A-59D, different orientations of the second portion 141" relative the first portion 141' are possible. In some embodiments, a connection between either the first portion 141' and the connecting portion 142, or between the second portion 141" and the connecting portion 142, may allow for a plurality of different connecting orientations. For example, a connection mechanism between the first portion 141' and the connecting portion 142 (or between the second portion 141" and the connecting portion 142) may possess a 90 degree rotational symmetry to allow the second portion 141' to be set in four different positions with respect to the first portion 141, each differing from the other by 90 degrees. Other degrees of rotational symmetry are of course possible, such as 30 degrees, 45 degrees, 60 degrees, 120 degrees, 180 degrees and so on. In other embodiments there are no connective mechanism between any of the first portion 141', the connecting portion 142, and the second portion 141" (i.e. the portions are made as one integral unit), and in such cases different variants of the device 140 can be achieved during manufacturing. In other embodiments, the connective mechanism between the first portion 141' and the connecting portion 142 (or between the second portion 141" and the connecting portion 142) is non-reversible, i.e. the first portion 141' and the second portion 141" may initially be handled as separate parts, but the orientation of the second portion 141" relative the first portion 141' cannot be changed once it has been selected and the parts have been connected via the connecting portion 142.

The different orientations of the second portion 141" relative the first portion 141' may be defined as the length direction of the second portion 141" having a relation or angle with respect to a length direction of the first portion 141'. Such angle may be 15 degrees, 30, 45, 60, 75 90, 105, 120, 135, 150, 165, 180, 195, 210, 225, 240, 255, 270, 285, 300, 315, 330, 345 or 360 degrees. In particular, the angle between the first portion 141' and the second portion 141" may be defined as an angle in the planes P1 and P2, or as an angle in a plane parallel to the tissue portion 610, when the remote unit 140 is implanted. In the embodiment illustrated in FIGS. 58A-58D, the length direction of the second portion 141" is angled by 0, 90, 180, and 270 degrees with respect to the length direction of the first portion 141'.

The second end 634 of the second portion 141" may comprise one or several connections for connecting to an implant being located in a caudal direction from a location of the remote unit in the patient. Hereby, when the remote unit 140 is implanted in a patient, preferably with the distal region 640 and second end 634 pointing downwards in a standing patient, the connections will be closer to the implant as the second end 634 will be pointing in the caudal direction whereas the first end 632 will be pointing in the cranial direction. It is also possible that the second end 634 of the second portion 141" is configured for connecting to an implant, i.e. the second end 634 may comprise a port, connector or other type of connective element for transmission of power, and/or signals.

Likewise, the first end 632 of the second portion 141" may comprise one or several connections for connecting to an implant being located in a cranial direction from a location of the remote unit in the patient. Hereby, when the remote unit 140 is implanted in a patient, preferably with the distal region 640 and second end 634 pointing downwards in a standing patient, the connections will be closer to the implant as the first end 632 will be pointing in the cranial direction whereas the second end 634 will be pointing in the caudal direction. It is also possible that the first end 632 of the second portion 141" is configured for connecting to an implant, i.e. the first end 632 may comprise a port, connector or other type of connective element for transmission of power, and/or signals.

Referring now to FIGS. 59E-K, 59L, 59M, 59N and 59O. The following will discuss some features of the first portion 141', and in some cases additionally or alternatively of the connecting portion 142, which enable the first portion 141' to increase its cross-sectional area in the first plane (i.e. to increase an area of the first surface configured to face the first tissue surface), and/or which enable the first portion 141' to be rotated, translated, or otherwise moved in relation to the connecting portion 142. In some embodiments, the first portion 141' will be configured to extend further away from the connecting portion 142 in or within the first plane. It is to be understood that these features can be combined with other features of the implantable energized medical device. In particular, the specific shape of the first portion, connecting portion and/or second portion in the illustrated embodiments are merely exemplary. Other shapes are possible, as discussed in the present disclosure. Accordingly, the elongated second portion 141" does not necessarily need to be elongated as shown for example in FIG. 59E, and furthermore, the first portion 141' does not necessarily need to have a semicircular shape.

Figure 59A:
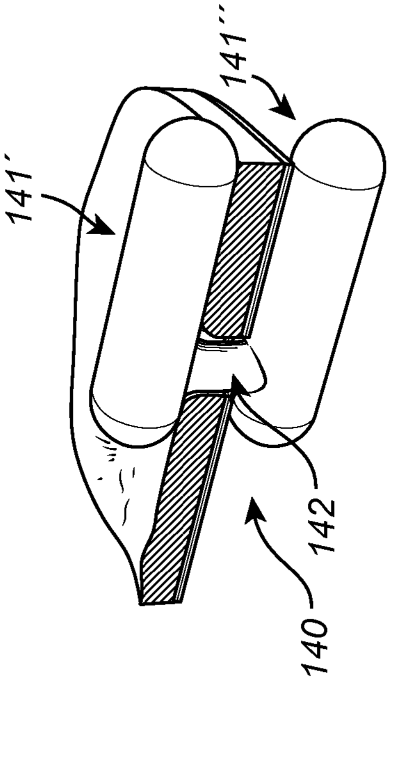
FIGS. 59A-O show embodiments of an implantable remote unit for powering an implantable medical device.
Figure 59B:
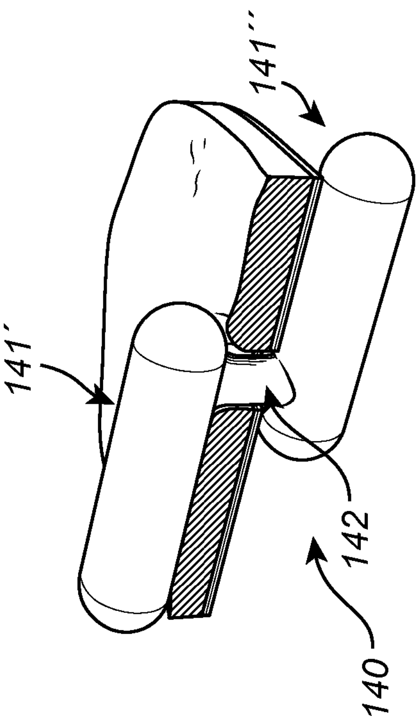
Figure 59C:
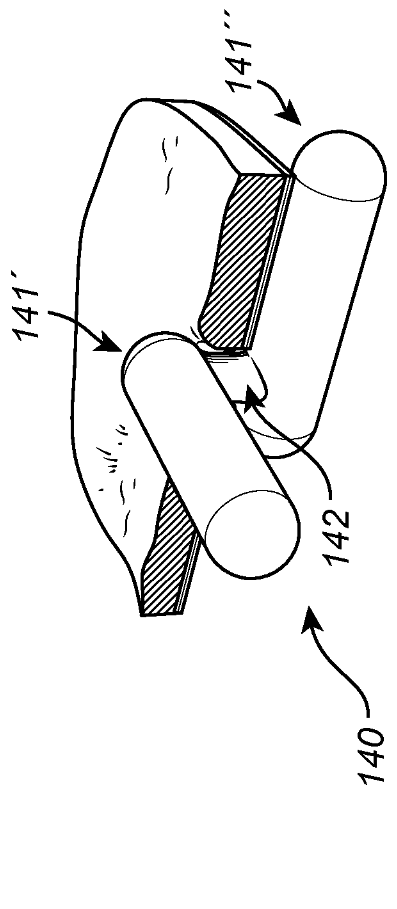
Figure 59D:
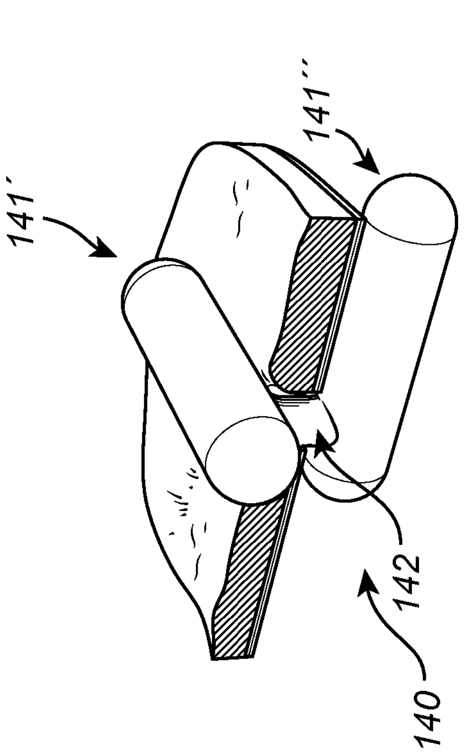
Figure 59E:
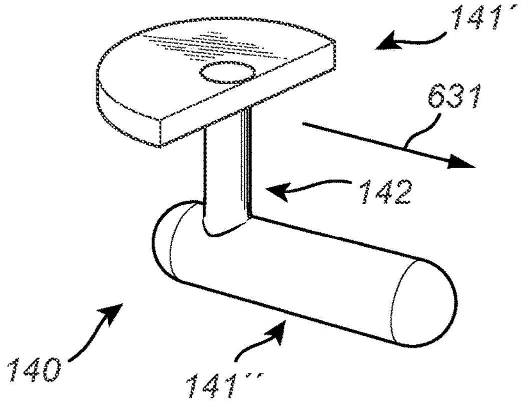

With reference to FIG. 59E, an implantable energized medical device 140 is shown, wherein the first portion 141' is configured and shaped such that an edge 710 of the first portion 141' is substantially aligned with the connecting portion 142 with regard to the first direction 631. In other words, no part of the first portion 141' protrudes forward of the connecting portion 142 with regard to the first direction 631. Hereby, insertion of the implantable energized medical device 140 may be facilitated, in particular when angled downwards, since the first portion 141' will not abut the tissue until most or all of the second portion 141" has been inserted through the hole in the tissue. Although the edge 710, as well as other edges of the first portion 141', are hereby shown as having no radius, radiused edges are possible. Thus, the edge 710 may have a radius, and/or the first portion 141', and/or the second portion 141", and/or the connecting portion 142, may comprise radiused edges.

Figure 59F:
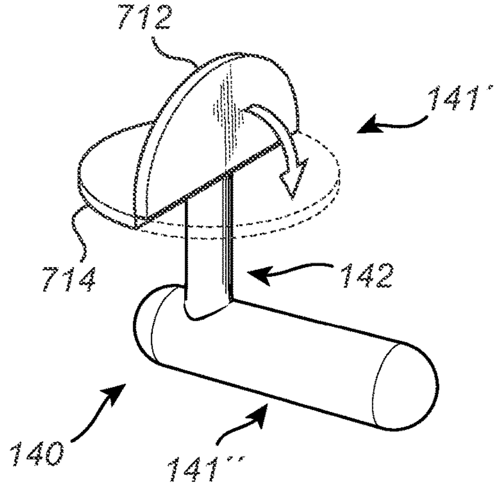
Figure 59G:
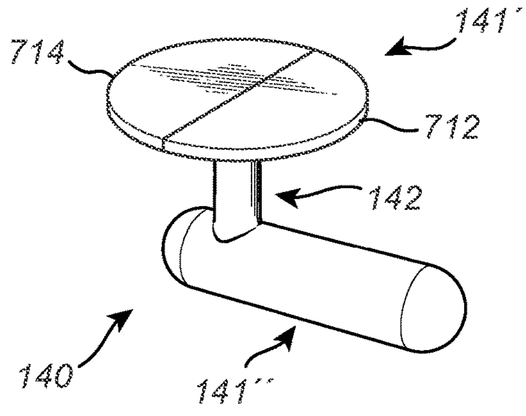

With reference to FIGS. 59F and 59G, a first portion 141' is shown being configured to have its surface area increased. Here, the first cross-sectional area is increased, thereby increasing an area of the first surface configured to face (and in some embodiments also configured to contact) the first tissue surface. In the illustrated embodiment, the first portion 141' comprises a first element 712 and a second element 714 being hingedly interconnected to allow the first element 712 to assume a first state (not shown) wherein the first element 712 is arranged on top of the second element 714, and a second state wherein the first element 712 is folded to be located adjacent or next to the second element 714. A similar configuration may be achieved by other means of interconnection between the first element 712 and second element 714, i.e. the configuration is not limited to a hinge-type connection. For example, the first element 712 and second element 714 may be constructed of a single piece of material being flexible enough to be able to fold over itself to assume the first and second state respectively.

Preferably, the first and second element 712, 714 are interconnected and formed such that a transition between the first and second element 712, 714 along the first direction 631 is flush. Furthermore, while in the first state, the first portion 141' may possess the same feature as discussed in conjunction with FIG. 59E, i.e. the first portion 141' may be substantially aligned with the connecting portion 142.

Figure 59H:
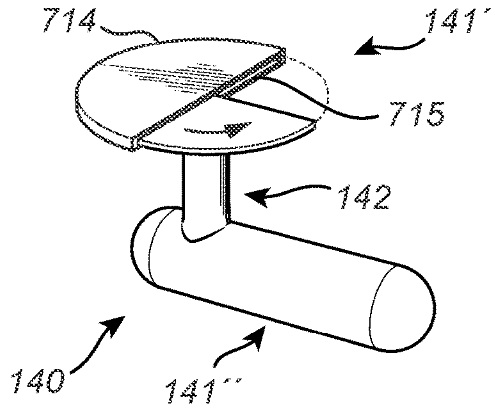
Figure 59I:
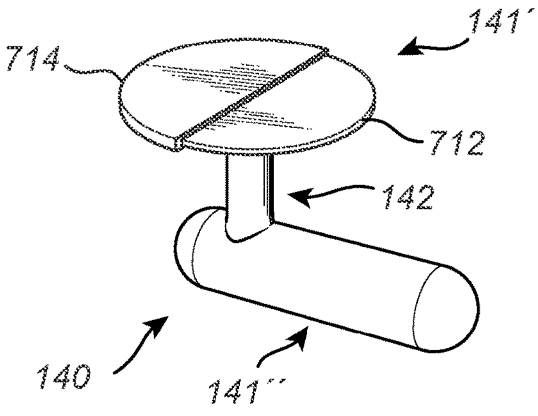

With reference to FIGS. 59H and 59I, a first portion 141' is shown being configured to have its surface area increased. Here, the first cross-sectional area is increased, thereby increasing an area of the first surface configured to face (and in some embodiments also configured to contact) the first tissue surface. In the illustrated embodiment, the first portion 141' comprises a first element 712 and a second element 714. The second element 714 here comprises a slot 715 configured to partially or fully house the first element 712. The first element 712 is configured to rotate about an axis to assume a first state, wherein the first element 712 is partially or completely housed in within the slot 715, and a second state wherein the first element 712 protrudes from the slot 715 to increase the first cross-sectional area. The first element 712 may be configured to rotate 180 degrees about the axis. In the illustrated example, the first and second elements 712, 714 are shaped as semi-circles and form a shape conforming to a full circle in the second state. However, it is also possible that the first element 712 only rotate about the axis up to 90 degrees, thus forming a shape conforming to three quarters of a circle in the second state. Other shapes are also possible, e.g. polygons.

Figure 59J:
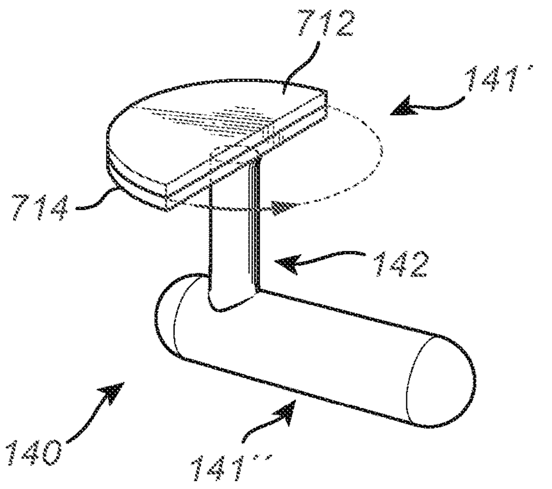
Figure 59K:
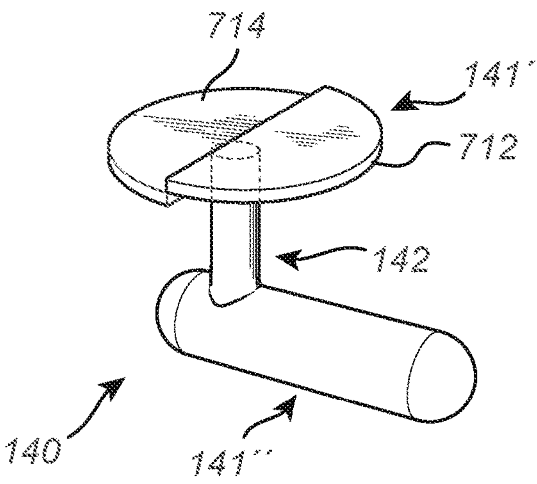

With reference to FIGS. 59J and 59K, a similar configuration as described with reference to FIGS. 59H and 59I is shown. However, here the second element 714 does not comprise a slot, and the first element is thus not housed in a slot. Instead, the first element 712 is arranged on top of the second element 714 (similar to the embodiment of FIGS. 59F and 59G). The first portion 141' is here configured to have its surface area increased, in particular the first cross-sectional area is increased, thereby increasing an area of the first surface configured to face (and in some embodiments also configured to contact) the first tissue surface. The first element 712 is configured to rotate about an axis to assume a first state, wherein the first element 712 is partially or completely arranged on top of the second element 714. Here, "completely arranged on top of" means that the first element 712 is confined within the borders of the second element 714. By rotation of the first element 712 about the axis, the first element 712 can assume a second state wherein the first element 712 protrudes over an edge or border of the second element 714 to increase the first cross-sectional area. The first element 712 may be configured to rotate 180 degrees about the axis. However, it is also possible that the first element 712 only rotate about the axis up to 90 degrees. Other shapes of the first and second element 712, 714 are also possible, e.g. polygons.

Figure 59L:
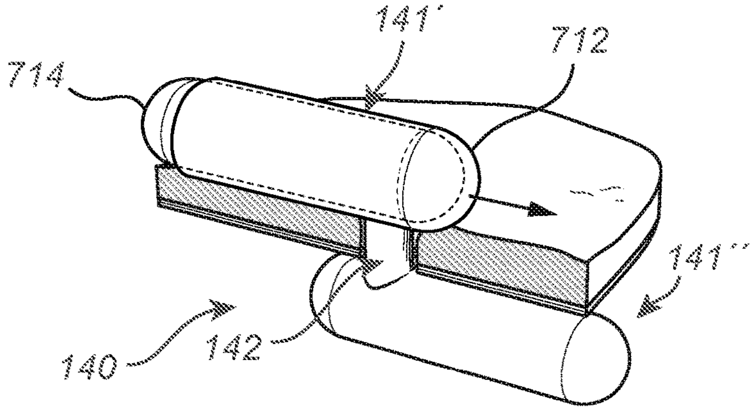
Figure 59M:
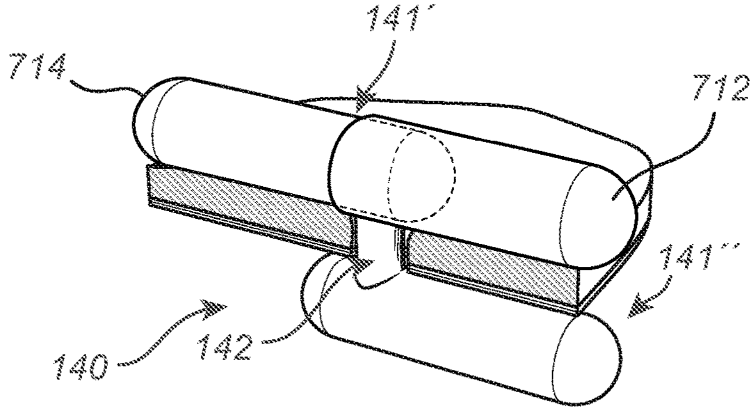

With reference to FIGS. 59L and 59M, a first portion 141' is shown being configured to have its surface area increased. Here, the first cross-sectional area is increased, thereby increasing an area of the first surface configured to face (and in some embodiments also configured to contact) the first tissue surface. In the illustrated embodiment, the first portion 141' comprises a first element 712 and a second element 714. The first element 712 here comprises a slot configured to partially or completely house the second element 714. The first element 712 is configured to assume a first state, as shown in FIG. 59L, wherein the second element 714 is arranged partially or fully within the slot of the first element 712, and a second state, as shown in FIG. 59M, wherein the first element 712 has been moved in a first direction to cause the second element 714 to protrude from the slot of the first element 712, and to cause the first element 712 to extend further away from the connecting portion 142 in the first plane. As will be understood, other variations are possible, e.g. the second element 714 may comprise the slot, and the first element 712 may be partially or fully housed within such slot, and subsequently the first element 712 or the second element 714 may be moved to protrude from such slot.

Figure 59N:
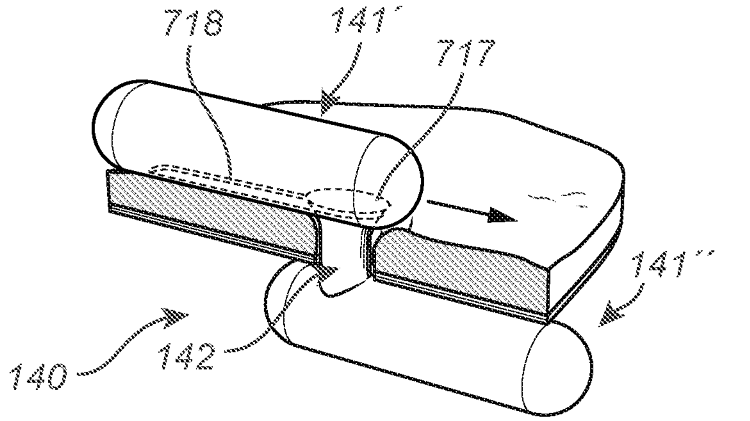
Figure 59O:
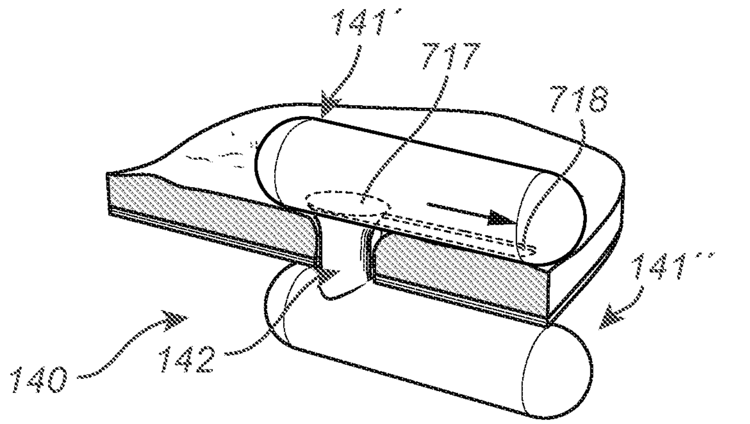

With reference to FIGS. 59N and 59O, a first portion 141' is shown being configured to be moved in relation to the connecting portion 142. The expression "configured to be moved" may in this context be interpreted as the first portion 141' being configured to assume at least two different positions with regard to the connecting portion 142 while still remaining in direct contact with the connecting portion. Here, the connecting portion 142 comprises a protruding element 717 and the first portion 141' comprises a slot 718, wherein the protruding element 717 is configured to slide within the slot 718 along a predetermined path, e.g. in a first direction and a direction opposite said first direction. The protruding element 717 may be configured to be interlocked within the slot 718 such that the protruding element 717 can only be removed from the slot 718 in a preconfigured position. In other embodiments, the protruding element 717 may be permanently enclosed within the slot 718. By sliding the first portion 141' in the first direction, an extension of the first portion 141' in the first plane with respect to the connecting portion 142 will be able to be adjusted. Any position between the endpoints of the slot 718 may be able to be assumed by the first portion 141'. In particular, first portion 141' and/or the connecting portion 142 may comprise a locking mechanism configured to secure a position of the first portion 141' in relation to the connecting portion 142. Such locking mechanism may rely on flexible parts being biased towards each other to maintain the first portion 141' and connecting portion 142 in a fixed position in relation to each other. Other possible locking mechanisms include the use of friction, snap-locking means, etc.

Figure 60:
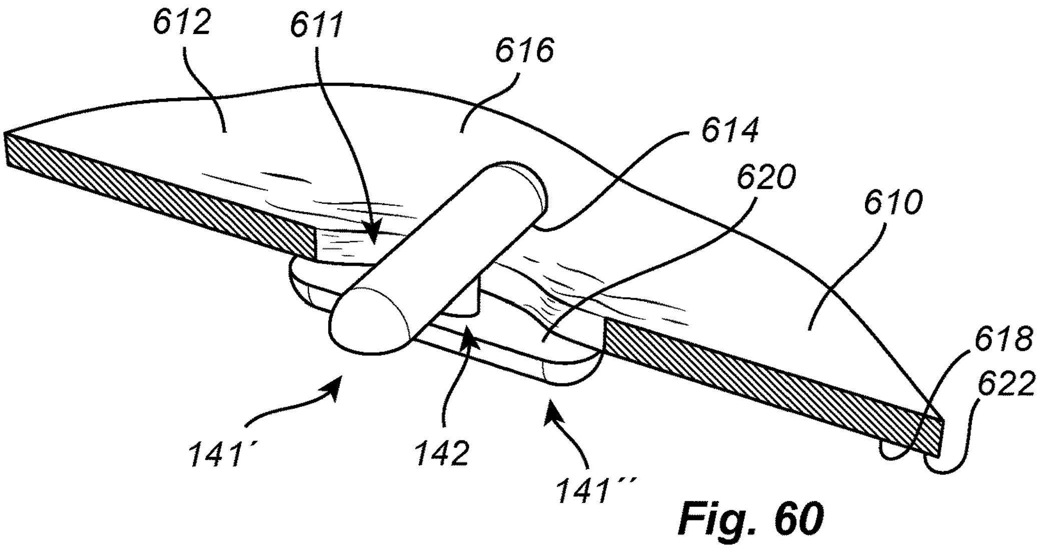
FIG. 60 shows a perspective elevated view from the right of an embodiment of an implantable remote unit for powering an implantable medical device.
Figure 61:
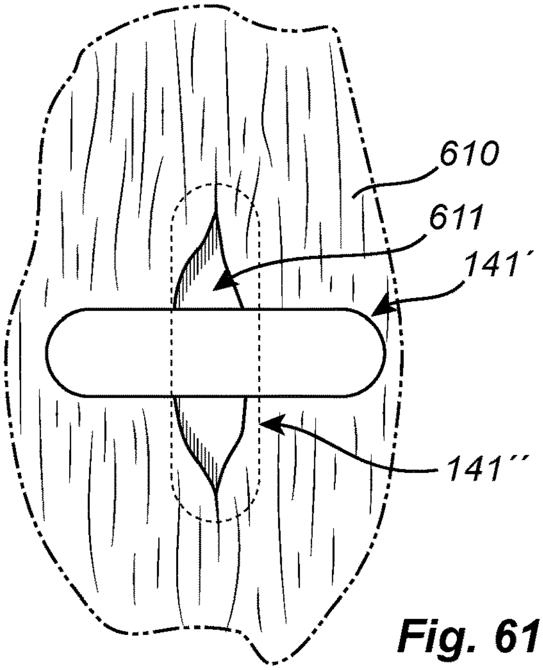
FIG. 61 shows a plain top view of an embodiment of an implantable remote unit for powering an implantable medical device.

With reference to FIGS. 60 and 61, an embodiment of an implantable remote unit 140 will be described. The remote unite 140 is configured to be held in position by a tissue portion 610 of a patient. The remote unit 140 comprises a first portion 141' configured to be placed on a first side 612 of the tissue portion 610, the first portion 141' having a first cross-sectional area in a first plane and comprising a first surface 614 configured to face and/or engage a first tissue surface 616 of the first side 612 of the tissue portion 610. The remote unit 140 further comprises a second portion 141" configured to be placed on a second side 618 of the tissue portion 610, the second side 618 opposing the first side 612, the second portion 141" having a second cross-sectional area in a second plane and comprising a second surface 620 configured to engage a second tissue surface 622 of the second side 618 of the tissue portion 610. The remote unit 140 further comprises a connecting portion 142 configured to be placed through a hole in the tissue portion 610 extending between the first and second sides 612, 618 of the tissue portion 610. The connecting portion 142 here has a third cross-sectional area in a third plane. The connecting portion 142 is configured to connect the first portion 141' to the second portion 141".

Figure 62A:
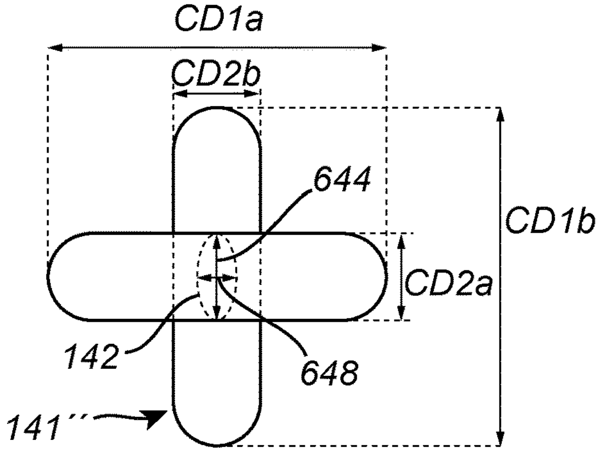
FIGS. 62A-B show, schematically, plain top views of two embodiments of implantable remote units for powering implantable medical devices.

With reference to FIG. 62*a*, the first cross-sectional area has a first cross-sectional distance CD1*a* and a second cross-sectional distance CD2*a*, the first and second cross-sectional distances CD1*a*, CD2*a* being perpendicular to each other and the first cross-sectional distance CD1*a* being longer than the second cross-sectional distance CD2*a*. Furthermore, the second cross-sectional area has a first cross-sectional distance CD1*b* and a second cross-sectional distance CD2*b*, the first and second cross-sectional distances CD2*a*, CD2*b* being perpendicular to each other and the first cross-sectional distance CD1*b* being longer than the second cross-sectional distance CD2*b*. The first cross-sectional distance CD1*a* of the first cross-sectional area and the first cross-sectional distance CD1*b* of the second cross-sectional area are rotationally displaced in relation to each other with an angle exceeding 45° to facilitate insertion of the second portion 141" through the hole in the tissue portion. In the embodiment illustrated in FIG. 62*a*, the rotational displacement is 90°.

The rotational displacement of the first portion 141' and the second portion 141" forms a cross-like structure, being particularly advantageous in that insertion through the hole in the tissue portion 610 may be facilitated, and once positioned in the hole in the tissue portion 610 a secure position may be achieved. In particular, if the remote unit 140 is positioned such that the second portion 141" has its first cross-sectional distance CD1*b* extending along a length extension of the hole 611 in the tissue portion 610, insertion of the second portion 141" through the hole 611 may be facilitated. Furthermore, if the first portion 141' is then displaced in relation to the second portion 141" such that the first cross-sectional distance CD1*a* of the first portion 141' is displaced in relation to a length extension of the hole 611, the first portion 141' may be prevented from travelling through the hole 611 in the tissue portion. In these cases, it is particularly advantageous if the hole 611 in the tissue portion is oblong, ellipsoidal, or at least has one dimension in one direction being longer than a dimension in another direction. Such oblong holes in a tissue portion may be formed for example in tissue having a fiber direction, where the longest dimension of the hole may be aligned with the fiber direction.

In the embodiment illustrated in FIG. 60, the first surface 614 of the first portion 141' is flat, thus providing a larger contact surface to the first tissue surface 616 and consequently less pressure on the tissue portion. A more stable position may also be achieved by the flat surface. Also the second surface 620 of the second portion 141" may be flat. However, other shapes, such as those described in other parts of the present disclosure, are possible.

As shown in FIG. 62*a*, the connecting portion 142 may have an elongated cross-section in the third plane. It may be particularly advantageous if the connecting portion 142 has a longer length 644 than width 648, said length 644 extending in the same direction as a length direction of the second portion 141", i.e. in the same direction as an elongation of the second portion 141". Hereby, the elongation of the connecting portion 142 may run in the same direction as an elongation of the hole in the tissue portion.

Figure 62B:
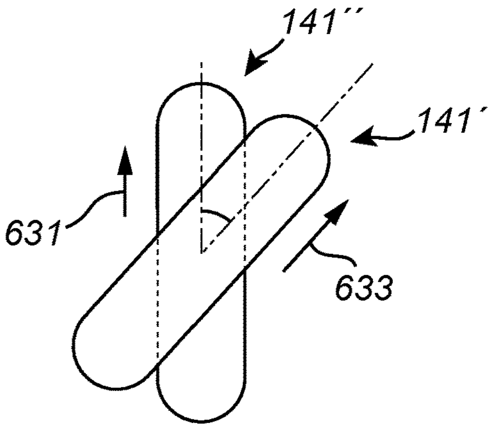

With reference to FIG. 62*b*, the rotational displacement of first cross-sectional distance of the first cross-sectional area and the first cross-sectional distance of the second cross-sectional area is shown, here at an angle about 45°. Accordingly, there is a rotational displacement, in the first, second and third planes, between a length direction 633 of the first portion 141' and a length direction 631 of the second portion 141". Other angles of rotational displacement are possible, such as 60°, 75, 90°, 105°, 120°, 135°, etc.

One and the same remote unit 140 may be capable of assuming several different arrangements with regards to rotational displacement of the first portion 141' and the second portion 141". In particular, this is possible when the first portion 141' and/or the second portion 141" is configured to detachably connect to the interconnecting portion 142. For example, a connection mechanism between the first portion 141' and the connecting portion 142, or between the second portion 141" and the connecting portion 142, may possess a rotational symmetry to allow the first portion 141' to be set in different positions in relation to the connecting portion 142 and in extension also in relation to the second portion 141". Likewise, such rotational symmetry may allow the second portion 142" to be set in different positions in relation to the connecting portion 142 and in extension also in relation to the first portion 141'.

Figure 63A:
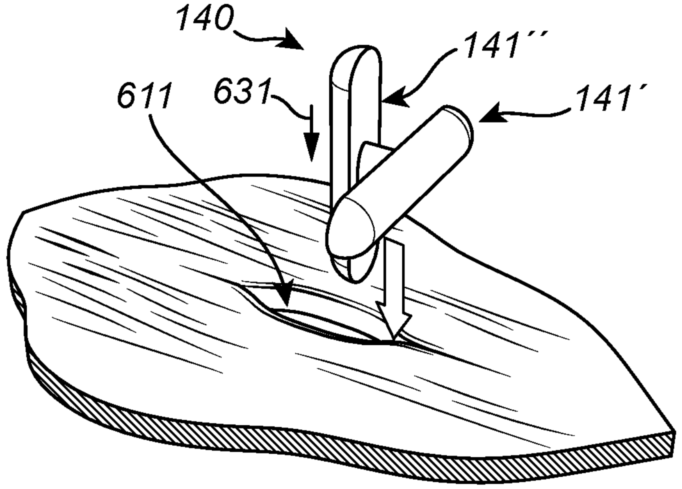
FIGS. 63A-C illustrate three stages of insertion and fixation of an embodiment of an implantable remote unit for powering an implantable medical device.
Figure 63B:
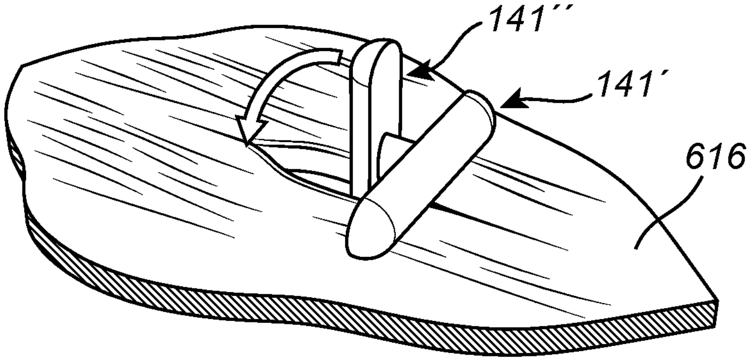
Figure 63C:
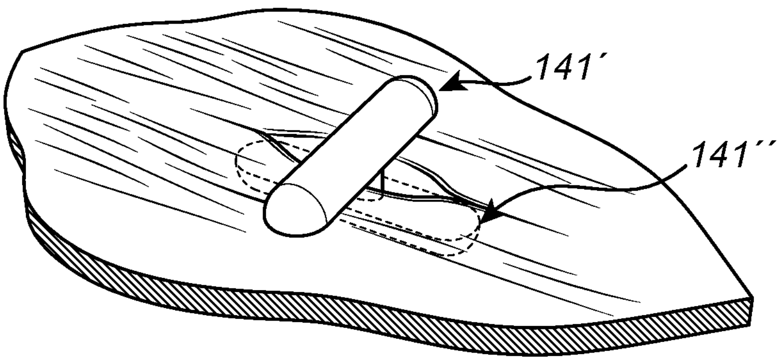

With reference to FIGS. 63*a*-63*c*, a procedure of insertion of the remote unit 140 in a tissue portion 610 will be described. The remote unit 140 may be oriented such that a length direction 631 of the second portion 141" points downwards into the hole 611. Preferably, the second portion 141" is positioned such that it is inserted close to an edge of the hole 611. The second portion 141" may then be inserted partially through the hole 611, until the point where the first portion 141' abuts the first tissue surface 616. Here, a 90° rotational displacement between the first portion 141' and the second portion 141", as described above, will allow a relatively large portion of the second portion 141" to be inserted before the first portion 141' abuts the first tissue surface 616. Subsequently, the remote unit 140 may be pivoted to slide or insert the remaining portion of the second portion 141" through the hole 611. While inserting the remaining portion of the second portion 141", the tissue may naturally flex and move to give way for the second portion 141". Upon having fully inserted the second portion 141" through the hole 611, such that the second portion 141" is completely located on the other side of the tissue portion 610, the tissue may naturally flex back.

With reference to FIG. 64, an embodiment of an implantable remote unit 140, which may be referred to as a remote unit in other parts of the present disclosure, will be described. The remote unit 140 is configured to be held in position by a tissue portion 610 of a patient. The remote unit 140 comprises a first portion 141' configured to be placed on a first side 612 of the tissue portion 610, the first portion 141' having a first cross-sectional area in a first plane and comprising a first surface 614 configured to face and/or engage a first tissue surface of the first side 612 of the tissue portion 610. The remote unit 140 further comprises a second portion 141" configured to be placed on a second side 618 of the tissue portion 610, the second side 618 opposing the first side 612, the second portion 141" having a second cross-sectional area in a second plane and comprising a second surface 620 configured to engage a second tissue surface of the second side 618 of the tissue portion 610. The remote unit 140 further comprises a connecting portion 142 configured to be placed through a hole in the tissue portion 610 extending between the first and second sides 612, 618 of the tissue portion 610. The connecting portion 142 here has a third cross-sectional area in a third plane. The connecting portion 142 is configured to connect the first portion 141' to the second portion 141".

At least one of the first portion and the second portion comprises at least one coil embedded in a ceramic material, the at least one coil being configured for at least one of: receiving energy transmitted wirelessly, transmitting energy wirelessly, receiving wireless communication, and transmitting wireless communication. In the illustrated embodiment, the first portion 141' comprises a first coil 658 and a second coil 660, and the second portion 141" comprises a third coil 662. The coils are embedded in a ceramic material 664

As discussed in other part of the present disclosure, the first portion 141' may comprise a first wireless energy receiver configured to receive energy transmitted wirelessly from an external wireless energy transmitter, and further the first portion 141' may comprise a first wireless communication receiver. The first wireless energy receiver and the first wireless communication receiver may comprise the first coil. Accordingly, the first coil may be configured to receive energy wirelessly, and/or to receive communication wirelessly.

By the expression "the receiver/transmitter comprising the coil" it is to be understood that said coil may form part of the receiver/transmitter.

The first portion 141' comprises a distal end 665 and a proximal end 666, here defined with respect to the connecting portion 142. In particular, the proximal end 665 is arranged closer to the connecting portion 142 and closer to the second portion 141" when the remote unit 140 is assembled. In the illustrated embodiment, the first coil 658 is arranged at the distal end 665.

The first portion 141' may comprise an internal wireless energy transmitter, and further a first wireless communication transmitter. In some embodiments, the internal wireless energy transmitter and/or the first wireless communication transmitter comprises the first coil 658. However, in some embodiments the internal wireless energy transmitter and/or the first wireless communication transmitter comprises the second coil 660. The second coil 660 is here arranged at the proximal end 665 of the first portion 141'. Such placement of the second coil 660 may provide for that energy and/or communication signals transmitted by the second coil 660 will not be attenuated by internal components of the first portion 141' when being transmitted to the second portion 141".

In some embodiments, the first wireless energy receiver and the internal wireless energy transmitter comprises a single coil embedded in a ceramic material. Accordingly, a single coil may be configured for receiving energy wirelessly and for transmitting energy wirelessly. Similarly, the first wireless communication receiver and the first wireless communication transmitter may comprise a single coil embedded in a ceramic material. Even further, in some embodiments a single coil may be configured for receiving and transmitting energy wirelessly, and for receiving and transmitting communication signals wirelessly.

The coils discussed herein are preferably arranged in a plane extending substantially parallel to the tissue portion 610.

The second portion 141" may comprise a second wireless energy receiver, and/or a second wireless communication receiver. In some embodiments, the third coil 662 in the second portion 141" comprises the second wireless energy receiver and/or the second wireless communication receiver.

The second portion 141" comprises a distal end 668 and a proximal end 670, here defined with respect to the connecting portion 142. In particular, the proximal end 668 is arranged closer to the connecting portion 142 and closer to the first portion 141' when the remote unit 140 is assembled. In the illustrated embodiment, the third coil 662 is arranged at the proximal end 668 of the second portion 141". Such placement of the third coil 662 may provide for that energy and/or communication signals received by the third coil 662 will not be attenuated by internal components of the second portion 141" when being received from the first portion 141'.

The first portion 141' may comprise a first controller 300*a* connected to the first coil 658, second coil 660, and/or third coil 662. The second portion 141" may comprise a second controller 300*b* connected to the first coil, 658, second coil 660, and/or third coil 662.

In the illustrated embodiment, the first portion 141' comprises a first energy storage unit 304*a* connected to the first wireless energy receiver 308*a*, i.e. the first coil 658. The second portion comprises a second energy storage unit 304*b* connected to the second wireless energy receiver 308*b*, i.e. the third coil 662. Such an energy storage unit may be a solid-state battery, such as a thionyl-chloride battery.

In some embodiments, the first coil 658 is configured to receive energy transmitted wirelessly by the external wireless energy transmitter and store the received energy in the first energy storage unit 304*a*. Furthermore, the first coil 658 and/or the second coil 660 may be configured to wirelessly transmit energy stored in the first energy storage unit 304*a* to the third coil 662, and the third coil 662 may be configured to receive energy transmitted wirelessly by the first coil 658 and/or the second coil 660 and store the received energy in the second energy storage unit 305*b*.

The first energy storage unit 304*a* may be configured to store less energy than the second energy storage unit 304*b*, and/or configured to be charged faster than the second energy storage unit 304*b*. Hereby, charging of the first energy storage unit 304*a* may be relatively quick, whereas transfer of energy from the first energy storage unit 304*a* to the second energy storage unit 304*b* may be relatively slow. Thus, a user can quickly charge the first energy storage unit 304*a*, and will not during such charging be restricted for a long period of time by being connected to an external wireless energy transmitter, e.g. at a particular location. After having charged the first energy storage unit 304*a*, the user may move freely while energy slowly transfers from the first energy storage unit 304*a* to the second energy storage unit 304*b*, via the first and/or second coil and the third coil.

As is readily understood by a person skilled in the art the system and embodiments disclosed in connection with FIGS. 40-45 may be integrated in any of the embodiments discussed with reference to FIGS. 1-38, as well as FIGS. 46-64, thus forming part of the disclosed embodiments, and/or be used in connection with such apparatuses 100 in order to address symptoms of a patient suffering from reflux disease.

The function and features of a controller for controlling the apparatuses according to any of the above aspects and embodiments will now described with reference to FIGS. 65A-E and 66A-N. The features of the controller described with reference to FIGS. 65A-E and 66A-N may be implemented and combined with any of the embodiments of implantable medical devices disclosed herein, such as for example FIGS. 1-38 and 40-64. The features may for example be implemented in the controllers shown and/or described with reference to FIGS. 1, 38A-B, 40, and 43-45. Any controller may reference to FIGS. 65A-E and 66A-N. The controller disclosed in this description, and any combination of features thereof, may comprise an internal computing unit, also called a processor or controller, for controlling a function of the implant, such as the electrical stimulation of muscle tissue and/or charging of the internal energy source, and it may comprise a communication unit and implement methods for communication, including verification, authentication and encryption of data, as described in the following.

In the following, the term "medical implant" should be understood as referring to any of the apparatuses, or part of the apparatuses, according to the above aspects. Thus, the medical implant may refer to the implantable movement restriction device, the electrode arrangement, the elongated core, the tubular cover, the implantable first and second portions, and/or the elongated support device.

The controller may comprise a collection of communication related sub-units such as a wired transceiver, a wireless transceiver, energy storage, an energy receiver, a computing unit, a memory, or a feedback unit. The sub-units of the controller may cooperate with each other or operate independently with different purposes. The sub-units of the controller may inherit the prefix "internal". This is to distinguish these sub-units from the sub-units of the external devices as similar sub-units may be present for both the implanted controller and the external devices. The sub-units of the external devices may similarly inherit the prefix "external".

A wireless transceiver may comprise both a wireless transmitter and a wireless receiver. The wireless transceiver may also comprise a first wireless transceiver and a second wireless transceiver. In this case, the wireless transceiver may be part of a first communication system (using the first wireless transceiver) and a second communication system (using the second wireless transceiver).

In some embodiments, two communication systems may be implemented using a single wireless transceiver in e.g. the medical implant and a single wireless transceiver in e.g. an external device (i.e. one antenna at the medical implant and one antenna at the external device), but where for example the network protocol used for data transmission from the external device to the medical implant is different from the network protocol used for data transmission from the medical implant to the external device, thus achieving two separate communication systems.

Alternatively, the wireless transceiver may be referred to as either a wireless transmitter or a wireless receiver as not all embodiments of secure wireless communication discussed herein require two-way communication capability of the wireless transceiver. The wireless transceiver may transmit or receive wireless communication via wireless connections. The wireless transceiver may connect to both the medical implant and to external devices, i.e. devices not implanted in the patient.

The wireless connections may be based on radio frequency identification (RFID), near field charge (NFC), Bluetooth, Bluetooth low energy (BLE), or wireless local area network (WLAN). The wireless connections may further be based on mobile telecommunication regimes such as 1G, 2G, 3G, 4G, or 5G. The wireless connections may further be based on modulation techniques such as amplitude modulation (AM), frequency modulation (FM), phase modulation (PM), or quadrature amplitude modulation (QAM). The wireless connection may further feature technologies such as time-division multiple access (TDMA), frequency-division multiple access (FDMA), or code-division multiple access (CDMA). The wireless connection may also be based on infra-red (IR) communication. The wireless connection may feature radio frequencies in the high frequency band (HF), very-high frequency band (VHF), and the ultra-high frequency band (UHF) as well as essentially any other applicable band for electromagnetic wave communication. The wireless connection may also be based on ultrasound communication to name at least one example that does not rely on electromagnetic waves.

A wired transceiver may comprise both a wired transmitter and a wired receiver. The wording wired transceiver aims to distinguish between it and the wireless transceiver. It may generally be considered a conductive transceiver. The wired transceiver may transmit or receive conductive communication via conductive connections. Conductive connections may alternatively be referred to as electrical connections or as wired connections. The wording wired however, does not imply there needs to be a physical wire for conducting the communication. The body tissue of the patient may be considered as the wire. Conductive connection may use the body of the patient as a conductor. Conductive connections may still use ohmic conductors such as metals to at least some extent, and more specifically at the interface between the wired transceiver and the chosen conductor.

Communication, conductive or wireless may be understood as digital or analogue. In analogue communication, the message signal is in analogue form i.e., a continuous time signal. In digital communication, usually digital data i.e., discrete time signals containing information is transmitted.

The controller may comprise a sensation generator. A sensation generator is a device or unit that generates a sensation. The generated sensation may be configured to be experienceable by the patient such that the patient may take actions to authenticate a device, connection, or communication. The sensation generator may be configured to generate a single sensation or a plurality of sensation components. The sensation or sensation components may comprise a vibration (e.g. a fixed frequency mechanical vibration), a sound (e.g. a superposition of fixed frequency mechanical vibrations), a photonic signal (e.g. a non-visible light pulse such as an infra-red pulse), a light signal (e.g. a visual light pulse), an electric signal (e.g. an electrical current pulse) or a heat signal (e.g. a thermal pulse). The sensation generator may be implanted, configured to be worn in contact with the skin of the patient or capable of creating sensation without being in physical contact with the patient, such as a beeping alarm. The sensations generated by the sensation generator may be configured to be experienceable by a sensory function or a sense of the patient from the list of tactile, pressure, pain, heat, cold, taste, smell, sight, and hearing. Sensations may be generated of varying power or force as to adapt to sensory variations in the patient. Power or force may be increased gradually until the patient is able to experience the sensation. Variations in power or force may be controlled via feedback. Sensation strength or force may be configured to stay within safety margins. The sensation generator may be connected to the medical implant. The sensation generator may be comprised within the medical implant or be a separate unit.

A motor, e.g. of the active device or unit of the medical implant, for controlling a physical function in the body of the patient may provide a secondary function as a sensation generator, generating a vibration or sound. Generation of vibrations or sounds of the motor may be achieved by operating the motor at specific frequencies. When functioning as to generate a sensation the motor may operate outside of its normal ranges for frequency controlling a physical function in the body. The power or force of the motor when operating to generate a sensation may also vary from its normal ranges for controlling a physical function in the body. The motor for use as an active device and a sensation generator could for example be an implantable brushless DC motor with integrated gear box, such as the motors provided by Maxon group or Dr. Fritz Faulhaber.

An external device is a device which is external to the patient in which the medical implant is implanted in. The external device may be also be enumerated (first, second, third, etc.) to separate different external devices from each other. Two or more external devices may be connected by means of a wired or wireless communication as described above, for example through IP (internet protocol), or a local area network (LAN). The wired or wireless communication may take place using a standard network protocol such as any suitable IP protocol (IPv4, IPv6) or Wireless Local Area Network (IEEE 802.11), Bluetooth, NFC, RFID etc. The wired or wireless communication may take place using a proprietary network protocol. Any external device may also be in communication with the medical implant using wired or wireless communication according to the above. Communication with implanted devices may be thus accomplished with a wired connection or with wireless radiofrequency (RF) telemetry. Other methods of wireless communication may be used to communicate with implants, including optical and ultrasound. Alternatively, the concept of intrabody communication may be used for wireless communication, which uses the conductive properties of the body to transmit signals, i.e. conductive (capacitive or galvanic) communication with the medical implant. Means for conductive communication between an external device and an implant may also be called "electrical connection" between an external device and an implant. The conductive communication may be achieved by placing a conductive member of the external device in contact with the skin of the patient. By doing this, the external device and/or the implant may assure that it is in direct electrical connection with the other device. The concept relies on using the inherent conductive or electrical properties of a human body. Signals may preferably be configured to affect the body or body functions minimally. For conductive communication this may mean using low currents. A current may flow from an external device to an implant or vice versa. Also, for conductive communication, each device may have a transceiver portion for transmitting or receiving the current. These may comprise amplifiers for amplifying at least the received current. The current may contain or carry a signal which may carry e.g. an authentication input, implant operation instructions, or information pertaining to the operation of the implant.

Alternatively, conductive communication may be referred to as electrical or ohmic or resistive communication.

The conductive member may be an integrated part of the external device (e.g. in the surface of a smartwatch that is intended to be in contact with the wrist of the person wearing it), or it may be a separate device which can be connected to the external device using a conductive interrace such as the charging port or the headphone port of a smartphone.

A conductive member may be considered any device or structure set up for data communication with the implant via electric conductive body tissue. The data communication to the implant may be achieved by e.g. current pulses transmitted from the conductive member through the body of the patient to be received by a receiver at the implant. Any suitable coding scheme known in the art may be employed. The conductive member may comprise an energy source such as a battery or receive energy from e.g. a connected external device.

The term conductive interface is representing any suitable interface configured for data exchange between the conductive member and the external device. The conductive member may in an alternative configuration receive and transmit data to the external device through a radio interface, NFC, and the like.

An external device may act as a relay for communication between an implant and a remote device, such as e.g. second, third, or other external devices. Generally, the methods of relaying communication via an external device may be preferable for a large number of reasons. The transmission capabilities of the implant may be reduced, reducing its technical complexity, physical dimensions, and medical effects on the patient in which the implant is implanted. Communication may also be more efficient as direct communication, i.e. without a relaying device, with an implant from a remote device may require higher energy transmissions to account for different mediums and different rates of attenuation for different communication means. Remote communication with lower transmission energy may also increase the security of the communication as the spatial area or volume where the communication may be at all noticeable may be made smaller. Utilizing such a relay system further enables the use of different communication means for communication with the implant and communication with remote devices that are more optimized for their respective mediums.

An external device may be any device having processing power or a processor to perform the methods and functions needed to provide safe operation of the implant and provide the patient or other stakeholders (caregiver, spouse, employer etc.) with information and feedback from the implant. Feedback parameters could include battery status, energy level at the controller, the electrical characteristics of the stimulation signal, number of stimulation cycles the electrode arrangement has delivered, properties, version number etc. relating to functionality of the apparatus. The external device may for example be a handset such as a smartphone, smartwatch, tablet etc. handled by the patient or other stakeholders. The external device may be a server or personal computer handled by the patient or other stakeholders. The external device may be cloud based or a virtual machine. In the drawings, the external device handled by the patient is often shown as a smart watch, or a device adapted to be worn by the patient at the wrist of the patient. This is merely by way of example and any other type of external device, depending on the context, is equally applicable.

Several external devices may exist such as a second external device, a third external device, or another external device. The above listed external devices may e.g. be available to and controllable by a patient, in which an implant is implanted, a caregiver of the patient, a healthcare professional of the patient, a trusted relative of the patient, an employer or professional superior of the patient, a supplier or producer of the implant or its related features. By controlling the external devices may provide options for e.g. controlling or safeguarding a function of the implant, monitoring the function of the implant, monitoring parameters of the patient, updating or amending software of the implant etc.

An external device under control by a supplier or producer of the implant may be connected to a database comprising data pertaining to control program updates and/or instructions. Such database may be regularly updated to provide new or improved functionality of the implant, or to mitigate for previously undetected flaws of the implant. When an update of a control program of an implant is scheduled, the updated control program may be transmitted from the database in a push mode and optionally routed via one or more further external devices before received by the implanted controller. In another embodiment, the update is received from the database by request from e.g. an external device under control by the patient having the implant implanted in his/her body, a pull mode.

The external device may require authentication to be operated in communication with other external devices or the implant. Passwords, multi-factor authentication, biometric identification (fingerprint, iris scanner, facial recognition, etc.) or any other way of authentication may be employed.

The external device may have a user interface (UI) for receiving input and displaying information/feedback from/to a user. The UI may be a graphical UI (GUI), a voice command interface, speaker, vibrators, lamps, etc.

The communication between external devices, or between an external device and the implant may be encrypted. Any suitable type of encryption may be employed such as symmetric or asymmetric encryption. The encryption may be a single key encryption or a multi-key encryption. In multi-key encryption, several keys are required to decrypt encrypted data. The several keys may be called first key, second key, third key, etc. or first part of a key, second part of the key, third part of the key, etc. The several keys are then combined in any suitable way (depending on the encryption method and use case) to derive a combined key which may be used for decryption. In some cases, deriving a combined key is intended to mean that each key is used one by one to decrypt data, and that the decrypted data is achieved when using the final key.

In other cases, the combination of the several key result in one "master key" which will decrypt the data. In other words, it is a form of secret sharing, where a secret is divided into parts, giving each participant (external device(s), internal device) its own unique part. To reconstruct the original message (decrypt), a minimum number of parts (keys) is required. In a threshold scheme this number is less than the total number of parts (e.g. the key at the implant and the key from one of the two external device are needed to decrypt the data). In other embodiments, all keys are needed to reconstruct the original secret, to achieve the combined key which may decrypt the data.

In should be noted that it is not necessary that the generator of a key for decryption is the unit that in the end sends the key to another unit to be used at that unit. In some cases, the generator of a key is merely a facilitator of encryption/decryption, and the working in behalf of another device/user.

A verification unit may comprise any suitable means for verifying or authenticating the use (i.e. user authentication) of a unit comprising or connected to the verification unit, e.g. the external device. For example, a verification unit may comprise or be connected to an interface (UI, GUI) for receiving authentication input from a user. The verification unit may comprise a communication interface for receiving authentication data from a device (separate from the external device) connected to the device comprising the verification unit. Authentication input/data may comprise a code, a key, biometric data based on any suitable techniques such as fingerprint, a palm vein structure, image recognition, face recognition, iris recognition, a retinal scan, a hand geometry, and genome comparison, etc. The verification/authentication may be provided using third party applications, installed at or in connection with the verification unit.

The verification unit may be used as one part of a two-part authentication procedure. The other part may e.g. comprise conductive communication authentication, sensation authentication, or parameter authentication.

The verification unit may comprise a card reader for reading a smart card. A smart card is a secure microcontroller that is typically used for generating, storing, and operating on cryptographic keys. Smart card authentication provides users with smart card devices for the purpose of authentication. Users connect their smart card to the verification unit. Software on the verification unit interacts with the keys material and other secrets stored on the smart card to authenticate the user. In order for the smart card to operate, a user may need to unlock it with a user-PIN. Smart cards are considered a very strong form of authentication because cryptographic keys and other secrets stored on the card are very well protected both physically and logically and are therefore hard to steal.

The verification unit may comprise a personal e-ID that is comparable to, for example, passport and driving license. The e-ID system comprises is a security software installed at the verification unit, and a e-ID which is downloaded from a web site of a trusted provided or provided via a smart card from the trusted provider.

The verification unit may comprise software for SMS-based two-factor authentication. Any other two-factor authentication systems may be used. Two-factor authentication requires two things to get authorized: something you know (your password, code, etc.) and something you have (an additional security code from your mobile device (e.g. a SMS, or a c-ID) or a physical token such as a smart card).

Other types of verification/user authentication may be employed. For example, a verification unit which communicate with an external device using visible light instead of wired communication or wireless communication using radio. A light source of the verification unit may transmit (e.g. by flashing in different patterns) secret keys or similar to the external device which uses the received data to verify the user, decrypt data or by any other means perform authentication. Light is easier to block and hide from an eavesdropping adversary than radio waves, which thus provides an advantage in this context. In similar embodiments, electromagnetic radiation is used instead of visible light for transmitting verification data to the external device.

Parameters relating to functionality of the implant may comprise for example a status indicator of the implant such as battery level, version of control program, properties of the implant, status of a motor of the implant, etc.

Data comprising operating instructions sent to the implant may comprise a new or updated control program, parameters relating to specific configurations of the implant, etc. Such data may for example comprise instructions how to operate the electrode arrangement for simulating and exercising the muscle tissue in a multi functionality implant, instructions to collect patient data at the implant, instructions to transmit feedback from the implant to an external device, etc.

The expressions "confirming the electrical connection between an implant and an external device" or "authenticating a connection between an implant and an external device", or similar expressions, are intended to encompass methods and processes for ensuring or be reasonably sure that the connection has not been compromised. Due to weaknesses in the wireless communication protocols, it is a simple task for a device to "listen" to the data and grab sensitive information, e.g. personal data regarding the patient sent from the implant, or even to try to compromise (hack) the implant by sending malicious commands or data to the implant. Encryption may not always be enough as a security measure (encryption schemes may be predictable), and other means of confirming or authenticating the external device being connected to the implant may be needed.

The expression "network protocol" is intended to encompass communication protocols used in computer networks. A communication protocol is a system of rules that allow two or more entities of a communications system to transmit information via any kind of variation of a physical quantity. The protocol defines the rules, syntax, semantics and synchronization of communication and possible error recovery methods. Protocols may be implemented by hardware, software, or a combination of both. Communication protocols have to be agreed upon by the parties involved. In this field, the term "standard" and "proprietary" is well defined. A communication protocol may be developed into a protocol standard by getting the approval of a standards organization. To get the approval the paper draft needs to enter and successfully complete the standardization process. When this is done, the network protocol can be referred to a "standard network protocol" or a "standard communication protocol". Standard protocols are agreed and accepted by whole industry. Standard protocols are not vendor specific. Standard protocols are often, as mentioned above, developed by collaborative effort of experts from different organizations.

Proprietary network protocols, on the other hand, are usually developed by a single company for the devices (or Operating System) which they manufacture. A proprietary network protocol is a communications protocol owned by a single organization or individual. Specifications for proprietary protocols may or may not be published, and implementations are not freely distributed. Consequently, any device may not communicate with another device using a proprietary network protocol, without having the license to use the proprietary network protocol, and knowledge of the specifications for proprietary protocol. Ownership by a single organization thus gives the owner the ability to place restrictions on the use of the protocol and to change the protocol unilaterally.

A control program is intended to define any software used for controlling the implant. Such software may comprise an operating system of the implant, of parts of an operating system or an application running on the implant such as software controlling a specific functionality of the implant (e.g. the active unit of the implant, feedback functionality of the implant, a transceiver of the implant, encoding/decoding functionality of the implant, etc.). The control program may thus control the medical function of the implant, for example the electrical stimulation of the muscle tissue, etc. Alternatively, or additionally, the control program may control internal hardware functionality of the implant such as energy usage, transceiver functionality, etc.

The controller may alternatively be called an internal control unit and may include any software or hardware for controlling the implant or the communication unit. The internal control unit may comprise an internal communication unit and a storage unit and a processor for running any control program or software. The term "internal control unit" may be used to encompass any part of the implant not being the active unit or body engaging unit.

The systems and methods disclosed hereinabove may be implemented as software, firmware, hardware, or a combination thereof. In a hardware implementation, the division of tasks between functional units referred to in the above description does not necessarily correspond to the division into physical units; to the contrary, one physical component may have multiple functionalities, and one task may be carried out by several physical components in cooperation. Certain components or all components may be implemented as software executed by a digital signal processor or microprocessor or be implemented as hardware or as an application-specific integrated circuit. Such software may be distributed on computer readable media, which may comprise computer storage media (or non-transitory media) and communication media (or transitory media). As is well known to a person skilled in the art, the term computer storage media includes both volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information, and which can be accessed by a computer. Further, it is well known to the skilled person that communication media typically embodies computer readable instructions, data structures, program modules or other data in a modulated data signal such as a carrier wave or other transport mechanism and includes any information delivery media.

Figure 65A:
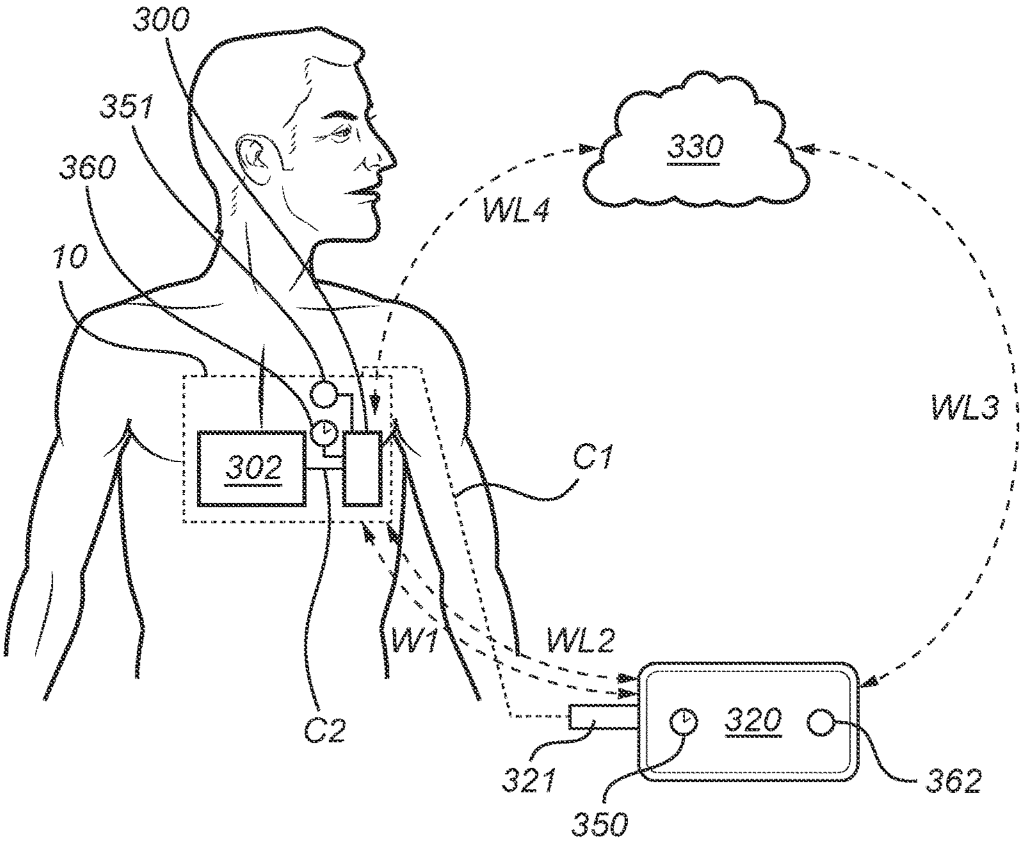

An embodiment of the system will now be described with reference to FIGS. 65A-N. FIG. 65A shows a patient with an implant 100. The implant 100 is in FIG. 65A an apparatus for treating reflux disease according to any one of the embodiments shown herein. The medical device 10 comprises an active unit 302, which is could be the part of the apparatus being adjustable or comprising electrodes for electrical stimulation. The medical device 10 may further comprise a remote unit which comprises the controller 300. The active unit 302 and/or remote unit (not shown) is connected to the controller 300 via an electrical connection C2. The controller 300 (further described with reference to FIG. 65B) is configured to communicate with an external device 320 (further described with reference to FIG. 65C). The controller 300 can communicate wirelessly with the external device 320 through a wireless connection WL1, and/or through an electrical connection C1.

Figure 65B:
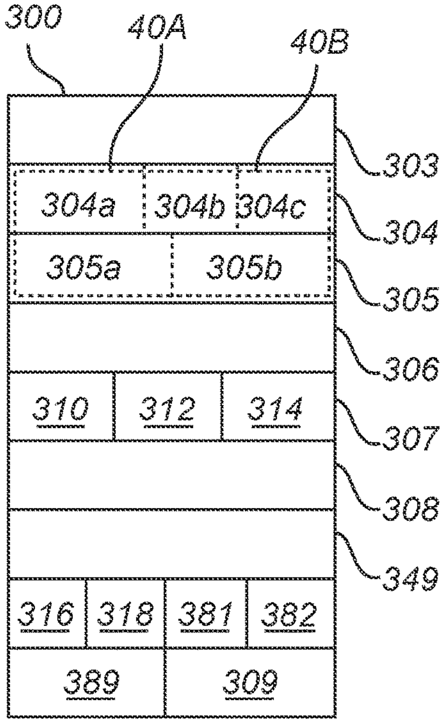
Figure 65B:
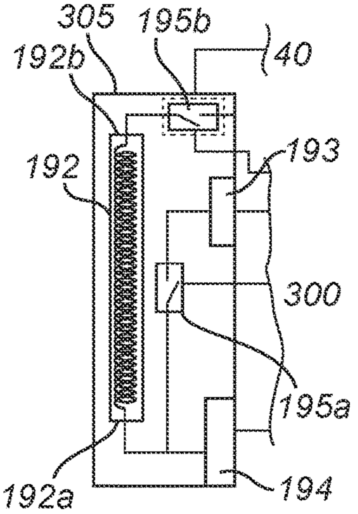

Referring now to FIG. 65B, one embodiment of the controller 300 will be describe in more detail. The controller 300 comprises an internal computing unit 306 configured to control the function performed by the implantable medical device 10. The computing unit 306 comprises an internal memory 307 configured to store programs thereon. In the embodiment described in FIG. 65B, the internal memory 307 comprises a first control program 310 which can control the function of the medical device 10. The first control program 310 may be seen as a program with minimum functionality to be run at the medical device only during updating of the second control program 312. When the medical device is running with the first control program 310, the medical device may be seen as running in safe mode, with reduced functionality. For example, the first control program 310 may result in that no sensor data is stored in the medical device while being run, or that no feedback is transmitted from the medical device while the first control program 310 is running. By having a low complexity first control program, memory at the medical device is saved, and the risk of failure of the medical device during updating of the second control program 312 is reduced.

The second control program 312 is the program controlling the medical device in normal circumstances, providing the medical device with full functionality and features.

The memory 307 can further comprise a second, updatable, control program 312. The term updatable is to be interpreted as the program being configured to receive incremental or iterative updates to its code, or be replaced by a new version of the code. Updates may provide new and/or improved functionality to the implant as well as fixing previous deficiencies in the code. The computing unit 306 can receive updates to the second control program 312 via the controller 300. The updates can be received wirelessly WL1 or via the electrical connection C1. As shown in FIG. 65B, the internal memory 307 of the controller 300 can possibly store a third program 314. The third program 314 can control the function of the implantable medical device 10 and the computing unit 306 may be configured to update the second program 312 to the third program 314. The third program 314 can be utilized when rebooting an original state of the second program 312. The third program 314 may thus be seen as providing a factory reset of the controller 300, e.g. restore it back to factory settings. The third program 314 may thus be included in the implant 300 in a secure part of the memory 307 to be used for resetting the software (second control program 312) found in the controller 300 to original manufacturer settings.

The controller 300 may comprise a reset function 316 connected to or part of the internal computing unit 306 or transmitted to said internal computing unit 306. The reset function 316 is configured to make the internal computing unit 306 switch from running the second control program 312 to the first control program 310. The reset function 316 could be configured to make the internal computing unit 306 delete the second control program 312 from the memory 307. The reset function 316 can be operated by palpating or pushing/put pressure on the skin of the patient. This could be performed by having a button on the implant. Alternatively, the reset function 316 can be invoked via a timer or a reset module. Temperature sensors and/or pressure sensors can be utilized for sensing the palpating. The reset function 316 could also be operated by penetrating the skin of the patient. It is further plausible that the reset function 316 can be operated by magnetic means. This could be performed by utilizing a magnetic sensor and applying a magnetic force from outside the body. The reset function 316 could be configured such that it only responds to magnetic forces applied for a duration of time exceeding a limit, such as 2 seconds. The time limit could equally plausible be 5 or 10 seconds, or longer. In these cases, the implant could comprise a timer. The reset function 316 may thus include or be connected to a sensor for sensing such magnetic force.

In addition to or as an alternative to the reset function described above, the implant may comprise an internal computing unit 306 (comprising an internal processor) comprising the second control program 312 for controlling a function of the implantable medical device, and a reset function 318. The reset function 318 may be configured to restart or reset said second control program 312 in response to: i, a timer of the reset function 318 has not been reset, or ii, a malfunction in the first control program 310.

The reset function 318 may comprise a first reset function, such as, for example, comprise a computer operating properly, COP, function connected to the internal computing unit 306. The first reset function may be configured to restart or reset the first or the second control program 312 using a second reset function. The first reset function comprises a timer, and the first or the second control program is configured to periodically reset the timer.

The reset function 318 may further comprise a third reset function connected to the internal computing unit and to the second reset function. The third reset function may in an example be configured to trigger a corrective function for correcting the first 310 or second control program 312, and the second reset function is configured to restart the first 310 or second control program 312 sometime after the corrective function has been triggered. The corrective function may be a soft reset or a hard reset.

The second or third reset function may, for example, configured to invoke a hardware reset by triggering a hardware reset by activating an internal or external pulse generator which is configured to create a reset pulse. Alternatively, the second or third reset function may be implemented by software.

The controller 300 may further comprise an internal wireless transceiver 308. The transceiver 308 communicates wirelessly with the external device 320 through the wireless connection WL The transceiver may further communicate with an external device 320, 300 via wireless connection WL2 or WL4. The transceiver may both transmit and receive data via either of the connections C1, WL1, WL2 and WL4. Optionally, the external devices 320 and 300, when present, may communicate with each other, for example via a wireless connection WL3.

The controller 300 can further be electrically connected C1 to the external device 320 and communicate by using the patient's body as a conductor. The controller 300 may thus comprise a wired transceiver 303 or an internal transceiver 303 for the electrical connection C1.

The confirmation/authentication of the electrical connection can be performed as described herein in the section for confirmation and/or authentication. In these cases, the implanted medical device and/or external device(s) 320 comprises the necessary features and functionality (described in the respective sections of this document) for performing such confirmation/authentication. By authenticating according to these aspects, security of the authentication may be increased as it may require a malicious third party to know or gain access to either the transient physiological parameter of the patient or detect randomized sensations generated at or within the patient.

Figure 65C:
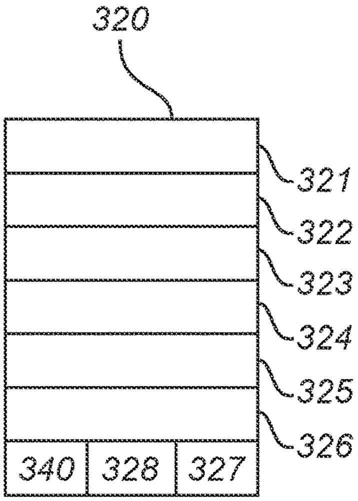

In FIGS. 65A-65C the patient is a human, but other mammals are equally plausible. It is also plausible that the communication is performed by inductive means. It is also plausible that the communication is direct.

The controller 300 of the implantable medical device 10 according to FIG. 65B further comprises a feedback unit 349. The feedback unit 349 provides feedback related to the switching from the second control program 312 to the first control program 310. The feedback could for example represent the information on when the update of the software, i.e. the second control program 312, has started, and when the update has finished. This feedback can be visually communicated to the patient, via for example a display on the external device 320. This display could be located on a watch, or a phone, or any other external device 320 coupled to the controller 300. Preferably, the feedback unit 349 provides this feedback signal wirelessly WL1 to the external device 320. Potentially, the words "Update started", or "Update finished", could be displayed to the patient, or similar terms with the same meaning. Another option could be to display different colors, where green for example could mean that the update has finished, and red or yellow that the update is ongoing. Obviously, any color is equally plausible, and the user could choose these depending on personal preference. Another possibility would be to flash a light on the external device 320. In this case the external device 320 comprises the light emitting device(s) needed. Such light could for example be a LED. Different colors could, again, represent the status of the program update. One way of representing that the update is ongoing and not yet finished could be to flash the light, i.e. turning the light on and off. Once the light stops flashing, the patient would be aware of that the update is finished. The feedback could also be audible, and provided by the implantable medical device 300 directly, or by the external device 320. In such cases, the implantable medical device 10 and external device 320 comprises means for providing audio. The feedback could also be tactile, for example in the form of a vibration that the user can sense. In such case, either the implantable medical device 10 or external device 320 comprises means for providing a tactile sensation, such as a vibration and/or a vibrator.

As seen in FIG. 65B, the controller 300 can further comprise a first energy storage unit 40A. The first energy storage unit 40A runs the first control program 310. The controller 300 further comprises a second energy storage unit 40B which runs the second control program 312. This may further increase security during update, since the first control program 310 has its own separate energy storage unit 40A. The energy storage unit 40A can comprise a first energy storage 304*a* and/or a first energy receiver 305*a*. The second energy storage unit 40B can comprise a second energy storage 304*b* and/or a second energy receiver 305*b*. The energy can be received wirelessly by inductive or conductive means. An external energy storage unit can for example transfer an amount of wireless energy to the energy receiver 305*a*, 305*b* inside the patient's body by utilizing an external coil which induces a voltage in an internal coil (not shown in figures). It is plausible that the first energy receiver 305*a* receives energy via a RFID pulse. The feedback unit 349 can provide feedback pertaining to the amount of energy received via the RFID pulse. The amount of RFID pulse energy that is being received can be adjusted based on the feedback, such that the pulse frequency is successively raised until a satisfying level is reached.

The controller 300 of the medical device 10 according to FIG. 65B further comprises a feedback unit and an electrical switch 309. The electrical switch 309 could be mechanically connected to an adjustment device for adjusting the size and/or shape of a portion of the apparatus, and/or connected to a member of the medical device configured to deliver an electric stimulation signal to improve long term implantation characteristics and reduce detrimental effects on muscle tissue against which the implant rests. The switch 309 could for example be bonded to a stimulation device controlling the stimulation signal delivered to the muscle tissue by the electrode arrangement to provide stimulation thereof, in any of the embodiments herein. Such a switch could for example be a switch 309 configured to switch if exposed to a temperature exceeding a threshold value, such as a bimetal switch which is switched by the heat created by the flow of current charging or discharging the battery. In the alternative, the switch 309 configured to switch if exposed to a temperature exceeding a threshold value could be placed at a different location on the medical device 10 to switch in case of exceeding temperatures, thereby hindering the medical device from overheating which may cause tissue damage.

The switch 309 could either be configured to cut the power to the operation device or to generate a control signal to the processor 306 of the implantable controller 300, such that the controller 300 can take appropriate action, such as reducing power or turning off the operation device.

The external device 320 is represented in FIG. 65C. The external device 320 can be placed anywhere on the patient's body, preferably on a convenient and comfortable place. The external device 320 could be a wristband, and/or have the shape of a watch. It is also plausible that the external device is a mobile phone or other device not attached directly to the patient. The external device as shown in FIG. 65C comprises a wired transceiver 323, and an energy storage 324. It also comprises a wireless transceiver 328 and an energy transmitter 325. It further comprises a computing unit 326 and a memory 327. The feedback unit 322 in the external device 320 is configured to provide feedback related to the computing unit 326. The feedback provided by the feedback unit 322 could be visual. The external device 320 could have a display showing such visual feedback to the patient. It is equally plausible that the feedback is audible, and that the external device 320 comprises means for providing audio. The feedback given by the feedback unit 322 could also be tactile, such as vibrating. The feedback could also be provided in the form of a wireless signal WL1, WL2, WL3, WL4.

The second, third or fourth communication methods WL2, WL3, WL4 may be a wireless form of communication. The second, third or fourth communication method WL2, WL3, WL4 may preferably be a form of electromagnetic or radio-based communication. The second, third and fourth communication method WL2, WL3, WL4 may be based on telecommunication methods. The second, third or fourth communication method WL2, WL3, WL4 may comprise or be related to the items of the following list: Wireless Local Arca Network (WLAN), Bluetooth, Bluetooth 5, BLE, GSM or 2G (2nd generation cellular technology), 3G, 4G or 5G.

The external device 320 may be adapted to be in electrical connection C1 with the medical device 10, using the body as a conductor. The electrical connection C1 is in this case used for conductive communication between the external device 320 and the medical device 10.

In one embodiment, the communication between controller 300 and the external device 320 over either of the communication methods WL2, WL3, WL4, C1 may be encrypted and/or decrypted with public and/or private keys, now described with reference to FIGS. 65A-65C. For example, the controller 300 may comprise a private key and a corresponding public key, and the external device 320 may comprise a private and a corresponding public key.

The controller 320 and the external device 320 may exchange public keys and the communication may thus be performed using public key encryption. The person skilled in the art may utilize any known method for exchanging the keys.

The controller may encrypt data to be sent to the external device 320 using a public key corresponding to the external device 320. The encrypted data may be transmitted over a wired, wireless or electrical communication channel C1, WL1, WL2, WL3 to the external device. The external device 320 may receive the encrypted data and decode it using the private key comprised in the external device 320, the private key corresponding to the public key with which the data has been encrypted. The external device 320 may transmit encrypted data to the controller 300. The external device 320 may encrypt the data to be sent using a public key corresponding to the private key of the controller 300. The external device 320 may transmit the encrypted data over a wired, wireless or electrical connection C1, WL1, WL2, WL3, WL4, directly or indirectly, to the controller of the implant. The controller may receive the data and decode it using the private key comprised in the controller 300.

In an alternative to the public key encryption, described with reference to FIGS. 65A-65C, the data to be sent between the controller 300 of the implantable medical device 10 and an external device 320, 330 or between an external device 320, 330 and the controller 300 may be signed. In a method for sending data from the controller 300 to the external device 320, 330, the data to be sent from the controller 300 may be signed using the private key of the controller 300. The data may be transmitted over a communication channel or connection C1, WL1, WL2, WL3. WL4. The external device 320, 330 may receive the message and verify the authenticity of the data using the public key corresponding to the private key of the controller 300. In this way, the external device 320, 330 may determine that the sender of the data was sent from the controller 300 and not from another device or source.

A method for communication between external devices and the controller 300 of the implantable medical device 10 using a combined key is now described with reference to FIGS. 65A-65C. A first step of the method comprises receiving, at the implant, by a wireless transmission WL1, WL2, WL3, WL4 or otherwise, a first key from an external device 320, 330. The method further comprises receiving, at the implant, by a wireless transmission WL1, WL2, WL3, a second key. The second key may be generated by a second external device, separate from the external device 320, 330 or by another external device being a generator of the second key on behalf of the second external device 320, 330. The second key may be received at the medical device from anyone of, the external device 320, the second external device 330, and the generator of the second key. The second external device may be controlled by a caretaker, or any other stakeholder. Said another external device may be controlled by a manufacturer of the implant, or medical staff, caretaker, etc.

In case the controller 300 is receiving the second key from the external device 320, this means that the second key is routed through the external device from the second external device 330 or from another external device (generator). In these cases, the implanted medical device and/or external device(s) comprises the necessary features and functionality (described in the respective sections of this document) for performing such routing. Using the external device 320 as a relay, with or without verification from the patient, may provide an extra layer of security as the external device 320 may not need to store or otherwise handle decrypted information. As such, the external device 320 may be lost without losing decrypted information. The controller 300 a computing unit 306 configured for deriving a combined key by combining the first key and the second key with a third key held by the controller 300, for example in memory 307 of the controller 300. The third key could for example be a license number of the implant or a chip number of the implantable medical device. The combined key may be used for decrypting, by the computing unit 306, encrypted data transmitted by a wireless transmission WL1 from the external device 320 to the controller 300. Optionally, the decrypted data may be used for altering, by the computing unit 306 an operation of the implantable medical device. The altering an operation of the implantable medical device may comprise controlling or switching an active unit 302 of the implantable medical device. In some embodiments, the method further comprises at least one of the steps of, based on the decrypted data, updating a control program running in the controller 300, and operating the implantable medical device 10 using operation instructions in the decrypted data.

Methods for encrypted communication between an external device 320 and the controller 300 are provided. These methods comprise:

- receiving, at the external device 320, by a wireless transceiver 328, a first key, the first key being generated by a second external device 330, separate from the external device 320 or by another external device being a generator of the second key on behalf of the second external device 330, the first key being received from anyone of the second external device 330 and the generator of the second key,
- receiving, at the external device 320 by the wireless transceiver 328, a second key from the controller 300,
- deriving a combined key, by a computing unit 326 of the external device 320, by combining the first key and the second key with a third key held by the external device 320 (e.g. in memory 307),
- transmitting encrypted data from the implant to the external device and receiving the encrypted data at the external device by the wireless transceiver 328, and
- decrypting, by the computing unit 326, the encrypted data, in the external device 320, using the combined key.

As described above, further keys may be necessary to decrypt the data. Consequently, the wireless transceiver 328 is configured for:

- receiving a fourth key from a third external device,
- wherein the computing unit 326 is configured for:
- deriving a combined key by combining the first, second and fourth key with the third key held by the external device, and
- decrypting the encrypted data using the combined key.

These embodiments further increase the security in the communication. The computing unit 326 may be configured to confirm the communication between the implantable medical device and the external device, wherein the confirmation comprises:

measuring a parameter of the patient, by the external device 320, receiving a measured parameter of the patient, from the implantable medical device 10, comparing the parameter measured by the implantable medical device 10 to the parameter measured by the external device 320, performing confirmation of the connection based on the comparison, and as a result of the confirmation, decrypting the encrypted data, in the external device, using the combined key.

The keys described in this section may in some embodiments be generated based on data sensed by sensors described herein under the twelfth or thirteenth aspect, e.g. using the sensed data as seed for the generated keys. A seed is an initial value that is fed into a pseudo random number generator to start the process of random number generation. The seed may thus be made hard to predict without access or knowledge of the physiological parameters of the patient which it is based on, providing an extra level of security to the generated keys.

Further, increased security for communication between an external device(s) and the implantable medical device is provided.

A method of communication between an external device 320 and an implantable medical device 10 is now described with reference to FIGS. 65A-65C, when the implantable medical device 10 is implanted in a patient and the external device 320 is positioned external to the body of the patient. The external device 320 is adapted to be in electrical connection C1 with the controller 300, using the body as a conductor. The electrical connection C1 is used for conductive communication between the external device 320 and the implantable medical device 10. The implantable medical device 10 comprises the controller 300. Both the controller 300 and the external device 320 comprises a wireless transceiver 308, 208 for wireless communication C1 between the controller 300 and the external device 320. The wireless transceiver 308 (included in the controller 300) may in some embodiments comprise sub-transceivers for receiving data from the external device 320 and other external devices, e.g. using different frequency bands, modulation schemes etc.

In a first step of the method, the electrical connection C1 between the controller 300 and the external device 320 is confirmed and thus authenticated. The confirmation and authentication of the electrical connection may be performed as described herein under the fifth, thirteenth and fifteenth aspect. In these cases, the implant and/or external device(s) comprises the necessary features and functionality (described in the respective sections of this document) for performing such authentication. By authenticating according to these aspects, security of the authentication may be increased as it may require a malicious third party to know or gain access to either the transient physiological parameter of the patient or detect randomized sensations generated at or within the patient.

The implant may comprise a first transceiver 303 configured to be in electrical connection C1 with the external device, using the body as a conductor. The implantable medical device may comprise a first external transmitter 203 configured to be in electrical connection C1 with the implantable medical device, using the body as a conductor, and the wireless transmitter 208 configured to transmit wireless communication W1 to the controller 300). The first transmitter 323 of the external device 320 may be wired or wireless. The first transmitter 323 and the wireless transmitter 208 may be the same or separate transmitters. The first transceiver 303 of the controller 300 may be wired or wireless. The first transceiver 303 and the wireless transceiver 102 may be the same or separate transceivers.

The controller 300 may comprise a computing unit 306 configured to confirm the electrical connection between the external device 320 and the internal transceiver 303 and accept wireless communication WL1 (of the data) from the external device 320 on the basis of the confirmation.

Data is transmitted from the external device 320 to the controller 300 wirelessly, e.g. using the respective wireless transceiver 308, 208 of the controller 300 and the external device 320. Data may alternatively be transmitted through the electrical connection C1. As a result of the confirmation, the received data may be used for instructing the implantable medical device 10. For example, a control program 310 running in the controller 300 may be updated, the controller 300 may be operated using operation instructions in the received data. This may be handled by the computing unit 306.

The method may comprise transmitting data from the external device 320 to the controller 300 wirelessly comprises transmitting encrypted data wirelessly. To decrypt the encrypted data (for example using the computing unit 306), several methods may be used.

In one embodiment, a key is transmitted using the confirmed conductive communication channel C1 (i.e. the electrical connection) from the external device 320 to the controller 300. The key is received at the controller (by the first internal transceiver 303). The key is then used for decrypting the encrypted data.

In some embodiments the key is enough to decrypt the encrypted data. In other embodiments, further keys are necessary to decrypt the data. In one embodiment, a key is transmitted using the confirmed conductive communication channel C1 (i.e. the electrical connection) from the external device 320 to the controller 300. The key is received at the controller 300 (by the first internal transceiver 303). A second key is transmitted (by the wireless transceiver 208) from the external device 320 using the wireless communication WL1 and received at the controller 300 by the wireless transceiver 308. The computing unit 306 is then deriving a combined key from the key and second key and uses this for decrypting the encrypted data.

In yet other embodiments, a key is transmitted using the confirmed conductive communication channel C1 (i.e. the electrical connection) from the external device 320 to the controller 300. The key is received at the controller (by the first internal transceiver 303). A third key is transmitted from a second external device 330, separate from the external device 320, to the implant wirelessly WL2. The third key may be received by a second wireless receiver (part of the wireless transceiver 308) of the controller 300 configured for receiving wireless communication WL2 from second external device 330.

The first and third key may be used to derive a combined key by the computing unit 306, which then decrypts the encrypted data. The decrypted data is then used for instructing the implantable medical device 10) as described above.

The second external device 330 may be controlled by for example a caregiver, to further increase security and validity of data sent and decrypted by the controller 300.

It should be noted that in some embodiments, the external device is further configured to receive WL2 secondary wireless communication from the second external device 330, and transmit data received from the secondary wireless communication WL2 to the implantable medical device.

This routing of data may be achieved using the wireless transceivers 308, 208 (i.e. the wireless connection WL1, or by using a further wireless connection WL4 between the controller 300 and the external device 320. In these cases, the medical device and/or external device(s) comprises the necessary features and functionality for performing such routing. Consequently, in some embodiments, the third key is generated by the second external device 330 and transmitted WL2 to the external device 320 which routes the third key to the controller 300 to be used for decryption of the encrypted data. In other words, the step of transmitting a third key from a second external device, separate from the external device, to the implant wirelessly, comprises routing the third key through the external device 320. Using the external device 320 as a relay, with or without verification from the patient, may provide an extra layer of security as the external device 320 may not need to store or otherwise handle decrypted information. As such, the external device 320 may be lost without losing decrypted information.

In yet other embodiments, a key is transmitted using the confirmed conductive communication channel C1 (i.e. the electrical connection) from the external device 320 to the controller 300. The key is received at the implant (by the first internal transceiver 303). A second key is transmitted from the external device 320 to the controller 300 wirelessly WL1, received at the at the controller 300. A third key is transmitted from the second external device, separate from the external device 320, to the controller 300 wirelessly WL4. Encrypted data transmitted from the external device 320 to the controller 300 is then decrypted using a derived combined key from the key, the second key and the third key. The external device may be a wearable external device.

The external device 320 may be a handset. The second external device 330 may be a handset. The second external device 330 may be a server. The second external device 330 may be cloud based.

In some embodiments, the electrical connection C1 between the external device 320 and the controller 300 is achieved by placing a conductive member 201, configured to be in connection with the external device 200, in electrical connection with a skin of the patient for conductive communication C1 with the medical device. In these cases, the medical device and/or external device(s) comprises the necessary features and functionality (described in the respective sections of this document) for performing such conductive communication. The communication may thus be provided with an extra layer of security in addition to the encryption by being electrically confined to the conducting path e.g. external device 320, conductive member 201, conductive connection C1, controller 300, meaning the communication will be excessively difficult to be intercepted by a third party not in physical contact with, or at least proximal to, the patient.

The keys described in this section may in some embodiments be generated based on data sensed by sensors described herein, e.g. using the sensed data as seed for the generated keys. A seed is an initial value that is fed into a pseudo random number generator to start the process of random number generation. The seed may thus be made hard to predict without access or knowledge of the physiological parameters of the patient which it is based on, providing an extra level of security to the generated keys.

Increased security for communication between an external device(s) and an implanted medical device is provided, now described with reference to FIGS. 65A-65C.

In these embodiments, a method for communication between an external device 320 and the implantable controller 300 is provided. The wireless transceiver 308 (included in the controller 300) may in some embodiments comprise sub-transceivers for receiving data from the external device 320 and other external devices 330, e.g. using different frequency bands, modulation schemes etc.

A first step of the method comprises receiving, at the implanted medical device, by a wireless transmission WL1 or otherwise, a first key from an external device 320. The method further comprises receiving, at the implanted medical device, by a wireless transmission WL1, WL2, WL3, a second key. The second key may be generated by a second external device 330, separate from the external device 320 or by another external device being a generator of the second key on behalf of the second external device 330. The second key may be received at the implanted medical device from anyone of, the external device 320, the second external device 330, and a generator of the second key. The second external device 330 may be controlled by a caretaker, or any other stakeholder. Said another external device may be controlled by a manufacturer of the medical device, or medical staff, caretaker, etc.

In case the medical device is receiving the second key from the external device 320, this means that the second key is routed through the external device from the second external device 330 or from the another external device (generator). In these cases, the medical device and/or external device(s) comprises the necessary features and functionality (described in the respective sections of this document) for performing such routing. Using the external device 320 as a relay, with or without verification from the patient, may provide an extra layer of security as the external device 320 may not need to store or otherwise handle decrypted information. As such, the external device 320 may be lost without losing decrypted information.

The controller 300 comprises a computing unit 306 configured for deriving a combined key by combining the first key and the second key with a third key held by the controller 300, for example in memory 307 of the controller. The combined key may be used for decrypting, by the computing unit 306, encrypted data transmitted by a wireless transmission WL1 from the external device 320 to the controller 300. Optionally, the decrypted data may be used for altering, by the computing unit 306 an operation of the implantable medical device 10. The altering an operation of the implantable medical device may comprise controlling or switching an active unit 302 of the medical device. In some embodiments, the method further comprises at least one of the steps of, based on the decrypted data, updating a control program running in the implant, and operating the implantable medical device 10 using operation instructions in the decrypted data.

In some embodiments, further keys are necessary to derive a combined key for decrypting the encrypted data received at the controller 300. In these embodiments, the first and second key are received as described above. Further, the method comprises receiving, at the implanted medical device, a fourth key from a third external device, the third external device being separate from the external device, deriving a combined key by combining the first, second and fourth key with the third key held by the controller 300, and decrypting the encrypted data, in the controller 300, using the combined key. Optionally, the decrypted data may be used for altering, by the computing unit 306, an operation of the implanted medical device as described above. In some embodiments, the fourth key is routed through the external device from the third external device.

In some embodiments, further security measures are needed before using the decrypted data for altering, by the computing unit 306, an operation of the implantable medical device. For example, an electrical connection C1 between the implantable medical device and the external device 320, using the body as a conductor, may be used for further verification of validity of the decrypted data. The electrical connection C1 may be achieved by placing a conductive member 201, configured to be in connection with the external device, in electrical connection with a skin of the patient for conductive communication C1 with the implantable medical device. The communication may thus be provided with an extra layer of security in addition to the encryption by being electrically confined to the conducting path e.g. external device 320, conductive member 201, conductive connection C1, controller 300, meaning the communication will be excessively difficult to be intercepted by a third party not in physical contact with, or at least proximal to, the patient.

Accordingly, in some embodiments, the method comprising confirming the electrical connection between the controller 300 and the external device 320, and as a result of the confirmation, altering an operation of the implantable medical device based on the decrypted data. The confirmation and authentication of the electrical connection may be performed as described herein under the general features section. In these cases, the implantable medical device and/or external device(s) 320 comprises the necessary features and functionality (described in the respective sections of this document) for performing such authentication. By authenticating according to these aspects, security of the authentication may be increased as it may require a malicious third party to know or gain access to either the transient physiological parameter of the patient or detect randomized sensations generated at or within the patient.

In some embodiments, the confirmation of the electrical connection comprises: measuring a parameter of the patient, by e.g. a sensor of the implantable medical device 10, measuring the parameter of the patient, by the external device 320, comparing the parameter measured by the implantable medical device to the parameter measured by the external device 320, and authenticating the connection based on the comparison. As mentioned above, as a result of the confirmation, an operation of the implantable medical device may be altered based on the decrypted data.

Further methods for encrypted communication between an external device 320 and an implantable medical device 10 are provided. These methods comprise:

- receiving, at the external device 320 by a wireless transceiver 328, a first key, the first key being generated by a second external device 330, separate from the external device 320 or by another external device being a generator of the second key on behalf of the second external device 320, the first key being received from anyone of the second external device 330 and the generator of the second key,
- receiving, at the external device 320 by the wireless transceiver 328, a second key from the controller 300,
- deriving a combined key, by a computing unit 326 of the external device 320, by combining the first key and the second key with a third key held by the external device 320 (e.g. in memory 327),
- transmitting encrypted data from the implant to the external device and receiving the encrypted data at the external device by the wireless transceiver 328, and
- decrypting, by the computing unit 326, the encrypted data, in the external device 320, using the combined key.

As described above, further keys may be necessary to decrypt the data. Consequently, the wireless transceiver 328 is configured for:

- receiving a fourth key from a third external device, wherein the computing unit 326 is configured for:
- deriving a combined key by combining the first, second and fourth key with the third key held by the external device, and
- decrypting the encrypted data using the combined key.

In some embodiments, the communication between the controller 300 and the external device 320 needs to be confirmed (authenticated) before decrypting the data. In these cases, the implantable medical device and/or external device(s) comprises the necessary features and functionality (described in the respective sections of this document) for performing such authentication.

These embodiments further increase the security in the communication. In these embodiments the computing unit 326 is configured to confirm the communication between the implantable medical device and the external device, wherein the confirmation comprises:

- measuring a parameter of the patient, by the external device 320,
- receiving a measured parameter of the patient, from the implantable medical device 10,
- comparing the parameter measured by the implantable medical device 320 to the parameter measured by the external device 320,
- performing confirmation of the connection based on the comparison, and
- as a result of the confirmation, decrypting the encrypted data, in the external device, using the combined key.

One or more of the first, second and third key may comprise a biometric key.

The keys described in this section may in some embodiments be generated based on data sensed by sensors, e.g. using the sensed data as seed for the generated keys. A seed is an initial value that is fed into a pseudo random number generator to start the process of random number generation. The seed may thus be made hard to predict without access or knowledge of the physiological parameters of the patient which it is based on, providing an extra level of security to the generated keys.

Further, increased security for communication between an external device(s) 320, 330 and an implantable medical device is provided, described with reference to FIGS. 65A-65C. The system being configured for enabling communication between an external device 320 and the controller 300 implanted in a patient. The system comprises a conductive member 321 configured to be in connection (electrical/conductive or wireless or otherwise) with the external device, the conductive member 321 being configured to be placed in electrical connection with a skin of the patient for conductive communication C1 with the implantable medical device 10. By using a conductive member 321 as defined herein, an increased security for communication between the external device and the implantable medical device may be achieved. For example, when a sensitive update of a control program of the controller 300 is to be made, or if sensitive data regarding physical parameters of the patient is to be sent to the external device 320 (or otherwise), the conductive member 321 may ensure that the patient is aware of such communication and actively participate in validating that the communication may take place. The conductive member may, by being placed in connection with the skin of the patient, open the conductive communication channel C1 between the external device and the controller to be used for data transmission.

Electrical or conductive communication, such as this or as described under the other embodiments, may be very hard to detect remotely, or at least relatively so, in relation to wireless communications such as radio transmissions. Direct electrical communication may further safeguard the connection between the implantable medical device 10 and the external device 320 from electromagnetic jamming i.e. high-power transmissions other a broad range of radio frequencies aimed at drowning other communications within the frequency range. Electrical or conductive communication will be excessively difficult to be intercepted by a third party not in physical contact with, or at least proximal to, the patient, providing an extra level of security to the communication.

In some embodiments, the conductive member comprises a conductive interface for connecting the conductive member to the external device.

In some embodiments, the conductive member 201 is a device which is plugged into the external device 200, and easily visible and identifiable for simplified usage by the patient. In other embodiments, the conductive member 321 is to a higher degree integrated with the external device 320, for example in the form of a case of the external device 320 comprising a capacitive area configured to be in electrical connection with a skin of the patient. In one example, the case is a mobile phone case (smartphone case) for a mobile phone, but the case may in other embodiments be a case for a personal computer, or a body worn camera or any other suitable type of external device as described herein. The case may for example be connected to the phone using a wire from the case and connected to the headphone port or charging port of the mobile phone.

The conductive communication C1 may be used both for communication between the controller 300 and the external device 320 in any or both directions. Consequently, according to some embodiments, the external device 320 is configured to transmit a conductive communication (conductive data) to the controller 300 via the conductive member 321.

According to some embodiments, the controller 300 is configured to transmit a conductive communication to the external device 320. These embodiments start by placing the conductive member 321, configured to be in connection with the external device 320, in electrical connection with a skin of the patient for conductive communication C1 with the controller 300. The conductive communication between the external device 320 and the controller 300 may follow an electrically/conductively confined path comprising e.g. the external device 320, conductive member 321, conductive connection C1, controller 300.

For the embodiments when the external device 320 transmits data to the controller, the communication may comprise transmitting a conductive communication to the controller 300 by the external device 320.

The transmitted data may comprise instructions for operating the implantable medical device 10. Consequently, some embodiments comprise operating the implantable medical device 10 using operation instructions, by an internal computing unit 306 of the controller 300, wherein the conductive communication C1 comprises instructions for operating the implantable medical device 10. The operation instruction may for example involve adjusting or setting up (e.g. properties or functionality of) the active unit 302 of the implantable medical device 10.

The transmitted data may comprise instructions for updating a control program 310 stored in memory 307 of the controller 300. Consequently, some embodiments comprise updating the control program 310 running in the controller 300, by the internal computing unit 306 of the implantable medical device, wherein the conductive communication comprises instructions for updating the control program 310.

For the embodiments when the controller 300 transmits data to the external device 320, the communication may comprise transmitting conductive communication C1 to the external device 320 by the controller 300. The conductive communication may comprise feedback parameters. Feedback parameters could include battery status, energy level at the controller, the fluid level of the hydraulic restriction device, number of operations that the restriction device has performed, properties, version number etc. relating to functionality of the implantable medical device 10. In other embodiments, the conductive communication C1 comprises data pertaining to least one physiological parameter of the patient, such as blood pressure etc. The physiological parameter(s) may be stored in memory 307 of the controller 300 or sensed in prior (in real time or with delay) to transmitting the conductive communication C1. Consequently, in some embodiments, the implantable medical device 10 comprises a sensor 150 for sensing at least one physiological parameter of the patient, wherein the conductive communication comprises said at least one physiological parameter of the patient.

To further increase security of the communication between the controller 300 and the external device 320, different types of authentication, verification and/or encryption may be employed. In some embodiments, the external device 320 comprises a verification unit 340. The verification unit 340 may be any type of unit suitable for verification of a user, i.e. configured to receive authentication input from a user, for authenticating the conductive communication between the implantable medical device and the external device. In some embodiments, the verification unit and the external device comprises means for collecting authentication input from the user (which may or may not be the patient). Such means may comprise a fingerprint reader, a retina scanner, a camera, a GUI for inputting a code, a microphone, device configured to draw blood, etc. The authentication input may thus comprise a code or any be based on a biometric technique selected from the list of: a fingerprint, a palm vein structure, image recognition, face recognition, iris recognition, a retinal scan, a hand geometry, and genome comparison. The means for collecting the authentication input may alternatively be part of the conductive member which comprise any of the above examples of functionality, such as a fingerprint reader or other type of biometric reader.

In some embodiments, the security may thus be increased by receiving an authentication input from a user by the verification unit 340 of the external device 320, and authenticating the conductive communication between the controller 300 and the external device using the authentication input. Upon a positive authentication, the conductive communication channel C1 may be employed for comprising transmitting a conductive communication to the controller 300 by external device 320 and/or transmitting a conductive communication to the external device 320 by the controller 300. In other embodiments, a positive authentication is needed prior to operating the implantable medical device 10 based on received conductive communication, and/or updating a control program running in the controller 300 as described above.

FIGS. 65A-65C further shows an implantable medical device 10 implanted in a patient and being connected to a sensation generator 381.

The sensation generator 381 may be configured to generate a sensation. The sensation generator 381 may be contained within the implantable medical device 10 or be a separate unit. The sensation generator 381 may be implanted. The sensation generator 381 may also be located so that it is not implanted as such but still is in connection with a patient so that only the patient may experience sensations generated. The controller 300 is configured for storing authentication data, related to the sensation generated by the sensation generator 381.

The controller 300 is further configured for receiving input authentication data from the external device 320. Authentication data related to the sensation generated may by stored by a memory 307 of the controller 3000). The authentication data may include information about the generated sensation such that it may be analyzed, e.g. compared, to input authentication data to authenticate the connection, communication or device. Input authentication data relates to information generated by a patient input to the external device 320. The input authentication data may be the actual patient input or an encoded version of the patient input, encoded by the external device 320. Authentication data and input authentication data may comprise a number of sensations or sensation components.

The authentication data may comprise a timestamp. The input authentication data may comprise a timestamp of the input from the patient. The timestamps may be a time of the event such as the generation of a sensation by the sensation generator 381 or the creation of input authentication data by the patient. The timestamps may be encoded. The timestamps may feature arbitrary time units, i.e. not the actual time. Timestamps may be provided by an internal clock 360 of the controller 300 and an external clock 362 of the external device 320. The clocks 360, 362 may be synchronized with each other. The clocks 360, 362 may be synchronized by using a conductive connection C1 or a wireless connection WL1 for communicating synchronization data from the external device 320, and its respective clock 362, to the controller 300, and its respective clock 360, and vice versa. Synchronization of the clocks 360, 362 may be performed continuously and may not be reliant on secure communication.

Authentication of the connection may comprise calculating a time difference between the timestamp of the sensation and the timestamp of the input from the patient, and upon determining that the time difference is less than a threshold, authenticating the connection. An example of a threshold may be Is. The analysis may also comprise a low threshold as to filter away input from the patient that is faster than normal human response times. The low threshold may e.g. be 50 ms.

Authentication data may comprise a number of times that the sensation is generated by the sensation generator, and wherein the input authentication data comprises an input from the patient relating to a number of times the patient detected the sensation. Authenticating the connection may then comprise: upon determining that the number of times that the authentication data and the input authentication data are equal, authenticating the connection.

A method of authenticating the connection between an implantable medical device 10 implanted in a patient, and an external device 320 according includes the following steps.

Generating, by a sensation generator 381, a sensation detectable by a sense of the patient. The sensation may comprise a plurality of sensation components. The sensation or sensation components may comprise a vibration (e.g. a fixed frequency mechanical vibration), a sound (e.g. a superposition of fixed frequency mechanical vibrations), a photonic signal (e.g. a non-visible light pulse such as an infra-red pulse), a light signal (e.g. a visual light pulse), an electric signal (e.g. an electrical current pulse) or a heat signal (e.g. a thermal pulse). The sensation generator may be implanted, configured to be worn in contact with the skin of the patient or capable of creating sensation without being in physical contact with the patient, such as a beeping alarm.

Sensations may be configured to be consistently felt by a sense of the patient while not risking harm to or affecting internal biological processes of the patient.

The sensation generator 381, may be contained within the controller 300 or be a separate entity connected to the controller 300. The sensation may be generated by a motor (denoted as M in several embodiments shown herein) of the implantable medical device 10, wherein the motor being the sensation generator 381. The sensation may be a vibration, or a sound created by running the motor. The sensation generator 381 may be located close to a skin of the patient and thus also the sensory receptors of the skin. Thereby the strength of some signal types may be reduced.

Storing, by the controller 300, authentication data, related to the generated sensation.

Providing, by the patient input to the external device, resulting in input authentication data. Providing the input may e.g. comprise an engaging an electrical switch, using a biometric input sensor or entry into digital interface running on the external device 320 to name just a few examples.

Transmitting the input authentication data from the external device to the controller 300. If the step was performed, the analysis may be performed by the controller 300.

Transmitting the authentication data from the implantable medical device 10 to the external device 320. If the step was performed, the analysis may be performed by the external device 320. The wireless connection WL1 or the conductive connection C1 may be used to transmit the authentication data or the input authentication data.

Authenticating the connection based on an analysis of the input authentication data and the authentication data e.g. by comparing a number of sensations generated and experienced or comparing timestamps of the authentication data and the input authentication data. If step was performed, the analysis may be performed by the implantable medical device 10.

Communicating further data between the controller 300 and the external device 320 following positive authentication. The wireless connection WL1 or the conductive connection C1 may be used to communicate the further data. The further data may comprise data for updating a control program 310 running in the controller 300 or operation instructions for operating the implantable medical device 10. The further data may also comprise data sensed by a sensor 150 connected to the controller 300. The controller may comprise at least one unit having a sleep mode and an active mode, and the unit consumes less energy in the sleep mode than in the active mode. The unit is configured to switch from the sleep mode to the active mode on the basis of at least one signal from the sensor. The unit could for example be a DSP (Digital Signal Processor), another type of processor or a wake-up circuit of the controller, which in turn activates the functions of the controller. The unit may be configured to switch from the sleep mode to the active mode on the basis of a signal from the sensor related to a sensed parameter of the patient, such as the patient swallowing.

If the analysis was performed by the controller 300, the external device 320 may continuously request or receive, information of an authentication status of the connection between the controller 300 and the external device 320, and upon determining, at the external device 320, that the connection is authenticated, transmitting further data from the external device 320 to the controller 300.

If the analysis was performed by the external device 320, the controller 300 may continuously request or receive, information of an authentication status of the connection between the controller 300 and the external device 320, and upon determining, at the controller 300, that the connection is authenticated, transmitting further data from the controller 300 to the external device 320.

A main advantage of authenticating a connection according to this method is that only the patient may be able to experience the sensation. Thus, only the patient may be able to authenticate the connection by providing authentication input corresponding to the sensation generation.

The sensation generator 381, sensation, sensation components, authentication data, input authentication data, and further data may be further described herein. In these cases, the implantable medical device 10 and/or external device(s) comprises the necessary features and functionality (described in the respective sections of this document). Further information and definitions can be found in this document in conjunction with the other aspects.

The method may further comprise transmitting further data between the controller 300 and the external device, wherein the further data is used or acted upon, only after authentication of the connection is performed.

The analysis or step of analyzing may be understood as a comparison or a step of comparing.

In one method, increased security for communication between an external device(s) and an implanted controller is provided. FIGS. 65A-65E show an implantable medical device 10 comprising a controller 300 and an external device 320 which may form a system.

The controller 300 comprises a transceiver 308, 303 configured to establish a connection with an external device 320, i.e. with a corresponding transceiver 328, 323. The connection may be an electrical connection C1 using the transceivers 303, 323, or a wireless connection WL1 using the transceivers 308, 328. The controller 300 further comprises a computing unit 306 configured to verify the authenticity of instructions received at the transceiver 308, 303 from the external device 320. In this aspect, the concept of using previously transmitted instructions for verifying a currently transmitted instructions are employed. Consequently, the transmitting node (in this case the external device) need to be aware of previously instructions transmitted to the implantable medical device, which reduces the risk of a malicious device instructing the implant without having the authority to do so.

In an embodiment, the computing unit 306 is configured to verify the authenticity of instructions received at the transceiver 308, 303 by extracting a previously transmitted set of instructions from a first combined set of instructions received by the transceiver. The external device 320 may thus comprise an external device comprising a computing unit 326 configured for: combining a first set of instructions with a previously transmitted set of instructions, forming a combined set of instructions, and transmitting the combined set of instructions to the implantable medical device. The previously transmitted set of instructions, or a representation thereof, may be stored in memory 327 of the external device 320.

The combined set of instructions may have a data format which facilitates such extraction, for example including metadata identifying data relating to the previously transmitted set of instructions in the combined set of instructions. In some embodiments, the combined set of instructions comprises the first set of instructions and a cryptographic hash of the previously transmitted set of instructions. Consequently, the method comprises combining, at the external device, a first set of instructions with a previously transmitted set of instructions, forming a first combined set of instructions. A cryptographic hash function is a special class of hash function that has certain properties which make it suitable for use in cryptography. It is a mathematical algorithm that maps data of arbitrary size to a bit string of a fixed size (a hash) and is designed to be a one-way function, that is, a function which is infeasible to invert. Examples include MD5, SHA1, SHA 256, etc. Increased security is thus achieved.

The first combined set of instructions is then transmitted to the implanted controller 300, where it is received by e.g. the transceiver 303, 308. The first combined set of instructions may be transmitted to the implantable medical device using a proprietary network protocol. The first combined set of instructions may be transmitted to the controller 300 using a standard network protocol. In these cases, the controller 300 and/or external device(s) comprises the necessary features and functionality (described in the respective sections of this document) for performing transmission of data. By using different communication protocols, at the external device 320, for communication with the controller 300 and with a second external device 330, an extra layer of security is added as the communication between controller 300 and the external device 320 may be made less directly accessible to remote third parties.

At the controller 300, the computing unit 306 verifies the authenticity of the received first combined set of instructions, by: extracting the previously transmitted set of instructions from the first combined set of instructions, and comparing the extracted previously transmitted set of instructions with previously received instructions stored in the implantable medical device.

Upon determining that the extracted previously transmitted set of instructions equals the previously received instructions stored in the controller 300, the authenticity of the received first combined set of instructions may be determined as valid, and consequently, the first set of instructions may be safely run at the controller 300, and the first combined set of instructions may be stored in memory 307 of the controller 300, to be used for verifying a subsequent received set of instructions.

In some embodiments, upon determining by the internal computing unit 306 that the extracted previously transmitted set of instructions differs from the previously received instructions stored in the controller 300, feedback related to an unauthorized attempt to instruct the implantable medical device 10 may be provided. For example, the transceiver 308, 303 may send out a distress signal to e.g. the external device 320 or to any other connected devices. The controller 300 may otherwise inform the patient that something is wrong by e.g. vibration or audio. The implantable medical device 10 may be run in safe mode, using a preconfigured control program which is stored in memory 307 of the controller 300 and specifically set up for these situations, e.g. by requiring specific encoding to instruct the implantable medical device 10, or only allow a predetermined device (e.g. provided by the manufacturer) to instruct the implantable medical device 10. In some embodiments, when receiving such feedback at the external device 320, the external device 320 retransmits the first combined set of instructions again, since the unauthorized attempt may in reality be an error in transmission (where bits of the combined set of instructions are lost in transmission), and where the attempt to instruct the implantable medical device 10 is indeed authorized.

The step of comparing the extracted previously transmitted set of instructions with previously received instructions stored in the controller 300 may be done in different ways. For example, the step of comparing the extracted previously transmitted set of instructions with previously received instructions stored in the controller 300 comprises calculating a difference between the extracted previously transmitted set of instructions with previously received instructions stored in the controller 300, and comparing the difference with a threshold value, wherein the extracted previously transmitted set of instructions is determined to equal the previously received instructions stored in the controller 300 in the case of the difference value not exceeding the threshold value. This embodiment may be used when received instructions is stored in clear text, or a representation thereof, in the controller 300, and where the combined set of instructions, transmitted from the external device also includes such a representation of the previously transmitted instructions. This embodiment may be robust against error in transmission where bits of information are lost or otherwise scrambled.

In other embodiments, the combined set of instructions comprises the first set of instructions and a cryptographic hash of the previously transmitted set of instructions, wherein the method further comprises, at the controller 300, calculating a cryptographic hash of the previously received instructions stored in the controller 300 and comparing the calculated cryptographic hash to the cryptographic hash included in the first combined set of instructions. This embodiment provides increased security since the cryptographic hash is difficult to decode or forge.

The above way of verifying the authenticity of received instructions at the controller 300 may be iteratively employed for further sets if instructions.

To further increase security, the transmission of a first set of instructions, to be stored at the controller 300 for verifying subsequent sets of combined instructions, where each set of received combined instructions will comprise data which in some form will represent, or be based on, the first set of instruction, may be performed.

In one example, the external device 320 may be adapted to communicate with the controller 300 using two separate communication methods. A communication range of a first communication method WL1 may be less than a communication range of a second communication method WL2. A method may comprise the steps of: sending a first part of a key from the external device 320 to the controller 300, using the first communication method WL1 and sending a second part of the key from the external device 320 to the controller 300, using the second communication method WL2. The method may further comprise deriving, in the controller 300, a combined key from the first part of the key and the second part of the key and decrypting the encrypted data, in the controller 300, using the combined key. The encrypted data may also be sent from the external device 320 to the controller 300 using the second communication method WL2. The method may then further comprise confirming an electrical connection C1 between the controller 300 and the external device 320 and as a result of the confirmation, decrypting the encrypted data in the controller 300 and using the decrypted data for instructing the controller 300.

The method may also comprise placing a conductive member 321, configured to be in connection with the external device 320, in electrical connection with a skin of the patient for conductive communication with the controller 300. By means of the electrical connection an extra layer of security is added as a potential hacker would have to be in contact with the patient to access or affect the operation of the implantable medical device 10.

Using a plurality of communication methods, may increase the security of the authentication and the communication with the implantable medical device 10 as more than one channel for communication may need to be hacked or hijacked by an unauthorized entity to gain access to the implantable medical device 10 or the communication.

The electrical connection C1 the conductive member 321 and conductive communication may be further described herein in the general definitions section. In these cases, the controller 300 and/or external device 320 comprise the necessary features and functionality (described in the respective sections of this document).

It should also be noted that any one of the first and second communication methods WL1, WL2 may be needed to be confirmed in order to decrypt the encrypted data in the controller 300 and using the decrypted data for instructing the implantable medical device 10.

The method may further comprise the step of wirelessly receiving, at the controller 300, a third part of the key from the second external device 330. In this case, the combined key may be derived from the first part of the key, the second part of the key and the third part of the key.

The first communication method WL1 may be a wireless form of communication. The first communication method WL1 may preferably be a form of electromagnetic or radio-based communication however, other forms of communication are not excluded. The first communication method WL1 may comprise or be related to the items of the following list: Radio-frequency identification (RFID), Bluetooth, Bluetooth 5, Bluetooth Low Energy (BLE), Near Field Communication (NFC), NFC-V, Infrared (IR) based communication, Ultrasound based communication.

RFID communication may enable the use of a passive receiver circuit such as those in a RFID access/key or payment card. IR based communication may comprise fiber optical communication and IR diodes. IR diodes may alternatively be used directly, without a fiber, such as in television remote control devices. Ultrasound based communication may be based on the non-invasive, ultrasound imaging found in use for medical purposes such as monitoring the development of mammal fetuses.

The first communication method WL1 may use a specific frequency band. The frequency band of the first communication method WL1 may have a center frequency of 13.56 MHz or 27.12 MHz. These bands may be referred to as industrial, scientific and medical (ISM) radio bands. Other ISM bands not mentioned here may also be utilized for the communication methods WL1, WL2. A bandwidth of the 13.56 MHz centered band may be 14 kHz and a bandwidth of the 27.12 MHz centered band may be 326 kHz.

The communication range of the first communication method WL1 may be less than 10 meters, preferably less than 2 meters, more preferably less than 1 meter and most preferably less than 20 centimeters. The communication range of the first communication method WL1 may be limited by adjusting a frequency and/or a phase of the communication. Different frequencies may have different rates of attenuation. By implementing a short communication range of the first communication method, security may be increased since it may be ensured or made probable that the external device is under control of the patient (holding the external device close to the implant)

The communication range of the first communication method WL1 should be evaluated by assuming that a patient's body, tissue, and bones present the propagation medium. Such a propagation medium may present different attenuation rates as compared to a free space of an air-filled atmosphere or a vacuum.

By restricting the communication range, it may be established that the external device communicating with the implanted controller 300 is in fact on, or at least proximal to, the patient. This may add extra security to the communication.

The second communication method WL2 may be a wireless form of communication. The second communication method WL2 may preferably be a form of electromagnetic or radio-based communication. The second communication method WL2 may be based on telecommunication methods. The second communication method WL2 may comprise or be related to the items of the following list: Wireless Local Area Network (WLAN), Bluetooth, Bluetooth 5, BLE, GSM or 2G (2nd generation cellular technology), 3G, 4G, 5G.

The second communication method WL2 may utilize the ISM bands as mentioned in the above for the first communication method WL1.

A communication range of the second communication method WL2 may be longer than the communication range of the first communication method WL1. The communication range of the second communication method WL2 may preferably be longer than 10 meters, more preferably longer than 50 meters, and most preferably longer than 100 meters.

Encrypted data may comprise instructions for updating a control program 310 running in the implantable medical device 10. Encrypted data may further comprise instructions for operating the implantable medical device 10.

In one embodiment, the implantable medical device 10 may transmit data to an external device 320 which may add an additional layer of encryption and transmit the data to a second external device 330, described with reference to FIGS. 65A-65E. By having the external device add an additional layer of encryption, less computing resources may be needed in the implanted controller 300, as the controller 300 may transmit unencrypted data or data encrypted using a less secure or less computing resource requiring encryption. In this way, data can still be relatively securely transmitted to a third device. The transmission of data can be performed using any of the method described herein in addition to the method or in the system described below.

Thus, in an embodiment, a system is provided. The system comprises an implantable medical device 10 comprising a controller 300 configured to transmit data from the body of the patient to an external device 320, and an encryption unit 382 for encrypting the data to be transmitted. The system further comprises an external device 320 configured to receive the data transmitted by the controller 300, encrypt the received data using a first key and transmit the encrypted received data to a third external device 330. The encryption can be performed using any of the keys described above or below. In some embodiments, the external device 320 is configured to decrypt the data received from the controller 300 before encrypting and transmitting the data. Alternatively, the external device 320 may encrypt and transmit the data received from the controller 300 without decrypting it first.

In one example, the encryption unit 382 is configured to encrypt the data to be transmitted using a second key. The first key or the second key may, for example, information specific to the implantable medical device 10, a secret key associated with the external device 320, an identifier of the implantable medical device 10 or an identifier of the controller 300. The second key could be a key transmitted by the external device 320 to the controller 300. In some examples, the second key is a combined key comprising a third key received by the controller 300 from the external device 320.

The first key may be a combined key comprising a fourth key, wherein the fourth key is received by the external device 320 from a fourth device. The fourth device may be a verification unit, either comprised in the external device, or external to the external device and connected to it. The verification unit may have a sensor 350 for verification, such as a fingerprint sensor. More details in regard to this will be described below. Alternatively, the verification unit may be a generator, as described above.

The system may be configured to perform a method for transmitting data using a sensed parameter. The method may comprise transmitting a parameter measured by the external device 320 from the external device 320 to the controller 300. In this case, the comparison of the parameter of the patient measured by the external device 320 and the parameter of the patient measured by the controller 300 may be performed by the controller 300. The implantable medical device 10 may comprise a first sensor 150 for measuring the parameter of the patient at the implantable medical device 10. The external device 320 may comprise an external sensor 350 for measuring the parameter of the patient at the external device 320.

Authentication of the connection between the controller 300 and the external device 320 may be performed automatically without input, authentication, or verification from a user or patient. This is because the comparison of parameters measured internally and externally, by the internal and external sensors 351, 350 respectively may be enough to authenticate the connection. This may typically be the case when the parameter of the patient is related to an automatically occurring physiological function of the patient such as e.g. a pulse of the patient. Certain types of authentication may however require actions from the patient, e.g. having the patient perform specific movements.

In the embodiments described herein, the controller 300 may comprise or be connected to a sensation generator 381 as described above. In response to an event in the implantable medical device, such as a reset, a restart, receipt of new instructions, receipt of a new configuration or update, installation or activation of new instructions or configuration or update, the controller 300 may be configured to cause the sensation generator 381 to generate a sensation detectable by the patient in which the implantable medical device 10 is implanted. In some examples, the user may after the sensation verify an action, for example via a user interface of an external device 320.

The implantable medical device 10 may further implement a method for improving the security of the data transmitted from the controller 300. The method, for encrypted communication between a controller 300, when implanted in a patient's body, and an external device 320, comprises encoding or encrypting, by the controller 300 or a processor 306 comprised in or connected to the controller 300, data relating to the implantable medical device 10 or the operation thereof; transmitting, by the controller 300, the data; receiving, by a second communication unit comprised the external device 320, the data; encrypting, by the external device 320, the data using an encryption key to obtain encrypted data; and transmitting the encrypted data to a third external device 330. In this way, the external device 320 may add or exchange the encryption, or add an extra layer of encryption, to the data transmitted by the controller 300. When the controller 300 encodes the data to be transmitted it may be configured to not encrypt the data before transmitting, or only using a light-weight encryption, thus not needing as much processing power as if the controller were to fully encrypt the data before the transmission.

The encrypting, by the controller 300, may comprise encrypting the data using a second key. The encryption using the second key may be a more light-weight encryption than the encryption performed by the external device using the second key, i.e. an encryption that does not require as much computing resources as the encryption performed by the external device 320.

The first or the second key may comprise a private key exchanged as described above with reference to encryption and authentication, or the first or the second key may comprise an information specific to the implantable medical device 10, a secret key associated with the external device, an identifier of the implantable medical device 10 or an identifier of the controller 300. They may be combined keys as described in this description, and the content of the keys, any combination of keys, and the exchange of a key or keys is described in the encryption and/or authentication section.

In an embodiment, the implantable medical device 10 comprises at least one sensor for sensing at least one physiological parameter of the patient or a functional parameter of the implantable medical device 10, now described with reference to FIGS. 65A-65C. The sensor 351 may, for example, be a pressure sensor, an electrical sensor, a clock, a temperature sensor, a motion sensor, an optical sensor, a acoustic sensor, an ultrasonic sensor. The sensor 351 is configured to periodically sense the parameter and the controller 300 is configured to, in response to the sensed parameter being above a predetermined threshold, wirelessly broadcast information relating to the sensed parameter. The controller 300 may be configured to broadcast the information using a short to mid-range transmitting protocol, such as a Radio Frequency type protocol, a RFID type protocol, a WLAN type protocol, a Bluetooth type protocol, a BLE type protocol, a NFC type protocol, a 3G/4G/5G type protocol, or a GSM type protocol.

The controller of the implant may be connected to the sensor 351 and be configured to anonymize the information before it is transmitted. The transmission of data may also be called broadcasting of data.

In addition to or as an alternative to transmitting the data when the sensed parameter is above a predetermined threshold, the controller 300 may be configured to broadcast the information periodically. The controller 300 may be configured to broadcast the information in response to a second parameter being above a predetermined threshold. The second parameter may, for example, be related to the controller 300 itself, such as a free memory or free storage space parameter, or a battery status parameter. When the implantable medical device 10 comprises an implantable energy storage unit and an energy storage unit indicator, the energy storage unit indicator is configured to indicate a functional status of the implantable energy storage unit and the indication may be comprised in the transmitted data. The functional status may indicate at least one of charge level and temperature of the implantable energy storage unit.

In some embodiments the external device 320 is configured to receive the broadcasted information, encrypt the received information using an encryption key and transmit the encrypted received information. In this way, the external device 320 may add an additional layer of encryption or exchange the encryption performed by the controller 300.

In an embodiment, the controller 300 is configured to transmit the data using the body of the patient as a conductor C1, and the external device 320 is configured to receive the data via the body. Alternatively, or in combination, the controller 300 of the implant is configured to transmit the data wirelessly to the external device WL2.

Thus, the controller 300 may implement a method for transmitting data from the controller 300 comprising a processor 306, comprising: obtaining sensor measurement data via a sensor 150 connected to or comprised in the controller 300, the sensor measurement relating to at least one physiological parameter of the patient or a functional parameter of the implantable medical device 10, and transmitting by the controller 300 the sensor measurement data in response to the sensor measurement being above a predetermined threshold, wherein the sensor 150 is configured to periodically sense the parameter. The method may further comprise broadcasting the sensor measurement data, to be received by an external device 320. The transmitting or broadcasting may comprise using at least one of a Radio Frequency type protocol, RFID type protocol, WLAN type protocol, Bluetooth type protocol, BLE type protocol, NFC type protocol, 3G/4G/5G type protocol, or a GSM type protocol.

The method may further comprise, at the processor 306, anonymizing, by the processor, the sensor measurement data before it is transmitted, or encrypting the sensor measurement data, using an encryptor 382 comprised in the processing unit 306, before it is transmitted. The transmitting of the data may further comprise to encode the data before the transmitting. The type of encoding may be dependent on the communication channel or the protocol used for the transmission.

The transmitting may be performed periodically, or in response to a signal received by the processor, for example, by an internal part of the implantable medical device 10 such as a sensor 150, or by an external device 320.

The parameter may, for example, be at least one of a functional parameter of the implantable medical device 10 (such as a battery parameter, a free memory parameter, a temperature, a pressure, an error count, a status of any of the control programs, or any other functional parameter mentioned in this description) or a parameter relating to the patient (such as a temperature, a blood pressure, or any other parameter mentioned in this description). In one example, the implantable medical device 10 comprises an implantable energy storage unit 40 and an energy storage unit indicator 304*c*, and the energy storage unit indicator 304*c* is configured to indicate a functional status of the implantable energy storage unit 40, and the sensor measurement comprises data related to the energy storage unit indicator.

In one example, the transmitting comprises transmitting the sensor measurement to an internal processor 306 configured to cause a sensation generator 381 to cause a sensation detectable by the patient in which the implantable medical device 100 is implanted.

The method may be implemented in a system comprising the implantable medical device 100 and an external device 320, and further comprise receiving the sensor measurement data at the external device 320), and, at the external device 320, encrypting the sensor measurement data using a key to obtain encrypted data, and, transmitting the encrypted data. The transmitting may, for example, be performed wirelessly WL3 or conductively C1.

In the examples or embodiments transmitting data from or to the implantable medical device 10, the following method may be implanted in order to verify the integrity of the data, described with reference to FIGS. 65A-65B. By verifying the integrity of the data, an external device 320 or a processor 306 comprised in the controller 300 may verify that the data has not been corrupted or tampered with during the transmission. In some examples, data integrity for data communicated between a controller 300 and an external device 320 or between an external device 320 and the controller 300 may be performed using a cyclic redundancy check.

Thus, in a first example, a method for evaluating a parameter of a controller 300 implanted in a patient is described. The controller 300 comprises a processor 306 and a sensor 150 for measuring the parameter. The method comprises measuring, using the sensor 150, the functional parameter to obtain measurement data; establishing a connection between the internal controller 300 and an external device 320 configured to receive data from the implant; determining, by the processor 306, a cryptographic hash or a metadata relating to the measurement data and adapted to be used by the external device 320 to verify the integrity of the received data; transmitting the cryptographic hash or metadata; and transmitting, from the controller 300, the measurement data.

The parameter may, for example, be a parameter of the controller 300, such as a temperature, a pressure, a battery status indicator, a time period length, s pressure at a restriction device, a pressure at a sphincter, or a physiological parameter of the patient, such as a pulse, a blood pressure, or a temperature. In some examples, multiple parameters may be used.

The method may further comprise evaluating the measurement data relating to the functional parameter. By evaluating it may be meant to determine if the parameter is exceeding or less than a predetermined value, to extract another parameter from the measurement data, compare the another parameter to a predetermined value, or displaying the another parameter to a user. For example, the method may further comprise, at the external device 320, to determining, based on the evaluating, that the implantable medical device 10 is functioning correctly, or determining based on the evaluating that the implantable medical device 10 is not functioning correctly.

If it is determined that the implantable medical device 10 is not functioning correctly, the method may further comprise sending, from the external device 320, a corrective command to the controller 300, receiving the corrective command at the controller 300, and by running the corrective command correcting the functioning of the implantable medical device 10 according to the corrective command.

The method may further comprise, at the external device 320, receiving the transmitted cryptographic hash or metadata, receiving the measurement data, and verifying the integrity of the measurement data using the cryptographic hash or metadata. The cryptographic hash algorithm be any type of hash algorithm, i.e. an algorithm comprising a one-way function configured to have an input data of any length as input and produce a fixed-length hash value. For example, the cryptographic hash algorithm may be MD5, SHA1, SHA 256, etc.

In some examples, the cryptographic hash is a signature obtained by using a private key of the controller 300, and wherein the verifying, by the external device 320, comprises verifying the signature using a public key corresponding to the private key.

When using a cryptographic hash, the method may further comprise calculating a second cryptographic hash for the received measurement data using a same cryptographic hash algorithm as the processor, and determining that the measurement data has been correctly received based on that the cryptographic hash and the second cryptographic hash are equal (i.e. have the same value).

When using a metadata the verifying the integrity of the data may comprises obtaining a second metadata for the received measurement data relating to the functional parameter, and determining that the data has been correctly received based on that metadata and the second metadata are equal. The metadata may, for example, be a length of the data or a timestamp. In some examples the measurement data is transmitted in a plurality of data packets. In those examples, the cryptographic hash or metadata comprises a plurality of cryptographic hashes or metadata each corresponding to a respective data packet, and the transmitting of each the cryptographic hashes or metadata is performed for each of the corresponding data packets.

A similar method may be utilized for communicating instructions from an external device 320 to a controller 300 implanted in a patient. The method comprises establishing a first connection between the external device 320 and the controller 300, establishing a second connection between a second external device 330 and the controller 300, transmitting, from the external device 320, a first set of instructions to the controller 300 over the first connection, transmitting, from the second external device 330, a first cryptographic hash or metadata corresponding to the first set of instructions to the controller 300, and, at the controller 300, verifying the integrity of the first set of instructions and the first cryptographic hash or metadata, based on the first cryptographic hash or metadata. The external device 320 may be separate from the second external device 330.

The first connections may be established between the controller 300 and a transceiver of the external communication unit 323. In some examples, the communication using the second connection is performed using a different protocol than a protocol used for communication using the first communication channel. In some examples, the first connection is a wireless connection and the second connection is an electrical connection. The second connection may, for example, be an electrical connection using the patient's body as a conductor (using 321). The protocols and ways of communicating may be any communication protocols described in this description with reference to C1, and WL1-WL4. The establishing of the first and second connections are performed according to the communication protocol used for each of the first and the second connections.

When using a cryptographic hash, the verifying the integrity of the first set of instructions may comprise calculating a second cryptographic hash for the received first set of instructions using a same cryptographic hash algorithm as the processor 306, and determining that the first set of instructions has been correctly received based on that the cryptographic hash and the second cryptographic hash are equal. The cryptographic hash may, for example, be a signature obtained by using a private key of the implantable medical device 10, and wherein the verifying comprises verifying the signature using a public key corresponding to the private key. In some examples, the cryptographic hash is a signature obtained by using a private key of the implantable medical device 10, and wherein the verifying comprises verifying the signature using a public key corresponding to the private key. The private keys and public keys, as well as the exchange or transmittal of keys have been described in this description. Alternatively, other well-known methods can be used for transmitting or exchanging a key or keys between the external device 320 and the controller 300.

When using a metadata, and wherein the verifying the integrity of the data may comprise obtaining a second metadata for the received first set of instructions, and determining that the first set of instructions has been correctly received based on that metadata and the second metadata are equal. The metadata may, for example, be any type of data relating to the data to be transmitted, in this example the first set of instructions. For example, the metadata may be a length of the data to be transmitted, a timestamp on which the data was transmitted or retrieved or obtained, a size, a number of packets, or a packet identifier.

In some examples, the controller 300 may transmit data to an external device 320 relating to the data information in order to verify that the received data is correct. The method may thus further comprise, transmitting, by the controller 300, information relating to the received first set of instructions, receiving, by the external device 320, the information, and verifying, by the external device 320, that the information corresponds to the first set of instructions sent by the external device 320. The information may, for example, comprise a length of the first set of instructions.

The method may further comprise, at the controller 300, verifying the authenticity of the first set of instructions by i. calculating a second cryptographic hash for the first set of instructions, ii. comparing the second cryptographic hash with the first cryptographic hash, iii. determining that the first set of instructions are authentic based on that the second cryptographic hash is equal to the first cryptographic hash, and upon verification of the authenticity of the first set of instructions, storing them at the controller 300.

In some examples, the first set of instructions comprises a cryptographic hash corresponding to a previous set of instruction, as described in other parts of this description.

In some examples, the first set of instructions may comprise a measurement relating to the patient of the body for authentication, as described in other parts of this description.

Figure 65D:
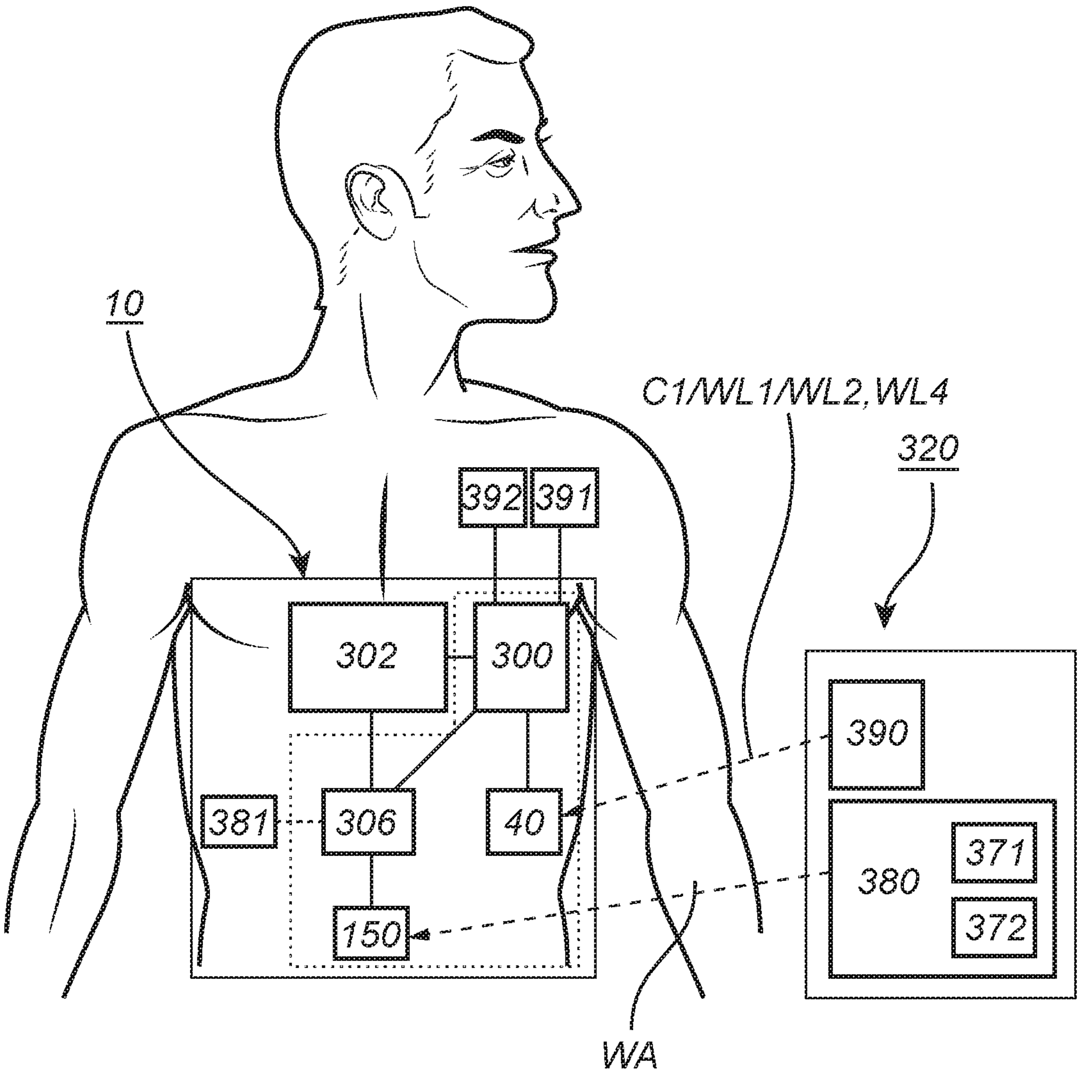
Figure 65E:
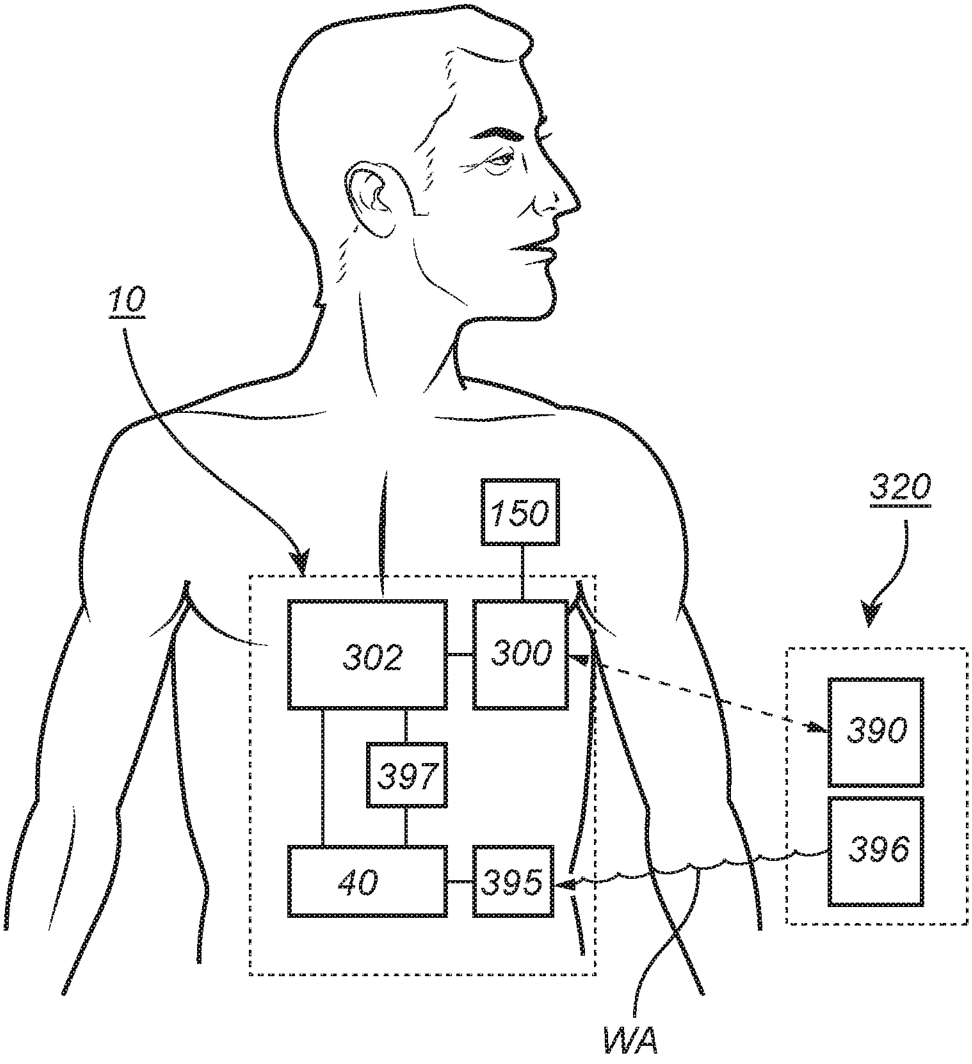

A system and a method for communication of instructions or control signals between an external device 320 and an implantable medical device 10 will now be described with reference to FIGS. 65A 65E.

The system shown in FIGS. 65A-65E comprises an implantable medical device 10, a first external device 320, and a second external device 330. The implantable medical device a controller 300. The controller 300 is adapted to receive an instruction from an external device 320 over the communication channel WL1, C1 and run the instruction to control a function of the medical device 10. The communication channel WL1, C1 may be any type of communication channel, such as a wireless connection WL1 or a conductive connection C1 described herein. For example, the wireless connection may comprise at least one of the following protocols: Radio Frequency type protocol, RFID type protocol, WLAN type protocol, Bluetooth type protocol, a BLE type protocol, a NFC type protocol, a 3G/4G/5G/6G type protocol, a GSM type protocol, and/or Bluetooth 5.

The first external device 320 is adapted to receive, such as through a user interface, or determine an instruction to be transmitted to the implantable medical device 10. The determination of the instruction may, for example, be based on received data from the implantable medical device 10, such as measurement data or data relating to a state of the implantable medical device 10, such as a battery status or a free memory status. The first external device 320 may be any type of device capable of transmitting information to the implantable medical device and capable of determining or receiving an instruction to be transmitted to the implantable medical device 10. In a preferred embodiment, the first external device 320) is a hand-held device, such as a smartphone, smartwatch, tablet etc. handled by the patient, having a user interface for receiving an instruction from a user, such as the patient or a caregiver.

The first external device 320 is further adapted to transmit the instruction to a second external device 330 via communication channel WL3. The second external device 320 is adapted to receive the instruction, encrypt the instruction using an encryption key, and then transmit the encrypted instruction to the implantable medical device 10. The implantable medical device 10 is configured to receive the instruction at the controller 300. The controller 300 thus comprises a wired transceiver or a wireless transceiver for receiving the instruction. The implantable medical device 10 is configured to decrypt the received instruction. The decryption may be performed using a decryption key corresponding to the encryption key. The encryption key, the decryption key and methods for encryption/decryption and exchange of keys may be performed as described in the "general definition of features" or as described with reference to FIGS. 65A-65E. Further, there are many known methods for encrypting data which the skilled person would understand to be usable in this example.

The second external device 330 may be any computing device capable of receiving, encrypting and transmitting data as described above. For example, the second external device 320 may be a network device, such as a network server, or it may be an encryption device communicatively coupled to the first external device.

The instruction may be a single instruction for running a specific function or method in the implantable medical device 10, a value for a parameter of the implantable medical device 10, or a set of sub-steps to be performed by the controller 300 comprised in the implantable medical device 10.

In this way, the instruction for controlling a function of the implantable medical device 10 may be received at the first external device 320 and transmitted to the implantable medical device 10 via the second external device 330. By having a second external device 330 encrypting the instruction before transmitting it to the implantable medical device 10, the instruction may be verified by the second external device 330 and the first external device 320 may function so as to relay the instruction. In some alternatives, the second external device 330 may transmit the instruction directly to the implantable medical device 10. This may provide an increased security as the instruction sent to the implantable medical device 10 may be verified by the second external device 330, which, for example, may be a proprietary device managed by the medical professional responsible for the implantable medical device 10. Further, by having the second external device 330 verifying and encrypting the instruction, the responsibility authenticity and/or correctness of the instruction may lie with the second external device 330, which may be beneficial for regulatory purposes, as the first external device 320 may not be considered as the instructor of the implantable medical device 10.

Further, the second external device 330 may verify that the instruction is correct before encrypting or signing and transmitting it to the implantable medical device 10. The second external device 330 may, for example, verify that the instruction is correct by comparing the instruction with a predetermined set of instructions, and if the instruction is comprised in the predetermined set of instructions determine that the instruction is correct. If the instruction comprises a plurality of sub-steps, the second external device 330 may determine that the instruction is correct if all the sub-steps are comprised in the predetermined set of instructions. If the instruction comprises a value for a parameter of the implantable medical device 10, the second external device 330 may verify that the value is within a predetermined range for the parameter. The second external device 320 may thus comprise a predetermined set of instructions, or a predetermined interval or threshold value for a value of a parameter, stored at an internal or external memory.

The second external device 330 may be configured to reject the instruction, i.e. to not encrypt and transmit the instruction to the implantable medical device 10, if the verification of the instruction would fail. For example, the second external device 330 determines that the instruction or any sub-step of the instruction is not comprised in the predetermined set of instructions, or if a value for a parameter is not within a predetermined interval, the second external device 330 may determine that the verification has failed.

In some embodiments, the implantable medical device 10 may be configured to verify the instruction. The verification of the instruction may be performed in the same way as described with reference to FIGS. 65A-65C. If the verification is performed by comparing the instruction or any sub-steps of the instruction with a predetermined set of instructions, the controller 300 may comprise a predetermined set of instructions. The predetermined set of instructions may, for example, be stored in an internal memory of the controller 300. Similarly, the controller 300 may store predetermined reference intervals for any parameter that can be set, and the controller 300 may be configured to compare a received value for a parameter to such a predetermined reference interval. If the verification of the instruction would fail, the controller 300 may be configured to reject the instruction, i.e. not run the instruction.

In an alternative to encrypting and decrypting the instruction, the instruction may be signed by the second external device 330 using a cryptographic hash, and the controller 300 may be configured to verify that the signature is correct before running the instruction.

A corresponding method for transmitting an instruction will now be described with reference to FIGS. 65A-65E. The instruction may relate to a function of the implantable medical device, such as an instruction to run a function or method of the implantable medical device, or to set a value of a parameter of the implantable medical device. The method comprises: transmitting an instruction for the implantable medical device from the first external device 300 to a second external device 320, the instruction relating to a function of the implantable medical device 10, encrypting, at the second external device 330 using a first encryption key, the instruction into an encrypted instruction, and transmitting the encrypted instruction from the second external device 330 to the implantable medical device 10, decrypting, at the implantable medical device, the instructions using a second encryption key corresponding to the first encryption key. The steps performed by or at the implantable medical device may be executed by the controller 300).

The instruction may be any type of instruction for controlling a function of the implantable medical device. For example, the instruction may be an instruction to run a function or method of the implantable medical device 10 or controller 300, an instruction comprising a plurality of sub-steps to be run at the controller 300, or a value for a parameter at the controller 300. The first external device 320 may, for example, receive the instruction from a user via a user interface displayed at or connected to the first external device 320. In another example, the first external device 320 may determine the instruction in response to data received from the implantable medical device 10, such as measurement data, or from another external device. Thus, in some examples, the method may further comprise receiving, at the first external device 320, an instruction to be transmitted to the implantable medical device 10. The method may further comprise displaying a user interface for receiving the instruction. In another example, the method comprises determining, at the first external device 320, an instruction to be transmitted to the implantable medical device 10.

In some embodiments, the transmitting of the encrypted instruction from the second external device 330 to the implantable medical device 10 comprises transmitting the encrypted instruction from the second external device 330 to the first external device 320, and transmitting the encrypted instruction from the first external device 320 to the controller 300 of the implantable medical device 10. In other words, the first external device 320 may relay the encrypted instruction from the second external device 330 to the controller 300, preferably without decrypting the instruction before transmitting it.

The method may further comprise to, at the controller 300, running the instruction or performing the instruction. The running of the instruction may be performed by an internal computing unit or a processor 306 comprised in the controller 300, and may, for example, cause the internal computing unit or processor 306 to instruct the implantable medical device 302 to perform an action.

The method may further comprise verifying, at the second external device 330, that the instructions are correct. The verifying may be performed as described above with reference to the corresponding system.

The method may further comprise verifying, at the controller 300, that the instructions are correct. The verifying may be performed as described above with reference to the corresponding system.

The method may further comprise authenticating the connection between the first external device 320 and the controller 300 over which the encrypted instruction is to be transmitted. The authentication may be performed as described herein.

As described above, a control program of the controller 300 may be updatable, configurable or replaceable. A system and a method for updating or configuring a control program of the controller 300 is now described with reference to FIGS. 65A-65E. The controller may comprise an internal computing unit 306 configured to control a function of the implantable medical device 10, the internal computing unit 306 comprises an internal memory 307 configured to store: i, a first control program 310 for controlling the internal computing unit, and ii, a second, configurable or updatable, with predefined program steps, control program 312 for controlling said function of the implantable medical device 10, and iii, a set of predefined program steps for updating the second control program 312. The controller 300 is configured to communicate with an external device 320. The internal computing unit 306 is configured to receive an update to the second control program 312 via the controller 300, and a verification function of, connected to, or transmitted to the controller 300. The verification function is configured to verify that the received update to the second control program 312 comprises program steps comprised in the set of predefined program steps. In this way, the updating or programming of the second control program may be performed using predefined program steps, which may decrease the risk that the new or updated control program is incorrect or comprises malicious software, such as a virus, spyware or a malware.

The predefined program steps may comprise setting a variable related to a pressure, a time, a minimum or maximum temperature, a current, a voltage, an intensity, a frequency, an amplitude of electrical stimulation, a feedback mode (sensorics or other), a post-operative mode or a normal mode, a catheter mode, a fibrotic tissue mode (for example semi-open), an time open after urination, a time open after urination before bed-time.

The verification function may be configured to reject the update in response to the update comprising program steps not comprised in the set of predefined program steps and/or be configured to allow the update in response to the update only comprising program steps comprised in the set of predefined program steps.

The internal computing unit 306 may be configured to install the update in response to a positive verification, for example by a user using an external device, by a button or similarly pressed by a user, or by another external signal.

The authentication or verification of communications between the implant and an external device has been described above.

When updating a control program of the controller 300, it may be beneficial to transmit a confirmation to a user or to an external device or system. Such a method is now described with reference to FIGS. 65A-65E.

The method for updating a control program of a controller 300 comprised in the implantable medical device 10 according to any of the embodiments herein. The controller 300 is adapted for communication with a first external device 320 and a second external device 330, which may comprise receiving, by the internal computing unit, an update or configuration to the control program from the first external device, wherein the update is received using a first communication channel; installing, by the internal computing unit 306, the update; and transmitting, by the internal computing unit, logging data relating to the receipt of the update or configuration and/or logging data relating to an installation of the update to the second external device 330 using the second communication channel; wherein the first and the second communication channels are different communication channels. By using a first and a second communication channels, in comparison to only using one, the security of the updating may be improved as any attempts to update the control program will be logged via the second communication channel, and thus, increasing the chances of finding incorrect or malicious update attempts.

The update or configuration comprises a set of instructions for the control program, and may, for examples comprise a set of predefined program steps as described above. The configuration or update may comprise a value for a predetermined parameter.

In some examples, the method further comprises confirming, by a user or by an external control unit, that the update or configuration is correct based on the received logging data.

The logging data may be related to the receipt of the update or configuration, and the controller 300 is configured to install the update or configuration in response to receipt of a confirmation that the logging data relates to a correct set of instructions. In this way, the controller 300 may receive data, transmit a logging entry relating to the receipt, and then install the data in response to a positive verification that the data should be installed.

In another example, or in combination with the one described above, the logging data is related to the installation or the update or configuration. In this example the logging data may be for information purposes only and not affect the installation, or the method may further comprise activating the installation in response to the confirmation that the update or configuration is correct.

If the update or configuration is transmitted to the controller 300 in one or more steps, the verification as described above may be performed for each of the steps.

The method may further comprise, after transmitting the logging data to the second external device, verifying the update via a confirmation from the second external device 330 via the second communication channel.

With reference to FIG. 65A-65E there may further be provided an implantable controller 300. The controller 300 is connected to a sensor 351 wherein the sensor 351 is at least one microphone sensor 351 configured to record acoustic signals. For instance, the controller 300 may be configured to register a sound related to at least one of a bodily function of the patient and a function of the implantable medical device 10. The controller 300 comprises a computing unit 306 configured to derive at least one of a pulse of the patient from the registered sound related to a bodily function, such as information related to the patient swallowing, from the registered sound related to a bodily function. In the alternative, the controller 300 could be configured to derive information related to a functional status of the implantable medical device 10 from the registered sound, such as RPM of the motor. To this end the computing unit 306 may be configured to perform signal processing on the registered sound (e.g. on a digital or analog signal representing the registered sound) so as to derive any of the above mentioned information related to a bodily function of the patient or a function of the implantable medical device 10. The signal processing may comprise filtering the registered sound signals of the microphone sensor 351.

The implantable controller is placed in an implantable housing for sealing against fluid, and the microphone sensor 351 is placed inside of the housing. Accordingly, the controller and the microphone sensor 351 do not come into contact with bodily fluids when implanted which ensures proper operation of the controller and the microphone sensor 351.

In some implementations, the computing unit 306 is configured to derive information related to the functional status of an active unit 302 of the implantable medical device 10, from the registered sound related to a function of the implantable medical device 10. Accordingly, the computing unit 306 may be configured to derive information related to the functional status of at least one of: a motor, a pump and a transmission of the active unit 302 of the implantable medical device 10, from the registered sound related to a function of the implantable medical device 10.

The controller may comprise a transceiver 303,308 configured to transmit a parameter derived from the sound registered by the at least one microphone sensor 351 using the transceiver 303,308. For example, the transceiver 303, 308 is a transceiver configured to transmit the parameter conductively (303) to an external device 320 or wirelessly (308) to an external device 320.

A method of authenticating the implantable medical device 10, the external device 320 or a communication signal or data stream between the external device 320 and the implantable medical device 10 is also described with reference to FIGS. 65A-65E. The method comprises the steps of registering a sound related to at least one of a bodily function and a function of the implantable medical device 10, using the at least one microphone sensor 351, connected to the controller 300. The method could in a first authentication embodiment comprise transmitting a signal derived from the registered sound, using the transceiver 303,308, receiving the signal in the external device 320, using the receiver 323,328 and comparing, in the external device 320, a parameter derived from the received signal with a reference parameter, using the computing unit 306. The method could in a second authentication embodiment comprise receiving a signal in the controller 300, from the external device 320, using the transceiver 323,328 and deriving a reference parameter from the received signal, using the computing unit 306 of the controller 300, and comparing, in the controller 300, a parameter derived from the received signal with the derived reference parameter, using the computing unit 306 of the controller 300. The methods further comprise the steps of the implantable controller 300 authenticating the external device 320, or the external device 320 authenticating the implantable controller 300, on the basis of the comparison. The registered sound could for example be related to the patient eating.

Embodiments relating to an implantable medical device 10 having a controller 300 having a processor 306 with a sleep mode and an active mode will now be described with reference to FIG. 65D. The implant, the internal communication unit and the external device(s) may have the features described above with reference to FIGS. 65A-65E.

In an embodiment in which the controller 300 comprises a processor 306 having a sleep mode and an active mode, the controller 300 comprises or is connected to a sensor 150 and a processing unit 306 having a sleep mode and an active mode. The sensor 150 is configured to periodically measure a physical parameter of the patient, and the controller 300 is further configured to, in response to a sensor measurement preceding a predetermined value, setting the processing unit 306 in an active mode. That is, the controller 300 may "wake up" or be set in an active mode in response to a measurement from, for example, the body. A physical parameter of the patient could for example be a local or systemic temperature, saturation/oxygenation, blood pressure or a parameter related to an ischemia marker such as lactate.

By sleeping mode it is meant a mode with less battery consumption and/or processing power used in the processing unit 306, and by "active mode" it may be meant that the processing unit 306 is not restricted in its processing.

The sensor 150 may, for example, be a pressure sensor. The pressure sensor may be adapted to measure a pressure in an organ of a patient, a hydraulic adjustment chamber of the implant or a pressure exerted in the body of the patient. The sensor 150 may be an analog sensor or a digital sensor, i.e. a sensor 150 implemented in part in software. In some examples, the sensor is adapted to measure one or more of a battery or energy storage status of the implantable medical device 10 and a temperature of the implantable medical device 10. In this way, the sensor 150 may periodically sense a pressure of the implantable medical device 10 or of the patient, and set the processing unit 306 in an active mode if the measured pressure is above a predetermined value. Thus, less power, i.e. less of for example a battery or energy storage comprised in the implant, may be used, thereby prolonging the lifetime of the implantable medical device 10 or increasing the time between charging occasions of the implantable medical device 10.

In some examples, the processor 306, when in set in the active mode, may cause a sensation generator 381 connected to the implant, comprised in the implantable medical device 10 or comprised in an external device 320, 330, to generate a sensation detectable by a sense of the patient. For example, the processor may cause the sensation generator to generate a sensation in response to a measure battery status, for example that the battery is above or below a predetermined level, that a measured pressure is above or below a predetermined level, or that another measured parameter has an abnormal value, i.e. less than or exceeding a predetermined interval or level. The sensation generator has been described in further detail earlier in this description.

The processing unit 306 may be configured to perform a corrective action in response to a measurement being below or above a predetermined level. Such a corrective action may, for example, be increasing or decreasing a pressure, increasing or decreasing electrical stimulation, increasing or decreasing power.

The controller 300 may comprise a signal transmitter 320 connected to the processing unit, and wherein the processing unit is configured to transmit data relating to the measurement via the transceiver 308 of the controller 300 or an additional internal signal transmitter 392. The transmitted data may be received by an external device 320.

The external device may have an external communication unit 390. The external device 320 may comprise a signal provider 380 for providing a wake signal to the controller 300. In some examples, the signal provider comprises a coil or magnet 371 for providing a magnetic wake signal.

The controller 300 may implement a corresponding method for controlling an implantable medical device 10 when implanted in a patient. The method comprises measuring, with a sensor of the controller 300 connected to or comprised in the controller 300, a physiological parameter of the patient or a parameter of the implantable medical device 10, and, in response to a sensor measurement having an abnormal value, setting, by the controller 300, a processor 306 of the controller 300 from a sleep mode to an active mode. The measuring may be carried out periodically. By "abnormal value" it may be meant a measured value exceeding or being less than a predetermined value, or a measured value being outside a predetermined interval. The method may further comprise generating, with a sensation generator 381 as described above, a sensation detectable by the patient. In some examples, the generating comprises requesting, by the processor, the sensation generator 381 to generate the sensation.

The method may further comprise to perform a medical intervention in response to a sensor measurement having an abnormal value, preferably after the processing unit has been set in the active mode.

According to one embodiment described with reference to FIG. 65A-65C, the communication unit 300 or internal controller 300 or control unit 300 comprises a wireless transceiver 308 for communicating wirelessly with an external device, a security module 389, and a central unit, also referred to herein as a computing unit 306, which is to be considered as equivalent. The central unit 306 is configured to be in communication with the wireless transceiver 308, the security module 389 and the implantable medical device or active unit 302. The wireless transceiver 308 is configured to receive communication from the external device 320 including at least one instruction to the implantable energized medical device 10 and transmit the received communication to the central unit or computing unit 306. The central unit or computing unit 306 is configured to send secure communication to the security module 389, derived from the received communication from the external device 320, and the security module 389 is configured to decrypt at least a portion of the secure communication and verify the authenticity of the secure communication. The security module is further configured to transmit a response communication to the central unit or computing unit 306 and the central unit or computing unit is configured to communicate the at least one instruction to the active unit 302. In the embodiment shown in FIG. 65A-65C, the at least one instruction is based on the response communication, or a combination of the response communication and the received communication from the external device 320.

In the embodiment shown in FIG. 65A-65C, the security module 389 comprises a set of rules for accepting communication from the central unit or computing unit 306. In the embodiment shown in FIG. 65A-65C, the wireless transceiver 308 is configured to be able to be placed in an off-mode, in which no wireless communication can be transmitted or received by the wireless transceiver 308. The set of rules comprises a rule stipulating that communication from the central unit or computing unit 306 to the security module 389 or to the active unit 302 is only accepted when the wireless transceiver 308 is placed in the off-mode.

In the embodiment shown in FIG. 656A-65C, the set of rules comprises a rule stipulating that communication from the central unit or computing unit 306 is only accepted when the wireless transceiver 308 has been placed in the off-mode for a specific time period.

In the embodiment shown in FIG. 65A-65C, the central unit or computing unit 306 is configured to verify a digital signature of the received communication from the external device 320. The digital signature could be a hash-based digital signature which could be based on a biometric signature from the patient or a medical professional. The set of rules further comprises a rule stipulating that communication from the central unit 306 is only accepted when the digital signature of the received communication has been verified by the central unit 306. The verification could for example comprise the step of comparing the digital signature or a portion of the digital signature with a previously verified digital signature stored in the central unit 306. The central unit 306 may be configured to verify the size of the received communication from the external device and the set of rules could comprise a rule stipulating that communication from the central unit 306 is only accepted when the size of the received communication has been verified by the central unit 306. The central unit could thus have a rule stipulating that communication above or below a specified size range is to be rejected.

In the embodiment shown in FIG. 65A-65C, the wireless transceiver is configured to receive a message from the external device 320 being encrypted with at least a first and second layer of encryption. The central unit 306 the decrypts the first layer of decryption and transmit at least a portion of the message comprising the second layer of encryption to the security model 389. The security module 389 then decrypts the second layer of encryption and transmits a response communication to the central unit 306 based on the portion of the message decrypted by the security module 389.

In the embodiment shown in FIG. 65A-65C, the central unit 306 is configured to decrypt a portion of the message comprising a digital signature, such that the digital signature can be verified by the central unit 306, also the central unit 306 is configured to decrypt a portion of the message comprising message size information, such that the message size can be verified by the central unit 306.

In the embodiment shown in FIG. 65A-65C, the central unit 306 is configured to decrypt a first and second portion of the message, and the first portion comprises a checksum for verifying the authenticity of the second portion.

In the embodiment shown in FIG. 65A-65C, the response communication transmitted from the security module 389 comprises a checksum, and the central unit 306 is configured to verify the authenticity of at least a portion of the message decrypted by the central unit 306 using the received checksum, i.e. by adding portions of the message decrypted by the central unit 306 and comparing the sum to the checksum.

In the embodiment shown in FIG. 65A-65C, the set of rules further comprise a rule related to the rate of data transfer between the central unit 306 and the security module 389. The rule could stipulate that the communication should be rejected or aborted if the rate of data transfer exceeds a set maximum rate of data transfer, which may make it harder for unauthorized persons to inject malicious code or instructions to the medical implant.

In the embodiment shown in FIG. 65A-65C, the security module 389 is configured to decrypt a portion of the message comprising the digital signature being encrypted with the second layer of encryption, such that the digital signature can be verified by the security module 389. The security module 389 then transmits a response communication to the central unit 306 based on the outcome of the verification, which can be used by the central unit 306 for further decryption of the message or for determining if instructions in the message should be communicated to the active unit 302.

In the embodiment shown in FIG. 65A-65C, the central unit 306 is only capable of decrypting a portion of the received communication from the external device 320 when the wireless transceiver 308 is placed in the off-mode. In the alternative, or as an additional layer of security, the central unit 306 may be limited such that the central unit 306 is only capable of communicating instructions to the active unit 302 of the implantable energized medical device 10 when the wireless transceiver 308 is placed in the off-mode. This ensures that no attacks can take place while the central unit 306 is communicating with the active unit 302.

In the embodiment shown in FIG. 65A-65C, the implantable controller 300 is configured to receive, using the wireless transceiver 308, a message from the external device 320 comprising a first un-encrypted portion and a second encrypted portion. The implantable controller 300 (e.g. the central unit 306 or the security module 389) then decrypts the encrypted portion, and uses the decrypted portion to verify the authenticity of the un-encrypted portion. As such, computing power and thereby energy can be saved by not encrypting the entire communication, but rather only the portion required to authenticate the rest of the message (such as a checksum and/or a digital signature)

In the embodiment shown in FIG. 65A-65C, the central unit 306 is configured to transmit an encrypted portion to the security module 389 and receive a response communication from the security module 389 based on information contained in the encrypted portion being decrypted by the security module. The central unit 306 is then configured to use the response communication to verify the authenticity of the un-encrypted portion. The un-encrypted portion could comprise at least a portion of the at least one instruction to the implantable medical device 306.

In the embodiment shown in FIG. 65A-65C, the implantable controller 300 is configured to receive, using the wireless transceiver 308, a message from the external device 320 comprising information related to at least one of: a physiological parameter of the patient and a physical parameter of the implantable energized medical device 10, and use the received information to verify the authenticity of the message. The physiological parameter of the patient could be a parameter such as a parameter based on one or more of: a temperature, a heart rate and a saturation value.

The physical parameter of the implantable energized medical device 10 could comprise at least one of a current setting or value of the implantable energized medical device 10, a prior instruction sent to the implantable energized medical device 10 or an ID of the implantable energized medical device 10.

The portion of the message comprising the information related to the physiological parameter of the patient and/or physical or functional parameter of the implantable energized medical device 10 could be encrypted, and the central unit 306 may be configured to transmit the encrypted portion to the security module 389 and receive a response communication from the security module 389 based on the information having been decrypted by the security module 389.

In the embodiment shown in FIG. 65A-65C, the security module 389 is a hardware security module comprising at least one hardware-based key. The security module 389 may have features that provide tamper evidence such as visible signs of tampering or logging and alerting. It may also be so that the security module 389 is "tamper resistant", which makes the security module 389 inoperable in the event that tampering is detected. For example, the response to tampering could include deleting keys is tampering is detected. The security module 389 could comprise one or more secure cryptoprocessor chip. The hardware-based key(s) in the security module 389 could have a corresponding hardware-based key placeable in the external device 320. The corresponding external hardware-based key could be placed on a key-card connectable to the external device 320.

In alternative embodiments, the security module 389 is a software security module comprising at least one software-based key, or a combination of a hardware and software-based security module and key. The software-based key may correspond to a software-based key in the external device 320. The software-based key may correspond to a software-based key on a key-card connectable to the external device 320.

In the embodiment shown in FIG. 65A-65C, the external device 320 is a handheld external device, however, in alternative embodiments, the external device may be a remote external device or a cloud based external device In the embodiment shown in FIG. 65A-65C, the at least one instruction to the implantable energized medical device 10 comprises an instruction for changing an operational state of the implantable energized medical device 10.

In the embodiment shown in FIG. 65A-65C, the wireless transceiver 308 is configured to communicate wirelessly with the external 320 device using electromagnetic waves at a frequency below 100 kHz, or more specifically below 40 kHz. The wireless transceiver 308 is thus configured to communicate with the external device 320 using "Very Low Frequency" communication (VLF). VLF signals have the ability to penetrate a titanium housing of the implantable energized medical device 10, such that the electronics of the implantable energized medical device 10 can be completely encapsulated in a titanium housing.

The wireless transceiver 308 is configured to communicate wirelessly with the external device 320 using a first communication protocol and the central unit 306 is configured to communicate with the security module 389 using a second, different, communication protocol. This adds an additional layer of security as security structures could be built into the electronics and/or software in the central unit 306 enabling the transfer from a first to a second communication protocol. The wireless transceiver 308 may be configured to communicate wirelessly with the external device using a standard network protocol, which could be one of an RFID type protocol, a WLAN type protocol, a Bluetooth (BT) type protocol, a BLE type protocol, an NFC type protocol, a 3G/4G/5G type protocol, and a GSM type protocol. In the alternative, or as a combination, the wireless transceiver 308 could be configured to communicate wirelessly with the external device 320 using a proprietary network protocol. The wireless transceiver 308 could comprises a Ultra-Wide Band (UWB) transceiver and the wireless communication between the implantable controller 300 and the external device 320 could thus be based on UWB. The use of UWB technology enables positioning of the remote control 320'' which can be used by the implantable energized medical device 10 as a way to establish that the external device 320 is at a position which the implantable energized medical device 10 and/or the patient can acknowledge as being correct, e.g. in the direct proximity to the implantable energized medical device 10 and/or the patient, such as within reach of the patient and/or within 1 or 2 meters of the implantable energized medical device 10. In the alternative, a combination of UWB and BT could be used, in which case the UWB communication can be used to authenticate the BT communication, as it is easier to transfer large data sets using BT.

According to one embodiment described with reference to FIG. 65A-65C, the communication unit 300 or controller of the implantable energized medical device 10 comprises a receiving unit 305 or energy receiver 305 comprising a coil 192 (specifically shown in FIG. 65B') configured for receiving transcutaneously transferred energy. The receiving unit further comprises a measurement unit 194 configured to measure a parameter related to the energy received by the coil 192 and a variable impedance 193 electrically connected to the coil 192. The receiving unit 305 further comprises a switch 195*a* placed between the variable impedance 193 and the coil 192 for switching off the electrical connection between the variable impedance 193 and the coil 192. The communication unit 300 or controller 300 is configured to control the variable impedance 193 for varying the impedance and thereby tune the coil 192 based on the measured parameter. The communication unit 300 or controller 300 is further configured to control the switch 195*a* for switching off the electrical connection between the variable impedance 193 and the coil 192 in response to the measured parameter exceeding a threshold value. The controller 300 may further be configured to vary the variable impedance in response to the measured parameter exceeding a threshold value. As such, the coil can be tuned or turned off to reduce the amount of received energy if the amount of received energy becomes excessive. The measurement unit 194 is configured to measure a parameter related to the energy received by the coil 192 over a time period and/or measure a parameter related to a change in energy received by the coil 192 by for example measure the derivative of the received energy over time. The variable impedance 193 is in the embodiment shown in FIG. 65B' placed in series with the coil 192. In alternative embodiments it is however conceivable that the variable impedance is placed parallel to the coil 192.

The first switch 195*a* is placed at a first end portion 192*a* of the coil 192, and the implantable energized medical device 10 further comprises a second switch 195*b* placed at a second end portion of the coil 192, such that the coil 192 can be completely disconnected from other portions of the implantable energized medical device 10. The receiving unit 305 is configured to receive transcutaneously transferred energy in pulses according to a pulse pattern. The measurement unit 194 is in the embodiment shown in FIG. 65B' configured to measure a parameter related to the pulse pattern. The controller 300 is configured to control the variable impedance in response to the pulse pattern deviating from a predefined pulse pattern. The controller 300 is configured to control the switch 195*a* for switching off the electrical connection between the variable impedance 193 and the coil 192 in response to the pulse pattern deviating from a predefined pulse pattern. The measurement unit is configured to measure a temperature in the implantable energized medical device 10 or in the body of the patient, and the controller 300 is configured to control the first and second switch 195*a*, 195*b* in response to the measured temperature.

The variable impedance 193 may comprise a resistor and a capacitor and/or a resistor and an inductor and/or an inductor and a capacitor. The variable impedance 193 may comprise a digitally tuned capacitor or a digital potentiometer. The variable impedance 193 may comprise a variable inductor. The first and second switch comprises a semiconductor, such as a MOSFET. The variation of the impedance is configured to lower the active power that is received by the receiving unit. As can be seen in FIG. 65B', the variable impedance 193, the first and second switch 195*a*, 195*b* and the measurement unit 194 are connected to the communication unit/controller 300 and the receiving unit 305 is connected to an energy storage unit 40 such that the energy storage unit 40 can store energy received by the receiving unit 305.

A system comprising an implantable medical device 10 having a controller 300 having a sleep mode and an active mode will now be described with reference to FIG. 65D. In one embodiment, the controller 300 comprises a sensor 150 adapted to detect a magnetic field and a processing unit 306 having a sleep mode and an active mode, now described with reference to FIGS. 65A-65C. The external control unit 320 comprises a signal provider 380 adapted to provide a magnetic field detectable by the internal sensor 150. The controller 300 is further configured to, in response to a detected magnetic field exceeding a predetermined value, setting the processing unit 306 in an active mode. In this way, the external device 320 may cause a sleeping controller 300 or processor 306 to "wake up".

The sensor 150 may, for example, be a hall effect sensor, a fluxgate sensor, an ultra-sensitive magnetic field sensor, a magneto-resistive sensor, an AMR or GMR sensor, or the sensor may comprise a third coil having an iron core.

The magnetic field provider 380 may have an off state, wherein it does not provide any magnetic field, and an on state, wherein it provides a magnetic field. For example, the magnetic field provider 380 may comprise a magnet 371, a coil 371, a coil having a core 371, or a permanent magnet 371. In some embodiments, the magnetic field provider 380 may comprise a shielding means for preventing a magnet 371 or permanent magnet 371 from providing a magnetic field in the off state. In order to provide a substantially even magnetic field, the magnetic field provider may comprise a first and a second coil arranged perpendicular to each other.

After the processing unit 306 has been set in an active mode, i.e. when the processing unit 306 has been woken, the implant may determine a frequency for further communication between the controller 300 and the external device 320. The controller 300 may thus comprise a frequency detector 39I for detecting a frequency for communication between the controller 300 and the second communication unit 390. The frequency detector 39I is, for example, an antenna. The external device 320 may comprise a frequency indicator 372, for transmitting a signal indicative of a frequency. The frequency indicator 372, may, for example, be a magnetic field provider capable of transmitting a magnetic field with a specific frequency. In some examples the frequency indicator is comprised in or the same as the magnetic field provider 371. In this way, the frequency signal is detected using means separate from the sensor, and can, for example, be detected using a pin on a chip.

Alternatively, the controller 300 and the external device 320 may communicate using a predetermined frequency or a frequency detected by means defined by a predetermined method according to a predetermined protocol to be used for the communication between the controller 300 and the external device 320.

In some embodiments, the sensor 150 may be used for the communication. The communication may in these embodiments be performed with such that a frequency of the magnetic field generated by the coil is 9-315 kHz, or the magnetic field generated by the coil is less than or equal to 125 kHz, preferably less than 58 kHz. The frequency may be less than 50 Hz, preferably less than 20 Hz, more preferably less than 10 Hz, in order to be transmittable through a titanium box.

In some embodiments, the controller 300 comprises a receiver unit 392, and the internal control unit and the external control unit are configured to transmit and/or receive data via the receiver unit 392 via magnetic induction. The receiver unit 392 may comprise a high-sensitivity magnetic field detector, or the receiver unit may comprise a fourth coil for receiving the magnetic induction.

The system may implement a method for controlling a medical implant implanted in a patient. The method comprises monitoring for signals by a sensor 150 comprised in the controller 300 communicatively coupled to the active unit 302, providing, from a signal provider 380 comprised in an external device 320, a wake signal, the external device 320 being adapted to be arranged outside of the patient's body, and setting, by the controller 300 and in response to a detected wake signal WS, a mode of a processing unit 306 comprised in the internal control unit from a sleep mode to an active mode.

The method may also comprise detecting, using a frequency detector 39I, a frequency for data communication between the controller 300 and a second communication unit 39O being associated with the external device 320. The frequency detector 39I is communicatively coupled to the controller 300 or the external device 320. The detection may be performed using a detection sequence for detecting the frequency. This detection sequence may, for example, be a detection sequence defined in the protocol to be used for communication between the controller 300 and the second communication unit 390. Potential protocols that may be used for communication between the controller 300 and the external device 320 has been described earlier in this description. Thus, the method may comprise determining, using the frequency detector 39I, the frequency for data communication, and initiating data communication between the controller 300 and the second communication unit 390. The data communication can, for example, comprise one or more control instructions for controlling the implantable medical device 10 transmitted from the external device 320, or, for example, comprise data related to the operation of the implantable medical device 10 and be transmitted from the controller 300.

In some examples, the implantable medical device may comprise or be connected to a power supply for powering the implantable medical device 10. This will now be described with reference to FIG. 65E. The medical device, the internal control unit, and the external device(s) may comprise all elements described above with reference to FIGS. 65A-65C and FIG. 65D. The power supply may comprise an implantable energy storage unit 40 for providing energy to the medical device, an energy provider 397 connected to the implantable energy storage unit 40 and connected to an energy consuming part of the implantable medical device 10, the energy provider 397 being configured to store energy to provide a burst of energy to the energy consuming part, wherein the energy provider 397 is configured to be charged by the implantable energy storage unit 40 and to provide the energy consuming part with electrical power during startup of the energy consuming part. The energy may for example be consumed when delivering the electrical stimulation signal, via the electrode arrangement, to the muscle tissue against which the implanted apparatus (such as the above-described movement restriction apparatuses) rests, or for adjusting the size and/or shape of an implantable component.

Alternatively, the implantable medical device 10 may comprise a first implantable energy storage unit 40 for providing energy to an energy consuming part of the implantable medical device 10, a second implantable energy storage unit 397 connected to the implantable energy storage unit 40 and connected to the energy consuming part, wherein the second implantable energy storage unit 397 is configured to be charged by the implantable energy storage unit 40 and to provide the energy consuming part with electrical power during startup of the energy consuming part. The second implantable energy storage unit 397 has a higher energy density than the first implantable energy storage unit 40. By having a "higher energy density" it may be meant that the second implantable energy storage unit 397 has a higher maximum energy output per time unit than the first implantable energy storage unit 40. The second energy storage 397 may be an energy provider as discussed below.

The energy consuming part may be any part of the implantable medical device 10, such as a processing or computing unit, a communication unit, a device for providing electrical stimulation to a tissue portion of the body of the patient, a CPU for encrypting information, a transmitting and/or receiving unit for communication with an external device (not shown as part of the energy consuming part in the drawings, that is, the communication unit may be connected to the energy storage unit 40 and to the energy provider 397), a measurement unit or a sensor, a data collection unit, a solenoid, a piezo-electrical element, a memory metal unit, a vibrator, a part configured to operate a valve comprised in the medical device, or a feedback unit.

In this way, an energy consuming part requiring a quick start or an energy consuming part which requires a high level or burst of energy for a start may be provided with sufficient energy. This may be beneficial as instead of having an idle component using energy, the component may be completely turned off and quickly turned on when needed. Further, this may allow the use of energy consuming parts needing a burst of energy for a startup while having a lower energy consumption when already in use. In this way, a battery or an energy storage unit having a slower discharging (or where a slower discharging is beneficial for the lifetime or health of the battery) may be used for the implant, as the extra energy needed for the startup is provided by the energy provider.

Energy losses may occur in a battery or energy storage unit of an implant if the battery or energy storage unit is discharged too fast. These energy losses may for example be in the form of heat, which may damage the battery or energy storage unit. By the apparatus described in these examples, energy may be provided from the battery or energy storage unit in a way that does not damage the battery or energy storage unit, which may improve the lifetime of the battery or energy storage unit and thereby the lifetime of the medical device.

In some examples, the discharging from the implantable energy storage unit 40 during startup of the energy consuming part is slower than the energy needed for startup of the energy consuming part, i.e. the implantable energy storage unit 40 is configured to have a slower discharging than the energy needed for startup of the energy consuming part. That is, there is a difference between the energy needed by the energy consuming part and the energy the implantable energy storage unit 40 is capable of providing without damaging the implantable energy storage unit 40. In other words, a maximum energy consumption of the energy consuming part may be higher than the maximum energy capable of being delivered by the implantable energy storage unit 40 without causing damage to the implantable energy storage unit, and the energy provider 397 may be adapted to deliver an energy burst corresponding to difference between the required energy consumption and the maximum energy capable of being delivered by the implantable energy storage unit 40. The implantable energy storage unit 40 may be configured to store a substantially larger amount of energy than the energy burst provider 397, but may be slower to charge.

The implantable energy storage unit 40 may be any type of energy storage unit suitable for an implant, such as a re-chargeable battery or a solid-state battery, such as a thionyl-chlorid battery. The implantable energy storage unit 40 may be connected to the energy consuming part and configured to power the energy consuming part after it has been started using the energy provider 397.

The energy provider 397 may be any type of part configured to provide a burst of energy for the energy consuming part. In some examples, the energy provider 397 is a capacitor, such as a start capacitor, a run capacitor, a dual run capacitor or a supercapacitor. The energy provider 397 may be connected to the implantable energy storage unit 40 and be adapted to be charged using the implantable energy storage unit 40. In some examples, the energy provider may be a second energy provider 397 configured to be charged by the implantable energy storage unit 40 and to provide the energy consuming part with electrical energy. The implantable medical device 10 may further comprising a temperature sensor for sensing a temperature of the capacitor and the temperature sensor may be integrated or connected to the controller 300 such that the sensed temperature can be used as input for controlling the implantable medical device 10 or as feedback to be sent to an external device 320.

A corresponding method for powering a medical device may also be contemplated. The method comprises the steps of initiating an energy consuming part 302 of the implant, the energy consuming part being connected to an implantable energy storage unit 40, providing an initial burst of energy to the energy consuming part using an energy provider 397 connected to the implantable energy storage unit 40) and to the energy consuming part 302, the energy provider 397 being adapted to provide a burst of energy to the energy consuming part, and subsequently powering the energy consuming part 302 using the implantable energy storage unit 40.

In some examples, a maximum energy consumption of the energy consuming part is higher than the maximum energy capable of being delivered by the implantable energy storage unit 40 without causing damage to the implantable energy storage unit 40, and the energy provider 397 is adapted to deliver an energy burst corresponding to difference between the required energy consumption and the maximum energy capable of being delivered by the implantable energy storage unit 40.

The method may further comprise the step of charging the energy provider 397 using the implantable energy storage unit 40.

Initiating an energy consuming part 302 may comprise transitioning a control unit of the medical device from a sleep mode to an operational or active mode.

The implantable energy storage unit 40 may be adapted to be wirelessly charged and the implantable energy storage unit may be connected to an internal charger 395 for receiving wireless energy from an external device 320 via an external charger 396, and the method may comprise wirelessly charging the implantable energy storage unit 40. In some examples, the method comprises controlling a receipt of electrical power from an external energy storage unit at the internal charger 395. The internal energy storage unit 40 may be charged via the receipt of a transmission of electrical power from an external energy storage unit 396 by the internal charger 395.

The embodiments described herein may advantageously be combined. For example, all the embodiments relating to the communication and controlling of the medical device may be combined with the embodiments relating to the programming of the implant, the methods and systems for improving energy consumption or the power supply. The embodiments relating to the programming of the medical device may be combined with any of the embodiments relating to improving the energy consumption or the power supply. The embodiments relating to the power supply maybe combined with the methods and systems for improving the energy consumption.

A computer program product of, or adapted to be run on, an internal computing unit or an external device is also provided, which comprises a computer-readable storage medium with instructions adapted to make the internal computing unit and/or the external device perform the actions as described in any embodiment or example above.

Figure 66A:
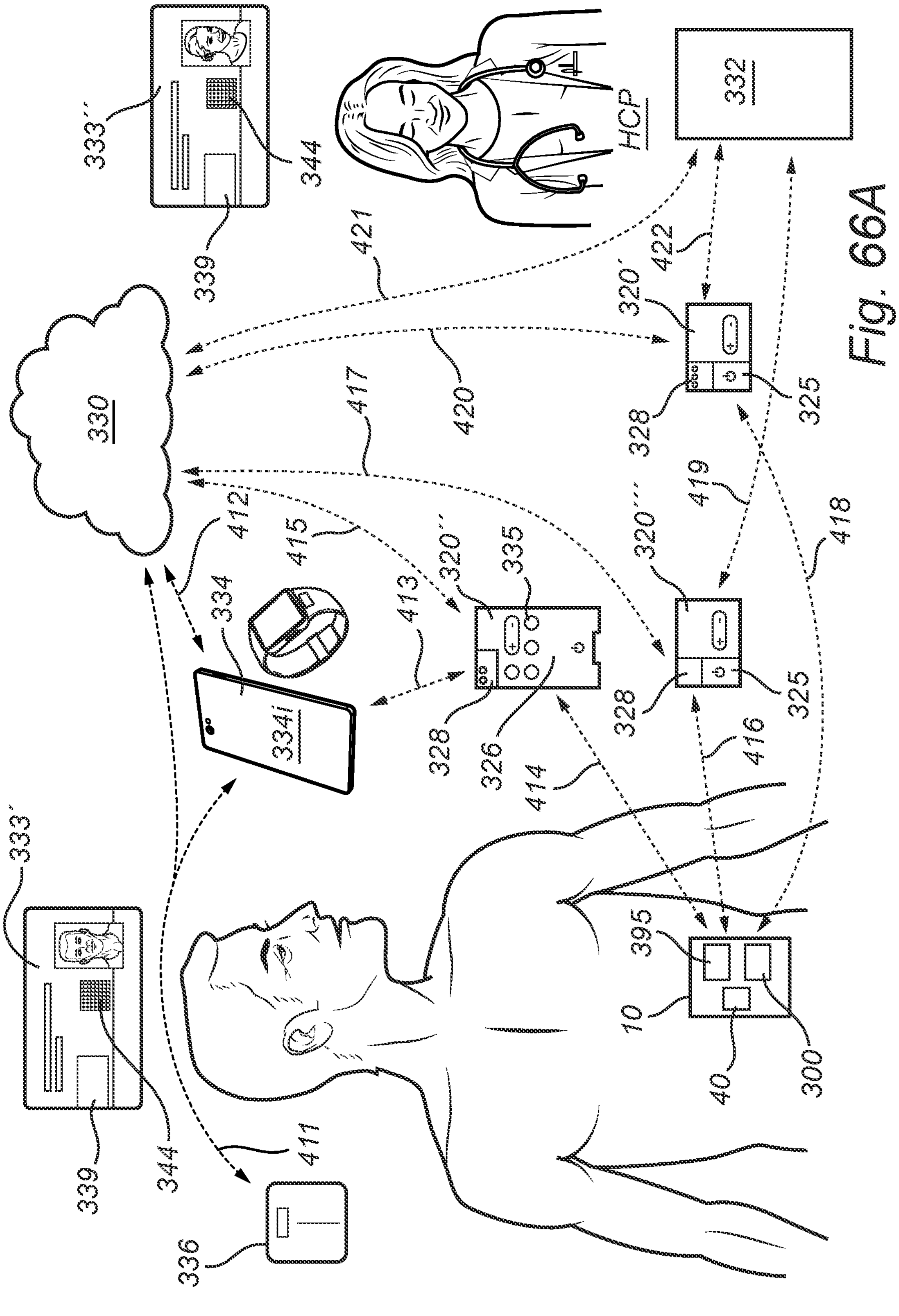

FIG. 66A shows one embodiment of a system for charging, programming and communicating with the controller 300 of the implanted medical device 100. FIG. 66A further describes the communication and interaction between different external devices which may be devices held and operated by the patient, by the health care provider (HCP) or by the Dedicated Data Infrastructure (DDI), which is an infrastructure supplier for example by the manufacturer of the implanted medical device 100 or the external devices 320', 320'', 320'''. The system of the embodiment of FIG. 66A comprises three external devices 320', 320'', 320''' capable of communicating with the controller 300.

The basic idea is to ensure the security of the communication with, and the operation of, the medical device 100 by having three external devices 320', 320'', 320''' with different levels of authority. The lowest level of authority is given to the patient operated remote control 320''. The remote control, also referred to as external device 320'' is authorized to operate functions of the implanted medical device 100 via the implanted controller 300, on the basis of patient input. The remote control 320'' is further authorized to fetch some necessary data from the controller 300. The remote control 320'' is only capable of operating the controller 300 by communicating with the software currently running on the controller 300, with the currently settings of the software. The next level of authority is given to the Patient External Interrogation Device (P-EID) 320''', which is a charging and communication unit which is held by the patient but may be partially remotely operated by the Health Care Provider (HCP) (Usually a medical doctor with the clinic providing the treatment with help of the implanted medical device 100).

The P-EID 320''' is authorized to make setting changes to the software running on the controller 300 of the implanted medical device 10 when remotely operated by the HCP.

The highest level of authority is given to the HCP-FID 320'. The HCP-EID 320' is a charging and communication unit which is held by the HCP physically at the clinic of the HCP. The HCP-EID 320' is authorized to freely alter or replace the software running on the controller 300, when the patient is physically in the clinic of the HCP.

Starting from the lowest level of authority, the remote control 320'' comprises a wireless transceiver 328 for communicating with the implanted medical device 10. The remote control 320'' is capable of controlling the operation of the implanted medical device 10 via the controller 300, by controlling pre-set functions of the implantable medical device 10, e.g. for operating an active portion of the implanted medical device 10 for performing the intended function of the implanted medical device 10. In the embodiment shown in FIG. 66A, the wireless transceiver 328 comprises a Bluetooth (BT) transceiver, and the remote control 320'' is configured to communicate with implanted medical device 10 using BT. In an alternative configuration, the remote control 320'' communicates with the implanted medical device 10 using a combination of Ultra-Wide Band (UWB) wireless communication and BT. The use of UWB technology enables positioning of the remote control 320'' which can be used by the implanted medical device 10 as a way to establish that the remote control 320'' is at a position which the implanted medical device 10 and/or the patient can acknowledge as being correct, e.g. in the direct proximity to the medical device 10 and/or the patient, such as within reach of the patient and/or within 1 or 2 meters of the implanted medical device 10.

UWB communication is performed by the generation of radio energy at specific time intervals and occupying a large bandwidth, thus enabling pulse-position or time modulation. The information can also be modulated on UWB signals (pulses) by encoding the polarity of the pulse, its amplitude and/or by using orthogonal pulses. A UWB radio system can be used to determine the "time of flight" of the transmission at various frequencies. This helps overcome multipath propagation, since some of the frequencies have a line-of-sight trajectory, while other indirect paths have longer delay. With a cooperative symmetric two-way metering technique, distances can be measured to high resolution and accuracy. UWB is useful for real-time location systems, and its precision capabilities and low power make it well-suited for radio-frequency-sensitive environments.

In embodiments in which a combination of BT and UWB technology is used, the UWB technology may be used for location-based authentication of the remote control 320", whereas the communication and/or data transfer could take place using BT. The UWB signal could in some embodiments also be used as a wake-up signal for the controller 300, or for the BT transceiver, such that the BT transceiver in the implanted medical device 10 can be turned off when not in use, which eliminates the risk that the BT is intercepted, or that the controller 300 of the implanted medical device 10 is hacked by means of BT communication. In embodiments in which a BT/UWB combination is used, the UWB connection may be used also for the transmission of data. In the alternative, the UWB connection could be used for the transmission of some portions of the data, such as sensitive portions of the data, or for the transmission of keys for the unlocking of encrypted communication sent over BT.

The remote control 320" comprises computing unit 326 which runs a software application for communicating with the implanted medical device 10. The computing unit 326 can receive input directly from control buttons 335 arranged on the remote control 320" or may receive input from a control interface **334*i* displayed on a display device 334 operated by the patient. In the embodiments in which the remote control 320" receives input from a control interface 334*i* displayed on a display device 334 operated by the patient, the remote control 320" transmits the control interface 334*i* in the form of a web-view, i.e. a remote interface that run in a sandbox environment on the patient's display device 334. A sandbox environment means that it runs on the display device 334 but can only use a tightly controlled set of resources, such as storage and memory space as well as network access, the ability to inspect the host system and read or write from other input devices connected to the display device 334. The computing unit 326 is further configured to the control interface before transmission to the display device 334, and the control commands before transmission to the implanted medical device 10. The computing unit 326 is further configured to transform the received user input into control commands for wireless transmission to the implantable medical device 10**.

The patient's display device 334 could for example be a mobile phone, a tablet or a smart watch. In the embodiment shown in FIG. 66A, the patient's display device 334 communicates with the remote control 320" by means of BT. The control interface **334*i* in the form of a web-view is transmitted from the remote control 320" to the patient's display device 334 over BT. Control commands in the form of inputs from the patient to the control interface 334*i* is transmitted from the patient's display device 334 to the remote control 320", providing input to the remote control 320" equivalent to the input that may be provided using the control buttons 335. The control commands created in the patient's display device 334 is encrypted in the patient's display device 334 and transmitted to the remote control 320'** using BT.

The patient's display device 334 may (in the case of the display device 334 being a mobile phone or tablet) comprise auxiliary radio transmitters for providing auxiliary radio connection, such as Wi-Fi or mobile connectivity (e.g. according to the 3G, 4G or 5G standards). The auxiliary radio connection(s) may have to be disconnected to enable communication with the remote control 320". Disconnecting the auxiliary radio connections reduces the risk that the integrity of the control interface **334*i* displayed on the patient's display device 334 is compromised, or that the control interface 334*i* displayed on the patient's display device 334** is remote controlled by an unauthorized device.

In alternative embodiments, control commands are generated and encrypted by the patient's display device and transmitted to the DDI 330. The DDI 330 could either alter the created control commands to commands readable by the remote control 320" before further encrypting the control commands for transmission to the remote control 320" or could simply add an extra layer of encryption before transmitting the control commands to the remote control 320", or could simply act as a router for relaying the control commands from the patients' display device 334 to the remote control 320". It is also conceivable that the DDI 330 adds a layer of end-to-end encryption directed at the implanted medical device 10, such that only the implanted medical device 10 can decrypt the control commands to perform the command intended by the patient.

The patient's display device 334 could have a first and second application related to the implanted medical device 10. The first application is the control application displaying the control interface **334*i* for control of the implanted medical device 10, whereas the second application is a general application for providing the patient with general information of the status of the implanted medical device 10 or information from the DDI 330 or HCP, or for providing an interface for the patient to provide general input to the DDI 330 or HCP related to the general wellbeing of the patient, the lifestyle of the patient or related to general input from the patient concerning the function of the implanted medical device 10. The second application, which do not provide input to the remote control 320" and/or the implanted medical device 10 thus handles data which is less sensitive. As such, the general application could be configured to function also when all auxiliary radio connections are activated, whereas switching to the control application which handles the more sensitive control commands and communication with the implanted medical device 10 could require that the auxiliary radio connections are temporarily de-activated. It is also conceivable that the control application is a sub-application running within the general application, in which case the activation of the control application as a sub-application in the general application could require the temporary de-activation of auxiliary radio connections. In the embodiment shown in FIG. 66A, access to the control application requires the use of the optical and/or NFC means of the hardware key 333'** in combination with biometric input to the patient's display device, whereas accessing the general application only requires biometric input to the patient's display device and/or a pin code. In the alternative, a two-factor authentication solution, such as a digital key in combination with a pin code could be used for accessing the general application and/or the control application.

In the embodiments in which the patients display device 334 is configured to only display and interact with a web-view provided by another unit in the system, it is conceivable that the web-view is a view of a back-end provided on the DDI 330, and in such embodiments, the patient interacting with the control interface on the patient's display device is equivalent to the patient interacting with an area of the DDI 330.

Moving now to the P-EID 320'". The P-EID 320'" is an external device which communicates with, and charges, the implanted medical device 10. The P-EID 320'" can be remotely controlled by the HCP to read information from the implanted medical device 10, control the operation of the implanted medical device 10, control the charging of the medical device 10, and adjusting the settings to the software running on the controller 300 of the implanted medical device 10, e.g. by adding or removing pre-defined program steps and/or by the selection of pre-defined parameters within a limited range. Just as the remote control 320", the P-EID 320''' could be configured to communicate with the implanted medical device 10 using BT or UWB communication. Just as with the remote control 320", it is also conceivable to use a combination of UWB wireless communication and BT for enabling positioning of the P-EID 320" as a way to establish that the P-EID 320" is at a position which the implanted medical device 10 and/or patient and/or HCP can acknowledge as being correct, e.g. in the direct proximity to the correct patient and/or the correct medical device 10. Just as for the remote control 320", in embodiments in which a combination of BT and UWB technology is used, the UWB technology may be used for location-based authentication of the P-EID 320", whereas the communication and/or data transfer could take place using BT. The P-EID 320" comprises a wireless transmitter/transceiver 328 for communication and also comprises a wireless transmitter 325 configured for transferring energy wirelessly, in the form of a magnetic field, to a wireless receiver 395 of the implanted medical device 10 configured to receive the energy in the form of a magnetic field and transform the energy into electric energy for storage in an implanted energy storage unit 40, and/or for consumption in an energy consuming part of the implanted medical device 10 (such as the operation device, controller 300 etc.). The magnetic field generated in the P-EID YY and received in the implanted medical device 10 is denoted charging signal. In addition to enabling the wireless transfer of energy from the P-EID to the implanted medical implant 10, the charging signal may also function as a means of communication. E.g., variations in the frequency of the transmission, and/or the amplitude of the signal may be uses as signaling means for enabling communication in one direction, from the P-EID to the implanted medical device 10, or in both directions between the P-EID and the implanted medical device 10. The charging signal in the embodiment shown in FIG. 66A is a signal in the range 120-140 kHz. and the communication follow a proprietary communication signaling protocol, i.e., it is not based on an open standard. In alternative embodiments, BT could be combined with communication using the charging signal, or communication using the charging signal could be combined with an UWB signal.

Just as for the remote control 320", the UWB signal could in some embodiments also be used as a wake-up signal for the controller 300, or for the BT transceiver, such that the BT transceiver in the implanted medical device 10 can be turned off when not in use, which eliminates the risk that the BT is intercepted, or that the controller 300 of the implanted medical device 10 is hacked by means of BT communication. In the alternative, the charging signal could be used as a wakeup signal for the BT, as the charging signal does not travel very far. Also, as a means of location-based authentication, the effect of the charging signal or the RSSI could be assessed by the controller 300 in the implanted medical device 10 to establish that the transmitter is within a defined range. In the BT/UWB combination, the UWB may be used also for transmission of data. In some embodiments, the UWB and/or the charging signal could be used for the transmission of some portions of the data, such as sensitive portions of the data, or for the transmission keys for unlocking encrypted communication sent by BT.

UWB could also be used for waking up the charging signal transmission, to start the wireless transfer of energy or for initiating communication using the charging signal. As the signal for transferring energy has a very high effect in relation to normal radio communication signals, the signal for transferring energy cannot be active all the time, as this signal may be hazardous e.g., by generating heat.

The P-EID 320''' communicates with the HCP over the Internet by means of a secure communication, such as over a VPN. The communication between the HCP and the P-EID 320''' is preferably encrypted. The communication from the HCP to the implanted medical device 10 may be performed using an end-to-end encryption, in which case the communication cannot be decrypted by the P-EID 320'''. In such embodiments, the P-EID 320''' acts as a router, only passing on encrypted communication from the HCP to the controller 300 of the implanted medical device 10. This solution further increases security as the keys for decrypting the information rests only with the HCP and with the implanted medical device 10, which reduces the risk that an unencrypted signal is intercepted by an unauthorized device.

When the implanted medical device 10 is to be controlled and/or updated remotely by the HCP, via the P-EID 320''', a HCP Dedicated Device (DD) 332 displays an interface in which predefined program steps or setting values are presented to the HCP. The HCP provides input to the HCP DD 332 by selecting program steps, altering settings and/or values or by altering the order in which pre-defined program steps is to be executed. The instructions/parameters inputted into the HCP DD 332 for remote operation is in the embodiment shown in FIG. **22*f* routed to the P-EID 320''' via the DDI 330, which may or may not be able to decrypt/read the instructions. The DDI 330 may store the instructions for a time period to later transfer the instructions in a package of created instructions to the P-EID 320'''. It is also conceivable that an additional layer of encryption is provided to the package by the DDI 330. The additional layer of encryption may be a layer of encryption to be decrypted by the P-EID 330, or a layer of encryption which may only be decrypted by the controller 300 of the implanted medical device 10, which reduces the risk that unencrypted instructions or packages are intercepted by unauthorized devices. The instructions/parameters are then provided to the P-EID 320", which then loads the instructions/parameters into the during the next charging/energy transfer to the implanted medical device 10** using any of the signal transferring means (wireless or conductive) disclosed herein.

The Health Care Provider EID (HCP EID) 320' have the same features as the P-EID 320" and can communicate with the implanted medical device 10 in the same alternative ways (and combinations of alternative ways) as the P-EID 320'''. However, in addition, the HCP EID 320' also enables the HCP to freely reprogram the controller 300 of the implanted medical device 10, including replacing the entire program code running in the controller 300. The idea is that the HCP EID 320' always remain with the HCP and as such, all updates to the program code or retrieval of data from the implanted medical device 10 using the HCP EID 320' is performed with the HCP present (i.e. not remote). The physical presence of the HCP is an additional layer of security for these updates which may be critical to the function of the implanted medical device 10.

In the embodiment shown in FIG. 66A, the HCP communicates with the HCP EID 320' using a HCP Dedicated Device 332 (HCP DD), which is a display device comprising a control interface for controlling and communicating with the HCP EID 320'. As the HCP EID 320' always stays physically at the HCP's clinic, communication between the HCP EID 320' and HCP DD 332 does not have to be sent over the Internet. Instead, the HCP DD 332 and the HCP EID 320' can communicate using one or more of BT, a proprietary wireless communication channel, or a wired connection. The alteration to the programming is then sent to the implanted medical device 10 directly via the HCP EID 320'. Inputting into the HCP DD 332 for direct operation by means of the HCP EID 320' is the same as inputting directly into the HCP EID 320', which then directly transfers the instructions into the implanted medical device 10.

In the embodiment shown in FIG. 66A, both the patient and the HCP has a combined hardware key 333',333". The combined keys 333',333" comprises a hardware component comprising a unique circuitry (providing the highest level of security), a wireless NFC-transmitter 339 for transmitting a specific code (providing mid-level security), and a printed QR-code 344 for optical recognition of the card (providing the lowest level of security).

The patient's key 333' in the embodiment shown in FIG. 66A is in the form of a key card having an interface for communicating with the P-EID 320'", such that the key card could be inserted into a key card slot in the P-EID 320". The NFC-transmitter 339 and/or the printed QR-code 344 can be used as means for accessing the control interface 334*i* of the display device 334. In addition, the display device 334 may require a pin-code and/or a biometric input, such as face recognition or fingerprint recognition.

The HCP's key 333" in the embodiment shown in FIG. 66A is in the form of a key card having an interface for communicating with the HCP-EID 320', such that the key card could be inserted into a key card slot in the HCP-EID 320'. The NFC-transmitter 339 and/or the printed QR-code 344 can be used as means for accessing the control interface of the HCP DD 332. In addition, the HCP DD 332 may require a pin-code and/or a biometric input, such as face recognition or fingerprint recognition.

In alternative embodiments, it is however conceivable that the hardware key solution is replaced by a two-factor authentication solution, such as a digital key in combination with a PIN code or a biometric input (such as face recognition and/or fingerprint recognition).

In the embodiment shown in FIG. 66A, communication over the Internet takes place over a Dedicated Data Infrastructure (DDI) 330, running on a cloud service. The DDI 330 handles communication between the HCP DD 332 and the P-EID 320'", between the HCP and the remote control 320", between the HCP and the patient's display device 334, as well as between the HCP and auxiliary devices 336 (such as tools for following up the patient's treatments e.g. a scale in obesity treatment example or a blood pressure monitor in a blood pressure treatment example). In some embodiments, the HCP DD 332 also handles the communication between the patient's display device 334 and the remote control 335. In all examples, the communication from the HCP to: the P-EID 320'", the remote control 320", the patient's display device 334 and the auxiliary devices 336 may be performed using an end-to-end encryption. In embodiments with end-to-end encryption, the communication cannot be decrypted by the DDI 330. In such embodiments, the DDI 330 acts as a router, only passing on encrypted communication from the HCP to various devices. This solution further increases security as the keys for decrypting the information rests only with the HCP and with the device sending or receiving the communication, which reduces the risk that an unencrypted signal is intercepted by an unauthorized device.

In addition to acting as an intermediary or router for communication, the DDI 330 collects data on the implanted medical device 10, on the treatment and on the patient. The data may be collected in an encrypted form, in an anonymized form or in an open form. The form of the collected data may depend on the sensitivity of the data or on the source from which the data is collected. In the embodiment shown in FIG. 66A, the DDI 330 sends a questionnaire to the patients display device 334. The questionnaire could comprise questions to the patient related to the general health of the patient, related to the way of life of the patient, or related specifically to the treatment provided by the implanted medical device 10 (such as for example a visual analogue scale for measuring pain). The DDI 330 could compile and/or combine input from several sources and communicate the input to the HCP which could use the provided information to create instructions to the various devices to be sent back over the DDI 330. The data collection performed by the DDI 330 could also be in the form a log to make sure that all communication between the units in the system can be back traced. Logging the communication ensures that all alterations to software or the settings of the software, as well as the frequency and operation of the implanted medical device 10 can be followed. Following the communication enables the DDI 330 or the HCP to follow the treatment and react it something in the communication indicates that the treatment does not provide the intended results or if something appears to be wrong with any of the components in the system.

In the specific embodiment disclosed in FIG. 66A, the wireless connections between the different units are as follows. The wireless connection 411 between the auxiliary device 336 and the DDI 330 is based on WiFi or a mobile telecommunication regime and the wireless connection 411 between the auxiliary device 336 and the patient's display device 334 is based on BT. The wireless connection 412 between the patient's display device 334 and the DDI 330 is based on WiFi or a mobile telecommunication regime. The wireless connection 413 between the patient's display device 334 and the remote control 320" is based on BT. The wireless connection 414 between the remote control 320" and the implanted medical device 10 is based on BT and UWB. The wireless connection 415 between the remote control 320" and the DDI 330 is based on WiFi or a mobile telecommunication regime. The wireless connection 416 between the P-EID 320'" and the implanted medical device 10 is based on BT, UWB and the charging signal. The wireless connection 417 between the P-EID 320'" and the DDI 330 is based on WiFi or a mobile telecommunication regime. The wireless connection 418 between the HCP-EID 320' and the implanted medical device 10 is based on BT, UWB and the charging signal. The wireless connection 419 between the P-EID 320'" and the HCP DD 332 is based on BT. The wireless connection 420 between the HPC-EID 320' and the DDI 330 is based on WiFi or a mobile telecommunication regime. The wireless connection 421 between the HPC DD 332 and the DDI 330 is based on WiFi or a mobile telecommunication regime. The wireless connection 422 between the HCP-EID 320' and the HCP DD 332 is based on BT.

The wireless connections specifically described in the embodiment shown in FIG. 66A may however be replaced or assisted by wireless connections based on radio frequency identification (RFID), near field charge (NFC), Bluetooth, Bluetooth low energy (BLE), or wireless local area network (WLAN). The mobile telecommunication regimes may for example be 1G, 2G, 3G, 4G, or 5G. The wireless connections may further be based on modulation techniques such as amplitude modulation (AM), frequency modulation (FM), phase modulation (PM), or quadrature amplitude modulation (QAM). The wireless connection may further feature technologies such as time-division multiple access (TDMA), frequency-division multiple access (FDMA), or code-division multiple access (CDMA). The wireless connection may also be based on infra-red (IR) communication. The wireless connection may feature radio frequencies in the high frequency band (HF), very-high frequency band (VHF), and the ultra-high frequency band (UHF) as well as essentially any other applicable band for electromagnetic wave communication. The wireless connection may also be based on ultrasound communication to name at least one example that does not rely on electromagnetic waves.

Although wireless transfer is primarily described in the embodiment disclosed with reference to FIG. 66A, the wireless communication between any of the external device may be substituted for wired communication. Also, some or all of the wireless communication between an external device and the implanted medical device 10 may be substituted for conductive communication using a portion of the human body as conductor (such as further described with reference to FIGS. 65A-65E).

Figure 66B:
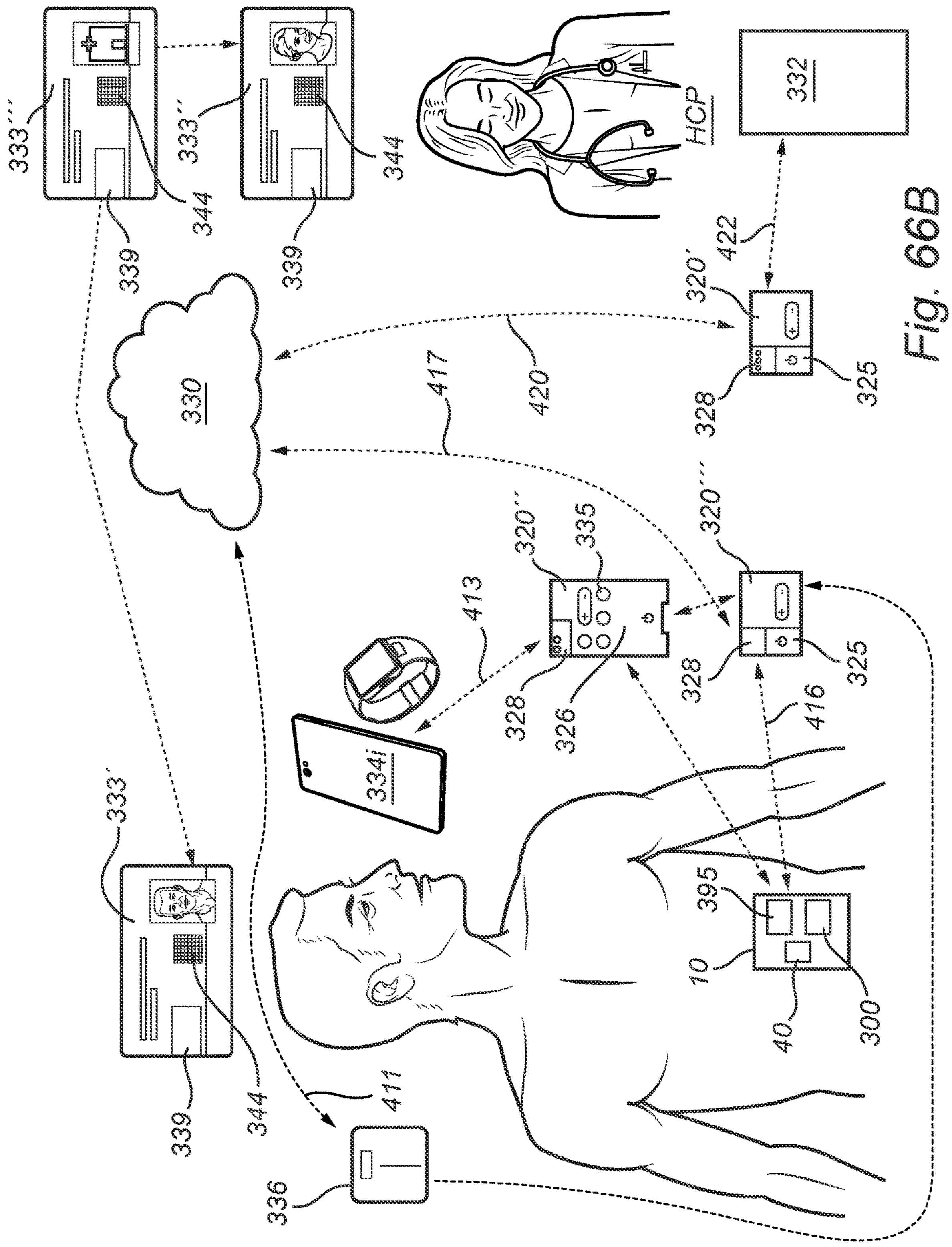

FIG. 66A and FIG. 66B show one embodiment of a system for charging, programming and communicating with the controller 300 of the implantable energized medical device 10. FIGS. 66A and 66B further describes the communication and interaction between different external devices which may be devices held and operated by the patient, by the health care provider (HCP) or by the Dedicated Data Infrastructure (DDI), which is an infrastructure supplier for example by the manufacturer of the implantable energized medical device 10 or the external devices 320', 320",320'". The system of the embodiment of FIGS. 66A and 66B comprises three external devices 320',320",320'" capable of communicating with the controller 300. The basic idea is to ensure the security of the communication with, and the operation of, the medical device 100 by having three external devices 320',320",320'" with different levels of authority. The lowest level of authority is given to the patient operated remote control 320". The remote control external device 320" is authorized to operate functions of the implantable energized medical device 10 via the implanted controller 300, on the basis of patient input. The remote control 320" is further authorized to fetch some necessary data from the controller 300. The remote control 320" is only capable of operating the controller 300 by communicating with the software currently running on the controller 300, with the currently settings of the software. The next level of authority is given to the Patient External Interrogation Device (P-EID) 320'", which is a charging and communication unit which is held by the patient but is partially remotely operated by the Health Care Provider (HCP) (Usually a medical doctor with the clinic providing the treatment with help of the implantable energized medical device 10).

The P-EID 320'" is authorized to make setting changes by selecting pre-programmed steps of the software or hardware running on the controller 300 of the implanted medical device 100. The P-EID is remotely operated by the HCP, and receives input from the HCP, via the DDI.

The highest level of authority is given to the HCP-EID 320' and its controller, referred to as the HCP Dedicated Display Device (DDD). The HCP-EID 320' is a charging and communication unit which may be located physically at the clinic of the HCP. The HCP-EID 320' may be authorized to freely alter or replace the software running on the controller 300, when the patient is physically in the clinic of the HCP. The HCP-EID 320' is controlled by the HCP DDD, which either may act on a "webview" portal from the HCP-EID or be a device closed down to any activities (which may include the absence of an internet connection) other than controlling and communicating with the HCP-EID. The webview portal does not necessarily mean internet based or HTML-protocol and the webview portal may be communicated over other communicating protocols such as Bluetooth or any other type of standard or proprietary protocol. The HCP DDD may also communicate with the HCP-EID over a local network or via Bluetooth or other standard or proprietary protocols.

Starting from the lowest level of authority, the patient remote control external device 320" beneficially may comprise a wireless transceiver 328 for communicating with the implanted medical device 100. The remote control 320" is capable of controlling the operation of the implanted medical device 100 via the controller 300, by controlling pre-set functions of the implantable medical device 100, e.g. for operating an active portion of the implanted medical device 100 for performing the intended function of the implanted medical device 100. The remote control 320" is able to communicate with the implanted medical device 100 using any standard or proprietary protocol designed for the purpose. In the embodiment shown in FIG. 66A, the wireless transceiver 328 comprises a Bluetooth (BT) transceiver, and the remote control 320" is configured to communicate with implanted medical device 100 using BT. In an alternative configurations, the remote control 320" communicates with the implanted medical device 100 using a combination of Ultra-Wide Band (UWB) wireless communication and BT. The use of UWB technology enables positioning of the remote control 320" which can be used by the implanted medical device 100 as a way to establish that the remote control 320" is at a position in which the implanted medical device 100 and/or the patient can acknowledge as being correct, e.g. in the direct proximity to the medical device 100 and/or the patient, such as within reach of the patient and/or within 1 or 2 meters of the implanted medical device 100.

UWB communication may be performed by the generation of radio energy at specific time intervals and occupying a large bandwidth, thus enabling pulse-position or time modulation. The information can also be modulated on UWB signals (pulses) by encoding the polarity of the pulses, their amplitude and/or by using orthogonal pulses. A UWB radio system can be used to determine the "time of flight" of the transmission at various frequencies. This helps overcome multipath propagation, since some of the frequencies have a line-of-sight trajectory, while other indirect paths have longer delay. With a cooperative symmetric two-way metering technique, distances can be measured at high resolution and accuracy. UWB is useful for real-time location systems, and its precision capabilities and low power make it well-suited for radio-frequency-sensitive environments, such as health care environments.

In embodiments in which a combination of BT and UWB technology is used, the UWB technology may be used for location-based authentication of the remote control 320", whereas the communication and/or data transfer could take place using BT or any other way of communicating different from the UWB. The UWB signal could in some embodiments also be used as a wake-up signal for the controller 300, or for the BT transceiver, such that the BT transceiver in the implanted medical device 100 can be turned off when not in use, which eliminates the risk that the BT is intercepted, or that the controller 300 of the implanted medical device 100 is hacked by means of BT communication. In embodiments in which a BT (or alternatives)/UWB combination is used, the UWB connection may be used also for the transmission of data. In the alternative, the UWB connection could be used for the transmission of some portions of the data, such as sensitive portions of the data, or for the transmission of keys for the unlocking of encrypted communication sent over BT.

The remote control 320" comprises a computing unit 326 configured to run a software application for communicating with the implanted medical device 100. The computing unit 326 can receive input directly from control buttons 335 arranged on the remote control 320" or may receive input from a control interface **334*i* displayed on a patient display device 334 operated by the patient. In the embodiments in which the remote control 320" receives input from a control interface 334*i* displayed on the patient display device 334 operated by the patient, the remote control 320" may transmit the control interface 334*i* in the form of a web-view portal, i.e. a remote interface running in a sandbox environment on the patient's display device 334. A sandbox environment is understood as running on the display device 334 but only displaying what is presented from the remote control, and only using a tightly controlled set of commands and resources, such as storage and memory space as well as network access. The ability to inspect the host system and read or write from other input devices connected to the display device 334** may therefore be extremely limited. Any action or command generated by the patient display device may be similar to controlling a webpage. All acting software may be located on the remote control that only displays its control interface onto the patient display unit.

The computing unit 326 may further be configured to encrypt the control interface before transmission to the patient display device 334, and encrypt the control commands before transmission to the implanted medical device 100. The computing unit 326 is further configured to transform the received user input into control commands for wireless transmission to the implantable medical device 100.

The patient's display device 334 could for example be a mobile phone, a tablet or a smart watch. In the embodiment shown in FIG. 66A, the patient's display device 334 communicates with the remote control 320" by means of BT. The control interface **334*i* in the form of a web-view portal is transmitted from the remote control 320" to the patient's display device 334 over BT. Control commands in the form of inputs from the patient to the control interface 334*i* may be transmitted from the patient's display device 334 to the remote control 320", providing input to the remote control 320" equivalent to the input that may be provided using the control buttons 335. The control commands created in the patient's display device 334 may be encrypted in the patient's display device 334 and transmitted to the remote control 320'** using BT or any other communication protocol.

The remote control may normally not be connected to the DDI or the Internet, thereby increasing security. In addition, the remote control 320" may in one embodiment have its own private key. In a specific embodiment, the remote control 320" may be activated by the patient's private key for a certain time period. This may activate the function of the patient's display device and the remote wed-view display portal supplied by the remote control to the patient's display device.

The patient's private key may be supplied in a patient private key device compromising a smartcard that may be inserted or provided close to the remote control 320" to activate a permission to communicate with the implant 100 for a certain time period.

The patient's display device 334 may (in the case of the display device 334 being a mobile phone or tablet) comprise auxiliary radio transmitters for providing an auxiliary radio connection, such as a Wi-Fi or mobile connectivity (e.g. according to the 3G, 4G or 5G standards). The auxiliary radio connection(s) may have to be disconnected to enable communication with the remote control 320". Disconnecting the auxiliary radio connections reduces the risk that the integrity of the control interface **334*i* displayed on the patient's display device 334 is compromised, or that the control interface 334*i* displayed on the patient's display device 334** is remotely controlled by an unauthorized device or entity.

In alternative embodiments, control commands are generated and encrypted by the patient's display device and transmitted to the DDI 330. The DDI 330 could either alter the created control commands to commands readable by the remote control 320" before further encrypting the control commands for transmission to the remote control 320", or could simply add an extra layer of encryption before transmitting the control commands to the remote control 320", or could simply act as a router for relaying the control commands from the patients' display device 334 to the remote control 320". It is also conceivable that the DDI 330 adds a layer of end-to-end encryption directed at the implanted medical device 100, such that only the implanted medical device 100 can decrypt the control commands to perform the commands intended by the patient. In the embodiments above, when the patient remote display device 334 is communicating with the DDI, the patient's display device 334 may be configured to only display and interact with a web-view portal provided by a section of the DDI. It is conceivable that the web-view portal is a view of a back-end provided on the DDI 330, and that in such embodiments the patient interacting with the control interface on the patient's display device 334 is equivalent to the patient interacting with an area of the DDI 330.

The patient's display device 334 could have a first and second application related to the implanted medical device 100. The first application is the control application displaying the control interface **334*i* for control of the implanted medical device 100, whereas the second application is a general application for providing the patient with general information of the status of the implanted medical device 100 or information from the DDI 330 or HCP, or for providing an interface for the patient to provide general input to the DDI 330 or HCP related to the general wellbeing of the patient, the lifestyle of the patient or related to general input from the patient concerning the function of the implanted medical device 100. The second application, which do not provide input to the remote control 320" and/or the implanted medical device 100 thus handles data which is less sensitive. As such, the general application could be configured to function also when all auxiliary radio connections are activated, whereas switching to the control application which handles the more sensitive control commands and communication with the implanted medical device 100 could require that the auxiliary radio connections are temporarily de-activated. It is also conceivable that the control application is a sub-application running within the general application, in which case the activation of the control application as a sub-application in the general application could require the temporary de-activation of auxiliary radio connections. In the embodiment shown in FIG. 66A, access to the control application requires the use of the optical and/or NFC means of the hardware key 333'** in combination with biometric input to the patient's display device, whereas accessing the general application only requires biometric input to the patient's display device and/or a pin code. In an example, a two-factor authentication solution, such as a digital key in combination with a pin code could be used for accessing the general application and/or the control application.

In general, a hardware key may be needed to activate the patient display device 334 for certain time period to control the web-view portal of the remote control 320", displaying the control interface 334*i* for control of the implanted medical device 100.

In the embodiments in which the patients display device 334 is configured to only display and interact with a web-view provided by another unit in the system, it is conceivable that the web-view portal is a view of a back-end provided on the DDI 330, and in such embodiments, the patient interacting with the control interface on the patient's display device is equivalent to the patient interacting with an area of the DDI 330.

Moving now to the P-EID 320'". The P-EID 320'" is an external device used by the patient, patient external device, configured to communicate with, and charge, the implanted medical device 100. The P-EID 320'" can be remotely controlled by the HCP to read information from the implanted medical device 100. The P-EID 320'" is adapted to control the operation of the implanted medical device 100, control the charging of the medical device 100, and adjust the settings on the controller 300 of the implanted medical device 100 by changing pre-defined pre-programmed steps and/or by the selection of pre-defined parameters within a defined range.

Similar to the remote control 320", the P-EID 320'" may be configured to communicate with the implanted medical device 100 using BT or UWB communication or any other proprietary or standard communication method. Since the device may be used for charging the implant, the charging signal and communication could be combined. Similar to the remote control 320", it is also possible to use a combination of UWB wireless communication and BT for enabling positioning of the P-EID 320" as a way to establish that the P-EID 320" is at a position which the implanted medical device 100 and/or patient and/or HCP can acknowledge as being correct, e.g. in the direct proximity to the correct patient and/or the correct medical device 100. Just as for the remote control 320", in embodiments in which a combination of BT and UWB technology is used, the UWB technology may be used for location-based authentication of the P-EID 320", whereas the communication and/or data transfer could take place using BT. The P-EID 320" comprises a wireless transmitter/transceiver 328 for communication and also comprises a wireless transmitter 325 configured for transferring energy wirelessly, which may be in the form of a magnetic field or any other signal such as electromagnetic, radio, light, sound or any other type of signal to transfer energy wirelessly to a wireless receiver 395 of the implanted medical device 100. The wireless receiver 395 of the implanted medical device 100 is configured to receive the energy in the form of the magnetic field and transform the energy into electric energy for storage in an implanted energy storage unit 40, and/or for consumption in an energy consuming part of the implanted medical device 100 (such as the operation device, controller 300 etc.). The magnetic field generated in the P-EID 320'" and received in the implanted medical device 100 is denoted charging signal. In addition to enabling the wireless transfer of energy from the P-EID 320'" to the implanted medical implant 10, the charging signal may also function as a means of communication. E.g., variations in the frequency of the transmission, and/or the amplitude of the signal may be uses as signaling means for enabling communication in one direction, from the P-EID 320'" to the implanted medical device 100, or in both directions between the P-EID 320'" and the implanted medical device 100. The charging signal in the embodiment shown in FIG. 66A is a signal in the range 10-65 kHz or 115-140 kHz and the communication follow a proprietary communication signaling protocol, i.e., it is not based on an open standard. In alternative embodiments, BT could be combined with communication using the charging signal, or communication using the charging signal could be combined with an UWB signal. The energy signal could also be used as a carrying signal for the communication signal.

Just as for the remote control 320", the UWB signal could in some embodiments also be used as a wake-up signal for the controller 300, or for the BT transceiver, such that the BT transceiver in the implanted medical device 100 can be turned off when not in use, which eliminates the risk that the BT is intercepted, or that the controller 300 of the implanted medical device 100 is hacked by means of BT communication. In some examples, the charging signal could be used as a wakeup signal for the BT, as the charging signal does not necessarily travel very far. Also, as a means of location-based authentication, the effect of the charging signal or the RSSI could be assessed by the controller 300 in the implanted medical device 100 to establish that the transmitter is within a defined range. In the BT/UWB combination, the UWB may be used also for transmission of data. In some embodiments, the UWB and/or the charging signal could be used for the transmission of some portions of the data, such as sensitive portions of the data, or for the transmission keys for unlocking encrypted communication sent by BT. Wake-up could be performed with any other signal.

UWB could also be used for waking up the charging signal transmission, to start the wireless transfer of energy or for initiating communication using the charging signal. As the signal for transferring energy has a very high effect in relation to normal radio communication signals, the signal for transferring energy cannot be active all the time, as this signal may be hazardous e.g., by generating heat.

The P-EID 320'" may communicate with the HCP over the Internet by means of a secure communication, such as over a VPN. The communication between the HCP and the P-EID 320'" is preferably encrypted. Preferably, the communication is sent via the DDI, which may only be relaying the information. The communication from the HCP to the implanted medical device 100 may be performed using an end-to-end encryption, in which case the communication cannot be decrypted by the P-EID 320'". In such embodiments, the P-EID 320'" acts as a router, only passing on encrypted communication from the HCP to the controller 300 of the implanted medical device 100 (without full decryption). This solution further increases security as the keys for decrypting the information rests only with the HCP and with the implanted medical device 100, which reduces the risk that an unencrypted signal is intercepted by an unauthorized device. The P-EID 320'" may add own encryption or information, specifically for security reasons. The P-EID 320'" may hold its own private key and may be allowed to communicate with the implant 100 based on confirmation from the patient's private key, which may be provided as a smartcard to be inserted in a slot of the P-EID 320'" or hold in close proximity thereto to be read by the P-EID 320'". These two keys will add a high level of security to the performed communication between the Implant 100 and the P-EID 320'" since the patient's hardware key in this example on the smartcard may activate and thereby allow the communication and action taken in relation to the implant. The P-EID 320''' may as previously described change the treatment setting of the implant by selecting pre-programmed steps of the treatment possibilities. Such pre-programmed treatment options may include for example to change:

at least one of the position, frequency and level of compression of an implanted heart compression device, the flow of an apparatus assisting the pump function of a heart of the patient, the flow of an apparatus assisting the pump function comprising a turbine bump placed within a patient's blood vessel for assisting the pump function of the heart, the function of an operable artificial heart valve, at least one of the function of, the valve opening pressure and time for closure of an operable artificial heart valve for increasing the blood flow to the coronary arteries.

at least one of the functions of, the amount and/or concentration of a drug from an implantable drug delivery device, at least one of the injection site and frequency as well as amount of drug delivered by an implantable drug delivery device for injecting directly into a blood vessel and change the position of the injection site, all from within the patient's body, at least one of the injection site and frequency as well as amount of drug delivered by an implantable drug delivery device for injecting potency enhancing drugs into an erectile tissue of the patient, at least one of the level of constriction, pressure or position of a hydraulic, mechanic, and/or electric constriction implant, the volume of an operable volume filling device, the constriction of an operable gastric band, at least one of the level and time of stretching and when such stretching occur in relation to food intake of a patient for an operable implant for stretching the stomach wall of the patient for creating satiety, when an action should be taken relating to an implant configured to sense the amount of food intake based on number of times a patient swallows solid food, at least one of the size and shape of an operable cosmetic implant.

at least one of the shape and size in the breast region of a patient of an operable cosmetic implant for adjustment, at least one of pressure, volume, sensor input or time of an implant controlling medical device for the emptying of a urinary bladder, at least one of the closing pressure, the time to close after urinating, how much extra pressure would be allowed at exercise of an implant hindering urinary leakage, at least one of the closing pressure, the time to close after revealing, how much extra pressure would be allowed at exercise of an implant hindering anal incontinence, parameters of an implant controlling the emptying of fecal matter, such as pressure, volume, pump or motor position etc., parameters of an implant monitoring an aneurysm, such as pressure, aneurysm expansion, volume, reservoir volume, etc., parameters of an implant for hindering the expansion of an aneurysm, such as pressure, aneurysm expansion, volume, reservoir volume, etc., parameters of an implant lubricating a joint, such as volume, reservoir volume, etc., parameters of an implant for affecting the blood flow to an erectile tissue of the patient, such as the level of constriction, pressure or position of a hydraulic, mechanic, and/or electric constriction implant, parameters of an implant for simulating the engorgement of an erectile tissue, such as the level of stimulation, frequency, or amplitude of an electrical stimulation.

parameters of an implant with a reservoir for holding bodily fluids, such as volume, reservoir volume, etc., parameters of an implant storing and/or emptying a bodily reservoir or a surgically created reservoir, such as stimulation parameters in a peristaltic wave, stretch or bending sensors, reservoir volume, etc., parameters of an implant communicating with a database outside the body, such as key handshake, new key pairing, signal amplitude etc., parameters of an implant able to be programmed from outside the body, parameters of an implant able to be programmed from outside the body with a wireless signal, parameters of an implant treating impotence, such as pressure, amount of drug delivered, time for erection period etc., parameters of an implant controlling the flow of eggs in the uterine tube, such as the level of constriction, time period, position of a hydraulic, mechanic, and/or electric constriction implant.

parameters of an implant controlling the flow of sperms in the uterine tube, such as the level of stimulation, frequency, or amplitude of an electrical stimulation, parameters of an implant controlling the flow of sperms in the vas deferens, such as the level of constriction, time period, position of a hydraulic, mechanic, and/or electric constriction implant, parameters of an implant for hindering the transportation of the sperm in the vas deferens, such as the level of constriction, time period, position of a hydraulic, mechanic, and/or electric constriction implant, parameters of an implant treating osteoarthritis, parameters of an implant performing a test of parameters inside the body, parameters of an implant controlling specific treatment parameters from inside the body, parameters of an implant controlling bodily parameters from inside the body, parameters of an implant controlling the blood pressure, parameters of an implant controlling the blood pressure by affecting the dilatation of the renal artery, such as heat and time period in relation to blood pressure, parameters of an implant controlling a drug treatment parameter, parameters of an implant controlling a parameter in the blood, parameters of an implant for adjusting or replacing any bone part of a body of the patient, parameters of an implant replacing an organ of the patient or part of an organ of the patient or the function thereof, parameters of a vascular treatment device, such as bending, expanding sensor, parameters of an implant adapted to move fluid inside the body of the patient, such as volume, pumping parameters, parameters of an implant configured to sense a parameter related to the patient swallowing, parameters of an implant configured to exercise a muscle with electrical or mechanical stimulation, such as stimulation parameters, amplitude frequency time period etc., parameters of an implant configured for emptying an intestine portion on command, such as electrical stimulation parameters, peristaltic wave adjustment etc., parameters of an operable implant configured to be invaginated in the stomach of the patient to reduce the volume of the stomach substantially more than the volume of the device, such as volume, parameters of an implant configured for emptying the urinary bladder from within the patient's body by compressing the bladder, such as pressure, volume and time parameters of an implant configured for draining fluid from within the patient's body, parameters of an implant configured for the active lubrication of a joint with an added lubrication fluid, such as frequency and/or volume of the drug supplied, parameters of an implant configured for removing clots and particles from the patient's blood stream, parameters of an implant configured for elongating or straightening a bone in the patient, to reduce scoliosis, force, length etc., parameters of a device to stimulate the brain for a several position to a focused point, parameters of an artificial stomach replacing the function of the natural stomach, parameters of an implant configured for adjusting the position of a female's urinary tract or bladder neck, parameters of an implant configured for stimulating the ampulla vas deference and creating temporary constriction.

When the implanted medical device 100 is to be controlled and/or updated remotely by the HCP, via the P-EID 320''', a HCP Dedicated Device (DD) 332 displays an interface in which predefined program steps or setting values are presented to the HCP. The HCP provides input to the HCP DD 332 by selecting program steps, altering settings and/or values or by altering the order in which pre-defined program steps is to be executed. The instructions/parameters inputted into the HCP DD 332 for remote operation is in the embodiment shown in FIG. 66A routed to the P-EID 320''' via the DDI 330, which may or may not be able to decrypt/read the instructions. The DDI 330 may store the instructions for a time period to later transfer the instructions in a package of created instructions to the P-EID 320'''. It is also conceivable that an additional layer of encryption is provided to the package by the DDI 330. The additional layer of encryption may be a layer of encryption to be decrypted by the P-EID 330, or a layer of encryption which may only be decrypted by the controller 300 of the implanted medical device 100, which reduces the risk that unencrypted instructions or packages are intercepted by unauthorized devices. The instructions/parameters are then provided to the P-EID 320'', which then loads the instructions/parameters into the during the next charging/energy transfer to the implanted medical device 100 using any of the signal transferring means (wireless or conductive) disclosed herein.

The Health Care Provider EID (HCP EID) 320' have the same features as the P-EID 320'' and can communicate with the implanted medical device 100 in the same alternative ways (and combinations of alternative ways) as the P-EID 320'''. However, in addition, the HCP EID 320' also enables the HCP to freely reprogram the controller 300 of the implanted medical device 100, including replacing the entire program code running in the controller 300. The idea is that the HCP EID 320' always remain with the HCP and as such, all updates to the program code or retrieval of data from the implanted medical device 100 using the HCP EID 320' is performed with the HCP and patient present (i.e. not remote). The physical presence of the HCP is an additional layer of security for these updates which may be critical to the function of the implanted medical device 100.

In the embodiment shown in FIG. 66A, the HCP communicates with the HCP EID 320' using a HCP Dedicated Display Device 332 (HCP DDD), which is a HCP display device comprising a control interface for controlling and communicating with the HCP EID 320'. As the HCP EID 320' always stays physically at the HCP's clinic, communication between the HCP EID 320' and HCP DDD 332 does not have to be sent over the Internet. Instead, the HCP DDD 332 and the HCP EID 320' can communicate using one or more of BT, a proprietary wireless communication channel, or a wired connection. The alteration to the programming is then sent to the implanted medical device 100 directly via the HCP EID 320'. Inputting into the HCP DDD 332 for direct operation by means of the HCP EID 320' is the same as inputting directly into the HCP EID 320', which then directly transfers the instructions into the implanted medical device 100.

In the embodiment shown in FIG. 66A, both the patient and the HCP has a combined hardware key 333', 333''. The combined keys 333', 333'' comprises a hardware component comprising a unique circuitry (providing the highest level of security), a wireless NFC-transmitter 339 for transmitting a specific code (providing mid-level security), and a printed QR-code 344 for optical recognition of the card (providing the lowest level of security). The HCP private key is supplied by a HCP private key device 333'' adapted to be provided to the HCP EID external device via at least one of: a reading slot or comparable for the HCP private key device 333'', an RFID communication or other close distance wireless activation communication to both the HCP EID 320' and the HCP DDD 332 if used. The HCP DDD 332 will be activated by such HCP private key device 333'', which for example may comprise at least one of, a smartcard, a key-ring device, a watch an arm or wrist band a neckless or any shape device.

The HCP EID external device may comprise at least one of;

a reading slot or comparable for the HCP private key device, an RFID communication and other close distance wireless activation communication means The HCP external device 320' may further comprise at least one wireless transceiver 328 configured for communication with a data infrastructure server, DDI, through a first network protocol.

A dedicated data infrastructure server, DDI, is in one embodiment adapted to receive commands from said HCP external device 320' and may be adapted to rely the received commands without opening said commands directed to the patient external device 320'', the DDI 330 comprising one wireless transceiver configured for communication with said patient external device 320''.

The patient EID external device 320'' is in one embodiment adapted to receive the commands relayed by the DDI, and further adapted to send these commands to the implanted medical device 100, which is adapted to receive commands from the HCP, Health Care Provider, via the DDI 330 to change the pre-programmed treatment steps of the implanted medical device 100. The patient EID is adapted to be activated and authenticated and allowed to perform the commands by the patient providing a patient private key device 333'. The patient's private key device is in one embodiment adapted to be provided to the patient external device by the patient via at least one of: a reading slot or comparable for the patient private key device 333', an RFID communication or other close distance wireless activation communication.

The patient EID external device, in one or more embodiments, comprises at least one of;

a reading slot or comparable for the HCP private key device.

an RFID communication, or other close distance wireless activation communication The patient EID external device may in one or more embodiments comprise at least one wireless transceiver configured for communication with the implanted medical device through a second network protocol.

The patient's key 333' is in the embodiment shown in FIG. 66A in the form of a key card having an interface for communicating with the P-EID 320''', such that the key card could be inserted into a key card slot in the P-EID 320''. The NFC-transmitter 339 and/or the printed QR-code 344 can be used as means for accessing the control interface **334*i* of the display device 334. In addition, the display device 334** may require a pin-code and/or a biometric input, such as face recognition or fingerprint recognition.

The HCP's key 333'', in the embodiment shown in FIG. 66A is in the form of a key card having an interface for communicating with the HCP-EID 320', such that in one embodiment the key card could be inserted into a key card slot in the HCP-EID 320'. The NFC-transmitter 339 and/or the printed QR-code 344 can be used as means for accessing the control interface of the HCP DDD 332. In addition, the HCP DDD 332 may require a pin-code and/or a biometric input, such as face recognition or fingerprint recognition.

In alternative embodiments, it is however conceivable that the hardware key solution is replaced by a two-factor authentication solution, such as a digital key in combination with a PIN code or a biometric input (such as face recognition and/or fingerprint recognition). The key could also be a software key, holding similar advance key features, such as the Swedish Bank ID being a good example thereof.

In the embodiment shown in FIG. 66A, communication over the Internet takes place over a Dedicated Data Infrastructure (DDI) 330, running on a cloud service. The DDI 330 in this case handles communication between the HCP DDD 332 and the P-EID 320''', however, the more likely scenario is that the HCP DDD 332 is closed down, such that only the necessary functions of the control application can function on the HCP DDD 332. In the closed down embodiment, the HCP DDD 332 is only able to give the necessary commands to HCP EID 320' to further update the pre-programmed treatment steps of the Implant 100 via the P-EID 320''' in direct contact, or more likely indirect contact via the DDI 332. If the patient is present locally, the HCP EID may communicate and act directly on the patient's implant. However, before anything is accepted by the implant, a patient private key device 333' has to be presented to the P EID 320''' or HCP EID 320' for maximum security.

The DDI 330 is logging information of the contact between the HCP and the remote control 320'' via implant feedback data supplied from the implant to P-EID 320'''. Data generated between the HCP and the patient's display device 334, as well as between the HCP and auxiliary devices 336 (such as tools for following up the patient's treatments e.g. a scale in obesity treatment example or a blood pressure monitor in a blood pressure treatment example) are logged by the DDI 330. In some embodiments, although less likely, the HCP DDD 332 may also handle the communication between the patient's display device 334 and the remote control 320''. In FIG. 66A, auxiliary devices 336 are connected to the P-EID as well and can thus provide input from the auxiliary devices 336 to the P-EID which can be used by the P-EID for altering the treatment or for follow up.

In all examples, the communication from the HCP to: the P-EID 320''', the remote control 320'', the patient's display device 334 and the auxiliary devices 336 may be performed using an end-to-end encryption In embodiments with end-to-end encryption, the communication cannot be decrypted by the DDI 330. In such embodiments, the DDI 330 acts as a router, only passing on encrypted communication from the HCP to various devices. This solution further increases security as the keys for decrypting the information rests only with the HCP and with the device sending or receiving the communication, which reduces the risk that an unencrypted signal is intercepted by an unauthorized device. The P-EID 320''' may also only pass on encrypted information.

In addition to acting as an intermediary or router for communication, the DDI 330 collects data on the implanted medical device 100, relating to the treatment and to the patient. The data may be collected in an encrypted form, in an anonymized form or in an open form. The form of the collected data may depend on the sensitivity of the data or on the source from which the data is collected. In the embodiment shown in FIG. 66A, the DDI 330 sends a questionnaire to the patient's display device 334. The questionnaire could comprise questions to the patient related to the general health of the patient, related to the way of life of the patient, or related specifically to the treatment provided by the implanted medical device 100 (such as for example a visual analogue scale for measuring pain). The DDI 330 could compile and/or combine input from several sources and communicate the input to the HCP which could use the provided information to create instructions to the various devices to be sent back over the DDI 330. The data collection performed by the DDI 330 could also be in the form a log to make sure that all communication between the units in the system can be back traced. Logging the communication ensures that all alterations to software or the settings of the software, as well as the frequency and operation of the implanted medical device 100 can be followed. Following the communication enables the DDI 330 or the HCP to follow the treatment and react it something in the communication indicates that the treatment does not provide the intended results or if something appears to be wrong with any of the components in the system. If patient feedback from the patient display device 334 indicates that a new treatment step of the implant is needed, such information must be confirmed by direct contact between HCP and patient.

In the specific embodiment disclosed in FIG. 66A, the wireless connections between the different units are as follows. The wireless connection 411 between the auxiliary device 336 and the DDI 330 is based on WiFi or a mobile telecommunication regime or may be sent to the DDI 330 via the P-EID 320'' and the wireless connection 411 between the auxiliary device 336 and the patient's display device 334 is based on BT or any other communication pathway disclosed herein. The wireless connection 412 between the patient's display device 334 and the DDI 330 is based on WiFi or a mobile telecommunication regime. The wireless connection 413 between the patient's display device 334 and the remote control 320" is based on BT or any other communication pathway disclosed herein. The wireless connection 414 between the patient remote control 320" and the implanted medical device 100 is based on BT and UWB or any other communication pathway disclosed herein. The wireless connection 415 between the remote control 320" and the DDI 330 is likely to not be used, and if present be based on WiFi or a mobile telecommunication regime. The wireless connection 416 between the P-EID 320'" and the implanted medical device 100 is based on BT, UWB and the charging signal or any other communication or energizing pathway disclosed herein. The wireless connection 417 between the P-EID 320'" and the DDI 330 is based on WiFi or a mobile telecommunication regime. The wireless connection 418 between the HCP-EID 320' and the implanted medical device 100 is based on at least one of the BT, UWB and the charging signal. The wireless connection 419 between the P-EID 320'" and the HCP DD 332 is based on BT or any other communication path disclosed herein. The wireless connection 420 between the HPC-EID 320' and the DDI 330 is based on WiFi or a mobile telecommunication regime. The wireless connection 421 between the HPC DD 332 and the DDI 330 is normally closed and not used and if so based on WiFi or a mobile telecommunication regime. The wireless connection 422 between the HCP-EID 320' and the HCP DD 332 is based on at least one of BT, UWB, local network or any other communication path disclosed herein.

The wireless connections specifically described in the embodiment shown in FIG. 66A may however be replaced or assisted by wireless connections based on radio frequency identification (RFID), near field communication (NFC), Bluetooth, Bluetooth low energy (BLE), or wireless local area network (WLAN). The mobile telecommunication regimes may for example be 1G, 2G, 3G, 4G, or 5G. The wireless connections may further be based on modulation techniques such as amplitude modulation (AM), frequency modulation (FM), phase modulation (PM), or quadrature amplitude modulation (QAM). The wireless connection may further feature technologies such as time-division multiple access (TDMA), frequency-division multiple access (FDMA), or code-division multiple access (CDMA). The wireless connection may also be based on infra-red (IR) communication. The wireless connection may feature radio frequencies in the high frequency band (HF), very-high frequency band (VHF), and the ultra-high frequency band (UHF) as well as essentially any other applicable band for electromagnetic wave communication. The wireless connection may also be based on ultrasound communication to name at least one example that does not rely on electromagnetic waves.

Figure 66C:
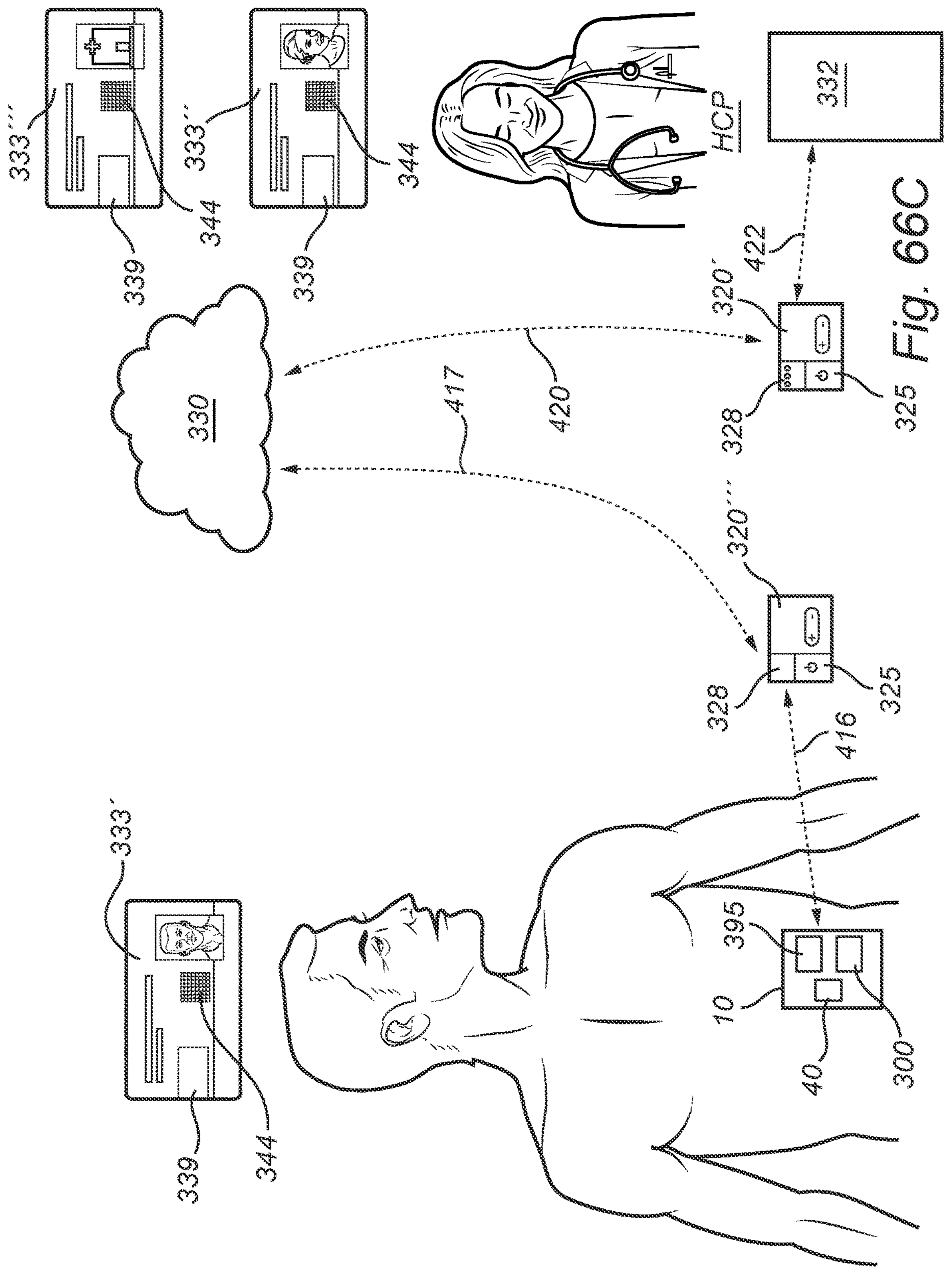

FIG. 66C also discloses a master private key 333'" device that allow issuance of new private key device wherein the HCP or HCP admin have such master private key 333'" device adapted to be able to replace and pair a new patient private key 333' device or HCP private key device 333" into the system, through the HCP EID external device 320'.

A system configured for changing pre-programmed treatment settings of an implantable medical device, when implanted in a patient, from a distant remote location in relation to the patient, will be discussed in the following.

FIG. 66A discloses a scenario in which at least one health care provider, HCP, external device 320' is adapted to receive a command from the HCP to change said pre-programmed treatment settings of an implanted medical device 100, further adapted to be activated and authenticated and allowed to perform said command by the HICP providing a HCP private key device 333". The HCP EID external device 320' further comprising at least one wireless transceiver 328 configured for communication with a patient EID external device 320'", through a first network protocol. The system comprises the patient EID external device 320'", the patient EID external 320'" device being adapted to receive command from said HCP external device 320', and to relay the received command without modifying said command to the implanted medical device 100. The patient EID external device 320'" comprises a wireless transceiver 328. The patient EID 320'" is adapted to send the command to the implanted medical device 100, to receive a command from the HCP to change said pre-programmed treatment settings of the implanted medical device 100, and further to be activated and authenticated and allowed to perform said command by the patient providing a patient private key 333' device comprising a patient private key.

Although wireless transfer is primarily described in the embodiment disclosed with reference to FIG. 66A the wireless communication between any of the external device may be substituted for wired communication. Also, some or all of the wireless communication between an external device and the implanted medical device 100 may be substituted for conductive communication using a portion of the human body as conductor.

FIG. 66B shows a portion of FIG. 66A, in which some of the components have been omitted to outline a specific scenario. In the scenario outlined in FIG. 66B, the system is configured for changing pre-programmed treatment settings of an implantable medical device 100, when implanted in a patient, from a distant remote location in relation to the patient. The system of FIG. 66B comprises at least one HCP EID 320' external device adapted to receive commands from the HCP to change said pre-programmed treatment settings of an implanted medical device 100. The HCP EID 320' external device is further adapted to be activated and authenticated and allowed to perform said command by the HCP providing a HCP private key device 333" adapted to be provided to the HCP EID external device 320'. The private key device 333" is adapted to be provided to the HCP EID external device 320' via at least one of: a reading slot or comparable for the HCP private key device 333", and an RFID communication or other close distance wireless activation communication.

The HCP EID external device 320' comprises at least one of: a reading slot or comparable for the HCP private key device 333", an RFID communication, and other close distance wireless activation communication or electrical direct contact. The HCP EID external device 320' further comprises at least one wireless transceiver 328 configured for communication with a dedicated data infrastructure server (DDI) 330, through a first network protocol. The system further comprises a dedicated data infrastructure server (DDI) 330, adapted to receive command from said HCP EID external device 320', adapted to relay the received commands without modifying said command to a patient EID external device 320'". The dedicated data infrastructure server (DDI) 330 further comprises a wireless transceiver 328 configured for communication with said patient external device. The system further comprises a patient EID external device 320'" adapted to receive the command relayed by the dedicated data infrastructure server (DDI) 330 and further adapted to send commands to the implanted medical device 100 and further adapted to receive commands from the HCP EID external device 320' via the dedicated data infrastructure server (DDI) 330 to change said pre-programmed treatment settings of the implanted medical device 100. The patient EID external device 320''' may further be adapted to be activated and authenticated and allowed to perform said command by the patient providing a patient private key device 333', which may be adapted to be provided to the patient EID external device 320''' by the patient via at least one of: a reading slot or comparable for the patient private key device 333', an RFID communication or other close distance wireless activation communication or electrical direct contact. The patient EID external device 320''' further comprises at least one of: a reading slot or comparable for the HCP private key device, an RFID communication and other close distance wireless activation communication or electrical direct contact. The patient EID external device 320''' further comprises at least one wireless transceiver 328 configured for communication with the implanted medical device 100 through a second network protocol. The implanted medical device 100 is in turn configured to treat the patient or perform a bodily function.

The scenario described with reference to FIG. 66B may in alternative embodiments be complemented with additional units or communication connections, or combined with any of the scenarios described with reference to FIGS. 66C-66F.

FIG. 66C shows a portion of FIG. 66A, in which some of the components have been omitted to outline a specific scenario. In the scenario outlined in FIG. 66C, a system configured for changing pre-programmed treatment settings of an implantable medical device 100 is disclosed. The changing of the pre-programmed treatment settings is performed by a health care provider (HCP) in the physical presence of the patient. The system comprises at least one HCP EID external device 320' adapted to receive commands from the HCP, directly or indirectly, to change said pre-programmed treatment settings in steps of an implantable medical device 100, when implanted. The HCP EID external device 320' is further adapted to be activated, authenticated, and allowed to perform said command by the HCP providing a HCP private key device 333" comprising a HCP private key. The HCP private key device in the embodiment of FIG. 119*c* comprises at least one of: a smart card, a keyring device, a watch, a arm or wrist band, a necklace, and any shaped device. The HCP EID external device 320' is adapted to be involved in at least one of: receiving information from the implant 100, receiving information from a patient remote external device 336, actuating the implanted medical device 100, changing pre-programmed settings, and updating software of the implantable medical device 100, when implanted. The HCP EID external device 320' is adapted to be activated, authenticated, and allowed to perform said command also by the patient, the system comprises a patient private key device 333' comprising a patient private key. The patient private key device 333' may comprise at least one of: a smart card, a keyring device, a watch, a arm or wrist band, a necklace, and any shaped device. The HCP private key 333" and the patient's private key may be required for performing said actions by the HCP EID external device 320' to at least one of: receive information from the implant 100, to receive information from a patient remote external device 336, to actuate the implanted medical device 100, to change pre-programmed settings, and to update software of the implantable medical device 100, when the implantable medical device is implanted.

Figure 66D:
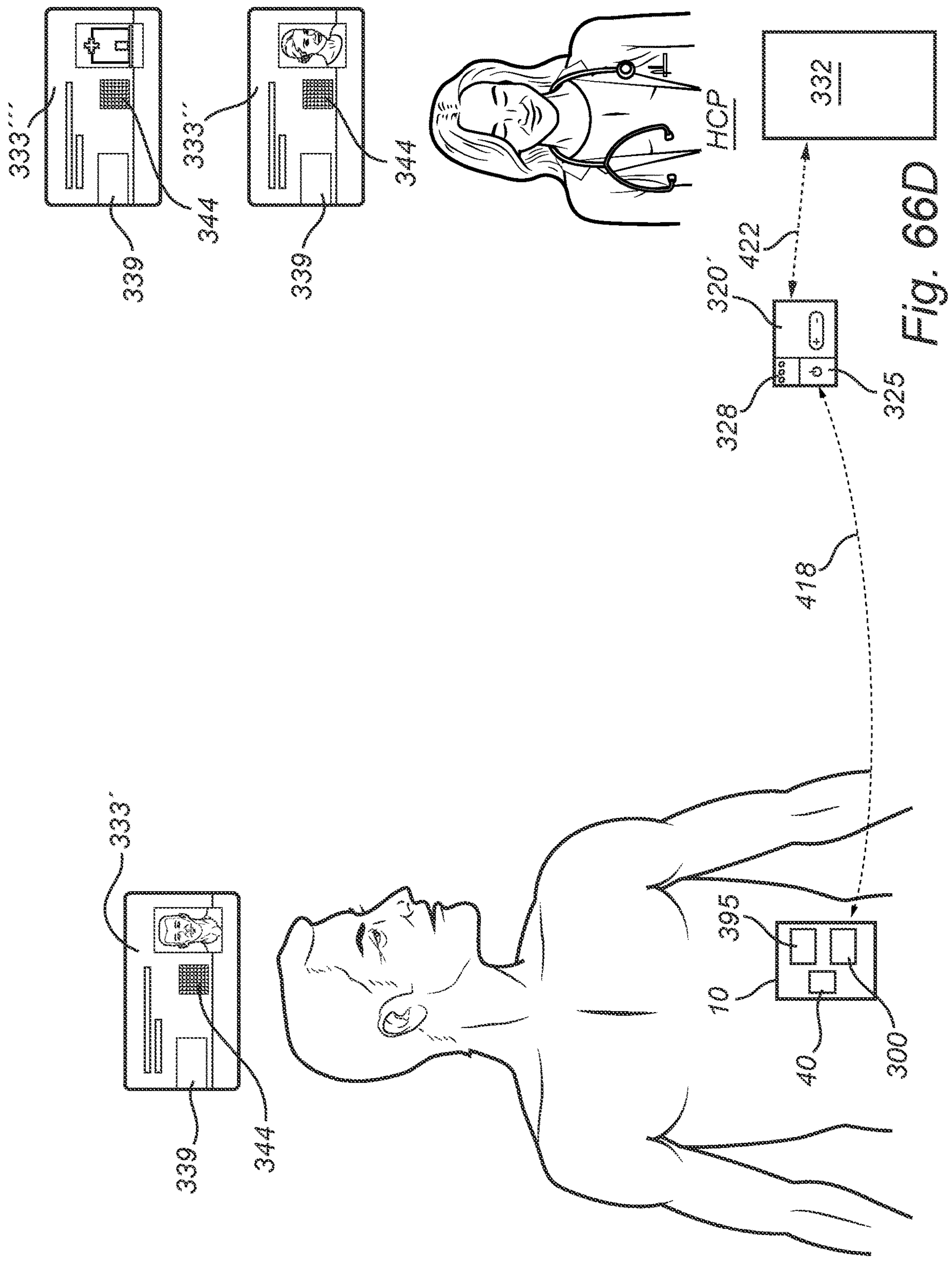

FIG. 66D) also outlines a scenario in which the system is configured for changing pre-programmed treatment settings in steps of an implantable medical device, when implanted in a patient, by a health care provider, HCP, wherein the patient may be located at a remote location, or on a distance. The system may comprise: at least one HCP EID external device 320' adapted to receive a command from the HCP, directly or indirectly, to change said pre-programmed treatment settings in steps of an implanted medical device The HCP EID external device 320' is further adapted to be activated, authenticated, and allowed to perform said command by the HCP. The action by the HCP EID external device 320' to change pre-programmed settings in the implant 100 and to update software of the implantable medical device 100, when the implantable medical device 100 is implanted, is adapted to be authenticated by a HCP private key device 333" and a patient private key device 333'.

The scenario described with reference to FIG. 66C may in alternative embodiments be complemented with additional units or communication connections, or combined with any of the scenarios described with reference to FIG. 66C, or 66E-66F.

Figure 66E:
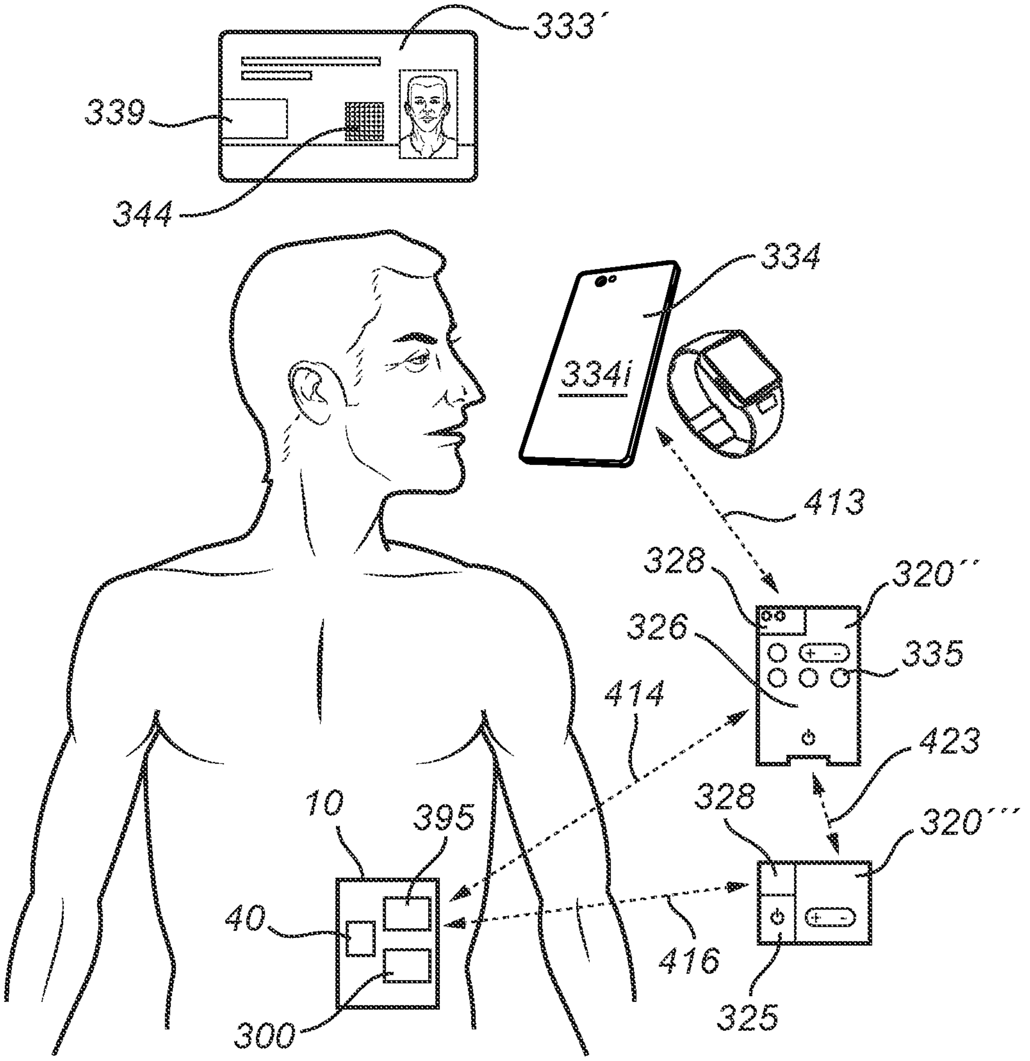

FIG. 66E shows a portion of FIG. 66A, in which some of the components have been omitted to outline a specific scenario. In the scenario outlined in FIG. 66E, a system configured to change pre-programmed and pre-selected treatment actions of an implantable medical device 100 by a command from the patient is described. The system comprises an implantable medical device 100, a patient remote external device 320", and a wireless transceiver 328 configured for communication with the implantable medical device 100, when the medical device is implanted, through a second network protocol. The system further comprises a remote display portal interface 334*i* configured to receive content delivered from the patient remote external device 320" to expose buttons to express the will to actuate the functions of the implanted medical device 100 by the patient through the patient remote external device 320". The remote external device 320" is further configured to present the display portal remotely on a patient display device 334 allowing the patient to actuate the functions of the implanted medical device 100 through the display portal of the patient remote external device 320" visualised on the patient display device 334. In FIG. 66E, a further wireless connection 423 between the patient remote external device 320" and the patient EID external device 320''' is provided. This further wireless connection 423 could be a wireless connection according to any one of the wireless signaling methods and protocols described herein, and the communication can be encrypted.

The scenario described with reference to FIG. 66E may in alternative embodiments be complemented with additional units or communication connections, or combined with any of the scenarios described with reference to FIG. 66C, 66D, or 66F.

Figure 66F:
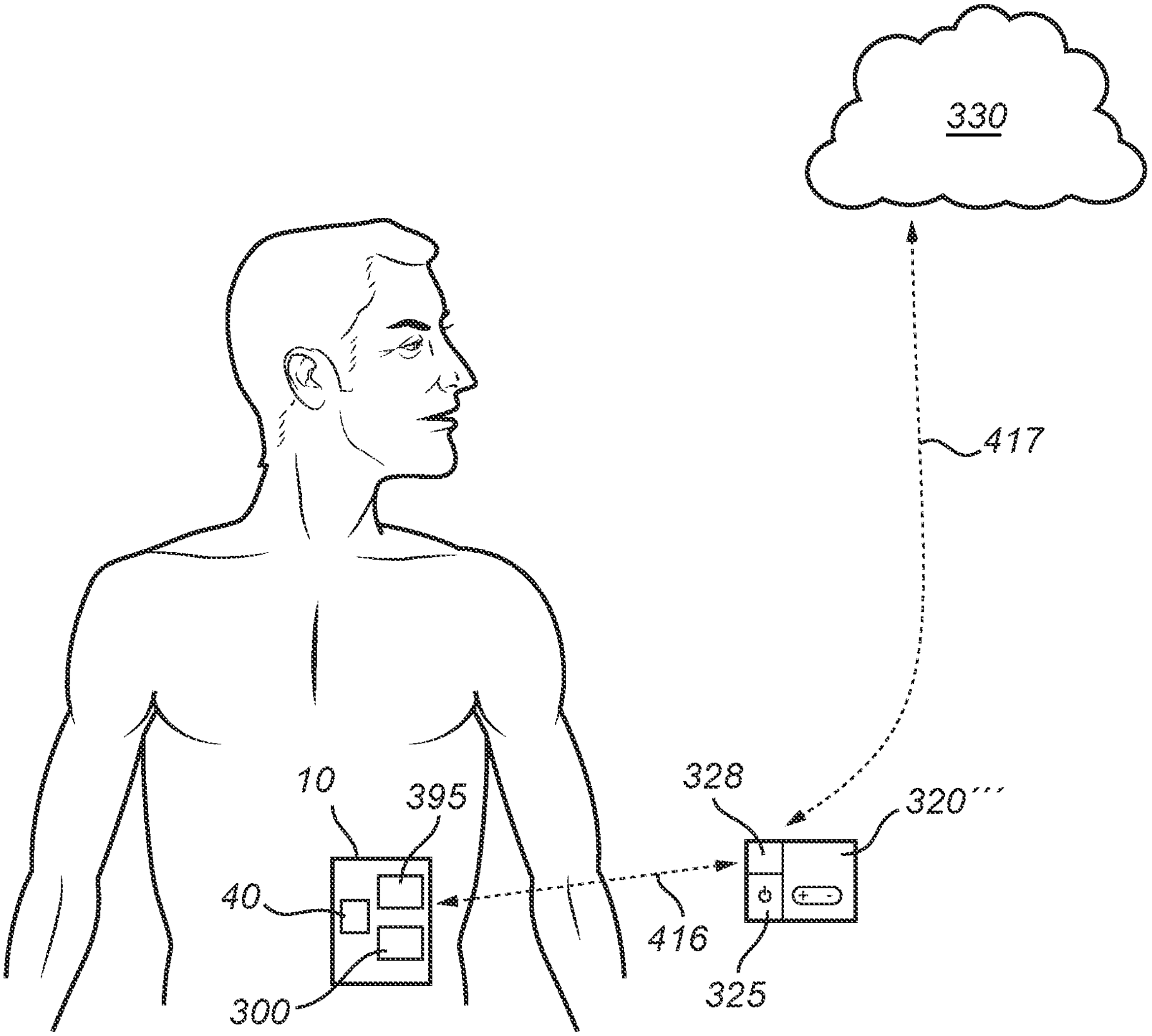

FIG. 66F shows a portion of FIG. 66A, in which some of the components have been omitted to outline a specific scenario. In the scenario outlined in FIG. 66F, a system configured for providing information from an implantable medical device 100, when implanted in a patient, from a distant remote location in relation to the patient is described. The system comprises at least one patient EID external device 320''' adapted to receive information from the implant 100, and to send such information further on to a server or dedicated data infrastructure, DDI, 330. The patient EID external device 320''' is further adapted to be activated and authenticated and allowed to receive said information from the implanted medical device 100 by the patient providing a private key. The patient private key device comprises the private key adapted to be provided to the patient EID external device 320''' via at least one of: a reading slot or comparable for the patient private key device, an RFID communication or other close distance wireless activation communication or direct electrical connection, The patient EID external device 320''' comprises at least one of: a reading slot or comparable for the patient private key device, an RFID communication and other close distance wireless activation communication or direct electrical contact. The patient EID external device 320''' further comprises at least one wireless transceiver 328 configured for communication with the DDI 330, through a first network protocol.

The scenario described with reference to FIG. 66F may in alternative embodiments be complemented with additional units or communication connections, or combined with any of the scenarios described with reference to FIGS. 66B-66E.

Figure 66G:
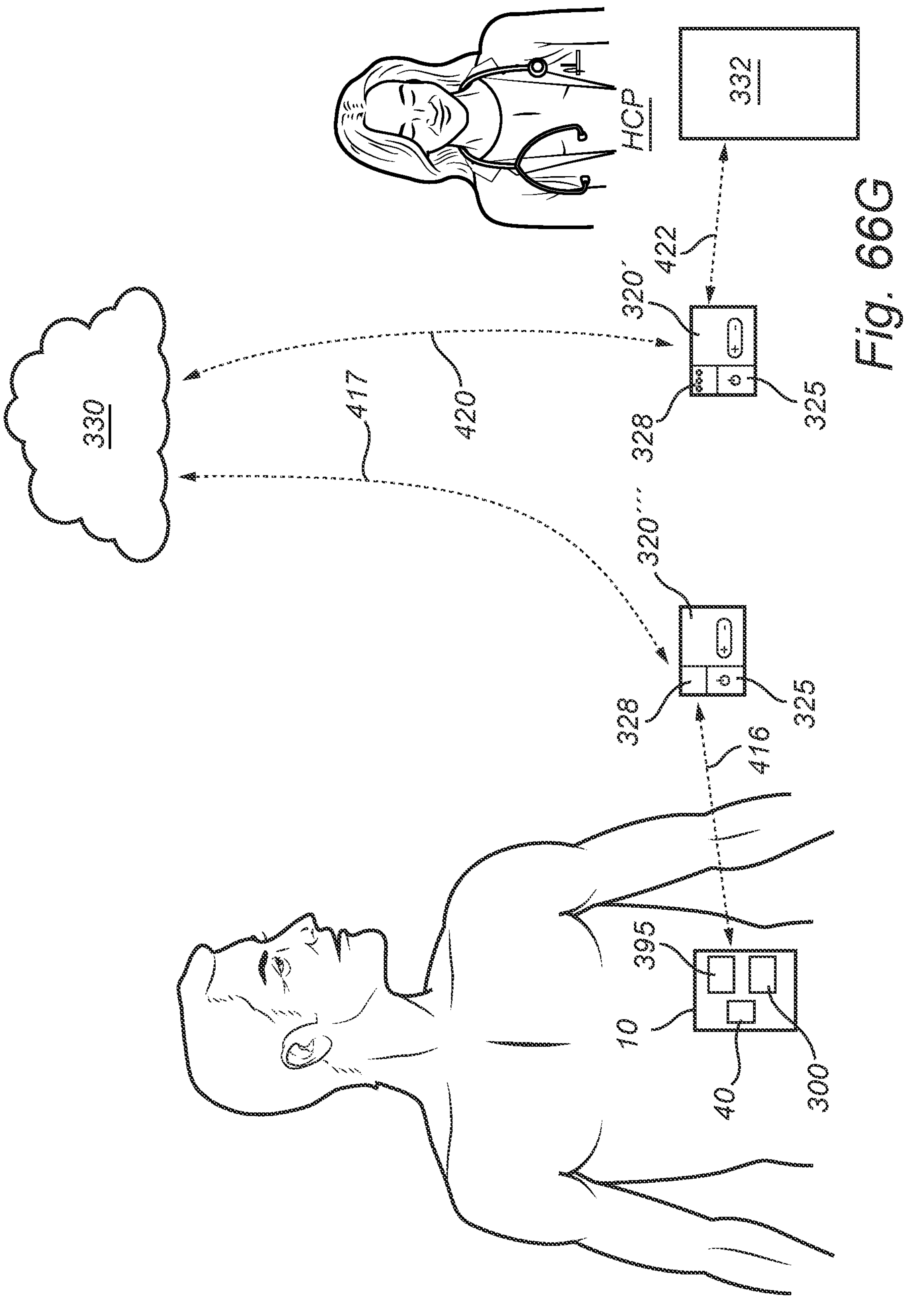

FIG. 66G shows a portion of FIG. 66A, in which some of the components have been omitted to outline a specific scenario. In the scenario outlined in FIG. 66G a system configured for changing pre-programmed treatment settings in steps of an implantable medical device 100, when implanted in a patient, by a health care provider, HCP, either in the physical presence of the patient or remotely with the patient on distance is described. The system comprises at least one HCP EID external device 320' adapted to receive a command directly or indirectly from the HCP to change said pre-programmed treatment settings in steps of the implantable medical device 100, when implanted, wherein the HCP EID external device 320' is further adapted to be activated, authenticated, and allowed to perform said command by the HCP providing a HCP private key device comprising a HCP private key. The HCP private key comprises at least one of: a smart card, a keyring device, a watch, an arm or wrist band, a necklace, and any shaped device. The system further comprises a patient private key device comprising a patient private key comprising at least one of: a smart card, a keyring device, a watch, an arm or wrist band, a necklace, and any shaped device. Both the HCP and patient private key is required for performing said action by the HCP EID external device 320' to change the pre-programmed settings in the implant 100 and to update software of the implantable medical device 100, when the implantable medical device 100 is implanted. The patient private key is adapted to activate, be authenticated, and allowed to perform said command provided by the HCP, cither via the HCP EID external device or when the action is performed remotely via a patient EID external device 320'. In the embodiment shown in FIG. 66G, the communication is routed over the DDI server 330.

The scenario described with reference to FIG. 66G may in alternative embodiments be complemented with additional units or communication connections, or combined with any of the scenarios described with reference to FIGS. 66C-66F.

Figure 66H:
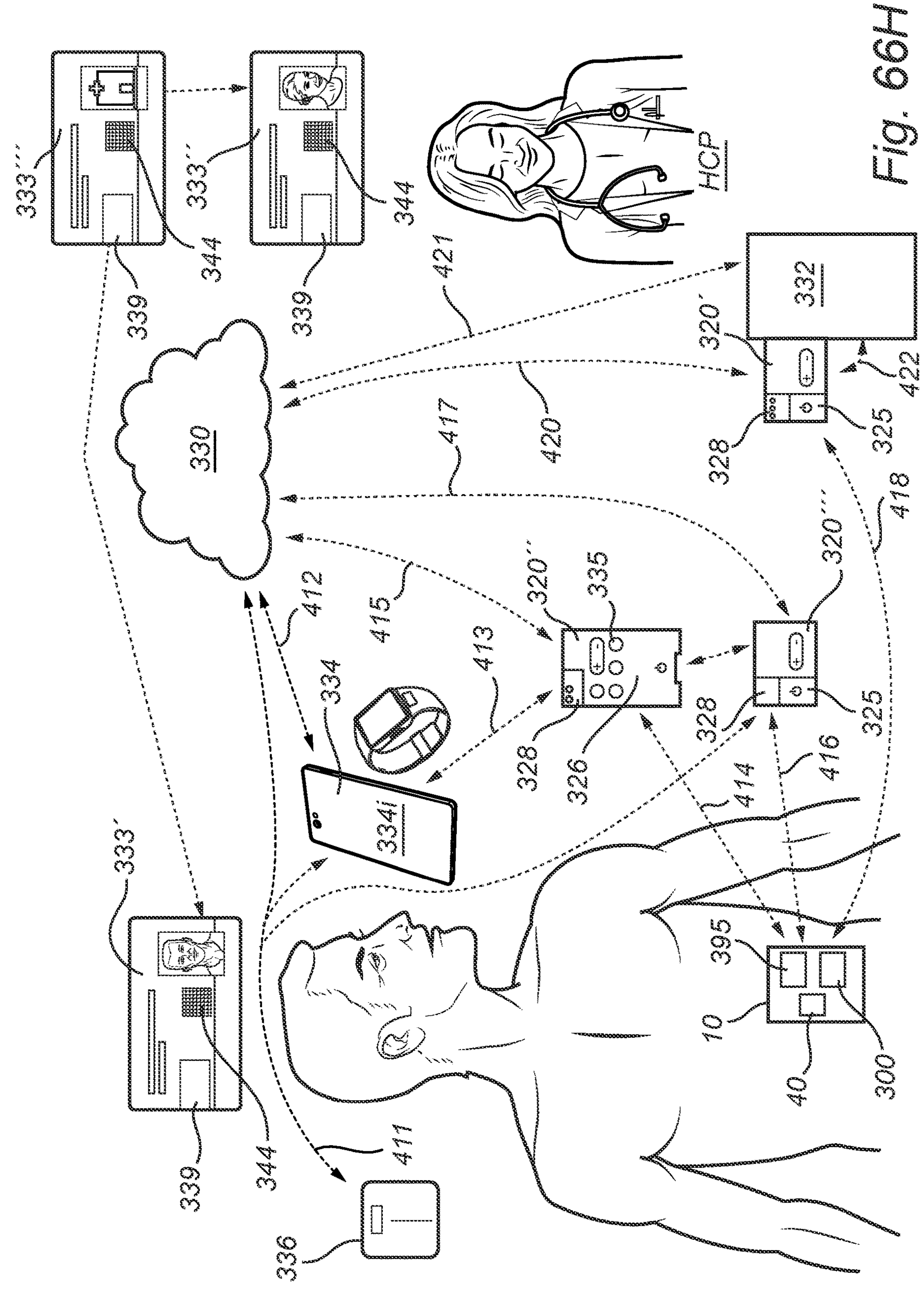

FIG. 66H shows an overview of an embodiment of the system, similar to the one described with reference to FIG. 66A, the difference being that the HCP EID and the HCP DDD are combined into a single device.

Figure 66I:
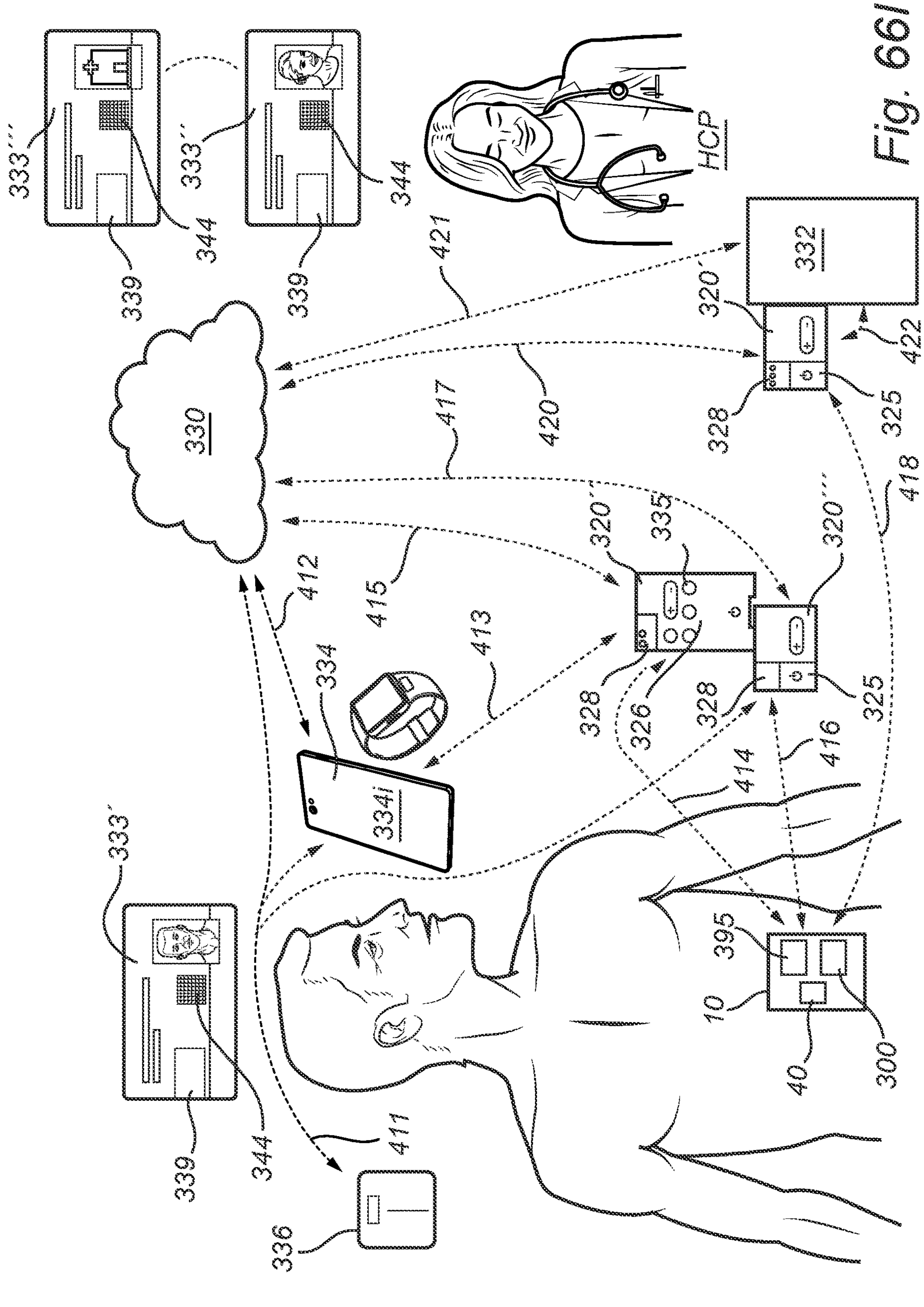

FIG. 66I shows an overview of an embodiment of the system, similar to that described with reference to FIG. 66A, the difference being that the HCP EID 320''' and the HCP DDD 332 are combined into a single device and the P EID 320''' and the patient remote control external device 320'' are combined into a single device.

One probable scenario/design of the communication system is for the purpose of changing pre-programmed treatment settings of an implantable medical device, when implanted in a patient, from a distant remote location in relation to the patient. The system comprises at least one health care provider, HCP, external device 320' adapted to receive a command from the HCP to change said pre-programmed treatment settings of an implanted medical device. The HCP external device 320' is further adapted to be activated and authenticated and allowed to perform said command by the HCP providing a HCP private key device 333'', which may be adapted to be provided to an HCP EID external device via at least one of: a reading slot or comparable for the HCP private key device, a RFID communication or other close distance wireless activation communication. The HCP EID external device comprises at least one of: a reading slot or comparable for the HCP private key device, a RFID communication, and other close distance wireless activation communication or electrical direct contact. The HCP EID external device further comprises at least one wireless transceiver configured for communication with a patient EID external device, through a first network protocol, wherein the system comprises the patient EID external device, the patient EID external device being adapted to receive command from said HCP external device, and to relay the received command without modifying said command to the implanted medical device. The patient EID external device comprising one wireless transceiver configured for communication with said patient external device. The patient FID is adapted to send the command to the implanted medical device, to receive a command from the HCP to change said pre-programmed treatment settings of the implanted medical device, and further to be activated and authenticated and allowed to perform said command by the patient providing a patient private key device comprising a patient private key.

Although the different scenarios outlined in FIGS. 66C-66I are described with specific units and method of signaling, these scenarios may very well be combined with each other or complemented with additional units or communication connections.

The embodiments described herein may advantageously be combined. A computer program product of, or adapted to be run on, an internal computing unit or an external device is also provided, which comprises a computer-readable storage medium with instructions adapted to make the internal computing unit and/or the external device perform the actions as described in any embodiment or example above.

The different aspects or any part of an aspect or different embodiments or any part of an embodiment may all be combined in any possible way. For example, all the embodiments relating to the communication and controlling of the implant may be combined with the embodiments relating to the programming of the implant, the methods, and systems for improving energy consumption or the power supply. The embodiments relating to the programming of the implant may be combined with any of the embodiments relating to improving the energy consumption or the power supply. The embodiments relating to the power supply maybe combined with the methods and systems for improving the energy consumption. Any method or any step of method may be seen also as an apparatus description, as well as, any apparatus embodiment, aspect or part of aspect or part of embodiment may be seen as a method description and all may be combined in any possible way down to the smallest detail. Any detailed description should be interpreted in its broadest outline as a general summary description, and please note that any embodiment or part of embodiment as well as any method or part of method could be combined in any way within the scope of the inventive concept, as defined by the appended claims. All examples herein should be seen as part of the general description and therefore possible to combine in any way in general terms.

As have been discussed before in this application, communication with a medical implant needs to be reliable and secure. For this purpose, it is desirable to have a standalone device as an external remote control (for example described as 320" in FIGS. 66A, 66B, 66C and 66H) for the medical implant, such that no other programs or applications run on the same device which may disturb or corrupt the communication to the medical implant. However, the smartphone or tablet (for example described as 334 in FIGS. 66A, 66B, 66E, 66H and 66I) has become an integrated part of everyday life for most people. This means that we almost always have our smartphones at hand. For this reason, it would have been convenient for the patient to communicate with the medical implant directly using the smartphone, such that no additional standalone device would have to be carried. However, as a lot of other applications are running on the smartphone, it does not fulfill the requirement of being a secure and reliable communication tool without interference from other communication. It is therefore desirable to split the tasks of providing secure communication between the external device and the implant from the task of communicating with the Internet and providing a familiar and intuitive user interface. For this purpose, and external device providing secure communication and tamperproof soft- and hardware, where the display device allows for intuitive and easy use is provided. In the embodiments described with reference to FIGS. 66J-66N a device fulfilling these combinatory needs will be described in the form of a standalone remote control external device integrated in a housing unit 320" connectable to a smartphone or another display device 334, such as a smart watch or a tablet.

Figure 66J:
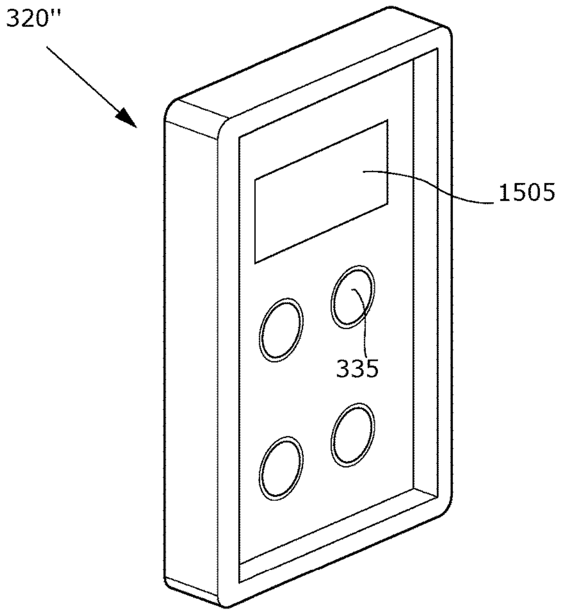
Figure 66K:
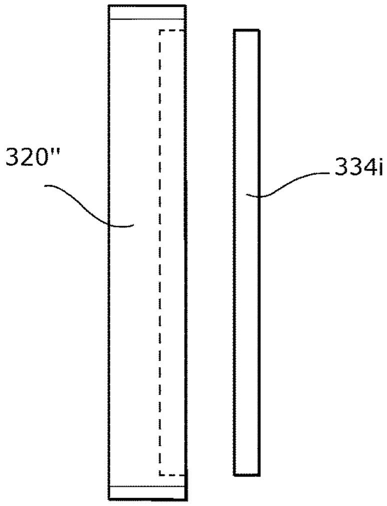

FIG. 66J shows the housing unit 320" in an elevated perspective view form the left, and FIG. 66K shows the housing unit 320" in a plain view from the left. In the embodiment shown in FIG. 66L, the housing unit 320" has a rectangular shape with rounded edges, having a height 1521 which is more than 1.5 times the width 1522. The housing unit 320" comprises recess 1525 configured to receive a display device 334, in the form of a smartphone, configured to be fitted in the housing unit 320" for mechanically, disconnectably connecting the display device 334 to the housing unit 320". The boundaries of the recess 1525 in the housing unit 320" forms an edge 1528 configured to encircle the display device 334, when the display device 334 is inserted into the recess 1525. In the embodiment shown in FIG. 66J, the recess 1525 has a depth 1526 configured to allow the display device 334 to be entirely inserted into the recess 1525. As such, the depth 1526 of the recess 1525 exceeds the depth 1531 of the display device 334. In the embodiment shown in FIGS. 66J and 66K, the edge is relatively thin, and has a width 1527 which is in the range ⅛-1⁄100 of the width of the display device 334, as such, the housing unit 320" has a width in the range 1.02-1.25 times the width 1522 of the housing unit 320". In the same way, the housing unit 320" has a height 1521 in the range 1·01-1.25 times the height 1521 of the display device 334. In the embodiment shown in FIGS. 66J-66K, the edges 1528 are configured to clasp the display device 334 and thereby mechanically fixate the display device 334 in the housing unit 320". The minimum bounding box of the housing unit 320" and the display device 334 when mechanically connected, is no more than, 10% wider, 10% longer or 100% higher, than the minimum bounding box of the display device 334.

For creating a clasping fixation, the edges of the housing unit 320" is made from an elastic material crating a tension between the edge 1528 and the display device 334 holding the display device 334 in place. The elastic material could be an elastic polymer material, or a thin sheet of elastic metal. For the purpose of further fixating the display device 334 in the housing unit 320", the inner surface of the edges 1528 may optionally comprise a recess or protrusion (not shown) corresponding to a recess or protrusion of the outer surface of the display device 334. The edges 1528 may in the alterative comprise concave portions for creating a snap-lock clasping mechanical fixation between the housing unit 320" and the display device 334.

In the embodiment shown in FIGS. 66J and 66K, the housing unit 320" functions as a remote control for communicating with an implanted medical device, including receiving information from, and providing instructions and updates to, the implanted medical device. Information could be information related to a state of the implanted medical device including any functional parameter of the implanted medical device or could be related to a state of the patient, including any physiological parameter pertaining to the body of the patient (further described on other sections of this disclosure). For the purpose of providing input to the implanted medical device and controlling and updating the functions of the housing unit 320", the housing unit 320" comprises a control interface comprising switches in the form of control buttons 335. The control buttons 335 are configured to be used when the external device is disconnected from the display device 334. The control interface further comprises a display 1505, which is a smaller and typically less sophisticated display 1505 than the display of the display device 334. In an alternative embodiment, the control buttons 335 and display 1505 are integrated into a single touch-responsive (touchscreen) display on which the control buttons may be displayed. In the embodiment shown in FIGS. 66J and 66K, one of the control buttons 335 is a control button for activating the implanted medical device and another of the control buttons 335 is a control button for deactivating the implanted medical device. When the display device 334 is attached to the housing unit 320", the control buttons 335 and the display is covered by the display device 334 and are as such not in an operational state. In the embodiment shown in FIGS. 66J and 66K, the housing unit 320" is configured to transmit information pertaining to the display of the user interface to the display device 334 and the display device 334 is configured to receive input pertaining to communication to or from the implantable medical device from the patient, and transmit signals based on the received input to the housing unit 320". The input may be a command to change the operational state of the implantable medical device. The display device 334 comprises a touch screen configured to display the user interface and receive the input from the patient. The display of the display device 334 may comprise one or more OLEDs or IPS LCDs elements. When the display device 334 is connected to the housing unit 320", the display device 334 is configured to display a control interface which is used to communicate with the housing unit 320", i.e. providing input to and receiving information from the housing unit 320". The input provided the housing unit 320" is then relayed to the implanted medical device—and in the same way information communicated from the implanted medical device to the housing unit 320" may be relayed or displayed on the display device 334. Having an external device comprising a combination of a housing unit 320" comprising the communication means for communicating with the implanted medical device and a display device 334 basically only functioning as and Input/Output device connected to the housing unit 320" makes it possible to have a secure communication between the housing unit 320" and the display device 334, which is out of reach from the Internet connection of the display device 334, which makes it much harder for an external attacker to get access to any of the vital communication portions of the housing unit 320". The communication between the housing unit and the display device 334 is very restricted and the only communication allowed from the display device 334 to the housing unit 320" is input from the patient or a healthcare professional, and authentication parameters created by an authentication application running on the display device 334. The authentication application running on the display device 334 could be a number-generating authenticator or a biometric authenticator for authenticating the patient or health care professional, and the authentication parameters could for example be parameters derived from a facial image or a fingerprint. In the opposite direction, i.e. from the housing unit 320" to the display device 334, the communication could be restricted to only communication needed for displaying information and/or a graphical user interface on the display device 334. The communication restrictions could for example be based on size of the communication packages or the frequency with which the communication takes place which reduces the risk that an un-authorized person makes multiple attempts to extract information from, or transit information to, the hand-held device.

In the embodiment shown with reference to FIGS. 66J and 66K, the housing unit 320" comprises a first communication unit providing a wireless connection 413 to the display device 334. The wireless connection 413 is in the embodiment shown in figs-66J and 66K based on NFC, but could in alternative embodiment be based on Bluetooth or any other communication pathway disclosed herein. The housing unit 320" further comprises a second communication unit providing a wireless connection with the implanted medical device. The wireless communication between the housing unit 320" and the implanted medical device is in the embodiment shown in FIGS. 66J and 66K based on Bluetooth, but could in alternative embodiments be based on NFC or UWB or any other communication pathway disclosed herein.

As mentioned, in the embodiment shown in FIGS. 66J and 66K, the wireless communication between the housing unit 320" and the display device 334 is based on NFC, while the wireless communication between the housing unit 320" and the is based on Bluetooth. As such, the first communication unit of the housing unit 320" is configured to communicate wirelessly with the display device 334' using a first communication frequency and the second communication unit of the housing unit 320" is configured to communicate wirelessly with the implantable medical device using a second different communication frequency. For this purpose, the first communication unit of the housing unit 320" comprises a first antenna configured for NFC-based wireless communication with the display device 334, and the second communication unit comprises a second antenna configured for Bluetooth-based wireless communication with the implantable medical device. The first and second antennae may be a wire-based antennae or a substrate-based antennae. As such, the first communication unit is configured to communicate wirelessly with the display device 334 on a first frequency and the second communication unit is configured to communicate wirelessly with the implantable medical device using a second different communication frequency. Also, first communication unit of the housing unit 320' is configured to communicate wirelessly with the display device 334 using a first communication protocol (the NFC-communication protocol), and the second communication unit is configured to communicate wirelessly with the implantable medical device using a second communication protocol (the Bluetooth communication protocol). The first and second communication protocols are different which adds an additional layer of security as security structures could be built into the electronics and/or software enabling the transfer from a first to a second communication protocol.

In an alternative embodiment, the second communication unit may be configured to communicate wirelessly with the implantable medical device using electromagnetic waves at a frequency below 100 kHz, or preferably at a frequency below 40 kHz. The second communication unit may thus be configured to communicate with the implantable medical device using "Very Low Frequency" communication (VLF). VLF signals have the ability to penetrate a titanium housing of the implant, such that the electronics of the implantable medical device can be completely encapsulated in a titanium housing. In yet further embodiments, the first and second communication units may be configured to communicate by means of an RFID type protocol, a WLAN type protocol, a BLE type protocol, a 3G/4G/5G type protocol, or a GSM type protocol.

In yet other alternative embodiments, it is conceivable that the mechanical connection between the housing unit 320" and the display device 334 comprises an electrical connection for creating a wire-based communication channel between the housing unit 320" and the display device 334. The electrical connection could also be configured to transfer electric energy from the display device 334 to the housing unit, such that the housing unit 320" may be powered or charged by the display device 334. A wired connection is even harder to access for a non-authorized entity than an NFC-based wireless connection, which further increases the security of the communication between the housing unit 320" and the display device 334.

In the embodiment shown with reference to FIGS. 66J and 66K, the display device 334 comprises a first communication unit providing a wireless connection 413 to the housing unit 320" based on NFC. The display device 334 further comprises a second communication unit providing a wireless connection with a further external device and/or with the Internet. The second external device may be far away, for example at a hospital or a place where a medical professional practice. The wireless communication between the display device 334 and a further external device is in the embodiment shown in FIGS. 66J and 66K based on WiFi, but could in alternative embodiments be based on for example Bluetooth.

As mentioned, in the embodiment shown in FIGS. 66J and 66K, the wireless communication between the display device 334 and the housing unit 320" is based on NFC, while the wireless communication between the display device and a further external unit is based on WiFi. As such, the first communication unit of the display device 334 is configured to communicate wirelessly with the housing unit 320" using a first communication frequency and the second communication unit of the display device 334 is configured to communicate wirelessly with a further external device using a second different communication frequency. For this purpose, the first communication unit of the display device 334 comprises a first antenna configured for NFC-based wireless communication with the housing unit 320", and the second communication unit comprises a second antenna configured for WiFi-based wireless communication with a further external device. The first and second antennae may be wire-based antennae or substrate-based antennae. As such, the first communication unit is configured to communicate wirelessly with the housing unit 320" on a first frequency and the second communication unit is configured to communicate wirelessly with the further external device using a second different communication frequency. Also, the first communication unit of the display device 334 is configured to communicate wirelessly with the housing unit 320" using a first communication protocol (the NFC communication protocol), and the second communication unit is configured to communicate wirelessly with the further external device using a second communication protocol (the WiFi communication protocol). The first and second communication protocols are different which adds an additional layer of security as security structures could be built into the electronics and/or software enabling the transfer from a first to a second communication protocol.

In alternative embodiments, the second communication unit of the display device 334 may be configured to communicate with the further external device by means of, a WLAN type protocol, or a 3G/4G/5G type protocol, or a GSM type protocol.

In the embodiment shown in FIGS. 66J and 66K, the communication range of the first communication unit of the housing unit 320" is less than a communication range of the second communication unit of the housing unit 320', such that the communication distance between the housing unit 320" and the medical implant may be longer than the communication distance between the housing unit 320" and the display device 334. In the embodiment shown in FIGS. 66J and 66K, the communication range of the first communication unit may be constrained to a length that is less than five times the longest dimension of the minimal bounding box of the display device 334, or more precisely constrained to a length that is less than three times the longest dimension of the minimal bounding box of the display device 334.

In the embodiment shown in FIGS. 66J and 66K, communication between the housing unit 320" and the display device 334 is only enabled when the housing unit 320" is connected to the display device 334. I.e. at least one of the housing unit 320" and the display device 334 is configured to allow communication between the housing unit 320" and the display device 334 on the basis of the distance between the housing unit 320" and the display device 334. In the alternative, the housing unit 320" and/or the display device 334 may comprise a sensor configured to estimate whether the housing unit 320" is attached to the display device 334 or not, such as a mechanically activated switch or a photo resistive sensor which providing sensor input when the housing unit 320" and display device 334 are mechanically connected to each other. The signal from the at least one sensor then may be used to permit usage of the communication unit configured for communication with the display device 334.

In the embodiment shown in FIGS. 66J and 66K, communication between the housing unit 320" and the implantable medical device is only enabled on the basis of a distance between the housing unit 320" and the implantable medical device. In the embodiment shown in FIGS. 66J and 66K, the distance should be less than twenty times the longest dimension of the minimal bounding box of the display device, or more specifically less than ten times the longest dimension of the minimal bounding box of the display device. The distance between the housing unit 320" and the medical implant may be measured using electromagnetic waves, or acoustic waves. The process of measuring the distance may comprise triangulation.

In the embodiment shown in FIGS. 66J and 66K, the second communication unit of the display device 334 need to be disabled to enable communication between the display device 334 and the housing unit 320", and further the second communication unit of the display device 334 needs to be disabled to enable communication between the housing unit 320" and the medical implant. Also, the second communication unit of the housing unit 320" needs to be disabled to enable communication between the housing unit 320" and the medical implant.

In the embodiment shown in FIGS. 66J and 66K, the housing unit 320" further comprises an encryption unit configured to encrypt communication received from the display device 334 before transmitting the communication to the implanted medical device. The encryption unit may for example be based on one of the following algorithms: AES, Blowfish, DES, Kalyna, Serpent or Twofish. For the purpose for handling the communication, I/O and encryption, the housing unit 320" comprises a processor which could be a general-purpose microprocessor and/or an instruction set processor and/or related chips sets and/or special purpose microprocessors such as ASICs (Application Specific Integrated Circuit). The processor also comprise memory for storing instruction and/or data.

Figure 66L:
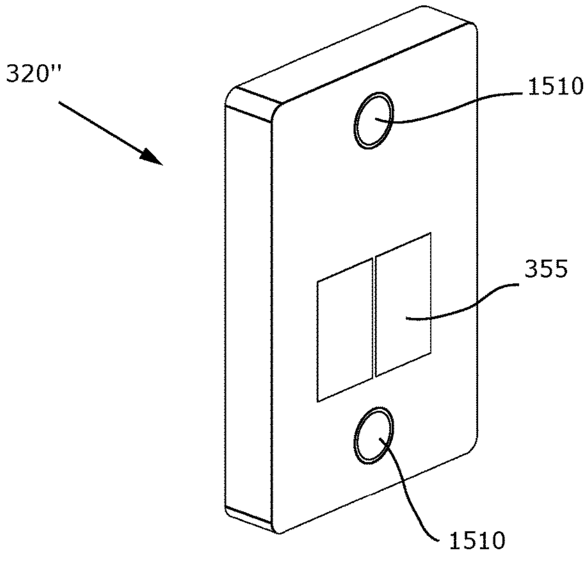
Figure 66M:
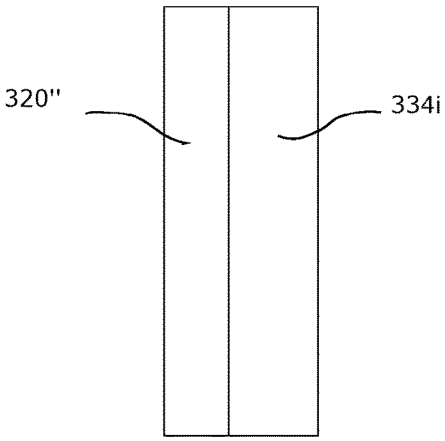

FIGS. 66I, and 66M shows an embodiment of the external device similar to the embodiment described with reference to FIGS. 66J and 66K. The difference being that in the embodiment of FIGS. 66L and 66M, the housing unit 320" does not clasp the display device 334. Instead, the housing unit comprises two magnets 1510 for magnetically fixating the display device 334 to the housing unit 320". In alternative embodiments, it is equally conceivable that the external device comprises an intermediate portion, which is fixedly fixated to the housing unit for providing a detachable connection with the display device 334. In the alternative, the intermediate device could be fixedly fixated to the display device 334 and provide a detachable connection with the housing unit 320".

Figure 66N:
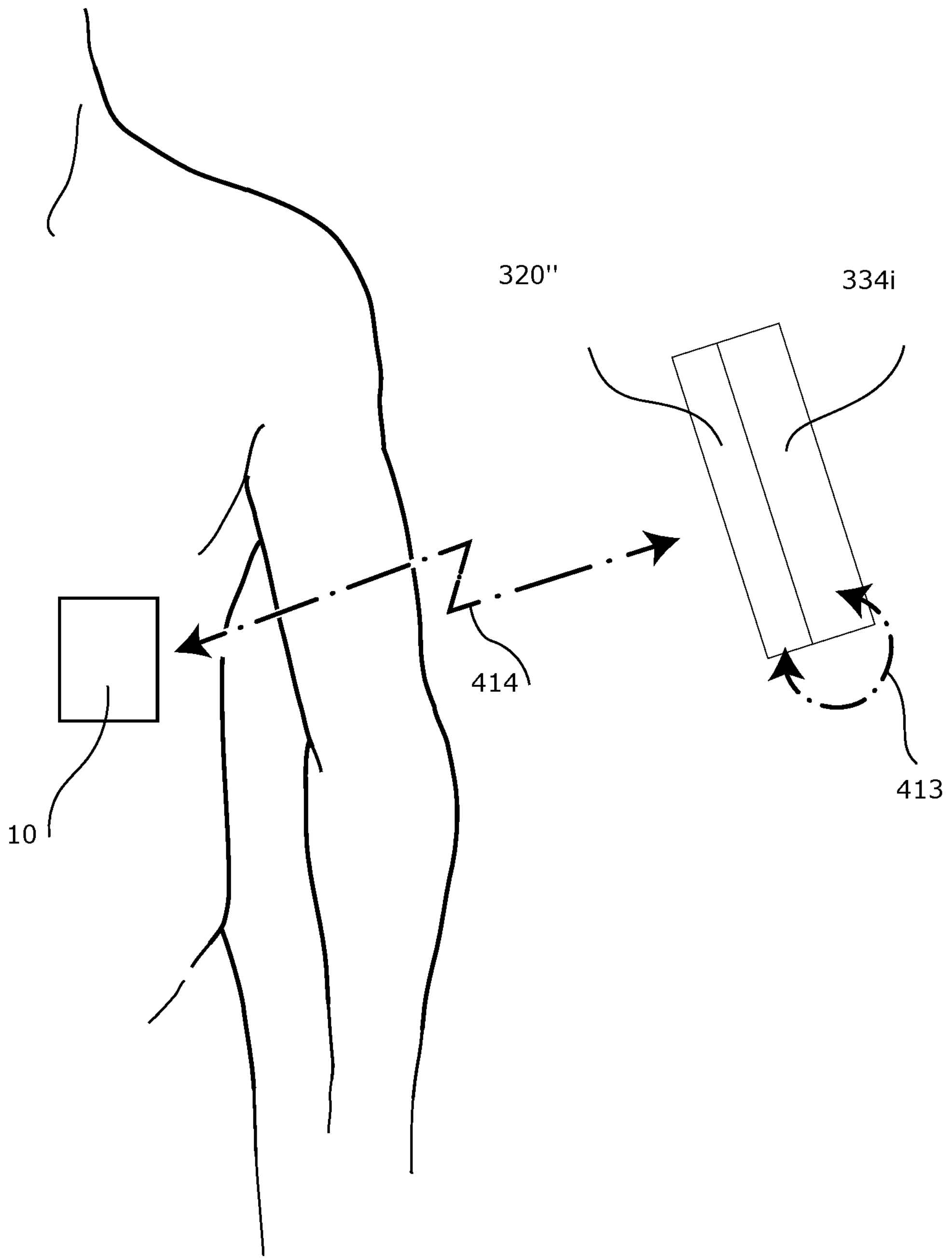

FIG. 66N shows a system overview of the external device (which could be the external device of the embodiment described with reference to FIGS. 66J and 66K, or of the embodiment described with reference to FIGS. 66L and 66M). The housing unit 320" is connected to the display device 334. A wireless connection 413 is provided between the housing unit 320" and the display device 334, and a further wireless connection 413 is provided between the housing unit 320" and the implantable energized medical device 10, such that the housing unit can send instructions and updates to the implantable energized medical device 10, and receive information, parameters (such as sensor values) and alarms from the implantable energized medical device 10. The communication between the external device and the medical implant 100 is further described in other portions of this disclosure.

In the following, numbered aspect groups 260SE-449ZPC of the present invention are provided. The different aspects are numbered individually within the groups and the references to other aspects relate to aspects within the same group. The scope of protection is however defined by the appended claims.

Aspect Group 260SE:
Reflux_Stop_Exercise_General

1. An apparatus (100) for treating reflux disease of a human patient, comprising:

an implantable movement restriction device (110) having a shape and size allowing it to be arranged to rest against a fundus wall portion (14) of the patient's stomach (10) and to be at least partly invaginated by the fundus wall portion, such that the movement restriction device is implanted at a position between the patient's diaphragm (30) and a lower portion of the fundus wall, and such that movement of the cardia (22) of the patient's stomach towards the diaphragm is restricted to hinder the cardia from sliding through the diaphragm opening (32) into the patient's thorax; and an electrode arrangement (150) configured to engage and electrically stimulate muscle tissue of the fundus wall portion to exercise the muscle tissue to improve the conditions for long term implantation of the movement restriction device.

2. The apparatus according to aspect 1, wherein the electrode arrangement is arranged on an outer surface of the movement restriction device.

3. The apparatus according to aspect 1 or 2, wherein the electrode arrangement comprises a plurality of electrode elements (152), each of which being configured to engage and electrically stimulate the muscle tissue.

4. The apparatus according to any of the preceding aspects, wherein the electrode arrangement comprises a coiled wire for increasing a contact surface between the electrode arrangement and the muscle tissue and for allowing the electrode arrangement to follow contraction and relaxation of the muscle tissue.

5. The apparatus according to any of the preceding aspects, wherein the electrode arrangement comprises a bare electrode portion (155) configured to form a metal-tissue interface with the muscle tissue, thereby allowing faradaic charge transfer to the be predominant charge transfer mechanism over said interface.

6. The apparatus according to any of the preceding aspects, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.

7. The apparatus according to any of the preceding aspects, wherein the electrode arrangement is further configured to be arranged to electrically stimulate the cardiac sphincter to cause the cardiac sphincter (26) to contract.

8. The apparatus according to aspect 7, wherein the electrode arrangement comprises at least two electrode elements (154) configured to be arranged on opposing sides of the cardiac sphincter.

9. The apparatus according to aspect 8, further comprising a holder configured to support the at least two electrode elements at the opposing sides of the cardiac sphincter.

10. The apparatus according to any of the preceding aspects, further comprising an implantable energy source (160) configured to provide the electrode with electrical power.

11. The apparatus according to aspect 10, wherein the implantable energy source is arranged inside the movement restriction device.

12. The apparatus according to aspect 10, wherein the implantable energy source is configured to be arranged outside the movement restriction device.

13. The apparatus according to aspect 12, wherein the implantable energy source is configured to be implanted subcutaneously.

14. The apparatus according to any of aspects 10-13, wherein the implantable energy source comprises a primary cell.

15. The apparatus according to any of aspects 10-14, wherein the implantable energy source comprises a secondary cell.

16. The apparatus according to aspect 14 or 15, further comprising a controller (170) configured to indicate a functional status of the implantable energy source.

17. The apparatus according to aspect 16, wherein the functional status indicates a charge level of the implantable energy source.

18. The apparatus according to aspect 16 or 17, wherein the functional status indicates a temperature of at least one of the implantable energy source, the muscle tissue and the electrode arrangement.

19. The apparatus according to any of aspects 16-18, wherein the implantable energy source is configured to be charged by an external energy source (165) arranged outside the patient's body.

20. The apparatus according to aspect 19, further comprising an implantable charger (190) configured to be electrically connected to the implantable energy source and enable charging of the implantable energy source by the external energy source.

21. The apparatus according to aspect 20, wherein the charger comprises an electromagnetic coil configured to receive electrical power wirelessly from the external energy source.

22. The apparatus according to aspect 19 or 20, wherein the charger is configured to control the charging of the implantable energy source based on the functional status.

23. The apparatus according to any of aspects 20-22, wherein the charger is configured to control the charging of the implantable energy source by controlling a receipt of electrical power from the external energy source at the implantable charger.

24. The apparatus according to any of aspects 20-22, wherein the charger is configured to control the charging of the implantable energy source by controlling a transmission of electrical power from the external energy source to the implantable charger.

25. The apparatus according to any of aspects 1-15, further comprising a controller (170) configured to be operably connected to the electrode arrangement for controlling the electrical stimulation of the muscle tissue.

26. The apparatus according to aspect 25, wherein the controller is configured to control the electrical stimulation such that the muscle tissue is stimulated by a series of electrical pulses (PL1, PL2, PL3, PL4).

27. The apparatus according to aspect 26, wherein the controller is configured to control the electrical stimulation such that a pulse of a first polarity is followed by a pulse of a second, reversed polarity.

28. The apparatus according to any of aspects 25-27, wherein the controller is configured to generate a pulsed electrical stimulation signal comprising a pulse frequency (F) of 0.01-150 Hz.

29. The apparatus according to aspect 28, wherein the electrical stimulation signal comprises a pulse duration (D) of 0.01-100 ms.

30. The apparatus according to aspect 28 or 29, wherein the electrical stimulation signal comprises a pulse amplitude (A) of 1-15 mA.

31. The apparatus according to any of aspects 28-30, wherein the electrical stimulation signal comprises a pulse frequency of 0.15-0.25 Hz, a pulse duration of 20-30 ms and a pulse amplitude of 3-10 mA.

32. The apparatus according to any of aspects 28-31, wherein the electrical stimulation signal comprises a build-up period (X1) of 0.01-2 s in which the amplitude is gradually increasing, a stimulation period (X2) of 1-60 s, and a stimulation pause (X4) of 0.01-60 s, wherein the electrical signal comprises a pulse frequency of 1-50 Hz and a pulse duration of 0.1-10 ms.
33. The apparatus according to any of aspects 25-32, wherein the controller comprises a wireless remote control (175).
34. The apparatus according to aspect 33, wherein the wireless remote control comprises an external signal transmitter, and wherein the controller comprises an implantable controller configured to receive a signal transmitted by the external signal transmitter and to control an operation of the apparatus based on said signal.
35. The apparatus according to aspect 35, wherein the signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.
36. The apparatus according to any of aspects 25-35, further comprising an implantable sensor (S1) configured to sense actions potentials generated by pacemaker cells of the muscle tissue, and wherein the controller is configured to control the electrical simulation based at least partly on the sensed action potentials.
37. The apparatus according to aspect 36, wherein the controller is configured to generate electrical pulses amplifying the sensed action potentials.
38. The apparatus according to any of the preceding aspects, wherein a volume of the movement restriction device is non-adjustable after implantation.
39. The apparatus according to any of aspects 1-37, wherein a volume of the movement restriction device is adjustable after implantation.
40. The apparatus according to aspect 39, wherein the volume of the movement restriction device is adjustable invasively or non-invasively.
41. The apparatus according to aspect 39 or 40, wherein the movement restriction device comprises an injection port (115) for allowing a fluid to be injected or extracted from the inside of the movement restriction device so as to vary a volume of the movement restriction device after implantation.
42. The apparatus according to any of the preceding aspects, wherein the movement restriction device comprises a biocompatible outer surface configured to rest against the fundus wall portion.
43. The apparatus according to any of the preceding aspects, wherein the movement restriction device is substantially spherical or egg-shaped.
44. The apparatus according to any of aspects 1-42, wherein the movement restriction device has a portion configured to be arranged to point away from the esophagus when implanted.
45. The apparatus according to any of the preceding aspects, wherein the movement restriction device is configured to be invaginated when placed on the outside of the fundus wall portion.
46. The apparatus according to any of aspects 1-44, wherein the movement restriction device is configured to be invaginated when placed on the inside of the fundus wall portion.
47. The apparatus according to any of the preceding aspects, wherein the movement restriction device is configured to be introduced in the patient's body by means of a gastroscope or an intraluminal instrument.
48. The apparatus according to aspect 47, wherein the movement restriction device is configured to change its shape to allow it to pass through a trocar during insertion into the patient's body.
49. The apparatus according to any of the preceding aspects, wherein the movement restriction device is formed of at least two distinct and separable parts (111, 113) configured to be assembled into the movement restriction device after insertion in the patient's body.
50. The apparatus according to any of the preceding aspects, wherein a minimum width of the movement restriction device, as measured from side to side, is 30 mm or larger, such as 40 mm or larger.
51. The apparatus according to any of the preceding aspects, wherein a minimum outer circumference of the movement restriction device is 150 mm or less, such as 130 mm or less, such as 110 mm or less, such as 90 mm or less, such as 70 mm or less, such as 50 mm or less, such as 30 mm or less.

Aspect Group 261SE: Reflux_Stop_Exercise_Torus

1. An apparatus (100) for treating reflux disease of a human patient, comprising:
  an at least partly ring-shaped implantable movement restriction device comprising a first portion (110) configured to be at least partly invaginated by a first wall portion of the patient's stomach (10) and arranged such that at least a part of the first portion is arranged above the cardiac notch (24) of the patient's stomach, and such that movement of the cardia (22) towards the diaphragm (30) is restricted to prevent the cardia from sliding through the diaphragm opening (32) into the patient's thorax; and an electrode arrangement (150) configured to electrically stimulate muscle tissue of the first wall portion to exercise the muscle tissue to improve the conditions for long term implantation of the movement restriction device.
2 The apparatus according to aspect 1, wherein the electrode arrangement is arranged on an outer surface of the movement restriction device.
3. The apparatus according to aspect 1 or 2, wherein the electrode arrangement comprises a plurality of electrode elements (152), each of which being configured to engage and electrically stimulate the muscle tissue.
4. The apparatus according to any of the preceding aspects, wherein the electrode arrangement comprises a coiled wire for increasing a contact surface between the electrode arrangement and the muscle tissue and for allowing the electrode arrangement to follow contraction and relaxation of the muscle tissue.
5. The apparatus according to any of the preceding aspects, wherein the electrode arrangement comprises a bare electrode portion (155) configured to form a metal-tissue interface with the muscle tissue, thereby allowing faradaic charge transfer to the be predominant charge transfer mechanism over said interface.
6. The apparatus according to any of the preceding aspects, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.
7. The apparatus according to any of the preceding aspects, wherein the electrode arrangement is further configured to be arranged to electrically stimulate the cardiac sphincter (26) of the patient to cause the cardiac sphincter to contract.
8. The apparatus according to aspect 7, wherein the electrode arrangement comprises at least two electrode elements (154) configured to be arranged on opposing sides of the cardiac sphincter.

9. The apparatus according to aspect 8, further comprising a holder (120) configured to support the at least two electrode elements at the opposing sides of the cardiac sphincter.

10. The apparatus according to any of the preceding aspects, further comprising an implantable energy source (160) configured to provide the electrode with electrical power.

11. The apparatus according to aspect 10, wherein the implantable energy source is arranged inside the movement restriction device.

12. The apparatus according to aspect 10, wherein the implantable energy source is configured to be arranged outside the movement restriction device.

13. The apparatus according to aspect 12, wherein the implantable energy source is configured to be implanted subcutaneously.

14. The apparatus according to any of aspects 10-13, wherein the implantable energy source comprises a primary cell.

15. The apparatus according to any of aspects 10-14, wherein the implantable energy source comprises a secondary cell.

16. The apparatus according to aspect 14 or 15, further comprising a controller (170) configured to indicate a functional status of the implantable energy source.

17. The apparatus according to aspect 16, wherein the functional status indicates a charge level of the implantable energy source.

18. The apparatus according to aspect 16 or 17, wherein the functional status indicates a temperature of at least one of the implantable energy source, the muscle tissue, and the electrode arrangement.

19. The apparatus according to any of aspects 16-18, wherein the implantable energy source is configured to be charged by an external energy source (165) arranged outside the patient's body.

20. The apparatus according to aspect 19, further comprising an implantable charger (190) configured to be electrically connected to the implantable energy source and enable charging of the implantable energy source by the external energy source.

21. The apparatus according to aspect 20, wherein the charger comprises an electromagnetic coil configured to receive electrical power wirelessly from the external energy source.

22. The apparatus according to aspect 20 or 21, wherein the charger is configured to control the charging of the implantable energy source based on the functional status.

23. The apparatus according to any of aspects 20-22, wherein the charger is configured to control the charging of the implantable energy source by controlling a receipt of electrical power from the external energy source at the implantable charger.

24. The apparatus according to any of aspects 20-22, wherein the charger is configured to control the charging of the implantable energy source by controlling a transmission of electrical power from the external energy source to the implantable charger.

25. The apparatus according to aspect 1, further comprising controller (170) configured to be operably connected to the electrode arrangement for controlling the electrical stimulation of the muscle tissue.

26. The apparatus according to aspect 25, wherein the controller is configured to control the electrical stimulation such that the muscle tissue is stimulated by a series of electrical pulses (PL1, PL2, PL3, PL4).

27. The apparatus according to aspect 26, wherein the controller is configured to control the electrical stimulation such that a pulse of a first polarity is followed by a pulse of a second, reversed polarity.

28. The apparatus according to any of aspects 25-27, wherein the controller is configured to generate a pulsed electrical stimulation signal comprising a pulse frequency (F) of 0.01-150 Hz.

29. The apparatus according to aspect 28, wherein the electrical stimulation signal comprises a pulse duration (D) of 0.01-100 ms.

30. The apparatus according to aspect 28 or 29, wherein the electrical stimulation signal comprises a pulse amplitude (A) of 1-15 mA.

31. The apparatus according to any of aspects 28-30, wherein the electrical stimulation signal comprises a pulse frequency of 0.15-0.25 Hz, a pulse duration of 20-30 ms and a pulse amplitude of 3-10 mA.

32. The apparatus according to any of aspects 28-31, wherein the electrical stimulation signal comprises a build-up period (X1) of 0.01-2 s in which the amplitude is gradually increasing, a stimulation period (X2) of 1-60 s, and a stimulation pause (X4) of 0.01-60 s, wherein the electrical signal comprises a pulse frequency of 1-50 Hz and a pulse duration of 0.1-10 ms.

33. The apparatus according to any of aspects 25-32, wherein the controller comprises a wireless remote control (175).

34. The apparatus according to aspect 33, wherein the wireless remote control comprises an external signal transmitter, and wherein the apparatus further comprises an implantable controller configured to receive a signal transmitted by the external signal transmitter and to control an operation of the apparatus based on said signal.

35. The apparatus according to aspect 35, wherein signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.

36. The apparatus according to any of aspects 25-35, further comprising an implantable sensor (S1) configured to sense actions potentials generated by pacemaker cells of the muscle tissue, and wherein the controller is configured to control the electrical simulation based at least partly on the sensed action potentials.

37. The apparatus according to aspect 36, wherein the controller is configured to generate electrical pulses amplifying the sensed action potentials.

38. The apparatus according to any of the preceding aspects, wherein a volume of the movement restriction device is non-adjustable after implantation.

39. The apparatus according to any of aspects 1-37, wherein a volume of the movement restriction device is adjustable after implantation.

40) The apparatus according to aspect 39, wherein the volume of the movement restriction device is adjustable invasively or non-invasively.

41. The apparatus according to aspect 39 or 40, wherein the movement restriction device comprises an injection port (115) for allowing a fluid to be injected or extracted from the inside of the movement restriction device so as to vary a volume of the movement restriction device after implantation.

42. The apparatus according to any of the preceding aspects, wherein the movement restriction device comprises a biocompatible outer surface configured to rest against the first wall portion.

43. The apparatus according to any of the preceding aspects, wherein the first wall portion is a fundus wall portion (14).

44. The apparatus according to aspect any of the preceding aspects, wherein the movement restriction device further comprises a second portion (120), and wherein the first and second portions of the movement restriction device are configured to be arranged on opposite sides of the cardia (22).

45. The apparatus according to aspect 44, wherein the movement restriction device is configured to be arranged such that a gap is formed between the second portion of the movement restriction device and the esophagus.

46. The apparatus according to aspect 44, wherein the second portion of the movement restriction device is configured to be at least partly invaginated by a second wall portion of the stomach.

47. The apparatus according to any of the preceding aspects, wherein the movement restriction device is configured to be arranged such that a portion of the first wall portion is arranged between the first portion of the movement restriction device and the esophagus.

48. The apparatus according to any of the preceding aspects, wherein the movement restriction device is configured to be at least partly invaginated by the first wall portion along at least half of the toroidal length of the movement restriction device.

49. The apparatus according to any of the preceding aspects, wherein the movement restriction device is configured to be invaginated when placed on the outside of the stomach wall.

50. The apparatus according to any of the preceding aspects, wherein the movement restriction device comprises two end portions configured to be coupled to each other to form a closed ring.

51. The apparatus according to aspect 50, wherein the end portions are configured to be releasably attached to each other.

52. The apparatus according to aspect 44, wherein a poloidal circumference of the movement restriction device is larger for the first portion and for the second portion.

53. The apparatus according to aspect 52, wherein a minimum width of the first portion of the movement restriction device, as measured from side to side, is 30 mm or larger, such as 40 mm or larger.

54. The apparatus according to aspect 52, wherein a minimum poloidal circumference of the first portion of the movement restriction device is 150 mm or less, such as 130 mm or less, such as 110 mm or less, such as 90 mm or less, such as 70 mm or less, such as 50 mm or less, such as 30 mm or less.

55. The apparatus according to any of the preceding aspects, wherein the movement restriction device has a shape conforming to a torus.

Aspect Group 262SE:
Reflux_Constricting-Band_Cover

1. An apparatus (100) for treating reflux disease of a human patient, comprising:

an elongated core (210) having a length allowing the core to at least partly encircle the esophagus (20) of the patient, wherein the length is variable to allow the core to be arranged in a constricting state for hindering fluid from passing from the stomach (10) into the esophagus and in an expanded state for allowing food to pass into the stomach in response to the patient swallowing; and a tubular cover (220) enclosing at least a part of the core and comprising a plurality of portions (224, 225, 226) adapted to bend relative to each other to allow the core to change between the constricting state and the expanded state, when the cover is at least partly covered by fibrotic tissue, without being substantially hindered or impeded by the presence of said fibrotic tissue.

2. The apparatus according to aspect 1, wherein the core is configured to allow a transition from the constricting state into the expanded state caused by the food passing through esophagus.

3. The apparatus according to aspect 1 or 2, wherein the core is configured to exert an encircling pressure on the esophagus in the constricting state.

4. The apparatus according to aspect 3, further comprising an attractor (212, 213) for resiliently attracting adjacent portions of the core to one another to generate the encircling pressure.

5. The apparatus according to aspect 4, wherein the attractor comprises an elastic element (212).

6. The apparatus according to aspect 4 or 5, wherein the attractor comprises at least two mutually attracting magnets (213).

7. The apparatus according to aspect 6, further comprising a link (214) connecting a first and a second one of said at least two magnets to each other.

8. The apparatus according to aspect 7, wherein the link is configured to extend into at least one of said magnets in response to said magnets moving towards each other.

9. The apparatus according to any of the preceding aspects, wherein the cover comprises an array of tubular segments (222).

10. The apparatus according to any of the preceding aspects, wherein the cover comprises a biocompatible outer surface for long-term implantation.

11. The apparatus according to any of the preceding aspects, wherein the cover is configured to rest against an outer surface of the esophagus.

12. The apparatus according to any of the preceding aspects, wherein the cover comprises a surface promoting tissue growth.

13. The apparatus according to any of the preceding aspects, wherein the cover is formed of a polymer material, such as silicone.

14. The apparatus according to any of the preceding aspects, wherein the cover is formed of a material having a thickness of 0.1 to 10 mm, such as 1-5 mm.

15. The apparatus according to any of the preceding aspects, wherein the cover comprises at least one predefined fold (224) along which the cover is allowed to fold in response to the core varying its length.

16. The apparatus according to any of the preceding aspects, wherein the cover comprises lowered and elevated portions (225, 226) allowing the cover to vary its length while maintaining its surface area.

17. The apparatus according to any of the preceding aspects, wherein the cover is configured to be compressible and expandable in its length direction.

18. The apparatus according to any of the preceding aspects, wherein a length of the cover enclosing said at least a part of the core exceeds a length of said at least a part of the core when said at least a part of the core is arranged in the constricting state.

19. The apparatus according to any of the preceding aspects, wherein the core comprises two end portions (216) configured to be coupled to each other to form a closed ring around the esophagus.

20. The apparatus according to aspect 21, wherein the end portions are configured to be releasably attached to each other.

21. The apparatus according to aspect 20 or 21, wherein the end portions comprise a respective interlockable attacher.

22. The apparatus according to aspect 1, wherein the core comprises a plurality of core elements configured to be arranged in an annular array around the esophagus.

23. The apparatus according to aspect 22, wherein the core further comprises a plurality of links, each of which extending between a respective pair of core elements arranged adjacent to each other.

24. The apparatus according to aspect 23, wherein each of the links is configured to allow the respective core elements to move towards and away from each other.

25. The apparatus according to aspect 24, wherein each of the links is configured to extend into at least one of the core elements of the respective pair of core elements as said core elements move towards each other.

26. The apparatus according to aspects 22-25, further comprising an attractor for resiliently attracting adjacent core elements of the annular array to each other.

27. The apparatus according to aspect 26, wherein the attractor comprises at least one of a magnet, an elastic member, and a spring.

28. The apparatus according to any of the preceding aspects, further comprising an electrode arrangement (150) configured to be arranged between the apparatus and the esophagus and to electrically stimulate muscle tissue of the outer wall of the esophagus to exercise the muscle tissue to improve the conditions for long term implantation of the movement restriction device.

29. The apparatus according to aspect 28, wherein the electrode arrangement is arranged on an outer surface of the cover.

30. The apparatus according to aspect 28 or 29, wherein the electrode arrangement comprises a plurality of electrode elements (154), each of which being configured to electrically stimulate the muscle tissue.

31. The apparatus according to any of aspects 28-30, wherein the electrode arrangement comprises a coiled wire for increasing a contact surface between the electrode arrangement and the muscle tissue and for allowing the electrode arrangement to follow contraction and relaxation of the muscle tissue.

32. The apparatus according to any of aspects 28-31, wherein the electrode arrangement comprises a bare electrode portion (155) configured to form a metal-tissue interface with the muscle tissue, thereby allowing faradaic charge transfer to the be predominant charge transfer mechanism over said interface.

33. The apparatus according to any of aspects 28-31, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.

34. The apparatus according to any of aspects 28-33, wherein the electrode arrangement is configured to be to electrically stimulate the cardiac sphincter (26) of the patient to cause the cardiac sphincter to contract.

35. The apparatus according to aspect 34, wherein the electrode arrangement comprises at least two electrode elements (154) configured to be arranged on opposing sides of the cardiac sphincter.

36. The apparatus according to any of aspects 28-35, further comprising an implantable energy source (160) configured to provide the electrode arrangement with electrical power.

37 The apparatus according to aspect 36, wherein the implantable energy source is arranged inside the cover.

38. The apparatus according to aspect 36, wherein the implantable energy source is configured to be arranged outside the cover.

39. The apparatus according to aspect 38, wherein the implantable energy source is configured to be implanted subcutaneously.

40. The apparatus according to any of aspects 36-39, wherein the implantable energy source comprises a primary cell.

41. The apparatus according to any of aspects 36-40, wherein the implantable energy source comprises a secondary cell.

42. The apparatus according to aspect 36-41, further comprising a controller (170) configured to indicate a functional status of the implantable energy source.

43. The apparatus according to aspect 42, wherein the functional status indicates a charge level of the implantable energy source.

44. The apparatus according to aspect 42 or 43, wherein the functional status indicates a temperature of at least one of the implantable energy source, the muscle tissue, and the electrode arrangement.

45. The apparatus according to any of aspects 36-44, wherein the implantable energy source is configured to be charged by an external energy source (165) arranged outside the patient's body.

46. The apparatus according to aspect 45, further comprising an implantable charger (190) configured to be electrically connected to the implantable energy source and enable charging of the implantable energy source by the external energy source.

47. The apparatus according to aspect 46, wherein the charger comprises an electromagnetic coil configured to receive electrical power wirelessly from the external energy source.

48. The apparatus according to aspect 46 or 47, wherein the charger is configured to control the charging of the implantable energy source based on the functional status.

49. The apparatus according to any of aspects 46-48, wherein the charger is configured to control the charging of the implantable energy source by controlling a receipt of electrical power from the external energy source at the implantable charger.

50. The apparatus according to any of aspects 46-48, wherein the charger is configured to control the charging of the implantable energy source by controlling a transmission of electrical power from the external energy source to the implantable charger.

51. The apparatus according to aspect 28, further comprising controller (170) configured to be operably connected to the electrode arrangement for controlling the electrical stimulation of the muscle tissue.

52. The apparatus according to aspect 51, wherein the controller is configured to control the electrical stimulation such that the muscle tissue is stimulated by a series of electrical pulses (PL1, PL2, PL3, PL4).

53. The apparatus according to aspect 52, wherein the controller is configured to control the electrical stimulation such that a pulse of a first polarity is followed by a pulse of a second, reversed polarity.

54. The apparatus according to any of aspects 51-53, wherein the controller is configured to generate a pulsed electrical stimulation signal comprising a pulse frequency (F) of 0.01-150 Hz.

55. The apparatus according to aspect 54, wherein the electrical stimulation signal comprises a pulse duration (D) of 0.01-100 ms.

56. The apparatus according to aspect 54 or 55, wherein the electrical stimulation signal comprises a pulse amplitude (A) of 1-15 mA.

57. The apparatus according to any of aspects 54-56, wherein the electrical stimulation signal comprises a pulse frequency of 0.15-0.25 Hz, a pulse duration of 20-30 ms and a pulse amplitude of 3-10 mA.

58. The apparatus according to any of aspects 54-57, wherein the electrical stimulation signal comprises a build-up period (X1) of 0.01-2 s in which the amplitude is gradually increasing, a stimulation period (X2) of 1-60 s, and a stimulation pause (X4) of 0.01-60 s, wherein the electrical signal comprises a pulse frequency of 1-50 Hz. and a pulse duration of 0.1-10 ms.

59. The apparatus according to any of aspects 51-58, wherein the controller comprises a wireless remote control (175).

60. The apparatus according to aspect 59, wherein the wireless remote control comprises an external signal transmitter, and wherein the apparatus further comprises an implantable controller configured to receive a signal transmitted by the external signal transmitter and to control an operation of the apparatus based on said signal.

61. The apparatus according to aspect 60, wherein signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.

62. The apparatus according to any of aspects 51-61, further comprising an implantable sensor (S1) configured to sense actions potentials generated by pacemaker cells of the muscle tissue, and wherein the controller is configured to control the electrical simulation based at least partly on the sensed action potentials.

63. The apparatus according to aspect 62, wherein the controller is configured to generate electrical pulses amplifying the sensed action potentials.

Aspect Group 263SE: Reflux_Constricting-Band_Stimulation

1. An apparatus (100) for treating reflux disease of a human patient, comprising:
   - an elongated core (210) having a length allowing the core to at least partly encircle the esophagus (20) of the patient, wherein the length is variable to allow the core to be arranged in a constricting state for hindering fluid from passing from the stomach (10) into the esophagus and in an expanded state for allowing food to pass into the stomach in response to the patient swallowing; and
   - an electrode arrangement (150) comprising an electrode element (154) supported by the core and configured to electrically stimulate muscle tissue of the esophagus.

2. The apparatus according to aspect 1, wherein the core is configured to allow a transition from the constricting state into the expanded state caused by the food passing through esophagus.

3. The apparatus according to aspect 1 or 2, wherein the core is configured to exert an encircling pressure on the esophagus in the constricting state.

4. The apparatus according to aspect 3, further comprising an attractor (212) for resiliently attracting adjacent portions (213) of the core to one another to generate the encircling pressure.

5. The apparatus according to aspect 4, wherein the attractor comprises an elastic element.

6. The apparatus according to aspect 4 or 5, wherein the attractor comprises at least two mutually attracting magnets.

7. The apparatus according to aspect 6, further comprising a link (214) connecting a first and a second one of said at least two magnets to each other.

8 The apparatus according to aspect 7, wherein the link is configured to extend into at least one of said magnets in response to said magnets moving towards each other.

9. The apparatus according to any of the preceding aspects, wherein the core comprises a biocompatible outer surface for long-term implantation.

10. The apparatus according to any of the preceding aspects, wherein the core comprises two end portions (216) configured to be coupled to each other to form a closed ring around the esophagus.

11. The apparatus according to aspect 10, wherein the end portions are configured to be releasably attached to each other.

12. The apparatus according to aspect 10 or 11, wherein the end portions comprise a respective interlockable attacher.

13. The apparatus according to aspect 1, wherein the core comprises a plurality of core elements configured to be arranged in an annular array around the esophagus.

14. The apparatus according to aspect 13, wherein the core further comprises a plurality of links, each of which extending between a respective pair of core elements arranged adjacent to each other.

15. The apparatus according to aspect 14, wherein each of the links is configured to allow the respective core elements to move towards and away from each other.

16. The apparatus according to aspect 15, wherein each of the links is configured to extend into at least one of the core elements of the respective pair of core elements as said core elements move towards each other.

17. The apparatus according to aspects 13-16, further comprising an attractor for resiliently attracting adjacent core elements of the annular array to each other.

18. The apparatus according to aspect 17, wherein the attractor comprises at least one of a magnet, an elastic member, and a spring.

19. The apparatus according to any of the preceding aspects, wherein the electrode arrangement is configured to electrically stimulate the muscle tissue so as to exercise the muscle tissue to improve the conditions for long term implantation of the core.

20. The apparatus according to any of the preceding aspects, wherein the electrode arrangement comprises a plurality of electrode elements (154), each of which being configured to electrically stimulate the muscle tissue.

21. The apparatus according to any of the preceding aspects, wherein the electrode arrangement comprises a coiled wire for allowing the electrode arrangement to follow a variation of the length of the core.

22. The apparatus according to any of the preceding aspects, wherein the electrode arrangement comprises a bare electrode portion (155) configured to form a metal-tissue interface with the muscle tissue, thereby allowing faradaic charge transfer to the be predominant charge transfer mechanism over said interface.

23. The apparatus according to any of aspects 1-21, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.

24. The apparatus according to any of the preceding aspects, wherein the electrode arrangement is configured to be to electrically stimulate the cardiac sphincter of the patient to cause the cardiac sphincter to contract.

25. The apparatus according to aspect 24, wherein the electrode arrangement comprises at least two electrode elements configured to be arranged on opposing sides of the cardiac sphincter.

26. The apparatus according to any of the preceding aspects, further comprising an implantable energy source (160) configured to provide the electrode arrangement with electrical power.

27. The apparatus according to aspect 26, wherein the implantable energy source is arranged inside the core.

28. The apparatus according to aspect 26, wherein the implantable energy source is configured to be arranged outside the core.

29. The apparatus according to aspect 28, wherein the implantable energy source is configured to be implanted subcutaneously.

30. The apparatus according to any of aspects 26-29, wherein the implantable energy source comprises a primary cell.

31. The apparatus according to any of aspects 26-30, wherein the implantable energy source comprises a secondary cell.

32. The apparatus according to aspect 26-31, further comprising a controller (170) configured to indicate a functional status of the implantable energy source.

33. The apparatus according to aspect 32, wherein the functional status indicates a charge level of the implantable energy source.

34. The apparatus according to aspect 32 or 33, wherein the functional status indicates a temperature of at least one of the implantable energy source, the muscle tissue, and the electrode arrangement.

35. The apparatus according to any of aspects 26-34, wherein the implantable energy source is configured to be charged by an external energy source (165) arranged outside the patient's body.

36. The apparatus according to aspect 35, further comprising an implantable charger (190) configured to be electrically connected to the implantable energy source and enable charging of the implantable energy source by the external energy source.

37. The apparatus according to aspect 36, wherein the charger comprises an electromagnetic coil configured to receive electrical power wirelessly from the external energy source.

38. The apparatus according to aspect 36 or 37, wherein the charger is configured to control the charging of the implantable energy source based on the functional status.

39. The apparatus according to any of aspects 36-38, wherein the charger is configured to control the charging of the implantable energy source by controlling a receipt of electrical power from the external energy source at the implantable charger.

40. The apparatus according to any of aspects 36-38, wherein the charger is configured to control the charging of the implantable energy source by controlling a transmission of electrical power from the external energy source to the implantable charger.

41. The apparatus according to any of the preceding aspects, further comprising a controller (170) configured to be operably connected to the electrode arrangement for controlling the electrical stimulation of the muscle tissue.

42. The apparatus according to aspect 41, wherein the controller is configured to control the electrical stimulation such that the muscle tissue is stimulated by a series of electrical pulses (PL1, PL2, PL3, PL4).

43. The apparatus according to aspect 42, wherein the controller is configured to control the electrical stimulation such that a pulse of a first polarity is followed by a pulse of a second, reversed polarity.

44. The apparatus according to any of aspects 41-43, wherein the controller is configured to generate a pulsed electrical stimulation signal comprising a pulse frequency (F) of 0.01-150 Hz.

45. The apparatus according to aspect 44, wherein the electrical stimulation signal comprises a pulse duration (D) of 0.01-100 ms.

46. The apparatus according to aspect 44 or 45, wherein the electrical stimulation signal comprises a pulse amplitude (A) of 1-15 mA.

47. The apparatus according to any of aspects 44-46, wherein the electrical stimulation signal comprises a pulse frequency of 0.15-0.25 Hz, a pulse duration of 20-30 ms and a pulse amplitude of 3-10 mA.

48. The apparatus according to any of aspects 44-47, wherein the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.

49. The apparatus according to any of aspects 41-48, wherein the controller comprises a wireless remote control (175).

50. The apparatus according to aspect 49, wherein the wireless remote control comprises an external signal transmitter, and wherein the apparatus further comprises an implantable controller configured to receive a signal transmitted by the external signal transmitter and to control an operation of the apparatus based on said signal.

51. The apparatus according to aspect 50, wherein signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.

52. The apparatus according to any of aspects 41-51, further comprising an implantable sensor (S1) configured to sense actions potentials generated by pacemaker cells of the muscle tissue, and wherein the controller is configured to control the electrical simulation based at least partly on the sensed action potentials.

53. The apparatus according to aspect 52, wherein the controller is configured to generate electrical pulses amplifying the sensed action potentials.

Aspect Group 264SE:
Reflux_Constricting-Band_No_Core

1. An apparatus (100) for treating reflux disease of a human patient, comprising:
 a tubular device (220) having a length allowing the tubular device to at least partly encircle the esophagus (20) of the patient, wherein the length is variable to allow the tubular cover to be arranged in a constricting state for hindering fluid from passing from the stomach (10) into the esophagus and in an expanded state for allowing food to pass into the stomach in response to the patient swallowing;
 wherein the outer surface of the tubular device comprises a plurality of portions (224, 225, 226) adapted to bend relative to each other to allow the tubular device to change between the constricting state and the expanded state, when the outer surface is at least partly covered by fibrotic tissue, without being substantially hindered or impeded by the presence of said fibrotic tissue.
2. The apparatus according to aspect 1, wherein the tubular device is configured to allow a transition from the constricting state into the expanded state caused by the food passing through esophagus.
3. The apparatus according to aspect 1 or 2, wherein the tubular device is configured to exert an encircling pressure on the esophagus in the constricting state.
4. The apparatus according to aspect 3, further comprising an attractor (212, 213) for resiliently attracting adjacent portions of the tubular device to one another to generate the encircling pressure.
5. The apparatus according to aspect 4, wherein the attractor comprises an elastic element (212).
6. The apparatus according to aspect 4 or 5, wherein the attractor comprises at least two mutually attracting magnets (213).
7. The apparatus according to aspect 6, further comprising a link (214) connecting a first and a second one of said at least two magnets to each other.
8. The apparatus according to aspect 7, wherein the link is configured to extend into at least one of said magnets in response to said magnets moving towards each other.
9. The apparatus according to any of the preceding aspects, wherein the tubular device comprises an array of tubular segments (222).
10. The apparatus according to any of the preceding aspects, wherein the tubular device comprises a biocompatible outer surface for long-term implantation.
11. The apparatus according to any of the preceding aspects, wherein the tubular device is configured to rest against an outer surface of the esophagus.
12. The apparatus according to any of the preceding aspects, wherein the tubular device comprises a surface promoting tissue growth.
13. The apparatus according to any of the preceding aspects, wherein the tubular device is formed of a polymer material, such as silicone.
14. The apparatus according to any of the preceding aspects, wherein the tubular device is formed of a material having a thickness of 0.1 to 10 mm, such as 1 to 5 mm.
15. The apparatus according to any of the preceding aspects, wherein the tubular device comprises at least one predefined fold (224) along which the tubular device is allowed to fold in response to the tubular device varying its length.
16. The apparatus according to any of the preceding aspects, wherein the tubular device comprises lowered and elevated portions (225, 226) allowing the tubular device to vary its length while maintaining its surface area.
17. The apparatus according to any of the preceding aspects, wherein the tubular device is configured to be compressible and expandable in its length direction.
18. The apparatus according to any of the preceding aspects, wherein the tubular device comprises two end portions (216) configured to be coupled to each other to form a closed ring around the esophagus.
19. The apparatus according to aspect 18, wherein the end portions are configured to be releasably attached to each other.
20. The apparatus according to aspect 18 or 19, wherein the end portions comprise a respective interlockable attacher.
21. The apparatus according to any of the preceding aspects, further comprising an elongated core (210) configured to be enclosed by the tubular device, and to vary its length in accordance with the varying length of the tubular device.
22. The apparatus according to aspect 21, wherein the core comprises a plurality of core elements configured to be arranged in an annular array around the esophagus.
23. The apparatus according to aspect 22, wherein the core further comprises a plurality of links, each of which extending between a respective pair of core elements arranged adjacent to each other.
24. The apparatus according to aspect 23, wherein each of the links is configured to allow the respective core elements to move towards and away from each other.
25. The apparatus according to aspect 24, wherein each of the links is configured to extend into at least one of the core elements of the respective pair of core elements as said core elements move towards each other.
26. The apparatus according to aspects 22-25, further comprising an attractor for resiliently attracting adjacent core elements of the annular array to each other.
27. The apparatus according to aspect 26, wherein the attractor comprises at least one of a magnet, an elastic member, and a spring.
28. The apparatus according to any of the preceding aspects, further comprising an electrode arrangement (150) configured to be arranged between the apparatus and the esophagus and to electrically stimulate muscle tissue of the outer wall of the esophagus to exercise the muscle tissue to improve the conditions for long term implantation of the movement restriction device.
29. The apparatus according to aspect 28, wherein the electrode arrangement is arranged on the outer surface of the tubular device.
30. The apparatus according to aspect 28 or 29, wherein the electrode arrangement comprises a plurality of electrode elements (154), each of which being configured to electrically stimulate the muscle tissue.
31. The apparatus according to any of aspects 28-30, wherein the electrode arrangement comprises a coiled wire for increasing a contact surface between the electrode arrangement and the muscle tissue and for allowing the electrode arrangement to follow contraction and relaxation of the muscle tissue.
32. The apparatus according to any of aspects 28-31, wherein the electrode arrangement comprises a bare electrode portion (155) configured to form a metal-tissue interface with the muscle tissue, thereby allowing faradaic charge transfer to the be predominant charge transfer mechanism over said interface.
33. The apparatus according to any of aspects 28-31, wherein the electrode arrangement comprises an electrode portion at least partly covered by a dielectric material (157)

configured to form a dielectric-tissue interface with the muscle tissue, thereby allowing for a faradaic portion of the charge transfer mechanism over said interface to be reduced.

34. The apparatus according to any of aspects 28-33, wherein the electrode arrangement is configured to be to electrically stimulate the cardiac sphincter (26) of the patient to cause the cardiac sphincter to contract.

35. The apparatus according to aspect 34, wherein the electrode arrangement comprises at least two electrode elements (154) configured to be arranged on opposing sides of the cardiac sphincter.

36. The apparatus according to any of aspects 28-35, further comprising an implantable energy source (160) configured to provide the electrode arrangement with electrical power.

37. The apparatus according to aspect 36, wherein the implantable energy source is arranged inside the cover.

38. The apparatus according to aspect 36, wherein the implantable energy source is configured to be arranged outside the cover.

39. The apparatus according to aspect 38, wherein the implantable energy source is configured to be implanted subcutaneously.

40. The apparatus according to any of aspects 36-39, wherein the implantable energy source comprises a primary cell.

41. The apparatus according to any of aspects 36-40, wherein the implantable energy source comprises a secondary cell.

42. The apparatus according to aspect 36-41, further comprising a controller (170) configured to indicate a functional status of the implantable energy source.

43. The apparatus according to aspect 42, wherein the functional status indicates a charge level of the implantable energy source.

44. The apparatus according to aspect 42 or 43, wherein the functional status indicates a temperature of at least one of the implantable energy source, the muscle tissue, and the electrode arrangement.

45. The apparatus according to any of aspects 36-44, wherein the implantable energy source is configured to be charged by an external energy source (165) arranged outside the patient's body.

46. The apparatus according to aspect 45, further comprising an implantable charger (190) configured to be electrically connected to the implantable energy source and enable charging of the implantable energy source by the external energy source.

47. The apparatus according to aspect 46, wherein the charger comprises an electromagnetic coil configured to receive electrical power wirelessly from the external energy source.

48. The apparatus according to aspect 46 or 47, wherein the charger is configured to control the charging of the implantable energy source based on the functional status.

49. The apparatus according to any of aspects 46-48, wherein the charger is configured to control the charging of the implantable energy source by controlling a receipt of electrical power from the external energy source at the implantable charger.

50. The apparatus according to any of aspects 46-48, wherein the charger is configured to control the charging of the implantable energy source by controlling a transmission of electrical power from the external energy source to the implantable charger.

51. The apparatus according to aspect 28, further comprising controller (170) configured to be operably connected to the electrode arrangement for controlling the electrical stimulation of the muscle tissue.

52. The apparatus according to aspect 51, wherein the controller is configured to control the electrical stimulation such that the muscle tissue is stimulated by a series of electrical pulses (PL1, PL2, PL3, PL4).

53. The apparatus according to aspect 52, wherein the controller is configured to control the electrical stimulation such that a pulse of a first polarity is followed by a pulse of a second, reversed polarity.

54. The apparatus according to any of aspects 51-53, wherein the controller is configured to generate a pulsed electrical stimulation signal comprising a pulse frequency (F) of 0.01-150 Hz.

55. The apparatus according to aspect 54, wherein the electrical stimulation signal comprises a pulse duration (D) of 0.01-100 ms.

56. The apparatus according to aspect 54 or 55, wherein the electrical stimulation signal comprises a pulse amplitude (A) of 1-15 mA.

57. The apparatus according to any of aspects 54-56, wherein the electrical stimulation signal comprises a pulse frequency of 0.15-0.25 Hz, a pulse duration of 20-30 ms and a pulse amplitude of 3-10 mA.

58. The apparatus according to any of aspects 54-57, wherein the electrical stimulation signal comprises a build-up period (X1) of 0.01-2 s in which the amplitude is gradually increasing, a stimulation period (X2) of 1-60 s, and a stimulation pause (X4) of 0.01-60 s, wherein the electrical signal comprises a pulse frequency of 1-50 Hz and a pulse duration of 0.1-10 ms.

59. The apparatus according to any of aspects 51-58, wherein the controller comprises a wireless remote control (175).

60. The apparatus according to aspect 59, wherein the wireless remote control comprises an external signal transmitter, and wherein the apparatus further comprises an implantable controller configured to receive a signal transmitted by the external signal transmitter and to control an operation of the apparatus based on said signal.

61. The apparatus according to aspect 60, wherein signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.

62. The apparatus according to any of aspects 51-61, further comprising an implantable sensor (S1) configured to sense actions potentials generated by pacemaker cells of the muscle tissue, and wherein the controller is configured to control the electrical simulation based at least partly on the sensed action potentials.

63. The apparatus according to aspect 62, wherein the controller is configured to generate electrical pulses amplifying the sensed action potentials.

Aspect Group 265SE: Reflux_Constricting-Band_Stop

1. An apparatus (100) for treating reflux disease of a human patient, comprising an elongated core (210) having a length allowing the core to at least partly encircle the esophagus (20) of the patient;

wherein the length is variable to allow the core to be arranged in a constricting state for hindering fluid from passing from the stomach (10) into the esophagus and in an expanded state for allowing food to pass into the stomach in response to the patient swallowing; and wherein the elongated core has a size allowing at least a portion of the elongated core to protrude above the cardiac sphincter of the patient, when implanted, such that movement of the cardia towards the diaphragm is restricted to hinder the cardia from sliding through the diaphragm opening (32) into the patient's thorax.

2. The apparatus according to aspect 1, wherein the elongated core has a maximum height exceeding 2 cm, as measured in a normal direction to the plane in which the elongated core extends when encircling the esophagus.

3. The apparatus according to aspect 2, wherein the maximum height is 3 cm or more, such as 4 cm or more, such as 5 cm or more.

4. The apparatus according to aspect 2 of 3, wherein the elongated core is configured to be implanted such that a portion of the elongated core having the maximum height is arranged at the fundus side of the esophagus.

5. The apparatus according to any of the preceding aspects, wherein the elongated core comprises a plurality of portions that are movable relative to each other.

6. The apparatus according to aspect 5, wherein the elongated core is configured to exert an encircling pressure on the esophagus in the constricting state.

7. The apparatus according to aspect 6, further comprising an attractor (212) for resiliently attracting adjacent portions (213) of the elongated core to one another to generate the encircling pressure.

8. The apparatus according to aspect 7, wherein the attractor comprises an elastic element.

9. The apparatus according to aspect 7, wherein the attractor comprises at least two mutually attracting magnets.

10. The apparatus according to aspect 9, further comprising a link (214) connecting a first and a second one of said at least two magnets to each other.

11. The apparatus according to any of the preceding aspects, further comprising a tubular cover (220) enclosing at least a part of the elongated core and comprising a plurality of cover portions (224, 225, 226) adapted to bend relative to each other to allow the elongated core to change between the constricting state and the expanded state, when the cover is at least partly covered by fibrotic tissue, without being substantially hindered or impeded by the presence of said fibrotic tissue.

12. The apparatus according to aspect 11, wherein the elongated core comprises an array of tubular segments (222).

13. The apparatus according to aspect 11 or 12, wherein the cover is formed of an inelastic material.

14. The apparatus according to any of aspects 11-13, wherein the cover comprises a biocompatible outer surface for long-term implantation.

15. The apparatus according to any of aspects 11-14, wherein the cover is configured to rest against an outer surface of the esophagus.

16. The apparatus according to any of aspects 11-15, wherein the cover comprises a surface promoting tissue growth.

17. The apparatus according to any of aspects 11-16, wherein the cover is formed of a polymer material, such as silicone.

18. The apparatus according to any of aspects 11-17, wherein the cover is formed of a material having a thickness of 0.1 to 10 mm, such as 1 to 5 mm.

19. The apparatus according to any of aspects 11-18, wherein the cover comprises at least one predefined fold (224) along which the cover is allowed to fold in response to the elongated core varying its length.

20. The apparatus according to any of aspects 11-19, wherein the cover comprises lowered and elevated portions (224, 225) allowing the cover to vary its length while maintaining its surface area.

21. The apparatus according to any of aspects 11-20, wherein the cover is configured to be compressible and expandable in its length direction.

22. The apparatus according to any of aspects 11-21, wherein a length of the cover enclosing said at least a part of elongated core exceeds a length of said at least a part of the elongated core when said at least a part of the second implantable portion is arranged in the constricting state.

23. The apparatus according to any of the preceding aspects, comprising two end portions (216) configured to be coupled to each other to form a closed ring around the esophagus.

24. The apparatus according to aspect 23, wherein the end portions are configured to be releasably attached to each other.

25. The apparatus according to aspect 23 or 24, wherein the end portions comprise a respective interlockable attacher.

26. The apparatus according to aspect 1, wherein the elongated core comprises a plurality of bodies (213) configured to be arranged in an annular array around the esophagus.

27. The apparatus according to aspect 26, wherein the elongated core further comprises a plurality of links (214), each of which extending between a respective pair of bodies arranged adjacent to each other.

28. The apparatus according to aspect 27, wherein the elongated core comprises at least some of the plurality bodies and at least some of the plurality of links, and wherein each of said links is configured to allow the respective ones of said bodies to move towards and away from each other.

29. The apparatus according to aspect 28, wherein each of said links is configured to extend into at least one of the respective ones of said bodies as said bodies move towards each other.

30. The apparatus according to aspects 26, wherein the elongated core comprises at least some of the plurality of bodies and at least some of the plurality of links, and wherein the apparatus further comprises an attractor for resiliently attracting adjacent ones of said bodies to each other.

31. The apparatus according to aspect 30, wherein the attractor comprises at least one of a magnet, an elastic member, and a spring.

32. The apparatus according to any of the preceding aspects, wherein the elongated core comprises a biocompatible outer surface configured to rest against the fundus wall portion.

33. The apparatus according to any of the preceding aspects, further comprising an electrode arrangement (150) configured to be arranged between the apparatus and the esophagus and to electrically stimulate muscle tissue of the outer wall of the esophagus to exercise the muscle tissue to improve the conditions for long term implantation of the movement restriction device.

34. The apparatus according to aspect 33, wherein the electrode arrangement is arranged on an outer surface of the elongated core.

35. The apparatus according to aspect 33 or 34, wherein the electrode arrangement comprises a plurality of electrode elements (152, 154), each of which being configured to electrically stimulate the muscle tissue.

36. The apparatus according to any of aspects 33-35, wherein the electrode arrangement comprises a coiled wire for increasing a contact surface between the electrode arrangement and the muscle tissue and for allowing the electrode arrangement to follow contraction and relaxation of the muscle tissue.

37. The apparatus according to any of aspects 33-36, wherein the electrode arrangement comprises a bare electrode portion (155) configured to form a metal-tissue interface with the muscle tissue, thereby allowing faradaic charge transfer to the be predominant charge transfer mechanism over said interface.

38. The apparatus according to any of aspects 33-36, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.

39. The apparatus according to any of aspects 33-38, wherein the electrode arrangement is configured be arranged to electrically stimulate the cardiac sphincter (26) of the patient to cause the cardiac sphincter to contract.

40. The apparatus according to aspect 39, wherein the electrode arrangement comprises at least two electrode elements (154) configured to be arranged on opposing sides of the cardiac sphincter.

41. The apparatus according to any of aspects 33-40, further comprising an implantable energy source (160) configured to provide the electrode arrangement with electrical power.

42. The apparatus according to aspect 41, wherein the implantable energy source comprises a primary cell and/or a secondary cell.

43. The apparatus according to aspect 41-42, further comprising a controller (170) configured to indicate a functional status of the implantable energy source.

44. The apparatus according to aspect 43, wherein the functional status indicates a charge level of the implantable energy source.

45. The apparatus according to aspect 43 or 44, wherein the functional status indicates a temperature of at least one of the implantable energy source, the muscle tissue, and the electrode arrangement.

46. The apparatus according to any of aspects 37-45, wherein the implantable energy source is configured to be charged by an external energy source (165) arranged outside the patient's body.

47. The apparatus according to aspect 46, further comprising an implantable charger (190) configured to be electrically connected to the implantable energy source and enable charging of the implantable energy source by the external energy source.

48. The apparatus according to aspect 47, wherein the charger comprises an electromagnetic coil configured to receive electrical power wirelessly from the external energy source.

49. The apparatus according to aspect 47 or 48, wherein the charger is configured to receive the functional status from the energy source indicator and control the charging of the implantable energy source based on the functional status.

50. The apparatus according to any of aspects 47-49, wherein the charger is configured to control the charging of the implantable energy source by controlling a receipt of electrical power from the external energy source at the implantable charger.

51. The apparatus according to any of aspects 47-49, wherein the charger is configured to control the charging of the implantable energy source by controlling a transmission of electrical power from the external energy source to the implantable charger.

52. The apparatus according to any of aspects 29-51, further comprising controller (170) configured to be operably connected to the electrode arrangement for controlling the electrical stimulation of the muscle tissue.

53. The apparatus according to aspect 52, wherein the controller is configured to control the electrical stimulation such that the muscle tissue is stimulated by a series of electrical pulses (PL1, PL2, PL3, PL4).

54. The apparatus according to aspect 53, wherein the controller is configured to control the electrical stimulation such that a pulse of a first polarity is followed by a pulse of a second, reversed polarity.

55. The apparatus according to any of aspects 52-54, wherein the controller is configured to generate a pulsed electrical stimulation signal comprising a pulse frequency (F) of 0.01-150 Hz.

56. The apparatus according to aspect 55, wherein the electrical stimulation signal comprises a pulse duration (D) of 0.01-100 ms.

57. The apparatus according to aspect 55 or 56, wherein the electrical stimulation signal comprises a pulse amplitude (A) of 1-15 mA.

58. The apparatus according to any of aspects 55-57, wherein the electrical stimulation signal comprises a pulse frequency of 0.15-0.25 Hz, a pulse duration of 20-30 ms and a pulse amplitude of 3-10 mA.

59. The apparatus according to any of aspects 55-58, wherein the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.

60. The apparatus according to any of aspects 52-59, wherein the controller comprises a wireless remote control (175).

61. The apparatus according to aspect 60, wherein the wireless remote control comprises an external signal transmitter, and wherein the apparatus further comprises an implantable controller configured to receive a signal transmitted by the external signal transmitter and to control an operation of the apparatus based on said signal.

62. The apparatus according to aspect 61, wherein signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.

63. The apparatus according to any of aspects 52-62, further comprising an implantable sensor (S1) configured to sense actions potentials generated by pacemaker cells of the muscle tissue, and wherein the controller is configured to control the electrical simulation based at least partly on the sensed action potentials.

64. The apparatus according to aspect 63, wherein the controller is configured to generate electrical pulses amplifying the sensed action potentials.

Aspect Group 265PC:
Reflux_Constricting-Band_Stop

1. An apparatus (100) for treating reflux disease of a human patient, comprising an elongated core (210) having a length allowing the core to at least partly encircle the esophagus (20) of the patient;

wherein the elongated core has a size allowing at least a portion of the elongated core to protrude clearly above the cardiac sphincter of the patient, when implanted, such that movement of the cardia towards the diaphragm is restricted to hinder the cardia from sliding towards the diaphragm as well as through the diaphragm opening (32) into the patient's thorax.

2. The apparatus according to aspect 1, wherein the elongated core has a maximum height exceeding 2 cm, as measured in a direction following esophagus in its cranial direction.

3. The apparatus according to aspect 1-2, wherein the maximum height is 3 cm or more, such as 4 cm or more, such as 5 cm or more.

4. The apparatus according to aspect 1 of 3, wherein the elongated core is configured to be implanted such that a portion of the elongated core having the maximum height is arranged at the fundus side of the esophagus.

5. The apparatus according to any of the preceding aspects, wherein the elongated core is configured to be implanted such that a portion of the elongated core having the maximum height is arranged at at least one of; the patient's right side, dorsal or ventral of the esophagus.

6. The apparatus according to aspect 5, wherein the elongated core is configured to not exert an encircling pressure on the esophagus.

7. The apparatus according to aspect 6, comprising an attractor which comprises an elastic element.

8. The apparatus according to aspect 7, wherein the attractor comprises at least two mutually attracting magnets.

9. The apparatus according to aspect 7, further comprising a link (214) connecting a first and a second one of said at least two magnets to each other.

10. The apparatus according to any of the preceding aspects, further comprising a tubular cover (220) enclosing at least a part of the elongated core and comprising a plurality of cover portions (224, 225, 226).

11. The apparatus according to any of the preceding aspects, wherein the tubular cover (220) comprising a plurality of cover portions (224, 225, 226) is adapted to bend relative to each other to allow the elongated core to change between a constricting state and an expanded state, when the cover is at least partly covered by fibrotic tissue, without being substantially hindered or impeded by the presence of said fibrotic tissue.

13. The apparatus according to aspect 11 or 12, wherein the cover is formed of an inelastic material.

14. The apparatus according to any of aspects 11-13, wherein the cover comprises a biocompatible outer surface for long-term implantation.

16. The apparatus according to any of aspects 11-15, wherein the cover comprises a surface promoting tissue growth.

17. The apparatus according to any of aspects 11-16, wherein the cover is formed of a polymer material, such as silicone.

18. The apparatus according to any of aspects 11-17, wherein the cover is formed of a material having a thickness of 0.1 to 10 mm, such as 1 to 5 mm.

19. The apparatus according to any of aspects 11-18, wherein the cover comprises at least one predefined fold (224) along which the cover is allowed to fold in response to the elongated core varying its length.

20. The apparatus according to any of aspects 11-19, wherein the cover comprises lowered and elevated portions (224, 225) allowing the cover to vary its length while maintaining its surface area.

21. The apparatus according to any of aspects 11-20, wherein the cover is configured to be compressible and expandable in its length direction.

22. The apparatus according to any of aspects 11-21, wherein a length of the cover enclosing said at least a part of elongated core exceeds a length of said at least a part of the elongated core when said at least a part of the second implantable portion is arranged in the constricting state.

23. The apparatus according to any of the preceding aspects, comprising two end portions (216) configured to be coupled to each other to form a closed ring around the esophagus.

24 The apparatus according to aspect 23, wherein the end portions are configured to be releasably attached to each other.

25. The apparatus according to aspect 23 or 24, wherein the end portions comprise a respective interlockable attacher.

26. The apparatus according to aspect 1, wherein the elongated core comprises a plurality of bodies (213) configured to be arranged in an annular array around the esophagus.

27. The apparatus according to aspect 26, wherein the elongated core further comprises a plurality of links (214), each of which extending between a respective pair of bodies arranged adjacent to each other.

28. The apparatus according to aspect 27, wherein the elongated core comprises at least some of the plurality bodies and at least some of the plurality of links, and wherein each of said links is configured to allow the respective ones of said bodies to move towards and away from each other.

29. The apparatus according to aspect 28, wherein each of said links is configured to extend into at least one of the respective ones of said bodies as said bodies move towards each other.

30. The apparatus according to aspects 26, wherein the elongated core comprises at least some of the plurality of bodies and at least some of the plurality of links, and wherein the apparatus further comprises an attractor for resiliently attracting adjacent ones of said bodies to each other.

33. The apparatus according to any of the preceding aspects, further comprising an electrode arrangement (150) configured to be arranged between the apparatus and the esophagus and to electrically stimulate muscle tissue of the outer wall of the esophagus to exercise the muscle tissue to improve the conditions for long term implantation of the movement restriction device.

34. The apparatus according to aspect 33, wherein the electrode arrangement is arranged on an outer surface of the elongated core.

35. The apparatus according to aspect 33 or 34, wherein the electrode arrangement comprises a plurality of electrode elements (152, 154), each of which being configured to electrically stimulate the muscle tissue.

36. The apparatus according to any of aspects 33-35, wherein the electrode arrangement comprises a coiled wire for increasing a contact surface between the electrode arrangement and the muscle tissue and for allowing the electrode arrangement to follow contraction and relaxation of the muscle tissue.

37. The apparatus according to any of aspects 33-36, wherein the electrode arrangement comprises a bare electrode portion (155) configured to form a metal-tissue interface with the muscle tissue, thereby allowing faradaic charge transfer to the be predominant charge transfer mechanism over said interface.

38. The apparatus according to any of aspects 33-36, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.

39. The apparatus according to any of aspects 33-38, wherein the electrode arrangement is configured be arranged to electrically stimulate the cardiac sphincter (26) of the patient to cause the cardiac sphincter to contract 40. The apparatus according to aspect 39, wherein the electrode arrangement comprises at least two electrode elements (154) configured to be arranged on opposing sides of the cardiac sphincter.

41. The apparatus according to any of aspects 33-40, further comprising an implantable energy source (160) configured to provide the electrode arrangement with electrical power.

42. The apparatus according to aspect 41, wherein the implantable energy source comprises a primary cell and/or a secondary cell.

43. The apparatus according to aspect 41-42, further comprising a controller (170) configured to indicate a functional status of the implantable energy source.

44. The apparatus according to aspect 43, wherein the functional status indicates a charge level of the implantable energy source.

45. The apparatus according to aspect 43 or 44, wherein the functional status indicates a temperature of at least one of the implantable energy source, the muscle tissue, and the electrode arrangement.

46. The apparatus according to any of aspects 37-45, wherein the implantable energy source is configured to be charged by an external energy source (165) arranged outside the patient's body.

47. The apparatus according to aspect 46, further comprising an implantable charger (190) configured to be electrically connected to the implantable energy source and enable charging of the implantable energy source by the external energy source.

48. The apparatus according to aspect 47, wherein the charger comprises an electromagnetic coil configured to receive electrical power wirelessly from the external energy source.

49. The apparatus according to aspect 47 or 48, wherein the charger is configured to receive the functional status from the energy source indicator and control the charging of the implantable energy source based on the functional status.

50. The apparatus according to any of aspects 47-49, wherein the charger is configured to control the charging of the implantable energy source by controlling a receipt of electrical power from the external energy source at the implantable charger.

51. The apparatus according to any of aspects 47-49, wherein the charger is configured to control the charging of the implantable energy source by controlling a transmission of electrical power from the external energy source to the implantable charger.

52. The apparatus according to any of aspects 29-51, further comprising controller (170) configured to be operably connected to the electrode arrangement for controlling the electrical stimulation of the muscle tissue.

53. The apparatus according to aspect 52, wherein the controller is configured to control the electrical stimulation such that the muscle tissue is stimulated by a series of electrical pulses (PL1, PL2, PL3, PL4).

54. The apparatus according to aspect 53, wherein the controller is configured to control the electrical stimulation such that a pulse of a first polarity is followed by a pulse of a second, reversed polarity.

55. The apparatus according to any of aspects 52-54, wherein the controller is configured to generate a pulsed electrical stimulation signal comprising a pulse frequency (F) of 0.01-150 Hz.

56. The apparatus according to aspect 55, wherein the electrical stimulation signal comprises a pulse duration (D) of 0.01-100 ms.

57. The apparatus according to aspect 55 or 56, wherein the electrical stimulation signal comprises a pulse amplitude (A) of 1-15 mA.

58. The apparatus according to any of aspects 55-57, wherein the electrical stimulation signal comprises a pulse frequency of 0.15-0.25 Hz, a pulse duration of 20-30 ms and a pulse amplitude of 3-10 mA.

59. The apparatus according to any of aspects 55-58, wherein the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.

60. The apparatus according to any of aspects 52-59, wherein the controller comprises a wireless remote control (175).

61. The apparatus according to aspect 60, wherein the wireless remote control comprises an external signal transmitter, and wherein the apparatus further comprises an implantable controller configured to receive a signal transmitted by the external signal transmitter and to control an operation of the apparatus based on said signal.

62. The apparatus according to aspect 61, wherein signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.

63. The apparatus according to any of aspects 52-62, further comprising an implantable sensor (S1) configured to sense actions potentials generated by pacemaker cells of the muscle tissue, and wherein the controller is configured to control the electrical simulation based at least partly on the sensed action potentials.

64. The apparatus according to aspect 63, wherein the controller is configured to generate electrical pulses amplifying the sensed action potentials.

Aspect Group 266SE:
Reflux_Constricting-Band_Stop_Invaginated

1. An apparatus (100) for treating reflux disease of a human patient, adapted to at least partly encircle the esophagus (20) of the patient, comprising:

a first implantable portion (110) having a shape and size allowing it to be arranged to rest against a fundus wall portion (14) of the patient's stomach (10) and to be at least partly invaginated by the fundus wall portion, such that the first implantable portion is implanted at a position between the patient's diaphragm (30) and a lower portion of the fundus wall, and such that movement of the cardia (22) of the patient's stomach towards the diaphragm is restricted to hinder the cardia from sliding through the diaphragm opening into the patient's thorax;

a second implantable portion (120) being elongated to at least partly encircle the esophagus and having a variable length for allowing the apparatus be arranged in a constricting state for hindering fluid from passing from the stomach into the esophagus and in an expanded state for allowing food to pass into the stomach in response to the patient swallowing.

2. The apparatus according to aspect 1, wherein the first portion has a substantially fixed shape during operation of the apparatus.

3. The apparatus according to aspect 1 or 2, wherein a maximum width of a cross section taken across a length direction of the first implantable portion is larger than a maximum width of a cross section taken across a length direction of the second implantable portion.

4. The apparatus according to any of the preceding aspects, wherein the second implantable portion is configured to allow a transition from the constricting state into the expanded state caused by the food passing through esophagus.

5. The apparatus according to any of the preceding aspects, wherein the second implantable portion is configured to exert an encircling pressure on the esophagus in the constricting state.

6. The apparatus according to aspect 5, further comprising an attractor (212) for resiliently attracting adjacent portions (213) of the second implantable portion to one another to generate the encircling pressure.

7 The apparatus according to aspect 6, wherein the attractor comprises an clastic element.

8. The apparatus according to aspect 6, wherein the attractor comprises at least two mutually attracting magnets.

9. The apparatus according to aspect 8, further comprising a link (214) connecting a first and a second one of said at least two magnets to each other.

10. The apparatus according to aspect 9, wherein the link is configured to extend into at least one of said magnets in response to said magnets moving towards each other.

11. The apparatus according to any of the preceding aspects, further comprising a tubular cover (220) enclosing at least a part of the second implantable portion and comprising a plurality of cover portions (224, 225, 226) adapted to bend relative to each other to allow the second implantable portion to change between the constricting state and the expanded state, when the cover is at least partly covered by fibrotic tissue, without being substantially hindered or impeded by the presence of said fibrotic tissue.

12. The apparatus according to aspect 11, wherein the second implantable portion comprises an array of tubular segments (222).

13. The apparatus according to aspect 11 or 12, wherein the cover is formed of an inelastic material.

14. The apparatus according to any of aspects 11-13, wherein the cover comprises a biocompatible outer surface for long-term implantation.

15. The apparatus according to any of aspects 11-14, wherein the cover is configured to rest against an outer surface of the esophagus.

16. The apparatus according to any of aspects 11-15, wherein the cover comprises a surface promoting tissue growth.

17. The apparatus according to any of aspects 11-16, wherein the cover is formed of a polymer material, such as silicone.

18. The apparatus according to any of aspects 11-17, wherein the cover is formed of a material having a thickness of 0.1 to 10 mm, such as 1 to 5 mm.

19. The apparatus according to any of aspects 11-18, wherein the cover comprises at least one predefined fold (224) along which the cover is allowed to fold in response to the second implantable portion varying its length.

20. The apparatus according to any of aspects 11-19, wherein the cover comprises lowered and elevated portions (224, 225) allowing the cover to vary its length while maintaining its surface area.

21. The apparatus according to any of aspects 11-20, wherein the cover is configured to be compressible and expandable in its length direction.

22. The apparatus according to any of aspects 11-21, wherein a length of the cover enclosing said at least a part of the second implantable portion exceeds a length of said at least a part of the second implantable portion when said at least a part of the second implantable portion is arranged in the constricting state.

23. The apparatus according to any of the preceding aspects, comprising two end portions (216) configured to be coupled to each other to form a closed ring around the esophagus.

24. The apparatus according to aspect 23, wherein the end portions are configured to be releasably attached to each other.

25 The apparatus according to aspect 23 or 24, wherein the end portions comprise a respective interlockable attacher.

26. The apparatus according to aspect 1, wherein at least one of the first and the second implantable portion comprises a plurality of bodies (213) configured to be arranged in an annular array around the esophagus.

27. The apparatus according to aspect 26, wherein at least one of the first and the second implantable portion further comprises a plurality of links (214), each of which extending between a respective pair of bodies arranged adjacent to each other.

28. The apparatus according to aspect 27, wherein the second implantable portion comprises at least some of the plurality bodies and at least some of the plurality of links, and wherein each of said links is configured to allow the respective ones of said bodies to move towards and away from each other.

29. The apparatus according to aspect 28, wherein each of said links is configured to extend into at least one of the respective ones of said bodies as said bodies move towards each other.

30. The apparatus according to aspects 26, wherein the second implantable portion comprises at least some of the plurality of bodies and at least some of the plurality of links, and wherein the apparatus further comprises an attractor for resiliently attracting adjacent ones of said bodies to each other.

31. The apparatus according to aspect 30, wherein the attractor comprises at least one of a magnet, an elastic member, and a spring.

32. The apparatus according to aspect 1, wherein the first implantable portion is formed of a single body and the second implantable portion is formed of an array of bodies, wherein the array of bodies is movable towards and away from each other.

33. The apparatus according to any of the preceding aspects, wherein a volume of the first implantable portion is non-adjustable.

34. The apparatus according to any of aspects 1-32, wherein a volume of the first implantable portion is adjustable after implantation.

35. The apparatus according to any of the preceding aspects, wherein the first implantable portion comprises a biocompatible outer surface configured to rest against the fundus wall portion.

36. The apparatus according to any of the preceding aspects, wherein the first implantable portion is configured to be arranged such that a part of the fundus wall portion is arranged between the first implantable portion of the apparatus and the esophagus.

37. The apparatus according to any of the preceding aspects, wherein the first implantable portion is configured to be at least partly invaginated by the fundus wall portion along at least half of a length of the apparatus.

38. The apparatus according to any one of the preceding aspects, further comprising an electrode arrangement (150) configured to be arranged between the apparatus and the esophagus and to electrically stimulate muscle tissue of the outer wall of the esophagus to exercise the muscle tissue to improve the conditions for long term implantation of the movement restriction device.

39. The apparatus according to aspect 38, wherein the electrode arrangement comprises a plurality of electrode elements (152, 154), each of which being configured to electrically stimulate the muscle tissue.

40. The apparatus according to any of aspects 38-39, wherein the electrode arrangement comprises a coiled wire for increasing a contact surface between the electrode arrangement and the muscle tissue and for allowing the electrode arrangement to follow contraction and relaxation of the muscle tissue.

41. The apparatus according to any of aspects 38-40, wherein the electrode arrangement comprises a bare electrode portion (155) configured to form a metal-tissue interface with the muscle tissue, thereby allowing faradaic charge transfer to the be predominant charge transfer mechanism over said interface.

42. The apparatus according to any of aspects 38-41, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.

43. The apparatus according to any of aspects 38-42, wherein the electrode arrangement is configured be arranged to electrically stimulate the cardiac sphincter (26) of the patient to cause the cardiac sphincter to contract.

44. The apparatus according to aspect 43, wherein the electrode arrangement comprises at least two electrode elements (154) configured to be arranged on opposing sides of the cardiac sphincter.

45. The apparatus according to any of aspects 38-44, further comprising an implantable energy source (160) configured to provide the electrode arrangement with electrical power.

46. The apparatus according to any of aspects 38-45, further comprising controller (170) configured to be operably connected to the electrode arrangement for controlling the electrical stimulation of the muscle tissue.

47. The apparatus according to aspect 46, wherein the controller is configured to control the electrical stimulation such that the muscle tissue is stimulated by a series of electrical pulses (PL1, PL2, PL3, PL4).

48. The apparatus according to aspect 47, wherein the controller is configured to control the electrical stimulation such that a pulse of a first polarity is followed by a pulse of a second, reversed polarity 49. The apparatus according to any of aspects 46-48, wherein the controller is configured to generate a pulsed electrical stimulation signal comprising a pulse frequency (F) of 0.01-150 Hz.

50. The apparatus according to aspect 49, wherein the electrical stimulation signal comprises a pulse duration (D) of 0.01-100 ms.

51. The apparatus according to aspect 49 or 50, wherein the electrical stimulation signal comprises a pulse amplitude (A) of 1-15 mA.

52. The apparatus according to any of aspects 49-51, wherein the electrical stimulation signal comprises a pulse frequency of 0.15-0.25 Hz, a pulse duration of 20-30 ms and a pulse amplitude of 3-10 mA.

53. The apparatus according to any of aspects 38-52, further comprising an implantable sensor (S1) configured to sense actions potentials generated by pacemaker cells of the muscle tissue, and wherein the controller is configured to control the electrical simulation based at least partly on the sensed action potentials.

54. The apparatus according to aspect 53, wherein the controller is configured to generate electrical pulses amplifying the sensed action potentials.

Aspect Group 267SE:
Reflux_Stimulating-Band_Stop_Invaginated

1. An apparatus (100) for treating reflux disease of a human patient, adapted to at least partly encircle the esophagus (20) of the patient, comprising:

a movement restriction device (110) having a shape and size allowing it to be arranged to rest against a fundus wall portion (14) of the patient's stomach (10) and to be at least partly invaginated by the fundus wall portion, such that the first implantable portion is implanted at a position between the patient's diaphragm (30) and a lower portion of the fundus wall, and such that movement of the cardia (22) of the patient's stomach towards the diaphragm is restricted to hinder the cardia from sliding through the diaphragm opening (32) into the patient's thorax; and an elongated support device (120) connected to the movement restriction device and configured to at least partly encircle the esophagus;

wherein the apparatus further comprises an electrode arrangement (150) comprising an electrode element (154) supported by the support device and configured to electrically stimulate muscle tissue of the esophagus; and wherein the support device comprises a rigidity that allows the position of the electrode element relative to the esophagus to be determined mainly by the position and orientation of the movement restriction device.

2. The apparatus according to aspect 1, wherein electrode arrangement comprises a plurality of electrode elements.

3. The apparatus according to aspect 1 or 2, wherein the electrode arrangement is configured to electrically stimulate the cardiac sphincter (26) of the patient to cause the cardiac sphincter to contract.

4. The apparatus according to aspect 3, wherein the electrode arrangement is configured to stimulate opposing sides of the cardiac sphincter.

5. The apparatus according to any of the preceding aspects, wherein the electrode arrangement is configured to exercise muscle tissue in contact with the apparatus to improve the conditions for long term implantation of the apparatus.

6. The apparatus according to aspect 2, wherein an electrode element of the plurality of electrode elements is configured to be arranged between the movement restriction device and the fundus wall portion to electrically stimulate muscle tissue of the fundus wall portion.

7. The apparatus according to any of the preceding aspects, wherein the electrode arrangement comprises a coiled wire for increasing a contact surface between the electrode arrangement and the muscle tissue.

8. The apparatus according to any of the preceding aspects, wherein a maximum width of a cross section taken across a length direction of the movement restriction device is larger than a maximum width of a cross section taken across a length direction of the support device.

9. The apparatus according to any of the preceding aspects, wherein the support device is formed as a band configured to be arranged around at least a part of the esophagus, and wherein a first and a second end portion of the band is coupled to the first implantable portion.

10. The apparatus according to any of the preceding aspects, wherein the apparatus comprises a biocompatible outer surface for long-term implantation.

11. The apparatus according to any of the preceding aspects, wherein the apparatus is formed of a polymer material, such as silicone.

12. The apparatus according to any of the preceding aspects, wherein the movement restriction device is configured to be arranged such that a part of the fundus wall portion is arranged between the movement restriction device and the esophagus.

13. The apparatus according to any of the preceding aspects, wherein the movement restriction device is configured to be fully invaginated by the fundus wall portion.

14. The apparatus according to any of the preceding aspects, wherein the apparatus is ring-shaped and configured to be at least partly invaginated by the fundus wall portion along at least half of a circumference of the apparatus.

15. The apparatus according to any of the preceding aspects, wherein the electrode arrangement comprises a bare electrode portion (155) configured to form a metal-tissue interface with the muscle tissue, thereby allowing faradaic charge transfer to the be predominant charge transfer mechanism over said interface.

16. The apparatus according to any of aspects 1-14, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.

17. The apparatus according to any of the preceding aspects, further comprising an implantable energy source (160) configured to provide the electrode arrangement with electrical power.

18. The apparatus according to aspect 17, wherein the implantable energy source is arranged within the movement restriction device or the support device.

19. The apparatus according to aspect 17, wherein the implantable energy source is configured to be arranged outside movement restriction device and the support device.

20. The apparatus according to aspect 19, wherein the implantable energy source is configured to be implanted subcutaneously.

21. The apparatus according to any of aspects 17-20, wherein the implantable energy source comprises a primary cell.

22. The apparatus according to any of aspects 17-31, wherein the implantable energy source comprises a secondary cell.

23. The apparatus according to aspect 17-22, further comprising a controller (170) configured to indicate a functional status of the implantable energy source.

24. The apparatus according to aspect 23, wherein the functional status indicates a charge level of the implantable energy source.

25. The apparatus according to aspect 23 or 24, wherein the functional status indicates a temperature of at least one of the implantable energy source, the muscle tissue, and the electrode arrangement.

26. The apparatus according to any of aspects 17-25, wherein the implantable energy source is configured to be charged by an external energy source arranged outside the patient's body.

27. The apparatus according to aspect 26, further comprising an implantable charger (190) configured to be electrically connected to the implantable energy source and enable charging of the implantable energy source by the external energy source.

28. The apparatus according to aspect 27, wherein the charger comprises an electromagnetic coil configured to receive electrical power wirelessly from the external energy source.

29. The apparatus according to aspect 27 or 28, wherein the charger is configured to receive the functional status from the energy source indicator and control the charging of the implantable energy source based on the functional status.

30. The apparatus according to any of aspects 27-29, wherein the charger is configured to control the charging of the implantable energy source by controlling a receipt of electrical power from the external energy source at the implantable charger.

31. The apparatus according to any of aspects 27-29, wherein the charger is configured to control the charging of the implantable energy source by controlling a transmission of electrical power from the external energy source to the implantable charger.

32. The apparatus according to any of the preceding aspects, further comprising controller (170) configured to be operably connected to the electrode arrangement for controlling the electrical stimulation of the muscle tissue.

33. The apparatus according to aspect 32, wherein the controller is configured to control the electrical stimulation such that the muscle tissue is stimulated by a series of electrical pulses (PL1, PL2, PL3, PL4).

34. The apparatus according to aspect 33, wherein the controller is configured to control the electrical stimulation such that a pulse of a first polarity is followed by a pulse of a second, reversed polarity.

35. The apparatus according to any of aspects 32-34, wherein the controller is configured to generate a pulsed electrical stimulation signal comprising a pulse frequency (F) of 0.01-150 Hz.

36. The apparatus according to aspect 35, wherein the electrical stimulation signal comprises a pulse duration (D) of 0.01-100 ms.

37. The apparatus according to aspect 35 or 36, wherein the electrical stimulation signal comprises a pulse amplitude (A) of 1-15 mA.

38. The apparatus according to any of aspects 35-37, wherein the electrical stimulation signal comprises a pulse frequency of 0.15-0.25 Hz, a pulse duration of 20-30 ms and a pulse amplitude of 3-10 mA.

39. The apparatus according to any of aspects 35-38, wherein the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.

40. The apparatus according to any of aspects 32-39, wherein the controller comprises a wireless remote control (175).

41. The apparatus according to aspect 40, wherein the wireless remote control comprises an external signal transmitter, and wherein the apparatus further comprises an implantable controller configured to receive a signal transmitted by the external signal transmitter and to control an operation of the apparatus based on said signal.

42. The apparatus according to aspect 41, wherein signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.

43. The apparatus according to any of aspects 32-42, further comprising an implantable sensor (S1) configured to sense actions potentials generated by pacemaker cells of the muscle tissue, and wherein the controller is configured to control the electrical simulation based at least partly on the sensed action potentials.

44. The apparatus according to aspect 43, wherein the controller is configured to generate electrical pulses amplifying the sensed action potentials.

Aspect Group 268SE: Reflux_Stop_His_Method

1. A method for treating reflux disease of a human patient by implanting a movement restriction device (100) such that the movement restriction device is arranged to restrict movement of the cardia (22) of the patient's stomach (10) towards the diaphragm (30) to hinder the cardia from sliding through the diaphragm opening (32) into the patient's thorax, wherein the method comprises:
- placing the movement restriction device such that a lower portion of the movement restriction device rests against the serosa at the angle of His (24), and such that an upper portion of the movement restriction device defines a gap between the movement restriction device and the patient's esophagus (20), when the lower portion rests against the angle of His;
- arranging a portion of the fundus (12) of the stomach in the gap; and
- attaching the fundus to the patient's esophagus to at least partly enclose the movement restriction device by the portion of the fundus.

2. The method according to aspect 1, wherein the movement restriction device has a rounded shape.

3. The method according to aspect 1 or 2, comprising arranging the upper portion to point away from the esophagus.

4. The method according to any of the preceding aspects, wherein the lower portion is wider that the upper portion.

5. The method according to any of the preceding aspects, wherein the movement restriction device has a C-shaped cross section.

6. The method according to any of the preceding aspects, wherein the upper portion comprises a recess defined in the outer surface of the movement restriction device.

7. The method according to any of the preceding aspects, wherein the lower portion comprises a curved outer surface, wherein the method further comprises arranging the curved outer surface to face the esophagus, and wherein the curved outer surface comprises a radius of curvature corresponding to or exceeding the radius of curvature of the esophagus.

8. The method according to any of the preceding aspects, further comprising at least partly invaginating an elongated support (117), protruding from the movement restriction device, in the portion of the fundus before attaching the fundus to the esophagus.

9. The method according to aspect 8, wherein the support is shaped as a lever, wherein the method further comprises orienting the support along the esophagus.

10. The method according to any of the preceding aspects, further comprising arranging an electrode arrangement (150) between the movement restriction device and the portion of the fundus and/or the serosa, wherein the electrode arrangement is configured to electrically stimulate muscle tissue of the portion of the fundus and/or the serosa to improve the conditions for long term implantation of the movement restriction device.

11. The method according to aspect 10, wherein the electrode arrangement comprises a plurality of electrode elements (152), each of which being configured to engage and electrically stimulate the muscle tissue.

12. The method according to aspect 10 or 11, wherein the electrode arrangement comprises a coiled wire for increasing a contact surface between the electrode arrangement and the muscle tissue and for allowing the electrode arrangement to follow contraction and relaxation of the muscle tissue.

13. The method according to any of aspects 10-12, wherein the electrode arrangement comprises a bare electrode portion (155) configured to form a metal-tissue interface with the muscle tissue, thereby allowing faradaic charge transfer to the be predominant charge transfer mechanism over said interface.

14. The method according to any aspects 10-12, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.

15. The method according to any of aspects 10-14, wherein the electrode arrangement is further configured to be arranged to electrically stimulate the cardiac sphincter (26) to cause the cardiac sphincter to contract.

16. The method according to aspect 15, wherein the electrode arrangement comprises at least two electrode elements (154), wherein the method further comprises arranging said electrode elements on opposing sides of the cardiac sphincter.

17. The method according to aspect 16, wherein the movement restriction device further comprises a holder (120) configured to support the at least two electrode elements at the opposing sides of the cardiac sphincter.

18. The method according to any of aspects 10-17, further comprising implanting an implantable energy source (160) configured to provide the electrode with electrical power.

19. The method according to aspect 18, wherein the implantable energy source is arranged inside the movement restriction device.

20. The method according to aspect 18, wherein the implantable energy source is configured to be arranged outside the movement restriction device, and wherein the method further comprises implanting the implantable energy source in the patient's body.

21. The method according to aspect 20, further comprising implanting the implantable energy source subcutaneously.

22. The method according to any of aspects 18-21, wherein the implantable energy source comprises a primary cell.

23. The method according to any of aspects 18-22, wherein the implantable energy source comprises a secondary cell.

24. The method according to aspect 18-23, further comprising implanting a controller (170) configured to indicate a functional status of the implantable energy source.

25. The method according to aspect 24, wherein the functional status indicates a charge level of the implantable energy source.
26. The method according to aspect 24 or 25, wherein the functional status indicates a temperature of at least one of the implantable energy source, the muscle tissue, and the electrode arrangement.
27. The method according to any of aspects 24-26, wherein the implantable energy source is configured to be charged by an external energy source (165) arranged outside the patient's body.
28. The method according to aspect 27, further comprising implanting an implantable charger (190) configured to be electrically connected to the implantable energy source and enable charging of the implantable energy source by the external energy source.
29. The method according to aspect 28, wherein the charger comprises an electromagnetic coil configured to receive electrical power wirelessly from the external energy source.
30. The method according to aspect 28 or 29, wherein the charger is configured to control the charging of the implantable energy source based on the functional status.
31. The method according to any of aspects 28-30, wherein the charger is configured to control the charging of the implantable energy source by controlling a receipt of electrical power from the external energy source at the implantable charger.
32. The method according to any of aspects 28-31, wherein the charger is configured to control the charging of the implantable energy source by controlling a transmission of electrical power from the external energy source to the implantable charger.
33. The method according to any of aspects 10-23, further comprising implanting a controller (170) configured to be operably connected to the electrode arrangement for controlling the electrical stimulation of the muscle tissue.
34. The method according to aspect 33, wherein the controller is configured to control the electrical stimulation such that the muscle tissue is stimulated by a series of electrical pulses (PL1, PL2, PL3, PL4).
35. The method according to aspect 34, wherein the controller is configured to control the electrical stimulation such that a pulse of a first polarity is followed by a pulse of a second, reversed polarity.
36. The method according to aspect 34 or 35, wherein the controller is configured to generate a pulsed electrical stimulation signal comprising a pulse frequency (F) of 0.01-150 Hz.
37. The method according to aspect 36, wherein the electrical stimulation signal comprises a pulse duration (D) of 0.01-100 ms.
38. The method according to aspect 36 or 37, wherein the electrical stimulation signal comprises a pulse amplitude (A) of 1-15 mA.
39 The method according to any of aspects 36-38, wherein the electrical stimulation signal comprises a pulse frequency of 0.15-0.25 Hz, a pulse duration of 20-30 ms and a pulse amplitude of 3-10 mA.
40. The method according to any of aspects 36-39, wherein the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.
41. The method according to any of aspects 33-43, further comprising implanting an implantable sensor (S1) configured to sense actions potentials generated by pacemaker cells of the muscle tissue, and wherein the controller is configured to control the electrical simulation based at least partly on the sensed action potentials.
42. The method according to aspect 44, wherein the controller is configured to generate electrical pulses amplifying the sensed action potentials.

Aspect Group 268PC_NEW: Reflux_Sleeve_Method

1. A method for treating reflux disease of a human patient by implanting a movement restriction device (100) such that the movement restriction device is arranged to restrict movement of the cardia (22) of the patient's stomach (10) towards the diaphragm (30) to hinder the cardia from moving towards and potentially sliding through the diaphragm opening (32) into the patient's thorax, wherein the method comprises:
- placing the movement restriction device such that a lower portion of the movement restriction device rests against the serosa of a surgically modified stomach on the greater curvature side of the stomach partly extirpated, such that an upper portion of the movement restriction device defines; a small gap between the movement restriction device positioned close to the diaphragm and the patient's esophagus (20), when the lower portion rests against the surgically modified stomach;
- arranging a portion of fat from the gastrophrenic and/or gastrosplenic ligament and/or greater omentum to cover the movement restriction device on at least one of the left, ventral and cranial side of the movement restriction device with the intention to avoid adherences to the nearby organs.

2. The method according to aspect 1, wherein the movement restriction device has a rounded shape.
3. The method according to aspect 1, wherein the part of the movement restriction device mounted towards the stomach is configured like an U-shaped arm.

Aspect Group 269SE: Reflux_Stop_Gastric-Sleeve

1. An apparatus (100) for treating reflux disease of a human patient, comprising:
- an implantable movement restriction device (110); and
- an elongated attacher (117) configured to be attached to the movement restriction device and to be at least one of; partly invaginated by a wall portion of the patient's stomach (10) and sutured to a previously sutured line of staplers in a surgically modified stomach:
- wherein the attacher comprises a shape and size allowing it to be invaginated by or sutured to the stapler reinforced wall portion to both hold the device in position as well as hinder rotation of the movement restriction device; and
- wherein the attacher is configured to be sutured to or invaginated by the wall portion such that the movement restriction device is arranged at a position between the patient's diaphragm (30) and the wall portion, close to esophagus, however, not contacting the patient's esophagus (20), high above the LES to restrict movement of the cardia (22) of the patient's stomach towards the diaphragm to also hinder.

2. The apparatus according to aspect 1, wherein a first end portion of the attacher is configured to be invaginated by the wall portion and a second end portion is configured to be attached to the movement restriction device.

3. The apparatus according to aspect 1 or 2, wherein the attacher comprises a first portion (118) and a second portion (119) extending in different directions relative to each other, wherein the first portion is configured to be invaginated by the wall portion to hinder rotation of the movement restriction device around a first axis, and wherein the second portion is configured to be invaginated by the wall portion to hinder rotation of the movement restriction device around a second axis, different from the first axis.
4. The apparatus according to aspect 3, wherein the first and second portions of the attacher are curved to follow a curvature of the wall portion.
5. The apparatus according to aspect 3 or 4, wherein the first portion and second portion are arranged at an angle to each other, the angle being in the interval of 60-120 degrees.
6. The apparatus according to any of the preceding aspects, wherein the attacher is configured to be releasably attached to the movement restriction device.
7. The apparatus according to any of the preceding aspects, wherein the movement restriction device has a rounded shape.
8 The apparatus according to any of the preceding aspects, wherein the movement restriction device has a shape conforming to a sphere.
9. The apparatus according to any of the preceding aspects, wherein the attacher is configured to allow a position of the movement restriction device to be adjusted after invagination of the attachment means.
10. The apparatus according to any of the preceding aspects, configured to allow a distance between the movement restriction device and the attacher to be varied to allow the position of the movement restriction device relative to the diaphragm to be adjusted.
11. The apparatus according to any of the preceding aspects, configured to allow an orientation of the movement restriction device relative to the attachments means to be varied to allow the position of the movement restriction device relative to the diaphragm or esophagus to be adjusted.
12. The apparatus according to aspect 3, wherein the attacher comprises a third portion, configured to be arranged to protrude from the wall portion when implanted, and to define a distance between the wall portion and the movement restriction device.
13. The apparatus according to aspect 12, wherein the third portion comprises a curvature allowing the third portion to be arranged to point away from the esophagus when implanted.
14. The apparatus according to aspect 1, wherein the movement restriction device and the attacher are integrally formed into a single piece.
15. The apparatus according to any of the preceding aspects, wherein each of the movement restriction device and the attachments means comprises a biocompatible outer surface.
16. The apparatus according to any of the preceding aspects, wherein the attacher comprises an outer surface configured to promote tissue growth.
17. The apparatus according to any of the preceding aspects, wherein the attacher is formed of a metal.
18. The apparatus according to any of aspects 1-16, wherein the movement restriction device is formed of a polymer.
19. The apparatus according to any of the preceding aspects, wherein a minimum width of the movement restriction device, as measured from side to side, is 30 mm or larger, such as 40 mm or larger.
20. The apparatus according to any of the preceding aspects, wherein an outer surface of the movement restriction device comprises a material for hindering growth of fibrotic tissue.
22. The apparatus according to any of the preceding aspects, further comprising an electrode arrangement (150) configured to be arranged between the apparatus and muscle tissue of at least one of the diaphragm and the wall portion, and to electrically stimulate muscle tissue to exercise the muscle tissue to improve the conditions for long term implantation of the apparatus.
23. The apparatus according to aspect 22, wherein the electrode arrangement comprises a plurality of electrode elements (152), each of which being configured to engage and electrically stimulate the muscle tissue.
24. The apparatus according to any of aspects 22 or 23, wherein the electrode arrangement comprises a bare electrode portion (155) configured to form a metal-tissue interface with the muscle tissue, thereby allowing faradaic charge transfer to the be predominant charge transfer mechanism over said interface.
25. The apparatus according to any aspects 22 or 23, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.
26. The apparatus according to any of aspects 22-25, further comprising an implantable energy source (160) configured to provide the electrode arrangement with electrical power.
27. The apparatus according to aspect 26, wherein the implantable energy source is arranged inside the movement restriction device or the attachment means.
28. The apparatus according to aspect 26, wherein the implantable energy source is configured to be arranged outside the movement restriction device and the attachment means.
29. The apparatus according to aspect 28, wherein the implantable energy source is configured to be implanted subcutaneously.
30. The apparatus according to any of aspects 26-29, wherein the implantable energy source comprises a primary cell.
31. The apparatus according to any of aspects 26-30, wherein the implantable energy source comprises a secondary cell.
32. The apparatus according to aspect 26-31, further comprising a controller (170) configured to indicate a functional status of the implantable energy source.
33. The apparatus according to aspect 32, wherein the functional status indicates a charge level of the implantable energy source.
34. The apparatus according to aspect 32 or 33, wherein the functional status indicates a temperature of at least one of the implantable energy source, the muscle tissue, and the electrode arrangement.
35. The apparatus according to any of aspects 32-34, wherein the implantable energy source is configured to be charged by an external energy source (165) arranged outside the patient's body.
36. The apparatus according to aspect 35, further comprising an implantable charger (190) configured to be electrically connected to the implantable energy source and enable charging of the implantable energy source by the external energy source.
37. The apparatus according to aspect 33, wherein the charger comprises an electromagnetic coil configured to receive electrical power wirelessly from the external energy source.

38. The apparatus according to aspect 36 or 37, wherein the charger is configured to control the charging of the implantable energy source based on the functional status.

39. The apparatus according to any of aspects 33-38, wherein the charger is configured to control the charging of the implantable energy source by controlling a receipt of electrical power from the external energy source at the implantable charger.

40. The apparatus according to any of aspects 36-39, wherein the charger is configured to control the charging of the implantable energy source by controlling a transmission of electrical power from the external energy source to the implantable charger.

41. The apparatus according to any of aspects 22-40, further comprising controller (170) configured to be operably connected to the electrode arrangement for controlling the electrical stimulation of the muscle tissue.

42. The apparatus according to aspect 41, wherein the controller is configured to control the electrical stimulation such that the muscle tissue is stimulated by a series of electrical pulses (PL1, PL2, PL3, PL4).

43. The apparatus according to aspect 42, wherein the controller is configured to control the electrical stimulation such that a pulse of a first polarity is followed by a pulse of a second, reversed polarity.

44. The apparatus according to aspect 42 or 43, wherein the controller is configured to generate a pulsed electrical stimulation signal comprising a pulse frequency (F) of 0.01-150 Hz.

45. The apparatus according to aspect 44, wherein the electrical stimulation signal comprises a pulse duration (D) of 0.01-100 ms.

46. The apparatus according to aspect 44 or 45, wherein the electrical stimulation signal comprises a pulse amplitude (A) of 1-15 mA.

47. The apparatus according to any of aspects 44-46, wherein the electrical stimulation signal comprises a pulse frequency of 0.15-0.25 Hz, a pulse duration of 20-30 ms and a pulse amplitude of 3-10 mA.

48. The apparatus according to any of aspects 44-47, wherein the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.

49. The apparatus according to any of aspects 41-48, wherein the controller comprises a wireless remote control (175).

50. The apparatus according to aspect 49, wherein the wireless remote control comprises an external signal transmitter, and wherein the controller comprises an implantable controller configured to receive a signal transmitted by the external signal transmitter and to control an operation of the apparatus based on said signal.

51. The apparatus according to aspect 50, wherein the signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.

52. The apparatus according to any of aspects 41-51, further comprising an implantable sensor (S1) configured to sense actions potentials generated by pacemaker cells of the muscle tissue, and wherein the controller is configured to control the electrical simulation based at least partly on the sensed action potentials.

53. The apparatus according to any of the preceding aspects, further comprising a support device (130) arranged to be attached to the outside of the stomach wall and further to support the elongated attacher (118).

54. The apparatus according to aspect 53, wherein the support device (130) is configured to be attached to a gastric sleeve seam formed during a gastric sleeve surgery.

55. The apparatus according to aspect 54, wherein the support device comprises a plurality of through-holes for receiving the fastening means, such as sutures or staples, used in the gastric sleeve seam.

56. The apparatus according to any of aspects 53-55, wherein the support device (130) is formed as a bar or flat rod having a U-shaped cross section profile adapted to follow an outer curvature of the stomach wall.

Aspect Group 269PC: Reflux_Stop_Gastric-Sleeve

1. An apparatus (100) for treating reflux disease of a human patient, comprising:
 an implantable movement restriction device (110); and
 an elongated attacher (117) configured to be attached to the movement restriction device and to be at least one of; partly invaginated by a wall portion of the patient's stomach (10) and sutured to a previously sutured line of staplers in a surgically modified stomach.
 wherein the attacher comprises a shape and size allowing it to be invaginated by or sutured to the stapler reinforced wall portion to both hold the device in position as well as hinder rotation of the movement restriction device; and
 wherein the attacher is configured to be sutured to or invaginated by the wall portion such that the movement restriction device is arranged at a position between the patient's diaphragm (30) and the wall portion, close to esophagus, however, not contacting the patient's esophagus (20), high above the LES to restrict movement of the cardia (22) of the patient's stomach towards the diaphragm to also hinder the cardia from sliding through the diaphragm opening (32) into the patient's thorax.

2. The apparatus according to aspect 1, wherein a first end portion of the attacher is configured to be invaginated by the wall portion and a second end portion is configured to be attached to the movement restriction device.

3. The apparatus according to aspect 1 or 2, wherein the attacher comprises a first portion (118) and a second portion (119) extending in different directions relative to each other, wherein the first portion is configured to be invaginated by the wall portion to hinder rotation of the movement restriction device around a first axis, and wherein the second portion is configured to be invaginated by the wall portion to hinder rotation of the movement restriction device around a second axis, different from the first axis.

4. The apparatus according to aspect 3, wherein the first and second portions of the attacher are curved to follow a curvature of the wall portion.

5. The apparatus according to aspect 3 or 4, wherein the first portion and second portion are arranged at an angle to each other, the angle being in the interval of 60-120 degrees.

6. The apparatus according to any of the preceding aspects, wherein the attacher is configured to be releasably attached to the movement restriction device.

7. The apparatus according to any of the preceding aspects, wherein the movement restriction device has a rounded shape.

8. The apparatus according to any of the preceding aspects, wherein the movement restriction device has a shape conforming to a sphere.
9. The apparatus according to any of the preceding aspects, wherein the attacher is configured to allow a position of the movement restriction device to be adjusted after invagination of the attachment means.
10. The apparatus according to any of the preceding aspects, configured to allow a distance between the movement restriction device and the attacher to be varied to allow the position of the movement restriction device relative to the diaphragm to be adjusted.
11. The apparatus according to any of the preceding aspects, configured to allow an orientation of the movement restriction device relative to the attachments means to be varied to allow the position of the movement restriction device relative to the diaphragm or esophagus to be the adjusted.
12. The apparatus according to aspect 3, wherein the attacher comprises a third portion, configured to be arranged to protrude from the wall portion when implanted, and to define a distance between the wall portion and the movement restriction device.
13. The apparatus according to aspect 12, wherein the third portion comprises a curvature allowing the third portion to be arranged to point away from the esophagus when implanted.
14. The apparatus according to aspect 1, wherein the movement restriction device and the attacher are integrally formed into a single piece.
15. The apparatus according to any of the preceding aspects, wherein each of the movement restriction device and the attachments means comprises a biocompatible outer surface.
16. The apparatus according to any of the preceding aspects, wherein the attacher comprises an outer surface configured to promote tissue growth.
17. The apparatus according to any of the preceding aspects, wherein the attacher is formed of a metal.
18. The apparatus according to any of aspects 1-16, wherein the movement restriction device is formed of a polymer.
19. The apparatus according to any of the preceding aspects, wherein a minimum width of the movement restriction device, as measured from side to side, is 30 mm or larger, such as 40 mm or larger.
20. The apparatus according to any of the preceding aspects, wherein an outer surface of the movement restriction device comprises a material for hindering growth of fibrotic tissue.
22. The apparatus according to any of the preceding aspects, further comprising an electrode arrangement (150) configured to be arranged between the apparatus and muscle tissue of at least one of the diaphragm and the wall portion, and to electrically stimulate muscle tissue to exercise the muscle tissue to improve the conditions for long term implantation of the apparatus.
23. The apparatus according to aspect 22, wherein the electrode arrangement comprises a plurality of electrode elements (152), each of which being configured to engage and electrically stimulate the muscle tissue.
24. The apparatus according to any of aspects 22 or 23, wherein the electrode arrangement comprises a bare electrode portion (155) configured to form a metal-tissue interface with the muscle tissue, thereby allowing faradaic charge transfer to the be predominant charge transfer mechanism over said interface.
25. The apparatus according to any aspects 22 or 23, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.
26. The apparatus according to any of aspects 22-25, further comprising an implantable energy source (160) configured to provide the electrode arrangement with electrical power.
27. The apparatus according to aspect 26, wherein the implantable energy source is arranged inside the movement restriction device or the attachment means.
28. The apparatus according to aspect 26, wherein the implantable energy source is configured to be arranged outside the movement restriction device and the attachment means.
29. The apparatus according to aspect 28, wherein the implantable energy source is configured to be implanted subcutaneously.
30. The apparatus according to any of aspects 26-29, wherein the implantable energy source comprises a primary cell.
31. The apparatus according to any of aspects 26-30, wherein the implantable energy source comprises a secondary cell.
32. The apparatus according to aspect 26-31, further comprising a controller (170) configured to indicate a functional status of the implantable energy source.
33. The apparatus according to aspect 32, wherein the functional status indicates a charge level of the implantable energy source.
34. The apparatus according to aspect 32 or 33, wherein the functional status indicates a temperature of at least one of the implantable energy source, the muscle tissue, and the electrode arrangement.
35. The apparatus according to any of aspects 32-34, wherein the implantable energy source is configured to be charged by an external energy source (165) arranged outside the patient's body.
36. The apparatus according to aspect 35, further comprising an implantable charger (190) configured to be electrically connected to the implantable energy source and enable charging of the implantable energy source by the external energy source.
37. The apparatus according to aspect 33, wherein the charger comprises an electromagnetic coil configured to receive electrical power wirelessly from the external energy source.
38. The apparatus according to aspect 36 or 37, wherein the charger is configured to control the charging of the implantable energy source based on the functional status.
39. The apparatus according to any of aspects 33-38, wherein the charger is configured to control the charging of the implantable energy source by controlling a receipt of electrical power from the external energy source at the implantable charger.
40. The apparatus according to any of aspects 36-39, wherein the charger is configured to control the charging of the implantable energy source by controlling a transmission of electrical power from the external energy source to the implantable charger.
41. The apparatus according to any of aspects 22-40, further comprising controller (170) configured to be operably connected to the electrode arrangement for controlling the electrical stimulation of the muscle tissue.
42. The apparatus according to aspect 41, wherein the controller is configured to control the electrical stimulation such that the muscle tissue is stimulated by a series of electrical pulses (PL1, PL2, PL3, PL4).

43. The apparatus according to aspect 42, wherein the controller is configured to control the electrical stimulation such that a pulse of a first polarity is followed by a pulse of a second, reversed polarity.

44. The apparatus according to aspect 42 or 43, wherein the controller is configured to generate a pulsed electrical stimulation signal comprising a pulse frequency (F) of 0.01-150 Hz.

45. The apparatus according to aspect 44, wherein the electrical stimulation signal comprises a pulse duration (D) of 0.01-100 ms.

46. The apparatus according to aspect 44 or 45, wherein the electrical stimulation signal comprises a pulse amplitude (A) of 1-15 mA.

47. The apparatus according to any of aspects 44-46, wherein the electrical stimulation signal comprises a pulse frequency of 0.15-0.25 Hz., a pulse duration of 20-30 ms and a pulse amplitude of 3-10 mA.

48. The apparatus according to any of aspects 44-47, wherein the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.

49. The apparatus according to any of aspects 41-48, wherein the controller comprises a wireless remote control (175).

50. The apparatus according to aspect 49, wherein the wireless remote control comprises an external signal transmitter, and wherein the controller comprises an implantable controller configured to receive a signal transmitted by the external signal transmitter and to control an operation of the apparatus based on said signal.

51. The apparatus according to aspect 50, wherein the signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.

52. The apparatus according to any of aspects 41-51, further comprising an implantable sensor (S1) configured to sense actions potentials generated by pacemaker cells of the muscle tissue, and wherein the controller is configured to control the electrical simulation based at least partly on the sensed action potentials.

53. The apparatus according to any of the preceding aspects, further comprising a support device (130) arranged to be attached to the outside of the stomach wall and further to support the elongated attacher (118).

54. The apparatus according to aspect 53, wherein the support device (130) is configured to be attached to a gastric sleeve seam formed during a gastric sleeve surgery.

55. The apparatus according to aspect 54, wherein the support device comprises a plurality of through-holes for receiving the fastening means, such as sutures or staples, used in the gastric sleeve seam.

56. The apparatus according to any of aspects 53-55, wherein the support device (130) is formed as a bar or flat rod having a U-shaped cross section profile adapted to follow an outer curvature of the stomach wall.

Aspect Group 270SE: Reflux_Band_Stop_Method

1. A method of treating reflux disease in a human patient by implanting an apparatus (100) comprising a movement restriction device (110) and an elongated support device (120), such that the support device at least partly encircles the esophagus (10) of the patient and such that the movement restriction device is at arranged on the fundus side of the esophagus to restrict the movement of the cardia (22) in relation to the diaphragm (30) to hinder the cardia to from sliding through the diaphragm opening (32) into the patient's thorax, the method comprising the steps of:

- introducing the apparatus into the abdominal cavity;
- placing the apparatus such that the movement restriction device rests against the outside of the stomach's fundus (12):
- wrapping a portion of the fundus around at least a part of the movement restriction device;
- affixing the fundus to the esophagus such that the movement restriction device is arranged at a position between the diaphragm and the cardiac sphincter, and such that a part of the fundus is arranged between the movement restriction device and the esophagus; and
- arranging the support device to at least partly encircle the esophagus;
- wherein the movement restriction device and the second portion form a ring-shaped body extending through the pouch to at least partly encircle the esophagus, supporting the movement restriction device to treat acid reflux.

2. The method according to aspect 1, comprising placing the apparatus such that the movement restriction device rests against the outside of the fundus at a position between the cardiac sphincter and the portion of the fundus that is to be affixed to the esophagus.

3. The method according to aspect 1, comprising placing the apparatus such that the portion of the fundus that is affixed to the esophagus is arranged between the cardiac sphincter (26) and the movement restriction device.

4. The method according to any of the preceding aspects, wherein the pouch is formed to be open in a least two positions to form a tunnel through which the apparatus extends.

5. The method according to any of the preceding aspects, further comprising affixing the portion of the fundus to the patient's diaphragm.

6. The method according to any of the preceding aspects, wherein affixing the portion of the fundus to the esophagus includes suturing or stapling.

7. The method according to any of the preceding aspects, wherein the support device comprises a first and a second end portion between which the esophagus can be introduced, and wherein the first and second end portions can be coupled to each other so as to fixate the support device to the esophagus in an encircling manner.

8. The method according to any of the preceding aspects, further comprising:

- inserting a needle or a tube-like instrument into the patient's abdomen;
- using the needle or tube-like instrument to fill the abdomen with a gas;
- placing at least two laparoscopic trocars in the abdomen;
- inserting a camera through one of the laparoscopic trocars into the abdomen:
- inserting at least one dissecting tool through one the laparoscopic trocars;
- dissecting a portion of the stomach; and
- at least partly closing the pouch by means of sutures, such as barbed sutures, or staples.

9. The method according to any of the preceding aspects, wherein the support device comprises a variable length for allowing the apparatus be arranged in a constricting state for hindering fluid from passing from the stomach into the esophagus and in an expanded state for allowing food to pass into the stomach in response to the patient swallowing.

10. The method according to aspect 9, wherein the movement restriction device has a substantially fixed shape during operation of the apparatus.

11. The method according to aspect 9 or 10, wherein the support device is configured to allow a transition from the constricting state into the expanded state caused by the food passing through esophagus.

12. The method according to any of aspects 9-11, wherein the support device is configured to exert an encircling pressure on the esophagus in the constricting state.

13. The method according to aspect 12, further comprising an attractor (212) for resiliently attracting adjacent portions (213) of the support device to one another to generate the encircling pressure.

14. The method according to aspect 13, wherein the attractor comprises an elastic element.

15. The method according to aspect 13, wherein the attractor comprises at least two mutually attracting magnets.

16. The method according to aspect 15, further comprising a link (214) connecting a first and a second one of said at least two magnets to each other.

17. The method according to aspect 16, wherein the link is configured to extend into at least one of said magnets in response to said magnets moving towards each other.

18. The method according to any of aspects 9-17, further comprising a tubular cover (220) enclosing at least a part of the support device and comprising a plurality of cover portions (224, 225, 226) adapted to bend relative to each other to allow the second support device to change between the constricting state and the expanded state, when the cover is at least partly covered by fibrotic tissue, without being substantially hindered or impeded by the presence of said fibrotic tissue.

19. The method according to aspect 18, wherein the cover comprises at least one predefined fold (224) along which the cover is allowed to fold in response to the support device varying its length.

20. The apparatus according to any of aspects 18-20, wherein the cover comprises lowered and elevated portions (225, 226) allowing the cover to vary its length while maintaining its surface area.

21. The method according to any of aspects 1-8, wherein the apparatus further comprises an electrode arrangement (150) comprising an electrode element (154) supported by the support device and configured to electrically stimulate muscle tissue of the esophagus.

22. The method according to aspect 21, wherein the electrode arrangement is configured to electrically stimulate the cardiac sphincter of the patient to cause the cardiac sphincter to contract.

23. The method according to aspect 22, wherein the electrode arrangement is configured to stimulate opposing sides of the cardiac sphincter.

24. The method according to any aspects 1-8, further comprising an electrode arrangement (150) configured to be arranged between the movement restriction device and the portion of the fundus to electrically stimulate muscle tissue of the portion of the fundus to exercise the muscle tissue to improve the conditions for long term implantation of the movement restriction device.

25. The method according to any of aspects 21-24, wherein the electrode arrangement comprises a bare electrode portion (155) configured to form a metal-tissue interface with the muscle tissue, thereby allowing faradaic charge transfer to the be predominant charge transfer mechanism over said interface.

26. The method according to any of aspects 21-24, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.

27. The method according to any of aspects 21-26, further comprising implanting an implantable energy source (160) in the patient's body, wherein the implantable energy source is configured to provide the electrode arrangement with electrical power.

28. The method according to aspect 27, wherein the implantable energy source is arranged inside the movement restriction device.

29. The method according to 27, comprising placing the implantable energy source outside the movement restriction device and the support device.

30. The method according to aspect 27, comprising implanting the implantable energy source subcutaneously.

31. The method according to any of aspects 27-30, further comprising implanting a controller (170) in the patient's body, wherein the controller is configured to indicate a functional status of the implantable energy source.

32. The method according to 31, wherein the functional status indicates a charge level of the implantable energy source.

33. The method according to aspect 32, wherein the functional status indicates a temperature of at least one of the implantable energy source, the muscle tissue, and the electrode arrangement.

34. The method according to any of aspects 31-33, further comprising implanting an implantable charger (190) in the patient's body, wherein the implantable charger is configured to be electrically connected to the implantable energy source and enable charging of the implantable energy source by an external energy source (165) arranged outside the body.

35. The method according to aspect 34, wherein the charger is configured to control the charging of the implantable energy source based on the functional status.

36. The method according to aspect 34 or 35, wherein the charger is configured to control the charging of the implantable energy source by controlling a receipt of electrical power from the external energy source at the implantable charger.

37. The method according to aspect 34 or 35, wherein the charger is configured to control the charging of the implantable energy source by controlling a transmission of electrical power from the external energy source to the implantable charger.

38. The method according to any of aspects 21-37, further comprising implanting a controller (170) in the patient's body, wherein the controller is configured to be operably connected to the electrode arrangement for controlling the electrical stimulation of the muscle tissue.

39. The method according to aspect 38, wherein the controller is configured to control the electrical stimulation such that the muscle tissue is stimulated by a series of electrical pulses (PL1, PL2, PL3, PL4).

40. The method according to aspect 39, wherein the controller is configured to control the electrical stimulation such that a pulse of a first polarity is followed by a pulse of a second, reversed polarity.

41. The method according to any of aspects 38-40, wherein the controller is configured to generate a pulsed electrical stimulation signal comprising a pulse frequency (F) of 0.01-150 Hz.

42. The method according to aspect 41, wherein the electrical stimulation signal comprises a pulse duration (D) of 0.01-100 ms.

43. The method according to aspect 41 or 42, wherein the electrical stimulation signal comprises a pulse amplitude (A) of 1-15 mA.

44. The method according to any of aspects 41-43, wherein the electrical stimulation signal comprises a pulse frequency of 0.15-0.25 Hz, a pulse duration of 20-30 ms and a pulse amplitude of 3-10 mA.

45. The method according to any of aspects 41-44, wherein the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.

Aspect Group 271SE:
Reflux_Modum-Forsell_Method

1. A method for affixing a fundus portion (14) of the stomach (10) of a human patient to the patient's esophagus (20), wherein the fundus portion extends from the angle of His (28) and in a direction away from the esophagus, the method comprising:

folding the fundus portion towards the esophagus such that the fundus portion rests against the esophagus, from the angle of His and upwards along the esophagus; and affixing the fundus portion to the esophagus by means of fasteners (230) arranged along a first line (231) and a second line (232);

wherein the first line and the second line extend along the esophagus and are arranged such that a distance between the first line and the second line increases with an increasing distance from the angle of His.

2. The method according to aspect 1, wherein the abdominal part of the esophagus and the fundus are divided by a plane into a ventral and a dorsal side, and wherein the method comprises providing the first line on the dorsal side of the plane and the second line on the ventral side of the plane.

3. The method according to aspect 1 or 2, comprising beginning the first line less than 1 cm above the angle of His and beginning the second line less than 3 cm above the angle of His.

4. The method according to any of the preceding aspects, comprising beginning the second line at a distance less than 2 cm from the first line.

5. The method according to any of the preceding aspects, wherein a separating angle between the first line and the second line is in the range of 90-150 degrees.

6. The method according to any of the preceding aspects, further comprising providing an additional fastener (233) between the first line and the second line, at the top of the fundus portion.

7. The method according to any of the preceding aspects, wherein the fasteners comprise staples.

8. The method according to any of aspects 1-6, wherein the fasteners comprise sutures, such as barbed sutures.

9. The method according to aspect 8, wherein the first line of fasteners comprises a first continuous suture, and wherein the second line of fasteners comprises a second continuous suture.

10. The method according to any of the preceding aspects, further comprising:

placing a movement restriction device (110) on the fundus:

forming a pouch in the fundus;

arranging the movement restriction device at least partly in the pouch;

invaginating the movement restriction device by the fundus by at least partly closing the pouch by fasteners;

wherein the movement restriction device is arranged at a position between the diaphragm (30) and the cardiac sphincter (26) to hinder the cardia (22) from sliding through the diaphragm opening (32) into the patient's thorax.

11. The method according to aspect 10, wherein the movement restriction device is invaginated after affixing the fundus portion to the esophagus.

12. The method according to aspect 10 or 11, wherein the pouch is formed to be open in a least two positions to form a tunnel through which the movement restriction device extends.

13. The method according to any of aspects 10-12, further comprising affixing the fundus to the diaphragm.

14. The method according to any of aspects 10-13, further comprising arranging an elongated support device (120) to at least partly encircle the esophagus, wherein the elongated support device and the movement restriction device form a respective portion of an implantable apparatus for treating reflux disease.

15. The method according to aspect 14, wherein the support device comprises a variable length for allowing the apparatus to be arranged in a constricting state for hindering fluid from passing from the stomach into the esophagus and in an expanded state for allowing food to pass into the stomach in response to the patient swallowing.

16. The method according to aspect 15, wherein the support device is configured to allow a transition from the constricting state into the expanded state caused by the food passing through the esophagus.

17. The method according to aspect 16, further comprising an attractor (212) for resiliently attracting adjacent portions (213) of the support device to one another to generate an encircling pressure on the esophagus.

18. The method according to aspect 17, wherein the attractor comprises an elastic element.

19. The method according to aspect 17, wherein the attractor comprises at least two mutually attracting magnets.

20. The method according to any of aspects 15-19, further comprising a tubular cover (220) enclosing at least a part of the support device and comprising a plurality of cover portions (224, 225, 226) adapted to bend relative to each other to allow the second support device to change between the constricting state and the expanded state, when the cover is at least partly covered by fibrotic tissue, without being substantially hindered or impeded by the presence of said fibrotic tissue.

21. The method according to aspect 20, wherein the cover comprises at least one predefined fold (224) along which the cover is allowed to fold in response to the support device varying its length.

22. The method according to any of aspects 15-21, wherein the apparatus further comprises an electrode arrangement (150) comprising an electrode element (154) supported by the support device and configured to electrically stimulate muscle tissue of the esophagus.

23. The method according to aspect 22, wherein the electrode arrangement is configured to electrically stimulate the cardiac sphincter of the patient to cause the cardiac sphincter to contract.

24. The method according to any aspects 10-14, further comprising an electrode arrangement (150) configured to be arranged between the movement restriction device and the fundus portion to electrically stimulate muscle tissue of the fundus portion to exercise the muscle tissue to improve the conditions for long term implantation of the movement restriction device.

25. The method according to any of aspects 10-24, wherein the electrode arrangement comprises a bare electrode portion (155) configured to form a metal-tissue interface with the muscle tissue, thereby allowing faradaic charge transfer to the be predominant charge transfer mechanism over said interface.

26. The method according to any of aspects 10-24, wherein the electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.

27. The method according to any of aspects 24-26, further comprising implanting an implantable energy source (160) in the patient's body, wherein the implantable energy source is configured to provide the electrode arrangement with electrical power.

28. The method according to aspect 27, wherein the implantable energy source is arranged inside the movement restriction device.

29. The method according to 27, comprising placing the implantable energy source outside the movement restriction device and the support device.

30. The method according to aspect 27, comprising implanting the implantable energy source subcutaneously.

31. The method according to any of aspects 27-30, further comprising implanting a controller (170) in the patient's body, wherein the controller is configured to indicate a functional status of the implantable energy source.

32. The method according to 31, wherein the functional status indicates a charge level of the implantable energy source.

33. The method according to aspect 32, wherein the functional status indicates a temperature of at least one of the implantable energy source, the muscle tissue, and the electrode arrangement.

34. The method according to any of aspects 31-33, further comprising implanting an implantable charger (190) in the patient's body, wherein the implantable charger is configured to be electrically connected to the implantable energy source and enable charging of the implantable energy source by an external energy source (165) arranged outside the body.

35. The method according to aspect 34, wherein the charger is configured to control the charging of the implantable energy source based on the functional status.

36. The method according to aspect 34 or 35, wherein the charger is configured to control the charging of the implantable energy source by controlling a receipt of electrical power from the external energy source at the implantable charger.

37 The method according to aspect 34 or 35, wherein the charger is configured to control the charging of the implantable energy source by controlling a transmission of electrical power from the external energy source to the implantable charger.

38. The method according to any of aspects 24-37, further comprising implanting a controller (170) in the patient's body, wherein the controller is configured to be operably connected to the electrode arrangement for controlling the electrical stimulation of the muscle tissue.

39. The method according to aspect 38, wherein the controller is configured to control the electrical stimulation such that the muscle tissue is stimulated by a series of electrical pulses (PL1, PL2, PL3, PL4).

40. The method according to aspect 39, wherein the controller is configured to control the electrical stimulation such that a pulse of a first polarity is followed by a pulse of a second, reversed polarity.

41. The method according to any of aspects 38-40, wherein the controller is configured to generate a pulsed electrical stimulation signal comprising a pulse frequency (F) of 0.01-150 Hz.

42. The method according to aspect 41, wherein the electrical stimulation signal comprises a pulse duration (D) of 0.01-100 ms.

43. The method according to aspect 41 or 42, wherein the electrical stimulation signal comprises a pulse amplitude (A) of 1-15 mA.

44. The method according to any of aspects 41-43, wherein the electrical stimulation signal comprises a pulse frequency of 0.15-0.25 Hz, a pulse duration of 20-30 ms and a pulse amplitude of 3-10 mA.

45. The method according to any of aspects 41-44, wherein the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.

Aspect Group 272SE:
Reflux_Muscle_Stimulation_Kit

1. An apparatus (100) for treating reflux disease in a human patient, comprising an electrode arrangement (150) for electrically stimulating the patient's muscle tissue to exercise the muscle tissue to improve the conditions for long term implantation of the apparatus, further comprising:

- an implantable energy source (160) configured to provide the electrode arrangement with electrical power; and
- a controller (170) operably connected to the electrode arrangement for controlling the electrical stimulation of the muscle tissue.

2. The apparatus according to aspect 1, wherein the electrode arrangement is configured to be arranged between the apparatus and the tissue onto which the apparatus is arranged to rest when implanted.

3. The apparatus according to aspect 1 or 2, wherein the electrode arrangement comprises an electrode element (152, 154, E1, E2) having a bare electrode portion (155) configured to form a metal-tissue interface with the muscle tissue, thereby allowing faradaic charge transfer to the be predominant charge transfer mechanism over said interface.

4. The apparatus according to aspect 1 or 2, wherein the electrode arrangement comprises an electrode element having a portion at least partly covered by a dielectric material (157) configured to form a dielectric-tissue interface with the muscle tissue, thereby allowing for a faradaic portion of the charge transfer mechanism over said interface to be reduced.

5. The apparatus according to any of the preceding aspects, wherein the controller is configured to control the electrical stimulation such that the muscle tissue is stimulated by a series of electrical pulses (PL1, PL2, PL3, PL4).

6. The apparatus according to aspect 5, wherein the controller is configured to control the electrical stimulation such that a pulse of a first polarity is followed by a pulse of a second, reversed polarity.

7. The apparatus according to aspect 5 or 6, wherein the controller is configured to generate a pulsed electrical stimulation signal comprising a pulse frequency (F) of 0.01-150 Hz.

8. The apparatus according to aspect 7, wherein the electrical stimulation signal comprises a pulse duration (D) of 0.01-100 ms.

9. The apparatus according to aspect 7 or 8, wherein the electrical stimulation signal comprises a pulse amplitude (A) of 1-15 mA.

10. The apparatus according to any of aspects 7-9, wherein the electrical stimulation signal comprises a pulse frequency of 0.15-0.25 Hz, a pulse duration of 20-30 ms and a pulse amplitude of 3-10 mA.

11. The apparatus according to any of aspects 7-10, wherein the electrical stimulation signal comprises a build-up period (X1) of 0.01-2 s in which the amplitude is gradually increasing, a stimulation period (X2) of 1-60 s, and a stimulation pause (X4) of 0.01-60 s, wherein the electrical signal comprises a pulse frequency of 1-50 Hz and a pulse duration of 0.1-10 ms.

12. The apparatus according to any of the preceding aspects, wherein the at least one electrode is configured to engage smooth muscle tissue.

13. The apparatus according to aspect 12, further comprising a sensor (S1) configured to sense action potentials generated by pacemaker cells of the muscle tissue, and wherein the controller is configured to control the electrical stimulation based at least partly on the sensed action potentials.

14. The apparatus according to aspect 13, wherein the controller is configured to generate electrical pulses amplifying the sensed action potentials.

15. The apparatus according to any preceding aspect, wherein the implantable energy source is configured to provide the electrode arrangement and/or the controller with electrical power.

16. The apparatus according to any of the preceding aspects, wherein the controller is further configured to indicate a functional status of the implantable energy source.

17. The apparatus according to aspect 16, wherein the functional status indicates at least one of charge level and temperature of the implantable energy source.

18. The apparatus according to aspect 16 or 17, wherein the controller is further configured to include the functional status in a signal transmitted to the outside of the body.

19. The apparatus according to any of the preceding aspects, further comprising a charger (190) configured to control a charging of the implantable energy source by controlling a receipt of electrical power from an external energy source at the implantable charger.

20. The apparatus according to aspect 19, wherein the charger comprises an electromagnetic coil configured to receive electrical power wirelessly from the external energy source.

21. The apparatus according to aspect 19 or 20, wherein the charger is configured to control the charging of the implantable energy source by controlling a transmission of electrical power from the external energy source to the implantable charger.

22. The apparatus according to any of the preceding aspects, wherein the controller comprises a wireless remote control.

23. The apparatus according to aspect 22, wherein the wireless remote control comprises an external signal transmitter, and wherein the controller comprises an implantable controller configured to receive a signal transmitted by the external signal transmitter and to control an operation of the apparatus based on said signal.

24. The apparatus according to aspect 19 wherein signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.

25. A method for exercising muscle tissue of a human patient to improve the conditions for long-term implantation of an apparatus for treating reflux disease of a human patient, the method comprises electrically stimulating the muscle against which the apparatus is arranged to rest when implanted.

26. The method according to aspect 25, comprising electrically stimulating the muscle tissue by means of an electrode arrangement arranged between the muscle tissue and the apparatus.

27. The method according to aspect 25 or 26, comprising electrically stimulating the muscle tissue with a pulsed signal (PL1, PL2, PL3, PL4).

28. The method according to aspect 27, wherein the pulsed signal comprises a pulse frequency (F) of 0.01-150 Hz, such as 0.1-150 Hz, such as 1-130 Hz, such as 10-100 Hz, such as 25-75 Hz.

29. The method according to aspect 27 or 28, wherein the pulsed signal comprises a pulse duration (D) of 0.01-100 ms, such as 0.1-50 ms, such as 1-10 ms.

30. The method according to any one of aspects 27-29, wherein the signal comprises a pulse amplitude (A) of 1-15 mA or less, such as 2-10 mA, such as 3-7 mA.

31. The method according to any one of aspects 27-30, wherein the signal comprises a pulse frequency of 0.2 Hz, a pulse duration of 0.3 ms and a pulse amplitude of 5 mA.

32. The method according to any one of aspects 27 to 31, wherein the signal comprises a pulse frequency of 0.15-0.25 Hz, a pulse duration of 20-30 ms and a pulse amplitude of 3-10 mA.

33. The method according to any of aspects 27-32, wherein the pulsed signal comprises a build-up period of 0.01-2 seconds, in which the amplitude is gradually increasing, a stimulation period of 1 to 60 seconds, a stimulation pause of 0.01 to 60 seconds, a pulse frequency of 1 to 50 Hz and a pulse duration of 0.1 to 10 ms.

34. The method according to any one of aspects 27-33, wherein the pulsed signal is applied by using the electrode arrangement as a cathode.

Aspect Group 273SE:
Reflux_Charging_Wireless_Kit

1. An apparatus (100) for treating reflux disease of a human patient, comprising an electrode arrangement (150), the apparatus comprising:

an implantable energy source (160) configured to provide the apparatus with electrical power, an external energy source (165) configured be arranged outside of the patient's body and configured to provide energy to the implantable energy source, and an implantable charger (190) configured to be electrically connected to the implantable energy source and enable charging of the implantable energy source by the external energy source.

2. The apparatus according to aspect 1, wherein the charger is configured to control the charging of the implantable energy source by controlling a receipt of electrical power from the external energy source at the implantable charger.

3. The apparatus according to aspect 1, wherein the charger is configured to control the charging of the implantable energy source by controlling a transmission of electrical power from the external energy source to the implantable charger.

4. The apparatus according to any preceding aspect, wherein the implantable energy source is configured to provide the electrode arrangement and/or the controller with electrical power.

5. The apparatus according to any of the preceding aspects, wherein the controller is further configured to indicate a functional status of the implantable energy source.

6. The apparatus according to aspect 5, wherein the functional status indicates at least one of charge level and temperature of the implantable energy source.

7. The apparatus according to aspect 5 or 6, wherein the controller is further configured to include the functional status in a signal transmitted to the outside of the body.

8. The apparatus according to aspect 1, wherein the charger comprises an electromagnetic coil configured to receive electrical power wirelessly from the external energy source.

9. The apparatus according to aspect 5-7, wherein the charger is configured to receive the functional status from the energy source indicator and control the charging of the implantable energy source based on the functional status.

10. The apparatus according to any of the preceding aspects, further comprising a controller (170) configured to be operably connected to the electrode arrangement for controlling the electrical stimulation of the muscle tissue.

11. The apparatus according to aspect 10, wherein the controller is configured to control the electrical stimulation such that the muscle tissue is stimulated by a series of electrical pulses (PL1, PL2, PL3, PL4).

12. The apparatus according to aspect 11, wherein the controller is configured to control the electrical stimulation such that a positive pulse is followed by a negative pulse.

13. The apparatus according to any of aspects 10-12, wherein the controller is configured to generate a pulsed electrical stimulation signal comprising a pulse frequency (F) of 0.01-150 Hz.

14. The apparatus according to aspect 13, wherein the electrical stimulation signal comprises a pulse duration (D) of 0.01-100 ms.

15. The apparatus according to aspect 13 or 14, wherein the electrical stimulation signal comprises a pulse amplitude (A) of 1-15 mA.

16. The apparatus according to any of aspects 13-15, wherein the electrical stimulation signal comprises a pulse frequency of 0.15-0.25 Hz, a pulse duration of 20-30 ms and a pulse amplitude of 3-10 mA.

17. The apparatus according to any of aspects 13-16, wherein the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.

18. The apparatus according to any of aspects 10-17, wherein the controller comprises a wireless remote control (175).

19. The apparatus according to aspect 18, wherein the wireless remote control comprises an external signal transmitter (176), and wherein the controller comprises an implantable controller configured to receive a signal transmitted by the external signal transmitter and to control an operation of the apparatus based on said signal.

20. The apparatus according to aspect 19 wherein signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.

21. The apparatus according to any of aspects 10-20, further comprising an implantable sensor (S1) configured to sense actions potentials generated by pacemaker cells of the muscle tissue, and wherein the controller is configured to control the electrical simulation based at least partly on the sensed action potentials.

22. The apparatus according to aspect 21, wherein the controller is configured to generate electrical pulses amplifying the sensed action potentials.

Aspect Group 274SE: Reflux_Communication_Kit

1. An apparatus (100) for treating reflux disease of a human patient, comprising an electrode arrangement (150), the apparatus further comprising:
- a controller (170) configured to be operably connected to the electrode arrangement for controlling the electrical stimulation of the muscle tissue, and
- wherein the controller comprises an implantable communicator (171) for transmitting and/or receiving a signal to/from the outside of the patient's body.

2. The apparatus according to aspect 1, wherein the signal comprises a functional status of an implantable energy source (160), wherein the implantable energy source is configured to provide the electrode arrangement and the controller with electrical power.

3. The apparatus according to aspect 2, wherein the functional status indicates a charge level of the implantable energy source.

4. The apparatus according to aspect 2 or 3, wherein the functional status indicates a temperature of at least one of the implantable energy source, the muscle tissue, and the electrode arrangement.

5. The apparatus according to any preceding aspect, wherein the controller further comprises an external controller configured to receive the signal.

6. The apparatus according to any preceding aspect, wherein the controller is configured to control the electrical stimulation such that the muscle tissue is stimulated by a series of electrical pulses (PL1, PL2, PL3, PLA).

7. The apparatus according to aspect 6, wherein the controller is configured to control the electrical stimulation such that a positive pulse is followed by a negative pulse.

8. The apparatus according to any preceding aspect, wherein the controller is configured to generate a pulsed electrical stimulation signal comprising a pulse frequency (F) of 0.01-150 Hz.

9. The apparatus according to any of aspects 6-8, wherein the electrical stimulation signal comprises a pulse duration (D) of 0.01-100 ms.

10. The apparatus according to any of aspects 6-9, wherein the electrical stimulation signal comprises a pulse frequency of 0.15-0.25 Hz, a pulse duration of 20-30 ms and a pulse amplitude of 3-10 mA.

11. The apparatus according to any of aspects 6-10, wherein the electrical stimulation signal comprises a build-up period of 0.01-2 s in which the amplitude is gradually increasing, a stimulation period of 1-60 s, and a stimulation pause of 0.01-60 s, wherein the electrical signal comprises a pulse frequency of 1-50 Hz and a pulse duration of 0.1-10 ms.

12. The apparatus according to any of the preceding aspects, wherein the controller comprises a wireless remote control (175).

13. The apparatus according to aspect 12, the apparatus further comprising an internal controller and an internal signal receiver connected to the internal controller, and wherein the wireless remote control comprises an external signal transmitter (176), and wherein the internal signal receiver implantable in the patient is configured to receive a signal transmitted by the external signal transmitter.

14. The apparatus according to aspect 13 wherein signal is selected from the group consisting of: a sound signal, an ultrasound signal, an electromagnetic signal, and infrared signal, a visible light signal, an ultra violet light signal, a laser signal, a microwave signal, a radio wave signal, an X-ray radiation signal and a gamma radiation signal.

15. The apparatus according to any of the preceding aspects, further comprising an implantable sensor (S1) configured to sense actions potentials generated by pacemaker cells of the muscle tissue, and wherein the controller is configured to control the electrical simulation based at least partly on the sensed action potentials.

16. The apparatus according to aspect 15, wherein the controller is configured to generate electrical pulses amplifying the sensed action potentials.

17. The apparatus according to any of the preceding aspects, further comprising an implantable energy source (160) configured to provide the electrode arrangement and the controller with electrical power.

18. The apparatus according to aspect 17, further comprising an implantable charger (190) configured to be electrically connected to the implantable energy source and enable recharging of the implantable energy source by an external energy source (165), wherein the charger is configured to control the charging of the implantable energy source by controlling the receipt of electrical power from the external energy source.

19. The apparatus according to aspect 18, wherein the charger comprises an electromagnetic coil configured to receive electrical power wirelessly from the external energy source.

20. The apparatus according to aspect 18-19, wherein the charger is configured to receive the functional status from the energy source indicator and control the charging of the implantable energy source based on the functional status.

Aspect Group 275SE: Reduced_Abutment

1. An apparatus (100) for treating reflux disease of a human patient, comprising:

an at least partly ring-shaped implantable movement restriction device configured to be arranged such that at a first, lower portion of the movement restriction device is arranged at the cardia of the patient's stomach and such that a second, upper portion of the movement restriction device is arranged to abut the diaphragm (30) of the patient, such that movement of the cardia (22) towards the diaphragm (30) is restricted to prevent the cardia from sliding through the diaphragm opening into the patient's thorax;

wherein the apparatus is configured to be arranged to define a gap or spacing between the second, upper portion of the movement restriction device and the outside of the esophagus (32) when the apparatus is implanted.

2. The apparatus according to aspect 1, wherein the movement restriction device has a shape conforming to a band or sleeve adapted to at least party encircle the esophagus.

3. The apparatus according to aspect 1 or 2, wherein a width of the movement restriction device is increasing towards the diaphragm of the patient, such that a first width (d1) of the first, lower portion of the movement restriction device is smaller than a second width (d2) of the second, upper portion of the movement restriction device.

4 The apparatus according to aspect 1 or 2, wherein a width of the movement restriction device is substantially constant along the esophagus at which it is configured to be implanted.

5. The apparatus according to any of the preceding aspects, wherein an inner surface of the movement restriction device is configured to be arranged at and angle ($\alpha$) relative an outer surface of the esophagus (32), thereby defining the gap or spacing between the movement restriction device and the esophagus.

6. The apparatus according to any of the preceding aspects, wherein the lower portion of the movement restriction device comprises a convex surface having a first curvature radius (R) and being configured to rest against the cardia, and wherein the upper portion of the movement restriction device comprises a concave surface having a second curvature radius (R') and being configured to define the gap between the movement restriction device and the esophagus (32).

7. The apparatus according to any of the preceding aspects, comprising a plurality of bodies (102) secured to each other by means of a holding device (104).

8. The apparatus according to aspect 7, wherein the plurality of bodies (102) are configured to be arranged in a sequence at least partly surrounding the esophagus (32), and wherein the holding device (104) comprises a sleeve or a string-shaped attachment means.

9. The apparatus according to aspect 7 or 8, wherein the plurality of bodies are elastically movable in relation to each other so as to allow the width of the movement restriction device to be varied.

10. The apparatus according to any of aspects 7-9, wherein the plurality of bodies are magnetic and configured to exert a constricting force on the cardia by means of an attractive magnetic force.

11. The apparatus according to any of aspects 7-10, wherein the bodies are elongated and configured to be arranged along the main direction of extension of the esophagus.

12. The apparatus according to any of aspects 7-11, wherein the bodies have a shape conforming to ellipsoids or rods.

Aspect Group 275BSE:
Reflux_Fixation_Two-Esophagus-Points

1. A method for treating reflux disease of a human patient by implanting a movement restriction device (110) such that the movement restriction device is arranged to restrict movement of the cardia (22) of the patient's stomach (10) towards the diaphragm (30) to hinder the cardia from sliding through the diaphragm opening (32) into the patient's thorax, wherein the method comprises:

attaching the fundus of the stomach of the patient to the esophagus of the patient in a first position, attaching the fundus of the stomach of the patient to the esophagus of the patient in a second position, at a distance from the first position in a cranial-caudal direction, and positioning the movement restriction device between the first and second position, such that the movement restriction device is secured in the cranial-caudal direction by the attachments between the fundus and the esophagus in the first and second positions.

2. The method according to aspect 1, wherein the step of attaching the fundus of the stomach of the patient to the esophagus of the patient in a second position is preceded by the step of positioning the movement restriction device between the first and second position.

3. The method according to any one of aspects 1 and 2, wherein at least one of the steps of: attaching the fundus of the stomach of the patient to the esophagus of the patient in a first position, and attaching the fundus of the stomach of the patient to the esophagus of the patient in a second position comprises suturing or stapling the fundus to the esophagus.

4. The method according to any one of the preceding aspects, wherein the steps of attaching the fundus of the stomach of the patient to the esophagus of the patient in a first position and attaching the fundus of the stomach of the patient to the esophagus of the patient in a second position are preceded by the step of dissecting the stomach of the patient.

5. The method according to any one of the preceding aspects, wherein at least one of the steps of attaching the fundus of the stomach of the patient to the esophagus of the patient in a first position and attaching the fundus of the stomach of the patient to the esophagus of the patient in a second position is performed using a translaminar instrument configured to be inserted through the esophagus of the patient.

6. The method according to any one of the preceding aspects, wherein the step of positioning the movement restriction device between the first and second position is performed using an abdominal instrument configured to enter the abdomen of the patient through an incision made in the skin of the patient.

7. The method according to any one of aspects 1-4 and 6, wherein at least one of the steps of attaching the fundus of the stomach of the patient to the esophagus of the patient in a first position and attaching the fundus of the stomach of the patient to the esophagus of the patient in a second position is performed using an abdominal instrument configured to enter the abdomen of the patient through an incision made in the skin of the patient.

8. The method according to any one of the preceding aspects, wherein the step of attaching the fundus of the stomach of the patient to the esophagus of the patient in a first position comprises attaching the fundus of the stomach of the patient to the esophagus of the patient at a distance from the angle of His exceeding 5 mm.

9. The method according to aspect 8, wherein the step of attaching the fundus of the stomach of the patient to the esophagus of the patient in a first position comprises attaching the fundus of the stomach of the patient to the esophagus of the patient at a distance from the angle of His exceeding 10 mm.

10. The method according to any one of the preceding aspects, wherein the step of attaching the fundus of the stomach of the patient to the esophagus of the patient in a second position comprises attaching the fundus of the stomach of the patient to the esophagus of the patient at a distance from the angle of His exceeding 20 mm.

11. The method according to any one of the preceding aspects, wherein the step of attaching the fundus of the stomach of the patient to the esophagus of the patient in a second position comprises attaching the fundus of the stomach of the patient to the esophagus of the patient at a distance from the angle of His exceeding 30 mm.

12. The method according to any one of the preceding aspects, wherein the step of positioning the movement restriction device between the first and second position comprises positioning the center of mass of the movement restriction device in a plane extending perpendicular to the cranial-caudal direction at a distance from the angle of His exceeding 20 mm.

13. The method according to aspect 12, wherein the step of positioning the movement restriction device between the first and second position comprises positioning the center of mass of the movement restriction device in a plane extending perpendicular to the cranial caudal direction extending at a distance from the angle of His exceeding 30 mm.

14. The method according to any one of the preceding aspects, wherein the step of positioning the movement restriction device between the first and second position comprises positioning the upper-most point of the movement restriction device in a plane extending perpendicular to the cranial-caudal direction at a distance from an upper-most point of the cardia exceeding 5 mm.

15. The method according to any one of the preceding aspects, wherein the step of positioning the movement restriction device between the first and second position comprises positioning the upper-most point of the movement restriction device in a plane extending perpendicular to the cranial-caudal direction at a distance from an upper-most point of the cardia exceeding 10 mm.

16. The method according to any one of the preceding aspects, wherein the step of positioning the movement restriction device between the first and second position comprises positioning the center of mass of the movement restriction device in a plane extending perpendicular to the cranial-caudal direction at a distance from an upper-most point of the cardia exceeding 1 mm.

17. The method according to any one of the preceding aspects, wherein the step of positioning the movement restriction device between the first and second position comprises positioning the center of mass of the movement restriction device in a plane extending perpendicular to the cranial-caudal direction at a distance from an upper-most point of the cardia exceeding 5 mm.

18. The method according to any one of the preceding aspects, wherein the step of positioning the movement restriction device between the first and second position comprises positioning the center of mass of the movement restriction device in a plane extending perpendicular to the cranial-caudal direction at a distance from an upper-most point of the cardia exceeding 10 mm.

19. The method according to any one of the preceding aspects, wherein the step of positioning the movement restriction device comprises positioning a movement restriction device having a rounded shape.

20. The method according to any one of the preceding aspects, wherein the step of positioning the movement restriction device comprises positioning a movement restriction device having a spherical shape.

21. The method according to any one of the preceding aspects, wherein the step of positioning the movement restriction device comprises positioning a movement restriction device encircling at least ⅓ of the esophagus in a plane extending perpendicular to the cranial-caudal direction.

22. The method according to any one of the preceding aspects, wherein the step of positioning the movement restriction device comprises positioning a movement restriction device encircling at least ½ of the esophagus in a plane extending perpendicular to the cranial-caudal direction.

23. The method according to any one of the preceding aspects, wherein the step of positioning the movement restriction device comprises positioning a movement restriction device encircling at least ⅔ of the esophagus in a plane extending perpendicular to the cranial-caudal direction.

24. The method according to any one of the preceding aspects, wherein the step of positioning the movement restriction device comprises positioning a movement restriction device encircling the esophagus in a plane extending perpendicular to the cranial-caudal direction.

25. The method according to any of the preceding aspects, wherein the step of positioning the movement restriction device comprises positioning a movement restriction device comprising a curved outer surface, such that the curved outer surface faces the esophagus.

26. The method according to aspect 25, wherein the step of positioning the movement restriction device such that the curved outer surface faces the esophagus, comprises positioning a movement restriction device comprising a curved outer surface comprising a radius of curvature corresponding to or exceeding the radius of curvature of the esophagus, such that the curved outer surface comprising a radius of curvature corresponding to or exceeding the radius of curvature of the esophagus.

27. The method according to any of the preceding aspects, wherein the step of positioning the movement restriction device comprises positioning a movement restriction device comprising an electrode arrangement configured to electrically stimulate muscle tissue of the portion of the fundus and/or the serosa to improve the conditions for long term implantation of the movement restriction device.

28. The method according to any of the preceding aspects, further comprising implanting an implantable energy source (160) configured to provide the electrode with electrical power.

29. The method according to aspect 28, wherein the implantable energy source is arranged inside the movement restriction device.

30. The method according to aspect 28, further comprising implanting the implantable energy source subcutaneously.

31. The method according to any one of aspects 28-30, further comprising implanting an implantable charger (190) configured to be electrically connected to the implantable energy source and enable charging of the implantable energy source by the external energy source.

32. The method according to any of aspects 27-31, further comprising implanting a controller (170) configured to be operably connected to the electrode arrangement for controlling the electrical stimulation of the muscle tissue.

33. The method according to aspect 32, wherein the controller is configured to control the electrical stimulation such that the muscle tissue is stimulated by a series of electrical pulses (PL1, PL2, PL3, PL4).

34 The method according to any of aspect 33, wherein the electrical stimulation signal comprises a pulse frequency of 0.15-0.25 Hz, a pulse duration of 20-30 ms and a pulse amplitude of 3-10 mA.

35. The apparatus according to any of aspects 32-34, wherein the controller comprises a wireless remote control (175).

36. The method according to any of the preceding aspects, wherein the step of positioning the movement restriction device comprises positioning a movement restriction device having a constricting state for hindering fluid from passing from the stomach into the esophagus and an expanded state for allowing food to pass into the stomach in response to the patient swallowing.

37. The method according to aspect 36, wherein the step of positioning the movement restriction device comprises positioning a movement restriction device configured to exert an encircling pressure on the esophagus in the constricting state.

38. The method according to aspect 37, wherein the step of positioning the movement restriction device comprises positioning a movement restriction device comprising at least one attractor (212) for resiliently attracting adjacent portions (213) of the movement restriction device to generate the encircling pressure.

39. The apparatus according to aspect 38, wherein the attractor comprises an elastic element.

40. The apparatus according to aspect 38, wherein the attractor comprises at least two mutually attracting magnets.

41. The apparatus according to aspect 40, further comprising a link (214) connecting a first and a second one of said at least two magnets to each other.

42. The method according to any one of the preceding aspects, wherein the step of positioning the movement restriction device comprises positioning a non-adjustable movement restriction device.

43. The method according to any one of the preceding aspects, wherein the step of positioning the movement restriction device comprises positioning a movement restriction device having an adjustable volume.

Aspect Group 275CSE: Reflux_Stimulating_Muscle-Cardia

1. An apparatus (100) for treating reflux disease of a human patient, comprising:
- an implantable movement restriction device (110) having a shape and size allowing it to be arranged to rest against a fundus wall portion (14) of the patient's stomach (10), such that the movement restriction device is implanted at a position between the patient's diaphragm (30) and a portion of the fundus wall, and such that movement of the cardia (22) of the patient's stomach towards the diaphragm is restricted to hinder the cardia from sliding through the diaphragm opening (32) into the patient's thorax, further comprising at least one of;
- a first electrode arrangement (150) configured to engage and electrically stimulate muscle tissue of the fundus wall portion to exercise the muscle tissue to improve the conditions for long term implantation of the movement restriction device, and
- a second electrode arrangement configured to engage and electrically stimulate the cardiac sphincter for causing contraction of the cardiac sphincter.

2. The apparatus according to aspect 1, wherein the first electrode arrangement is arranged on an outer surface of the movement restriction device.

3. The apparatus according to aspect 1 or 2, wherein the first electrode arrangement comprises a plurality of electrode elements (152), each of which being configured to engage and electrically stimulate the muscle tissue.

4. The apparatus according to any of the preceding aspects, wherein the first electrode arrangement comprises a coiled wire for increasing a contact surface between the first electrode arrangement and the muscle tissue and for allowing the first electrode arrangement to follow contraction and relaxation of the muscle tissue.

5. The apparatus according to any of the preceding aspects, wherein at least one of the first and second electrode arrangement comprises a bare electrode portion (155) configured to form a metal-tissue interface with the muscle tissue, thereby allowing faradaic charge transfer to the be predominant charge transfer mechanism over said interface.

6. The apparatus according to any of the preceding aspects, wherein at least one of the first and second electrode arrangement comprises an electrode portion at least partly covered by a dielectric material (157) configured to form a dielectric-tissue interface with the muscle tissue, thereby allowing for a faradaic portion of the charge transfer mechanism over said interface to be reduced.

7. The apparatus according to any one of the preceding aspects, wherein the second electrode arrangement comprises at least two electrode elements (154) configured to be arranged on opposing sides of the cardiac sphincter.

8. The apparatus according to aspect 7, further comprising a holder configured to support the at least two electrode elements at the opposing sides of the cardiac sphincter.

9. The apparatus according to any of the preceding aspects, further comprising an implantable energy source (160) configured to provide the electrode with electrical power.

10. The apparatus according to aspect 9, wherein the implantable energy source is arranged inside the movement restriction device.

11. The apparatus according to aspect 9, wherein the implantable energy source is configured to be arranged outside the movement restriction device.

12. The apparatus according to aspect 11, wherein the implantable energy source is configured to be implanted subcutaneously.

13. The apparatus according to any of aspects 9-12, wherein the implantable energy source comprises a primary cell.

14. The apparatus according to any of aspects 9-13, wherein the implantable energy source comprises a secondary cell.

15. The apparatus according to any of the preceding aspects, further comprising a controller configured to be operably connected to the electrode arrangement for controlling the electrical stimulation of the muscle tissue.

16. The apparatus according to aspect 15, wherein the controller is configured to control the electrical stimulation such that the muscle tissue is stimulated by a series of electrical pulses (PL1, PL2, PL3, PL4).

17. The apparatus according to aspect 16, wherein the controller is configured to control the electrical stimulation such that a pulse of a first polarity is followed by a pulse of a second, reversed polarity.

18. The apparatus according to any of aspects 15-17, wherein the controller is configured to generate a pulsed electrical stimulation signal comprising a pulse frequency (F) of 0.01-150 Hz.

19. The apparatus according to aspect 18, wherein the electrical stimulation signal comprises a pulse duration (D) of 0.01-100 ms.

20. The apparatus according to aspect 18 or 19, wherein the electrical stimulation signal comprises a pulse amplitude (A) of 1-15 mA.

21. The apparatus according to any of aspects 18-20, wherein the electrical stimulation signal comprises a pulse frequency of 0.15-0.25 Hz, a pulse duration of 20-30 ms and a pulse amplitude of 3-10 mA.

22. The apparatus according to any of aspects 18-21, wherein the electrical stimulation signal comprises a build-up period (X1) of 0.01-2 s in which the amplitude is gradually increasing, a stimulation period (X2) of 1-60 s, and a stimulation pause (X4) of 0.01-60 s, wherein the electrical signal comprises a pulse frequency of 1-50 Hz and a pulse duration of 0.1-10 ms.

23. The apparatus according to any of aspects 15-22, wherein the controller comprises a wireless remote control.

24. The apparatus according to any of aspects 13-23, wherein the controller is further configured to indicate a functional status of the implantable energy source.

25. The apparatus according to aspect 24, wherein the functional status indicates a charge level of the implantable energy source.

26. The apparatus according to aspect 24 or 25, wherein the functional status indicates a temperature of at least one of the implantable energy source, the muscle tissue and the electrode arrangement.

27. The apparatus according to any of aspects 9-26, wherein the implantable energy source is configured to be charged by an external energy source arranged outside the patient's body.

28. The apparatus according to aspect 27, further comprising an implantable charger configured to be electrically connected to the implantable energy source and enable charging of the implantable energy source by the external energy source.

29. The apparatus according to aspect 28, wherein the charger comprises an electromagnetic coil configured to receive electrical power wirelessly from the external energy source.

30. The apparatus according to aspect 28 or 29, wherein the charger is configured to control the charging of the implantable energy source based on the functional status.

31. The apparatus according to any of aspects 28-30, wherein the charger is configured to control the charging of the implantable energy source by controlling a receipt of electrical power from the external energy source at the implantable charger.

32. The apparatus according to any of aspects 28-31, wherein the charger is configured to control the charging of the implantable energy source by controlling a transmission of electrical power from the external energy source to the implantable charger.

33. The apparatus according to any of aspects 15-32, further comprising an implantable sensor (S1) configured to sense actions potentials generated by pacemaker cells of the muscle tissue, and wherein the controller is configured to control the electrical simulation based at least partly on the sensed action potentials.

34. The apparatus according to aspect 33, wherein the controller is configured to generate electrical pulses amplifying the sensed action potentials.

35. The apparatus according to any of the preceding aspects, wherein a volume of the movement restriction device is non-adjustable after implantation.

36. The apparatus according to any of aspects 1-34, wherein a volume of the movement restriction device is adjustable after implantation.

37. The apparatus according to aspect 36, wherein the movement restriction device comprises an injection port (115) for allowing a fluid to be injected or extracted from the inside of the movement restriction device so as to vary a volume of the movement restriction device after implantation.

38. The apparatus according to any of the preceding aspects, wherein the movement restriction device comprises a biocompatible outer surface configured to rest against the fundus wall portion.

39. The apparatus according to any of the preceding aspects, wherein the movement restriction device is substantially spherical or egg-shaped.

40. The apparatus according to any of the preceding aspects, wherein the movement restriction device is configured to be at least partially invaginated by the fundus wall.

41. The apparatus according to any of the preceding aspects, wherein the movement restriction device is configured to be introduced in the patient's body by means of a gastroscope or an intraluminal instrument.

42. The apparatus according to aspect 41, wherein the movement restriction device is configured to change its shape to allow it to pass through a trocar during insertion into the patient's body.

43. The apparatus according to any of the preceding aspects, wherein the movement restriction device is formed of at least two distinct and separable parts configured to be assembled into the movement restriction device after insertion in the patient's body.

44. The apparatus according to any of the preceding aspects, wherein a minimum width of the movement restriction device, as measured from side to side, is 30 mm or larger, such as 40 mm or larger.

45. The apparatus according to any of the preceding aspects, wherein a minimum outer circumference of the movement restriction device is 150 mm or less, such as 130 mm or less, such as 110 mm or less, such as 90 mm or less, such as 70 mm or less, such as 50 mm or less, such as 30 mm or less.

Aspect Group 275C2PC: Reflux_Stimulating_Cardia_Supression

1. An apparatus (100) for treating reflux disease of a human patient, the apparatus comprising:
   - an implantable movement restriction device (110) having a shape and size allowing it to be arranged to rest against a fundus wall portion (14) of the patient's stomach (10), such that the movement restriction device is implanted at a position between the thoracic diaphragm (30) of the patient and a portion of the fundus wall, and such that movement of the lower esophageal sphincter (26) of the patient's stomach towards the thoracic diaphragm is restricted to hinder the lower esophageal sphincter from sliding through the opening (32) in the thoracic diaphragm into the patient's thorax,
   - a first electrode arrangement configured to engage and electrically stimulate the lower esophageal sphincter (26) for causing contraction of the lower esophageal sphincter, and
   - a suppression electrode arrangement (150') configured to deliver an electrical suppression signal to the vagus nerve.

2. The apparatus according to aspect 1, further comprising a controller (170) configured to generate the suppression signal to be transferred to the suppression electrode arrangement (150').

3. The apparatus according to aspect 2, wherein the controller is configured to generate a time-varying signal having a frequency component that varies in the range of 1-10 kHz.

4. The apparatus according to aspect 3, wherein the controller is configured to generate a time-varying signal having a frequency component that varies in the range of 2-8 kHz.

5. The apparatus according to aspect 4, wherein the controller is configured to generate a time-varying signal having a frequency component that varies in the range of 4-6 kHz.

6. The apparatus according to any one of the preceding aspects, wherein the first electrode arrangement comprises at least two electrode elements (152) configured to be arranged on opposing sides of the lower esophageal sphincter.

7. The apparatus according to aspect 6, further comprising a holder configured to support the at least two electrode elements at the opposing sides of the cardiac sphincter.

8. The apparatus according to any of the preceding aspects, further comprising an implantable energy source (160) configured to provide the electrode with electrical power.

9. The apparatus according to aspect 8, wherein the implantable energy source is arranged inside the movement restriction device.

10. The apparatus according to any one of the preceding aspects, wherein the controller (170) is configured to control the first electrode arrangement such that the lower esophageal sphincter is stimulated by a series of electrical pulses (PL1, PL2, PL3, PL4).

11. The apparatus according to aspect 10, wherein the controller is configured to control the electrical stimulation such that a pulse of a first polarity is followed by a pulse of a second, reversed polarity.

12. The apparatus according to any of aspects 10-11, wherein the controller is configured to generate a pulsed electrical stimulation signal comprising a pulse frequency (F) of 0.01-150 Hz.

13. The apparatus according to aspect 12, wherein the electrical stimulation signal comprises a pulse duration (D) of 0.01-100 ms.

14. The apparatus according to aspect 12 or 13, wherein the electrical stimulation signal comprises a pulse amplitude (A) of 1-15 mA.

15. The apparatus according to any of aspects 12-14, wherein the electrical stimulation signal comprises a pulse frequency of 0.15-0.25 Hz, a pulse duration of 20-30 ms and a pulse amplitude of 3-10 mA.

16. The apparatus according to any of aspects 12-15, wherein the electrical stimulation signal comprises a build-up period (X1) of 0.01-2 s in which the amplitude is gradually increasing, a stimulation period (X2) of 1-60 s, and a stimulation pause (X4) of 0.01-60 s, wherein the electrical signal comprises a pulse frequency of 1-50 Hz and a pulse duration of 0.1-10 ms.

Aspect Group 275C3PC: Reflux_Stimulating_Cardia_Impedance

1. An apparatus (100) for treating reflux disease of a human patient, the apparatus comprising:
   - an implantable movement restriction device (110) having a shape and size allowing it to be arranged to rest against a fundus wall portion (14) of the patient's stomach (10), such that the movement restriction device is implanted at a position between the thoracic diaphragm (30) of the patient and a portion of the fundus wall, and such that movement of the lower esophageal sphincter (26) of the patient's stomach towards the thoracic diaphragm is restricted to hinder the lower esophageal sphincter from sliding through the opening (32) in the thoracic diaphragm into the patient's thorax,
   - an electrode arrangement configured to engage and electrically stimulate the lower esophageal sphincter (26) for causing contraction of the lower esophageal sphincter,
   - an electric impedance sensor configured to measure a change in electrical impedance in the tissue of the lower esophageal sphincter or in the esophagus tissue for detecting the patient swallowing, and a stimulation controller (170) configured to control the electrical stimulation of the lower esophageal sphincter (26) in response to signals from the electric impedance sensor.

2. The apparatus according to aspect 1, further comprising a reference electrode connected to the stimulation controller, and wherein the stimulation controller (170) is configured to generate the output from the sensor based on an electrical interaction between the electric impedance sensor and the reference electrode.

3. The apparatus according to any one of aspects 1 and 2, wherein the stimulation controller (170) is configured to generate a time-varying signal having a frequency component that varies in the range of 1-10 kHz.

4. The apparatus according to aspect 3, wherein the stimulation controller (170) is configured to generate a time-varying signal having a frequency component that varies in the range of 2-8 kHz.

5. The apparatus according to aspect 4, wherein the stimulation controller (170) is configured to generate a time-varying signal having a frequency component that varies in the range of 4-6 kHz.

6. The apparatus according to any one of the preceding aspects, wherein the electrode arrangement comprises at least two electrode elements (152) configured to be arranged on opposing sides of the lower esophageal sphincter.

7. The apparatus according to aspect 6, further comprising a holder configured to support the at least two electrode elements at the opposing sides of the cardiac sphincter.

8. The apparatus according to any of the preceding aspects, further comprising an implantable energy source (160) configured to provide the electrode with electrical power.

9. The apparatus according to aspect 8, wherein the implantable energy source is arranged inside the movement restriction device.

10. The apparatus according to any one of the preceding aspects, wherein the stimulation controller (170) is configured to control the electrode arrangement such that the lower esophageal sphincter is stimulated by a series of electrical pulses (PL1, PL2, PL3, PL4).

11. The apparatus according to aspect 10, wherein the stimulation controller (170) is configured to control the electrical stimulation such that a pulse of a first polarity is followed by a pulse of a second, reversed polarity.

12. The apparatus according to any of aspects 10-11, wherein the stimulation controller (170) is configured to generate a pulsed electrical stimulation signal comprising a pulse frequency (F) of 0.01-150 Hz.

13. The apparatus according to aspect 12, wherein the electrical stimulation signal comprises a pulse duration (D) of 0.01-100 ms.

14. The apparatus according to aspect 12 or 13, wherein the electrical stimulation signal comprises a pulse amplitude (A) of 1-15 mA.

15. The apparatus according to any of aspects 12-14, wherein the electrical stimulation signal comprises a pulse frequency of 0.15-0.25 Hz, a pulse duration of 20-30 ms and a pulse amplitude of 3-10 mA.

16. The apparatus according to any of aspects 12-15, wherein the electrical stimulation signal comprises a build-up period (X1) of 0.01-2 s in which the amplitude is gradually increasing, a stimulation period (X2) of 1-60 s, and a stimulation pause (X4) of 0.01-60 s, wherein the electrical signal comprises a pulse frequency of 1-50 Hz and a pulse duration of 0.1-10 ms.

Aspect Group 275DSE: Reflux_Adjustable_Height

1. An apparatus for treating reflux disease of a human patient, the apparatus comprises an implantable movement restriction device (110) configured to be fixated between an upper portion of the stomach and the thoracic diaphragm of the patient, for restricting the movement of the cardia (22) of the patient towards the thoracic diaphragm (30), the implantable movement restriction device (110) having a first cross-sectional distance and a second cross-sectional distance, and wherein the movement restriction device (110) is configured to be implanted such that:

the first cross-sectional distance is more parallel than perpendicular to the cranial-caudal axis of the patient, and the second cross-sectional distance is more perpendicular than parallel to the cranial-caudal axis of the patient, and wherein the implantable movement restriction device (110) is adjustable in situ, such that the shape of the implantable movement restriction device (110) can be adjusted by the adjustment of the length of the first cross-sectional distance, such that the length of the first cross-sectional distance can be increased relative to the length of the second cross-sectional distance.

2. The apparatus according to aspect 1, wherein the shape of the implantable movement restriction device (110) can be adjusted by an increase of the length of the first cross-sectional distance relative to the length of the second cross-sectional distance while the length of a circumference of a cross-section of the implantable movement restriction device (110), in a plane parallel to the coronal plane of the patient remains constant.

3. The apparatus according to any one of aspects 1 and 2, wherein the shape of the implantable movement restriction device (110) can be adjusted to an elongated shape by an increase of the length of the first cross-sectional distance relative to the length of the second cross-sectional distance.

4. The apparatus according to any one of the preceding aspects, wherein the shape of the implantable movement restriction device (110) can be adjusted by an increase of the length of the first cross-sectional distance relative to the length of the second cross-sectional distance, such that the length of the circumference of a cross-section of the implantable movement restriction device (110), in a plane parallel to the coronal plane of the patient, is increased relative to the length of the circumference of a cross-section of the implantable movement restriction device (110), in a plane parallel to the transverse plane of the patient.

5. The apparatus according to any one of the preceding aspects, wherein the implantable movement restriction device (110) comprises a lower portion configured to, directly or indirectly, engage the stomach of the patient in a region of the angle of his, such that the function of the implantable movement restriction device (110) is supported by tissue of the stomach in the region of the angle of his.

6. The apparatus according to any one of the preceding aspects, wherein the implantable movement restriction device (110) comprises an upper portion configured to, directly or indirectly, engage the thoracic diaphragm of the patient, and wherein the upper portion comprises at least one curvature.

7. The apparatus according to any one of the preceding aspects, wherein the implantable movement restriction device (110) is configured to be at least partially invaginated by the stomach wall.

8. The apparatus according to aspect 7, wherein the implantable movement restriction device (110) is configured to be at least partially invaginated by the stomach wall of the fundus.
9. The apparatus according to any one of the preceding aspects, wherein the movement restriction device comprises a curved cross-section in a plane parallel to the transverse plane of the patient, and wherein the curve is configured to partially enclose the esophagus of the patient.
10. The apparatus according to aspect 9, wherein the movement restriction device is configured to encircle at least ⅓ of the esophagus in a plane parallel to the transverse plane of the patient.
11. The apparatus according to aspect 10, wherein the movement restriction device is configured to encircle at least ½ of the esophagus in a plane parallel to the transverse plane of the patient.
12. The apparatus according to aspect 9, wherein the movement restriction device comprises a C-shaped cross-section in a plane parallel to the transverse plane of the patient, and wherein the C-shaped cross-section is configured to partially enclose the esophagus of the patient.
13. The method according to aspect 12, wherein the movement restriction device is configured to encircle at least ⅔ of the esophagus in a plane parallel to the transverse plane of the patient.
14. The apparatus according to any one of aspects 1-9, wherein a cross-section of the movement restriction device in a plane parallel to the transverse plane of the patient comprises a closed curve configured to enclose the esophagus of the patient.
15. The apparatus according to any one of the preceding aspects, wherein the movement restriction device is hydraulically adjustable.
16. The apparatus according to aspect 15, wherein the movement restriction device comprises a conduit configured to connect the hydraulically adjustable movement restriction device to an implantable injection port.
17. The apparatus according to aspect 15, wherein the movement restriction device comprises an injection port, such that the hydraulically adjustable movement restriction device can be adjusted by the injection or withdrawal of a hydraulic fluid into the hydraulically adjustable movement restriction device.
18. The apparatus according to any one of aspects 15-17, wherein a portion of the movement restriction device comprises a bellows, and wherein the injection or withdrawal of a hydraulic fluid into the hydraulically adjustable movement restriction adjusts a length of the bellows.
19. The apparatus according to any one of aspects 1518, wherein the movement restriction device comprises a wall enclosing a hydraulic adjustment chamber, and wherein the thickness of the wall varies affecting the alteration of the shape of the movement restriction device as fluid is injected into or withdrawn from the movement restriction device.
20. The apparatus according to aspect 19, wherein the shape of the movement restriction device is altered by a thinner portion of the wall enclosing the hydraulic adjustment chamber being deformed more than thicker portions of the wall enclosing the hydraulic adjustment chamber.
21. The apparatus according to any one of aspects 1-14, wherein the movement restriction device is mechanically adjustable.
22. The apparatus according to aspect 21, wherein the movement restriction device comprises mechanical operation device.
23. The apparatus according to aspect 22, wherein the movement restriction device comprises a transferring element configured to transfer at least one of:
electrical energy, and
mechanical force to the mechanically adjustable movement restriction device.
24. The apparatus according to aspect 23, wherein the transferring element comprises at least one of:
an electrical lead,
a shaft for transferring rotating force, and
a shaft for transferring linear force.
25. The apparatus according to any one of aspects 22-24, wherein the mechanical operation device comprises an electrical motor.
26. The apparatus according to any one of aspects 25, wherein the mechanical operation device comprises a transmission configured to transform a rotating force generated by the electrical motor into a linear force for adjusting the length of the first cross-sectional distance.
27. The apparatus according to any one of aspects 22-26, wherein a portion of the movement restriction device comprises a bellows, and wherein the operation of the mechanical operation device adjusts a length of the bellows.
28. The apparatus according to any one of aspects 1-14, wherein the movement restriction device is electrically adjustable.
29. The apparatus according to aspect 28, wherein the movement restriction device comprises at least one material configured to alter shape when exposed to an electrical current or an electrical voltage.
30. The apparatus according to aspect 29, wherein the movement restriction device comprises at least one electroactive polymer.
31. The apparatus according to aspect 30, wherein the electroactive polymer is at least one electroactive polymer selected from a list consisting of: ferroelectric polymers, electrostrictive graft polymers, electrostrictive paper, piezoelectric polymers and liquid crystal elastomers.
32. The apparatus according to aspect 31, wherein the movement restriction device further comprises a transferring element configured to transfer electrical energy to the movement restriction device.
33. The apparatus according to any one of the preceding aspects, wherein the length of the first cross-sectional distance is adjustable in situ such that the length of the first cross-sectional distance is 1.2 times the length of the second cross-sectional distance, or 1.3 times the length of the second cross-sectional distance, or 1.5 times the length of the second cross-sectional distance.
34. The apparatus according to any one of the preceding aspects, wherein the length of the first cross-sectional distance is adjustable in situ such that the length of the circumference of a cross-section of the implantable movement restriction device (110), in a plane parallel to the coronal plane of the patient, is 1.2 times the length of the circumference of a cross-section of the implantable movement restriction device (110), in a plane parallel to the transverse plane of the patient, or 1.3 times the length of the circumference of a cross-section of the implantable movement restriction device (110), in a plane parallel to the transverse plane of the patient, or 1.5 times the length of the circumference of a cross-section of the implantable movement restriction device (110), in a plane parallel to the transverse plane of the patient.
35. The apparatus according to any one of the preceding aspects, wherein the length of the first cross-sectional distance is adjustable in situ such that the center of mass of the movement restriction device in a plane parallel to the transverse plane of the patient is positioned at a distance from the angle of His exceeding 20 mm, or exceeding 30 mm.

36. The apparatus according to any one of the preceding aspects, wherein the length of the first cross-sectional distance is adjustable in situ such that the center of mass of the movement restriction device in a plane parallel to the transverse plane of the patient is positioned at a distance from an upper-most point of the cardia exceeding 5 mm, or exceeding 10 mm.

37. The apparatus according to any one of the preceding aspects, wherein the movement restriction device comprises at least two parts.

38. The apparatus according to any of the preceding aspects, further comprising an implantable energy source (160) configured to provide the adjustable implantable movement restriction device (110) with electrical power.

39. The apparatus according to aspect 38, wherein the implantable energy source is arranged inside the movement restriction device.

40. The apparatus according to aspect 38, wherein the implantable energy source is configured to be arranged subcutaneously.

41. The apparatus according to any one of the preceding aspects, further comprising at least one electrode for electrically stimulating at least one tissue portion of the patient.

42. The apparatus according to any one of the preceding aspects, wherein the movement restriction device comprises has a constricting state for hindering fluid from passing from the stomach into the esophagus and an expanded state for allowing food to pass into the stomach in response to the patient swallowing.

43. The apparatus according to aspect 42, wherein the movement restriction device comprises at least one attractor for resiliently attracting adjacent portions (213) of the movement restriction device to generate an encircling pressure on the esophagus.

44. The apparatus according to aspect 43, wherein the attractor comprises an elastic element.

45. The apparatus according to aspect 43, wherein the attractor comprises at least two mutually attracting magnets.

Aspect Group 275ESE: Reflux_Decreased_Weight

1. An apparatus for treating reflux disease of a human patient, the apparatus comprises an implantable movement restriction device (110) configured to be fixated between an upper portion of the stomach and the thoracic diaphragm of the patient, for restricting the movement of the cardia (22) of the patient towards the thoracic diaphragm (30), the implantable movement restriction device (110) comprising:
- a first portion having a first volume enclosed by material of the implantable movement restriction device (110), and
- a second portion, different from the first portion, having a second volume enclosed by material of the implantable movement restriction device (110), wherein:
  - the first volume and the second volumes are equally large,
  - the first volume has a higher density than the second volume, and the second volume has
  - a density below 1000 kg/m3.

2. The apparatus according to aspect 1, wherein the first volume comprises a first solid material.

3. The apparatus according to aspect 2, wherein the first solid material comprises a polymer material.

4. The apparatus according to aspect 3, wherein the first solid material comprises at least one of silicone-based material and a polyurethane-based material.

5. The apparatus according to any one of aspects 1-4, wherein the second volume comprises a second solid material.

6. The apparatus according to aspect 5, wherein the second solid material comprises a polymer material.

7. The apparatus according to aspect 6, wherein the second solid material comprises a at least one of a polypropylene-based and a polyethylene-based material.

8. The apparatus according to any one of aspects 5-7, wherein the first volume comprises a solid material having a density above 1000 kg/m3 and the second volume comprises a solid material having a density below 1000 kg/m3.

9. The apparatus according to aspect 1-4, wherein the second volume comprises a fluid.

10. The apparatus according to aspect 9, wherein the second volume comprises a liquid having a density a below 1000 kg/m3.

11. The apparatus according to aspect 10, wherein the liquid comprises at least one selected from a list of:
- oil-based liquids, and
- alcohol based liquids.

12. The apparatus according to aspect 9, wherein the second volume comprises a gas.

13. The apparatus according to aspect 12, wherein the second volume comprises a plurality of volumes of gas enclosed by an enclosing material.

14. The apparatus according to aspect 13, wherein the second volume comprises a solid polymer material enclosing the enclosing material, and wherein the enclosing material is harder than the solid polymer material.

15. The apparatus according to any one of aspects 13 and 14, wherein the plurality of volumes of gas enclosed by an enclosing material makes up at least 10 volume percent of the second volume, more preferably at least 20 volume percent of the second volume, and even more preferably at least 30 volume percent of the second volume.

16. The apparatus according to any one of aspects 13-15, wherein the enclosing material comprises glass.

17. The apparatus according to any one of the preceding aspects, wherein the movement restriction device has an average density below 1100 kg/m3.

18. The apparatus according to any one of the preceding aspects, wherein the movement restriction device has an average density below 1050 kg/m3.

19. The apparatus according to any one of the preceding aspects, wherein the movement restriction device has an average density below 1000 kg/m3.

20. The apparatus according to any one of the preceding aspects, wherein the movement restriction device comprises a first cross-sectional distance and a second cross-sectional distance, and wherein the movement restriction device (110) is configured to be implanted such that:
- the first cross-sectional distance is more parallel than perpendicular to the cranial-caudal axis of the patient, and
- the second cross-sectional distance is more perpendicular than parallel to the cranial-caudal axis of the patient, and wherein
- the implantable movement restriction device (110) is adjustable in situ, such that the shape of the implantable movement restriction device (110) can be adjusted by the adjustment of the length of the first cross-sectional distance, such that the length of the first cross-sectional distance can be increased relative to the length of the second cross-sectional distance.

21. The apparatus according to aspect 20, wherein the shape of the implantable movement restriction device (110) can be adjusted by an increase of the length of the first cross-sectional distance relative to the length of the second cross-sectional distance while the length of a circumference of a cross-section of the implantable movement restriction device (110), in a plane parallel to the coronal plane of the patient remains constant.

22. The apparatus according to any one of the preceding aspects, wherein the implantable movement restriction device (110) comprises a lower portion configured to, directly or indirectly, engage the stomach of the patient in a region of the angle of his, such that the function of the implantable movement restriction device (110) is supported by tissue of the stomach in the region of the angle of his.

23. The apparatus according to any one of the preceding aspects, wherein the implantable movement restriction device (110) comprises an upper portion configured to, directly or indirectly, engage the thoracic diaphragm of the patient, and wherein the upper portion comprises at least one curvature.

24. The apparatus according to any one of the preceding aspects, wherein the implantable movement restriction device (110) is configured to be at least partially invaginated by the stomach wall.

25. The apparatus according to aspect 24, wherein the implantable movement restriction device (110) is configured to be at least partially invaginated by the stomach wall of the fundus.

26. The apparatus according to any one of the preceding aspects, wherein the implantable movement restriction device (110) comprises at least one circular cross-section.

27. The apparatus according to any one of the preceding aspects, wherein the implantable movement restriction device comprises at least two parts.

28. The apparatus according to aspect 27, wherein the at least two parts are configured to be assembled to form the implantable movement restriction device.

29. The apparatus according to aspect 28, wherein the at least two parts are configured to be connected to each other to form the implantable movement restriction device.

30. The apparatus according to any one of aspects 27-29, further comprising an interconnecting part configured to connect to the at least two parts.

31. The apparatus according to any one of aspects 27-30, wherein at least one of the two parts and the interconnecting part comprises a connecting recess, and at least one of the two parts and the interconnecting part comprises a connecting protrusion, and wherein at least one connecting protrusion and one connecting recess are configured to be interconnected for forming the implantable movement restriction device.

32. The apparatus according to any one of the preceding aspects, wherein the movement restriction device comprises a curved cross-section in a plane parallel to the transverse plane of the patient, and wherein the curve is configured to partially enclose the esophagus of the patient.

33. The apparatus according to aspect 32, wherein the movement restriction device is configured to encircle at least ⅓ of the esophagus in a plane parallel to the transverse plane of the patient.

34. The apparatus according to aspect 33, wherein the movement restriction device is configured to encircle at least ½ of the esophagus in a plane parallel to the transverse plane of the patient.

35. The apparatus according to aspect 32, wherein the movement restriction device comprises a C-shaped cross-section in a plane parallel to the transverse plane of the patient, and wherein the C-shaped cross-section is configured to partially enclose the esophagus of the patient.

36. The method according to aspect 35, wherein the movement restriction device is configured to encircle at least ⅔ of the esophagus in a plane parallel to the transverse plane of the patient.

37. The apparatus according to any one of aspects 1-31, wherein a cross-section of the movement restriction device in a plane parallel to the transverse plane of the patient comprises a closed curve configured to enclose the esophagus of the patient.

38. The apparatus according to any one of the preceding aspects, wherein the movement restriction device has a constricting state for hindering fluid from passing from the stomach into the esophagus and an expanded state for allowing food to pass into the stomach in response to the patient swallowing.

39. The apparatus according to aspect 38, wherein the movement restriction device comprises at least one attractor (212) for resiliently attracting adjacent portions (213) of the movement restriction device to generate an encircling pressure in the esophagus.

40. The apparatus according to aspect 39, wherein the attractor comprises an elastic element.

41. The apparatus according to aspect 39, wherein the attractor comprises at least two mutually attracting magnets.

Aspect Group 275FSE:
Reflux_Elongated_Plural_Device

1. An apparatus for treating reflux disease of a human patient, the apparatus comprises an implantable movement restriction device (110) configured to be at least partly invaginated by the stomach wall of the patient for restricting the movement of the cardia (22) of the patient towards the thoracic diaphragm (30), the implantable movement restriction device (110) having a first cross-sectional distance and a second cross-sectional distance, the first cross-sectional distance has a first length and the second cross-sectional distance has a second length, and wherein the first length is more than 1.5 times the second length, wherein the movement restriction device (110) is configured to be implanted such that:

the first cross-sectional distance is more parallel than perpendicular to the cranial-caudal axis of the patient, and the second cross-sectional distance is more perpendicular than parallel to the cranial-caudal axis of the patient, the implantable movement restriction device comprises at least a first and a second part configured to be connected to form the implantable movement restriction device, wherein the center of gravity of the first part is positioned on a plane extending perpendicularly from a first half of the first cross-sectional distance and the center of gravity of the second part is positioned on a plane extending perpendicularly from a second half of the first cross-sectional distance, a lower portion of the first part comprises a first connecting portion and the upper portion of the second part comprises a second connecting portion, and wherein:

the first and second connecting portions are configured to be connected to each other, the first and second connecting portions are configured to remain connected to each other by at least one of the first and second parts being supported or compressed by the invagination of the implantable movement restriction device in the stomach wall of the patient, and
the first and second parts are capable of disconnecting and separating if the support or compression from at least one of the first and second parts the stomach wall decreases.

2. The apparatus according to aspect 1, wherein the first and second connecting portions are configured to be directly connected to each other.

3. The apparatus according to aspect 1, further comprising an interconnecting part, and wherein the first and second connecting portions are configured to be connected to the interconnecting part.

4. The apparatus according to aspect 3, wherein the first and second connecting portions are configured to be indirectly connected to each other by the connections to the interconnecting part.

5. The apparatus according to any one of the preceding aspects, wherein at least one of: the first part, the second part, and the interconnecting part comprises a connecting recess, and at least one of: the first part, the second part, and the interconnecting part comprises a connecting protrusion and wherein at least one connecting protrusion and one connecting recess are configured to be interconnected for forming the implantable movement restriction device.

6. The apparatus according to any one of the preceding aspects, wherein at least one of the first and second connecting portions comprises a resilient connecting portion and wherein the resilient connecting portion is, directly or indirectly, supported or compressed by the invagination of the implantable movement for connecting, directly or indirectly, the first part to the second part.

7. The apparatus according to aspect 6, wherein the resilient connecting portion comprises a resilient protrusion configured to engage a recess for connecting, directly or indirectly, the first part to the second part.

8. The apparatus according to aspect 7, wherein the resilient protrusion is configured to connect and disconnect from a recess in a direction substantially perpendicular to the direction of the first cross-sectional distance.

9. The apparatus according to any one of the preceding aspects, wherein at least one of: the first part comprises a first sub-part and a second sub-part, and the second part comprises a first sub-part and a second sub-part.

10. The apparatus according to aspect 9, the first and second sub-parts each comprises a connecting portion, and wherein each of the first and second sub-parts are configured to connect and disconnect from the connecting portion of the first part, or the second part of the interconnecting part in a direction substantially perpendicular to the direction of the first cross-sectional distance.

11. The apparatus according to any one of aspects 9 and 10, wherein the first sub-part and the second sub-part are configured to remain connected to each other by at least one of the first and second parts being supported or compressed by the invagination of the implantable movement restriction device in the stomach wall of the patient, and wherein the first sub-part and the second sub-part are capable of disconnecting from each other and separating if the support or compression from the stomach wall on at least one of the first and second parts decreases.

12. The apparatus according to aspect 11, wherein the first part comprises a first and second sub-part, and wherein the first and second sub-parts are configured to remain connected by the first and second sub-parts being supported or compressed by the connecting portion of the second part.

13. The apparatus according to aspect 12, wherein the second part is configured to exert a supporting or compressing force on the first part derived from a supporting or compressing force exerted by the stomach wall on the second part.

14. The apparatus according to any one of the preceding aspects, wherein:
the first part comprises a first sub-part and a second sub-part, and
the second part comprises a first sub-part and a second sub-part, and wherein:
the first and second sub-parts of the first part are configured to remain connected to each other by a supporting or compressing force exerted by at least one of the second part and the stomach wall, and
the first and second sub-parts of the second part are configured to remain connected to each other by a supporting or compressing force exerted by the stomach wall.

15. The apparatus according to any one of the preceding aspects, wherein the implantable movement restriction device further comprises a third part, and wherein the lower portion of the second part comprises a third connecting portion and the upper portion of the third part comprises a fourth connecting portion, such that the first, second and third parts can be connected for forming the implantable medical device.

16. The apparatus according to aspect 15, wherein the second part is configured to exert a supporting or compressing force on the first part derived from a supporting or compressing force exerted by the third part on the second part, and wherein the third part is configured to exert a supporting or compressing force on the second part derived from a supporting or compressing force exerted by the stomach wall on the third part.

17. The apparatus according to any one of aspects 15 and 16, further comprising a second interconnecting part, and wherein the third and fourth connecting portions are configured to be connected to the second interconnecting part, such that the first interconnecting part connects the first part to the second part and the second interconnecting part connects the third part to the fourth part.

18. The apparatus according to any one of the aspects 15-17, wherein the first and second resilient connecting portions are supported or compressed by a supporting or compressing force exerted by the third part on the second part.

19. The apparatus according to any one of aspects 15-18, wherein:
the first part comprises a first sub-part and a second sub-part.
the second part comprises a first sub-part and a second sub-part, and
the third part comprises a first sub-part and a second sub-part, and wherein:
the first and second sub-parts of the first part are configured to remain connected to each other by a supporting or compressing force exerted by at least one of the second part and the stomach wall,
the first and second sub-parts of the second part are configured to remain connected to each other by a supporting or compressing force exerted by at least one of the third part and the stomach wall, and
the first and second sub-parts of the third part are configured to remain connected to each other by a supporting or compressing force exerted by the stomach wall.

20. The apparatus according to any one of the preceding aspects, wherein at least one of:

the first part comprises a first, second and third sub-part, the second part comprises a first, second and third sub-part, and the third part comprises a first, second and third sub-part.

21. The apparatus according to any one of the preceding aspects, wherein at least one of:

the first part comprises a first, second, third and fourth sub-part, the second part comprises a first, second, third and fourth sub-part, and the third part comprises a first, second, third and fourth sub-part.

22. The apparatus according to any one of the preceding aspects, wherein the movement restriction device is elongated and wherein the first length is more than 2 times the second length, preferably more than 2.5 times the second length and even more preferably more than 3 times the second length.

23. The apparatus according to any one of the preceding aspects, wherein the implantable movement restriction device (110) comprises at least one circular cross-section.

24. The apparatus according to any one of the preceding aspects, wherein the implantable movement restriction device (110) comprises a first, second and third cross-section in planes spaced apart and parallel to each other, wherein the first and third cross-sections have the same area, and the second cross-section is located between the first and third cross-section and have a smaller area.

25. The apparatus according to any one of the preceding aspects, wherein the implantable movement restriction device (110) further comprises a fourth and fifth cross-section in planes spaced apart and parallel to the planes of the first, second and third cross-sections, wherein the third and fifth cross-sections have the same area, and the fourth cross-section is located between the third and fifth cross-sections and have a smaller area.

26. The apparatus according to any one of the preceding aspects, wherein the implantable movement restriction device (110) is configured to be fully invaginated.

27. The apparatus according to any one of the preceding aspects, wherein a first portion of the implantable movement restriction device (110) has a first volume enclosed by material of the implantable movement restriction device (110), and a second portion of the movement restriction device (110), separate from the first portion, has a second volume enclosed by material of the implantable movement restriction device (110), and wherein the first volume and the second volumes are equally large, the first volume has a higher density than the second volume, and the second volume has a density below 1000 kg/m3.

28. The apparatus according to aspect 27, wherein the first volume comprises a first solid material.

29. The apparatus according to aspect 28, wherein the first solid material comprises a polymer material.

30. The apparatus according to aspect 29, wherein the first solid material comprises at least one of silicone-based material and a polyurethane-based material.

31. The apparatus according to any one of aspects 27-30, wherein the second volume comprises a second solid material.

32. The apparatus according to aspect 31, wherein the second solid material comprises a polymer material.

33. The apparatus according to aspect 32, wherein the second solid material comprises a at least one of a polypropylene-based and a polyethylene-based material.

34. The apparatus according to any one of aspects 31-33, wherein the first volume comprises a solid material having a density above 1000 kg/m3 and the second volume comprises a solid material having a density below 1000 kg/m3.

35. The apparatus according to aspect 31-34, wherein the second volume comprises a fluid.

36. The apparatus according to aspect 35, wherein the second volume comprises a liquid having a density a below 1000 kg/m3.

37. The apparatus according to aspect 36, wherein the liquid comprises at least one selected from a list of:

oil-based liquids, and alcohol based liquids.

38. The apparatus according to aspect 35, wherein the second volume comprises a gas.

39. The apparatus according to aspect 38, wherein the second volume comprises a plurality of volumes of gas enclosed by an enclosing material.

40. The apparatus according to aspect 39, wherein the second volume comprises a solid polymer material enclosing the enclosing material, and wherein the enclosing material is harder than the solid polymer material.

41. The apparatus according to any one of aspects 39 and 40, wherein the plurality of volumes of gas enclosed by an enclosing material makes up at least 10 volume percent of the second volume, more preferably at least 20 volume percent of the second volume, and even more preferably at least 30 volume percent of the second volume.

42. The apparatus according to any one of aspects 39-41, wherein the enclosing material comprises glass.

43. The apparatus according to any one of the preceding aspects, wherein the movement restriction device has an average density below 1100 kg/m3.

44. The apparatus according to any one of the preceding aspects, wherein the movement restriction device has an average density below 1050 kg/m3.

45. The apparatus according to any one of the preceding aspects, wherein the movement restriction device has an average density below 1000 kg/m3.

46. The apparatus according to any one of the preceding aspects, wherein the movement restriction device comprises a first cross-sectional distance and a second cross-sectional distance, and wherein the implantable movement restriction device (110) is adjustable in situ, such that the shape of the implantable movement restriction device (110) can be adjusted by the adjustment of the length of the first cross-sectional distance, such that the length of the first cross-sectional distance can be increased relative to the length of the second cross-sectional distance.

47. The apparatus according to aspect 46, wherein the shape of the implantable movement restriction device (110) can be adjusted by an increase of the length of the first cross-sectional distance relative to the length of the second cross-sectional distance while the length of a circumference of a cross-section of the implantable movement restriction device (110), in a plane parallel to the coronal plane of the patient remains constant.

48. The apparatus according to any one of the preceding aspects, wherein the first part comprises an upper portion configured to, directly or indirectly, engage the thoracic diaphragm of the patient, and wherein the upper portion comprises at least one curvature.

Aspect Group 275GSE:
Reflux_Device_Pressure_Sensor

1. An apparatus for treating reflux disease of a human patient, the apparatus comprises an implantable movement restriction device (110) configured to be at least partly invaginated by the stomach wall of the patient for restricting the movement of the cardia (22) of the patient towards the thoracic diaphragm (30), the implantable movement restriction device (110) comprising sensor (S1) configured to sense at least one of a force and a pressure, for monitoring a pressure or force exerted by the implantable movement restriction device on the stomach wall of the patient.

2. The apparatus according to aspect 1, wherein the sensor is at least one of: fixated to a surface of the implantable movement restriction device (110), or integrated in the implantable movement restriction device (110).

3. The apparatus according to any one of aspects 1 and 2, wherein the sensor (106) comprises a strain gauge-based sensor.

4. The apparatus according to aspect 3, wherein the sensor comprises a piezoresistive or piezoelectric strain gauge-based sensor.

5. The apparatus according to aspect 3, wherein the sensor comprises an optical strain gauge-based sensor.

6. The apparatus according to any one of aspects 1-3, wherein the sensor comprises a capacitive sensor.

7. The apparatus according to any one of aspects 1-3, wherein the sensor comprises an electromagnetic sensor.

8. The apparatus according to any one of the preceding aspects, wherein the implantable movement restriction device (110) comprises at least one enclosed chamber comprising a fluid, and wherein the sensor is configured the sense a pressure in the fluid.

9. The apparatus according to aspect 8, wherein the apparatus further comprises at least one conduit and a sensor unit configured to house the sensor, and wherein the conduit is in fluid connection with the enclosed chamber of the implantable movement restriction device and with the sensor unit, such that the sensor can sense the pressure in the fluid in the enclosed chamber of the implantable movement restriction device through the fluid connection provided by the conduit.

10. The apparatus according to any one of the preceding aspects, further comprising an implantable energy source for powering the sensor.

11. The apparatus according to any one of the preceding aspects, further comprising an implantable controller connected to the sensor.

12. The apparatus according to aspect 11, wherein the implantable controller comprises a wireless transceiver, and wherein the implantable controller is configured to receive a sensor signal from the sensor and transmit a wireless signal derived from the sensor signal to a unit external to the body of the patient.

13. The apparatus according to any one of the preceding aspects, wherein the implantable movement restriction device has a size such that the implantable movement restriction device can be fully invaginated by the fundus wall of the patient.

13. The apparatus according to any one of the preceding aspects, wherein the apparatus comprises at least one lead connected to the sensor, and wherein the lead is configured to connect the sensor to an external device configured to remain outside the patient's body.

14. The apparatus according to aspect 13, further comprising a connector for detachably connecting the sensor to the lead, such that the lead can be disconnected from the sensor.

15. The apparatus according to aspect 13, wherein the sensor is detachably attached to the implantable movement restriction device, such that the sensor can be detached from the implantable movement restriction device by pulling on the lead.

16. The apparatus according to aspect 15, wherein the sensor is detachably attached to the implantable movement restriction device using an adhesive.

17. The apparatus according to any one of the preceding aspects, wherein the implantable movement restriction device has a size of less than 200 cm2, preferably less than 100 cm2, and more preferably less than 50 cm2.

18. The apparatus according to any one of the preceding aspects, wherein the movement restriction device is elongated and wherein a first cross-sectional distance has a first length, and a second cross-sectional distance has a second length, and wherein the first length is more than 1.2 times the second length, preferably more than 1.5 times the second length and even more preferably more than 2 times the second length.

19. The apparatus according to any one of the preceding aspects, wherein the implantable movement restriction device (110) comprises at least one circular cross-section.

20. The apparatus according to any one of the preceding aspects, wherein the implantable movement restriction device (110) comprises a first, second and third cross-section in planes spaced apart and parallel to each other, wherein the first and third cross-sections have the same area, and the second cross-section is located between the first and third cross-section and have a smaller area.

21. The apparatus according to any one of the preceding aspects, wherein the implantable movement restriction device comprises at least two parts, or at least three parts, or at least 4 parts.

22. The apparatus according to aspect 21, wherein the at least two parts are configured to be assembled to form the implantable movement restriction device.

23. The apparatus according to aspect 22, wherein the at least two parts are configured to be connected to each other to form the implantable movement restriction device.

24. The apparatus according to any one of the preceding aspects, wherein the movement restriction device comprises a curved cross-section in a plane parallel to the transverse plane of the patient, and wherein the curve is configured to partially enclose the esophagus of the patient.

25. The apparatus according to aspect 24, wherein the movement restriction device is configured to encircle at least ⅓ of the esophagus in a plane parallel to the transverse plane of the patient.

26. The apparatus according to aspect 25, wherein the movement restriction device is configured to encircle at least ½ of the esophagus in a plane parallel to the transverse plane of the patient.

27. The apparatus according to aspect 25, wherein the movement restriction device comprises a C-shaped cross-section in a plane parallel to the transverse plane of the patient, and wherein the C-shaped cross-section is configured to partially enclose the esophagus of the patient.

28. The method according to aspect 27, wherein the movement restriction device is configured to encircle at least ⅔ of the esophagus in a plane parallel to the transverse plane of the patient.

29. The apparatus according to aspect 24, wherein a cross-section of the movement restriction device in a plane parallel to the transverse plane of the patient comprises a closed curve configured to enclose the esophagus of the patient.

30. The apparatus according to any one of the preceding aspects, wherein the implantable movement restriction device (110) comprises at least one circular cross-section.

Aspect Group 275HSE: Reflux_Instrument_Pressure_Sensor

1. A surgical instrument for assisting in a surgical procedure for implanting an implantable movement restriction device (110) configured to be at least partly invaginated by the stomach wall of the patient for restricting the movement of the cardia (22) of the patient towards the thoracic diaphragm (30), the surgical instrument comprising:

a handling portion configured to remain outside of the body of the patient in use, a distal portion configured to be inserted into the body of the patient, and a lead at least partially attached to the distal portion and configured to be connected to a sensor for sensing at least one of a force and a pressure, for monitoring a pressure or force exerted by the implantable movement restriction device on the stomach wall of the patient during implantation.

2. The surgical instrument according to aspect 1, wherein the distal portion comprises a holding device (901) connected to the handling portion and configured to be inserted into the body of the patient and to engage the movement restriction device.

3. The surgical instrument according to aspect 2, wherein the holding device (901) comprises an elongated portion configured to be inserted into the implantable movement restriction device.

4. The surgical instrument according to aspect 2, wherein the holding device (901) comprises a gripping portion configured to grip the implantable movement restriction device.

5. The surgical instrument according to any one of aspects 2-4, wherein the surgical instrument is configured for placement of the implantable movement restriction device, and wherein the surgical instrument further comprises a sleeve connected to the handling portion, and wherein the holding device is configured to be partially placed within the sleeve and be displaceable in relation to the sleeve, and wherein the handling of the handling portion creates relative displacement of the holding device in relation to the sleeve, which disengages the holding device from the movement restriction device for performing the placement of the movement restriction device.

6. The surgical instrument according to any one of the preceding aspects, wherein the distal portion is bent in relation to the primary length axis of the surgical instrument.

7. The surgical instrument according to aspect 8, wherein the distal portion is bent more than 20° in relation to the primary length axis of the instrument.

8. The surgical instrument according to any one of the preceding aspects, wherein the distal portion is flexible.

9. The surgical instrument according to any one of the preceding aspects, wherein the distal portion is bendable.

10. The surgical instrument according to aspect 9, wherein the bending of the distal portion is controllable from the handling portion.

11. The surgical instrument according to any one of the preceding aspects, wherein the surgical instrument is an abdominal instrument configured to be inserted into the abdomen of the patent during an open surgical procedure.

12. The surgical instrument according to any one of aspects 1-10, wherein the surgical instrument is a laparoscopic instrument configured to be inserted into the abdomen of the patient through a trocar.

13. The surgical instrument according to any one of aspects 1-10, wherein the surgical instrument is a gastroscopic instrument configured to be inserted into the body of the patient through the esophagus of the patient.

14. The surgical instrument according to any one of the preceding aspects, wherein the surgical instrument further comprises the sensor.

15. The surgical instrument according to aspect 14, wherein the sensor is configured to be detachably attached to the implantable movement restriction device, such that the sensor can be detached from the implantable movement restriction device and removed from the body of the patient during the surgical procedure.

16. The surgical instrument according to any one of the preceding aspects, wherein the sensor is at least one of: configured to be attached to a surface of the implantable movement restriction device (110) or attached in the implantable movement restriction device (110).

17. The surgical instrument according to any one of aspects 14 and 15, wherein the sensor is configured to be detachably attached to the implantable movement restriction device using an adhesive.

18. The surgical instrument according to any one of the preceding aspects, further comprising a connector for detachably connecting the sensor to the lead, such that the lead can be disconnected from the sensor.

19. The surgical instrument according to any one of the preceding aspects, wherein the sensor comprises a strain gauge-based sensor.

20. The surgical instrument according to aspect 19, wherein the sensor comprises a piezoresistive or piezoelectric strain gauge-based sensor.

21. The surgical instrument according to aspect 19, wherein the sensor comprises an optical strain gauge-based sensor.

22. The surgical instrument according to any one of aspects 14-19, wherein the sensor comprises a capacitive sensor.

23. The surgical instrument according to any one of aspects 14-19, wherein the sensor comprises an electromagnetic sensor.

24. The surgical instrument according to any one of the preceding aspects, wherein the implantable movement restriction device (110) comprises at least one enclosed chamber comprising a fluid, and wherein the sensor is a sensor configured the sense a pressure in a fluid.

25. The surgical instrument according to any one of the preceding aspects, further comprising an energy source for powering the sensor.

26. The surgical instrument according to any one of the preceding aspects, further comprising a controller connected to the sensor.

27. The surgical instrument according to aspect 26, wherein the controller is an external device configured to remain on the outside of the patient when the surgical instrument is in use, and wherein the controller is configured to receive a sensor signal from the sensor via the lead and provide an output on the basis the sensor signal.

28. The surgical instrument according to aspect 27, wherein the controller comprises an output device configured to provide an output to a person, wherein the output device comprises at least one unit selected from a list consisting of:

a unit providing audio output, a unit providing visual output, such as a lighting unit or a display unit, and a unit providing haptic output.

Aspect Group 275ISE:
Reflux_Constricting-Band_Adjustable_Length

1. An apparatus (100) for treating reflux disease of a human patient, the apparatus comprising an elongated core (210) having a length allowing the core to at least partly encircle the esophagus (20) of the patient, wherein the core comprises:

a first length variability function allowing the core to be arranged in a constricting state for hindering fluid from passing from the stomach (10) into the esophagus and in an expanded state for allowing food to pass into the stomach in response to the patient swallowing; and a second length variability function for post-operatively adjusting the length that the core has in its constricting state.

2. The apparatus according to aspect 1, wherein the second length variability function comprises a hydraulic length variability function.

3. The apparatus according to aspect 2, wherein the second hydraulic length variability function comprises at least one hydraulic chamber, and wherein the length of the core can be post-operatively adjusted by injection of a fluid into, or withdrawal of a fluid from the at least one hydraulic chamber.

4. The apparatus according to aspect 3, wherein the hydraulic chamber comprises at least one pleated portion.

5. The apparatus according to aspect 4, wherein the hydraulic chamber comprises at least one bellows.

6. The apparatus according to any one of aspects 3-5, wherein the elongated core (210) comprises a wall enclosing the hydraulic chamber, and wherein the thickness of the wall varies affecting the alteration of the shape of the hydraulic chamber as fluid is injected into or withdrawn from the hydraulic chamber.

7. The apparatus according to aspect 6, wherein the shape of the movement restriction device is altered by thinner portion of the wall enclosing the hydraulic adjustment chamber being deformed more than thicker portions of the wall enclosing the hydraulic adjustment chamber.

8. The apparatus according to any one of aspects 3-7, wherein the hydraulic chamber comprises at least one implantable injection port or is connected to at least one implantable injection port.

9. The apparatus according to aspect 1, wherein the second length variability function comprises a mechanical length variability function.

10. The apparatus according to aspect 9, wherein the mechanical length variability function comprises a powered mechanical length variability function.

11. The apparatus according to aspect 10, wherein the powered mechanical length variability function comprises at least one of: an electrical motor, an electromagnet, and an electroactive material.

12. The apparatus according to any one of aspects 9-11, wherein the movement restriction device comprises a transferring element configured to transfer at least one of:

electrical energy, and mechanical force to the mechanical length variability function.

13. The apparatus according to aspect 12, wherein the transferring element comprises at least one of:

an electrical lead, a shaft for transferring rotating force, and a shaft for transferring linear force.

14. The apparatus according to any one of aspects 11-13, wherein the mechanical operation device comprises a transmission configured to transform a rotating force generated by the electrical motor into a linear force for adjusting the length of the first cross-sectional distance.

15. The apparatus according to any of the preceding aspects, wherein the first length variability function comprises a plurality of portions that are movable relative to each other.

16. The apparatus according to aspect 15, wherein the first length variability function comprises an attractor (212) for resiliently attracting adjacent portions (213) of the elongated core to one another.

17. The apparatus according to aspect 16, wherein the attractor comprises an elastic element.

18. The apparatus according to aspect 16, wherein the attractor comprises at least two mutually attracting magnets.

19. The apparatus according to aspect 18, further comprising a link (214) connecting a first and a second one of said at least two magnets to each other.

20. The apparatus according to any one of the preceding aspects, wherein the elongated core is configured to exert an encircling pressure on the esophagus in the constricting state.

21. The apparatus according to any one of the preceding aspects, comprising two end portions (216) configured to be coupled to each other to form a closed ring around the esophagus.

22. The apparatus according to aspect 21, wherein the end portions are configured to be releasably attached to each other.

23. The apparatus according to aspect 22, wherein the end portions comprise a respective interlockable attacher.

24. The apparatus according to any one of the preceding aspects, wherein the elongated core comprises a plurality of bodies (213) configured to be arranged in an annular array around the esophagus.

25. The apparatus according to aspect 24, wherein the elongated core further comprises a plurality of links (214), each of which extending between a respective pair of bodies arranged adjacent to each other.

26. The apparatus according to any one of aspects 24-25, wherein at least one of the plurality of bodies (213) comprises the second length variability function for post-operatively adjusting the length of the core in its constricting state.

27. The apparatus according to aspect 26, wherein at least one of the plurality of bodies (213) comprises the hydraulic chamber for post-operatively adjusting the length of the core in its constricting state.

28. The apparatus according to any one of the preceding aspects, wherein the elongated core has a size allowing at least a portion of the elongated core to protrude above the cardiac sphincter of the patient, when implanted, such that movement of the cardia towards the diaphragm is restricted to hinder the cardia from sliding through the diaphragm opening (32) into the patient's thorax.

29. The apparatus according to any one of the preceding aspects, wherein the elongated core has a maximum height exceeding 2 cm, as measured in a normal direction to the plane in which the elongated core extends when encircling the esophagus.

30. The apparatus according to aspect 29, wherein the maximum height is 3 cm or more, such as 4 cm or more, such as 5 cm or more.

31. The apparatus according to any one of aspects 29 and 30, wherein the elongated core is configured to be implanted such that a portion of the elongated core having the maximum height is arranged at the fundus side of the esophagus.

32. The apparatus according to any one of the preceding aspects, wherein the elongated core has a first cross-sectional distance and a second cross-sectional distance, and wherein the elongated core is configured to be implanted such that:

the first cross-sectional distance is more parallel than perpendicular to the cranial-caudal axis of the patient, and the second cross-sectional distance is more perpendicular than parallel to the cranial-caudal axis of the patient, and wherein the elongated core is adjustable in situ, such that the shape of the elongated core can be adjusted by the adjustment of the length of the first cross-sectional distance, such that the length of the first cross-sectional distance can be increased relative to the length of the second cross-sectional distance.

33. The apparatus according to aspect 32, wherein the shape of the elongated core can be adjusted by an increase of the length of the first cross-sectional distance relative to the length of the second cross-sectional distance while the length of a circumference of a cross-section of the elongated core, in a plane parallel to the coronal plane of the patient remains constant.

34. The apparatus according to any one of aspects 32 and 33, wherein the shape of a cross-section of the elongated core can be adjusted to an elongated shape by an increase of the length of the first cross-sectional distance relative to the length of the second cross-sectional distance.

35. The apparatus according to any one of the preceding aspects, wherein the elongated core comprises a lower portion configured to, directly or indirectly, engage the stomach of the patient in a region of the angle of his, such that the function of the elongated core is supported by tissue of the stomach in the region of the angle of his.

36. The apparatus according to any one of the preceding aspects, wherein the elongated core comprises an upper portion configured to, directly or indirectly, engage the thoracic diaphragm of the patient, and wherein the upper portion comprises at least one curvature.

37. The apparatus according to any one of the preceding aspects, wherein the elongated core is configured to be at least partially invaginated by the stomach wall.

38. The apparatus according to aspect 37, wherein the elongated core is configured to be at least partially invaginated by the stomach wall of the fundus.

39. The apparatus according to any one of the preceding aspects, wherein the elongated core comprises a curved cross-section in a plane parallel to the transverse plane of the patient, and wherein the curve is configured to partially enclose the esophagus of the patient.

40. The apparatus according to aspect 39, wherein the movement restriction device is configured to encircle at least ⅓ of the esophagus in a plane parallel to the transverse plane of the patient.

41. The apparatus according to aspect 40, wherein the movement restriction device is configured to encircle at least ½ of the esophagus in a plane parallel to the transverse plane of the patient.

42. The apparatus according to aspect 41, wherein the movement restriction device comprises a C-shaped cross-section in a plane parallel to the transverse plane of the patient, and wherein the C-shaped cross-section is configured to partially enclose the esophagus of the patient.

43. The apparatus according to any one of aspects 41 and 42, wherein the movement restriction device is configured to encircle at least ⅔ of the esophagus in a plane parallel to the transverse plane of the patient.

44. The apparatus according to any one of the preceding aspects, wherein a cross-section of the movement restriction device in a plane parallel to the transverse plane of the patient comprises a closed curve configured to enclose the esophagus of the patient.

45. The apparatus according to any one of the preceding aspects, wherein the second length variability function is configured for post-operatively adjusting the length that the core has in its constricting state with more than 5%, or with more than 10%, or with more than 15% or with more than 20%.

46. The apparatus according to any one of the preceding aspects, further comprising at least one electrode for electrically stimulating at least one tissue portion of the patient.

Aspect Group 275JSE:
Reflux_Constricting-Band_Protruding-Element

1. An apparatus (100) for treating reflux disease of a human patient, the apparatus comprising an elongated core (210) having a length allowing the elongated core to at least partly encircle the esophagus (20) of the patient, wherein the elongated core comprises:

a first length variability function allowing the core to be arranged in a constricting state for hindering fluid from passing from the stomach (10) into the esophagus and in an expanded state for allowing food to pass into the stomach in response to the patient swallowing; and a protruding portion configured to protrude from the first length variability function in a direction more parallel than perpendicular to the cranial-caudal axis of the patient, in a substantially cranial direction, when the elongated core (210) is implanted, wherein:

the protruding portion is configured to protrude a distance of at least 10 mm in a substantially cranial direction from a plane extending perpendicularly from the cranial-caudal axis of the patient and comprising the center of gravity of the elongated core (210), and the protruding portion is configured to directly or indirectly engage the thoracic diaphragm of the patient for restricting the movement of the cardia (22) of the patient (10).

2. The apparatus according to aspect 1, wherein the protruding portion is configured to protrude a distance of at least 20 mm in a substantially cranial direction from a plane extending perpendicularly from the cranial-caudal axis of the patient and comprising the center of gravity of the elongated core (210).

3. The apparatus according to any one of aspects 1 and 2, wherein the protruding portion is configured to protrude in a substantially cranial direction from a plane extending perpendicularly from the cranial-caudal axis of the patient and comprising the center of gravity of the elongated core (210) a distance such that an upper portion of the protruding portion is placed at least 5 mm above the cardiac sphincter.

4. The apparatus according to aspect 3, wherein the protruding portion is configured to protrude in a substantially cranial direction from a plane extending perpendicularly from the cranial-caudal axis of the patient and comprising the center of gravity of the elongated core (210) a distance such that an upper portion of the protruding portion is placed at least 10 mm above the cardiac sphincter.

5. The apparatus according to aspect 4, wherein the protruding portion is configured to protrude in a substantially cranial direction from a plane extending perpendicularly from the cranial-caudal axis of the patient and comprising the center of gravity of the elongated core (2.10)) a distance such that an upper portion of the protruding portion is placed at least 15 mm above the cardiac sphincter.

6. The apparatus according to any one of the preceding aspects, wherein the elongated core has a first cross-sectional area in a first plane extending perpendicularly from the cranial-caudal axis of the patient, and the protruding portion has a second cross-sectional area in a second plane parallel to the first plane, and wherein the first cross-sectional area is more than 1.5 times the size of the second cross-sectional area.

7. The apparatus according to aspect 6, wherein the second cross-sectional area is an average cross-sectional area of the protruding portion.

8. The apparatus according to any one of aspects 6-7, wherein the protruding portion has a third cross-sectional area in a third plane parallel to the first plane, and wherein the second plane is positioned between the first and third planes, and wherein the third cross-sectional area is more than 1.5 times the size of the second cross-sectional area.

9. The apparatus according to any one of the preceding aspects, further comprising a second elongated core (210) having a length allowing the second elongated core to at least partly encircle the esophagus (20) of the patient, and wherein the protruding portion connects first elongated core to the second elongated core.

10. The apparatus according to any one of the preceding aspects, wherein the elongated core comprises a lower portion configured to, directly or indirectly, engage the stomach of the patient in a region of the angle of his, such that the function of the elongated core is supported by tissue of the stomach in the region of the angle of his.

11. The apparatus according to any one of the preceding aspects, wherein the protruding portion comprises an upper portion configured to, directly or indirectly, engage the thoracic diaphragm of the patient, and wherein the upper portion comprises at least one curvature.

12. The apparatus according to any one of the preceding aspects, wherein at least one of the first elongated core, the second elongate core and the protruding portion is configured to be at least partially invaginated by the stomach wall.

13. The apparatus according to any one of the preceding aspects, wherein protruding portion is adjustable in situ, such that the length that the protruding portion protrudes from the plane extending perpendicularly from the cranial-caudal axis of the patient and comprising the center of gravity of the elongated core (210) can be adjusted.

14. The apparatus according to aspect 13, wherein the protruding portion is hydraulically adjustable.

15. The apparatus according to aspect 14, wherein the apparatus further comprises a conduit configured to connect the hydraulically adjustable protruding portion to an implantable injection port.

16. The apparatus according to aspect 14, wherein at least one of the protruding portion and the elongated core comprises an injection port, such that the hydraulically adjustable protruding portion can be adjusted by the injection or withdrawal of a hydraulic fluid into the injection port.

17. The apparatus according to any one of aspects 14-16, wherein the protruding portion comprises a bellows, and wherein the injection or withdrawal of a hydraulic fluid into the injection port adjusts a length of the bellows.

18. The apparatus according to any one of aspects 14-17, wherein the protruding portion comprises a wall enclosing a hydraulic adjustment chamber, and wherein the thickness of the wall varies affecting the alteration of the shape of the protruding portion as fluid is injected into or withdrawn from the protruding portion.

19. The apparatus according to aspect 18, wherein the shape of the protruding portion is altered by thinner portion of the wall enclosing the hydraulic adjustment chamber being deformed more than thicker portions of the wall enclosing the hydraulic adjustment chamber.

20. The apparatus according to any one of aspects 1-13, wherein the protruding portion is mechanically adjustable.

21. The apparatus according to aspect 20, wherein the apparatus comprises a mechanical operation device for mechanically adjusting the protruding portion.

22. The apparatus according to aspect 21, wherein the movement restriction device comprises a transferring element configured to transfer at least one of:

electrical energy, and mechanical force to the mechanically adjustable protruding portion.

23. The apparatus according to aspect 22, wherein the transferring element comprises at least one of:

an electrical lead, a shaft for transferring rotating force, and a shaft for transferring linear force.

24. The apparatus according to any one of aspects 21-23, wherein the mechanical operation device comprises an electrical motor.

25. The apparatus according to aspect 24, wherein the mechanical operation device comprises a transmission configured to transform a rotating force generated by the electrical motor into a linear force for adjusting the length of the protruding portion.

26. The apparatus according to any one of aspects 21-25, wherein a portion of the protruding portion comprises a bellows, and wherein the operation of the mechanical operation device adjusts a length of the bellows.

27. The apparatus according to any one of aspects 1-13, wherein the protruding portion is electrically adjustable.

28. The apparatus according to aspect 27, wherein the apparatus comprises at least one material configured to alter shape when exposed to an electrical current or an electrical voltage.

29. The apparatus according to aspect 28, wherein the movement restriction device comprises at least one electroactive polymer.

30. The apparatus according to aspect 29, wherein the electroactive polymer is at least one electroactive polymer selected from a list consisting of: ferroelectric polymers, electrostrictive graft polymers, electrostrictive paper, piezoelectric polymers and liquid crystal elastomers.

31. The apparatus according to any one of the preceding aspects, wherein the length of the protruding portion is adjustable in situ more than 1.2 times, or more than 1.3 times, or more than 1.5 times.

32. The apparatus according to any one of the preceding aspects, wherein the elongated core comprises a curved cross-section in a plane parallel to the transverse plane of the patient, and wherein the curve is configured to partially enclose the esophagus of the patient.

33. The apparatus according to aspect 32, wherein the elongated core is configured to encircle at least ⅓ of the esophagus in a plane parallel to the transverse plane of the patient.

34. The apparatus according to aspect 33, wherein the elongated core is configured to encircle at least ½ of the esophagus in a plane parallel to the transverse plane of the patient.

35. The apparatus according to aspect 32, wherein the elongated core comprises a C-shaped cross-section in a plane parallel to the transverse plane of the patient, and wherein the C-shaped cross-section is configured to partially enclose the esophagus of the patient.

36. The apparatus according to aspect 34, wherein the elongated core is configured to encircle at least ⅔ of the esophagus in a plane parallel to the transverse plane of the patient.

37. The apparatus according to any one of the preceding aspects, wherein a cross-section of the elongated core in a plane parallel to the transverse plane of the patient comprises a closed curve configured to enclose the esophagus of the patient.

38. The apparatus according to any one of the preceding aspects, wherein the first length variability function comprises an attractor (212) for resiliently attracting adjacent portions (213) of the elongated core to one another.

39. The apparatus according to aspect 38, wherein the attractor comprises an elastic element.

40. The apparatus according to aspect 38, wherein the attractor comprises at least two mutually attracting magnets.

41. The apparatus according to aspect 40, further comprising a link (214) connecting a first and a second one of said at least two magnets to each other.

42. The apparatus according to any one of the preceding aspects, wherein the elongated core is configured to exert an encircling pressure on the esophagus in the constricting state.

43. The apparatus according to any one of the preceding aspects, comprising two end portions (216) configured to be coupled to each other to form a closed ring around the esophagus.

44. The apparatus according to aspect 43, wherein the end portions are configured to be releasably attached to each other.

45. The apparatus according to aspect 44, wherein the end portions comprise a respective interlockable attacher.

46. The apparatus according to any one of the preceding aspects, wherein the elongated core comprises a plurality of bodies (213) configured to be arranged in an annular array around the esophagus.

47. The apparatus according to aspect 46, wherein the elongated core further comprises a plurality of links (214), each of which extending between a respective pair of bodies arranged adjacent to each other.

48. The apparatus according to any one of the preceding aspects, wherein the elongated core is configured to be implanted such that the protruding portion is arranged at the fundus side of the esophagus.

45. The apparatus according to any one of the preceding aspects, further comprising a second length variability function configured for post-operatively adjusting the length that the elongated core has in its constricting state with more than 5%, or with more than 10%, or with more than 15% or with more than 20%.

46. The apparatus according to any one of the preceding aspects, further comprising at least one electrode for electrically stimulating at least one tissue portion of the patient.

Aspect Group 275KSE: Reflux_Constricting-Band_Stop_High-Placement-Method

1. A method for treating reflux disease of a human patient by implanting a movement restriction device (110) such that the movement restriction device is arranged to restrict movement of the cardia (22) of the patient's stomach (10) towards the diaphragm (30) to hinder the cardia from sliding through the diaphragm opening (32) into the patient's thorax, the movement restriction device (110) comprises a curved inner surface configured to face the curved outer surface of the esophagus (20), the method comprising positioning and fixating the movement restriction device such that:

the curved inner surface encircles at least ⅓ of the esophagus in a plane extending perpendicular to the cranial-caudal axis, and the center of mass of the movement restriction device is placed in a plane extending perpendicular to the cranial-caudal axis, and wherein the shortest distance from a point on the plane to the angle of His exceeds 20 mm.

2. The method according to aspect 1, wherein the method comprises the step of attaching the fundus of the stomach of the patient to the esophagus of the patient in a first position below the center of mass of the movement restriction device, such that the movement restriction device is supported by the attachment of the fundus to the esophagus.

3. The method according to aspect 2, wherein the step of attaching the fundus of the stomach of the patient to the esophagus of the patient in a first position comprises attaching the fundus of the stomach of the patient to the esophagus of the patient at a distance from the angle of His exceeding 5 mm.

4. The method according to any one of aspects 1-3, wherein the step of positioning and fixating the movement restriction device comprises positioning and fixating the movement restriction device such that the upper most point of the movement restriction device is placed in a second plane extending perpendicular to the cranial-caudal axis, and wherein the shortest distance from a point on the second plane to the angle of His exceeds 40 mm.

5. The method according to aspect 4, wherein the step of positioning and fixating the movement restriction device comprises positioning and fixating the movement restriction device such that the upper most point of the movement restriction device is placed in a second plane extending perpendicular to the cranial-caudal axis, and wherein the shortest distance from a point on the second plane to the angle of His exceeds 50 mm.

6. The method according to any one of aspects 1-5, wherein the step of positioning and fixating the movement restriction device comprises positioning and fixating the movement restriction device such that the lower most point of the movement restriction device is placed in a third plane extending perpendicular to the cranial-caudal axis, and wherein the shortest distance from a point on the third plane to the angle of His exceeds 10 mm.

7. The method according to aspect 6, wherein the step of positioning and fixating the movement restriction device comprises positioning and fixating the movement restriction device such that the lower most point of the movement restriction device is placed in a third plane extending perpendicular to the cranial-caudal axis, and wherein the shortest distance from a point on the third plane to the angle of His exceeds 20 mm.

8. The method according to any one of the preceding aspects, wherein the step of positioning and fixating the movement restriction device comprises positioning and fixating the movement restriction device such that the upper most point of the movement restriction device is placed in a second plane extending perpendicular to the cranial-caudal axis, and wherein the shortest distance from a point on the second plane to an upper-most point of the cardia exceeds 5 mm.

9. The method according to aspect 8, wherein the step of positioning and fixating the movement restriction device comprises positioning and fixating the movement restriction device such that the upper most point of the movement restriction device is placed in a second plane extending perpendicular to the cranial-caudal axis, and wherein the shortest distance from a point on the second plane to an upper-most point of the cardia exceeds 10 mm.

10. The method according to any one of the preceding aspects, wherein the step of positioning and fixating the movement restriction device comprises positioning the center of mass of the movement restriction device in the second plane extending perpendicular to the cranial-caudal direction, and wherein the shortest distance from a point on the second plane to an upper-most point of the cardia exceeds 5 mm.

11. The method according to any one of the preceding aspects, wherein the step of positioning and fixating the movement restriction device comprises positioning the center of mass of the movement restriction device in the second plane extending perpendicular to the cranial-caudal direction, and wherein the shortest distance from a point on the second plane to an upper-most point of the cardia exceeds 10 mm.

12. The method according to any one of the preceding aspects, wherein the step of positioning and fixating the movement restriction device comprises positioning a movement restriction device encircling at least ½ of the esophagus in a plane extending perpendicular to the cranial-caudal direction.

13. The method according to aspect 12, wherein the step of positioning and fixating the movement restriction device comprises positioning a movement restriction device encircling at least ⅔ of the esophagus in a plane extending perpendicular to the cranial-caudal direction.

14. The method according to aspect 13, wherein the step of positioning and fixating the movement restriction device comprises positioning a movement restriction device encircling the esophagus in a plane extending perpendicular to the cranial-caudal direction.

15. The method according to any of the preceding aspects, wherein the curved inner surface configured to face the curved outer surface of the esophagus (20) comprises a radius of curvature corresponding to or exceeding the radius of curvature of the esophagus, such that the curved inner surface comprises a radius of curvature corresponding to or exceeding the radius of curvature of the esophagus.

16. The method according to any of the preceding aspects, wherein the step of positioning and fixating the movement restriction device comprises positioning a movement restriction device comprising an electrode arrangement configured to electrically stimulate muscle tissue of the portion of the fundus and/or the serosa to improve the conditions for long term implantation of the movement restriction device.

17. The method according to aspect 16, further comprising implanting an implantable energy source configured to provide the electrode with electrical power.

18. The method according to any of the preceding aspects, wherein the step of positioning and fixating the movement restriction device comprises positioning a movement restriction device having a constricting state for hindering fluid from passing from the stomach into the esophagus and an expanded state for allowing food to pass into the stomach in response to the patient swallowing.

19. The method according to any one of the preceding aspects, wherein the step of positioning the movement restriction device comprises positioning a movement restriction device configured to exert an encircling pressure on the esophagus in the constricting state.

20. The method according to aspect 19, wherein the step of positioning and fixating the movement restriction device comprises positioning a movement restriction device comprising at least one attractor (212) for resiliently attracting adjacent portions (213) of the movement restriction device to generate the encircling pressure.

21. The apparatus according to aspect 20, wherein the attractor comprises an elastic element.

22. The apparatus according to aspect 20, wherein the attractor comprises at least two mutually attracting magnets.

23. The apparatus according to aspect 22, further comprising a link (214) connecting a first and a second one of said at least two magnets to each other.

24. The method according to any one of the preceding aspects, wherein the step of positioning and fixating the movement restriction device comprises positioning and fixating a movement restriction device having an adjustable volume.

Aspect Group 275LSE:
Reflux_Stop_Migration-Reducing-Gel_Device

1. An apparatus for treating reflux disease of a human patient, the apparatus comprises an implantable movement restriction device (100) configured to be at least partly invaginated by the stomach wall of the patient for restricting the movement of the cardia (22) of the patient (10) towards the thoracic diaphragm (30), the implantable movement restriction device (100) comprising a surface friction reducing coating covering at least a part of the surface of the implantable movement restriction device, wherein the surface friction reducing coating is configured to reduce the friction between the implantable movement restriction device and the tissue of the stomach wall by which the implantable movement restriction device is at least partially invaginated.

2. The apparatus according to aspect 1, wherein the surface friction reducing coating is covering the entire surface of the movement restriction device.

3. The apparatus according to any preceding aspect, wherein the surface friction reducing coating is selected from natural polymers, polysaccharide coatings, oils, hydrogels, and lubricating jellies.

4. The apparatus according to any preceding aspect, wherein the surface friction reducing coating is selected from methylcelluloses, such as hydroxypropyl methylcellulose (HPMC) and carboxymethylcellulose, ethylcelluloses, such as hydroxyethylcellulose, racine oil, mineral oil, glycerin, and polyethylene glycol (PEG).

5. The apparatus according to any preceding aspect, wherein the surface friction reducing coating is comprising an active agent selected from bactericides, antibiotics, bacteriostatics, analgesics and anesthetics.

6. The apparatus according to any preceding aspect, wherein the surface friction reducing coating provides antiseptic properties.

7. The apparatus according to any preceding aspect, wherein the surface friction reducing coating provides softening of adjacent tissues.

8. The apparatus according to any preceding aspect, wherein the surface friction reducing coating contains pH-adjusting compounds.

9. The apparatus according to any one of the preceding aspects, wherein the surface friction reducing coating is a viscous medium.

10. The apparatus according to any one of the preceding aspects, wherein the surface friction reducing coating has a higher viscosity than water.

11. The apparatus according to any one of the preceding aspects, wherein the surface friction reducing coating has a viscosity of at least 10 mPa·s at a shear rate of 50 s 1 at room temperature.

12. The apparatus according to aspect 11, wherein the surface friction reducing coating has a viscosity of at least 100 mPa·s at a shear rate of 50 s 1 at room temperature.

13. The apparatus according to any one of the preceding aspects, wherein the implantable movement restriction device has a size such that the implantable movement restriction device can be fully invaginated by the fundus wall of the patient.
14. The apparatus according to any one of the preceding aspects, wherein the implantable movement restriction device has a size of less than 200 $cm^2$, preferably less than 100 $cm^2$, and more preferably less than 50 $cm^2$.
15. The apparatus according to any one of the preceding aspects, wherein the movement restriction device is elongated and wherein a first cross-sectional distance has a first length, and a second cross-sectional distance has a second length, and wherein the first length is more than 1.2 times the second length, preferably more than 1.5 times the second length and even more preferably more than 2 times the second length.
16. The apparatus according to any one of the preceding aspects, wherein the implantable movement restriction device (100) comprises at least one circular cross-section.
17. The apparatus according to any one of the preceding aspects, wherein the implantable movement restriction device (100) comprises a first, second and third cross-section in planes spaced apart and parallel to each other, wherein the first and third cross-sections have the same area, and the second cross-section is located between the first and third cross-section and have a smaller area.
18. The apparatus according to any one of the preceding aspects, wherein the implantable movement restriction device comprises at least two parts, or at least three parts, or at least 4 parts.
19. The apparatus according to aspect 18, wherein the at least two parts are configured to be assembled to form the implantable movement restriction device.
20. The apparatus according to aspect 19, wherein the at least two parts are configured to be connected to each other to form the implantable movement restriction device.
21. The apparatus according to any one of the preceding aspects, wherein the movement restriction device comprises a curved cross-section in a plane parallel to the transverse plane of the patient, and wherein the curve is configured to partially enclose the esophagus of the patient.
22. The apparatus according to aspect 21, wherein the movement restriction device is configured to encircle at least ⅓ of the esophagus in a plane parallel to the transverse plane of the patient.
23. The apparatus according to aspect 22, wherein the movement restriction device is configured to encircle at least ½ of the esophagus in a plane parallel to the transverse plane of the patient.
24. The apparatus according to aspect 23, wherein the movement restriction device comprises a C-shaped cross-section in a plane parallel to the transverse plane of the patient, and wherein the C-shaped cross-section is configured to partially enclose the esophagus of the patient.
25. The method according to aspect 23, wherein the movement restriction device is configured to encircle at least ⅔ of the esophagus in a plane parallel to the transverse plane of the patient.
26. The apparatus according to aspect 21, wherein a cross-section of the movement restriction device in a plane parallel to the transverse plane of the patient comprises a closed curve configured to enclose the esophagus of the patient.
27. The apparatus according to any one of the preceding aspects, wherein the implantable movement restriction device (100) comprises at least one circular cross-section.

Aspect Group 275MSE: Reflux_Stop_Migration-Reducing-Gel_Method-Compound_and-Use

1. A method for treating reflux disease of a human patient by implanting a movement restriction device (100) the method comprises:
   at least partially invaginating the movement restriction device in the stomach of the patient such that the movement restriction device restricts movement of the cardia (22) of the patient's stomach (10) towards the thoracic diaphragm (30) to hinder the cardia from sliding through the diaphragm opening (32) into the patient's thorax, wherein the surface of the movement restriction device is at least partially covered by a surface friction reducing coating.
2. The method according to aspect 1, wherein the method comprises the step of applying the surface friction reducing coating onto the movement restriction device prior to implantation in the body of the patient.
3. The method according to aspect 1, wherein the method comprises the step applying the surface friction reducing coating in situ between the movement restriction device and tissue of the stomach wall of the patient.
4. The method according to aspect 3, wherein the method comprises the steps of:
   partially invaginating the movement restriction device in the stomach of the patient,
   applying the surface friction reducing coating in situ between the movement restriction device and tissue of the stomach wall of the patient, and
   further invaginating the movement restriction device in the stomach of the patient.
5. The method according to any one of the preceding aspects, wherein the step of at least partially invaginating the movement restriction device in the stomach of the patient comprises fully invaginating the movement restriction device in the stomach of the patient.
6. The method according to any one of the preceding aspects, wherein the method is a laparoscopic surgical method, and the method further comprises the step of introducing the movement restriction device into the body of the patient through a laparoscopic trocar after the surface friction reducing coating has been applied.
7. The method according to aspect 3, wherein the method is a laparoscopic surgical method, and wherein the step applying the surface friction reducing coating in situ between the movement restriction device and tissue of the stomach wall of the patient comprises applying the surface friction reducing coating in situ using a laparoscopic instrument inserted into the body of the patient though a laparoscopic trocar.
8. The method according to any one of aspects 1-5, wherein the method is a gastroscopic method, and the method further comprises the step of introducing the movement restriction device into the body of the patient through the esophagus of the patient after the surface friction reducing coating has been applied.
9. The method according to any one of aspects 1-5, wherein the method is a gastroscopic method, and wherein the step applying the surface friction reducing coating in situ between the movement restriction device and tissue of the stomach wall of the patient comprises applying the surface friction reducing coating in situ using a gastroscopic instrument inserted into the body of the patient though the esophagus.
10. The method according to any one of the preceding aspects, wherein the step of at least partially invaginating a movement restriction device comprises at least partially invaginating a movement restriction device comprising a surface friction reducing coating covering the entire surface of the movement restriction device.

11. The method according to any one of the preceding aspects, wherein the step of at least partially invaginating a movement restriction device comprises at least partially invaginating a movement restriction device comprising a surface friction reducing coating selected from natural polymers, polysaccharide coatings, oils, hydrogels, and lubricating jellies.

12. The method according to any one of the preceding aspects, wherein the step of at least partially invaginating a movement restriction device comprises at least partially invaginating a movement restriction device comprising a surface friction reducing coating selected from methylcelluloses, such as hydroxypropyl methylcellulose (HPMC) and carboxymethylcellulose, ethylcelluloses, such as hydroxyethylcellulose, racine oil, mineral oil, glycerin, and polyethylene glycol (PEG).

13. The method according to any one of the preceding aspects, wherein the step of at least partially invaginating a movement restriction device comprises at least partially invaginating a movement restriction device comprising a surface friction reducing coating comprising an active agent selected from bactericides, antibiotics, bacteriostatics, analgesics and anesthetics.

14. The method according to any one of the preceding aspects, wherein the step of at least partially invaginating a movement restriction device comprises at least partially invaginating a movement restriction device comprising a surface friction reducing coating providing antiseptic properties.

15. The method according to any one of the preceding aspects, wherein the step of at least partially invaginating a movement restriction device comprises at least partially invaginating a movement restriction device comprising a surface friction reducing coating providing softening of adjacent tissues.

16. The method according to any one of the preceding aspects, wherein the step of at least partially invaginating a movement restriction device comprises at least partially invaginating a movement restriction device comprising a surface friction reducing coating that contains pH-adjusting compounds.

17. The method according to any one of the preceding aspects, wherein the surface friction reducing coating is a viscous medium.

18. The method according to any one of the preceding aspects, wherein the surface friction reducing coating has a higher viscosity than water.

19. The method according to any one of the preceding aspects, wherein the surface friction reducing coating has a viscosity of at least 10 mPa·s at a shear rate of 50 $s^{-1}$ at room temperature.

20. The method according to aspect 19, wherein the surface friction reducing coating has a viscosity of at least 100 mPa·s at a shear rate of 50 $s^{-1}$ at room temperature.

21. The method according to any one of the preceding aspects, wherein the step of at least partially invaginating a movement restriction device comprises at least partially invaginating a movement restriction device having a size such that the implantable movement restriction device can be fully invaginated by the fundus wall of the patient.

22. The method according to any one of the preceding aspects, wherein the step of at least partially invaginating a movement restriction device comprises at least partially invaginating a movement restriction device having a size of less than 200 $cm^2$, preferably less than 100 $cm^2$, and more preferably less than 50 $cm^2$.

23. The method according to any one of the preceding aspects, wherein the step of at least partially invaginating a movement restriction device comprises at least partially invaginating a movement restriction device being elongated and having a first cross-sectional distance having a first length, and a second cross-sectional distance having a second length, and wherein the first length is more than 1.2 times the second length, preferably more than 1.5 times the second length and even more preferably more than 2 times the second length.

24. The method according to any one of the preceding aspects, wherein the step of at least partially invaginating a movement restriction device comprises at least partially invaginating a movement restriction device comprising at least one circular cross-section.

25. The method according to any one of the preceding aspects, wherein the step of at least partially invaginating a movement restriction device comprises at least partially invaginating a movement restriction device comprising a first, second and third cross-section in planes spaced apart and parallel to each other, wherein the first and third cross-sections have the same area, and the second cross-section is located between the first and third cross-section and have a smaller area.

26. The method according to any one of the preceding aspects, wherein the step of at least partially invaginating a movement restriction device comprises at least partially invaginating a movement restriction device comprising at least two parts, or at least three parts, or at least 4 parts.

27. The method according to aspect 26, wherein the step of at least partially invaginating a movement restriction device comprises assembling at least two parts for forming the implantable movement restriction device.

28. The method according to any one of the preceding aspects, wherein the step of at least partially invaginating a movement restriction device comprises at least partially invaginating a movement restriction device comprising a curved cross-section in a plane parallel to the transverse plane of the patient, and wherein the curve is configured to partially enclose the esophagus of the patient.

28. The method according to any one of the preceding aspects, wherein the step of at least partially invaginating a movement restriction device comprises at least partially in vaginating a movement restriction device comprising at least one circular cross-section.

29. A friction-reducing composition for use in the method according to any one of aspects 1-28.

30. Use of a composition selected from natural polymers, polysaccharide coatings, oils, hydrogels, and lubricating jellies as a surface friction reducing coating of at least part of the surface of an implantable movement restriction device for treating reflux disease of a human patient, wherein the movement restriction device (100) is configured to be at least partially invaginated by a stomach wall of a patient and arranged to restrict movement of the cardia (22) of a patient's stomach (10) towards the diaphragm (30) to hinder the cardia from sliding through the diaphragm opening (32) into the patient's thorax.

31. The use according to aspect 30, wherein the surface friction reducing coating is selected from methylcelluloses, such as hydroxypropyl methylcellulose (HPMC) and carboxymethylcellulose, ethylcelluloses, such as hydroxyethylcellulose, racine oil, mineral oil, glycerin, and polyethylene glycol (PEG).

32. The use according to any one of aspects 30-31, wherein the surface friction reducing coating is comprising an active agent selected from bactericides, antibiotics, bacteriostatics, analgesics and anesthetics.

33. The use according to any one of aspects 30-32, wherein the surface friction reducing coating provides antiseptic properties.

34. The use according to any one of aspects 30-33, wherein the surface friction reducing coating provides softening of adjacent tissues.

35. The use according to any one of aspects 30-34, wherein the surface friction reducing coating contains pH-adjusting compounds.

Aspect Group 449APC: Reflux Device Distance v.1

1. An implantable medical device for treating reflux disease, the implantable medical device comprising a movement restriction device configured to hindering movement of the lower esophageal sphincter relative to the thoracic diaphragm, the movement restriction device comprises:

a first part, a second part, and a first distance element, wherein:

the first and second part are configured to be connected to each other for forming at least a portion of a functional movement restriction device, the first and second part are capable of disconnecting from each other, such that the first and second part individually can pass through the gastro-intestinal tract, and the first distance element is configured to create a space located between the first and second part, wherein the space is configured to allow in-growth of fibrotic tissue between portions of the first and second parts, and wherein the space is confined at least partially by a first surface of the first part and a second surface of the second part and wherein the first and second surfaces are positioned opposite each other when the first and second parts are connected, and wherein:

a line segment of a first straight line is bounded by a first point on the first surface and a second point on the second surface, the line segment of the first straight line is more than 1 mm, a line segment of a second straight line is bounded by a third point on the first surface and a fourth point on the second surface, the line segment of the second straight line is more than 1 mm, the first straight line is parallel to the second straight line, the first and second straight lines intersect a third straight line which also intersects the center of gravity of the functional movement restriction device, and a distance between the first and second straight lines is more than 2 mm for allowing in-growth of fibrotic tissue for aiding in the fixation of the functional movement restriction device to the stomach wall.

The Distance Element

2. The implantable medical device according to aspect 1, wherein the first distance element is integrated in at least one of the first and second part.

3. The implantable medical device according to aspect 2, wherein the first distance element protrudes from a surface of at least one of the first and second part.

4. The implantable medical device according to aspect 1, further comprising a first separate distance part comprising the first distance element.

5. The implantable medical device according to aspect 4, wherein at least one of the first and second part further comprises a recess configured to receive a portion of the first distance element.

6. The implantable medical device according to any one of aspects 1-5, wherein the first distance element comprises at least a first and second portion configured to be placed at a distance from each other.

7. The implantable medical device according to any one of aspects 1-6, further comprising at least a third part, and wherein the first, second and third part are configured to be connected to each other for forming at least a portion of the functional movement restriction device.

8. The implantable medical device according to aspect 7, further comprising a second distance element, and wherein the first distance element is configured to create a space between the first and second part and the second distance element is configured to create a space between the first and third part.

9. The implantable medical device according to aspect 8, wherein the first and second distance element are portions of a separate distance part.

10. The implantable medical device according to any one of aspects 1-9, wherein at least one of the first, second and third parts comprises a recess configured to receive a portion of the distance element.

11. The implantable medical device according to any one of the preceding aspects, wherein the space has a volume exceeding 100 mm3.

12. The implantable medical device according to any one of the preceding aspects, wherein the space forms a recess in the implantable medical device, and wherein the recess has a depth exceeding 2 mm and a width exceeding 1 mm.

13. The implantable medical device according to any one of aspects 1-12, wherein the distance element is configured to prevent at least one of:

a. rotation between the first and second part, b. linear movement between the first and second part in a first direction, and c. linear movement between the first and second part in a first and second direction.

14. The implantable medical device according to any one of aspects 4-13, wherein the first separate distance part is configured to be placed centrally in the functional movement restriction device.

15. The implantable medical device according to aspect 14, wherein the center of gravity of the first separate distance part substantially coincides with the center of gravity of the functional movement restriction device.

16. The implantable medical device according to any one of aspects 4-15, wherein the first separate distance part comprises at least one rim comprising at least a first and a second surface, and wherein the first surface of the rim is configured to engage a surface of the first part and the second surface of the flange is configured to engage a surface of the second part.

17. The implantable medical device according to aspect 16, wherein the first and second surfaces of the at least one rim are parallel.

18. The implantable medical device according to any one of aspects 16-17, wherein the first separate distance part comprises at least two rims, and wherein:

the first rim comprises at least a first and a second surface, and wherein the first surface of the first rim is configured to engage a surface of the first part and the second surface of the first rim is configured to engage a surface of the second part, the second rim comprises at least a first and a second surface, and wherein the first surface of the second rim is configured to engage a surface of the first part and the second surface of the second rim is configured to engage a surface of the third part.

19. The implantable medical device according to aspect 18, wherein the first surfaces of the first rim and the first surface of the second rim are angled relative to each other with an angle in the range 20°-70°.

20. The implantable medical device according to aspect 19, wherein the first surfaces of the first rim and the first surface of the second rim are angled relative to each other with an angle in the range 40°-50°.

21. The implantable medical device according to aspect 19, wherein the first surfaces of the first rim and the first surface of the second rim are perpendicular.

22. The implantable medical device according to any one of aspects 5-21, wherein the first distance element is configured to engage the recess in at least one of the first and second part in a direction of a length axis of the distance element, and wherein the portion of the first distance element configured to enter the recess of the second part comprises at least one surface being angled relative to the length axis of the distance element.

23. The implantable medical device according to aspect 22, wherein the surface of the first distance element being angled is configured to face a surface of the recess in at least one of the first and second part being angled with an angle different from the angle of the first distance element, and wherein a point on the angled surface of the first distance element is configured to abut a point on the angled surface of the recess.

24. The implantable medical device according to aspect 23, wherein the angled surface of the first distance element abuts the angled surface of the recess over a length being less than half of the length of the angled surface of the first distance element.

25. The implantable medical device according to aspect 24, wherein the angled surface of the first distance element abuts the angled surface of the recess over a length being less than one third of the length of the angled surface of the first distance element.

26. The implantable medical device according to aspect 23, wherein the angled surface of the first distance element abuts the angled surface of the recess over a length being less than half of the depth of the recess, measured in a direction coinciding with the direction of the length axis of the first distance element, when the portion of the first distance element is inserted into the recess.

27. The implantable medical device according to any one of aspects 22-26, wherein the portion of the first distance element configured to enter the recess of the second part comprises a tapered portion.

28. The implantable medical device according to aspect 27, wherein the tapered portion is tapered with an angle in the range 20°-100°.

29. The implantable medical device according to any one of aspects 5-28, wherein the recess in at least one of the first and second part is tapered, such that two surfaces on opposite sides of the tapered portion of the first distance element faces two surfaces on opposite sides of the tapered recess, when the tapered portion of the first distance element is inserted into the recess.

30. The implantable medical device according to aspect 27, wherein the tapered recess is tapered with an angle in the range 30°-135°.

31. The implantable medical device according to any one of aspects 29 and 30, wherein the tapered portion of the first distance element is tapered with a first angle and the tapered recess in at least one of the first and second part is tapered with a second angle, and wherein the second angle is larger than the first angle.

32. The implantable medical device according to aspect 31, wherein the second angle is more than 3° larger than the first angle.

33. The implantable medical device according to aspect 32, wherein the second angle is more than 5° larger than the first angle.

34. The implantable medical device according to aspect 33, wherein the second angle is more than 10° larger than the first angle.

35. The implantable medical device according to any one of aspects 27-34, wherein at least one of:

the tapered portion of the first distance element, and the tapered recess in at least one of the first and second part is conical or frustum-conical.

36. The implantable medical device according to any one of aspects 27-34, wherein the tapered portion of the first distance element has the shape of a pyramid with a polygonal base.

37. The implantable medical device according to any one of aspects 5-21, wherein the portion of the first distance element configured to enter the recess of the first or second part comprises at least one surface having a curvature.

38. The implantable medical device according to aspect 37, wherein the surface of the first distance element having a curvature is configured to face a surface of the recess in at least one of the first and second part, and wherein a point on the surface of the first distance element having the curvature is configured to abut a point on the surface of the recess.

39. The implantable medical device according to aspect 38, wherein the surface of the first distance element having a curvature abuts the surface of the recess over a length being less than half of the length of the angled surface of the first distance element, when the first distance element has been positioned in the recess in at least one of the first and second part.

40. The implantable medical device according to aspect 39, wherein the surface of the first distance element having a curvature abuts the surface of the recess over a length being less than one third of the length of the angled surface of the first distance element, when the portion of the first distance element is inserted into the recess.

41. The implantable medical device according to aspect 38, wherein the surface of the first distance element having a curvature abuts the surface of the recess over a length being less than one third of the length of the angled surface of the first distance element, when the portion of the first distance element is inserted into the recess.

42. The implantable medical device according to aspect 38, wherein the surface of the first distance element having a curvature abuts the surface of the recess over a length being less than half of the depth of the recess, measured in a direction coinciding with the direction of the length axis of the first distance element, when the portion of the first distance element is inserted into the recess.

43. The implantable medical device according to any one of aspects 39-42, wherein the portion of the first distance element configured to enter the recess of the second part comprises at least one surface having a first and second curvature extending in perpendicular directions.

44. The implantable medical device according to aspect 43, wherein the portion of the first distance element configured to enter the recess of the second part comprises at least one spherical surface.

45. The implantable medical device according to any one of aspects 39-44, wherein the recess in at least one of the first and second part is tapered, such that two curved surfaces on opposite sides of the portion of the first distance element configured to enter the recess of the first or second part faces two surfaces on opposite sides of the tapered recess, when the portion of the first distance element configured to enter the recess of the first or second part is inserted into the recess.

46. The implantable medical device according to any one of aspects 5-28 and 37-44, wherein the recess in at least one of the first and second part comprises at least one surface having a curvature.

47. The implantable medical device according to aspect 46, wherein the recess in at least one of the first and second part comprises at least one surface having a first and second curvature extending in perpendicular directions.

48. The implantable medical device according to aspect 47, wherein the recess in at least one of the first and second part comprises at least one spherical surface.

49. The implantable medical device according to any one of aspects 37-48, wherein the portion of the first distance element configured to enter the recess of the first or second part comprises at least one surface having a curvature with a first radius and the recess in at least one of the first and second part comprises at least one surface having a curvature with a second radius, and wherein the second radius is longer than the first radius.

50. The implantable medical device according to aspect 49, wherein the portion of the first distance element configured to enter the recess of the first or second part comprises at least one surface having a first and second curvature extending in perpendicular directions, and wherein the recess in at least one of the first and second part comprises at least one surface having a first and second curvature extending in perpendicular directions, and wherein the sum of the radii of the first and second curvatures of the recess in at least one of the first and second part is longer than the sum of the radii of the first and second curvature of the portion of the first distance element configured to enter the recess.

Shapes of the Parts and the Functional Movement Restriction Device

51. The implantable medical device according to any one of the preceding aspects, wherein the functional movement restriction device or the boundary of the functional movement restriction device is elongated.

52. The implantable medical device according to aspect 51, wherein the functional movement restriction device is elongated such that a longest length is more than 1.5 times a widest width.

53. The implantable medical device according to any one of aspects 51 and 52, wherein the functional movement restriction device comprises a bend, and wherein the functional movement restriction device comprises a bent center axis following the elongation of the functional movement restriction device.

54. The implantable medical device according to aspect 53, wherein a first portion of the functional movement restriction device is configured to be positioned such that a first portion of the bent center axis is parallel to the caudal-cranial axis of the patient, and a second portion of the bent center axis is angled relative to the caudal-cranial axis of the patient, with an angle exceeding 5°.

55. The implantable medical device according to aspect 54, wherein the second portion of the bent center axis is configured to be positioned in the stomach such that it is angled towards the esophagus.

56. The implantable medical device according to any one of the preceding aspects, wherein at least one of the first and second part has a shape corresponding to an ellipsoid wedge or a truncated ellipsoid wedge.

57. The implantable medical device according to aspect 56, wherein at least one of the first and second part has a shape corresponding to a spherical wedge or a truncated spherical wedge.

58. The implantable medical device according to any one of aspects 1-55, wherein at least one of the first and second part has a shape corresponding to a portion of an ellipsoid wedge or a portion of a truncated ellipsoid wedge.

59. The implantable medical device according to aspect 58, wherein at least one of the first and second part has a shape corresponding to a hemiellipsoid wedge or a truncated hemiellipsoid wedge.

60. The implantable medical device according to aspect 59, wherein at least one of the first and second part has a shape corresponding to a portion of a spherical wedge or a portion of a truncated spherical wedge.

61. The implantable medical device according to aspect 60, wherein at least one of the first and second part has a shape corresponding to a hemispherical wedge or a truncated hemispherical wedge.

62. The implantable medical device according to any one of aspects 1-55, wherein at least one of the first and second part has a shape corresponding to an ellipsoid segment or a portion of an ellipsoid segment.

63. The implantable medical device according to aspect 62, wherein at least one of the first and second part has a shape corresponding to a spherical segment or a portion of a spherical segment.

64. The implantable medical device according to any one of the preceding aspects, wherein the functional movement restriction device, or the boundary of the functional movement restriction device, has a shape corresponding to an ellipsoid or a truncated ellipsoid.

65. The implantable medical device according to aspect 64, wherein the functional movement restriction device, or the boundary of the functional movement restriction device, has a shape corresponding to a sphere or a truncated sphere.

66. The implantable medical device according to any one of aspects 1-55, wherein at least the periphery of at least one of the first and second part has a shape corresponding to a cylinder.

67. The implantable medical device according to aspect 66, wherein the combined periphery of the first and second part has a shape corresponding to a cylinder.

68. The implantable medical device according to aspect 67, wherein the periphery of the first part has a shape corresponding to a first cylinder having a first radius, and the periphery of the second part has a shape corresponding to a second cylinder having a second radius, and wherein the first and second radii are different.

69. The implantable medical device according to any one of aspects 1-55 and 67-68, wherein the functional movement restriction device, or the boundary of the functional movement restriction device, comprises a stadium shaped cross-section, or a truncated stadium shaped cross-section.

70. The implantable medical device according to any one of aspects 1-55 and 67-68, wherein the functional movement restriction device comprises a bent stadium shaped cross-section, or a truncated bent stadium shaped cross-section.

71. The implantable medical device according to any one of aspects 1-3, 22-34, 51-55 and 64-70, wherein a periphery of the first part has a shape corresponding to a cylinder or an ellipsoid segment, and a periphery of the second part has a shape corresponding to a cylinder or an ellipsoid segment, and wherein the first part comprises at least one protrusion protruding from a first base surface and wherein the second part comprises at least one recess in a first base surface, and wherein the at least one protrusion is adapted to be placed at least partially in the at least one recess.

72. The implantable medical device according to aspect 71, wherein the at least one protrusion is adapted to engage the at least one recess.

73. The implantable medical device according to any one of aspects 71 and 72, wherein the first part further comprises at least one recess in a second base surface.

74. The implantable medical device according to aspect 73, wherein the position of the at least one protrusion coincides with the position of the at least one recess, such that the recess overlaps the protrusion when the first part is viewed in a direction normal to the first base surface.

75. The implantable medical device according to aspect 74, wherein the at least one recess recesses into the at least one protrusion.

76. The implantable medical device according to any one of aspects 71-75, wherein the at least one protrusion has the shape of a pyramid with a polygonal base.

77. The implantable medical device according to any one of aspects 71-76, wherein the first part further comprises at least one protrusion in a second base surface.

78. The implantable medical device according to any one of aspects 71-77, wherein the second part further comprises at least one protrusion in a second base surface.

79. The implantable medical device according to any one of aspects 71-78, wherein the second part further comprises at least one recess in a second base surface.

80. The implantable medical device according to aspect 71, further comprising a third part, and wherein:

- the first part further comprises a recess in a second base surface,
- the second part further comprises a protrusion protruding from a second base surface,
- the third part comprises a protrusion protruding from a first base surface and a recess in a second base surface,
- the protrusion of the first part is configured to be at least partially inserted into the recess of the second part,
- the protrusion of the second part is configured to be at least partially inserted into the recess of the third part, and wherein the first, second and third parts are configured to be assembled for forming at least a portion of a functional implantable medical device, and wherein the recesses and protrusions stabilize the parts relative to each other when assembled.

81. The implantable medical device according to any one of aspects 71-80, wherein the area of the first base surface of the first part is smaller than the area of the first base surface of the second part.

82. The implantable medical device according to any one of aspects 71-81, wherein the at least one protrusion protruding from the first base surface of the first part comprises the distance element.

Obesity Treatment

83. The implantable medical device according to any one of aspects 1-82, wherein the medical device is further configured to treat obesity by the movement restriction device being configured to protrude into the stomach and thereby reducing the volume of the cavity of the stomach.

84. The implantable medical device according to aspect 83, wherein the functional movement restriction device has a volume in the range 100 $cm^3$-1000 $cm^3$.

85. The implantable medical device according to aspect 84, wherein the functional movement restriction device has a volume in the range 100 $cm^3$-500 $cm^3$.

86. The implantable medical device according to any one of aspects 83-85, wherein the functional implantable medical device has a length in the range 2.5 cm-15 cm.

87. The implantable medical device according to aspect 86, wherein the functional implantable medical device has a length in the range 5 cm-15 cm.

88. The implantable medical device according to aspect 87, wherein the functional implantable medical device has a length in the range 7 cm-15 cm.

89. The implantable medical devices according to aspect 88, wherein the functional implantable medical device has a length in the range 8 cm-15 cm.

90. The implantable medical device according to aspect 89, wherein the functional implantable medical device has a length in the range 8 cm-12 cm.

Additional

91. The implantable medical device according to any one of the preceding aspects, wherein the movement restriction device comprises a surface friction reducing coating covering at least a part of the surface of the movement restriction device, wherein the surface friction reducing coating is configured to reduce the friction between the movement restriction device and the tissue of the stomach wall by which the movement restriction device is at least partially invaginated.

92. The implantable medical device according to any one of the preceding aspects, wherein the movement restriction device comprises a sensor configured to sense at least one of a force and a pressure, for monitoring a pressure or force exerted by the implantable movement restriction device on the stomach wall of the patient.

The implantable medical device according to any one of the preceding aspects, wherein the movement restriction device comprises a first portion having a first volume enclosed by material of the implantable movement restriction device and a second portion, different from the first portion, having a second volume enclosed by material of the implantable movement restriction device, wherein the first volume and the second volumes are equally large, the first volume has a higher density than the second volume, and the second volume has a density below 1000 kg/m3. Aspect group 449BPC: Reflux Device Distance v.2

1. An implantable medical device for treating reflux disease, the implantable medical device is configured to act as a movement restriction device for hindering movement of the lower esophageal sphincter relative to the thoracic diaphragm and adapted to be positioned between the angle of His and the diaphragm, the movement restriction device comprises:

- a first part,
- a second part, and
- a distance element, wherein:

the first and second part are configured to be connected to each other for forming at least a portion of a functional movement restriction device, the first and second part are capable of disconnecting from each other if at least one of the first and second part becomes positioned inside of the stomach, such that the first and second part individually can pass through the gastro-intestinal tract, and the distance element is configured to create a space between the first and second part, wherein the space is configured to allow in-growth of fibrotic tissue between portions of the first and second parts, and wherein the space forms a recess in the functional movement restriction device, and wherein the recess is more than 1 mm wide and more than 2 mm deep for allowing in-growth of fibrotic tissue for aiding in the fixation of the functional movement restriction device to the stomach wall.

The Distance Element

2. The implantable medical device according to aspect 1, wherein the first distance element is integrated in at least one of the first and second part.

3. The implantable medical device according to aspect 2, wherein the first distance element protrudes from a surface of at least one of the first and second part.

4. The implantable medical device according to aspect 1, further comprising a first separate distance part comprising the first distance element.

5. The implantable medical device according to aspect 4, wherein at least one of the first and second part further comprises a recess configured to receive a portion of the first distance element.

6. The implantable medical device according to any one of aspects 1-5, wherein the first distance element comprises at least a first and second portion configured to be placed at a distance from each other.

7. The implantable medical device according to any one of aspects 1-6, further comprising at least a third part, and wherein the first, second and third part are configured to be connected to each other for forming at least a portion of the functional movement restriction device.

8. The implantable medical device according to aspect 7, further comprising a second distance element, and wherein the first distance element is configured to create a space between the first and second part and the second distance element is configured to create a space between the first and third part.

9. The implantable medical device according to aspect 8, wherein the first and second distance element are portions of a separate distance part.

10. The implantable medical device according to any one of aspects 1-9, wherein at least one of the first, second and third parts comprises a recess configured to receive a portion of the distance element.

11. The implantable medical device according to any one of the preceding aspects, wherein the space has a volume exceeding 100 mm3.

12. The implantable medical device according to any one of the preceding aspects, wherein the space forms a recess in the implantable medical device, and wherein the recess has a depth exceeding 2 mm and a width exceeding 1 mm.

13. The implantable medical device according to any one of aspects 1-12, wherein the distance element is configured to prevent at least one of:

a. rotation between the first and second part,
b. linear movement between the first and second part in a first direction, and
c. linear movement between the first and second part in a first and second direction.

14. The implantable medical device according to any one of aspects 4-13, wherein the first separate distance part is configured to be placed centrally in the functional movement restriction device.

15. The implantable medical device according to aspect 14, wherein the center of gravity of the first separate distance part substantially coincides with the center of gravity of the functional movement restriction device.

16. The implantable medical device according to any one of aspects 4-15, wherein the first separate distance part comprises at least one rim comprising at least a first and a second surface, and wherein the first surface of the rim is configured to engage a surface of the first part and the second surface of the flange is configured to engage a surface of the second part.

17. The implantable medical device according to aspect 16, wherein the first and second surfaces of the at least one rim are parallel.

18. The implantable medical device according to any one of aspects 16-17, wherein the first separate distance part comprises at least two rims, and wherein:

the first rim comprises at least a first and a second surface, and wherein the first surface of the first rim is configured to engage a surface of the first part and the second surface of the first rim is configured to engage a surface of the second part, the second rim comprises at least a first and a second surface, and wherein the first surface of the second rim is configured to engage a surface of the first part and the second surface of the second rim is configured to engage a surface of the third part.

19. The implantable medical device according to aspect 18, wherein the first surfaces of the first rim and the first surface of the second rim are angled relative to each other with an angle in the range 20°-70°.

20. The implantable medical device according to aspect 19, wherein the first surfaces of the first rim and the first surface of the second rim are angled relative to each other with an angle in the range 40°-50°.

21. The implantable medical device according to aspect 19, wherein the first surfaces of the first rim and the first surface of the second rim are perpendicular.

22. The implantable medical device according to any one of aspects 5-21, wherein the first distance element is configured to engage the recess in at least one of the first and second part in a direction of a length axis of the distance element, and wherein the portion of the first distance element configured to enter the recess of the second part comprises at least one surface being angled relative to the length axis of the distance element.

23. The implantable medical device according to aspect 22, wherein the surface of the first distance element being angled is configured to face a surface of the recess in at least one of the first and second part being angled with an angle different from the angle of the first distance element, and wherein a point on the angled surface of the first distance element is configured to abut a point on the angled surface of the recess.

24. The implantable medical device according to aspect 23, wherein the angled surface of the first distance element abuts the angled surface of the recess over a length being less than half of the length of the angled surface of the first distance element.

25. The implantable medical device according to aspect 24, wherein the angled surface of the first distance element abuts the angled surface of the recess over a length being less than one third of the length of the angled surface of the first distance element.

26. The implantable medical device according to aspect 23, wherein the angled surface of the first distance element abuts the angled surface of the recess over a length being less than half of the depth of the recess, measured in a direction coinciding with the direction of the length axis of the first distance element, when the portion of the first distance element is inserted into the recess.

27. The implantable medical device according to any one of aspects 22-26, wherein the portion of the first distance element configured to enter the recess of the second part comprises a tapered portion.

28. The implantable medical device according to aspect 27, wherein the tapered portion is tapered with an angle in the range 200°-100°.

29. The implantable medical device according to any one of aspects 5-28, wherein the recess in at least one of the first and second part is tapered, such that two surfaces on opposite sides of the tapered portion of the first distance element faces two surfaces on opposite sides of the tapered recess, when the tapered portion of the first distance element is inserted into the recess.

30. The implantable medical device according to aspect 27, wherein the tapered recess is tapered with an angle in the range 30°-135°.

31. The implantable medical device according to any one of aspects 29 and 30, wherein the tapered portion of the first distance element is tapered with a first angle and the tapered recess in at least one of the first and second part is tapered with a second angle, and wherein the second angle is larger than the first angle.

32. The implantable medical device according to aspect 31, wherein the second angle is more than 3° larger than the first angle.

33. The implantable medical device according to aspect 32, wherein the second angle is more than 5° larger than the first angle.

34. The implantable medical device according to aspect 33, wherein the second angle is more than 10° larger than the first angle.

35. The implantable medical device according to any one of aspects 27-34, wherein at least one of:

the tapered portion of the first distance element, and the tapered recess in at least one of the first and second part is conical or frustum-conical.

36. The implantable medical device according to any one of aspects 27-34, wherein the tapered portion of the first distance element has the shape of a pyramid with a polygonal base.

37. The implantable medical device according to any one of aspects 5-21, wherein the portion of the first distance element configured to enter the recess of the first or second part comprises at least one surface having a curvature.

38. The implantable medical device according to aspect 37, wherein the surface of the first distance element having a curvature is configured to face a surface of the recess in at least one of the first and second part, and wherein a point on the surface of the first distance element having the curvature is configured to abut a point on the surface of the recess.

39. The implantable medical device according to aspect 38, wherein the surface of the first distance element having a curvature abuts the surface of the recess over a length being less than half of the length of the angled surface of the first distance element, when the first distance element has been positioned in the recess in at least one of the first and second part.

40. The implantable medical device according to aspect 39, wherein the surface of the first distance element having a curvature abuts the surface of the recess over a length being less than one third of the length of the angled surface of the first distance element, when the portion of the first distance element is inserted into the recess.

41. The implantable medical device according to aspect 38, wherein the surface of the first distance element having a curvature abuts the surface of the recess over a length being less than one third of the length of the angled surface of the first distance element, when the portion of the first distance element is inserted into the recess.

42. The implantable medical device according to aspect 38, wherein the surface of the first distance element having a curvature abuts the surface of the recess over a length being less than half of the depth of the recess, measured in a direction coinciding with the direction of the length axis of the first distance element, when the portion of the first distance element is inserted into the recess.

43. The implantable medical device according to any one of aspects 39-42, wherein the portion of the first distance element configured to enter the recess of the second part comprises at least one surface having a first and second curvature extending in perpendicular directions.

44. The implantable medical device according to aspect 43, wherein the portion of the first distance element configured to enter the recess of the second part comprises at least one spherical surface.

45. The implantable medical device according to any one of aspects 39-44, wherein the recess in at least one of the first and second part is tapered, such that two curved surfaces on opposite sides of the portion of the first distance element configured to enter the recess of the first or second part faces two surfaces on opposite sides of the tapered recess, when the portion of the first distance element configured to enter the recess of the first or second part is inserted into the recess.

46. The implantable medical device according to any one of aspects 5-28 and 37-44, wherein the recess in at least one of the first and second part comprises at least one surface having a curvature.

47. The implantable medical device according to aspect 46, wherein the recess in at least one of the first and second part comprises at least one surface having a first and second curvature extending in perpendicular directions.

48. The implantable medical device according to aspect 47, wherein the recess in at least one of the first and second part comprises at least one spherical surface.

49. The implantable medical device according to any one of aspects 37-48, wherein the portion of the first distance element configured to enter the recess of the first or second part comprises at least one surface having a curvature with a first radius and the recess in at least one of the first and second part comprises at least one surface having a curvature with a second radius, and wherein the second radius is longer than the first radius.

50. The implantable medical device according to aspect 49, wherein the portion of the first distance element configured to enter the recess of the first or second part comprises at least one surface having a first and second curvature extending in perpendicular directions, and wherein the recess in at least one of the first and second part comprises at least one surface having a first and second curvature extending in perpendicular directions, and wherein the sum of the radii of the first and second curvatures of the recess in at least one of the first and second part is longer than the sum of the radii of the first and second curvature of the portion of the first distance element configured to enter the recess.

Shapes of the Parts and the Functional Movement Restriction Device

51. The implantable medical device according to any one of the preceding aspects, wherein the functional movement restriction device or the boundary of the functional movement restriction device is elongated.

52. The implantable medical device according to aspect 51, wherein the functional movement restriction device is elongated such that a longest length is more than 1.5 times a widest width.

53. The implantable medical device according to any one of aspects 51 and 52, wherein the functional movement restriction device comprises a bend, and wherein the functional movement restriction device comprises a bent center axis following the elongation of the functional movement restriction device.

54. The implantable medical device according to aspect 53, wherein a first portion of the functional movement restriction device is configured to be positioned such that a first portion of the bent center axis is parallel to the caudal-cranial axis of the patient, and a second portion of the bent center axis is angled relative to the caudal-cranial axis of the patient, with an angle exceeding 5°.

55. The implantable medical device according to aspect 54, wherein the second portion of the bent center axis is configured to be positioned in the stomach such that it is angled towards the esophagus.

56. The implantable medical device according to any one of the preceding aspects, wherein at least one of the first and second part has a shape corresponding to an ellipsoid wedge or a truncated ellipsoid wedge.

57. The implantable medical device according to aspect 56, wherein at least one of the first and second part has a shape corresponding to a spherical wedge or a truncated spherical wedge.

58. The implantable medical device according to any one of aspects 1-55, wherein at least one of the first and second part has a shape corresponding to a portion of an ellipsoid wedge or a portion of a truncated ellipsoid wedge.

59. The implantable medical device according to aspect 58, wherein at least one of the first and second part has a shape corresponding to a hemiellipsoid wedge or a truncated hemiellipsoid wedge.

60. The implantable medical device according to aspect 59, wherein at least one of the first and second part has a shape corresponding to a portion of a spherical wedge or a portion of a truncated spherical wedge.

61. The implantable medical device according to aspect 60, wherein at least one of the first and second part has a shape corresponding to a hemispherical wedge or a truncated hemispherical wedge.

62. The implantable medical device according to any one of aspects 1-55, wherein at least one of the first and second part has a shape corresponding to an ellipsoid segment or a portion of an ellipsoid segment.

63. The implantable medical device according to aspect 62, wherein at least one of the first and second part has a shape corresponding to a spherical segment or a portion of a spherical segment.

64. The implantable medical device according to any one of the preceding aspects, wherein the functional movement restriction device, or the boundary of the functional movement restriction device, has a shape corresponding to an ellipsoid or a truncated ellipsoid.

65. The implantable medical device according to aspect 64, wherein the functional movement restriction device, or the boundary of the functional movement restriction device, has a shape corresponding to a sphere or a truncated sphere.

66. The implantable medical device according to any one of aspects 1-55, wherein at least the periphery of at least one of the first and second part has a shape corresponding to a cylinder.

67. The implantable medical device according to aspect 66, wherein the combined periphery of the first and second part has a shape corresponding to a cylinder.

68. The implantable medical device according to aspect 67, wherein the periphery of the first part has a shape corresponding to a first cylinder having a first radius, and the periphery of the second part has a shape corresponding to a second cylinder having a second radius, and wherein the first and second radii are different.

69. The implantable medical device according to any one of aspects 1-55 and 67-68, wherein the functional movement restriction device, or the boundary of the functional movement restriction device, comprises a stadium shaped cross-section, or a truncated stadium shaped cross-section.

70. The implantable medical device according to any one of aspects 1-55 and 67-68, wherein the functional movement restriction device comprises a bent stadium shaped cross-section, or a truncated bent stadium shaped cross-section.

71. The implantable medical device according to any one of aspects 1-3, 22-34, 51-55 and 64-70, wherein a periphery of the first part has a shape corresponding to a cylinder or an ellipsoid segment, and a periphery of the second part has a shape corresponding to a cylinder or an ellipsoid segment, and wherein the first part comprises at least one protrusion protruding from a first base surface and wherein the second part comprises at least one recess in a first base surface, and wherein the at least one protrusion is adapted to be placed at least partially in the at least one recess.

72. The implantable medical device according to aspect 71, wherein the at least one protrusion is adapted to engage the at least one recess.

73. The implantable medical device according to any one of aspects 71 and 72, wherein the first part further comprises at least one recess in a second base surface.

74. The implantable medical device according to aspect 73, wherein the position of the at least one protrusion coincides with the position of the at least one recess, such that the recess overlaps the protrusion when the first part is viewed in a direction normal to the first base surface.

75. The implantable medical device according to aspect 74, wherein the at least one recess recesses into the at least one protrusion.

76. The implantable medical device according to any one of aspects 71-75, wherein the at least one protrusion has the shape of a pyramid with a polygonal base.

77. The implantable medical device according to any one of aspects 71-76, wherein the first part further comprises at least one protrusion in a second base surface.

78. The implantable medical device according to any one of aspects 71-77, wherein the second part further comprises at least one protrusion in a second base surface.

79. The implantable medical device according to any one of aspects 71-78, wherein the second part further comprises at least one recess in a second base surface.

80. The implantable medical device according to aspect 71, further comprising a third part, and wherein:

- the first part further comprises a recess in a second base surface,
- the second part further comprises a protrusion protruding from a second base surface,
- the third part comprises a protrusion protruding from a first base surface and a recess in a second base surface, the protrusion of the first part is configured to be at least partially inserted into the recess of the second part.

the protrusion of the second part is configured to be at least partially inserted into the recess of the third part, and wherein the first, second and third parts are configured to be assembled for forming at least a portion of a functional implantable medical device, and wherein the recesses and protrusions stabilize the parts relative to each other when assembled.

81. The implantable medical device according to any one of aspects 71-80, wherein the area of the first base surface of the first part is smaller than the area of the first base surface of the second part.

82. The implantable medical device according to any one of aspects 71-81, wherein the at least one protrusion protruding from the first base surface of the first part comprises the distance element.

Obesity Treatment

83. The implantable medical device according to any one of aspects 1-82, wherein the medical device is further configured to treat obesity by the movement restriction device being configured to protrude into the stomach and thereby reducing the volume of the cavity of the stomach.

84. The implantable medical device according to aspect 83, wherein the functional movement restriction device has a volume in the range 100 $cm^3$-1000 $cm^3$.

85. The implantable medical device according to aspect 84, wherein the functional movement restriction device has a volume in the range 100 $cm^3$-500 $cm^3$.

86. The implantable medical device according to any one of aspects 83-85, wherein the functional implantable medical device has a length in the range 2.5 cm-15 cm.

87. The implantable medical device according to aspect 86, wherein the functional implantable medical device has a length in the range 5 cm-15 cm.

88. The implantable medical device according to aspect 87, wherein the functional implantable medical device has a length in the range 7 cm-15 cm.

89. The implantable medical device according to aspect 88, wherein the functional implantable medical device has a length in the range 8 cm-15 cm.

90. The implantable medical device according to aspect 89, wherein the functional implantable medical device has a length in the range 8 cm-12 cm.

Additional

91. The implantable medical device according to any one of the preceding aspects, wherein the movement restriction device comprises a surface friction reducing coating covering at least a part of the surface of the movement restriction device, wherein the surface friction reducing coating is configured to reduce the friction between the movement restriction device and the tissue of the stomach wall by which the movement restriction device is at least partially invaginated.

92. The implantable medical device according to any one of the preceding aspects, wherein the movement restriction device comprises a sensor configured to sense at least one of a force and a pressure, for monitoring a pressure or force exerted by the implantable movement restriction device on the stomach wall of the patient.

93. The implantable medical device according to any one of the preceding aspects, wherein the movement restriction device comprises a first portion having a first volume enclosed by material of the implantable movement restriction device and a second portion, different from the first portion, having a second volume enclosed by material of the implantable movement restriction device, wherein the first volume and the second volumes are equally large, the first volume has a higher density than the second volume, and the second volume has a density below 1000 kg/m3.

Aspect Group 449CPC: Reflux2 Plural Discs

1. An implantable medical device for treating reflux disease, the implantable medical device comprising a movement restriction device configured to be fixated to the stomach wall for hindering movement of the lower esophageal sphincter relative to the thoracic diaphragm, the movement restriction device comprises a first part and a second part, wherein:

the first and second parts are configured to be connected to each other for forming at least a portion of a functional movement restriction device, the first and second part are capable of disconnecting from each other, such that the first and second part individually can pass through the gastro-intestinal tract, and a periphery of the first part has a shape corresponding to a cylinder or an ellipsoid segment, and a periphery of the second part has a shape corresponding to a cylinder or an ellipsoid segment, the first part comprises at least one protrusion protruding from a first base surface and the second part comprises at least one recess in a first base surface, and the at least one protrusion is adapted to be placed at least partially in the at least one recess for stabilizing the first and second parts relative to each other.

2. The implantable medical device according to aspect 1, wherein the at least one protrusion is adapted to engage the at least one recess.

3. The implantable medical device according to any one of aspects 1 and 2, wherein the first part further comprises at least one recess in a second base surface.

4. The implantable medical device according to aspect 3, wherein the position of the at least one protrusion coincides with the position of the at least one recess, such that the recess overlaps the protrusion when the first part is viewed in a direction normal to the first base surface.

5. The implantable medical device according to aspect 4, wherein the at least one recess recesses into the at least one protrusion.

6. The implantable medical device according to any one of aspects 1-5, wherein the at least one protrusion is adapted to engage the at least one recess in a direction of a length axis of the protrusion, and wherein the portion of the protrusion adapted to be placed at least partially in the at least one recess comprises at least one surface being angled relative to the length axis of the protrusion.

7. The implantable medical device according to aspect 6, wherein the surface of the protrusion being angled is configured to face a surface of the recess in the second part being angled with an angle different from the angle of the protrusion, and wherein a point on the angled surface of the protrusion is configured to abut a point on the angled surface of the recess.

8. The implantable medical device according to aspect 7, wherein the angled surface of the protrusion abuts the angled surface of the recess over a length being less than half of the length of the angled surface of the protrusion.

9. The implantable medical device according to aspect 8, wherein the angled surface of the protrusion abuts the angled surface of the recess over a length being less than one third of the length of the angled surface of protrusion.

10. The implantable medical device according to aspect 9, wherein the angled surface of the protrusion abuts the angled surface of the recess over a length being less than half of the depth of the recess, measured in a direction coinciding with the direction of the length axis of the protrusion, when the portion of the protrusion is inserted into the recess.

11. The implantable medical device according to any one of aspects 1-10, wherein the portion of the protrusion configured to enter the recess of the second part comprises a tapered portion.

12. The implantable medical device according to aspect 11, wherein the tapered portion is tapered with an angle in the range 20°-150°.

13. The implantable medical device according to any one of aspects 1-12, wherein the recess in at least one of the first and second part is tapered, such that two surfaces on opposite sides of the tapered portion of the protrusion faces two surfaces on opposite sides of the tapered recess, when the tapered portion of the first distance element is inserted into the recess.

14. The implantable medical device according to aspect 13, wherein the tapered recess is tapered with an angle in the range 30°-155°.

15. The implantable medical device according to any one of aspects 13 and 14, wherein the tapered portion of the protrusion is tapered with a first angle and the tapered recess in at least one of the first and second part is tapered with a second angle, and wherein the second angle is larger than the first angle.

16. The implantable medical device according to aspect 15, wherein the second angle is more than 3° larger than the first angle.

17. The implantable medical device according to aspect 16, wherein the second angle is more than 5° larger than the first angle.

18. The implantable medical device according to aspect 17, wherein the second angle is more than 10° larger than the first angle.

19. The implantable medical device according to any one of aspects 6-18, wherein the at least one protrusion has the shape of a pyramid with a polygonal base.

20. The implantable medical device according to any one of aspects 1-19, wherein the first part further comprises at least one protrusion in a second base surface.

21. The implantable medical device according to any one of aspects 1-20, wherein the second part further comprises at least one protrusion in a second base surface.

22. The implantable medical device according to any one of aspects 1-21, wherein the second part further comprises at least one recess in a second base surface.

23. The implantable medical device according to aspect 1, further comprising a third part, and wherein:
- the first part further comprises a recess in a second base surface,
- the second part further comprises a protrusion protruding from a second base surface,
- the third part comprises a protrusion protruding from a first base surface and a recess in a second base surface,
- the protrusion of the first part is configured to be at least partially inserted into the recess of the second part,
- the protrusion of the second part is configured to be at least partially inserted into the recess of the third part, and wherein the first, second and third parts are configured to be assembled for forming at least a portion of a functional implantable medical device, and wherein the recesses and protrusions stabilize the parts relative to each other when assembled.

24. The implantable medical device according to any one of aspects 1-23, wherein the area of the first base surface of the first part is smaller than the area of the first base surface of the second part.

Shape of the Functional Movement Restriction Device

25. The implantable medical device according to any one of the preceding aspects, wherein the functional movement restriction device, or the boundary of the functional movement restriction device, has a shape corresponding to an ellipsoid or a truncated ellipsoid.

26. The implantable medical device according to aspect 25, wherein the functional movement restriction device, or the boundary of the functional movement restriction device, has a shape corresponding to a sphere or a truncated sphere.

27. The implantable medical device according to any one of aspects 1-26, wherein at least a periphery of at least one of the first and second part has a shape corresponding to a cylinder.

28. The implantable medical device according to aspect 27, wherein a combined periphery of the first and second part has a shape corresponding to a cylinder.

29. The implantable medical device according to aspect 28, wherein the periphery of the first part has a shape corresponding to a first cylinder having a first radius, and the periphery of the second part has a shape corresponding to a second cylinder having a second radius, and wherein the first and second radii are different.

30. The implantable medical device according to any one of aspects 1-24 and 27-29, wherein the functional movement restriction device, or the boundary of the functional movement restriction device, comprises a stadium shaped cross-section, or a truncated stadium shaped cross-section.

31. The implantable medical device according to any one of aspects 1-24 and 27-29, wherein the functional movement restriction device, or the boundary of the functional movement restriction device, comprises a bent stadium shaped cross-section, or a truncated bent stadium shaped cross-section.

32. The implantable medical device according to any one of the preceding aspects, wherein the functional movement restriction device is elongated.

33. The implantable medical device according to aspect 32, wherein the functional movement restriction device is elongated such that a longest length is more than 1.5 times a widest width.

34. The implantable medical device according to any one of aspects 32 and 33, wherein the functional movement restriction device comprises a bend, and wherein the functional movement restriction device comprises a bent center axis following the elongation of the functional movement restriction device.

35. The implantable medical device according to aspect 34, wherein a first portion of the functional movement restriction device is configured to be positioned such that a first portion of the bent center axis is parallel to the caudal-cranial axis of the patient, and a second portion of the bent center axis is angled relative to the caudal-cranial axis of the patient, with an angle exceeding 5°.

36. The implantable medical device according to aspect 35, wherein the second portion of the bent center axis is configured to be positioned in the stomach such that it is angled towards the esophagus.

Distance

37. The implantable medical device according to any one of the preceding aspects, wherein the protrusion comprises a first distance element configured to create a space located between the first and second part, wherein the space is configured to allow in-growth of fibrotic tissue between portions of the first and second parts, and wherein the space is confined at least partially by a first surface of the first part and a second surface of the second part and wherein the first and second surfaces are positioned opposite each other when the first and second parts are connected, and wherein:

a line segment of a first straight line is bounded by a first point on the first surface and a second point on the second surface, the line segment of the first straight line is more than 1 mm, a line segment of a second straight line is bounded by a third point on the first surface and a fourth point on the second surface, the line segment of the second straight line is more than 1 mm, the first straight line is parallel to the second straight line, the first and second straight lines intersect a third straight line which also intersects the center of gravity of the functional movement restriction device, and a distance between the first and second straight lines is more than 2 mm for allowing in-growth of fibrotic tissue for aiding in the fixation of the functional movement restriction device to the stomach wall.

38. The implantable medical device according to any one of the preceding aspects, wherein the protrusion comprises a first distance element configured to create a space located between the first and second part, wherein the space is configured to allow in-growth of fibrotic tissue between portions of the first and second parts, and wherein the space forms a recess in the functional implantable medical device, and wherein the recess is more than 1 mm wide and more than 2 mm deep for allowing in-growth of fibrotic tissue for aiding in the fixation of the functional implantable medical device to the stomach wall.

Obesity Treatment

39. The implantable medical device according to any one of aspects 1-38, wherein the medical device is further configured to treat obesity by the movement restriction device being configured to protrude into the stomach and thereby reducing the volume of the cavity of the stomach.

40. The implantable medical device according to aspect 39, wherein the functional movement restriction device has a volume in the range 100 $cm^3$-1000 $cm^3$.

41. The implantable medical device according to aspect 40, wherein the functional movement restriction device has a volume in the range 100 $cm^3$-500 $cm^3$.

42. The implantable medical device according to any one of aspects 39-41, wherein the functional implantable medical device has a length in the range 2.5 cm-15 cm.

43. The implantable medical device according to aspect 42, wherein the functional implantable medical device has a length in the range 5 cm-15 cm.

44. The implantable medical device according to aspect 43, wherein the functional implantable medical device has a length in the range 7 cm-15 cm.

45. The implantable medical device according to aspect 44, wherein the functional implantable medical device has a length in the range 8 cm-15 cm.

46. The implantable medical device according to aspect 45, wherein the functional implantable medical device has a length in the range 8 cm-12 cm.

Additional

47. The implantable medical device according to any one of the preceding aspects, wherein the movement restriction device comprises a surface friction reducing coating covering at least a part of the surface of the movement restriction device, wherein the surface friction reducing coating is configured to reduce the friction between the movement restriction device and the tissue of the stomach wall by which the movement restriction device is at least partially invaginated.

48. The implantable medical device according to any one of the preceding aspects, wherein the movement restriction device comprises a sensor configured to sense at least one of a force and a pressure, for monitoring a pressure or force exerted by the implantable movement restriction device on the stomach wall of the patient.

49. The implantable medical device according to any one of the preceding aspects, wherein the movement restriction device comprises a first portion having a first volume enclosed by material of the implantable movement restriction device and a second portion, different from the first portion, having a second volume enclosed by material of the implantable movement restriction device, wherein the first volume and the second volumes are equally large, the first volume has a higher density than the second volume, and the second volume has a density below 1000 kg/m3.

Aspect Group 449DPC: Reflux Obesity Treatment Distance

1. An implantable medical device for treating obesity, the implantable medical device is configured to be fixated to the stomach wall and protrude into the stomach and thereby reduce the volume of the cavity of the stomach, the implantable medical device comprising:

a first part, a second part, and a first distance element, wherein:

the first and second part are configured to be connected to each other for forming at least a portion of a functional implantable medical device, the first and second part are capable of disconnecting from each other, such that the first and second part individually can pass through the gastro-intestinal tract, and the first distance element is configured to create a space located between the first and second part, wherein the space is configured to allow in-growth of fibrotic tissue between portions of the first and second parts, and wherein the space is confined at least partially by a first surface of the first part and a second surface of the second part and wherein the first and second surfaces are positioned opposite each other when the first and second parts are connected, and wherein:

a line segment of a first straight line is bounded by a first point on the first surface and a second point on the second surface, the line segment of the first straight line is more than 1 mm, a line segment of a second straight line is bounded by a third point on the first surface and a fourth point on the second surface, the line segment of the second straight line is more than 1 mm, the first straight line is parallel to the second straight line, the first and second straight lines intersect a third straight line which also intersects the center of gravity of the functional medical device, and a distance between the first and second straight lines is more than 2 mm for allowing in-growth of fibrotic tissue for aiding in the fixation of the functional implantable medical device to the stomach wall.

2. The implantable medical device according to aspect 1, wherein the functional implantable medical device has a volume in the range 100 $cm^3$-1000 $cm^3$.

3. The implantable medical device according to aspect 2, wherein the functional implantable medical device has a volume in the range 100 $cm^3$-500 $cm^3$.

4. The implantable medical device according to any one of aspects 1-3, wherein the functional implantable medical device has a length in the range 2.5 cm-15 cm.

5. The implantable medical device according to aspect 4, wherein the functional implantable medical device has a length in the range 5 cm-15 cm.

6. The implantable medical device according to aspect 5, wherein the functional implantable medical device has a length in the range 7 cm-15 cm.

7. The implantable medical device according to aspect 6, wherein the functional implantable medical device has a length in the range 8 cm-15 cm.

8. The implantable medical device according to aspect 7, wherein the functional implantable medical device has a length in the range 8 cm-12 cm.

The Distance Element

9. The implantable medical device according to any one of aspects 1-8, wherein the first distance element is integrated in at least one of the first and second part.

10. The implantable medical device according to aspect 9, wherein the first distance element protrudes from a surface of at least one of the first and second part.

11. The implantable medical device according to any one of aspects 1-8, further comprising a first separate distance part comprising the first distance element.

12. The implantable medical device according to aspect 11, wherein at least one of the first and second part further comprises a recess configured to receive a portion of the first distance element.

13. The implantable medical device according to any one of aspects 1-12, wherein the first distance element comprises at least a first and second portion configured to be placed at a distance from each other.

14. The implantable medical device according to any one of aspects 1-13, further comprising at least a third part, and wherein the first, second and third part are configured to be connected to each other for forming at least a portion of the functional implantable medical device.

15. The implantable medical device according to aspect 14, further comprising a second distance element, and wherein the first distance element is configured to create a space between the first and second part and the second distance element is configured to create a space between the first and third part.

16. The implantable medical device according to aspect 15, wherein the first and second distance element are portions of a separate distance part.

17. The implantable medical device according to any one of aspects 1-16, wherein at least one of the first, second and third parts comprises a recess configured to receive a portion of the distance element.

18. The implantable medical device according to any one of the preceding aspects, wherein the space has a volume exceeding 100 mm3.

19. The implantable medical device according to any one of the preceding aspects, wherein the space forms a recess in the implantable medical device, and wherein the recess has a depth exceeding 2 mm and a width exceeding 1 mm.

20. The implantable medical device according to any one of aspects 1-19, wherein the distance element is configured to prevent at least one of:

a. rotation between the first and second part,
b. linear movement between the first and second part in a first direction, and
c. linear movement between the first and second part in a first and second direction.

21. The implantable medical device according to any one of aspects 4-20, wherein the first separate distance part is configured to be placed centrally in the functional implantable medical device.

22. The implantable medical device according to aspect 21, wherein the center of gravity of the first separate distance part substantially coincides with the center of gravity of the functional implantable medical device.

23. The implantable medical device according to any one of aspects 11-22, wherein the first separate distance part comprises at least one rim comprising at least a first and a second surface, and wherein the first surface of the rim is configured to engage a surface of the first part and the second surface of the flange is configured to engage a surface of the second part.

24. The implantable medical device according to aspect 23, wherein the first and second surfaces of the at least one rim are parallel.

25. The implantable medical device according to any one of aspects 2.3-24, wherein the first separate distance part comprises at least two rims, and wherein:

the first rim comprises at least a first and a second surface, and wherein the first surface of the first rim is configured to engage a surface of the first part and the second surface of the first rim is configured to engage a surface of the second part, the second rim comprises at least a first and a second surface, and wherein the first surface of the second rim is configured to engage a surface of the first part and the second surface of the second rim is configured to engage a surface of the third part.

26. The implantable medical device according to aspect 25, wherein the first surfaces of the first rim and the first surface of the second rim are angled relative to each other with an angle in the range 20°-70°.

27. The implantable medical device according to aspect 26, wherein the first surfaces of the first rim and the first surface of the second rim are angled relative to each other with an angle in the range 40°-50°.

28. The implantable medical device according to aspect 26, wherein the first surfaces of the first rim and the first surface of the second rim are perpendicular.

29. The implantable medical device according to any one of aspects 12-28, wherein the first distance element is configured to engage the recess in at least one of the first and second part in a direction of a length axis of the distance element, and wherein the portion of the first distance element configured to enter the recess of the second part comprises at least one surface being angled relative to the length axis of the distance element.

30. The implantable medical device according to aspect 29, wherein the surface of the first distance element being angled is configured to face a surface of the recess in at least one of the first and second part being angled with an angle different from the angle of the first distance element, and wherein a point on the angled surface of the first distance element is configured to abut a point on the angled surface of the recess.

31. The implantable medical device according to aspect 30, wherein the angled surface of the first distance element abuts the angled surface of the recess over a length being less than half of the length of the angled surface of the first distance element.

32. The implantable medical device according to aspect 31, wherein the angled surface of the first distance element abuts the angled surface of the recess over a length being less than one third of the length of the angled surface of the first distance element.

33. The implantable medical device according to aspect 30, wherein the angled surface of the first distance element abuts the angled surface of the recess over a length being less than half of the depth of the recess, measured in a direction coinciding with the direction of the length axis of the first distance element, when the portion of the first distance element is inserted into the recess.

34. The implantable medical device according to any one of aspects 29-33, wherein the portion of the first distance element configured to enter the recess of the second part comprises a tapered portion.

35. The implantable medical device according to aspect 34, wherein the tapered portion is tapered with an angle in the range 20°-100°.

36. The implantable medical device according to any one of aspects 12-35, wherein the recess in at least one of the first and second part is tapered, such that two surfaces on opposite sides of the tapered portion of the first distance element faces two surfaces on opposite sides of the tapered recess, when the tapered portion of the first distance element is inserted into the recess.

37. The implantable medical device according to aspect 34, wherein the tapered recess is tapered with an angle in the range 30°-135°.

38. The implantable medical device according to any one of aspects 36 and 37, wherein the tapered portion of the first distance element is tapered with a first angle and the tapered recess in at least one of the first and second part is tapered with a second angle, and wherein the second angle is larger than the first angle.

39. The implantable medical device according to aspect 38, wherein the second angle is more than 3° larger than the first angle.

40. The implantable medical device according to aspect 39, wherein the second angle is more than 5° larger than the first angle.

41. The implantable medical device according to aspect 40, wherein the second angle is more than 10° larger than the first angle.

42. The implantable medical device according to any one of aspects 34-41, wherein at least one of:

- the tapered portion of the first distance element, and
- the tapered recess in at least one of the first and second part is conical or frustum-conical.

43. The implantable medical device according to any one of aspects 34-41, wherein the tapered portion of the first distance element has the shape of a pyramid with a polygonal base.

44. The implantable medical device according to any one of aspects 12-28, wherein the portion of the first distance element configured to enter the recess of the first or second part comprises at least one surface having a curvature.

45. The implantable medical device according to aspect 44, wherein the surface of the first distance element having a curvature is configured to face a surface of the recess in at least one of the first and second part, and wherein a point on the surface of the first distance element having the curvature is configured to abut a point on the surface of the recess.

46. The implantable medical device according to aspect 45, wherein the surface of the first distance element having a curvature abuts the surface of the recess over a length being less than half of the length of the angled surface of the first distance element, when the first distance element has been positioned in the recess in at least one of the first and second part.

47. The implantable medical device according to aspect 46, wherein the surface of the first distance element having a curvature abuts the surface of the recess over a length being less than one third of the length of the angled surface of the first distance element, when the portion of the first distance element is inserted into the recess.

48. The implantable medical device according to aspect 45, wherein the surface of the first distance element having a curvature abuts the surface of the recess over a length being less than one third of the length of the angled surface of the first distance element, when the portion of the first distance element is inserted into the recess.

49. The implantable medical device according to aspect 45, wherein the surface of the first distance element having a curvature abuts the surface of the recess over a length being less than half of the depth of the recess, measured in a direction coinciding with the direction of the length axis of the first distance element, when the portion of the first distance element is inserted into the recess.

50. The implantable medical device according to any one of aspects 46-49, wherein the portion of the first distance element configured to enter the recess of the second part comprises at least one surface having a first and second curvature extending in perpendicular directions.

51. The implantable medical device according to aspect 50, wherein the portion of the first distance element configured to enter the recess of the second part comprises at least one spherical surface.

52. The implantable medical device according to any one of aspects 46-51, wherein the recess in at least one of the first and second part is tapered, such that two curved surfaces on opposite sides of the portion of the first distance element configured to enter the recess of the first or second part faces two surfaces on opposite sides of the tapered recess, when the portion of the first distance element configured to enter the recess of the first or second part is inserted into the recess.

53. The implantable medical device according to any one of aspects 12-35 and 44-51, wherein the recess in at least one of the first and second part comprises at least one surface having a curvature.

54. The implantable medical device according to aspect 53, wherein the recess in at least one of the first and second part comprises at least one surface having a first and second curvature extending in perpendicular directions.

55. The implantable medical device according to aspect 54, wherein the recess in at least one of the first and second part comprises at least one spherical surface.

56. The implantable medical device according to any one of aspects 44-55, wherein the portion of the first distance element configured to enter the recess of the first or second part comprises at least one surface having a curvature with a first radius and the recess in at least one of the first and second part comprises at least one surface having a curvature with a second radius, and wherein the second radius is longer than the first radius.

57. The implantable medical device according to aspect 56, wherein the portion of the first distance element configured to enter the recess of the first or second part comprises at least one surface having a first and second curvature extending in perpendicular directions, and wherein the recess in at least one of the first and second part comprises at least one surface having a first and second curvature extending in perpendicular directions, and wherein the sum of the radii of the first and second curvatures of the recess in at least one of the first and second part is longer than the sum of the radii of the first and second curvature of the portion of the first distance element configured to enter the recess.

Shapes of the Parts and the Functional Implantable Medical Device

58. The implantable medical device according to any one of the preceding aspects, wherein the functional implantable medical device or the boundary of the functional implantable medical device is elongated.

59. The implantable medical device according to aspect 58, wherein the functional implantable medical device is elongated such that a longest length is more than 1.5 times a widest width.

60. The implantable medical device according to any one of aspects 58 and 59, wherein the functional implantable medical device comprises a bend, and wherein the functional implantable medical device comprises a bent center axis following the elongation of the functional implantable medical device.

61. The implantable medical device according to aspect 60, wherein a first portion of the functional implantable medical device is configured to be positioned such that a first portion of the bent center axis is parallel to the caudal-cranial axis of the patient, and a second portion of the bent center axis is angled relative to the caudal-cranial axis of the patient, with an angle exceeding 5°.

62. The implantable medical device according to aspect 61, wherein the second portion of the bent center axis is configured to be positioned in the stomach such that it is angled towards the esophagus.

63. The implantable medical device according to any one of the preceding aspects, wherein at least one of the first and second part has a shape corresponding to an ellipsoid wedge or a truncated ellipsoid wedge.

64. The implantable medical device according to aspect 63, wherein at least one of the first and second part has a shape corresponding to a spherical wedge or a truncated spherical wedge.

65. The implantable medical device according to any one of aspects 1-62, wherein at least one of the first and second part has a shape corresponding to a portion of an ellipsoid wedge or a portion of a truncated ellipsoid wedge.

66. The implantable medical device according to aspect 65, wherein at least one of the first and second part has a shape corresponding to a hemiellipsoid wedge or a truncated hemiellipsoid wedge.

67. The implantable medical device according to aspect 66, wherein at least one of the first and second part has a shape corresponding to a portion of a spherical wedge or a portion of a truncated spherical wedge.

68. The implantable medical device according to aspect 67, wherein at least one of the first and second part has a shape corresponding to a hemispherical wedge or a truncated hemispherical wedge.

69. The implantable medical device according to any one of aspects 1-62, wherein at least one of the first and second part has a shape corresponding to an ellipsoid segment or a portion of an ellipsoid segment.

70. The implantable medical device according to aspect 69, wherein at least one of the first and second part has a shape corresponding to a spherical segment or a portion of a spherical segment.

71. The implantable medical device according to any one of the preceding aspects, wherein the functional implantable medical device, or the boundary of the functional implantable medical device, has a shape corresponding to an ellipsoid or a truncated ellipsoid.

72. The implantable medical device according to aspect 71, wherein the functional implantable medical device, or the boundary of the functional implantable medical device, has a shape corresponding to a sphere or a truncated sphere.

73. The implantable medical device according to any one of aspects 1-62, wherein at least the periphery of at least one of the first and second part has a shape corresponding to a cylinder.

74. The implantable medical device according to aspect 73, wherein the combined periphery of the first and second part has a shape corresponding to a cylinder.

75. The implantable medical device according to aspect 74, wherein the periphery of the first part has a shape corresponding to a first cylinder having a first radius, and the periphery of the second part has a shape corresponding to a second cylinder having a second radius, and wherein the first and second radii are different.

76. The implantable medical device according to any one of aspects 1-62 and 74-75, wherein the functional implantable medical device, or the boundary of the functional implantable medical device, comprises a stadium shaped cross-section, or a truncated stadium shaped cross-section.

77. The implantable medical device according to any one of aspects 1-62 and 74-75, wherein the functional implantable medical device comprises a bent stadium shaped cross-section, or a truncated bent stadium shaped cross-section.

78. The implantable medical device according to any one of aspects 1-10, 29-41, 51-55 and 58-62, wherein a periphery of the first part has a shape corresponding to a cylinder or an ellipsoid segment, and a periphery of the second part has a shape corresponding to a cylinder or an ellipsoid segment, and wherein the first part comprises at least one protrusion protruding from a first base surface and wherein the second part comprises at least one recess in a first base surface, and wherein the at least one protrusion is adapted to be placed at least partially in the at least one recess.

79. The implantable medical device according to aspect 78, wherein the at least one protrusion is adapted to engage the at least one recess.

80. The implantable medical device according to any one of aspects 78 and 79, wherein the first part further comprises at least one recess in a second base surface.

81. The implantable medical device according to aspect 80, wherein the position of the at least one protrusion coincides with the position of the at least one recess, such that the recess overlaps the protrusion when the first part is viewed in a direction normal to the first base surface.

82. The implantable medical device according to aspect 81, wherein the at least one recess recesses into the at least one protrusion.

83. The implantable medical device according to any one of aspects 78-82, wherein the at least one protrusion has the shape of a pyramid with a polygonal base.

84. The implantable medical device according to any one of aspects 78-83, wherein the first part further comprises at least one protrusion in a second base surface.

85. The implantable medical device according to any one of aspects 78-84, wherein the second part further comprises at least one protrusion in a second base surface.

86. The implantable medical device according to any one of aspects 78-85, wherein the second part further comprises at least one recess in a second base surface.

87. The implantable medical device according to aspect 78, further comprising a third part, and wherein:

the first part further comprises a recess in a second base surface, the second part further comprises a protrusion protruding from a second base surface, the third part comprises a protrusion protruding from a first base surface and a recess in a second base surface, the protrusion of the first part is configured to be at least partially inserted into the recess of the second part, the protrusion of the second part is configured to be at least partially inserted into the recess of the third part, and wherein the first, second and third parts are configured to be assembled for forming at least a portion of a functional implantable medical device, and wherein the recesses and protrusions stabilize the parts relative to each other when assembled.

88. The implantable medical device according to any one of aspects 78-87, wherein the area of the first base surface of the first part is smaller than the area of the first base surface of the second part.

89. The implantable medical device according to any one of aspects 78-88, wherein the at least one protrusion protruding from the first base surface of the first part comprises the distance element.

Additional

90. The implantable medical device according to any one of the preceding aspects, wherein the implantable medical device comprises a surface friction reducing coating covering at least a part of the surface of the implantable medical device, wherein the surface friction reducing coating is configured to reduce the friction between the implantable medical device and the tissue of the stomach wall by which the implantable medical device is at least partially invaginated.

91. The implantable medical device according to any one of the preceding aspects, wherein the implantable medical device comprises a sensor configured to sense at least one of a force and a pressure, for monitoring a pressure or force exerted by the implantable medical device on the stomach wall of the patient.

92. The implantable medical device according to any one of the preceding aspects, wherein the implantable medical device comprises a first portion having a first volume enclosed by material of the implantable medical device and a second portion, different from the first portion, having a second volume enclosed by material of the implantable medical device, wherein the first volume and the second volumes are equally large, the first volume has a higher density than the second volume, and the second volume has a density below 1000 kg/m3.

Aspect Group 449EPC: Reflux Method Lateral Sutures

1. A surgical method of treating reflux disease comprising the steps of:

a. dissecting the fundus at least partially down on the posterior side thereof; in the approximate direction towards bursa Omentalis, as well as away from the spleen, b. dissecting the esophagus such that the esophagus is disconnected from the surrounding tissue at least 3 cm in a cranial direction from the angle of his, c. connecting the fundus to the esophagus by:

i. placing at least two posterior single sutures in a posterior suture line or use a continuous suture line, connecting the fundus to the esophagus, on the sinister-posterior side of the esophagus, and ii. placing at least two anterior sutures, in a anterior suture line or use a continuous suture line connecting the fundus to the esophagus, on the sinister-anterior side of the esophagus, and d. placing an implantable movement restriction device between the angle of His and the diaphragm, such that the lower esophageal sphincter is prevented from sliding through the esophageal hiatus.

Dissecting the Fundus

2. The surgical method according to aspect 1, wherein the step of dissecting the fundus at least partially on the posterior side thereof comprises at least partially freeing the fundus from at least one of the Gastrophrenic ligament and the Gastrosplenic ligament.

3. The surgical method according to any one of the preceding aspects, wherein the step of dissecting the fundus at least partially on the posterior side thereof comprises dissecting the fundus at least 0.5 cm posterior to a coronal plane intersecting a most cranial point of the fundus.

4. The surgical method according to any one of the preceding aspects, wherein the step of dissecting the fundus at least partially on the posterior side thereof comprises dissecting the fundus at least 1 cm posterior to a coronal plane intersecting a most cranial point of the fundus.

5. The surgical method according to any one of the preceding aspects, wherein the step of dissecting the fundus at least partially on the posterior side thereof comprises dissecting the fundus at least 0.5 cm posterior to the most anterior fixation point of the Gastrophrenic ligament on the fundus.

6. The surgical method according to any one of the preceding aspects, wherein the step of dissecting the fundus at least partially on the posterior side thereof comprises dissecting the fundus at least 1 cm posterior to the most anterior fixation point of the Gastrophrenic ligament on the fundus.

7. The surgical method according to any one of the preceding aspects, wherein the step of dissecting the fundus at least partially on the posterior side thereof comprises dissecting the fundus at least 0.5 cm posterior to the extension of the greater curvature of the stomach in the region of the fundus.

8. The surgical method according to any one of the preceding aspects, wherein the step of dissecting the fundus at least partially on the posterior side thereof comprises dissecting the fundus at least 1 cm posterior to the extension of the greater curvature of the stomach in the region of the fundus.

9. The surgical method according to any one of the preceding aspects, wherein the step of dissecting the fundus further comprises to dissect the gastric brevis/short gastrics and ligating at least one of them.

10. The surgical method according to any one of the preceding aspects, wherein the step of dissecting the fundus further comprises to dissect the gastric brevis/short gastrics and ligating at least two of them.

11. The surgical method according to any one of the preceding aspects, wherein the step of dissecting the fundus further comprises to dissect the gastric brevis/short gastrics and ligating at least three of them.

Dissecting the Esophagus

12. The surgical method according to any one of the preceding aspects, wherein the step of dissecting the esophagus comprises dissecting the esophagus such that the esophagus is disconnected from the surrounding tissue at least 4 cm in a cranial direction from the angle of his, preferably at least 5 cm in a cranial direction from the angle of his and most preferably at least 6 cm in a cranial direction from the angle of his.

13. The surgical method according to any one of the preceding aspects, wherein the step of dissecting the esophagus such that the esophagus is disconnected from the surrounding tissue comprises dissecting the esophagus into mediastinum.

14. The surgical method according to aspect 12-13, wherein the step of dissecting the esophagus into mediastinum comprises dissecting the esophagus into mediastinum such that the esophagus is disconnected from the surrounding tissue at least 1 cm in a cranial direction from the distal edge of the esophageal hiatus, preferably at least 2 cm in a cranial direction from the distal edge of the esophageal hiatus and most preferably at least 3 cm in a cranial direction from the distal edge of the esophageal hiatus.

15. The surgical method according to any one of the aspects presented herein, wherein the step of dissecting the esophagus into mediastinum comprises dissecting the esophagus into mediastinum such that the esophagus is disconnected from the surrounding tissue providing at least 4 cm of abdominal esophagus in a cranial direction from the distal edge of the repaired esophageal hiatus, preferably at least 5 cm of abdominal esophagus and most preferably at least 6 cm of abdominal esophagus from the distal edge of the repaired esophageal hiatus.

16. The surgical method according to any one of the aspects presented herein, wherein the step of dissecting the esophagus such that the esophagus is disconnected from the surrounding tissue comprises identifying the anterior and posterior nervus vagus trunk to avoid risk for nerve damage.

Plication

17. The surgical method according to any one of the preceding aspects, wherein at least one of:

the step of placing at least two posterior sutures, connecting the fundus to the esophagus, on the sinister-posterior side of the esophagus comprises placing at least one continuous suture connecting the fundus to the esophagus, on the sinister-posterior side of the esophagus, and the step of placing at least two anterior sutures, connecting the fundus to the esophagus, on the sinister-anterior side of the esophagus comprises placing at least one continuous suture connecting the fundus to the esophagus, on the sinister-anterior side of the esophagus.

18. The surgical method according to any one of the aspects presented herein, wherein at least one of starting and ending of the continuous sutures is performed in the serosa of the stomach wall for securing the sutures to the serosa of the stomach wall.

19. The surgical method according to any one of the aspects presented herein, wherein both of the starting and ending of the continuous sutures is performed in the serosa of the stomach wall for securing the sutures.

20.

21. The surgical method according to any one of the preceding aspects, wherein at least one of:

the step of placing at least two posterior sutures, connecting the fundus to the esophagus, on the sinister-posterior side of the esophagus comprises placing at least two lateral sutures substantially along a cranial-caudal axis, on the sinister-posterior side of the esophagus, and the step of placing at least two anterior sutures, connecting the fundus to the esophagus, on the sinister-anterior side of the esophagus comprises placing at least two lateral sutures substantially along a cranial-caudal axis, on the sinister-anterior side of the esophagus.

22. The surgical method according to any one of the preceding aspects, wherein at least one of:

the step of placing at least two posterior sutures, connecting the fundus to the esophagus, on the sinister-posterior side of the esophagus, comprises placing the at least two posterior sutures or staplers at least 0.5 cm posterior to a coronal plane intersecting a most cranial point of the fundus, and the step of placing at least two anterior sutures, connecting the fundus to the esophagus, on the sinister-anterior side of the esophagus, comprises placing the at least two anterior sutures or staplers at least 0.5 cm anterior from the coronal plane intersecting the most cranial point of the fundus.

23. The surgical method according to any one of the preceding aspects, wherein at least one of:

the step of placing at least two posterior sutures, connecting the fundus to the esophagus, on the sinister-posterior side of the esophagus comprises placing the most caudal suture or stapler at least 0.5 cm from the angle of His, and the step of placing at least two anterior sutures, connecting the fundus to the esophagus, on the sinister-anterior side of the esophagus comprises placing the most caudal suture or stapler at least 0.5 cm from the angle of His.

24. The surgical method according to any one of the preceding aspects, wherein at least one of:

the step of placing at least two posterior sutures, connecting the fundus to the esophagus, on the sinister-posterior side of the esophagus comprises placing the most caudal suture, and the step of placing at least two anterior sutures, connecting the fundus to the esophagus, on the sinister-anterior side of the esophagus comprises placing the most caudal suture, comprising placing at least one of the most caudal suture in the region of the angle of His.

25. The surgical method according to any one of the preceding aspects, wherein at least one of:

the step of placing at least two posterior sutures, connecting the fundus to the esophagus, on the sinister-posterior side of the esophagus comprises placing the most caudal suture, and the step of placing at least two anterior sutures, connecting the fundus to the esophagus, on the sinister-anterior side of the esophagus comprises placing the most caudal suture, comprising placing at least one of the two most caudal sutures in the region at least 1.5 cm above the angle of His.

26. The surgical method according to any one of the aspects presented herein, wherein at least one of:

the step of placing at least two posterior sutures, connecting the fundus to the esophagus, on the sinister-posterior side of the esophagus comprises placing the most caudal suture at least 1.5 cm from the angle of His, and the step of placing at least two anterior sutures or staplers, connecting the fundus to the esophagus, on the sinister-anterior side of the esophagus comprises placing the most caudal suture or stapler at least 1.5 cm from the angle of His.

27. The surgical method according to any one of the aspects presented herein, comprising one of the steps of:

placing the most caudal suture or stapler of the at least two posterior sutures or staplers, connecting the fundus to the esophagus, on the sinister-posterior side of the esophagus at least 0.5 cm from the angle of His and placing the most caudal suture or stapler of the at least two anterior sutures or staplers, connecting the fundus to the esophagus, on the sinister-anterior side of the esophagus at least 1.5 cm from the angle of His, and placing the most caudal suture or stapler of the at least two posterior sutures or staplers, connecting the fundus to the esophagus, on the sinister-posterior side of the esophagus at least 1.5 cm from the angle of His and placing the most caudal suture or stapler of the at least two anterior sutures or staplers, connecting the fundus to the esophagus, on the sinister-anterior side of the esophagus at least 0.5 cm from the angle of His.

28. The surgical method according to any one of the preceding aspects, wherein the step of connecting the fundus to the esophagus further comprises placing at least one central suture on a cranial-caudal axis extending between the at least two posterior sutures or continuous suture line and the at least two anterior sutures or continuous suture line, placing at least one suture most cranial and preferable a line of sutures in between the posterior and anterior suture line, placing with a distance of one cm of esophagus circumference to both the anterior and posterior suture lines.

29. The surgical method according to any one of the preceding aspects, wherein the step of connecting the fundus to the esophagus further comprises placing at least one central suture on a cranial-caudal axis extending between the at least two posterior sutures or continuous suture line and the at least two anterior sutures or continuous suture line, placing a third continuous suture line in between the posterior and anterior suture line, placing with a targeted distance of one cm of esophagus circumference to both the anterior and posterior suture lines.

30. The surgical method according to aspects 17-29, wherein the step of placing at least one central in between suture line on a cranial-caudal axis comprises placing this central suture line disconnected from the anterior suture line and from the posterior suture line, for maintaining the possibility of radial expansion the esophagus for limiting the disk of dysphagia.

31. The surgical method according to any one of aspects 1-31 or any aspect presented herein, wherein at least one of the steps of: placing at least two posterior sutures or a continuous suture, connecting the fundus to the esophagus, on the sinister-posterior side of the esophagus, and placing at least two anterior sutures or a continuous suture, connecting the fundus to the esophagus, on the sinister-anterior side of the esophagus, comprises using an at least partially barbed suture.

Invagination

32. The surgical method according to any one of the preceding aspects or any aspect presented herein, wherein the step of stabilising the implantable movement restriction device in relation to the fundus comprises placing a continuous multibite/purse-string type roof suture in the region of the greater curvature of the stomach, in the region of the fundus, such that the stomach tissue can be contracted and formed to a hat over the implantable movement restriction device when implanted by pulling the ends of the purse-string sutures.

33. The surgical method according to aspect 32, wherein the step of placing roof sutures comprises placing at least one of the continuous purse-string roof sutures at least 1 cm preferable 2 cm behind the greater curvature of the stomach, in the caudal region of the fundus.

34. The surgical method according to any one of aspects 32 and 33, wherein the step of placing the continuous purse-string roof suture comprises placing the continuous purse-string roof suture using an at least partially un-barbed suture, leaving a loose suture loop.

35. The surgical method according to any one of aspects 32-34, wherein the step of placing the continuous purse-string roof sutures comprises ending the continuous purse-string roof sutures at least 1 cm away from the esophagus to stomach anterior suture line.

36. The surgical method according to any one of aspects 32-35, wherein the step of placing the continuous purse-string roof sutures comprises placing the continuous purse-string roof suture using a suture ending with a loop and lacking barbes close to the loop, such that the suture can be drawn through the loop for contracting the stomach tissue, but in a loose loop manner.

37. The surgical method according to any one of aspects 32-36, wherein the step of placing the continuous purse-string roof suture comprises using a barbed free suture that preferable only partly should be closed or loosely closed for contracting the stomach tissue, forming a hat over the implantable movement restriction device when implanted, but in a loose manner.

38. The surgical method according to any one of aspects 32-37, wherein the step of fixating the implantable movement restriction device to the fundus comprises inserting the implantable movement restriction device into the abdomen of the patient.

39. The surgical method according to aspect 38, wherein the step of inserting the implantable movement restriction device into the abdomen of the patient comprises inserting the implantable movement restriction device into the abdomen of the patient using an elongated insertion instrument having an elongated abdominal portion.

40. The surgical method according to any one of aspects 38-39 or anyone aspect presented herein, wherein the step of fixating the implantable movement restriction device to the fundus comprises pushing the implantable movement restriction device into the fundus in a cranial direction close to esophagus using the instrument having the elongated abdominal portion.

41. The surgical method according to aspect 39, wherein the step of pushing the implantable movement restriction device into the fundus in a cranial direction using the instrument having the elongated abdominal portion comprises pushing the implantable movement restriction device using the elongated insertion instrument such that a portion of the implantable movement restriction device ends up dorsal to the roof sutures presenting a hat to the movement restriction device.

42. The surgical method according to any one of the preceding aspects or anyone aspect presented herein, wherein the step of stabilising the implantable movement restriction device in relation to the fundus comprises placing a continuous purse-string base or floor suture in the region below the movement restriction device or proximal on fundus/proximal on the elongated insertion instrument holding the implantable movement restriction device to stabilize its position.

43. The surgical method according to aspect 42, wherein the step of placing the continuous purse-string floor suture in the region of the caudal end of the implantable movement restriction device comprising placing at least two of the continuous purse-string floor suture bites following an arc, preferable patient left to right at least from the equator to equator in an arc around the movement restriction device to stabilize its position.

44. The surgical method according to aspect 43, wherein the step of placing continuous purse-string base or floor suture following an arc comprises placing continuous purse-string floor sutures following an arc below the elongated abdominal portion of the instrument holding the implantable movement restriction device.

45. The surgical method according to aspect 43-44, wherein the step of placing continuous purse-string base sutures in the region of the caudal end of the implantable movement restriction device comprising placing the continuous purse-string base suture such that the continuous purse-string base suture bites forms a closed curve, closed loop to bring stomach from left and right of the elongated insertion instrument to contact each other above the instrument.
46. The surgical method according to any one of aspects 41-45, wherein the step of stabilising the implantable movement restriction device in relation to the fundus comprises placing at least one suture from stomach wall to stomach wall around the movement restriction device and around the elongated insertion instrument to close the suture loop above the elongated abdominal portion of the instrument holding the implantable movement restriction device.
47.
48. The surgical method according to any one of the preceding aspects or anyone aspect presented herein, wherein the step of stabilising the implantable movement restriction device to the fundus comprises releasing the elongated abdominal portion of the instrument from the implantable movement restriction device.
49. The surgical method according to aspect 48, further comprising placing at least one suture to close the opening in the stomach wall in the region from which the elongated abdominal portion of the instrument was removed, for closing the hole through which the elongated abdominal portion of the instrument passed.
50. The surgical method according to any one of aspects 42-49, wherein the continuous purse-string base suture comprises un-barbed suture for enabling the contraction and relaxation of the stomach wall during the surgical procedure.
51. The surgical method according to any one of aspects 32-50, wherein the step of stabilising the implantable movement restriction device to the fundus comprises contracting a first portion of the stomach wall by pulling on the purse-string roof sutures and contracting a second portion of the stomach wall by pulling on the purse-string base sutures, and wherein the implantable movement restriction device is held on the stomach wall between the first contracted portion and the second contracted portion.
52. The surgical method according to any one of the preceding aspects or anyone aspect presented herein, wherein the step of fixating the implantable movement restriction device to the fundus comprising invaginating the remaining not yet covered implantable movement restriction device in the fundus wall from the outside thereof suturing caudal to cranial with single sutures or a continuous suture.
53. The surgical method according to aspect 51-52, wherein the step of invaginating the implantable movement restriction device in the fundus wall from the outside thereof comprises placing at least two more sutures from stomach wall to stomach wall for connecting stomach wall to stomach wall around the implantable movement restriction device and thereby enclose the implantable movement restriction device in a pouch formed by the stomach wall of the fundus.

Aspect Group 449FPC: Reflux Method Lateral Sutures 2

1. A surgical method of treating reflux disease comprising the steps of:
   a. connecting the fundus to the esophagus by:
      i. placing at least two posterior lateral sutures or at least one continuous suture line substantially along a cranial-caudal axis on the sinister-posterior side of the esophagus, connecting the fundus to the esophagus on the sinister-posterior side of the esophagus,
      ii. placing at least two more anterior lateral sutures or at least one continuous suture line substantially along a cranial-caudal axis either more anterior on the sinister-posterior side of the esophagus or on the sinister-anterior side of esophagus, connecting the fundus to the esophagus on the sinister-posterior side of the esophagus, and
   b. stabilizing an implantable movement restriction device in relation to the fundus, such that the lower esophageal sphincter is prevented from sliding through the esophageal hiatus.
2. The surgical method according to aspect 1, wherein at least one of:
   the step of placing at least one continuous suture line connecting the fundus to the esophagus, on the sinister-posterior side of the esophagus, and
   the step of placing at least one continuous suture line connecting the fundus to the esophagus, either more anterior on the sinister-posterior side of the esophagus or on the sinister-anterior side of the esophagus comprising using at least one barbed suture line.
3. The surgical method according to aspect 2, wherein at least one of starting and ending of the continuous sutures is performed in the serosa of the stomach wall for securing the sutures to the serosa of the stomach wall.
4. The surgical method according to any one of the aspects presented herein, wherein both of the starting and ending of the continuous sutures is performed in the serosa of the stomach wall for securing the sutures.
5. The surgical method according to any one of the preceding aspects, wherein at least one of:
   the step of placing at least two posterior sutures, connecting the fundus to the esophagus, on the sinister-posterior side of the esophagus comprises placing at least two lateral sutures substantially along a cranial-caudal axis, on the sinister-posterior side of the esophagus, and
   the step of placing at least two anterior sutures, connecting the fundus to the esophagus, on the sinister-anterior side of the esophagus comprises placing at least two lateral sutures substantially along a cranial-caudal axis, on the sinister-anterior side of the esophagus.
6. The surgical method according to any one of the preceding aspects, wherein at least one of:
   the step of placing at least two posterior sutures, connecting the fundus to the esophagus, on the sinister-posterior side of the esophagus, comprises placing the at least two posterior sutures at least 0.5 cm posterior to a coronal plane intersecting a most cranial point of the fundus, and
   the step of placing at least two anterior sutures, connecting the fundus to the esophagus, on the sinister-anterior side of the esophagus, comprises placing the at least two anterior sutures at least 0.5 cm anterior from the coronal plane intersecting the most cranial point of the fundus.
7. The surgical method according to any one of the preceding aspects, wherein at least one of:
   the step of placing at least two posterior sutures, connecting the fundus to the esophagus, on the sinister-posterior side of the esophagus comprises placing the most caudal suture at least 0.5 cm from the angle of His, and
   the step of placing at least two anterior sutures, connecting the fundus to the esophagus, on the sinister-anterior side of the esophagus comprises placing the most caudal suture at least 0.5 cm from the angle of His.

8. The surgical method according to any one of the preceding aspects, wherein at least one of:

the step of placing at least two posterior sutures, connecting the fundus to the esophagus, on the sinister-posterior side of the esophagus comprises placing the most caudal suture, and the step of placing at least two anterior sutures, connecting the fundus to the esophagus, on the sinister-anterior side of the esophagus comprises placing the most caudal suture, comprising placing at least one of the most caudal suture in the region of the angle of His.

9. The surgical method according to any one of the preceding aspects, wherein at least one of:

the step of placing at least two posterior sutures, connecting the fundus to the esophagus, on the sinister-posterior side of the esophagus comprises placing the most caudal suture, and the step of placing at least two anterior sutures, connecting the fundus to the esophagus, on the sinister-anterior side of the esophagus comprises placing the most caudal suture, comprising placing at least one of the two most caudal sutures in the region at least 1.5 cm above the angle of His.

10. The surgical method according to any one of the preceding aspects, wherein at least one of:

the step of placing at least two posterior sutures, connecting the fundus to the esophagus, on the sinister-posterior side of the esophagus comprises placing the most caudal suture or stapler at least 1.5 cm from the angle of His, and the step of placing at least two anterior sutures, connecting the fundus to the esophagus, on the sinister-anterior side of the esophagus comprises placing the most caudal suture or stapler at least 1.5 cm from the angle of His.

11. The surgical method according to any one of the preceding aspects or any one aspect presented herein, comprising one of the steps of:

placing the most caudal suture or stapler of the at least two posterior sutures or staplers, connecting the fundus to the esophagus, on the sinister-posterior side of the esophagus at least 0.5 cm from the angle of His and placing the most caudal suture or stapler of the at least two anterior sutures or staplers, connecting the fundus to the esophagus, on the sinister-anterior side of the esophagus at least 1.5 cm from the angle of His, and placing the most caudal suture or stapler of the at least two posterior sutures or staplers, connecting the fundus to the esophagus, on the sinister-posterior side of the esophagus at least 1.5 cm from the angle of His and placing the most caudal suture or stapler of the at least two anterior sutures or staplers, connecting the fundus to the esophagus, on the sinister-anterior side of the esophagus at least 0.5 cm from the angle of His.

12. The surgical method according to any one of the preceding aspects, wherein the step of connecting the fundus to the esophagus further comprises placing at least one central suture on a cranial-caudal axis extending between the at least two posterior sutures or continuous suture line and the at least two anterior sutures or continuous suture line, placing at least one suture most cranial and preferable a line of sutures in between the posterior and anterior suture lines, placing with a distance of one cm of esophagus circumference to both the anterior and posterior suture lines.

13. The surgical method according to any one of the preceding aspects, wherein the step of connecting the fundus to the esophagus further comprises placing at least one central suture on a cranial-caudal axis extending between the at least two posterior sutures or one continuous suture line and the at least two anterior sutures or one continuous suture line, placing at least one suture most cranial and preferable a line of sutures in between the posterior and anterior suture line, placing with a targeted distance of one cm of esophagus circumference to both the anterior and posterior suture lines.

14. The surgical method according to aspect 9-13, wherein the step of placing at least one central suture on a cranial-caudal axis comprises placing at least one central suture in between the anterior and posterior suture lines and being disconnected therefrom, for maintaining the possibility of radial expansion the esophagus for limiting the disk of dysphagia.

15. The surgical method according to any one of aspects 1-10 or any aspect presented herein, wherein at least one of the steps of: placing the at least two posterior sutures or continuous suture, connecting the fundus to the esophagus, on the sinister-posterior side of the esophagus, and placing the at least two anterior sutures or continuous suture, connecting the fundus to the esophagus, on the sinister-anterior side of the esophagus, comprises using at least one, at least partially barbed suture.

Aspect Group 449GPC: Reflux Method Posterior Dissection

1. A surgical method of treating reflux disease comprising the steps of:

dissecting the fundus at least partially caudal on the posterior side thereof, in the approximate direction of bursa Omentalis, as well as away from the spleen area, wherein the step of dissecting the fundus at least partially on the posterior side thereof comprises at least partially freeing the fundus from at least one of the Gastrophrenic ligament and the Gastrosplenic ligament, and stabilizing an implantable movement restriction device in relation to the fundus, such that the lower esophageal sphincter is prevented from moving towards or through the esophageal hiatus.

2. The surgical method according to aspect 1 or any aspect presented herein, wherein the step of dissecting the fundus at least partially on the posterior side thereof comprises dissecting the fundus at least 0.5 cm posterior to a coronal plane intersecting a most cranial point of the fundus.

3. The surgical method according to aspect 2 or any aspect presented herein, wherein the step of dissecting the fundus at least partially on the posterior side thereof comprises dissecting the fundus at least 1 cm posterior to a coronal plane intersecting a most cranial point of the fundus.

4. The surgical method according to any one of the preceding aspects or any aspect presented herein, wherein the step of dissecting the fundus at least partially on the posterior side thereof comprises dissecting the fundus at least 0.5 cm posterior to the most anterior fixation point of the Gastrophrenic ligament on the fundus.

5. The surgical method according to any one of the preceding aspects or any aspect presented herein, wherein the step of dissecting the fundus at least partially on the posterior side thereof comprises dissecting the fundus at least 1 cm posterior to the most anterior fixation point of the Gastrophrenic ligament on the fundus.

6. The surgical method according to any one of the preceding aspects or any aspect presented herein, wherein the step of dissecting the fundus at least partially on the posterior side thereof comprises dissecting the fundus at least 0.5 cm posterior to extension of the greater curvature of the stomach in the region of the fundus.

7. The surgical method according to any one of the preceding aspects or any aspect presented herein, wherein the step of dissecting the fundus at least partially on the posterior side thereof comprises dissecting the fundus at least 1 cm posterior to extension of the greater curvature of the stomach in the region of the fundus.

8. The surgical method according to any one of the preceding aspects or any aspect presented herein, wherein the step of dissecting the fundus further comprises to dissect the gastric brevis/short gastrics and ligating at least one of them.

9. The surgical method according to any one of the preceding aspects or any aspect presented herein, wherein the step of dissecting the fundus further comprises to dissect the gastric brevis/short gastrics and ligating at least two of them.

10. The surgical method according to any one of the preceding aspects or any aspect presented herein, wherein the step of dissecting the fundus further comprises to dissect the gastric brevis/short gastrics and ligating at least three of them.

11. The surgical method according to any one of the preceding aspects or any aspect presented herein, wherein the step of stabilising the implantable movement restriction device in relation to the fundus comprises placing a continuous purse-string roof suture in the region of the greater curvature of the stomach, in the region of the fundus, such that the stomach tissue can be contracted and forming a hat over the implantable movement restriction device when implanted by pulling the ends of the purse-string sutures.

12. The surgical method according to aspect 11 or any aspect presented herein, wherein the step of placing roof sutures comprises placing one continuous purse-string roof suture at least 1 cm preferable 2 cm behind the sail of the greater curvature of the stomach, in the region of the fundus.

13. The surgical method according to any one of aspects 11 and 12, wherein the step of placing the continuous purse-string roof suture comprises placing the continuous purse-string roof suture using an at least partially un-barbed suture, leaving a loose suture loop.

14. The surgical method according to any one of aspects 11-13, wherein the step of placing the continuous purse-string roof sutures comprises ending the continuous purse-string roof sutures at least 1 cm away from the esophagus to stomach anterior suture line.

15. The surgical method according to any one of aspects 11-14, w or any aspect presented herein the step of placing the continuous purse-string roof sutures comprises placing the continuous purse-string roof sutures using a suture ending with a loop, such that the needle of the suture can be drawn through the loop for contracting the stomach tissue in a loose loop manner, without fully close the suture loop due to lack of barbes close to the loop for the needle entrance.

16. The surgical method according to any one of aspects 1-15 or any aspect presented herein, wherein the step of placing the continuous purse-string roof suture comprises using a barbed free suture that preferable only partly should be closed or loosely closed for contracting the stomach tissue, forming a hat over the implantable movement restriction device when implanted, but in a loose manner.

17. The surgical method according to any one of aspects 11-16, wherein the step of stabilising the implantable movement restriction device to the fundus comprises inserting the implantable movement restriction device into the abdomen of the patient.

18. The surgical method according to aspect 17, wherein the step of inserting the implantable movement restriction device into the abdomen of the patient comprises inserting the implantable movement restriction device into the abdomen of the patient using an elongated insertion instrument having an elongated abdominal portion.

19. The surgical method according to any one of aspects 17-18, wherein the step of stabilising the implantable movement restriction device to the fundus comprises pushing the implantable movement restriction device into the fundus in a cranial direction using the instrument having the elongated abdominal portion.

20. The surgical method according to aspect 19 or any aspect presented herein, wherein the step of pushing the implantable movement restriction device into the fundus in a dorsal direction using the instrument having the elongated abdominal portion comprises pushing the elongated insertion instrument such that a portion of the movement restriction device ends up dorsal to the roof sutures presenting a hat to the movement restriction device.

21. The surgical method according to any one of the preceding aspects or any aspect presented herein, wherein the step of stabilising the implantable movement restriction device in relation to the fundus comprises placing a continuous purse-string base or floor suture in the region below of the caudal end of the implantable movement restriction device being proximal on fundus and proximal on the elongated insertion instrument, holding the implantable movement restriction device to stabilize its position.

22. The surgical method according to aspect 21, wherein the step of placing the continuous purse-string base or floor suture in the region of the caudal end of the implantable movement restriction device comprising placing at least two of the continuous purse-string floor suture bites following an arc.

23. The surgical method according to aspect 22, wherein the step of placing the continuous purse-string base suture following an arc around the movement restriction device with bites as a purse string also below the elongated abdominal portion of the instrument holding the implantable movement restriction device.

24. The surgical method according to aspect 22-23, wherein the step of placing continuous purse-string base sutures in the region of the caudal end of the implantable movement restriction device comprising placing the continuous purse-string base sutures such that the continuous purse-string base sutures forms a closed loop by bringing stomach from left and right of the elongated insertion instrument to contact each other above the instrument when closing the suture loop.

25. The surgical method according to any one of aspects 16-20, wherein the step of stabilising the implantable movement restriction device in relation to the fundus comprises placing at least one suture from stomach wall to stomach wall around the movement restriction device and around the elongated insertion instrument to close the suture loop above the elongated abdominal portion of the instrument holding the implantable movement restriction device.

26. The surgical method according to any one of the preceding aspects or anyone aspect presented herein, wherein the step of stabilising the implantable movement restriction device to the fundus comprises releasing the elongated abdominal portion of the instrument from the implantable movement restriction device.

27. The surgical method according to aspect 26, further comprising placing at least one suture to close the opening in the stomach wall in the region from which the elongated abdominal portion of the instrument was removed, for closing the hole through which the elongated abdominal portion of the instrument passed.

28. The surgical method according to any one of aspects 20-27 or any aspect presented herein, wherein the continuous purse-string base sutures comprises an un-barbed suture for enabling the contraction and relaxation of the stomach wall during the surgical procedure.

29. The surgical method according to any one of aspects 1-28 or any aspect presented herein, wherein the step of stabilising the implantable movement restriction device to the fundus comprises contracting a first portion of the stomach wall by pulling on the purse-string roof sutures and contracting a second portion of the stomach wall by pulling on the purse-string base sutures, and wherein the implantable movement restriction device is held on the stomach wall between the first contracted portion and the second contracted portion.

30. The surgical method according to any one of the preceding aspects or any aspect presented herein, wherein the step of stabilising the remaining not yet covered part of the implantable movement restriction device to the fundus comprising invaginating the implantable movement restriction device in the fundus wall from the outside thereof suturing caudal to cranial with using the at least two single sutures or continuous suture.

31. The surgical method according to aspect 30, wherein the step of invaginating the implantable movement restriction device in the fundus wall from the outside thereof comprises placing at least two sutures from stomach wall to stomach wall for connecting stomach wall to stomach wall around the implantable movement restriction device and thereby enclose the implantable movement restriction device in a pouch formed by the stomach wall of the fundus.

Aspect Group 449HPC: Reflux Method Mediastinum Dissection

2. A surgical method of treating reflux disease comprising the steps of:
   - dissecting the esophagus such that the esophagus is disconnected from the surrounding tissue at least 3 cm in a cranial direction from the angle of his,
   - stabilizing an implantable movement restriction device to the fundus, such that the lower esophageal sphincter is prevented from moving towards the diaphragm and/or sliding through the esophageal hiatus.

3. The surgical method according to any one of the preceding aspects, wherein the step of dissecting the esophagus comprises dissecting the esophagus such that the esophagus is disconnected from the surrounding tissue at least 4 cm in a cranial direction from the angle of his, preferably at least 5 cm in a cranial direction from the angle of his and most preferably at least 6 cm in a cranial direction from the angle of his.

4. The surgical method according to any one of the preceding aspects, wherein the step of dissecting the esophagus such that the esophagus is disconnected from the surrounding tissue comprises dissecting the esophagus into mediastinum.

5. The surgical method according to aspect 3, wherein the step of dissecting the esophagus into mediastinum comprises dissecting the esophagus into mediastinum such that the esophagus is disconnected from the surrounding tissue at least 3 cm in a cranial direction from the distal edge of the esophageal hiatus, preferably at least 4 cm in a cranial direction from the distal edge of the esophageal hiatus and most preferably at least 5 cm in a cranial direction from the distal edge of the esophageal hiatus.

6. The surgical method according to any one of the aspects presented herein, wherein the step of dissecting the esophagus into mediastinum comprises dissecting the esophagus into mediastinum such that the esophagus is disconnected from the surrounding tissue providing at least 4 cm of abdominal esophagus in a cranial direction from the distal edge of the repaired esophageal hiatus, preferably at least 5 cm of abdominal esophagus and most preferably at least 6 cm of abdominal esophagus from the distal edge of the repaired esophageal hiatus.

7. The surgical method according to any one of the aspects presented herein, wherein the step of dissecting the esophagus such that the esophagus is disconnected from the surrounding tissue comprises identifying the anterior and posterior nervus vagus trunc to avoid risk for nerve damage.

8. The surgical method according to any one of the preceding aspects, wherein the step of dissecting the esophagus comprises freeing the esophagus from the crus muscles.

Plication

9. The surgical method according to any one of the preceding aspects, further comprising connecting the fundus to the esophagus by:
   - placing at least two posterior sutures or at least one continuous suture line, connecting the fundus to the esophagus, on the sinister-posterior side of the esophagus, and
   - placing at least two anterior sutures or at least one continuous suture line, connecting the fundus to the esophagus, on the sinister-anterior side of the esophagus, 10. The surgical method according to aspect 7, wherein at least one of:
   - the step of placing at least two posterior sutures connecting the fundus to the esophagus, on the sinister-posterior side of the esophagus, comprises placing at least one continuous suture connecting the fundus to the esophagus, on the sinister-posterior side of the esophagus, and
   - the step of placing at least two anterior sutures connecting the fundus to the esophagus, on the sinister-anterior side of the esophagus, comprises placing at least one continuous suture connecting the fundus to the esophagus, on the sinister-anterior side of the esophagus.

11. The surgical method according to aspect 8 or any one of the aspects presented herein, wherein at least one of starting and ending of the continuous sutures is performed in the serosa of the stomach wall for securing the sutures to the serosa of the stomach wall.

12. The surgical method according to any one of the aspects presented herein, wherein both of the starting and ending of the continuous sutures is performed in the serosa of the stomach wall for securing the sutures.

13. The surgical method according to any one of the preceding aspects or any one of the aspects presented herein, wherein at least one of:
   - the step of placing at least two posterior sutures or at least one continuous suture, connecting the fundus to the esophagus, on the sinister-posterior side of the esophagus comprises placing at least two lateral sutures or continuous suture substantially along a cranial-caudal axis, on the sinister-posterior side of the esophagus, and the step of placing at least two anterior sutures or at least one continuous suture, connecting the fundus to the esophagus, on the sinister-anterior side of the esophagus comprises placing at least two lateral sutures or continuous suture substantially along a cranial-caudal axis, on the sinister-anterior side of the esophagus.

14. The surgical method according to any one of the preceding aspects, wherein at least one of:

the step of placing at least two posterior sutures or at least one continuous suture, connecting the fundus to the esophagus, on the sinister-posterior side of the esophagus, comprises placing the at least two posterior sutures or continuous suture bites at least 0.5 cm posterior to a coronal plane intersecting a most cranial point of the fundus, and the step of placing at least two anterior sutures or at least one continuous suture, connecting the fundus to the esophagus, on the sinister-anterior side of the esophagus, comprises placing the at least two anterior sutures or continuous bites at least 0.5 cm anterior from the coronal plane intersecting the most cranial point of the fundus.

15. The surgical method according to any one of the preceding aspects, wherein at least one of:

the step of placing at least two posterior sutures or at least one continuous suture, connecting the fundus to the esophagus, on the sinister-posterior side of the esophagus comprises placing the most caudal suture or continuous suture bites at least 0.5 cm from the angle of His, and the step of placing at least two anterior sutures or at least one continuous suture, connecting the fundus to the esophagus, on the sinister-anterior side of the esophagus comprises placing the most caudal suture or continuous suture bites at least 0.5 cm from the angle of His.

16. The surgical method according to any one of the preceding aspects, wherein at least one of:

the step of placing at least two posterior sutures or at least one continuous suture, connecting the fundus to the esophagus, on the sinister-posterior side of the esophagus comprises placing the most caudal suture or continuous suture bite at least 1.5 cm from the angle of His, and the step of placing at least two anterior sutures or at least one continuous suture, connecting the fundus to the esophagus, on the sinister-anterior side of the esophagus comprises placing the most caudal suture or continuous suture bite at least 1.5 cm from the angle of His.

17. The surgical method according to any one of the preceding aspects, comprising one of the steps of:

placing the most caudal suture or stapler of the at least two posterior sutures or at least one continuous suture, connecting the fundus to the esophagus, on the sinister-posterior side of the esophagus at least 0.5 cm from the angle of His and placing the most caudal suture of the at least two anterior sutures or continuous suture bite, connecting the fundus to the esophagus, on the sinister-anterior side of the esophagus at least 1.5 cm from the angle of His, and placing the most caudal suture or stapler of the at least two posterior sutures, connecting the fundus to the esophagus, on the sinister-posterior side of the esophagus at least 1.5 cm from the angle of His and placing the most caudal suture of the at least two anterior sutures, or continuous suture bite connecting the fundus to the esophagus, on the sinister-anterior side of the esophagus at least 0.5 cm from the angle of His.

18. The surgical method according to any one of the preceding aspects, wherein the step of connecting the fundus to the esophagus further comprises placing at least one central suture or continuous suture line on a cranial-caudal axis extending between the at least two posterior sutures or continuous suture line and the at least two anterior sutures or continuous suture line, placing at least one suture most cranial and preferable a line of sutures in between the posterior and anterior suture line, placing with a distance of one cm of esophagus circumference to both the anterior and posterior suture lines.

19. The surgical method according to any one of the preceding aspects, wherein the step of connecting the fundus to the esophagus further comprises placing at least one central suture on a cranial-caudal axis extending between the at least two posterior sutures or continuous suture line and the at least two anterior sutures or continuous suture line, placing a third continuous suture line in between the posterior and anterior suture line, placing with a targeted distance of one cm of esophagus circumference to both the anterior and posterior suture lines.

20. The surgical method according to aspect 15, wherein the step of placing at least one central suture or stapler on a cranial-caudal axis comprises placing at least one central suture or stapler being disconnected from the at least two anterior sutures or staplers and from the at least two posterior sutures or staplers, for maintaining the possibility of radial expansion the esophagus for limiting the disk of dysphagia.

21. The surgical method according to any one of aspects 1-20, wherein at least one of the steps of: placing at least two posterior sutures or continuous suture, connecting the fundus to the esophagus, on the sinister-posterior side of the esophagus, and placing at least two anterior sutures or continuous suture, connecting the fundus to the esophagus, on the sinister-anterior side of the esophagus, comprises using an at least partially barbed suture.

Aspect Group 449IPC: Reflux_Stop_Surface Roughness

1. An apparatus (100) for treating reflux disease of a human patient, comprising:

an implantable movement restriction device (110) having a shape and size allowing it to be arranged to rest against a fundus wall portion (14) of the patient's stomach (10), such that the movement restriction device is implanted at a position between the patient's diaphragm (30) and a portion of the fundus wall, and such that movement of the cardia (22) of the patient's stomach towards the diaphragm is restricted to hinder the cardia from sliding through the diaphragm opening (32) into the patient's thorax, wherein the implantable movement restriction device comprises an outer surface configured to rest against the stomach wall portion (14), and wherein an average surface roughness measured on the outer surface is less than 300'000 μm.

2. The apparatus (100) according to aspect 1, wherein the average surface roughness is $R_a$ as defined according to ISO 21920-2:2021.

3. The apparatus (100) according to aspect 1, wherein the average surface roughness is $S_a$ as defined according to ISO 25178-2-2021.

4. The apparatus (100) according to any one of aspects 1-3, wherein the average surface roughness is in the range of 0.01-0.1 μm, >0.1-0.5 μm, >0.5-10 μm, >10-80 μm, >80-200 μm, >200-10'000 μm, >10'000-500'000 μm.

5. The apparatus (100) according to any one of aspects 1-4, wherein the average surface roughness is in the range of 0.1-0.3 mm.

6. The apparatus according to any one of aspects 1-5, wherein the implantable movement restriction device comprises a polymer material.

7. The apparatus according to aspect 6, wherein the implantable movement restriction device comprises at least one of a silicone-based material and a polyurethane-based material.

8. The apparatus according to aspect 6, wherein the second solid material comprises at least one of a polypropylene-based and a polyethylene-based material.

9. The apparatus according to any one of aspects 1-8, wherein an indentation hardness on the Shore A scale measured on the outer surface is at least 50.

10. The apparatus according to aspect 9, wherein the indentation hardness is indentation hardness is measured by the durometer method defined in part 4 of ISO 48-4:2018.

11. The apparatus according to aspect 6 or 7, wherein an indentation hardness on the Shore A scale measured on the outer surface is no more than 70.

12. The apparatus according to any one of aspects 9-11, wherein an indentation hardness on the Shore A scale measured on the outer surface is in the range of 55 to 65.

13. The apparatus according to any one of the preceding aspects, wherein the movement restriction device comprises a first cross-sectional distance and a second cross-sectional distance, and wherein the movement restriction device (110) is configured to be implanted such that:

the first cross-sectional distance is more parallel than perpendicular to the cranial-caudal axis of the patient, and the second cross-sectional distance is more perpendicular than parallel to the cranial-caudal axis of the patient, and wherein the implantable movement restriction device (110) is adjustable in situ, such that the shape of the implantable movement restriction device (110) can be adjusted by the adjustment of the length of the first cross-sectional distance, such that the length of the first cross-sectional distance can be increased relative to the length of the second cross-sectional distance.

14. The apparatus according to aspect 13, wherein the shape of the implantable movement restriction device (110) can be adjusted by an increase of the length of the first cross-sectional distance relative to the length of the second cross-sectional distance while the length of a circumference of a cross-section of the implantable movement restriction device (110), in a plane parallel to the coronal plane of the patient remains constant.

15. The apparatus according to any one of the preceding aspects, wherein the implantable movement restriction device (110)) comprises a lower portion configured to, directly or indirectly, engage the stomach of the patient in a region of the angle of his, such that the function of the implantable movement restriction device (110) is supported by tissue of the stomach in the region of the angle of his.

16. The apparatus according to any one of the preceding aspects, wherein the implantable movement restriction device (110) comprises an upper portion configured to, directly or indirectly, engage the thoracic diaphragm of the patient, and wherein the upper portion comprises at least one curvature.

17. The apparatus according to any one of the preceding aspects, wherein the implantable movement restriction device (110) is configured to be at least partially invaginated by the stomach wall.

18. The apparatus according to aspect 17, wherein the implantable movement restriction device (110) is configured to be at least partially invaginated by the stomach wall of the fundus.

19. The apparatus according to any one of the preceding aspects, wherein the implantable movement restriction device (110) comprises at least one circular cross-section.

20. The apparatus according to any one of the preceding aspects, wherein the implantable movement restriction device comprises at least two parts.

21. The apparatus according to aspect 20, wherein the at least two parts are configured to be assembled to form the implantable movement restriction device.

22. The apparatus according to aspect 21, wherein the at least two parts are configured to be connected to each other to form the implantable movement restriction device.

23. The apparatus according to any one of aspects 20-22, further comprising an interconnecting part configured to connect to the at least two parts.

24. The apparatus according to any one of aspects 20-23, wherein at least one of the two parts and the interconnecting part comprises a connecting recess, and at least one of the two parts and the interconnecting part comprises a connecting protrusion, and wherein at least one connecting protrusion and one connecting recess are configured to be interconnected for forming the implantable movement restriction device.

25. The apparatus according to any one of the preceding aspects, wherein the movement restriction device comprises a curved cross-section in a plane parallel to the transverse plane of the patient, and wherein the curve is configured to partially enclose the esophagus of the patient.

26. The apparatus according to aspect 25, wherein the movement restriction device is configured to encircle at least ⅓ of the esophagus in a plane parallel to the transverse plane of the patient.

27. The apparatus according to aspect 28, wherein the movement restriction device is configured to encircle at least ½ of the esophagus in a plane parallel to the transverse plane of the patient.

28. The apparatus according to aspect 25, wherein the movement restriction device comprises a C-shaped cross-section in a plane parallel to the transverse plane of the patient, and wherein the C-shaped cross-section is configured to partially enclose the esophagus of the patient.

29. The method according to aspect 28, wherein the movement restriction device is configured to encircle at least ⅔ of the esophagus in a plane parallel to the transverse plane of the patient.

30. The apparatus according to any one of aspects 1-24, wherein a cross-section of the movement restriction device in a plane parallel to the transverse plane of the patient comprises a closed curve configured to enclose the esophagus of the patient.

31. The apparatus according to any one of the preceding aspects, wherein the movement restriction device has a constricting state for hindering fluid from passing from the stomach into the esophagus and an expanded state for allowing food to pass into the stomach in response to the patient swallowing.

32. The apparatus according to aspect 31, wherein the movement restriction device comprises at least one attractor (212) for resiliently attracting adjacent portions (213) of the movement restriction device to generate an encircling pressure in the esophagus.

33. The apparatus according to aspect 32, wherein the attractor comprises an elastic element.

34. The apparatus according to aspect 32, wherein the attractor comprises at least two mutually attracting magnets.

35. The apparatus according to any one of the preceding aspects, the implantable movement restriction device comprises a contrast agent.

36. The apparatus according to aspect 35, wherein the contrast agent is BaSO4.

37. The apparatus according to aspect 35 or 36, wherein the implantable movement restriction device comprises the contrast agent in an amount of 1-15% by weight of the implantable movement restriction device.

38. The apparatus according to aspect 37, wherein the implantable movement restriction device comprises the contrast agent in an amount of 1-6% by weight of the implantable movement restriction device.

39. The apparatus according to aspect 37, the implantable movement restriction device comprises the contrast agent in an amount of 8-15% by weight of the implantable movement restriction device.

Aspect Group 449JPC: Reflux_Stop Elasticity

1. An apparatus (100) for treating reflux disease of a human patient, comprising:

- an implantable movement restriction device (110) having a shape and size allowing it to be arranged to rest against a fundus wall portion (14) of the patient's stomach (10), such that the movement restriction device is implanted at a position between the patient's diaphragm (30) and a portion of the fundus wall, and such that movement of the cardia (22) of the patient's stomach towards the diaphragm is restricted to hinder the cardia from sliding through the diaphragm opening (32) into the patient's thorax, wherein the implantable movement restriction device comprises an outer surface configured to rest against the stomach wall portion (14), and wherein an indentation hardness on the Shore A scale measured on the outer surface is at least 25.

2. The apparatus according to aspect 1, wherein the indentation hardness is indentation hardness is measured by the durometer method defined in part 4 of ISO 48-4:2018.

3. The apparatus according to aspect 1 or 2, wherein an indentation hardness on the Shore A scale measured on the outer surface is no more than 70.

4. The apparatus according to any one of aspects 1 to 3, wherein an indentation hardness on the Shore A scale measured on the outer surface is in the range of 55 to 65.

5. The apparatus according to any one of aspects 1-3, wherein the implantable movement restriction device comprises a polymer material.

4. The apparatus according to aspect 4, wherein the implantable movement restriction device comprises at least one of silicone-based material and a polyurethane-based material.

5. The apparatus according to aspect 4, wherein the second solid material comprises at least one of a polypropylene-based and a polyethylene-based material.

6. The apparatus according to any one of aspects 1-5, wherein the implantable movement restriction device comprises an outer surface configured to rest against the stomach wall portion (14), and wherein an average surface roughness measured on the outer surface is no more than 300'000 μm.

7. The apparatus (100) according to aspect 6, wherein the average surface roughness is $R_a$ as defined according to ISO 21920-2:2021.

8. The apparatus (100) according to aspect 6, wherein the average surface roughness is Sa as defined according to ISO 25178-2:2021.

9. The apparatus (100) according to any one of aspects 6-8, wherein the average surface roughness is in the range 0.01-0.1 μm, or in the range >0.1-0.5 μm, or in the range >0.5-10 μm, or in the range >10-80 μm, or in the range >80-200 μm, or in the range >200-10'000 μm, or in the range >10'000-500'000 μm.

10. The apparatus (100)) according to any one of aspects 6-9, wherein the average surface roughness is in the range of 0.1-0.3 μm.

11. The apparatus according to any one of the preceding aspects, wherein the movement restriction device comprises a first cross-sectional distance and a second cross-sectional distance, and wherein the movement restriction device (110) is configured to be implanted such that:

- the first cross-sectional distance is more parallel than perpendicular to the cranial-caudal axis of the patient, and
- the second cross-sectional distance is more perpendicular than parallel to the cranial-caudal axis of the patient, and wherein
- the implantable movement restriction device (110) is adjustable in situ, such that the shape of the implantable movement restriction device (110) can be adjusted by the adjustment of the length of the first cross-sectional distance, such that the length of the first cross-sectional distance can be increased relative to the length of the second cross-sectional distance.

12. The apparatus according to aspect 11, wherein the shape of the implantable movement restriction device (110) can be adjusted by an increase of the length of the first cross-sectional distance relative to the length of the second cross-sectional distance while the length of a circumference of a cross-section of the implantable movement restriction device (110), in a plane parallel to the coronal plane of the patient remains constant.

13. The apparatus according to any one of the preceding aspects, wherein the implantable movement restriction device (110) comprises a lower portion configured to, directly or indirectly, engage the stomach of the patient in a region of the angle of his, such that the function of the implantable movement restriction device (110) is supported by tissue of the stomach in the region of the angle of his.

14. The apparatus according to any one of the preceding aspects, wherein the implantable movement restriction device (110) comprises an upper portion configured to, directly or indirectly, engage the thoracic diaphragm of the patient, and wherein the upper portion comprises at least one curvature.

15. The apparatus according to any one of the preceding aspects, wherein the implantable movement restriction device (110) is configured to be at least partially invaginated by the stomach wall.

16. The apparatus according to aspect 14, wherein the implantable movement restriction device (110) is configured to be at least partially invaginated by the stomach wall of the fundus.

17. The apparatus according to any one of the preceding aspects, wherein the implantable movement restriction device (110) comprises at least one circular cross-section.

18. The apparatus according to any one of the preceding aspects, wherein the implantable movement restriction device comprises at least two parts.
19. The apparatus according to aspect 18, wherein the at least two parts are configured to be assembled to form the implantable movement restriction device.
20. The apparatus according to aspect 19, wherein the at least two parts are configured to be connected to each other to form the implantable movement restriction device.
21. The apparatus according to any one of aspects 18-20, further comprising an interconnecting part configured to connect to the at least two parts.
22. The apparatus according to any one of aspects 18-21, wherein at least one of the two parts and the interconnecting part comprises a connecting recess, and at least one of the two parts and the interconnecting part comprises a connecting protrusion, and wherein at least one connecting protrusion and one connecting recess are configured to be interconnected for forming the implantable movement restriction device.
23. The apparatus according to any one of the preceding aspects, wherein the movement restriction device comprises a curved cross-section in a plane parallel to the transverse plane of the patient, and wherein the curve is configured to partially enclose the esophagus of the patient.
24. The apparatus according to aspect 23, wherein the movement restriction device is configured to encircle at least ⅓ of the esophagus in a plane parallel to the transverse plane of the patient.
25. The apparatus according to aspect 24, wherein the movement restriction device is configured to encircle at least ½ of the esophagus in a plane parallel to the transverse plane of the patient.
26. The apparatus according to aspect 23, wherein the movement restriction device comprises a C-shaped cross-section in a plane parallel to the transverse plane of the patient, and wherein the C-shaped cross-section is configured to partially enclose the esophagus of the patient.
27. The method according to aspect 26, wherein the movement restriction device is configured to encircle at least ⅔ of the esophagus in a plane parallel to the transverse plane of the patient.
28. The apparatus according to any one of aspects 1-22, wherein a cross-section of the movement restriction device in a plane parallel to the transverse plane of the patient comprises a closed curve configured to enclose the esophagus of the patient.
29. The apparatus according to any one of the preceding aspects, wherein the movement restriction device has a constricting state for hindering fluid from passing from the stomach into the esophagus and an expanded state for allowing food to pass into the stomach in response to the patient swallowing.
30. The apparatus according to aspect 29, wherein the movement restriction device comprises at least one attractor (212) for resiliently attracting adjacent portions (213) of the movement restriction device to generate an encircling pressure in the esophagus.
31. The apparatus according to aspect 30, wherein the attractor comprises an elastic element.
32. The apparatus according to aspect 30, wherein the attractor comprises at least two mutually attracting magnets.
33. The apparatus according to any one of the preceding aspects, wherein the implantable movement restriction device comprises a contrast agent.
34. The apparatus according to aspect 33, wherein the contrast agent is BaSO4.
35. The apparatus according to aspect 34 or 35, wherein the implantable movement restriction device comprises the contrast agent in an amount of 1-15% by weight of the implantable movement restriction device.
36. The apparatus according to aspect 35, wherein the implantable movement restriction device comprises the contrast agent in an amount of 1-6% by weight of the implantable movement restriction device.
37. The apparatus according to aspect 35, the implantable movement restriction device comprises the contrast agent in an amount of 8-15% by weight of the implantable movement restriction device.

Aspect Group 449KPC: Reflux_Stop_Increased Weight in Core

1. An apparatus (100) for treating reflux disease of a human patient, comprising:
   an implantable movement restriction device (110) having a shape and size allowing it to be arranged to rest against a fundus wall portion (14) of the patient's stomach (10), such that the movement restriction device is implanted at a position between the patient's diaphragm (30) and a portion of the fundus wall, and such that movement of the cardia (22) of the patient's stomach towards the diaphragm is restricted to hinder the cardia from sliding through the diaphragm opening (32) into the patient's thorax, wherein the implantable movement restriction device comprises a plurality of segments, wherein the plurality of segments are comprised of a core part and a plurality of outer parts, and wherein the core part has an average density of above 1000 $kg/m^3$.
2. The apparatus according to aspect 1, wherein at least one outer part in the plurality of outer parts has an average density below 1000 $kg/m^3$.
3. The apparatus according to aspect 2, wherein the average density of the at least one outer part and the average density of the core part differ by at least 10 $kg/m^3$.
4. The apparatus according to any one of the preceding aspects, wherein the average density of the at least one outer part and the average density of the core part differ by at least 20 $kg/m^3$.
5. The apparatus according to any one of the preceding aspects, wherein the plurality of outer parts comprises at least 3 outer parts.
6. The apparatus according to any one of the preceding aspects, wherein the plurality of outer parts comprises at least 4 outer parts.
7. The apparatus according to any one of the preceding aspects, wherein all outer parts in the plurality of outer parts have an average density below 1000 $kg/m^3$.
8. The apparatus according any one of the preceding aspects, wherein the at least one core part comprises a first solid material.
9. The apparatus according to aspect 8, wherein the first solid material comprises a polymer material.
10. The apparatus according to aspect 3, wherein the first solid material comprises at least one of silicone-based material and a polyurethane-based material.
11. The apparatus according to any one of aspects 1-10, wherein the at least one outer part comprises a second solid material.
12. The apparatus according to aspect 11, wherein the second solid material comprises a polymer material.

13. The apparatus according to aspect 12, wherein the second solid material comprises a at least one of a polypropylene-based and a polyethylene-based material.

14. The apparatus according to aspect 1-4, wherein the at least one outer part comprises a fluid.

15. The apparatus according to aspect 24, wherein the at least one outer part comprises a liquid having a density a below 1000 kg/m3.

16. The apparatus according to aspect 15, wherein the liquid comprises at least one selected from a list of:
- oil-based liquids, and
- alcohol based liquids.

17. The apparatus according to aspect 14, wherein the at least one outer part comprises a gas.

18. The apparatus according to aspect 17, wherein the at least one outer part comprises a plurality of volumes of gas enclosed by an enclosing material.

19. The apparatus according to aspect 18, wherein the at least one outer part comprises a solid polymer material enclosing the enclosing material, and wherein the enclosing material is harder than the solid polymer material.

20. The apparatus according to any one of aspects 18 and 19, wherein the plurality of volumes of gas enclosed by an enclosing material makes up at least 10 volume percent of the second volume, more preferably at least 20 volume percent of the second volume, and even more preferably at least 30 volume percent of the at least one outer part.

21. The apparatus according to any one of aspects 18-20, wherein the enclosing material comprises glass.

22. The apparatus according to any one of the preceding aspects, wherein the movement restriction device has an average density below 1100 kg/m3.

23. The apparatus according to any one of the preceding aspects, wherein the movement restriction device has an average density below 1050 kg/m3.

24. The apparatus according to any one of the preceding aspects, wherein the movement restriction device has an average density below 1000 kg/m3.

25. The apparatus according to any one of the preceding aspects, wherein the movement restriction device comprises a first cross-sectional distance and a second cross-sectional distance, and wherein the movement restriction device (110) is configured to be implanted such that:
- the first cross-sectional distance is more parallel than perpendicular to the cranial-caudal axis of the patient, and
- the second cross-sectional distance is more perpendicular than parallel to the cranial-caudal axis of the patient, and wherein
- the implantable movement restriction device (110) is adjustable in situ, such that the shape of the implantable movement restriction device (110) can be adjusted by the adjustment of the length of the first cross-sectional distance, such that the length of the first cross-sectional distance can be increased relative to the length of the second cross-sectional distance.

26. The apparatus according to aspect 25, wherein the shape of the implantable movement restriction device (110) can be adjusted by an increase of the length of the first cross-sectional distance relative to the length of the second cross-sectional distance while the length of a circumference of a cross-section of the implantable movement restriction device (110), in a plane parallel to the coronal plane of the patient remains constant.

27. The apparatus according to any one of the preceding aspects, wherein the implantable movement restriction device (110) comprises a lower portion configured to, directly or indirectly, engage the stomach of the patient in a region of the angle of his, such that the function of the implantable movement restriction device (110) is supported by tissue of the stomach in the region of the angle of his.

28. The apparatus according to any one of the preceding aspects, wherein the implantable movement restriction device (110) comprises an upper portion configured to, directly or indirectly, engage the thoracic diaphragm of the patient, and wherein the upper portion comprises at least one curvature.

29. The apparatus according to any one of the preceding aspects, wherein the implantable movement restriction device (110) is configured to be at least partially invaginated by the stomach wall.

30. The apparatus according to aspect 14, wherein the implantable movement restriction device (110) is configured to be at least partially invaginated by the stomach wall of the fundus.

31. The apparatus according to any one of the preceding aspects, wherein the implantable movement restriction device (110) comprises at least one circular cross-section.

32. The apparatus according to any one of the preceding aspects, wherein the implantable movement restriction device comprises at least two parts.

33. The apparatus according to aspect 32, wherein the at least two parts are configured to be assembled to form the implantable movement restriction device.

34. The apparatus according to aspect 33, wherein the at least two parts are configured to be connected to each other to form the implantable movement restriction device.

35. The apparatus according to any one of aspects 32-34, further comprising an interconnecting part configured to connect to the at least two parts.

36. The apparatus according to any one of aspects 32-35, wherein at least one of the two parts and the interconnecting part comprises a connecting recess, and at least one of the two parts and the interconnecting part comprises a connecting protrusion, and wherein at least one connecting protrusion and one connecting recess are configured to be interconnected for forming the implantable movement restriction device.

37. The apparatus according to any one of the preceding aspects, wherein the movement restriction device comprises a curved cross-section in a plane parallel to the transverse plane of the patient, and wherein the curve is configured to partially enclose the esophagus of the patient.

38. The apparatus according to aspect 37, wherein the movement restriction device is configured to encircle at least ⅓ of the esophagus in a plane parallel to the transverse plane of the patient.

39. The apparatus according to aspect 38, wherein the movement restriction device is configured to encircle at least ½ of the esophagus in a plane parallel to the transverse plane of the patient.

40. The apparatus according to aspect 37, wherein the movement restriction device comprises a C-shaped cross-section in a plane parallel to the transverse plane of the patient, and wherein the C-shaped cross-section is configured to partially enclose the esophagus of the patient.

41. The method according to aspect 40, wherein the movement restriction device is configured to encircle at least ⅔ of the esophagus in a plane parallel to the transverse plane of the patient.

42. The apparatus according to any one of aspects 1-36, wherein a cross-section of the movement restriction device in a plane parallel to the transverse plane of the patient comprises a closed curve configured to enclose the esophagus of the patient.

43. The apparatus according to any one of the preceding aspects, wherein the movement restriction device has a constricting state for hindering fluid from passing from the stomach into the esophagus and an expanded state for allowing food to pass into the stomach in response to the patient swallowing.

44. The apparatus according to aspect 43, wherein the movement restriction device comprises at least one attractor (212) for resiliently attracting adjacent portions (213) of the movement restriction device to generate an encircling pressure in the esophagus.

45. The apparatus according to aspect 44, wherein the attractor comprises an clastic element.

46. The apparatus according to aspect 44, wherein the attractor comprises at least two mutually attracting magnets.

47. The apparatus according to any one of the preceding aspects, wherein the core part comprises a fluid.

48. The apparatus according to aspect 47, wherein the core part comprises a liquid having a density a below 1000 kg/m3.

49. The apparatus according to aspect 48, wherein the liquid comprises at least one selected from a list of:

oil-based liquids, and alcohol based liquids.

50. The apparatus according to aspect 47, wherein the core part comprises a gas.

51. The apparatus according to aspect 50, wherein the core part comprises a plurality of volumes of gas enclosed by an enclosing material.

52. The apparatus according to aspect 51, wherein the core part comprises a solid polymer material enclosing the enclosing material, and wherein the enclosing material is harder than the solid polymer material.

53. The apparatus according to any one of aspects 51 and 52, wherein the plurality of volumes of gas enclosed by an enclosing material makes up at least 10 volume percent of the second volume, more preferably at least 20 volume percent of the second volume, and even more preferably at least 30 volume percent of the at least one outer part, and even more preferably at least 40 volume percent of the second volume, and even more preferably at least 50 volume percent of the second volume, and even more preferably at least 60 volume percent of the second volume, and even more preferably at least 70 volume percent of the second volume, and even more preferably at least 80 volume percent of the second volume, and even more preferably at least 90 volume percent of the second volume.

54. The apparatus according to any one of aspects 51-53, wherein the enclosing material comprises glass.

55. The apparatus according to any one of the preceding aspects, wherein the implantable movement restriction device comprises a contrast agent.

56. The apparatus according to aspect 55 wherein the contrast agent is BaSO4.

57. The apparatus according to aspect 55 or 56, wherein the implantable movement restriction device comprises the contrast agent in an amount of 1-15% by weight of the implantable movement restriction device.

58. The apparatus according to aspect 57, wherein the implantable movement restriction device comprises the contrast agent in an amount of 1-6% by weight of the implantable movement restriction device.

59. The apparatus according to aspect 57, the implantable movement restriction device comprises the contrast agent in an amount of 8-15% by weight of the implantable movement restriction device.

60. The apparatus according to any one of aspects 55-60, wherein the core part comprises the contrast agent.

61 The apparatus according to aspect 60, wherein the core part comprises the contrast agent in an amount of 8-15% by weight of the core part.

62. The apparatus according to any one of aspects 55-61, wherein the at least one outer part comprises the contrast agent.

63 The apparatus according to aspect 62, wherein the at least one outer part comprises the contrast agent in an amount of 8-15% by weight of the at least one outer part.

Aspect Group 449LPC: Reflux Device Configuration Flat Surfaces_1

1. An implantable medical device for treating reflux disease, the implantable medical device comprising a movement restriction device configured to be fixated to the stomach wall for hindering movement of the lower esophageal sphincter relative to the thoracic diaphragm, the movement restriction device comprises:

a, a central part, and b. at least two outer parts, wherein the central part and the at least two outer parts are configured to be connected to each other for forming at least a portion of a functional movement restriction device, the central part and the at least two outer parts are capable of disconnecting from each other, such that the central part and the at least two outer parts individually can pass through the gastro-intestinal tract, wherein the outer surface of the functional movement restriction device comprises at least four flat surfaces separated from each other and interspaced by at least four curved surfaces, and wherein the combined area of the at least four flat surfaces exceeds 40% of the total surface area of the functional movement restriction device.

2. The implantable medical device according to aspect 1, wherein the outer surface of the functional movement restriction device comprises at least five flat surfaces.

3. The implantable medical device according to aspect 1, wherein the outer surface of the functional movement restriction device comprises at least six flat surfaces.

4. The implantable medical device according to aspect 1, wherein the outer surface of the functional movement restriction device comprises at least seven flat surfaces.

5. The implantable medical device according to aspect 1, wherein the outer surface of the functional movement restriction device comprises at least eight flat surfaces.

6. The implantable medical device according to any one of the preceding aspects, wherein at least one of the flat surfaces is elliptical.

7. The implantable medical device according to any one of the preceding aspects, wherein at least one of the flat surfaces is circular.

8. The implantable medical device according to any one of the preceding aspects, wherein at least one of the flat surfaces is polygonal.

9. The apparatus according to any one of the preceding aspects, wherein the implantable movement restriction device (110) comprises a first portion having a first volume enclosed by material of the implantable movement restriction device (110), and a second portion, different from the first portion, having a second volume enclosed by material of the implantable movement restriction device (110), wherein:

the first volume has a higher density than the second volume, and the second volume has a density below 1000 kg/m3.

10. The apparatus according to aspect 9, wherein the first volume comprises a first solid material.

11. The apparatus according to aspect 10, wherein the first solid material comprises a polymer material, a metal, a ceramic or carbon material or a mixture thereof.

12. The apparatus according to aspect 11, wherein the first solid material comprises at least one of silicone-based material and a polyurethane-based material, an ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.

13. The apparatus according to any one of aspects 9-12, wherein the second volume comprises a second solid material.

14. The apparatus according to aspect 13, wherein the second solid material comprises a polymer material, a metal, a ceramic or carbon material or a mixture thereof.

15. The apparatus according to aspect 14, wherein the second solid material comprises a at least one of a polypropylene-based and a polyethylene-based material, an ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.

16. The apparatus according to any one of aspects 13-15, wherein the first volume comprises a solid material having a density above 1000 kg/m3 and the second volume comprises a solid material having a density below 1000 kg/m3.

17. The apparatus according to any one of aspects 9-16, wherein the second volume comprises a gas.

18. The apparatus according to any one of aspects 9-17, wherein the second volume comprises a plurality of volumes of gas enclosed by an enclosing material.

19. The apparatus according to aspect 18, wherein the second volume comprises a solid polymer material enclosing the enclosing material, and wherein the enclosing material is harder than the solid polymer material.

20. The apparatus according to any one of aspects 18 and 19, wherein the plurality of volumes of gas enclosed by an enclosing material makes up at least 10 volume percent of the second volume, more preferably at least 20 volume percent of the second volume, and even more preferably at least 30 volume percent of the second volume, and even more preferably at least 40 volume percent of the second volume, and even more preferably at least 50 volume percent of the second volume, and even more preferably at least 60 volume percent of the second volume, and even more preferably at least 70 volume percent of the second volume, and even more preferably at least 80 volume percent of the second volume, and even more preferably at least 90 volume percent of the second volume.

21. The apparatus according to any one of aspects 18-20, wherein the enclosing material comprises glass.

22. The apparatus according to any one of the preceding aspects, wherein the implantable movement restriction device comprises an outer surface configured to rest against the stomach wall portion, and wherein an average surface roughness measured on the outer surface is no more than 300'000 μm.

23. The apparatus (100) according to aspect 22, wherein the average surface roughness is $R_a$ as defined according to ISO 21920-2:2021.

24. The apparatus (100) according to aspect 22, wherein the average surface roughness is Sa as defined according to ISO 25178-2:2021.

25. The apparatus (100) according to any one of aspects 22-24, wherein the average surface roughness is in the range of at least one of; 0.01-0.1 μm, >0.1-0.5 μm, >0.5-10 μm, >10-80 μm, >80-200 μm, >200-10'000 μm, >10'000-500'000 μm.

26. The apparatus (100) according to any one of aspects 22-25, wherein the average surface roughness is in the range of 0.1-0.3 mm.

27. The apparatus according to any one of the preceding aspects, wherein an indentation hardness on the Shore A scale measured on the outer surface of the movement restriction device is at least 50.

28. The apparatus according to aspect 27, wherein the indentation hardness is indentation hardness is measured by the durometer method defined in part 4 of ISO 48-4:2018.

29. The apparatus according to aspects 27-28, wherein an indentation hardness on the Shore A scale measured on the outer surface is no more than 70.

30. The apparatus according to any one of aspects 27-29, wherein an indentation hardness on the Shore A scale measured on the outer surface is in the range of 55 to 65, or 5-25 or >25-50, or >65.

31. The apparatus according to any one of the preceding aspects, wherein the implantable movement restriction device comprises a contrast agent.

32. The apparatus according to aspect 31, wherein the contrast agent is BaSO4.

33. The apparatus according to aspect 31 or 32, wherein the implantable movement restriction device comprises the contrast agent in an amount of 1-15% by weight of the implantable movement restriction device.

34. The apparatus according to aspect 33, wherein the implantable movement restriction device comprises the contrast agent in an amount of 1-6% by weight of the implantable movement restriction device.

35. The apparatus according to aspect 34, the implantable movement restriction device comprises the contrast agent in an amount of 8-15% by weight of the implantable movement restriction device.

Aspect Group 449MPC: Reflux Device Configuration Flat Surfaces_2

1. An implantable medical device for treating reflux disease, the implantable medical device comprising a movement restriction device configured to be fixated to the stomach wall for hindering movement of the lower esophageal sphincter relative to the thoracic diaphragm, the movement restriction device comprises:

a. a central part, and b. at least two outer parts, wherein the central part and the at least two outer parts are configured to be connected to each other for forming at least a portion of a functional movement restriction device, the central part and the at least two outer parts are capable of disconnecting from each other, such that the central part and the at least two outer parts individually can pass through the gastro-intestinal tract, wherein the outer surface of the functional movement restriction device comprises at least four flat surfaces separated from each other and interspaced by at least four curved surfaces, and wherein the combined area of the at least four flat surfaces is in the interval 10%-20% of the total surface area of the functional movement restriction device.

2. The implantable medical device according to aspect 1, wherein the outer surface of the functional movement restriction device comprises at least five flat surfaces.

3. The implantable medical device according to aspect 1, wherein the outer surface of the functional movement restriction device comprises at least six flat surfaces.

4. The implantable medical device according to aspect 1, wherein the outer surface of the functional movement restriction device comprises at least seven flat surfaces.

5. The implantable medical device according to aspect 1, wherein the outer surface of the functional movement restriction device comprises at least eight flat surfaces.

6. The implantable medical device according to any one of the preceding aspects, wherein at least one of the flat surfaces is elliptical.

7. The implantable medical device according to any one of the preceding aspects, wherein at least one of the flat surfaces is circular.

8. The implantable medical device according to any one of the preceding aspects, wherein at least one of the flat surfaces is polygonal.

9. The apparatus according to any one of the preceding aspects, wherein the implantable movement restriction device (110) comprises

- a first portion having a first volume enclosed by material of the implantable movement restriction device (110), and
- a second portion, different from the first portion, having a second volume enclosed by material of the implantable movement restriction device (110), wherein:
  - the first volume has a higher density than the second volume, and the second volume has a density below 1000 kg/m3.

10. The apparatus according to aspect 9, wherein the first volume comprises a first solid material.

11. The apparatus according to aspect 10, wherein the first solid material comprises a polymer material, a metal, a ceramic or carbon material or a mixture thereof.

12. The apparatus according to aspect 11, wherein the first solid material comprises at least one of silicone-based material and a polyurethane-based material, an ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.

13. The apparatus according to any one of aspects 9-12, wherein the second volume comprises a second solid material.

14. The apparatus according to aspect 13, wherein the second solid material comprises a polymer material, a metal, a ceramic or carbon material or a mixture thereof.

15. The apparatus according to aspect 14, wherein the second solid material comprises a at least one of a polypropylene-based and a polyethylene-based material, an ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.

16. The apparatus according to any one of aspects 13-15, wherein the first volume comprises a solid material having a density above 1000 kg/m3 and the second volume comprises a solid material having a density below 1000 kg/m3.

17. The apparatus according to any one of aspects 9-16, wherein the second volume comprises a gas.

18. The apparatus according to any one of aspects 9-17, wherein the second volume comprises a plurality of volumes of gas enclosed by an enclosing material.

19. The apparatus according to aspect 18, wherein the second volume comprises a solid polymer material enclosing the enclosing material, and wherein the enclosing material is harder than the solid polymer material.

20. The apparatus according to any one of aspects 18 and 19, wherein the plurality of volumes of gas enclosed by an enclosing material makes up at least 10 volume percent of the second volume, more preferably at least 20 volume percent of the second volume, and even more preferably at least 30 volume percent of the second volume, and even more preferably at least 40 volume percent of the second volume, and even more preferably at least 50 volume percent of the second volume, and even more preferably at least 60 volume percent of the second volume, and even more preferably at least 70 volume percent of the second volume, and even more preferably at least 80 volume percent of the second volume, and even more preferably at least 90 volume percent of the second volume.

21. The apparatus according to any one of aspects 18-20, wherein the enclosing material comprises glass.

22. The apparatus according to any one of the preceding aspects, wherein the implantable movement restriction device comprises an outer surface configured to rest against the stomach wall portion, and wherein an average surface roughness measured on the outer surface is no more than 300'000 μm.

23. The apparatus (100) according to aspect 22, wherein the average surface roughness is $R_a$ as defined according to ISO 21920-2:2021.

24. The apparatus (100) according to aspect 22, wherein the average surface roughness is $S_a$ as defined according to ISO 25178-2:2021.

25. The apparatus (100) according to any one of aspects 22-24, wherein the average surface roughness is in the range of at least one of; 0.01-0.1 μm, >0.1-0.5 μm, >0.5-10 μm, >10-80 μm, >80-200 μm, >200-10'000 μm, >10'000-500'000 μm.

26. The apparatus (100) according to any one of aspects 22-25, wherein the average surface roughness is in the range of 0.1-0.3 mm.

27. The apparatus according to any one of the preceding aspects, wherein an indentation hardness on the Shore A scale measured on the outer surface of the movement restriction device is at least 50.

28. The apparatus according to aspect 27, wherein the indentation hardness is indentation hardness is measured by the durometer method defined in part 4 of ISO 48-4:2018.

29. The apparatus according to aspects 27-28, wherein an indentation hardness on the Shore A scale measured on the outer surface is no more than 70.

30. The apparatus according to any one of aspects 27-29, wherein an indentation hardness on the Shore A scale measured on the outer surface is in the range of 55 to 65, or 5-25 or >25-50, or >65.

31. The apparatus according to any one of the preceding aspects, wherein the implantable movement restriction device comprises a contrast agent.

32. The apparatus according to aspect 31, wherein the contrast agent is $BaSO_4$.

33. The apparatus according to aspect 31 or 32, wherein the implantable movement restriction device comprises the contrast agent in an amount of 1-15% by weight of the implantable movement restriction device.

34. The apparatus according to aspect 33, wherein the implantable movement restriction device comprises the contrast agent in an amount of 1-6% by weight of the implantable movement restriction device.
35. The apparatus according to aspect 34, the implantable movement restriction device comprises the contrast agent in an amount of 8-15% by weight of the implantable movement restriction device.

Aspect Group 449NPC: Reflux Device Configuration Volume

1. An implantable medical device for treating reflux disease, the implantable medical device comprising a movement restriction device configured to be hindering movement of the lower esophageal sphincter relative to the thoracic diaphragm and adapted to be positioned between the angle of His and the diaphragm, the movement restriction device comprises:
a. a central part, and
b. at least two outer parts, wherein
the central part and the at least two outer parts are configured to be connected to each other for forming at least a portion of a functional movement restriction device, the central part and the at least two outer parts are capable of disconnecting from each other, such that the central part and the at least two outer parts individually can pass through the gastro-intestinal tract, wherein at least one of the functional movement restriction device and the boundary of the functional movement restriction device has a volume in the range 7.3 $cm^3$-8 $cm^3$.
2. The implantable medical device according to any one of the herein presented aspects, wherein at least one of the functional movement restriction device and the boundary of the functional movement restriction device has a volume in the range >6.6 $cm^3$-<7.3 $cm^3$.
3. The implantable medical device according to any one of the herein presented aspects, wherein at least one of the functional movement restriction device and the boundary of the functional movement restriction device has a volume in the range >5.8 $cm^3$. 6.6 $cm^3$.
4. The implantable medical device according to any one of the herein presented aspects, wherein at least one of the movement restriction device and the boundary of the movement restriction device has a volume in the range 5.0 $cm^3$-5.8 $cm^3$.
5. The implantable medical device according to any one of the herein presented aspects, wherein at least one of the functional movement restriction device and the boundary of the functional movement restriction device has a volume in the range >8 $cm^3$-<200 $cm^3$.
6. The implantable medical device according to any one of the herein presented aspects, wherein at least one of the functional movement restriction device and the boundary of the functional movement restriction device has a surface area in the range >23 $cm^2$-50 $cm^2$.
7. The implantable medical device according to any one of the herein presented aspects, wherein at least one of the functional movement restriction device and the boundary of the functional movement restriction device has a surface area in the range 22.5 $cm^2$-45 $cm^2$.
8. The implantable medical device according to any one of the herein presented aspects, wherein at least one of the functional movement restriction device and the boundary of the functional movement restriction device has a surface area in the range 21 $cm^2$-41 $cm^2$.
9. The implantable medical device according to any one of the herein presented aspects, wherein at least one of the functional movement restriction device and the boundary of the functional movement restriction device has a surface area in the range 19 $cm^2$-29 $cm^2$.
10. The implantable medical device according to any one of the herein presented aspects, wherein at least one of the movement restriction device and the boundary of the movement restriction device has a surface area >41 $cm^2$.
11. The implantable medical device according to any one of the herein presented aspects, wherein at least one of the movement restriction device and the boundary of the movement restriction device has a surface area of at least one of 22.5 $cm^2$-225 and >225-599 $cm^2$.
12. The implantable medical device according to any one of the herein presented aspects, wherein at least one of the movement restriction device and the boundary of the movement restriction device has a surface area of at least one of 20.5 $cm^2$-200 $cm^2$, >200 $cm^2$-350 $cm^2$, >350 $cm^2$-450 $cm^2$ and, >450-599 $cm^2$.
13. The apparatus according to any one of the herein presented aspects, wherein the implantable movement restriction device (110) comprises
A first material having a first density,
A second material having a second density, and wherein:
the first material has a higher density than the second material, and the second material has a density below 1000 kg/m3.
14. The apparatus according to any one of the herein presented aspects, wherein the first material comprises a polymer material.
15. The apparatus according to any one of the herein presented aspects, wherein the first material comprises a plastic, metal, ceramic or carbon material or a mixture thereof.
16. The apparatus according to any one of the herein presented aspects, wherein the first material comprises at least one of a silicone-based, an ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.
17. The apparatus according to any one of aspects 17-20, wherein the first material having a density above 1000 kg/m3 and the second material having a density below 1000 kg/m3.
18. The apparatus according to aspect 17-21, wherein the second material comprises at least one of a silicone-based, a ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.
19. The apparatus according to any one of the herein presented aspects, wherein the second material is a gas.
20. The apparatus according to any one of the herein presented aspects, wherein the second material comprises a plurality of volumes of gas enclosed by an enclosing material.
21. The apparatus according to any one of the herein presented aspects, wherein the enclosing material comprises glass.
22. The apparatus according to any one of the herein presented aspects, wherein the plurality of volumes of gas enclosed by an enclosing material makes up at least 10 volume percent of the volume of the second material, more preferably at least 20 volume percent of the second volume, and even more preferably at least 30 volume percent of the second volume.

23. The apparatus according to any one of the herein presented aspects, wherein the plurality of volumes of gas enclosed by an enclosing material makes up at least 40 volume percent of the volume of the second material, more preferably at least 50 volume percent of the second volume.

24. The apparatus according to any one of the herein presented aspects, wherein the plurality of volumes of gas enclosed by an enclosing material makes up at least 60 volume percent of the volume of the second material, more preferably at least 70 volume percent of the second volume.

25. The apparatus according to any one of the herein presented aspects, wherein the plurality of volumes of gas enclosed by an enclosing material makes up at least 80 volume percent of the volume of the second material, more preferably at least 90 volume percent of the second volume.

26. The apparatus according to any one of the preceding aspects, wherein the implantable movement restriction device comprises an outer surface configured to rest against the stomach wall portion, and wherein an average surface roughness measured on the outer surface is no more than 300'000 μm.

27. The apparatus (100) according to any one of the herein presented aspects, wherein the average surface roughness is $R_a$ as defined according to ISO 21920-2:2021.

28. The apparatus (100) according to any one of the herein presented aspects, wherein the average surface roughness is $S_a$ as defined according to ISO 25178-2:2021.

29. The apparatus (100) according to any one of the herein presented aspects, wherein the average surface roughness is in the range of at least one of; 0.01-0.1 μm, >0.1-0.5 μm, >0.5-10 μm, >10-80 μm, >80-200 μm, >200-10'000 μm, >10'000-500'000 μm.

30. The apparatus (100) according to any one of the herein presented aspects, wherein the average surface roughness is in the range of 0.1-0.3 mm.

31. The apparatus according to any one of the preceding aspects, wherein an indentation hardness on the Shore A scale measured on the outer surface of the movement restriction device is at least 50.

32. The apparatus according to any one of the herein presented aspects, wherein the indentation hardness is measured by the durometer method defined in part 4 of ISO 48-4:2018.

33. The apparatus according to any one of the herein presented aspects, wherein an indentation hardness on the Shore A scale measured on the outer surface is no more than 65.

34. The apparatus according to any one of the herein presented aspects, wherein an indentation hardness on the Shore A scale measured on the outer surface is in the range of 50 to 65.

35. The apparatus according to any one of the preceding aspects, wherein an indentation hardness on the Shore A scale measured on the outer surface is in the range of 5-25 or >25-50, or >65.

36. The apparatus according to any one of the herein presented aspects, wherein the implantable movement restriction device comprises a contrast agent.

37. The apparatus according to any one of the herein presented aspects, wherein the contrast agent is BaSO4.

38. The apparatus according to any one of the herein presented aspects, wherein the implantable movement restriction device comprises the contrast agent in an amount of 1-15% by weight of the implantable movement restriction device.

39. The apparatus according to any one of the herein presented aspects, wherein the implantable movement restriction device comprises the contrast agent in an amount of 1-6% by weight of the implantable movement restriction device.

40. The apparatus according to any one of the herein presented aspects, the implantable movement restriction device comprises the contrast agent in an amount of 8-15% by weight of the implantable movement restriction device.

Aspect Group 4490PC: Reflux Device Configuration Height

1. An implantable medical device for treating reflux disease, the implantable medical device comprising a movement restriction device configured to be hindering movement of the lower esophageal sphincter relative to the thoracic diaphragm and adapted to be positioned between the angle of His and the diaphragm, the movement restriction device comprises at least two parts, wherein the parts are configured to be connected to each other for forming at least a portion of a functional movement restriction device, and the at least two parts are capable of disconnecting from each other, such that the at least two parts individually can pass through the gastro-intestinal tract, wherein the functional movement restriction device has a height >1 inch.

2. The implantable medical device according to aspects 1-2, wherein the functional movement restriction device has a height in the range 1 inch-6 cm.

3. The implantable medical device according to aspect 1, wherein the functional movement restriction device has a height in the range 3.5 cm-6 cm.

4. The implantable medical device according to aspect 1, wherein the functional movement restriction device has a height in the range 4 cm-6 cm.

5. The implantable medical device according to any one of the preceding aspects, further comprising a central part, wherein the at least two parts are configured to be connected to the central part for forming at least a portion of the functional movement restriction device, the central part and the at least two parts are capable of disconnecting from each other, such that the central part and the at least two parts individually can pass through the gastro-intestinal tract.

6. The implantable medical device according to any one of the preceding aspects, wherein the complete movement restriction device is elongated and wherein the height is a longest cross-sectional distance, and wherein the movement restriction device further comprises a width, being a longest cross-sectional distance perpendicular to the height, and wherein the height is longer than the width.

7. The implantable medical device according to aspect 1, wherein at least one of the functional movement restriction device and the boundary of the functional movement restriction device has a surface area in the range 22.5 $cm^2$-50 $cm^2$, or in the range 20.5 $cm^2$-40 $cm^2$.

8. The apparatus according to any one of the preceding aspects, wherein the volume of the implantable movement restriction device (110) comprises a first material having a first density, a second material having a second density, and wherein:

the first material has a higher density than the second material, and the second material has a density below 1000 kg/m3.

9. The apparatus according to any one of the herein presented aspects, wherein the first material comprises a polymer material.

10. The apparatus according to any one of the herein presented aspects, wherein the first solid material comprises at least one of silicone-based material and a polyurethane-based material.

11. The apparatus according to any one of the herein presented aspects, wherein the first material comprises a plastic, metal, ceramic or carbon material or a mixture thereof.

12. The apparatus according to any one of the herein presented aspects, wherein the first material comprises at least one of a silicone-based, a ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.

13. The apparatus according to any one of the herein presented aspects, wherein the first material having a density above 1000 kg/m3 and the second material having a density below 1000 kg/m3.

14. The apparatus according to any one of the herein presented aspects, wherein the second material comprises at least one of a silicone-based, a ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.

15. The apparatus according to any one of the herein presented aspects, wherein the second material is a gas.

16. The apparatus according to any one of the herein presented aspects, wherein the second material comprises a plurality of volumes of gas enclosed by an enclosing material.

17. The apparatus according to any one of the herein presented aspects, wherein the plurality of volumes of gas enclosed by an enclosing material makes up at least 10 volume percent of the volume of the second material, more preferably at least 20 volume percent of the second volume, and even more preferably at least 30 volume percent of the second volume.

18. The apparatus according to any one of the herein presented aspects, wherein the plurality of volumes of gas enclosed by an enclosing material makes up at least 40 volume percent of the volume of the second material, more preferably at least 50 volume percent of the second volume.

19. The apparatus according to any one of the herein presented aspects, wherein the plurality of volumes of gas enclosed by an enclosing material makes up at least 60 volume percent of the volume of the second material, more preferably at least 70 volume percent of the second volume.

20. The apparatus according to any one of the herein presented aspects, wherein the plurality of volumes of gas enclosed by an enclosing material makes up at least 80 volume percent of the volume of the second material, more preferably at least 90 volume percent of the second volume.

21. The apparatus according to any one of the preceding aspects, wherein the implantable movement restriction device comprises an outer surface configured to rest against the stomach wall portion, and wherein an average surface roughness measured on the outer surface is no more than 300'000 μm.

22. The apparatus (100) according to any one of the herein presented aspects, wherein the average surface roughness is $R_a$ as defined according to ISO 21920-2:2021.

23. The apparatus (100) according to any one of the herein presented aspects, wherein the average surface roughness is $S_a$ as defined according to ISO 25178-2:2021.

24. The apparatus (100) according to any one of aspects 22-24, wherein the average surface roughness is in the range of at least one of; 0.01-0.1 μm, >0.1-0.5 μm, >0.5-10 μm, >10-80 μm, >80-200 μm, >200-10'000 μm, >10'000-500'000 μm.

25. The apparatus (100) according to any one of the herein presented aspects, wherein the average surface roughness is in the range of 0.1-0.3 mm.

26. The apparatus according to any one of the preceding aspects, wherein an indentation hardness on the Shore A scale measured on the outer surface of the movement restriction device is at least 50.

27. The apparatus according to any one of the herein presented aspects, wherein the indentation hardness is measured by the durometer method defined in part 4 of ISO 48-4:2018.

28. The apparatus according to any one of the herein presented aspects, wherein an indentation hardness on the Shore A scale measured on the outer surface is no more than 65.

29. The apparatus according to any one of the herein presented aspects, wherein an indentation hardness on the Shore A scale measured on the outer surface is in the range of 50 to 65.

30. The apparatus according to any one of the herein presented aspects, wherein an indentation hardness on the Shore A scale measured on the outer surface is in the range of 5-25 or >25-50, or >65.

31. The apparatus according to any one of the herein presented aspects, wherein the implantable movement restriction device comprises a contrast agent.

32. The apparatus according to any one of the herein presented aspects, wherein the contrast agent is BaSO4.

33. The apparatus according to any one of the herein presented aspects, wherein the implantable movement restriction device comprises the contrast agent in an amount of 1-15% by weight of the implantable movement restriction device.

34. The apparatus according to any one of the herein presented aspects, wherein the implantable movement restriction device comprises the contrast agent in an amount of 1-6% by weight of the implantable movement restriction device.

35. The apparatus according to any one of the herein presented aspects, the implantable movement restriction device comprises the contrast agent in an amount of 8-15% by weight of the implantable movement restriction device.

Aspect Group 449PPC: Reflux Device Configuration Wedge_1

1. An implantable medical device for treating reflux disease, the implantable medical device comprising a movement restriction device configured to be fixated to the stomach wall for hindering movement of the lower esophageal sphincter relative to the thoracic diaphragm, the movement restriction device comprises:

a. a central part, and b. at least two outer parts, wherein the central part and the at least two outer parts are configured to be connected to each other for forming at least a portion of a functional movement restriction device, the central part and the at least two outer parts are capable of disconnecting from each other, such that the central part and the at least two outer parts individually can pass through the gastro-intestinal tract, wherein at least one of the two outer parts comprises a wedge-shaped portion and wherein the central part comprises a wedge-shaped portion, and wherein the wedge-shaped portion of the at least one outer part is configured to be placed in the wedge-shaped portion of the central part, and wherein:

the wedge-shaped portion of the at least one outer part is wedge-shaped with a first angle, and the wedge-shaped portion of the central part is wedge-shaped with a second angle, and wherein the first angle is more than 7° larger than the second angle.

2. The implantable medical device according to aspect 1, wherein the first angle is more than 10° larger than the second angle.

3. The implantable medical device according to aspect 2, wherein the first angle is more than 12° larger than the second angle.

4. The implantable medical device according to aspect 3, wherein the first angle is more than 15° larger than the second angle.

5. The implantable medical device according to any one of aspects 1-4, wherein the wedge-shaped portion of the at least one outer part comprises a wedge-shaped recess.

6. The implantable medical device according to any one of aspects 1-4, wherein the wedge-shaped portion of the at least one outer part comprises a wedge-shaped protrusion.

7. The implantable medical device according to any one of aspects 1-4 or 6, wherein the wedge-shaped portion of the central part comprises a wedge-shaped recess.

8. The implantable medical device according to any one of aspects 1-4 or 5, wherein the wedge-shaped portion of the central part comprises a wedge-shaped protrusion.

9. The apparatus according to any one of the preceding aspects, wherein the implantable movement restriction device (110) comprises a first portion having a first volume enclosed by material of the implantable movement restriction device (110), and a second portion, different from the first portion, having a second volume enclosed by material of the implantable movement restriction device (110), wherein:

the first volume has a higher density than the second volume, and the second volume has a density below 1000 kg/m3.

10. The apparatus according to aspect 9, wherein the first volume comprises a first solid material.

11. The apparatus according to aspect 10, wherein the first solid material comprises a polymer material, a metal, a ceramic or carbon material or a mixture thereof.

12. The apparatus according to aspect 11, wherein the first solid material comprises at least one of silicone-based material and a polyurethane-based material, an ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.

13. The apparatus according to any one of aspects 9-12, wherein the second volume comprises a second solid material.

14. The apparatus according to aspect 13, wherein the second solid material comprises a polymer material, a metal, a ceramic or carbon material or a mixture thereof.

15. The apparatus according to aspect 14, wherein the second solid material comprises a at least one of a polypropylene-based and a polyethylene-based material, an ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.

16. The apparatus according to any one of aspects 13-15, wherein the first volume comprises a solid material having a density above 1000 kg/m3 and the second volume comprises a solid material having a density below 1000 kg/m3.

17. The apparatus according to any one of aspects 9-16, wherein the second volume comprises a gas.

18. The apparatus according to any one of aspects 9-17, wherein the second volume comprises a plurality of volumes of gas enclosed by an enclosing material.

19. The apparatus according to aspect 18, wherein the second volume comprises a solid polymer material enclosing the enclosing material, and wherein the enclosing material is harder than the solid polymer material.

20. The apparatus according to any one of aspects 18 and 19, wherein the plurality of volumes of gas enclosed by an enclosing material makes up at least 10 volume percent of the second volume, more preferably at least 20 volume percent of the second volume, and even more preferably at least 30 volume percent of the second volume, and even more preferably at least 40 volume percent of the second volume, and even more preferably at least 50 volume percent of the second volume, and even more preferably at least 60 volume percent of the second volume, and even more preferably at least 70 volume percent of the second volume, and even more preferably at least 80 volume percent of the second volume, and even more preferably at least 90 volume percent of the second volume.

21. The apparatus according to any one of aspects 18-20, wherein the enclosing material comprises glass.

22. The apparatus according to any one of the preceding aspects, wherein the implantable movement restriction device comprises an outer surface configured to rest against the stomach wall portion, and wherein an average surface roughness measured on the outer surface is no more than 300'000 μm.

23. The apparatus (100) according to aspect 22, wherein the average surface roughness is $R_a$ as defined according to ISO 21920-2:2021.

24. The apparatus (100) according to aspect 22, wherein the average surface roughness is $S_a$ as defined according to ISO 25178-2:2021.

25. The apparatus (100) according to any one of aspects 22-24, wherein the average surface roughness is in the range of at least one of; 0.01-0.1 μm, >0.1-0.5 μm, >0.5-10 μm, >10-80 μm, >80-200 μm, >200-10'000 μm, >10'000-500'000 μm.

26. The apparatus (100) according to any one of aspects 22-25, wherein the average surface roughness is in the range of 0.1-0.3 mm.

27. The apparatus according to any one of the preceding aspects, wherein an indentation hardness on the Shore A scale measured on the outer surface of the movement restriction device is at least 50.

28. The apparatus according to aspect 27, wherein the indentation hardness is indentation hardness is measured by the durometer method defined in part 4 of ISO 48-4:2018.

29. The apparatus according to aspects 27-28, wherein an indentation hardness on the Shore A scale measured on the outer surface is no more than 70.

30. The apparatus according to any one of aspects 27-29, wherein an indentation hardness on the Shore A scale measured on the outer surface is in the range of 55 to 65, or 5-25 or >25-50, or >65.

31. The apparatus according to any one of the preceding aspects, wherein the implantable movement restriction device comprises a contrast agent.

32. The apparatus according to aspect 31, wherein the contrast agent is $BaSO_4$.

33. The apparatus according to aspect 31 or 32, wherein the implantable movement restriction device comprises the contrast agent in an amount of 1-15% by weight of the implantable movement restriction device.

34. The apparatus according to aspect 33, wherein the implantable movement restriction device comprises the contrast agent in an amount of 1-6% by weight of the implantable movement restriction device.

35. The apparatus according to aspect 34, the implantable movement restriction device comprises the contrast agent in an amount of 8-15% by weight of the implantable movement restriction device.

Aspect Group 449QPC: Reflux Device Configuration Wedge_2

1. An implantable medical device for treating reflux disease, the implantable medical device comprising a movement restriction device configured to be fixated to the stomach wall for hindering movement of the lower esophageal sphincter relative to the thoracic diaphragm, the movement restriction device comprises:
   - a. a central part, and
   - b. at least two outer parts, wherein the central part and the at least two outer parts are configured to be connected to each other for forming at least a portion of a functional movement restriction device, the central part and the at least two outer parts are capable of disconnecting from each other, such that the central part and the at least two outer parts individually can pass through the gastro-intestinal tract, wherein at least one of the two outer parts comprises a wedge-shaped portion and wherein the central part comprises a wedge-shaped portion, and wherein the wedge-shaped portion of the central part is configured to be placed in the wedge-shaped portion of the central part, and wherein:
   - the wedge-shaped portion of the at least one outer part is wedge-shaped with a first angle, and
   - the wedge-shaped portion of the central part is wedge-shaped with a second angle, and wherein the second angle is more than 7° larger than the first angle.

2. The implantable medical device according to aspect 1, wherein the second angle is more than 10° larger than the first angle.

3. The implantable medical device according to aspect 2, wherein the second angle is more than 12° larger than the first angle.

4. The implantable medical device according to aspect 3, wherein the second angle is more than 15° larger than the first angle.

5. The implantable medical device according to any one of aspects 1-4, wherein the wedge-shaped portion of the at least one outer part comprises a wedge-shaped recess.

6. The implantable medical device according to any one of aspects 1-4, wherein the wedge-shaped portion of the at least one outer part comprises a wedge-shaped protrusion.

7. The implantable medical device according to any one of aspects 1-4 or 6, wherein the wedge-shaped portion of the central part comprises a wedge-shaped recess.

8. The implantable medical device according to any one of aspects 1-4 or 5, wherein the wedge-shaped portion of the central part comprises a wedge-shaped protrusion.

9. The apparatus according to any one of the preceding aspects, wherein the implantable movement restriction device (110) comprises
   - a first portion having a first volume enclosed by material of the implantable movement restriction device (110), and
   - a second portion, different from the first portion, having a second volume enclosed by material of the implantable movement restriction device (110), wherein:
     - the first volume has a higher density than the second volume, and the second volume has a density below 1000 kg/m3.

10. The apparatus according to aspect 9, wherein the first volume comprises a first solid material.

11. The apparatus according to aspect 10, wherein the first solid material comprises a polymer material, a metal, a ceramic or carbon material or a mixture thereof.

12. The apparatus according to aspect 11, wherein the first solid material comprises at least one of silicone-based material and a polyurethane-based material, an ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.

13. The apparatus according to any one of aspects 9-12, wherein the second volume comprises a second solid material.

14. The apparatus according to aspect 13, wherein the second solid material comprises a polymer material, a metal, a ceramic or carbon material or a mixture thereof.

15. The apparatus according to aspect 14, wherein the second solid material comprises a at least one of a polypropylene-based and a polyethylene-based material, an ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.

16. The apparatus according to any one of aspects 13-15, wherein the first volume comprises a solid material having a density above 1000 kg/m3 and the second volume comprises a solid material having a density below 1000 kg/m3.

17. The apparatus according to any one of aspects 9-16, wherein the second volume comprises a gas.

18. The apparatus according to any one of aspects 9-17, wherein the second volume comprises a plurality of volumes of gas enclosed by an enclosing material.

19. The apparatus according to aspect 18, wherein the second volume comprises a solid polymer material enclosing the enclosing material, and wherein the enclosing material is harder than the solid polymer material.

20. The apparatus according to any one of aspects 18 and 19, wherein the plurality of volumes of gas enclosed by an enclosing material makes up at least 10 volume percent of the second volume, more preferably at least 20 volume percent of the second volume, and even more preferably at least 30 volume percent of the second volume, and even more preferably at least 40 volume percent of the second volume, and even more preferably at least 50 volume percent of the second volume, and even more preferably at least 60 volume percent of the second volume, and even more preferably at least 70 volume percent of the second volume, and even more preferably at least 80 volume percent of the second volume, and even more preferably at least 90 volume percent of the second volume.

21. The apparatus according to any one of aspects 18-20, wherein the enclosing material comprises glass.

22. The apparatus according to any one of the preceding aspects, wherein the implantable movement restriction device comprises an outer surface configured to rest against the stomach wall portion, and wherein an average surface roughness measured on the outer surface is no more than 300'000 μm.

23. The apparatus (100) according to aspect 22, wherein the average surface roughness is $R_a$ as defined according to ISO 21920-2:202.1.

24. The apparatus (100) according to aspect 22, wherein the average surface roughness is $S_a$ as defined according to ISO 25178-2:2021.

25. The apparatus (100) according to any one of aspects 22-24, wherein the average surface roughness is in the range of at least one of; 0.01-0.1 μm, >0.1-0.5 μm, >0.5-10 μm, >10-80 μm, >80-200 μm, >200-10'000 μm, >10'000-500'000 μm.

26. The apparatus (100) according to any one of aspects 22-25, wherein the average surface roughness is in the range of 0.1-0.3 mm.

27. The apparatus according to any one of the preceding aspects, wherein an indentation hardness on the Shore A scale measured on the outer surface of the movement restriction device is at least 50.

28. The apparatus according to aspect 27, wherein the indentation hardness is indentation hardness is measured by the durometer method defined in part 4 of ISO 48-4:2018.

29. The apparatus according to aspects 27-28, wherein an indentation hardness on the Shore A scale measured on the outer surface is no more than 70.

30. The apparatus according to any one of aspects 27-29, wherein an indentation hardness on the Shore A scale measured on the outer surface is in the range of 55 to 65, or 5-25 or >25-50, or >65.

31. The apparatus according to any one of the preceding aspects, wherein the implantable movement restriction device comprises a contrast agent.

32. The apparatus according to aspect 31, wherein the contrast agent is BaSO4.

33. The apparatus according to aspect 31 or 32, wherein the implantable movement restriction device comprises the contrast agent in an amount of 1-15% by weight of the implantable movement restriction device.

34. The apparatus according to aspect 33, wherein the implantable movement restriction device comprises the contrast agent in an amount of 1-6% by weight of the implantable movement restriction device.

35. The apparatus according to aspect 34, the implantable movement restriction device comprises the contrast agent in an amount of 8-15% by weight of the implantable movement restriction device.

Aspect Group 449RPC: Reflux Device Configuration Curved Surfaces

1. An implantable medical device for treating reflux disease, the implantable medical device comprising a movement restriction device configured to be fixated to the stomach wall for hindering movement of the lower esophageal sphincter relative to the thoracic diaphragm, the movement restriction device comprises:

a. a central part, and b. at least two outer parts, wherein the central part and the at least two outer parts are configured to be connected to each other for forming at least a portion of a functional movement restriction device, the central part and the at least two outer parts are capable of disconnecting from each other, such that the central part and the at least two outer parts individually can pass through the gastro-intestinal tract, wherein at least one of the two outer parts comprises a contacting surface configured to be placed in contact with a contacting surface of the central part, and wherein at least one of:

- the contacting surface of the at least one outer part is curved, and
- the contacting surface of the central part is curved.

2. The implantable medical device according to aspect 1, wherein at least one of:

- the contacting surface of the at least one outer part is convex, and
- the contacting surface of the central part is convex.

3. The implantable medical device according to aspect 1, wherein at least one of:

- the contacting surface of the at least one outer part is concave, and
- the contacting surface of the central part is concave.

4. The implantable medical device according to any one of aspects 1 and 2, wherein at least one of:

- the contacting surface of the at least one outer part comprises an elliptic point, and
- the contacting surface of the central part comprises an elliptic point.

5. The implantable medical device according to any one of the preceding aspects wherein the contacting surface of the at least one outer part contacts the contacting surface of the central part over less than half of the area of the contacting surface of the at least one outer part.

6. The implantable medical device according to aspect 5 wherein the contacting surface of the at least one outer part contacts the contacting surface of the central part over less than one third of the area of the contacting surface of the at least one outer part.

7. The implantable medical device according to any one of aspects 1-6, wherein the functional movement restriction device has a height in the range 3.5 cm-6 cm, or in the range 4 cm-5 cm, or in the range 4 cm-6 cm.

8. The implantable medical device according to any one of the preceding aspects, wherein at least one of the functional movement restriction device and the boundary of the functional movement restriction device has a surface area in the range 25 $cm^2$-50 $cm^2$, or in the range 25 $cm^2$-40 $cm^2$.

9. The apparatus according to any one of the preceding aspects, wherein the implantable movement restriction device (110) comprises

- a first portion having a first volume enclosed by material of the implantable movement restriction device (110), and
- a second portion, different from the first portion, having a second volume enclosed by material of the implantable movement restriction device (110), wherein:
  - the first volume has a higher density than the second volume, and the second volume has a density below 1000 kg/m3.

10. The apparatus according to aspect 9, wherein the first volume comprises a first solid material.

11. The apparatus according to aspect 10, wherein the first solid material comprises a polymer material, a metal, a ceramic or carbon material or a mixture thereof.

12. The apparatus according to aspect 11, wherein the first solid material comprises at least one of silicone-based material and a polyurethane-based material, an ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.

13. The apparatus according to any one of aspects 9-12, wherein the second volume comprises a second solid material.

14. The apparatus according to aspect 13, wherein the second solid material comprises a polymer material, a metal, a ceramic or carbon material or a mixture thereof.

15. The apparatus according to aspect 14, wherein the second solid material comprises a at least one of a polypropylene-based and a polyethylene-based material, an ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.

16. The apparatus according to any one of aspects 13-15, wherein the first volume comprises a solid material having a density above 1000 kg/m3 and the second volume comprises a solid material having a density below 1000 kg/m3.

17. The apparatus according to any one of aspects 9-16, wherein the second volume comprises a gas.

18. The apparatus according to any one of aspects 9-17, wherein the second volume comprises a plurality of volumes of gas enclosed by an enclosing material.

19. The apparatus according to aspect 18, wherein the second volume comprises a solid polymer material enclosing the enclosing material, and wherein the enclosing material is harder than the solid polymer material.

20. The apparatus according to any one of aspects 18 and 19, wherein the plurality of volumes of gas enclosed by an enclosing material makes up at least 10 volume percent of the second volume, more preferably at least 20 volume percent of the second volume, and even more preferably at least 30 volume percent of the second volume, and even more preferably at least 40 volume percent of the second volume, and even more preferably at least 50 volume percent of the second volume, and even more preferably at least 60 volume percent of the second volume, and even more preferably at least 70 volume percent of the second volume, and even more preferably at least 80 volume percent of the second volume, and even more preferably at least 90 volume percent of the second volume.

21. The apparatus according to any one of aspects 18-20, wherein the enclosing material comprises glass.

22. The apparatus according to any one of the preceding aspects, wherein the implantable movement restriction device comprises an outer surface configured to rest against the stomach wall portion, and wherein an average surface roughness measured on the outer surface is no more than 300'000 μm.

23. The apparatus (100) according to aspect 22, wherein the average surface roughness is $R_a$ as defined according to ISO 21920-2:2021.

24. The apparatus (100) according to aspect 22, wherein the average surface roughness is $S_a$ as defined according to ISO 25178-2:2021.

25. The apparatus (100) according to any one of aspects 22-24, wherein the average surface roughness is in the range of at least one of: 0.01-0.1 μm, >0.1-0.5 μm, >0.5-10 μm, >10-80 μm, >80-200 μm, >200-10'000 μm, >10'000-500'000 μm.

26. The apparatus (100) according to any one of aspects 22-25, wherein the average surface roughness is in the range of 0.1-0.3 mm.

27. The apparatus according to any one of the preceding aspects, wherein an indentation hardness on the Shore A scale measured on the outer surface of the movement restriction device is at least 50.

28. The apparatus according to aspect 27, wherein the indentation hardness is indentation hardness is measured by the durometer method defined in part 4 of ISO 48-4:2018.

29. The apparatus according to aspects 27-28, wherein an indentation hardness on the Shore A scale measured on the outer surface is no more than 70.

30. The apparatus according to any one of aspects 27-29, wherein an indentation hardness on the Shore A scale measured on the outer surface is in the range of 55 to 65, or 5-25 or >25, 50, or >65.

31. The apparatus according to any one of the preceding aspects, wherein the implantable movement restriction device comprises a contrast agent.

32. The apparatus according to aspect 31, wherein the contrast agent is $BaSO_4$.

33. The apparatus according to aspect 31 or 32, wherein the implantable movement restriction device comprises the contrast agent in an amount of 1-15% by weight of the implantable movement restriction device.

34. The apparatus according to aspect 33, wherein the implantable movement restriction device comprises the contrast agent in an amount of 1-6% by weight of the implantable movement restriction device.

35. The apparatus according to aspect 34, the implantable movement restriction device comprises the contrast agent in an amount of 8-15% by weight of the implantable movement restriction device.

Aspect Group 449SPC: Reflux Device Configuration Vertical Rims

1. An implantable medical device for treating reflux disease, the implantable medical device comprising a movement restriction device configured to be hindering movement of the lower esophageal sphincter relative to the thoracic diaphragm, the movement restriction device comprises:

a. a central part, and b. at least two outer parts, wherein the central part and the at least two outer parts are configured to be connected to each other for forming at least a portion of a functional movement restriction device, the central part and the at least two outer parts are capable of disconnecting from each other, such that the central part and the at least two outer parts individually can pass through the gastro-intestinal tract, wherein the central part comprises at least three vertically extending rims being spaced apart, and wherein each the at least three vertically extending rims have at least one contacting surface configured to contact at least one surface of the at least two outer parts, and wherein at least a portion of the at least three vertically extending rims is wedge-shaped with an angle in the range 20°-60°.

2. The implantable medical device according to aspect 1, wherein a portion of the at least three vertically extending rims is wedge-shaped with an angle exceeding 25°, or an angle exceeding 30°, or an angle exceeding 35°.

3. The implantable medical device according to any one of aspects 1-2, wherein the wedge-shaped portion of the at least one vertically extending rim is tapered in a direction away from the center of gravity of the central part.

4. The implantable medical device according to any one of aspects 1-2, wherein the vertically extending rim having the wedge-shaped portion is elongated, and wherein the wedge-shaped portion of the vertically extending rim is tapered in a direction of the elongation of the vertically extending rim.

5. The implantable medical device according to any one of aspects 1-4, further comprising at least one horizontally extending rim extending substantially perpendicularly from at least one of the vertically extending rims.

6. The implantable medical device according to aspects 5, wherein the horizontally extending rim comprises a wedge-shaped portion.

7. The implantable medical device according to aspects 6, wherein the wedge-shaped portion of the horizontally extending rim is tapered in a direction away from the center of gravity of the central part.

8. The implantable medical device according to any one of aspects 6 and 7, wherein the wedge-shaped portion of the horizontally extending rim is wedge-shaped with an angle in the range 20°-60°.

9. The apparatus according to any one of the preceding aspects, wherein the implantable movement restriction device (110) comprises a first portion having a first volume enclosed by material of the implantable movement restriction device (110), and a second portion, different from the first portion, having a second volume enclosed by material of the implantable movement restriction device (110), wherein:

the first volume has a higher density than the second volume, and the second volume has a density below 1000 kg/m3.

10. The apparatus according to aspect 9, wherein the first volume comprises a first solid material.

11. The apparatus according to aspect 10, wherein the first solid material comprises a polymer material, a metal, a ceramic or carbon material or a mixture thereof.

12. The apparatus according to aspect 11, wherein the first solid material comprises at least one of silicone-based material and a polyurethane-based material, an ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.

13. The apparatus according to any one of aspects 9-12, wherein the second volume comprises a second solid material.

14. The apparatus according to aspect 13, wherein the second solid material comprises a polymer material, a metal, a ceramic or carbon material or a mixture thereof.

15. The apparatus according to aspect 14, wherein the second solid material comprises a at least one of a polypropylene-based and a polyethylene-based material, an ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.

16. The apparatus according to any one of aspects 13-15, wherein the first volume comprises a solid material having a density above 1000 kg/m3 and the second volume comprises a solid material having a density below 1000 kg/m3.

17. The apparatus according to any one of aspects 9-16, wherein the second volume comprises a gas.

18. The apparatus according to any one of aspects 9-17, wherein the second volume comprises a plurality of volumes of gas enclosed by an enclosing material.

19. The apparatus according to aspect 18, wherein the second volume comprises a solid polymer material enclosing the enclosing material, and wherein the enclosing material is harder than the solid polymer material.

20. The apparatus according to any one of aspects 18 and 19, wherein the plurality of volumes of gas enclosed by an enclosing material makes up at least 10 volume percent of the second volume, more preferably at least 20 volume percent of the second volume, and even more preferably at least 30 volume percent of the second volume, and even more preferably at least 40 volume percent of the second volume, and even more preferably at least 50 volume percent of the second volume, and even more preferably at least 60 volume percent of the second volume, and even more preferably at least 70 volume percent of the second volume, and even more preferably at least 80 volume percent of the second volume, and even more preferably at least 90 volume percent of the second volume.

21. The apparatus according to any one of aspects 18-20, wherein the enclosing material comprises glass.

22. The apparatus according to any one of the preceding aspects, wherein the implantable movement restriction device comprises an outer surface configured to rest against the stomach wall portion, and wherein an average surface roughness measured on the outer surface is no more than 300'000 μm.

23. The apparatus (100) according to aspect 22, wherein the average surface roughness is $R_a$ as defined according to ISO 21920-2:2021.

24. The apparatus (100) according to aspect 22, wherein the average surface roughness is $S_a$ as defined according to ISO 25178-2:2021.

25. The apparatus (100) according to any one of aspects 22-24, wherein the average surface roughness is in the range of at least one of: 0.01-0.1 μm, >0.1-0.5 μm, >0.5-10μ, >10-80 μm, >80-200 μm, >200-10'000 μm, >10'000-500'000 μm.

26. The apparatus (100) according to any one of aspects 22-25, wherein the average surface roughness is in the range of 0.1-0.3 mm.

27. The apparatus according to any one of the preceding aspects, wherein an indentation hardness on the Shore A scale measured on the outer surface of the movement restriction device is at least 50.

28. The apparatus according to aspect 27, wherein the indentation hardness is indentation hardness is measured by the durometer method defined in part 4 of ISO 48-4:2018.

29. The apparatus according to aspects 27-28, wherein an indentation hardness on the Shore A scale measured on the outer surface is no more than 70.

30. The apparatus according to any one of aspects 27-29, wherein an indentation hardness on the Shore A scale measured on the outer surface is in the range of 55 to 65, or 5-25 or >25-50, or >65.

31. The apparatus according to any one of the preceding aspects, wherein the implantable movement restriction device comprises a contrast agent.

32. The apparatus according to aspect 31, wherein the contrast agent is BaSO4.

33. The apparatus according to aspect 31 or 32, wherein the implantable movement restriction device comprises the contrast agent in an amount of 1-15% by weight of the implantable movement restriction device.

34. The apparatus according to aspect 33, wherein the implantable movement restriction device comprises the contrast agent in an amount of 1-6% by weight of the implantable movement restriction device.

35. The apparatus according to aspect 34, the implantable movement restriction device comprises the contrast agent in an amount of 8-15% by weight of the implantable movement restriction device.

Aspect Group 449TPC: Reflux Device Configuration Horizontal Rim

1. An implantable medical device for treating reflux disease, the implantable medical device comprising a movement restriction device configured to be hindering movement of the lower esophageal sphincter relative to the thoracic diaphragm, the movement restriction device comprises:

a. a central part, and b. at least two outer parts, wherein the at least two outer parts are configured to be connected to each other along a vertical plane and wherein the at least two outer parts are configured to be connected to the central part for forming at least a portion of a functional movement restriction device, the central part and the at least two outer parts are capable of disconnecting from each other, such that the central part and the at least two outer parts individually can pass through the gastro-intestinal tract, wherein the central part comprises at least one horizontally extending rim extending in a direction perpendicular to the vertical plane and wherein the central part has at least one contacting surface configured to contact at least one surface of the at least two outer parts, and wherein a portion of the horizontally extending rim is wedge-shaped with an angle in the range 20°-60°.

2. The implantable medical device according to aspect 1, wherein the portion of the horizontally extending rim is wedge-shaped with an angle exceeding 25°.

3. The implantable medical device according to aspect 1, wherein a portion of the horizontally extending rim is wedge-shaped with an angle exceeding 30° or exceeding 35°.

4. The implantable medical device according to any one of aspects 1-4, wherein the wedge-shaped portion of the horizontally extending rim is tapered in a direction away from the center of gravity of the central part.

5. The implantable medical device according to any one of aspects 1-5, further comprising at least two vertically extending rims extending substantially perpendicularly from the horizontally extending rim.

6. The implantable medical device according to aspects 6, wherein the vertically extending rims comprises wedge-shaped portions.

7. The implantable medical device according to aspects 7, wherein the wedge-shaped portion of the vertically extending rims are tapered in a direction away from the center of gravity of the central part.

8. The implantable medical device according to any one of aspects 7 and 8, wherein the wedge-shaped portions of the vertically extending rims are wedge-shaped with an angle in the range 20°-60°.

9. The apparatus according to any one of the preceding aspects, wherein the implantable movement restriction device (110) comprises a first portion having a first volume enclosed by material of the implantable movement restriction device (110), and a second portion, different from the first portion, having a second volume enclosed by material of the implantable movement restriction device (110), wherein:

the first volume has a higher density than the second volume, and the second volume has a density below 1000 kg/m3.

10. The apparatus according to aspect 9, wherein the first volume comprises a first solid material.

11. The apparatus according to aspect 10, wherein the first solid material comprises a polymer material, a metal, a ceramic or carbon material or a mixture thereof.

12. The apparatus according to aspect 11, wherein the first solid material comprises at least one of silicone-based material and a polyurethane-based material, an ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.

13. The apparatus according to any one of aspects 9-12, wherein the second volume comprises a second solid material.

14. The apparatus according to aspect 13, wherein the second solid material comprises a polymer material, a metal, a ceramic or carbon material or a mixture thereof.

15. The apparatus according to aspect 14, wherein the second solid material comprises a at least one of a polypropylene-based and a polyethylene-based material, an ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.

16. The apparatus according to any one of aspects 13-15, wherein the first volume comprises a solid material having a density above 1000 kg/m3 and the second volume comprises a solid material having a density below 1000 kg/m3.

17. The apparatus according to any one of aspects 9-16, wherein the second volume comprises a gas.

18. The apparatus according to any one of aspects 9-17, wherein the second volume comprises a plurality of volumes of gas enclosed by an enclosing material.

19. The apparatus according to aspect 18, wherein the second volume comprises a solid polymer material enclosing the enclosing material, and wherein the enclosing material is harder than the solid polymer material.

20. The apparatus according to any one of aspects 18 and 19, wherein the plurality of volumes of gas enclosed by an enclosing material makes up at least 10 volume percent of the second volume, more preferably at least 20 volume percent of the second volume, and even more preferably at least 30 volume percent of the second volume, and even more preferably at least 40 volume percent of the second volume, and even more preferably at least 50 volume percent of the second volume, and even more preferably at least 60 volume percent of the second volume, and even more preferably at least 70 volume percent of the second volume, and even more preferably at least 80 volume percent of the second volume, and even more preferably at least 90 volume percent of the second volume.

21. The apparatus according to any one of aspects 18-20, wherein the enclosing material comprises glass.

22. The apparatus according to any one of the preceding aspects, wherein the implantable movement restriction device comprises an outer surface configured to rest against the stomach wall portion, and wherein an average surface roughness measured on the outer surface is no more than 300'000 μm.

23. The apparatus (100) according to aspect 22, wherein the average surface roughness is $R_a$ as defined according to ISO 21920-2:2021.

24. The apparatus (100) according to aspect 22, wherein the average surface roughness is $S_a$ as defined according to ISO 25178-2:2021.

25. The apparatus (100) according to any one of aspects 22-24, wherein the average surface roughness is in the range of at least one of; 0.01-0.1 μm, >0.1-0.5 μm, >0.5-10 μm, >10-80 μm, >80-200 μm, >200-10'000 μm, >10'000-500'000 μm.

26. The apparatus (100) according to any one of aspects 22-25, wherein the average surface roughness is in the range of 0.1-0.3 mm.

27. The apparatus according to any one of the preceding aspects, wherein an indentation hardness on the Shore A scale measured on the outer surface of the movement restriction device is at least 50.

28. The apparatus according to aspect 27, wherein the indentation hardness is indentation hardness is measured by the durometer method defined in part 4 of ISO 48-4:2018.

29. The apparatus according to aspects 27-28, wherein an indentation hardness on the Shore A scale measured on the outer surface is no more than 70.

30. The apparatus according to any one of aspects 27-29, wherein an indentation hardness on the Shore A scale measured on the outer surface is in the range of 55 to 65, or 5-25 or >25-50, or >65.

31. The apparatus according to any one of the preceding aspects, wherein the implantable movement restriction device comprises a contrast agent.

32. The apparatus according to aspect 31, wherein the contrast agent is BaSO4.

33. The apparatus according to aspect 31 or 32, wherein the implantable movement restriction device comprises the contrast agent in an amount of 1-15% by weight of the implantable movement restriction device.

34. The apparatus according to aspect 33, wherein the implantable movement restriction device comprises the contrast agent in an amount of 1-6% by weight of the implantable movement restriction device.

35. The apparatus according to aspect 34, the implantable movement restriction device comprises the contrast agent in an amount of 8-15% by weight of the implantable movement restriction device.

Aspect Group 449UPC: Reflux Device Configuration Central Part Mass

1. An implantable medical device for treating reflux disease, the implantable medical device comprising a movement restriction device configured to be hindering movement of the lower esophageal sphincter relative to the thoracic diaphragm, the movement restriction device comprises:

a. a central part, and b. at least two outer parts, wherein the at least two outer parts are configured to be connected to each other along a vertical plane and wherein the at least two outer parts are configured to be connected to the central part for forming at least a portion of a functional movement restriction device, the central part and the at least two outer parts are capable of disconnecting from each other, such that the central part and the at least two outer parts individually can pass through the gastro-intestinal tract, wherein the mass of the central part exceeds the mass of at least one of the outer parts.

2. The implantable medical device according to aspect 1, wherein the mass of the central part exceeds the mass of at least one of the outer parts by at least 10%.

3. The implantable medical device according to aspect 1, wherein the mass of the central part exceeds the mass of at least one of the outer parts by at least 20%.

4. The implantable medical device according to aspect 1, wherein the mass of the central part exceeds the mass of at least one of the outer parts by at least 30%.

5. The implantable medical device according to any one of aspects 1-4, wherein the volume of the central part exceeds the volume of at least one of the outer parts by at least 10%.

6. The implantable medical device according to aspect 1, wherein the volume of the central part exceeds the volume of at least one of the outer parts by at least 20%.

7. The implantable medical device according to aspect 1, wherein the volume of the central part exceeds the volume of at least one of the outer parts by at least 30%.

8. The implantable medical device according to aspect 1, wherein the volume of the central part exceeds the volume of at least one of the outer parts by at least 40%.

9. The apparatus according to any one of the preceding aspects, wherein the implantable movement restriction device (110) comprises a first portion having a first volume enclosed by material of the implantable movement restriction device (110), and a second portion, different from the first portion, having a second volume enclosed by material of the implantable movement restriction device (110), wherein:

the first volume has a higher density than the second volume, and the second volume has a density below 1000 kg/m3.

10. The apparatus according to aspect 9, wherein the first volume comprises a first solid material.

11. The apparatus according to aspect 10, wherein the first solid material comprises a polymer material, a metal, a ceramic or carbon material or a mixture thereof.

12. The apparatus according to aspect 11, wherein the first solid material comprises at least one of silicone-based material and a polyurethane-based material, an ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.

13. The apparatus according to any one of aspects 9-12, wherein the second volume comprises a second solid material.

14. The apparatus according to aspect 13, wherein the second solid material comprises a polymer material, a metal, a ceramic or carbon material or a mixture thereof.

15. The apparatus according to aspect 14, wherein the second solid material comprises a at least one of a polypropylene-based and a polyethylene-based material, an ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.

16. The apparatus according to any one of aspects 13-15, wherein the first volume comprises a solid material having a density above 1000 kg/m3 and the second volume comprises a solid material having a density below 1000 kg/m3.

17. The apparatus according to any one of aspects 9-16, wherein the second volume comprises a gas.

18. The apparatus according to any one of aspects 9-17, wherein the second volume comprises a plurality of volumes of gas enclosed by an enclosing material.

19. The apparatus according to aspect 18, wherein the second volume comprises a solid polymer material enclosing the enclosing material, and wherein the enclosing material is harder than the solid polymer material.

20. The apparatus according to any one of aspects 18 and 19, wherein the plurality of volumes of gas enclosed by an enclosing material makes up at least 10 volume percent of the second volume, more preferably at least 20 volume percent of the second volume, and even more preferably at least 30 volume percent of the second volume, and even more preferably at least 40 volume percent of the second volume, and even more preferably at least 50 volume percent of the second volume, and even more preferably at least 60 volume percent of the second volume, and even more preferably at least 70 volume percent of the second volume, and even more preferably at least 80 volume percent of the second volume, and even more preferably at least 90 volume percent of the second volume.

21. The apparatus according to any one of aspects 18-20, wherein the enclosing material comprises glass.

22. The apparatus according to any one of the preceding aspects, wherein the implantable movement restriction device comprises an outer surface configured to rest against the stomach wall portion, and wherein an average surface roughness measured on the outer surface is more than 300'000 μm.

23. The apparatus (100) according to aspect 22, wherein the average surface roughness is $R_a$ as defined according to ISO 21920-2:2021.

24. The apparatus (100) according to aspect 22, wherein the average surface roughness is $S_a$ as defined according to ISO 25178-2:2021.

25. The apparatus (100) according to any one of aspects 22-24, wherein the average surface roughness is in the range of at least one of; 0.01-0.1 μm, >0.1-0.5 μm, >0.5-10 μm, >10-80 μm, >80-200 μm, >200-10'000 μm, >10'000-500'000 μm.

26. The apparatus (100) according to any one of aspects 22-25, wherein the average surface roughness is in the range of 0.1-0.3 mm.

27. The apparatus according to any one of the preceding aspects, wherein an indentation hardness on the Shore A scale measured on the outer surface of the movement restriction device is at least 50.

28. The apparatus according to aspect 27, wherein the indentation hardness is indentation hardness is measured by the durometer method defined in part 4 of ISO 48-4:2018.

29. The apparatus according to aspects 27-28, wherein an indentation hardness on the Shore A scale measured on the outer surface is no more than 70.

30. The apparatus according to any one of aspects 27-29, wherein an indentation hardness on the Shore A scale measured on the outer surface is in the range of 55 to 65, or 5-25 or >25-50, or >65.

31. The apparatus according to any one of the preceding aspects, wherein the implantable movement restriction device comprises a contrast agent.

32. The apparatus according to aspect 31, wherein the contrast agent is $BaSO_4$.

33. The apparatus according to aspect 31 or 32, wherein the implantable movement restriction device comprises the contrast agent in an amount of 1-15% by weight of the implantable movement restriction device.

34. The apparatus according to aspect 33, wherein the implantable movement restriction device comprises the contrast agent in an amount of 1-6% by weight of the implantable movement restriction device.

35. The apparatus according to aspect 34, the implantable movement restriction device comprises the contrast agent in an amount of 8-15% by weight of the implantable movement restriction device.

Aspect Group 449VPC: Reflux Device Configuration Distance

1. An implantable medical device for treating reflux disease, the implantable medical device comprising a movement restriction device configured to be hindering movement of the lower esophageal sphincter relative to the thoracic diaphragm, the movement restriction device comprises:

a. a central part, and b. at least two outer parts, wherein the at least two outer parts are configured to be connected to each other along a vertical plane and wherein the at least two outer parts are configured to be connected to the central part for forming at least a portion of a functional movement restriction device, the central part and the at least two outer parts are capable of disconnecting from each other, such that the central part and the at least two outer parts individually can pass through the gastro-intestinal tract, wherein the longest cross-sectional distance of at least one of the outer parts exceeds the longest cross-sectional distance of the central part by at least 20%.

2. The implantable medical device according to aspect 1, wherein the longest cross-sectional distance of at least one of the outer parts exceeds the longest cross-sectional distance of the central part by at least 30%.

3. The implantable medical device according to aspect 1, wherein the longest cross-sectional distance of at least one of the outer parts exceeds the longest cross-sectional distance of the central part by at least 40%.

4. The implantable medical device according to aspect 1, wherein the longest cross-sectional distance of at least one of the outer parts exceeds the longest cross-sectional distance of the central part by at least 50%.

5. The implantable medical device according to any one of the preceding aspects, wherein the longest cross-sectional distance of at least one of the outer parts is in the range 25 mm-60 mm.

6. The implantable medical device according to any one of the preceding aspects, wherein the longest cross-sectional distance of at least one of the outer parts is in the range 25 mm-50 mm.

7. The implantable medical device according to any one of the preceding aspects, wherein the longest cross-sectional distance of at least one of the outer parts is in the range 25 mm-40 mm.

8. The implantable medical device according to any one of aspects 1-6, wherein the longest cross-sectional distance of at least one of the outer parts is in the range 35 mm-60 mm.

9. The apparatus according to any one of the preceding aspects, wherein the implantable movement restriction device (110) comprises a first portion having a first volume enclosed by material of the implantable movement restriction device (110), and a second portion, different from the first portion, having a second volume enclosed by material of the implantable movement restriction device (110), wherein:

the first volume has a higher density than the second volume, and the second volume has a density below 1000 kg/m3.

10. The apparatus according to aspect 9, wherein the first volume comprises a first solid material.

11. The apparatus according to aspect 10, wherein the first solid material comprises a polymer material, a metal, a ceramic or carbon material or a mixture thereof.

12. The apparatus according to aspect 11, wherein the first solid material comprises at least one of silicone-based material and a polyurethane-based material, an ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.

13. The apparatus according to any one of aspects 9-12, wherein the second volume comprises a second solid material.

14. The apparatus according to aspect 13, wherein the second solid material comprises a polymer material, a metal, a ceramic or carbon material or a mixture thereof.

15. The apparatus according to aspect 14, wherein the second solid material comprises a at least one of a polypropylene-based and a polyethylene-based material, an ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.

16. The apparatus according to any one of aspects 13-15, wherein the first volume comprises a solid material having a density above 1000 kg/m3 and the second volume comprises a solid material having a density below 1000 kg/m3.

17. The apparatus according to any one of aspects 9-16, wherein the second volume comprises a gas.

18. The apparatus according to any one of aspects 9-17, wherein the second volume comprises a plurality of volumes of gas enclosed by an enclosing material.

19. The apparatus according to aspect 18, wherein the second volume comprises a solid polymer material enclosing the enclosing material, and wherein the enclosing material is harder than the solid polymer material.

20. The apparatus according to any one of aspects 18 and 19, wherein the plurality of volumes of gas enclosed by an enclosing material makes up at least 10 volume percent of the second volume, more preferably at least 20 volume percent of the second volume, and even more preferably at least 30 volume percent of the second volume, and even more preferably at least 40 volume percent of the second volume, and even more preferably at least 50 volume percent of the second volume, and even more preferably at least 60 volume percent of the second volume, and even more preferably at least 70 volume percent of the second volume, and even more preferably at least 80 volume percent of the second volume, and even more preferably at least 90 volume percent of the second volume.

21. The apparatus according to any one of aspects 18-20, wherein the enclosing material comprises glass.

22. The apparatus according to any one of the preceding aspects, wherein the implantable movement restriction device comprises an outer surface configured to rest against the stomach wall portion, and wherein an average surface roughness measured on the outer surface is more than 300'000 μm.

23. The apparatus (100) according to aspect 22, wherein the average surface roughness is $R_a$ as defined according to ISO 21920-2:2021.

24. The apparatus (100) according to aspect 22, wherein the average surface roughness is $S_a$ as defined according to ISO 25178-2:2021.

25. The apparatus (100) according to any one of aspects 22-24, wherein the average surface roughness is in the range of at least one of; 0.01-0.1 μm, >0.1-0.5 μm, >0.5-10μ, >10-80 μm, >80-200 μm, >200-10'000 μm, >10'000-500'000 μm.

26. The apparatus (100) according to any one of aspects 22-25, wherein the average surface roughness is in the range of 0.1-0.3 mm.

27. The apparatus according to any one of the preceding aspects, wherein an indentation hardness on the Shore A scale measured on the outer surface of the movement restriction device is at least 50.

28. The apparatus according to aspect 27, wherein the indentation hardness is indentation hardness is measured by the durometer method defined in part 4 of ISO 48-4:2018.

29. The apparatus according to aspects 27-28, wherein an indentation hardness on the Shore A scale measured on the outer surface is no more than 70.

30. The apparatus according to any one of aspects 27-29, wherein an indentation hardness on the Shore A scale measured on the outer surface is in the range of 55 to 65, or 5-25 or >25-50, or >65.

31. The apparatus according to any one of the preceding aspects, wherein the implantable movement restriction device comprises a contrast agent.

32. The apparatus according to aspect 31, wherein the contrast agent is BaSO4.

33. The apparatus according to aspect 31 or 32, wherein the implantable movement restriction device comprises the contrast agent in an amount of 1-15% by weight of the implantable movement restriction device.

34. The apparatus according to aspect 33, wherein the implantable movement restriction device comprises the contrast agent in an amount of 1-6% by weight of the implantable movement restriction device.

35. The apparatus according to aspect 34, the implantable movement restriction device comprises the contrast agent in an amount of 8-15% by weight of the implantable movement restriction device.

Aspect Group 449WPC: Reflux Device Configuration Surface

1. An implantable medical device for treating reflux disease, the implantable medical device comprising a movement restriction device configured to be hindering movement of the lower esophageal sphincter relative to the thoracic diaphragm, the movement restriction device comprises at least two parts, wherein the parts are configured to be connected to each other for forming at least a portion of a functional movement restriction device, and the at least two parts are capable of disconnecting from each other, such that the at least two parts individually can pass through the gastro-intestinal tract, wherein at least one of the functional movement restriction device and the boundary of the functional movement restriction device has a surface area in the range 20 $cm^2$-50 $cm^2$.

2. The implantable medical device according to aspect 1, wherein at least one of the functional movement restriction device and the boundary of the functional movement restriction device has a surface area in the range 22.5 $cm^2$-40 $cm^2$.

3. The implantable medical device according to aspect 2, wherein at least one of the functional movement restriction device and the boundary of the functional movement restriction device has a surface area in the range 20.5 $cm^2$-35 $cm^2$.

4. The implantable medical device according to aspect 1, wherein at least one of the functional movement restriction device and the boundary of the functional movement restriction device has a surface area in the range 20 $cm^2$-40 $cm^2$.

5. The implantable medical device according to aspect 4, wherein at least one of the functional movement restriction device and the boundary of the functional movement restriction device has a surface area in the range 20 $cm^2$-35 $cm^2$.

6. The implantable medical device according to aspect 5, wherein at least one of the functional movement restriction device and the boundary of the functional movement restriction device has a surface area in the range 20 $cm^2$-30 $cm^2$.

7. The implantable medical device according to any one of aspects 1-6, wherein the functional movement restriction device is elongated and has a height, being a longest cross-sectional distance, and a width, being a longest cross-sectional distance perpendicular to the height, and wherein the height is in the range 1.2 times-2 times longer than the width.

8. The implantable medical device according to aspect 1, wherein the height is in the range 1.3 times-2 times longer than the width.

9. The implantable medical device according to aspect 1, wherein the height is in the range 1.2 times-1.8 times longer than the width.

10. The implantable medical device according to aspect 1, wherein the height is in the range 1.3 times-1.6 times longer than the width.

11. The implantable medical device according to any one of the preceding aspects, wherein the functional movement restriction device has a height in the range 3 cm-5 cm.

12. The implantable medical device according to any one of the preceding aspects, wherein the functional movement restriction device has a height in the range 3.5 cm-6 cm.

13. The implantable medical device according to any one of the preceding aspects, wherein the functional movement restriction device has a height in the range 4 cm-5 cm.

14. The implantable medical device according to any one of the preceding aspects, wherein the functional movement restriction device has a height in the range 4 cm-6 cm.

15. The implantable medical device according to any one of the preceding aspects, further comprising a central part, wherein the at least two parts are configured to be connected to the central part for forming at least a portion of the functional movement restriction device, the central part and the at least two parts are capable of disconnecting from each other, such that the central part and the at least two parts individually can pass through the gastro-intestinal tract.

17. The apparatus according to any one of the preceding aspects, wherein the implantable movement restriction device (110) comprises a first portion having a first volume enclosed by material of the implantable movement restriction device (110), and a second portion, different from the first portion, having a second volume enclosed by material of the implantable movement restriction device (110), wherein:

the first volume has a higher density than the second volume, and the second volume has a density below 1000 kg/m3.

18. The apparatus according to aspect 17, wherein the first volume comprises a first solid material.

19. The apparatus according to aspect 18, wherein the first solid material comprises a polymer material, a metal, a ceramic or carbon material or a mixture thereof.

20. The apparatus according to aspect 19, wherein the first solid material comprises at least one of silicone-based material and a polyurethane-based material, an ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.

21. The apparatus according to any one of aspects 17-20, wherein the second volume comprises a second solid material.

22. The apparatus according to aspect 21, wherein the second solid material comprises a polymer material, a metal, a ceramic or carbon material or a mixture thereof.

23. The apparatus according to aspect 22, wherein the second solid material comprises a at least one of a polypropylene-based and a polyethylene-based material.

24. The apparatus according to any one of aspects 21-23, wherein the first volume comprises a solid material having a density above 1000 kg/m3 and the second volume comprises a solid material having a density below 1000 kg/m3.

25. The apparatus according to any one of aspects 17-24, wherein the second volume comprises a gas.

26. The apparatus according to any one of aspects 17-25, wherein the second volume comprises a plurality of volumes of gas enclosed by an enclosing material.

27. The apparatus according to aspect 26, wherein the second volume comprises a solid polymer material enclosing the enclosing material, and wherein the enclosing material is harder than the solid polymer material.

28. The apparatus according to any one of aspects 26 and 27, wherein the plurality of volumes of gas enclosed by an enclosing material makes up at least 10 volume percent of the second volume, more preferably at least 20 volume percent of the second volume, and even more preferably at least 30 volume percent of the second volume, and even more preferably at least 40 volume percent of the second volume, and even more preferably at least 50 volume percent of the second volume, and even more preferably at least 60 volume percent of the second volume, and even more preferably at least 70 volume percent of the second volume, and even more preferably at least 80 volume percent of the second volume, and even more preferably at least 90 volume percent of the second volume.

29. The apparatus according to any one of aspects 26-28, wherein the enclosing material comprises glass.

30. The apparatus according to any one of the preceding aspects, wherein the implantable movement restriction device comprises an outer surface configured to rest against the stomach wall portion, and wherein an average surface roughness measured on the outer surface is no more than 300'000 μm.

31. The apparatus (100) according to aspect 30, wherein the average surface roughness is $R_a$ as defined according to ISO 21920-2:2021.

32. The apparatus (100) according to aspect 30, wherein the average surface roughness is $S_a$ as defined according to ISO 25178-2:2021.

33. The apparatus (100) according to any one of aspects 30-32, wherein the average surface roughness is in the range of at least one of: 0.01-0.1 μm, >0.1-0.5 μm, >0.5-10 μm, >10-80 μm, >80-200 μm, >200-10'000 μm, >10'000-500'000 μm.

34. The apparatus (100) according to any one of aspects 30-33, wherein the average surface roughness is in the range of 0.1-0.3 mm.

35. The apparatus according to any one of the preceding aspects, wherein an indentation hardness on the Shore A scale measured on the outer surface of the movement restriction device is at least 50) 36. The apparatus according to aspect 35, wherein the indentation hardness is indentation hardness is measured by the durometer method defined in part 4 of ISO 48-4:2018.

37. The apparatus according to aspects 35-36, wherein an indentation hardness on the Shore A scale measured on the outer surface is no more than 70.

38. The apparatus according to any one of aspects 35-37, wherein an indentation hardness on the Shore A scale measured on the outer surface is in the range of 55 to 65, or 5-25 or >25-50, or >65.

39. The apparatus according to any one of the preceding aspects, wherein the implantable movement restriction device comprises a contrast agent.

40. The apparatus according to aspect 39, wherein the contrast agent is BaSO4.
41. The apparatus according to aspect 39 or 40, wherein the implantable movement restriction device comprises the contrast agent in an amount of 1-15% by weight of the implantable movement restriction device.
42. The apparatus according to aspect 41, wherein the implantable movement restriction device comprises the contrast agent in an amount of 1-6% by weight of the implantable movement restriction device.
43. The apparatus according to aspect 42, the implantable movement restriction device comprises the contrast agent in an amount of 8-15% by weight of the implantable movement restriction device.

Aspect Group 449XPC: Reflux Device Configuration Width

1. An implantable medical device for treating reflux disease, the implantable medical device comprising a movement restriction device configured to be fixated to the stomach wall for hindering movement of the lower esophageal sphincter relative to the thoracic diaphragm, the movement restriction device comprises at least two parts, wherein the parts are configured to be connected to each other for forming at least a portion of a functional movement restriction device, and the at least two parts are capable of disconnecting from each other, such that the at least two parts individually can pass through the gastro-intestinal tract, wherein the functional movement restriction device is elongated and has a height, being a longest cross-sectional distance, and a width, being a longest cross-sectional distance perpendicular to the height, and wherein the height is in the range 1.2-2 times longer than the width.
2. The implantable medical device according to aspect 1, wherein the height is in the range 1.3-2 times longer than the width.
3. The implantable medical device according to aspect 1, wherein the height is in the range 1.2-1.8 times longer than the width.
4. The implantable medical device according to aspect 1, wherein the height is in the range 1.3-1.6 times longer than the width.
5. The implantable medical device according to any one of aspects 1-4, wherein the functional movement restriction device has a height of more than 1 inch.
6. The implantable medical device according to any one of aspects 1-4, wherein the functional movement restriction device has a height in the range 1 inch-3.5 cm, 3.5 cm-6 cm, or in the range 4 cm-5 cm, or in the range 4 cm-6 cm.
7. The implantable medical device according to aspect 1, wherein at least one of the functional movement restriction device and the boundary of the functional movement restriction device has a surface area in the range, 19 $cm^2$-29 $cm^2$, or in the range 21 $cm^2$-41 $cm^2$, or in the range 22.5 $cm^2$-50 $cm^2$, or in the range 23 $m^2$-45 $cm^2$, or in the range 22.5 $cm^2$-225, or in the range >225-599 $cm^2$, or in the range 20.5 $cm^2$-200 $cm^2$, or in the range >200 $cm^2$-350 $cm^2$, or in the range >350 $cm^2$-450 $cm^2$, or in the range >450-599 $cm^2$.
8. The implantable medical device according to any one of the preceding aspects, further comprising a central part, wherein the at least two parts are configured to be connected to the central part for forming at least a portion of the functional movement restriction device, the central part and the at least two parts are capable of disconnecting from each other, such that the central part and the at least two parts individually can pass through the gastro-intestinal tract.
9. The apparatus according to any one of the preceding aspects, wherein the implantable movement restriction device (110) comprises
- a first portion having a first volume enclosed by material of the implantable movement restriction device (110), and
- a second portion, different from the first portion, having a second volume enclosed by material of the implantable movement restriction device (110), wherein:
  - the first volume has a higher density than the second volume, and the second volume has a density below 1000 kg/m3.

10. The apparatus according to aspect 9, wherein the first volume comprises a first solid material.
11. The apparatus according to aspect 10, wherein the first solid material comprises a polymer material, a metal, a ceramic or carbon material or a mixture thereof.
12. The apparatus according to aspect 11, wherein the first solid material comprises at least one of silicone-based material and a polyurethane-based material, an ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.
13. The apparatus according to any one of aspects 9-12, wherein the second volume comprises a second solid material.
14. The apparatus according to aspect 13, wherein the second solid material comprises a polymer material, a metal, a ceramic or carbon material or a mixture thereof.
15. The apparatus according to aspect 14, wherein the second solid material comprises a at least one of a polypropylene-based and a polyethylene-based material, an ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.
16. The apparatus according to any one of aspects 13-15, wherein the first volume comprises a solid material having a density above 1000 kg/m3 and the second volume comprises a solid material having a density below 1000 kg/m3.
17. The apparatus according to any one of aspects 9-16, wherein the second volume comprises a gas.
18. The apparatus according to any one of aspects 9-17, wherein the second volume comprises a plurality of volumes of gas enclosed by an enclosing material.
19. The apparatus according to aspect 18, wherein the second volume comprises a solid polymer material enclosing the enclosing material, and wherein the enclosing material is harder than the solid polymer material.
20. The apparatus according to any one of aspects 18 and 19, wherein the plurality of volumes of gas enclosed by an enclosing material makes up at least 10 volume percent of the second volume, more preferably at least 20 volume percent of the second volume, and even more preferably at least 30 volume percent of the second volume, and even more preferably at least 40 volume percent of the second volume, and even more preferably at least 50 volume percent of the second volume, and even more preferably at least 60 volume percent of the second volume, and even more preferably at least 70 volume percent of the second volume, and even more preferably at least 80 volume percent of the second volume, and even more preferably at least 90 volume percent of the second volume.
21. The apparatus according to any one of aspects 18-20, wherein the enclosing material comprises glass.

22. The apparatus according to any one of the preceding aspects, wherein the implantable movement restriction device comprises an outer surface configured to rest against the stomach wall portion, and wherein an average surface roughness measured on the outer surface is no more than 300'000 μm.

23. The apparatus (100) according to aspect 22, wherein the average surface roughness is $R_a$ as defined according to ISO 21920-2:2021.

24. The apparatus (100) according to aspect 22, wherein the average surface roughness is $S_a$ as defined according to ISO 25178-2:2021.

25. The apparatus (100) according to any one of aspects 22-24, wherein the average surface roughness is in the range of at least one of; 0.01-0.1 μm, >0.1-0.5 μm, >0.5-10 μm, >10-80 μm, >80-200 μm, >200-10'000 μm, >10'000-500'000 μm.

26. The apparatus (100) according to any one of aspects 22-25, wherein the average surface roughness is in the range of 0.1-0.3 mm.

27. The apparatus according to any one of the preceding aspects, wherein an indentation hardness on the Shore A scale measured on the outer surface of the movement restriction device is at least 50.

28. The apparatus according to aspect 27, wherein the indentation hardness is indentation hardness is measured by the durometer method defined in part 4 of ISO 48-4:2018.

29. The apparatus according to aspects 27-28, wherein an indentation hardness on the Shore A scale measured on the outer surface is no more than 70.

30. The apparatus according to any one of aspects 27-29, wherein an indentation hardness on the Shore A scale measured on the outer surface is in the range of 55 to 65, or 5-25 or >25-50, or >65.

31. The apparatus according to any one of the preceding aspects, wherein the implantable movement restriction device comprises a contrast agent.

32. The apparatus according to aspect 31, wherein the contrast agent is BaSO4.

33. The apparatus according to aspect 31 or 32, wherein the implantable movement restriction device comprises the contrast agent in an amount of 1-15% by weight of the implantable movement restriction device.

34. The apparatus according to aspect 33, wherein the implantable movement restriction device comprises the contrast agent in an amount of 1-6% by weight of the implantable movement restriction device.

35. The apparatus according to aspect 34, the implantable movement restriction device comprises the contrast agent in an amount of 8-15% by weight of the implantable movement restriction device.

Aspect Group 449YPC: Reflux Surgical Kit

1. A surgical kit for performing a surgical procedure for treating reflux disease, the surgical kit comprising:
- an implantable movement restriction device configured to be hindering movement of the lower esophageal sphincter relative to the thoracic diaphragm, placed at least partly between the angle of His and the diaphragm,
- a lubricant including at least a bacteriostatic substance for use with the implantable movement restriction device,
- at least one resorbable suture.

2. The surgical kit according to aspect 1, further comprising at least one at least partly barbed suture.

3. The surgical kit according to any one of the preceding aspects, wherein a portion of the barbed suture is without barbs at least 2 cm long.

4. The surgical kit according to aspect 3, wherein the at least one partially barbed suture comprises a loop for use in fixating the at least one partially barbed suture.

5. The surgical kit according to any aspect presented herein, wherein the bacteriostatic substance comprises at least one of the substances Chlorhexidine and Lidocain.

6. The surgical kit according to any one of the preceding aspects, wherein the at least one barbed suture comprises at least one of the following materials:
- a. PTFE,
- b. Gore Tex®
- c. Polybutester
- d. Polypropolene, and
- e. Polyester.

7. The surgical kit according to any one of the preceding aspects, wherein the at least one resorbable suture comprises at least one of the following materials:
- a. Polyglactin,
- b. GlycolideDioxanone
- c. Trimethylene carbonat
- d. Catgut
- e. Collagen
- f. Polylactide
- g. Copolymer
- h. Poly-4-hydroxybutyrate
- i. PHA
- j. Tephaflex
- k. Polycaprolactone
- 1. Polyhydroxyalkanoates
- m. Maxon
- n. PDS
- o. Polyglycolide 8. The surgical kit according to any one of the preceding aspects, wherein the at least one of:
- the at least partially barbed suture, and
- the at least one resorbable suture
- is a monofilament suture.

9. The surgical kit according to any one of the preceding aspects, wherein the at least one of:
- the at least partially barbed suture, and
- the at least one resorbable suture,
- is a braided suture.

10. The surgical kit according to any one of aspects 8 and 9, wherein the suture comprises a coating.

11. The surgical kit according to any one of the preceding aspects, wherein the movement restriction device comprises at least two parts, wherein the parts are configured to be connected to each other for forming at least a portion of a functional movement restriction device, and the at least two parts are capable of disconnecting from each other, such that the at least two parts individually can pass through the gastro-intestinal tract.

12. The surgical kit according to aspect 11, further comprising a central part, wherein the at least two parts are configured to be connected to the central part for forming at least a portion of the functional movement restriction device, the central part and the at least two parts are capable of disconnecting from each other, such that the central part and the at least two parts individually can pass through the gastro-intestinal tract.

13. The surgical kit according to any one of the preceding aspects, wherein the functional movement restriction device is elongated.

Aspect Group 449ZPC: Reflux Device Configuration Broad

1. An implantable medical device for treating reflux disease, the implantable medical device comprising a movement restriction device configured to be hindering movement of the lower esophageal sphincter relative to the thoracic diaphragm and adapted to be positioned between the angle of His and the diaphragm.
2. The implantable medical device according to claim 1, wherein the complete movement restriction device is elongated and has a height, being a longest cross-sectional distance, and a width, being a longest cross-sectional distance perpendicular to the height, and wherein the height is longer than the width.
3. The implantable medical device according to any one of aspects 1-2, wherein the movement restriction device has a height of >1 inch.
4. The implantable medical device according to any one of aspects 1-2, wherein the movement restriction device has a height in the range 1 inch-3.5 cm, >3.5 cm-6 cm, or in the range 4 cm-5 cm, or in the range 4 cm-6 cm.
5. The implantable medical device according to any one of the herein presented aspects, wherein at least one of the movement restriction device and the boundary of the movement restriction device has a volume in the range 7.3 $cm^3$-8 $cm^3$.
6. The implantable medical device according to any one of the herein presented aspects, wherein at least one of the movement restriction device and the boundary of the movement restriction device has a volume in the range >6.6 $cm^3$-<7.3 $cm^3$.
7. The implantable medical device according to any one of the herein presented aspects, wherein at least one of the movement restriction device and the boundary of the movement restriction device has a volume in the range >5.8 $cm^3$-6.6 $cm^3$.
8. The implantable medical device according to any one of the herein presented aspects, wherein at least one of the movement restriction device and the boundary of the movement restriction device has a volume in the range 5.0 $cm^3$-5.8 $cm^3$.
9. The implantable medical device according to any one of the herein presented aspects, wherein at least one of the movement restriction device and the boundary of the movement restriction device has a volume in the range >8 $cm^3$-<200 $cm^3$.
10. The implantable medical device according to any one of the herein presented aspects, wherein at least one of the movement restriction device and the boundary of the movement restriction device has a surface area in the range >23 $cm^2$-50 $cm^2$.
11. The implantable medical device according to any one of the herein presented aspects, wherein at least one of the movement restriction device and the boundary of the movement restriction device has a surface area in the range 22.5 $cm^2$-45 $cm^2$.
12. The implantable medical device according to any one of the herein presented aspects, wherein at least one of the movement restriction device and the boundary of the movement restriction device has a surface area in the range 21 $cm^2$-41 $cm^2$.
13. The implantable medical device according to any one of the herein presented aspects, wherein at least one of the movement restriction device and the boundary of the movement restriction device has a surface area in the range 19 $cm^2$-29 $cm^2$.
14. The implantable medical device according to any one of the herein presented aspects, wherein at least one of the movement restriction device and the boundary of the movement restriction device has a surface area >41 $cm^2$.
15. The implantable medical device according to any one of the herein presented aspects, wherein at least one of the movement restriction device and the boundary of the movement restriction device has a surface area of at least one of 22.5 $cm^2$-225 and >225-599 $cm^2$.
16. The implantable medical device according to any one of the herein presented aspects, wherein at least one of the movement restriction device and the boundary of the movement restriction device has a surface area of at least one of 20.5 $cm^2$-200 $cm^2$, >200 $cm^2$-350 cm, >350 $cm^2$-450 $cm^2$ and >450-599 $cm^2$
17. The apparatus according to any one of the herein presented aspects, wherein the volume of the implantable movement restriction device (110) comprises,
  A first material having a first density,
  A second material having a second density, and wherein:
    the first material has a higher density than the second material, and the second material has a density below 1000 kg/m3.
18. The apparatus according to aspect 17, wherein the first material comprises a polymer, material.
19. The apparatus according to aspect 17, wherein the first material comprises a plastic, metal, ceramic or carbon material or a mixture thereof.
20. The apparatus according to aspect 18, wherein the first material comprises at least one of a silicone-based, an ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof. 21. The apparatus according to any one of aspects 17-20, wherein the first material having a density above 1000 kg/m3 and the second material having a density below 1000 kg/m3.
22. The apparatus according to aspect 17-21, wherein the second material comprises at least one of a silicone-based, a ethylene-based, a polypropylene-based, a polyethylene-based, a PTFE-based, a polyurethane-based, a PEEK-based, a SRP-based, a PPSU-based, a PSU-based, carbon-based material, or bio ceramic-based, material or any mixture thereof.
23. The apparatus according to any one of aspects 17-22, wherein the second material is a gas.
24. The apparatus according to any one of aspects 17-23, wherein the second material comprises a plurality of volumes of gas enclosed by an enclosing material.
25. The apparatus according to any one of aspects 24, wherein the enclosing material comprises glass.
26. The apparatus according to any one of aspects 24 and 25, wherein the plurality of volumes of gas enclosed by an enclosing material makes up at least 10 volume percent of the volume of the second material, more preferably at least 20 volume percent of the second volume, and even more preferably at least 30 volume percent of the second volume.
27. The apparatus according to any one of aspects 24-26, wherein the plurality of volumes of gas enclosed by an enclosing material makes up at least 40 volume percent of the volume of the second material, more preferably at least 50 volume percent of the second volume.
28. The apparatus according to any one of aspects 24-27, wherein the plurality of volumes of gas enclosed by an enclosing material makes up at least 60 volume percent of the volume of the second material, more preferably at least 70) volume percent of the second volume.

29. The apparatus according to any one of aspects 24-28, wherein the plurality of volumes of gas enclosed by an enclosing material makes up at least 80 volume percent of the volume of the second material, more preferably at least 90 volume percent of the second volume.

30. The apparatus according to any one of the preceding aspects, wherein the implantable movement restriction device comprises an outer surface configured to rest against the stomach wall portion, and wherein an average surface roughness measured on the outer surface is no more than 300'000 μm.

31. The apparatus (100) according to aspect 30, wherein the average surface roughness is $R_a$ as defined according to ISO 21920-2:2021.

32. The apparatus (100) according to aspect 30, wherein the average surface roughness is $S_a$ as defined according to ISO 25178-2:2021.

33. The apparatus (100) according to any one of aspects 30-32, wherein the average surface roughness is in the range of at least one of; 0.01-0.1 μm, >0.1-0.5 μm, >0.5-10 μm, >10-80 μm, >80-200 μm, >200-10'000 μm, >10'000-500'000 μm.

34. The apparatus (100) according to any one of aspects 30-33, wherein the average surface roughness is in the range of 0.1-0.3 mm.

35. The apparatus according to any one of the preceding aspects, wherein an indentation hardness on the Shore A scale measured on the outer surface of the movement restriction device is at least 50.

36. The apparatus according to aspect 35, wherein the indentation hardness is indentation hardness is measured by the durometer method defined in part 4 of ISO 48-4:2018.

37. The apparatus according to aspects 35-36, wherein an indentation hardness on the Shore A scale measured on the outer surface is no more than 65.

38. The apparatus according to any one of aspects 35-37, wherein an indentation hardness on the Shore A scale measured on the outer surface is in the range of 50 to 65.

39. The apparatus according to any one of aspects 35-37, wherein an indentation hardness on the Shore A scale measured on the outer surface is in the range of 5-25 or >25-50, or >65.

40. The apparatus according to any one of the herein presented aspects, wherein the implantable movement restriction device comprises a contrast agent.

41. The apparatus according to aspect 40, wherein the contrast agent is $BaSO_4$.

42. The apparatus according to aspect 40 or 41, wherein the implantable movement restriction device comprises the contrast agent in an amount of 1-15% by weight of the implantable movement restriction device.

43. The apparatus according to aspect 42, wherein the implantable movement restriction device comprises the contrast agent in an amount of 1-6% by weight of the implantable movement restriction device.

44. The apparatus according to aspect 43, the implantable movement restriction device comprises the contrast agent in an amount of 8-15% by weight of the implantable movement restriction device.

The invention claimed is:

1. A surgical method of treating reflux disease comprising the steps of:

a. dissecting an outside of a fundus of a stomach at least partially down on a posterior side of the outside of the fundus; in an approximate direction towards bursa Omentalis, as well as away from a spleen, b. dissecting an esophagus such that the esophagus is disconnected from surrounding tissue at least 3 cm in a cranial direction from an angle of His, c. connecting the fundus to the esophagus by:

i. placing at least two posterior single sutures in a posterior suture line, or a posterior continuous suture line, connecting the fundus to the esophagus, on a sinister-posterior side of the esophagus, and ii. placing at least two anterior sutures, in an anterior suture line, or an anterior continuous suture line, connecting the fundus to the esophagus, on the sinister-anterior side of the esophagus, and d. placing an implantable movement restriction device between an angle of His and a diaphragm, such that a lower esophageal sphincter is prevented from sliding through an esophageal hiatus.

2. The surgical method according to claim 1, wherein the step of dissecting the fundus at least partially on the posterior side thereof comprises at least partially freeing the fundus from at least one of a Gastrophrenic ligament and a Gastrosplenic ligament.

3. The surgical method according to claim 1, wherein the step of dissecting the fundus at least partially on the posterior side thereof comprises dissecting the fundus at least 1 cm posterior to a coronal plane intersecting a most cranial point of the fundus.

4. The surgical method according to claim 1, wherein the step of dissecting the fundus at least partially on the posterior side thereof comprises dissecting the fundus at least 1 cm posterior to a most anterior fixation point of the Gastrophrenic ligament on the fundus.

5. The surgical method according to claim 1, wherein the step of dissecting the fundus at least partially on the posterior side thereof comprises dissecting the fundus at least 1 cm posterior to an extension of a greater curvature of the stomach in the region of the fundus.

6. The surgical method according to claim 1, wherein the step of dissecting the fundus further comprises dissecting a gastric brevis and/or short gastrics and ligating at least one of them.

7. The surgical method according to claim 1, wherein the step of dissecting the esophagus comprises dissecting the esophagus such that the esophagus is disconnected from the surrounding tissue at least 4 cm in a cranial direction from the angle of his.

8. The surgical method according to claim 1, wherein the step of dissecting the esophagus such that the esophagus is disconnected from the surrounding tissue comprises dissecting the esophagus into mediastinum.

9. The surgical method according to claim 1, wherein the step of dissecting the esophagus into mediastinum comprises dissecting the esophagus into mediastinum such that the esophagus is disconnected from the surrounding tissue at least 1 cm in a cranial direction from a distal edge of the esophageal hiatus.

10. The surgical method according to claim 1, wherein at least one of:

the step of placing at least two posterior sutures, connecting the fundus to the esophagus, on the sinister-posterior side of the esophagus comprises placing at least two lateral sutures substantially along a cranial-caudal axis, on the sinister-posterior side of the esophagus, and the step of placing at least two anterior sutures, connecting the fundus to the esophagus, on the sinister-anterior side of the esophagus comprises placing at least two lateral sutures substantially along a cranial-caudal axis, on the sinister-anterior side of the esophagus.

11. The surgical method according to claim 1, wherein at least one of:

the step of placing at least two posterior sutures, connecting the fundus to the esophagus, on the sinister-posterior side of the esophagus, comprises placing the at least two posterior sutures at least 0.5 cm posterior to a coronal plane intersecting a most cranial point of the fundus, and the step of placing at least two anterior sutures, connecting the fundus to the esophagus, on the sinister-anterior side of the esophagus, comprises placing the at least two anterior sutures at least 0.5 cm anterior from the coronal plane intersecting a most cranial point of the fundus.

12. The surgical method according to claim 1, wherein at least one of:

the step of placing at least two posterior sutures, connecting the fundus to the esophagus, on the sinister-posterior side of the esophagus comprises placing a most caudal suture at least 0.5 cm from the angle of His, and the step of placing at least two anterior sutures, connecting the fundus to the esophagus, on the sinister-anterior side of the esophagus comprises placing a most caudal suture at least 0.5 cm from the angle of His.

13. The surgical method according to claim 1, wherein at least one of:

the step of placing at least two posterior sutures, connecting the fundus to the esophagus, on the sinister-posterior side of the esophagus comprises placing a most caudal suture at least 1.5 cm from the angle of His, and the step of placing at least two anterior sutures or staplers, connecting the fundus to the esophagus, on the sinister-anterior side of the esophagus comprises placing a most caudal suture or stapler at least 1.5 cm from the angle of His.

14. The surgical method according to claim 1, comprising one of the steps of:

placing a most caudal suture of the at least two posterior sutures or staplers, connecting the fundus to the esophagus, on the sinister-posterior side of the esophagus at least 0.5 cm from the angle of His and placing a most caudal suture or stapler of the at least two anterior sutures or staplers, connecting the fundus to the esophagus, on the sinister-anterior side of the esophagus at least 1.5 cm from the angle of His, and placing a most caudal suture of the at least two posterior sutures or staplers, connecting the fundus to the esophagus, on the sinister-posterior side of the esophagus at least 1.5 cm from the angle of His and placing a most caudal suture of the at least two anterior sutures or staplers, connecting the fundus to the esophagus, on the sinister-anterior side of the esophagus at least 0.5 cm from the angle of His.

15. The surgical method according to claim 1, wherein the step of connecting the fundus to the esophagus further comprises placing at least one central suture on a cranial-caudal axis extending between the at least two posterior sutures or continuous suture line and the at least two anterior sutures or continuous suture line.

16. The surgical method according to claim 1, wherein the step of placing an implantable movement restriction device between the angle of His and the diaphragm comprises placing a continuous purse-string type roof suture in the region of a greater curvature of the stomach, in a region of the fundus, such that the stomach tissue can be contracted and formed to a hat over the implantable movement restriction device when implanted by pulling ends of the purse-string sutures.

17. The surgical method according to claim 16, wherein the step of placing roof sutures comprises placing at least one of the continuous purse-string roof sutures at least 1 cm behind the greater curvature of the stomach, in a caudal region of the fundus.

18. The surgical method according to claim 1, wherein the step of placing an implantable movement restriction device between the angle of His comprises placing a continuous purse-string base or floor suture in the region below the movement restriction device to stabilize its position.

19. The surgical method according to claim 18, wherein the step of placing the continuous purse-string floor suture comprises placing at least two of continuous purse-string floor suture bites following an arc to stabilize the position of the movement restriction device.

20. The surgical method according to claim 19, wherein the step of placing continuous purse-string base or floor suture following an arc comprises placing continuous purse-string floor sutures following an arc below an elongated abdominal portion of an instrument holding the implantable movement restriction device.

* * * * *